US011771715B2

(12) United States Patent
Horhota et al.

(10) Patent No.: US 11,771,715 B2
(45) **Date of Patent: *Oct. 3, 2023**

(54) CIRCULAR RNA COMPOSITIONS AND METHODS

(71) Applicant: Orna Therapeutics, Inc., Cambridge, MA (US)

(72) Inventors: Allen T. Horhota, Cambridge, MA (US); Brian Goodman, Cambridge, MA (US); Robert Alexander Wesselhoeft, Cambridge, MA (US); Junghoon Yang, Cambridge, MA (US)

(73) Assignee: Orna Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/503,208

(22) Filed: Oct. 15, 2021

(65) Prior Publication Data

US 2023/0058784 A1 Feb. 23, 2023

Related U.S. Application Data

(63) Continuation of application No. 17/202,223, filed on Mar. 15, 2021, which is a continuation of application No. PCT/US2020/063494, filed on Dec. 4, 2020.

(60) Provisional application No. 63/087,582, filed on Oct. 5, 2020, provisional application No. 63/022,248, filed on May 8, 2020, provisional application No. 62/972,194, filed on Feb. 10, 2020, provisional application No. 62/943,779, filed on Dec. 4, 2019, provisional application No. 62/943,797, filed on Dec. 4, 2019.

(51) Int. Cl.
*A61K 31/7105* (2006.01)
*A61K 47/22* (2006.01)

(52) U.S. Cl.
CPC .......... *A61K 31/7105* (2013.01); *A61K 47/22* (2013.01)

(58) Field of Classification Search
CPC .. A61K 48/005; A61K 48/0025; C12N 15/11; C12N 15/64; C12N 15/67; C12N 15/79; C12N 15/113; C12N 2830/42; C12N 2840/203; C12P 19/34
USPC ...... 424/9.1; 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 4,323,689 | A | 4/1982 | Vogel et al. |
| 4,661,450 | A | 4/1987 | Kempe et al. |
| 5,434,261 | A | 7/1995 | Schoen et al. |
| 5,580,859 | A | 12/1996 | Felgner et al. |
| 5,591,737 | A | 1/1997 | Doherty et al. |
| 5,625,047 | A | 4/1997 | Been et al. |
| 5,629,304 | A | 5/1997 | Murakata et al. |
| 5,656,606 | A | 8/1997 | Nargund et al. |
| 5,672,596 | A | 9/1997 | Wyvratt et al. |
| 5,712,128 | A | 1/1998 | Been et al. |
| 5,747,485 | A | 5/1998 | Doherty et al. |
| 5,755,903 | A | 5/1998 | Garant et al. |
| 5,766,903 | A | 6/1998 | Sarnow |
| 5,773,244 | A | 6/1998 | Ares, Jr. et al. |
| 5,972,964 | A | 10/1999 | Perregaard |
| 6,043,026 | A | 3/2000 | Patchett et al. |
| 6,210,931 | B1 | 4/2001 | Feldstein et al. |
| 6,211,174 | B1 | 4/2001 | Devita et al. |
| 6,368,802 | B1 | 4/2002 | Kool |
| 6,576,628 | B1 | 6/2003 | Grams et al. |
| 6,620,597 | B1 | 9/2003 | Chen et al. |
| 8,829,170 | B2 | 9/2014 | Dale et al. |
| 11,203,767 | B2 | 12/2021 | Anderson et al. |
| 11,352,640 | B2 | 6/2022 | Anderson et al. |
| 11,352,641 | B2 | 6/2022 | Anderson et al. |
| 2006/0199851 | A1 | 9/2006 | Kempf et al. |
| 2010/0137407 | A1 | 6/2010 | Abe et al. |
| 2010/0305197 | A1 | 12/2010 | Che |
| 2011/0019782 | A1 | 1/2011 | Kobayashi et al. |
| 2015/0079630 | A1 | 3/2015 | Abe et al. |
| 2016/0194368 | A1 | 7/2016 | Hoge et al. |
| 2016/0331828 | A1 | 11/2016 | Ciaramella et al. |

(Continued)

FOREIGN PATENT DOCUMENTS

| | | | |
|---|---|---|---|
| CN | 101016264 | A | 8/2007 |
| CN | 105176981 | A | 12/2015 |

(Continued)

OTHER PUBLICATIONS

U.S. Appl. No. 17/548,241, filed 2019.*

(Continued)

*Primary Examiner* — Jane J Zara
(74) *Attorney, Agent, or Firm* — Goodwin Procter LLP

(57) ABSTRACT

Disclosed herein are circular RNAs and transfer vehicles, along with related compositions and methods of treatment. The circular RNAs can comprise group I intron fragments, spacers, an IRES, duplex forming regions, and/or an expression sequence, thereby having the features of improved expression, functional stability, low immunogenicity, ease of manufacturing, and/or extended half-life compared to linear RNA. Pharmaceutical compositions comprising such circular RNAs and transfer vehicles are particularly suitable for efficient protein expression in immune cells in vivo. Also disclosed are precursor RNAs and materials useful in producing the precursor or circular RNAs, which have improved circularization efficiency and/or are compatible with effective circular RNA purification methods.

25 Claims, 75 Drawing Sheets

Specification includes a Sequence Listing.

(56) References Cited

U.S. PATENT DOCUMENTS

| | | | | |
|---|---|---|---|---|
| 2017/0204422 | A1 | 7/2017 | Nelson et al. | |
| 2018/0010175 | A1 | 1/2018 | Cheng | |
| 2018/0311343 | A1 | 11/2018 | Huang et al. | |
| 2018/0326045 | A1 | 11/2018 | Ciaramella et al. | |
| 2019/0290694 | A1 | 9/2019 | Gautron et al. | |
| 2019/0314291 | A1 | 10/2019 | Besin et al. | |
| 2019/0328769 | A1 | 10/2019 | Uchida et al. | |
| 2019/0345503 | A1 | 11/2019 | Chang et al. | |
| 2020/0040370 | A1 | 2/2020 | Eber et al. | |
| 2020/0080106 | A1 | 3/2020 | Anderson et al. | |
| 2021/0085719 | A1 | 3/2021 | Jensen | |
| 2021/0198688 | A1* | 7/2021 | Anderson .......... | A61K 31/7105 |
| 2021/0363540 | A1 | 11/2021 | Anderson et al. | |
| 2021/0371494 | A1 | 12/2021 | Wesselhoeft et al. | |
| 2021/0403944 | A1 | 12/2021 | Anderson et al. | |
| 2022/0025395 | A1 | 1/2022 | Anderson et al. | |
| 2022/0106259 | A1 | 4/2022 | Benenato et al. | |
| 2022/0177540 | A1 | 6/2022 | Wesselhoeft et al. | |

FOREIGN PATENT DOCUMENTS

| | | | | |
|---|---|---|---|---|
| CN | 106801050 | A | 6/2017 | |
| EP | 2819377 | A1 | 12/2014 | |
| EP | 3630966 | A1 | 4/2020 | |
| EP | 3819377 | A1 | 5/2021 | |
| GB | 2308064 | A | 6/1997 | |
| JP | 2016/521133 | A | 7/2016 | |
| JP | 2017043556 | A | 3/2017 | |
| JP | 6284181 | B2 | 2/2018 | |
| KR | 2011/0095439 | A | 8/2011 | |
| WO | 1995/011029 | A1 | 4/1995 | |
| WO | 1995/024207 | A1 | 9/1995 | |
| WO | 2005/044201 | A2 | 5/2005 | |
| WO | 2005/079803 | A1 | 9/2005 | |
| WO | 2006/138380 | A2 | 12/2006 | |
| WO | 2007/044627 | A2 | 4/2007 | |
| WO | 2009/035541 | A1 | 3/2009 | |
| WO | 2010/084371 | A1 | 7/2010 | |
| WO | 2010/138652 | A1 | 12/2010 | |
| WO | 2010/138659 | A1 | 12/2010 | |
| WO | 2010/138685 | A1 | 12/2010 | |
| WO | 2010/138695 | A1 | 12/2010 | |
| WO | 2010/138706 | A1 | 12/2010 | |
| WO | 2010/138758 | A1 | 12/2010 | |
| WO | 2013/076509 | A1 | 5/2013 | |
| WO | 2013/118878 | A1 | 8/2013 | |
| WO | 2014/144871 | A1 | 9/2014 | |
| WO | 2014/186334 | A1 | 11/2014 | |
| WO | 2014/193857 | A1 | 12/2014 | |
| WO | 2015/034925 | A1 | 3/2015 | |
| WO | 2015/095340 | A1 | 6/2015 | |
| WO | 2016/020373 | A1 | 2/2016 | |
| WO | 2016/197121 | A1 | 12/2016 | |
| WO | 2017/046203 | A1 | 3/2017 | |
| WO | 2017/049245 | A2 | 3/2017 | |
| WO | 2017/055487 | A2 | 4/2017 | |
| WO | 2017/059357 | A1 | 4/2017 | |
| WO | 2017/118734 | A1 | 7/2017 | |
| WO | 2017/201332 | A1 | 11/2017 | |
| WO | 2017/201333 | A1 | 11/2017 | |
| WO | 2017/201340 | A2 | 11/2017 | |
| WO | 2017/201342 | A1 | 11/2017 | |
| WO | 2017/201346 | A1 | 11/2017 | |
| WO | 2017/201348 | A1 | 11/2017 | |
| WO | 2017/201349 | A1 | 11/2017 | |
| WO | 2017/201350 | A1 | 11/2017 | |
| WO | 2017/222911 | A1 | 12/2017 | |
| WO | 2018/144775 | A1 | 8/2018 | |
| WO | 2018/157009 | A1 | 8/2018 | |
| WO | 2018/170260 | A1 | 9/2018 | |
| WO | 2018/170306 | A1 | 9/2018 | |
| WO | WO-2018170306 | A1 * | 9/2018 | ......... A61K 38/1816 |
| WO | 2018/191722 | A1 | 10/2018 | |
| WO | 2018/237372 | A1 | 12/2018 | |
| WO | 2019/118919 | A1 | 6/2019 | |
| WO | 2019/213308 | A1 | 11/2019 | |
| WO | 2019/222275 | A2 | 11/2019 | |
| WO | 2019/236673 | A1 | 12/2019 | |
| WO | 2020/010242 | A1 | 1/2020 | |
| WO | 2020/023595 | A1 | 1/2020 | |
| WO | 2020/035070 | A1 | 2/2020 | |
| WO | 2020/061367 | A1 | 3/2020 | |
| WO | 2020/198403 | A2 | 10/2020 | |
| WO | 2020/237227 | A1 | 11/2020 | |
| WO | 2020/252436 | A1 | 12/2020 | |
| WO | 2021/041541 | A1 | 3/2021 | |
| WO | WO-2021055849 | A1 * | 3/2021 | ......... A61K 31/7052 |
| WO | 2021/113777 | A2 | 6/2021 | |

OTHER PUBLICATIONS

U.S. Appl. No. 17/202,223, filed 2019.*

Benenato, Ciaramella, and Huang. "Structures of Lipids," 2022, 28 pages.

Final Office Action for U.S. Appl. No. 17/384,460, dated Jul. 22, 2022.

Koos et al. "Influence of structure on antimicrobial activity of some heterocycles. IV. 1-(3-alkylamino-2-hydroxypropyl)-2-methyl-5-nitroimidazoles," Chem Papers. 1994, 48(1):54-57.

Non-Final Office Action for U.S. Appl. No. 17/548,241, dated May 24, 2022.

Notice of Allowance for U.S. Appl. No. 17/492,512, dated Apr. 26, 2022.

Notice of Allowance for U.S. Appl. No. 17/548,247, dated Jul. 22, 2022.

STN Registry Database Entry for 1333432-38-4 entered STN Sep. 27, 2011.

STN Registry Database Entry for 1333626-46-2 entered STN Sep. 28, 2011.

STN Registry Database Entry for 156811-31-3 entered STN Aug. 5, 1994.

STN Registry Database Entry for 157493-54-4 entered STN Sep. 7, 1994.

STN Registry Database Entry for 1609534-48-6 entered STN Jun. 4, 2014.

STN Registry Database Entry for 2086785-24-0 entered STN Mar. 17, 2017.

STN Registry Database Entry for 2086785-25-1 entered STN Mar. 17, 2017.

STN Registry Database Entry for 2086785-26-2 entered STN Mar. 17, 2017.

STN Registry Database Entry for 2086785-27-3 entered STN Mar. 17, 2017.

STN Registry Database Entry for 2086785-32-0 entered STN Mar. 17, 2017.

STN Registry Database Entry for 2086785-33-1 entered STN Mar. 17, 2017.

STN Registry Database Entry for 2089251-16-9 entered STN Apr. 10, 2017.

STN Registry Database Entry for 79111-60-7 entered STN Nov. 16, 1984.

Unpublished U.S. Appl. No. 17/853,576, entitled "Circular RNA Vectors Encoding Chimeric Antigen Receptors Targeting BCMA," Filed Jun. 29, 2022; Inventors: Robert Alexander Wesselhoeft, Kristen Ott, Thomas Barnes, Gregory Motz, Amy M. Becker, Allen T. Horhota, and Brian Goodman.

Van Esch et al. "Aggregation behavior and copper-binding properties of surfactants containing imidazole and pyrazole ligands," Reel Trav Chim Pays-Bas. 1994, 113(4): 186-193.

Wang et al. "Combinatorially designed lipid-like nanoparticles for intracellular delivery of cytotoxic protein for cancer therapy," Angew Chem Int Ed Engl. 2014, 53(11):2893-2898.

Badelt et al. "Computational Design of a Circular RNA with Prionlike Behavior," Artif Life., 2016, 22(2):172-84.

Bail et al. "Tri- to be mono- for bacterial mRNA decay," Structure, 2009, 17(3):317-9.

Barrett et al. "Circular RNAs: analysis, expression and potential functions," Development, 2016, 1143(11):1838-47.

(56) References Cited

OTHER PUBLICATIONS

Bohjanen, P. R. et al., "A small circular TAR RNA decoy specifically inhibits Tat-activated HIV-1 transcription,", Nucleic Acids Res., vol. 24; No. 19; 3733-3738 (1996).
Bohjanen, P. R., et al., "TAR RNA decoys inhibit Tat-activated HIV-1 transcription after preinitiation complex formation", Nucleic Acids Res., vol. 25; 4481-4486 (1997).
Borchardt et al. "Inducing circular RNA formation using the CRISPR endoribonuclease Csy4," RNA, 2017, 23 (5):619-627.
Branch et al. "Unusual properties of two branched RNA's with circular and linear components," Nucleic Acids Res., 1985, 13(13):14889-903.
Cech, T.R., "Self-Splicing of Group 1 Introns," Ann. Rev. Biochem., vol. 59; 543-568 (1990).
Chen et al. "Promising diagnostic and therapeutic circRNAs for skeletal and chondral disorders," Int J Biol Sci., 2021, 17(5):1428-1439.
Chen et al. "Sensing Self and Foreign Circular RNAs by Intron Identify," Molecular Cell, 2017, 67:228-238.
Chen, C. and Sarnow, P., "Initiation of protein synthesis by the eukaryotic translational apparatus on circular RNAs," America Association for the Advancement of Science, Abstract 268.5209; p. 415 (1995).
Costello et al. "Reinventing the Wheel: Synthetic Circular RNAs for Mammalian Cell Engineering." Trends Biotechnol., 2020, 38(2):217-230.
Dahlman, J.E., et al., "Barcoded nanoparticles for high throughput in vivo discovery of targeted therapeutics," PNAS, vol. 114; No. 8; 2060-2065 (2017).
Devaux, Y. et al., "Circular RNAs in heart failure", European Journal of Heart Failure, vol. 19; 701-709 (2017).
Durymanov, M. and Reineke, J., "Non-viral Delivery of Nucleic Acids: Insight Into Mechanisms of Overcoming Intracellular Barriers," Frontiers in Pharmacology, vol. 9; Article 971; 15 pages (2018).
Examination Report issued in EP19739422.4 dated Mar. 17, 2022. 6 pages.
Fenton et al., "Customizable Lipid Nanoparticle Materials for the Delivery of siRNAs and mRNAs," Angew Chem Int Ed Engl. 57(41): 13582-86 (2018).
Final Office Action for U.S. Appl. No. 17/191,697, dated Sep. 30, 2021.
Final Office Action for U.S. Appl. No. 17/202,223, dated Mar. 7, 2022.
Foster et al. "Purification of mRNA Encoding Chimeric Antigen Receptor Is Critical for Generation of a Robust T-Cell Response," Hum Gene Ther, 2019, 30(2):168-178.
Greene, J. et al., "Circular RNAs: Biogenesis, Function and Role in Human Diseases", Frontiers in Molecular Biosciences, vol. 4; Article 38; 11 pages (2017).
Han et al. "Multi-antigen-targeted chimeric antigen receptor T cells for cancer therapy," J Hematol Oncol., 2019, 12(1):128.
Harrer et al. "RNA-transfection of gamma/delta T cells with a chimeric antigen receptor or an alpha/beta T-cell receptor: a safer alternative to genetically engineered alpha/beta T cells for the immunotherapy of melanoma," BMC Cancer, 2017, 17:551, 17 pages.
He, J. et al., "Cicular RNAs and cancer", Cancer Letters, vol. 396, 138-144 (2017).
Holdt et al. "Circular RNAs as Therapeutic Agents and Targets," Front Physiol., 2018, 9:1262.
International Preliminary Report on Patentability and Written Opinion for International Application No. PCT/US2019/035531, dated Dec. 8, 2020, 8 pages.
International Preliminary Report on Patentability for International Application No. PCT/US2019/035531, entitled: "Circular RNA for Translation in Eukaryotic Cells," dated Dec. 17, 2020 (9 pages).
International Preliminary Report on Patentability for International Application No. PCT/US2020/034418 dated Nov. 16, 2021. 8 pages.
International Search Report and Written Opinion for International Application No. PCT/US2019/035531, entitled: "Circular RNA for Translation in Eukaryotic Cells," dated Sep. 27, 2019 (17 pages).
International Search Report and Written Opinion for International Application No. PCT/US2020/034418, dated Sep. 28, 2020, 15 pages.
International Search Report and Written Opinion for International Application No. PCT/US2020/063494, dated Aug. 6, 2021, 24 pages.
International Search Report and Written Opinion for International Application No. PCT/US2021/023540 dated Oct. 11, 2021.
International Search Report and Written Opinion for International Application No. PCT/US2021/031629 dated Feb. 4, 2022.
International Search Report and Written Opinion for International Appliction No. PCT/US2021/033276 dated Oct. 18, 2021.
Invitation to Pay Additional Fees and, Where Applicable, Protest Fee for International Application No. PCT/JS2020/063494, dated Apr. 28, 2021, 12 pages.
Jeck et al. "Detecting and characterizing circular RNAs," Nat Biotechnol., 2014, 32(5):453-61.
Jemielity et al. "Synthetic mRNA cap analogs with a modified triphosphate bridge—synthesis, applications and prospects," New Journal of Chemistry, 2010, 34:829-844.
Kaczmarek et al. "Advances in the Delivery of RNA Therapeutics: from Concept to Clinical Reality," Genome Medicine, 2017, 9(1):60.
Kariko, K. et al., "Generating the optimal mRNA for therapy: HPLC purification eliminates immune activation and improves translation of nucleoside-modified, protein-encoding mRNA", Nucleic Acids Research, vol. 39; No. 21; e142, 10 pages (2011).
Kariko, K. et al., "Incorporation of Pseudouridine Into mRNA Yields Superior Nonimmunogenic Vector With Increased Translational Capacity and Biological Stability," Molecular Therapy, Vo. 16; No. 11; 1833-1840 (2008).
Kauffman, K.J. et al., "Efficacy and Immunogenicity of Unmodified and Pseudouridine-Modified mRNA Delivered Systemically with Lipid Nanoparticles in Vivo," Biomaterials, vol. 109; 78-87 (2016).
Kauffman, K.J. et al., "Rapid, Single-cell Analysis and Discovery of Vectored mRNA Transfection in Vivo wth a IoxP-Flanked tdTomato Reporter Mouse," Molecular Therapy: Nucleic Acids, vol. 10; 55-63 (2018).
Kauffman, K.J., "Optimization and analysis of lipid nanoparticles for in vivo mRNA delivery," Ph D. Thesis, Massachusetts Institute of Technology, Department of Chemical Engineering; 167 pages (2017).
Kotterman, M.A. and Schaffer, D.V., "Engineering adeno-associated viruses for clinical gene therapy," Nature Reviews, vol. 15; 445-451 (2014).
Legnini, I. et al., "Circ-ZNF609 Is a Circular RNA that Can Be Translated and Functions in Myogenesis," Molecular Cell, vol. 66; No. 1; 22-37 (2017).
Lenzi et al., "Gene Transfer Research: The Evolution of the Clinical Science," NCBI Bookshelf, A Service of the National Library of Medicine, National Institutes of Health, 16 pages (2014).
Li et al. "The Biogenesis, Functions, and Challenges of Circular RNAs," Mol Cell., 2018, 71(3):428-442.
Litke et al. "Trans ligation of RNAs to generate hybrid circular RNAs using highly efficient autocatalytic transcripts," Methods, 2021, S1046-2023(21)00135-3.
Mao et al. "Biological roles and therapeutic potential of circular RNAs in osteoarthritis," Mol Ther Nucleic Acids, 2021, 24:856-867.
Meganck et al. "Engineering highly efficient backsplicing and translation of synthetic circRNAs," Mol Ther Nucleic Acids, 2021, 23:821-834.
Memczak, S. et al., "Circular RNAs and a large class of animal RNAs with regulatory potency," Nature, vol. 495; 333-338 (2013).
Metzgar et al. "Abrupt emergence of diverse species B adenoviruses at US military recruit training centers," J Infect Dis. 2007, 196(10):1465-73.
Mu, X. et al., "An origin of the immunogenicity of in vitro transcribed RNA," Nucleic Acids Research, vol. 46; No. 10; 5239-5249 (2018).

(56) References Cited

OTHER PUBLICATIONS

Nakamoto et al. "Chemical Synthesis of Circular RNAs with Phosphoramidate Linkages for Rolling-Circle Translation," Curr Protoc., 2021, 1(3):e43.
Non-Final Office Action for U.S. Appl. No. 17/191,697, dated Jun. 18, 2021.
Non-Final Office Action for U.S. Appl. No. 17/374,497, dated Dec. 7, 2021.
Non-Final Office Action for U.S. Appl. No. 17/468,100, dated Dec. 8, 2021.
Non-Final Office Action for U.S. Appl. No. 17/492,512, dated Mar. 1, 2022.
Non-Final Office Action for U.S. Appl. No. 17/202,223, dated Apr. 18, 2022.
Non-Final Office Action for U.S. Appl. No. 17/202,223, dated Aug. 20, 2021.
Non-Final Office Action for U.S. Appl. No. 17/384,460, dated Mar. 24, 2022.
Non-Final Office Action for U.S. Appl. No. 17/548,247, dated Apr. 1, 2022.
Notice of Allowance for U.S. Appl. No. 17/191,697, dated Nov. 2, 2021.
Notice of Allowance for U.S. Appl. No. 17/374,497, dated Apr. 13, 2022.
Notice of Allowance for U.S. Appl. No. 17/468,100, dated Apr. 8, 2022.
Oberli et al. "Lipid Nanoparticle Assisted mRNA Delivery for Potent Cancer Immunotherapy," Nano Letters, 2017, 17:1326-1335.
Obi et al. "The design and synthesis of circular RNAs," Methods, 2021, S1046-2023(21)00065-7.
Ochi, A., et al., Nucleic Acids Symp. Ser. vol. 53, pp. 275-276 (2009).
Pamudurti, N.R. et al., "Translation of CircRNAs," Molecular Cell, vol. 66; No. 1; 9-21 (2017).
Petkovic et al. "RNA Circularization Strategies in vivo and in vitro," Nucleic Acids Research, 2015, 43(4):12454-2465.
Puttaraju et al. "Group I Permuted Intron-exon (PIE) Sequences Self-splice to Produce Circular Exons," Nucleic Acids Research, 1992, 20(20):15357-5364.
Puttaraju, M. and Been, M. D., Circular Ribozymes Generated in *Escherichia coli* Using Group I Self-splicing Permuted Intron-Exon Sequences, J Biol Chem., vol. 271, pp. 26081-26087 (1996).
Rafiq et al. "Targeted delivery of a PD-1-blocking scFv by CAR-T cells enhances anti-tumor efficacy in vivo," Nat Biotechnol., 2018, 36(9):847-856.
Rausch et al. "Characterizing and circumventing sequence restrictions for synthesis of circular RNA in vitro," Nucleic Acids Res., 2021, 49(6):e35.
Sahin, U. et al., "mRNA-based therapeutics—developing a new class of drugs," Nature Reviews, vol. 13; 759-780 (2014).
Shim, G. et al., "Nonviral Delivery Systems for Cancer Gene Therapy: Strategies and Challenges," Current Gene Therapy, vol. 17; 18 pages (2017).
Sullenger et al. "From the RNA world to the clinic," Science, 2016, 352(6292):1417-1420.
Umekage et al. "In vivo circular RNA production using a constitutive promoter for high-level expression," J Biosci Bioeng, 2009, 108(4):354-6.
Umekage, U. et al., In Vivo Circular RNA Expression by the Permuted Intron-Exon Method, Innovations in Biotechnology, Chapter 4, 17 pages (2012).
Unpublished U.S. Appl. No. 17/202,223, entitled: "Circular RNA Compositions and Methods," Filed Mar. 15, 2021; Inventors: Brian Goodman, Alexander Wesselhoeft, Allen T. Horhota, Jung-hoon Yang, and Kristen Ott.
Unpublished U.S. Appl. No. 17/374,497, entitled: "Circular RNA for Translation in Eukaryotic Cells," Filed Jul. 13, 2021, Inventors: Daniel G. Anderson, Robert Alexander Wesselhoeft, and Piotr S. Kowalski.
Unpublished U.S. Appl. No. 17/384,460, entitled: "Circular RNA Compositions and Methods," Filed Jul. 23, 2021; Inventors: Alexander Wesselhoeft, Daniel G. Anderson, Shinichiro Fuse, Brian Goodman, Allen Horhota, and Raffaella Squilloni.
Unpublished U.S. Appl. No. 17/468,100, entitled: "Circular RNA for Translation in Eukaryotic Cells," Filed Sep. 7, 2021, Inventors: Daniel G. Anderson, Robert Alexander Wesselhoeft, and Piotr S. Kowalski.
Unpublished U.S. Appl. No. 17/492,512, entitled: "Circular RNA for Translation in Eukaryotic Cells," Filed Oct. 1, 2021, Inventors: Daniel G. Anderson, Robert Alexander Wesselhoeft, and Piotr S. Kowalski.
Unpublished U.S. Appl. No. 17/548,241, entitled "Circular RNA Compositions and Methods," Filed Dec. 10, 2021; Inventors: Brian Goodman, Alexander Wesselhoeft, Allen Horhota, and Junghoon Yang.
Unpublished U.S. Appl. No. 17/548,247, entitled "Circular RNA Compositions and Methods," Filed Dec. 10, 2021; Inventors: Alexander Wesselhoeft, Daniel G. Anderson, Shinichiro Fuse, Brian Goodman, Allen Horhota, and Ratfaella Squilloni.
Valdmanis, P.N. and Kay, M.A., "The Expanding Repertoire of Circular RNAs," The American Society of Gene and Cell Therapy, vol. 21; No. 6; 1112-1114 (2013).
Wang, Y. and Wang, Z., "Efficient backsplicing produces translatable circular mRNAs," RNA, vol. 21; No. 2; 172-179 (2014).
Wesselhoeft et al. "Engineering Circular RNA for Potent and Stable Translation in Eukaryotic Cells," Nature Communications, 2018, 9(1):2629, 10 pages.
Wesselhoeft et al. "RNA Circulation Diminishes Immunogenicity and can Extend Translation Duration In Vivo," Molecular Cell, 2019, 74(3):508-520.
Wiesinger et al. "Clinical-Scale Production of CAR-T Cells for the Treatment of Melanoma Patients by mRNA Transfection of a CSPG4-Specific CAR under Full GMP Compliance," Cancers (Basel), 2019, 11(8):1198.
Xue et al. "Lipid-based nanocarriers for RNA delivery," Curr Pharm Des, 2015, 21(22):3140-7.
Yang et al. "Circular RNAs: Expression, localization, and therapeutic potentials," Mol Ther, 2021, 29(5):1683-1702.
Yang, E. et al., "Decay Rates of Human mRNAs: Correlation with Functional Characteristics and Sequence Attributes," Genome Research, vol. 13; 1863-1872 (2003).
Yeku et al. "Armored CAR T-cells: utilizing cytokines and pro-inflammatory ligands to enhance CAR T-cell anti-tumour efficacy," Biochem Soc Trans, 2016, 44(2):412-8.
Zeng et al., "A Circular RNA Binds to and Activates AKT Phosphorylation and Nuclear Localization Reducing Apoptosis and Enhancing Cardia Repair," Theranostics 7(16):3842-3855 (2017).
Petkovic et al. "RNA Circularization Strategies in vivo and in vitro," Nucleic Acids Research, 2015, 43(4):2454-2465.
Puttaraju et al. "Group I Permuted Intron-exon (PIE) Sequences Self-splice to Produce Circular Exons," Nucleic Acids Research, 1992, 20(20):5357-5364.
Unpublished U.S. Appl. No. 17/548,247, entitled "Circular RNA Compositions and Methods," Filed Dec. 10, 2021; Inventors: Alexander Wesselhoeft, Daniel G. Anderson, Shinichiro Fuse, Brian Goodman, Allen Horhota, and Raffaella Squilloni.
U.S. Appl. No. 17/202,223, filed Mar. 15, 2021, Brian Goodman et al.
U.S. Appl. No. 17/548,241, filed Dec. 10, 2021, Brian Goodman et al.
U.S. Appl. No. 17/384,460, filed Jul. 23, 2021, Robert Alexander Wesselhoeft et al.
U.S. Appl. No. 17/548,247, filed Dec. 10, 2021, Robert Alexander Wesselhoeft et al.
U.S. Appl. No. 17/374,497, filed Jul. 13, 2021, Daniel G. Anderson et al.
U.S. Appl. No. 17/492,512, filed Oct. 1, 2021, Daniel G. Anderson et al.
U.S. Appl. No. 17/468,100, filed Sep. 7, 2021, Daniel G. Anderson et al.
Liang et al. "Short intronic repeat sequences facilitate circular RNA production," Genes & Development, 2014, 28:2233-2247.

(56) References Cited

OTHER PUBLICATIONS

Liang et al. "The Output of Protein-Coding Genes Shifts to Circular RNAs When the Pre-mRNA Processing Machinery is Limiting," Molecular Cell, 2017, 68:940-954.
Starke et al. "Exon Circularization Requires Canonical Splice Signals," Cell Reports, 2015, 10:103-111.
Unpublished U.S. Appl. No. 17/894,141, entitled "Circular RNA for Translation in Eukaryotic Cells," Filed Aug. 23, 2022; Inventors: Daniel G. Anderson, Robert Alexander Wesselhoeft, and Piotr S. Kowalski.

* cited by examiner

CIRCULAR RNA COMPOSITIONS AND METHODS

CROSS REFERENCE TO RELATED APPLICATIONS

This application is a continuation of U.S. application Ser. No. 17/202,223, filed on Mar. 15, 2021, which is a continuation of International Application No. PCT/US2020/063494, filed on Dec. 4, 2020, which claims the benefit of U.S. Provisional Application No. 62/943,779, filed on Dec. 4, 2019; U.S. Provisional Application No. 62/972,194, filed on Feb. 10, 2020; U.S. Provisional Application No. 63/022,248, filed on May 8, 2020; U.S. Provisional Application No. 63/087,582, filed on Oct. 5, 2020; and U.S. Provisional Application No. 62/943,797, filed on Dec. 4, 2019, the contents of each of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Oct. 14, 2021, is named OBS-011WOC2_Sequence_Listing.txt and is 589,790 bytes in size.

BACKGROUND

Conventional gene therapy involves the use of DNA for insertion of desired genetic information into host cells. The DNA introduced into the cell is usually integrated to a certain extent into the genome of one or more transfected cells, allowing for long-lasting action of the introduced genetic material in the host. While there may be substantial benefits to such sustained action, integration of exogenous DNA into a host genome may also have many deleterious effects. For example, it is possible that the introduced DNA will be inserted into an intact gene, resulting in a mutation which impedes or even totally eliminates the function of the endogenous gene. Thus, gene therapy with DNA may result in the impairment of a vital genetic function in the treated host, such as, e.g., elimination or deleteriously reduced production of an essential enzyme or interruption of a gene critical for the regulation of cell growth, resulting in unregulated or cancerous cell proliferation. In addition, with conventional DNA based gene therapy it is necessary for effective expression of the desired gene product to include a strong promoter sequence, which again may lead to undesirable changes in the regulation of normal gene expression in the cell. It is also possible that the DNA based genetic material will result in the induction of undesired anti-DNA antibodies, which in turn, may trigger a possibly fatal immune response. Gene therapy approaches using viral vectors can also result in an adverse immune response. In some circumstances, the viral vector may even integrate into the host genome. In addition, production of clinical grade viral vectors is also expensive and time consuming. Targeting delivery of the introduced genetic material using viral vectors can also be difficult to control. Thus, while DNA based gene therapy has been evaluated for delivery of secreted proteins using viral vectors (U.S. Pat. No. 6,066,626; US2004/0110709), these approaches may be limited for these various reasons.

In contrast to DNA, the use of RNA as a gene therapy agent is substantially safer because RNA does not involve the risk of being stably integrated into the genome of the transfected cell, thus eliminating the concern that the introduced genetic material will disrupt the normal functioning of an essential gene, or cause a mutation that results in deleterious or oncogenic effects, and extraneous promoter sequences are not required for effective translation of the encoded protein, again avoiding possible deleterious side effects. In addition, it is not necessary for mRNA to enter the nucleus to perform its function, while DNA must overcome this major barrier.

Circular RNA is useful in the design and production of stable forms of RNA. The circularization of an RNA molecule provides an advantage to the study of RNA structure and function, especially in the case of molecules that are prone to folding in an inactive conformation (Wang and Ruffner, 1998). Circular RNA can also be particularly interesting and useful for in vivo applications, especially in the research area of RNA-based control of gene expression and therapeutics, including protein replacement therapy and vaccination.

Prior to this invention, there were three main techniques for making circularized RNA in vitro: the splint-mediated method, the permuted intron-exon method, and the RNA ligase-mediated method. However, the existing methodologies are limited by the size of RNA that can be circularized, thus limiting their therapeutic application.

SUMMARY

The present application provides circular RNAs and transfer vehicles, along with related compositions and methods of treatment. The transfer vehicles can comprise, e.g., ionizable lipid, PEG-modified lipid, and/or structural lipid, thereby forming lipid nanoparticles encapsulating the circular RNAs. The circular RNAs can comprise group I intron fragments, spacers, an IRES, duplex forming regions, and/or an expression sequence, thereby having the features of improved expression, functional stability, low immunogenicity, ease of manufacturing, and/or extended half-life compared to linear RNA. Pharmaceutical compositions comprising such circular RNAs and transfer vehicles are particularly suitable for efficient protein expression in immune cells in vivo. The present application also provides precursor RNAs and materials useful in producing the precursor or circular RNAs, which have improved circularization efficiency and/or are compatible with effective circular RNA purification methods.

Accordingly, one aspect of the present application provides a pharmaceutical composition comprising a circular RNA polynucleotide and a transfer vehicle comprising an ionizable lipid represented by Formula (1):

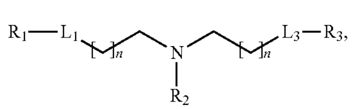

Formula (1)

wherein:

each n is independently an integer from 2-15;

$L_1$ and $L_3$ are each independently —OC(O)—* or —C(O)O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

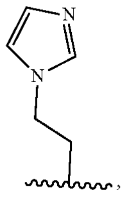,
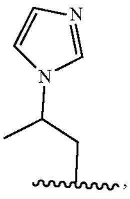,
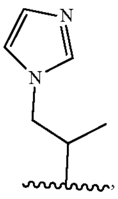,
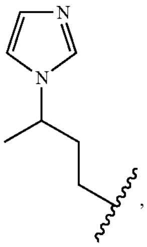,
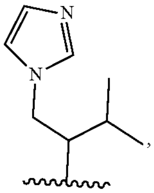,
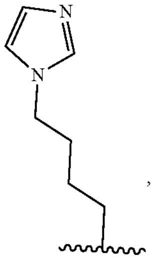,
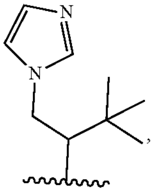,
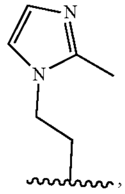,
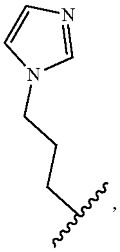,
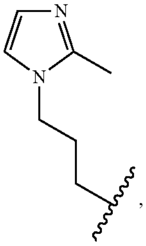,
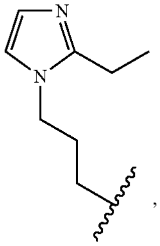,
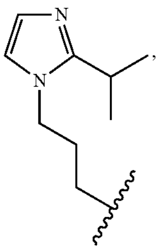,
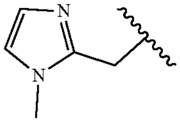,
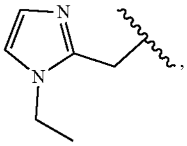,
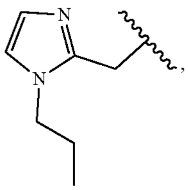,
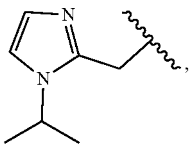, -continued

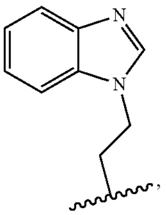,
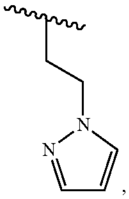,
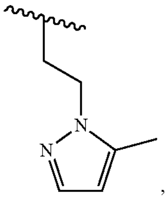, and
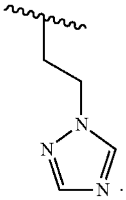.

In some embodiments, $R_1$ and $R_3$ are each independently selected from a group consisting of:

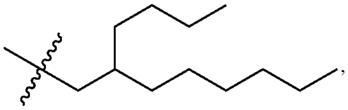,
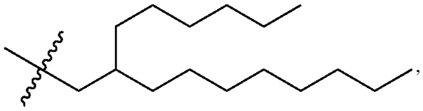,
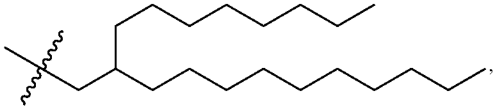,
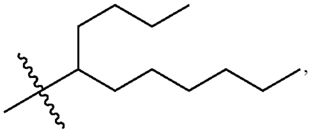,
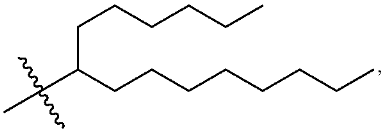,
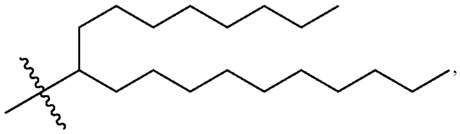,
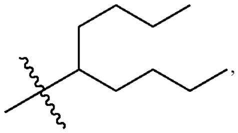,
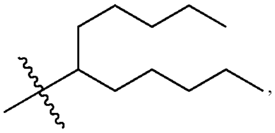,
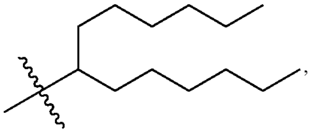, -continued
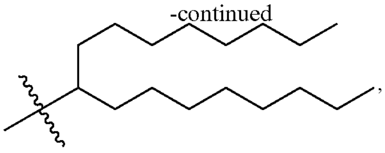
, and
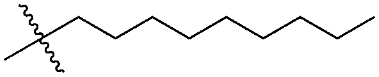
.
In some embodiments, $R_1$ and $R_3$ are the same. In some embodiments, $R_1$ and $R_3$ are different.
In some embodiments, the ionizable lipid of Formula (1) is represented by Formula (1-1) or Formula (1-2):
Formula (1-1)
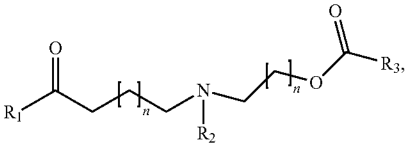
Formula (1-2)
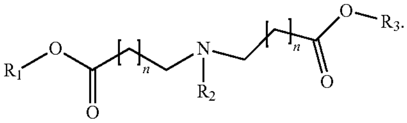
In some embodiments, the ionizable lipid is selected from the group consisting of:
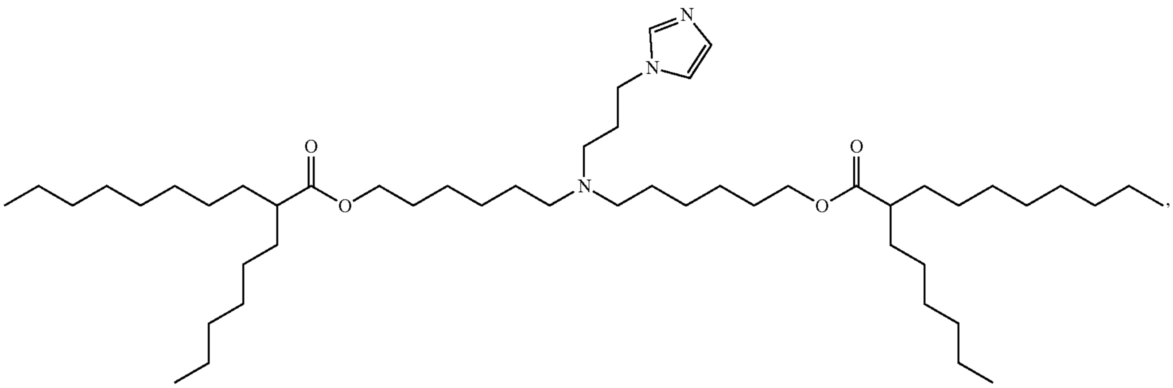
,
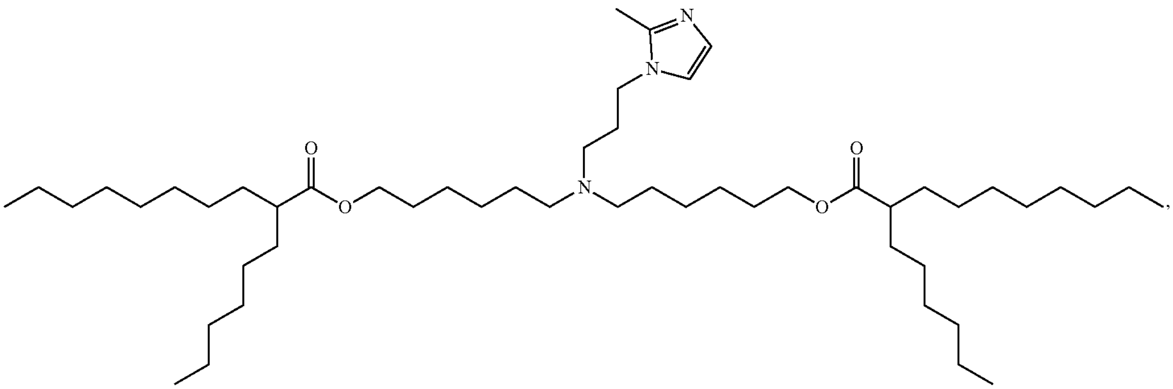
,
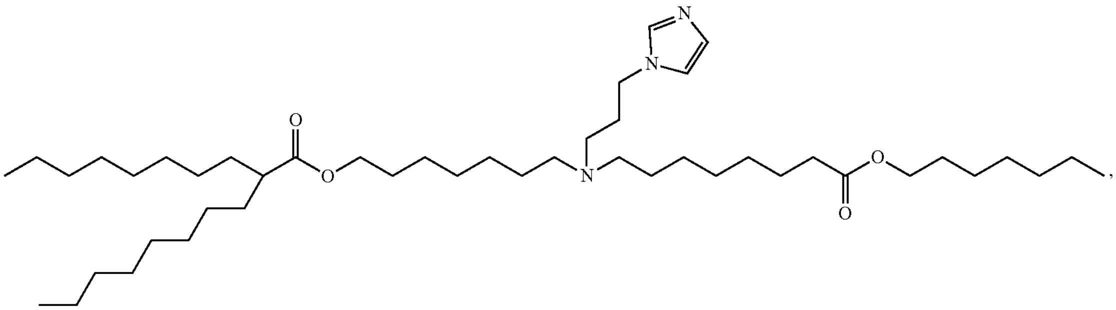
, and -continued
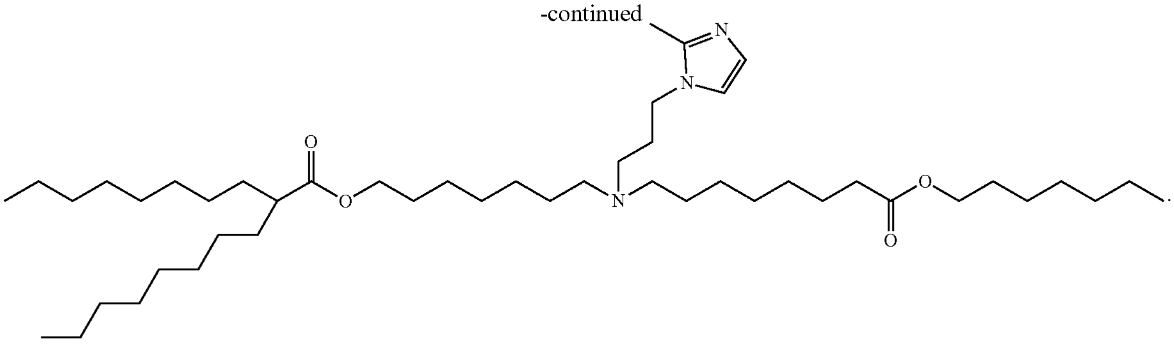
.
In another aspect, the present application provides a pharmaceutical composition comprising: a circular RNA polynucleotide and a transfer vehicle comprising an ionizable lipid represented by Formula (2):
Formula (2)
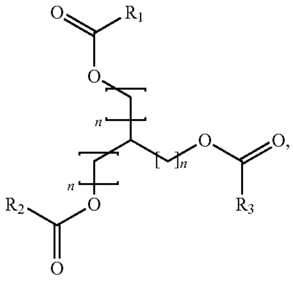
wherein:
each n is independently an integer from 1-15;
$R_1$ and $R_2$ are each independently selected from a group consisting of:
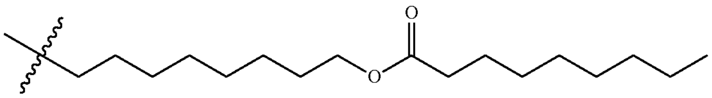
,
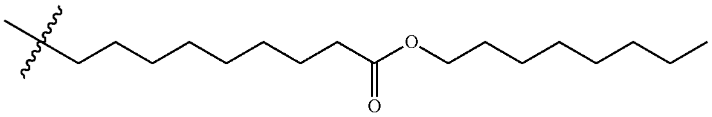
,
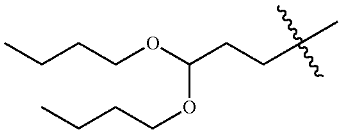
,
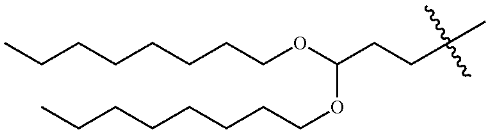
,
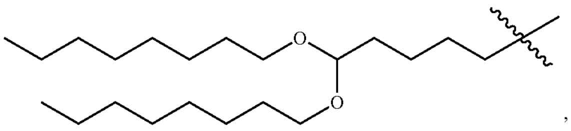
,
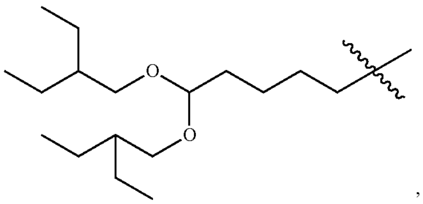
, -continued
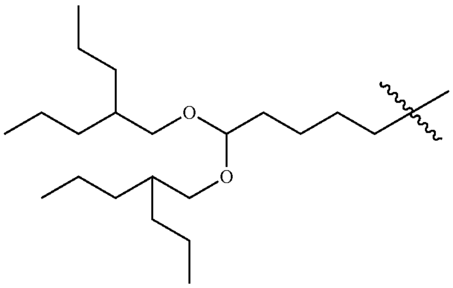
,
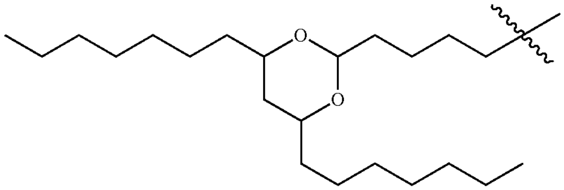
,
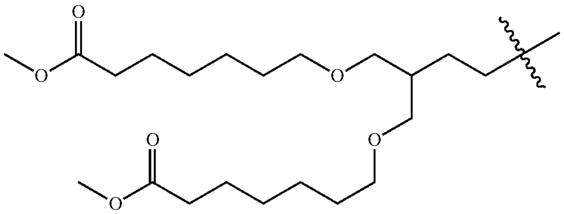
,
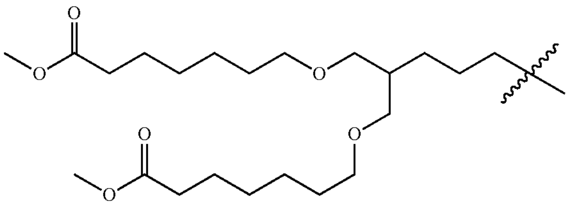
,
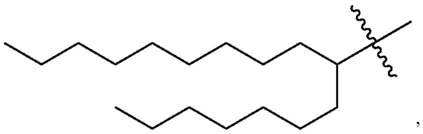
,
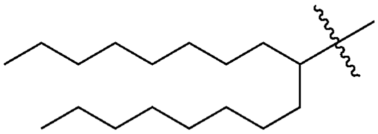
,
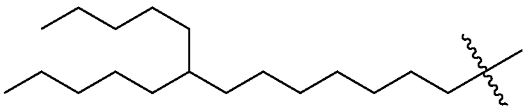
,
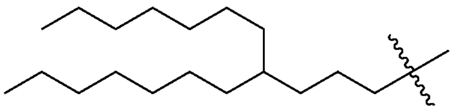
,
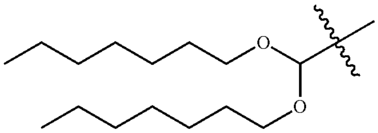
,
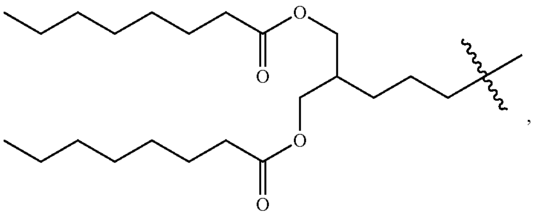
,
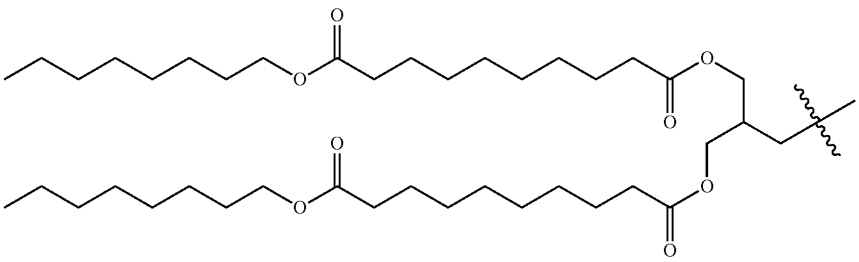
,
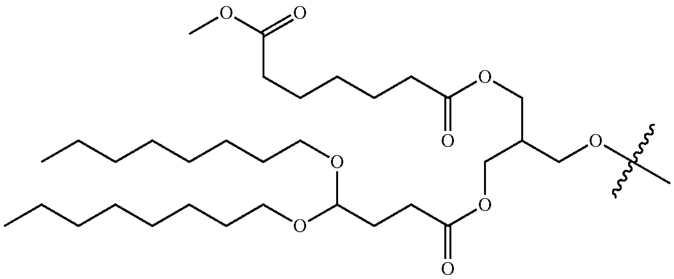
,
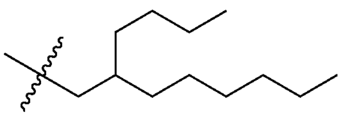
,
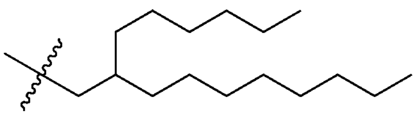
,
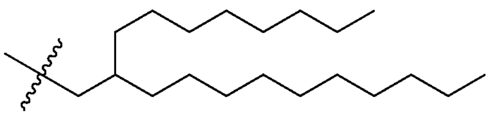
, -continued

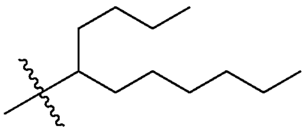,
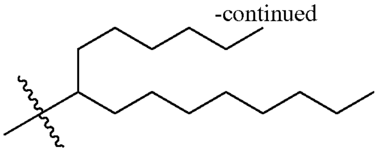,
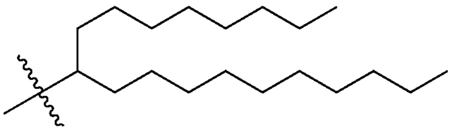,
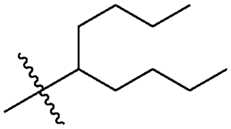,
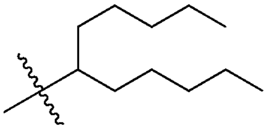,
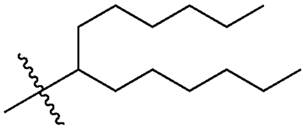,
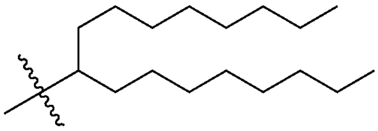,
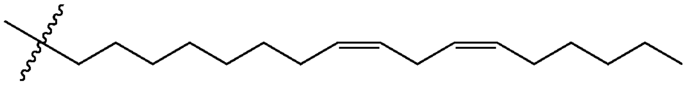,
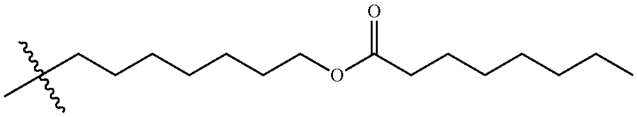, and
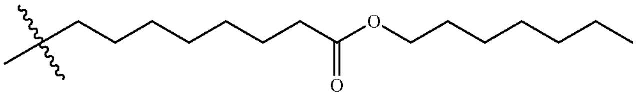;

and $R_3$ is selected from a group consiting of:

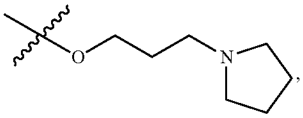

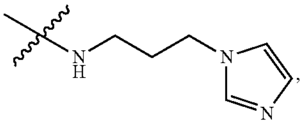

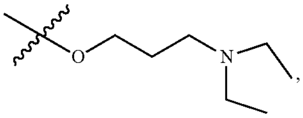

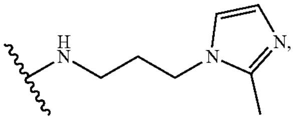

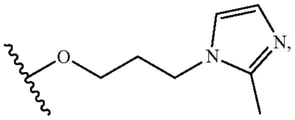
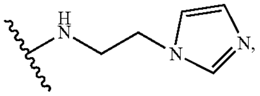

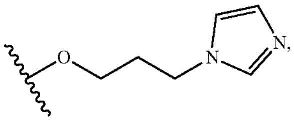

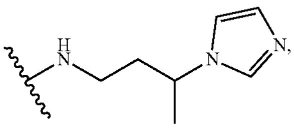

-continued

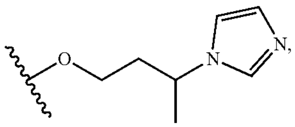
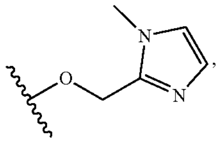

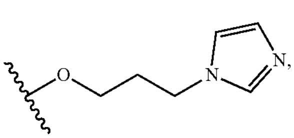 and 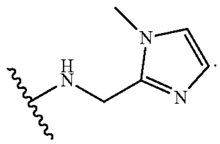

In another aspect, the present application provides a pharmaceutical composition comprising: a circular RNA polynucleotide, and a transfer vehicle comprising an ionizable lipid represented by Formula (3):

Formula (3)

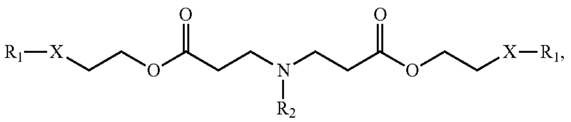

wherein:

X is selected from —O—, —S—, or —OC(O)—*, wherein * indicates the attachment point to $R_1$;

$R_1$ is selected from a group consisting of:

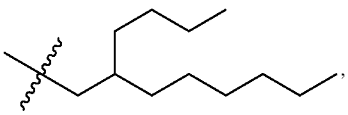

-continued
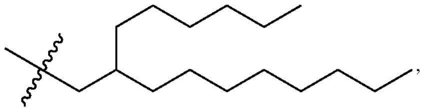,
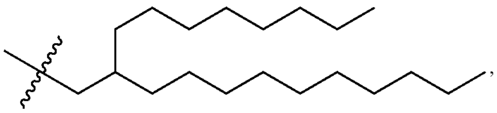,
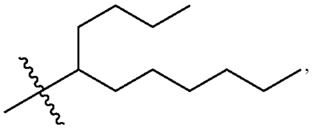,
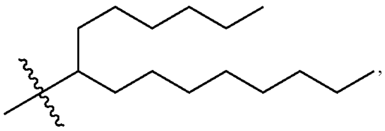,
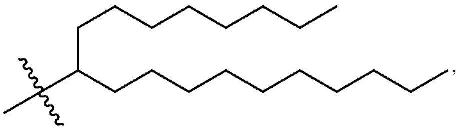,
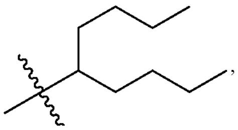, 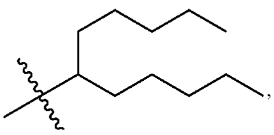,
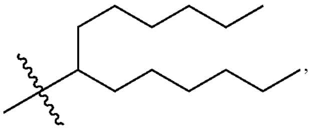, and
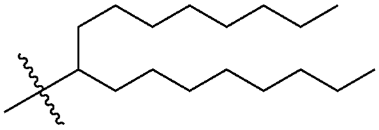; and
$R_2$ is selected from a group consisting of:
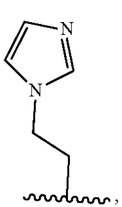, 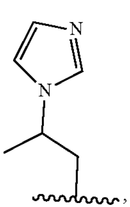, 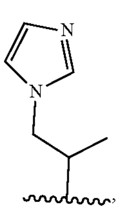, 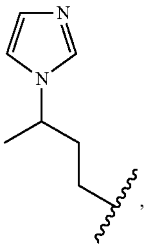,
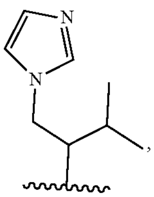, 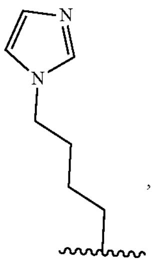, 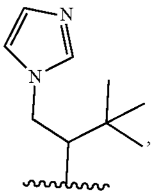,
-continued
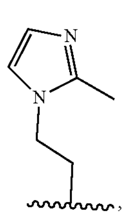, 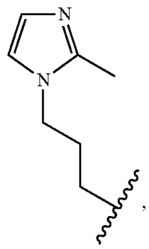, 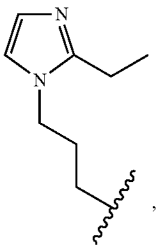,
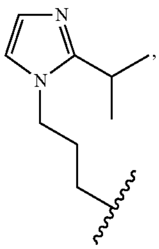, 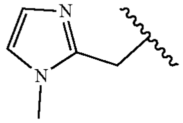, 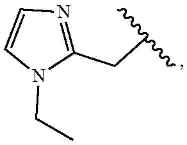,
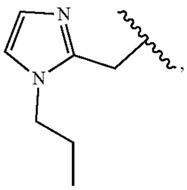, 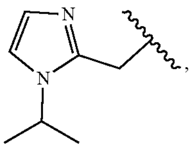,
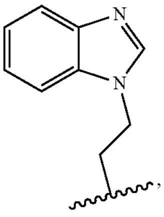, 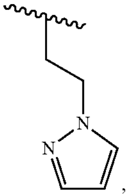, 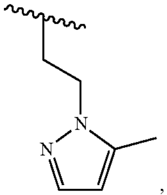,
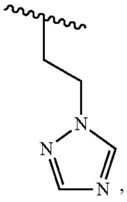, and 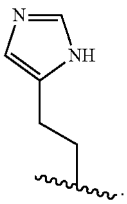.
In some embodiments, the ionizable lipid of Formula (3) is represented by Formula (3-1), Formula (3-2), or Formula (3-3):
Formula (3-1)
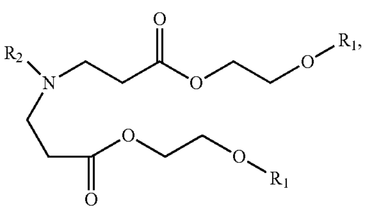

-continued

Formula (3-2)

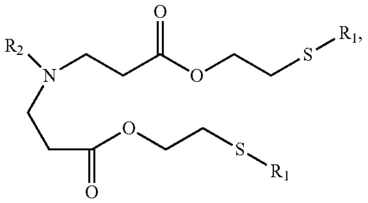

Formula (3-3)

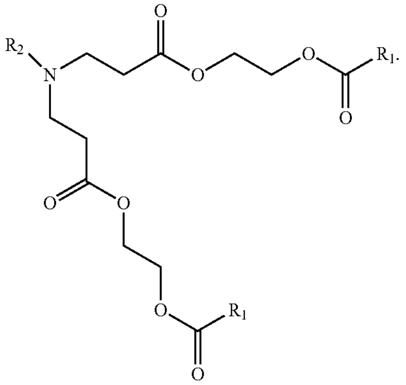

In another aspect, the present application provides a pharmaceutical composition comprising: a circular RNA polynucleotide, and a transfer vehicle comprising an ionizable Formula (4)

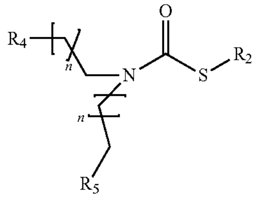

wherein: each n is independently an integer from 2-15; and $R_2$ is defined in Formula (1).

In another aspect, the present application provides a pharmaceutical composition comprising: a circular RNA polynucleotide, and a transfer vehicle comprising an ionizable lipid selected from Table 10a.

In some embodiments, the circular RNA comprises a first expression sequence. In some embodiments, the first expression sequence encodes a therapeutic protein. In some embodiments, the first expression sequence encodes a cytokine or a functional fragment thereof. In some embodiments, the first expression sequence encodes a transcription factor. In some embodiments, the first expression sequence encodes an immune checkpoint inhibitor. In some embodiments, the first expression sequence encodes a chimeric antigen receptor.

In some embodiments, the circular RNA polynucleotide further comprises a second expression sequence. In some embodiments, the circular RNA polynucleotide further comprises an internal ribosome entry site (IRES).

In some embodiments, the first and second expression sequences are separated by a ribosomal skipping element or a nucleotide sequence encoding a protease cleavage site. In some embodiments, the first expression sequence encodes a first T-cell receptor (TCR) chain and the second expression sequence encodes a second TCR chain.

In some embodiments, the circular RNA polynucleotide comprises one or more microRNA binding sites. the microRNA binding site is recognized by a microRNA expressed in the liver. In some embodiments, the microRNA binding site is recognized by miR-122.

In some embodiments, the circular RNA polynucleotide comprises a first IRES associated with greater protein expression in a human immune cell than in a reference human cell. In some embodiments, the human immune cell is a T cell, an NK cell, an NKT cell, a macrophage, or a neutrophil. In some embodiments, the reference human cell is a hepatic cell.

In some embodiments, the circular RNA polynucleotide comprises, in the following order: a) a post-splicing intron fragment of a 3' group I intron fragment, b) an IRES, c) an expression sequence, and d) a post-splicing intron fragment of a 5' group I intron fragment. In some embodiments, the circular RNA polynucleotide comprises. In some embodiments, the circular RNA polynucleotide comprises a first spacer before the post-splicing intron fragment of the 3' group I intron fragment, and a second spacer after the post-splicing intron fragment of the 5' group I intron fragment. In some embodiments, the first and second spacers each have a length of about 10 to about 60 nucleotides.

In some embodiments, the circular RNA polynucleotide is made via circularization of a RNA polynucleotide comprising, in the following order: a 3' group I intron fragment, an IRES, an expression sequence, and a 5' group I intron fragment.

In some embodiments, the circular RNA polynucleotide is made via circularization of a RNA polynucleotide comprising, in the following order: a 5' external duplex forming region, a 3' group I intron fragment, a 5' internal spacer optionally comprising a 5' internal duplex forming region, an IRES, an expression sequence, a 3' internal spacer optionally comprising a 3' internal duplex forming region, a 5' group I intron fragment, and a 3' external duplex forming region.

In some embodiments, the circular RNA polynucleotide is made via circularization of a RNA polynucleotide comprising, in the following order: a 5' external duplex forming region, a 5' external spacer, a 3' group I intron fragment, a 5' internal spacer optionally comprising a 5' internal duplex forming region, an IRES, an expression sequence, a 3' internal spacer optionally comprising a 3' internal duplex forming region, a 5' group I intron fragment, a 3' external spacer, and a 3' external duplex forming region.

In some embodiments, the circular RNA polynucleotide is made via circularization of a RNA polynucleotide comprising, in the following order: a 3' group I intron fragment, a 5' internal spacer comprising a 5' internal duplex forming region, an IRES, an expression sequence, a 3' internal spacer comprising a 3' internal duplex forming region, and a 5' group I intron fragment.

In some embodiments, the circular RNA polynucleotide is made via circularization of a RNA polynucleotide comprising, in the following order: a 5' external duplex forming region, a 5' external spacer, a 3' group I intron fragment, a 5' internal spacer comprising a 5' internal duplex forming region, an IRES, an expression sequence, a 3' internal spacer comprising a 3' internal duplex forming region, a 5' group I intron fragment, a 3' external spacer, and a 3' external duplex forming region.

In some embodiments, the circular RNA polynucleotide is made via circularization of a RNA polynucleotide comprising, in the following order: a first polyA sequence, a 5' external duplex forming region, a 5' external spacer, a 3' group I intron fragment, a 5' internal spacer comprising a 5' internal duplex forming region, an IRES, an expression sequence, a 3' internal spacer comprising a 3' internal duplex forming region, a 5' group I intron fragment, a 3' external spacer, a 3' external duplex forming region, and a second polyA sequence.

In some embodiments, the circular RNA polynucleotide is made via circularization of a RNA polynucleotide comprising, in the following order: a first polyA sequence, a 5' external spacer, a 3' group I intron fragment, a 5' internal spacer comprising a 5' internal duplex forming region, an IRES, an expression sequence, a 3' internal spacer comprising a 3' internal duplex forming region, a 5' group I intron fragment, a 3' external spacer, and a second polyA sequence.

In some embodiments, the circular RNA polynucleotide is made via circularization of a RNA polynucleotide comprising, in the following order: a first polyA sequence, a 5' external spacer, a 3' group I intron fragment, a 5' internal spacer comprising a 5' internal duplex forming region, an IRES, an expression sequence, a stop condon, a 3' internal spacer comprising a 3' internal duplex forming region, a 5' group I intron fragment, a 3' external spacer, and a second polyA sequence.

In some embodiments, at least one of the 3' or 5' internal or external spacers has a length of about 8 to about 60 nucleotides. In some embodiments, the 3' and 5' external duplex forming regions each has a length of about 10-50 nucleotides. In some embodiments, the 3' and 5' internal duplex forming regions each has a length of about 6-30 nucleotides.

In some embodiments, the IRES is selected from Table 17, or is a functional fragment or variant thereof. In some embodiments, the IRES has a sequence of an IRES from Taura syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, *Homalodisca coagulata* virus-1, Human Immunodeficiency Virus type 1, *Homalodisca coagulata* virus-1, Himetobi P virus, Hepatitis C virus, Hepatitis A virus, Hepatitis GB virus, Foot and mouth disease virus, Human enterovirus 71, Equine rhinitis virus, *Ectropis obliqua* picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAPI, Human c-myc, Human eIF4G, Mouse NDST4L, Human LEF1, Mouse HIF1 alpha, Human n.myc, Mouse Gtx, Human p27kipl, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, Apodemus Agrarius Picornavirus, Caprine Kobuvirus, Parabovirus, Salivirus A BN5, Salivirus A BN2, Salivirus A 02394, Salivirus A GUT, Salivirus A CH, Salivirus A SZ1, Salivirus FHB, CVB3, CVB1, Echovirus 7, CVB5, EVA71, CVA3, CVA12, EV24, or an aptamer to eIF4G.

In some embodiments, the first and second polyA sequences each have a length of about 15-50 nt. In some embodiments, the first and second polyA sequences each have a length of about 20-25 nt.

In some embodiments, the circular RNA polynucleotide contains at least about 80%, at least about 90%, at least about 95%, or at least about 99% naturally occurring nucleotides. In some embodiments, the circular RNA polynucleotide consists of naturally occurring nucleotides.

In some embodiments, the expression sequence is codon optimized. In some embodiments, the circular RNA polynucleotide is optimized to lack at least one microRNA binding site present in an equivalent pre-optimized polynucleotide. In some embodiments, the circular RNA polynucleotide is optimized to lack at least one microRNA binding site capable of binding to a microRNA present in a cell within which the circular RNA polynucleotide is expressed. In some embodiments, the circular RNA polynucleotide is optimized to lack at least one endonuclease susceptible site present in an equivalent pre-optimized polynucleotide. In some embodiments, the circular RNA polynucleotide is optimized to lack at least one endonuclease susceptible site capable of being cleaved by an endonuclease present in a cell within which the endonuclease is expressed. In some embodiments, the circular RNA polynucleotide is optimized to lack at least one RNA editing susceptible site present in an equivalent pre-optimized polynucleotide.

In some embodiments, the circular RNA polynucleotide is from about 100 nt to about 10,000 nt in length. In some embodiments, the circular RNA polynucleotide is from about 100 nt to about 15,000 nt in length. In some embodiments, the circular RNA is more compact than a reference linear RNA polynucleotide having the same expression sequence as the circular RNA polynucleotide.

In some embodiments, the pharmaceutical composition has a duration of therapeutic effect in a human cell greater than or equal to that of a composition comprising a reference linear RNA polynucleotide having the same expression sequence as the circular RNA polynucleotide. In some embodiments, the reference linear RNA polynucleotide is a linear, unmodified or nucleoside-modified, fully-processed mRNA comprising a cap1 structure and a polyA tail at least 80 nt in length.

In some embodiments, the pharmaceutical composition has a duration of therapeutic effect in vivo in humans greater than that of a composition comprising a reference linear RNA polynucleotide having the same expression sequence as the circular RNA polynucleotide. In some embodiments, the pharmaceutical composition has an duration of therapeutic effect in vivo in humans of at least about 10, at least about 20, at least about 30, at least about 40, at least about 50, at least about 60, at least about 70, at least about 80, at least about 90, or at least about 100 hours.

In some embodiments, the pharmaceutical composition has a functional half-life in a human cell greater than or equal to that of a pre-determined threshold value. In some embodiments, the pharmaceutical composition has a functional half-life in vivo in humans greater than that of a pre-determined threshold value. In some embodiments, the functional half-life is determined by a functional protein assay. In some embodiments, the functional protein assay is an in vitro luciferase assay. In some embodiments, the functional protein assay comprises measuring levels of protein encoded by the expression sequence of the circular RNA polynucleotide in a patient serum or tissue sample. In some embodiments, wherein the pre-determined threshold value is the functional half-life of a reference linear RNA polynucleotide comprising the same expression sequence as the circular RNA polynucleotide. In some embodiments, the pharmaceutical composition has a functional half-life of at least about 20 hours.

In some embodiments, the pharmaceutic composition comprises a structural lipid and a PEG-modified lipid. In some embodiments, the structural lipid binds to C1q and/or promotes the binding of the transfer vehicle comprising said lipid to C1q compared to a control transfer vehicle lacking the structural lipid and/or increases uptake of C1q-bound transfer vehicle into an immune cell compared to a control transfer vehicle lacking the structural lipid. In some embodiments, the immune cell is a T cell, an NK cell, an NKT cell, a macrophage, or a neutrophil.

In some embodiments, the structural lipid is cholesterol. In some embodiments, the structural lipid is beta-sitosterol. In some embodiments, the structural lipid is not beta-sitosterol.

In some embodiments, the PEG-modified lipid is DSPE-PEG, DMG-PEG, or PEG-1. In some embodiments, the PEG-modified lipid is DSPE-PEG(2000).

In some embodiments, the pharmaceutic composition further comprises a helper lipid. In some embodiments, the helper lipid is DSPC or DOPE.

In some embodiments, the pharmaceutic composition comprises DOPE, cholesterol, and DSPE-PEG.

In some embodiments, the transfer vehicle comprises about 0.5% to about 4% PEG-modified lipids by molar ratio. In some embodiments, the transfer vehicle comprises about 1% to about 2% PEG-modified lipids by molar ratio.

In some embodiments, the transfer vehicle comprises a. an ionizable lipid is represented by

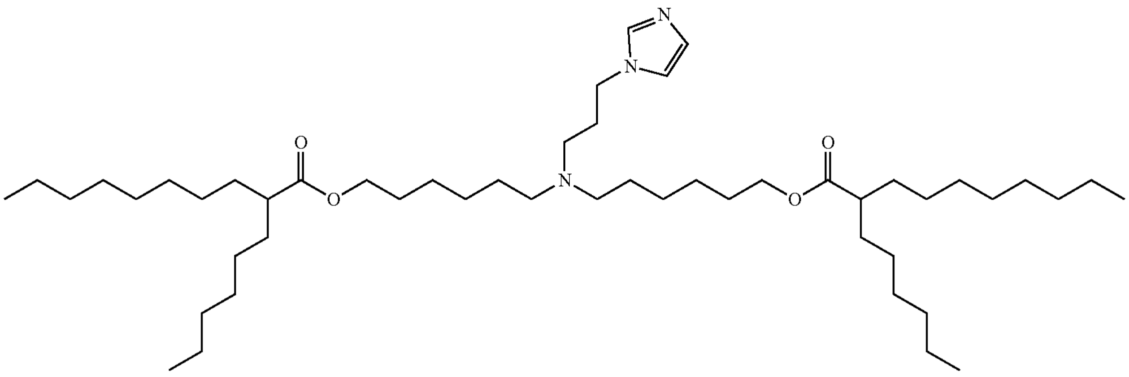

or

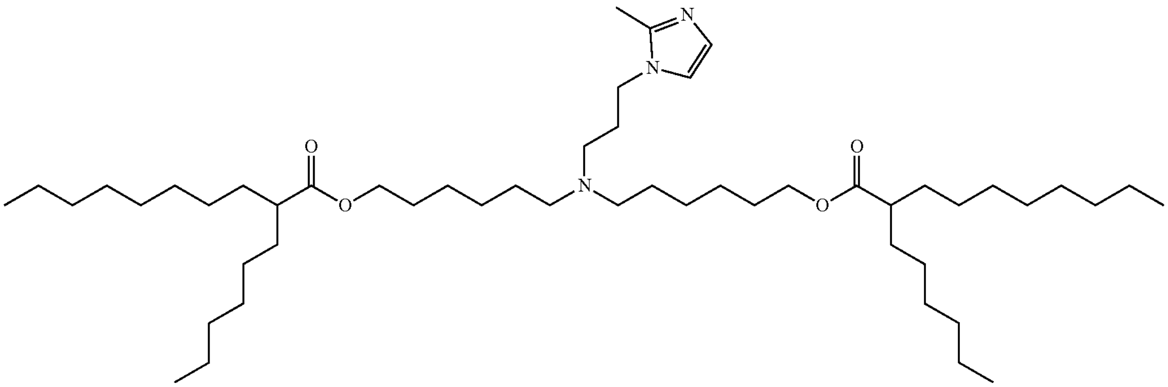

b. DOPE, c. cholesterol, and d. DSPE-PEG(2000).

In some embodiments, the molar ration of ionizable lipid:DSPC:cholesterol:DSPE-PEG(2000) is 62:4:33:1.

In some embodiments, the transfer vehicle comprises
a. an ionizable lipid is represented by selected from the group consisting of CD2, CD3, CD5, CD7, CD8, CD4, beta7 integrin, beta2 integrin, and C1q.

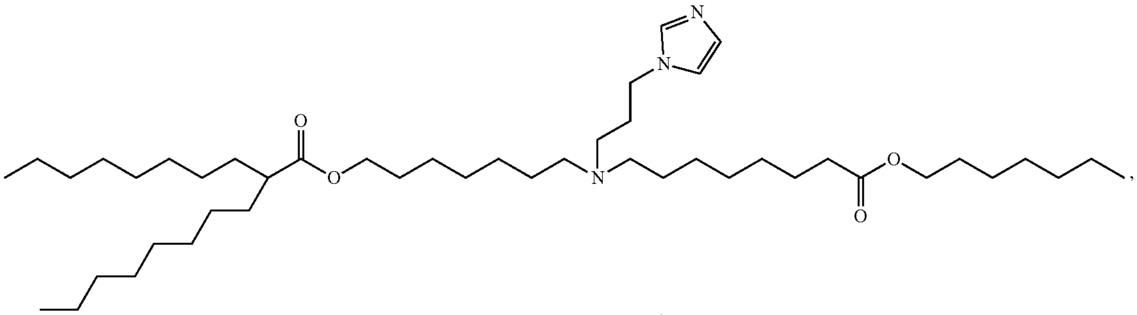

, or

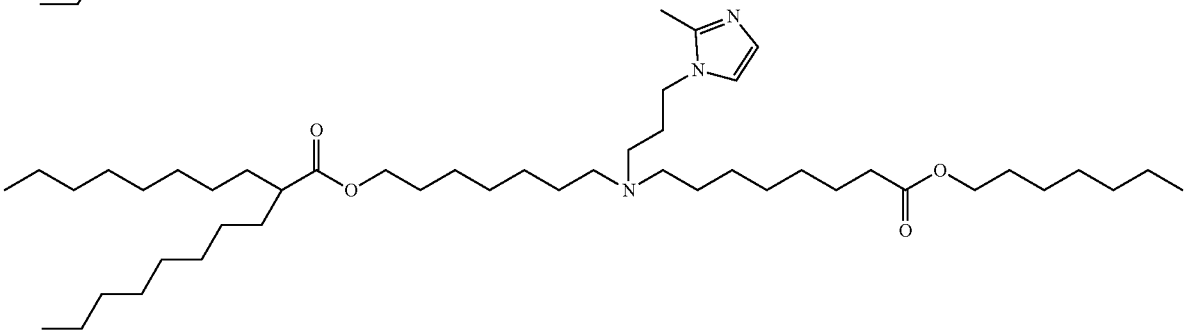

b. DOPE,
c. cholesterol, and
d. DSPE-PEG(2000).

In some embodiments, the molar ration of ionizable lipid:DSPC:cholesterol:DSPE-PEG(2000) is 50:10:38.5:1.5.

In some embodiments, the transfer vehicle has a nitrogen:phosphate (N:P) ratio of about 3 to about 6.

In some embodiments, the transfer vehicle is formulated for endosomal release of the circular RNA polynucleotide.

In some embodiments, the transfer vehicle is capable of binding to APOE. In some embodiments, the transfer vehicle interacts with apolipoprotein E (APOE) less than an equivalent transfer vehicle loaded with a reference linear RNA having the same expression sequence as the circular RNA polynucleotide. In some embodiments, the exterior surface of the transfer vehicle is substantially free of APOE binding sites.

In some embodiments, the transfer vehicle has a diameter of less than about 120 nm. In some embodiments, the transfer vehicle does not form aggregates with a diameter of more than 300 nm.

In some embodiments, the transfer vehicle has an in vivo half-life of less than about 30 hours.

In some embodiments, the transfer vehicle is capable of low density lipoprotein receptor (LDLR) dependent uptake into a cell. In some embodiments, the transfer vehicle is capable of LDLR independent uptake into a cell.

In some embodiments, the pharmaceutical composition is substantially free of linear RNA.

In some embodiments, the pharmaceutical composition further comprises a targeting moiety operably connected to the transfer vehicle. In some embodiments, the targeting moiety specifically binds an immune cell antigen or indirectly. In some embodiments, the immune cell antigen is a T cell antigen. In some embodiments, the T cell antigen is selected from the group consisting of CD2, CD3, CD5, CD7, CD8, CD4, beta7 integrin, beta2 integrin, and C1q.

In some embodiments, the pharmaceutical composition further comprises an adapter molecule comprising a transfer vehicle binding moiety and a cell binding moiety, wherein the targeting moiety specifically binds the transfer vehicle binding moiety and the cell binding moiety specifically binds a target cell antigen. In some embodiments, the target cell antigen is an immune cell antigen. In some embodiments, the immune cell antigen is a T cell antigen, an NK cell, an NKT cell, a macrophage, or a neutrophil. In some embodiments, the T cell antigen is selected from the group consisting of CD2, CD3, CD5, CD7, CD8, CD4, beta7 integrin, beta2 integrin, CD25, CD39, CD73, A2a Receptor, A2b Receptor, and C1q. In some embodiments, the immune cell antigen is a macrophage antigen. In some embodiments, the macrophage antigen is selected from the group consisting of mannose receptor, CD206, and C1q.

In some embodiments, the targeting moiety is a small molecule. In some embodiments, the small molecule binds to an ectoenzyme on an immune cell, wherein the ectoenzyme is selected from the group consisting of CD38, CD73, adenosine 2a receptor, and adenosine 2b receptor. In some embodiments, the small molecule is mannose, a lectin, acivicin, biotin, or digoxigenin.

In some embodiments, the targeting moiety is a single chain Fv (scFv) fragment, nanobody, peptide, peptide-based macrocycle, minibody, small molecule ligand such as folate, arginylglycylaspartic acid (RGD), or phenol-soluble modulin alpha 1 peptide (PSMA1), heavy chain variable region, light chain variable region or fragment thereof.

In some embodiments, the ionizable lipid has a half-life in a cell membrane less than about 2 weeks. In some embodiments, the ionizable lipid has a half-life in a cell membrane less than about 1 week. In some embodiments, the ionizable lipid has a half-life in a cell membrane less than about 30 hours. In some embodiments, the ionizable lipid has a half-life in a cell membrane less than the functional half-life of the circular RNA polynucleotide.

In another aspect, the present application provides a method of treating or preventing a disease, disorder, or condition, comprising administering an effective amount of a pharmaceutical composition disclosed herein. In some embodiments, the disease, disorder, or condition is associated with aberrant expression, activity, or localization of a polypeptide selected from Tables 27 or 28. In some embodiments, the circular RNA polynucleotide encodes a therapeutic protein. In some embodiments, therapeutic protein expression in the spleen is higher than therapeutic protein expression in the liver. In some embodiments, therapeutic protein expression in the spleen is at least about 2.9× therapeutic protein expression in the liver. In some embodiments, the therapeutic protein is not expressed at functional levels in the liver. In some embodiments, the therapeutic protein is not expressed at detectable levels in the liver. In some embodiments, therapeutic protein expression in the spleen is at least about 63% of total therapeutic protein expression.

In another aspect, the present application provides a linear RNA polynucleotide comprising, from 5' to 3', a 3' group I intron fragment, an Internal Ribosome Entry Site (IRES), an expression sequence, and a 5' group I intron fragment, further comprising a first spacer 5' to the 3' group I intron fragment and/or a second spacer 3' to the 5' group I intron fragment.

In some embodiments, the linear RNA polynucleotide comprises a first spacer 5' to the 3' group I intron fragment. In some embodiments, the first spacer has a length of 10-50 nucleotides, optionally 10-20 nucleotides, further optionally about 15 nucleotides. In some embodiments, the first spacer comprises a polyA sequence.

In some embodiments, the linear RNA polynucleotide comprises a second spacer 3' to the 5' group I intron fragment. In some embodiments, the second spacer has a length of 10-50 nucleotides, optionally 10-20 nucleotides, further optionally about 15 nucleotides. In some embodiments, the second spacer comprises a polyA sequence.

In some embodiments, the linear RNA polynucleotide further comprises a third spacer between the 3' group I intron fragment and IRES. In some embodiments, the third spacer has a length of about 10 to about 60 nucleotides. In some embodiments, the linear RNA polynucleotide further comprises a first and a second duplex forming regions capable of forming a duplex. In some embodiments, the first and second duplex forming regions each have a length of about 9 to 19 nucleotides. In some embodiments, the first and second duplex forming regions each have a length of about 30 nucleotides.

In some embodiments, the linear RNA polynucleotide has enhanced expression, circularization efficiency, functional stability, and/or stability as compared to a reference linear RNA polynucleotide, wherein the reference linear RNA polynucleotide comprises, from 5' to 3', a first polyA sequence, a 5' external spacer, a 3' group I intron fragment, a 5' internal spacer comprising a 5' internal duplex forming region, an IRES, an expression sequence, a stop condon, a 3' internal spacer comprising a 3' internal duplex forming region, a 5' group I intron fragment, a 3' external spacer, and a second polyA sequence.

In some embodiments, the linear RNA polynucleotide has enhanced expression, circularization efficiency, functional stability, and/or stability as compared to a reference linear RNA polynucleotide, wherein the reference linear RNA polynucleotide comprises, from 5' to 3', a reference 3' group I intron fragment, a reference IRES, a reference expression sequence, and a reference 5' group I intron fragment, and does not comprise a spacer 5' to the 3' group I intron fragment or a spacer 3' to the 5' group I intron fragment. In some embodiments, the expression sequence and the reference expression sequence have the same sequence. In some embodiments, the IRES and the reference IRES have the same sequence.

In some embodiments, the linear RNA polynucleotide comprises a 3' anabaena group I intron fragment and a 5' anabaena group I intron fragment. In some embodiments, the reference RNA polynucleotide comprises a reference 3' anabaena group I intron fragment and a reference 5' anabaena group I intron fragment. In some embodiments, the reference 3' anabaena group I intron fragment and reference 5' anabaena group I intron fragment were generated using the L6-5 permutation site. In some embodiments, the 3' anabaena group I intron fragment and 5' anabaena group I intron fragment were not generated using the L6-5 permutation site. In some embodiments, the 3' anabaena group I intron fragment comprises or consists of a sequence selected from SEQ ID NO: 112-123 and 125-150. In some embodiments, the 5' anabaena group I intron fragment comprises a corresponding sequence selected from SEQ ID NO: 73-84 and 86-111. In some embodiments, the 5' anabaena group I intron fragment comprises or consists of a sequence selected from SEQ ID NO: 73-84 and 86-111. In some embodiments, the 3' anabaena group I intron fragment comprises or consists of a corresponding sequence selected from SEQ ID NO: 112-124 and 125-150.

In some embodiments, the IRES comprises a nucleotide sequence selected from SEQ ID NOs: 348-351. In some embodiments, the reference IRES is CVB3. In some embodiments, the IRES is not CVB3. In some embodiments, the IRES comprises a sequence selected from SEQ ID NOs: 1-64 and 66-72.

In another aspect, the present application discloses a circular RNA polynucleotide produced from the linear RNA disclosed herein.

In another aspect, the present application discloses a circular RNA comprising, from 5' to 3', a 3' group I intron fragment, an IRES, an expression sequence, and a 5' group I intron fragment, wherein the IRES comprises a nucleotide sequence selected from SEQ ID NOs: 348-351.

In some embodiments, the circular RNA polynucleotide further comprises a spacer between the 3' group I intron fragment and the IRES.

In some embodiments, the circular RNA polynucleotide further comprises a first and a second duplex forming regions capable of forming a duplex. In some embodiments, the first and second duplex forming regions each have a length of about 9 to 19 nucleotides. In some embodiments, the first and second duplex forming regions each have a length of about nucleotides.

In some embodiments, the expression sequence has a size of at least about 1,000 nt, at least about 2,000 nt, at least about 3,000 nt, at least about 4,000 nt, or at least about 5,000 nt.

In some embodiments, the RNA polynucleotide comprises natural nucleotides. In some embodiments, the expression sequence is codon optimized. In some embodiments, the RNA polynucleotide further comprises a translation termination cassette comprising at least one stop codon in each reading frame. In some embodiments, the translation termination cassette comprises at least two stop codons in the reading frame of the expression sequence. In some embodiments, the RNA polynucleotide is optimized to lack at least one microRNA binding site present in an equivalent pre-optimized polynucleotide. In some embodiments, the RNA polynucleotide is optimized to lack at least one endonuclease susceptible site present in an equivalent pre-optimized polynucleotide. In some embodiments, the RNA polynucleotide is optimized to lack at least one RNA editing susceptible site present in an equivalent pre-optimized polynucleotide.

In some embodiments, the RNA polynucleotide comprises at least 2 expression sequences. In some embodiments, each expression sequence encodes a different therapeutic protein.

In some embodiments, a circular RNA polynucleotide disclosed herein is from about 100 to 15,000 nucleotides, optionally about 100 to 12,000 nucleotides, further optionally about 100 to 10,000 nucleotides in length.

In some embodiments, a circular RNA polynucleotide disclosed herein has an in vivo duration of therapeutic effect in humans of at least about 20 hours. In some embodiments, a circular RNA polynucleotide disclosed herein has a functional half-life of at least about 20 hours. In some embodiments, the circular RNA polynucleotide has a duration of therapeutic effect in a human cell greater than or equal to that of an equivalent linear RNA polynucleotide comprising the same expression sequence. In some embodiments, the circular RNA polynucleotide has a functional half-life in a human cell greater than or equal to that of an equivalent linear RNA polynucleotide comprising the same expression sequence. In some embodiments, the circular RNA polynucleotide has an in vivo duration of therapeutic effect in humans greater than that of an equivalent linear RNA polynucleotide having the same expression sequence. In some embodiments, the circular RNA polynucleotide has an in vivo functional half-life in humans greater than that of an equivalent linear RNA polynucleotide having the same expression sequence.

In another aspect, the present disclosure provides a composition comprising a circular RNA polynucleotide disclosed herein, a nanoparticle, and optionally, a targeting moiety operably connected to the nanoparticle. In some embodiments, the nanoparticle is a lipid nanoparticle, a core-shell nanoparticle, a biodegradable nanoparticle, a biodegradable lipid nanoparticle, a polymer nanoparticle, or a biodegradable polymer nanoparticle. In some embodiments, the pharmaceutical composition comprises a targeting moiety, wherein the targeting moiety mediates receptor-mediated endocytosis or direct fusion selectively into cells of a selected cell population or tissue in the absence of cell isolation or purification. In some embodiments, the targeting moiety is a scfv, nanobody, peptide, minibody, polynucleotide aptamer, heavy chain variable region, light chain variable region or fragment thereof. In some embodiments, wherein less than 1%, by weight, of the polynucleotides in the composition are double stranded RNA, DNA splints, or triphosphorylated RNA. In some embodiments, less than 1%, by weight, of the polynucleotides and proteins in the pharmaceutical composition are double stranded RNA, DNA splints, triphosphorylated RNA, phosphatase proteins, protein ligases, and capping enzymes.

In another aspect, the present disclosure provides a method of treating a subject in need thereof comprising administering a therapeutically effective amount of a composition comprising the circular RNA polynucleotide disclosed herein, a nanoparticle, and optionally, a targeting moiety operably connected to the nanoparticle.

In another aspect, the present disclosure provides a method of treating a subject in need thereof comprising administering a therapeutically effective amount of the pharmaceutical composition disclosed herein. In some embodiments, the targeting moiety is an scfv, nanobody, peptide, minibody, heavy chain variable region, light chain variable region, an extracellular domain of a TCR, or a fragment thereof. In some embodiments, the nanoparticle is a lipid nanoparticle, a core-shell nanoparticle, or a biodegradable nanoparticle. In some embodiments, the nanoparticle comprises one or more cationic lipids, ionizable lipids, or poly β-amino esters. In some embodiments, the nanoparticle comprises one or more non-cationic lipids. In some embodiments, the nanoparticle comprises one or more PEG-modified lipids, polyglutamic acid lipids, or Hyaluronic acid lipids. In some embodiments, the nanoparticle comprises cholesterol. In some embodiments, the nanoparticle comprises arachidonic acid or oleic acid.

In some embodiments, a provided pharmaceutical composition comprises a targeting moiety, wherein the targeting moiety mediates receptor-mediated endocytosis selectively into cells of a selected cell population in the absence of cell selection or purification.

In some embodiments, a provided nanoparticle comprises more than one circular RNA polynucleotide.

In another aspect, the present application provides a DNA vector encoding the RNA polynucleotide disclosed herein. In some embodiments, the DNA vector further comprises a transcription regulatory sequence. In some embodiments, the transcription regulatory sequence comprises a promoter and/or an enhancer. In some embodiments, the promoter comprises a T7 promoter. In some embodiments, the DNA vector comprises a circular DNA. In some embodiments, the DNA vector comprises a linear DNA.

In another aspect, the present application provides a prokaryotic cell comprising the DNA vector disclosed herein.

In another aspect, the present application provides a eukaryotic cell comprising the circular RNA polynucleotide disclosed herein. In some embodiments, the eukaryotic cell is a human cell.

In another aspect, the present application provides a method of producing a circular RNA polynucleotide, the method comprising incubating the linear RNA polynucleotide disclosed herein under suitable conditions for circularization. In some embodiments, the method comprises incubating the DNA disclosed herein under suitable conditions for transcription. In some embodiments, the DNA is transcribed in vitro. In some embodiments, the suitable conditions comprises adenosine triphosphate (ATP), guanine triphosphate (GTP), cytosine triphosphate (CTP), uridine triphosphate (UTP), and an RNA polymerase. In some embodiments, the suitable conditions further comprises guanine monophosphate (GMP). In some embodiments, the ratio of GMP concentration to GTP concentration is within the range of about 3:1 to about 15:1, optionally about 4:1, 5:1, or 6:1.

In another aspect, the present application provides a method of producing a circular RNA polynucleotide, the method comprising culturing the prokaryotic cell disclosed herein under suitable conditions for transcribing the DNA in the cell. In some embodiments, the method further comprising purifying a circular RNA polynucleotide. In some embodiments, the circular RNA polynucleotide is purified by negative selection using an affinity oligonucleotide that hybridizes with the first or second spacer conjugated to a solid surface. In some embodiments, the first or second spacer comprises a polyA sequence, and wherein the affinity oligonucleotide is a deoxythymine oligonucleotide.

BRIEF DESCRIPTION OF THE DRAWINGS

(FIG. 1B), or 1C1C7 (FIG. 1C) cells 24 hours after transfection with circular RNA comprising a *Gaussia* luciferase expression sequence and various IRES sequences.

FIGS. 13A and 3B depicts HPLC chromatograms (FIG. 13A) and circularization efficiencies (FIG. 13B) of 3 RNA constructs with or without homology arms.

FIGS. 27A, 27B, 27C, 27D, 27E and 27F depicts molecular characterization of Lipids 26 and 27 from Table 10a. FIG. 27A shows the proton nuclear magnetic resonance (NMR) spectrum of Lipid 26. FIG. 27B shows the retention time of Lipid 26 measured by liquid chromatography-mass spectrometry (LC-MS). FIG. 27C shows the mass spectrum of Lipid 26. FIG. 27D shows the proton NMR spectrum of Lipid 27. FIG. 27E shows the retention time of Lipid 27 measured by LC-MS. FIG. 27F shows the mass spectrum of Lipid 27.

FIG. 28A depicts the NMR spectrum of 2-(tetradecylthio)ethan-1-ol. FIG. 28B depicts the NMR spectrum of 2-(tetradecylthio)ethyl acrylate. FIG. 28C depicts the NMR spectrum of bis(2-(tetradecylthio)ethyl) 3,3'-((3-(2-methyl-1H-imidazol-1-yl)propyl)azanediyl)dipropionate (Lipid 22-S14).

FIG. 30A shows the proton NMR spectrum of Lipid 54. FIG. 30B shows the retention time of Lipid 54 measured by LC-MS. FIG. 30C shows the mass spectrum of Lipid 54.

FIG. 31A shows the proton NMR spectrum of Lipid 53. FIG. 31B shows the retention time of Lipid 53 measured by LC-MS. FIG. 31C shows the mass spectrum of Lipid 53.

DETAILED DESCRIPTION

Figure 1A:
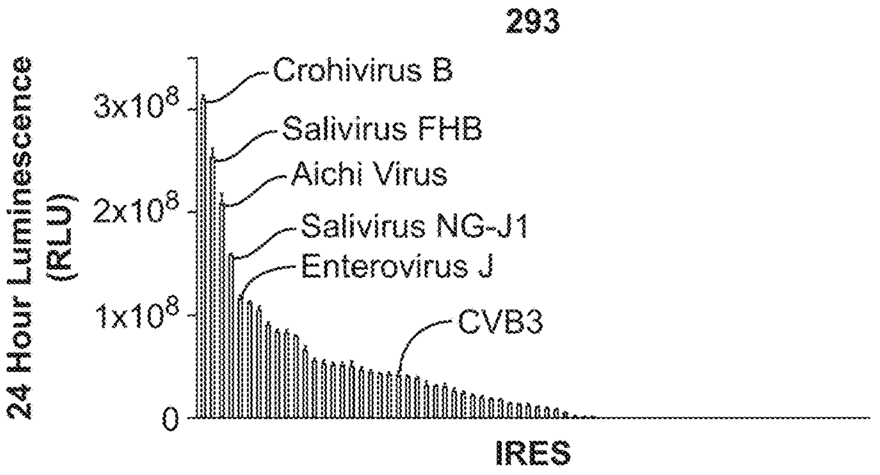
FIG. 1A, 1B, 1C, 1D, and 1E depicts luminescence in supernatants of HEK293 (FIGS. 1A, 1D, and 1E), HepG2

Provided herein are pharmaceutical compositions and transfer vehicles, e.g., lipid nanoparticles, comprising circular RNA. The circular RNA provided herein may be delivered and/or targeted to a cell in a transfer vehicle, e.g., a nanoparticle, or a composition comprising a transfer vehicle. In some embodiments, the circular RNA may also be delivered to a subject in a transfer vehicle or a composition comprising a transfer vehicle. In some embodiments, the transfer vehicle is a nanoparticle. In some embodiments, the nanoparticle is a lipid nanoparticle, a polymeric core-shell nanoparticle, or a biodegradable nanoparticle. In some embodiments, the nanoparticle is a lipid nanoparticle. In some embodiments, the transfer vehicle comprises one or more ionizable lipids, PEG modified lipids, helper lipids, and/or structural lipids.

In some embodiments, a transfer vehicle encapsulates circular RNA and comprises an ionizable lipid, a structural lipid, and a PEG-modified lipid. In some embodiments, a transfer vehicle encapsulates circular RNA and comprises an ionizable lipid, a structural lipid, a PEG-modified lipid, and a helper lipid.

In some embodiments, the transfer vehicle comprises an ionizable lipid described herein. In some embodiments, the transfer vehicle comprises an ionizable lipid shown in any one of Tables 1-10, 10a, 10b, 11-15, and 15b. In some embodiments, the transfer vehicle comprises an ionizable lipid shown in Table 10a.

In some embodiments, the RNA in a transfer vehicle is at least about 80%, 85%, 90%, 91%, 92%, 93%, 94%, 95%, 96%, 97%, 98%, 99%, 99.5%, 99.9%, or more circular RNA. In some embodiments, less than 5%, 10%, 15%, 20%, 25%, 30%, 35%, 40%, 45%, 50%, 55%, 60%, 65%, or 70% of loaded RNA is on or associated with a transfer vehicle exterior surface.

In some embodiments, the transfer vehicle is capable of binding to APOE. In some embodiments, the surface of the transfer vehicle comprises APOE binding sites. In some embodiments, the surface of the transfer vehicle is substantially free of APOE binding sites. In some embodiments, a transfer vehicle interacts with APOE less than an equivalent transfer vehicle loaded with linear RNA. In some embodiments, APOE interaction may be measured by comparing nanoparticle uptake in cells in APO depleted serum or APO complement serum.

Without wishing to be bound by theory, it is contemplated that transfer vehicles comprising APOE binding sites deliver circular RNAs more efficiently to the liver. Accordingly, in some embodiments, the transfer vehicle comprising the ionizable lipids described herein and loaded with circular RNA substantially comprises APOEbinding sites on the transfer vehicle surface, thereby delivering the circular RNA to the liver at a higher efficiency compared to a transfer vehicle substantially lacking APOE binding sites on the surface. In some embodiments, the transfer vehicle comprising the ionizable lipids described herein and loaded with circular RNA substantially lacks APOE binding sites on the transfer vehicle surface, thereby delivering the circular RNA to the liver at a lower efficiency compared to a transfer vehicle comprising APOE binding sites on the surface.

In some embodiments, the transfer vehicle delivers, or is capable of delivering, circular RNA to the spleen. In some embodiments, a circular RNA encodes a therapeutic protein. In some embodiments, at least about 10%, 15%, 20%, 25%, 30%, 35%, 40%, 45%, 50%, 55%, 60%, 65%, 70%, 75%, 80%, 85%, 90%, 95%, or 99% of the total therapeutic protein expressed in the subject is expressed in the spleen. In some embodiments, more therapeutic protein is expressed in the spleen than in the liver (e.g., 2×, 3×, 4×, or 5×more). In some embodiments, the lipid nanoparticle has an ionizable lipid:phosphate ratio of 3-7. In some embodiments, the lipid nanoparticlehas an ionizable lipid:phosphate ratio of 4-6. In some embodiments, the lipid nanoparticlehas an ionizable lipid:phosphate ratio of 4.5. In some embodiments, the lipid nanoparticlehas an nitrogen:phosphate (N:P) ratio of 3-6. In some embodiments, the lipid nanoparticlehas an N:P ratio of 5-6. In some embodiments, the lipid nanoparticlehas an N:P ratio of 5.7. In some embodiments, expression of a nonsecreted protein may be measured using an ELISA, normalizing to tissue weight.

Without wishing to be bound by theory, it is thought that transfer vehicles described herein shield encapsulated circular RNA from degradation and provide for effective delivery of circular RNA to target cells in vivo and in vitro.

Embodiments of the present disclosure provide lipid compositions described according to the respective molar ratios of the component lipids in the formulation. In one embodiment, the mol-% of the ionizable lipid may be from about 10 mol-% to about 80 mol-%. In one embodiment, the mol-% of the ionizable lipid may be from about 20 mol-% to about 70 mol-%. In one embodiment, the mol-% of the ionizable lipid may be from about 30 mol-% to about 60 mol-%. In one embodiment, the mol-% of the ionizable lipid may be from about 35 mol-% to about 55 mol-%. In one embodiment, the mol-% of the ionizable lipid may be from about 40 mol-% to about 50 mol-%. In some embodiments, the ionizable lipid mol-% of the transfer vehicle batch will be ±30%, ±25%, ±20%, ±15%, ±10%, ±5%, or ±2.5% of the target mol-%. In certain embodiments, transfer vehicle inter-lot variability will be less than 15%, less than 10% or less than 5%.

In one embodiment, the mol-% of the helper lipid may be from about 1 mol-% to about 50 mol-%. In one embodiment, the mol-% of the helper lipid may be from about 2 mol-% to about 45 mol-%. In one embodiment, the mol-% of the helper lipid may be from about 3 mol-% to about 40 mol-%. In one embodiment, the mol-% of the helper lipid may be from about 4 mol-% to about 35 mol-%. In one embodiment, the mol-% of the helper lipid may be from about 5 mol-% to about 30 mol-%. In one embodiment, the mol-% of the helper lipid may be from about 10 mol-% to about 20 mol-%. In some embodiments, the helper lipid mol-% of the transfer vehicle batch will be ±30%, ±25%, ±20%, ±15%, ±10%, ±5%, or ±2.5% of the target mol-%.

In one embodiment, the mol-% of the structural lipid may be from about 10 mol-% to about 80 mol-%. In one embodiment, the mol-% of the structural lipid may be from about 20 mol-% to about 70 mol-%. In one embodiment, the mol-% of the structural lipid may be from about 30 mol-% to about 60 mol-%. In one embodiment, the mol-% of the structural lipid may be from about 35 mol-% to about 55 mol-%. In one embodiment, the mol-% of the structural lipid may be from about 40 mol-% to about 50 mol-%. In some embodiments, the structural lipid mol-% of the transfer vehicle batch will be ±30%, ±25%, ±20%, ±15%, ±10%, ±5%, or ±2.5% of the target mol-%.

In one embodiment, the mol-% of the PEG modified lipid may be from about 0.1 mol-% to about 10 mol-%. In one embodiment, the mol-% of the PEG modified lipid may be from about 0.2 mol-% to about 5 mol-%. In one embodiment, the mol-% of the PEG modified lipid may be from about 0.5 mol-% to about 3 mol-%. In one embodiment, the mol-% of the PEG modified lipid may be from about 1 mol-% to about 2 mol-%. In one embodiment, the mol-% of the PEG modified lipid may be about 1.5 mol-%. In some embodiments, the PEG modified lipid mol-% of the transfer vehicle batch will be ±30%, ±25%, ±20%, ±15%, ±10%, ±5%, or ±2.5% of the target mol-%.

Also contemplated are pharmaceutical compositions, and in particular transfer vehicles, that comprise one or more of the compounds disclosed herein. In certain embodiments, such transfer vehicles comprise one or more of PEG-modified lipids, an ionizable lipid, a helper lipid, and/or a structural lipid disclosed herein. Also contemplated are transfer vehicles that comprise one or more of the compounds disclosed herein and that further comprise one or more additional lipids. In certain embodiments, such transfer vehicles are loaded with or otherwise encapsulate circular RNA.

Transfer vehicles of the invention encapsulate circular RNA. In certain embodiments, the polynucleotides encapsulated by the compounds or pharmaceutical and liposomal compositions of the invention include RNA encoding a protein or enzyme (e.g., circRNA encoding, for example, phenylalanine hydroxylase (PAH)). The present invention contemplates the use of such polynucleotides as a therapeutic that is capable of being expressed by target cells to thereby facilitate the production (and in certain instances, the excretion) of a functional enzyme or protein as disclosed bu such target cells, for example, in International Application No. PCT/US2010/058457 and in U.S. Provisional Application No. 61/494,881, filed Jun. 8, 2011, the teachings of which are both incorporated herein by reference in their entirety. For example, in certain embodiments, upon the expression of one or more polynucleotides by target cells, the production of a functional enzyme or protein in which a subject is deficient (e.g., a urea cycle enzyme or an enzyme associated with a lysosomal storage disorder) may be observed. As another example, circular RNA encapsulated by a transfer vehicle may encode one or both polypeptide chains of a T cell receptor protein or encode a chimeric antigen receptor (CAR).

Also provided herein are methods of treating a disease in a subject by administering an effective amount of a composition comprising circular RNA encoding a functional protein and a transfer vehicle described herein to the subject. In some embodiments, the circular RNA is encapsulated within the transfer vehicle. In certain embodiments, such methods may enhance (e.g., increase) the expression of a polynucleotide and/or increase the production and secretion of a functional polypeptide product in one or more target cells and tissues (e.g., immune cells or hepatocytes). Generally, such methods comprise contacting the target cells with one or more compounds and/or transfer vehicles that comprise or otherwise encapsulate the circRNA.

In certain embodiments, the transfer vehicles (e.g., lipid nanoparticles) are formulated based in part upon their ability to facilitate the transfection (e.g., of a circular RNA) of a target cell. In another embodiment, the transfer vehicles (e.g., lipid nanoparticles) may be selected and/or prepared to optimize delivery of circular RNA to a target cell, tissue or organ. For example, if the target cell is a hepatocyte, or if the target organ is the spleen, the properties of the pharmaceutical and/or liposomal compositions (e.g., size, charge and/or pH) may be optimized to effectively deliver such composition (e.g., lipid nanoparticles) to the target cell or organ, reduce immune clearance and/or promote retention in the target cell or organ. Alternatively, if the target tissue is the central nervous system, the selection and preparation of the transfer vehicle must consider penetration of, and retention within. the blood brain barrier and/or the use of alternate means of directly delivering such compositions (e.g., lipid nanoparticles) to such target tissue (e.g., via intracerebrovascular administration). In certain embodiments, the transfer vehicles may be combined with agents that facilitate the transfer of encapsulated materials across the blood brain barrier (e.g., agents which disrupt or improve the permeability of the blood brain barrier and thereby enhance the transfer of circular RNA to the target cells). While the transfer vehicles described herein (e.g., lipid nanoparticles) can facilitate introduction of circRNA into target cells, the addition of polycations (e.g., poly L-lysine and protamine) to, for example, one or more of the lipid nanoparticles that comprise the pharmaceutical compositions as a copolymer can also facilitate, and in some instances markedly enhance, the transfection efficiency of several types of transfer vehicles by 2-28 fold in a number of cell lines both in vitro and in vivo (See, N. J. Caplen, et al., Gene Ther. 1995; 2: 603; S. Li, et al., Gene Ther. 1997; 4, 891.). In some embodiments, a target cell is an immune cell. In some embodiments, a target cell is a T cell.

In certain embodiments, the transfer vehicles described herein (e.g., lipid nanoparticles) are prepared by combining multiple lipid components (e.g., one or more of the compounds disclosed herein) with one or more polymer components. For example, a lipid nanoparticle may be prepared using HGT4003, DOPE, cholesterol and DMG-PEG2000. A lipid nanoparticle may be comprised of additional lipid combinations in various ratios, including for example, HGT4001, DOPE and DMG-PEG2000. The selection of ionizable lipids, helper lipids, structural lipids, and/or PEG-modified lipids which comprise the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, charge, pH, pKa, fusogenicity and toxicity of the selected lipid(s).

Transfer vehicles described herein can allow the encapsulated polynucleotide to reach the target cell or may preferentially allow the encapsulated polynucleotide to reach the target cells or organs on a discriminatory basis (e.g., the transfer vehicles may concentrate in the liver or spleen of a subject to which such transfer vehicles are administered). Alternatively, the transfer vehicles may limit the delivery of encapsulated polynucleotides to other non-targeted cells or organs where the presence of the encapsulated polynucleotides may be undesirable or of limited utility.

Loading or encapsulating a polynucleotide, e.g., circRNA, into a transfer vehicle may serve to protect the polynucleotide from an environment (e.g., serum) which may contain enzymes or chemicals that degrade such polynucleotides and/or systems or receptors that cause the rapid excretion of such polynucleotides. Accordingly, in some embodiments, the compositions described herein are capable of enhancing the stability of the encapsulated polynucleotide (s), particularly with respect to the environments into which such polynucleotides will be exposed.

In certain embodiments, provided herein is a vector for making circular RNA, the vector comprising a 5' duplex forming region, a 3' group I intron fragment, optionally a first spacer, an Internal Ribosome Entry Site (IRES), an expression sequence, optionally a second spacer, a 5' group I intron fragment, and a 3' duplex forming region. In some embodiments, these elements are positioned in the vector in the above order. In some embodiments, the vector further comprises an internal 5' duplex forming region between the 3' group I intron fragment and the IRES and an internal 3' duplex forming region between the expression sequence and the 5' group I intron fragment. In some embodiments, the internal duplex forming regions are capable of forming a duplex between each other but not with the external duplex forming regions. In some embodiments, the internal duplex forming regions are part of the first and second spacers. Additional embodiments include circular RNA polynucleotides, including circular RNA polynucleotides made using the vectors provided herein, compositions comprising such circular RNA, cells comprising such circular RNA, methods of using and making such vectors, circular RNA, compositions and cells.

In some embodiments, provided herein are methods comprising administration of circular RNA polynucleotides provided herein into cells for therapy or production of useful proteins, such as PAH. In some embodiments, the method is advantageous in providing the production of a desired polypeptide inside eukaryotic cells with a longer half-life than linear RNA, due to the resistance of the circular RNA to ribonucleases.

Circular RNA polynucleotides lack the free ends necessary for exonuclease-mediated degradation, causing them to be resistant to several mechanisms of RNA degradation and granting extended half-lives when compared to an equivalent linear RNA. Circularization may allow for the stabilization of RNA polynucleotides that generally suffer from short half-lives and may improve the overall efficacy of exogenous mRNA in a variety of applications. In an embodiment, the half-life of the circular RNA polynucleotides provided herein in eukaryotic cells (e.g., mammalian cells, such as human cells) is at least 20 hours (e.g., at least 80 hours).

1. Definitions

As used herein, the terms "circRNA" or "circular polyribonucleotide" or "circular RNA" or "oRNA" are used interchangeably and refers to a polyribonucleotide that forms a circular structure through covalent bonds.

As used herein, the term "3' group I intron fragment" refers to a sequence with 75% or higher similarity to the 3'-proximal end of a natural group I intron including the splice site dinucleotide and optionally a stretch of natural exon sequence.

As used herein, the term "5' group I intron fragment" refers to a sequence with 75% or higher similarity to the 5'-proximal end of a natural group I intron including the splice site dinucleotide and optionally a stretch of natural exon sequence.

As used herein, the term "permutation site" refers to the site in a group I intron where a cut is made prior to permutation of the intron. This cut generates 3' and 5' group I intron fragments that are permuted to be on either side of a stretch of precursor RNA to be circularized.

As used herein, the term "splice site" refers to a dinucleotide that is partially or fully included in a group I intron and between which a phosphodiester bond is cleaved during RNA circularization.

As used herein, the term "therapeutic protein" refers to any protein that, when administered to a subject directly or indirectly in the form of a translated nucleic acid, has a therapeutic, diagnostic, and/or prophylactic effect and/or elicits a desired biological and/or pharmacological effect.

As used herein, the term "immunogenic" refers to a potential to induce an immune response to a substance. An immune response may be induced when an immune system of an organism or a certain type of immune cells is exposed to an immunogenic substance. The term "non-immunogenic" refers to a lack of or absence of an immune response above a detectable threshold to a substance. No immune response is detected when an immune system of an organism or a certain type of immune cells is exposed to a non-immunogenic substance. In some embodiments, a non-immunogenic circular polyribonucleotide as provided herein, does not induce an immune response above a predetermined threshold when measured by an immunogenicity assay. In some embodiments, no innate immune response is detected when an immune system of an organism or a certain type of immune cells is exposed to a non-immunogenic circular polyribonucleotide as provided herein. In some embodiments, no adaptive immune response is detected when an immune system of an organism or a certain type of immune cell is exposed to a non-immunogenic circular polyribonucleotide as provided herein.

As used herein, the term "circularization efficiency" refers to a measurement of resultant circular polyribonucleotide as compared to its linear starting material.

As used herein, the term "translation efficiency" refers to a rate or amount of protein or peptide production from a ribonucleotide transcript. In some embodiments, translation efficiency can be expressed as amount of protein or peptide produced per given amount of transcript that codes for the protein or peptide.

The term "nucleotide" refers to a ribonucleotide, a deoxyribonucleotide, a modified form thereof, or an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety as defined herein. Nucleotide analogs are also meant to include nucleotides with bases such as inosine, queuosine, xanthine; sugars such as 2'-methyl ribose; non-natural phosphodiester linkages such as methylphosphonate, phosphorothioate and peptide linkages. Nucleotide analogs include 5-methoxyuridine, 1-methylpseudouridine, and 6-methyladenosine.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, or up to about 10,000 or more bases, composed of nucleotides, e.g., deoxyribonucleotides or ribonucleotides, and may be produced enzymatically or synthetically (e.g., as described in U.S. Pat. No. 5,948,902 and the references cited therein), which can hybridize with naturally occurring nucleic acids in a sequence specific manner analogous to that of two naturally occurring nucleic acids, e.g., can participate in Watson-Crick base pairing interactions. Naturally occurring nucleic acids are comprised of nucleotides including guanine, cytosine, adenine, thymine, and uracil (G, C, A, T, and U respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (for example, in some embodiments, a compound, a polynucleotide, a protein, a polypeptide, a polynucleotide composition, or a polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90%-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is more than as it is found naturally.

The terms "duplexed," "double-stranded," or "hybridized" as used herein refer to nucleic acids formed by hybridization of two single strands of nucleic acids containing complementary sequences. In most cases, genomic DNA is double-stranded. Sequences can be fully complementary or partially complementary.

As used herein, "unstructured" with regard to RNA refers to an RNA sequence that is not predicted by the RNAFold software or similar predictive tools to form a structure (e.g., a hairpin loop) with itself or other sequences in the same RNA molecule. In some embodiments, unstructured RNA can be functionally characterized using nuclease protection assays.

As used herein, "structured" with regard to RNA refers to an RNA sequence that is predicted by the RNAFold software or similar predictive tools to form a structure (e.g., a hairpin loop) with itself or other sequences in the same RNA molecule.

As used herein, two "duplex forming regions," "homology arms," or "homology regions," may be any two regions that are thermodynamically favored to cross-pair in a sequence specific interaction. In some embodiments, two duplex forming regions, homology arms, or homology regions, share a sufficient level of sequence identity to one another's reverse complement to act as substrates for a hybridization reaction. As used herein polynucleotide sequences have "homology" when they are either identical or share sequence identity to a reverse complement or "complementary" sequence. The percent sequence identity between a homology region and a counterpart homology region's reverse complement can be any percent of sequence identity that allows for hybridization to occur. In some embodiments, an internal duplex forming region of an inventive polynucleotide is capable of forming a duplex with another internal duplex forming region and does not form a duplex with an external duplex forming region.

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end nucleotide of a polynucleotide at which a new linkage would be to a 5' carbon is its 5' terminal nucleotide. The end nucleotide of a polynucleotide at which a new linkage would be to a 3' carbon is its 3' terminal nucleotide. A terminal nucleotide, as used herein, is the nucleotide at the end position of the 3'- or 5'-terminus "Transcription" means the formation or synthesis of an RNA molecule by an RNA polymerase using a DNA molecule as a template. The invention is not limited with respect to the RNA polymerase that is used for transcription. For example, in some embodiments, a T7-type RNA polymerase can be used.

"Translation" means the formation of a polypeptide molecule by a ribosome based upon an RNA template.

It is to be understood that the terminology used herein is for the purpose of describing particular embodiments only, and is not intended to be limiting. As used in this specification and the appended claims, the singular forms "a," "an," and "the" include plural referents unless the content clearly dictates otherwise. Thus, for example, reference to "a cell" includes combinations of two or more cells, or entire cultures of cells; reference to "a polynucleotide" includes, as a practical matter, many copies of that polynucleotide. Unless specifically stated or obvious from context, as used herein, the term "or" is understood to be inclusive. Unless defined herein and below in the reminder of the specification, all technical and scientific terms used herein have the same meaning as commonly understood by one of ordinary skill in the art to which the invention pertains.

Unless specifically stated or obvious from context, as used herein, the term "about," is understood as within a range of normal tolerance in the art, for example within 2 standard deviations of the mean. "About" can be understood as within 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the stated value. Unless otherwise clear from the context, all numerical values provided herein are modified by the term "about."

As used herein, the term "encode" refers broadly to any process whereby the information in a polymeric macromolecule is used to direct the production of a second molecule that is different from the first. The second molecule may have a chemical structure that is different from the chemical nature of the first molecule.

By "co-administering" is meant administering a therapeutic agent provided herein in conjunction with one or more additional therapeutic agents sufficiently close in time such that the therapeutic agent provided herein can enhance the effect of the one or more additional therapeutic agents, or vice versa.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. The treatment or prevention provided by the method disclosed herein can include treatment or prevention of one or more conditions or symptoms of the disease. Also, for purposes herein, "prevention" can encompass delaying the onset of the disease, or a symptom or condition thereof.

As used herein, the term "expression sequence" refers to a nucleic acid sequence that encodes a product, e.g., a peptide or polypeptide, regulatory nucleic acid, or non-coding nucleic acid. An exemplary expression sequence that codes for a peptide or polypeptide can comprise a plurality of nucleotide triads, each of which can code for an amino acid and is termed as a "codon".

As used herein, a "spacer" refers to a region of a polynucleotide sequence ranging from 1 nucleotide to hundreds or thousands of nucleotides separating two other elements along a polynucleotide sequence. The sequences can be defined or can be random. A spacer is typically non-coding. In some embodiments, spacers include duplex forming regions.

As used herein, "splice site" refers to the dinucleotide or dinucleotides between which cleavage of the phosphodiester bond occurs during a splicing reaction. A "5' splice site" refers to the natural 5' dinucleotide of the intron e.g., group I intron, while a "3' splice site" refers to the natural 3' dinucleotide of the intron.

As used herein, an "internal ribosome entry site" or "IRES" refers to an RNA sequence or structural element ranging in size from 10 nt to 1000 nt or more, capable of initiating translation of a polypeptide in the absence of a typical RNA cap structure. An IRES is typically about 500 nt to about 700 nt in length.

As used herein, a "miRNA site" refers to a stretch of nucleotides within a polynucleotide that is capable of forming a duplex with at least 8 nucleotides of a natural miRNA sequence.

As used herein, an "endonuclease site" refers to a stretch of nucleotides within a polynucleotide that is capable of being recognized and cleaved by an endonuclease protein.

As used herein, "bicistronic RNA" refers to a polynucleotide that includes two expression sequences coding for two distinct proteins. These expression sequences can be separated by a nucleotide sequence encoding a cleavable peptide such as a protease cleavage site. They can also be separated by a ribosomal skipping element.

As used herein, the term"ribosomal skipping element" refers to a nucleotide sequence encoding a short peptide sequence capable of causing generation of two peptide chains from translation of one RNA molecule. While not wishing to be bound by theory, it is hypothesized that ribosomal skipping elements function by (1) terminating translation of the first peptide chain and re-initiating translation of the second peptide chain; or (2) cleavage of a peptide bond in the peptide sequence encoded by the ribosomai skipping element by an intrinsic protease activity of the encoded peptide, or by another protease in the environment (e.g., cytosol).

As used herein, the term "co-formulate" refers to a nanoparticle formulation comprising two or more nucleic acids or a nucleic acid and other active drug substance. Typically, the ratios are equimolar or defined in the ratiometric amount of the two or more nucleic acids or the nucleic acid and other active drug substance.

As used herein, "transfer vehicle" includes any of the standard pharmaceutical carriers, diluents, excipients, and the like, which are generally intended for use in connection with the administration of biologically active agents, including nucleic acids.

As used herein, the phrase "lipid nanoparticle" refers to a transfer vehicle comprising one or more lipids (e.g., in some embodiments, cationic lipids, non-cationic lipids, and PEG-modified lipids).

As used herein, the phrase "ionizable lipid" refers to any of a number of lipid species that carry a net positive charge at a selected pH, such as physiological pH 4 and a neutral charge at other pHs such as physiological pH 7.

In some embodiments, a lipid, e.g., an ionizable lipid, disclosed herein comprises one or more cleavable groups. The terms "cleave" and "cleavable" are used herein to mean that one or more chemical bonds (e.g., one or more of covalent bonds, hydrogen-bonds, van der Waals' forces and/or ionic interactions) between atoms in or adjacent to the subject functional group are broken (e.g., hydrolyzed) or are capable of being broken upon exposure to selected conditions (e.g., upon exposure to enzymatic conditions). In certain embodiments, the cleavable group is a disulfide functional group, and in particular embodiments is a disulfide group that is capable of being cleaved upon exposure to selected biological conditions (e.g., intracellular conditions). In certain embodiments, the cleavable group is an ester functional group that is capable of being cleaved upon exposure to selected biological conditions. For example, the disulfide groups may be cleaved enzymatically or by a hydrolysis, oxidation or reduction reaction. Upon cleavage of such disulfide functional group, the one or more functional moieties or groups (e.g., one or more of a head-group and/or a tail-group) that are bound thereto may be liberated. Exemplary cleavable groups may include, but are not limited to, disulfide groups, ester groups, ether groups, and any derivatives thereof (e.g., alkyl and aryl esters). In certain embodiments, the cleavable group is not an ester group or an ether group. In some embodiments, a cleavable group is bound (e.g., bound by one or more of hydrogen-bonds, van der Waals' forces, ionic interactions and covalent bonds) to one or more functional moieties or groups (e.g., at least one head-group and at least one tail-group). In certain embodiments, at least one of the functional moieties or groups is hydrophilic (e.g., a hydrophilic head-group comprising one or more of imidazole, guanidinium, amino, imine, enamine, optionally-substituted alkyl amino and pyridyl).

As used herein, the term "hydrophilic" is used to indicate in qualitative terms that a functional group is water-preferring, and typically such groups are water-soluble. For example, disclosed herein are compounds that comprise a cleavable disulfide (S-S) functional group bound to one or more hydrophilic groups (e.g., a hydrophilic head-group), wherein such hydrophilic groups comprise or are selected from the group consisting of imidazole, guanidinium, amino, imine, enamine, an optionally-substituted alkyl amino (e.g., an alkyl amino such as dimethylamino) and pyridyl.

In certain embodiments, at least one of the functional groups of moieties that comprise the compounds disclosed herein is hydrophobic in nature (e.g., a hydrophobic tail-group comprising a naturally occurring lipid such as cholesterol). As used herein, the term "hydrophobic" is used to indicate in qualitative terms that a functional group is water-avoiding, and typically such groups are not water soluble. For example, disclosed herein are compounds that comprise a cleavable functional group (e.g., a disulfide (S-S) group) bound to one or more hydrophobic groups, wherein such hydrophobic groups comprise one or more naturally occurring lipids such as cholesterol, and/or an optionally substituted, variably saturated or unsaturated $C_6$-$C_{20}$ alkyl and/or an optionally substituted, variably saturated or unsaturated $C_6$-$C_{20}$ acyl.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

When a range of values is listed, it is intended to encompass each value and sub-range within the range. For example, "$C_{1-6}$alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

In certain embodiments, the compounds disclosed herein comprise, for example, at least one hydrophilic head-group and at least one hydrophobic tail-group, each bound to at least one cleavable group, thereby rendering such compounds amphiphilic. As used herein to describe a compound or composition, the term "amphiphilic" means the ability to dissolve in both polar (e.g., water) and non-polar (e.g., lipid) environments. For example, in certain embodiments, the compounds disclosed herein comprise at least one lipophilic tail-group (e.g., cholesterol or a $C_6$-$C_{20}$ alkyl) and at least one hydrophilic head-group (e.g., imidazole), each bound to a cleavable group (e.g., disulfide).

It should be noted that the terms "head-group" and "tail-group" as used describe the compounds of the present invention, and in particular functional groups that comprise such compounds, are used for ease of reference to describe the orientation of one or more functional groups relative to other functional groups. For example, in certain embodiments a hydrophilic head-group (e.g., guanidinium) is bound (e.g., by one or more of hydrogen-bonds, van der Waals' forces, ionic interactions and covalent bonds) to a cleavable functional group (e.g., a disulfide group), which in turn is bound to a hydrophobic tail-group (e.g., cholesterol).

As used herein, the term "alkyl" refers to both straight and branched chain $C_1$-$C_{40}$ hydrocarbons (e.g., $C_6$-$C_{20}$ hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). In certain embodiments, a contemplated alkyl includes (9Z,12Z)-octadeca-9,12-dien. The use of designations such as, for example, "$C_6$-$C_{20}$" is intended to refer to an alkyl (e.g., straight or branched chain and inclusive of alkenes and alkyls) having the recited range carbon atoms. In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-s}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-s}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl).

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. The terms "heterocycle," "heterocyclyl," "heterocyclyl ring," "heterocyclic group," "heterocyclic moiety," and "heterocyclic radical," may be used interchangeably.

As used herein, "cyano" refers to —CN.

The terms "halo" and "halogen" as used herein refer to an atom selected from fluorine (fluoro, —F), chlorine (chloro, —Cl), bromine (bromo, —Br), and iodine (iodo, —I). In certain embodiments, the halo group is either fluoro or chloro.

The term "alkoxy," as used herein, refers to an alkyl group which is attached to another moiety via an oxygen atom (—O(alkyl)). Non-limiting examples include e.g., methoxy, ethoxy, propoxy, and butoxy.

As used herein, "oxo" refers to —C═O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

In certain embodiments the compounds and the transfer vehicles of which such compounds are a component (e.g., lipid nanoparticles) exhibit an enhanced (e.g., increased) ability to transfect one or more target cells. Accordingly, also provided herein are methods of transfecting one or more target cells. Such methods generally comprise the step of contacting the one or more target cells with the compounds and/or pharmaceutical compositions disclosed herein such that the one or more target cells are transfected with the circular RNA encapsulated therein. As used herein, the terms "transfect" or "transfection" refer to the intracellular introduction of one or more encapsulated materials (e.g., nucleic acids and/or polynucleotides) into a cell, or preferably into a target cell. The term "transfection efficiency" refers to the relative amount of such encapsulated material (e.g., polynucleotides) up-taken by, introduced into and/or expressed by the target cell which is subject to transfection. In some embodiments, transfection efficiency may be estimated by the amount of a reporter polynucleotide product produced by the target cells following transfection. In some embodiments, a transfer vehicle has high transfection efficiency. In some embodiments, a transfer vehicle has at least about 10%, 20%, 30%, 40%, 50%, 60%, 70%, 80%, or 90% transfection efficiency.

As used herein, the term "liposome" generally refers to a vesicle composed of lipids (e.g., amphiphilic lipids) arranged in one or more spherical bilayer or bilayers. In certain embodiments, the liposome is a lipid nanoparticle (e.g., a lipid nanoparticle comprising one or more of the ionizable lipid compounds disclosed herein). Such liposomes may be unilamellar or multilamellar vesicles which have a membrane formed from a lipophilic material and an aqueous interior that contains the encapsulated circRNA to be delivered to one or more target cells, tissues and organs. In certain embodiments, the compositions described herein comprise one or more lipid nanoparticles. Examples of suitable lipids (e.g., ionizable lipids) that may be used to form the liposomes and lipid nanoparticles contemplated include one or more of the compounds disclosed herein (e.g., HGT4001, HGT4002, HGT4003, HGT4004 and/or HGT4005). Such liposomes and lipid nanoparticles may also comprise additional ionizable lipids such as C12-200, DLin-KC2-DMA, and/or HGT5001, helper lipids, structural lipids, PEG-modified lipids, MC3, DLinDMA, DLinkC2DMA, cKK-E12, ICE, HGT5000, DODAC, DDAB, DMRIE, DOSPA, DOGS, DODAP, DODMA, DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, HGT4003, and combinations thereof.

As used herein, the phrases "non-cationic lipid", "non-cationic helper lipid", and "helper lipid" are used interchangeably and refer to any neutral, zwitterionic or anionic lipid.

As used herein, the phrase "anionic lipid" refers to any of a number of lipid species that carry a net negative charge at a selected pH, such as physiological pH.

As used herein, the phrase "biodegradable lipid" or "degradable lipid" refers to any of a number of lipid species that are broken down in a host environment on the order of minutes, hours, or days ideally making them less toxic and unlikely to accumulate in a host over time. Common modifications to lipids include ester bonds, and disulfide bonds among others to increase the biodegradability of a lipid.

As used herein, the phrase "biodegradable PEG lipid" or "degradable PEG lipid" refers to any of a number of lipid species where the PEG molecules are cleaved from the lipid in a host environment on the order of minutes, hours, or days ideally making them less immunogenic. Common modifications to PEG lipids include ester bonds, and disulfide bonds among others to increase the biodegradability of a lipid.

In certain embodiments of the present invention, the transfer vehicles (e.g., lipid nanoparticles) are prepared to encapsulate one or more materials or therapeutic agents (e.g., circRNA). The process of incorporating a desired therapeutic agent (e.g., circRNA) into a transfer vehicle is referred to herein as or "loading" or "encapsulating" (Lasic, et al., FEBS Lett., 312: 255-258, 1992). The transfer vehicle-loaded or -encapsulated materials (e.g., circRNA) may be completely or partially located in the interior space of the transfer vehicle, within a bilayer membrane of the transfer vehicle, or associated with the exterior surface of the transfer vehicle.

As used herein, the term "structural lipid" refers to sterols and also to lipids containing sterol moieties.

As defined herein, "sterols" are a subgroup of steroids consisting of steroid alcohols.

As used herein, the term "structural lipid" refers to sterols and also to lipids containing sterol moieties.

As used herein, the term "PEG" means any polyethylene glycol or other polyalkylene ether polymer.

As generally defined herein, a "PEG-OH lipid" (also referred to herein as "hydroxy-PEGylated lipid") is a PEGylated lipid having one or more hydroxyl (—OH) groups on the lipid.

As used herein, a "phospholipid" is a lipid that includes a phosphate moiety and one or more carbon chains, such as unsaturated fatty acid chains.

All nucleotide sequences disclosed herein can represent an RNA sequence or a corresponding DNA sequence. It is understood that deoxythymidine (dT or T) in a DNA is transcribed into a uridine (U) in an RNA. As such, "T" and "U" are used interchangeably herein in nucleotide sequences.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

2. Vectors, Precursor RNA, and Circular RNA

Also provided herein are circular RNAs, precursor RNAs that can circularize into the circular RNAs, and vectors (e.g., DNA vectors) that can be transcribed into the precursor RNAs or the circular RNAs.

Two types of spacers have been designed for improving precursor RNA circularization and/or gene expression from circular RNA. The first type of spacer is external spacer, i.e., present in a precursor RNA but removed upon circularization. While not wishing to be bound by theory, it is contemplated that an external spacer may improve ribozyme-mediated circularization by maintaining the structure of the ribozyme itself and preventing other neighboring sequence elements from interfering with its folding and function. The second type of spacer is internal spacer, i.e., present in a precursor RNA and retained in a resulting circular RNA. While not wishing to be bound by theory, it is contemplated that an internal spacer may improve ribozyme-mediated circularization by maintaining the structure of the ribozyme itself and preventing other neighboring sequence elements, particularly the neighboring IRES and coding region, from interfering with its folding and function. It is also contemplated that an internal spacer may improve protein expression from the IRES by preventing neighboring sequence elements, particularly the intron elements, from hybridizing with sequences within the IRES and inhibiting its ability to fold into its most preferred and active conformation.

For driving protein expression, the circular RNA comprises an IRES operably linked to a protein coding sequence. Exemplary IRES sequences are provided in Table 17 below. In some embodiments, the circular RNA disclosed herein comprises an IRES sequence at least 80%, 85%, 90%, 91%, 92%, 93%, 94%, 95%, 96%, 97%, 98%, or 99% identical to an IRES sequence in Table 17. In some embodiments, the circular RNA disclosed herein comprises an IRES sequence in Table 17. Modifications of IRES and accessory sequences are disclosed herein to increase or reduce IRES activities, for example, by truncating the 5' and/or 3' ends of the IRES, adding a spacer 5' to the IRES, modifying the 6 nucleotides 5' to the translation initiation site (Kozak sequence), modification of alternative translation initiation sites, and creating chimeric/hybrid IRES sequences. In some embodiments, the IRES sequence in the circular RNA disclosed herein comprises one or more of these modifications relative to a native IRES (e.g., a native IRES disclosed in Table 17).

In certain aspects, provided herein are circular RNA polynucleotides comprising a 3' post splicing group I intron fragment, optionally a first spacer, an Internal Ribosome Entry Site (IRES), an expression sequence, optionally a second spacer, and a 5' post splicing group I intron fragment. In some embodiments, these regions are in that order. In some embodiments, the circular RNA is made by a method provided herein or from a vector provided herein.

In certain embodiments, transcription of a vector provided herein (e.g., comprising a 5' homology region, a 3' group I intron fragment, optionally a first spacer, an Internal Ribosome Entry Site (IRES), an expression sequence, optionally a second spacer, a 5' group I intron fragment, and a 3' homology region) results in the formation of a precursor linear RNA polynucleotide capable of circularizing. In some embodiments, this precursor linear RNA polynucleotide circularizes when incubated in the presence of guanosine nucleotide or nucleoside (e.g., GTP) and divalent cation (e.g., $Mg^{2+}$).

In some embodiments, the vectors and precursor RNA polynucleotides provided herein comprise a first (5') duplex forming region and a second (3') duplex forming region. In certain embodiments, the first and second homology regions may form perfect or imperfect duplexes. Thus, in certain embodiments at least 75%, 80%, 85%, 90%, 91%, 92%, 93%, 94%, 95%, 96%, 97%, 98%, 99% or 100% of the first and second duplex forming regions may be base paired with one another. In some embodiments, the duplex forming regions are predicted to have less than 50% (e.g., less than 45%, less than 40%, less than 35%, less than 30%, less than 25%) base pairing with unintended sequences in the RNA (e.g., non-duplex forming region sequences). In some embodiments, including such duplex forming regions on the ends of the precursor RNA strand, and adjacent or very close to the group I intron fragment, bring the group I intron fragments in close proximity to each other, increasing splicing efficiency. In some embodiments, the duplex forming regions are 3 to 100 nucleotides in length (e.g., 3-75 nucleotides in length, 3-50 nucleotides in length, 20-50 nucleotides in length, 35-50 nucleotides in length, 5-25 nucleotides in length, 9-19 nucleotides in length). In some embodiments, the duplex forming regions are about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some embodiments, the duplex forming regions have a length of about 9 to about 50 nucleotides. In one embodiment, the duplex forming regions have a length of about 9 to about 19 nucleotides. In some embodiments, the duplex forming regions have a length of about 20 to about 40 nucleotides. In certain embodiments, the duplex forming regions have a length of about 30 nucleotides.

In certain embodiments, the vectors, precursor RNA and circular RNA provided herein comprise a first (5') and/or a second (3') spacer. In some embodiments, including a spacer between the 3' group I intron fragment and the IRES may conserve secondary structures in those regions by preventing them from interacting, thus increasing splicing efficiency. In some embodiments, the first (between 3' group I intron fragment and IRES) and second (between the expression sequence and 5' group I intron fragment) spacers comprise additional base pairing regions that are predicted to base pair with each other and not to the first and second duplex forming regions. In some embodiments, such spacer base pairing brings the group I intron fragments in close proximity to each other, further increasing splicing efficiency. Additionally, in some embodiments, the combination of base pairing between the first and second duplex forming regions, and separately, base pairing between the first and second spacers, promotes the formation of a splicing bubble containing the group I intron fragments flanked by adjacent regions of base pairing. Typical spacers are contiguous sequences with one or more of the following qualities: 1) predicted to avoid interfering with proximal structures, for example, the IRES, expression sequence, or intron; 2) is at least 7 nt long and no longer than 100 nt; 3) is located after and adjacent to the 3' intron fragment and/or before and adjacent to the 5' intron fragment; and 4) contains one or more of the following: a) an unstructured region at least 5 nt long, b) a region of base pairing at least 5 nt long to a distal sequence, including another spacer, and c) a structured region at least 7 nt long limited in scope to the sequence of the spacer. Spacers may have several regions, including an unstructured region, abase pairing region, a hairpin/structured region, and combinations thereof. In an embodiment, the spacer has a structured region with high GC content. In an embodiment, a region within a spacer base pairs with another region within the same spacer. In an embodiment, a region within a spacer base pairs with a region within another spacer. In an embodiment, a spacer comprises one or more hairpin structures. In an embodiment, a spacer comprises one or more hairpin structures with a stem of 4 to 12 nucleotides and a loop of 2 to 10 nucleotides. In an embodiment, there is an additional spacer between the 3' group I intron fragment and the IRES. In an embodiment, this additional spacer prevents the structured regions of the IRES from interfering with the folding of the 3' group I intron fragment or reduces the extent to which this occurs. In some embodiments, the 5' spacer sequence is at least 7, 8, 9, 10, 11, 12, 13, 14, 15, 16, 17, 18, 19, 20, 25 or 30 nucleotides in length. In some embodiments, the 5' spacer sequence is no more than 100, 90, 80, 70, 60, 50, 45, 40, 35 or 30 nucleotides in length. In some embodiments the 5' spacer sequence is between 5 and 50, 10 and 50, 20 and 50, 20 and 40, and/or 25 and 35 nucleotides in length. In certain embodiments, the 5' spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In one embodiment, the 5' spacer sequence is a polyA sequence. In another embodiment, the 5' spacer sequence is a polyAC sequence. In one embodiment, a spacer comprises about 10%, 20%, 30%, 40%, 50%, 60%, 70%, 80%, 90%, or 100% polyAC content. In one embodiment, a spacer comprises about 10%, 20%, 30%, 40%, 50%, 60%, 70%, 80%, 90%, or 100% polypyrimidine (C/T or C/U) content.

In certain embodiments, a 3' group I intron fragment is a contiguous sequence at least 75% identical (e.g., at least 80%, 85%, 90%, 91%, 92%, 93%, 94%, 95%, 96%, 97%, 98%, 99% or 100% identical) to a 3' proximal fragment of a natural group I intron including the 3' splice site dinucleotide and optionally the adjacent exon sequence at least 1 nt in length (e.g., at least 2, 3, 4, 5, 6, 7, 8, 9, 10, 15, 20, 25 or 30 nt in length) and at most the length of the exon. Typically, a 5' group I intron fragment is a contiguous sequence at least 75% identical (e.g., at least 80%, 85%, 90%, 91%, 92%, 93%, 94%, 95%, 96%, 97%, 98%, 99% or 100% identical) to a 5' proximal fragment of a natural group I intron including the 5' splice site dinucleotide and optionally the adjacent exon sequence at least 1 nt in length (e.g., at least 2, 3, 4, 5, 6, 7, 8, 9, 10, 15, 20, 25 or 30 nt in length) and at most the length of the exon. As described by Umekage et al. (2012), external portions of the 3' group I intron fragment and 5' group I intron fragment are removed in circularization, causing the circular RNA provided herein to comprise only the portion of the 3' group I intron fragment formed by the optional exon sequence of at least 1 nt in length and 5' group I intron fragment formed by the optional exon sequence of at least 1 nt in length, if such sequences were present on the non-circularized precursor RNA. The part of the 3' group I intron fragment that is retained by a circular RNA is referred to herein as the post splicing 3' group I intron fragment. The part of the 5' group I intron fragment that is retained by a circular RNA is referred to herein as the post splicing 5' group I intron fragment.

In certain embodiments, the vectors, precursor RNA and circular RNA provided herein comprise an internal ribosome entry site (IRES). Inclusion of an IRES permits the translation of one or more open reading frames from a circular RNA (e.g., open reading frames that form the expression sequence). The IRES element attracts a eukaryotic ribosomal translation initiation complex and promotes translation initiation. See, e.g., Kaufman et al., Nuc. Acids Res. (1991) 19:4485-4490; Gurtu et al., Biochem. Biophys. Res. Comm. (1996) 229:295-298; Rees et al., BioTechniques (1996) 20: 102-110; Kobayashi et al., BioTechniques (1996) 21:399-402; and Mosser et al., BioTechniques 1997 22 150-161).

A multitude of IRES sequences are available and include sequences derived from a wide variety of viruses, such as from leader sequences of picornaviruses such as the encephalomyocarditis virus (EMCV) UTR (Jang et al. J. Virol. (1989) 63: 1651-1660), the polio leader sequence, the hepatitis A virus leader, the hepatitis C virus IRES, human rhinovirus type 2 IRES (Dobrikova et al., Proc. Natl. Acad. Sci. (2003) 100(25): 15125-15130), an IRES element from the foot and mouth disease virus (Ramesh et al., Nucl. Acid Res. (1996) 24:2697-2700), a giardiavirus IRES (Garlapati et al., J. Biol. Chem. (2004) 279(5):3389-3397), and the like.

In some embodiments, the IRES is an IRES sequence of Taura syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, *Homalodisca coagulata* virus-1, Human Immunodeficiency Virus type 1, Himetobi P virus, Hepatitis C virus, Hepatitis A virus, Hepatitis GB virus, Foot and mouth disease virus, Human enterovirus 71, Equine rhinitis virus, *Ectropis obliqua* picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAPI, Human c-myc, Human eIF4G, Mouse NDST4L, Human LEF1, Mouse HIF1 alpha, Human n.myc, Mouse Gtx, Human p27kipl, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SH1, Salivirus FHB, Salivirus NG-J1, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, Salivirus A BN5, Salivirus A BN2, Salivirus A 02394, Salivirus A GUT, Salivirus A CH, Salivirus A SZ1, Salivirus FHB, CVB3, CVB1, Echovirus 7, CVB5, EVA71, CVA3, CVA 12, EV24 or an aptamer to eIF4G.

In some embodiments, the polynucleotides herein comprise an expression sequence. In some embodiments, the expression sequence encodes a therapeutic protein.

In some embodiments, the circular RNA encodes two or more polypeptides. In some embodiments, the circular RNA is a bicistronic RNA. The sequences encoding the two or more polypeptides can be separated by a ribosomal skipping element or a nucleotide sequence encoding a protease cleavage site. In certain embodiments, the ribosomai skipping element encodes thosea-asigna virus 2A peptide (T2A), porcine teschovirus-1 2 Apeptide (P2A), foot-and-mouth disease virus 2 A peptide (F2A), equine rhinitis A vims 2A peptide (E2A), cytoplasmic polyhedrosis vims 2A peptide (BmCPV 2A), or flacherie vims of *B. mori* 2A peptide (BmIFV 2A).

In certain embodiments, the vectors provided herein comprise a 3' UTR. In some embodiments, the 3' UTR is from human beta globin, human alpha globin xenopus beta globin, xenopus alpha globin, human prolactin, human GAP-43, human eEFlal, human Tau, human TNFα, dengue virus, hantavirus small mRNA, bunyavirus small mRNA, turnip yellow mosaic virus, hepatitis C virus, rubella virus, tobacco mosaic virus, human IL-8, human actin, human GAPDH, human tubulin, hibiscus chlorotic ringspot virus, woodchuck hepatitis virus post translationally regulated element, sindbis virus, turnip crinkle virus, tobacco etch virus, or Venezuelan equine encephalitis virus.

In some embodiments, the vectors provided herein comprise a 5' UTR. In some embodiments, the 5' UTR is from human beta globin, *Xenopus laevis* beta globin, human alpha globin, *Xenopus laevis* alpha globin, rubella virus, tobacco mosaic virus, mouse Gtx, dengue virus, heat shock protein 70 kDa protein 1A, tobacco alcohol dehydrogenase, tobacco etch virus, turnip crinkle virus, or the adenovirus tripartite leader.

In some embodiments, a vector provided herein comprises a polyA region external of the 3' and/or 5' group I intron fragments. In some embodiments the polyA region is at least 15, 30, or 60 nucleotides long. In some embodiments, one or both polyA regions is 15-50 nucleotides long. In some embodiments, one or both polyA regions is 20-25 nucleotides long. The polyA sequence is removed upon circularization. Thus, an oligonucleotide hybridizing with the polyA sequence, such as a deoxythymine oligonucleotide (oligo(dT)) conjugated to a solid surface (e.g., a resin), can be used to separate circular RNA from its precursor RNA. Other sequences can also be disposed 5' to the 3' group I intron fragment or 3' to the 5' group I intron fragment and a complementary sequence can similarly be used for circular RNA purification.

In some embodiments, the DNA (e.g., vector), linear RNA (e.g., precursor RNA), and/or circular RNA polynucleotide provided herein is between 300 and 10000, 400 and 9000, 500 and 8000, 600 and 7000, 700 and 6000, 800 and 5000, 900 and 5000, 1000 and 5000, 1100 and 5000, 1200 and 5000, 1300 and 5000, 1400 and 5000, and/or 1500 and 5000 nucleotides in length. In some embodiments, the polynucleotide is at least 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, or 5000 nt in length. In some embodiments, the polynucleotide is no more than 3000 nt, 3500 nt, 4000 nt, 4500 nt, 5000 nt, 6000 nt, 7000 nt, 8000 nt, 9000 nt, or 10000 nt in length. In some embodiments, the length of a DNA, linear RNA, and/or circular RNA polynucleotide provided herein is about 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, 5000 nt, 6000 nt, 7000 nt, 8000 nt, 9000 nt, or 10000 nt.

In some embodiments, provided herein is a vector. In certain embodiments, the vector comprises, in the following order, a) a 5' homology region, b) a 3' group I intron fragment, c) optionally, a first spacer sequence, d) an IRES, e) an expression sequence, f) optionally, a second spacer sequence, g) a 5' group I intron fragment, and h) a 3' homology region. In some embodiments, the vector comprises a transcriptional promoter upstream of the 5' homology region. In certain embodiments, the precursor RNA comprises, in the following order, a) a polyA sequence, b) an external spacer, c) a 3' group I intron fragment, d) a duplex forming region, e) an internal spacer, f) an IRES, g) an expression sequence, h) a stop codon cassette, i) optionally, an internal spacer, j) a duplex forming region capable of forming a duplex with the duplex forming region of d, k) a 5' group I intron fragment, 1) an external spacer, and m) a polyA sequence.

In some embodiments, provided herein is a precursor RNA. In certain embodiments, the precursor RNA is a linear RNA produced by in vitro transcription of a vector provided herein. In some embodiments, the precursor RNA comprises, in the following order, a) a 5' homology region, b) a 3' group I intron fragment, c) optionally, a first spacer sequence, d) an IRES, e) an expression sequence, f) optionally, a second spacer sequence, g) a 5' group I intron fragment, and h) a 3' homology region. The precursor RNA can be unmodified, partially modified or completely modified.

In certain embodiments, provided herein is a circular RNA. In certain embodiments, the circular RNA is a circular RNA produced by a vector provided herein. In some embodiments, the circular RNA is circular RNA produced by circularization of a precursor RNA provided herein. In some embodiments, the circular RNA comprises, in the following sequence, a) a first spacer sequence, b) an IRES, c) an expression sequence, and d) a second spacer sequence. In some embodiments, the circular RNA further comprises the portion of the 3' group I intron fragment that is 3' of the 3' splice site. In some embodiments, the circular RNA further comprises the portion of the 5' group I intron fragment that is 5' of the 5' splice site. In some embodiments, the circular RNA is at least 500, 600, 700, 800, 900, 1000, 1500, 2000, 2500, 3000, 3500, 4000 or 4500 nucleotides in size. The circular RNA can be unmodified, partially modified or completely modified.

In some embodiments, the circular RNA provided herein has higher functional stability than mRNA comprising the same expression sequence. In some embodiments, the circular RNA provided herein has higher functional stability than mRNA comprising the same expression sequence, 5moU modifications, an optimized UTR, a cap, and/or a polyA tail.

In some embodiments, the circular RNA polynucleotide provided herein has a functional half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a functional half-life of 5-80, 10-70, 15-60, and/or 20-50 hours. In some embodiments, the circular RNA polynucleotide provided herein has a functional half-life greater than (e.g., at least 1.5-fold greater than, at least 2-fold greater than) that of an equivalent linear RNA polynucleotide encoding the same protein. In some embodiments, functional half-life can be assessed through the detection of functional protein synthesis.

In some embodiments, the circular RNA polynucleotide provided herein has a half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a half-life of 5-80, 10-70, 15-60, and/or 20-50 hours. In some embodiments, the circular RNA polynucleotide provided herein has a half-life greater than (e.g., at least 1.5-fold greater than, at least 2-fold greater than) that of an equivalent linear RNA polynucleotide encoding the same protein. In some embodiments, the circular RNA polynucleotide, or pharmaceutical composition thereof, has a functional half-life in a human cell greater than or equal to that of a pre-determined threshold value. In some embodiments the functional half-life is determined by a functional protein assay. For example in some embodiments, the functional half-life is determined by an in vitro luciferase assay, wherein the activity of *Gaussia* luciferase (GLuc) is measured in the media of human cells (e.g. HepG2) expressing the circular RNA polynucleotide every 1, 2, 6, 12, or 24 hours over 1, 2, 3, 4, 5, 6, 7, or 14 days. In other embodiments, the functional half-life is determined by an in vivo assay, wherein levels of a protein encoded by the expression sequence of the circular RNA polynucleotide are measured in patient serum or tissue samples every 1, 2, 6, 12, or 24 hours over 1, 2, 3, 4, 5, 6, 7, or 14 days. In some embodiments, the pre-determined threshold value is the functional half-life of a reference linear RNA polynucleotide comprising the same expression sequence as the circular RNA polynucleotide.

In some embodiments, the circular RNA provided herein may have a higher magnitude of expression than equivalent linear mRNA, e.g., a higher magnitude of expression 24 hours after administration of RNA to cells. In some embodiments, the circular RNA provided herein has a higher magnitude of expression than mRNA comprising the same expression sequence, SmoU modifications, an optimized UTR, a cap, and/or a polyA tail.

In some embodiments, the circular RNA provided herein may be less immunogenic than an equivalent mRNA when exposed to an immune system of an organism or a certain type of immune cell. In some embodiments, the circular RNA provided herein is associated with modulated production of cytokines when exposed to an immune system of an organism or a certain type of immune cell. For example, in some embodiments, the circular RNA provided herein is associated with reduced production of IFN-β1, RIG-I, IL-2, IL-6, IFNγ, and/or TNFα when exposed to an immune system of an organism or a certain type of immune cell as compared to mRNA comprising the same expression sequence. In some embodiments, the circular RNA provided herein is associated with less IFN-β1, RIG-I, IL-2, IL-6, IFNγ, and/or TNFα transcript induction when exposed to an immune system of an organism or a certain type of immune cell as compared to mRNA comprising the same expression sequence. In some embodiments, the circular RNA provided herein is less immunogenic than mRNA comprising the same expression sequence. In some embodiments, the circular RNA provided herein is less immunogenic than mRNA comprising the same expression sequence, 5moU modifications, an optimized UTR, a cap, and/or a polyA tail.

In certain embodiments, the circular RNA provided herein can be transfected into a cell as is, or can be transfected in DNA vector form and transcribed in the cell. Transcription of circular RNA from a transfected DNA vector can be via added polymerases or poylmerases encoded by nucleic acids transfected into the cell, or preferably via endogenous polymerases.

In certain embodiments, a circular RNA polynucleotide provided herein comprises modified RNA nucleotides and/or modified nucleosides. In some embodiments, the modified nucleoside is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is Ψ (pseudouridine). In another embodiment, the modified nucleoside is Um (2'-O-methyluridine). In other embodiments, the modified nucleoside is $m^1A$ (1-methyladenosine); $m^2A$ (2-methyladenosine); Am (2'-O-methyladenosine); $ms^2m^6A$ (2-methylthio-$N^6$-methyladenosine); $i^6A$ ($N^6$-isopentenyladenosine); $ms^2i6A$ (2-methylthio-$N^6$ isopentenyladenosine); $io^6A$ ($N^6$-(cis-hydroxyisopentenyl)adenosine); $ms^2io^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); miG (1-methylguanosine); $m^2G$ ($N^2$-methylguanosine); $m^7G$ (7-methylguanosine); Gm (2'-O-methylguanosine); $m^2{}_2G$ ($N^2$,$N^2$-dimethylguanosine); $m^2Gm$ ($N^2$,2'-O-dimethylguanosine); $m^2{}_2Gm$ ($N^2$,$N^2$, 2'-O-trimethylguanosine); Gr(p) (2'-O-ribosylguanosine (phosphate)); yW (wybutosine); $o_2$yW (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); preQ$_0$ (7-cyano-7-deazaguanosine); preQ$_1$ (7-aminomethyl-7-deazaguanosine); G* (archaeosine); D (dihydrouridine); m$^5$Um (5,2'-O-dimethyluridine); s$^4$U (4-thiouridine); m$^5$s$^2$U (5-methyl-2-thiouridine); s$^2$Um (2-thio-2'-O-methyluridine); acp$^3$U (3-(3-amino-3-carboxypropyl)uridine); ho$^5$U (5-hydroxyuridine); mo$^5$U (5-methoxyuridine); cmo$^5$U (uridine 5-oxyacetic acid); mcmo$^5$U (uridine 5-oxyacetic acid methyl ester); chm$^5$U (5-(carboxyhydroxymethyl)uridine)); mchm$^5$U (5-(carboxyhydroxymethyl)uridine methyl ester); mcm$^5$U (5-methoxycarbonylmethyluridine); mcm$^5$Um (5-methoxycarbonylmethyl-2'-o-methyluridine); mcm$^5$s$^2$U (5-methoxycarbonylmethyl-2-thiouridine); nm$^5$S$^2$U (5-aminomethyl-2-thiouridine); mnm$^5$U (5-methylaminomethyluridine); mnm$^5$s$^2$U (5-methylaminomethyl-2-thiouridine); mnm$^5$se$^2$U (5-methylaminomethyl-2-selenouridine); ncm$^5$U (5-carbamoylmethyluridine); ncm$^5$Um (5-carbamoylmethyl-2'-O-methyluridine); cmnm$^5$U (5-carboxymethylaminomethyluridine); cmnm$^5$Um (5-carboxymethylaminomethyl-2'-O-methyluridine); cmnm$^5$s$^2$U (5-carboxymethylaminomethyl-2-thiouridine); m$^6$ $_2$A (N$^6$, N$^6$-dimethyladenosine); Im (2'-O-methylinosine); m$^4$C (N$^4$-methylcytidine); m$^4$Cm (N$^4$,2'-O-dimethylcytidine); hm$^5$C (5-hydroxymethylcytidine); m$^3$U (3-methyluridine); cm$^5$U (5-carboxymethyluridine); m$^6$Am (N$^6$,2'-O-dimethyladenosine); m$^6$ $_2$Am (N$^6$,N$^6$,O-2'-trimethyladenosine); m$^{2,7}$G (N$^2$,7-dimethylguanosine); m$^{2,2,7}$G (N$^2$,N$^2$,7-trimethylguanosine); m$^3$Um (3,2'-O-dimethyluridine); m$^5$D (5-methyldihydrouridine); f$^5$Cm (5-formyl-2'-O-methylcytidine); m$^1$Gm (1,2'-O-dimethylguanosine); m$^1$Am (1,2'-O-dimethyladenosine); Tm $^5$U (5-taurinomethyluridine); Ttm$^5$s$^2$U (5-taurinomethyl-2-thiouridine)); imG-14 (4-demethylwyosine); imG2 (isowyosine); or ac$^6$A (N$^6$-acetyladenosine).

In some embodiments, the modified nucleoside may include a compound selected from the group of: pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-m ethoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine. In another embodiment, the modifications are independently selected from the group consisting of 5-methylcytosine, pseudouridine and 1-methylpseudouridine.

In some embodiments, the modified ribonucleosides include 5-methylcytidine, 5-methoxyuridine, 1-methyl-pseudouridine, N6-methyladenosine, and/or pseudouridine. In some embodiments, such modified nucleosides provide additional stability and resistance to immune activation.

In particular embodiments, polynucleotides may be codon-optimized. A codon optimized sequence may be one in which codons in a polynucleotide encoding a polypeptide have been substituted in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid. In some embodiments, a codon optimized polynucleotide may minimize ribozyme collisions and/or limit structural interference between the expression sequence and the IRES.

In certain embodiments circular RNA provided herein is produced inside a cell. In some embodiments, precursor RNA is transcribed using a DNA template (e.g., in some embodiments, using a vector provided herein) in the cytoplasm by a bacteriophage RNA polymerase, or in the nucleus by host RNA polymerase II and then circularized.

In certain embodiments, the circular RNA provided herein is injected into an animal (e.g., a human), such that a polypeptide encoded by the circular RNA molecule is expressed inside the animal.

3. Payload

In some embodiments, the expression sequence encodes a therapeutic protein. In some embodiments, the therapeutic protein is selected from the proteins listed in the following table.

| Payload | Sequence | Target cell/ organ | Preferred delivery formulation |
|---|---|---|---|
| CD 19 CAR | Any of sequences 309-314 | T cells | 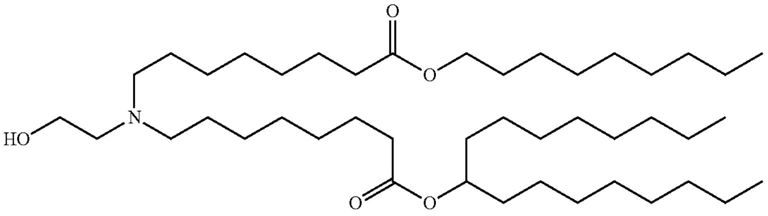 [SMILES: CCCCCCCCCOC(=O)CCCCCCCN(CCO)CCCCCCCC(=O)OC(CCCCCCCC)CCCCCCCC]<br>(50 mol %)<br>DSPC (10 mol %)<br>Beta-sitosterol (28.5% mol %)<br>Cholesterol (10 mol %)<br>PEG DMG (1.5 mol %) |
| BCMA CAR | MALPVTALLLPLALLL<br>HAARPDIVLTQSPASLA<br>VSLGERATINCRASESV<br>SVIGAHLIHWYQQKPG<br>QPPKLLIYLASNLETGV<br>PARFSGSGSGTDFTLTIS<br>SLQAEDAAIYYCLQSRI<br>FPRTFGQGTKLEIKGST<br>SGSGKPGSGEGSTKGQ<br>VQLVQSGSELKKPGAS<br>VKVSCKASGYTFTDYSI<br>NWVRQAPGQGLEWMG<br>WINTETREPAYAYDFR<br>GRFVFSLDTSVSTAYLQ<br>ISSLKAEDTAVYYCAR<br>DYSYAMDYWGQGTLV<br>TVSSAAATTTPAPRPPT<br>PAPTIASQPLSLRPEACR<br>PAAGGAVHTRGLDFAC<br>DIYIWAPLAGTCGVLLL<br>SLVITLYCKRGRKKLLY<br>IFKQPFMRPVQTTQEED<br>GCSCRFPEEEEGGCELR<br>VKFSRSADAPAYQQGQ<br>NQLYNELNLGRREEYD<br>VLDKRRGRDPEMGGKP<br>RRKNPQEGLYNELQKD<br>KMAEAYSEIGMKGERR<br>RGKGHDGLYQGLSTAT<br>KDTYDALHMQALPPR | T cells | 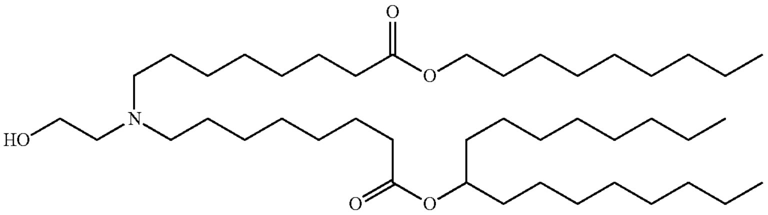 [SMILES: CCCCCCCCCOC(=O)CCCCCCCN(CCO)CCCCCCCC(=O)OC(CCCCCCCC)CCCCCCCC]<br>(50 mol %)<br>DSPC (10 mol %)<br>Beta-sitosterol (28.5% mol %)<br>Cholesterol (10 mol %)<br>PEG DMG (1.5 mol %) |
| MAGE-A4 TCR | TCR alpha chain:<br>KNQVEQSPQSLIILEGK<br>NCTLQCNYTVSPFSNLR<br>WYKQDTGRGPVSLTIM<br>TFSENTKSNGRYTATLD<br>ADTKQSSLHITASQLSD<br>SASYICVVNHSGGSYIP<br>TFGRGTSLIVHPYIQKP<br>DPAVYQLRDSKSSDKS<br>VCLFTDFDSQTNVSQSK<br>DSDVYITDKTVLDMRS<br>MDFKSNSAVAWSNKS<br>DFACANAFNNSIIPEDT<br>FFPSPESS<br>TCR beta chain:<br>DVKVTQSSRYLVKRTG<br>EKVFLECVQDMDHEN<br>MFWYRQDPGLGLRLIY<br>FSYDVKMKEKGDIPEG<br>YSVSREKKERFSLILES<br>ASTNQTSMYLCASSFL<br>MTSGDPYEQYFGPGTR<br>LTVTEDLKNVFPPEVA<br>VFEPSEAEISHTQKATL<br>VCLATGFYPDHVELSW<br>WVNGKEVHSGVSTDPQ<br>PLKEQPALNDSRYCLSS<br>RLRVSATFWQNPRNHF | T cells | 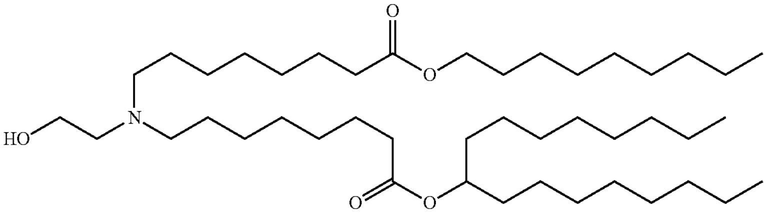 [SMILES: CCCCCCCCCOC(=O)CCCCCCCN(CCO)CCCCCCCC(=O)OC(CCCCCCCC)CCCCCCCC]<br>(50 mol %)<br>DSPC (10 mol %)<br>Beta-sitosterol (28.5% mol %)<br>Cholesterol (10 mol %)<br>PEG DMG (1.5 mol %) |

-continued

| Payload | Sequence | Target cell/ organ | Preferred delivery formulation |
|---|---|---|---|
| | RCQVQFYGLSENDEWT<br>QDRAKPVTQIVSAEAW<br>GRAD | | |
| NY-ESO TCR | TCRalpha extracellular sequence<br>MQEVTQIPAALSVPEGE<br>NLVLNCSFTDSAIYNLQ<br>WFRQDPGKGLTSLLLIQ<br>SSQREQTSGRLNASLDK<br>SSGRSTLYIAASQPGDS<br>ATYLCAVRPTSGGSYIP<br>TFGRGTSLIVHPY<br>TCRbeta extracellular sequence<br>MGVTQTPKFQVLKTGQ<br>SMTLQCAQDMNHEYM<br>SWYRQDPGMGLRLIHY<br>SVGAGITDQGEVPNGY<br>NVSRSTTEDFPLRLLSA<br>APSQTSVYFCASSYVG<br>NTGELFFGEGSRLTVL | T cells | 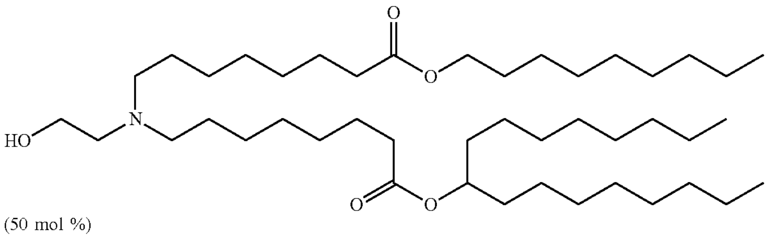<br>(50 mol %)<br>DSPC (10 mol %)<br>Beta-sitosterol (28.5% mol %)<br>Cholesterol (10 mol %)<br>PEG DMG (1.5 mol %) |
| EPO | APPRLICDSRVLERYLL<br>EAKEAENITTGCAEHCS<br>LNENITVPDTKVNFYA<br>WKRMEVGQQAVEVW<br>QGLALLSEAVLRGQAL<br>LVNSSQPWEPLQLHVD<br>KAVSGLRSLTTLLRALG<br>AQKEAISPPDAASAAPL<br>RTITADTFRKLFRVYSN<br>FLRGKLKLYTGEACRT<br>GDR | Kidney or bone marrow | |
| PAH | MSTAVLENPGLGRKLS<br>DFGQETSYIEDNCNQN<br>GAISLIFSLKEEVGALA<br>KVLRLFEENDVNLTHIE<br>SRPSRLKKDEYEFFTHL<br>DKRSLPALTNIIKILRHD<br>IGATVHELSRDKKKDT<br>VPWFPRTIQELDRFANQ<br>ILSYGAELDADHPGFKD<br>PVYRARRKQFADIAYN<br>YRHGQPIPRVEYMEEE<br>KKTWGTVFKTLKSLYK<br>THACYEYNHIFPLLEKY<br>CGFHEDNIPQLEDVSQF<br>LQTCTGFRLRPVAGLLS<br>SRDFLGGLAFRVFHCT<br>QYIRHGSKPMYTPEPDI<br>CHELLGHVPLFSDRSFA<br>QFSQEIGLASLGAPDEY<br>IEKLATIYWFTVEFGLC<br>KQGDSIKAYGAGLLSSF<br>GELQYCLSEKPKLLPLE<br>LEKTAIQNYTVTEFQPL<br>YYVAESFNDAKEKVRN<br>FAATIPRPFSVRYDPYT<br>QRIEVLDNTQQLKILAD<br>SINSEIGILCSALQKIK | Hepatic cells | 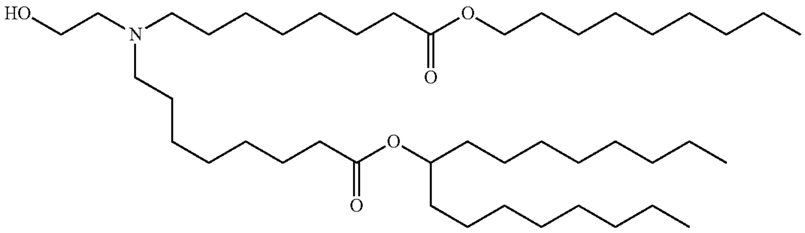 [SMILES: CCCCCCCCCOC(=O)CCCCCCCN(CCO)CCCCCCCC(=O)OC(CCCCCCCC)CCCCCCCC]<br>(50 mol %)<br>DSPC (10 mol %)<br>Cholesterol (38.5% mol %)<br>PEG-DMG (1.5%)<br>OR<br>MC3 (50 mol %)<br>DSPC (10 mol %)<br>Cholesterol (38.5% mol %)<br>PEG-DMG (1.5%) |
| CPS1 | LSVKAQTAHIVLEDGT<br>KMKGYSFGHPSSVAGE<br>VVFNTGLGGYPEAITDP<br>AYKGQILTMANPIIGNG<br>GAPDTTALDELGLSKY<br>LESNGIKVSGLLVLDYS<br>KDYNHWLATKSLGQW<br>LQEEKVPAIYGVDTRM<br>LTKIIRDKGTMLGKIEF<br>EGQPVDFVDPNKQNLI<br>AEVSTKDVKVYGKGNP<br>TKVVAVDCGIKNNVIR<br>LLVKRGAEVHLVPWN | Hepatic cells | 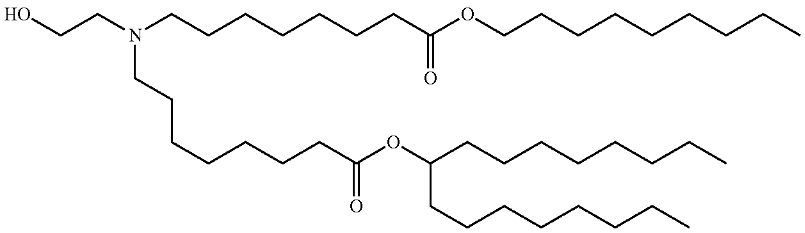 [SMILES: CCCCCCCCCOC(=O)CCCCCCCN(CCO)CCCCCCCC(=O)OC(CCCCCCCC)CCCCCCCC]<br>(50 mol %)<br>DSPC (10 mol %) |

-continued

| Payload | Sequence | Target cell/ organ | Preferred delivery formulation |
|---|---|---|---|
| | HDFTKMEYDGILIAGGP<br>GNPALAEPLIQNVRKIL<br>ESDRKEPLFGISTGNLIT<br>GLAAGAKTYKMSMAN<br>RGQNQPVLNITNKQAFI<br>TAQNHGYALDNTLPAG<br>WKPLFVNVNDQTNEGI<br>MHESKPFFAVQFHPEV<br>TPGPIDTEYLFDSFFSLI<br>KKGKATTITSVLPKPAL<br>VASRVEVSKVLILGSGG<br>LSIGQAGEFDYSGSQAV<br>KAMKEENVKTVLMNP<br>NIASVQTNEVGLKQAD<br>TVYFLPITPQFVTEVIKA<br>EQPDGLILGMGGQTAL<br>NCGVELFKRGVLKEYG<br>VKVLGTSVESIMATED<br>RQLFSDKLNEINEKIAPS<br>FAVESIEDALKAADTIG<br>YPVMIRSAYALGGLGS<br>GICPNRETLMDLSTKAF<br>AMTNQILVEKSVTGWK<br>EIEYEVVRDADDNCVT<br>VCNMENVDAMGVHTG<br>DSVVVAPAQTLSNAEF<br>QMLRRTSINVVRHLGIV<br>GECNIQFALHPTSMEYC<br>IIEVNARLSRSSALASK<br>ATGYPLAFIAAKIALGIP<br>LPEIKNVVSGKTSACFE<br>PSLDYMVTKIPRWDLD<br>RFHGTSSRIGSSMKSVG<br>EVMAIGRTFEESFQKAL<br>RMCHPSIEGFTPRLPMN<br>KEWPSNLDLRKELSEPS<br>STRIYAIAKAIDDNMSL<br>DEIEKLTYIDKWFLYK<br>MRDILNMEKTLKGLNS<br>ESMTEETLKRAKEIGFS<br>DKQISKCLGLTEAQTRE<br>LRLKKNIHPWVKQIDTL<br>AAEYPSVTNYLYVTYN<br>GQEHDVNFDDHGMMV<br>LGCGPYHIGSSVEFDW<br>CAVSSIRTLRQLGKKTV<br>VVNCNPETVSTDFDEC<br>DKLYFEELSLERILDIYH<br>QEACGGCIISVGGQIPN<br>NLAVPLYKNGVKIMGT<br>SPLQIDRAEDRSIFSAVL<br>DELKVAQAPWKAVNT<br>LNEALEFAKSVDYPCLL<br>RPSYVLSGSAMNVVFS<br>EDEMKKFLEEATRVSQ<br>EHPVVLTKFVEGAREV<br>EMDAVGKDGRVISHAI<br>SEHVEDAGVHSGDATL<br>MLPTQTISQGAIEKVKD<br>ATRKIAKAFAISGPFNV<br>QFLVKGNDVLVIECNL<br>RASRSFPFVSKTLGVDF<br>IDVATKVMIGENVDEK<br>HLPTLDHPIIPADYVAIK<br>APMFSWPRLRDADPILR<br>CEMASTGEVACFGEGI<br>HTAFLKAMLSTGFKIPQ<br>KGILIGIQQSFRPRFLGV<br>AEQLHNEGFKLFATEA<br>TSDWLNANNVPATPVA | | Cholesterol (38.5% mol %)<br>PEG-DMG (1.5%)<br>OR<br>MC3 (50 mol %)<br>DSPC (10 mol %)<br>Cholesterol (38.5% mol %)<br>PEG-DMG (1.5%) |

-continued

| Payload | Sequence | Target cell/ organ | Preferred delivery formulation |
|---|---|---|---|
| | WPSQEGQNPSLSSIRKLI RDGSIDLVINLPNNNTK FVHDNYVIRRTAVDSGI PLLTNFQVTKLFAEAV QKSRKVDSKSLFHYRQ YSAGKAA | | |
| Cas9 | MKRNYILGLDIGITSVG YGIIDYETRDVIDAGVR LFKEANVENNEGRRSK RGARRLKRRRRHRIQR VKKLLFDYNLLTDHSE LSGINPYEARVKGLSQK LSEEEFSAALLHLAKRR GVHNVNEVEEDTGNEL STKEQISRNSKALEEKY VAELQLERLKKDGEVR GSINRFKTSDYVKEAK QLLKVQKAYHQLDQSF IDTYIDLLETRRTYYEG PGEGSPFGWKDIKEWY EMLMGHCTYFPEELRS VKYAYNADLYNALND LNNLVITRDENEKLEYY EKFQIIENVFKQKKKPT LKQIAKEILVNEEDIKG YRVTSTGKPEFTNLKV YHDIKDITARKEIIENAE LLDQIAKILTIYQSSEDI QEELTNLNSELTQEEIE QISNLKGYTGTHNLSLK AINLILDELWHTNDNQI AIFNRLKLVPKKVDLSQ QKEIPTTLVDDFILSPVV KRSFIQSIKVINAIIKKY GLPNDIIIELAREKNSKD AQKMINEMQKRNRQT NERIEEIIRTTGKENAKY LIEKIKLHDMQEGKCLY SLEAIPLEDLLNNPFNY EVDHIIPRSVSFDNSFNN KVLVKQEENSKKGNRT PFQYLSSSDSKISYETFK KHILNLAKGKGRISKTK KEYLLEERDINRFSVQK DFINRNLVDTRYATRG LMNLLRSYFRVNNLDV KVKSINGGFTSFLRRK WKFKKERNKGYKHHA EDALIIANADFIFKEWK KLDKAKKVMENQMFE EKQAESMPEIETEQEYK EIFITPHQIKHIKDFKDY KYSHRVDKKPNRELIN DTLYSTRKDDKGNTLI VNNLNGLYDKDNDKL KKLINKSPEKLLMYHH DPQTYQKLKLIMEQYG DEKNPLYKYYEETGNY LTKYSKKDNGPVIKKIK YYGNKLNAHLDITDDY PNSRNKVVKLSLKPYR FDVYLDNGVYKFVTVK NLDVIKKENYYEVNSK CYEEAKKLKKISNQAEF IASFYNNDLIKINGELY RVIGVNNDLLNRIEVN MIDITYREYLENMNDK RPPRIIKTIASKTQSIKK YSTDILGNLYEVKSKK HPQIIKKG | Immune cells | 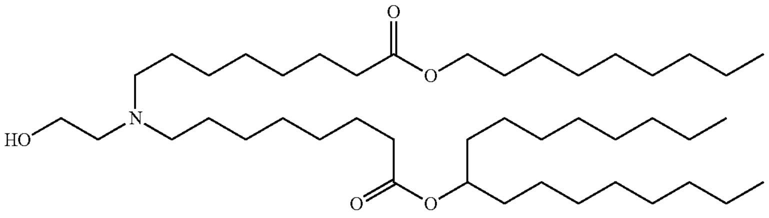 [SMILES: CCCCCCCCCOC(=O)CCCCCCCN(CCO)CCCCCCCC(=O)OC(CCCCCCCC)CCCCCCCC] (50 mol %) DSPC (10 mol %) Beta-sitosterol (28.5% mol %) Cholesterol (10 mol %) PEG DMG (1.5 mol %) |

-continued

| Payload | Sequence | Target cell/ organ | Preferred delivery formulation |
|---|---|---|---|
| ADAM TS13 | AAGGILHLELLVAVGP DVFQAHQEDTERYVLT NLNIGAELLRDPSLGAQ FRVHLVKMVILTEPEG APNITANLTSSLLSVCG WSQTINPEDDTDPGHA DLVLYITRFDLELPDGN RQVRGVTQLGGACSPT WSCLITEDTGFDLGVTI AHEIGHSFGLEHDGAPG SGCGPSGHVMASDGAA PRAGLAWSPCSRRQLL SLLSAGRARCVWDPPR PQPGSAGHPPDAQPGL YYSANEQCRVAFGPKA VACTFAREHLDMCQAL SCHTDPLDQSSCSRLLV PLLDGTECGVEKWCSK GRCRSLVELTPIAAVHG RWSSWGPRSPCSRSCG GGVVTRRRQCNNPRPA FGGRACVGADLQAEM CNTQACEKTQLEFMSQ QCARTDGQPLRSSPGG ASFYHWGAAVPHSQG DALCRHMCRAIGESFIM KRGDSFLDGTRCMPSG PREDGTLSLCVSGSCRT FGCDGRMDSQQVWDR CQVCGGDNSTCSPRKG SFTAGRAREYVTFLTVT PNLTSVYIANHRPLFTH LAVRIGGRYVVAGKMS ISPNTTYPSLLEDGRVE YRVALTEDRLPRLEEIRI WGPLQEDADIQVYRRY GEEYGNLTRPDITFTYF QPKPRQAWVWAAVRG PCSVSCGAGLRWVNYS CLDQARKELVETVQCQ GSQQPPAWPEACVLEP CPPYWAVGDFGPCSAS CGGGLRERPVRCVEAQ GSLLKTLPPARCRAGA QQPAVALETCNPQPCP ARWEVSEPSSCTSAGG AGLALENETCVPGADG LEAPVTEGPGSVDEKLP APEPCVGMSCPPGWGH LDATSAGEKAPSPWGSI RTGAQAAHVWTPAAG SCSVSCGRGLMELRFLC MDSALRVPVQEELCGL ASKPGSRREVCQAVPC PARWQYKLAACSVSCG RGVVRRILYCARAHGE DDGEEILLDTQCQGLPR PEPQEACSLEPCPPRWK VMSLGPCSASCGLGTA RRSVACVQLDQGQDVE VDEAACAALVRPEASV PCLIADCTYRWHVGTW MECSVSCGDGIQRRRD TCLGPQAQAPVPADFC QHLPKPVTVRGCWAGP CVGQGTPSLVPHEEAA APGRTTATPAGASLEW SQARGLLFSPAPQPRRL LPGPQENSVQSSACGR QHLEPTGTIDMRGPGQ ADCAVAIGRPLGEVVT LRVLESSLNCSAGDML LLWGRLTWRKMCRKL LDMTFSSKTNTLVVRQ RCGRPGGGVLLRYGSQ LAPETFYRECDMQLFG | Hepatic cells | 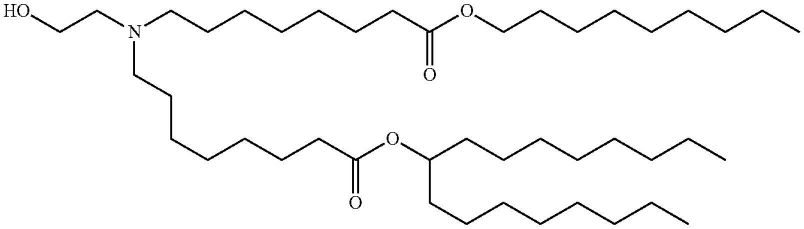 [SMILES: CCCCCCCCCOC(=O)CCCCCCCN(CCO)CCCCCCCC(=O)OC(CCCCCCCC)CCCCCCCC] (50 mol %) DSPC (10 mol %) Cholesterol (38.5% mol %) PEG-DMG (1.5%) OR MC3 (50 mol %) DSPC (10 mol %) Cholesterol (38.5% mol %) PEG-DMG (1.5%) |

-continued

| Payload | Sequence | Target cell/ organ | Preferred delivery formulation |
|---|---|---|---|
| | PWGEIVSPSLSPATSNA GGCRLFINVAPHARIAI HALATNMGAGTEGAN ASYILIRDTHSLRTTAFH GQQVLYWESESSQAEM EFSEGFLKAQASLRGQ YWTLQSWVPEMQDPQ SWKGKEGT | | |
| FOXP3 | MPNPRPGKPSAPSLALG PSPGASPSWRAAPKAS DLLGARGPGGTFQGRD LRGGAHASSSSLNPMPP SQLQLPTLPLVMVAPSG ARLGPLPHLQALLQDR PHFMHQLSTVDAHART PVLQVHPLESPAMISLT PPTTATGVFSLKARPGL PPGINVASLEWVSREPA LLCTFPNPSAPRKDSTL SAVPQSSYPLLANGVC KWPGCEKVFEEPEDFL KHCQADHLLDEKGRA QCLLQREMVQSLEQQL VLEKEKLSAMQAHLAG KMALTKASSVASSDKG SCCIVAAGSQGPVVPA WSGPREAPDSLFAVRR HLWGSHGNSTFPEFLH NMDYFKFHNMRPPFTY ATLIRWAILEAPEKQRT LNEIYHWFTRMFAFFR NHPATWKNAIRHNLSL HKCFVRVESEKGAVWT VDELEFRKKRSQRPSRC SNPTPGP | Immune cells | 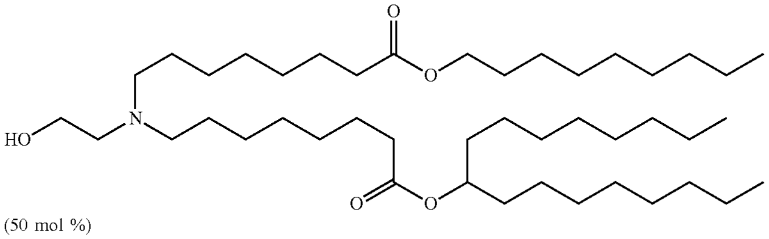<br>(50 mol %)<br>DSPC (10 mol %)<br>Beta-sitosterol (28.5% mol %)<br>Cholesterol (10 mol %)<br>PEG DMG (1.5 mol %) |
| IL-10 | SPGQGTQSENSCTHFPG NLPNMLRDLRDAFSRV KTFFQMKDQLDNLLLK ESLLEDFKGYLGCQALS EMIQFYLEEVMPQAEN QDPDIKAHVNSLGENL KTLRLRLRRCHRFLPCE NKSKAVEQVKNAFNKL QEKGIYKAMSEFDIFIN YIEAYMTMKIRN | Immune cells | 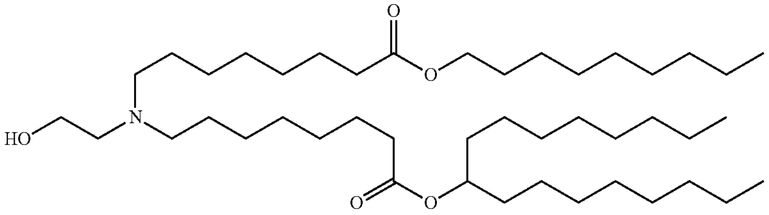 [SMILES: CCCCCCCCCOC(=O)CCCCCCCN(CCO)CCCCCCCC(=O)OC(CCCCCCCC)CCCCCCCC]<br>(50 mol %)<br>DSPC (10 mol %)<br>Beta-sitosterol (28.5% mol %)<br>Cholesterol (10 mol %)<br>PEG DMG(1.5mol%) |
| IL-2 | APTSSSTKKTQLQLEHL LLDLQMILNGINNYKNP KLTRMLTFKFYMPKKA TELKHLQCLEEELKPLE EVLNLAQSKNFHLRPR DLISNINVIVLELKGSET TFMCEYADETATIVEFL NRWITFCQSIISTLT | Immune cells | 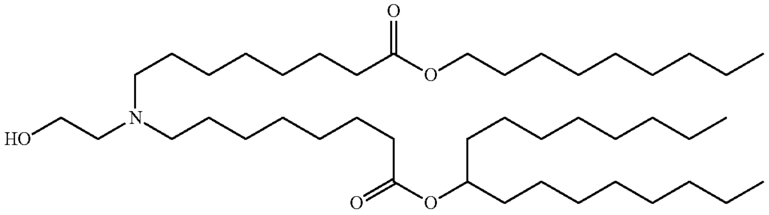 [SMILES: CCCCCCCCCOC(=O)CCCCCCCN(CCO)CCCCCCCC(=O)OC(CCCCCCCC)CCCCCCCC]<br>(50 mol %)<br>DSPC (10 mol %)<br>Beta-sitosterol (28.5% mol %)<br>Cholesterol (10 mol %)<br>PEG DMG (1.5 mol %) |

In some embodiments, the expression sequence encodes a therapeutic protein. In some embodiments, the expression sequence encodes a cytokine, e.g., IL-12p70, IL-15, IL-2, IL-18, IL-21, IFN-α, IFN-β, IL-10, TGF-beta, IL-4, or IL-35, or a functional fragment thereof. In some embodiments, the expression sequence encodes an immune checkpoint inhibitor. In some embodiments, the expression sequence encodes an agonist (e.g., a TNFR family member such as CD137L, OX40L, ICOSL, LIGHT, or CD70). In some embodiments, the expression sequence encodes a chimeric antigen receptor. In some embodiments, the expression sequence encodes an inhibitory receptor agonist (e.g., PDL1, PDL2, Galectin-9, VISTA, B7H4, or MHCII) or inhibitory receptor (e.g., PD1, CTLA4, TIGIT, LAG3, or TIM3). In some embodiments, the expression sequence encodes an inhibitory receptor antagonist. In some embodiments, the expression sequence encodes one or more TCR chains (alpha and beta chains or gamma and delta chains). In some embodiments, the expression sequence encodes a secreted T cell or immune cell engager (e.g., a bispecific antibody such as BiTE, targeting, e.g., CD3, CD137, or CD28 and a tumor-expressed protein e.g., CD19, CD20, or BCMA etc.). In some embodiments, the expression sequence encodes a transcription factor (e.g., FOXP3, HELIOS, TOX1, or TOX2). In some embodiments, the expression sequence encodes an immunosuppressive enzyme (e.g., IDO or CD39/CD73). In some embodiments, the expression sequence encodes a GvHD (e.g., anti-HLA-A2 CAR-Tregs).

In some embodiments, a polynucleotide encodes a protein that is made up of subunits that are encoded by more than one gene. For example, the protein may be a heterodimer, wherein each chain or subunit of the protein is encoded by a separate gene. It is possible that more than one circRNA molecule is delivered in the transfer vehicle and each circRNA encodes a separate subunit of the protein. Alternatively, a single circRNA may be engineered to encode more than one subunit. In certain embodiments, separate circRNA molecules encoding the individual subunits may be administered in separate transfer vehicles.

3.1 Cytokines

Descriptions and/or amino acid sequences of IL-2, IL-7, IL-10, IL-12, IL-15, IL-18, IL-27beta, IFNgamma, and/or TGFbeta1 are provided herein and at the www.uniprot.org database at accession numbers: P60568 (IL-2), P29459 (IL-12A), P29460 (IL-12B), P13232 (IL-7), P22301 (IL-10), P40933 (IL-15), Q14116 (IL-18), Q14213 (IL-27beta), P01579 (IFNgamma), and/or P01137 (TGFbeta1).

3.2 PD-1 and PD-L1 Antagonists

In some embodiments, a PD-1 inhibitor is pembrolizumab, pidilizumab, or nivolumab. In some embodiments, Nivolumab is described in WO2006/121168. In some embodiments, Pembrolizumab is described in WO2009/114335. In some embodiments, Pidilizumab is described in WO2009/101611. Additional anti-PD1 antibodies are described in U.S. Pat. No. 8,609,089, US 2010028330, US 20120114649, WO2010/027827 and WO2011/066342.

In some embodiments, a PD-L1 inhibitor is atezolizumab, avelumab, durvalumab, BMS-936559, or CK-301.

Descriptions and/or amino acid sequences of heavy and light chains of PD-1, and/or PD-L1 antibodies are provided herein and at the www.drugbank.ca database at accession numbers: DB09037 (Pembrolizumab), DB09035 (Nivolumab), DB15383 (Pidilizumab), DB11595 (Atezolizumab), DB11945 (Avelumab), and DB11714 (Durvalumab).

3.3 T Cell Receptors

TCRs are described using the International Immunogenetics (IMGT) TCR nomenclature, and links to the IMGT public database of TCR sequences. Native alpha-beta heterodimeric TCRs have an alpha chain and a beta chain. Broadly, each chain may comprise variable, joining and constant regions, and the beta chain also usually contains a short diversity region between the variable and joining regions, but this diversity region is often considered as part of the joining region. Each variable region may comprise three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number. Thus, "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. In the same way, "TRBV5-1" defines a TCR VP region having unique framework and CDR1 and CDR2 sequences, but with only a partly defined CDR3 sequence.

The joining regions of the TCR are similarly defined by the unique IMGT TRAJ and TRBJ nomenclature, and the constant regions by the IMGT TRAC and TRBC nomenclature.

The beta chain diversity region is referred to in IMGT nomenclature by the abbreviation TRBD, and, as mentioned, the concatenated TRBD/TRBJ regions are often considered together as the joining region.

The unique sequences defined by the IMGT nomenclature are widely known and accessible to those working in the TCR field. For example, they can be found in the IMGT public database. The "T cell Receptor Factsbook", (2001) LeFranc and LeFranc, Academic Press, ISBN 0-12-441352-8 also discloses sequences defined by the IMGT nomenclature, but because of its publication date and consequent time-lag, the information therein sometimes needs to be confirmed by reference to the IMGT database.

Native TCRs exist in heterodimeric αβ or γδ forms. However, recombinant TCRs consisting of αα or β βhomodimers have previously been shown to bind to peptide MHC molecules. Therefore, the TCR of the invention may be a heterodimeric αβ TCR or may be an aa or RR homodimeric TCR.

For use in adoptive therapy, an αβ heterodimeric TCR may, for example, be transfected as full length chains having both cytoplasmic and transmembrane domains. In certain embodiments TCRs of the invention may have an introduced disulfide bond between residues of the respective constant domains, as described, for example, in WO 2006/000830.

TCRs of the invention, particularly alpha-beta heterodimeric TCRs, may comprise an alpha chain TRAC constant domain sequence and/or a beta chain TRBC1 or TRBC2 constant domain sequence. The alpha and beta chain constant domain sequences may be modified by truncation or substitution to delete the native disulfide bond between Cys4 of exon 2 of TRAC and Cys2 of exon 2 of TRBC1 or TRBC2. The alpha and/or beta chain constant domain sequence(s) may also be modified by substitution of cysteine residues for Thr 48 of TRAC and Ser 57 of TRBC1 or TRBC2, the said cysteines forming a disulfide bond between the alpha and beta constant domains of the TCR.

Binding affinity (inversely proportional to the equilibrium constant $K_D$) and binding half-life (expressed as T½) can be determined by any appropriate method. It will be appreciated that doubling the affinity of a TCR results in halving the $K_D$. T½ is calculated as In 2 divided by the off-rate (koff). So doubling of T½ results in a halving in koff. $K_D$ and koff values for TCRs are usually measured for soluble forms of the TCR, i.e. those forms which are truncated to remove cytoplasmic and transmembrane domain residues. Therefore, it is to be understood that a given TCR has an improved binding affinity for, and/or a binding half-life for the parental TCR if a soluble form of that TCR has the said characteristics. Preferably the binding affinity or binding half-life of a given TCR is measured several times, for example 3 or more times, using the same assay protocol, and an average of the results is taken.

Since the TCRs of the invention have utility in adoptive therapy, the invention includes a non-naturally occurring and/or purified and/or engineered cell, especially a T-cell, presenting a TCR of the invention. There are a number of methods suitable for the transfection of T cells with nucleic acid (such as DNA, cDNA or RNA) encoding the TCRs of the invention (see for example Robbins et al., (2008) J Immunol. 180: 6116-6131). T cells expressing the TCRs of the invention will be suitable for use in adoptive therapy-based treatment of cancers such as those of the pancreas and liver. As will be known to those skilled in the art, there are a number of suitable methods by which adoptive therapy can be carried out (see for example Rosenberg et al., (2008) Nat Rev Cancer 8(4): 299-308).

As is well-known in the art, TCRs of the invention may be subject to post-translational modifications when expressed by transfected cells. Glycosylation is one such modification, which may comprise the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Glycosylation of transfected TCRs may be controlled by mutations of the transfected gene (Kuball J et al. (2009), J Exp Med 206(2):463-475). Such mutations are also encompassed in this invention.

A TCR may be specific for an antigen in the group MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2 (HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RARa fusion protein, PTPRK, K-ras, N-ras, Triosephosphate isomeras, GnTV, Herv-K-mel, Lage-1, Mage-C2, NA-88, Lage-2, SP17, and TRP2-Int2, (MART-I), gp100 (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, pi85erbB2, pi80erbB-3, c-met, nm-23H1, PSA, TAG-72-4, CA 19-9, CA 72-4, CAM 17.1, NuMa, K-ras, .beta.-Catenin, CDK4, Mum-1, p16, TAGE, PSMA, PSCA, CT7, telomerase, 43-9F, 5T4, 791Tgp72, α-fetoprotein (AFP), 13HCG, BCA225, BTAA, CA 125, CA 15-3 (CA 27.29\BCAA), CA 195, CA 242, CA-50, CAM43, CD68KP1, CO-029, FGF-5, G250, Ga733 (EpCAM), HTgp-175, M344, MA-50, MG7-Ag, MOV18, NB\170K, NY-CO-1, RCAS i, SDCCAGi6, TA-90 (Mac-2 binding protein\cyclophilin C-associated protein), TAAL6, TAG72, TLP, and TPS.

3.4 Transcription Factors

Regulatory T cells (Treg) are important in maintaining homeostasis, controlling the magnitude and duration of the inflammatory response, and in preventing autoimmune and allergic responses.

In general, Tregs are thought to be mainly involved in suppressing immune responses, functioning in part as a "self-check" for the immune system to prevent excessive reactions. In particular, Tregs are involved in maintaining tolerance to self-antigens, harmless agents such as pollen or food, and abrogating autoimmune disease.

Tregs are found throughout the body including, without limitation, the gut, skin, lung, and liver. Additionally, Treg cells may also be found in certain compartments of the body that are not directly exposed to the external environment such as the spleen, lymph nodes, and even adipose tissue. Each of these Treg cell populations is known or suspected to have one or more unique features and additional information may be found in Lehtimaki and Lahesmaa, Regulatory T cells control immune responses through their non-redundant tissue specific features, 2013, FRONTIERS IN IMMUNOL., 4(294): 1-10, the disclosure of which is hereby incorporated in its entirety.

Typically, Tregs are known to require TGF-β and IL-2 for proper activation and development. Tregs, expressing abundant amounts of the IL-2 receptor (IL-2R), are reliant on IL-2 produced by activated T cells. Tregs are known to produce both IL-10 and TGF-β, both potent immunosuppressive cytokines. Additionally, Tregs are known to inhibit the ability of antigen presenting cells (APCs) to stimulate T cells. One proposed mechanism for APC inhibition is via CTLA-4, which is expressed by Foxp3+ Treg. It is thought that CTLA-4 may bind to B7 molecules on APCs and either block these molecules or remove them by causing internalization resulting in reduced availability of B7 and an inability to provide adequate co-stimulation for immune responses. Additional discussion regarding the origin, differentiation and function of Treg may be found in Dhamne et al., Peripheral and thymic Foxp3+ regulatory T cells in search of origin, distinction, and function, 2013, Frontiers in Immunol., 4 (253): 1-11, the disclosure of which is hereby incorporated in its entirety.

Descriptions and/or amino acid sequences of FOXP3, STAT5B, and/or HELIOS are provided herein and at the www.uniprot.org database at accession numbers: Q9BZS1 (FOXP3), P51692 (STAT5b), and/or Q9UKS7 (HELIOS).

Foxp3

In some embodiments, a transcription factor is the Forkhead box P3 transcription factor (Foxp3). Foxp3 has been shown to be a key regulator in the differentiation and activity of Treg. In fact, loss-of-function mutations in the Foxp3 gene have been shown to lead to the lethal IPEX syndrome (immune dysregulation, polyendocrinopathy, enteropathy, X-linked). Patients with IPEX suffer from severe autoimmune responses, persistent eczema, and colitis. Regulatory T (Treg) cells expressing Foxp3 play a key role in limiting inflammatory responses in the intestine (Josefowicz, S. Z. et al. Nature, 2012, 482, 395-U1510).

STAT

Members of the signal transducer and activator of transcription (STAT) protein family are intracellular transcription factors that mediate many aspects of cellular immunity, proliferation, apoptosis and differentiation. They are primarily activated by membrane receptor-associated Janus kinases (JAK). Dysregulation of this pathway is frequently observed in primary tumors and leads to increased angiogenesis, enhanced survival of tumors and immunosuppression. Gene knockout studies have provided evidence that STAT proteins are involved in the development and function of the immune system and play a role in maintaining immune tolerance and tumor surveillance.

There are seven mammalian STAT family members that have been identified: STAT1, STAT2, STAT3, STAT4, STAT5 (including STAT5A and STAT5B), and STATE.

Extracellular binding of cytokines or growth factors induce activation of receptor-associated Janus kinases, which phosphorylate a specific tyrosine residue within the STAT protein promoting dimerization via their SH2 domains. The phosphorylated dimer is then actively transported to the nucleus via an importin α/β ternary complex. Originally, STAT proteins were described as latent cytoplasmic transcription factors as phosphorylation was thought to be required for nuclear retention. However, unphosphorylated STAT proteins also shuttle between the cytosol and nucleus, and play a role in gene expression. Once STAT reaches the nucleus, it binds to a consensus DNA-recognition motif called gamma-activated sites (GAS) in the promoter region of cytokine-inducible genes and activates transcription. The STAT protein can be dephosphorylated by nuclear phosphatases, which leads to inactivation of STAT and subsequent transport out of the nucleus by a exportin-RanGTP complex.

In some embodiments, a STAT protein of the present disclosure may be a STAT protein that comprises a modification that modulates its expression level or activity. In some embodiments such modifications include, among other things, mutations that effect STAT dimerization, STAT protein binding to signaling partners, STAT protein localization or STAT protein degradation. In some embodiments, a STAT protein of the present disclosure is constitutively active. In some embodiments, a STAT protein of the present disclosure is constitutively active due to constitutive dimerization. In some embodiments, a STAT protein of the present disclosure is constitutively active due to constitutive phosphorylation as described in Onishi, M. et al., Mol. Cell. Biol. July 1998 vol. 18 no. 7 3871-3879 the entirety of which is herein incorporated by reference.

3.5 Chimeric Antigen Receptors

Chimeric antigen receptors (CARs or CAR-Ts) are genetically-engineered receptors. These engineered receptors may be inserted into and expressed by immune cells, including T cells via circular RNA as described herein. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell. In some embodiments, the CAR encoded by the polynucleotide comprises (i) an antigen-binding molecule that specifically binds to a target antigen, (ii) a hinge domain, a transmembrane domain, and an intracellular domain, and (iii) an activating domain.

In some embodiments, an orientation of the CARs in accordance with the disclosure comprises an antigen binding domain (such as an scFv) in tandem with a costimulatory domain and an activating domain. The costimulatory domain may comprise one or more of an extracellular portion, a transmembrane portion, and an intracellular portion. In other embodiments, multiple costimulatory domains may be utilized in tandem.

Antigen Binding Domain

CARs may be engineered to bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment (scFv). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are useful in chimeric antigen receptors because they may be engineered to be expressed as part of a single chain along with the other CAR components. Id. See also Krause et al., J. Exp. Med., Volume 188, No. 4, 1998 (619-626); Finney et al., Journal of Immunology, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

In some embodiments, the antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids.

In some embodiments, the antigen binding molecule comprises a nanobody. In some embodiments, the antigen binding molecule comprises a DARPin. In some embodiments, the antigen binding molecule comprises an anticalin or other synthetic protein capable of specific binding to target protein.

In some embodiments, the CAR comprises an antigen binding domain specific for an antigen selected from the group CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GalNAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EP-CAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-Ireceptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), thyroid stimulating hormone receptor (TSHR), G protein-coupled receptor class C group 5, member D (GPRC5D), chromosome X open reading frame 61 (CXORF61), CD97, CD179a, anaplastic lymphoma kinase (ALK), Polysialic acid, placenta-specific 1 (PLAC1), hexasaccharide portion of globoH glycoceramide (GloboH), mammary gland differentiation antigen (NY-BR-1), uroplakin 2 (UPK2), Hepatitis A virus cellular receptor 1 (HAVCR1), adrenoceptor beta 3 (ADRB3), pannexin 3 (PANX3), G protein-coupled receptor 20 (GPR20), lymphocyte antigen 6 complex, locus K 9 (LY6K), Olfactory receptor 51E2 (OR51E2), TCR Gamma Alternate Reading Frame Protein (TARP), Wilms tumor protein (WT1), Cancer/testis antigen 1 (NY-ESO-1), Cancer/testis antigen 2 (LAGE-la), MAGE family members (including MAGE-A1, MAGE-A3 and MAGE-A4), ETS translocation-variant gene 6, located on chromosome 12p (ETV6-AML), sperm protein 17 (SPA17), X Antigen Family, Member 1A (XAGE1), angiopoietin-binding cell surface receptor 2 (Tie 2), melanoma cancer testis antigen-1 (MAD-CT-1), melanoma cancer testis antigen-2 (MAD-CT-2), Fos-related antigen 1, tumor protein p53 (p53), p53 mutant, prostein, surviving, telomerase, prostate carcinoma tumor antigen-1, melanoma antigen recognized by T cells 1, Rat sarcoma (Ras) mutant, human Telomerase reverse transcriptase (hTERT), sarcoma translocation breakpoints, melanoma inhibitor of apoptosis (ML-IAP), ERG (transmembrane protease, serine 2 (TMPRSS2) ETS fusion gene), N-Acetyl glucosaminyl-transferase V (NA 17), paired box protein Pax-3 (PAX3), Androgen receptor, Cyclin B1, v-myc avian myelocytomatosis viral oncogene neuroblastoma derived homolog (MYCN), Ras Homolog Family Member C (RhoC), Tyrosinase-related protein 2 (TRP-2), Cytochrome P450 1B1 (CYP1B1), CCCTC-Binding Factor (Zinc Finger Protein)-Like, Squamous Cell Carcinoma Antigen Recognized By T Cells 3 (SART3), Paired box protein Pax-5 (PAX5), proacrosin binding protein sp32 (OY-TES1), lymphocyte-specific protein tyrosine kinase (LCK), A kinase anchor protein 4 (AKAP-4), synovial sarcoma, X breakpoint 2 (SSX2), Receptor for Advanced Glycation Endproducts (RAGE-1), renal ubiquitous 1 (RU1), renal ubiquitous 2 (RU2), legumain, human papilloma virus E6 (HPV E6), human papilloma virus E7 (HPV E7), intestinal carboxyl esterase, heat shock protein 70-2 mutated (mut hsp70-2), CD79a, CD79b, CD72, Leukocyte-associated immunoglobulin-like receptor 1 (LAIR1), Fc fragment of IgA receptor (FCAR or CD89), Leukocyte immunoglobulin-like receptor subfamily A member 2 (LILRA2), CD300 molecule-like family member f (CD300LF), C-type lectin domain family 12 member A (CLEC12A), bone marrow stromal cell antigen 2 (BST2), EGF-like module-containing mucin-like hormone receptor-like 2 (EMR2), lymphocyte antigen 75 (LY75), Glypican-3 (GPC3), Fc receptor-like 5 (FCRL5), MUC16, 5T4, 8H9, αvβθ integrin, αvβ6 integrin, alphafetoprotein (AFP), B7-H6, ca-125, CA9, CD44, CD44v7/8, CD52, E-cadherin, EMA (epithelial membrane antigen), epithelial glycoprotein-2 (EGP-2), epithelial glycoprotein-40 (EGP-40), ErbB4, epithelial tumor antigen (ETA), folate binding protein (FBP), kinase insert domain receptor (KDR), k-light chain, L1 cell adhesion molecule, MUC18, NKG2D, oncofetal antigen (h5T4), tumor/testis-antigen 1B, GAGE, GAGE-1, BAGE, SCP-1, CTZ9, SAGE, CAGE, CT10, MART-1, immunoglobulin lambda-like polypeptide 1 (IGLL1), Hepatitis B Surface Antigen Binding Protein (HBsAg), viral capsid antigen (VCA), early antigen (EA), EBV nuclear antigen (EBNA), HHV-6p41 early antigen, HHV-6B U94 latent antigen, HHV-6B p98 late antigen, cytomegalovirus (CMV) antigen, large T antigen, small T antigen, adenovirus antigen, respiratory syncytial virus (RSV) antigen, haemagglutinin (HA), neuraminidase (NA), parainfluenza type 1 antigen, parainfluenza type 2 antigen, parainfluenza type 3 antigen, parainfluenza type 4 antigen, Human Metapneumovirus (HMPV) antigen, hepatitis C virus (HCV) core antigen, HIV p24 antigen, human T-cell lympotrophic virus (HTLV-1) antigen, Merkel cell polyoma virus small T antigen, Merkel cell polyoma virus large T antigen, Kaposi sarcoma-associated herpesvirus (KSHV) lytic nuclear antigen and KSHV latent nuclear antigen. In some embodiments, an antigen binding domain comprises SEQ ID NO: 321 and/or 322.

Hinge/Spacer Domain

In some embodiments, a CAR of the instant disclosure comprises a hinge or spacer domain. In some embodiments, the hinge/spacer domain may comprise a truncated hinge/spacer domain (THD) the THD domain is a truncated version of a complete hinge/spacer domain ("CHD"). In some embodiments, an extracellular domain is from or derived from (e.g., comprises all or a fragment of) ErbB2, glycophorin A (GpA), CD2, CD3 delta, CD3 epsilon, CD3 gamma, CD4, CD7, CD8a, CD8[T CDl la (IT GAL), CDl lb (IT GAM), CDl lc (ITGAX), CDl ld (IT GAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRT AM), CD357 (TNFRSF18), inducible T cell co-stimulator (ICOS), LFA-1 (CDl la/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof. A hinge or spacer domain may be derived either from a natural or from a synthetic source.

In some embodiments, a hinge or spacer domain is positioned between an antigen binding molecule (e.g., an scFv) and a transmembrane domain. In this orientation, the hinge/spacer domain provides distance between the antigen binding molecule and the surface of a cell membrane on which the CAR is expressed. In some embodiments, a hinge or spacer domain is from or derived from an immunoglobulin. In some embodiments, a hinge or spacer domain is selected from the hinge/spacer regions of IgG1, IgG2, IgG3, IgG4, IgA, IgD, IgE, IgM, or a fragment thereof. In some embodiments, a hinge or spacer domain comprises, is from, or is derived from the hinge/spacer region of CD8 alpha. In some embodiments, a hinge or spacer domain comprises, is from, or is derived from the hinge/spacer region of CD28. In some embodiments, a hinge or spacer domain comprises a fragment of the hinge/spacer region of CD8 alpha or a fragment of the hinge/spacer region of CD28, wherein the fragment is anything less than the whole hinge/spacer region. In some embodiments, the fragment of the CD8 alpha hinge/spacer region or the fragment of the CD28 hinge/spacer region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge/spacer region, or of the CD28 hinge/spacer region.

Transmembrane Domain

The CAR of the present disclosure may further comprise a transmembrane domain and/or an intracellular signaling domain. The transmembrane domain may be designed to be fused to the extracellular domain of the CAR. It may similarly be fused to the intracellular domain of the CAR. In some embodiments, the transmembrane domain that naturally is associated with one of the domains in a CAR is used. In some instances, the transmembrane domain may be selected or modified (e.g., by an amino acid substitution) to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein.

Transmembrane regions may be derived from (i.e. comprise) a receptor tyrosine kinase (e.g., ErbB2), glycophorin A (GpA), 4-1BB/CD137, activating NKcell receptors, an immunoglobulin protein, B7-H3, BAFFR, BFAME (SEAMF8), BTEA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD1 la, CD1 lb, CD1 1c, CD1 Id, CDS, CEACAM1, CRT AM, cytokine receptor, DAP-10, DNAM1 (CD226), Fc gamma receptor, GADS, GITR, HVEM (EIGHTR), IA4, ICAM-1, ICAM-1, Ig alpha (CD79a), IE-2R beta, IE-2R gamma, IE-7R alpha, inducible T cell costimulator (ICOS), integrins, ITGA4, ITGA4, ITGA6, IT GAD, ITGAE, ITGAE, IT GAM, ITGAX, ITGB2, ITGB7, ITGB1, KIRDS2, EAT, LFA-1, LFA-1, a ligand that specifically binds with CD83, LIGHT, LIGHT, LTBR, Ly9 (CD229), lymphocyte function-associated antigen-1 (LFA-1; CD1-la/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMFI; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, suitable intracellular signaling domain include, but are not limited to, activating Macrophage/Myeloid cell receptors CSFR1, MYD88, CD14, TIE2, TLR4, CR3, CD64, TREM2, DAP10, DAP12, CD169, DECTIN1, CD206, CD47, CD163, CD36, MARCO, TIM4, MERTK, F4/80, CD91, ClQR, LOX-1, CD68, SRA, BAI-1, ABCA7, CD36, CD31, Lactoferrin, or a fragment, truncation, or combination thereof.

In some embodiments, a receptor tyrosine kinase may be derived from (e.g., comprise) Insulin receptor (InsR), Insulin-like growth factor I receptor (IGF1R), Insulin receptor-related receptor (IRR), platelet derived growth factor receptor alpha (PDGFRa), platelet derived growth factor receptor beta (PDGFRfi). KIT proto-oncogene receptor tyrosine kinase (Kit), colony stimulating factor 1 receptor (CSFR), fms related tyrosine kinase 3 (FLT3), fms related tyrosine kinase 1 (VEGFR-1), kinase insert domain receptor (VEGFR-2), fms related tyrosine kinase 4 (VEGFR-3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), protein tyrosine kinase 7 (CCK4), neurotrophic receptor tyrosine kinase 1 (trkA), neurotrophic receptor tyrosine kinase 2 (trkB), neurotrophic receptor tyrosine kinase 3 (trkC), receptor tyrosine kinase like orphan receptor 1 (ROR1), receptor tyrosine kinase like orphan receptor 2 (ROR2), muscle associated receptor tyrosine kinase (MuSK), MET proto-oncogene, receptor tyrosine kinase (MET), macrophage stimulating 1 receptor (Ron), AXL receptor tyrosine kinase (Ax1), TYR03 protein tyrosine kinase (Tyro3), MER proto-oncogene, tyrosine kinase (Mer), tyrosine kinase with immunoglobulin like and EGF like domains 1 (TIE1), TEK receptor tyrosine kinase (TIE2), EPH receptor A 1 (EphAl), EPH receptor A2 (EphA2), (EPH receptor A3) EphA3, EPH receptor A4 (EphA4), EPH receptor A5 (EphA5), EPH receptor A6 (EphA6), EPH receptor A7 (EphA7), EPH receptor A8 (EphA8), EPH receptor A10 (EphAlO), EPH receptor B1 (EphB1), EPH receptor B2 (EphB2), EPH receptor B3 (EphB3), EPH receptor B4 (EphB4), EPH receptor B6 (EphB6), ret proto oncogene (Ret), receptor-like tyrosine kinase (RYK), discoidin domain receptor tyrosine kinase 1 (DDR1), discoidin domain receptor tyrosine kinase 2 (DDR2), c-ros oncogene 1, receptor tyrosine kinase (ROS), apoptosis associated tyrosine kinase (Lmrl), lemur tyrosine kinase 2 (Lmr2), lemur tyrosine kinase 3 (Lmr3), leukocyte receptor tyrosine kinase (LTK), ALK receptor tyrosine kinase (ALK), or serine/threonine/tyrosine kinase 1 (STYK1).

Costimulatory Domain

In certain embodiments, the CAR comprises a costimulatory domain. In some embodiments, the costimulatory domain comprises 4-1BB (CD137), CD28, or both, and/or an intracellular T cell signaling domain. In a preferred embodiment, the costimulatory domain is human CD28, human 4-1BB, or both, and the intracellular T cell signaling domain is human CD3 zeta (( ). 4-1BB, CD28, CD3 zeta may comprise less than the whole 4-1BB, CD28 or CD3 zeta, respectively. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Amur. Rev. Pharmacol. Toxicol. 56:59-83 (2016).

In some embodiments, a costimulatory domain comprises the amino acid sequence of SEQ ID NO: 318 or 320.

Intracellular Signaling Domain

The intracellular (signaling) domain of the engineered T cells disclosed herein may provide signaling to an activating domain, which then activates at least one of the normal effector functions of the immune cell. Effector function of a T cell, for example, may be cytolytic activity or helper activity including the secretion of cytokines.

In some embodiments, suitable intracellular signaling domain include (e.g., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD 19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD1 la, CD1 lb, CD1 11, CD1 1d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, LFA-1, ligand that specifically binds with CD83, LIGHT, LTBR, Ly9 (CD229), Ly108, lymphocyte function-associated antigen-1 (LFA-1; CDl-la/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

CD3 is an element of the T cell receptor on native T cells, and has been shown to be an important intracellular activating element in CARs. In some embodiments, the CD3 is CD3 zeta. In some embodiments, the activating domain comprises an amino acid sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of SEQ ID NO: 319.

3.6 Trispecific Antigen-Binding Proteins and Bispecific Antigen-Binding Proteins Disclosed herein are circular RNA polypeptides encoding trispecific antigen-binding proteins (TRITEs), bispecific antigen-binding proteins (BITEs), functional fragments thereof, and pharmaceutical compositions thereof. Recombinant expression vectors useful for making circular RNA encoding trispecific antigen-binding proteins or bispecific antigen binding proteins, and cells comprising the inventive circular RNA are also provided herein. Also provided are methods of using the disclosed trispecific antigen-binding proteins or the bispecific antigen-binding proteins in the prevention and/or treatment of liver diseases, conditions and disorders. The trispecific antigen-binding proteins are capable of specifically binding to a target antigen, e.g., a cancer antigen, as well as CD3, TCR, CD16A, or NKp46, and a liver retention domain or a half-life extension domain, such as a domain binding human serum albumin (HSA). In some embodiments, the *TRITE* or BITE is created within a patient's liver post-administration of a composition comprising the inventive circular RNA polypeptides to a patient in need thereof.

In one aspect, trispecific antigen-binding proteins comprise a domain (A) which specifically binds to CD3, TCR, CD16A, or NKp46, a domain (B) which specifically binds to a half-life extension molecule or a liver retention molecule, and a domain (C) which specifically binds to a target antigen, e.g., a cancer cell antigen. The three domains in trispecific antigen-binding proteins may be arranged in any order. Thus, it is contemplated that the domain order of the trispecific antigen-binding proteins are in any of the following orders: (A)-(B)-(C), (A)-(C)-(B), (B)-(A)-(C), (B)-(C)-(A), (C)-(B)-(A), or (C)-(A)-(B).

In some embodiments, the trispecific antigen-binding proteins have a domain order of (A)-(B)-(C). In some embodiments, the trispecific antigen-binding proteins have a domain order of (A)-(C)-(B). In some embodiments, the trispecific antigen binding proteins have a domain order of (B)-(A)-(C). In some embodiments, the trispecific antigen-binding proteins have a domain order of (B)-(C)-(A). In some embodiments, the trispecific antigen-binding proteins have a domain order of (C)-(B)-(A). In some embodiments, the trispecific antigen-binding proteins have a domain order of (C)-(A)-(B).

In an embodiment, a bispecific antigen-binding protein comprises a domain (A) which specifically binds to CD3, TCR, CD16A, or NKp46, and a domain (B) which specifically binds to a target antigen. The two domains in a bispecific antigen-binding protein are arranged in any order. Thus, it is contemplated that the domain order of the bispecific antigen-binding proteins may be: (A)-(B), or (B)-(A).

The trispecific antigen-binding proteins or bispecific antigen-binding proteins described herein are designed to allow specific targeting of cells expressing a target antigen by recruiting cytotoxic T cells or NK cells. This improves efficacy compared to ADCC (antibody dependent cell-mediated cytotoxicity), which uses full length antibodies directed to a sole antigen and is not capable of directly recruiting cytotoxic T cells. In contrast, by engaging CD3 molecules expressed specifically on these cells, the trispecific antigen-binding proteins or bispecific antigen-binding proteins can crosslink cytotoxic T cells or NK cells with cells expressing a target antigen in a highly specific fashion, thereby directing the cytotoxic potential of the recruited T cell or NK cell towards the target cell. The trispecific antigen-binding proteins or bispecific antigen-binding proteins described herein engage cytotoxic T cells via binding to the surface-expressed CD3 proteins, which form part of the TCR, or CD16A or NKp46, which activates NK cells. Simultaneous binding of several trispecific antigen-binding protein or bispecific antigen-binding proteins to CD3 and to a target antigen expressed on the surface of particular cells causes T cell activation and mediates the subsequent lysis of the particular target antigen expressing cell. Thus, trispecific antigen-binding or bispecific antigen-binding proteins are contemplated to display strong, specific and efficient target cell killing. In some embodiments, the trispecific antigen-binding proteins or bispecific antigen-binding proteins described herein stimulate target cell killing by cytotoxic T cells to eliminate pathogenic cells (e.g., tumor cells, virally or bacterially infected cells, autoreactive T cells, etc). In some embodiments, cells are eliminated selectively, thereby reducing the potential for toxic side effects. In some embodiments anti-41bb or CD137 binding domains are used as the t cell engager.

Immune Cell Binding Domain

The specificity of the response of T cells is mediated by the recognition of antigen (displayed in context of a major histocompatibility complex, MHC) by the TCR. As part of the TCR, CD3 is a protein complex that includes a CD3γ (gamma) chain, a CD3δ (delta) chain, and two CD3ε (epsilon) chains which are present on the cell surface. CD3 associates with the α (alpha) and β (beta) chains of the TCR as well as CD3 ζ (zeta) altogether to comprise the complete TCR. Clustering of CD3 on T cells, such as by immobilized anti-CD3 antibodies leads to T cell activation similar to the engagement of the T cell receptor but independent of its clone-typical specificity.

In one aspect, the bispecific and trispecific proteins described herein comprise a domain which specifically binds to CD3. In one aspect, the trispecific proteins described herein comprise a domain which specifically binds to human CD3. In some embodiments, the trispecific proteins described herein comprise a domain which specifically binds to CD3γ. In some embodiments, the trispecific proteins described herein comprise a domain which specifically binds to CD36. In some embodiments, the trispecific proteins described herein comprise a domain which specifically binds to CD3g.

In further embodiments, the trispecific proteins described herein comprise a domain which specifically binds to the TCR. In certain instances, the trispecific proteins described herein comprise a domain which specifically binds the α chain of the TCR. In certain instances, the trispecific proteins described herein comprise a domain which specifically binds the R chain of the TCR.

In some embodiments, a trispecific antigen binding protein or bispecific antigen binding protein comprises a NKp46 specific binder. In some embodiments, a trispecific antigen binding protein or bispecific antigen binding protein comprises a CD16A specific binder.

In some embodiments, the CD3, TCR, NKp46, or CD16A binding domain of the antigen-binding protein can be any domain that binds to CD3, TCR, NKp46, or CD16A including but not limited to domains from a monoclonal antibody, a polyclonal antibody, a recombinant antibody, a human antibody, a humanized antibody. In some instances, it is beneficial for the CD3, TCR, NKp46, or CD16A binding domain to be derived from the same species in which the trispecific antigen-binding protein will ultimately be used in. For example, for use in humans, it may be beneficial for the CD3, TCR, NKp46, or CD16A binding domain of the trispecific antigen-binding protein to comprise human or humanized residues from the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-CD3, TCR, NKp46, or CD16A binding domain comprises one or more (e.g., all three) light chain complementary determining region 1 (LC CDR1), light chain complementary determining region 2 (LC CDR2), and light chain complementary determining region 3 (LC CDR3) of a humanized or human anti-CD3, TCR, NKp46, or CD16A binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-CD3, TCR, NKp46, or CD16A binding domain described herein, e.g., a humanized or human anti-CD3, TCR, NKp46, or CD16A binding domain comprising one or more, e.g., all three, LC CDRs and one or more, e.g., all three, HC CDRs.

In some embodiments, the humanized or human anti-CD3, TCR, NKp46, or CD16A binding domain comprises a humanized or human heavy chain variable region specific to CD3, TCR, NKp46, or CD16A where the heavy chain variable region specific to CD3, TCR, NKp46, or CD16A comprises human or non-human heavy chain CDRs in a human heavy chain framework region.

In certain instances, the complementary determining regions of the heavy chain and/or the light chain are derived from known anti-CD3 antibodies, such as, for example, muromonab-CD3 (OKT3), otelixizumab (TRX4), teplizumab (MGA031), visilizumab (Nuvion), SP34, TR-66 or X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In some embodiments, an anti-NKp46 binding domain comprises an antibody or fragment thereof described in U.S. patent application Ser. No. 16/451,051. In some embodiments, an anti-NKp46 binding domain comprises the antibodies BAB281, 9E2, 195314 or a fragment thereof.

In one embodiment, the anti-CD3, TCR, NKp46, or CD16A binding domain is a single chain variable fragment (scFv) comprising a light chain and a heavy chain of an amino acid sequence provided herein. In an embodiment, the anti-CD3, TCR, NKp46, or CD16A binding domain comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-CD3 binding domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be, e.g., in any of the following orientations: light chain variable region-scFv linker-heavy chain variable region or heavy chain variable region-scFv linker-light chain variable region.

In some embodiments, CD3, TCR, NKp46, or CD16A binding domain of trispecific antigen-binding protein has an affinity to CD3, TCR, NKp46, or CD16A on CD3, TCR, NKp46, or CD16A expressing cells with a KD of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In some embodiments, the CD3 binding domain of MSLN trispecific antigen-binding protein has an affinity to CD3g, 7, or 6 with a KD of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In further embodiments, CD3, TCR, NKp46, or CD16A binding domain of trispecific antigen-binding protein has low affinity to CD3, TCR, NKp46, or CD16A, i.e., about 100 nM or greater.

The affinity to bind to CD3, TCR, NKp46, or CD16A can be determined, for example, by the ability of the trispecific antigen-binding protein itself or its CD3, TCR, NKp46, or CD16A binding domain to bind to CD3, TCR, NKp46, or CD16A coated on an assay plate; displayed on a microbial cell surface; in solution; etc. The binding activity of the trispecific antigen-binding protein itself or its CD3, TCR, NKp46, or CD16A binding domain of the present disclosure to CD3, TCR, NKp46, or CD16A can be assayed by immobilizing the ligand (e.g., CD3, TCR, NKp46, or CD16A) or the trispecific antigen-binding protein itself or its CD3, TCR, NKp46, or CD16A binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

In some embodiments, a bispecific antigen binding protein or bispecific antigen binding protein comprises a TCR binding domain. In some embodiments, a TCR binding domain is a viral antigen or a fragment thereof. In some embodiments, a viral antigen is from the families: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., Ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviruses and rotaviruses); Bornaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the agent of delta hepatitis (thought to be a defective satellite of hepatitis B virus), Hepatitis C; Norwalk and related viruses, and astroviruses).

Linkers

In the trispecific proteins described herein, the domains are linked by internal linkers L1 and L2, where L1 links the first and second domain of the trispecific proteins and L2 links the second and third domains of the trispecific proteins. In some embodiments, linkers L1 and L2 have an optimized length and/or amino acid composition. In some embodiments, linkers L1 and L2 are the same length and amino acid composition. In other embodiments, L1 and L2 are different. In certain embodiments, internal linkers L1 and/or L2 consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, internal linkers L1 and/or L2 consist of 15, 20 or 25 amino acid residues. In some embodiments, these internal linkers consist of about 3 to about 15, for example 8, 9 or 10 contiguous amino acid residues. Regarding the amino acid composition of the internal linkers L1 and L2, peptides are selected with properties that confer flexibility to the trispecific proteins, do not interfere with the binding domains as well as resist cleavage from proteases. For example, glycine and serine residues generally provide protease resistance. Examples of internal linkers suitable for linking the domains in the trispecific proteins include but are not limited to (GS)n, (GGS)n, (GGGS)n, (GGSG)n, (GGSGG)n, (GGGGS)n, (GGGGG)n, or (GGG)n, wherein n is 1, 2, 3, 4, 5, 6, 7, 8, 9, or 10. In one embodiment, internal linker L1 and/or L2 is (GGGGS)4 or $(GGGGS)_3$.

Half-Life Extension Domain

Contemplated herein are domains which extend the half-life of an antigen-binding domain. Such domains are contemplated to include but are not limited to Albumin binding domains, Fc domains, small molecules, and other half-life extension domains known in the art.

Human albumin (ALB) is the most abundant protein in plasma, present at about 50 mg/ml and has a half-life of around 20 days in humans. ALB serves to maintain plasma pH, contributes to colloidal blood pressure, functions as carrier of many metabolites and fatty acids, and serves as a major drug transport protein in plasma.

Noncovalent association with albumin extends the elimination half-time of short lived proteins.

In one aspect, the trispecific proteins described herein comprise a half-life extension domain, for example a domain which specifically binds to ALB. In some embodiments, the ALB binding domain of a trispecific antigen-binding protein can be any domain that binds to ALB including but not limited to domains from a monoclonal antibody, a polyclonal antibody, a recombinant antibody, a human antibody, a humanized antibody. In some embodiments, the ALB binding domain is a single chain variable fragments (scFv), single-domain antibody such as a heavy chain variable domain (VH), a light chain variable domain (VL) and a variable domain (VHH) of camelid derived single domain antibody, peptide, ligand or small molecule entity specific for HSA. In certain embodiments, the ALB binding domain is a single-domain antibody. In other embodiments, the HSA binding domain is a peptide. In further embodiments, the HSA binding domain is a small molecule. It is contemplated that the HSA binding domain of MSLN trispecific antigen-binding protein is fairly small and no more than 25 kD, no more than 20 kD, no more than 15 kD, or no more than 10 kD in some embodiments. In certain instances, the ALB binding is 5 kD or less if it is a peptide or small molecule entity.

The half-life extension domain of a trispecific antigen-binding protein provides for altered pharmacodynamics and pharmacokinetics of the trispecific antigen-binding protein itself. As above, the half-life extension domain extends the elimination half-time. The half-life extension domain also alters pharmacodynamic properties including alteration of tissue distribution, penetration, and diffusion of the trispecific antigen-binding protein. In some embodiments, the half-life extension domain provides for improved tissue (including tumor) targeting, tissue distribution, tissue penetration, diffusion within the tissue, and enhanced efficacy as compared with a protein without a half-life extension domain. In one embodiment, therapeutic methods effectively and efficiently utilize a reduced amount of the trispecific antigen-binding protein, resulting in reduced side effects, such as reduced non-tumor cell cytotoxicity.

Further, the binding affinity of the half-life extension domain can be selected so as to target a specific elimination half-time in a particular trispecific antigen-binding protein. Thus, in some embodiments, the half-life extension domain has a high binding affinity. In other embodiments, the half-life extension domain has a medium binding affinity. In yet other embodiments, the half-life extension domain has a low or marginal binding affinity. Exemplary binding affinities include KD concentrations at 10 nM or less (high), between 10 nM and 100 nM (medium), and greater than 100 nM (low). As above, binding affinities to ALB are determined by known methods such as Surface Plasmon Resonance (SPR).

Liver Retention Domain

Contemplated herein are domains which allows for and promotes a higher retention of the trispecific antigen-binding protein within liver. The liver retention domain of the trispecific antigen-binding protein is directed to targeting a liver cell moiety. In an embodiment, a liver cell includes but is not limited to a hepatocyte, hepatic stellate cell, sinusoidal endothelial cell.

In an embodiment, a liver cell contains a receptor that binds to a liver targeting moiety. In an embodiment, the liver targeting moiety includes, but is not limited to lactose, cyanuric chloride, cellobiose, polylsine, polyarginine, Mannose-6-phosphate, PDGF, human serum albumin, galactoside, galactosamine, linoleic acid, Apoliopoprotein A-1, Acetyl CKNEKKNIERNNKLKQPP-amide, glycyrrhizin, lactobionic acid, Mannose-BSA, BSA, poly-ACO-HAS, KLGR peptide, hyaluronic acid, IFN-alpha, cRGD peptide, 6-phosphate-HSA, retinol, lactobiotin, galactoside, pullulan, soybean sterylglucoside, asialoorosomucoid, glycyrrhetinic acid/glycyrrhizin, linoleic acid, AMD3100, cleavable hyaluronic acid-glycyrrhetinic acid, Hepatitis B virus pre-S1 derived lipoprotein, Apo-A 1, or LDL. In an embodiment, the liver cell receptor includes but is not limited to galactose receptor, mannose receptor, scavenger receptor, low-density lipoprotein receptor, HARE, CD44, IFNareceptor, collagen type VI receptor, 6-phosphate/insulin-like growth factor 2 receptor, platelet-derived growth factor receptor β, RBP receptor, αVβ3 integrin receptor, ASGP receptor, glycyrrhetinic acid/glycyrrhizin receptor, PPAR, Heparan sulfate glycosaminoglycan receptor, CXC receptor type 4, glycyrrhetinic acid receptor, HBVP receptor, HDL receptor, scavenger receptor class B member 1 LDL receptor or combination thereof.

Target Antigen Binding Domain

The trispecific antigen-binding proteins and bispecific antigen-binding proteins described herein comprise a domain that binds to a target antigen. A target antigen is involved in and/or associated with a disease, disorder or condition, e.g., cancer. In some embodiments, a target antigen is a tumor antigen. In some embodiments, the target antigen is NY-ESO-1, SSX-2, Sp 17, AFP, Glypican-3, Gpa33, Annexin-A2, WT1, PSMA, Midkine, PRAME, Survivin, MUC-1. P53, CEA, RAS, Hsp70, Hsp27, squamous cell carcinoma antigen (SCCA), GP73, TAG-72, or a protein in the MAGE family.

In some embodiments, a target antigen is one found on a non-liver tumor cell that has metastasized into the liver. In some embodiments, a bispecific antigen-binding protein or trispecific antigen binding protein comprises a target antigen binding domain specific for group CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GaINAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, HER2, HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), claudin 18.2 (CLDN18.2), thyroid stimulating hormone receptor (TSHR), G protein-coupled receptor class C group 5, member D (GPRC5D), chromosome X open reading frame 61 (CXORF61), CD97, or CD179a. In some embodiments, a target antigen is an antigen associated with a viral disease, e.g., a viral antigen. In some embodiments, a target antigen is a hepatitis A, hepatitis B, hepatitis C, hepatitis D or hepatitis E antigen.

The design of the trispecific antigen-binding proteins described herein allows the binding domain to a liver target antigen to be flexible in that the binding domain to a liver target antigen can be any type of binding domain, including but not limited to, domains from a monoclonal antibody, a polyclonal antibody, a recombinant antibody, a human antibody, a humanized antibody. In some embodiments, the binding domain to a liver target antigen is a single chain variable fragments (scFv), single-domain antibody such as a heavy chain variable domain (VH), a light chain variable domain (VL) and a variable domain (VHH) of camelid derived single domain antibody. In other embodiments, the binding domain to a liver target antigen is a non-Ig binding domain, i.e., antibody mimetic, such as anticalins, affilins, affibody molecules, affimers, affitins, alphabodies, avimers, DARPins, fynomers, kunitz domain peptides, and monobodies. In further embodiments, the binding domain to a liver target antigen is a ligand or peptide that binds to or associates with a target antigen.

3.7 PAH

In some embodiments, the present invention provides methods and compositions for delivering circRNA encoding PAH to a subject for the treatment of phenylketonuria (PKU). A suitable PAH circRNA encodes any full length, fragment or portion of a PAH protein which can be substituted for naturally-occurring PAH protein activity and/or reduce the intensity, severity, and/or frequency of one or more symptoms associated with PKU.

In some embodiments, a suitable RNA sequence for the present invention comprises a circRNA sequence encoding human PAH protein.

In some embodiments, a suitable RNA sequence may be an RNA sequence that encodes a homolog or an analog of human PAH. As used herein, a homolog or an analog of human PAH protein may be a modified human PAH protein containing one or more amino acid substitutions, deletions, and/or insertions as compared to a wild-type or naturally-occurring human PAH protein while retaining substantial PAH protein activity.

The present invention may be used to treat a subject who is suffering from or susceptible to Phenylketonuria (PKU). PKU is an autosomal recessive metabolic genetic disorder characterized by a mutation in the gene for the hepatic enzyme phenylalanine hydroxylase (PAH), rendering it non-functional. PAH is necessary to metabolize the amino acid phenylalanine (Phe) to the amino acid tyrosine (Tyr). When PAH activity is reduced, phenylalanine accumulates and is converted into phenylpyruvate (also known as phenylketone) which can be detected in the urine.

Phenylalanine is a large, neutral amino acid (LNAA). LNAAs compete for transport across the blood-brain barrier (BBB) via the large neutral amino acid transporter (LNAAT). Excess Phe in the blood saturates the transporter and tends to decrease the levels of other LNAAs in the brain. Because several of these other amino acids are necessary for protein and neurotransmitter synthesis, Phe buildup hinders the development of the brain, and can cause mental retardation.

In addition to hindered brain development, the disease can present clinically with a variety of symptoms including seizures, albinism hyperactivity, stunted growth, skin rashes (eczema), microcephaly, and/or a "musty" odor to the baby's sweat and urine, due to phenylacetate, one of the ketones produced). Untreated children are typically normal at birth, but have delayed mental and social skills, have a head size significantly below normal, and often demonstrate progressive impairment of cerebral function. As the child grows and develops, additional symptoms including hyperactivity, jerking movements of the arms or legs, EEG abnormalities, skin rashes, tremors, seizures, and severe learning disabilities tend to develop. However, PKU is commonly included in the routine newborn screening panel of most countries that is typically performed 2-7 days after birth.

If PKU is diagnosed early enough, an affected newborn can grow up with relatively normal brain development, but only by managing and controlling Phe levels through diet, or a combination of diet and medication. All PKU patients must adhere to a special diet low in Phe for optimal brain development. The diet requires severely restricting or eliminating foods high in Phe, such as meat, chicken, fish, eggs, nuts, cheese, legumes, milk and other dairy products. Starchy foods, such as potatoes, bread, pasta, and corn, must be monitored. Infants may still be breastfed to provide all of the benefits of breastmilk, but the quantity must also be monitored and supplementation for missing nutrients will be required. The sweetener aspartame, present in many diet foods and soft drinks, must also be avoided, as aspartame contains phenylalanine.

Throughout life, patients can use supplementary infant formulas, pills or specially formulated foods to acquire amino acids and other necessary nutrients that would otherwise be deficient in a low-phenylalanine diet. Some Phe is required for the synthesis of many proteins and is required for appropriate growth, but levels of it must be strictly controlled in PKU patients. Additionally, PKU patients must take supplements of tyrosine, which is normally derived from phenylalanine. Other supplements can include fish oil, to replace the long chain fatty acids missing from a standard Phe-free diet and improve neurological development and iron or carnitine. Another potential therapy for PKU is tetrahydrobiopterin (BH4), a cofactor for the oxidation of Phe that can reduce blood levels of Phe in certain patients. Patients who respond to BH4 therapy may also be able to increase the amount of natural protein that they can eat.

In some embodiments, the expression of PAH protein is detectable in liver, kidney, heart, spleen, serum, brain, skeletal muscle, lymph nodes, skin, and/or cerebrospinal fluid.

In some embodiments, administering the provided composition results in the expression of a PAH protein level at or above about 100 ng/mg, about 200 ng/mg, about 300 ng/mg, about 400 ng/mg, about 500 ng/mg, about 600 ng/mg, about 700 ng/mg, about 800 ng/mg, about 900 ng/mg, about 1000 ng/mg, about 1200 ng/mg or about 1400 ng/mg of total protein in the liver.

In some embodiments, the expression of the PAH protein is detectable 1 to 96 hours after administration. For example, in some embodiments, expression of PAH protein is detectable 1 to 84 hours, 1 to 72 hours, 1 to 60 hours, 1 to 48 hours, 1 to 36 hours, 1 to 24 hours, 1 to 12 hours, 1 to 10 hours, 1 to 8 hours, 1 to 6 hours, 1 to 4 hours, 1 to 2 hours, 2 to 96 hours, 2 to 84 hours, 2 to 72 hours, 2 to 60 hours, 2 to 48 hours, 2 to 36 hours, 2 to 24 hours, 2 to 12 hours, 2 to 10 hours, 2 to 8 hours, 2 to 6 hours, 2 to 4 hours, 4 to 96 hours, 4 to 84 hours, 4 to 72 hours, 4 to 60 hours, 4 to 48 hours, 4 to 36 hours, 4 to 24 hours, 4 to 12 hours, 4 to 10 hours, 4 to 8 hours, 4 to 6 hours, 6 to 96 hours, 6 to 84 hours, 6 to 72 hours, 6 to 60 hours, 6 to 48 hours, 6 to 36 hours, 6 to 24 hours, 6 to 12 hours, 6 to 10 hours, 6 to 8 hours, 8 to 96 hours, 8 to 84 hours, 8 to 72 hours, 8 to 60 hours, 8 to 48 hours, 8 to 36 hours, 8 to 24 hours, 8 to 12 hours, 8 to 10 hours, 10 to 96 hours, 10 to 84 hours, 10 to 72 hours, 10 to 60 hours, 10 to 48 hours, 10 to 36 hours, 10 to 24 hours, 10 to 12 hours, 12 to 96 hours, 12 to 84 hours, 12 to 72 hours, 12 to 60 hours, 12 to 48 hours, 12 to 36 hours, 12 to 24 hours, 24 to 96 hours, 24 to 84 hours, 24 to 72 hours, 24 to 60 hours, 24 to 48 hours, 24 to 36 hours, 36 to 96 hours, 36 to 84 hours, 36 to 72 hours, 36 to 60 hours, 36 to 48 hours, 48 to 96 hours, 48 to 84 hours, 48 to 72 hours, 48 to 60 hours, 48 to 84 hours, 48 to 72 hours, 48 to 60 hours, 60 to 96 hours, 60 to 84 hours, 60 to 72 hours, 72 hours to 96 hours, 72 hours to 84 hours, or 84 hours to 96 hours after administration. For example, in certain embodiments, the expression of the PAH protein is detectable 6, 12, 18, 24, 30, 36, 42, 48, 54, 60, 66, and/or 72 hours after the administration. In some embodiments, the expression of the PAH protein is detectable 1 day to 7 days after the administration. For example, in some embodiments, PAH protein is detectable 1 day, 2 days, 3 days, 4 days, 5 days, 6 days, and/or 7 days after the administration. In some embodiments, the expression of the PAH protein is detectable 1 week to 8 weeks after the administration. For example, in some embodiments, the expression of the PAH protein is detectable 1 week, 2 weeks, 3 weeks, and/or 4 weeks after the administration. In some embodiments, the expression of the PAH protein is detectable after a month after the administration.

3.8 CPS1

In some embodiments, the present invention provides methods and compositions for delivering circRNA encoding CPS1 to a subject for the treatment of CPS1 deficiency. A suitable CPS1 circRNA encodes any full length, fragment or portion of a CPS1 protein which can be substituted for naturally-occurring CPS1 protein activity and/or reduce the intensity, severity, and/or frequency of one or more symptoms associated with CPS1 deficiency.

In some embodiments, a suitable RNA sequence for the present invention comprises a circRNA sequence encoding human CPS1 protein.

In some embodiments, a suitable RNA sequence may be an RNA sequence that encodes a homolog or an analog of human CPS1. As used herein, a homolog or an analog of human CPS 1 protein may be a modified human CPS1 protein containing one or more amino acid substitutions, deletions, and/or insertions as compared to a wild-type or naturally-occurring human CPS1 protein while retaining substantial CPS 1 protein activity.

Carbamoyl phosphate synthetase I (CPS1) catalyzes the conversion of ammonia, bicarbonate and 2 ATP with formation of carbamoyl phosphate in the first step of the urea cycle. It also plays a role in the biosynthesis of arginine, which in turn is a substrate for the biosynthesis of NO, e.g. in the case of an endotoxin shock (c.f. Shoko Tabuchi et al., Regulation of Genes for Inducible Nitric Oxide Synthase and Urea Cycle Enzymes in Rat Liver in Endotoxin Shock, Biochemical and Biophysical Research Communications 268, 221-224 (2000)). CPS 1 should be distinguished from the cytosolic enzyme CPS 2, which likewise plays a role in the urea cycle but processes the substrate glutamine. It is known that CPS 1 is localized in mitochondria and occurs in this form in large amounts in liver tissue (it accounts for 2-6% of total liver protein). Its amino acid sequence and genetic localization have long been known (c.f. Haraguchi Y. et al., Cloning and sequence of a cDNA encoding human carbamyl phosphate synthetase I: molecular analysis of hyperammonemia, Gene 1991, Nov. 1; 107 (2); 335-340; cf. also the publication WO 03/089933 A1 of the Applicant). Regarding its physiological role, reference may be made to review articles such as, for example, H. M. Holder et al., Carbamoyl phosphate synthetase: an amazing biochemical odyssey from substrate to product, CMLS, Cell. Mol. Life Sci. 56 (1999) 507-522, and the literature referred to therein, and the introduction to the publication by Mikiko Ozaki et al., Enzyme-Linked Immunosorbent Assay of Carbamoylphosphate Synthetase I: Plasma Enzyme in Rat Experimental Hepatitis and Its Clearance, Enzyme Protein 1994, 95:48:213-221.

Carbamoyl phosphate synthetase I (CPS1) deficiency is a genetic disorder characterized by a mutation in the gene for the enzyme Carbamoyl phosphate synthetase I, affecting its ability to catalyze synthesis of carbamoyl phosphate from ammonia and bicarbonate. This reaction is the first step of the urea cycle, which is important in the removal of excess urea from cells. Defects in the CPS 1 protein disrupt the urea cycle and prevent the liver from properly processing excess nitrogen into urea.

In some embodiments, administering the provided composition results in the expression of a CPS1 protein level at or above about 100 ng/mg, about 200 ng/mg, about 300 ng/mg, about 400 ng/mg, about 500 ng/mg, about 600 ng/mg, about 700 ng/mg, about 800 ng/mg, about 900 ng/mg, about 1000 ng/mg, about 1200 ng/mg or about 1400 ng/mg of total protein in the liver.

In some embodiments, the expression of the CPS1 protein is detectable 1 to 96 hours after administration. For example, in some embodiments, expression of CPS 1 protein is detectable 1 to 84 hours, 1 to 72 hours, 1 to 60 hours, 1 to 48 hours, 1 to 36 hours, 1 to 24 hours, 1 to 12 hours, 1 to 10 hours, 1 to 8 hours, 1 to 6 hours, 1 to 4 hours, 1 to 2 hours, 2 to 96 hours, 2 to 84 hours, 2 to 72 hours, 2 to 60 hours, 2 to 48 hours, 2 to 36 hours, 2 to 24 hours, 2 to 12 hours, 2 to 10 hours, 2 to 8 hours, 2 to 6 hours, 2 to 4 hours, 4 to 96 hours, 4 to 84 hours, 4 to 72 hours, 4 to 60 hours, 4 to 48 hours, 4 to 36 hours, 4 to 24 hours, 4 to 12 hours, 4 to 10 hours, 4 to 8 hours, 4 to 6 hours, 6 to 96 hours, 6 to 84 hours, 6 to 72 hours, 6 to 60 hours, 6 to 48 hours, 6 to 36 hours, 6 to 24 hours, 6 to 12 hours, 6 to 10 hours, 6 to 8 hours, 8 to 96 hours, 8 to 84 hours, 8 to 72 hours, 8 to 60 hours, 8 to 48 hours, 8 to 36 hours, 8 to 24 hours, 8 to 12 hours, 8 to 10 hours, 10 to 96 hours, 10 to 84 hours, 10 to 72 hours, 10 to 60 hours, 10 to 48 hours, 10 to 36 hours, 10 to 24 hours, 10 to 12 hours, 12 to 96 hours, 12 to 84 hours, 12 to 72 hours, 12 to 60 hours, 12 to 48 hours, 12 to 36 hours, 12 to 24 hours, 24 to 96 hours, 24 to 84 hours, 24 to 72 hours, 24 to 60 hours, 24 to 48 hours, 24 to 36 hours, 36 to 96 hours, 36 to 84 hours, 36 to 72 hours, 36 to 60 hours, 36 to 48 hours, 48 to 96 hours, 48 to 84 hours, 48 to 72 hours, 48 to 60 hours, 48 to 84 hours, 48 to 72 hours, 48 to 60 hours, 60 to 96 hours, 60 to 84 hours, 60 to 72 hours, 72 hours to 96 hours, 72 hours to 84 hours, or 84 hours to 96 hours after administration. For example, in certain embodiments, the expression of the CPS1 protein is detectable 6, 12, 18, 24, 30, 36, 42, 48, 54, 60, 66, and/or 72 hours after the administration. In some embodiments, the expression of the CPS1 protein is detectable 1 day to 7 days after the administration. For example, in some embodiments, CPS1 protein is detectable 1 day, 2 days, 3 days, 4 days, 5 days, 6 days, and/or 7 days after the administration. In some embodiments, the expression of the CPS1 protein is detectable 1 week to 8 weeks after the administration. For example, in some embodiments, CPS1 protein is detectable 1 week, 2 weeks, 3 weeks, and/or 4 weeks after the administration. In some embodiments, the expression of the CPS1 protein is detectable after a month after the administration.

In some embodiments, administering of the composition results in reduced ammonia levels in a subject as compared to baseline levels before treatment. Typically, baseline levels are measured in the subject immediately before treatment. Typically, ammonia levels are measured in a biological sample. Suitable biological samples include, for example, whole blood, plasma, serum, urine or cerebral spinal fluid.

In some embodiments, administering the composition results in reduced ammonia levels in a biological sample (e.g., a serum, plasma, or urine sample) by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline levels in a subject immediately before treatment.

In some embodiments, administering the composition provided herein results in reduced ammonia levels in plasma or serum as compared to baseline ammonia levels in a subject immediately before treatment. In some embodiments, administering the provided composition results in reduced ammonia levels in plasma or serum as compared to the ammonia levels in subjects who are not treated. In some embodiments, administering the composition results in reduction of ammonia levels to about 3000 μmol/L or less, about 2750 μmol/L or less, about 2500 μmol/L or less, about 2250 μmol/L or less, about 2000 μmol/L or less, about 1750 μmol/L or less, about 1500 μmol/L or less, about 1250

μmol/L or less, about 1000 μmol/L or less, about 750 μmol/L or less, about 500 μmol/L or less, about 250 μmol/L or less, about 100 μmol/L or less or about 50 μmol/L or less in the plasma or serum of the subject. In a particular embodiment, administering the composition results in reduction of ammonia levels to about 50 μmol/L or less in the plasma or serum.

3.9 ADAMTS13

In some embodiments, the present invention provides methods and compositions for delivering circRNA encoding ADAMTS13 to a subject for the treatment of thrombotic thrombocytopenic purpura (TTP). A suitable ADAMTS13 circRNA encodes any full length ADAMTS13 protein, or functional fragment or portion thereof, which can be substituted for naturally-occurring ADAMTS13 protein and/or reduce the intensity, severity, and/or frequency of one or more symptoms associated with TTP.

In some embodiments, the RNA sequence of the present invention comprises a circRNA sequence encoding human ADAMTS13 protein.

In some embodiments, the RNA sequence may be an RNA sequence that encodes a homolog or an analog of human ADAMTS13. As used herein, a homolog or an analog of human ADAMTS13 protein may be a modified human ADAMTS13 protein containing one or more amino acid substitutions, deletions, and/or insertions as compared to a wild-type or naturally-occurring human ADAMTS13 protein while retaining substantial ADAMTS13 protein activity.

The ADAMTS13 enzyme cleaves von Willebrand factor, which, in its un-cleaved form, interacts with platelets and causes them to stick together and adhere to the walls of blood vessels, forming clots. Defects in ADAMTS13 are associated with TTP.

In some embodiments, administering the provided composition results in the expression of a ADAMTS13 protein level at or above about 100 ng/mg, about 200 ng/mg, about 300 ng/mg, about 400 ng/mg, about 500 ng/mg, about 600 ng/mg, about 700 ng/mg, about 800 ng/mg, about 900 ng/mg, about 1000 ng/mg, about 1200 ng/mg or about 1400 ng/mg of total protein in the liver.

In some embodiments, the expression of the ADAMTS13 protein is detectable 1 to 96 hours after administration. For example, in some embodiments, expression of ADAMTS13 protein is detectable 1 to 84 hours, 1 to 72 hours, 1 to 60 hours, 1 to 48 hours, 1 to 36 hours, 1 to 24 hours, 1 to 12 hours, 1 to 10 hours, 1 to 8 hours, 1 to 6 hours, 1 to 4 hours, 1 to 2 hours, 2 to 96 hours, 2 to 84 hours, 2 to 72 hours, 2 to 60 hours, 2 to 48 hours, 2 to 36 hours, 2 to 24 hours, 2 to 12 hours, 2 to 10 hours, 2 to 8 hours, 2 to 6 hours, 2 to 4 hours, 4 to 96 hours, 4 to 84 hours, 4 to 72 hours, 4 to 60 hours, 4 to 48 hours, 4 to 36 hours, 4 to 24 hours, 4 to 12 hours, 4 to 10 hours, 4 to 8 hours, 4 to 6 hours, 6 to 96 hours, 6 to 84 hours, 6 to 72 hours, 6 to 60 hours, 6 to 48 hours, 6 to 36 hours, 6 to 24 hours, 6 to 12 hours, 6 to 10 hours, 6 to 8 hours, 8 to 96 hours, 8 to 84 hours, 8 to 72 hours, 8 to 60 hours, 8 to 48 hours, 8 to 36 hours, 8 to 24 hours, 8 to 12 hours, 8 to 10 hours, 10 to 96 hours, 10 to 84 hours, 10 to 72 hours, 10 to 60 hours, 10 to 48 hours, 10 to 36 hours, 10 to 24 hours, 10 to 12 hours, 12 to 96 hours, 12 to 84 hours, 12 to 72 hours, 12 to 60 hours, 12 to 48 hours, 12 to 36 hours, 12 to 24 hours, 24 to 96 hours, 24 to 84 hours, 24 to 72 hours, 24 to 60 hours, 24 to 48 hours, 24 to 36 hours, 36 to 96 hours, 36 to 84 hours, 36 to 72 hours, 36 to 60 hours, 36 to 48 hours, 48 to 96 hours, 48 to 84 hours, 48 to 72 hours, 48 to 60 hours, 48 to 84 hours, 48 to 72 hours, 48 to 60 hours, 60 to 96 hours, 60 to 84 hours, 60 to 72 hours, 72 hours to 96 hours, 72 hours to 84 hours, or 84 hours to 96 hours after administration. For example, in certain embodiments, the expression of the ADAMTS13 protein is detectable 6, 12, 18, 24, 30, 36, 42, 48, 54, 60, 66, and/or 72 hours after the administration. In some embodiments, the expression of the ADAMTS13 protein is detectable 1 day to 7 days after the administration. For example, in some embodiments, ADAMTS13 protein is detectable 1 day, 2 days, 3 days, 4 days, 5 days, 6 days, and/or 7 days after the administration. In some embodiments, the expression of the ADAMTS13 protein is detectable 1 week to 8 weeks after the administration. For example, in some embodiments, ADAMTS13 protein is detectable 1 week, 2 weeks, 3 weeks, and/or 4 weeks after the administration. In some embodiments, the expression of the ADAMTS13 protein is detectable after a month after the administration.

In some embodiments, administering the composition results in reduced von Willebrand factor (vWF) levels in a subject as compared to baseline vWR levels before treatment. Typically, the baseline levels are measured in the subject immediately before treatment. Typically, vWF levels are measured in a biological sample. Suitable biological samples include, for example, whole blood, plasma or serum.

In some embodiments, administering the composition results in reduced vWF levels in a biological sample taken from the subject by at least about 10%, 20%, 30%, 40%, 50%, 60%, 70%, 80%, 90%, or 95% as compared to baseline vWF levels immediately before treatment. In some embodiments, administering the composition results in reduced plasma vWF levels in the subject to less than about 2000 μM, 1500 μM, 1000 μM, 750 μM, 500 μM, 250 μM, 100 μM, 90 μM, 80 μM, 70 μM, 60 μM, 50 μM, 40 μM, or 30 μM.

In some embodiments, administering the provided composition results in reduced vWF levels in plasma or serum samples taken from the subject as compared to baseline vWF levels immediately before treatment. In some embodiments, administering the provided composition results in reduced vWF levels in plasma or serum as compared to vWF levels in subjects who are not treated. In some embodiments, administering the composition results in reduction of vWF levels to about 3000 μmol/L or less, about 2750 μmol/L or less, about 2500 μmol/L or less, about 2250 μmol/L or less, about 2000 μmol/L or less, about 1750 μmol/L or less, about 1500 μmol/L or less, about 1250 μmol/L or less, about 1000 μmol/L or less, about 750 μmol/L or less, about 500 μmol/L or less, about 250 μmol/L or less, about 100 μmol/L or less or about 50 μmol/L or less in the plasma or serum. In a particular embodiment, administering the composition results in reduction of vWF levels to about 50 μmol/L or less in the plasma or serum 4. Production of Polynucleotides The vectors provided herein can be made using standard techniques of molecular biology. For example, the various elements of the vectors provided herein can be obtained using recombinant methods, such as by screening cDNA and genomic libraries from cells, or by deriving the polynucleotides from a vector known to include the same.

The various elements of the vectors provided herein can also be produced synthetically, rather than cloned, based on the known sequences. The complete sequence can be assembled from overlapping oligonucleotides prepared by standard methods and assembled into the complete sequence. See, e.g., Edge, Nature (1981) 292:756; Nambair et al., Science (1984) 223: 1299; and Jay et al., J. Biol. Chem. (1984) 259:631 1.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. One method of obtaining nucleotide sequences encoding the desired vector elements is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al., Proc. Natl. Acad. Sci. USA (1991) 88:4084-4088. Additionally, oligonucleotide-directed synthesis (Jones et al., Nature (1986) 54:75-82), oligonucleotide directed mutagenesis of preexisting nucleotide regions (Riechmann et al., Nature (1988) 332:323-327 and Verhoeyen et al., Science (1988) 239: 1534-1536), and enzymatic filling-in of gapped oligonucleotides using T4 DNA polymerase (Queen et al., Proc. Natl. Acad. Sci. USA (1989) 86: 10029-10033) can be used.

The precursor RNA provided herein can be generated by incubating a vector provided herein under conditions permissive of transcription of the precursor RNA encoded by the vector. For example, in some embodiments a precursor RNA is synthesized by incubating a vector provided herein that comprises an RNA polymerase promoter upstream of its 5' duplex forming region and/or expression sequence with a compatible RNA polymerase enzyme under conditions permissive of in vitro transcription. In some embodiments, the vector is incubated inside of a cell by a bacteriophage RNA polymerase or in the nucleus of a cell by host RNA polymerase II.

In certain embodiments, provided herein is a method of generating precursor RNA by performing in vitro transcription using a vector provided herein as a template (e.g., a vector provided herein with a RNA polymerase promoter positioned upstream of the 5' homology region).

In certain embodiments, the resulting precursor RNA can be used to generate circular RNA (e.g., a circular RNA polynucleotide provided herein) by incubating it in the presence of magnesium ions and guanosine nucleotide or nucleoside at a temperature at which RNA circularization occurs (e.g., between 20° C. and 60° C.).

Thus, in certain embodiments provided herein is a method of making circular RNA. In certain embodiments, the method comprises synthesizing precursor RNA by transcription (e.g., run-off transcription) using a vector provided herein (e.g., a vector comprising, in the following order, a 5' homology region, a 3' group I intron fragment, a first spacer, an Internal Ribosome Entry Site (IRES), an expression sequence, a second spacer, a 5' group I intron fragment, and a 3' homology region) as a template, and incubating the resulting precursor RNA in the presence of divalent cations (e.g., magnesium ions) and GTP such that it circularizes to form circular RNA. In some embodiments, the precursor RNA disclosed herein is capable of circularizing in the absence of magnesium ions and GTP and/or without the step of incubation with magnesium ions and GTP. It has been discovered that circular RNA has reduced immunogenicity relative to a corresponding mRNA, at least partially because the mRNA contains an immunogenic 5' cap. When transcribing a DNA vector from certain promoters (e.g., a T7 promoter) to produce a precursor RNA, it is understood that the 5' end of the precursor RNA is G. To reduce the immunogenicity of a circular RNA composition that contains a low level of contaminant linear mRNA, an excess of GMP relative to GTP can be provided during transcription such that most transcripts contain a 5' GMP, which cannot be capped. Therefore, in some embodiments, transcription is carried out in the presence of an excess of GMP. In some embodiments, transcription is carried out where the ratio of GMP concentration to GTP concentration is within the range of about 3:1 to about 15:1, for example, about 3:1 to about 10:1, about 3:1 to about 5:1, about 3:1, about 4:1, or about 5:1.

In some embodiments, a composition comprising circular RNA has been purified. Circular RNA may be purified by any known method commonly used in the art, such as column chromatography, gel filtration chromatography, and size exclusion chromatography. In some embodiments, purification comprises one or more of the following steps: phosphatase treatment, HPLC size exclusion purification, and RNase R digestion. In some embodiments, purification comprises the following steps in order: RNase R digestion, phosphatase treatment, and HPLC size exclusion purification. In some embodiments, purification comprises reverse phase HPLC. In some embodiments, a purified composition contains less double stranded RNA, DNA splints, triphosphorylated RNA, phosphatase proteins, protein ligases, capping enzymes and/or nicked RNA than unpurified RNA. In some embodiments, a purified composition is less immunogenic than an unpurified composition. In some embodiments, immune cells exposed to a purified composition produce less IFN-β1, RIG-I, IL-2, IL-6, IFNδ, and/or TNFα than immune cells exposed to an unpurified composition.

5. Ionizable Lipids

In certain embodiments disclosed herein are ionizable lipids that may be used as a component of a transfer vehicle to facilitate or enhance the delivery and release of circular RNA to one or more target cells (e.g., by permeating or fusing with the lipid membranes of such target cells). In certain embodiments, an ionizable lipid comprises one or more cleavable functional groups (e.g., a disulfide) that allow, for example, a hydrophilic functional head-group to dissociate from a lipophilic functional tail-group of the compound (e.g., upon exposure to oxidative, reducing or acidic conditions), thereby facilitating a phase transition in the lipid bilayer of the one or more target cells.

In some embodiments, an ionizable lipid is a lipid as described in international patent application PCT/US2018/058555.

In some of embodiments, a cationic lipid has the following formula:

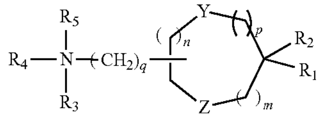

wherein:

$R^1$ and $R^2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R^4$ are either the same or different and independently optionally substituted $C_1$-$C_6$ alkyl, optionally substituted $C_2$-$C_6$ alkenyl, or optionally substituted $C_2$-$C_6$ alkynyl or R3 and $R^4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl; m, n, and p are either the same or different and independently either 0 or 1 with the proviso that m, n, and p are not simultaneously 0; q is 0, 1, 2, 3, or 4; and Y and Z are either the same or different and independently O, S, or NH.

In one embodiment, $R_1$ and $R^2$ are each linoleyl, and the amino lipid is a dilinoleyl amino lipid.

In one embodiment, the amino lipid is a dilinoleyl amino lipid.

In various other embodiments, a cationic lipid has the following structure:

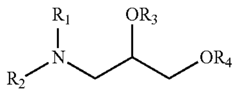

or a pharmaceutically acceptable salt, tautomer, prodrug or stereoisomer thereof, wherein:

$R_1$ and $R_2$ are each independently selected from the group consisting of H and $C_1$-$C_3$ alkyls; and $R_3$ and $R_4$ are each independently an alkyl group having from about 10 to about 20 carbon atoms, wherein at least one of $R_3$ and $R_4$ comprises at least two sites of unsaturation.

In some embodiments, $R_3$ and $R_4$ are each independently selected from dodecadienyl, tetradecadienyl, hexadecadienyl, linoleyl, and icosadienyl. In an embodiment, $R_3$ and $R_4$ and are both linoleyl. In some embodiments, $R_3$ and/or $R_4$ may comprise at least three sites of unsaturation (e.g., $R_3$ and/or $R_4$ may be, for example, dodecatrienyl, tetradectrienyl, hexadecatrienyl, linolenyl, and icosatrienyl).

In some embodiments, a cationic lipid has the following structure:

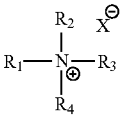

or a pharmaceutically acceptable salt, tautomer, prodrug or stereoisomer thereof, wherein:

$R_1$ and $R_2$ are each independently selected from H and $C_1$-$C_3$ alkyls;

$R_3$ and $R_4$ are each independently an alkyl group having from about 10 to about 20 carbon atoms, wherein at least one of $R_3$ and $R_4$ comprises at least two sites of unsaturation.

In one embodiment, $R_3$ and $R_4$ are the same, for example, in some embodiments $R_3$ and $R_4$ are both linoleyl ($C_{18}$-alkyl). In another embodiment, $R_3$ and $R_4$ are different, for example, in some embodiments, $R_3$ is tetradectrienyl ($C_{14}$-alkyl) and $R_4$ is linoleyl ($C_{18}$-alkyl). In a preferred embodiment, the cationic lipid(s) of the present invention are symmetrical, i.e., $R_3$ and $R_4$ are the same. In another preferred embodiment, both $R_3$ and $R_4$ comprise at least two sites of unsaturation. In some embodiments, $R_3$ and $R_4$ are each independently selected from dodecadienyl, tetradecadienyl, hexadecadienyl, linoleyl, and icosadienyl. In an embodiment, $R_3$ and $R_4$ are both linoleyl. In some embodiments, $R_3$ and/or $R_4$ comprise at least three sites of unsaturation and are each independently selected from dodecatrienyl, tetradectrienyl, hexadecatrienyl, linolenyl, and icosatrienyl.

In various embodiments, a cationic lipid has the formula:

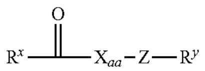

or a pharmaceutically acceptable salt, tautomer, prodrug or stereoisomer thereof, wherein:

$X_{aa}$ is a D- or L-amino acid residue having the formula —$NR^N$—$CR^1R^2$—C(C═O)—, or a peptide or a peptide of amino acid residues having the formula —{$NR^N$—$CR^1R^2$—C(C═O)}$_n$—, wherein n is an integer from 2 to 20;

$R^1$ is independently, for each occurrence, a non-hydrogen or a substituted or unsubstituted side chain of an amino acid;

$R^2$ and $R^N$ are independently, for each occurrence, hydrogen, an organic group consisting of carbon, oxygen, nitrogen, sulfur, and hydrogen atoms, or any combination of the foregoing, and having from 1 to 20 carbon atoms, $C_{(1-5)}$ alkyl, cycloalkyl, cycloalkylalkyl, $C_{(1-5)}$alkenyl, $C_{(1-5)}$alkynyl, $C_{(1-5)}$alkanoyl, $C_{(1-5)}$alkanoyloxy, $C_{(1-5)}$alkoxy, $C_{(1-5)}$ alkoxy-$C_{(1-5)}$alkyl, $C_{(1-5)}$alkoxy-$C_{(1-5)}$alkoxy, $C_{(1-5)}$alkyl-amino-$C_{(1-5)}$alkyl-, $C_{(1-5)}$dialkyl-amino-$C_{(1-5)}$ alkyl-, nitro-$C_{(1-5)}$alkyl, cyano-$C_{(1-5)}$alkyl, aryl-$C_{(1-5)}$alkyl, 4-biphenyl-$C_{(1-5)}$alkyl, carboxyl, or hydroxyl; Z is —NH—, —O—, —S—, —$CH_2$S—, —$CH_2$S(O)—, or an organic linker consisting of 1-40 atoms selected from hydrogen, carbon, oxygen, nitrogen, and sulfur atoms (preferably, Z is —NH— or —O—);

$R^x$ and $R^y$ are, independently, (i) a lipophilic tail derived from a lipid (which can be naturally occurring or synthetic), e.g., a phospholipid, a glycolipid, a triacylglycerol, a glycerophospholipid, a sphingolipid, a ceramide, a sphingomyelin, a cerebroside, or a ganglioside, wherein the tail optionally includes a steroid; (ii) an amino acid terminal group selected from hydrogen, hydroxyl, amino, and an organic protecting group; or (iii) a substituted or unsubstituted $C_{(3-22)}$alkyl, $C_{(6-12)}$cycloalkyl, $C_{(6-12)}$cycloalkyl-$C_{(3-22)}$alkyl, $C_{(3-22)}$alkenyl, $C_{(3-22)}$alkynyl, $C_{(3-22)}$alkoxy, or $C_{(6-12)}$-alkoxy $C_{(3-22)}$alkyl;

In some embodiments, one of $R^x$ and $R^y$ is a lipophilic tail as defined above and the other is an amino acid terminal group. In some embodiments, both $R^x$ and $R^y$ are lipophilic tails.

In some embodiments, at least one of $R^x$ and $R^y$ is interrupted by one or more biodegradable groups (e.g., —OC(O)—, —C(O)O—, —SC(O)—, —C(O)S—, —OC(S)—, —C(S)O—, —S—S—, —C(O)($NR^5$)—, —N($R^5$)C(O)—, —C(S)($NR^5$)—, —N($R^5$)C(O)—, —N($R^5$)C(O)N($R^5$)—, —OC(O)O—, —OSi($R^5$)$_2$O—, —C(O)($CR^3R^4$)C(O)O—, —OC(O)($CR^3R^4$)C(O)—, or

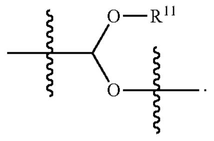

In some embodiments, $R^{11}$ is a $C_2$-$C_8$alkyl or alkenyl.

In some embodiments, each occurrence of $R^5$ is, independently, H or alkyl.

In some embodiments, each occurrence of $R^3$ and $R^4$ are, independently H, halogen, OH, alkyl, alkoxy, —$NH_2$, alkylamino, or dialkylamino; or $R_3$ and $R_4$, together with the carbon atom to which they are directly attached, form a cycloalkyl group. In some particular embodiments, each occurrence of $R^3$ and $R^4$ are, independently H or $C_1$-$C_4$alkyl.

In some embodiments, $R^x$ and $R^y$ each, independently, have one or more carbon-carbon double bonds.

In some embodiments, the cationic lipid is one of the following:

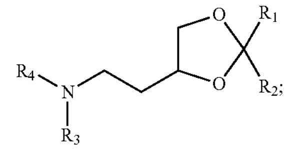

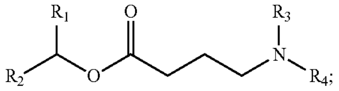

or

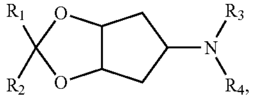

or a pharmaceutically acceptable salt, tautomer, prodrug or stereoisomer thereof, wherein:

$R_1$ and $R_2$ are each independently alkyl, alkenyl, or alkynyl, each of which can optionally substituted;

$R_3$ and $R_4$ are each independently a $C_1$-$C_6$ alkyl, or $R_3$ and $R_4$ are taken together to form an optionally substituted heterocyclic ring.

A representative useful dilinoleyl amino lipid has the formula:

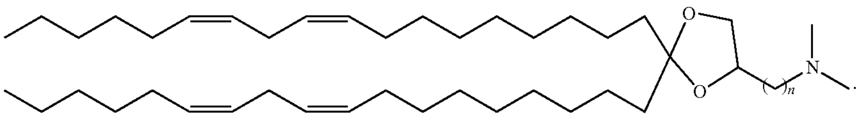

wherein n is 0, 1, 2, 3, or 4.

In one embodiment, a cationic lipid is DLin-K-DMA. In one embodiment, a cationic lipid is DLin-KC2-DMA (DLin-K-DMA above, wherein n is 2).

In one embodiment, a cationic lipid has the following structure:

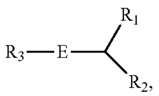

or a pharmaceutically acceptable salt, tautomer, prodrug or stereoisomer thereof, wherein:

$R_1$ and $R_2$ are each independently for each occurrence optionally substituted $C_{10}$-$C_{30}$ alkyl, optionally substituted $C_{10}$-$C_{30}$ alkenyl, optionally substituted $C_{10}$-$C_{30}$ alkynyl or optionally substituted $C_{10}$-$C_{30}$ acyl;

$R_3$ is H, optionally substituted $C_2$-$C_{10}$ alkyl, optionally substituted $C_2$-$C_{10}$ alkenyl, optionally substituted $C_2$-$C_{10}$ alkylyl, alkylhetrocycle, alkylpbosphate, alkylphosphorothioate, alkylphosphorodithioate, alkylphosphonate, alkylamine, hydroxyalkyl, ω-aminoalkyl, ω-(substituted)aminoalkyl, ω-phosphoalkyl, ω-thiophosphoalkyl, optionally substituted polyethylene glycol (PEG, mw 100-40K), optionally substituted mPEG (mw 120-40K), heteroaryl, or heterocycle, or a linker ligand, for example, in some embodiments, $R_3$ is $(CH_3)_2N(CH_2)_n$—, wherein n is 1, 2, 3 or 4;

E is O, S, N(O), C(O), OC(O), C(O)O, N(O)C(O), C(O)N(O), (O)N(CO)O, O(CO)N(O), S(O), $NS(O)_2N(O)$, $S(O)_2$, $N(O)S(O)_2$, SS, O═N, aryl, heteroaryl, cyclic or heterocycle, for example —C(O)O, wherein — is a point of connection to $R_3$; and Q is H, alkyl, ω-aminoalkyl, ω-(substitutcd)aminoalkyl, ω-phosphoalkyl or ω-thioplosploalkyl.

In one specific embodiment, the cationic lipid of Embodiments 1, 2, 3, 4 or 5 has the following structure:

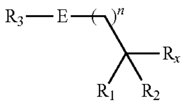

or a pharmaceutically acceptable salt, tautomer, prodrug or stereoisomer thereof, wherein:

E is O, S, N(O), C(O), N(O)C(O), C(O)N(O), (O)N(CO)O, O(CO)N(O), S(O), $NS(O)_2N(O)$, $S(O)_2$, $N(O)S(O)_2$, SS, O═N, aryl, heteroaryl, cyclic or heterocycle;

Q is H, alkyl, Ω-aminoalkyl, ω-(substituted)aminoalkyl, Ω-phosphoalkyl or Ω-thiophosphoalkyl;

$R_1$ and $R_2$ and $R_x$ are each independently for each occurrence H, optionally substituted $C_1$-$C_{10}$alkyl, optionally substituted $C_{10}$-$C_{30}$ alkyl, optionally substituted $C_{10}$-$C_{30}$ alkenyl, optionally substituted $C_{10}$-$C_{30}$ alkynyl, optionally substituted $C_{10}$-$C_{30}$ acyl, or linker-ligand, provided that at least one of $R_1$, $R_2$ and $R_x$ is not H;

$R_3$ is H, optionally substituted $C_1$-$C_{10}$ alkyl, optionally substituted $C_2$-$C_{10}$alkenyl, optionally substituted $C_2$-$C_{10}$ alkynyl, alkylhetrocycle, alkylphosphate, alkylphosphorothioate, alkylphosphorodithioate, alkylphosphonate, alkylamine, hydroxyalkyl, ω-aminoalkyl, ω-(substituted)aminoalkyl, ω-phosphoalkyl, ω-thiophosphoalkyl, optionally substituted polyethylene glycol (PEG, mw 100-40K), optionally substituted mPEG (mw 120-40K), heteroaryl, or heterocycle, or linker-ligand; and n is 0, 1, 2, or 3.

In one embodiment, the cationic lipid of Embodiments 1, 2, 3, 4 or 5 has the structure of Formula I:

I

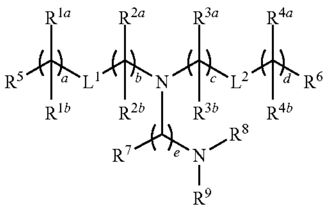

or a pharmaceutically acceptable salt, tautomer, prodrug or stereoisomer thereof, wherein:

one of $L^1$ or $L^2$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, $NR^aC$(═O)$NR^a$—, —OC(═O)$NR^a$— or —$NR^aC$(═O)O—, and the other of $L^1$ or $L^2$ is —O(C═O)—, —(C═O)O—, —C(═O)—, —O—, —$S(O)_x$—, —S—S—, —C(═O)S—, SC(═O)—, —$NR^aC$(═O)—, —C(═O)$NR^a$—, —$NR^aC$(═O)$NR^a$—, —OC(═O)$NR^a$— or —$NR^aC$(═O)O— or a direct bond;

$R^a$ is H or $C_1$-$C_{12}$ alkyl;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent Rib and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24;

e is 1 or 2; and x is 0, 1 or 2.

In some embodiments of Formula I, $L^1$ and $L^2$ are independently —O(C═O)— or —(C═O)O—.

In certain embodiments of Formula I, at least one of $R^{1a}$, $R^{2a}$, $R^{3a}$ or $R^{4a}$ is $C_1$-$C_{12}$ alkyl, or at least one of $L^1$ or $L^2$ is —O(C═O)— or —(C═O)O—. In other embodiments, $R^{1a}$ and $R^{1b}$ are not isopropyl when a is 6 or n-butyl when a is 8. In still further embodiments of Formula I, at least one of $R^{1a}$, $R^{2a}$, $R^{3a}$ or $R^{4a}$ is $C_1$-$C_{12}$ alkyl, or at least one of $L^1$ or $L^2$ is —O(C═O)— or —(C═O)O—; and $R^{1a}$ and $R^{lb}$ are not isopropyl when a is 6 or n-butyl when a is 8.

In other embodiments of Formula I, $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

In certain embodiments of Formula I, any one of $L^1$ or $L^2$ may be —O(C═O)— or a carbon-carbon double bond. $L^1$ and $L^2$ may each be —O(C═O)— or may each be a carbon-carbon double bond.

In some embodiments of Formula I, one of $L^1$ or $L^2$ is —O(C═O)—. In other embodiments, both $L^1$ and $L^2$ are —O(C═O)—.

In some embodiments of Formula I, one of $L^1$ or $L^2$ is —(C═O)O—. In other embodiments, both $L^1$ and $L^2$ are —(C═O)O—.

In some other embodiments of Formula I, one of $L^1$ or $L^2$ is a carbon-carbon double bond. In other embodiments, both $L^1$ and $L^2$ are a carbon-carbon double bond.

In still other embodiments of Formula I, one of $L^1$ or $L^2$ is —O(C═O)— and the other of $L^1$ or $L^2$ is —(C═O)O—. In more embodiments, one of $L^1$ or $L^2$ is —O(C═O)— and the other of $L^1$ or $L^2$ is a carbon-carbon double bond. In yet more embodiments, one of $L^1$ or $L^2$ is —(C═O)O— and the other of $L^1$ or $L^2$ is a carbon-carbon double bond.

It is understood that "carbon-carbon" double bond, as used throughout the specification, refers to one of the following structures:

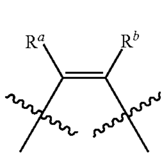

or

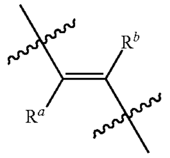

wherein $R^a$ and $R^b$ are, at each occurrence, independently H or a substituent. For example, in some embodiments $R^a$ and R are, at each occurrence, independently H, $C_1$-$C_{12}$ alkyl or cycloalkyl, for example H or $C_1$-$C_{12}$ alkyl.

In other embodiments, the lipid compounds of Formula I have the following Formula (Ia):

(Ia)

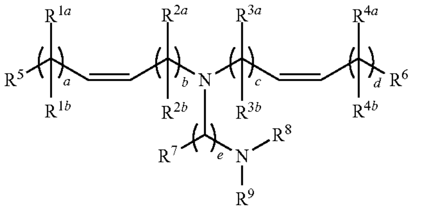

In other embodiments, the lipid compounds of Formula I have the following Formula (Ib):

(Ib)

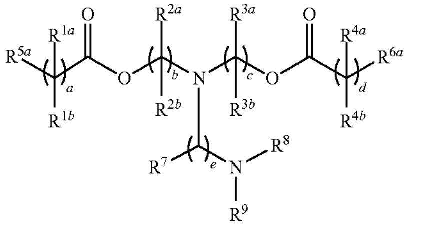

In yet other embodiments, the lipid compounds of Formula I have the following Formula (Ic):

(Ic)

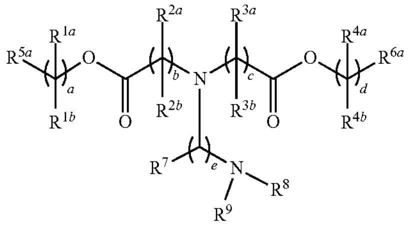

In certain embodiments of the lipid compound of Formula I, a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some other embodiments of Formula I, b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some more embodiments of Formula I, c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain other embodiments of Formula I, d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some other various embodiments of Formula I, a and d are the same. In some other embodiments, b and c are the same. In some other specific embodiments, a and d are the same and b and c are the same.

The sum of a and b and the sum of c and d in Formula I are factors which may be varied to obtain a lipid of formula I having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such the sum of a and b and the sum of c and d is 12 or greater.

In some embodiments of Formula I, e is 1. In other embodiments, e is 2.

The substituents at $R^{1a}$, $R^{2a}$, $R^{3a}$ and $R^{4a}$ of Formula I are not particularly limited. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula I, $R^{1a}$, $R^{1b}$, $R^{4a}$ and $R^{4b}$ are $C_1$-$C_{12}$ alkyl at each occurrence.

In further embodiments of Formula I, at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula I, $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula I are not particularly limited in the foregoing embodiments. In certain embodiments one or both of $R^5$ or $R^6$ is methyl. In certain other embodiments one or both of $R^5$ or $R^6$ is cycloalkyl for example cyclohexyl. In these embodiments the cycloalkyl may be substituted or not substituted. In certain other embodiments the cycloalkyl is substituted with $C_1$-$C_{12}$ alkyl, for example tert-butyl.

The substituents at $R^7$ are not particularly limited in the foregoing embodiments of Formula I. In certain embodiments at least one $R^7$ is H. In some other embodiments, $R^7$ is H at each occurrence. In certain other embodiments $R^7$ is $C_1$-$C_{12}$ alkyl.

In certain other of the foregoing embodiments of Formula I, one of $R^8$ or $R^9$ is methyl. In other embodiments, both $R^8$ and $R^9$ are methyl.

In some different embodiments of Formula I, $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring.

In some embodiments of Embodiment 3, the first and second cationic lipids are each, independently selected from a lipid of Formula I.

In various different embodiments, the lipid of Formula I has one of the structures set forth in Table 1 below.

TABLE 1
| Representative Lipids of Formula 1 | | |
|---|---|---|
| No. | Structure | pKa |
| I-1 | 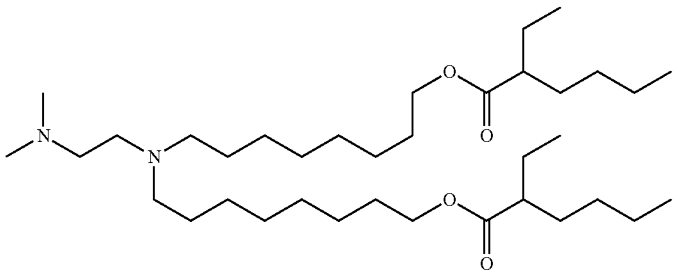 [SMILES: CCCCC(CC)C(=O)OCCCCCCCCN(CCCCCCCCOC(=O)C(CC)CCCC)CCN(C)C] | — |
| I-2 | 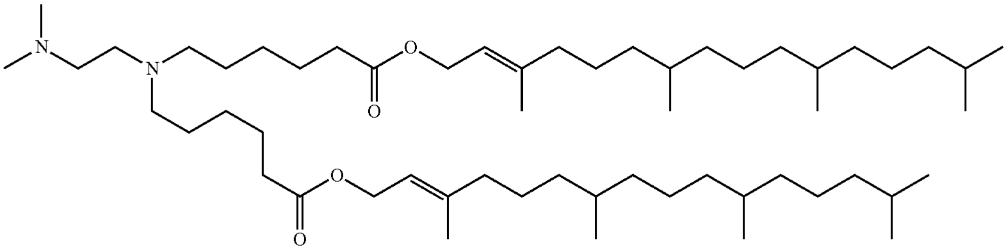 [SMILES: C/C(=C\COC(=O)CCCCCN(CCCCCC(=O)OC/C=C(\C)CCCC(C)CCCC(C)CCCC(C)C)CCN(C)C)CCCC(C)CCCC(C)CCCC(C)C] | 5.64 |
| I-3 | 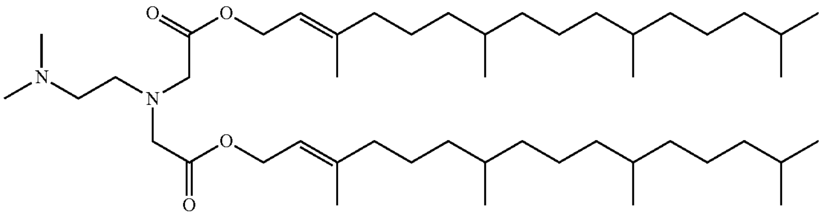 [SMILES: C/C(=C\COC(=O)CN(CCN(C)C)CC(=O)OC/C=C(\C)CCCC(C)CCCC(C)CCCC(C)C)CCCC(C)CCCC(C)CCCC(C)C] | 7.15 |
| I-4 | 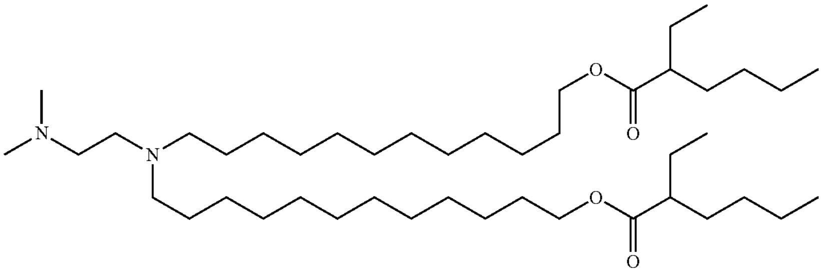 [SMILES: CCCCC(CC)C(=O)OCCCCCCCCCCCCN(CCCCCCCCCCCCOC(=O)C(CC)CCCC)CCN(C)C] | 6.43 |
| I-5 | 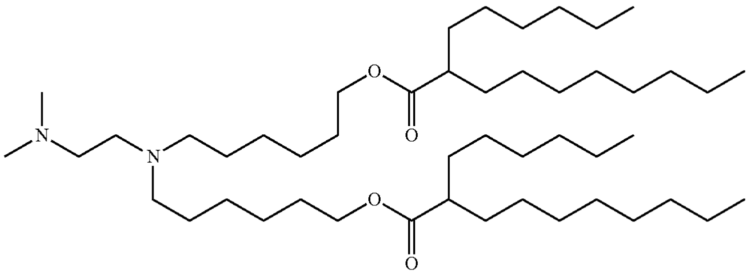 [SMILES: CCCCCCCCC(CCCCCC)C(=O)OCCCCCCN(CCCCCCOC(=O)C(CCCCCC)CCCCCCCC)CCN(C)C] | 6.28 |

TABLE 1-continued
| Representative Lipids of Formula 1 | | |
|---|---|---|
| No. | Structure | pKa |
| I-6 | 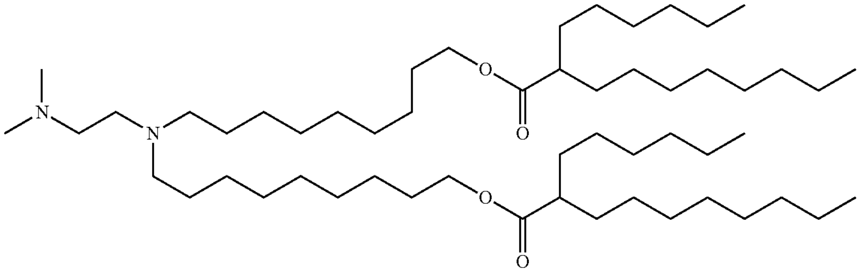 [SMILES: CCCCCCCCC(CCCCCC)C(=O)OCCCCCCCCCN(CCCCCCCCCOC(=O)C(CCCCCC)CCCCCCCC)CCN(C)C] | 6.12 |
| I-7 | 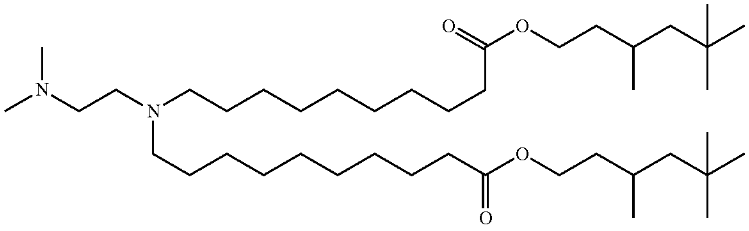 [SMILES: CC(CCOC(=O)CCCCCCCCCN(CCCCCCCCCC(=O)OCCC(C)CC(C)(C)C)CCN(C)C)CC(C)(C)C] | — |
| I-8 | 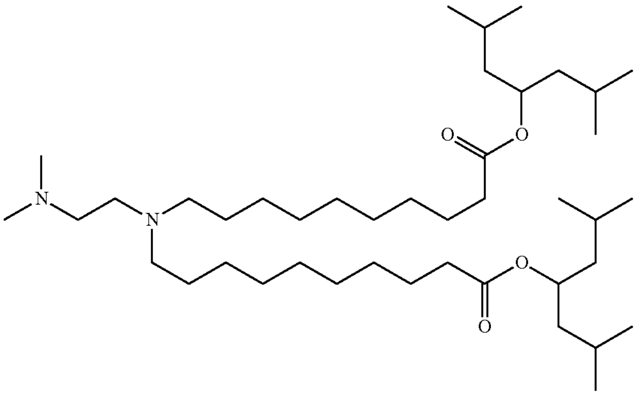 [SMILES: CC(C)CC(CC(C)C)OC(=O)CCCCCCCCCN(CCCCCCCCCC(=O)OC(CC(C)C)CC(C)C)CCN(C)C] | — |
| I-9 | 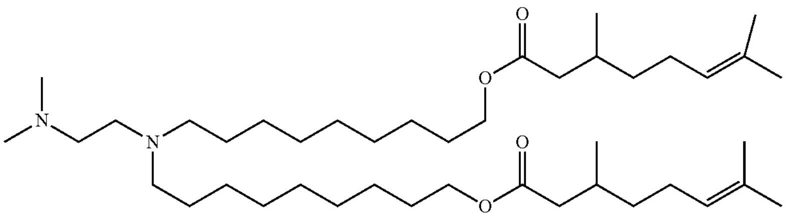 [SMILES: CC(C)=CCCC(C)CC(=O)OCCCCCCCCCN(CCCCCCCCCOC(=O)CC(C)CCC=C(C)C)CCN(C)C] | — |
| I-10 | 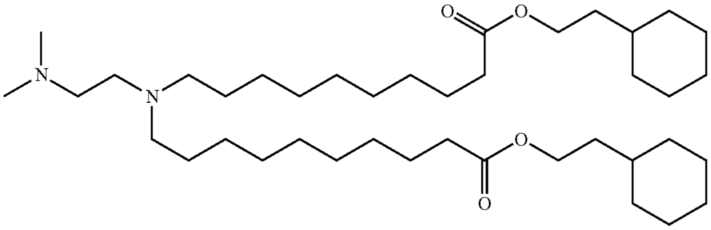 [SMILES: CN(C)CCN(CCCCCCCCCC(=O)OCCC1CCCCC1)CCCCCCCCCC(=O)OCCC1CCCCC1] | — |

TABLE 1-continued
| Representative Lipids of Formula 1 | | |
|---|---|---|
| No. | Structure | pKa |
| I-11 | 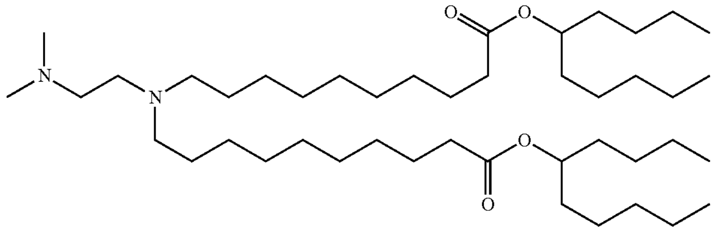 [SMILES: CCCCCC(CCCC)OC(=O)CCCCCCCCCN(CCCCCCCCCC(=O)OC(CCCC)CCCCC)CCN(C)C] | 6.36 |
| I-12 | 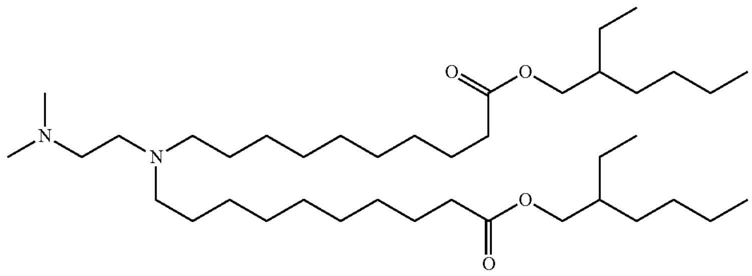 [SMILES: CCCCC(CC)COC(=O)CCCCCCCCCN(CCCCCCCCCC(=O)OCC(CC)CCCC)CCN(C)C] | — |
| I-13 | 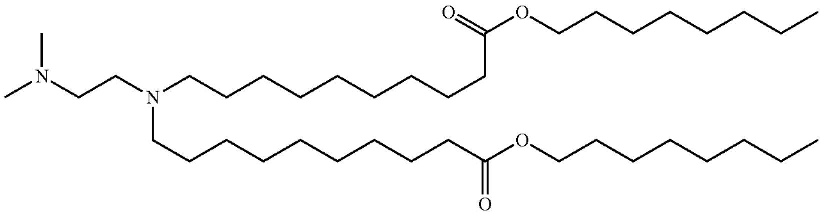 [SMILES: CCCCCCCCOC(=O)CCCCCCCCCN(CCCCCCCCCC(=O)OCCCCCCCC)CCN(C)C] | 6.51 |
| I-14 | 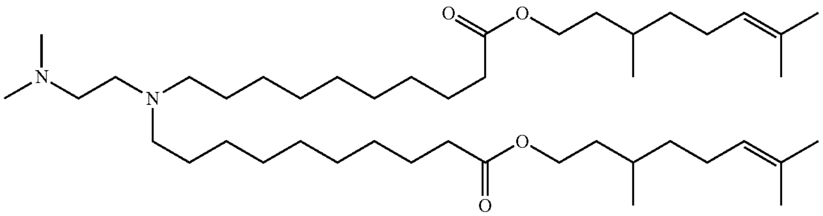 [SMILES: CC(C)=CCCC(C)CCOC(=O)CCCCCCCCCN(CCCCCCCCCC(=O)OCCC(C)CCC=C(C)C)CCN(C)C] | — |
| I-15 | 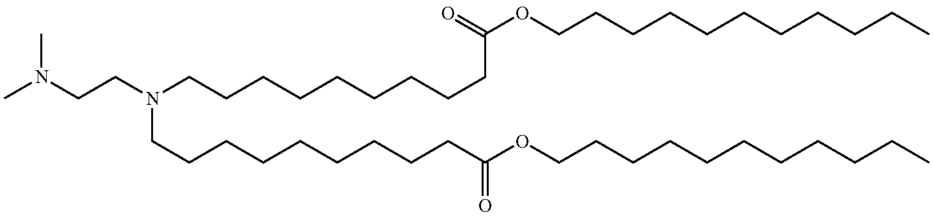 [SMILES: CCCCCCCCCCCOC(=O)CCCCCCCCCN(CCCCCCCCCC(=O)OCCCCCCCCCCC)CCN(C)C] | 6.30 |
| I-16 | 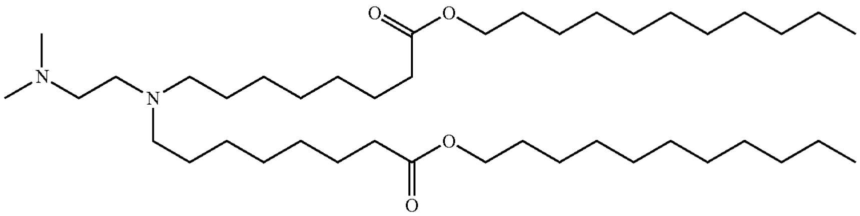 [SMILES: CCCCCCCCCCCOC(=O)CCCCCCCN(CCCCCCCC(=O)OCCCCCCCCCCC)CCN(C)C] | 6.63 |

TABLE 1-continued
| Representative Lipids of Formula 1 | | |
|---|---|---|
| No. | Structure | pKa |
| I-17 | 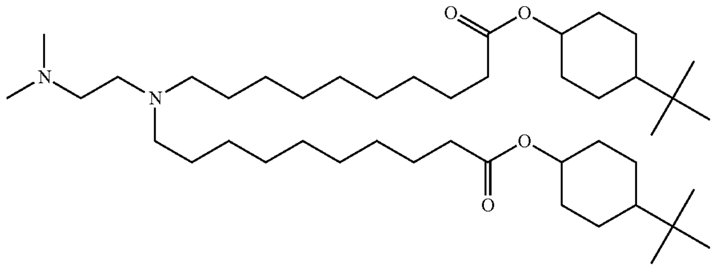 [SMILES: CN(C)CCN(CCCCCCCCCC(=O)OC1CCC(C(C)(C)C)CC1)CCCCCCCCCC(=O)OC1CCC(C(C)(C)C)CC1] | — |
| I-18 | 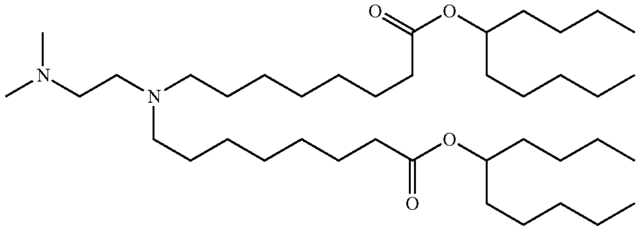 [SMILES: CCCCCC(CCCC)OC(=O)CCCCCCCN(CCCCCCCC(=O)OC(CCCC)CCCCC)CCN(C)C] | — |
| I-19 | 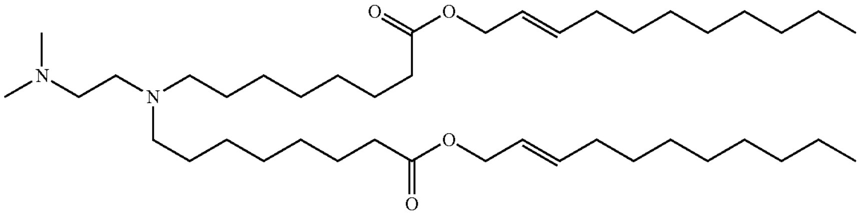 [SMILES: CCCCCCCC/C=C/COC(=O)CCCCCCCN(CCCCCCCC(=O)OC/C=C/CCCCCCCC)CCN(C)C] | 6.72 |
| I-20 | 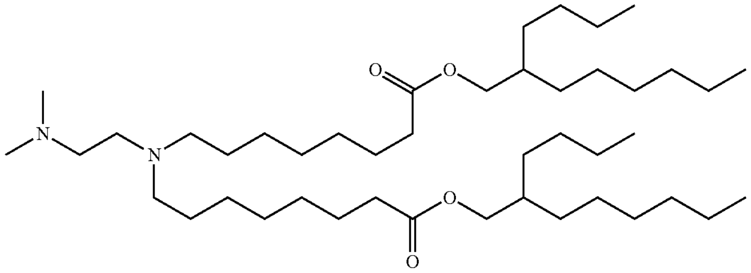 [SMILES: CCCCCCC(CCCC)COC(=O)CCCCCCCN(CCCCCCCC(=O)OCC(CCCC)CCCCCC)CCN(C)C] | 6.44 |
| I-21 | 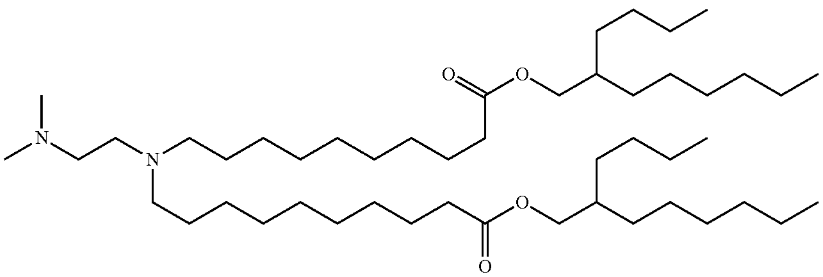 [SMILES: CCCCCCC(CCCC)COC(=O)CCCCCCCCCN(CCCCCCCCCC(=O)OCC(CCCC)CCCCCC)CCN(C)C] | 6.28 |

TABLE 1-continued
| Representative Lipids of Formula 1 | | |
|---|---|---|
| No. | Structure | pKa |
| I-22 | 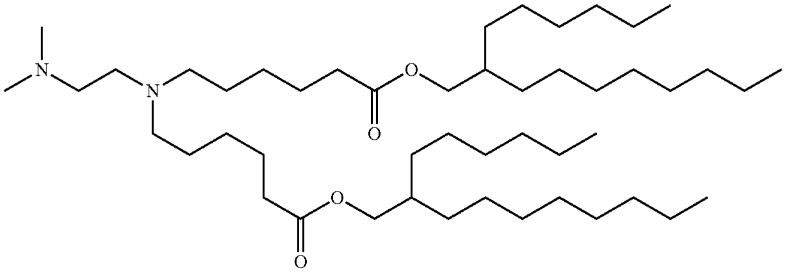 [SMILES: CCCCCCCCC(CCCCCC)COC(=O)CCCCCN(CCCCCC(=O)OCC(CCCCCC)CCCCCCCC)CCN(C)C] | 6.53 |
| I-23 | 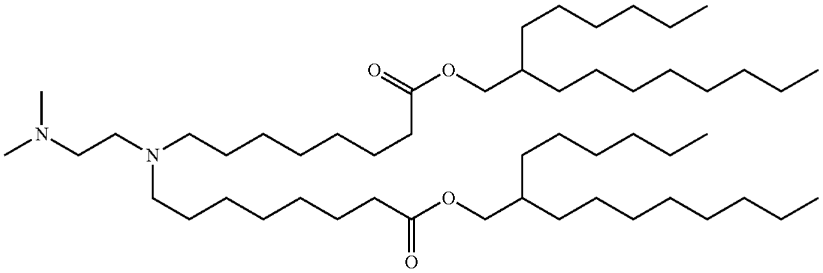 [SMILES: CCCCCCCCC(CCCCCC)COC(=O)CCCCCCCN(CCCCCCCC(=O)OCC(CCCCCC)CCCCCCCC)CCN(C)C] | 6.24 |
| I-24 | 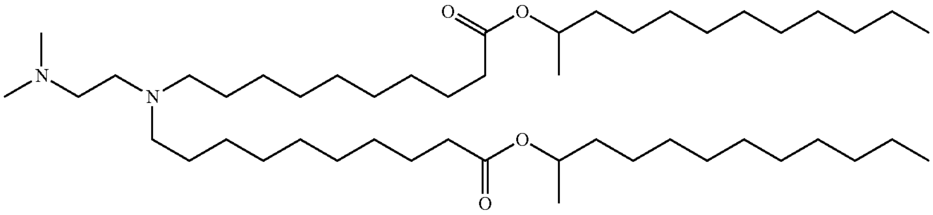 [SMILES: CCCCCCCCCCC(C)OC(=O)CCCCCCCCCN(CCCCCCCCCC(=O)OC(C)CCCCCCCCCC)CCN(C)C] | 6.28 |
| I-25 | 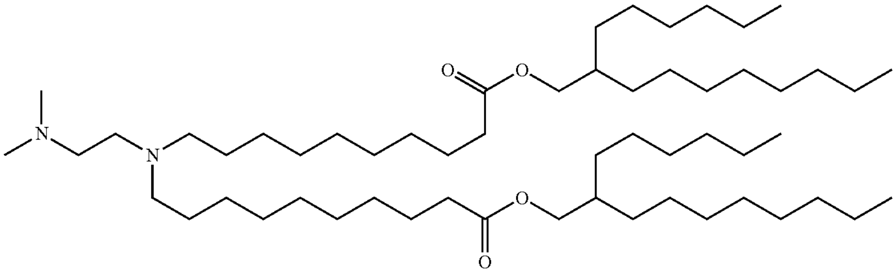 [SMILES: CCCCCCCCC(CCCCCC)COC(=O)CCCCCCCCCN(CCCCCCCCCC(=O)OCC(CCCCCC)CCCCCCCC)CCN(C)C] | 6.20 |
| I-33 | 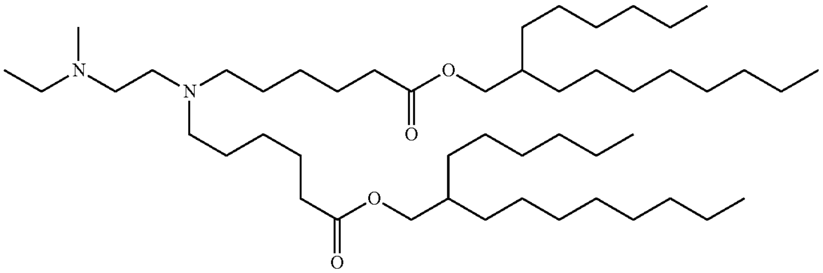 [SMILES: CCCCCCCCC(CCCCCC)COC(=O)CCCCCN(CCCCCC(=O)OCC(CCCCCC)CCCCCCCC)CCN(C)CC] | 6.27 |

TABLE 1-continued
| Representative Lipids of Formula 1 | | |
|---|---|---|
| No. | Structure | pKa |
| I-34 | 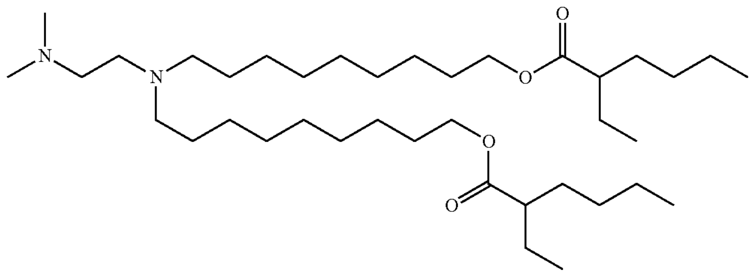 [SMILES: CCCCC(CC)C(=O)OCCCCCCCCCN(CCCCCCCCCOC(=O)C(CC)CCCC)CCN(C)C] | — |
| I-35 | 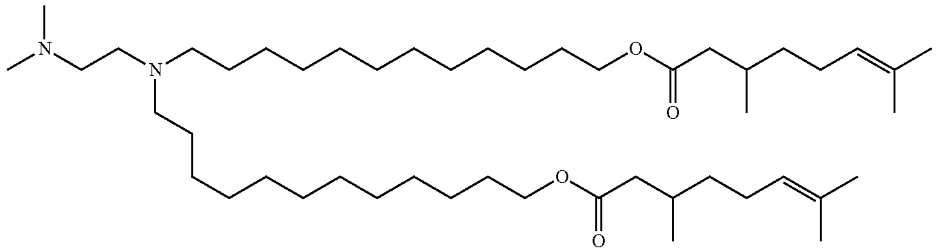 [SMILES: CC(C)=CCCC(C)CC(=O)OCCCCCCCCCCCCN(CCCCCCCCCCCCOC(=O)CC(C)CCC=C(C)C)CCN(C)C] | 6.21 |
| I-36 | 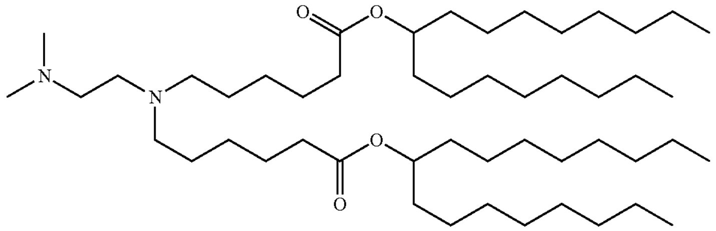 [SMILES: CCCCCCCCC(CCCCCCCC)OC(=O)CCCCCN(CCCCCC(=O)OC(CCCCCCCC)CCCCCCCC)CCN(C)C] | — |
| I-37 | 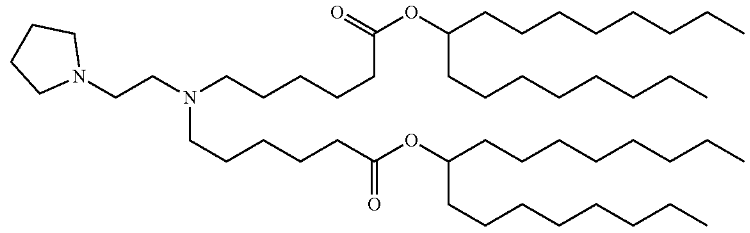 [SMILES: CCCCCCCCC(CCCCCCCC)OC(=O)CCCCCN(CCCCCC(=O)OC(CCCCCCCC)CCCCCCCC)CCN1CCCC1] | — |
| I-38 | 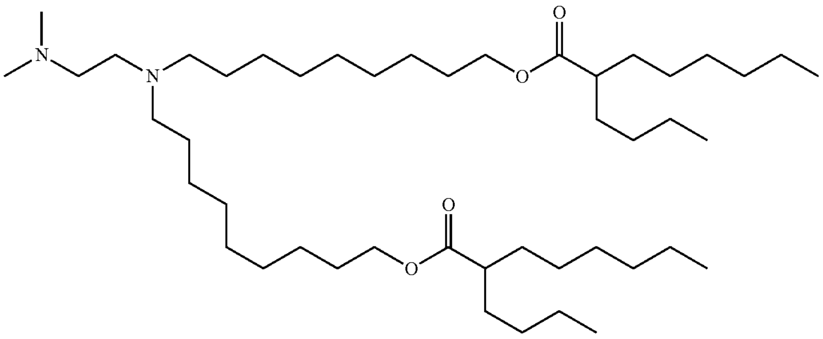 [SMILES: CCCCCCC(CCCC)C(=O)OCCCCCCCCCN(CCCCCCCCCOC(=O)C(CCCC)CCCCCC)CCN(C)C] | 6.24 |

TABLE 1-continued

| Representative Lipids of Formula 1 | | |
|---|---|---|
| No. | Structure | pKa |
| I-39 | 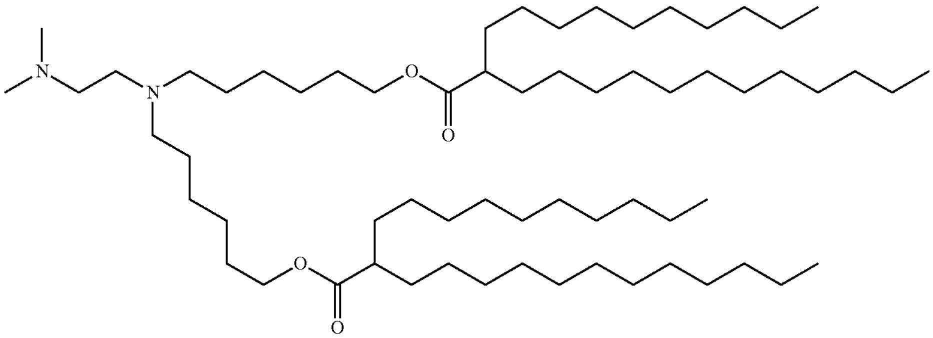 [SMILES: CCCCCCCCCCCCC(CCCCCCCCCC)C(=O)OCCCCCCN(CCCCCCOC(=O)C(CCCCCCCCCC)CCCCCCCCCCCC)CCN(C)C] | 5.82 |
| I-40 | 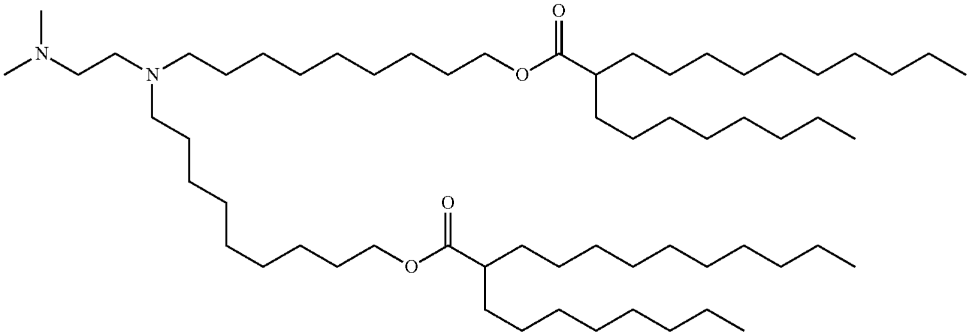 [SMILES: CCCCCCCCCCC(CCCCCCCC)C(=O)OCCCCCCCCCN(CCCCCCCCCOC(=O)C(CCCCCCCC)CCCCCCCCCC)CCN(C)C] | 6.38 |
| I-41 | 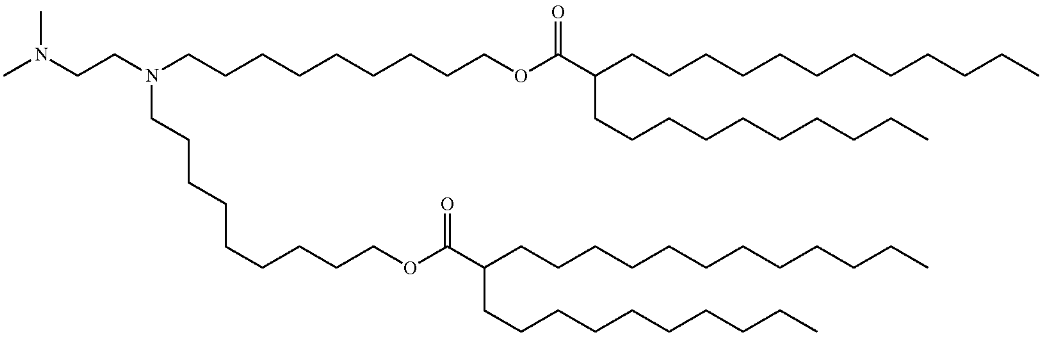 [SMILES: CCCCCCCCCCCCC(CCCCCCCCCC)C(=O)OCCCCCCCCCN(CCCCCCCCCOC(=O)C(CCCCCCCCCC)CCCCCCCCCCCC)CCN(C)C] | 5.91 |

In some embodiments, the cationic lipid of Embodiments 1, 2, 3, 4 or 5 has a structure of Formula II:

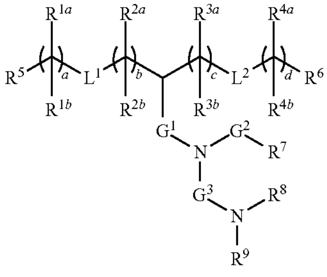

II or a pharmaceutically acceptable salt, tautomer, prodrug or stereoisomer thereof, wherein:

one of $L^1$ or $L^2$ is —O(C═O)—, —(C═O)O—, —C(═O)—, —O—, —$S(O)_x$—, —S—S—, —C(═O)S—, SC(═O)—, —$NR^a$C(═O)—, —C(═O)$NR^a$—, $NR^a$C(═O)$NR^a$—, —OC(═O)$NR^a$— or —$NR^a$C(═O)O—, and the other of $L^1$ or $L^2$ is —O(C═O)—, —(C═O)O—, —C(═O)—, —O—, —$S(O)_x$—, —S—S—, —C(═O)S—, SC(═O)—, —$NR^a$C(═O)—, —C(═O)$NR^a$, $NR^a$C(═O)$NR^a$—, —OC(═O)$NR^a$— or —$NR^a$C(═O)O— or a direct bond;

$G^1$ is $C_1$-$C_2$ alkylene, —(C═O)—, —O(C═O)—, —SC(═O)—, —$NR^a$C(═O)— or a direct bond;

$G^2$ is —C(═O)—, —(C═O)O—, —C(═O)S—, —C(═O)$NR^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In some embodiments of Formula (II), $L^1$ and $L^2$ are each independently —O(C=O)—, —(C=O)O— or a direct bond. In other embodiments, $G^1$ and $G^2$ are each independently —(C=O)— or a direct bond. In some different embodiments, $L^1$ and $L^2$ are each independently —O(C=O)—, —(C=O)O— or a direct bond; and $G^1$ and $G^2$ are each independently —(C=O)— or a direct bond.

In some different embodiments of Formula (II), $L^1$ and $L^2$ are each independently —C(=O)—, —O—, —$S(O)_x$—, —S—S—, —C(=O)S—, —SC(=O)—, —$NR^a$—, —$NR^a$C(=O)—, —C(=O)$NR^a$—, —$NR^a$C(=O)$NR^a$, —OC(=O)$NR^a$—, —$NR^a$C(=O)O—, —$NR^aS(O)_xNR^a$—, —$NR^a$S $(O)_x$ or —$S(O)_xNR^a$—

In other of the foregoing embodiments of Formula (II), the lipid compound has one of the following Formulae (IIA) or (IIB):

(IIA)

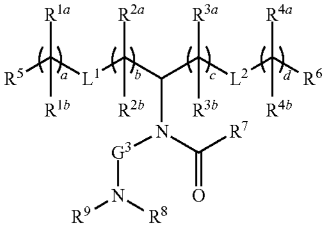

or (IIB)

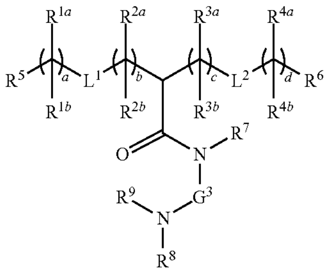

In some embodiments of Formula (II), the lipid compound has Formula (IIA). In other embodiments, the lipid compound has Formula (IIB).

In any of the foregoing embodiments of Formula (II), one of $L^1$ or $L^2$ is —O(C=O)—. For example, in some embodiments each of $L^1$ and $L^2$ are —O(C=O)—.

In some different embodiments of Formula (II), one of $L^1$ or $L^2$ is —(C=O)O—. For example, in some embodiments each of $L^1$ and $L^2$ is —(C=O)O—.

In different embodiments of Formula (II), one of $L^1$ or $L^2$ is a direct bond. As used herein, a "direct bond" means the group (e.g., $L^1$ or $L^2$) is absent. For example, in some embodiments each of $L^1$ and $L^2$ is a direct bond.

In other different embodiments of Formula (II), for at least one occurrence of $R^{1a}$ and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of Formula (II), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of Formula (II), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of Formula (II), for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

In various other embodiments of Formula (II), the lipid compound has one of the following Formulae (IIC) or (IID):

(IIC)

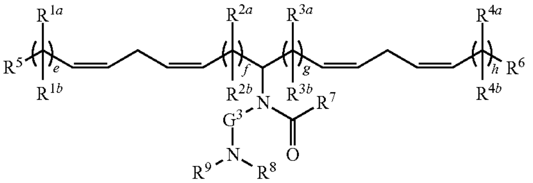

or (IID)

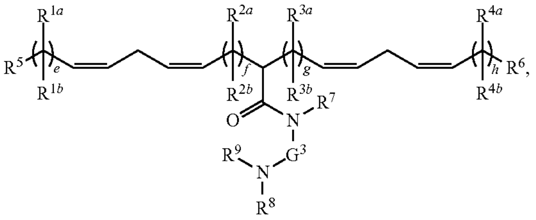

wherein e, f, g and h are each independently an integer from 1 to 12.

In some embodiments of Formula (II), the lipid compound has Formula (IIC). In other embodiments, the lipid compound has Formula (IID).

In various embodiments of Formulae (IIC) or (IID), e, f, g and h are each independently an integer from 4 to 10.

In certain embodiments of Formula (II), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7.

In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of Formula (II), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of Formula (II), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments of Formula (II), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of Formula (II), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of Formula (II), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of Formula (II), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of Formula (II), h is 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, h is 11. In yet other embodiments, h is 12.

In some other various embodiments of Formula (II), a and d are the same. In some other embodiments, b and c are the same. In some other specific embodiments and a and d are the same and b and c are the same.

The sum of a and b and the sum of c and d of Formula (II) are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such that the sum of a and b and the sum of c and d is 12 or greater.

The substituents at $R^1$, $R^{2a}$, $R^{3a}$ and $R^{4a}$ of Formula (II) are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (II), $R^{1a}$, $R^{1b}$, $R^{4a}$ and $R^{4b}$ are $C_1$-$C_2$ alkyl at each occurrence.

In further embodiments of Formula (II), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula (II), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (II) are not particularly limited in the foregoing embodiments. In certain embodiments one of $R^5$ or $R^6$ is methyl. In other embodiments each of $R^5$ or $R^6$ is methyl.

The substituents at $R^7$ of Formula (II) are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with $-(C{=}O)OR^b$, $-O(C{=}O)R$, $-C({=}O)R^b$, $-OR^b$, $-S(O)_xR^b$, $-S-SR^b$, $-C({=}O)SR^b$, $-SC({=}O)R^b$, $-NR^aR^b$, $-NR^aC({=}O)R^b$, $-C({=}O)NR^aR^b$, $-NR^aC({=}O)NR^aR^b$, $-OC({=}O)NR^aR^b$, $-NR^aC({=}O)OR^b$, $-NR^aS(O)_xNR^aR^b$, $-NR^aS(O)_xR^b$ or $-S(O)_xNR^aR^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with $-(C{=}O)OR^b$ or $-O(C{=}O)R^b$.

In some of the foregoing embodiments of Formula (II), $R^b$ is branched $C_1$-$C_{16}$ alkyl. For example, in some embodiments $R^b$ has one of the following structures:

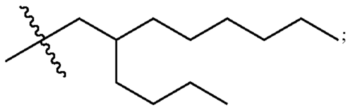
;

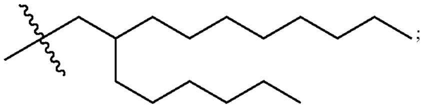
;

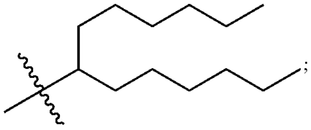
;

-continued

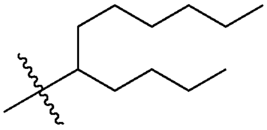

;

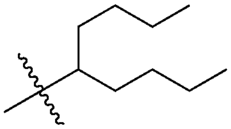

or

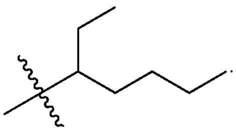

.

In certain other of the foregoing embodiments of Formula (II), one of $R^8$ or $R^9$ is methyl. In other embodiments, both $R^8$ and $R^9$ are methyl.

In some different embodiments of Formula (II), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring. In some different embodiments of the foregoing, $R^8$ and $R^9$, together with the nitrogen atom to which they are attached, form a 6-membered heterocyclic ring, for example a piperazinyl ring.

In certain embodiments of Embodiment 3, the first and second cationic lipids are each, independently selected from a lipid of Formula II.

In still other embodiments of the foregoing lipids of Formula (II), $G^3$ is $C_2$-$C_4$ alkylene, for example $C_3$ alkylene. In various different embodiments, the lipid compound has one of the structures set forth in Table 2 below

TABLE 2

| Representative Lipids of Formula (II) | | |
|---|---|---|
| No. | Structure | pKa |
| II-1 | 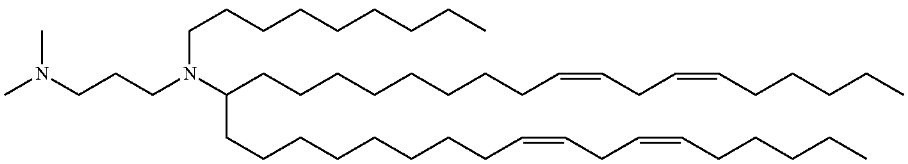 [SMILES: CCCCC/C=C\C/C=C\CCCCCCCCC(CCCCCCCC/C=C\C/C=C\CCCCC)N(CCCCCCCCC)CCCN(C)C] | 5.64 |
| II-2 | 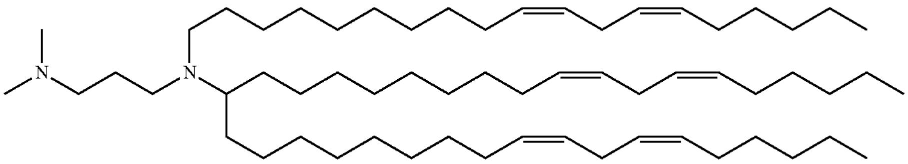 [SMILES: CCCCC/C=C\C/C=C\CCCCCCCCCN(CCCN(C)C)C(CCCCCCCC/C=C\C/C=C\CCCCC)CCCCCCCC/C=C\C/C=C\CCCCC] | — |
| II-3 | 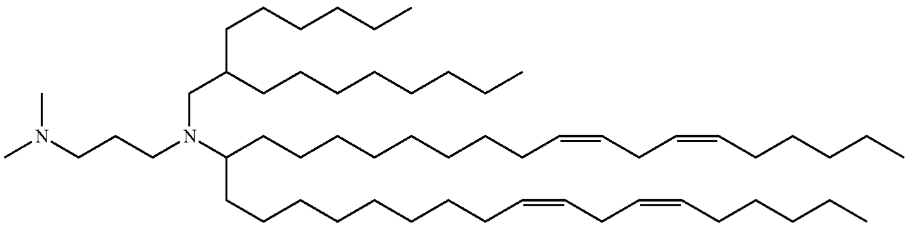 [SMILES: CCCCC/C=C\C/C=C\CCCCCCCCC(CCCCCCCC/C=C\C/C=C\CCCCC)N(CCCN(C)C)CC(CCCCCC)CCCCCCCC] | — |
| II-4 | 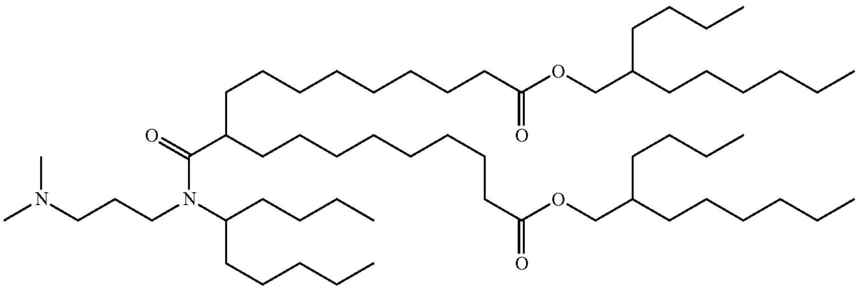 [SMILES: CCCCCCC(CCCC)COC(=O)CCCCCCCCC(CCCCCCCCC(=O)OCC(CCCC)CCCCCC)C(=O)N(CCCN(C)C)C(CCCC)CCCCC] | — |
| II-5 | 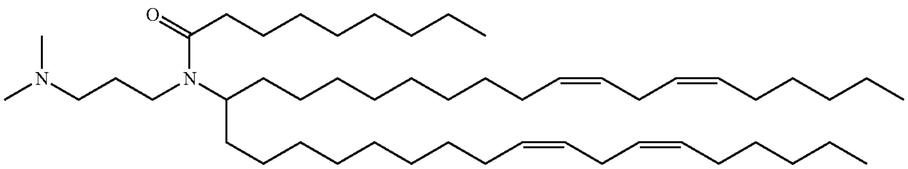 [SMILES: CCCCC/C=C\C/C=C\CCCCCCCCC(CCCCCCCC/C=C\C/C=C\CCCCC)N(CCCN(C)C)C(=O)CCCCCCCC] | 6.27 |

TABLE 2-continued
| Representative Lipids of Formula (II) | | |
|---|---|---|
| No. | Structure | pKa |
| II-6 | 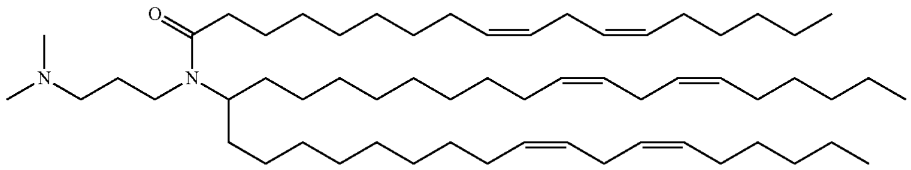 [SMILES: CCCCC/C=C\C/C=C\CCCCCCCCC(CCCCCCCC/C=C\C/C=C\CCCCC)N(CCCN(C)C)C(=O)CCCCCCC/C=C\C/C=C\CCCCC] | 6.14 |
| II-7 | 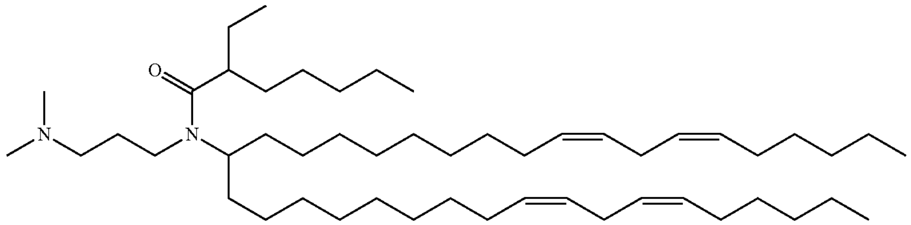 [SMILES: CCCCC/C=C\C/C=C\CCCCCCCCC(CCCCCCCC/C=C\C/C=C\CCCCC)N(CCCN(C)C)C(=O)C(CC)CCCCC] | 5.93 |
| II-8 | 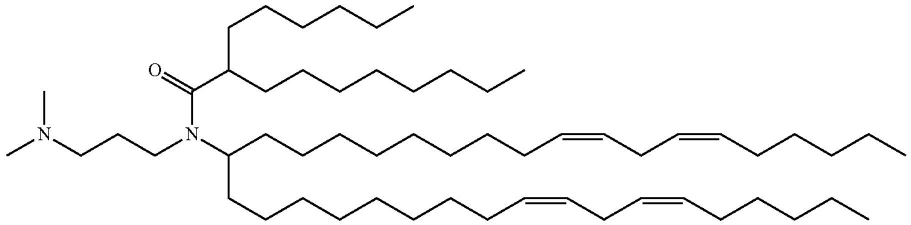 [SMILES: CCCCC/C=C\C/C=C\CCCCCCCCC(CCCCCCCC/C=C\C/C=C\CCCCC)N(CCCN(C)C)C(=O)C(CCCCCC)CCCCCCCC] | 5.35 |
| II-9 | 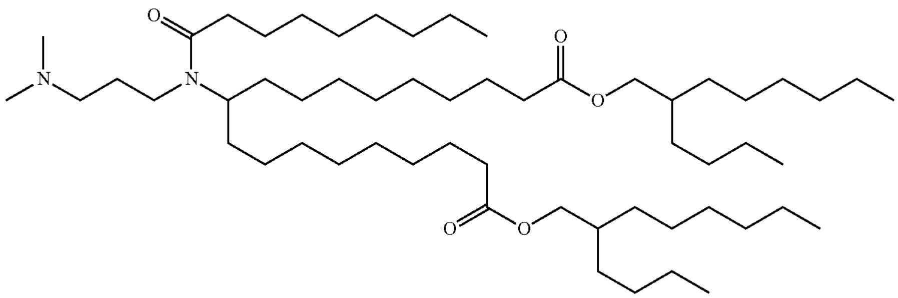 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC] | 6.27 |
| II-10 | 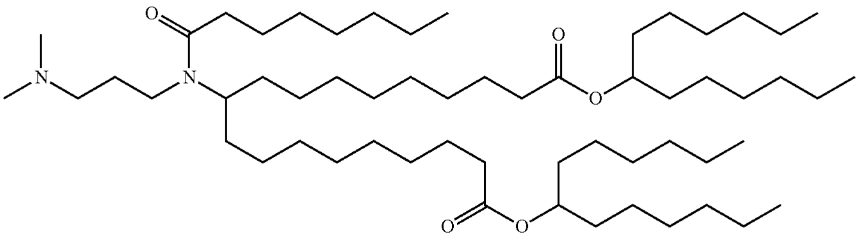 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC] | 6.16 |
| II-11 | 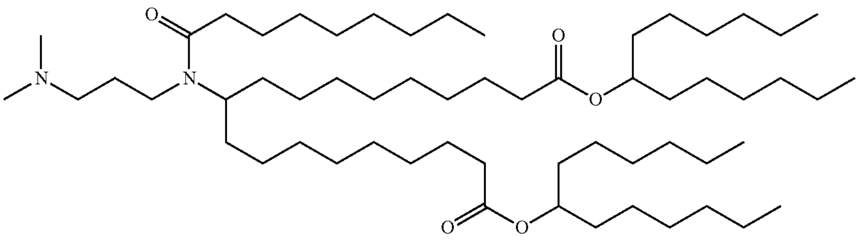 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC] | 6.13 |

TABLE 2-continued
| Representative Lipids of Formula (II) | | |
|---|---|---|
| No. | Structure | pKa |
| II-12 | 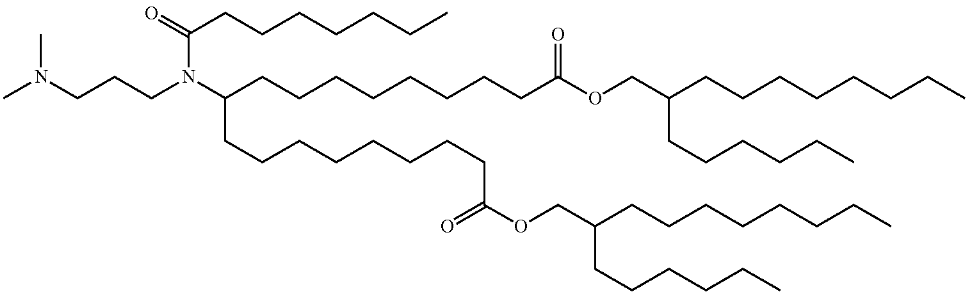 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC] | 6.21 |
| II-13 | 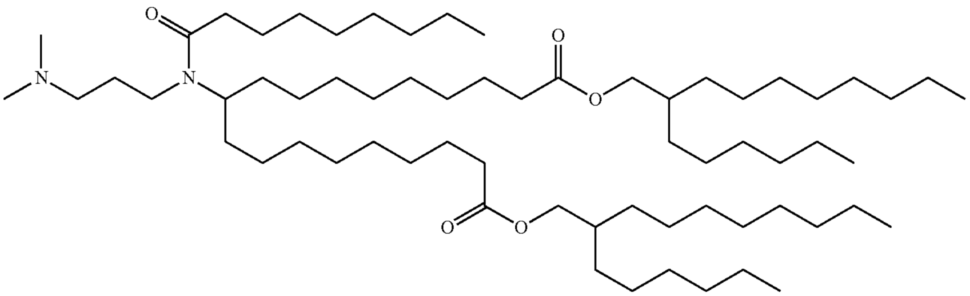 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC] | 6.22 |
| II-14 | 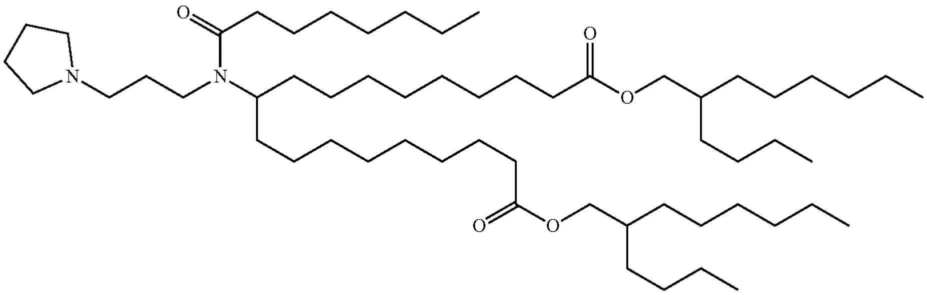 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC] | 6.33 |
| II-15 | 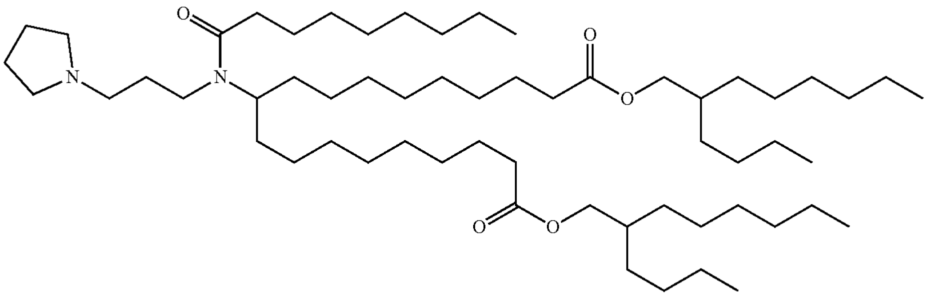 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC] | 6.32 |
| II-16 | 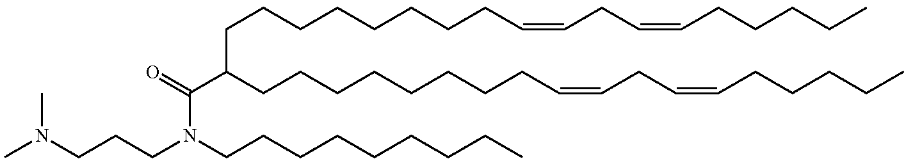 [SMILES: CCCCC/C=C\C/C=C\CCCCCCCCC(CCCCCCCC/C=C\C/C=C\CCCCC)C(=O)N(CCCCCCCCC)CCCN(C)C] | 6.37 |

TABLE 2-continued
| No. | Representative Lipids of Formula (II)<br>Structure | pKa |
|---|---|---|
| II-17 | 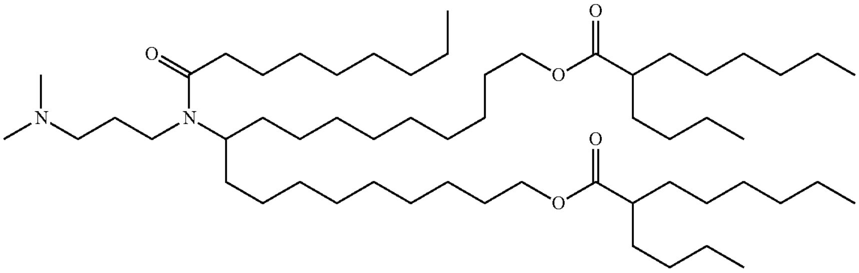 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC] | 6.27 |
| II-18 | 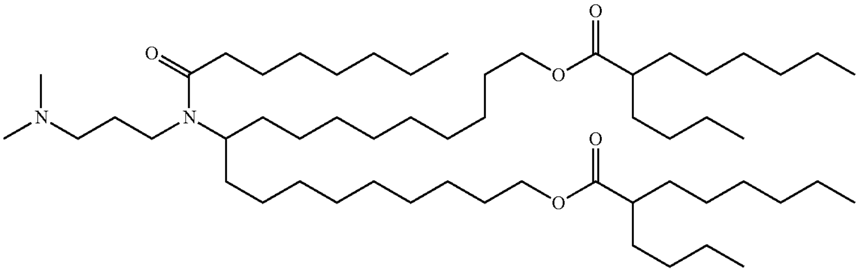 [SMILES: CCCCCCCC(=O)N(CCCN(C)C)C(CCCCCCCCCOC(=O)C(CCCC)CCCCCC)CCCCCCCCCOC(=O)C(CCCC)CCCCCC] | — |
| II-19 | 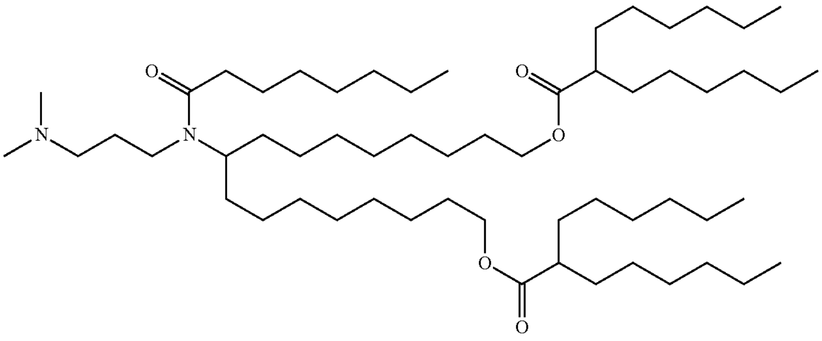 [SMILES: CCCCCCCC(=O)N(CCCN(C)C)C(CCCCCCCCOC(=O)C(CCCCCC)CCCCCC)CCCCCCCCOC(=O)C(CCCCCC)CCCCCC] | — |
| II-20 | 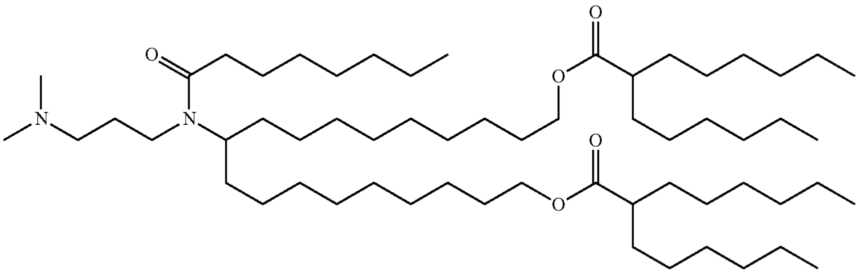 | — |
| II-21 | 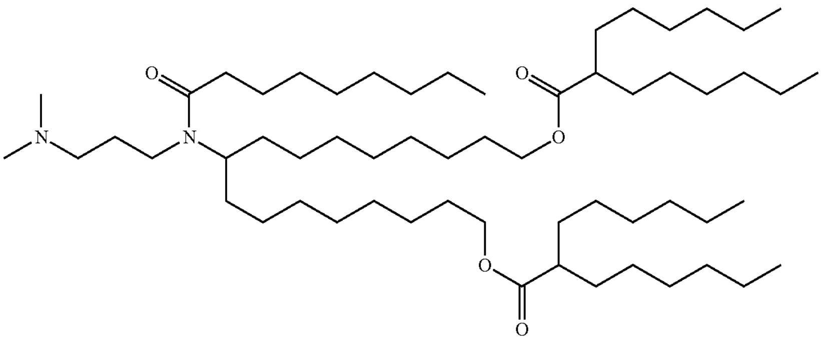 [SMILES: CCCCCCCCC(=O)N(CCCN(C)C)C(CCCCCCCCOC(=O)C(CCCCCC)CCCCCC)CCCCCCCCOC(=O)C(CCCCCC)CCCCCC] | — |

TABLE 2-continued
| Representative Lipids of Formula (II) | | |
|---|---|---|
| No. | Structure | pKa |
| II-22 | 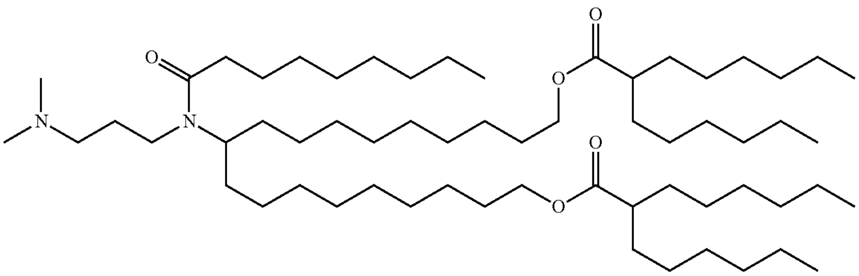 [SMILES: CCCCCCCCC(=O)N(CCCN(C)C)C(CCCCCCCCCOC(=O)C(CCCCCC)CCCCCC)CCCCCCCCCOC(=O)C(CCCCCC)CCCCCC] | — |
| II-23 | 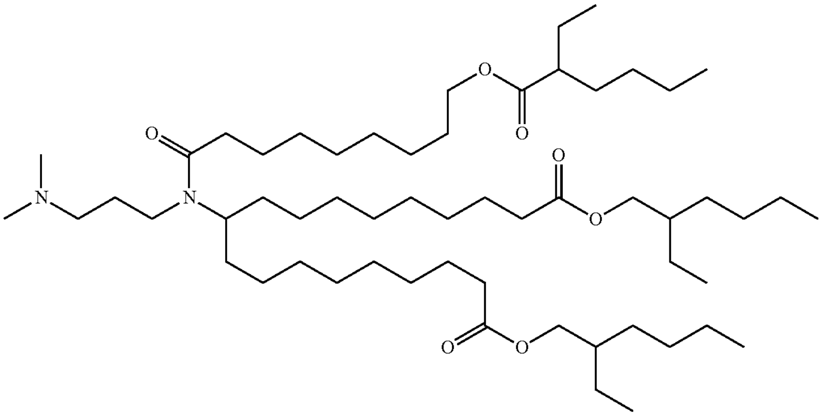 [SMILES: CCCCC(CC)COC(=O)CCCCCCCCC(CCCCCCCCC(=O)OCC(CC)CCCC)N(CCCN(C)C)C(=O)CCCCCCCCOC(=O)C(CC)CCCC] | — |
| II-24 | 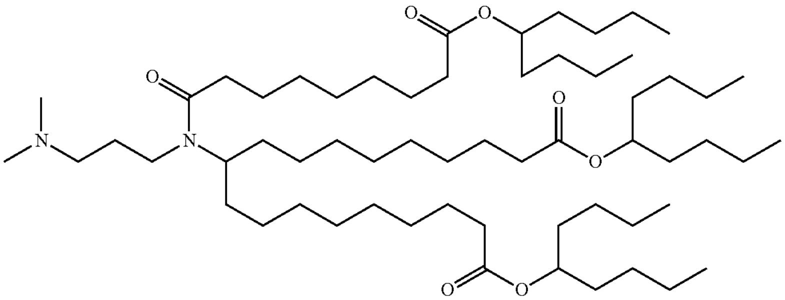 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC] | 6.14 |
| II-25 | 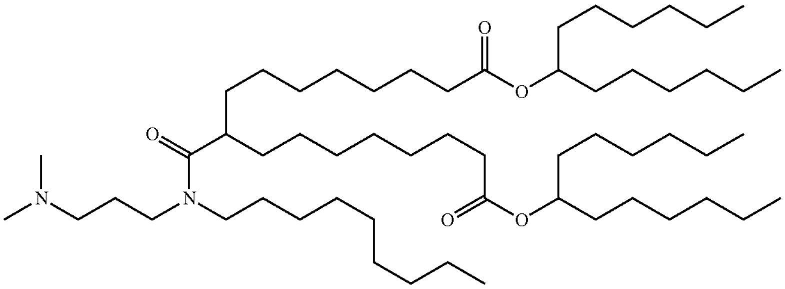 [SMILES: CCCCCCCCCN(CCCN(C)C)C(=O)C(CCCCCCCC(=O)OC(CCCCCC)CCCCCC)CCCCCCCC(=O)OC(CCCCCC)CCCCCC] | — |

TABLE 2-continued
| No. | Representative Lipids of Formula (II)<br>Structure | pKa |
| --- | --- | --- |
| II-26 | 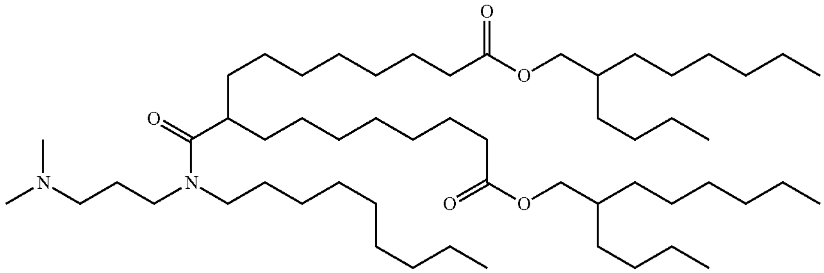 [SMILES: CCCCCCCCCN(CCCN(C)C)C(=O)C(CCCCCCCC(=O)OCC(CCCC)CCCCCC)CCCCCCCC(=O)OCC(CCCC)CCCCCC] | — |
| II-27 | 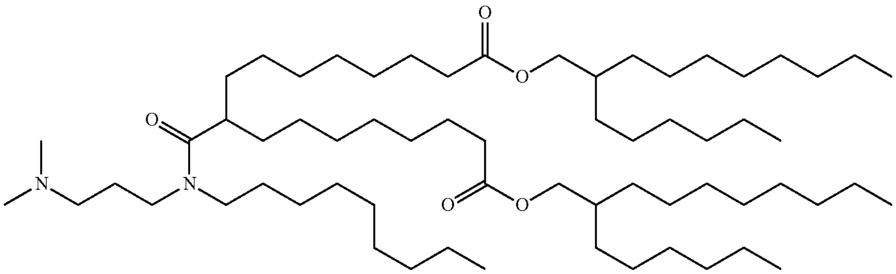 [SMILES: CCCCCCCCCN(CCCN(C)C)C(=O)C(CCCCCCCC(=O)OCC(CCCCCC)CCCCCCCC)CCCCCCCC(=O)OCC(CCCCCC)CCCCCCCC] | — |
| II-28 | 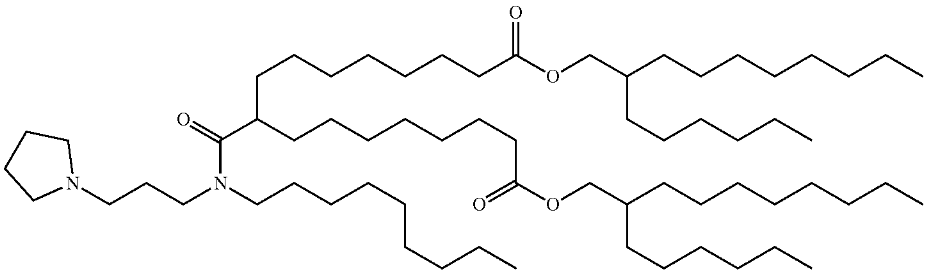 [SMILES: CCCCCCCCCN(CCCN1CCCC1)C(=O)C(CCCCCCCC(=O)OCC(CCCCCC)CCCCCCCC)CCCCCCCC(=O)OCC(CCCCCC)CCCCCCCC] | — |
| II-29 | 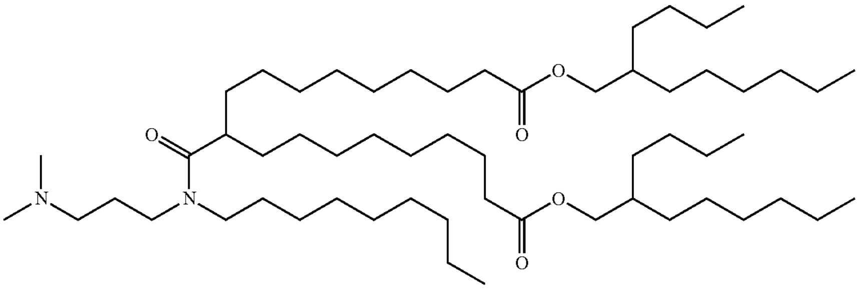 [SMILES: CCCCCCCCCN(CCCN(C)C)C(=O)C(CCCCCCCCC(=O)OCC(CCCC)CCCCCC)CCCCCCCCC(=O)OCC(CCCC)CCCCCC] | — |
| II-30 | 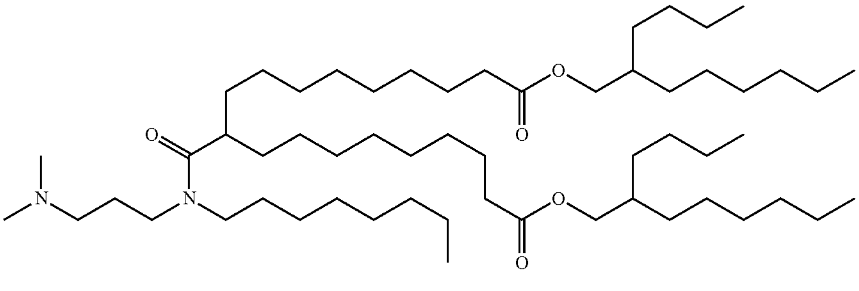 [SMILES: CCCCCCCCN(CCCN(C)C)C(=O)C(CCCCCCCCC(=O)OCC(CCCC)CCCCCC)CCCCCCCCC(=O)OCC(CCCC)CCCCCC] | — |

TABLE 2-continued
| Representative Lipids of Formula (II) | | |
|---|---|---|
| No. | Structure | pKa |
| II-31 | 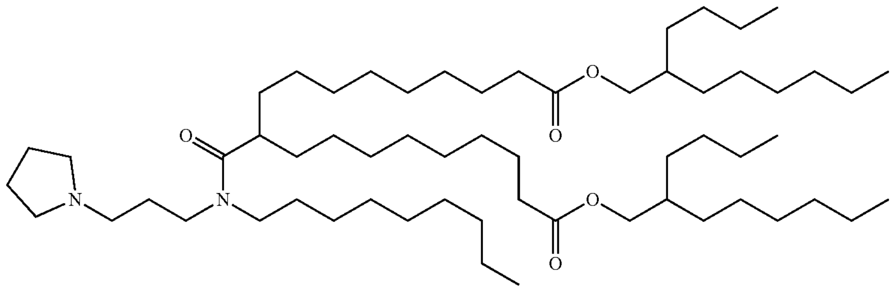 [SMILES: CCCCCCCCCN(CCCN1CCCC1)C(=O)C(CCCCCCCCC(=O)OCC(CCCC)CCCCCC)CCCCCCCCC(=O)OCC(CCCC)CCCCCC] | — |
| II-32 | 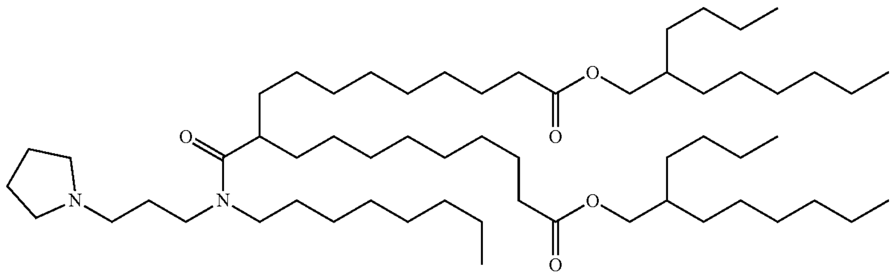 [SMILES: CCCCCCCCN(CCCN1CCCC1)C(=O)C(CCCCCCCCC(=O)OCC(CCCC)CCCCCC)CCCCCCCCC(=O)OCC(CCCC)CCCCCC] | — |
| II-33 | 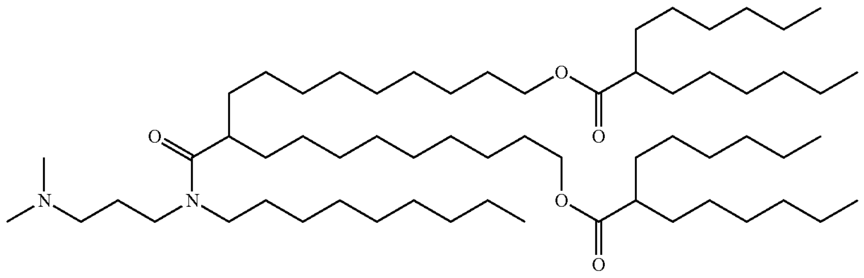 [SMILES: CCCCCCCCCN(CCCN(C)C)C(=O)C(CCCCCCCCCOC(=O)C(CCCCCC)CCCCCC)CCCCCCCCCOC(=O)C(CCCCCC)CCCCCC] | — |
| II-34 | 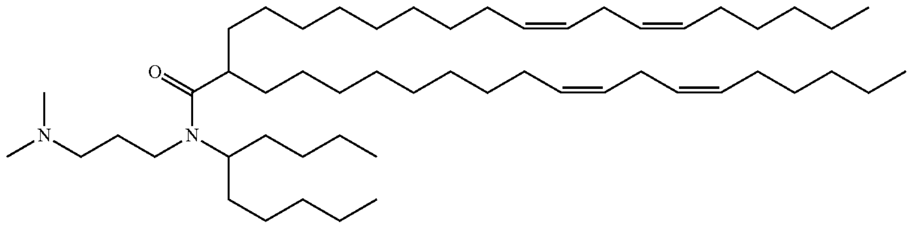 [SMILES: CCCCC/C=C\C/C=C\CCCCCCCCC(CCCCCCCC/C=C\C/C=C\CCCCC)C(=O)N(CCCN(C)C)C(CCCC)CCCCC] | — |
| II-35 | 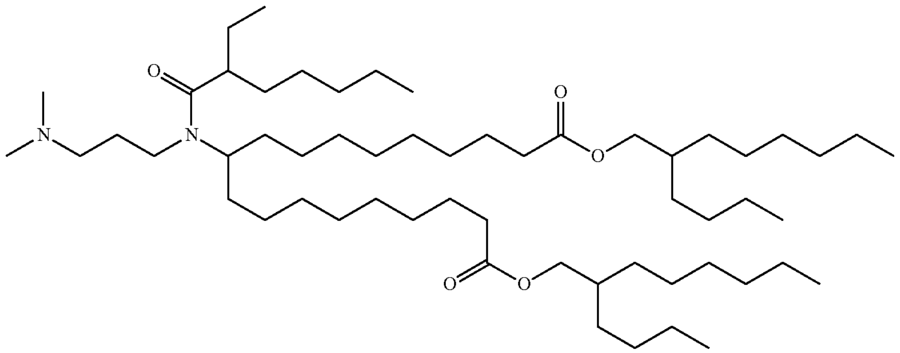 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC] | 5.97 |

TABLE 2-continued
| No. | Structure | pKa |
| --- | --- | --- |
| | Representative Lipids of Formula (II) | |
| II-36 | 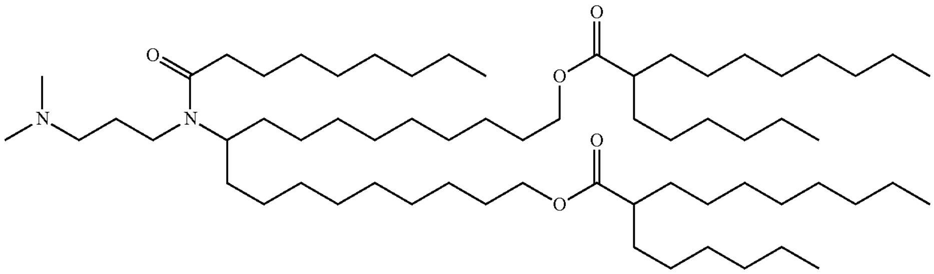 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC] | 6.13 |
| II-37 | 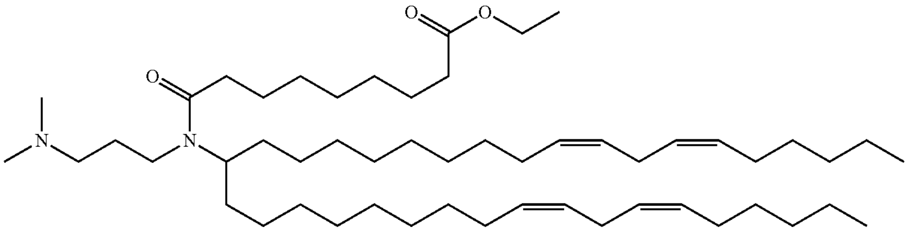 [SMILES: CCCCC/C=C\C/C=C\CCCCCCCCC(CCCCCCCC/C=C\C/C=C\CCCCC)N(CCCN(C)C)C(=O)CCCCCCCC(=O)OCC] | 5.61 |
| II-38 | 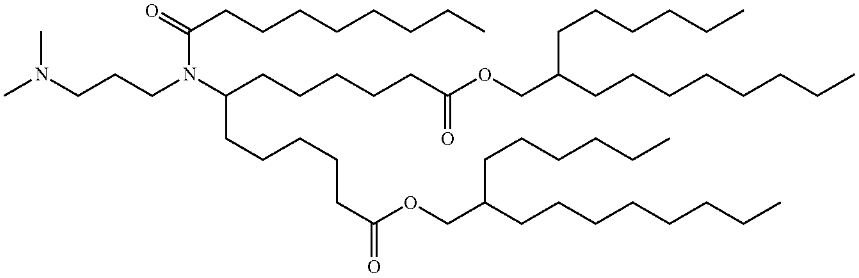 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC] | 6.45 |
| II-39 | 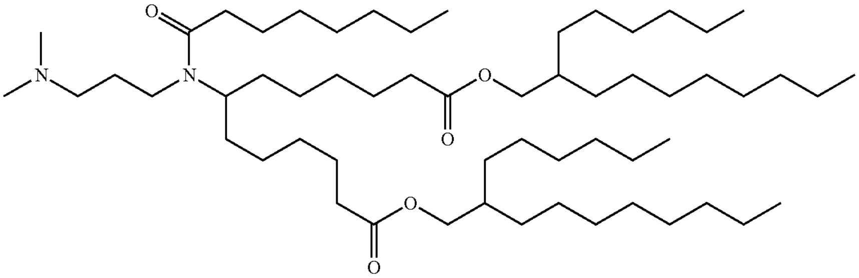 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC] | 6.45 |
| II-40 | 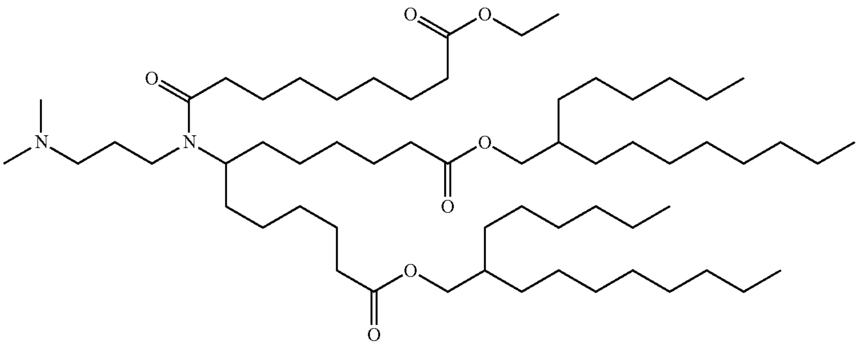 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC] | 6.57 |

TABLE 2-continued
| Representative Lipids of Formula (II) | | |
|---|---|---|
| No. | Structure | pKa |
| II-41 | 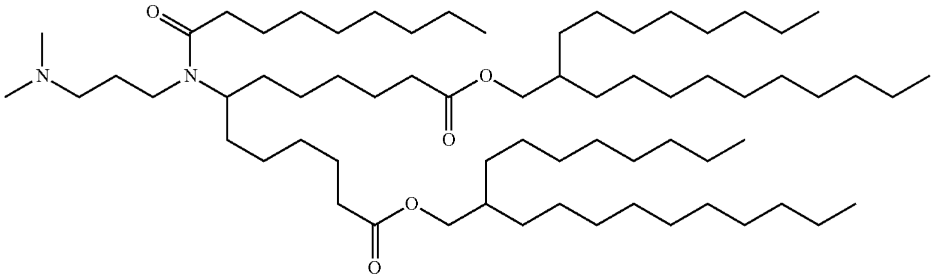 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC] | — |
| II-42 | 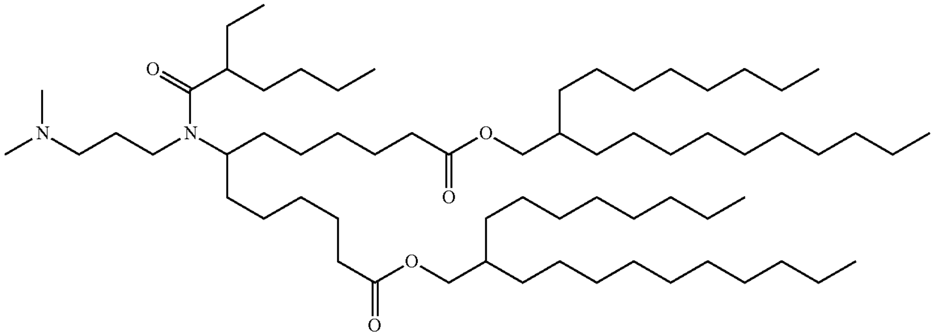 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)C(CC)CCCC] | — |
| II-43 | 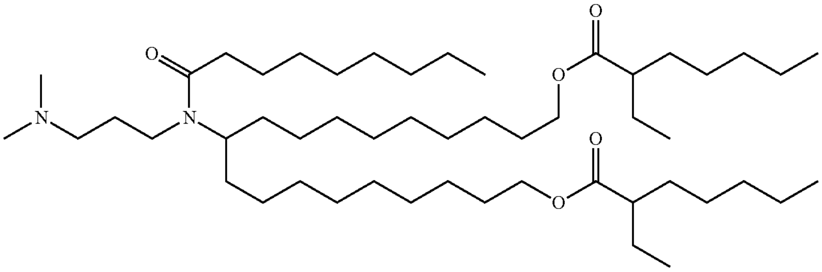 [SMILES: CCCCCCCCC(=O)N(CCCN(C)C)C(CCCCCCCCCOC(=O)C(CC)CCCCC)CCCCCCCCCOC(=O)C(CC)CCCCC] | — |
| II-44 | 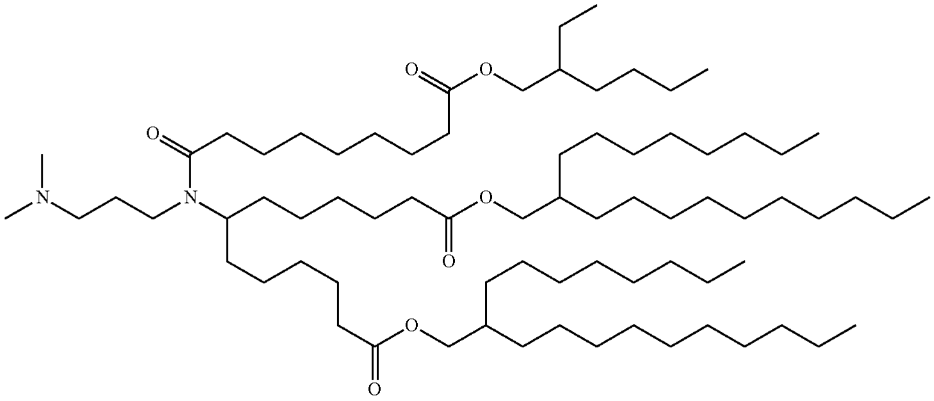 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC(=O)OCC(CC)CCCC] | — |

TABLE 2-continued

Representative Lipids of Formula (II)

| No. | Structure | pKa |
| --- | --- | --- |
| II-45 | 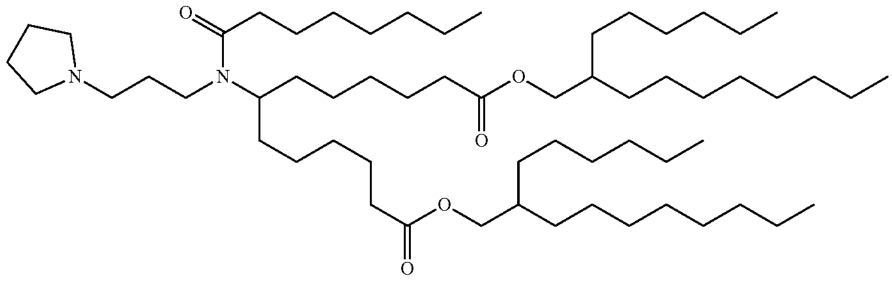 [SMILES: CCCCCCCCC(CCCCCC)COC(=O)CCCCCC(CCCCCC(=O)OCC(CCCCCC)CCCCCCCC)N(CCCN1CCCC1)C(=O)CCCCCCC] | — |
| II-46 | 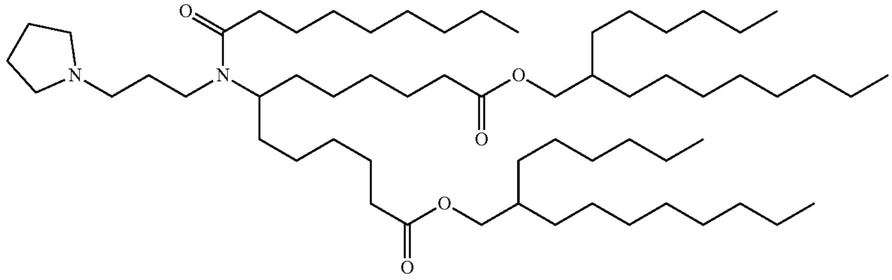 [SMILES: CCCCCCCCC(=O)N(CCCN1CCCC1)C(CCCCCC(=O)OCC(CCCCCC)CCCCCCCC)CCCCCC(=O)OCC(CCCCCC)CCCCCCCC] | — |

In some other embodiments, the cationic lipid of Embodiments 1, 2, 3, 4 or 5 has a structure of Formula III:

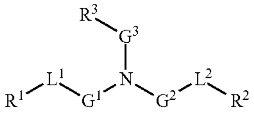

III or a pharmaceutically acceptable salt, prodrug or stereoisomer thereof, wherein:

one of $L^1$ or $L^2$ is —O(C═O)—, —(C═O)O—, —C(═O)—, —O—, —S(O)$_x$—, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O—, and the other of $L^1$ or $L^2$ is —O(C═O)—, —(C═O)O—, —C(═O)—, —O—, —S(O)$_x$—, —S-S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(═O)OR$^4$, —OC(═O)R$^4$ or —NR$^5$C(═O)R$^4$;

$R^4$ is $C_1$-$C_{12}$ alkyl;

$R^5$ is H or $C_1$-$C_6$ alkyl; and x is 0, 1 or 2.

In some of the foregoing embodiments of Formula (III), the lipid has one of the following Formulae (IIIA) or (IIIB):

(IIIA)

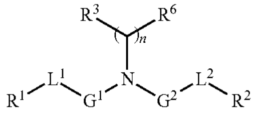

or (IIIB)

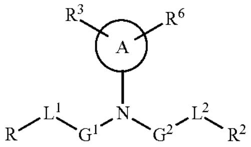

wherein:

A is a 3 to 8-membered cycloalkyl or cycloalkylene ring;

$R^6$ is, at each occurrence, independently H, OH or $C_1$-$C_{24}$ alkyl;

n is an integer ranging from 1 to 15.

In some of the foregoing embodiments of Formula (III), the lipid has Formula (IIIA), and in other embodiments, the lipid has Formula (IIIB).

In other embodiments of Formula (III), the lipid has one of the following Formulae (IIC) or (IIID):

(IIIC)

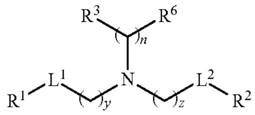

or

-continued (IIID)

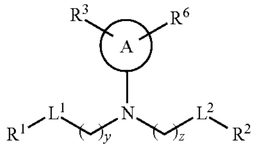

wherein y and z are each independently integers ranging from 1 to 12.

In any of the foregoing embodiments of Formula (III), one of $L^1$ or $L^2$ is —O(C═O)—. For example, in some embodiments each of $L^1$ and $L^2$ are —O(C═O)—. In some different embodiments of any of the foregoing, $L^1$ and $L^2$ are each independently —(C═O)O— or —O(C═O)—. For example, in some embodiments each of L and $L^2$ is —(C═O)O—.

In some different embodiments of Formula (III), the lipid has one of the following Formulae (IIIE) or (IIIF):

(IIIE)

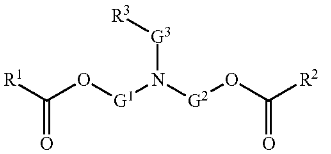

or (IIIF)

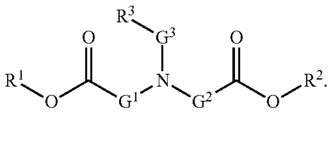

In some of the foregoing embodiments of Formula (III), the lipid has one of the following Formulae (IIIG), (IIIH), (IIII), or (IIIJ):

(IIIG)

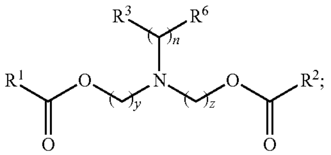

;

(IIIH)

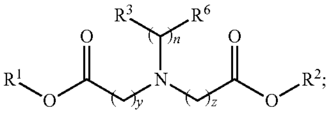

;

(IIII)

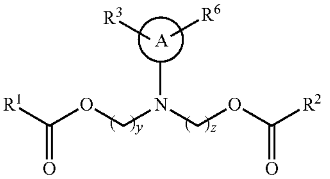

or (IIIJ)

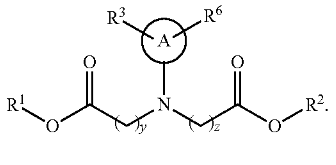

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some other foregoing embodiments of Formula (III), $R^1$ or $R^2$, or both, is $C_6$-$C_{24}$ alkenyl. For example, in some embodiments, $R^1$ and $R_2$ each, independently have the following structure:

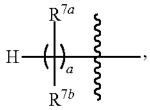

, wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of Formula (III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (III), $R^1$ or $R^2$, or both, has one of the following structures:

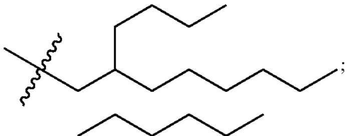

;

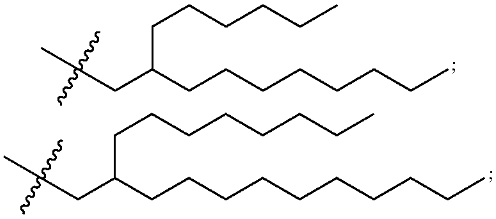

;

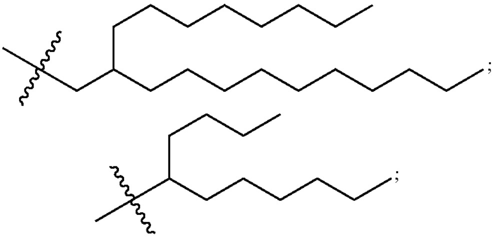

;

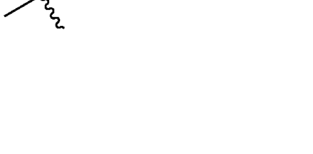

;

-continued

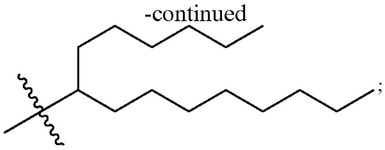
;

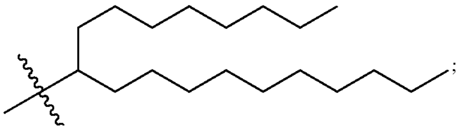
;

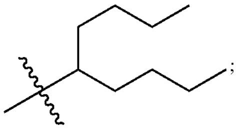
;

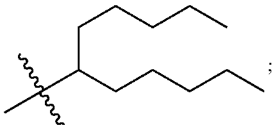
;

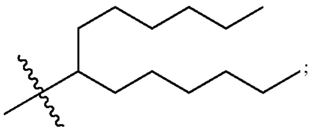
;

-continued

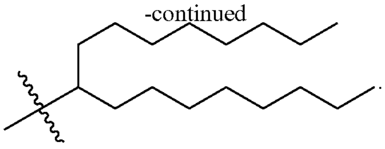
.

In some of the foregoing embodiments of Formula (III), $R^3$ is OH, CN, —C(═O)OR$^4$, —OC(═O)R$^4$ or —NHC(═O)R$^4$. In some embodiments, $R^4$ is methyl or ethyl.

In some specific embodiments of Embodiment 3, the first and second cationic lipids are each, independently selected from a lipid of Formula III.

In various different embodiments, a cationic lipid of any one of the disclosed embodiments (e.g., the cationic lipid, the first cationic lipid, the second cationic lipid) of Formula (III) has one of the structures set forth in Table 3 below.

TABLE 3

Representative Compounds of Formula (III)

| No. | Structure | pKa |
|---|---|---|
| III-1 | 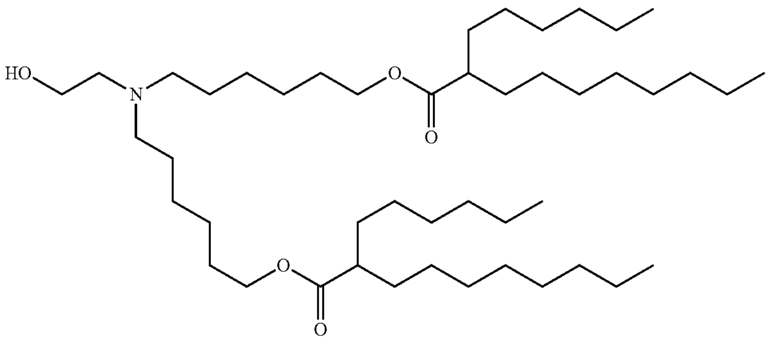 [SMILES: CCCCCCCCC(CCCCCC)C(=O)OCCCCCCN(CCO)CCCCCCOC(=O)C(CCCCCC)CCCCCCCC] | 5.89 |
| III-2 | 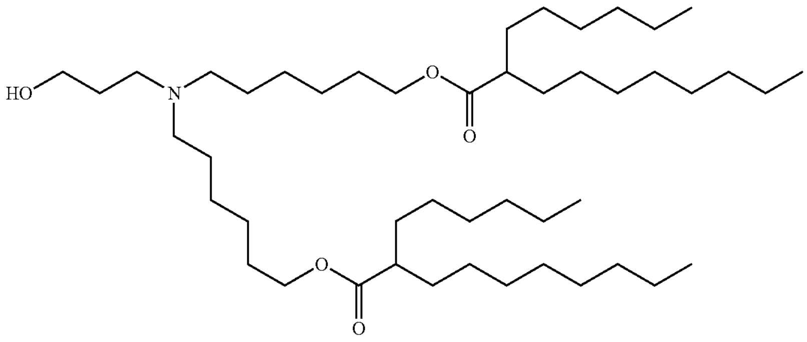 [SMILES: CCCCCCCCC(CCCCCC)C(=O)OCCCCCCN(CCCO)CCCCCCOC(=O)C(CCCCCC)CCCCCCCC] | 6.05 |

TABLE 3-continued
| Representative Compounds of Formula (III) | | |
|---|---|---|
| No. | Structure | pKa |
| III-3 | 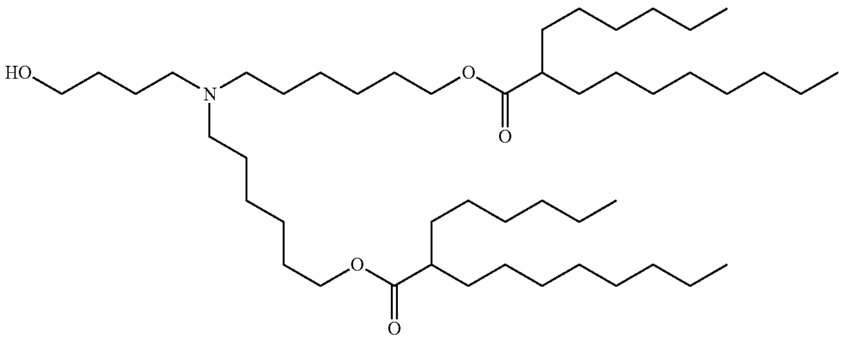 [SMILES: CCCCCCCCC(CCCCCC)C(=O)OCCCCCCN(CCCCO)CCCCCCOC(=O)C(CCCCCC)CCCCCCCC] | 6.09 |
| III-4 | 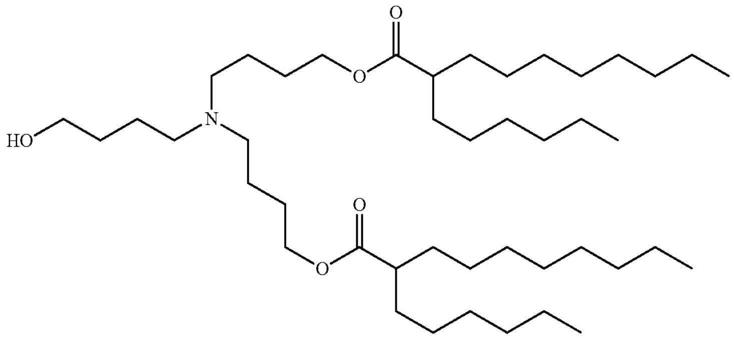 [SMILES: CCCCCCCCC(CCCCCC)C(=O)OCCCCN(CCCCO)CCCCOC(=O)C(CCCCCC)CCCCCCCC] | 5.60 |
| III-5 | 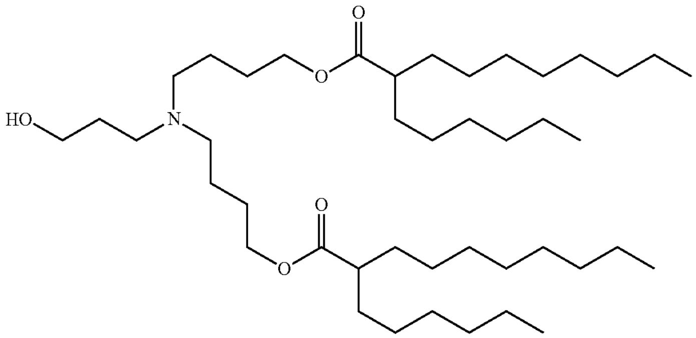 [SMILES: CCCCCCCCC(CCCCCC)C(=O)OCCCCN(CCCO)CCCCOC(=O)C(CCCCCC)CCCCCCCC] | 5.59 |
| III-6 | 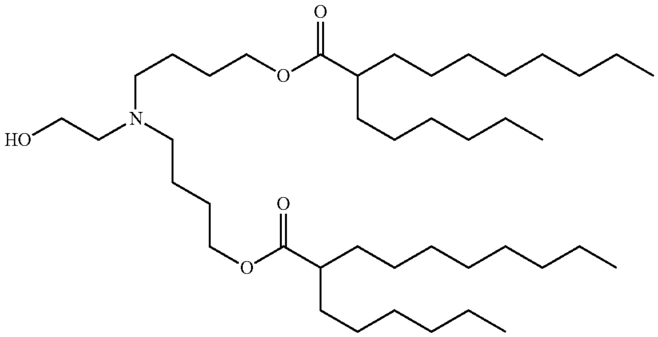 [SMILES: CCCCCCCCC(CCCCCC)C(=O)OCCCCN(CCO)CCCCOC(=O)C(CCCCCC)CCCCCCCC] | 5.42 |

TABLE 3-continued
Representative Compounds of Formula (III)
| No. | Structure | pKa |
| --- | --- | --- |
| III-7 | 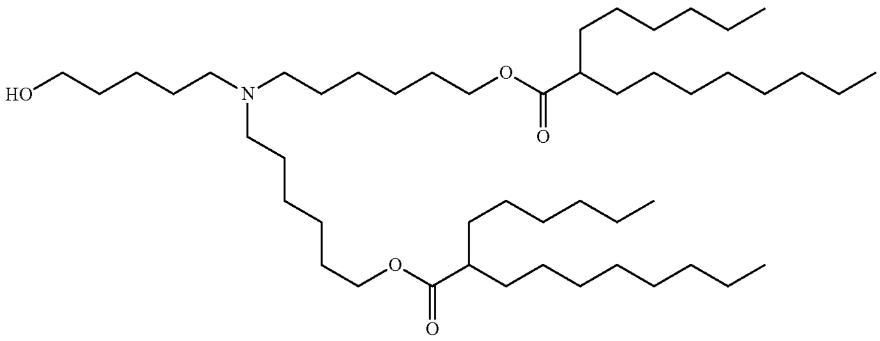 [SMILES: CCCCCCCCC(CCCCCC)C(=O)OCCCCCCN(CCCCCO)CCCCCCOC(=O)C(CCCCCC)CCCCCCCC] | 6.11 |
| III-8 | 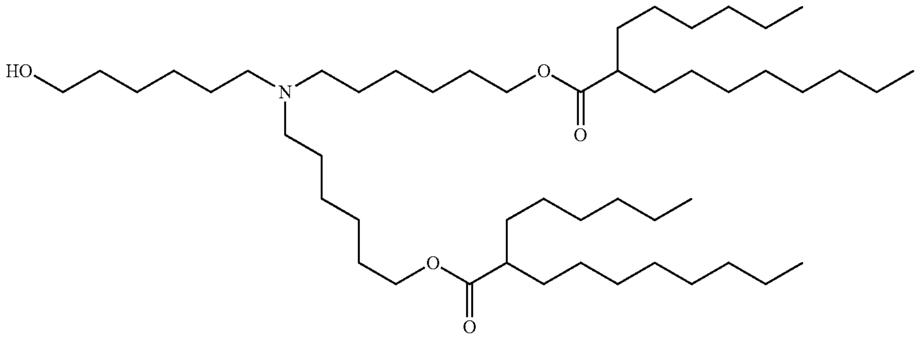 [SMILES: CCCCCCCCC(CCCCCC)C(=O)OCCCCCCN(CCCCCCO)CCCCCCOC(=O)C(CCCCCC)CCCCCCCC] | 5.84 |
| III-9 | 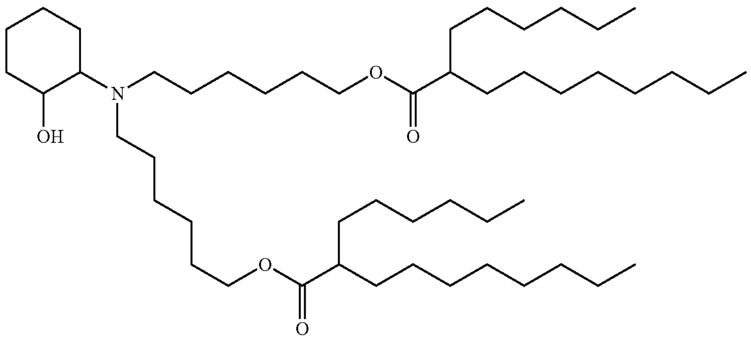 [SMILES: CCCCCCCCC(CCCCCC)C(=O)OCCCCCCN(CCCCCCOC(=O)C(CCCCCC)CCCCCCCC)C1CCCCC1O] | — |
| III-10 | 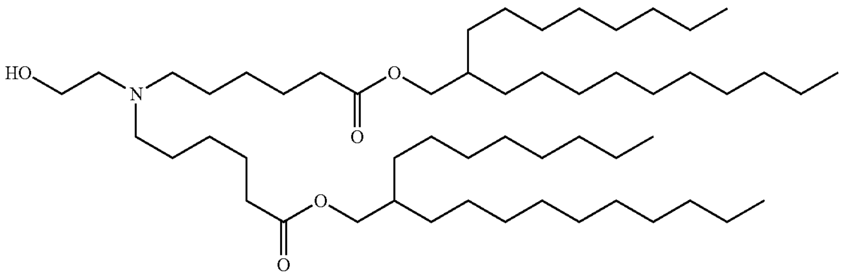 [SMILES: CCCCCCCCCCC(CCCCCCCC)COC(=O)CCCCCN(CCO)CCCCCC(=O)OCC(CCCCCCCC)CCCCCCCCCC] | — |

TABLE 3-continued
Representative Compounds of Formula (III)
| No. | Structure | pKa |
| --- | --- | --- |
| III-11 | 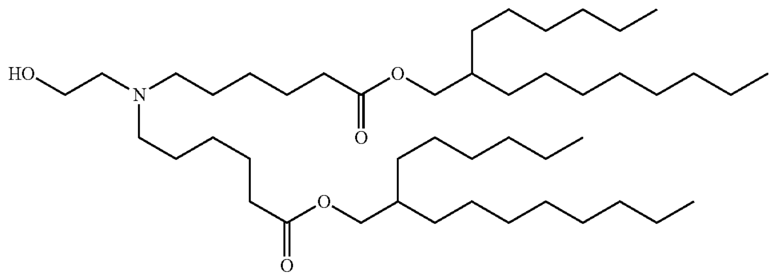 [SMILES: CCCCCCCCC(CCCCCC)COC(=O)CCCCCN(CCO)CCCCCC(=O)OCC(CCCCCC)CCCCCCCC] | — |
| III-12 | 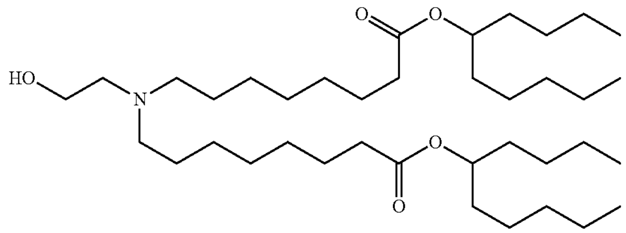 [SMILES: CCCCCC(CCCC)OC(=O)CCCCCCCN(CCO)CCCCCCCC(=O)OC(CCCC)CCCCC] | — |
| III-13 | 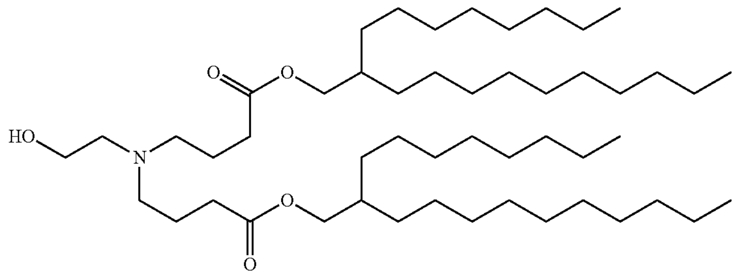 [SMILES: CCCCCCCCCCC(CCCCCCCC)COC(=O)CCCN(CCO)CCCC(=O)OCC(CCCCCCCC)CCCCCCCCCC] | — |
| III-14 | 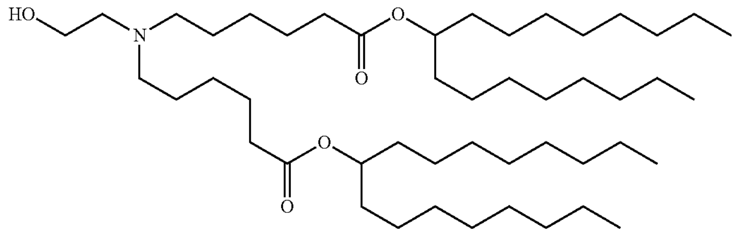 [SMILES: CCCCCCCCC(CCCCCCCC)OC(=O)CCCCCN(CCO)CCCCCC(=O)OC(CCCCCCCC)CCCCCCCC] | — |
| III-15 | 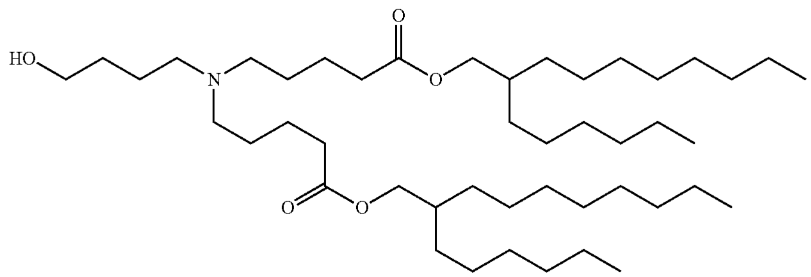 [SMILES: CCCCCCCCC(CCCCCC)COC(=O)CCCCN(CCCCO)CCCCC(=O)OCC(CCCCCC)CCCCCCCC] | 6.14 |

TABLE 3-continued
| Representative Compounds of Formula (III) | | |
|---|---|---|
| No. | Structure | pKa |
| III-16 | 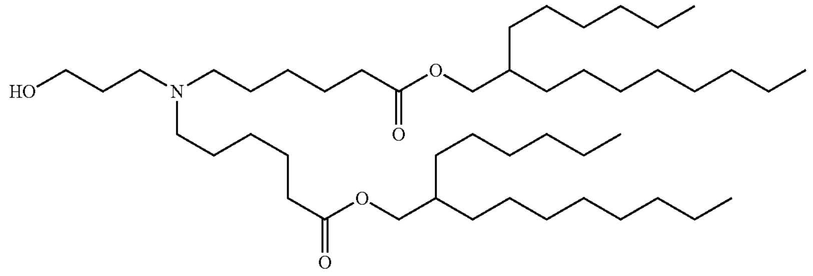 [SMILES: CCCCCCCCC(CCCCCC)COC(=O)CCCCCN(CCCO)CCCCCC(=O)OCC(CCCCCC)CCCCCCCC] | 6.31 |
| III-17 | 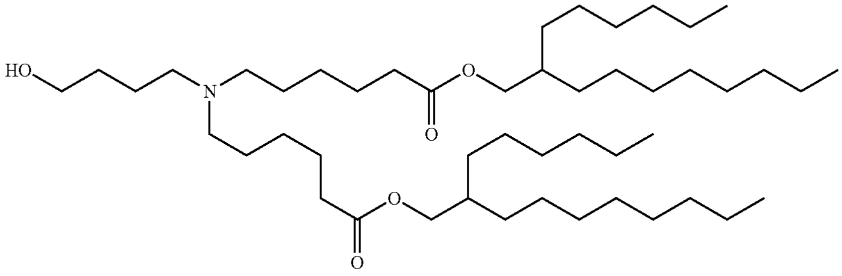 [SMILES: CCCCCCCCC(CCCCCC)COC(=O)CCCCCN(CCCCO)CCCCCC(=O)OCC(CCCCCC)CCCCCCCC] | 6.28 |
| III-18 | 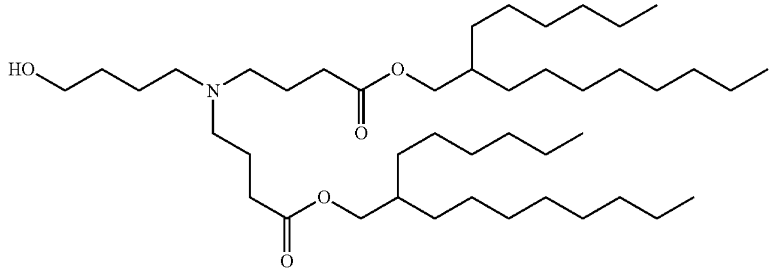 [SMILES: CCCCCCCCC(CCCCCC)COC(=O)CCCN(CCCCO)CCCC(=O)OCC(CCCCCC)CCCCCCCC] | — |
| III-19 | 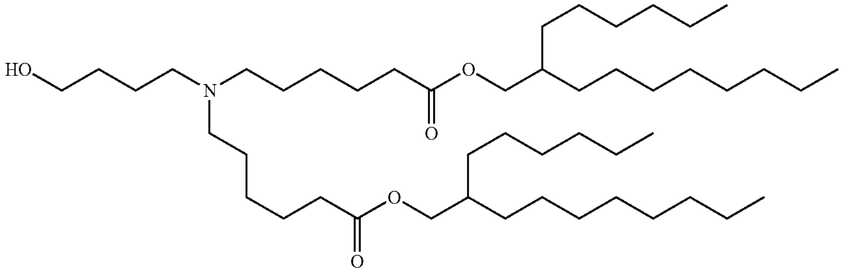 [SMILES: CCCCCCCCC(CCCCCC)COC(=O)CCCCCN(CCCCO)CCCCCC(=O)OCC(CCCCCC)CCCCCCCC] | — |
| III-20 | 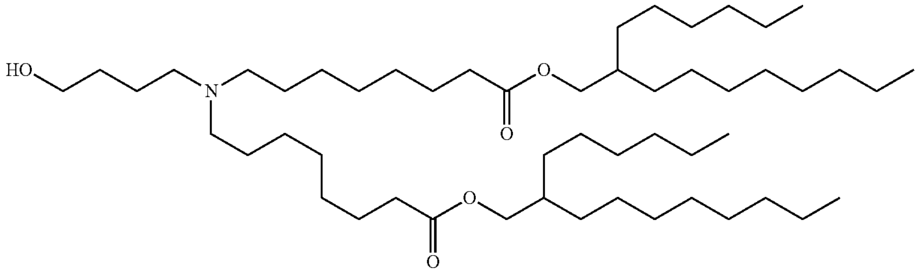 [SMILES: CCCCCCCCC(CCCCCC)COC(=O)CCCCCCCN(CCCCO)CCCCCCCC(=O)OCC(CCCCCC)CCCCCCCC] | 6.36 |

TABLE 3-continued
| Representative Compounds of Formula (III) | | |
|---|---|---|
| No. | Structure | pKa |
| III-21 | 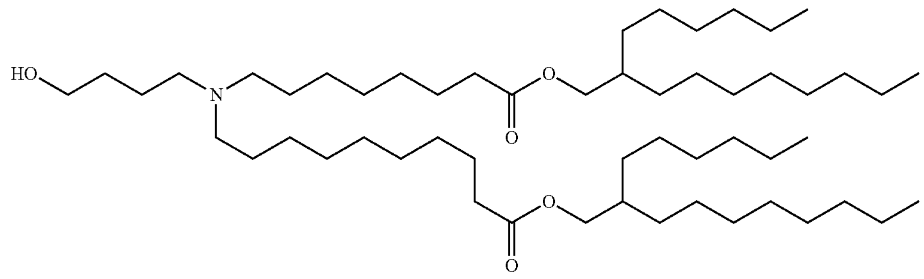 [SMILES: CCCCCCCCC(CCCCCC)COC(=O)CCCCCCCCCN(CCCCO)CCCCCCCC(=O)OCC(CCCCCC)CCCCCCCC] | — |
| III-22 | 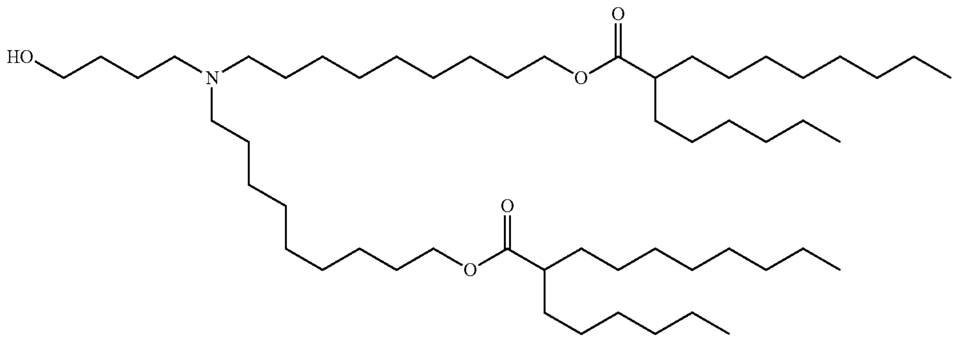 [SMILES: CCCCCCCCC(CCCCCC)C(=O)OCCCCCCCCCN(CCCCO)CCCCCCCCCOC(=O)C(CCCCCC)CCCCCCCC] | 6.10 |
| III-23 | 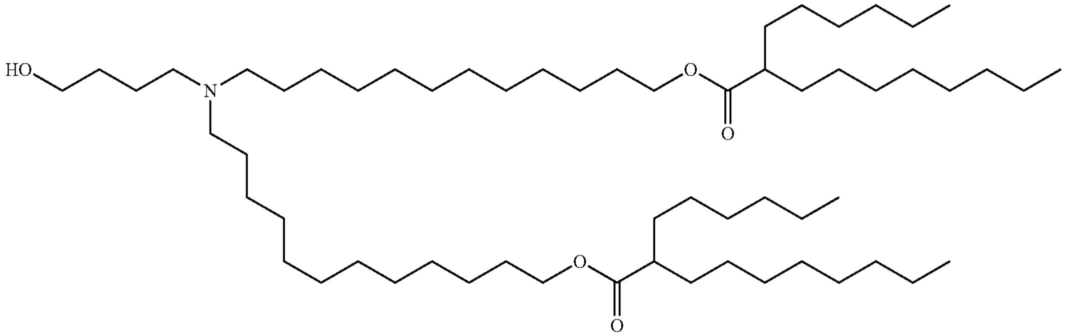 [SMILES: CCCCCCCCC(CCCCCC)C(=O)OCCCCCCCCCCCCN(CCCCO)CCCCCCCCCCCCOC(=O)C(CCCCCC)CCCCCCCC] | 5.98 |
| III-24 | 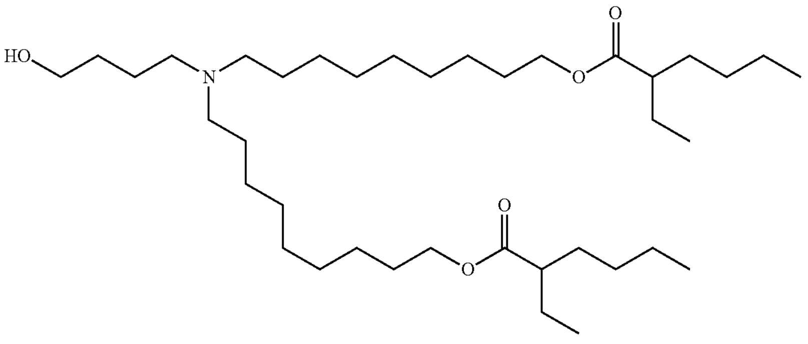 [SMILES: CCCCC(CC)C(=O)OCCCCCCCCCN(CCCCO)CCCCCCCCCOC(=O)C(CC)CCCC] | — |

TABLE 3-continued
| Representative Compounds of Formula (III) | | |
|---|---|---|
| No. | Structure | pKa |
| III-25 | 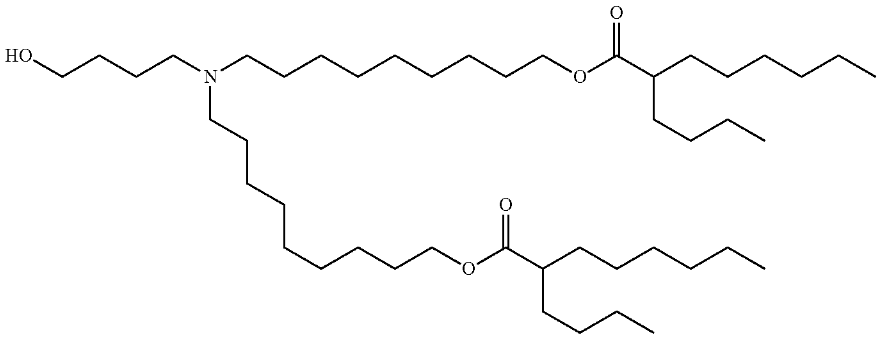 [SMILES: CCCCCCC(CCCC)C(=O)OCCCCCCCCCN(CCCCO)CCCCCCCCCOC(=O)C(CCCC)CCCCCC] | 6.22 |
| III-26 | 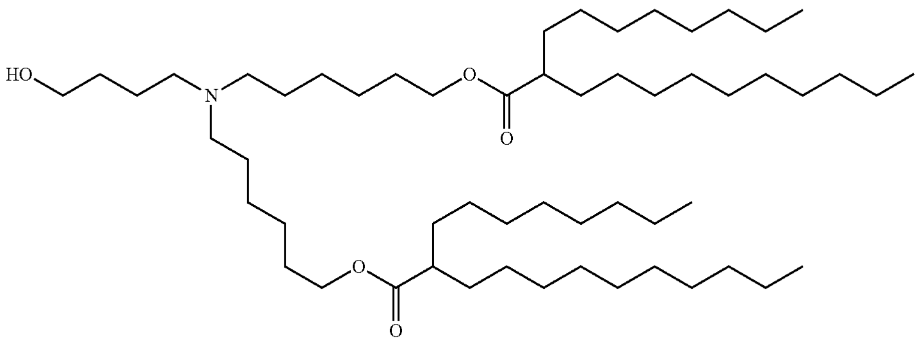 [SMILES: CCCCCCCCCCC(CCCCCCCC)C(=O)OCCCCCCN(CCCCO)CCCCCCOC(=O)C(CCCCCCCC)CCCCCCCCCC] | 5.84 |
| III-27 | 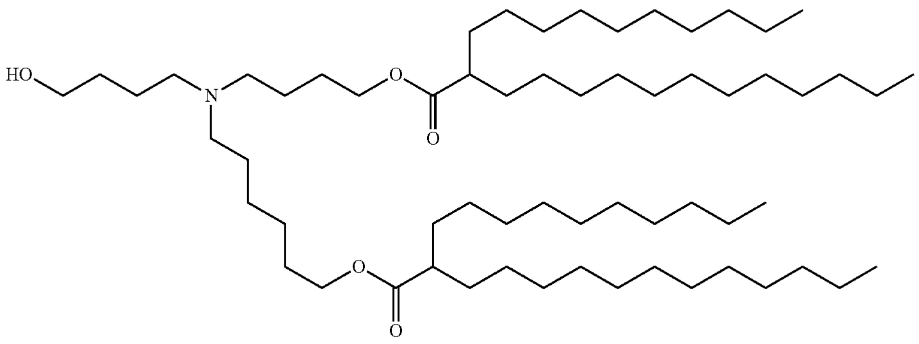 [SMILES: CCCCCCCCCCCCC(CCCCCCCCCC)C(=O)OCCCCCCN(CCCCO)CCCCOC(=O)C(CCCCCCCCCC)CCCCCCCCCCCC] | 5.77 |
| III-28 | 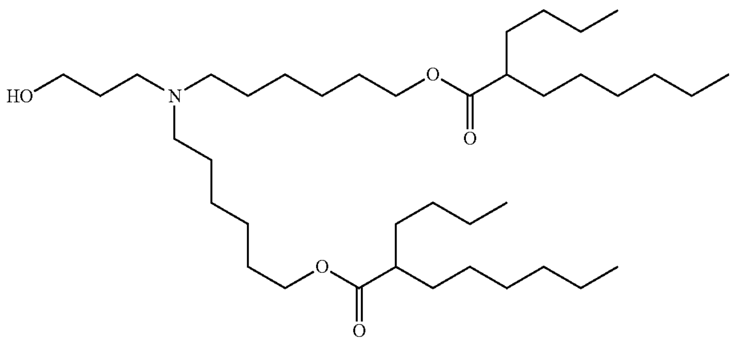 [SMILES: CCCCCCC(CCCC)C(=O)OCCCCCCN(CCCO)CCCCCCOC(=O)C(CCCC)CCCCCC] | — |

TABLE 3-continued
| Representative Compounds of Formula (III) | | |
|---|---|---|
| No. | Structure | pKa |
| III-29 | 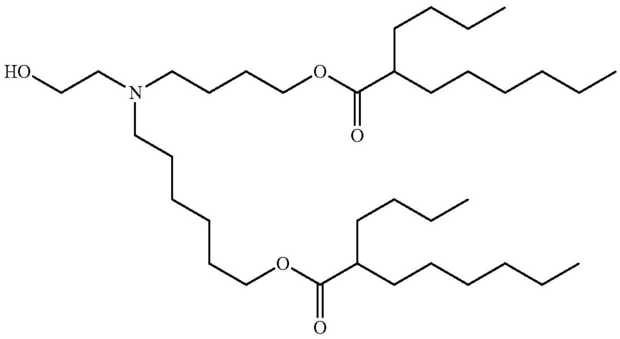 [SMILES: CCCCCCC(CCCC)C(=O)OCCCCCCN(CCO)CCCCOC(=O)C(CCCC)CCCCCC] | — |
| III-30 | 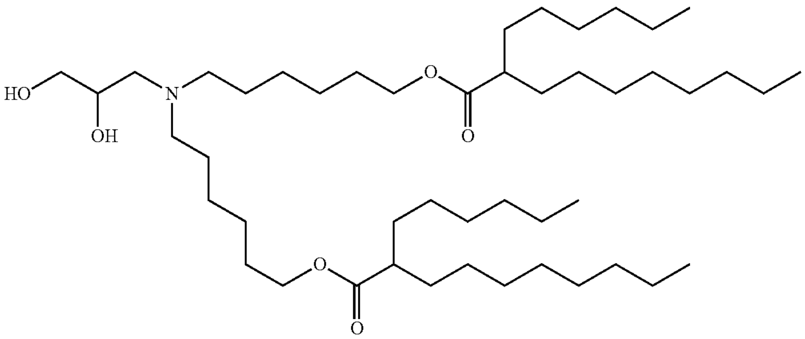 [SMILES: CCCCCCCCC(CCCCCC)C(=O)OCCCCCCN(CCCCCCOC(=O)C(CCCCCC)CCCCCCCC)CC(O)CO] | 6.09 |
| III-31 | 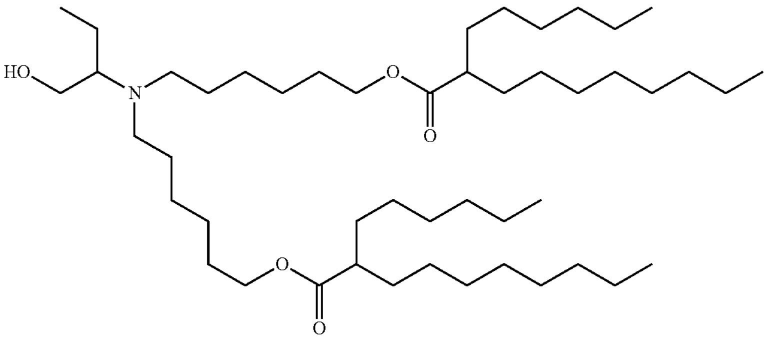 [SMILES: CCCCCCCCC(CCCCCC)C(=O)OCCCCCCN(CCCCCCOC(=O)C(CCCCCC)CCCCCCCC)C(CC)CO] | — |
| III-32 | 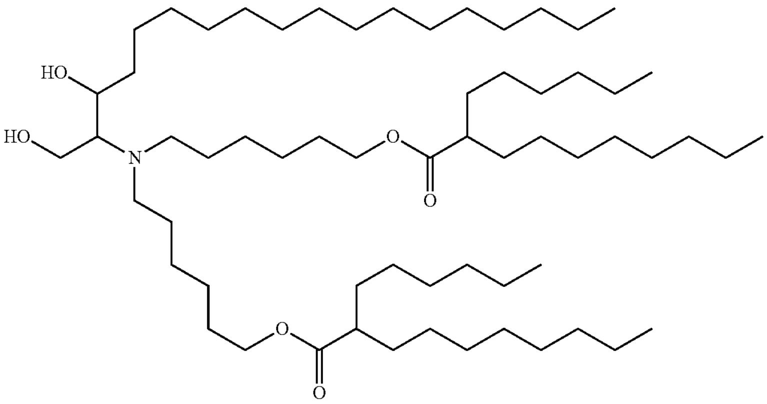 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] | — |

TABLE 3-continued
| Representative Compounds of Formula (III) | | |
|---|---|---|
| No. | Structure | pKa |
| III-33 | 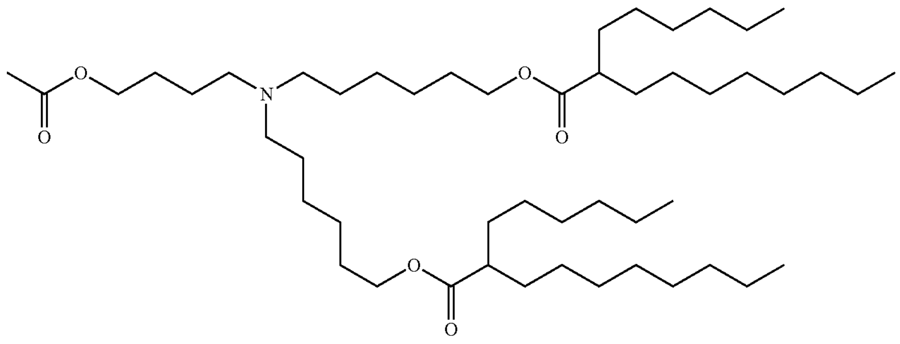 | — |
| III-34 | 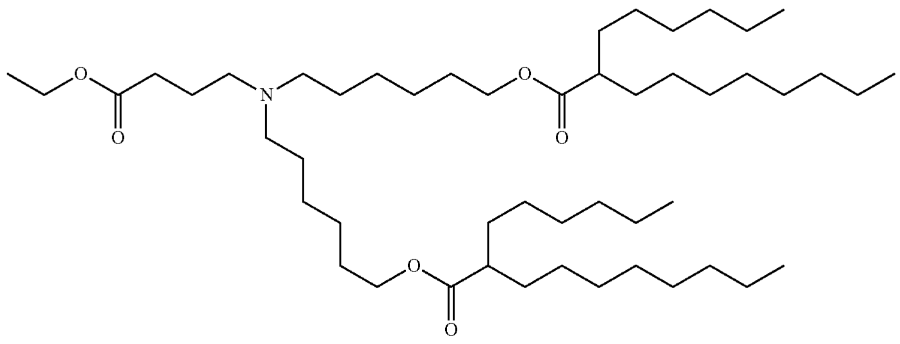 [SMILES: CCCCCCCCC(CCCCCC)C(=O)OCCCCCCN(CCCCCCOC(=O)C(CCCCCC)CCCCCCCC)CCCC(=O)OCC] | — |
| III-35 | 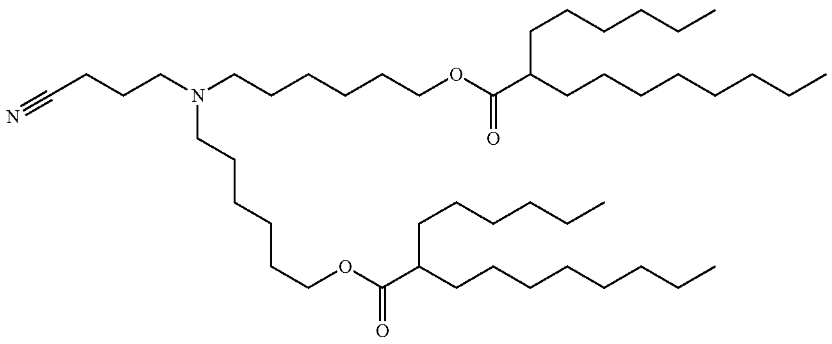 [SMILES: CCCCCCCCC(CCCCCC)C(=O)OCCCCCCN(CCCC#N)CCCCCCOC(=O)C(CCCCCC)CCCCCCCC] | — |
| III-36 | 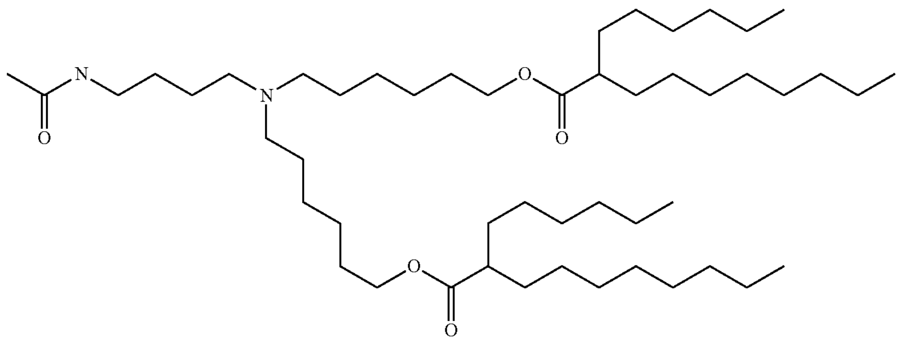 [SMILES: CCCCCCCCC(CCCCCC)C(=O)OCCCCCCN(CCCCCCOC(=O)C(CCCCCC)CCCCCCCC)CCCCNC(C)=O] | — |

TABLE 3-continued
| Representative Compounds of Formula (III) | | |
|---|---|---|
| No. | Structure | pKa |
| III-37 | 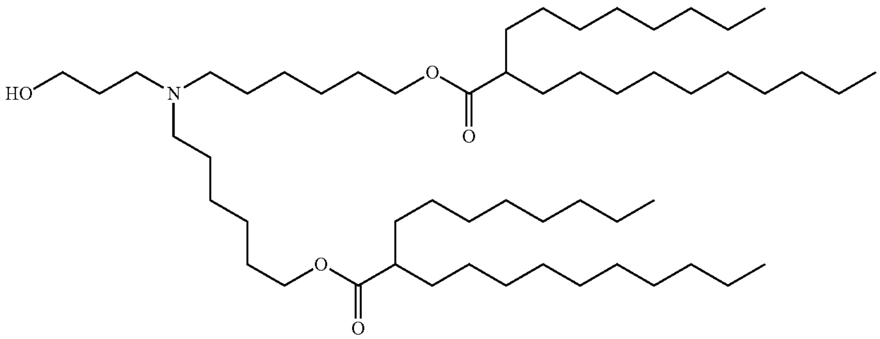 [SMILES: CCCCCCCCCCC(CCCCCCCC)C(=O)OCCCCCCN(CCCO)CCCCCCOC(=O)C(CCCCCCCC)CCCCCCCCCC] | — |
| III-38 | 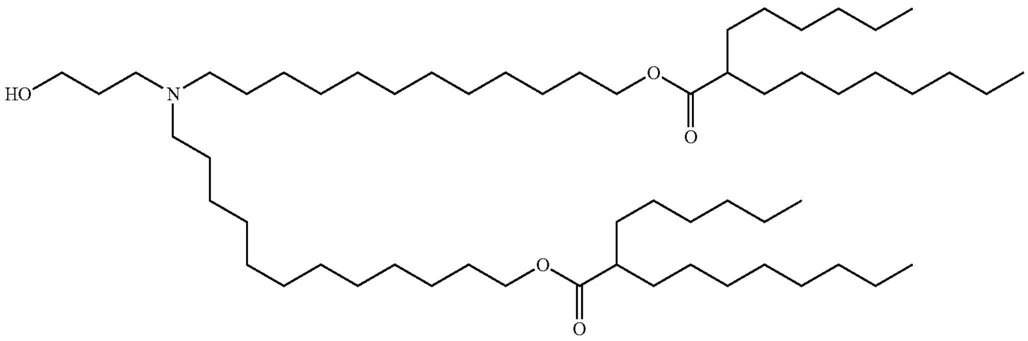 [SMILES: CCCCCCCCC(CCCCCC)C(=O)OCCCCCCCCCCCCN(CCCO)CCCCCCCCCCCCOC(=O)C(CCCCCC)CCCCCCCC] | — |
| III-39 | 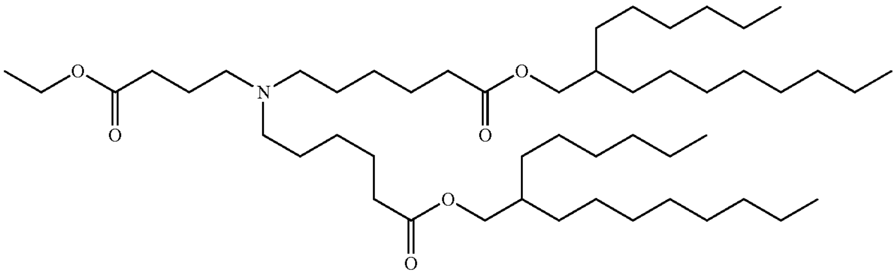 [SMILES: CCCCCCCCC(CCCCCC)COC(=O)CCCCCN(CCCCCC(=O)OCC(CCCCCC)CCCCCCCC)CCCC(=O)OCC] | — |
| III-40 | 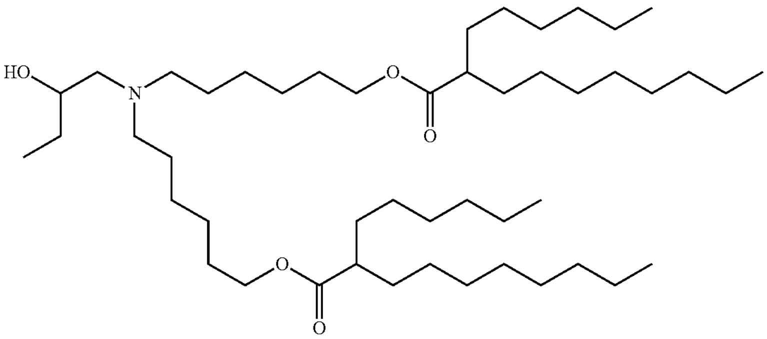 [SMILES: CCCCCCCCC(CCCCCC)C(=O)OCCCCCCN(CCCCCCOC(=O)C(CCCCCC)CCCCCCCC)CC(O)CC] | — |

TABLE 3-continued
| Representative Compounds of Formula (III) | | |
|---|---|---|
| No. | Structure | pKa |
| III-41 | 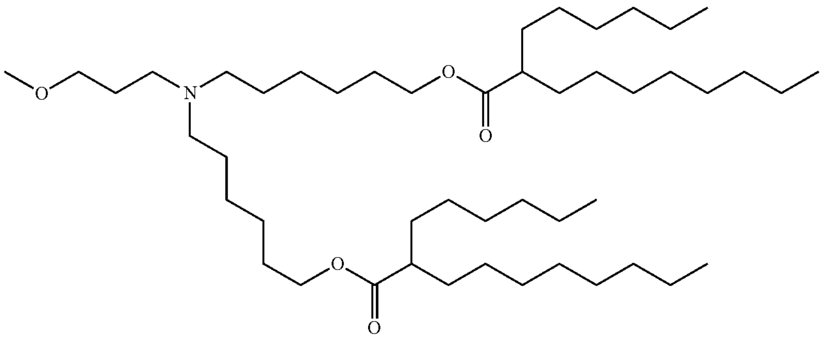 [SMILES: CCCCCCCCC(CCCCCC)C(=O)OCCCCCCN(CCCCCCOC(=O)C(CCCCCC)CCCCCCCC)CCCOC] | — |
| III-42 | 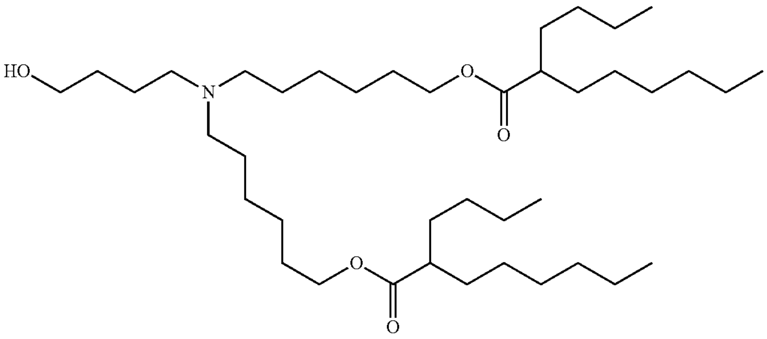 [SMILES: CCCCCCC(CCCC)C(=O)OCCCCCCN(CCCCO)CCCCCCOC(=O)C(CCCC)CCCCCC] | — |
| III-43 | 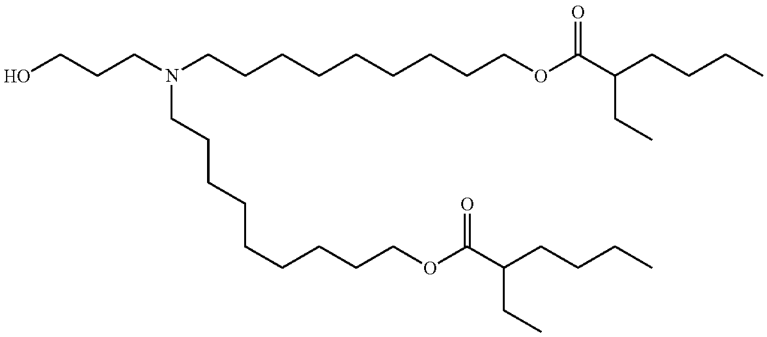 [SMILES: CCCCC(CC)C(=O)OCCCCCCCCCN(CCCO)CCCCCCCCCOC(=O)C(CC)CCCC] | — |
| III-44 | 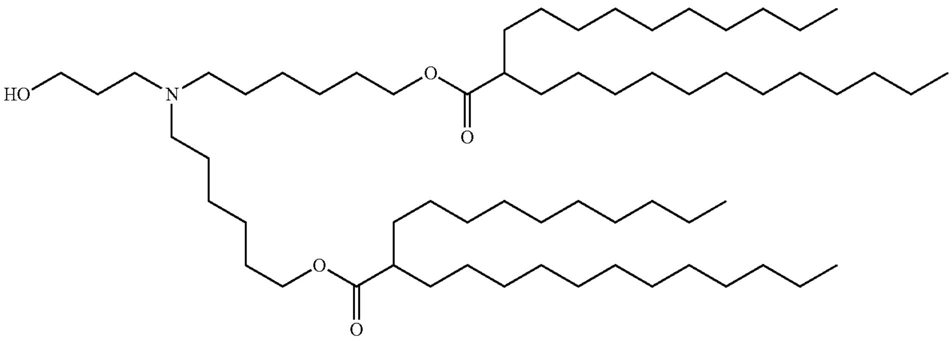 [SMILES: CCCCCCCCCCCCC(CCCCCCCCCC)C(=O)OCCCCCCN(CCCO)CCCCCCOC(=O)C(CCCCCCCCCC)CCCCCCCCCCCC] | — |

TABLE 3-continued
| Representative Compounds of Formula (III) | | |
|---|---|---|
| No. | Structure | pKa |
| III-45 | 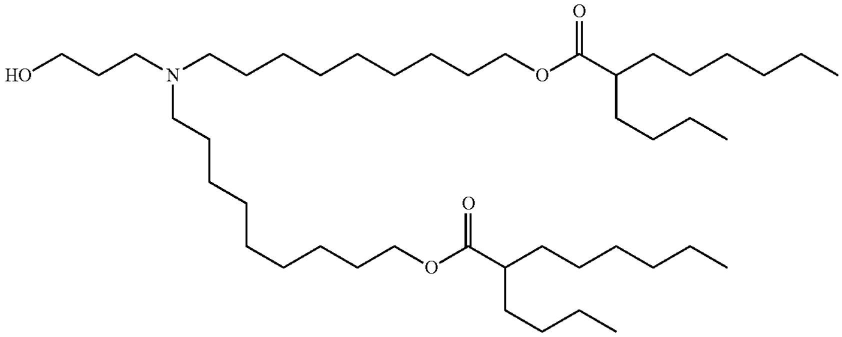 [SMILES: CCCCCCC(CCCC)C(=O)OCCCCCCCCCN(CCCO)CCCCCCCCCOC(=O)C(CCCC)CCCCCC] | — |
| III-46 | 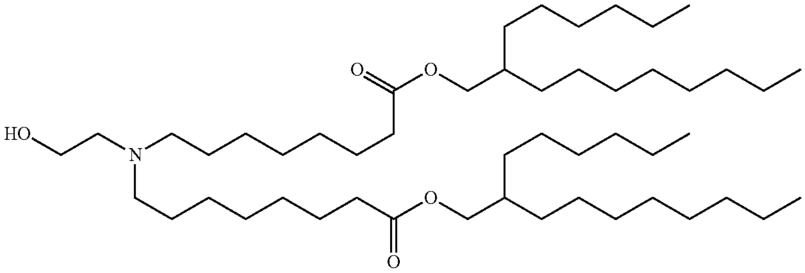 [SMILES: CCCCCCCCC(CCCCCC)COC(=O)CCCCCCCN(CCO)CCCCCCCC(=O)OCC(CCCCCC)CCCCCCCC] | — |
| III-47 | 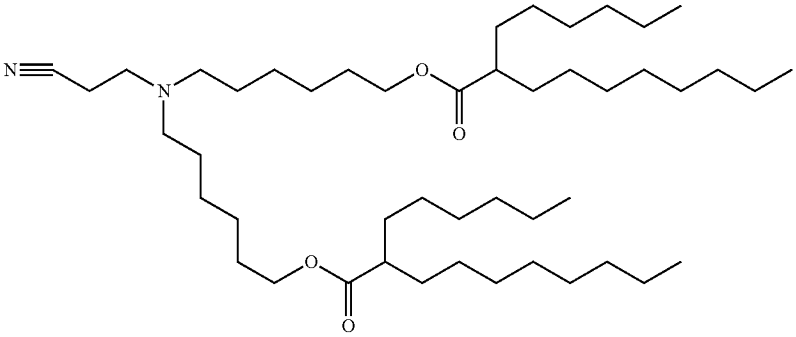 [SMILES: CCCCCCCCC(CCCCCC)C(=O)OCCCCCCN(CCC#N)CCCCCCOC(=O)C(CCCCCC)CCCCCCCC] | — |
| III-48 | 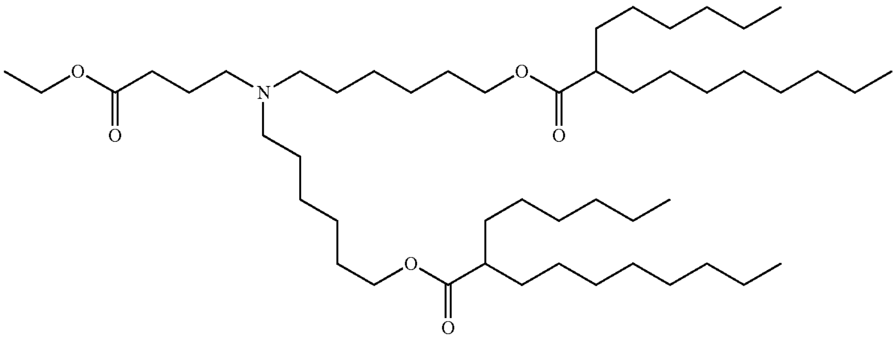 [SMILES: CCCCCCCCC(CCCCCC)C(=O)OCCCCCCN(CCCCCCOC(=O)C(CCCCCC)CCCCCCCC)CCCC(=O)OCC] | — |

TABLE 3-continued

Representative Compounds of Formula (III)

| No. | Structure | pKa |
| --- | --- | --- |
| III-49 | 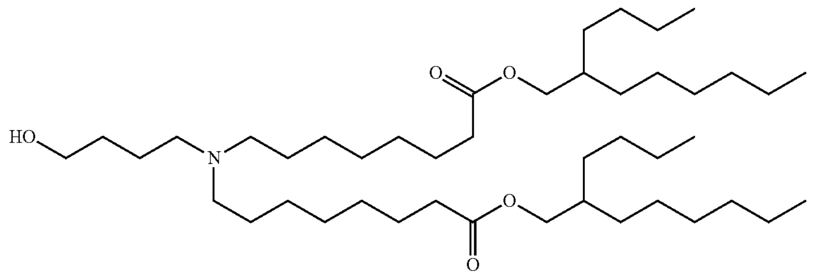 [SMILES: CCCCCCC(CCCC)COC(=O)CCCCCCCN(CCCCO)CCCCCCCC(=O)OCC(CCCC)CCCCCC] | — |

In one embodiment, the cationic lipid of any one of Embodiments 1, 2, 3, 4 or 5 has a structure of Formula (IV):

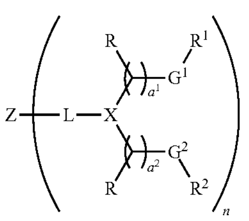

(IV)

or a pharmaceutically acceptable salt, prodrug or stereoisomer thereof, wherein:

one of $G^1$ or $G^2$ is, at each occurrence, —O(C═O)—, —(C═O)O—, —C(═O)—, —O—, —S(O)$_y$—, —S—S—, —C(═O)S—, SC(═O)—, —N($R^a$)C(═O)—, —C(═O)N($R^a$)—, —N($R^a$)C(═O)N($R^a$)—, —OC(═O)N($R^a$)— or —N($R^a$)C(═O)O—, and the other of $G^1$ or $G^2$ is, at each occurrence, —O(C═O)—, —(C═O)O—, —C(═O)—, —O—, —S(O)$_y$—, —S—S—, —C(═O)S—, —SC(═O)—, —N($R^a$)C(═O)—, —C(═O)N($R^a$)—, —N($R^a$)C(═O)N($R^a$)—, —OC(═O)N($R^a$)— or —N($R^a$)C(═O)O— or a direct bond;

L is, at each occurrence, ~O(C═O)—, wherein ~ represents a covalent bond to X;

X is $CR^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

$R^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

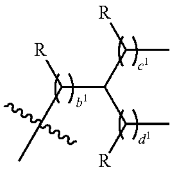 and 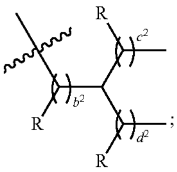;

$R^1$ $R^2$ $a^1$ and $a^2$ are, at each occurrence, independently an integer from 3 to 12;

$b^1$ and $b^2$ are, at each occurrence, independently 0 or 1;

$c^1$ and $c^2$ are, at each occurrence, independently an integer from 5 to 10;

$d^1$ and $d^2$ are, at each occurrence, independently an integer from 5 to 10;

y is, at each occurrence, independently an integer from 0 to 2; and n is an integer from 1 to 6, wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In some embodiments of Formula (IV), $G^1$ and $G^2$ are each independently

—O(C═O)— or —(C═O)O—.

In other embodiments of Formula (IV), X is CH.

In different embodiments of Formula (IV), the sum of $a^1+b^1+c^1$ or the sum of $a^2+b^2+c^2$ is an integer from 12 to 26.

In still other embodiments of Formula (IV), $a^1$ and $a^2$ are independently an integer from 3 to 10. For example, in some embodiments at and $a^2$ are independently an integer from 4 to 9.

In various embodiments of Formula (IV), $b^1$ and $b^2$ are 0. In different embodiments, $b^1$ and $b^2$ are 1.

In more embodiments of Formula (IV), $c^1$, $c^2$, $d^1$ and $d^2$ are independently an integer from 6 to 8.

In other embodiments of Formula (IV), $c^1$ and $c^2$ are, at each occurrence, independently an integer from 6 to 10, and $d^1$ and $d^2$ are, at each occurrence, independently an integer from 6 to 10.

In other embodiments of Formula (IV), $c^1$ and $c^2$ are, at each occurrence, independently an integer from 5 to 9, and $d^1$ and $d^2$ are, at each occurrence, independently an integer from 5 to 9.

In more embodiments of Formula (IV), Z is alkyl, cycloalkyl or a monovalent moiety comprising at least one polar functional group when n is 1. In other embodiments, Z is alkyl.

In various embodiments of the foregoing Formula (IV), R is, at each occurrence, independently either: (a) H or methyl; or (b) R together with the carbon atom to which it is bound is taken together with an adjacent R and the carbon atom to which it is bound to form a carbon-carbon double bond. In certain embodiments, each R is H. In other embodiments at least one R together with the carbon atom to which it is bound is taken together with an adjacent R and the carbon atom to which it is bound to form a carbon-carbon double bond.

In other embodiments of the compound of Formula (IV), $R^1$ and $R^2$ independently have one of the following structures:

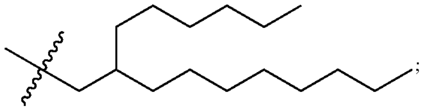

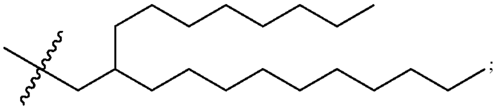

-continued

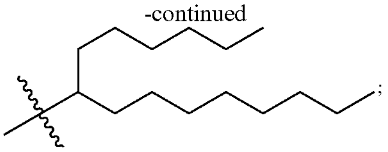

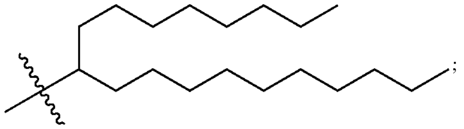

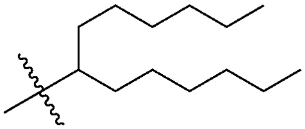

or

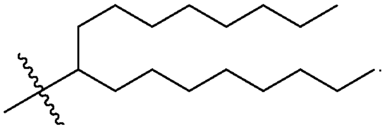

In certain embodiments of Formula (IV), the compound has one of the following structures:

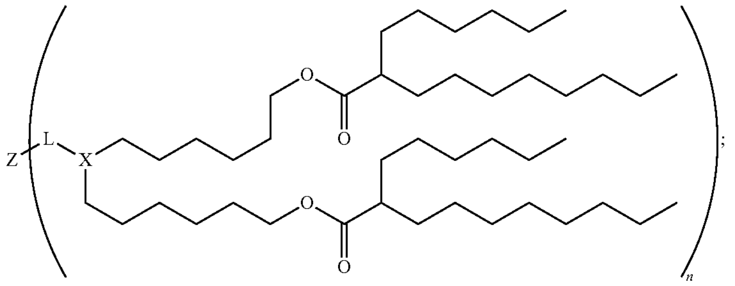

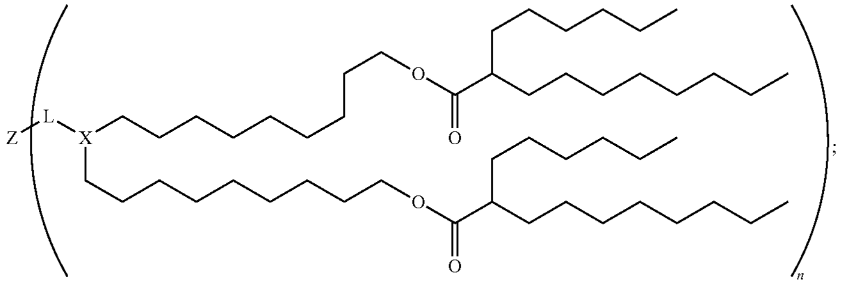

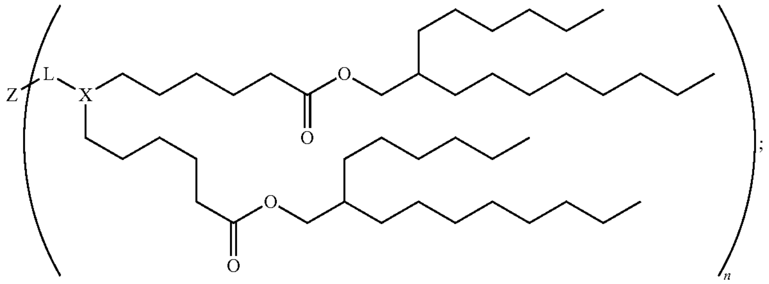

-continued
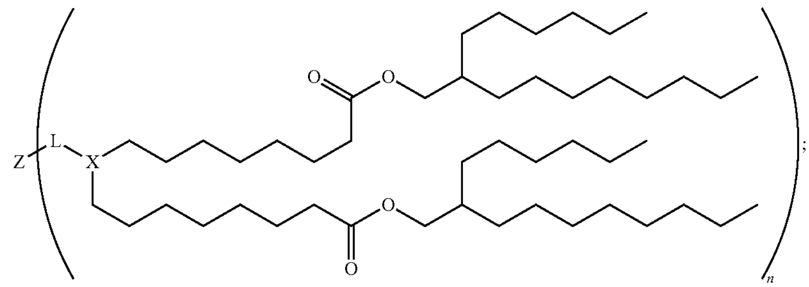
;
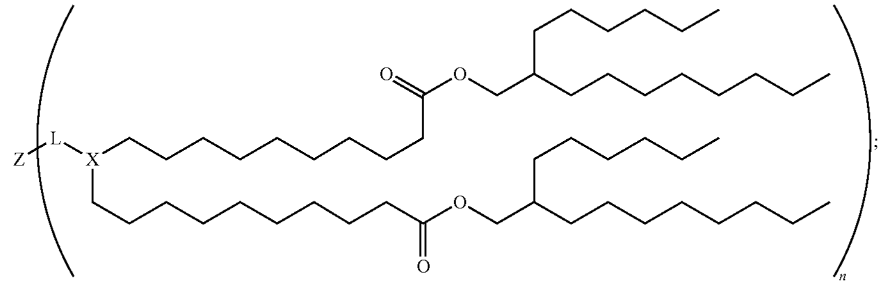
;
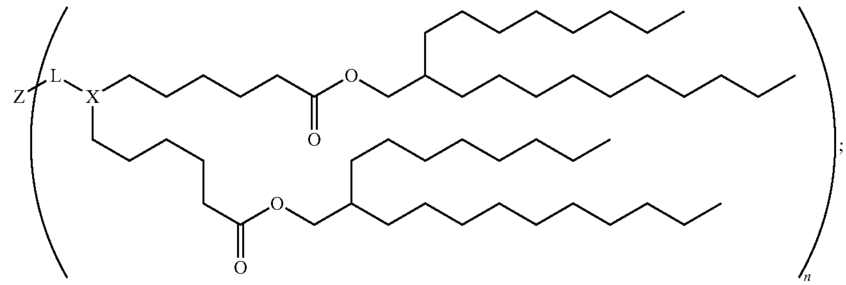
;
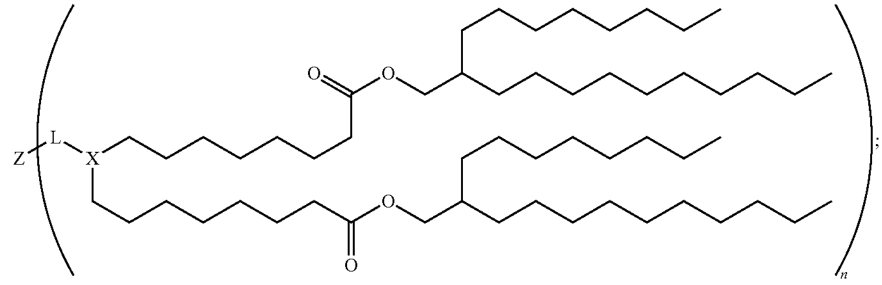
;
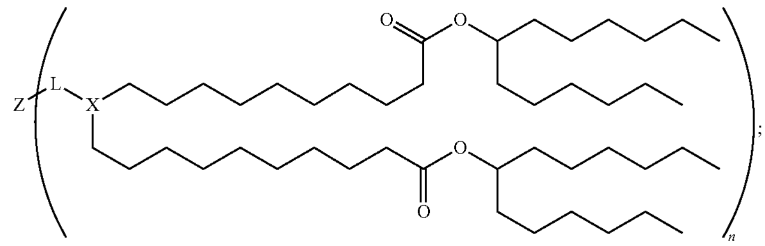
;
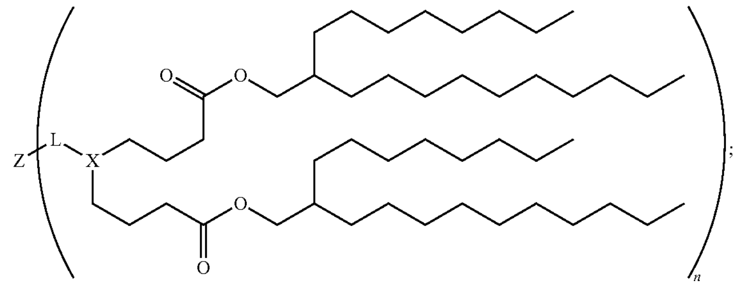
;

-continued
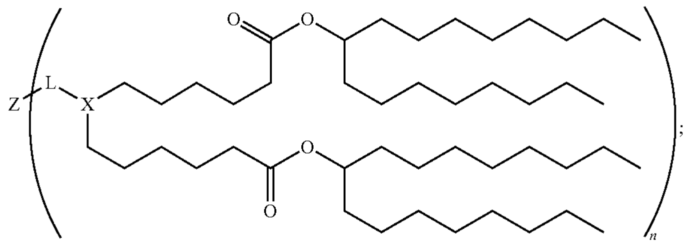
;
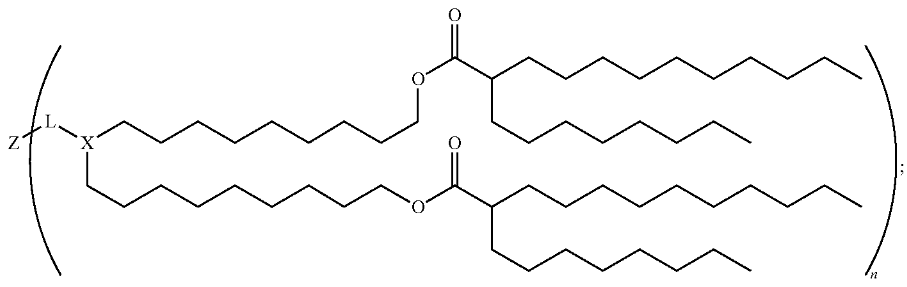
;
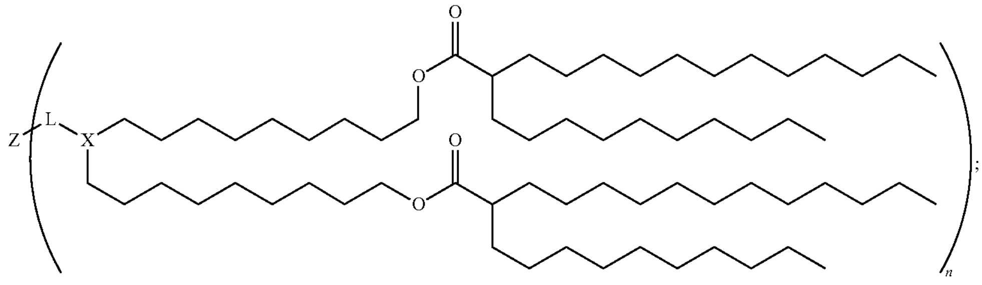
;
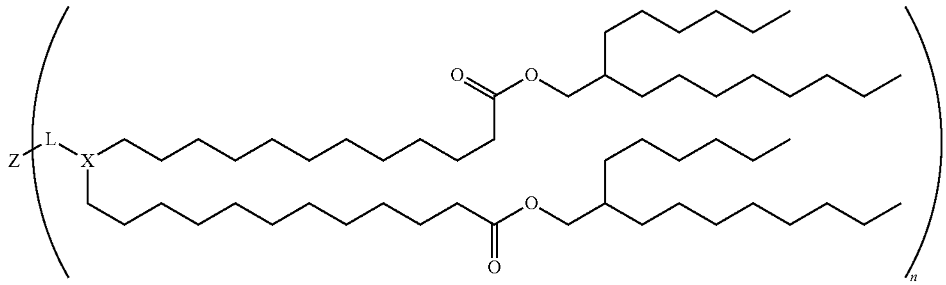
or
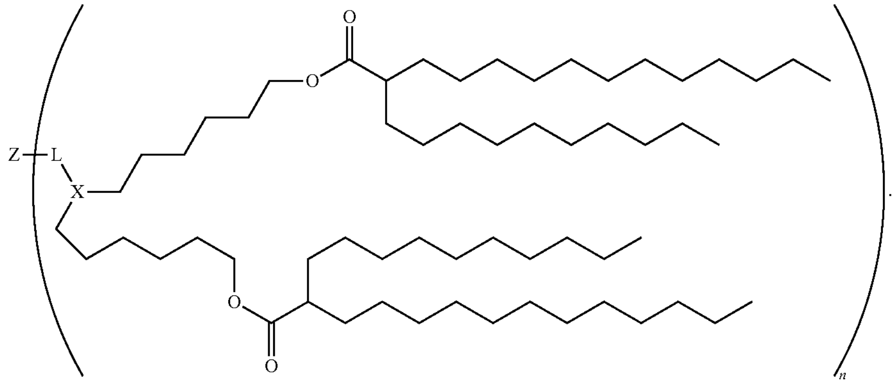
.

In still different embodiments the cationic lipid of Embodiments 1, 2, 3, 4 or 5 has the structure of Formula (V):

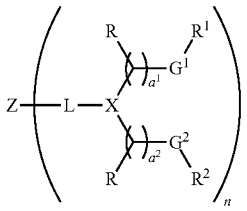

(V)

or a pharmaceutically acceptable salt, prodrug or stereoisomer thereof, wherein:

one of $G^1$ or $G^2$ is, at each occurrence, —O(C═O)—, —(C═O)O—, —C(═O)—, —O—, —S(O)$_y$—, —S—S—, —C(═O)S—, SC(═O)—, —N($R^a$)C(═O)—, —C(═O)N($R^a$)—, —N($R^a$)C(═O)N($R^a$)—, —OC(═O)N($R^a$)— or —N($R^a$)C(═O)O—, and the other of $G^1$ or $G^2$ is, at each occurrence, —O(C═O)—, —(C═O)O—, —C(═O)—, —O—, —S(O)$_y$—, —S—S—, —C(═O)S—, —SC(═O)—, —N($R^a$)C(═O)—, —C(═O)N($R^a$)—, —N($R^a$)C(═O)N($R^a$)—, —OC(═O)N($R^a$)— or —N($R^a$)C(═O)O— or a direct bond;

L is, at each occurrence, ~O(C═O)—, wherein ~ represents a covalent bond to X;

X is $CR^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

$R^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

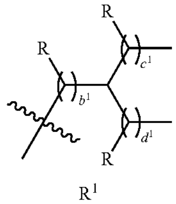 and 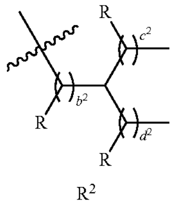;

$R^1$ $R^2$

R' is, at each occurrence, independently H or $C_1$-$C_{12}$ alkyl;

$a^1$ and $a^2$ are, at each occurrence, independently an integer from 3 to 12;

$b^1$ and $b^2$ are, at each occurrence, independently 0 or 1;

$c^1$ and $c^2$ are, at each occurrence, independently an integer from 2 to 12;

$d^1$ and $d^2$ are, at each occurrence, independently an integer from 2 to 12;

y is, at each occurrence, independently an integer from 0 to 2; and n is an integer from 1 to 6, wherein $a^1$, $a^2$, $c^1$, $c^2$, $d^1$ and $d^2$ are selected such that the sum of $a^1$+$c^1$+$d^1$ is an integer from 18 to 30, and the sum of $a^2$+$c^2$+$d^2$ is an integer from 18 to 30, and wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In certain embodiments of Formula (V), $G^1$ and $G^2$ are each independently —O(C═O)— or —(C═O)O—.

In other embodiments of Formula (V), X is CH.

In some embodiments of Formula (V), the sum of $a^1$+$c^1$+$d^1$ is an integer from 20 to 30, and the sum of $a^2$+$c^2$+$d^2$ is an integer from 18 to 30. In other embodiments, the sum of $a^1$+$c^1$+$d^1$ is an integer from 20 to 30, and the sum of $a^2$+$c^2$±$d^2$ is an integer from 20 to 30. In more embodiments of Formula (V), the sum of $a^1$+$b^1$+$c^1$ or the sum of $a^2$+$b^2$+$c^2$ is an integer from 12 to 26. In other embodiments, $a^1$, $a^2$, $c^1$, $c^2$, $d^1$ and $d^2$ are selected such that the sum of $a^1$+$c^1$+$d^1$ is an integer from 18 to 28, and the sum of $a^2$+$c^2$+$d^2$ is an integer from 18 to 28, In still other embodiments of Formula (V), $a^1$ and $a^2$ are independently an integer from 3 to 10, for example an integer from 4 to 9.

In yet other embodiments of Formula (V), $b^1$ and $b^2$ are 0. In different embodiments $b^1$ and $b^2$ are 1.

In certain other embodiments of Formula (V), $c^1$, $c^2$, $d^1$ and $d^2$ are independently an integer from 6 to 8.

In different other embodiments of Formula (V), Z is alkyl or a monovalent moiety comprising at least one polar functional group when n is 1; or Z is alkylene or a polyvalent moiety comprising at least one polar functional group when n is greater than 1.

In more embodiments of Formula (V), Z is alkyl, cycloalkyl or a monovalent moiety comprising at least one polar functional group when n is 1. In other embodiments, Z is alkyl.

In other different embodiments of Formula (V), R is, at each occurrence, independently either: (a) H or methyl; or (b) R together with the carbon atom to which it is bound is taken together with an adjacent R and the carbon atom to which it is bound to form a carbon-carbon double bond. For example in some embodiments each R is H. In other embodiments at least one R together with the carbon atom to which it is bound is taken together with an adjacent R and the carbon atom to which it is bound to form a carbon-carbon double bond.

In more embodiments, each R' is H.

In certain embodiments of Formula (V), the sum of $a^1$+$c^1$+$d^1$ is an integer from 20 to 25, and the sum of $a^2$+$c^2$+$d^2$ is an integer from 20 to 25.

In other embodiments of Formula (V), $R^1$ and $R^2$ independently have one of the following structures:

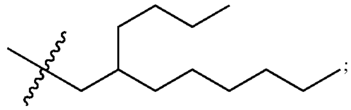;

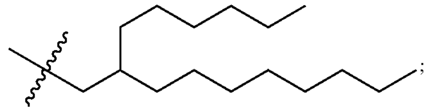;

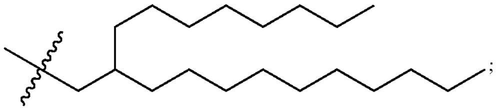;

-continued
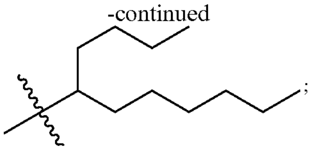;
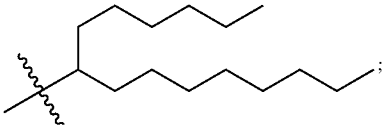;
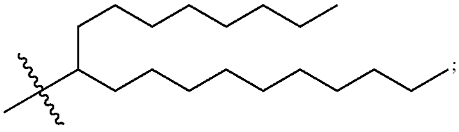;
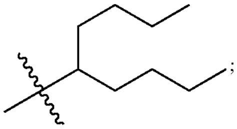; 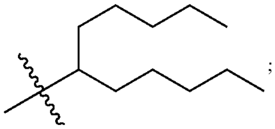;
-continued
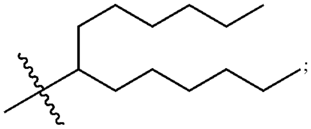;
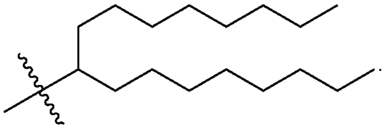.
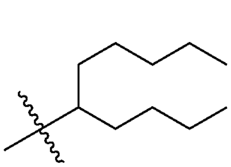 or 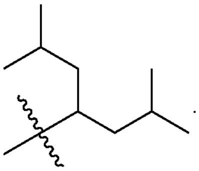.
In more embodiments of Formula (V), the compound has one of the following structures:
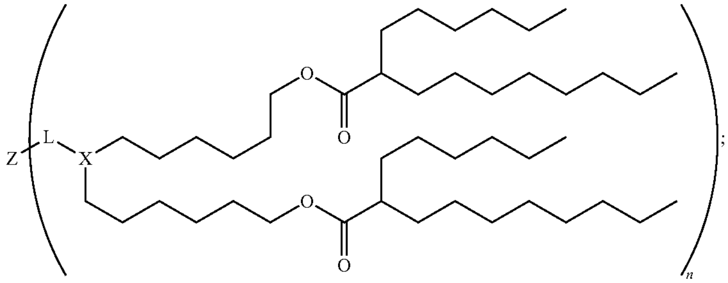;
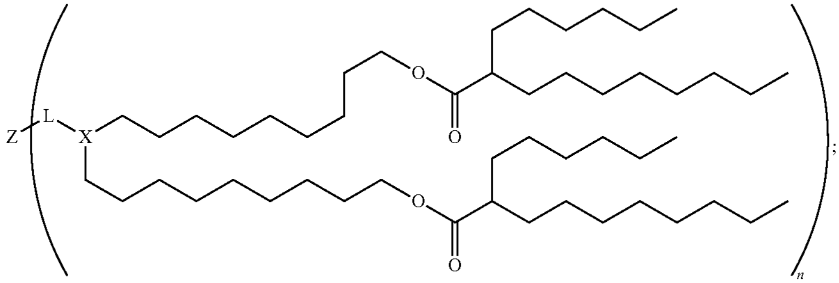;
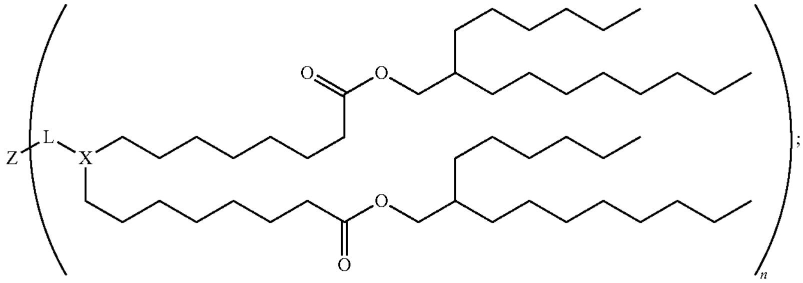;
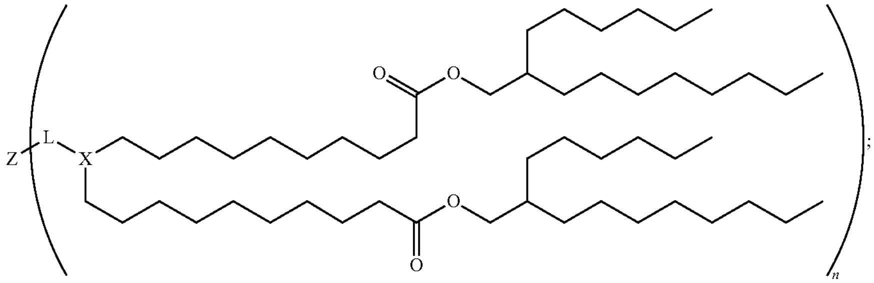;

-continued
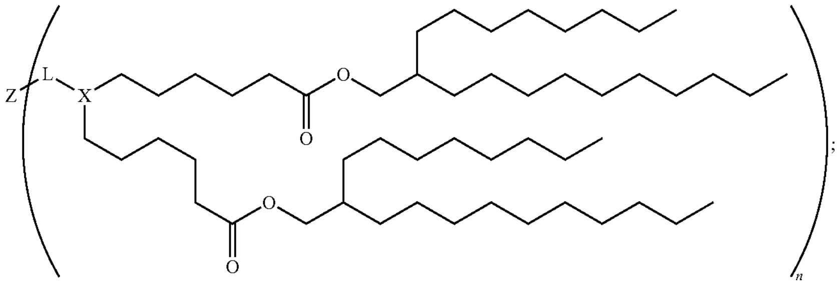
;
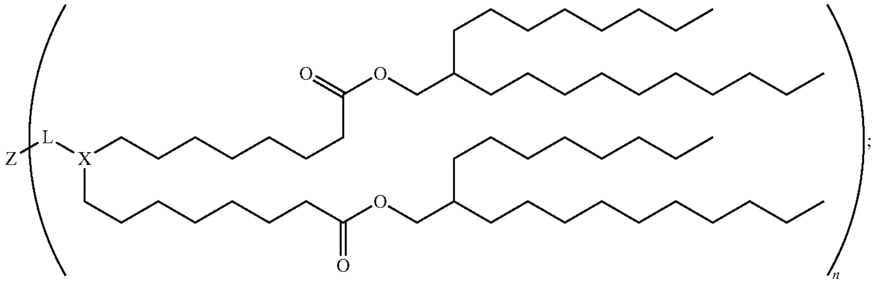
;
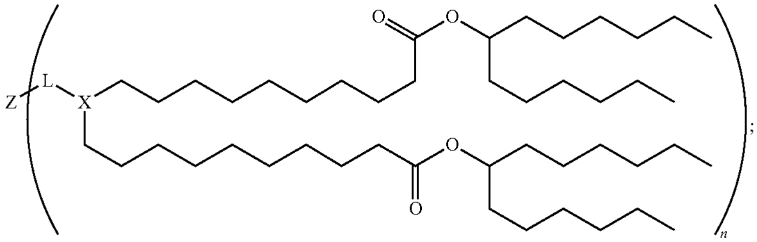
;
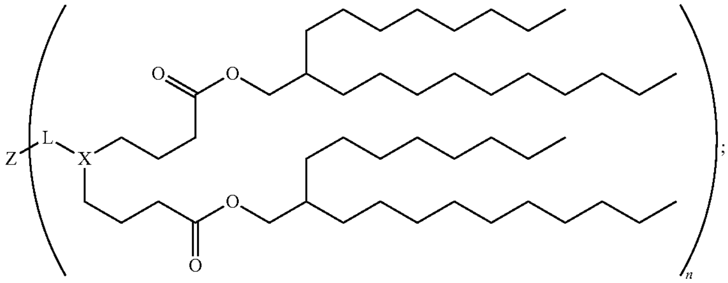
;
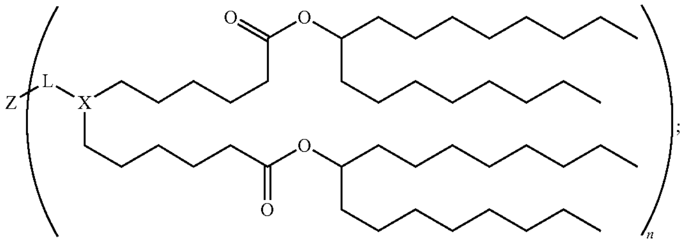
;
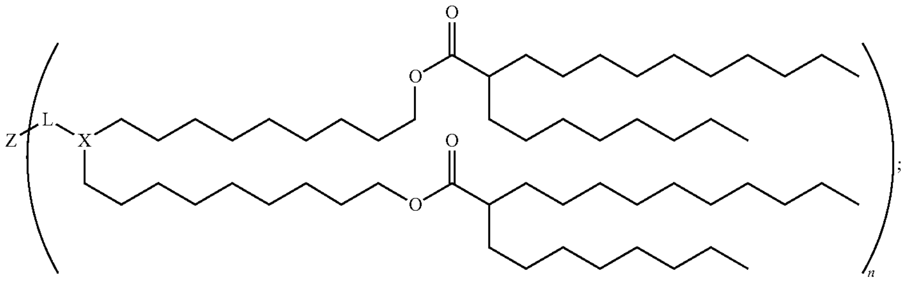
;

-continued

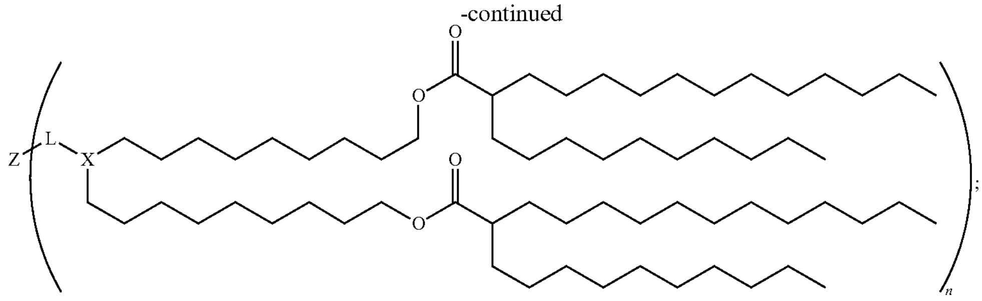

;

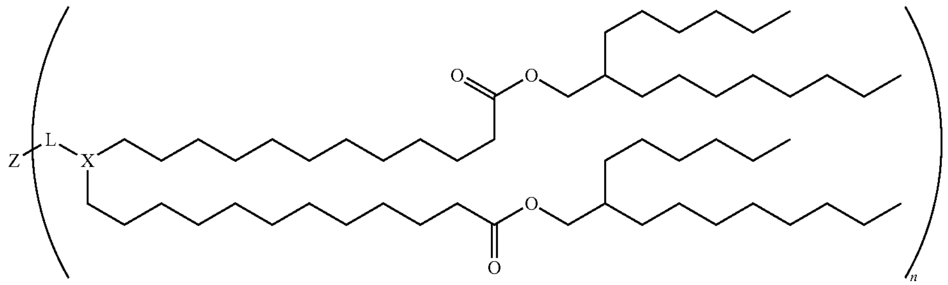

or

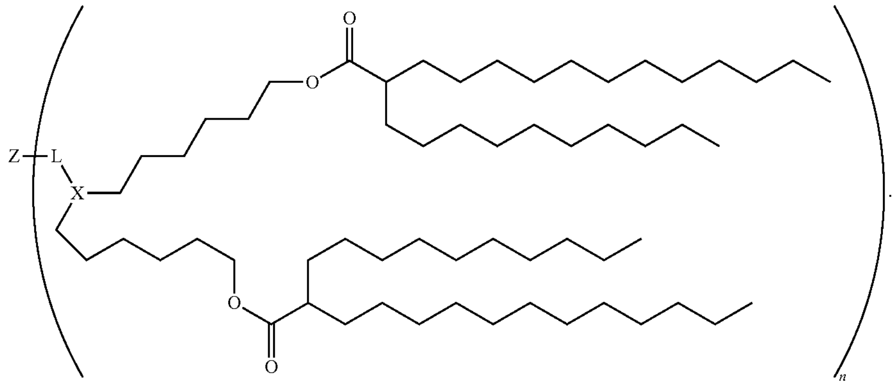

.

In any of the foregoing embodiments of Formula (IV) or (V), n is 1. In other of the foregoing embodiments of Formula (IV) or (V), n is greater than 1.

In more of any of the foregoing embodiments of Formula (IV) or (V), Z is a mono- or polyvalent moiety comprising at least one polar functional group. In some embodiments, Z is a monovalent moiety comprising at least one polar functional group. In other embodiments, Z is a polyvalent moiety comprising at least one polar functional group.

In more of any of the foregoing embodiments of Formula (IV) or (V), the polar functional group is a hydroxyl, alkoxy, ester, cyano, amide, amino, alkylaminyl, heterocyclyl or heteroaryl functional group.

In any of the foregoing embodiments of Formula (IV) or (V), Z is hydroxyl, hydroxylalkyl, alkoxyalkyl, amino, aminoalkyl, alkylaminyl, alkylaminylalkyl, heterocyclyl or heterocyclylalkyl.

In some other embodiments of Formula (IV) or (V), Z has the following structure:

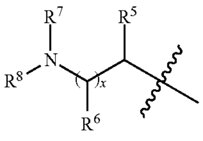

wherein:

$R^5$ and $R^6$ are independently H or $C_1$-$C_6$ alkyl;

$R^7$ and $R^8$ are independently H or $C_1$-$C_6$ alkyl or $R^7$ and $R^8$, together with the nitrogen atom to which they are attached, join to form a 3-7 membered heterocyclic ring; and x is an integer from 0 to 6.

In still different embodiments of Formula (IV) or (V), Z has the following structure:

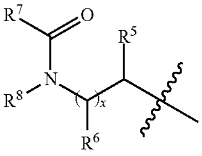

wherein:

$R^5$ and $R^6$ are independently H or $C_1$-$C_6$ alkyl;

$R^7$ and $R^8$ are independently H or $C_1$-$C_6$ alkyl or $R^1$ and $R^8$, together with the nitrogen atom to which they are attached, join to form a 3-7 membered heterocyclic ring; and x is an integer from 0 to 6.

In still different embodiments of formula (IV) or (V), Z has the following structure:

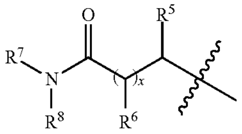

wherein:

$R^5$ and $R^6$ are independently H or $C_1$-$C_6$ alkyl;

$R^7$ and $R^8$ are independently H or $C_1$-$C_6$ alkyl or $R^7$ and $R^8$, together with the nitrogen atom to which they are attached, join to form a 3-7 membered heterocyclic ring; and x is an integer from 0 to 6.

In some other embodiments of Formula (IV) or (V), Z is hydroxylalkyl, cyanoalkyl or an alkyl substituted with one or more ester or amide groups.

For example, in any of the foregoing embodiments of Formula (IV) or (V), Z has one of the following structures:

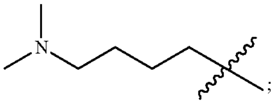
;
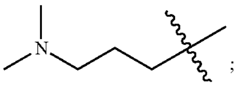
;
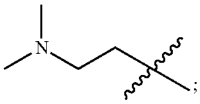
;
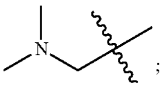
;
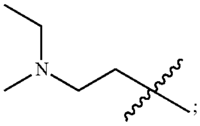
;
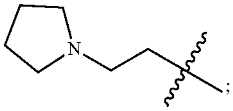
;
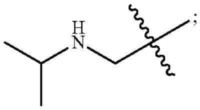
;
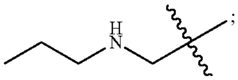
;
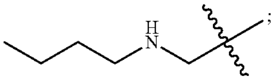
;
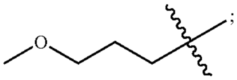
;
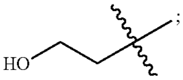
;
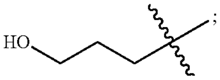
;
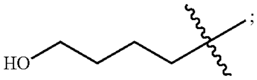
;
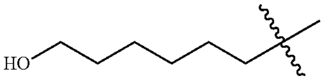
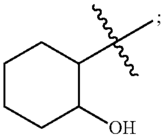
;
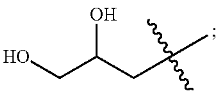
;
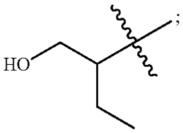
;
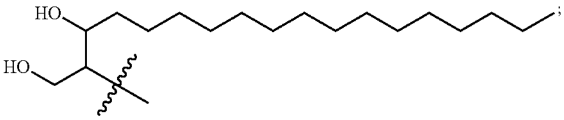
;
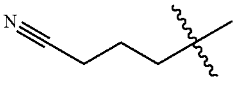
or -continued

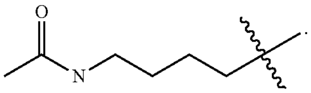
.

In other embodiments of Formula (IV) or (V), Z-L has one of the following structures:

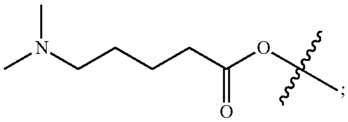
;
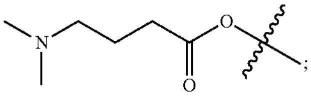
;
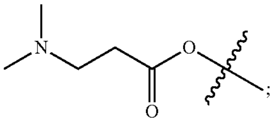
;
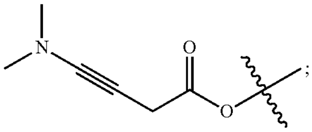
;
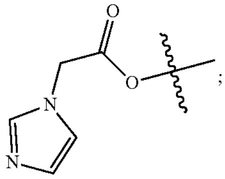
;
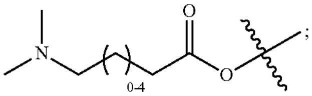
;
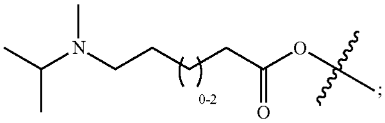
;
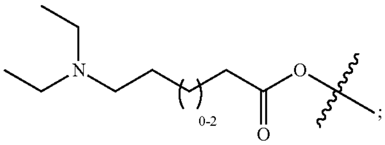
;
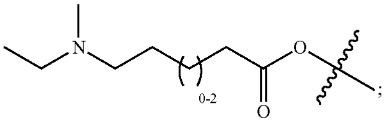
;
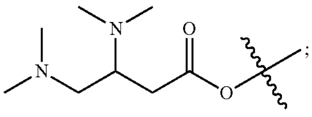
;
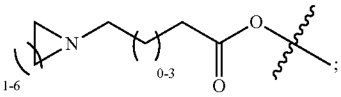
;
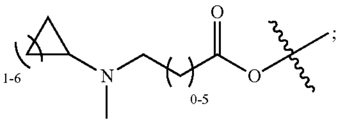
;
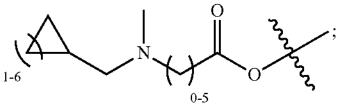
;

-continued
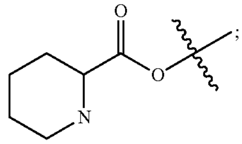
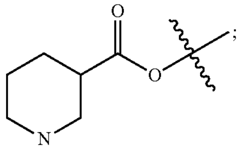
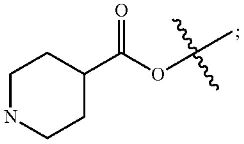
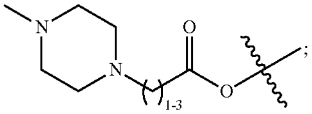
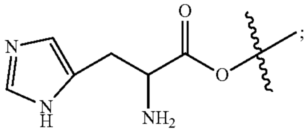
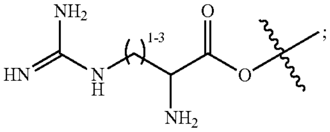
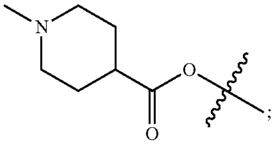
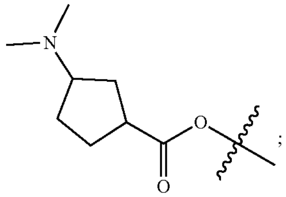
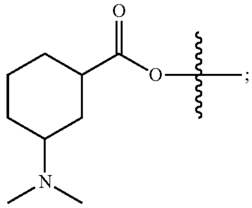
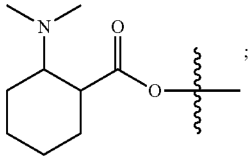
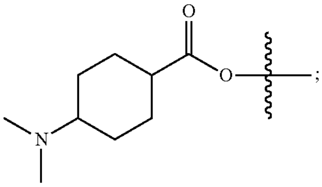
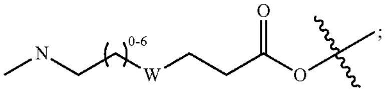
W = O, S, NH, NMe
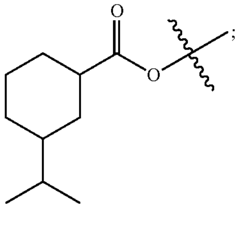
-continued
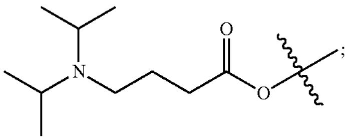
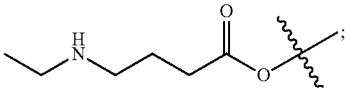
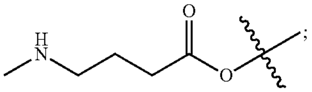
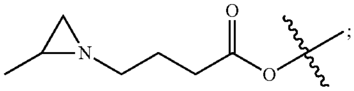
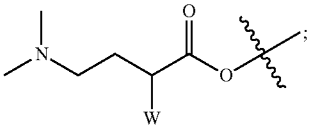
W = Me, OH, Cl
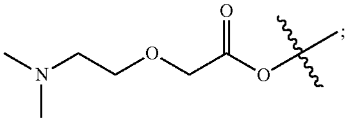
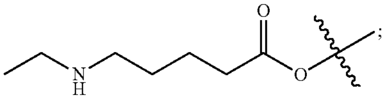
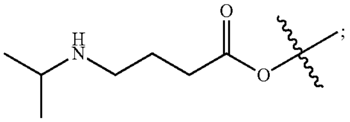
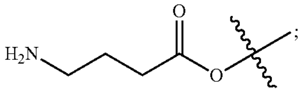
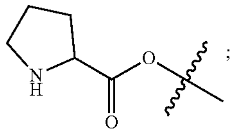
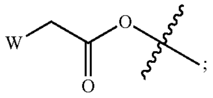
W = H, Me, Et, iPr
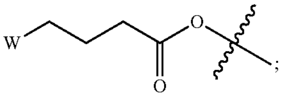
W = H, Me, Et, iPr
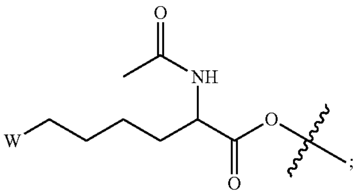
W = H, Me, Et, iPr
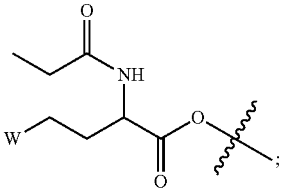
W = H, Me, Et, iPr -continued
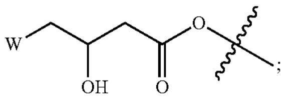
W = H, Me, Et, iPr
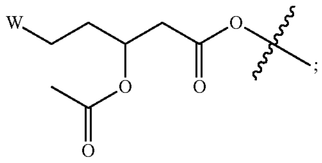
W = H, Me, Et, iPr
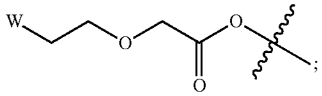
W = H, Me, Et, iPr
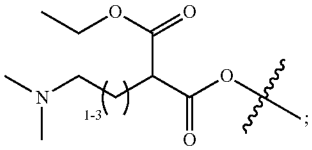
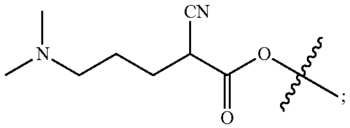
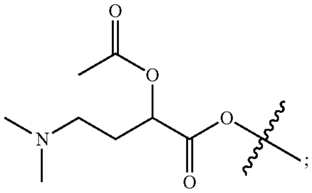
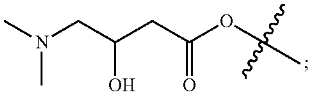
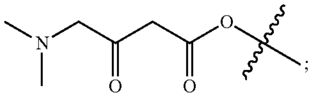
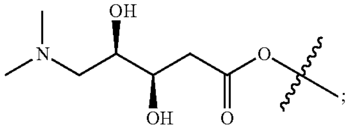
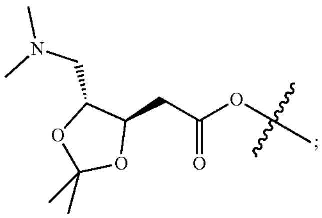
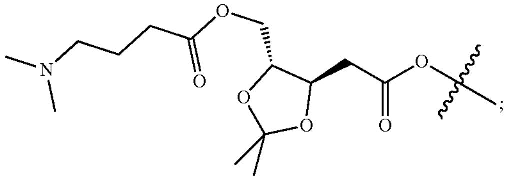
-continued
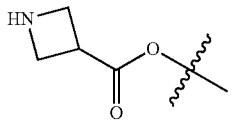
or
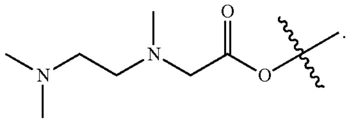
In other embodiments, Z-L has one of the following structures:
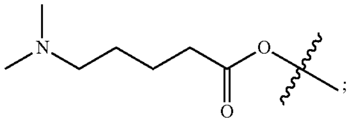
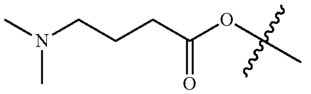
or
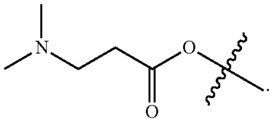
In still other embodiments, X is CH and Z-L has one of the following structures:
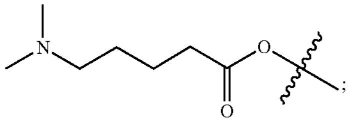
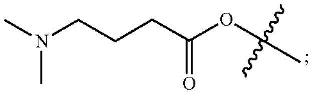
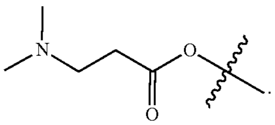
In various different embodiments, a cationic lipid of any one Embodiments 1, 2, 3, 4 or 5 has one of the structures set forth in Table 4 below.

TABLE 4

| Representative Compounds of Formula (IV) or (V) | |
|---|---|
| No. | Structure |
| IV-1 | 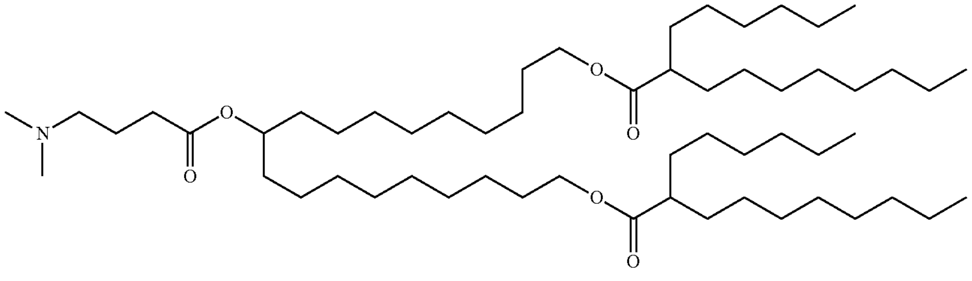 [SMILES: CCCCCCCCC(CCCCCC)C(=O)OCCCCCCCCCC(CCCCCCCCCOC(=O)C(CCCCCC)CCCCCCCC)OC(=O)CCCN(C)C] |
| IV-2 | 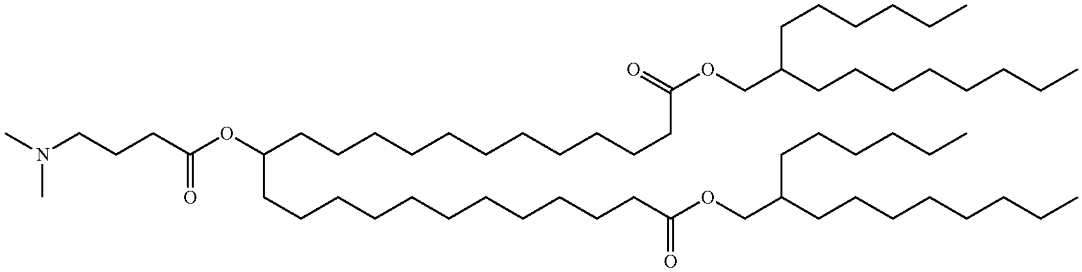 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C] |
| IV-3 | 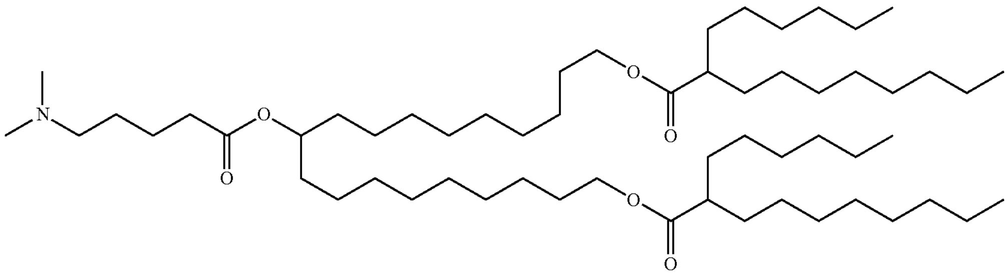 [SMILES: CCCCCCCCC(CCCCCC)C(=O)OCCCCCCCCCC(CCCCCCCCCOC(=O)C(CCCCCC)CCCCCCCC)OC(=O)CCCCN(C)C] |

In one embodiment, the cationic lipid is a compound having the following structure (VI):

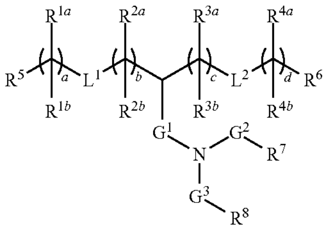

(VI)

or a pharmaceutically acceptable salt, tautomer, prodrug or stereoisomer thereof, wherein:

$L^1$ and $L^2$ are each independently —O(C═O)—, —(C═O)O—, —C(═O)—, —O—, —S(O)$_x$—, —S—S—, —C(═O)S—, —SC(═O)—, —NR$^a$C(═O)—, —C(═O)NR$^a$—, —NR$^a$C(═O)NR$^a$—, —OC(═O)NR$^a$—, —NR$^a$C(═O)O— or a direct bond;

$G^1$ is $C_1$-$C_2$ alkylene, —(C═O)—, —O(C═O)—, —SC(═O)—, —NR$^a$C(═O)— or a direct bond;

$G^2$ is —C(═O)—, —(C═O)O—-, —C(═O)S—, —C(═O)NR$^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is H or $C_1$-$C_{20}$ alkyl;

$R^8$ is OH, —N($R^9$)(C═O)$R^{10}$, —(C═O)N$R^9R^{10}$, —N$R^9R^{11}$, —(C═O)O$R^{11}$ or —O(C═O)$R^{11}$, provided that $G^3$ is $C_4$-$C_6$ alkylene when $R^8$ is —N$R^9R^{10}$, $R^9$ and $R^{10}$ are each independently H or $C_1$-$C_{12}$ alkyl;

$R^{11}$ is aralkyl;

a, b, c and d are each independently an integer from 1 to 24; and x is 0, 1 or 2, wherein each alkyl, alkylene and aralkyl is optionally substituted.

In some embodiments of structure (VI), $L^1$ and $L^2$ are each independently —O(C═O)—, —(C═O)O— or a direct bond. In other embodiments, $G^1$ and $G^2$ are each independently —(C═O)— or a direct bond. In some different embodiments, $L^1$ and $L^2$ are each independently —O(C═O)—, —(C═O)O— or a direct bond; and $G^1$ and $G^2$ are each independently —(C═O)— or a direct bond.

In some different embodiments of structure (VI), $L^1$ and $L^2$ are each independently —C(═O)—, —O—, —S(O)$_x$—, —S—S—, —C(═O)S—, —SC(═O)—, —NR$^a$—, —NR$^a$C(═O)—, —C(═O)NR$^a$—, —NR$^a$C(═O)NR$^a$, —OC(═O)NR$^a$—, —NR$^a$C(═O)O—, —NR$^a$S(O)$_x$NR$^a$—, —NR$^a$S(O)— or —S(O)$_x$NR$^a$—.

In other of the foregoing embodiments of structure (VI), the compound has one of the following structures (VIA) or (VIB):

(VIA)

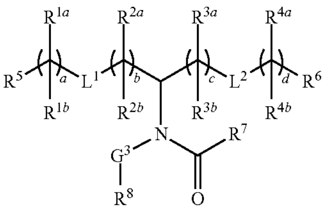

or (VIB)

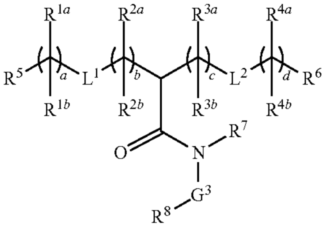

In some embodiments, the compound has structure (VIA). In other embodiments, the compound has structure (VIB).

In any of the foregoing embodiments of structure (VI), one of $L^1$ or $L^2$ is —O(C═O)—. For example, in some embodiments each of $L^1$ and $L^2$ are —O(C═O)—.

In some different embodiments of any of the foregoing, one of $L^1$ or $L^2$ is —(C═O)O—. For example, in some embodiments each of $L^1$ and $L^2$ is —(C═O)O—.

In different embodiments of structure (VI), one of $L^1$ or $L^2$ is a direct bond. As used herein, a "direct bond" means the group (e.g., $L^1$ or $L^2$) is absent. For example, in some embodiments each of $L^1$ and $L^2$ is a direct bond.

In other different embodiments of the foregoing, for at least one occurrence of $R^{1a}$ and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of structure (VI), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of structure (VI), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of any of the foregoing, for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

It is understood that "carbon-carbon" double bond refers to one of the following structures:

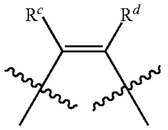

or

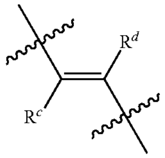

wherein $R^c$ and $R^d$ are, at each occurrence, independently H or a substituent. For example, in some embodiments $R^c$ and $R^d$ are, at each occurrence, independently H, $C_1$-$C_{12}$ alkyl or cycloalkyl, for example H or $C_1$-$C_{12}$ alkyl.

In various other embodiments, the compound has one of the following structures (VIC) or (VID):

(VIC)

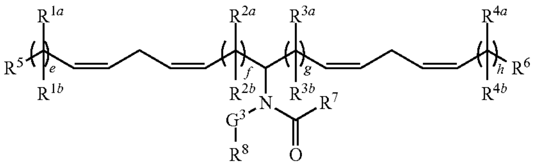

or (VID)

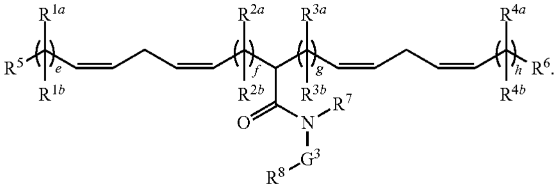

wherein e, f, g and h are each independently an integer from 1 to 12.

In some embodiments, the compound has structure (VIC). In other embodiments, the compound has structure (VID).

In various embodiments of the compounds of structures (VIC) or (VID), e, f g and h are each independently an integer from 4 to 10.

In other different embodiments,

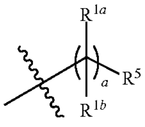

or

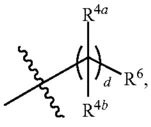

or both, independently has one of the following structures.

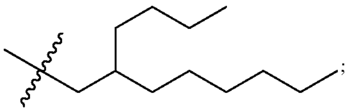
;
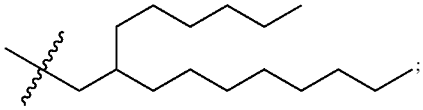
;
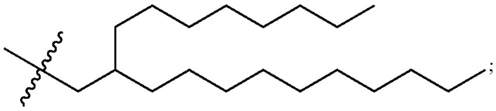
;
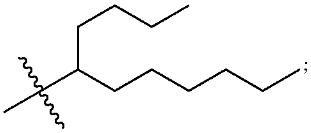
;
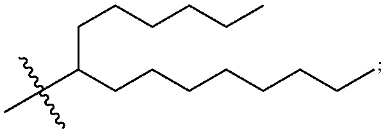
;
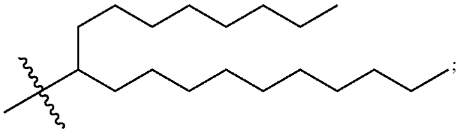
;
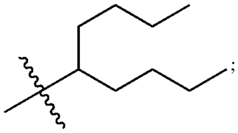
;
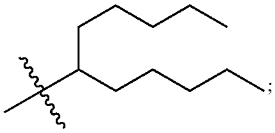
;
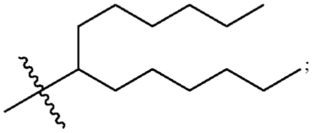
;
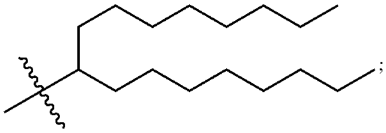
;
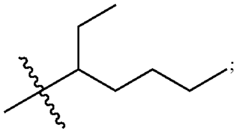
;
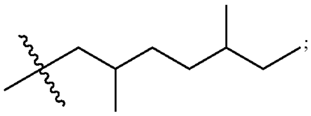
;
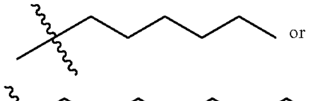
or
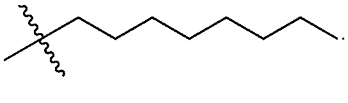
.

In certain embodiments of the foregoing, a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7.

In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of structure (VI), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of structure (VI), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments of structure (VI), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of structure (VI), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of structure (VI), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of structure (VI), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of structure (VI), h is 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, h is 11. In yet other embodiments, h is 12.

In some other various embodiments of structure (VI), a and d are the same. In some other embodiments, b and c are the same. In some other specific embodiments a and d are the same and b and c are the same.

The sum of a and b and the sum of c and d are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such that the sum of a and b and the sum of c and d is 12 or greater.

The substituents at $R^{1a}$, $R^{2a}$, $R^{3a}$ and $R^{4a}$ are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of the foregoing, $R^{1a}$, $R^{1b}$, $R^{4a}$ and $R^{4b}$ are $C_1$-$C_{12}$ alkyl at each occurrence.

In further embodiments of the foregoing, at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of the foregoing, $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ are not particularly limited in the foregoing embodiments. In certain embodiments one of $R^5$ or $R^6$ is methyl. In other embodiments each of $R^5$ or $R^6$ is methyl.

The substituents at $R^7$ are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with —(C═O)OR$^b$, —O(C═O)R$^b$, —C(═O)R$^b$, —OR$^b$, —S(O)$_x$R$^b$, —S—SR$^b$, —C(═O)SR$^b$, —SC(═O)R$^b$, —NR$^a$R$^b$, —NR$^a$C(═O)R$^b$, —C(═O)NR$^a$R$^b$, —NR$^a$C(═O)NR$^a$R$^b$, —OC(═O)NR$^a$R$^b$, —NR$^a$C(═O)OR$^b$, —NR$^a$S(O)$_x$NR$^a$R$^b$, —NR$^a$S(O)$_x$R$^b$ or —S(O)$_x$NR$^a$R$^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with —(C═O)OR$^b$ or —O(C═O)R$^b$.

In various of the foregoing embodiments of structure (VI), $R^b$ is branched $C_3$-$C_{15}$ alkyl. For example, in some embodiments $R^b$ has one of the following structures:

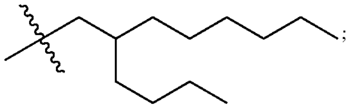

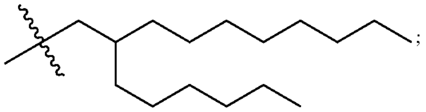

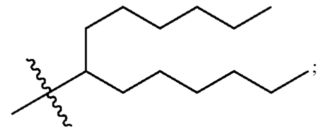

-continued

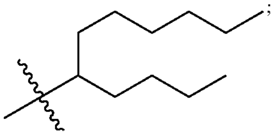

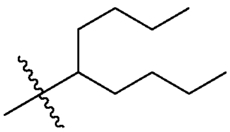

or

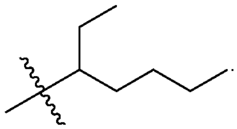

In certain embodiments, $R^8$ is OH.

In other embodiments of structure (VI), $R^8$ is —N(R$^9$)(C═O)R$^{10}$. In some other embodiments, $R^8$ is —(C═O)NR$^9$R$^{10}$. In still more embodiments, $R^8$ is —NR$^9$R$^{10}$. In some of the foregoing embodiments, $R^9$ and $R^{10}$ are each independently H or $C_1$-$C_8$ alkyl, for example H or $C_1$-$C_3$ alkyl. In more specific of these embodiments, the $C_1$-$C_8$ alkyl or $C_1$-$C_3$ alkyl is unsubstituted or substituted with hydroxyl. In other of these embodiments, $R^9$ and $R^{10}$ are each methyl.

In yet more embodiments of structure (VI), $R^8$ is —(C═O)OR$^{11}$. In some of these embodiments $R^{11}$ is benzyl.

In yet more specific embodiments of structure (VI), $R^8$ has one of the following structures:

-OH;

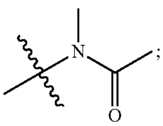

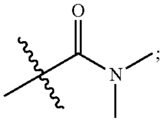

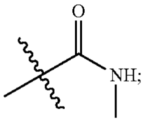

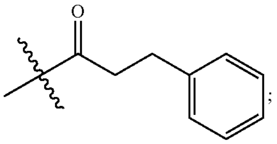

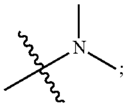

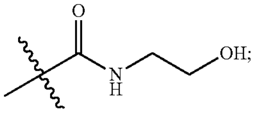

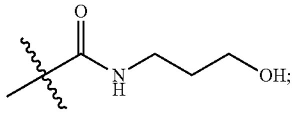

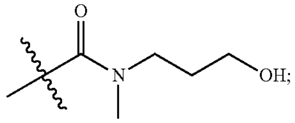

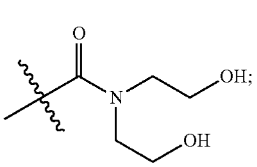

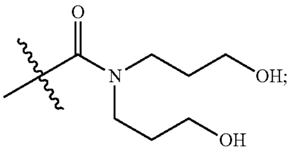

-continued

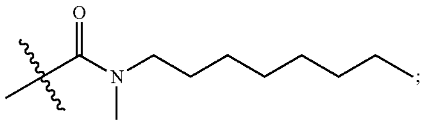

;

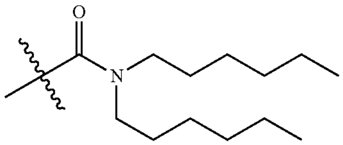

or

-continued

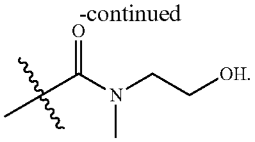

In still other embodiments of the foregoing compounds, $G^3$ is $C_2$-$C_5$ alkylene, for example $C_2$-$C_4$ alkylene, $C_3$ alkylene or $C_4$ alkylene. In some of these embodiments, $R^8$ is OH. In other embodiments, $G^2$ is absent and $R^7$ is $C_1$-$C_2$ alkylene, such as methyl.

In various different embodiments, the compound has one of the structures set forth in Table 5 below.

TABLE 5

Representative cationic lipids of structure (VI)

| No. | Structure |
| --- | --- |
| VI-1 | 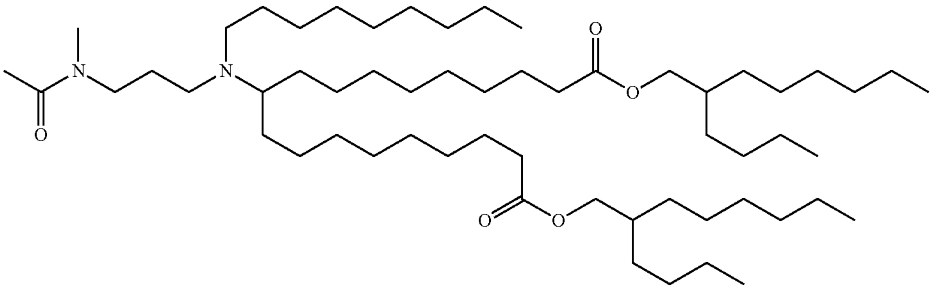 [SMILES: CCCCCCCCCN(CCCN(C)C(C)=O)C(CCCCCCCCC(=O)OCC(CCCC)CCCCCC)CCCCCCCCC(=O)OCC(CCCC)CCCCCC] |
| VI-2 | 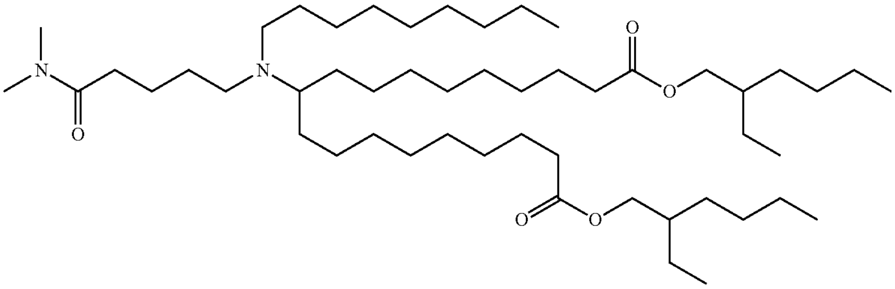 [SMILES: CCCCCCCCCN(CCCCC(=O)N(C)C)C(CCCCCCCCC(=O)OCC(CC)CCCC)CCCCCCCCC(=O)OCC(CC)CCCC] |
| VI-3 | 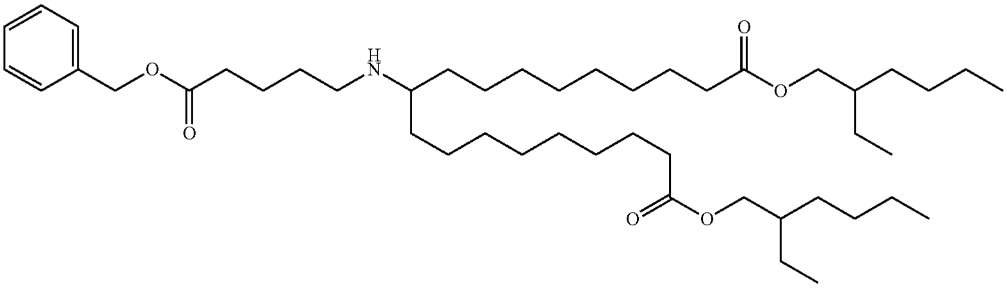 [SMILES: CCCCC(CC)COC(=O)CCCCCCCCC(CCCCCCCCC(=O)OCC(CC)CCCC)NCCCCC(=O)OCc1ccccc1] |

TABLE 5-continued
Representative cationic lipids of structure (VI)
| No. | Structure |
| --- | --- |
| VI-4 | 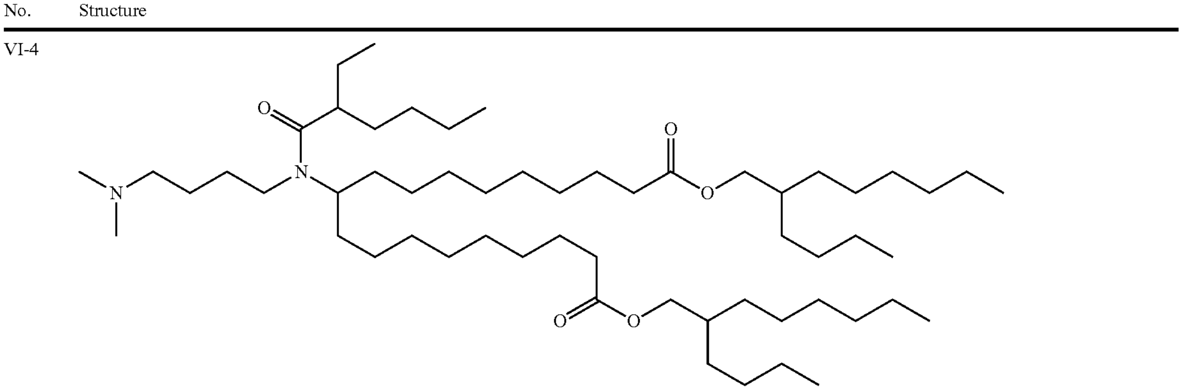 |
| VI-5 | 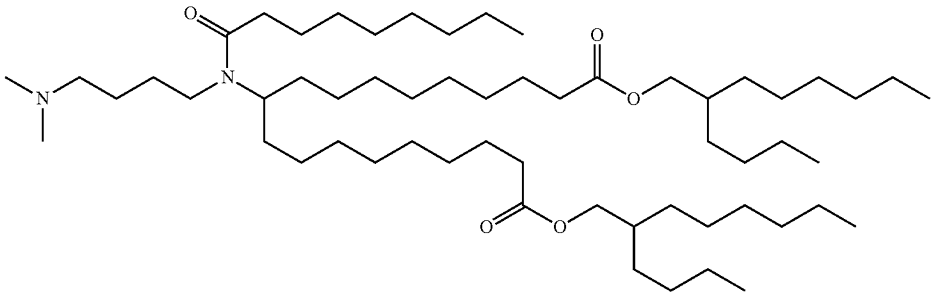 [SMILES: CCCCCCCCC(=O)N(CCCCN(C)C)C(CCCCCCCCC(=O)OCC(CCCC)CCCCCC)CCCCCCCCC(=O)OCC(CCCC)CCCCCC] |
| VI-6 | 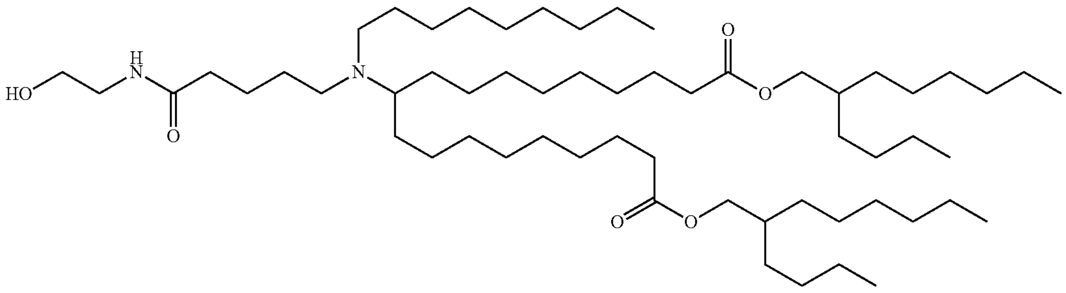 [SMILES: CCCCCCCCCN(CCCCC(=O)NCCO)C(CCCCCCCCC(=O)OCC(CCCC)CCCCCC)CCCCCCCCC(=O)OCC(CCCC)CCCCCC] |
| VI-7 | 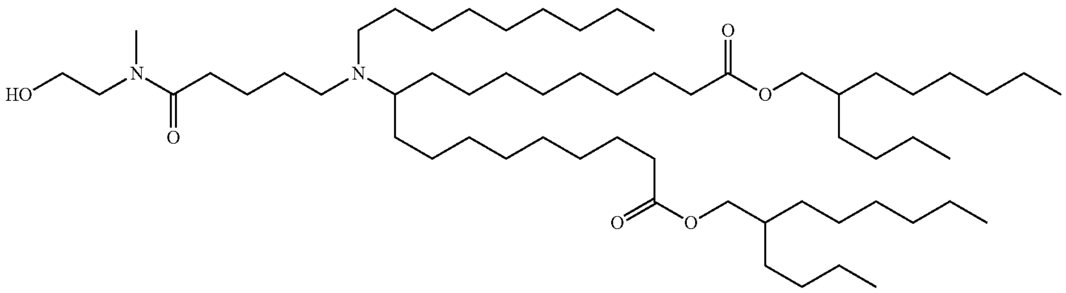 [SMILES: CCCCCCCCCN(CCCCC(=O)N(C)CCO)C(CCCCCCCCC(=O)OCC(CCCC)CCCCCC)CCCCCCCCC(=O)OCC(CCCC)CCCCCC] |
| VI-8 | 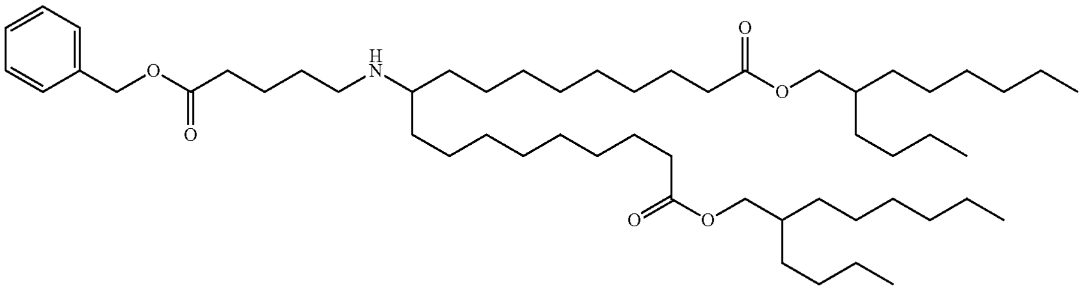 [SMILES: CCCCCCC(CCCC)COC(=O)CCCCCCCCC(CCCCCCCCC(=O)OCC(CCCC)CCCCCC)NCCCCC(=O)OCc1ccccc1] |

TABLE 5-continued
| Representative cationic lipids of structure (VI) | |
|---|---|
| No. | Structure |
| VI-9 | 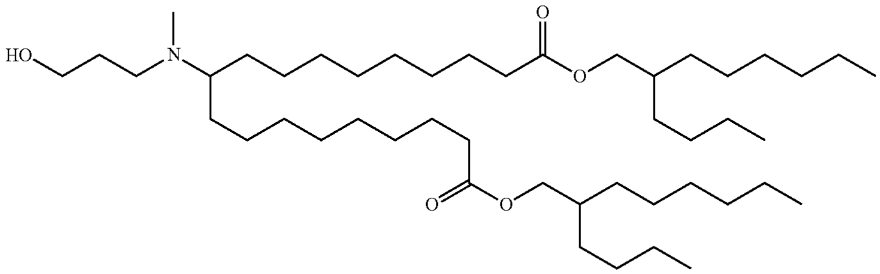 [SMILES: CCCCCCC(CCCC)COC(=O)CCCCCCCCC(CCCCCCCCC(=O)OCC(CCCC)CCCCCC)N(C)CCCO] |
| VI-10 | 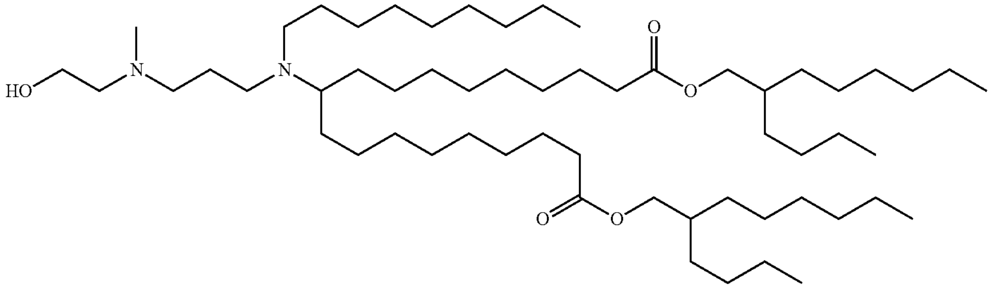 [SMILES: CCCCCCCCCN(CCCN(C)CCO)C(CCCCCCCCC(=O)OCC(CCCC)CCCCCC)CCCCCCCCC(=O)OCC(CCCC)CCCCCC] |
| VI-11 | 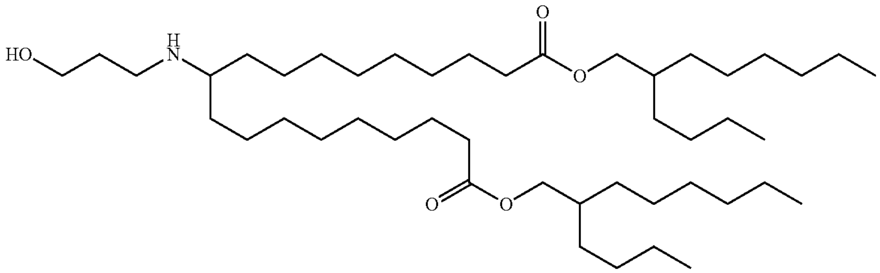 [SMILES: CCCCCCC(CCCC)COC(=O)CCCCCCCCC(CCCCCCCCC(=O)OCC(CCCC)CCCCCC)NCCCO] |
| VI-12 | 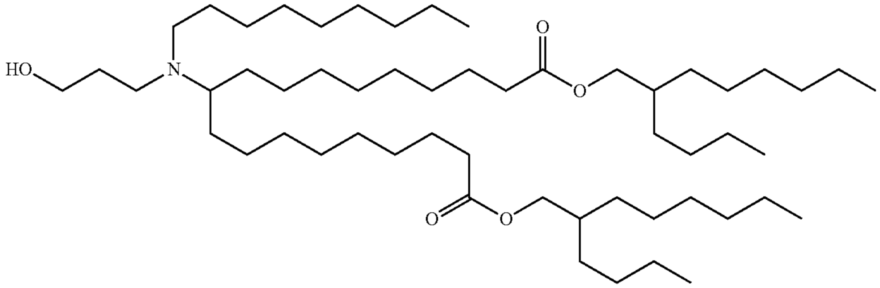 [SMILES: CCCCCCCCCN(CCCO)C(CCCCCCCCC(=O)OCC(CCCC)CCCCCC)CCCCCCCCC(=O)OCC(CCCC)CCCCCC] |
| VI-13 | 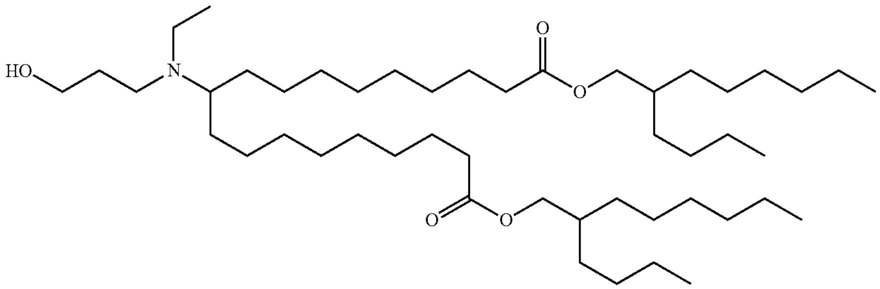 [SMILES: CCCCCCC(CCCC)COC(=O)CCCCCCCCC(CCCCCCCCC(=O)OCC(CCCC)CCCCCC)N(CC)CCCO] |

TABLE 5-continued
Representative cationic lipids of structure (VI)
| No. | Structure |
|---|---|
| VI-14 | 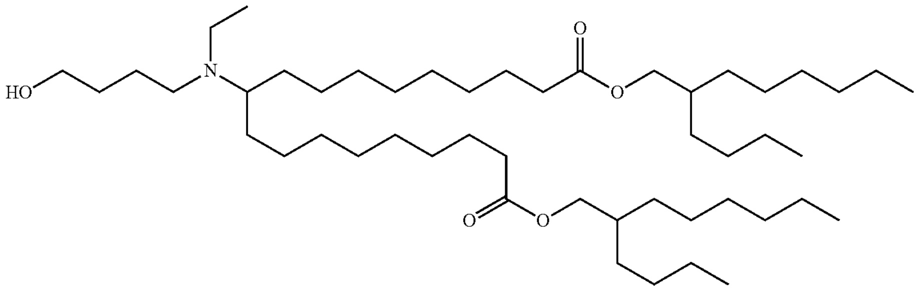 [SMILES: CCCCCCC(CCCC)COC(=O)CCCCCCCCC(CCCCCCCCC(=O)OCC(CCCC)CCCCCC)N(CC)CCCCO] |
| VI-15 | 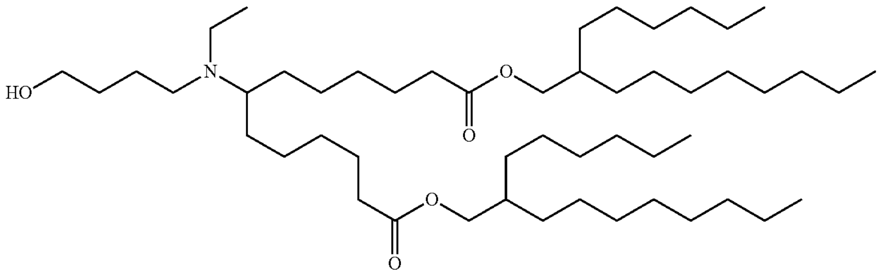 [SMILES: CCCCCCCCC(CCCCCC)COC(=O)CCCCCC(CCCCCC(=O)OCC(CCCCCC)CCCCCCCC)N(CC)CCCCO] |
| VI-16 | 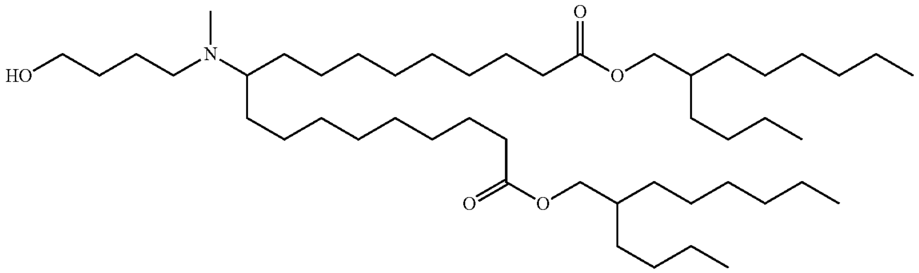 [SMILES: CCCCCCC(CCCC)COC(=O)CCCCCCCCC(CCCCCCCCC(=O)OCC(CCCC)CCCCCC)N(C)CCCCO] |
| VI-17 | 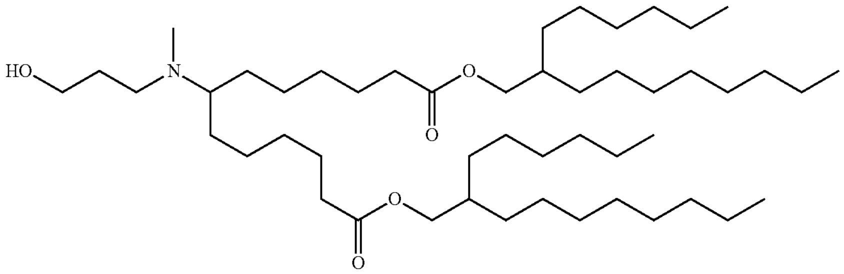 [SMILES: CCCCCCCCC(CCCCCC)COC(=O)CCCCCC(CCCCCC(=O)OCC(CCCCCC)CCCCCCCC)N(C)CCCO] |
| VI-18 | 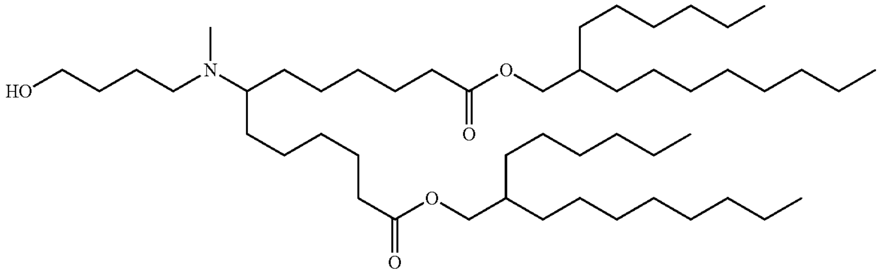 [SMILES: CCCCCCCCC(CCCCCC)COC(=O)CCCCCC(CCCCCC(=O)OCC(CCCCCC)CCCCCCCC)N(C)CCCCO] |

TABLE 5-continued
| Representative cationic lipids of structure (VI) | |
|---|---|
| No. | Structure |
| VI-19 | 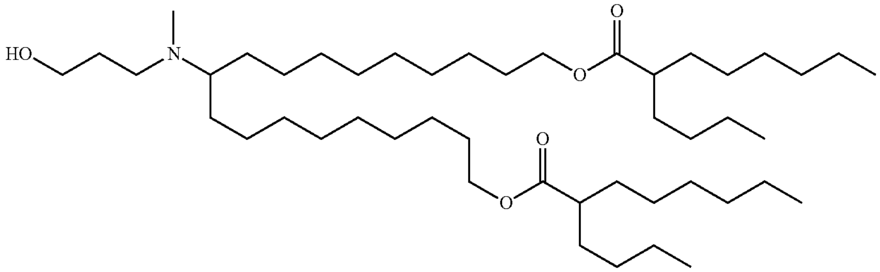 [SMILES: CCCCCCC(CCCC)C(=O)OCCCCCCCCCC(CCCCCCCCCOC(=O)C(CCCC)CCCCCC)N(C)CCCO] |
| VI-20 | 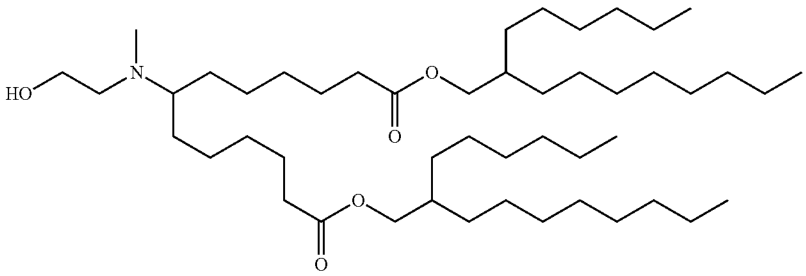 [SMILES: CCCCCCCCC(CCCCCC)COC(=O)CCCCCC(CCCCCC(=O)OCC(CCCCCC)CCCCCCCC)N(C)CCO] |
| VI-21 | 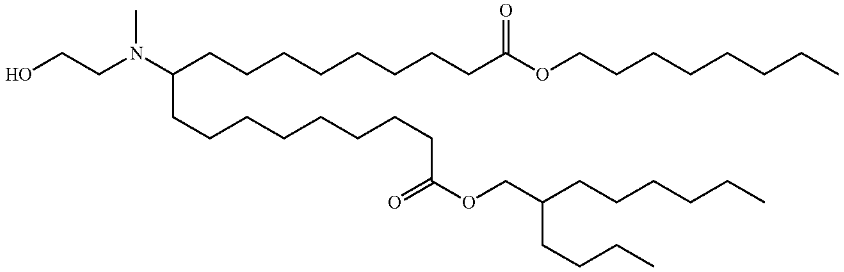 [SMILES: CCCCCCCCOC(=O)CCCCCCCCC(CCCCCCCCC(=O)OCC(CCCC)CCCCCC)N(C)CCO] |
| VI-22 | 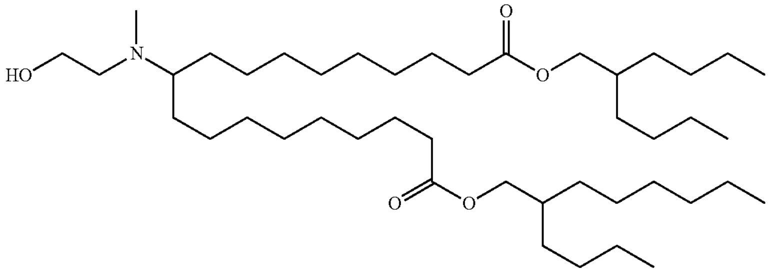 [SMILES: CCCCCCC(CCCC)COC(=O)CCCCCCCCC(CCCCCCCCC(=O)OCC(CCCC)CCCC)N(C)CCO] |
| VI-23 | 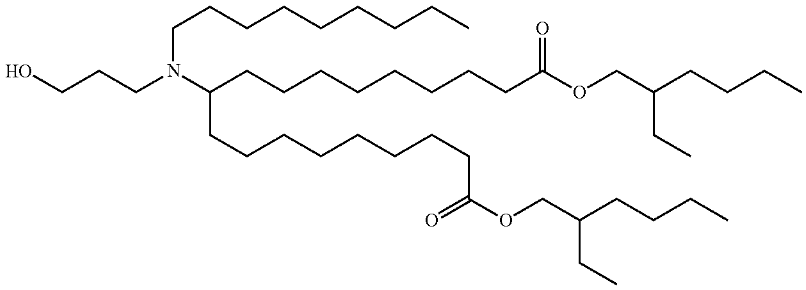 [SMILES: CCCCCCCCCN(CCCO)C(CCCCCCCCC(=O)OCC(CC)CCCC)CCCCCCCCC(=O)OCC(CC)CCCC] |

TABLE 5-continued
| Representative cationic lipids of structure (VI) | |
|---|---|
| No. | Structure |
| VI-24 | 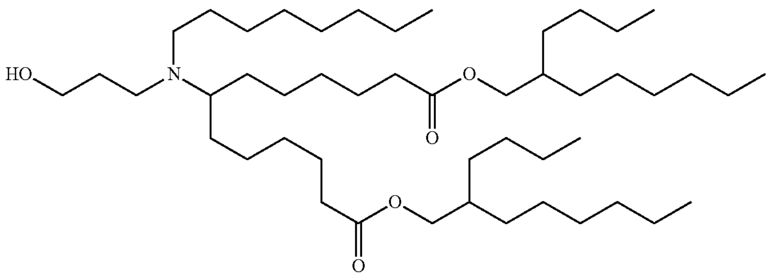 [SMILES: CCCCCCCCN(CCCO)C(CCCCCC(=O)OCC(CCCC)CCCCCC)CCCCCC(=O)OCC(CCCC)CCCCCC] |
| VI-25 | 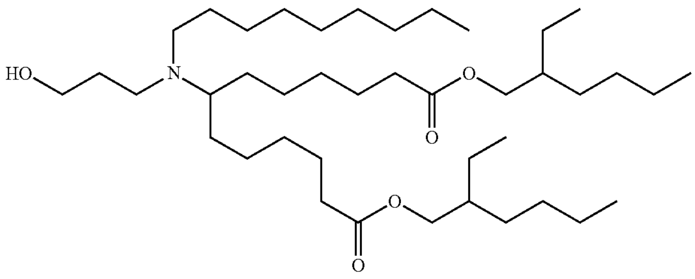 [SMILES: CCCCCCCCCN(CCCO)C(CCCCCC(=O)OCC(CC)CCCC)CCCCCC(=O)OCC(CC)CCCC] |
| VI-26 | 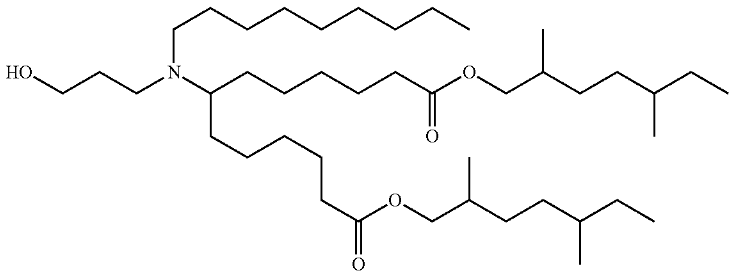 [SMILES: CCCCCCCCCN(CCCO)C(CCCCCC(=O)OCC(C)CCC(C)CC)CCCCCC(=O)OCC(C)CCC(C)CC] |
| VI-27 | 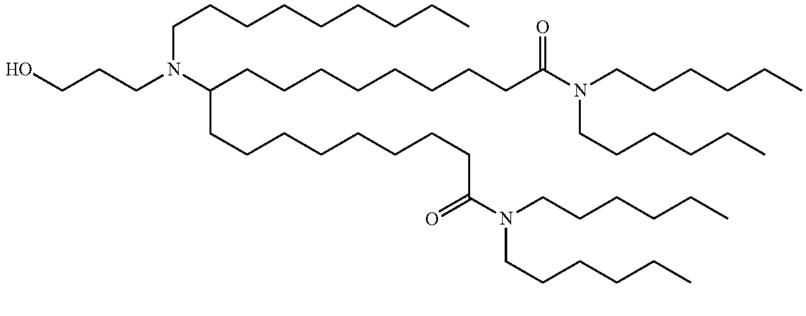 [SMILES: CCCCCCCCCN(CCCO)C(CCCCCCCCC(=O)N(CCCCCC)CCCCCC)CCCCCCCCC(=O)N(CCCCCC)CCCCCC] |
| VI-28 | 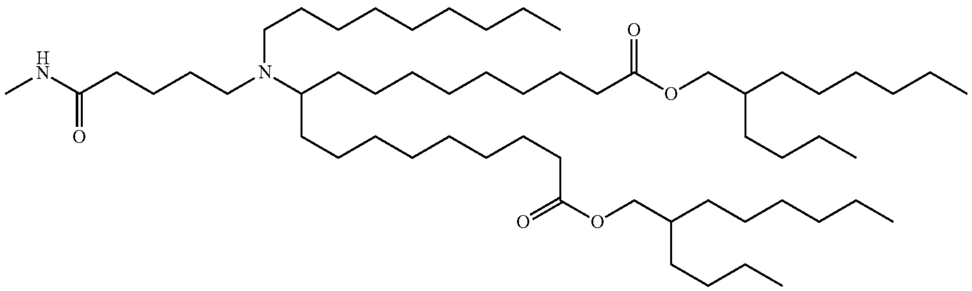 [SMILES: CCCCCCCCCN(CCCCC(=O)NC)C(CCCCCCCCC(=O)OCC(CCCC)CCCCCC)CCCCCCCCC(=O)OCC(CCCC)CCCCCC] |

TABLE 5-continued
| Representative cationic lipids of structure (VI) | |
|---|---|
| No. | Structure |
| VI-29 | 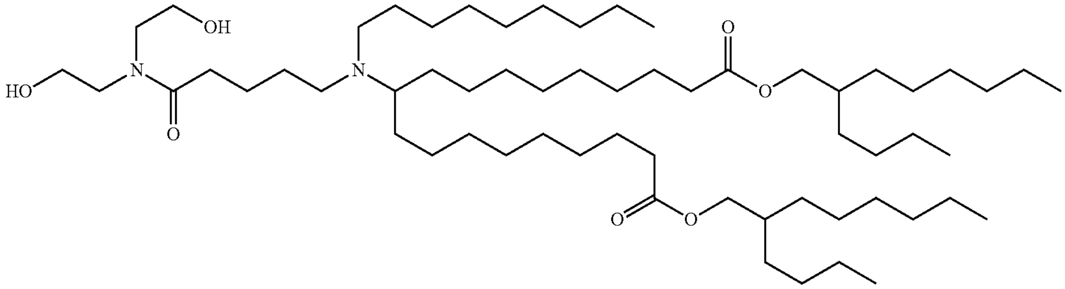 [SMILES: CCCCCCCCCN(CCCCC(=O)N(CCO)CCO)C(CCCCCCCCC(=O)OCC(CCCC)CCCCCC)CCCCCCCCC(=O)OCC(CCCC)CCCCCC] |
| VI-30 | 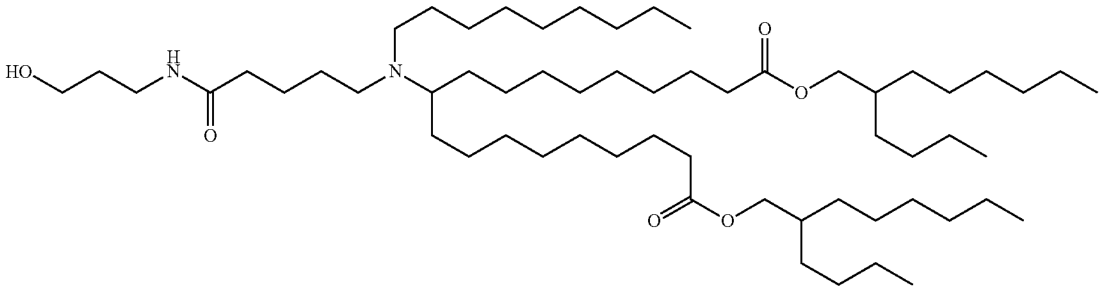 [SMILES: CCCCCCCCCN(CCCCC(=O)NCCCO)C(CCCCCCCCC(=O)OCC(CCCC)CCCCCC)CCCCCCCCC(=O)OCC(CCCC)CCCCCC] |
| VI-31 | 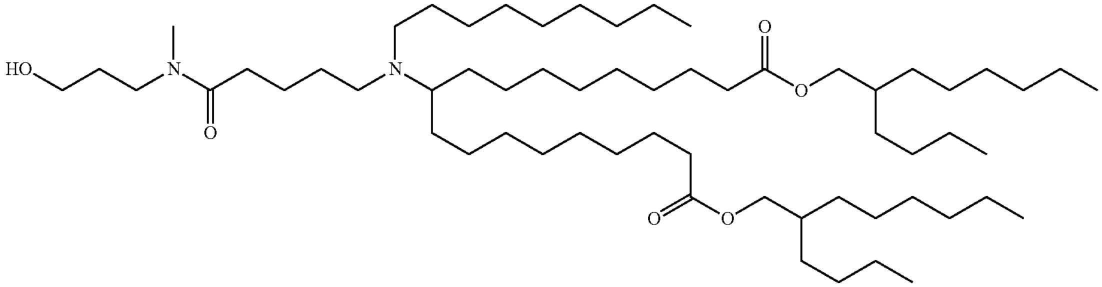 [SMILES: CCCCCCCCCN(CCCCC(=O)N(C)CCCO)C(CCCCCCCCC(=O)OCC(CCCC)CCCCCC)CCCCCCCCC(=O)OCC(CCCC)CCCCCC] |
| VI-32 | 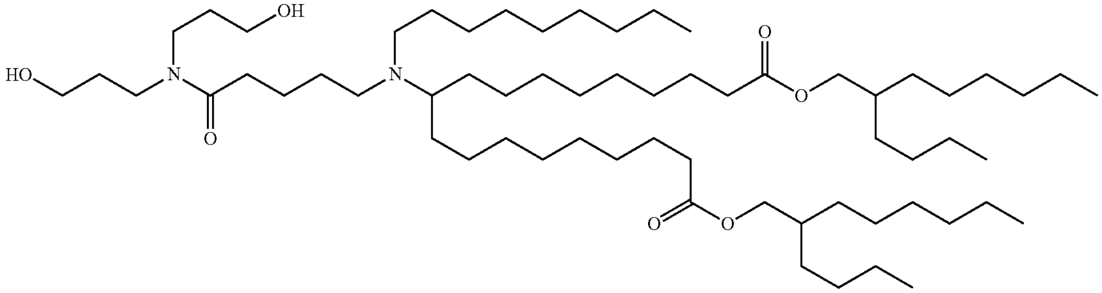 [SMILES: CCCCCCCCCN(CCCCC(=O)N(CCCO)CCCO)C(CCCCCCCCC(=O)OCC(CCCC)CCCCCC)CCCCCCCCC(=O)OCC(CCCC)CCCCCC] |
| VI-33 | 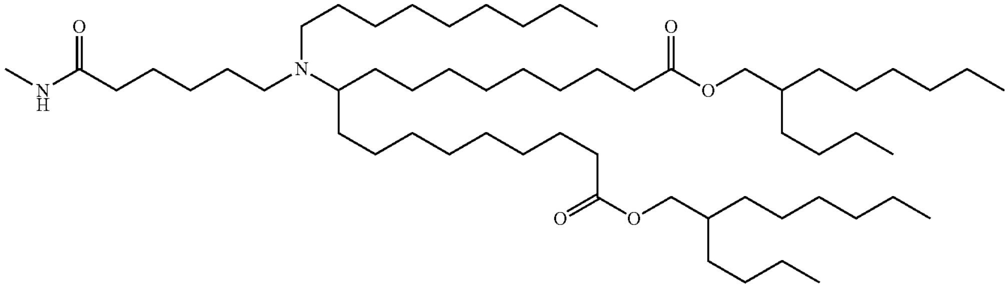 [SMILES: CCCCCCCCCN(CCCCCC(=O)NC)C(CCCCCCCCC(=O)OCC(CCCC)CCCCCC)CCCCCCCCC(=O)OCC(CCCC)CCCCCC] |

TABLE 5-continued

| Representative cationic lipids of structure (VI) | |
|---|---|
| No. | Structure |
| VI-34 | 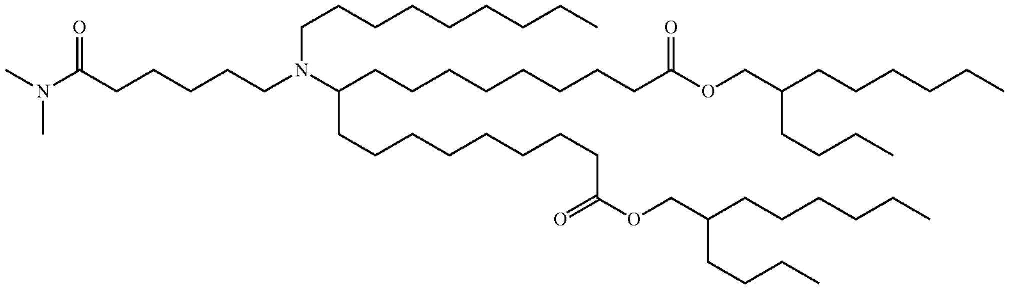 [SMILES: CCCCCCCCCN(CCCCCC(=O)N(C)C)C(CCCCCCCCC(=O)OCC(CCCC)CCCCCC)CCCCCCCCC(=O)OCC(CCCC)CCCCCC] |
| VI-35 | 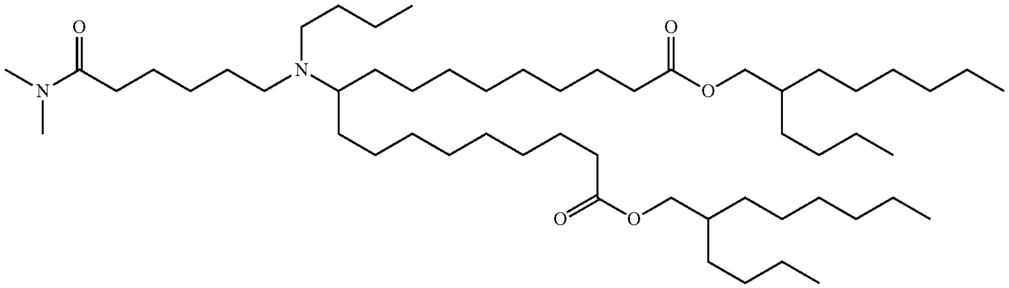 [SMILES: CCCCCCC(CCCC)COC(=O)CCCCCCCCC(CCCCCCCCC(=O)OCC(CCCC)CCCCCC)N(CCCC)CCCCCC(=O)N(C)C] |
| VI-36 | 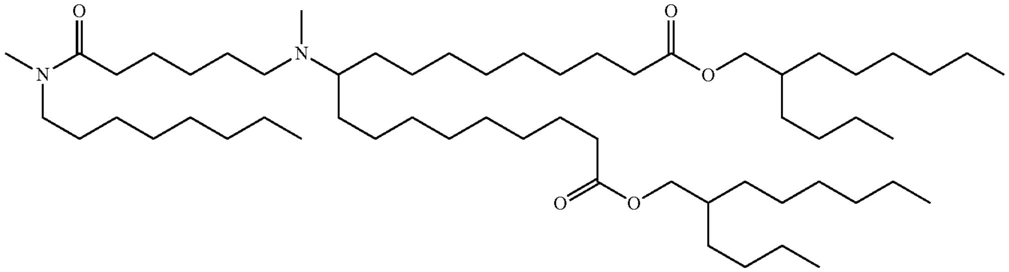 [SMILES: CCCCCCCCN(C)C(=O)CCCCCN(C)C(CCCCCCCCC(=O)OCC(CCCC)CCCCCC)CCCCCCCCC(=O)OCC(CCCC)CCCCCC] |
| VI-37 | 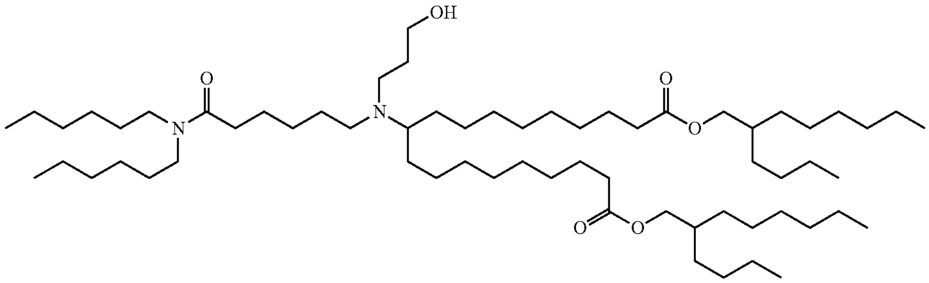 [SMILES: CCCCCCC(CCCC)COC(=O)CCCCCCCCC(CCCCCCCCC(=O)OCC(CCCC)CCCCCC)N(CCCO)CCCCCC(=O)N(CCCCCC)CCCCCC] |

In one embodiment, the cationic lipid is a compound having the following structure (VII):

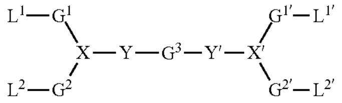

(VII)

or a pharmaceutically acceptable salt, prodrug or stereoisomer thereof, wherein:

X and X' are each independently N or CR;

Y and Y' are each independently absent, —O(C═O)—, —(C═O)O— or NR, provided that:

a)Y is absent when X is N;

b) Y' is absent when X' is N;

c) Y is —O(C═O)—, —(C═O)O— or NR when X is CR; and d) Y' is —O(C═O)—, —(C═O)O— or NR when X' is CR, $L^1$ and $L^{1'}$ are each independently —O(C═O)$R^1$, —(C═O)O$R^1$, —C(═O)$R^1$, —O$R^1$, —S(O)$_z$$R^1$, —S—S$R^1$, —C(═O)S$R^1$, —SC(═O)$R^1$, —N$R^a$C(═O)$R^1$, —C(═O)N$R^bR^c$, —N$R^a$C(═O)N$R^bR^c$, —OC(═O)N$R^bR^c$ or —N$R^a$C(═O)O$R^1$;

$L^2$ and $L^{2'}$ are each independently —O(C═O)$R^2$, —(C═O)O$R^2$, —C(═O)$R^2$, —O$R^2$, —S(O)$_z$$R^2$, —S—S$R^2$, —C(═O)S$R^2$, —SC(═O)$R^2$, —N$R^d$C(═O)$R^2$, —C(=O)$NR^eR^f$, —$NR^d$C(=O)$NR^eR^f$, —OC(=O)$NR^eR^f$; —$NR^d$C(=O)$OR^2$ or a direct bond to $R^2$;

$G^1$, $G^{1'}$, $G^2$ and $G^{2'}$ are each independently $C_2$-$C_{12}$ alkylene or $C_2$-$C_{12}$ alkenylene;

$G^3$ is $C_2$-$C_{24}$ heteroalkylene or $C_2$-$C_{24}$ heteroalkenylene;

$R^a$, $R^b$, $R^d$ and $R^e$ are, at each occurrence, independently H, $C_1$-$C_{12}$ alkyl or $C_2$-$C_{12}$ alkenyl;

$R^e$ and $R^f$ are, at each occurrence, independently $C_1$-$C_{12}$ alkyl or $C_2$-$C_{12}$ alkenyl;

R is, at each occurrence, independently H or $C_1$-$C_{12}$ alkyl;

$R^1$ and $R^2$ are, at each occurrence, independently branched $C_6$-$C_{24}$ alkyl or branched $C_6$-$C_{24}$ alkenyl;

z is 0, 1 or 2, and wherein each alkyl, alkenyl, alkylene, alkenylene, heteroalkylene and heteroalkenylene is independently substituted or unsubstituted unless otherwise specified.

In other different embodiments of structure (VII):

X and X' are each independently N or CR;

Y and Y' are each independently absent or NR, provided that:

a)Y is absent when X is N;

b) Y' is absent when X is N;

c) Y is NR when X is CR; and d) Y' is NR when X' is CR, $L^1$ and $L^{1'}$ are each independently —O(C=O)$R^1$, —(C=O)$OR^1$, —C(=O)$R^1$, —$OR^1$, —S(O)$_z R^1$, —S—$SR^1$, —C(=O)$SR^1$, —SC(=O)$R^1$, —$NR^a$C(=O)$R^1$, —C(=O)$NR^bR^c$, —$NR^a$C(=O)$NR^bR^c$, —OC(=O)$NR^bR^c$ or —$NR^a$C(=O)$OR^1$;

$L^2$ and $L^2$ are each independently —O(C=O)$R^2$, —(C=O)$OR^2$, —C(=O)$R^2$, —$OR^2$, —S(O)$_z R^2$, —S—$SR^2$, —C(=O)$SR^2$, —SC(=O)$R^2$, —$NR^d$C(=O)$R^2$, —C(=O)$NR^eR^f$, —$NR^d$C(=O)$NR^eR^f$, —OC(=O)$NR^eR^f$; —$NR^d$C(=O)$OR^2$ or a direct bond to $R^2$ $G^1$, $G^{1'}$, $G^2$ and $G^{2'}$ are each independently $C_2$-$C_{12}$ alkylene or $C_2$-$C_{12}$ alkenylene;

$G^3$ is $C_2$-$C_{24}$ alkyleneoxide or $C_2$-$C_{24}$ alkenyleneoxide;

$R^a$, $R^b$, $R^d$ and $R^e$ are, at each occurrence, independently H, $C_1$-$C_{12}$ alkyl or $C_2$-$C_{12}$ alkenyl;

$R^e$ and $R^f$ are, at each occurrence, independently $C_1$-$C_{12}$ alkyl or $C_2$-$C_{12}$ alkenyl;

R is, at each occurrence, independently H or $C_1$-$C_{12}$ alkyl;

$R^1$ and $R^2$ are, at each occurrence, independently branched $C_6$-$C_{24}$ alkyl or branched $C_6$-$C_{24}$ alkenyl;

z is 0, 1 or 2, and wherein each alkyl, alkenyl, alkylene, alkenylene, alkyleneoxide and alkenyleneoxide is independently substituted or unsubstituted unless otherwise specified.

In some embodiments of structure (VII), $G^3$ is $C_2$-$C_{24}$ alkyleneoxide or $C_2$-$C_{24}$ alkenyleneoxide. In certain embodiments, $G^3$ is unsubstituted. In other embodiments, $G^3$ is substituted, for example substituted with hydroxyl. In more specific embodiments $G^3$ is $C_2$-$C_{12}$ alkyleneoxide, for example, in some embodiments $G^3$ is $C_3$-$C_7$ alkyleneoxide or in other embodiments $G^3$ is $C_3$-$C_{12}$ alkyleneoxide.

In other embodiments of structure (VII), $G^3$ is $C_2$-$C_{24}$ alkyleneaminyl or $C_2$-$C_{24}$ alkenyleneaminyl, for example $C_6$-$C_{12}$ alkyleneaminyl. In some of these embodiments, $G^3$ is unsubstituted. In other of these embodiments, $G^3$ is substituted with $C_1$-$C_6$ alkyl.

In some embodiments of structure (VII), X and X' are each N, and Y and Y' are each absent. In other embodiments, X and X' are each CR, and Y and Y' are each NR. In some of these embodiments, R is H.

In certain embodiments of structure (VII), X and X' are each CR, and Y and Y' are each independently —O(C=O)— or —(C=O)O—.

In some of the foregoing embodiments of structure (VII), the compound has one of the following structures (VIIA), (VIIB), (VIIC), (VIID), (VIIE), (VIIF), (VIIG) or (VIIH):

(VIIA)

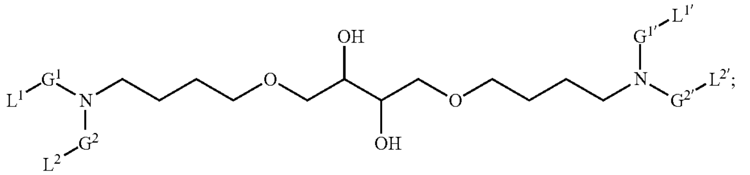

(VIIB)

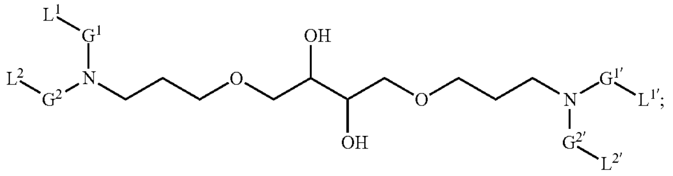

(VIIC)

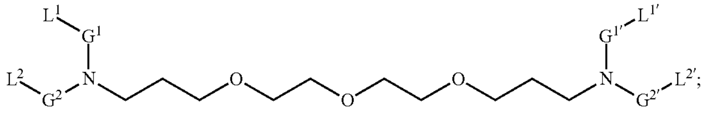

(VIID)

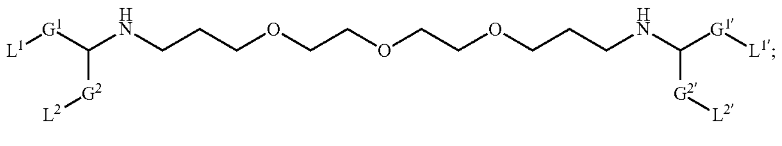

-continued (VIIE)

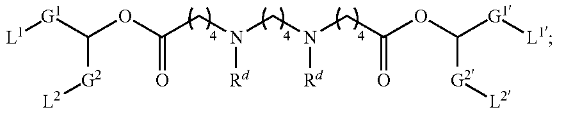

(VIIF)

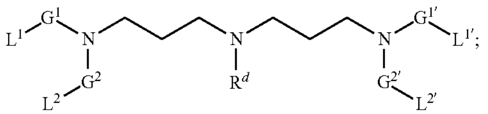

(VIIG)

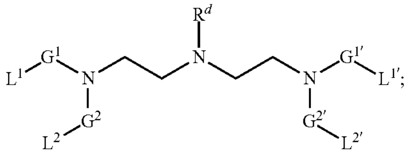

or (VIIH)

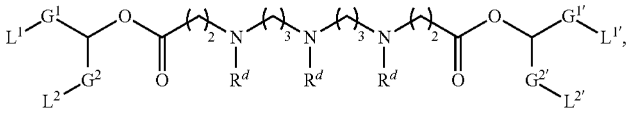

wherein $R^d$ is, at each occurrence, independently H or optionally substituted $C_1$-$C_6$ alkyl. For example, in some embodiments $R^d$ is H. In other embodiments, $R^d$ is $C_1$-$C_6$ alkyl, such as methyl. In other embodiments, $R^d$ is substituted $C_1$-$C_6$ alkyl, such as $C_1$-$C_6$ alkyl substituted with —O(C═O)R, —(C═O)OR, —NRC(═O)R or —C(═O)N(R)$_2$, wherein R is, at each occurrence, independently H or $C_1$-$C_{12}$ alkyl.

In some of the foregoing embodiments of structure (VII), $L^1$ and $L^{1'}$ are each independently —O(C═O)$R^1$, —(C═O)O$R^1$ or —C(═O)N$R^bR^c$, and $L^2$ and $L^{2'}$ are each independently —O(C═O)$R^2$, —(C═O)O$R^2$ or —C(═O)N$R^eR^f$. For example, in some embodiments $L^1$ and $L^{1'}$ are each —(C═O)O$R^1$, and $L^2$ and $L^{2'}$ are each —(C═O)O$R^2$. In other embodiments $L^1$ and $L^{1'}$ are each —(C═O)O$R^1$, and $L^2$ and $L^{2'}$ are each —C(═O)N$R^eR^f$. In other embodiments $L^1$ and $L^{1'}$ are each —C(═O)N$R^bR^c$, and $L^2$ and $L^{2'}$ are each —C(═O)N$R^eR^f$.

In some embodiments of the foregoing, $G^1$, $G^{1'}$, $G^2$ and $G^{2'}$ are each independently $C_2$-$C_8$ alkylene, for example $C_4$-$C_8$ alkylene.

In some of the foregoing embodiments of structure (VII), $R^1$ or $R^2$, are each, at each occurrence, independently branched $C_6$-$C_{24}$ alkyl. For example, in some embodiments, $R^1$ and $R^2$ at each occurrence, independently have the following structure:

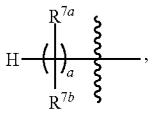

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (VII), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of structure (VII), $R^1$ or $R^2$, or both, at each occurrence independently has one of the following structures:

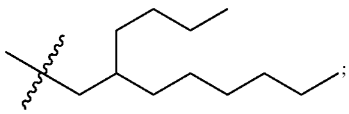

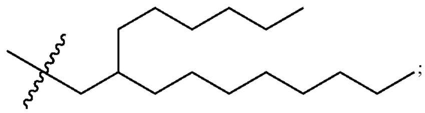

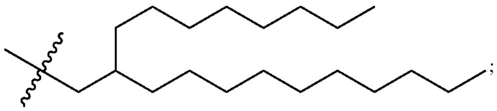

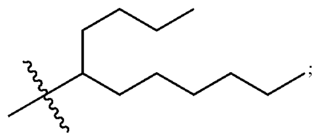

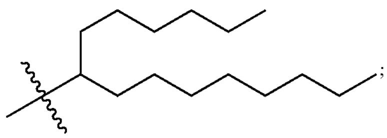

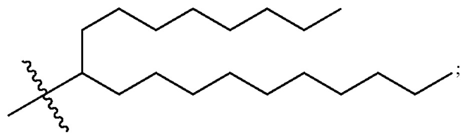

-continued

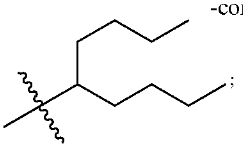

;

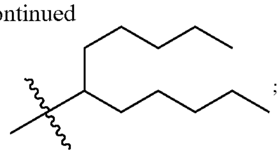

;

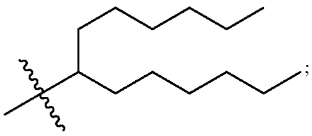

;

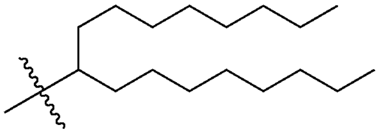

or

-continued

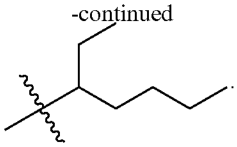

.

In some of the foregoing embodiments of structure (VII), $R^b$, $R^c$, $R^e$ and $R^f$, when present, are each independently $C_3$-$C_{12}$ alkyl. For example, in some embodiments $R^b$, $R^c$, $R^e$ and $R^f$, when present, are n-hexyl and in other embodiments $R^b$, $R^c$, $R^e$ and $R^f$, when present, are n-octyl.

In various different embodiments of structure (VII), the cationic lipid has one of the structures set forth in Table 6 below.

TABLE 6

| Representative cationic lipids of structure (VII) | |
|---|---|
| No. | Structure |
| VII-1 | 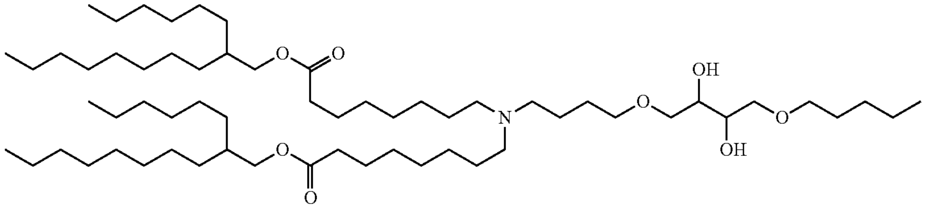 |
| | 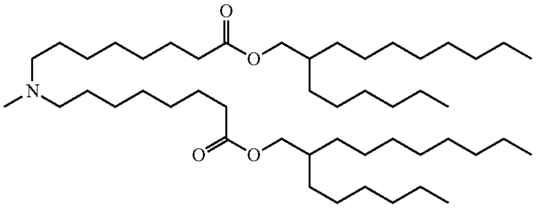 |
| VII-2 | 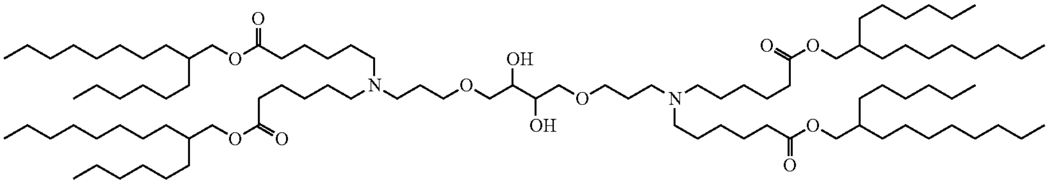 [SMILES: CCCCCCCCC(CCCCCC)COC(=O)CCCCCN(CCCCCC(=O)OCC(CCCCCC)CCCCCCCC)CCCOCC(O)C(O)COCCCN(CCCCCC(=O)OCC(CCCCCC)CCCCCCCC)CCCCCC(=O)OCC(CCCCCC)CCCCCCCC] |
| VII-3 | 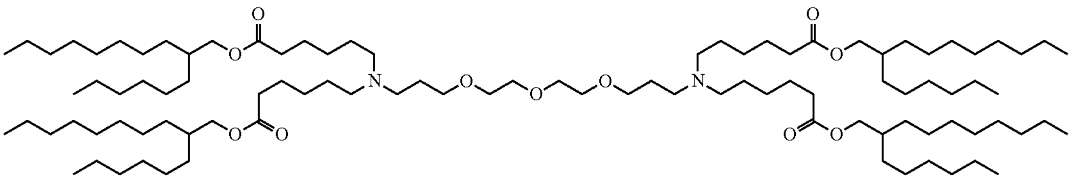 [SMILES: CCCCCCCCC(CCCCCC)COC(=O)CCCCCN(CCCCCC(=O)OCC(CCCCCC)CCCCCCCC)CCCOCCOCCOCCCN(CCCCCC(=O)OCC(CCCCCC)CCCCCCCC)CCCCCC(=O)OCC(CCCCCC)CCCCCCCC] |
| VII-4 | 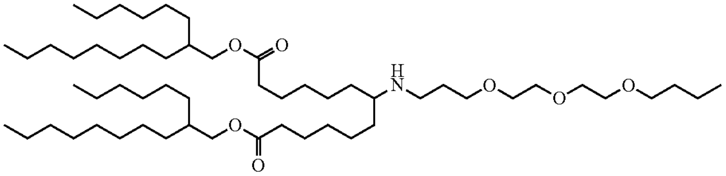 |

TABLE 6-continued
Representative cationic lipids of structure (VII)
| No. | Structure |
|---|---|
| | 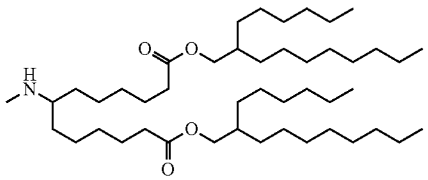 |
| VII-5 | 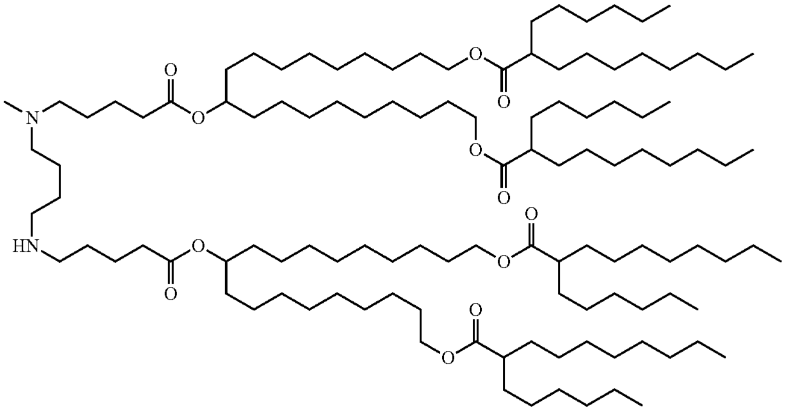 [SMILES: CCCCCCCCC(CCCCCC)C(=O)OCCCCCCCCCC(CCCCCCCCCOC(=O)C(CCCCCC)CCCCCCCC)OC(=O)CCCCNCCCCN(C)CCCCC(=O)OC(CCCCCCCCCOC(=O)C(CCCCCC)CCCCCCCC)CCCCCCCCCOC(=O)C(CCCCCC)CCCCCCCC] |
| VII-6 | 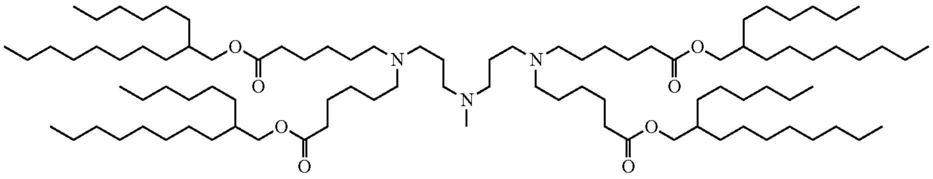 [SMILES: CCCCCCCCC(CCCCCC)COC(=O)CCCCCN(CCCCCC(=O)OCC(CCCCCC)CCCCCCCC)CCCN(C)CCCN(CCCCCC(=O)OCC(CCCCCC)CCCCCCCC)CCCCCC(=O)OCC(CCCCCC)CCCCCCCC] |
| VII-7 | 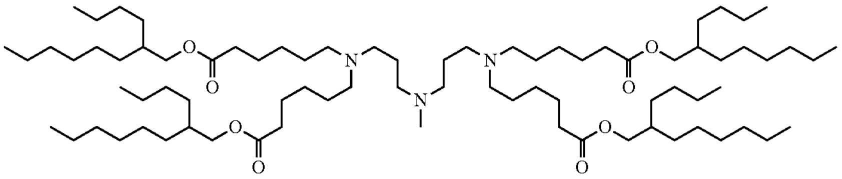 [SMILES: CCCCCCC(CCCC)COC(=O)CCCCCN(CCCCCC(=O)OCC(CCCC)CCCCCC)CCCN(C)CCCN(CCCCCC(=O)OCC(CCCC)CCCCCC)CCCCCC(=O)OCC(CCCC)CCCCCC] |
| VII-8 | 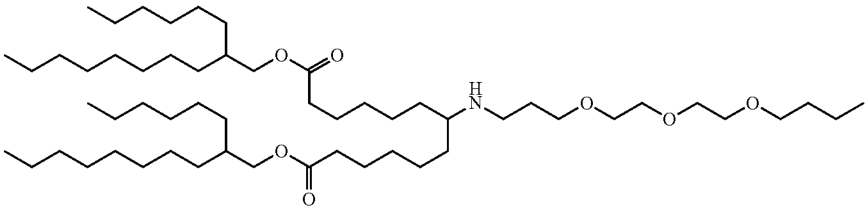 |
| | 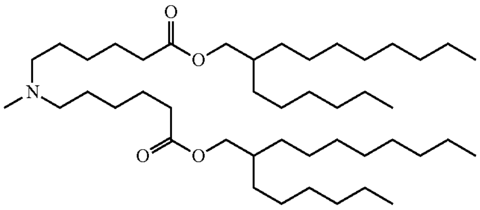 |

TABLE 6-continued

Representative cationic lipids of structure (VII)

| No. | Structure |
| --- | --- |
| VII-9 | 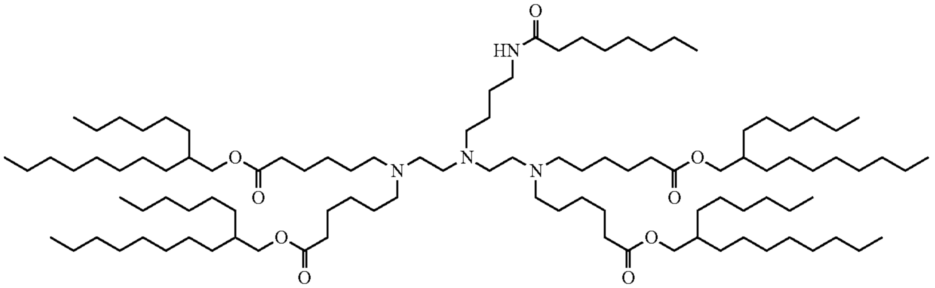 [SMILES: CCCCCCCCC(CCCCCC)COC(=O)CCCCCN(CCCCCC(=O)OCC(CCCCCC)CCCCCCCC)CCN(CCCCNC(=O)CCCCCCC)CCN(CCCCCC(=O)OCC(CCCCCC)CCCCCCCC)CCCCCC(=O)OCC(CCCCCC)CCCCCCCC] |
| VII-10 | 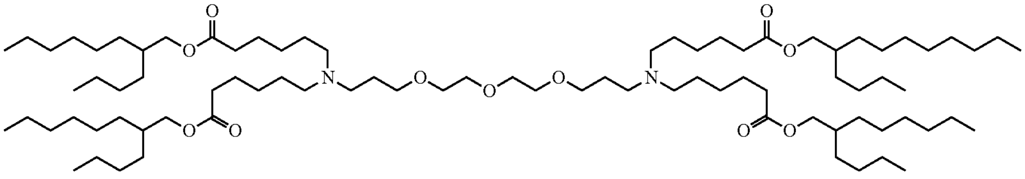 [SMILES: CCCCCCCCC(CCCC)COC(=O)CCCCCN(CCCCCC(=O)OCC(CCCC)CCCCCC)CCCOCCOCCOCCCN(CCCCCC(=O)OCC(CCCC)CCCCCC)CCCCCC(=O)OCC(CCCC)CCCCCC] |
| VII-11 | 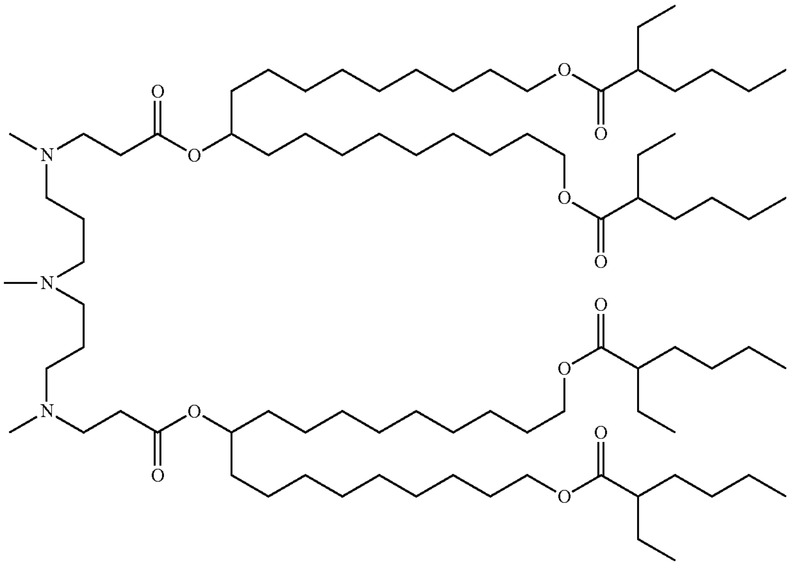 [SMILES: CCCCC(CC)C(=O)OCCCCCCCCCC(CCCCCCCCCOC(=O)C(CC)CCCC)OC(=O)CCN(C)CCCN(C)CCCN(C)CCC(=O)OC(CCCCCCCCCOC(=O)C(CC)CCCC)CCCCCCCCCOC(=O)C(CC)CCCC] |

In one embodiment, the cationic lipid is a compound having the following structure (VIII):

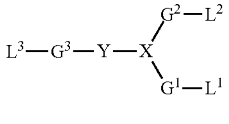

(VIII)

or a pharmaceutically acceptable salt, prodrug or stereoisomer thereof, wherein:

X is N, and Y is absent; or X is CR, and Y is NR;

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$; —N$R^d$C(═O)O$R^2$ or a direct bond to $R^2$;

$L^3$ is —O(C═O)$R^3$ or —(C═O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene;

$R^a$, $R^b$, $R^d$ and Re are each independently H or $C_1$-$C_{12}$ alkyl or $C_1$-$C_{12}$ alkenyl;

$R^e$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In more embodiments of structure (I)

X is N, and Y is absent; or X is CR, and Y is NR;

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$; —N$R^d$C(═O)O$R^2$ or a direct bond to $R^2$;

$L^3$ is —O(C═O)$R^3$ or —(C═O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene when X is CR, and Y is NR; and $G^3$ is $C_1$-$C_{24}$ heteroalkylene or $C_2$-$C_{24}$ heteroalkenylene when X is N, and Y is absent;

$R^a$, $R^b$, $R^d$ and $R^e$ are each independently H or $C_1$-$C_{12}$ alkyl or $C_1$-$C_{12}$ alkenyl;

$R^e$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In other embodiments of structure (I):

X is N and Y is absent, or X is CR and Y is NR;

$L^f$ is —O(C═O)$R^1$, —(C═O)O$R^1$, —C(═O)$R^1$, —O$R^1$, —S(O)$_x$$R^f$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^b$, —OC(═O)N$R^b$$R^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$; —N$R^d$C(═O)O$R^2$ or a direct bond to $R^2$;

$L^3$ is —O(C═O)$R^3$ or —(C═O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene;

$R^a$, $R^b$, $R^d$ and Re are each independently H or $C_1$-$C_{12}$ alkyl or $C_1$-$C_{12}$ alkenyl;

$R^e$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently branched $C_6$-$C_{24}$ alkyl or branched $C_6$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In certain embodiments of structure (VIII), $G^3$ is unsubstituted. In more specific embodiments $G^3$ is $C_2$-$C_{12}$ alkylene, for example, in some embodiments $G^3$ is $C_3$-$C_7$ alkylene or in other embodiments $G^3$ is $C_3$-$C_{12}$ alkylene. In some embodiments, $G^3$ is $C_2$ or $C_3$ alkylene.

In other embodiments of structure (VIII), $G^3$ is $C_1$-$C_{12}$ heteroalkylene, for example $C_1$-$C_{12}$ aminylalkylene.

In certain embodiments of structure (VIII), X is N and Y is absent. In other embodiments, X is CR and Y is NR, for example in some of these embodiments R is H.

In some of the foregoing embodiments of structure (VIII), the compound has one of the following structures (VIIIA), (VIIIB), (VIIIC) or (VIIID):

(VIIIA)

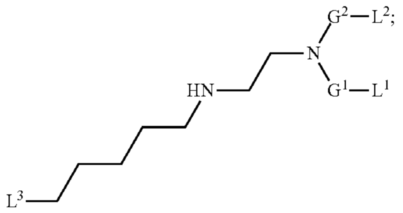

(VIIIB)

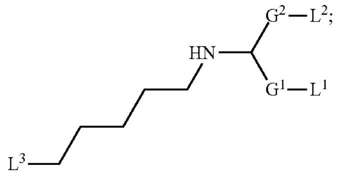

(VIIIC)

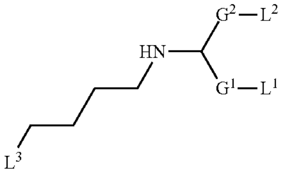

or (VIIID)

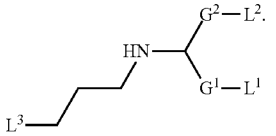

In some of the foregoing embodiments of structure (VIII), $L^1$ is —O(C═O)$R^1$, —(C═O)OR or —C(═O)N$R^b$$R^c$, and $L^2$ is —O(C═O)$R^2$, —(C═O)O$R^2$ or —C(═O)N$R^e$$R^f$. In other specific embodiments, $L^1$ is —(C═O)O$R^1$ and $L^2$ is —(C═O)O$R^2$. In any of the foregoing embodiments, $L^3$ is —(C═O)O$R^3$.

In some of the foregoing embodiments of structure (VIII), $G^1$ and $G^2$ are each independently $C_2$-$C_{12}$ alkylene, for example $C_4$-$C_{10}$ alkylene.

In some of the foregoing embodiments of structure (VIII), $R^1$, $R^2$ and $R^3$ are each, independently branched $C_6$-$C_{24}$ alkyl. For example, in some embodiments, $R^1$, $R^2$ and $R^3$ each, independently have the following structure:

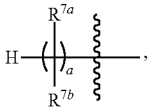

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (VIII), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In some of the foregoing embodiments of structure (VIII), X is CR, Y is NR and $R^3$ is $C_1$-$C_{12}$ alkyl, such as ethyl, propyl or butyl. In some of these embodiments, $R^1$ and $R^2$ are each independently branched $C_6$-$C_{24}$ alkyl.

In different embodiments of structure (VIII), $R^1$, $R^2$ and $R^3$ each, independently have one of the following structures:

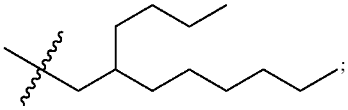
;
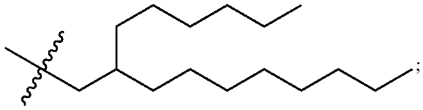
;
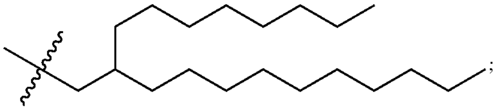
;
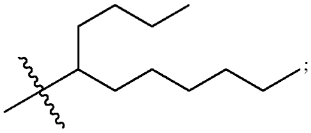
;
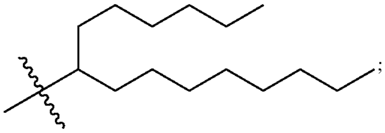
;
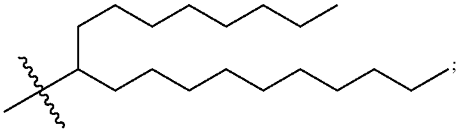
;

-continued

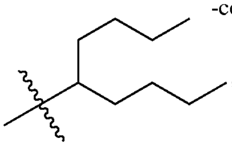
;
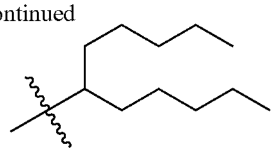
;
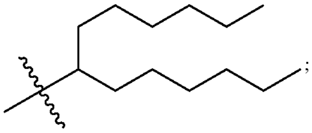
;
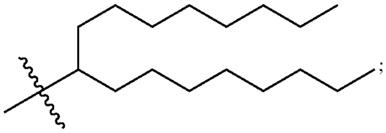
;
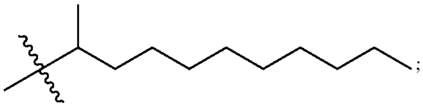
;
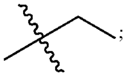
;
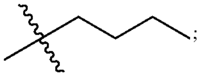
;
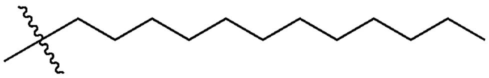
or
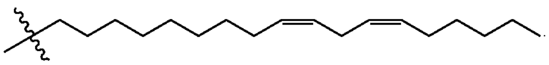
.

In certain embodiments of structure (VIII), $R^1$ and $R^2$ and $R^3$ are each, independently, branched $C_6$-$C_{24}$ alkyl and $R^3$ is $C_1$-$C_{24}$ alkyl or $C_2$-$C_{24}$ alkenyl.

In some of the foregoing embodiments of structure (VIII), $R^b$, $R^c$, $R^e$ and $R^f$ are each independently $C_3$-$C_{12}$ alkyl. For example, in some embodiments $R^b$, $R^c$, $R^e$ and $R^f$ are n-hexyl and in other embodiments $R^b$, $R^c$, $R^e$ and $R^f$ are n-octyl.

In various different embodiments of structure (VIII), the compound has one of the structures set forth in Table 7 below.

TABLE 7

Representative cationic lipids of structure (VIII)

| No. | Structure |
| --- | --- |
| VIII-1 | 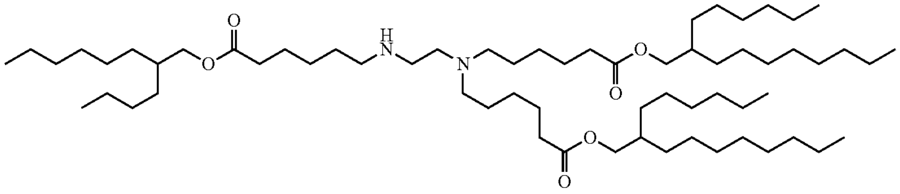 [SMILES: CCCCCCCCC(CCCCCC)COC(=O)CCCCCN(CCCCCC(=O)OCC(CCCCCC)CCCCCCCC)CCNCCCCCC(=O)OCC(CCCC)CCCCCC] |
| VIII-2 | 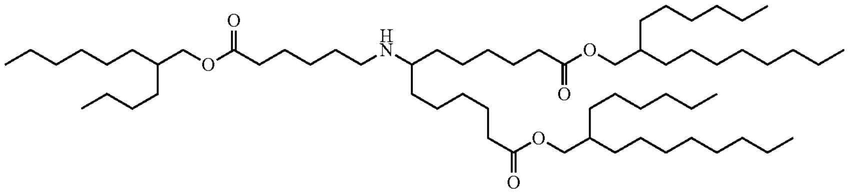 [SMILES: CCCCCCCCC(CCCCCC)COC(=O)CCCCCC(CCCCCC(=O)OCC(CCCCCC)CCCCCCCC)NCCCCCC(=O)OCC(CCCC)CCCCCC] |

TABLE 7-continued
Representative cationic lipids of structure (VIII)
| No. | Structure |
| --- | --- |
| VIII-3 | 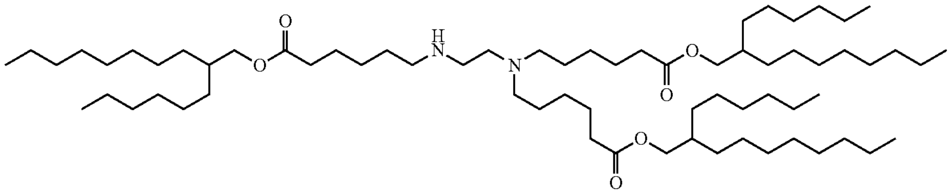 [SMILES: CCCCCCCCC(CCCCCC)COC(=O)CCCCCNCCN(CCCCCC(=O)OCC(CCCCCC)CCCCCCCC)CCCCCC(=O)OCC(CCCCCC)CCCCCCCC] |
| VIII-4 | 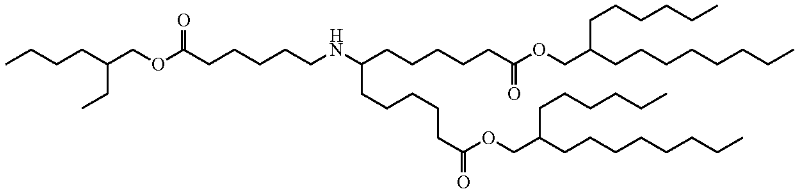 [SMILES: CCCCCCCCC(CCCCCC)COC(=O)CCCCCC(CCCCCC(=O)OCC(CCCCCC)CCCCCCCC)NCCCCCC(=O)OCC(CC)CCCC] |
| VIII-5 | 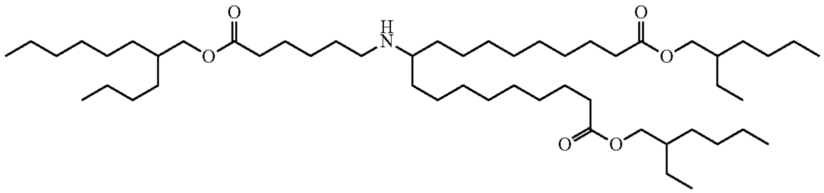 [SMILES: CCCCCCC(CCCC)COC(=O)CCCCCNC(CCCCCCCCC(=O)OCC(CC)CCCC)CCCCCCCCC(=O)OCC(CC)CCCC] |
| VIII-6 | 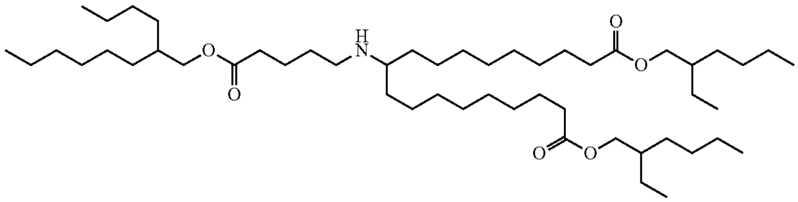 [SMILES: CCCCCCC(CCCC)COC(=O)CCCCNC(CCCCCCCCC(=O)OCC(CC)CCCC)CCCCCCCCC(=O)OCC(CC)CCCC] |
| VIII-7 | 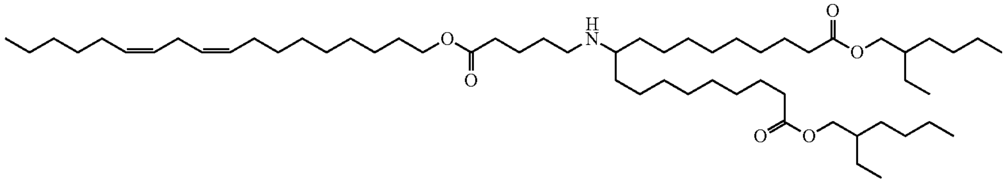 [SMILES: CCCCC/C=C\C/C=C\CCCCCCCCOC(=O)CCCCNC(CCCCCCCCC(=O)OCC(CC)CCCC)CCCCCCCCC(=O)OCC(CC)CCCC] |
| VIII-8 | 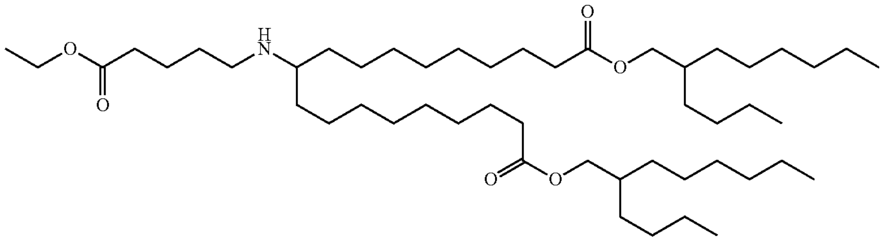 [SMILES: CCCCCCC(CCCC)COC(=O)CCCCCCCCC(CCCCCCCCC(=O)OCC(CCCC)CCCCCC)NCCCCC(=O)OCC] |
| VIII-9 | 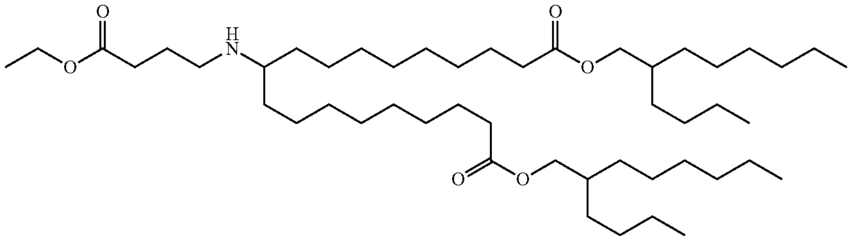 [SMILES: CCCCCCC(CCCC)COC(=O)CCCCCCCCC(CCCCCCCCC(=O)OCC(CCCC)CCCCCC)NCCCC(=O)OCC] |

TABLE 7-continued

| Representative cationic lipids of structure (VIII) | |
|---|---|
| No. | Structure |
| VIII-10 | 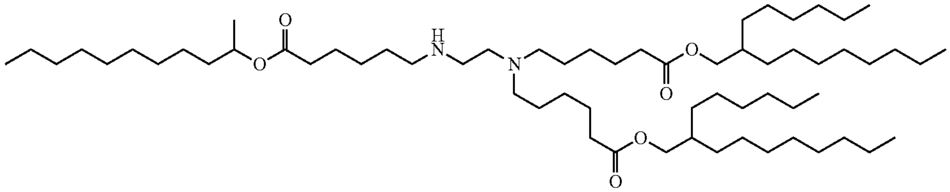 [SMILES: CCCCCCCCCC(C)OC(=O)CCCCCNCCN(CCCCCC(=O)OCC(CCCCCC)CCCCCCCC)CCCCCC(=O)OCC(CCCCCC)CCCCCCCC] |
| VIII-11 | 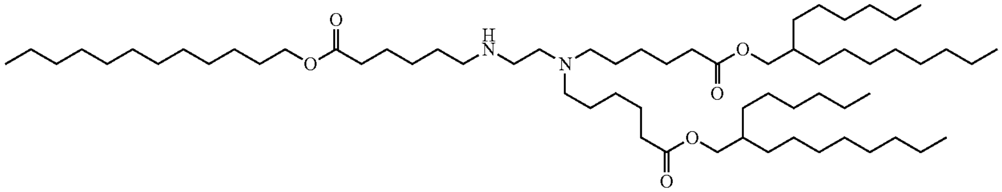 [SMILES: CCCCCCCCCCCCOC(=O)CCCCCNCCN(CCCCCC(=O)OCC(CCCCCC)CCCCCCCC)CCCCCC(=O)OCC(CCCCCC)CCCCCCCC] |
| VIII-12 | 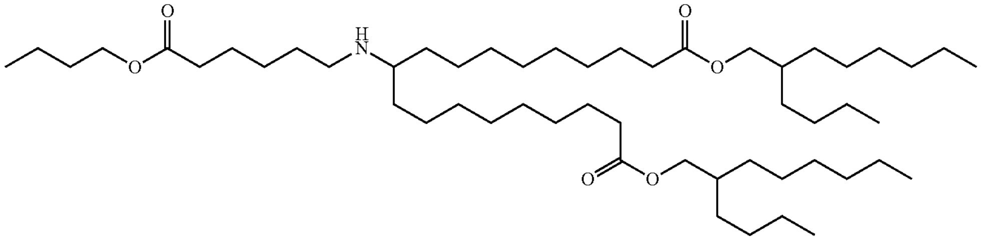 [SMILES: CCCCCCC(CCCC)COC(=O)CCCCCCCCC(CCCCCCCCC(=O)OCC(CCCC)CCCCCC)NCCCCCC(=O)OCCCC] |

In one embodiment, the cationic lipid is a compound having the following structure (IX):

(IX)

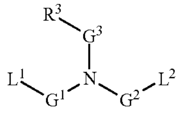

or a pharmaceutically acceptable salt, prodrug or stereoisomer thereof, wherein:

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^bR^c$, —N$R^a$C(═O)N$R^bR^c$, —OC(═O)N$R^bR^c$ or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^eR^f$, —N$R^d$C(═O)N$R^eR^f$, —OC(═O)N$R^eR^f$, —N$R^d$C(═O)O$R^2$ or a direct bond to $R^2$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_1$-$C_{12}$ alkenyl;

$R^e$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^3$ is —N($R^4$)$R^5$;

$R^4$ is $C_1$-$C_{12}$ alkyl;

$R^5$ is substituted $C_1$-$C_{12}$ alkyl; and x is 0, 1 or 2, and wherein each alkyl, alkenyl, alkylene, alkenylene, cycloalkylene, cycloalkenylene, aryl and aralkyl is independently substituted or unsubstituted unless otherwise specified.

In certain embodiments of structure (XI), $G^3$ is unsubstituted. In more specific embodiments $G^3$ is $C_2$-$C_{12}$ alkylene, for example, in some embodiments $G^3$ is $C_3$-$C_7$ alkylene or in other embodiments $G^3$ is $C_3$-$C_{12}$ alkylene. In some embodiments, $G^3$ is $C_2$ or $C_3$ alkylene.

In some of the foregoing embodiments of structure (IX), the compound has the following structure (IX A):

(IXA)

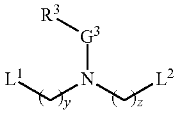

wherein y and z are each independently integers ranging from 2 to 12, for example an integer from 2 to 6, from 4 to 10, or for example 4 or 5. In certain embodiments, y and z are each the same and selected from 4, 5, 6, 7, 8 and 9.

In some of the foregoing embodiments of structure (IX), $L_1$ is —O(C═O)$R^1$, —(C═O)O$R^1$ or —C(═O)N$R^bR^c$, and $L^2$ is —O(C═O)$R^2$, —(C═O)O$R^2$ or —C(═O)N$R^eR^f$. For example, in some embodiments $L^1$ and $L^2$ are —(C═O)O$R^1$ and —(C═O)O$R^2$, respectively. In other embodiments $L_1$ is —(C═O)O$R^1$ and $L^2$ is —C(═O)N$R^eR^f$. In other embodiments $L_1$ is —C(═O)N$R^bR^c$ and $L^2$ is —C(═O)N$R^eR^f$.

In other embodiments of the foregoing, the compound has one of the following structures (IXB), (IXC), (IXD) or (IXE):

(IXB)

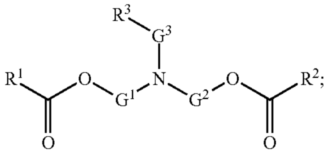

(IXC)

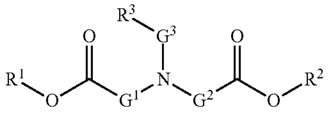

(IXD)

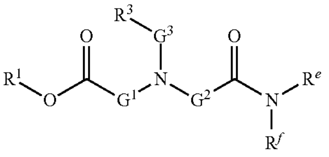

or (IXE)

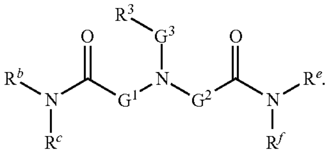

In some of the foregoing embodiments, the compound has structure (IXB), in other embodiments, the compound has structure (IXC) and in still other embodiments the compound has the structure (IXD). In other embodiments, the compound has structure (IXE).

In some different embodiments of the foregoing, the compound has one of the following structures (IXF), (IXG), (IXH) or (IXJ):

(IXF)

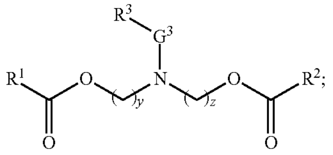

(IXG)

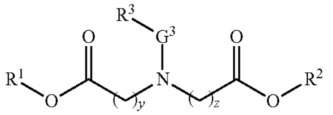

(IXH)

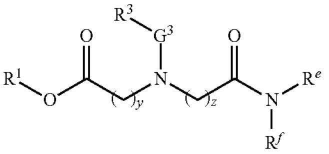

or (IXJ)

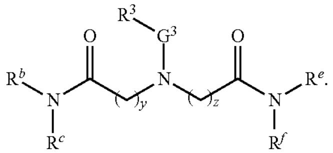

wherein y and z are each independently integers ranging from 2 to 12, for example an integer from 2 to 6, for example 4.

In some of the foregoing embodiments of structure (IX), y and z are each independently an integer ranging from 2 to 10, 2 to 8, from 4 to 10 or from 4 to 7. For example, in some embodiments, y is 4, 5, 6, 7, 8, 9, 10, 11 or 12. In some embodiments, z is 4, 5, 6, 7, 8, 9, 10, 11 or 12. In some embodiments, y and z are the same, while in other embodiments y and z are different.

In some of the foregoing embodiments of structure (IX), $R^1$ or $R^2$, or both is branched $C_6$-$C_{24}$ alkyl. For example, in some embodiments, $R^1$ and $R^2$ each, independently have the following structure:

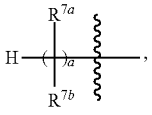

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (IX), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of structure (IX), $R^1$ or $R^2$, or both, has one of the following structures:

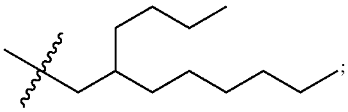

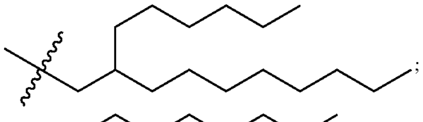

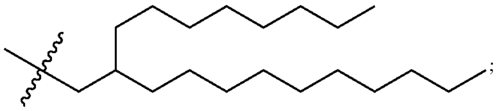

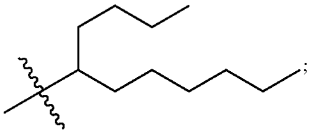

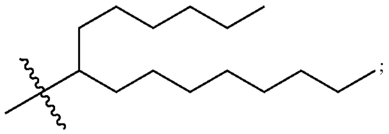

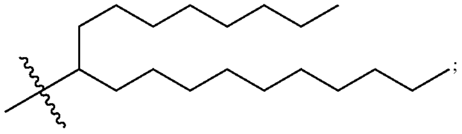

-continued

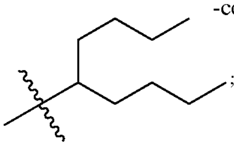;
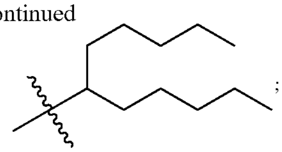;
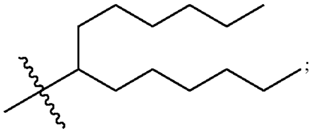;
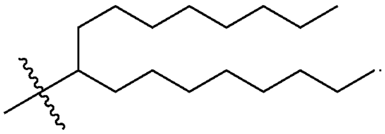.

In some of the foregoing embodiments of structure (IX), $R^b$, $R^c$, $R^e$ and $R^f$ are each independently $C_3$-$C_{12}$ alkyl. For example, in some embodiments $R^b$, $R^c$, $R^e$ and $R^f$ are n-hexyl and in other embodiments $R^b$, $R^c$, $R^e$ and $R^f$ are n-octyl.

In any of the foregoing embodiments of structure (IX), $R^4$ is substituted or unsubstituted: methyl, ethyl, propyl, n-butyl, n-hexyl, n-octyl or n-nonyl. For example, in some embodiments $R^4$ is unsubstituted. In other $R^4$ is substituted with one or more substituents selected from the group consisting of —$OR^g$, —$NR^gC(=O)R^h$, —$C(=O)NR^gR^h$, —$C(=O)R^h$, —$OC(=O)R^h$, —$C(=O)OR^h$ and —$OR^iOH$, wherein:

$R^g$ is, at each occurrence independently H or $C_1$-$C_6$ alkyl;

$R^h$ is at each occurrence independently $C_1$-$C_6$ alkyl; and $R^1$ is, at each occurrence independently $C_1$-$C_6$ alkylene.

In other of the foregoing embodiments of structure (IX), $R^5$ is substituted: methyl, ethyl, propyl, n-butyl, n-hexyl, n-octyl or n-nonyl. In some embodiments, $R^5$ is substituted ethyl or substituted propyl. In other different embodiments, $R^5$ is substituted with hydroxyl. In still more embodiments, $R^5$ is substituted with one or more substituents selected from the group consisting of —$OR^g$, —$NR^gC(=O)R^h$, —$C(=O)NR^gR^h$, —$C(=O)R^h$, —$OC(=O)R^h$, —$C(=O)OR^g$ and —$OR^iOH$, wherein:

$R^g$ is, at each occurrence independently H or $C_1$-$C_6$ alkyl;

$R^h$ is at each occurrence independently $C_1$-$C_6$ alkyl; and $R^i$ is, at each occurrence independently $C_1$-$C_6$ alkylene.

In other embodiments of structure (IX), $R^4$ is unsubstituted methyl, and $R^5$ is substituted: methyl, ethyl, propyl, n-butyl, n-hexyl, n-octyl or n-nonyl. In some of these embodiments, $R^5$ is substituted with hydroxyl.

In some other specific embodiments of structure (IX), $R^3$ has one of the following structures:

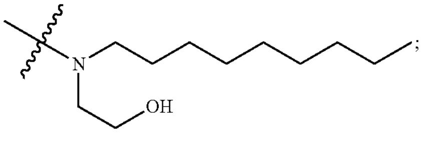;
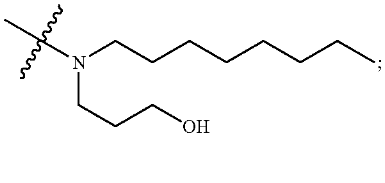;

-continued

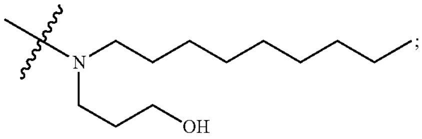;
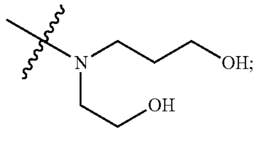;
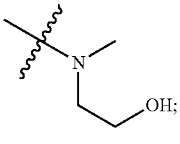;
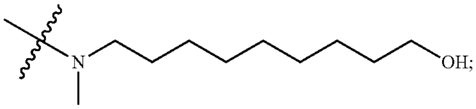;
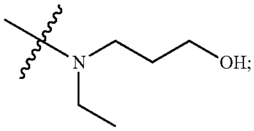;
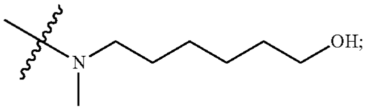;
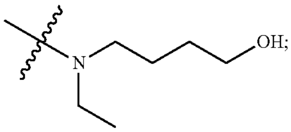;
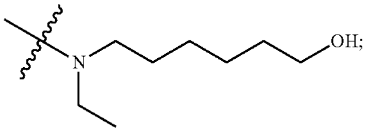;
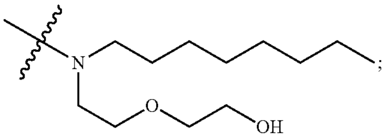;
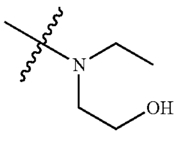
or
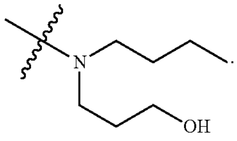.

In various different embodiments of structure (IX), the cationic lipid has one of the structures set forth in Table 8 below.

TABLE 8
| Representative cationic lipids of structure (IX) | |
|---|---|
| No. | Structure |
| IX-1 | 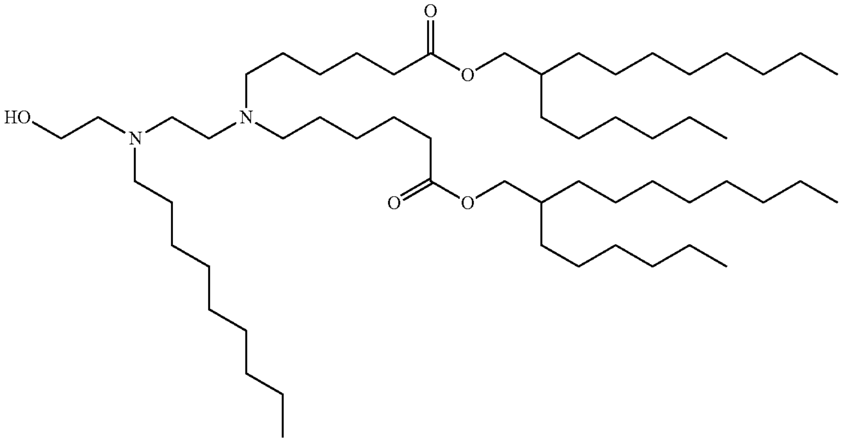 [SMILES: CCCCCCCCCN(CCO)CCN(CCCCCC(=O)OCC(CCCCCC)CCCCCCCC)CCCCCC(=O)OCC(CCCCCC)CCCCCCCC] |
| IX-2 | 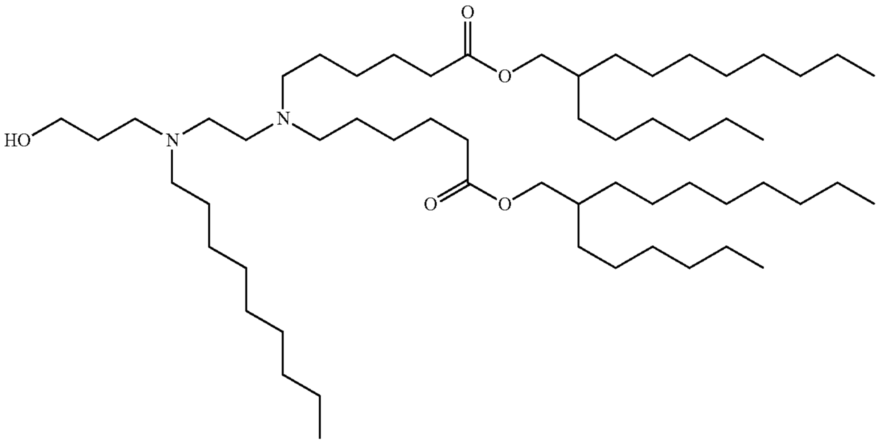 [SMILES: CCCCCCCCCN(CCCO)CCN(CCCCCC(=O)OCC(CCCCCC)CCCCCCCC)CCCCCC(=O)OCC(CCCCCC)CCCCCCCC] |
| IX-3 | 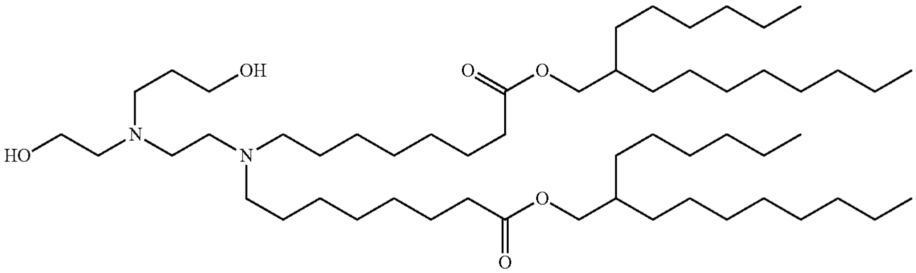 [SMILES: CCCCCCCCC(CCCCCC)COC(=O)CCCCCCCN(CCCCCCCC(=O)OCC(CCCCCC)CCCCCCCC)CCN(CCO)CCCO] |
| IX-4 | 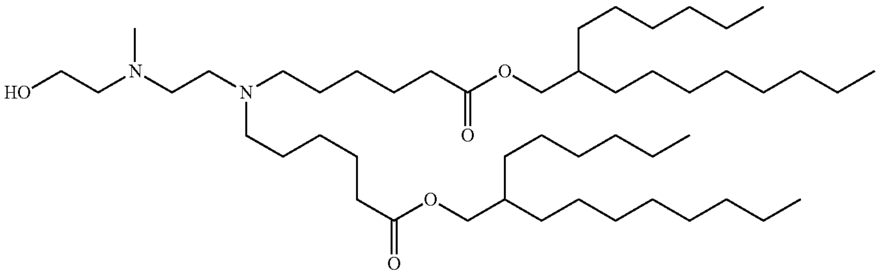 [SMILES: CCCCCCCCC(CCCCCC)COC(=O)CCCCCN(CCCCCC(=O)OCC(CCCCCC)CCCCCCCC)CCN(C)CCO] |

TABLE 8-continued
| Representative cationic lipids of structure (IX) | |
|---|---|
| No. | Structure |
| IX-5 | 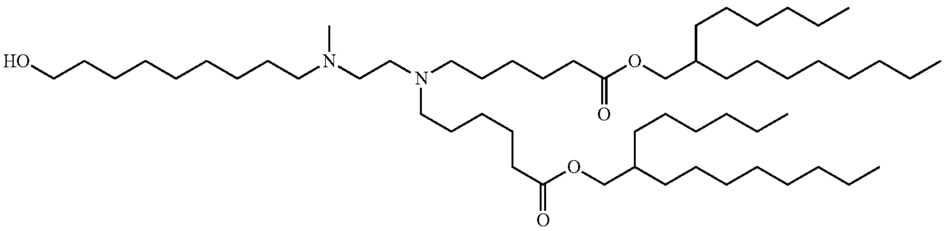 [SMILES: CCCCCCCCC(CCCCCC)COC(=O)CCCCCN(CCCCCC(=O)OCC(CCCCCC)CCCCCCCC)CCN(C)CCCCCCCCCO] |
| IX-6 | 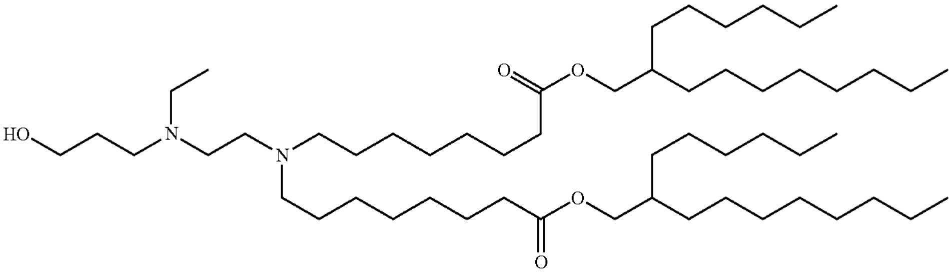 [SMILES: CCCCCCCCC(CCCCCC)COC(=O)CCCCCCCN(CCCCCCCC(=O)OCC(CCCCCC)CCCCCCCC)CCN(CC)CCCO] |
| IX-7 | 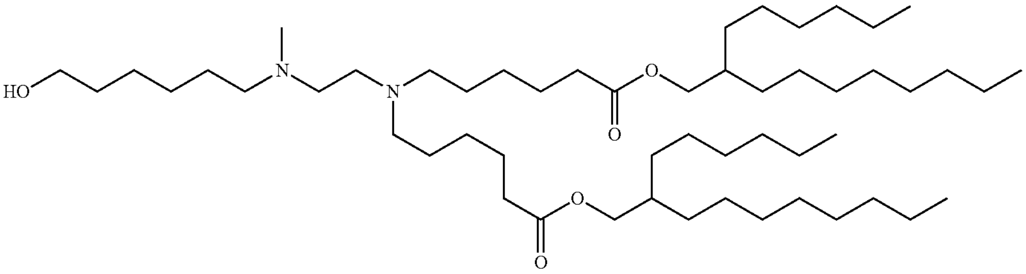 [SMILES: CCCCCCCCC(CCCCCC)COC(=O)CCCCCN(CCCCCC(=O)OCC(CCCCCC)CCCCCCCC)CCN(C)CCCCCCO] |
| IX-8 | 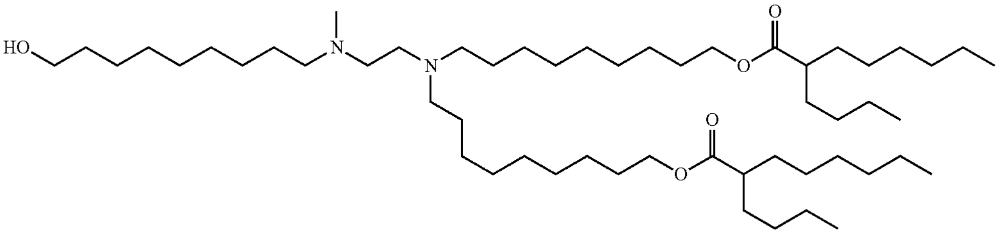 [SMILES: CCCCCCC(CCCC)C(=O)OCCCCCCCCCN(CCCCCCCCCOC(=O)C(CCCC)CCCCCC)CCN(C)CCCCCCCCCO] |
| IX-9 | 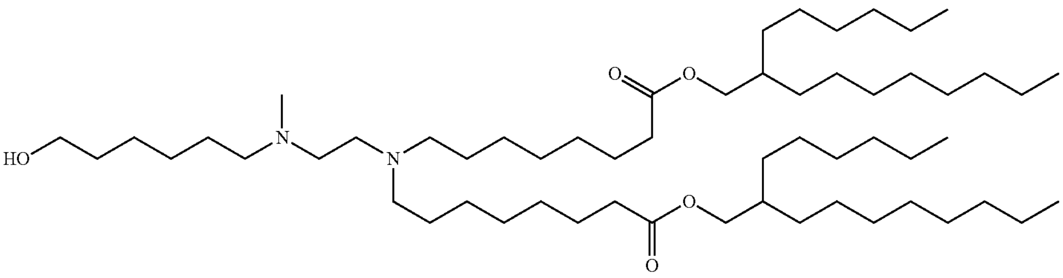 [SMILES: CCCCCCCCC(CCCCCC)COC(=O)CCCCCCCN(CCCCCCCC(=O)OCC(CCCCCC)CCCCCCCC)CCN(C)CCCCCCO] |

TABLE 8-continued
| Representative cationic lipids of structure (IX) | |
|---|---|
| No. | Structure |
| IX-10 | 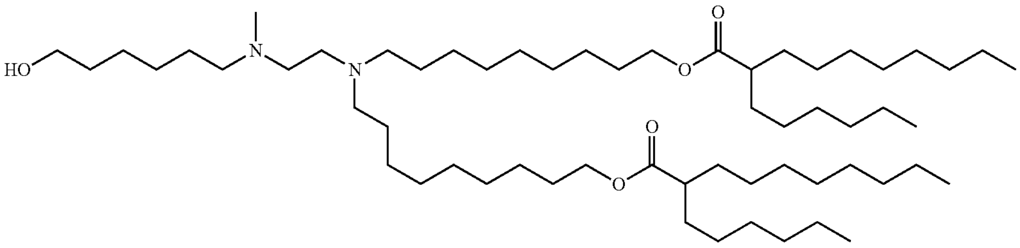 [SMILES: CCCCCCCCC(CCCCCC)C(=O)OCCCCCCCCCN(CCCCCCCCCOC(=O)C(CCCCCC)CCCCCCCC)CCN(C)CCCCCCO] |
| IX-11 | 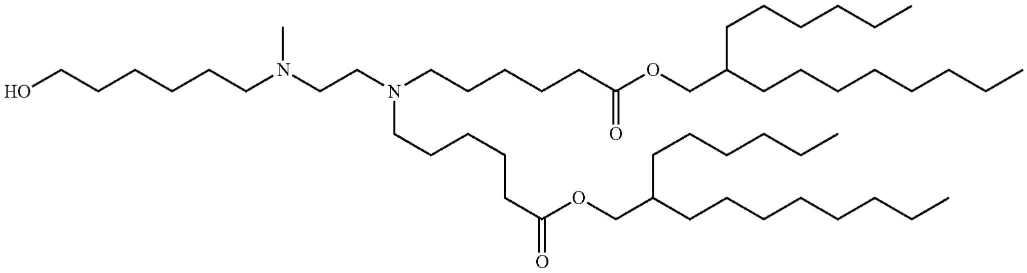 [SMILES: CCCCCCCCC(CCCCCC)COC(=O)CCCCCN(CCCCCC(=O)OCC(CCCCCC)CCCCCCCC)CCN(C)CCCCCCO] |
| IX-12 | 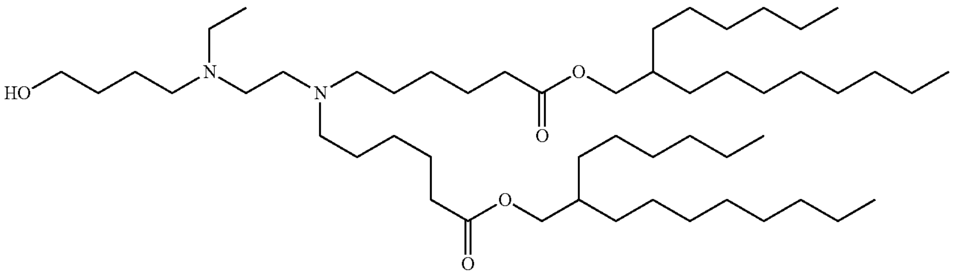 [SMILES: CCCCCCCCC(CCCCCC)COC(=O)CCCCCN(CCCCCC(=O)OCC(CCCCCC)CCCCCCCC)CCN(CC)CCCCO] |
| IX-13 | 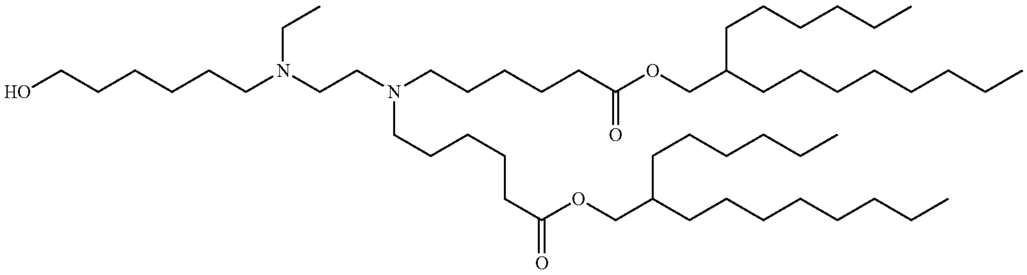 [SMILES: CCCCCCCCC(CCCCCC)COC(=O)CCCCCN(CCCCCC(=O)OCC(CCCCCC)CCCCCCCC)CCN(CC)CCCCCCO] |
| IX-14 | 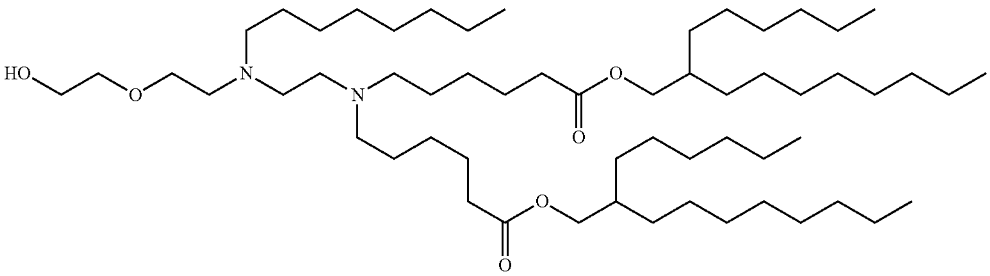 [SMILES: CCCCCCCCC(CCCCCC)COC(=O)CCCCCN(CCCCCC(=O)OCC(CCCCCC)CCCCCCCC)CCN(CCCCCCCC)CCOCCO] |

TABLE 8-continued

| No. | Structure |
| --- | --- |
| | Representative cationic lipids of structure (IX) |
| IX-15 | 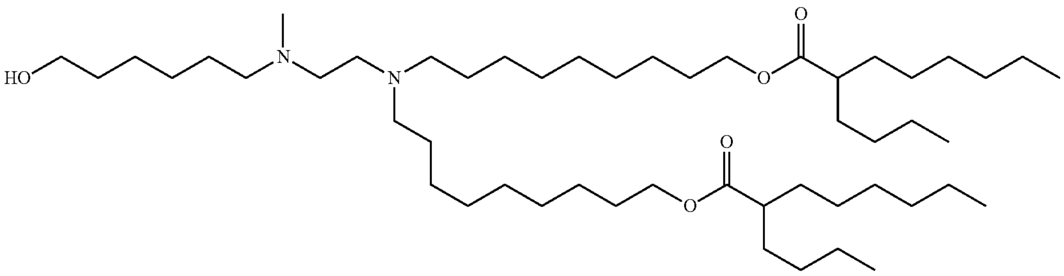 [SMILES: CCCCCCC(CCCC)C(=O)OCCCCCCCCCN(CCCCCCCCCOC(=O)C(CCCC)CCCCCC)CCN(C)CCCCCCO] |
| IX-16 | 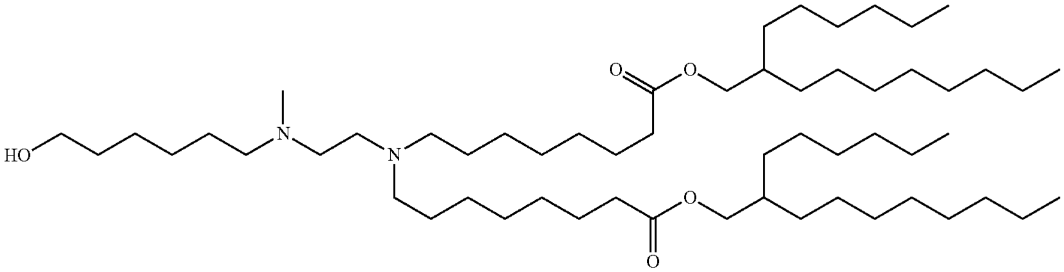 [SMILES: CCCCCCCCC(CCCCCC)COC(=O)CCCCCCCN(CCCCCCCC(=O)OCC(CCCCCC)CCCCCCCC)CCN(C)CCCCCCO] |
| IX-17 | 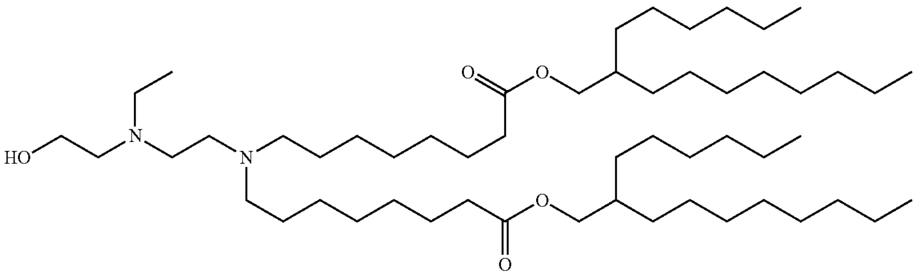 [SMILES: CCCCCCCCC(CCCCCC)COC(=O)CCCCCCCN(CCCCCCCC(=O)OCC(CCCCCC)CCCCCCCC)CCN(CC)CCO] |
| IX-18 | 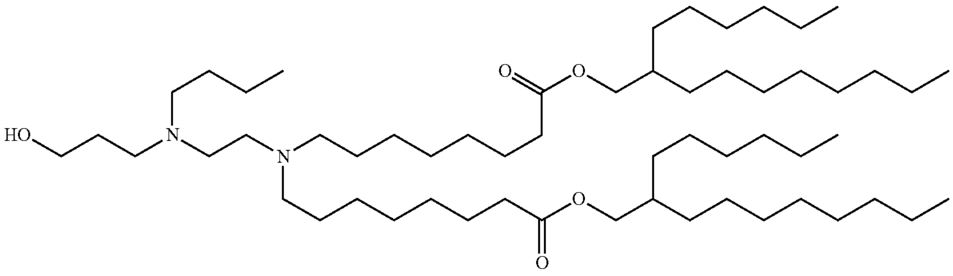 [SMILES: CCCCCCCCC(CCCCCC)COC(=O)CCCCCCCN(CCCCCCCC(=O)OCC(CCCCCC)CCCCCCCC)CCN(CCCC)CCCO] |

In one embodiment, the cationic lipid is a compound having the following structure (X):

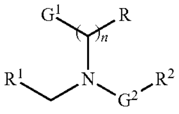

(X)

or a pharmaceutically acceptable salt, tautomer, prodrug or stereoisomer thereof, wherein:

$G^1$ is —OH, —$NR^3R^4$, —(C═O)$NR^5$ or —$NR^3$(C═O)$R^5$;

$G^2$ is —$CH_2$— or —(C═O)—;

R is, at each occurrence, independently H or OH;

$R^1$ and $R^2$ are each independently branched, saturated or unsaturated $C_{12}$-$C_{36}$ alkyl;

$R^3$ and $R^4$ are each independently H or straight or branched, saturated or unsaturated $C_1$-$C_6$ alkyl;

$R^5$ is straight or branched, saturated or unsaturated $C_1$-$C_6$ alkyl; and n is an integer from 2 to 6.

In some embodiments, $R^1$ and $R^2$ are each independently branched, saturated or unsaturated $C_{12}$-$C_{30}$ alkyl, $C_{12}$-$C_{20}$ alkyl, or $C_{15}$-$C_{20}$ alkyl. In some specific embodiments, $R^1$ and $R^2$ are each saturated. In certain embodiments, at least one of $R^1$ and $R^2$ is unsaturated.

In some of the foregoing embodiments of structure (X), $R^1$ and $R^2$ have the following structure:

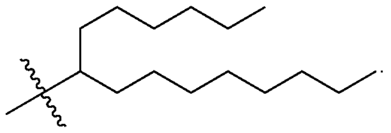 [SMILES: *C(CCCCCC)CCCCCCCC]

In some of the foregoing embodiments of structure (X), the compound has the following structure (XA):

(XA)

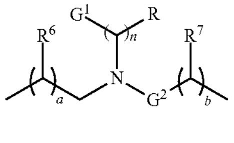

wherein:

$R^6$ and $R^7$ are, at each occurrence, independently H or straight or branched, saturated or unsaturated $C_1$-$C_{14}$ alkyl;

a and b are each independently an integer ranging from 1 to 15, provided that $R^6$ and a, and $R^7$ and b, are each independently selected such that $R^1$ and $R^2$, respectively, are each independently branched, saturated or unsaturated $C_{12}$-$C_{36}$ alkyl.

In some of the foregoing embodiments, the compound has the following structure (XB):

(XB)

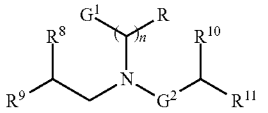

wherein:

$R^8$, $R^9$, $R^{10}$ and $R^{11}$ are each independently straight or branched, saturated or unsaturated $C_4$-$C_{12}$ alkyl, provided that $R^1$ and $R^9$, and $R^{10}$ and $R^{11}$, are each independently selected such that $R^1$ and $R^2$, respectively, are each independently branched, saturated or unsaturated $C_{12}$-$C_{36}$ alkyl. In some embodiments of (XB), $R^8$, $R^9$, $R^{10}$ and $R^{11}$ are each independently straight or branched, saturated or unsaturated $C_6$-$C_{10}$ alkyl. In certain embodiments of (XB), at least one of $R^8$, $R^9$, $R^{10}$ and $R^{11}$ is unsaturated. In other certain specific embodiments of (XB), each of $R^8$, $R^9$, $R^{10}$ and $R^{11}$ is saturated.

In some of the foregoing embodiments, the compound has structure (XA), and in other embodiments, the compound has structure (XB).

In some of the foregoing embodiments, $G^1$ is —OH, and in some embodiments $G^1$ is —$NR^3R^4$. For example, in some embodiments, $G^1$ is —$NH_2$, —$NHCH_3$ or —$N(CH_3)_2$. In certain embodiments, $G^1$ is —(C═O)$NR^5$. In certain other embodiments, $G^1$ is —$NR^3$(C═O)$R^5$. For example, in some embodiments $G^1$ is —NH(C═O)$CH_3$ or —NH(C═O)$CH_2CH_2CH_3$.

In some of the foregoing embodiments of structure (X), $G^2$ is —$CH_2$—. In some different embodiments, $G^2$ is —(C═O)—.

In some of the foregoing embodiments of structure (X), n is an integer ranging from 2 to 6, for example, in some embodiments n is 2, 3, 4, 5 or 6. In some embodiments, n is 2. In some embodiments, n is 3. In some embodiments, n is 4.

In certain of the foregoing embodiments of structure (X), at least one of $R^1$, $R^2$, $R^3$, $R^4$ and $R^5$ is unsubstituted. For example, in some embodiments, $R^1$, $R^2$, $R^3$, $R^4$ and $R^5$ are each unsubstituted. In some embodiments, $R^3$ is substituted. In other embodiments $R^4$ is substituted. In still more embodiments, $R^5$ is substituted. In certain specific embodiments, each of $R^3$ and $R^4$ are substituted. In some embodiments, a substituent on $R^3$, $R^4$ or $R^5$ is hydroxyl. In certain embodiments, $R^3$ and $R^4$ are each substituted with hydroxyl.

In some of the foregoing embodiments of structure (X), at least one R is OH. In other embodiments, each R is H.

In various different embodiments of structure (X), the compound has one of the structures set forth in Table 9 below.

TABLE 9

Representative cationic lipids of structure (X)

| No. | Structure |
| --- | --- |
| X-1 | 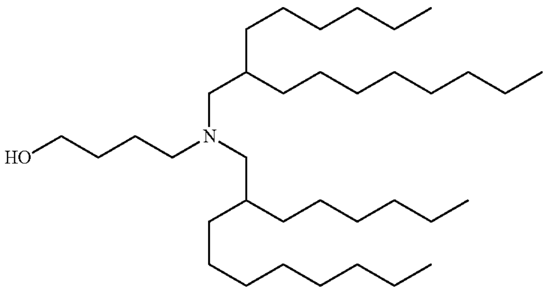 [SMILES: CCCCCCCCC(CCCCCC)CN(CCCCO)CC(CCCCCC)CCCCCCCC] |

TABLE 9-continued
| Representative cationic lipids of structure (X) | |
|---|---|
| No. | Structure |
| X-2 | 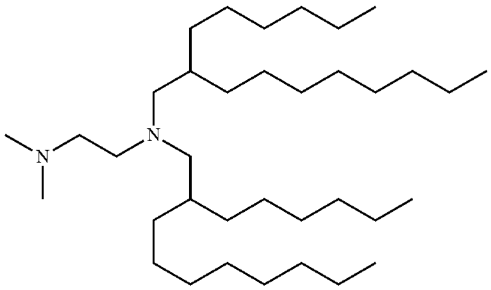 [SMILES: CCCCCCCCC(CCCCCC)CN(CCN(C)C)CC(CCCCCC)CCCCCCCC] |
| X-3 | 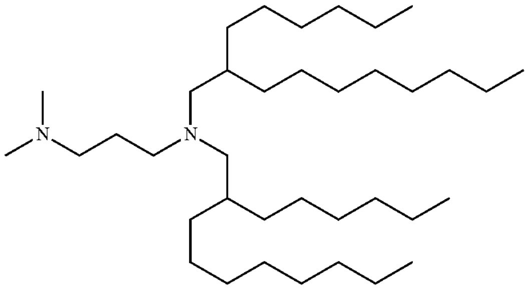 [SMILES: CCCCCCCCC(CCCCCC)CN(CCCN(C)C)CC(CCCCCC)CCCCCCCC] |
| X-4 | 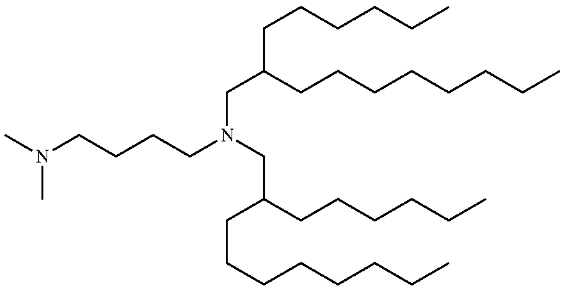 [SMILES: CCCCCCCCC(CCCCCC)CN(CCCCN(C)C)CC(CCCCCC)CCCCCCCC] |
| X-5 | 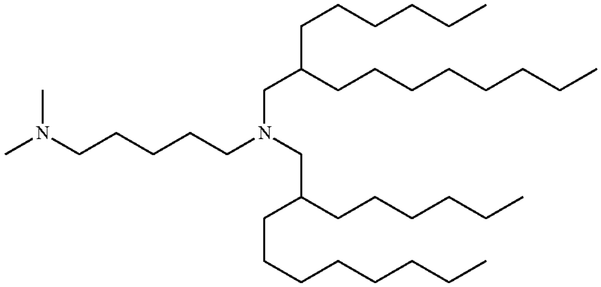 [SMILES: CCCCCCCCC(CCCCCC)CN(CCCCCN(C)C)CC(CCCCCC)CCCCCCCC] |
| X-6 | 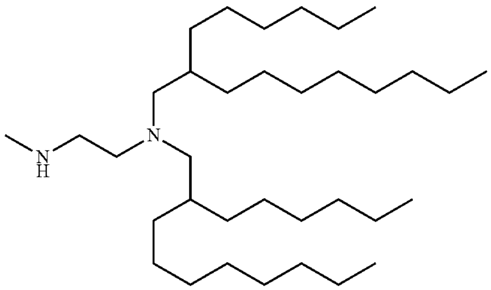 [SMILES: CCCCCCCCC(CCCCCC)CN(CCNC)CC(CCCCCC)CCCCCCCC] |

TABLE 9-continued
| Representative cationic lipids of structure (X) | |
|---|---|
| No. | Structure |
| X-7 | 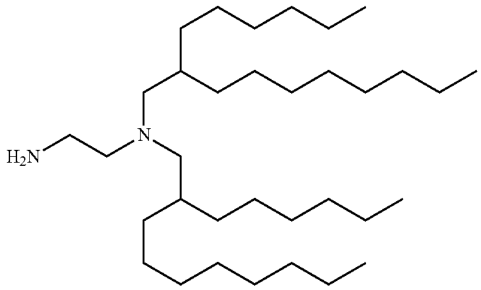 [SMILES: CCCCCCCCC(CCCCCC)CN(CCN)CC(CCCCCC)CCCCCCCC] |
| X-8 | 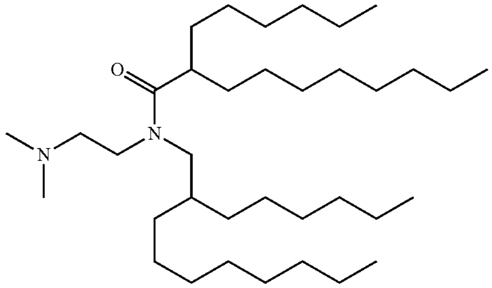 [SMILES: CCCCCCCCC(CCCCCC)CN(CCN(C)C)C(=O)C(CCCCCC)CCCCCCCC] |
| X-9 | 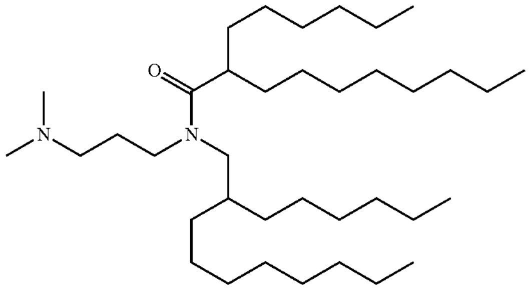 [SMILES: CCCCCCCCC(CCCCCC)CN(CCCN(C)C)C(=O)C(CCCCCC)CCCCCCCC] |
| X-10 | 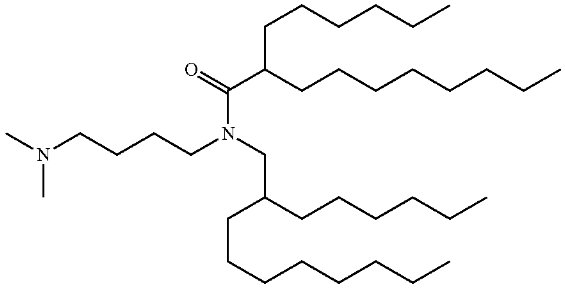 [SMILES: CCCCCCCCC(CCCCCC)CN(CCCCN(C)C)C(=O)C(CCCCCC)CCCCCCCC] |
| X-11 | 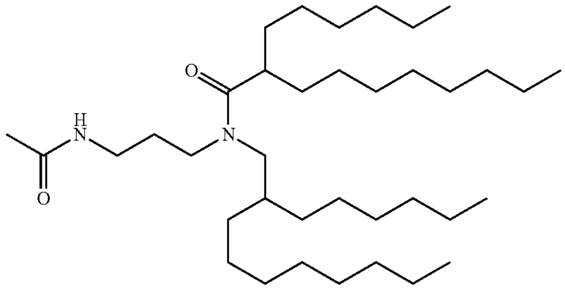 [SMILES: CCCCCCCCC(CCCCCC)CN(CCCNC(C)=O)C(=O)C(CCCCCC)CCCCCCCC] |

TABLE 9-continued
Representative cationic lipids of structure (X)
| No. | Structure |
| --- | --- |
| X-12 | 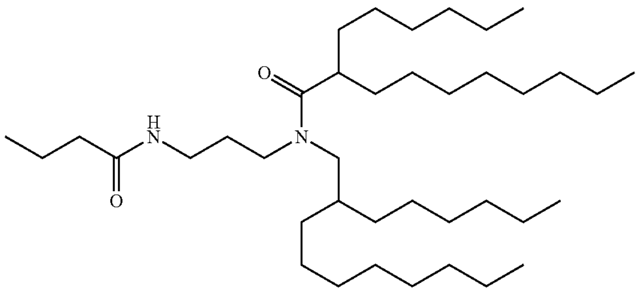 [SMILES: CCCCCCCCC(CCCCCC)CN(CCCNC(=O)CCC)C(=O)C(CCCCCC)CCCCCCCC] |
| X-13 | 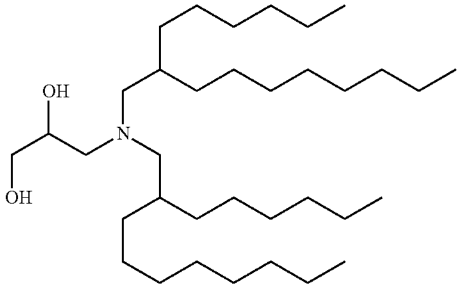 [SMILES: CCCCCCCCC(CCCCCC)CN(CC(O)CO)CC(CCCCCC)CCCCCCCC] |
| X-14 | 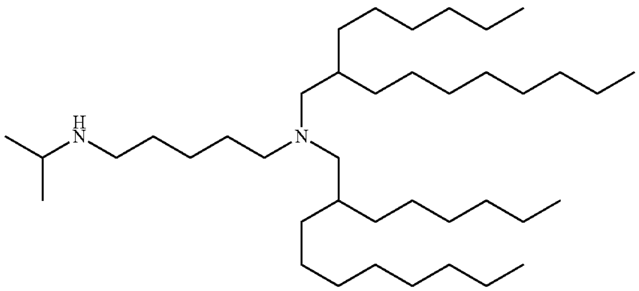 [SMILES: CCCCCCCCC(CCCCCC)CN(CCCCCNC(C)C)CC(CCCCCC)CCCCCCCC] |
| X-15 | 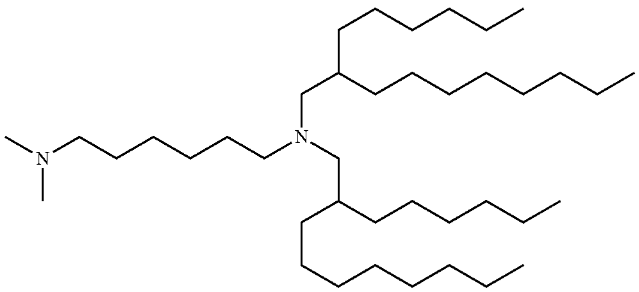 [SMILES: CCCCCCCCC(CCCCCC)CN(CCCCCCN(C)C)CC(CCCCCC)CCCCCCCC] |
| X-16 | 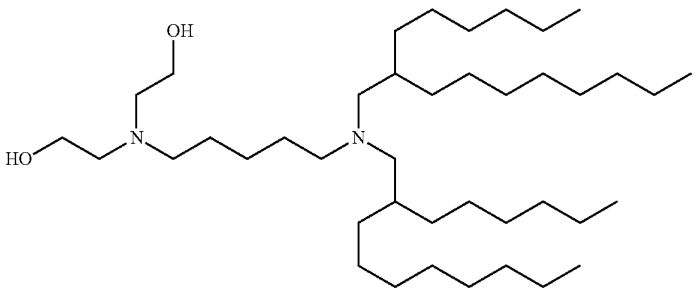 [SMILES: CCCCCCCCC(CCCCCC)CN(CCCCCN(CCO)CCO)CC(CCCCCC)CCCCCCCC] |

TABLE 9-continued

| Representative cationic lipids of structure (X) | |
|---|---|
| No. | Structure |
| X-17 | 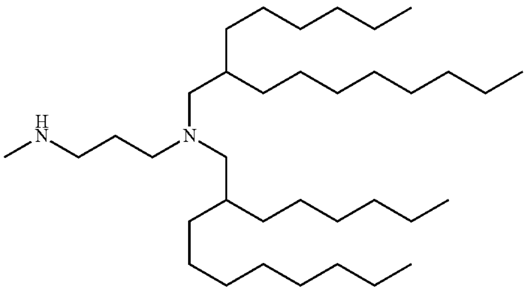 [SMILES: CCCCCCCCC(CCCCCC)CN(CCCNC)CC(CCCCCC)CCCCCCCC] |

In any of Embodiments 1, 2, 3, 4 or 5, the LNPs further comprise a neutral lipid. In various embodiments, the molar ratio of the cationic lipid to the neutral lipid ranges from about 2:1 to about 8:1. In certain embodiments, the neutral lipid is present in any of the foregoing LNPs in a concentration ranging from 5 to 10 mol percent, from 5 to 15 mol percent, 7 to 13 mol percent, or 9 to 11 mol percent. In certain specific embodiments, the neutral lipid is present in a concentration of about 9.5, or 10.5 mol percent. In some embodiments, the molar ratio of cationic lipid to the neutral lipid ranges from about 4.1:1.0 to about 4.9:1.0, from about 4.5:1.01 to about 4.8:1.0, or from about 4.7:1.0 to 4.8:1.0. In some embodiments, the molar ratio of total cationic lipid to the neutral lipid ranges from about 4.1:1.0 to about 4.9:1.0, from about 4.5:1.0 to about 4.8:1.0, or from about 4.7:1.0 to 4.8:1.0.

Exemplary neutral lipids for use in any of Embodiments 1, 2, 3, 4 or 5 include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE), and 1,2-dielaidoyl-sn-glycero-3-phophoethanolamine (transDOPE). In one embodiment, the neutral lipid is 1,2-distearoyl-sn-glycero-3phosphocholine (DSPC). In some embodiments, the neutral lipid is selected from DSPC, DPPC, DMPC, DOPC, POPC, DOPE and SM. In some embodiments, the neutral lipid is DSPC.

In various embodiments of Embodiments 1, 2, 3, 4 or 5, any of the disclosed lipid nanoparticles comprise a steroid or steroid analogue. In certain embodiments, the steroid or steroid analogue is cholesterol. In some embodiments, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent. In certain specific embodiments, the steroid is present in a concentration of 40, 41, 42, 43, 44, 45, or 46 molar percent.

In certain embodiments, the molar ratio of cationic lipid to the steroid ranges from 1.0:0.9 to 1.0:1.2, or from 1.0:1.0 to 1.0:1.2. In some of these embodiments, the molar ratio of cationic lipid to cholesterol ranges from about 5:1 to 1:1. In certain embodiments, the steroid is present in a concentration ranging from 32 to 40 mol percent of the steroid.

In certain embodiments, the molar ratio of total cationic to the steroid ranges from 1.0:0.9 to 1.0:1.2, or from 1.0:1.0 to 1.0:1.2. In some of these embodiments, the molar ratio of total cationic lipid to cholesterol ranges from about 5:1 to 1:1. In certain embodiments, the steroid is present in a concentration ranging from 32 to 40 mol percent of the steroid.

In some embodiments of Embodiments 1, 2, 3 4 or 5, the LNPs further comprise a polymer conjugated lipid. In various other embodiments of Embodiments 1, 2, 3 4 or 5, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2', 3'-di(tetradecanoyloxy) propyl-1-O-(o-methoxy(polyethoxy)ethyl)butanedioate (PEG-S-DMG), a pegylated ceramide (PEG-cer), or a PEG dialkoxypropylcarbamate such as (o-methoxy(polyethoxy) ethyl-N-(2,3-di(tetradecanoxy)propyl)carbamate or 2,3-di (tetradecanoxy)propyl-N-(o-methoxy(polyethoxy)ethyl)carbamate.

In various embodiments, the polymer conjugated lipid is present in a concentration ranging from 1.0 to 2.5 molar percent. In certain specific embodiments, the polymer conjugated lipid is present in a concentration of about 1.7 molar percent. In some embodiments, the polymer conjugated lipid is present in a concentration of about 1.5 molar percent.

In certain embodiments, the molar ratio of cationic lipid to the polymer conjugated lipid ranges from about 35:1 to about 25:1. In some embodiments, the molar ratio of cationic lipid to polymer conjugated lipid ranges from about 100:1 to about 20:1.

In certain embodiments, the molar ratio of total cationic lipid (i.e., the sum of the first and second cationic lipid) to the polymer conjugated lipid ranges from about 35:1 to about 25:1. In some embodiments, the molar ratio of total cationic lipid to polymer conjugated lipid ranges from about 100:1 to about 20:1.

In some embodiments of Embodiments 1, 2, 3 4 or 5, the pegylated lipid, when present, has the following Formula (XI):

(XI)

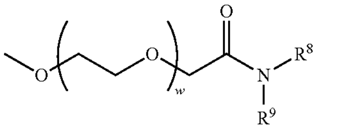

or a pharmaceutically acceptable salt, tautomer or stereoisomer thereof, wherein:

$R^{12}$ and $R^{13}$ are each independently a straight or branched, saturated or unsaturated alkyl chain containing from 10 to 30 carbon atoms, wherein the alkyl chain is optionally interrupted by one or more ester bonds; and w has a mean value ranging from 30 to 60.

In some embodiments, $R^{12}$ and $R^{13}$ are each independently straight, saturated alkyl chains containing from 12 to 16 carbon atoms. In other embodiments, the average w ranges from 42 to 55, for example, the average w is 42, 43, 44, 45, 46, 47, 48, 49, 50, 51, 52, 53, 54 or 55. In some specific embodiments, the average w is about 49.

In some embodiments, the pegylated lipid has the following Formula (XIa):

(XIa)

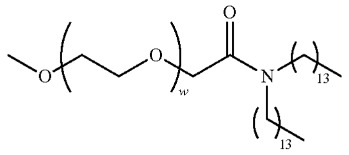

wherein the average w is about 49.

In some embodiments of Embodiments 1, 2, 3 4 or 5, the nucleic acid is selected from antisense and messenger RNA. For example, messenger RNA may be used to induce an immune response (e.g., as a vaccine), for example by translation of immunogenic proteins.

In an embodiment, the transfer vehicle comprises a lipid or an ionizable lipid described in US patent publication number 20190314524.

Some embodiments of the present invention provide nucleic acid-lipid nanoparticle compositions comprising one or more of the novel cationic lipids described herein as structures listed in Table 10, that provide increased activity of the nucleic acid and improved tolerability of the compositions in vivo.

In one embodiment, an ionizable lipid has the following structure (XII):

(XII)

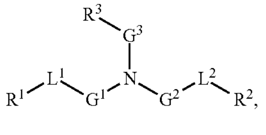

or a pharmaceutically acceptable salt, tautomer, pro rug or stereoisomer thereof, wherein:

one of $L^1$ or $L^2$is —O(C═O)—, —(C═O)O—, —C(═O)—, —O—, —S(O)$_x$—, —S—S—, —C(═O)S—, —SC(═O)—, —NR$^a$C(═O)—, —C(═O)NR$^a$—, —NR$^a$C(═)NR$^a$—, —OC(═O)NR$^a$— or —NR$^a$C(═O)O—, and the other of $L^1$ or $L^2$ is —O(C═O)—, (C═O)O—, —C(═O)—, —O—, —S(O)$_x$—, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, C(═O)$OR^4$, OC(═O)$R^4$ or —NR$^5$C(═O)$R^4$;

$R^4$ is $C_1$-$C_{12}$ alkyl;

$R^5$ is H or $C_1$-$C_6$ alkyl; and x is 0, 1 or 2.

In some embodiments, an ionizable lipid has one of the following structures (XIIA) or (XIIB):

(XIIA)

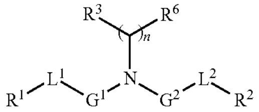

(XIIB)

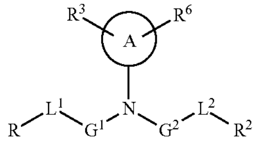

wherein:

A is a 3 to 8-membered cycloalkyl or cycloalkylene ring;

$R^6$ is, at each occurrence, independently H, OH or $C_1$-$C_{24}$ alkyl; and n is an integer ranging from 1 to 15.

In some embodiments, the ionizable lipid has structure (XIIA), and in other embodiments, the ionizable lipid has structure (XIIB).

In other embodiments, an ionizable lipid has one of the following structures (XIIC) or (XIID):

(XIIC)

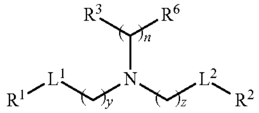

(XIID)

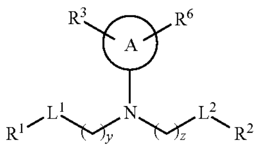

wherein y and z are each independently integers ranging from 1 to 12.

In some embodiments, one of $L^1$ or $L^2$is —O(C═O)—. For example, in some embodiments each of $L^1$ and $L^2$ are —O(C═O)—. In some different embodiments of any of the foregoing, $L^1$ and $L^2$ are each independently —(C═O)O— or —O(C═O)—. For example, in some embodiments each of $L^1$ and $L^2$ is —(C═O)O—.

In some embodiments, an ionizable lipid has one of the following structures (XIIE) or (XIIF):

(XIIE)

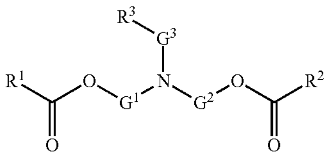

(XIIF)

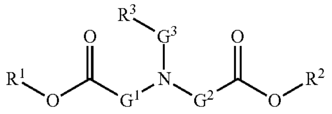

In some embodiments, an ionizable lipid has one of the following structures (XIIG), (XIIH), (XIII), or (XIIJ):

(XIIG)

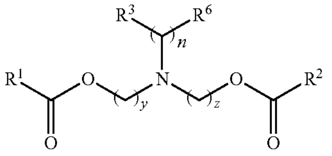

(XIIH)

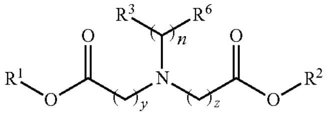

(XIII)

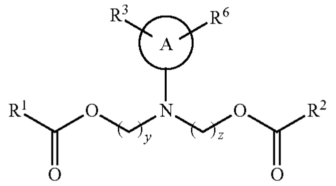

(XIIJ)

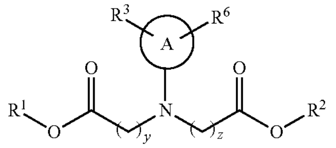

In some embodiments, n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some embodiments, y and z are each independently an integer ranging from 2 to 10. For example, in some embodiments, y and z are each independently an integer ranging from 4 to 9 or from 4 to 6.

In some embodiments, $R^6$ is H. In other embodiments, $R^6$ is $C_1$-$C_{24}$ alkyl. In other embodiments, $R^6$ is OH.

In some embodiments, $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some embodiments, $R^1$ or $R^2$, or both, is $C_6$-$C_{24}$ alkenyl. For example, in some embodiments, $R^1$ and $R^2$ each, independently have the following structure:

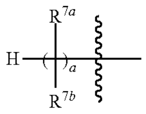

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$each independently comprise from 6 to 20 carbon atoms.

In some embodiments, a is an integer ranging from 5 to 9 or from 8 to 12.

In some embodiments, at least one occurrence of $R^{7a}$ is H. For example, in some embodiments, $R^{7a}$ is H at each occurrence. In other different embodiments, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments, $R^1$ or $R^2$, or both, has one of the following structures:

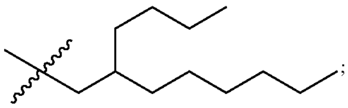
;

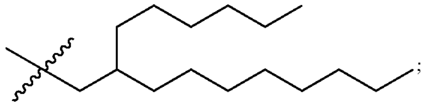
;

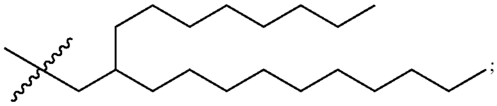
;

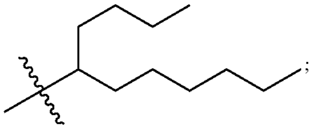
;

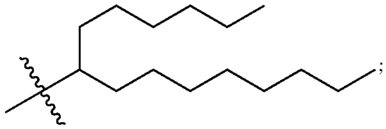
;

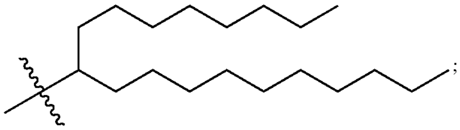
;

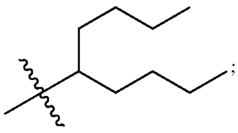
;

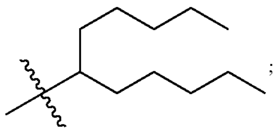
;

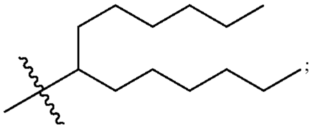
;

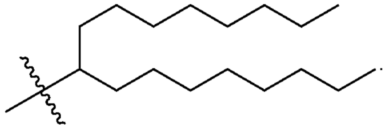
.

In some embodiments, $R^3$ is —OH, —CN, —C(═O)$OR^4$, —OC(═O)$R^4$ or —NHC(═O)$R^4$. In some embodiments, $R^4$ is methyl or ethyl.

In some embodiments, an ionizable lipid is a compound of Formula (1):

Formula (1)

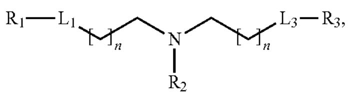

wherein:

each n is independently 1, 2, 3, 4, 5, 6, 7, 8, 9, 10, 11, 12, 13, 14, or 15; and $L_1$ and $L_3$ are each independently —OC(O)—* or —C(O)O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl.

In some embodiments, $R_1$ and $R_3$ are the same. In some embodiments, $R_1$ and $R_3$ are different.

In some embodiments, $R_1$ and $R_3$ are each independently a branched saturated $C_9$-$C_{20}$ alkyl. In some embodiments, one of $R_1$ and $R_3$ is a branched saturated $C_9$-$C_{20}$ alkyl, and the other is an unbranched saturated $C_9$-$C_{20}$ alkyl. In some embodiments, $R_1$ and $R_3$ are each independently selected from a group consisting of:

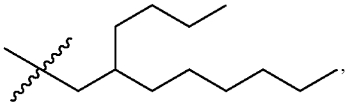,

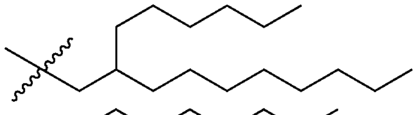,

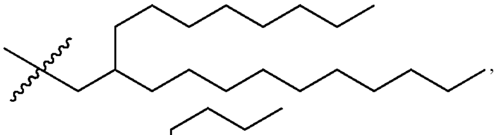,

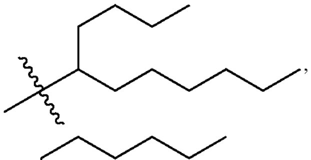,

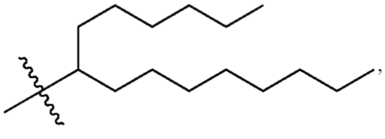,

-continued

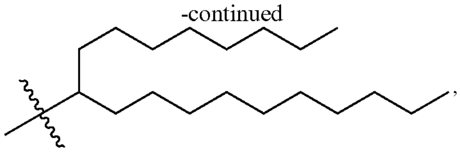,

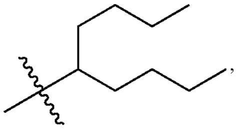, 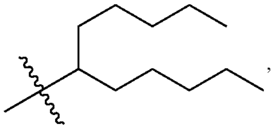,

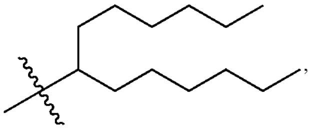,

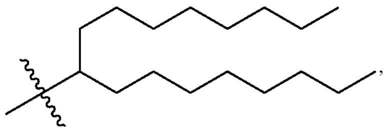, and

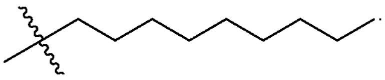.

In various embodiments $R_2$ is selected from a group consisting of:

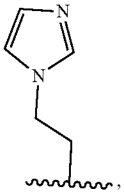, 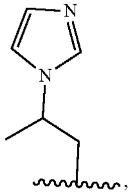, 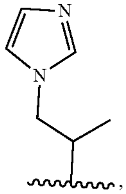,

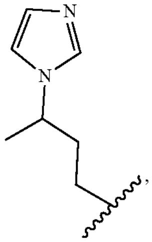, 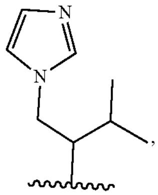, 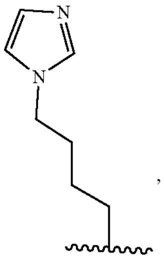,

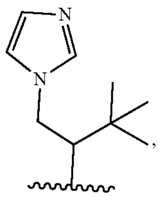, 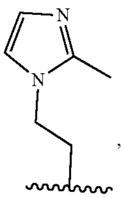, 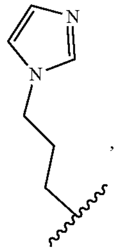, 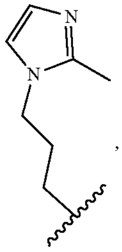,

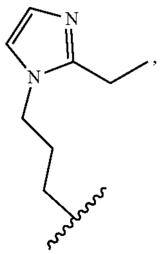, 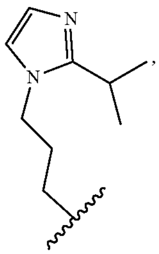, 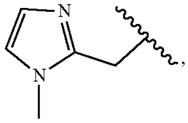,

-continued

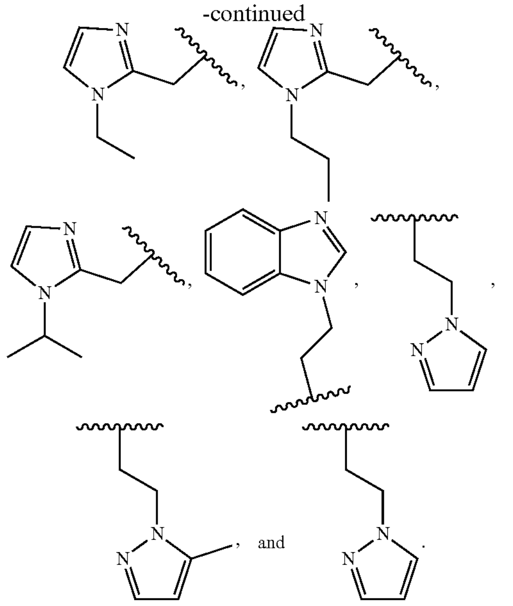

and

In some embodiments, $R^2$ may be as described in International Pat. Pub. No. WO2019/152848 A 1, which is incorporated herein by reference in its entirety.

In some embodiments, an ionizable lipid is a compound of Formula (1-1) or Formula (1-2):

Formula (1-1)

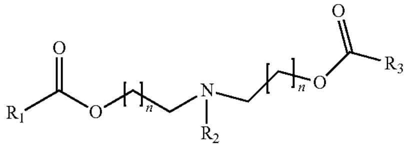

Formula (1-2)

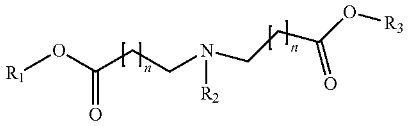

wherein n, $R_1$, $R_2$, and $R_3$ are as defined in Formula (1).

Preparation methods for the above compounds and compositions are described herein below and/or known in the art.

It will be appreciated by those skilled in the art that in the process described herein the functional groups of intermediate compounds may need to be protected by suitable protecting groups. Such functional groups include, e.g., hydroxyl, amino, mercapto, and carboxylic acid. Suitable protecting groups for hydroxyl include, e.g., trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino, and guanidino include, e.g., t-butoxycarbonyl, benzyloxycarbonyl, and the like. Suitable protecting groups for mercapto include, e.g., —C(O)—R" (where R" is alkyl, aryl, or arylalkyl), p-methoxybenzyl, trityl, and the like. Suitable protecting groups for carboxylic acid include, e.g., alkyl, aryl, or arylalkyl esters. Protecting groups may be added or removed in accordance with standard techniques, which are known to one skilled in the art and as described herein. The use of protecting groups is described in detail in, e.g., Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin, or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as prodrugs. All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can also be converted to their free base or acid form by standard techniques.

The following reaction scheme illustrates an exemplary method to make compounds of Formula (1):

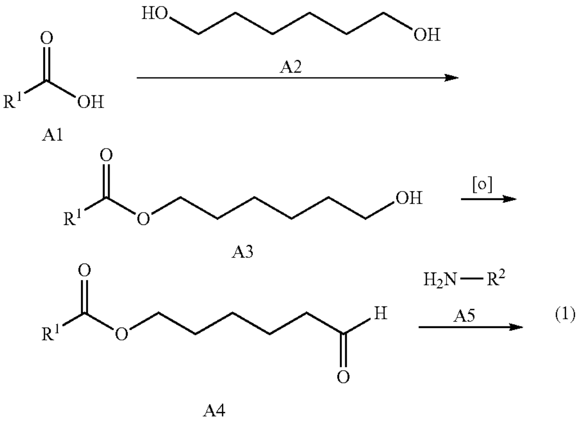

A1 are purchased or prepared according to methods known in the art. Reaction of A1 with diol A2under appropriate condensation conditions (e.g., DCC) yields ester/alcohol A3, which can then be oxidized (e.g., with PCC) to aldehyde A4. Reaction of A4 with amine A5 under reductive amination conditions yields a compound of Formula (1).

The following reaction scheme illustrates a second exemplary method to make compounds of Formula (1), wherein $R_1$ and $R_3$ are the same:

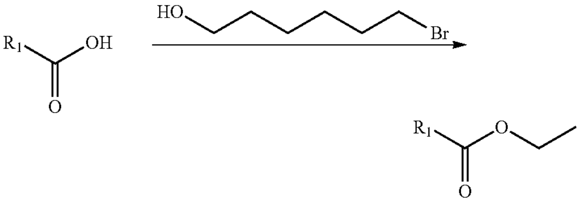

Modifications to the above reaction scheme, such as using protecting groups, may yield compounds wherein $R_1$ and $R_3$ are different. The use of protecting groups, as well as other modification methods, to the above reaction scheme will be readily apparent to one of ordinary skill in the art.

It is understood that one skilled in the art may be able to make these compounds by similar methods or by combining other methods known to one skilled in the art. It is also understood that one skilled in the art would be able to make other compounds of Formula (1) not specifically illustrated herein by using the appropriate starting materials and modifying the parameters of the synthesis. In general, starting materials may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention.

In some embodiments, an ionizable lipid is a compound of Formula (2):

Formula (2)

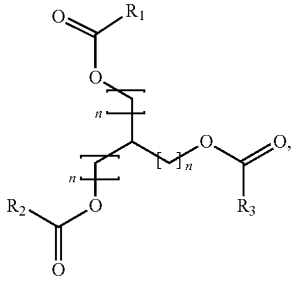

wherein each n is independently 1, 2, 3, 4, 5, 6, 7, 8, 9, 10, 11, 12, 13, 14, or 15.

In some embodiments, as used in Formula (2), $R_1$ and $R_2$ are as defined in Formula (1).

In some embodiments, as used in Formula (2), $R_1$ and $R_2$ are each independently selected from a group consisting of:

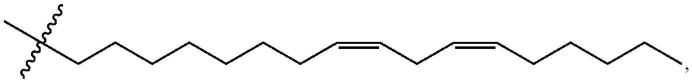
,
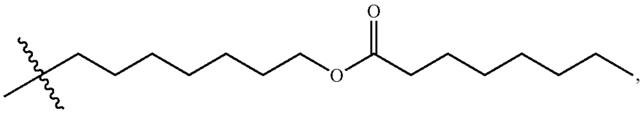
,
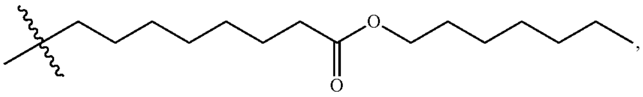
,
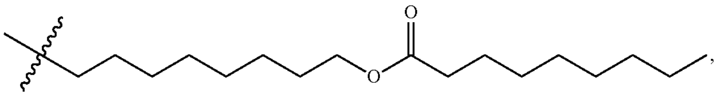
,
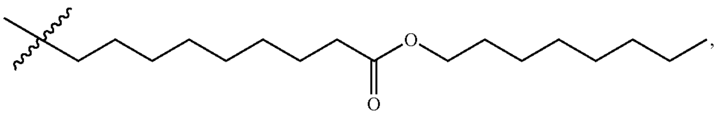
,
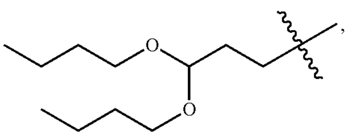
,
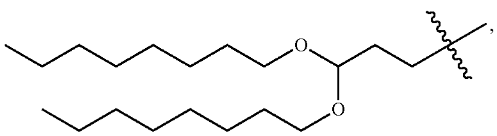
,
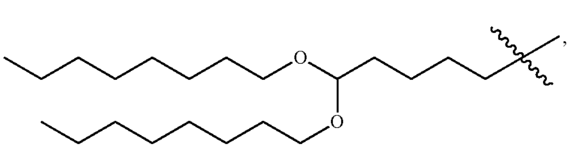
,
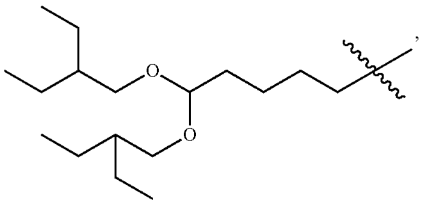
, -continued
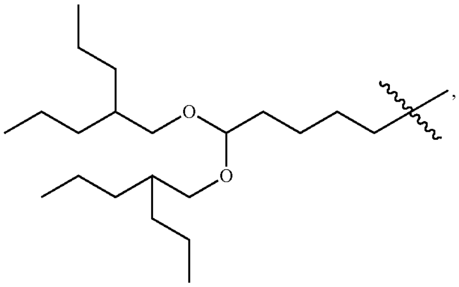,
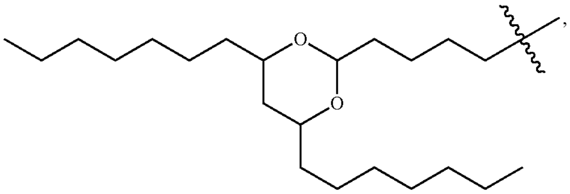,
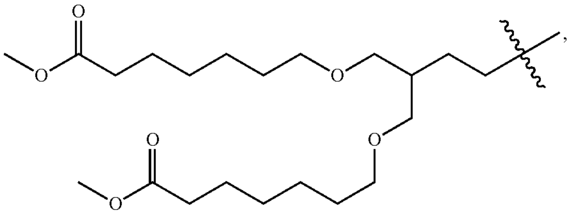,
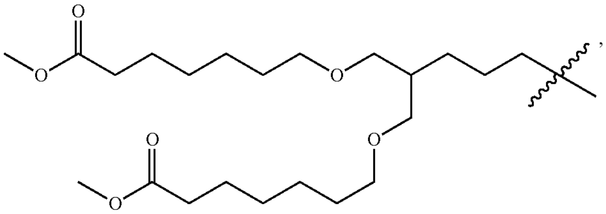,
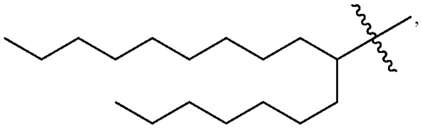,
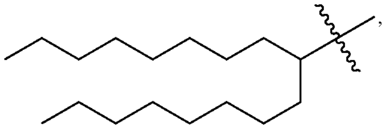,
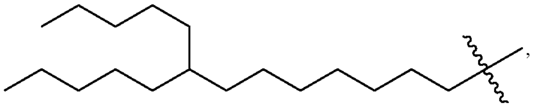,
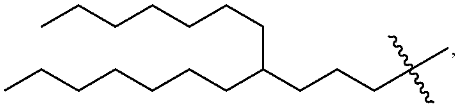,
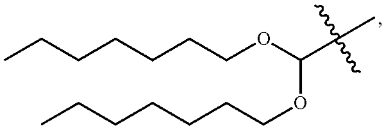,
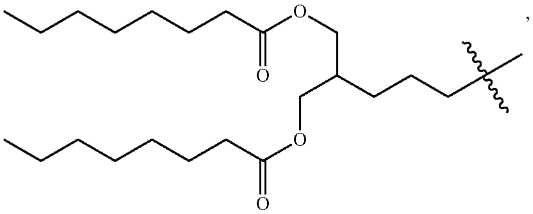,
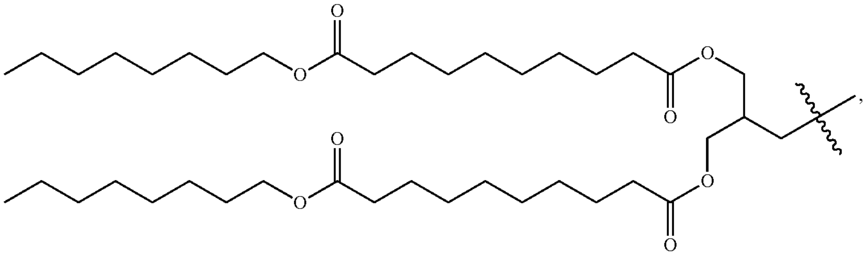,
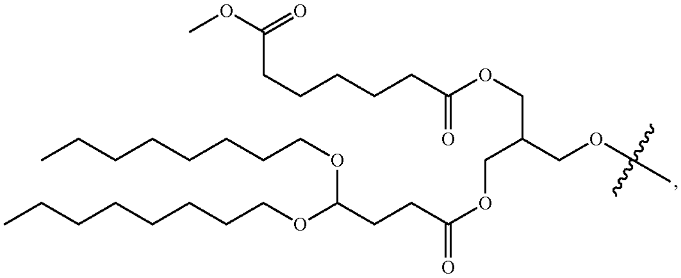,
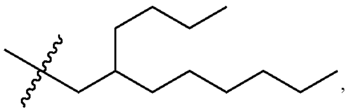,
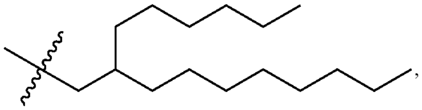,
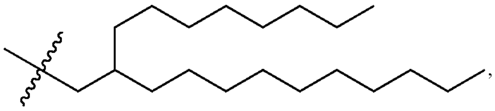, -continued

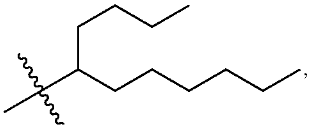,
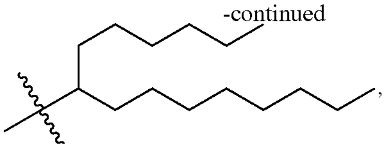,
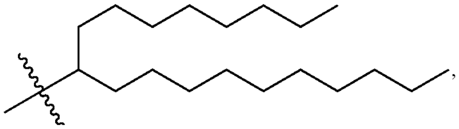,
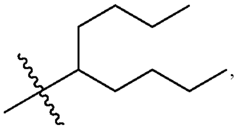,
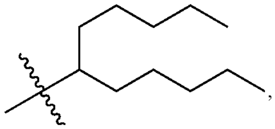,
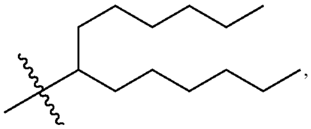, and
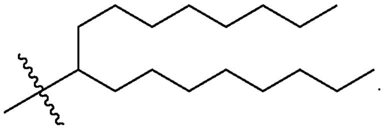.

In some embodiments, $R_1$ and/or $R_2$ as used in Formula (2) may be as described in International Pat. Pub. No. WO2015/095340 A 1, which is incorporated herein by reference in its entirety. In some embodiments, $R_1$ as used in Formula (2) may be as described in International Pat. Pub. No. WO2019/152557 A 1, which is incorporated herein by reference in its entirety.

In some embodiments, as used in Formula (2), $R_3$ is selected from a group consisting of:

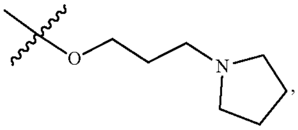,

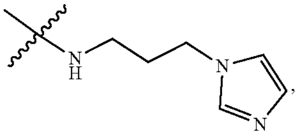,

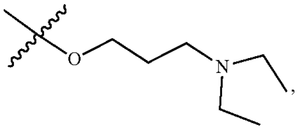,

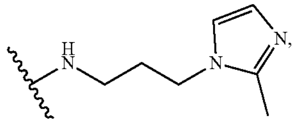,

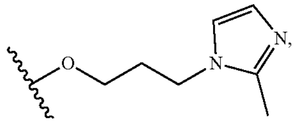,

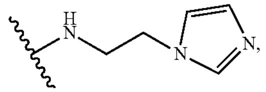,
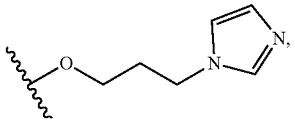,

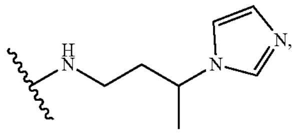

-continued

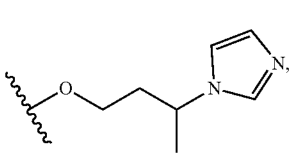,
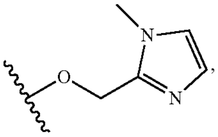,

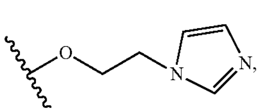, and
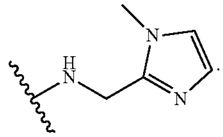.

In some embodiments, an ionizable lipid is a compound of Formula (3)

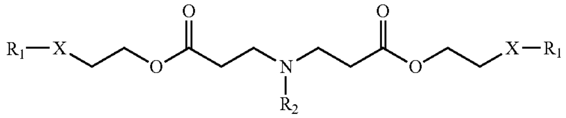

wherein X is selected from —O—, —S—, or —OC(O)—*, wherein * indicates the attachment point to $R_1$.

In some embodiments, an ionizable lipid is a compound of Formula (3-1): (3-1).

(3-1)

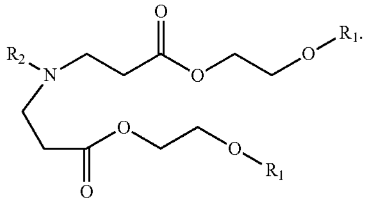

In some embodiments, an ionizable lipid is a compound of Formula (3-2):

(3-2)

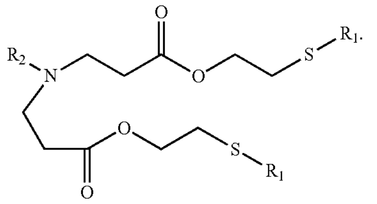

In some embodiments, an ionizable lipid is a compound of Formula (3-3):

(3-3)

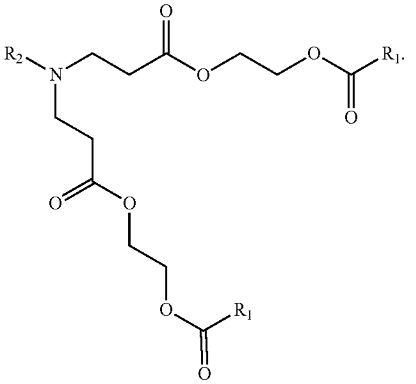

In some embodiments, as used in Formula (3-1), (3-2), or (3-3), each $R_1$ is independently a branched saturated $C_9$-$C_{2M}$ alkyl. In some embodiments, each $R_1$ is independently selected from a group consisting of:

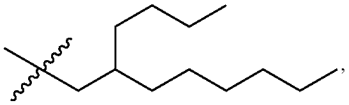,

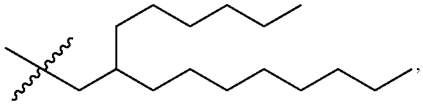,

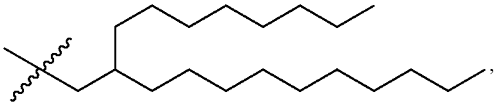,

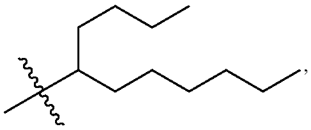,

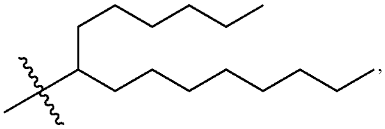,

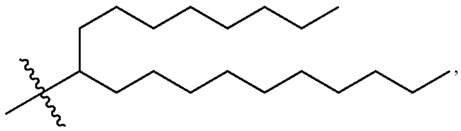,

-continued

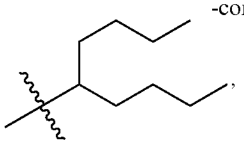,

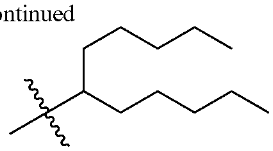,

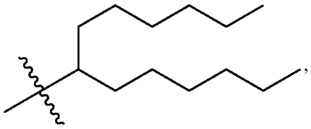, and

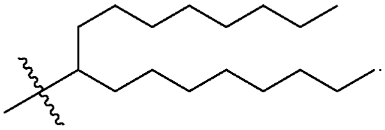.

In some embodiments, each $R_1$ in Formula (3-1), (3-2), or (3-3) are the same.

In some embodiments, as used in Formula (3-1), (3-2), or (3-3), $R_2$ is selected from a group consisting of:

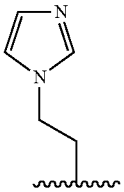,

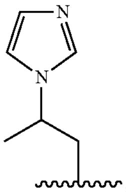,

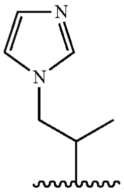,

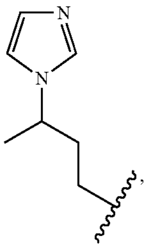,

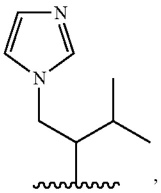,

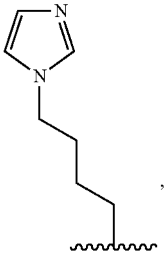,

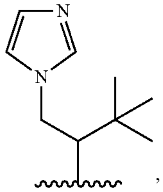,

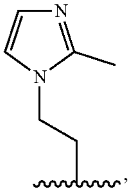,

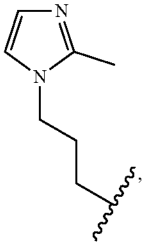,

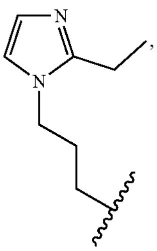,

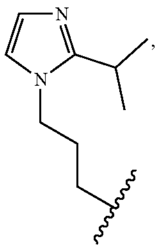,

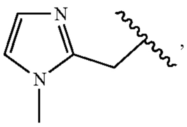,

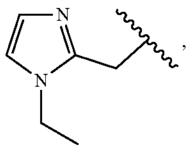,

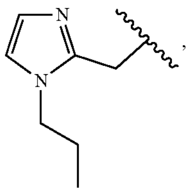,

-continued

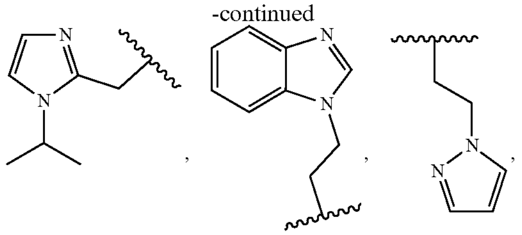

and

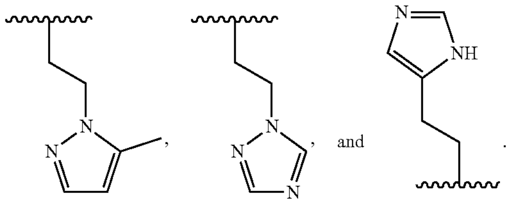

In some embodiments, $R^2$ as used in Formula (3-1), (3-2), or (3-3) may be as described in International Pat. Pub. No. WO2019/152848A1, which is incorporated herein by reference in its entirety.

In some embodiments, an ionizable lipid is a compound of Formula (5):

(5)

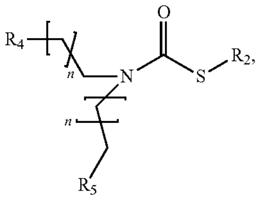

wherein:

each n is independently 1, 2, 3, 4, 5, 6, 7, 8, 9, 10, 11, 12, 13, 14, or 15; and $R_2$ is as defined in Formula (1).

In some embodiments, as used in Formula (5), $R_4$ and $R_5$ are defined as $R_1$ and $R_3$, respectively, in Formula (1). In some embodiments, as used in Formula (5), $R_4$ and $R_5$ may be as described in International Pat. Pub. No. WO2019/191780 A1, which is incorporated herein by reference in its entirety.

In some embodiments, an ionizable lipid of the disclosure is selected from Table 10a. In some embodiments, the ionizable lipid is Lipid 26 in Table 10a. In some embodiments, the ionizable lipid is Lipid 27 in Table 10a. In some embodiments, the ionizable lipid is Lipid 53 in Table 10a. In some embodiments, the ionizable lipid is Lipid 54 in Table 10a.

In some embodiments, an ionizable lipid of the disclosure is selected from the group consisting of:

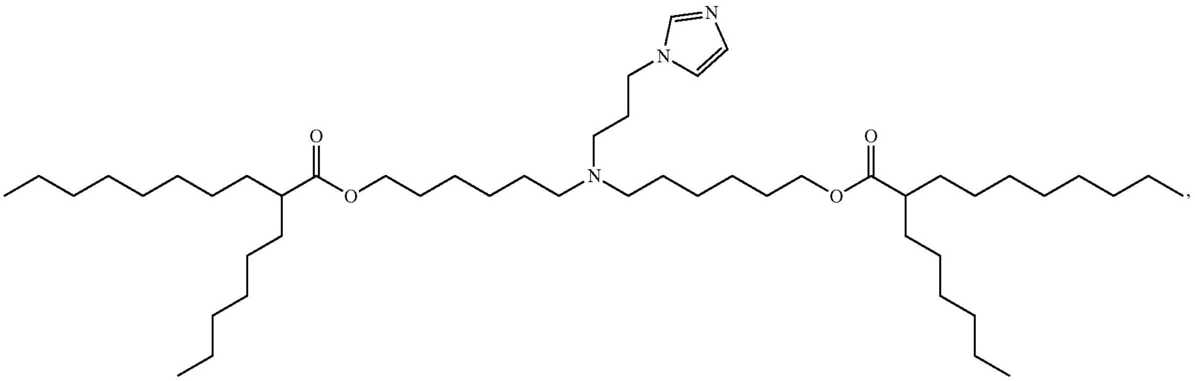

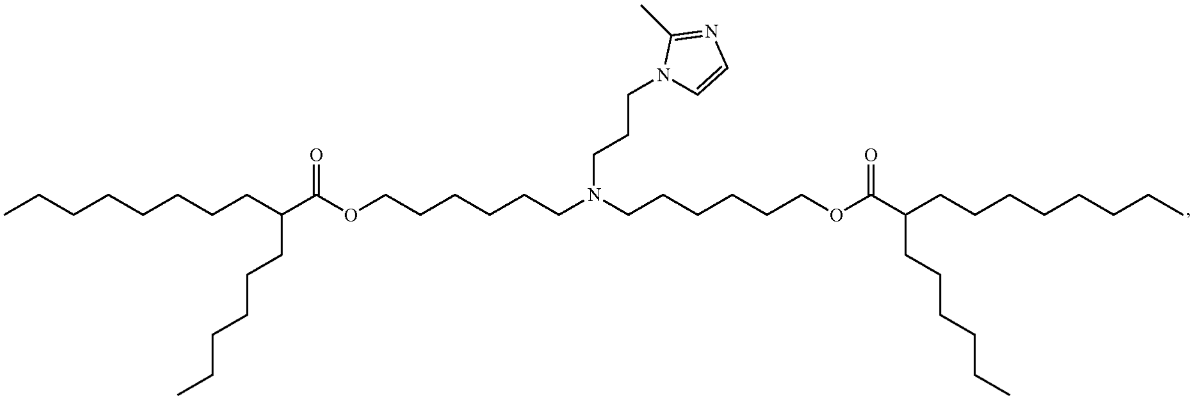

-continued
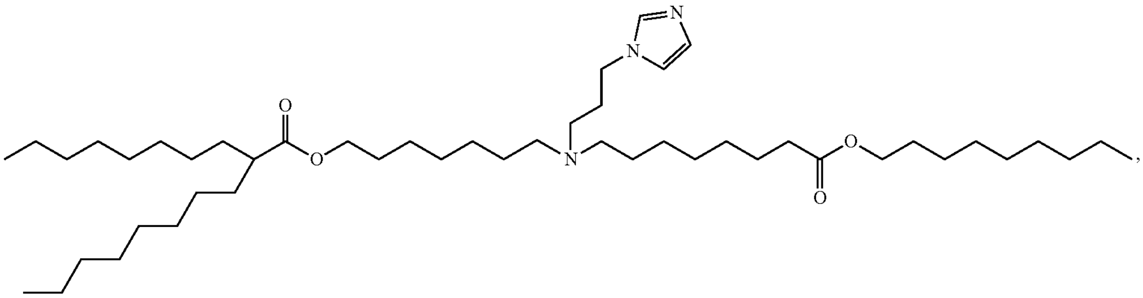
, and
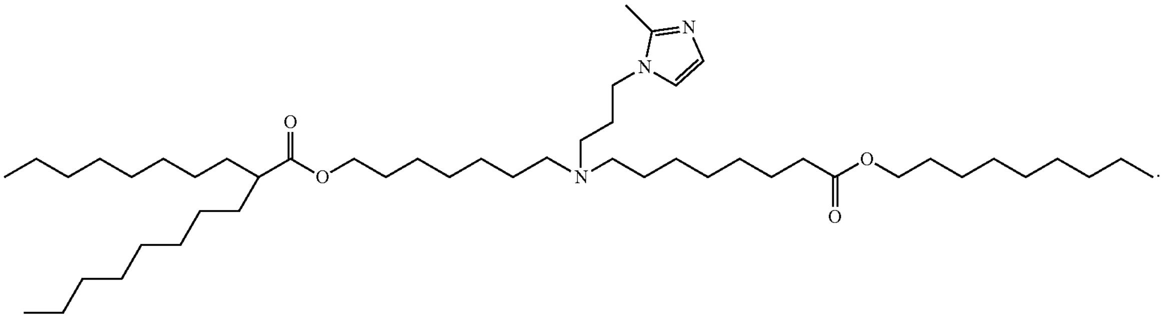
.
TABLE 10a
| Ionizable lipid number | Structure |
|---|---|
| 1 | 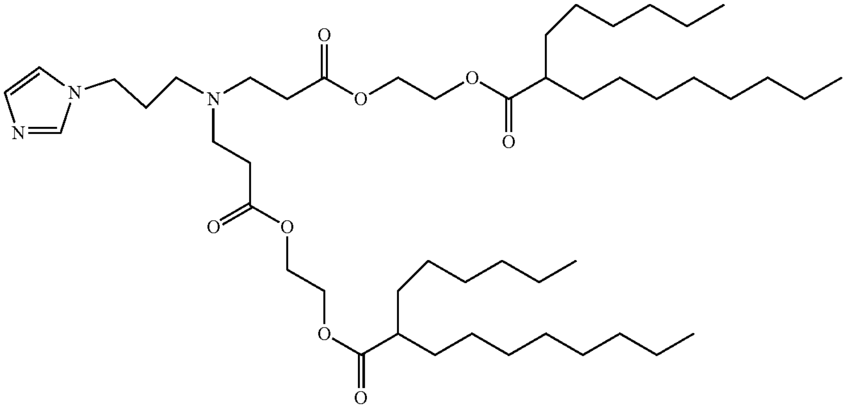 [SMILES: CCCCCCCCC(CCCCCC)C(=O)OCCOC(=O)CCN(CCCn1ccnc1)CCC(=O)OCCOC(=O)C(CCCCCC)CCCCCCCC] |
| 2 | 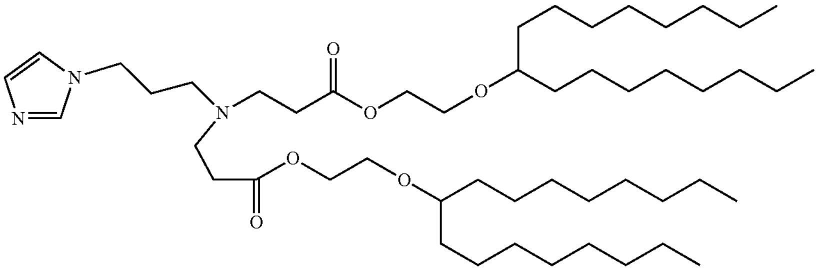 [SMILES: CCCCCCCCC(CCCCCCCC)OCCOC(=O)CCN(CCCn1ccnc1)CCC(=O)OCCOC(CCCCCCCC)CCCCCCCC] |

TABLE 10a-continued
| Ionizable lipid number | Structure |
|---|---|
| 3 | 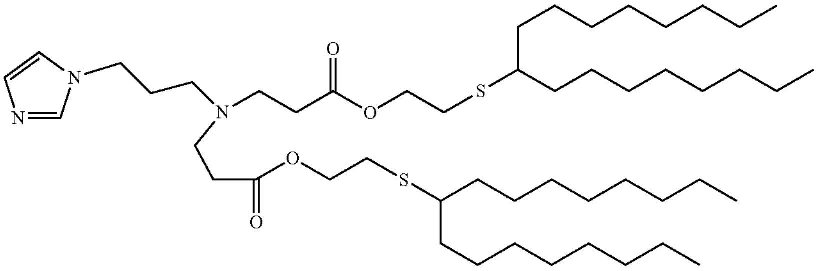 [SMILES: CCCCCCCCC(CCCCCCCC)SCCOC(=O)CCN(CCCn1ccnc1)CCC(=O)OCCSC(CCCCCCCC)CCCCCCCC] |
| 4 | 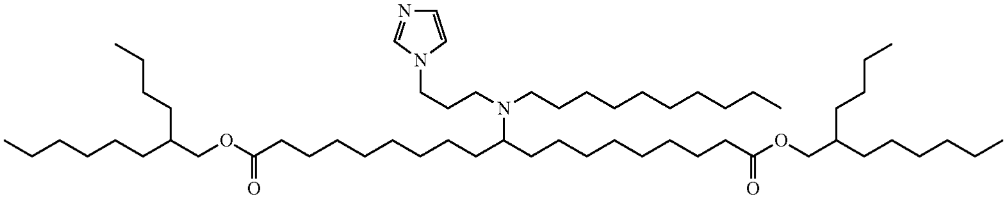 [SMILES: CCCCCCCCCCN(CCCn1ccnc1)C(CCCCCCCCC(=O)OCC(CCCC)CCCCCC)CCCCCCCCC(=O)OCC(CCCC)CCCCCC] |
| 5 | 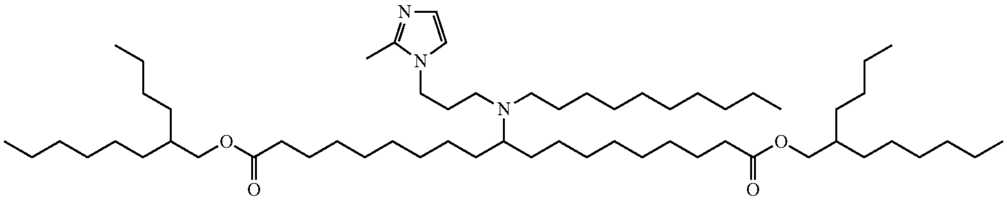 [SMILES: CCCCCCCCCCN(CCCn1ccnc1C)C(CCCCCCCCC(=O)OCC(CCCC)CCCCCC)CCCCCCCCC(=O)OCC(CCCC)CCCCCC] |
| 6 | 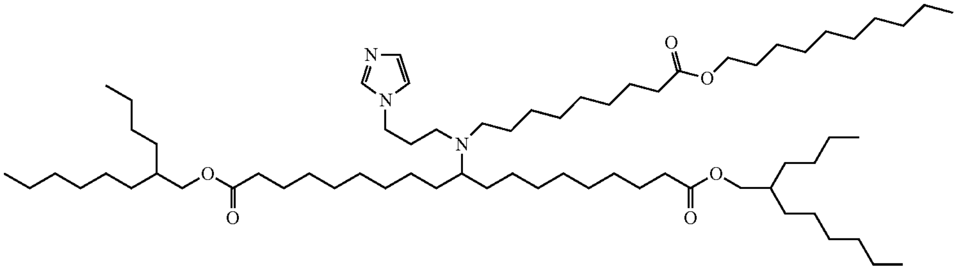 [SMILES: CCCCCCCCCCOC(=O)CCCCCCCCN(CCCn1ccnc1)C(CCCCCCCCC(=O)OCC(CCCC)CCCCCC)CCCCCCCCC(=O)OCC(CCCC)CCCCCC] |
| 7 | 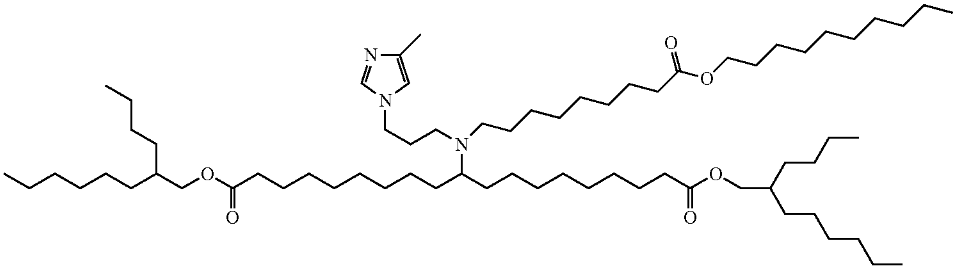 [SMILES: CCCCCCCCCCOC(=O)CCCCCCCCN(CCCn1cnc(C)c1)C(CCCCCCCCC(=O)OCC(CCCC)CCCCCC)CCCCCCCCC(=O)OCC(CCCC)CCCCCC] |
| 8 | 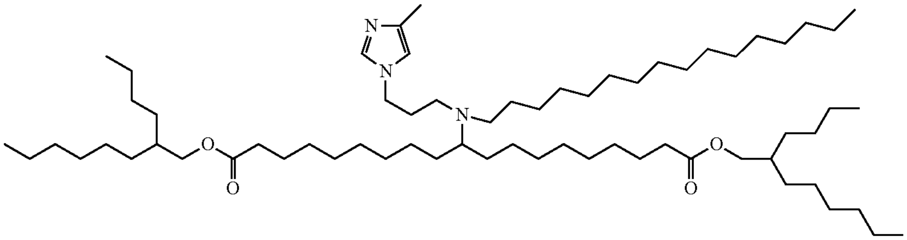 [SMILES: CCCCCCCCCCCCCCCCN(CCCn1cnc(C)c1)C(CCCCCCCCC(=O)OCC(CCCC)CCCCCC)CCCCCCCCC(=O)OCC(CCCC)CCCCCC] |

TABLE 10a-continued
| Ionizable lipid number | Structure |
|---|---|
| 9 | 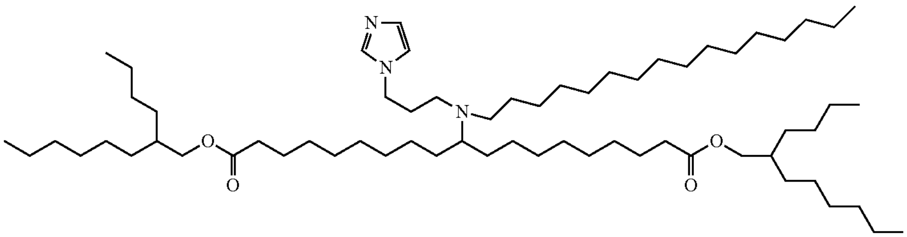 [SMILES: CCCCCCCCCCCCCCCCN(CCCn1ccnc1)C(CCCCCCCCC(=O)OCC(CCCC)CCCCCC)CCCCCCCCC(=O)OCC(CCCC)CCCCCC] |
| 10 | 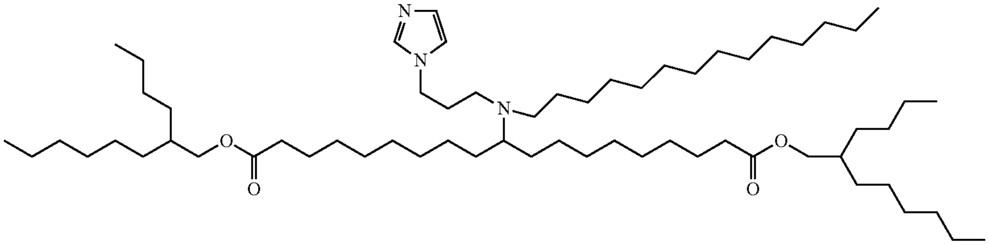 [SMILES: CCCCCCCCCCCCCCN(CCCn1ccnc1)C(CCCCCCCCC(=O)OCC(CCCC)CCCCCC)CCCCCCCCC(=O)OCC(CCCC)CCCCCC] |
| 11 | 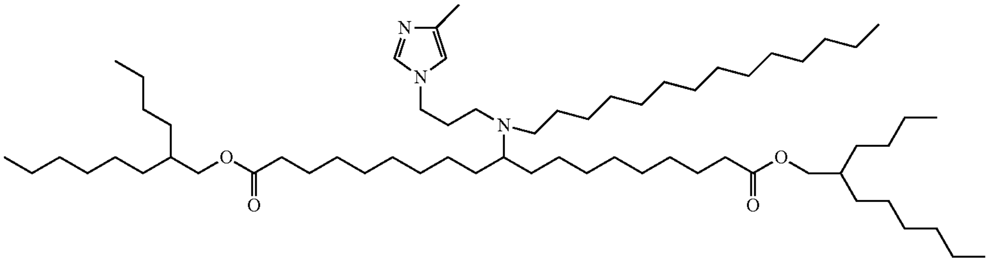 [SMILES: CCCCCCCCCCCCCCN(CCCn1cnc(C)c1)C(CCCCCCCCC(=O)OCC(CCCC)CCCCCC)CCCCCCCCC(=O)OCC(CCCC)CCCCCC] |
| 12 | 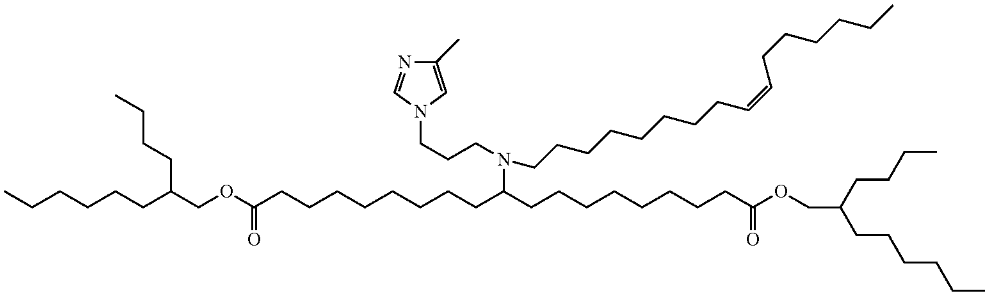 [SMILES: CCCCCC/C=C\CCCCCCCCN(CCCn1cnc(C)c1)C(CCCCCCCCC(=O)OCC(CCCC)CCCCCC)CCCCCCCCC(=O)OCC(CCCC)CCCCCC] |
| 13 | 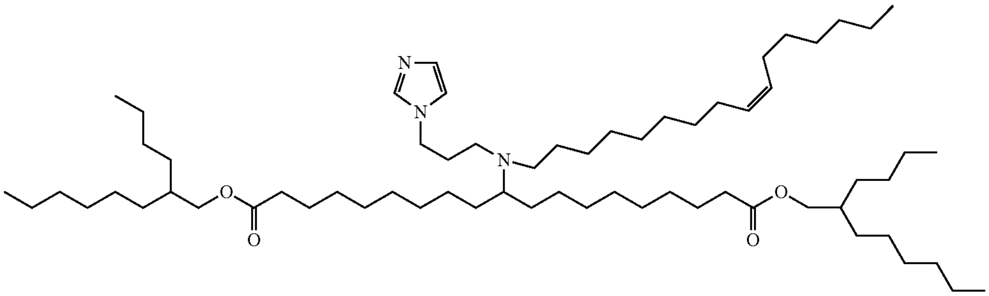 [SMILES: CCCCCC/C=C\CCCCCCCCN(CCCn1ccnc1)C(CCCCCCCCC(=O)OCC(CCCC)CCCCCC)CCCCCCCCC(=O)OCC(CCCC)CCCCCC] |

TABLE 10a-continued
| Ionizable lipid number | Structure |
|---|---|
| 14 | 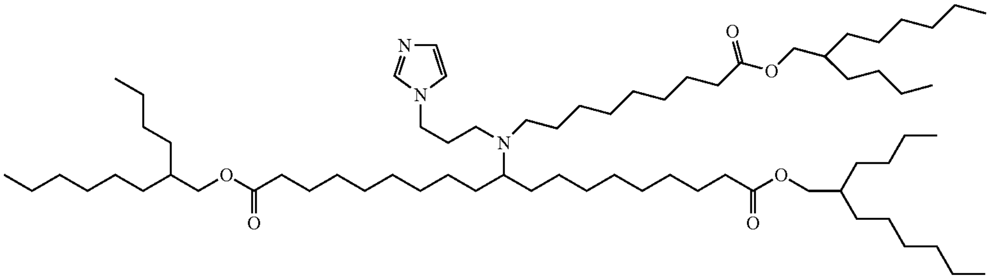 [SMILES: CCCCCCC(CCCC)COC(=O)CCCCCCCCC(CCCCCCCCC(=O)OCC(CCCC)CCCCCC)N(CCCCCCCCC(=O)OCC(CCCC)CCCCCC)CCCn1ccnc1] |
| 15 | 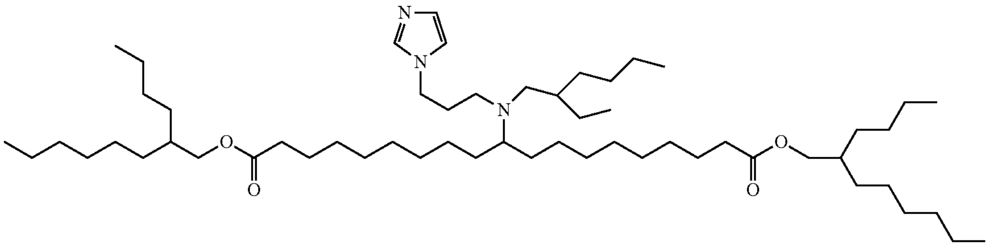 [SMILES: CCCCCCC(CCCC)COC(=O)CCCCCCCCC(CCCCCCCCC(=O)OCC(CCCC)CCCCCC)N(CCCn1ccnc1)CC(CC)CCCC] |
| 16 | 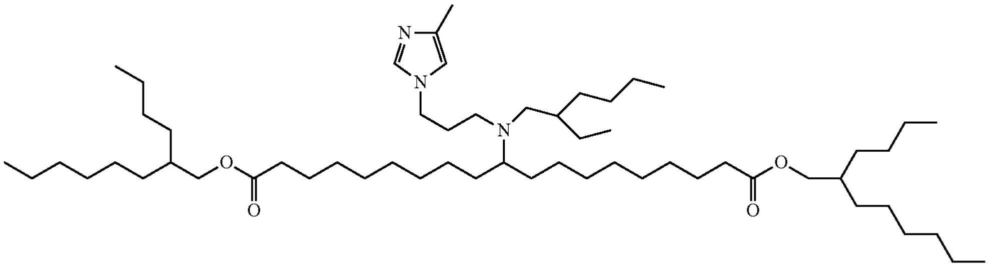 [SMILES: CCCCCCC(CCCC)COC(=O)CCCCCCCCC(CCCCCCCCC(=O)OCC(CCCC)CCCCCC)N(CCCn1cnc(C)c1)CC(CC)CCCC] |
| 17 | 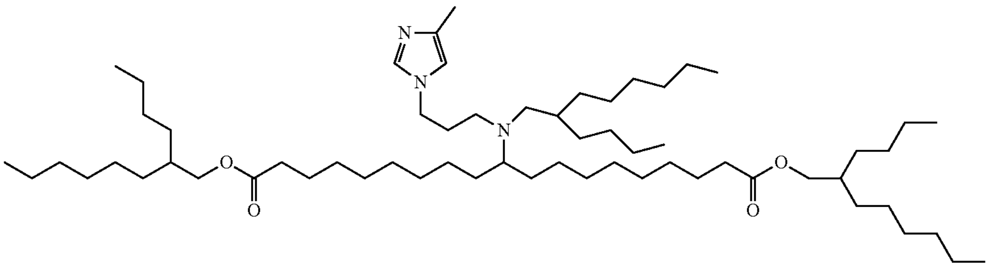 [SMILES: CCCCCCC(CCCC)COC(=O)CCCCCCCCC(CCCCCCCCC(=O)OCC(CCCC)CCCCCC)N(CCCn1cnc(C)c1)CC(CCCC)CCCCCC] |
| 18 | 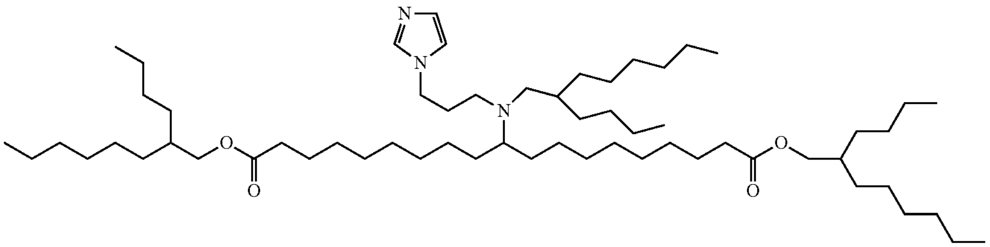 [SMILES: CCCCCCC(CCCC)COC(=O)CCCCCCCCC(CCCCCCCCC(=O)OCC(CCCC)CCCCCC)N(CCCn1ccnc1)CC(CCCC)CCCCCC] |
| 19 | 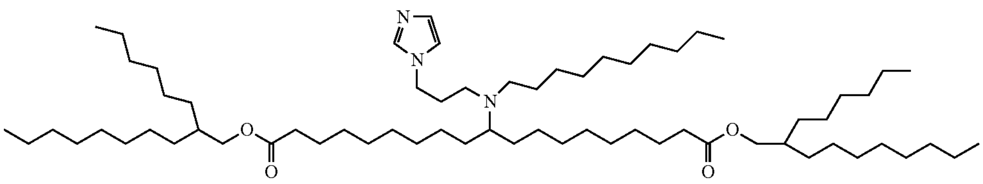 [SMILES: CCCCCCCCCCN(CCCn1ccnc1)C(CCCCCCCCC(=O)OCC(CCCCCC)CCCCCCCC)CCCCCCCCC(=O)OCC(CCCCCC)CCCCCCCC] |

TABLE 10a-continued
| Ionizable lipid number | Structure |
| --- | --- |
| 20 | 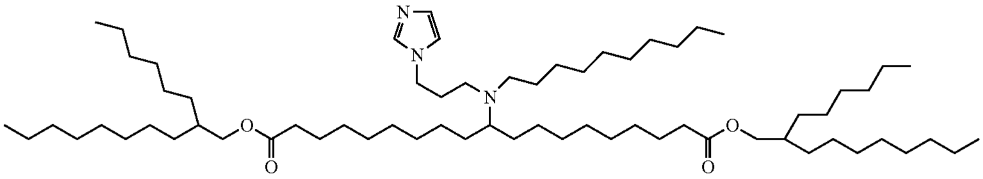 [SMILES: CCCCCCCCCCN(CCCn1ccnc1)C(CCCCCCCCC(=O)OCC(CCCCCC)CCCCCCCC)CCCCCCCCC(=O)OCC(CCCCCC)CCCCCCCC] |
| 21 | 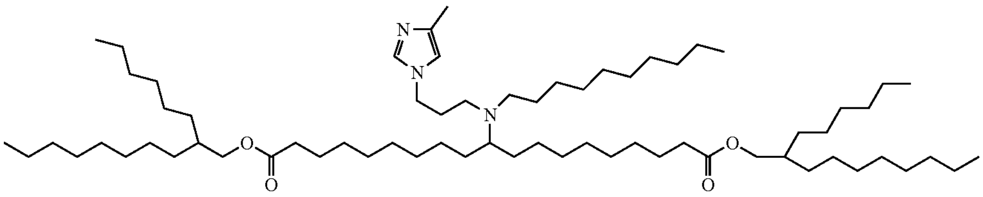 [SMILES: CCCCCCCCCCN(CCCn1cnc(C)c1)C(CCCCCCCCC(=O)OCC(CCCCCC)CCCCCCCC)CCCCCCCCC(=O)OCC(CCCCCC)CCCCCCCC] |
| 22 | 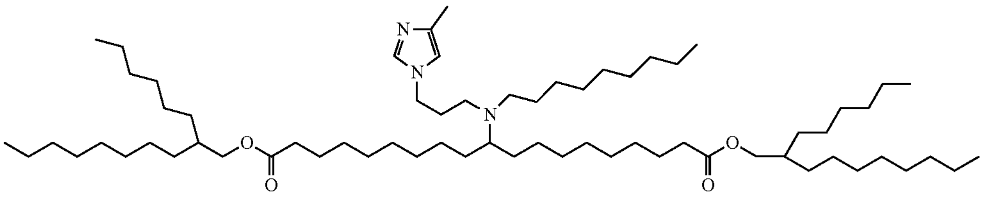 [SMILES: CCCCCCCCCN(CCCn1cnc(C)c1)C(CCCCCCCCC(=O)OCC(CCCCCC)CCCCCCCC)CCCCCCCCC(=O)OCC(CCCCCC)CCCCCCCC] |
| 23 | 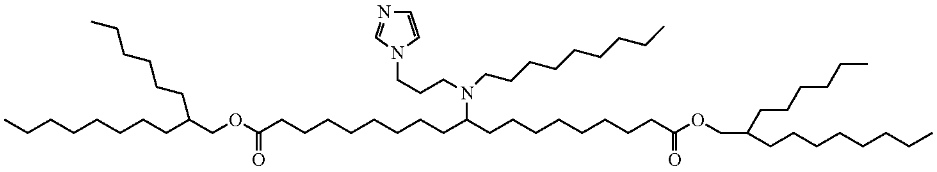 [SMILES: CCCCCCCCCN(CCCn1ccnc1)C(CCCCCCCCC(=O)OCC(CCCCCC)CCCCCCCC)CCCCCCCCC(=O)OCC(CCCCCC)CCCCCCCC] |
| 24 | 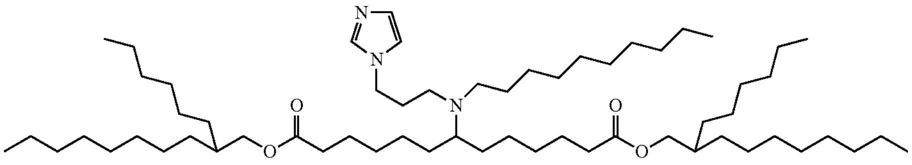 [SMILES: CCCCCCCCCCN(CCCn1ccnc1)C(CCCCCC(=O)OCC(CCCCCC)CCCCCCCC)CCCCCC(=O)OCC(CCCCCC)CCCCCCCC] |
| 25 | 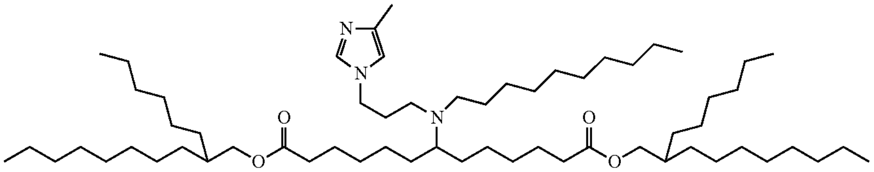 [SMILES: CCCCCCCCCCN(CCCn1cnc(C)c1)C(CCCCCC(=O)OCC(CCCCCC)CCCCCCCC)CCCCCC(=O)OCC(CCCCCC)CCCCCCCC] |
| 26 | 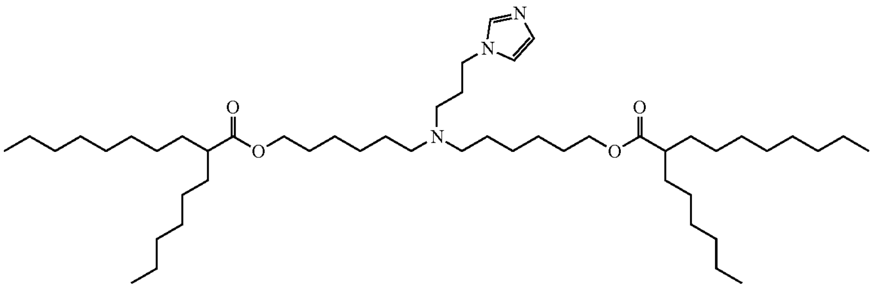 [SMILES: CCCCCCCCC(CCCCCC)C(=O)OCCCCCCN(CCCCCCOC(=O)C(CCCCCC)CCCCCCCC)CCCn1ccnc1] |

TABLE 10a-continued
| Ionizable lipid number | Structure |
|---|---|
| 27 | 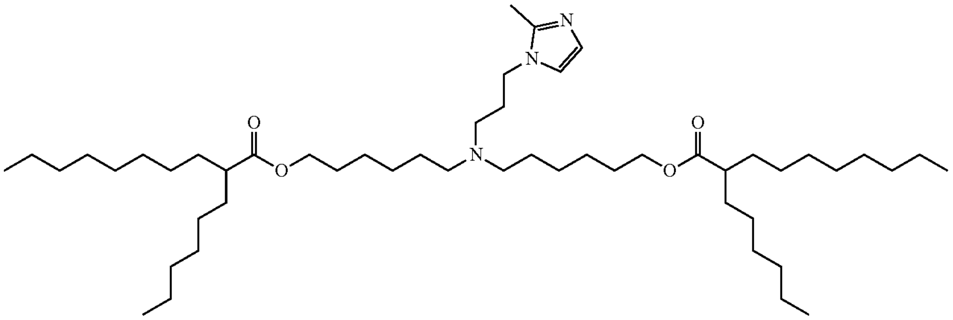 [SMILES: CCCCCCCCC(CCCCCC)C(=O)OCCCCCCN(CCCCCCOC(=O)C(CCCCCC)CCCCCCCC)CCCn1ccnc1C] |
| 28 | 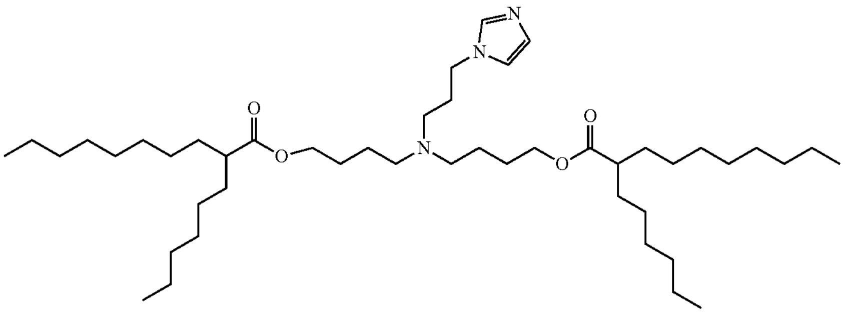 [SMILES: CCCCCCCCC(CCCCCC)C(=O)OCCCCN(CCCCOC(=O)C(CCCCCC)CCCCCCCC)CCCn1ccnc1] |
| 29 | 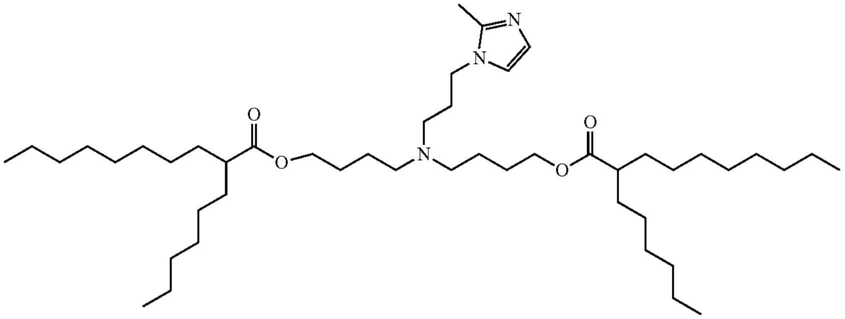 [SMILES: CCCCCCCCC(CCCCCC)C(=O)OCCCCN(CCCCOC(=O)C(CCCCCC)CCCCCCCC)CCCn1ccnc1C] |
| 30 | 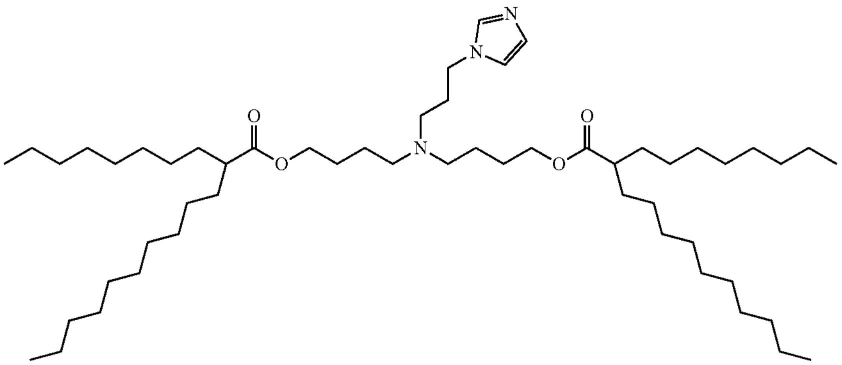 [SMILES: CCCCCCCCCCC(CCCCCCCC)C(=O)OCCCCN(CCCCOC(=O)C(CCCCCCCC)CCCCCCCCCC)CCCn1ccnc1] |

TABLE 10a-continued
| Ionizable lipid number | Structure |
|---|---|
| 31 | 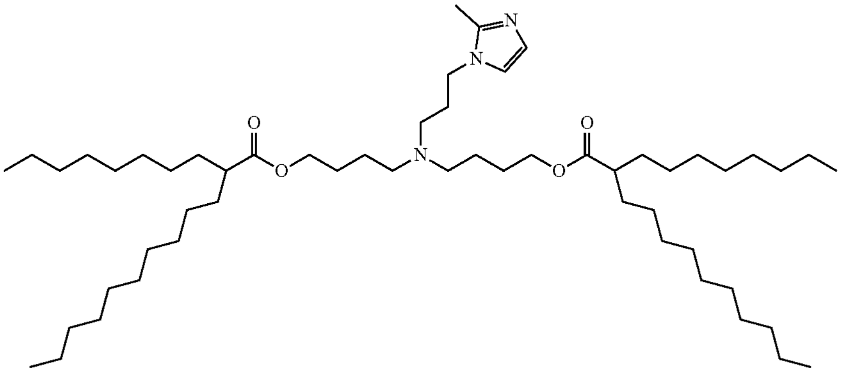 [SMILES: CCCCCCCCCCC(CCCCCCCC)C(=O)OCCCCN(CCCCOC(=O)C(CCCCCCCC)CCCCCCCCCC)CCCn1ccnc1C] |
| 32 | 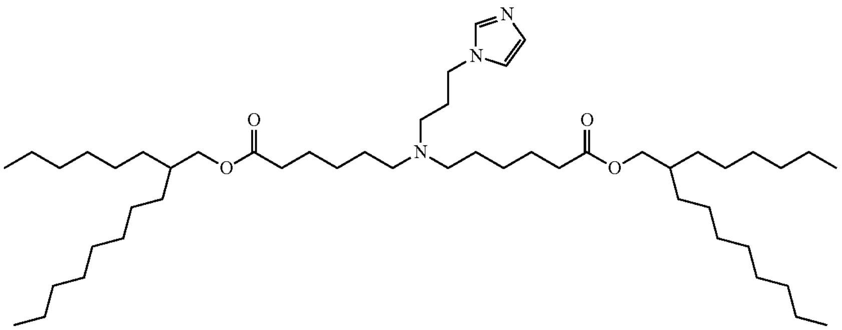 [SMILES: CCCCCCCCC(CCCCCC)COC(=O)CCCCCN(CCCCCC(=O)OCC(CCCCCC)CCCCCCCC)CCCn1ccnc1] |
| 33 | 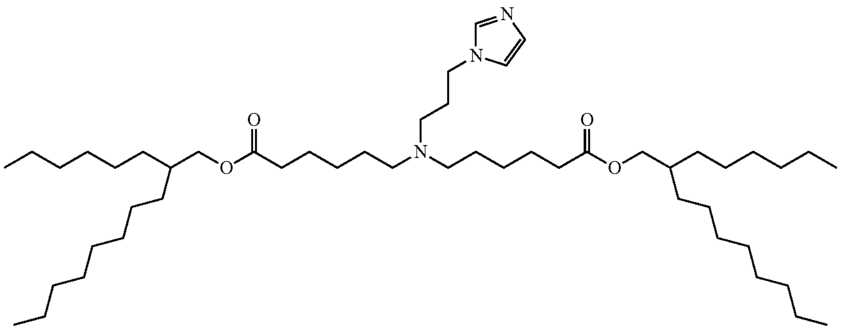 [SMILES: CCCCCCCCC(CCCCCC)COC(=O)CCCCCN(CCCCCC(=O)OCC(CCCCCC)CCCCCCCC)CCCn1ccnc1] |
| 34 | 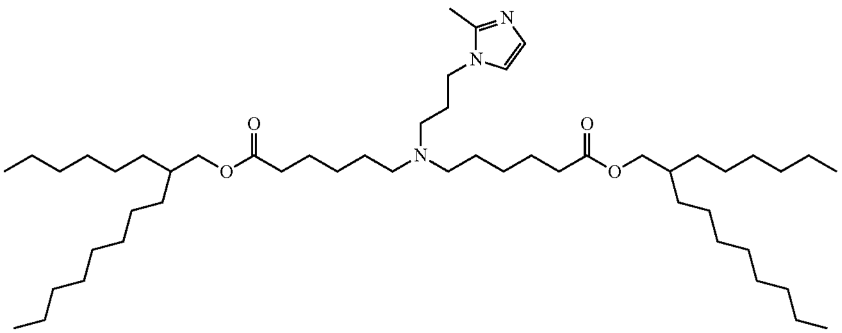 [SMILES: CCCCCCCCC(CCCCCC)COC(=O)CCCCCN(CCCCCC(=O)OCC(CCCCCC)CCCCCCCC)CCCn1ccnc1C] |

TABLE 10a-continued
| Ionizable lipid number | Structure |
| --- | --- |
| 35 | 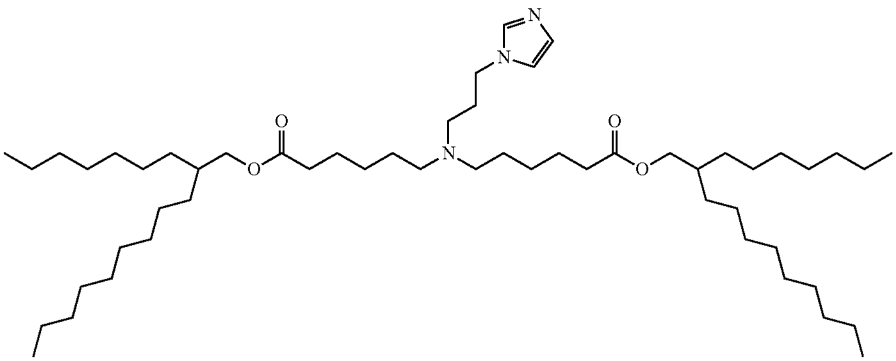 [SMILES: CCCCCCCCCC(CCCCCCC)COC(=O)CCCCCN(CCCCCC(=O)OCC(CCCCCCC)CCCCCCCCC)CCCn1ccnc1] |
| 36 | 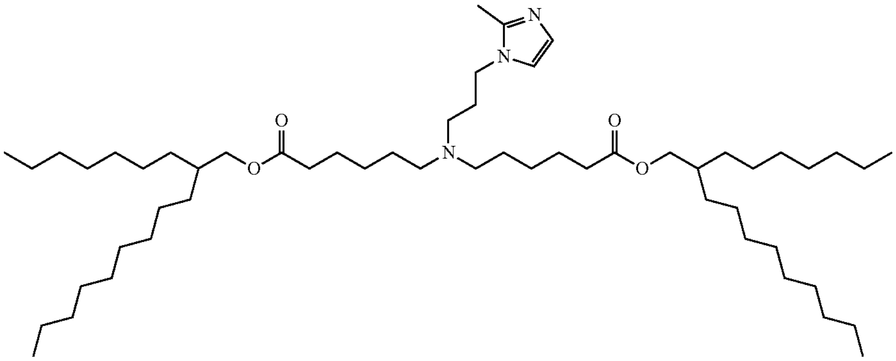 [SMILES: CCCCCCCCCC(CCCCCCC)COC(=O)CCCCCN(CCCCCC(=O)OCC(CCCCCCC)CCCCCCCCC)CCCn1ccnc1C] |
| 37 | 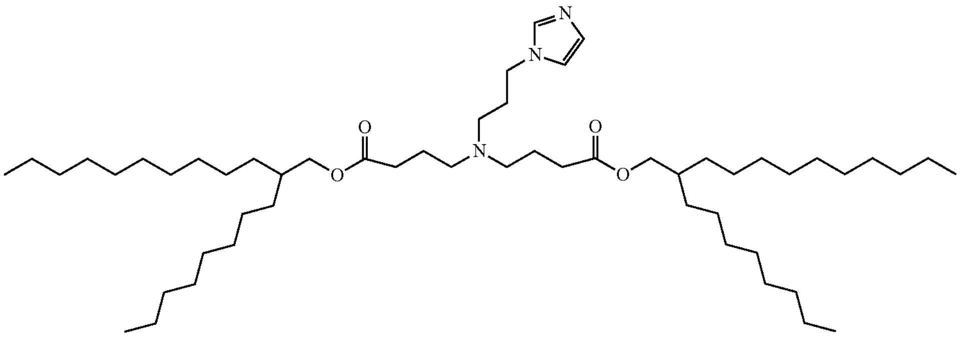 [SMILES: CCCCCCCCCCC(CCCCCCCC)COC(=O)CCCN(CCCC(=O)OCC(CCCCCCCC)CCCCCCCCCC)CCCn1ccnc1] |
| 38 | 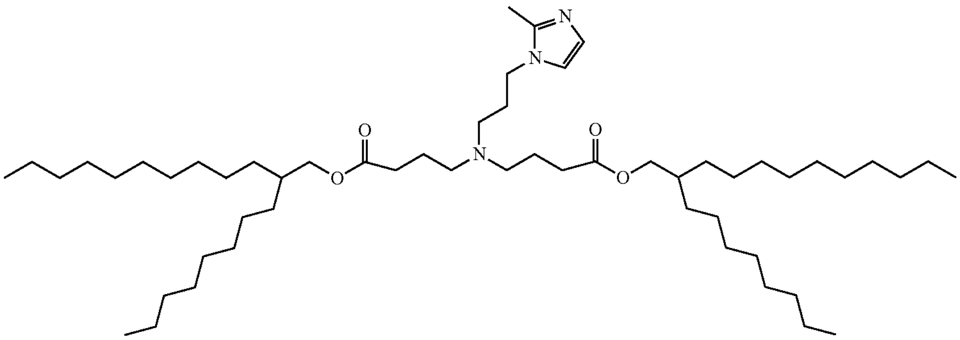 [SMILES: CCCCCCCCCCC(CCCCCCCC)COC(=O)CCCN(CCCC(=O)OCC(CCCCCCCC)CCCCCCCCCC)CCCn1ccnc1C] |

TABLE 10a-continued
| Ionizable lipid number | Structure |
|---|---|
| 39 | 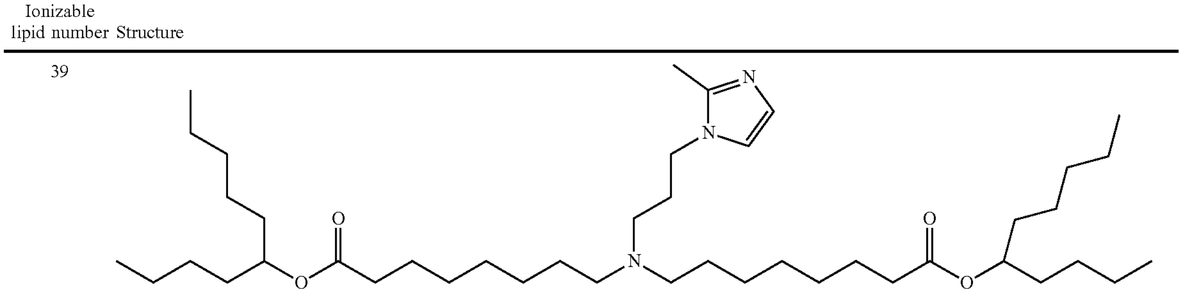 |
| 40 | 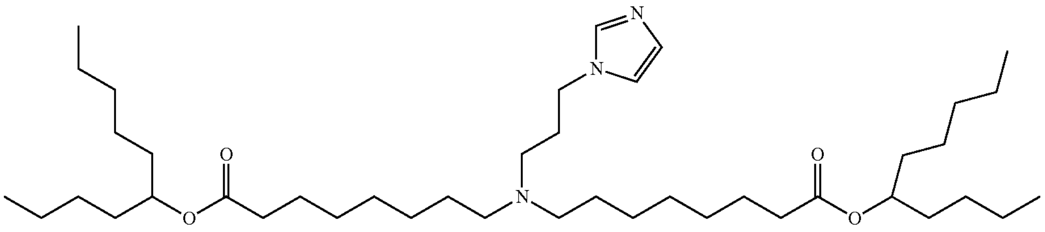 [SMILES: CCCCCC(CCCC)OC(=O)CCCCCCCN(CCCCCCCC(=O)OC(CCCC)CCCCC)CCCn1ccnc1] |
| 41 | 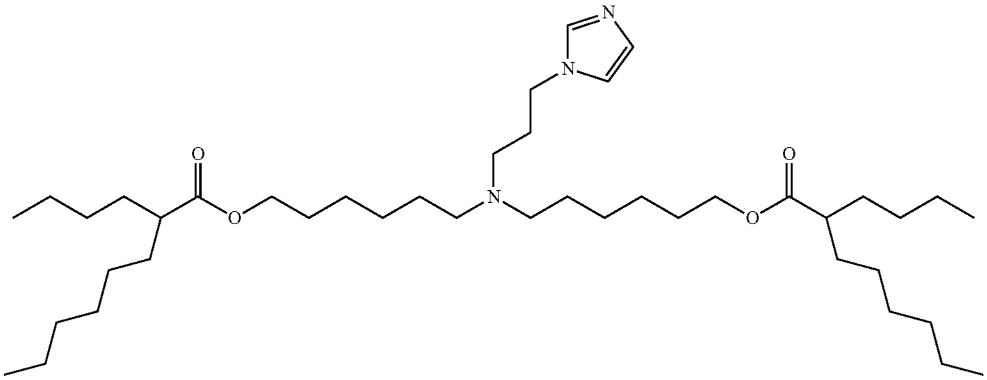 [SMILES: CCCCCCC(CCCC)C(=O)OCCCCCCN(CCCCCCOC(=O)C(CCCC)CCCCCC)CCCn1ccnc1] |
| 42 | 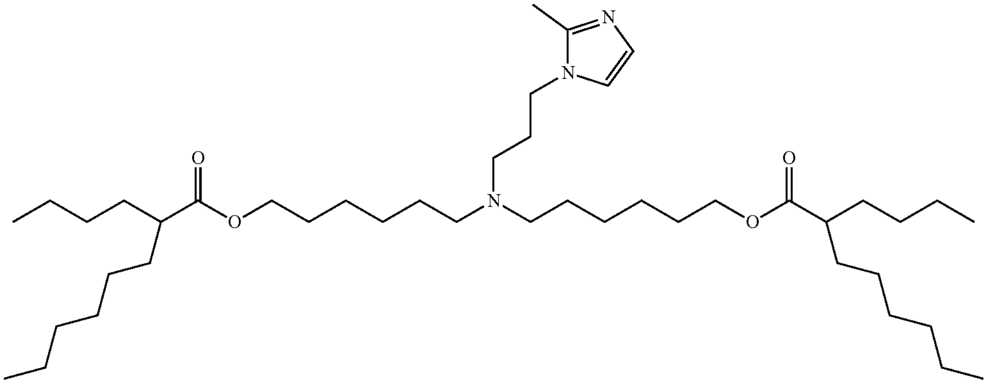 [SMILES: CCCCCCC(CCCC)C(=O)OCCCCCCN(CCCCCCOC(=O)C(CCCC)CCCCCC)CCCn1ccnc1C] |
| 43 | 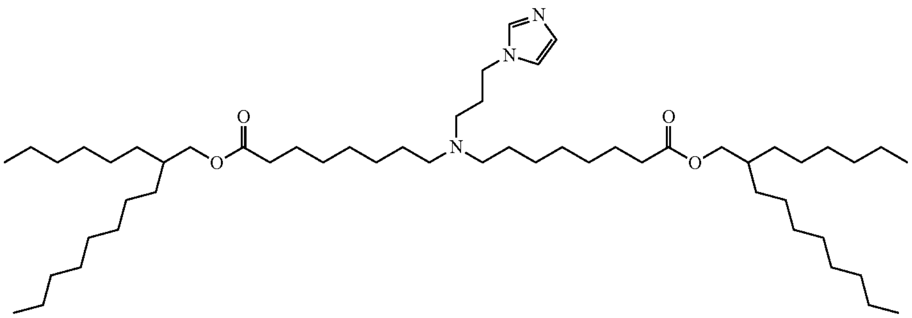 [SMILES: CCCCCCCCC(CCCCCC)COC(=O)CCCCCCCN(CCCCCCCC(=O)OCC(CCCCCC)CCCCCCCC)CCCn1ccnc1] |

TABLE 10a-continued
| Ionizable lipid number | Structure |
|---|---|
| 44 | 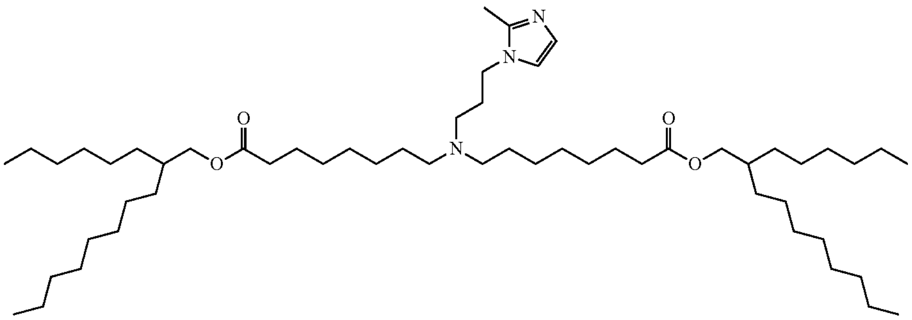 [SMILES: CCCCCCCCC(CCCCCC)COC(=O)CCCCCCCN(CCCCCCCC(=O)OCC(CCCCCC)CCCCCCCC)CCCn1ccnc1C] |
| 45 | 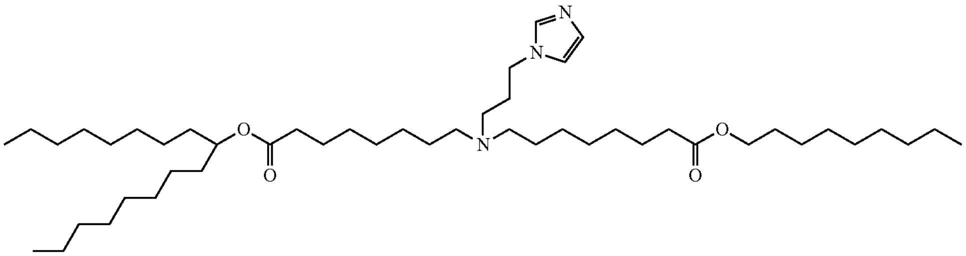 [SMILES: CCCCCCCCCOC(=O)CCCCCCCN(CCCCCCCC(=O)OC(CCCCCCCC)CCCCCCCC)CCCn1ccnc1] |
| 46 | 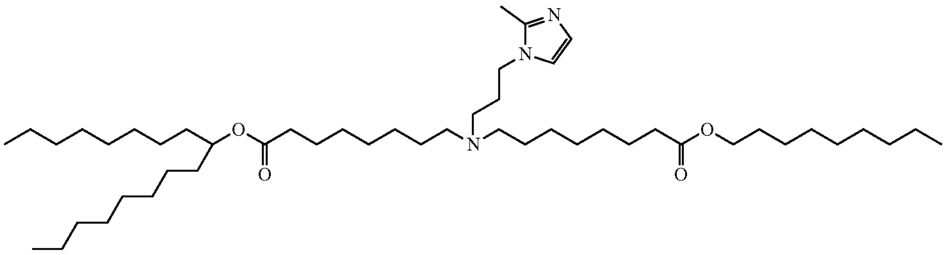 [SMILES: CCCCCCCCCOC(=O)CCCCCCCN(CCCCCCCC(=O)OC(CCCCCCCC)CCCCCCCC)CCCn1ccnc1C] |
| 47 | 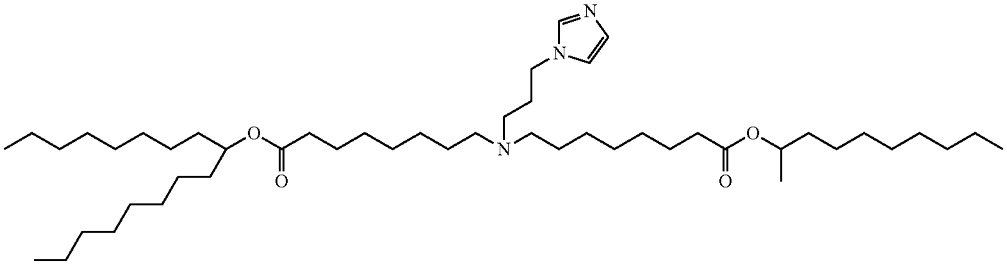 [SMILES: CCCCCCCCC(C)OC(=O)CCCCCCCN(CCCCCCCC(=O)OC(CCCCCCCC)CCCCCCCC)CCCn1ccnc1] |
| 48 | 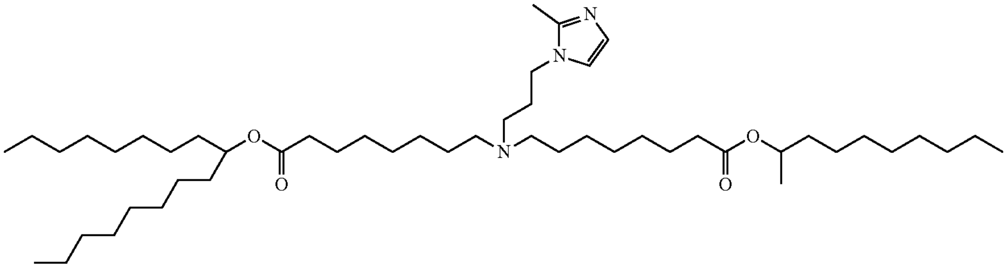 [SMILES: CCCCCCCCC(C)OC(=O)CCCCCCCN(CCCCCCCC(=O)OC(CCCCCCCC)CCCCCCCC)CCCn1ccnc1C] |

TABLE 10a-continued
| Ionizable lipid number | Structure |
|---|---|
| 49 | 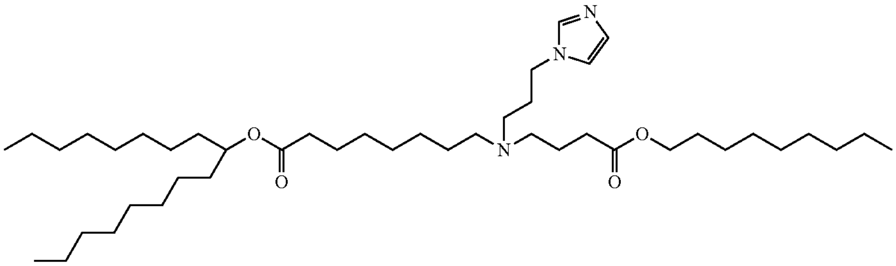 [SMILES: CCCCCCCCCOC(=O)CCCN(CCCCCCCC(=O)OC(CCCCCCCC)CCCCCCCC)CCCn1ccnc1] |
| 50 | 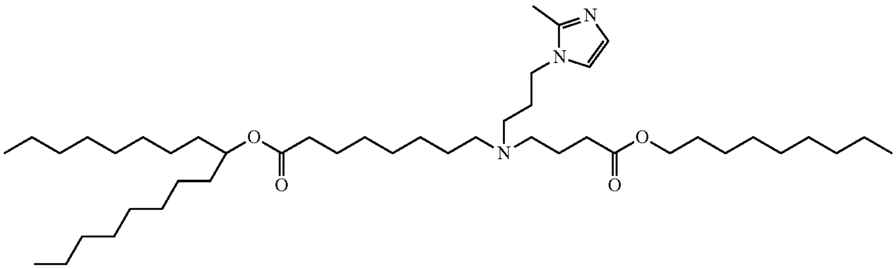 [SMILES: CCCCCCCCCOC(=O)CCCN(CCCCCCCC(=O)OC(CCCCCCCC)CCCCCCCC)CCCn1ccnc1C] |
| 51 | 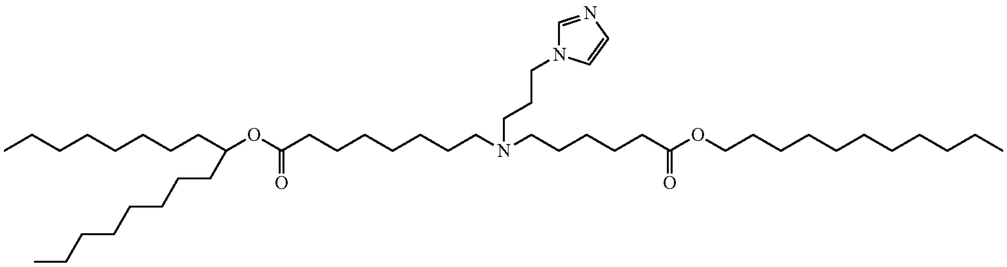 [SMILES: CCCCCCCCCCCOC(=O)CCCCCN(CCCCCCCC(=O)OC(CCCCCCCC)CCCCCCCC)CCCn1ccnc1] |
| 52 | 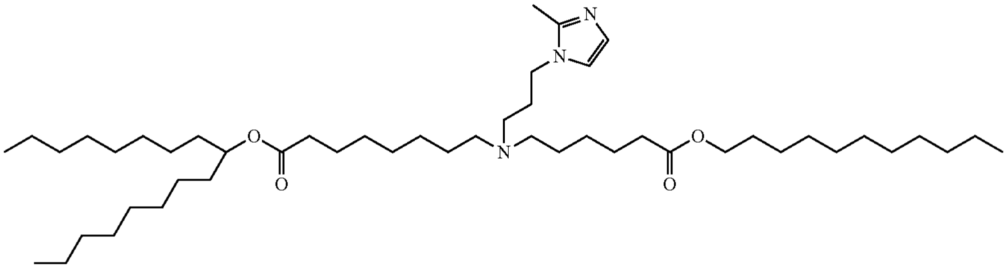 [SMILES: CCCCCCCCCCCOC(=O)CCCCCN(CCCCCCCC(=O)OC(CCCCCCCC)CCCCCCCC)CCCn1ccnc1C] |
| 53 | 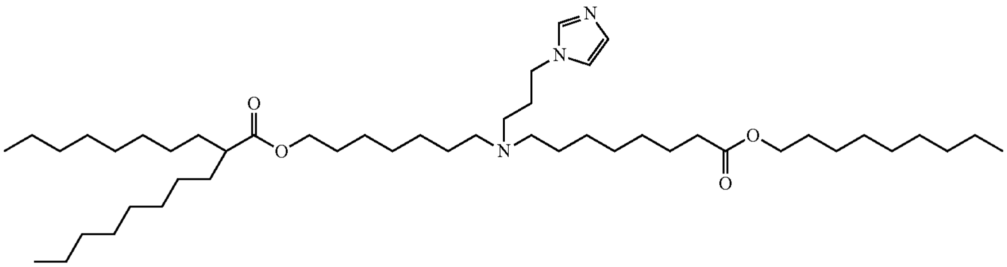 [SMILES: CCCCCCCCCOC(=O)CCCCCCCN(CCCCCCCOC(=O)C(CCCCCCCC)CCCCCCCC)CCCn1ccnc1] |

TABLE 10a-continued
| Ionizable lipid number | Structure |
|---|---|
| 54 | 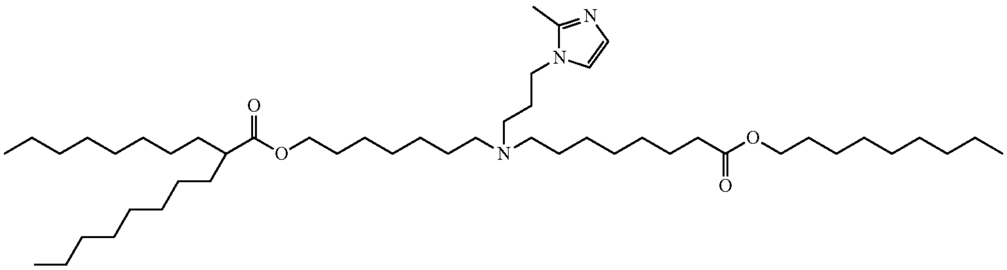 [SMILES: CCCCCCCCCOC(=O)CCCCCCCN(CCCCCCCOC(=O)C(CCCCCCCC)CCCCCCCC)CCCn1ccnc1C] |
| 55 | 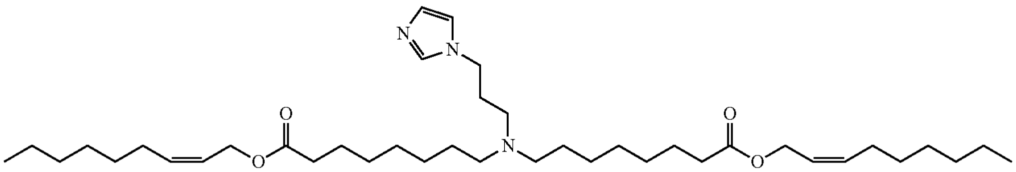 [SMILES: CCCCCC/C=C\COC(=O)CCCCCCCN(CCCCCCCC(=O)OC/C=C\CCCCCC)CCCn1ccnc1] |
| 56 | 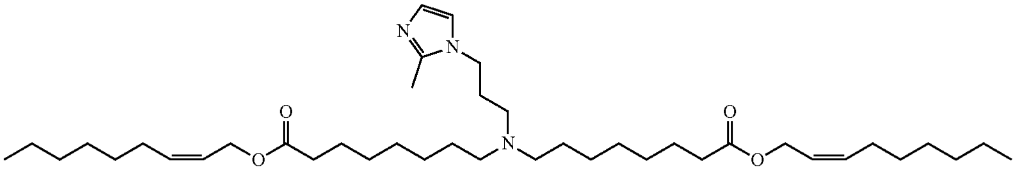 [SMILES: CCCCCC/C=C\COC(=O)CCCCCCCN(CCCCCCCC(=O)OC/C=C\CCCCCC)CCCn1ccnc1C] |
| 57 | 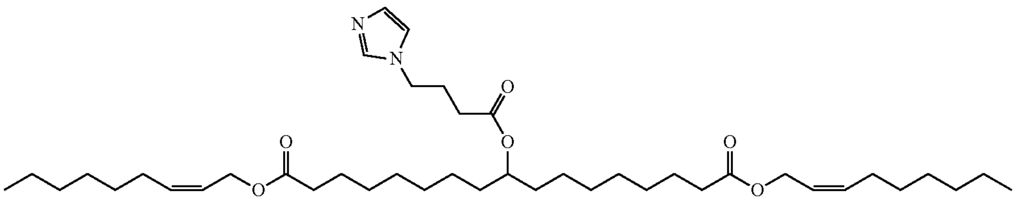 |
| 58 | 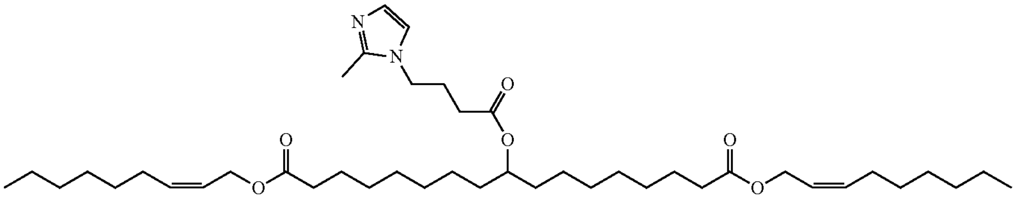 [SMILES: CCCCCC/C=C\COC(=O)CCCCCCCC(CCCCCCCC(=O)OC/C=C\CCCCCC)OC(=O)CCCn1ccnc1] |
| 59 | 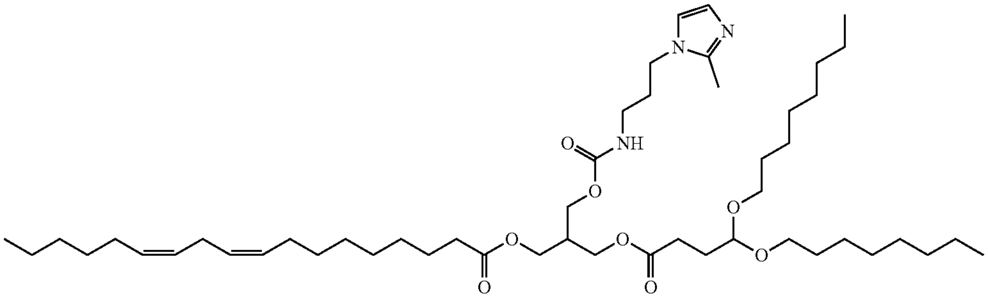 |

TABLE 10a-continued
| Ionizable lipid number | Structure |
|---|---|
| 60 | 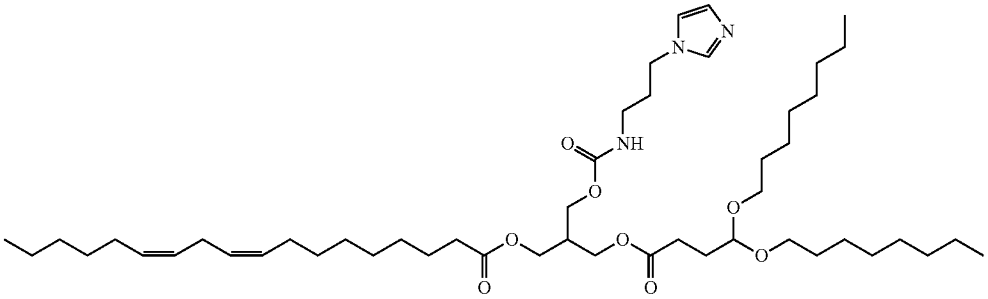 [SMILES: CCCCC/C=C\C/C=C\CCCCCCCC(=O)OCC(COC(=O)CCC(OCCCCCCCC)OCCCCCCCC)COC(=O)NCCCn1ccnc1] |
| 61 | 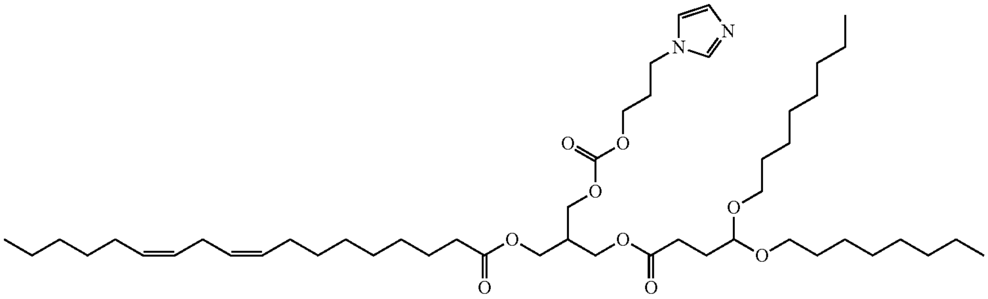 [SMILES: CCCCC/C=C\C/C=C\CCCCCCCC(=O)OCC(COC(=O)CCC(OCCCCCCCC)OCCCCCCCC)COC(=O)OCCCn1ccnc1] |
| 62 | 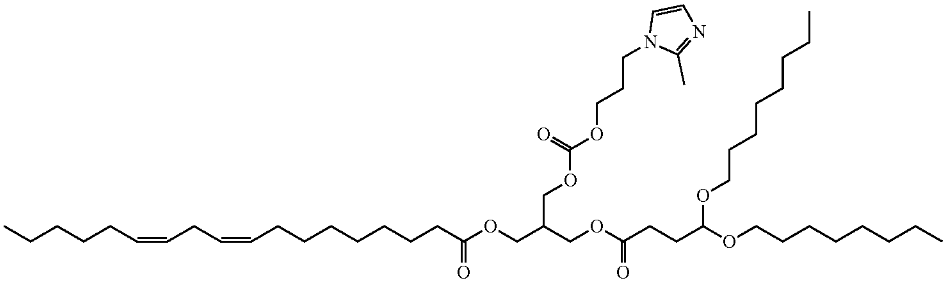 [SMILES: CCCCC/C=C\C/C=C\CCCCCCCC(=O)OCC(COC(=O)CCC(OCCCCCCCC)OCCCCCCCC)COC(=O)OCCCn1ccnc1C] |
| 63 | 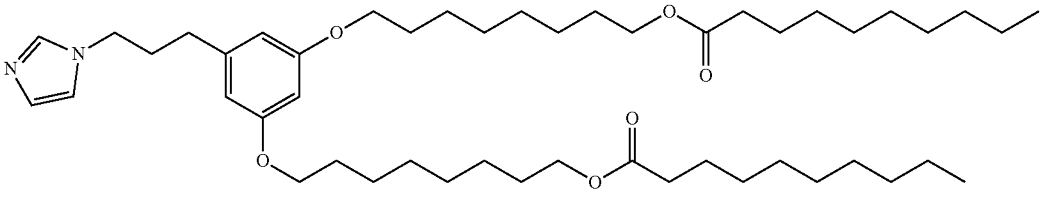 [SMILES: CCCCCCCCCC(=O)OCCCCCCCCOc1cc(CCCn2ccnc2)cc(OCCCCCCCCOC(=O)CCCCCCCCC)c1] |
| 64 | 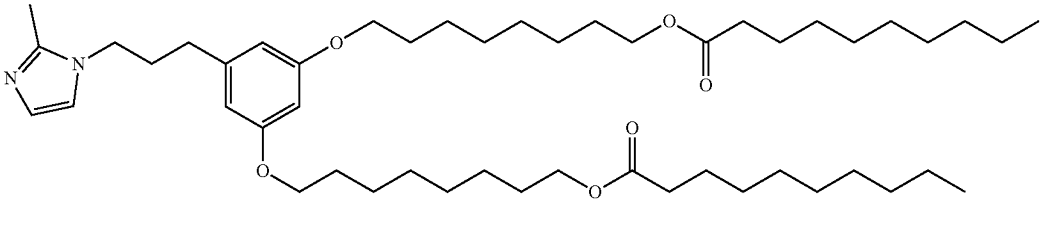 [SMILES: CCCCCCCCCC(=O)OCCCCCCCCOc1cc(CCCn2ccnc2C)cc(OCCCCCCCCOC(=O)CCCCCCCCC)c1] |
| 65 | 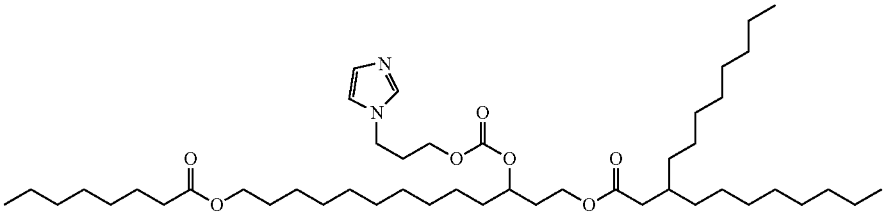 [SMILES: CCCCCCCCC(CCCCCCCC)CC(=O)OCCC(CCCCCCCCCCOC(=O)CCCCCCC)OC(=O)OCCCn1ccnc1] |

TABLE 10a-continued
| Ionizable lipid number | Structure |
|---|---|
| 66 | 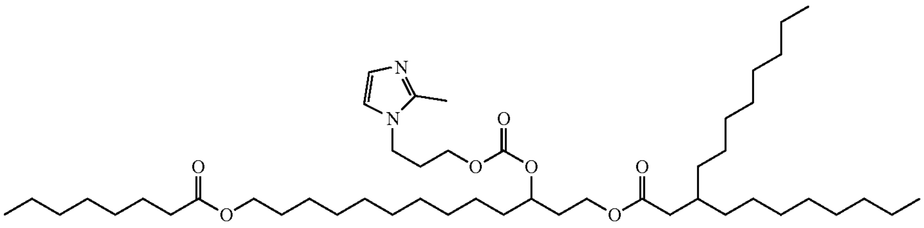 [SMILES: CCCCCCCCC(CCCCCCCC)CC(=O)OCCC(CCCCCCCCCCOC(=O)CCCCCCC)OC(=O)OCCCn1ccnc1C] |
| 67 | 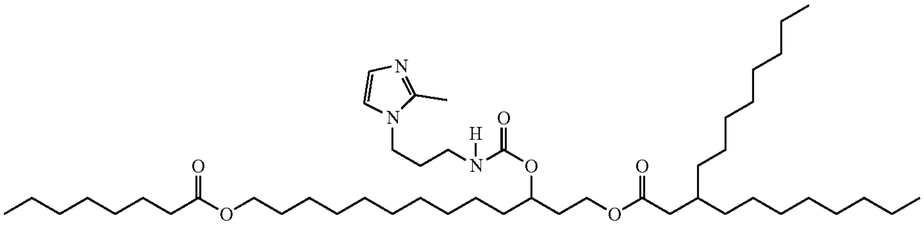 [SMILES: CCCCCCCCC(CCCCCCCC)CC(=O)OCCC(CCCCCCCCCCOC(=O)CCCCCCC)OC(=O)NCCCn1ccnc1C] |
| 68 | 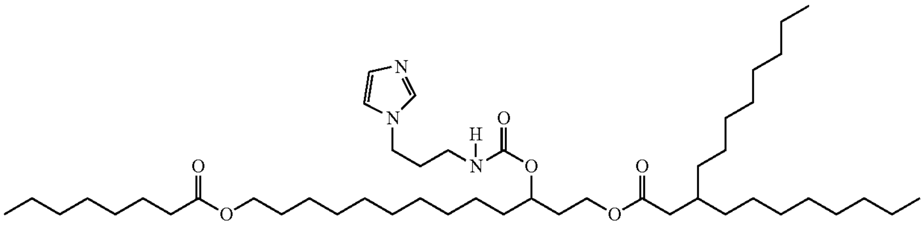 [SMILES: CCCCCCCCC(CCCCCCCC)CC(=O)OCCC(CCCCCCCCCCOC(=O)CCCCCCC)OC(=O)NCCCn1ccnc1] |
| 69 | 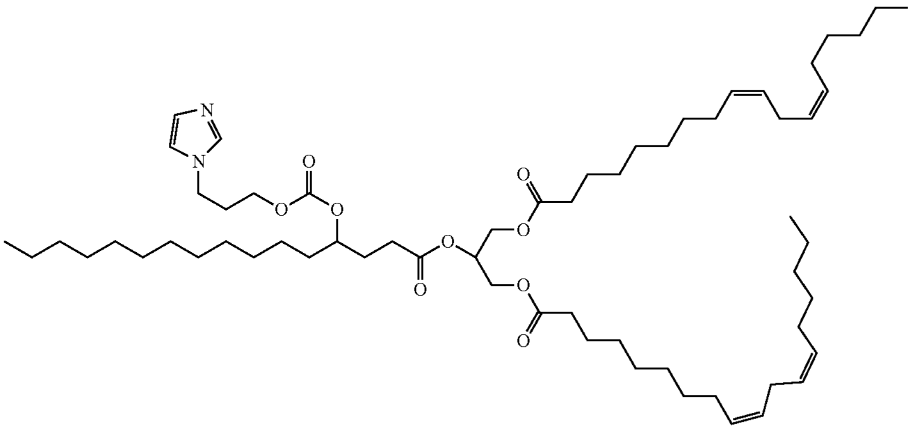 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCn1ccnc1] |
| 70 | 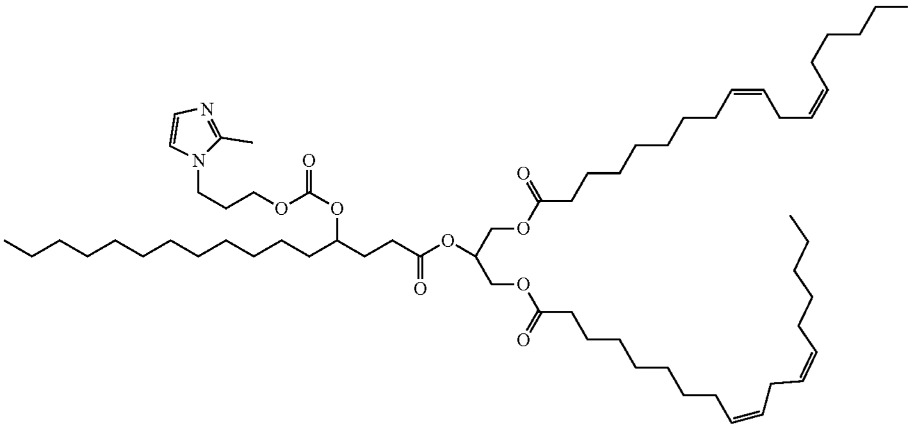 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCn1ccnc1C] |

TABLE 10a-continued
| Ionizable lipid number | Structure |
| --- | --- |
| 71 | 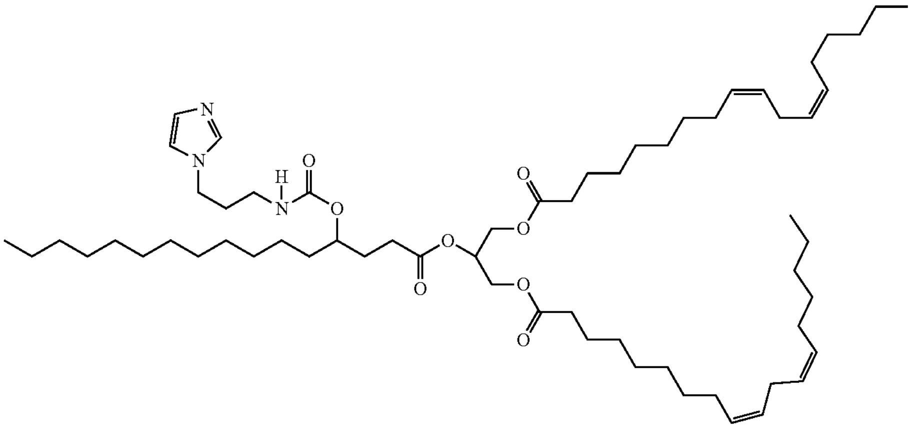 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCCn1ccnc1] |
| 72 | 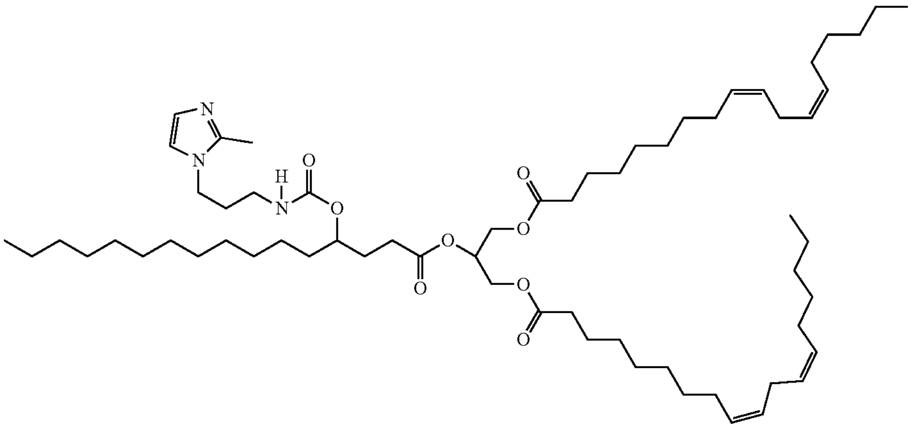 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)NCCCn1ccnc1C] |
| 73 | 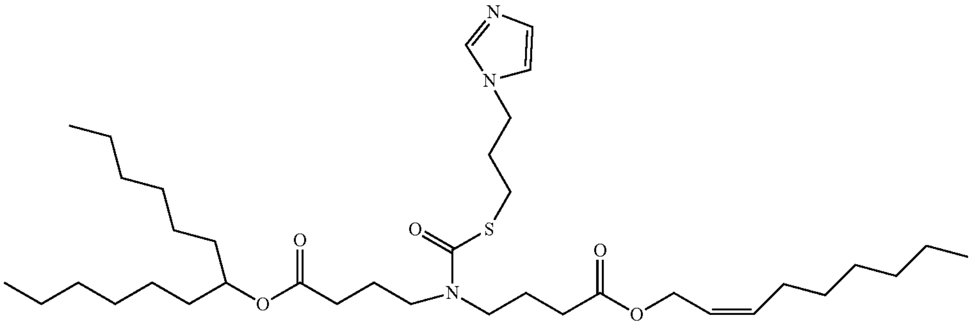 [SMILES: CCCCCC/C=C\COC(=O)CCCN(CCCC(=O)OC(CCCCCC)CCCCCC)C(=O)SCCCn1ccnc1] |
| 74 | 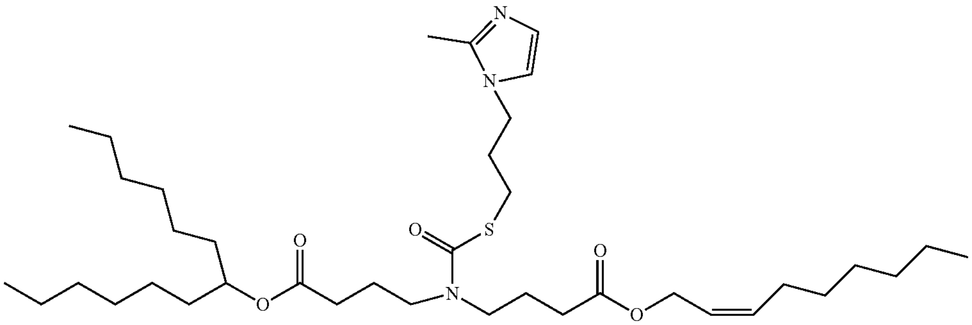 [SMILES: CCCCCC/C=C\COC(=O)CCCN(CCCC(=O)OC(CCCCCC)CCCCCC)C(=O)SCCCn1ccnc1C] |

TABLE 10a-continued
| Ionizable lipid number | Structure |
|---|---|
| 75 | 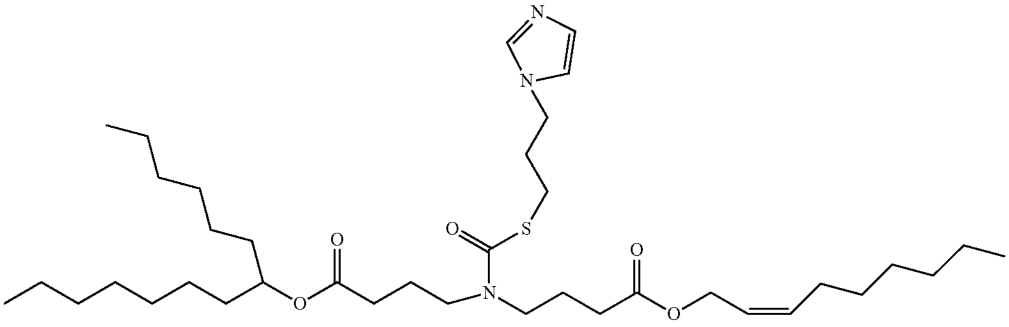 [SMILES: CCCCCC/C=C\COC(=O)CCCN(CCCC(=O)OC(CCCCCC)CCCCCCC)C(=O)SCCCn1ccnc1] |
| 76 | 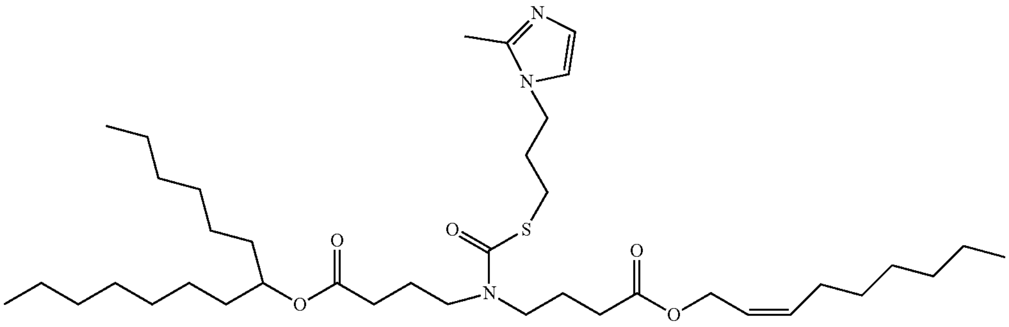 [SMILES: CCCCCC/C=C\COC(=O)CCCN(CCCC(=O)OC(CCCCCC)CCCCCCC)C(=O)SCCCn1ccnc1C] |
| 77 | 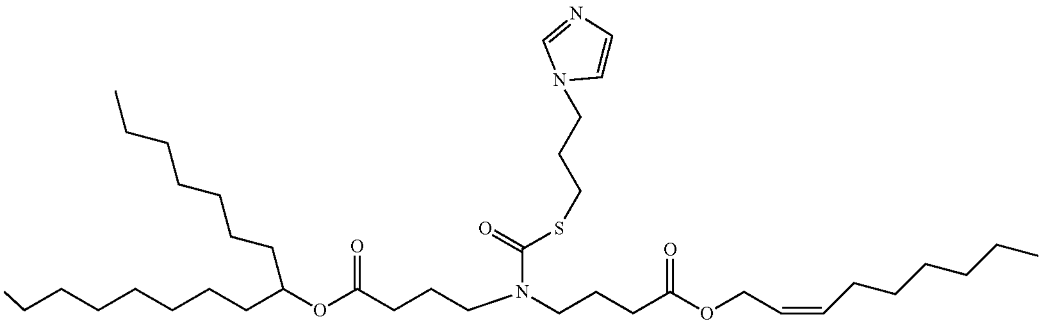 [SMILES: CCCCCC/C=C\COC(=O)CCCN(CCCC(=O)OC(CCCCCCC)CCCCCCCC)C(=O)SCCCn1ccnc1] |
| 78 | 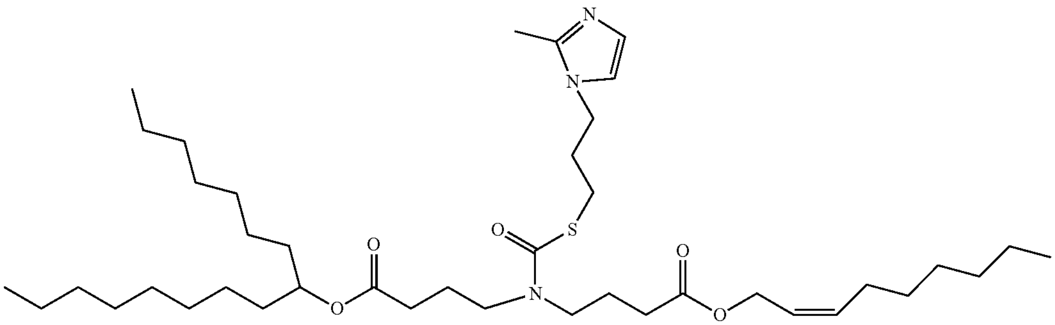 [SMILES: CCCCCC/C=C\COC(=O)CCCN(CCCC(=O)OC(CCCCCCC)CCCCCCCC)C(=O)SCCCn1ccnc1C] |

TABLE 10a-continued
| Ionizable lipid number | Structure |
|---|---|
| 79 | 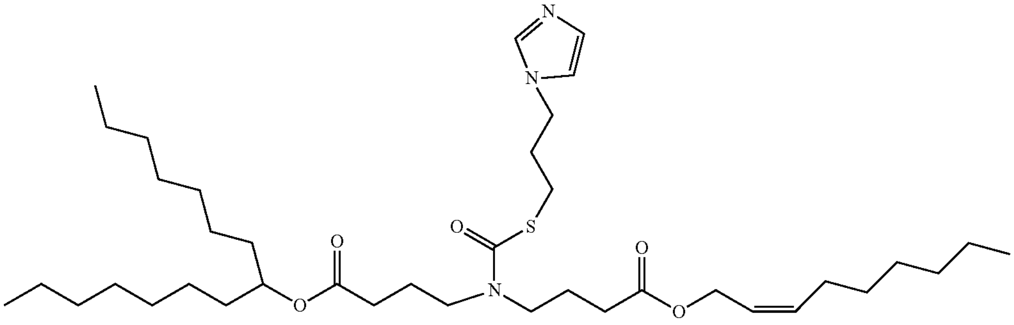 [SMILES: CCCCCC/C=C\COC(=O)CCCN(CCCC(=O)OC(CCCCCCC)CCCCCCC)C(=O)SCCCn1ccnc1] |
| 80 | 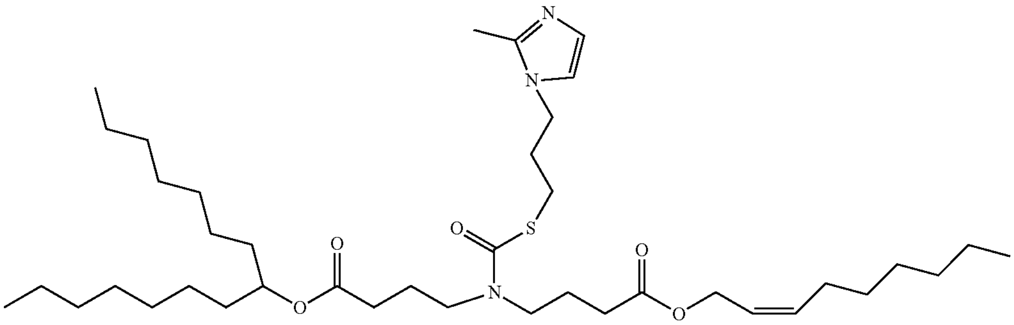 [SMILES: CCCCCC/C=C\COC(=O)CCCN(CCCC(=O)OC(CCCCCCC)CCCCCCC)C(=O)SCCCn1ccnc1C] |
| 81 | 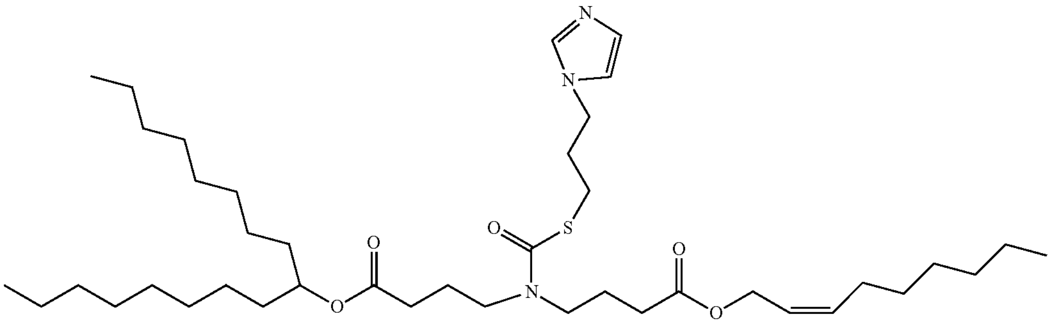 [SMILES: CCCCCC/C=C\COC(=O)CCCN(CCCC(=O)OC(CCCCCCCC)CCCCCCCC)C(=O)SCCCn1ccnc1] |
| 82 | 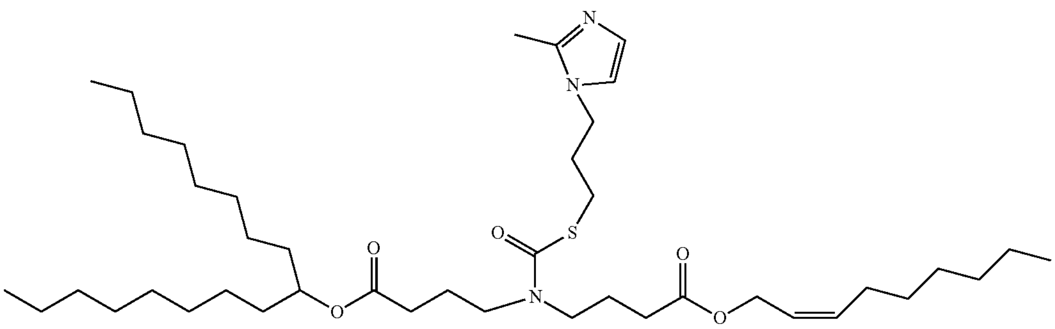 [SMILES: CCCCCC/C=C\COC(=O)CCCN(CCCC(=O)OC(CCCCCCCC)CCCCCCCC)C(=O)SCCCn1ccnc1C] |

TABLE 10a-continued
| Ionizable lipid number | Structure |
|---|---|
| 83 | 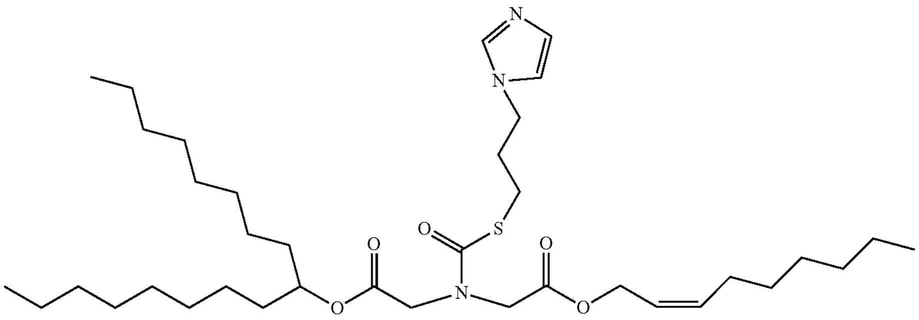 [SMILES: CCCCCC/C=C\COC(=O)CN(CC(=O)OC(CCCCCCCC)CCCCCCCC)C(=O)SCCCn1ccnc1] |
| 84 | 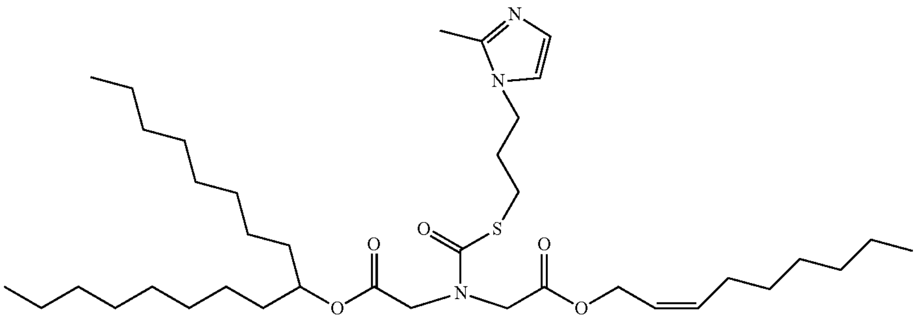 [SMILES: CCCCCC/C=C\COC(=O)CN(CC(=O)OC(CCCCCCCC)CCCCCCCC)C(=O)SCCCn1ccnc1C] |
| 85 | 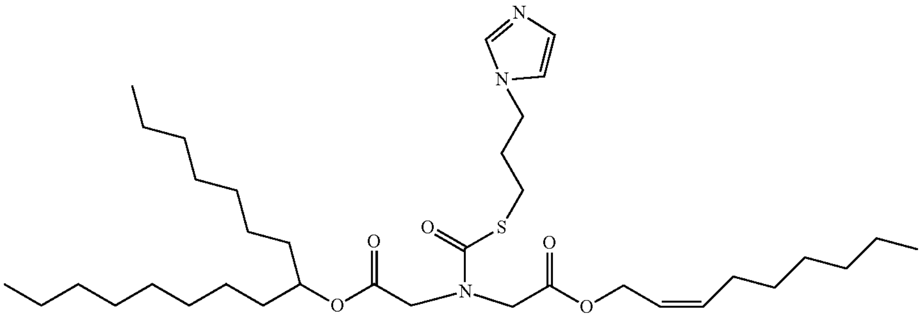 [SMILES: CCCCCC/C=C\COC(=O)CN(CC(=O)OC(CCCCCCC)CCCCCCCC)C(=O)SCCCn1ccnc1] |
| 86 | 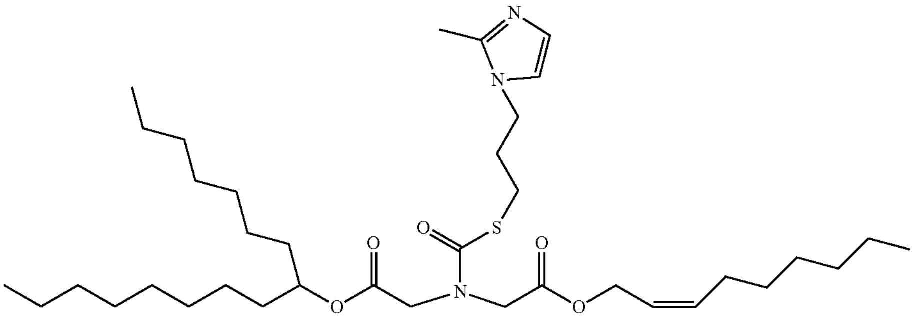 [SMILES: CCCCCC/C=C\COC(=O)CN(CC(=O)OC(CCCCCCC)CCCCCCCC)C(=O)SCCCn1ccnc1C] |

TABLE 10a-continued
| Ionizable lipid number | Structure |
| --- | --- |
| 87 | 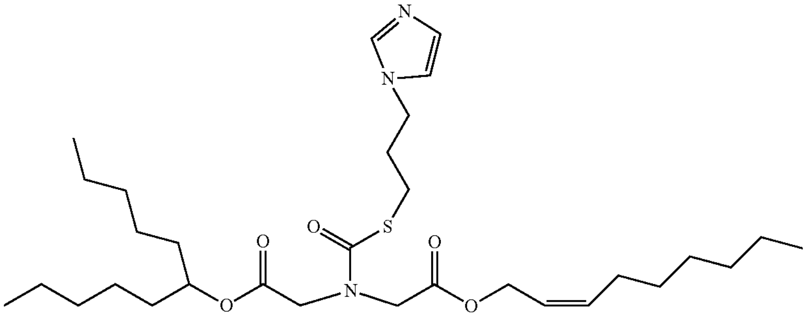 [SMILES: CCCCCC/C=C\COC(=O)CN(CC(=O)OC(CCCCC)CCCCC)C(=O)SCCCn1ccnc1] |
| 88 | 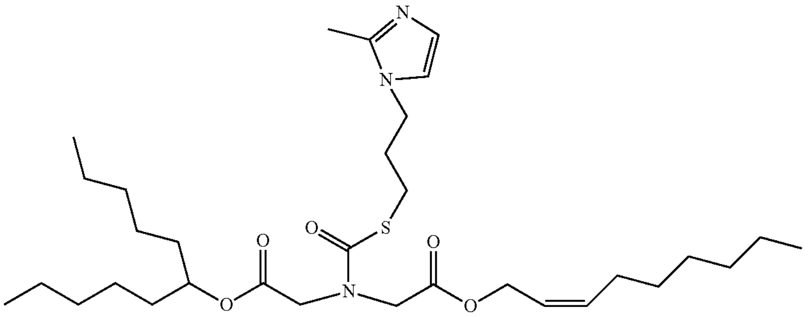 [SMILES: CCCCCC/C=C\COC(=O)CN(CC(=O)OC(CCCCC)CCCCC)C(=O)SCCCn1ccnc1C] |
| 89 | 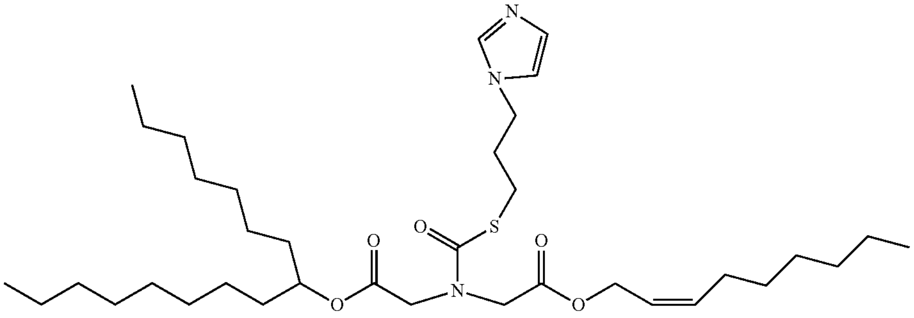 [SMILES: CCCCCC/C=C\COC(=O)CN(CC(=O)OC(CCCCCCC)CCCCCCCC)C(=O)SCCCn1ccnc1] |
| 90 | 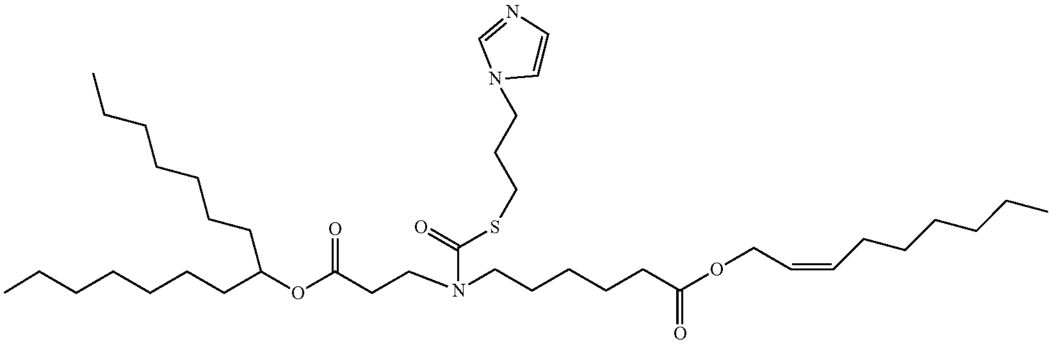 [SMILES: CCCCCC/C=C\COC(=O)CCCCCN(CCC(=O)OC(CCCCCCC)CCCCCCC)C(=O)SCCCn1ccnc1] |

TABLE 10a-continued
| Ionizable lipid number | Structure |
| --- | --- |
| 91 | 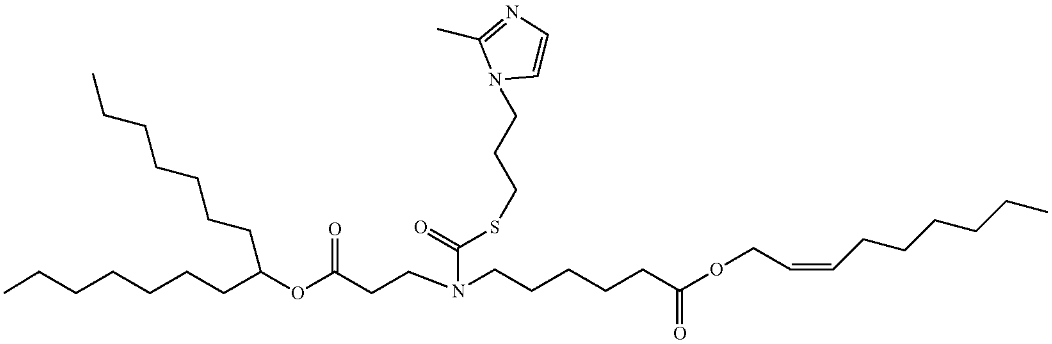 [SMILES: CCCCCC/C=C\COC(=O)CCCCCN(CCC(=O)OC(CCCCCCC)CCCCCCC)C(=O)SCCCn1ccnc1C] |
| 92 | 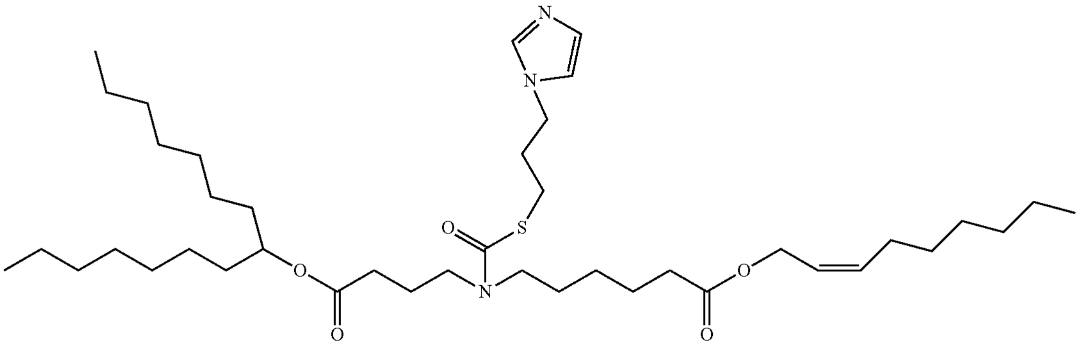 [SMILES: CCCCCC/C=C\COC(=O)CCCCCN(CCCC(=O)OC(CCCCCCC)CCCCCCC)C(=O)SCCCn1ccnc1] |
| 93 | 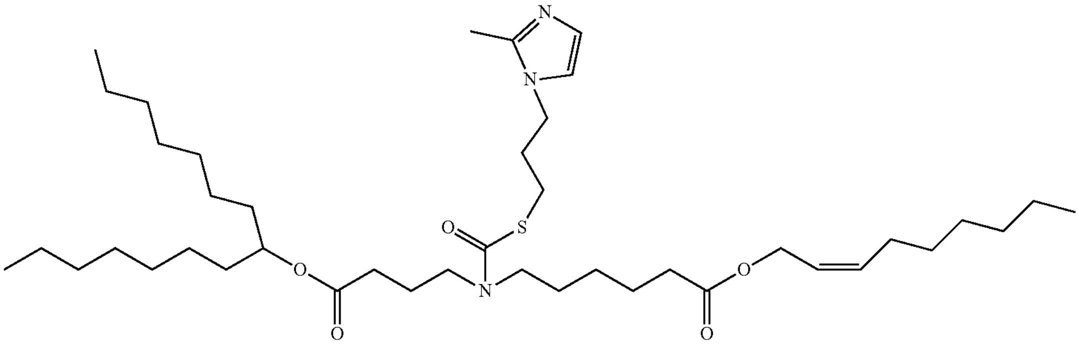 [SMILES: CCCCCC/C=C\COC(=O)CCCCCN(CCCC(=O)OC(CCCCCCC)CCCCCCC)C(=O)SCCCn1ccnc1C] |
| 94 | 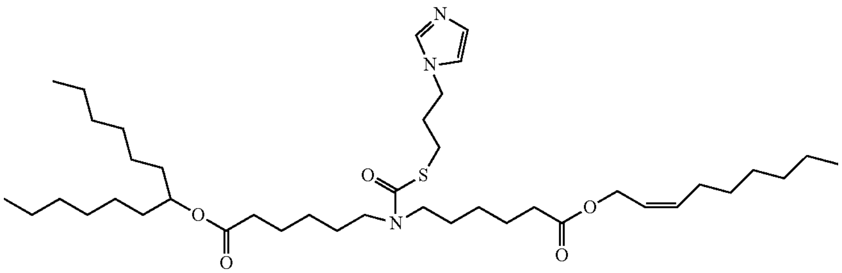 [SMILES: CCCCCC/C=C\COC(=O)CCCCCN(CCCCCC(=O)OC(CCCCCC)CCCCCC)C(=O)SCCCn1ccnc1] |

TABLE 10a-continued
| Ionizable lipid number | Structure |
| --- | --- |
| 95 | 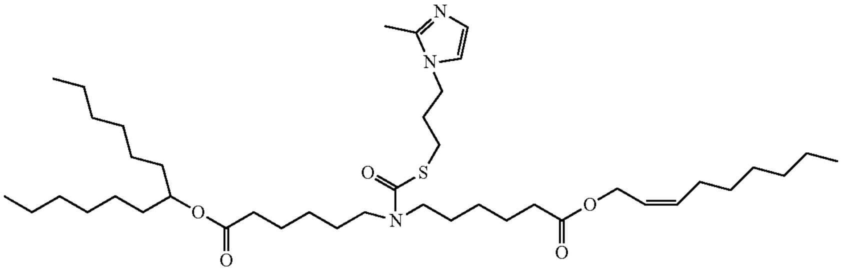 [SMILES: CCCCCC/C=C\COC(=O)CCCCCN(CCCCCC(=O)OC(CCCCCC)CCCCCC)C(=O)SCCCn1ccnc1C] |
| 96 | 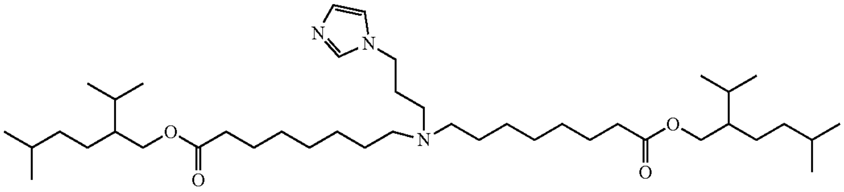 [SMILES: CC(C)CCC(COC(=O)CCCCCCCN(CCCCCCCC(=O)OCC(CCC(C)C)C(C)C)CCCn1ccnc1)C(C)C] |
| 97 | 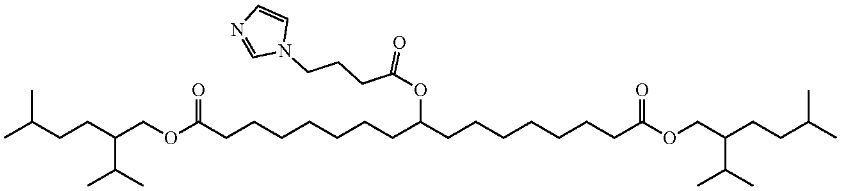 [SMILES: CC(C)CCC(COC(=O)CCCCCCCC(CCCCCCCC(=O)OCC(CCC(C)C)C(C)C)OC(=O)CCCn1ccnc1)C(C)C] |
| 98 | 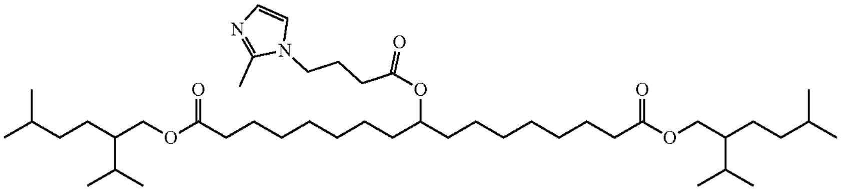 [SMILES: Cc1nccn1CCCC(=O)OC(CCCCCCCC(=O)OCC(CCC(C)C)C(C)C)CCCCCCCC(=O)OCC(CCC(C)C)C(C)C] |
| 99 | 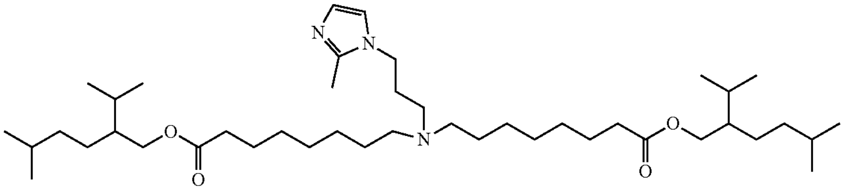 [SMILES: Cc1nccn1CCCN(CCCCCCCC(=O)OCC(CCC(C)C)C(C)C)CCCCCCCC(=O)OCC(CCC(C)C)C(C)C] |
| 100 | 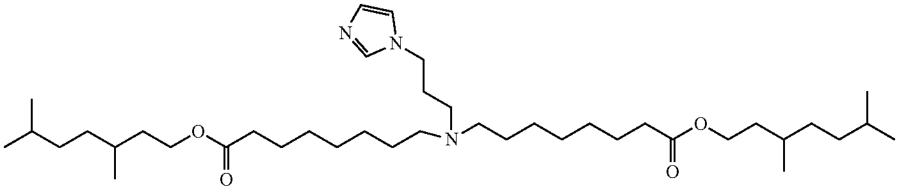 [SMILES: CC(C)CCC(C)CCOC(=O)CCCCCCCN(CCCCCCCC(=O)OCCC(C)CCC(C)C)CCCn1ccnc1] |
| 101 | 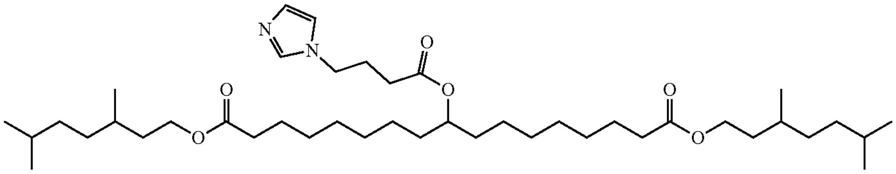 [SMILES: CC(C)CCC(C)CCOC(=O)CCCCCCCC(CCCCCCCC(=O)OCCC(C)CCC(C)C)OC(=O)CCCn1ccnc1] |

TABLE 10a-continued
| Ionizable lipid number | Structure |
|---|---|
| 102 | 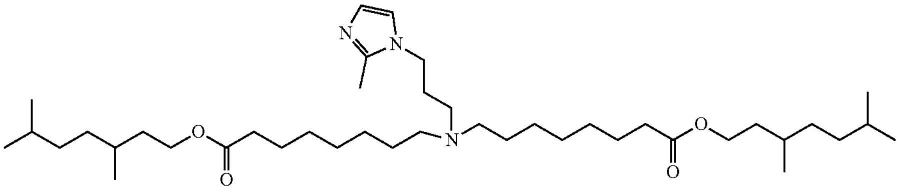 [SMILES: Cc1nccn1CCCN(CCCCCCCC(=O)OCCC(C)CCC(C)C)CCCCCCCC(=O)OCCC(C)CCC(C)C] |
| 103 | 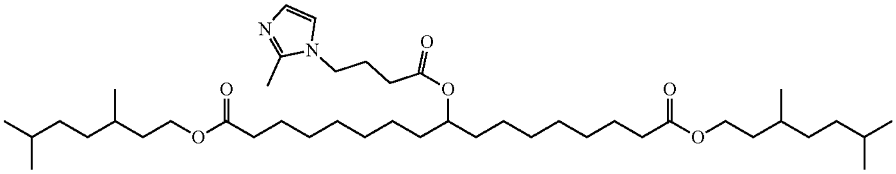 [SMILES: Cc1nccn1CCCC(=O)OC(CCCCCCCC(=O)OCCC(C)CCC(C)C)CCCCCCCC(=O)OCCC(C)CCC(C)C] |
| 104 | 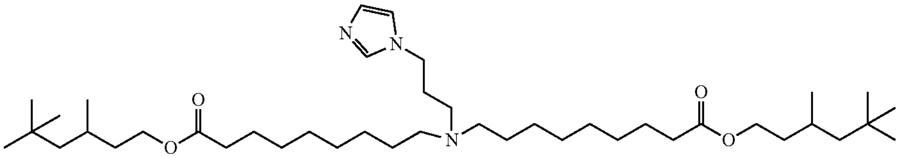 [SMILES: CC(CCOC(=O)CCCCCCCCN(CCCCCCCCC(=O)OCCC(C)CC(C)(C)C)CCCn1ccnc1)CC(C)(C)C] |
| 105 | 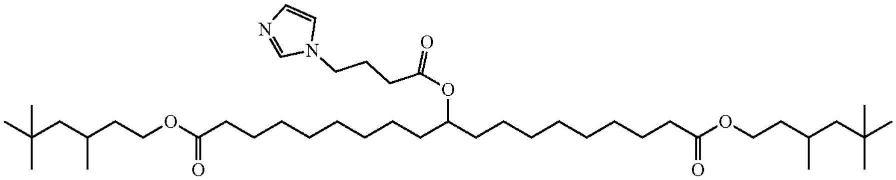 [SMILES: CC(CCOC(=O)CCCCCCCCC(CCCCCCCCC(=O)OCCC(C)CC(C)(C)C)OC(=O)CCCn1ccnc1)CC(C)(C)C] |
| 106 | 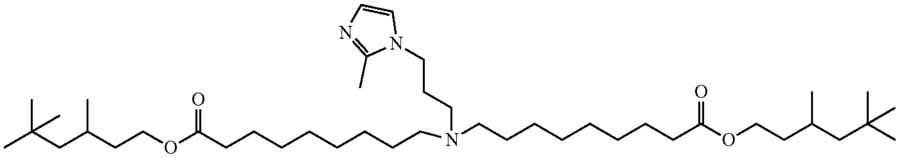 [SMILES: Cc1nccn1CCCN(CCCCCCCCC(=O)OCCC(C)CC(C)(C)C)CCCCCCCCC(=O)OCCC(C)CC(C)(C)C] |
| 107 | 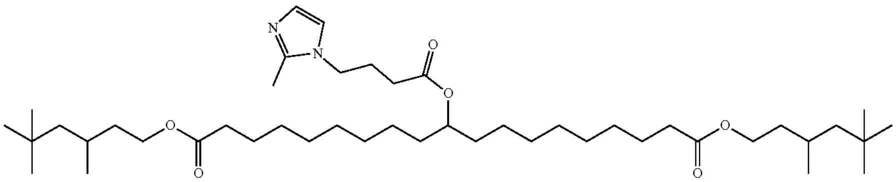 [SMILES: Cc1nccn1CCCC(=O)OC(CCCCCCCCC(=O)OCCC(C)CC(C)(C)C)CCCCCCCCC(=O)OCCC(C)CC(C)(C)C] |
| 108 | 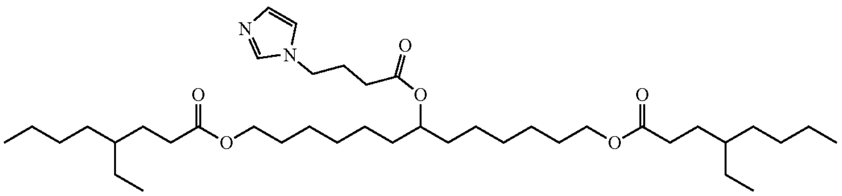 [SMILES: CCCCC(CC)CCC(=O)OCCCCCCC(CCCCCCOC(=O)CCC(CC)CCCC)OC(=O)CCCn1ccnc1] |
| 109 | 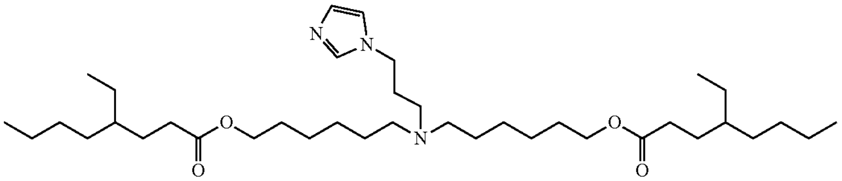 [SMILES: CCCCC(CC)CCC(=O)OCCCCCCN(CCCCCCOC(=O)CCC(CC)CCCC)CCCn1ccnc1] |

TABLE 10a-continued
| Ionizable lipid number | Structure |
| --- | --- |
| 110 | 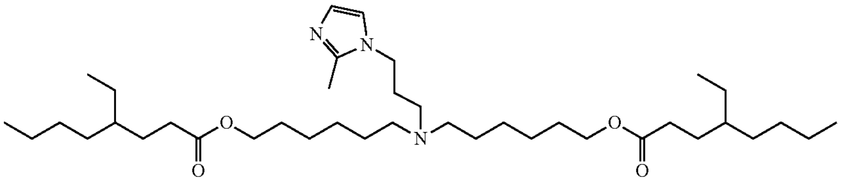 [SMILES: CCCCC(CC)CCC(=O)OCCCCCCN(CCCCCCOC(=O)CCC(CC)CCCC)CCCn1ccnc1C] |
| 111 | 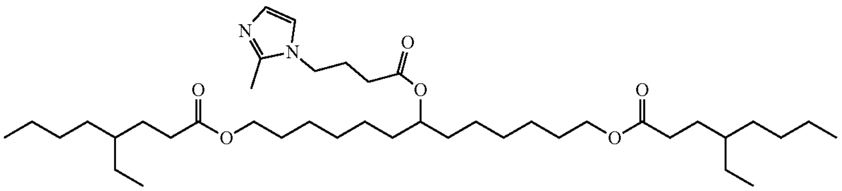 [SMILES: CCCCC(CC)CCC(=O)OCCCCCCC(CCCCCCOC(=O)CCC(CC)CCCC)OC(=O)CCCn1ccnc1C] |
| 112 | 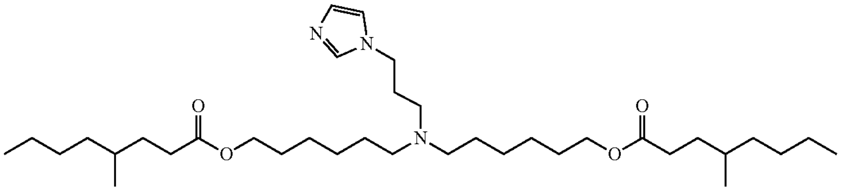 [SMILES: CCCCC(C)CCC(=O)OCCCCCCN(CCCCCCOC(=O)CCC(C)CCCC)CCCn1ccnc1] |
| 113 | 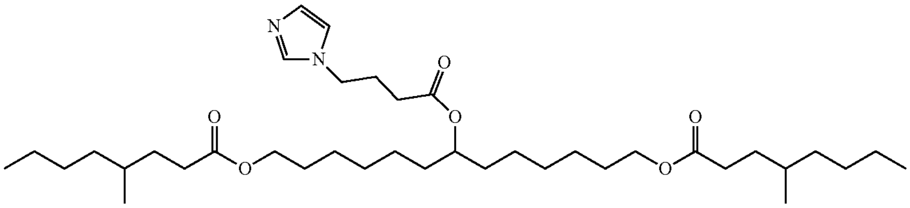 [SMILES: CCCCC(C)CCC(=O)OCCCCCCC(CCCCCCOC(=O)CCC(C)CCCC)OC(=O)CCCn1ccnc1] |
| 114 | 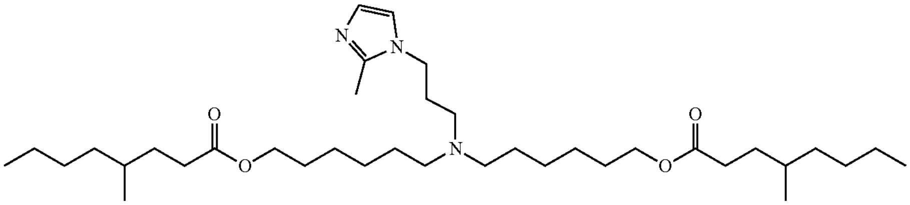 [SMILES: CCCCC(C)CCC(=O)OCCCCCCN(CCCCCCOC(=O)CCC(C)CCCC)CCCn1ccnc1C] |
| 115 | 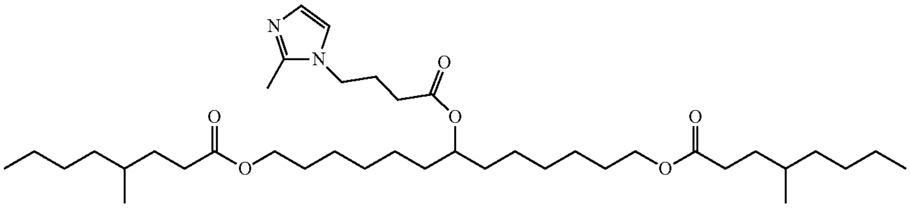 [SMILES: CCCCC(C)CCC(=O)OCCCCCCC(CCCCCCOC(=O)CCC(C)CCCC)OC(=O)CCCn1ccnc1C] |
| 116 | 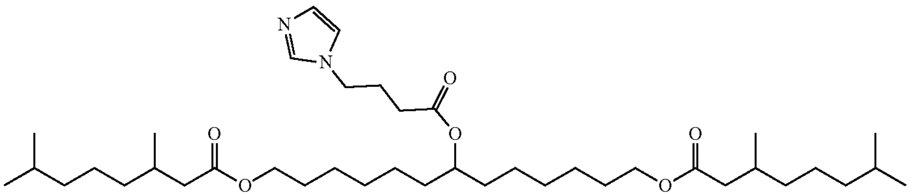 [SMILES: CC(C)CCCC(C)CC(=O)OCCCCCCC(CCCCCCOC(=O)CC(C)CCCC(C)C)OC(=O)CCCn1ccnc1] |

TABLE 10a-continued
| Ionizable lipid number | Structure |
|---|---|
| 117 | 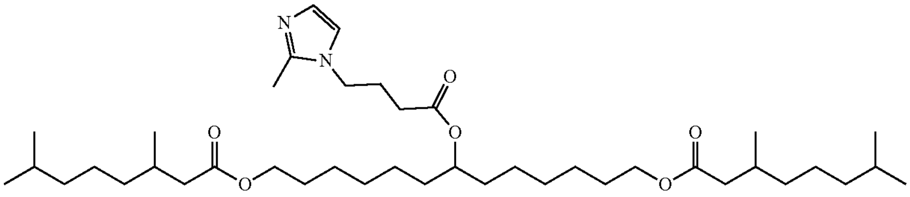 [SMILES: Cc1nccn1CCCC(=O)OC(CCCCCCOC(=O)CC(C)CCCC(C)C)CCCCCCOC(=O)CC(C)CCCC(C)C] |
| 118 | 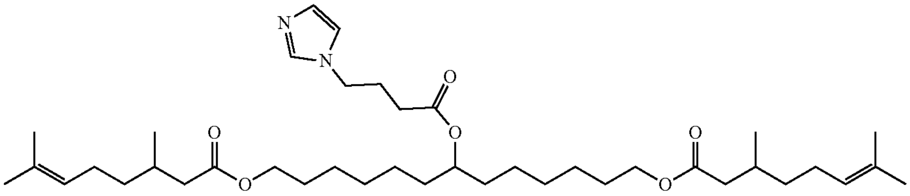 [SMILES: CC(C)=CCCC(C)CC(=O)OCCCCCCC(CCCCCCOC(=O)CC(C)CCC=C(C)C)OC(=O)CCCn1ccnc1] |
| 119 | 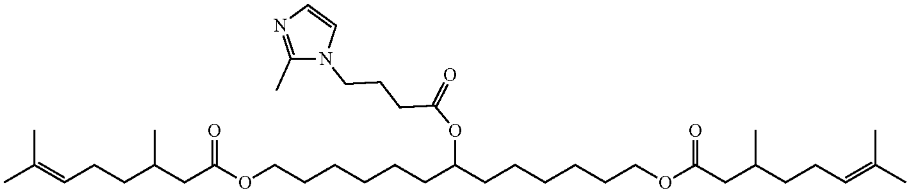 [SMILES: CC(C)=CCCC(C)CC(=O)OCCCCCCC(CCCCCCOC(=O)CC(C)CCC=C(C)C)OC(=O)CCCn1ccnc1C] |
| 120 | 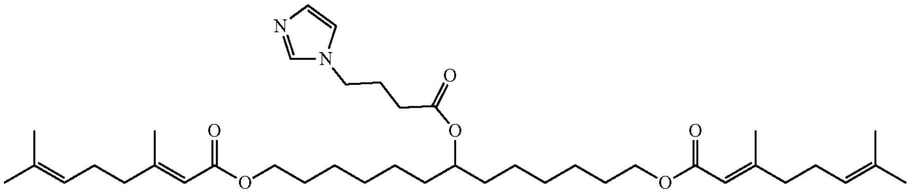 [SMILES: CC(C)=CCC/C(C)=C/C(=O)OCCCCCCC(CCCCCCOC(=O)/C=C(\C)CCC=C(C)C)OC(=O)CCCn1ccnc1] |
| 121 | 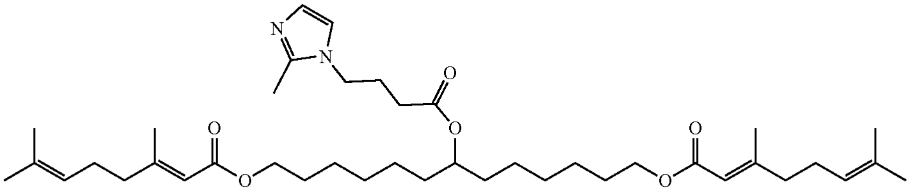 [SMILES: CC(C)=CCC/C(C)=C/C(=O)OCCCCCCC(CCCCCCOC(=O)/C=C(\C)CCC=C(C)C)OC(=O)CCCn1ccnc1C] |
| 122 | 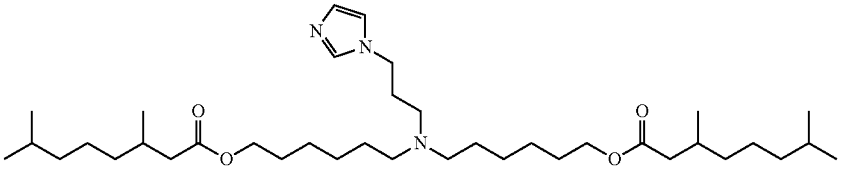 [SMILES: CC(C)CCCC(C)CC(=O)OCCCCCCN(CCCCCCOC(=O)CC(C)CCCC(C)C)CCCn1ccnc1] |
| 123 | 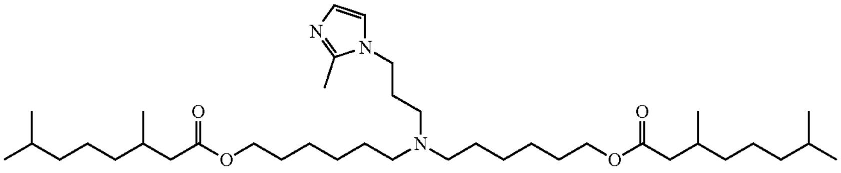 [SMILES: Cc1nccn1CCCN(CCCCCCOC(=O)CC(C)CCCC(C)C)CCCCCCOC(=O)CC(C)CCCC(C)C] |
| 124 | 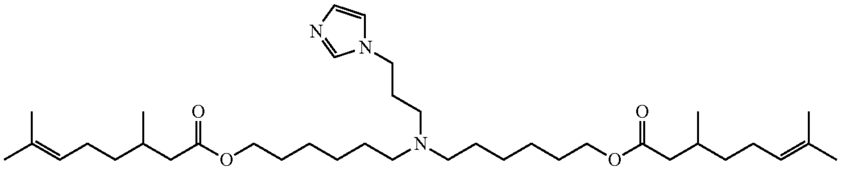 [SMILES: CC(C)=CCCC(C)CC(=O)OCCCCCCN(CCCCCCOC(=O)CC(C)CCC=C(C)C)CCCn1ccnc1] |

TABLE 10a-continued
| Ionizable lipid number | Structure |
|---|---|
| 125 | 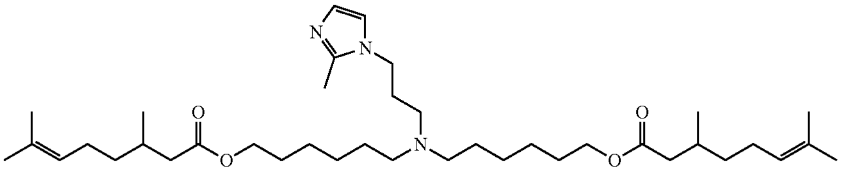 [SMILES: CC(C)=CCCC(C)CC(=O)OCCCCCCN(CCCCCCOC(=O)CC(C)CCC=C(C)C)CCCn1ccnc1C] |
| 126 | 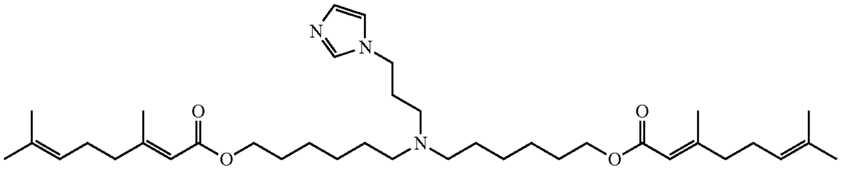 [SMILES: CC(C)=CCC/C(C)=C/C(=O)OCCCCCCN(CCCCCCOC(=O)/C=C(\C)CCC=C(C)C)CCCn1ccnc1] |
| 127 | 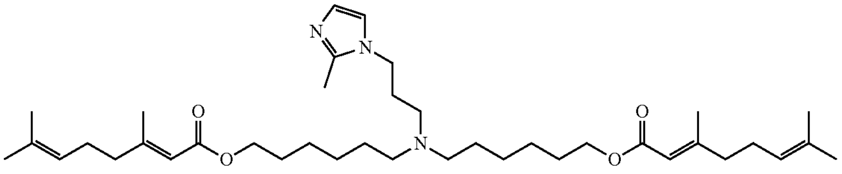 [SMILES: CC(C)=CCC/C(C)=C/C(=O)OCCCCCCN(CCCCCCOC(=O)/C=C(\C)CCC=C(C)C)CCCn1ccnc1C] |
| 128 | 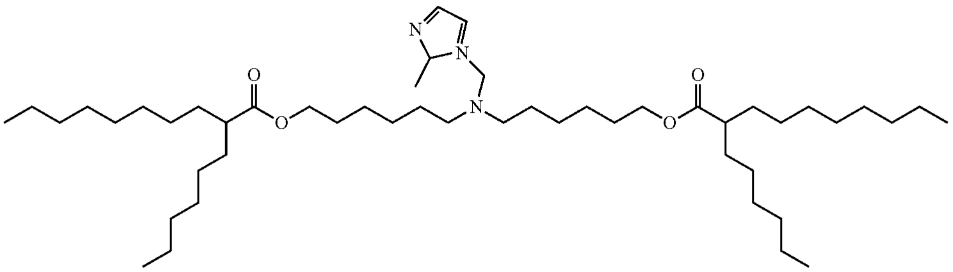 |
| 129 | 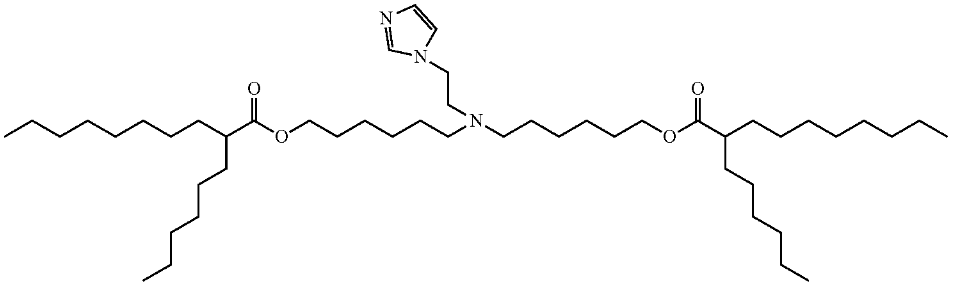 [SMILES: CCCCCCCCC(CCCCCC)C(=O)OCCCCCCN(CCCCCCOC(=O)C(CCCCCC)CCCCCCCC)CCn1ccnc1] |
| 130 | 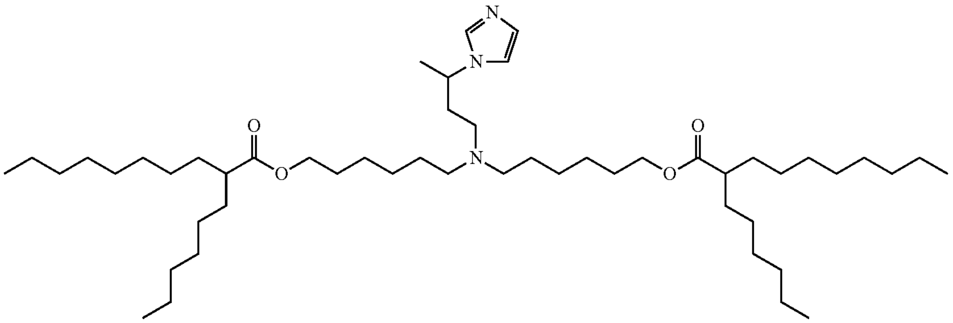 [SMILES: CCCCCCCCC(CCCCCC)C(=O)OCCCCCCN(CCCCCCOC(=O)C(CCCCCC)CCCCCCCC)CCC(C)n1ccnc1] |

TABLE 10a-continued
| Ionizable lipid number | Structure |
|---|---|
| 131 | 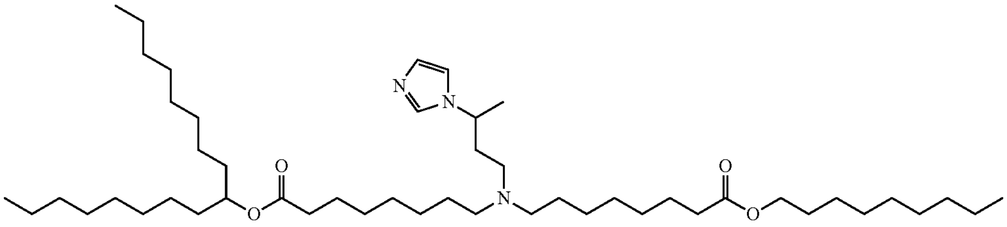 |
| 132 | 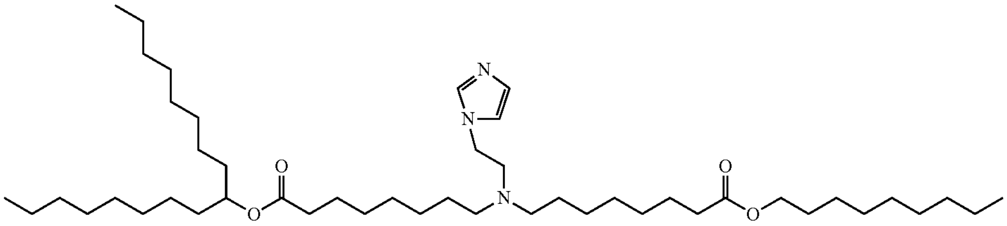 |
| 133 | 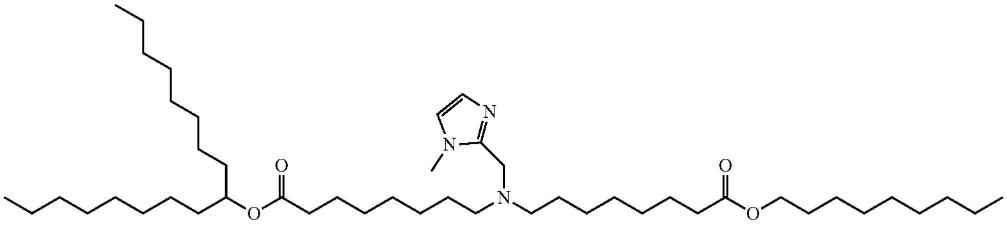 |
| 134 | 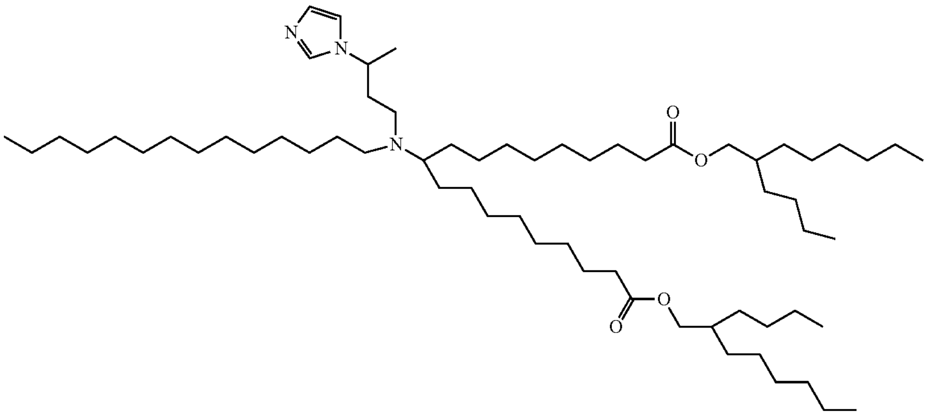 [SMILES: CCCCCCCCCCCCCCN(CCC(C)n1ccnc1)C(CCCCCCCCC(=O)OCC(CCCC)CCCCCC)CCCCCCCCC(=O)OCC(CCCC)CCCCCC] |
| 135 | 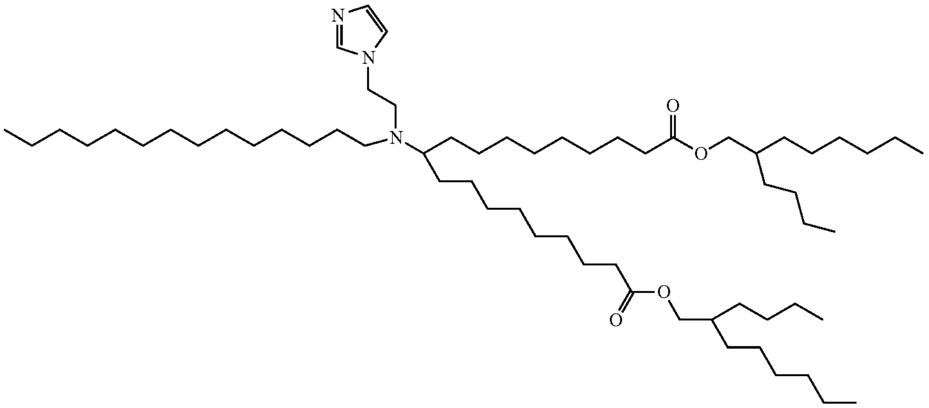 [SMILES: CCCCCCCCCCCCCCN(CCn1ccnc1)C(CCCCCCCCC(=O)OCC(CCCC)CCCCCC)CCCCCCCCC(=O)OCC(CCCC)CCCCCC] |

TABLE 10a-continued

| Ionizable lipid number | Structure |
|---|---|
| 136 | 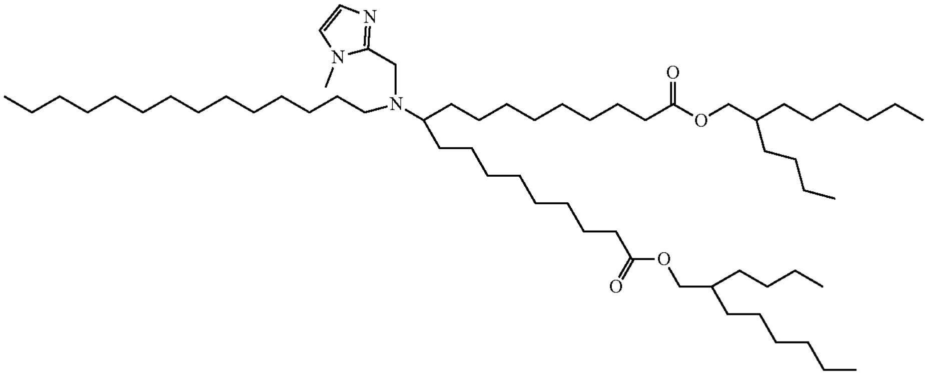 [SMILES: CCCCCCCCCCCCCCN(Cc1nccn1C)C(CCCCCCCCC(=O)OCC(CCCC)CCCCCC)CCCCCCCCC(=O)OCC(CCCC)CCCCCC] |

In some embodiments, the ionizable lipid has a beta-hydroxyl amine head group. In some embodiments, the ionizable lipid has a gamma-hydroxyl amine head group.

In some embodiments, an ionizable lipid of the disclosure is a lipid selected from Table 10b. In some embodiments, an ionizable lipid of the disclosure is Lipid 15 from Table 10b. In an embodiment, the ionizable lipid is described in US patent publication number US20170210697A1. In an embodiment, the ionizable lipid is described in US patent publication number US20170119904A1.

TABLE 10b

| Ionizable lipid number | Structure |
|---|---|
| 1 | 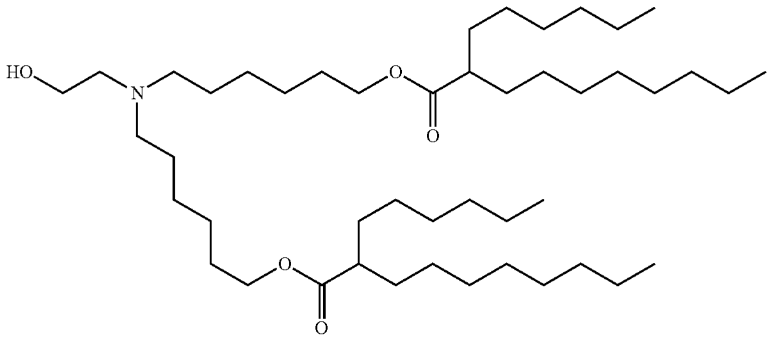 [SMILES: CCCCCCCCC(CCCCCC)C(=O)OCCCCCCN(CCO)CCCCCCOC(=O)C(CCCCCC)CCCCCCCC] |
| 2 | 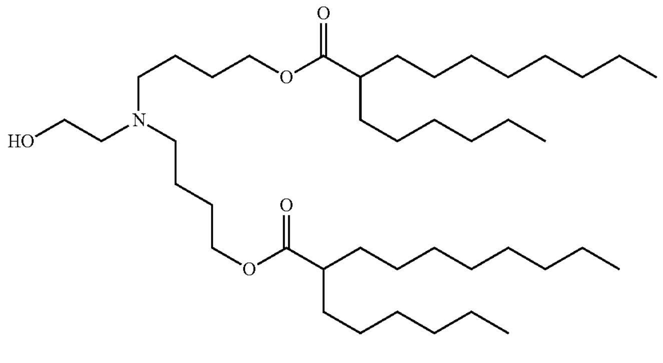 [SMILES: CCCCCCCCC(CCCCCC)C(=O)OCCCCN(CCO)CCCCOC(=O)C(CCCCCC)CCCCCCCC] |

TABLE 10b-continued
| Ionizable lipid number | Structure |
|---|---|
| 3 | 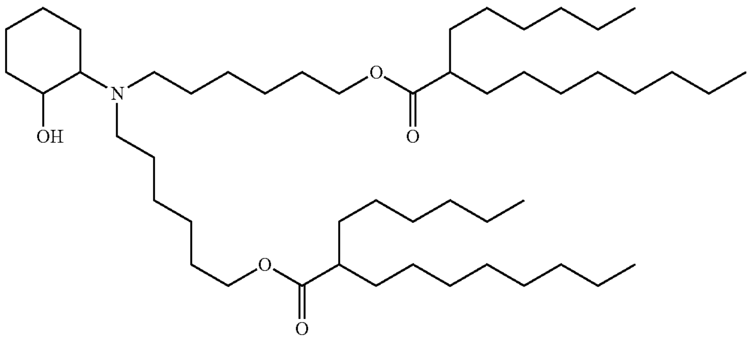 [SMILES: CCCCCCCCC(CCCCCC)C(=O)OCCCCCCN(CCCCCCOC(=O)C(CCCCCC)CCCCCCCC)C1CCCCC1O] |
| 4 | 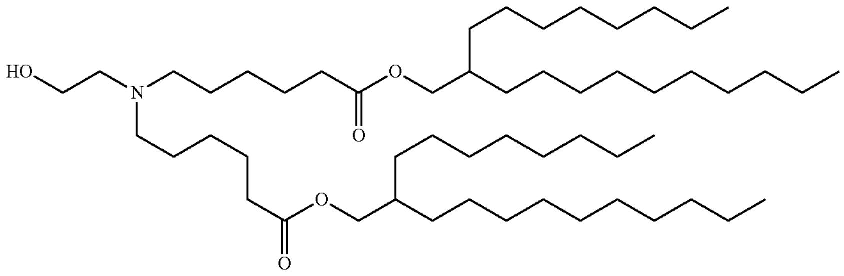 [SMILES: CCCCCCCCCCC(CCCCCCCC)COC(=O)CCCCCN(CCO)CCCCCC(=O)OCC(CCCCCCCC)CCCCCCCCCC] |
| 5 | 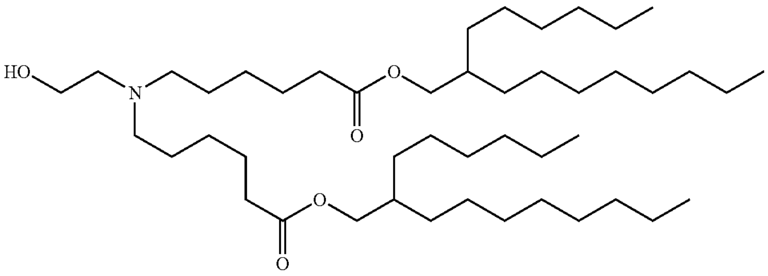 [SMILES: CCCCCCCCC(CCCCCC)COC(=O)CCCCCN(CCO)CCCCCC(=O)OCC(CCCCCC)CCCCCCCC] |
| 6 | 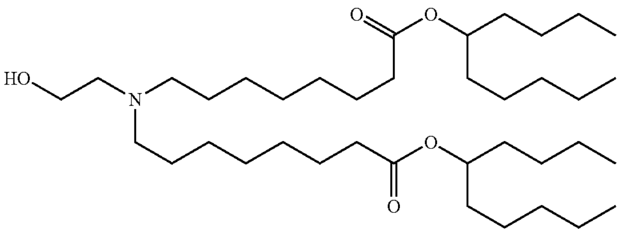 [SMILES: CCCCCC(CCCC)OC(=O)CCCCCCCN(CCO)CCCCCCCC(=O)OC(CCCC)CCCCC] |
| 7 | 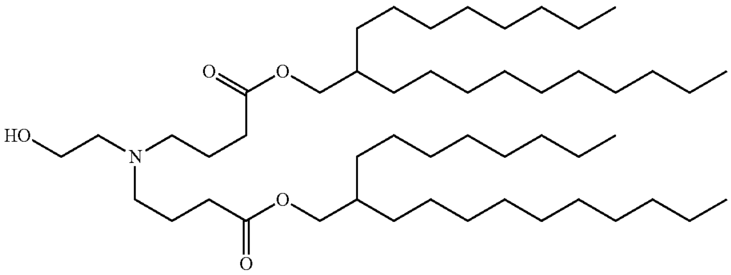 [SMILES: CCCCCCCCCCC(CCCCCCCC)COC(=O)CCCN(CCO)CCCC(=O)OCC(CCCCCCCC)CCCCCCCCCC] |

TABLE 10b-continued
| Ionizable lipid number | Structure |
|---|---|
| 8 | 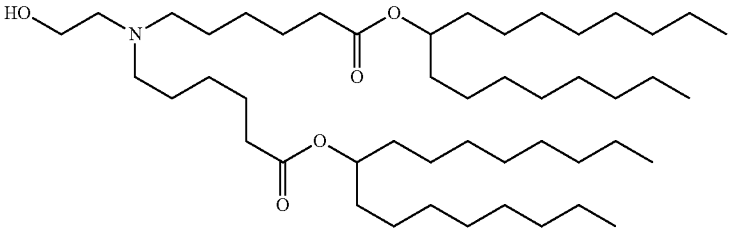 [SMILES: CCCCCCCCC(CCCCCCCC)OC(=O)CCCCCN(CCO)CCCCCC(=O)OC(CCCCCCCC)CCCCCCCC] |
| 9 | 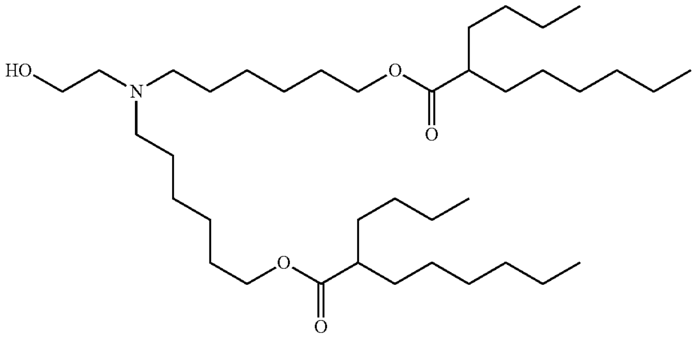 [SMILES: CCCCCCC(CCCC)C(=O)OCCCCCCN(CCO)CCCCCCOC(=O)C(CCCC)CCCCCC] |
| 10 | 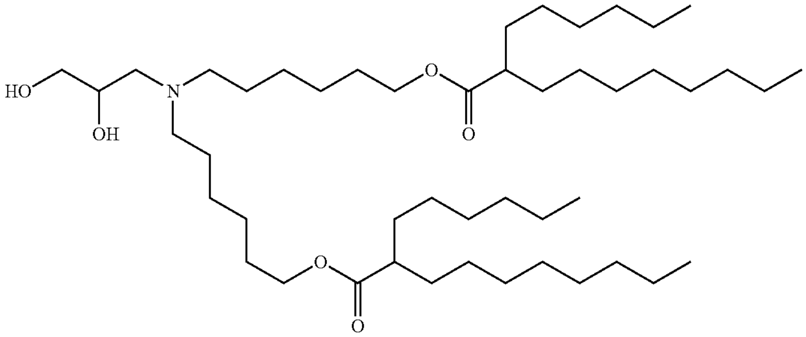 [SMILES: CCCCCCCCC(CCCCCC)C(=O)OCCCCCCN(CCCCCCOC(=O)C(CCCCCC)CCCCCCCC)CC(O)CO] |
| 11 | 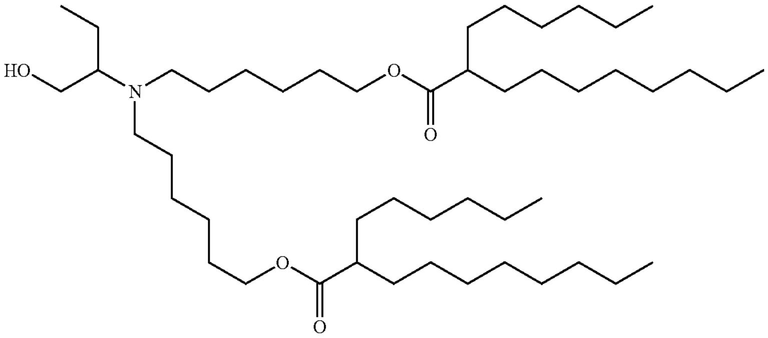 [SMILES: CCCCCCCCC(CCCCCC)C(=O)OCCCCCCN(CCCCCCOC(=O)C(CCCCCC)CCCCCCCC)C(CC)CO] |

TABLE 10b-continued
| Ionizable lipid number | Structure |
|---|---|
| 12 | 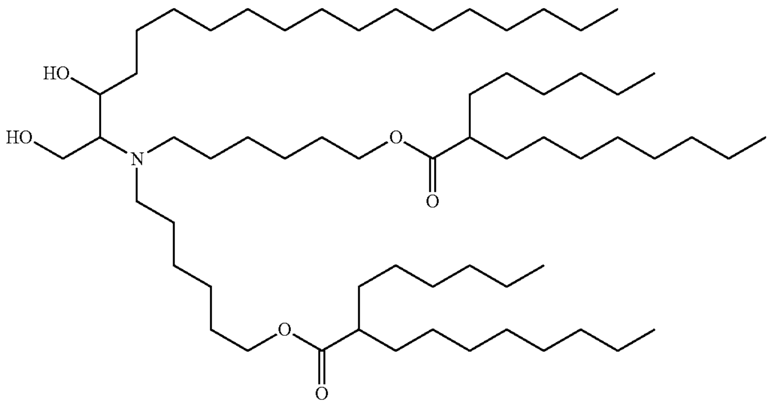 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |
| 13 | 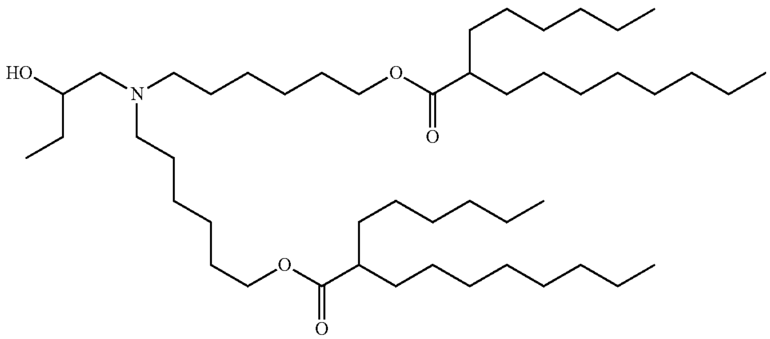 [SMILES: CCCCCCCCC(CCCCCC)C(=O)OCCCCCCN(CCCCCCOC(=O)C(CCCCCC)CCCCCCCC)CC(O)CC] |
| 14 | 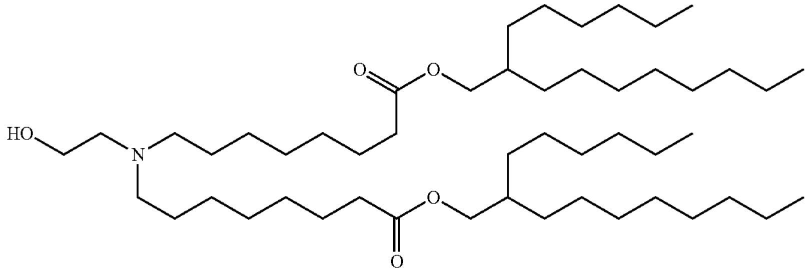 [SMILES: CCCCCCCCC(CCCCCC)COC(=O)CCCCCCCN(CCO)CCCCCCCC(=O)OCC(CCCCCC)CCCCCCCC] |
| 15 | 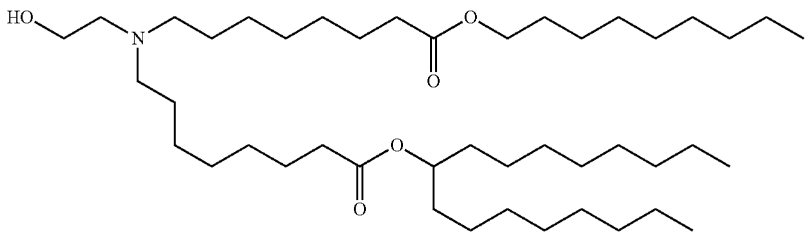 [SMILES: CCCCCCCCCOC(=O)CCCCCCCN(CCO)CCCCCCCC(=O)OC(CCCCCCCC)CCCCCCCC] |

TABLE 10b-continued
| Ionizable lipid number | Structure |
|---|---|
| 16 | 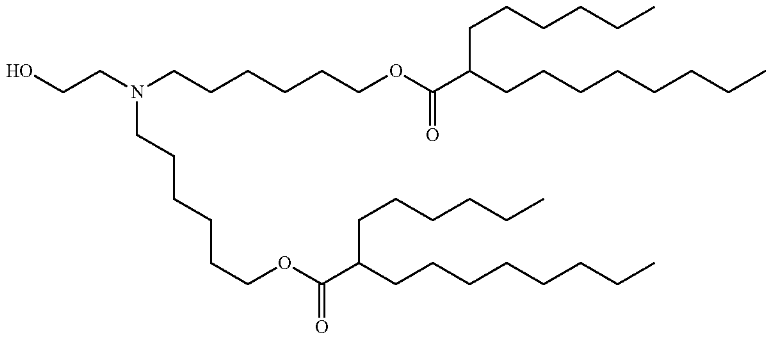 [SMILES: CCCCCCCCC(CCCCCC)C(=O)OCCCCCCN(CCO)CCCCCCOC(=O)C(CCCCCC)CCCCCCCC] |
| 17 | 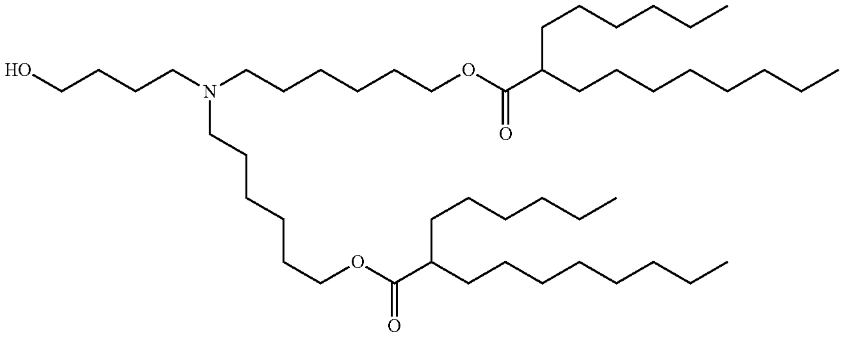 [SMILES: CCCCCCCCC(CCCCCC)C(=O)OCCCCCCN(CCCCO)CCCCCCOC(=O)C(CCCCCC)CCCCCCCC] |
| 18 | 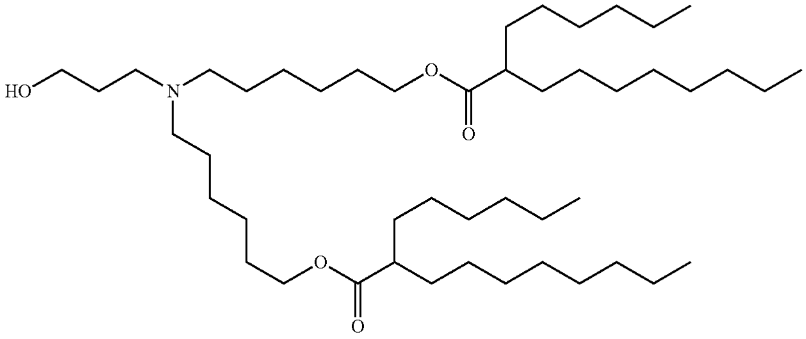 [SMILES: CCCCCCCCC(CCCCCC)C(=O)OCCCCCCN(CCCO)CCCCCCOC(=O)C(CCCCCC)CCCCCCCC] |
| 19 | 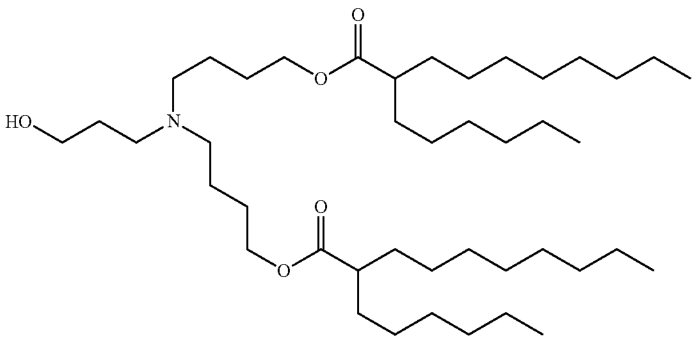 [SMILES: CCCCCCCCC(CCCCCC)C(=O)OCCCCN(CCCO)CCCCOC(=O)C(CCCCCC)CCCCCCCC] |

TABLE 10b-continued
| Ionizable lipid number | Structure |
| --- | --- |
| 20 | 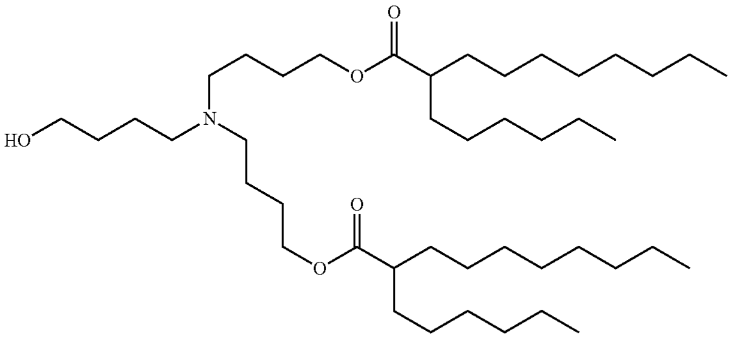 [SMILES: CCCCCCCCC(CCCCCC)C(=O)OCCCCN(CCCCO)CCCCOC(=O)C(CCCCCC)CCCCCCCC] |
| 21 | 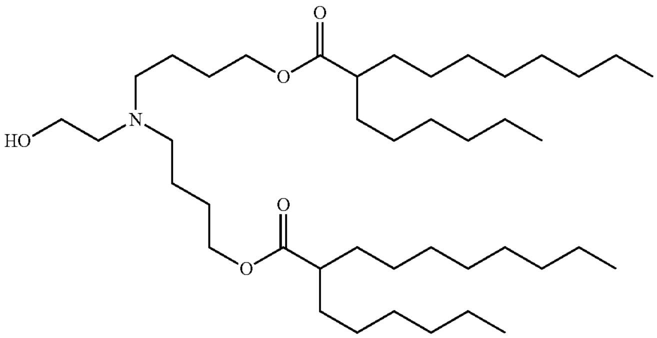 [SMILES: CCCCCCCCC(CCCCCC)C(=O)OCCCCN(CCO)CCCCOC(=O)C(CCCCCC)CCCCCCCC] |
| 22 | 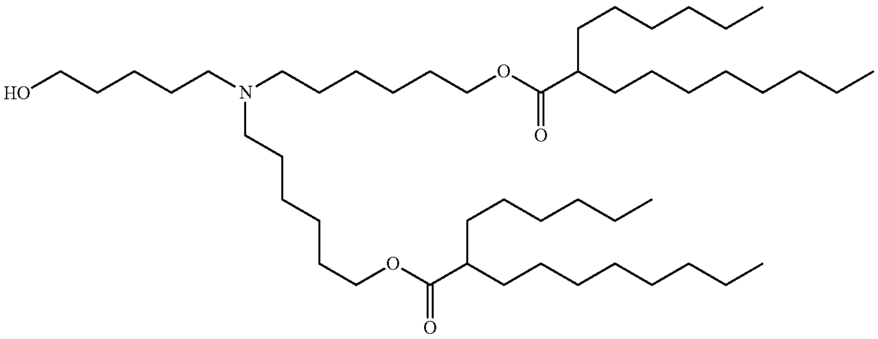 [SMILES: CCCCCCCCC(CCCCCC)C(=O)OCCCCCCN(CCCCCO)CCCCCCOC(=O)C(CCCCCC)CCCCCCCC] |
| 23 | 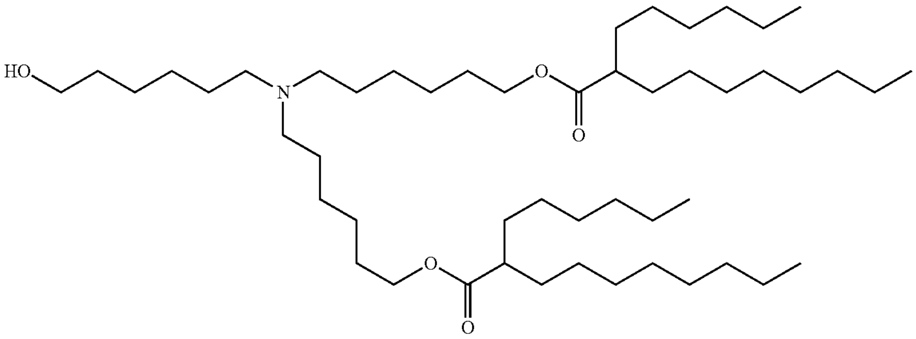 [SMILES: CCCCCCCCC(CCCCCC)C(=O)OCCCCCCN(CCCCCCO)CCCCCCOC(=O)C(CCCCCC)CCCCCCCC] |

TABLE 10b-continued
| Ionizable lipid number | Structure |
|---|---|
| 24 | 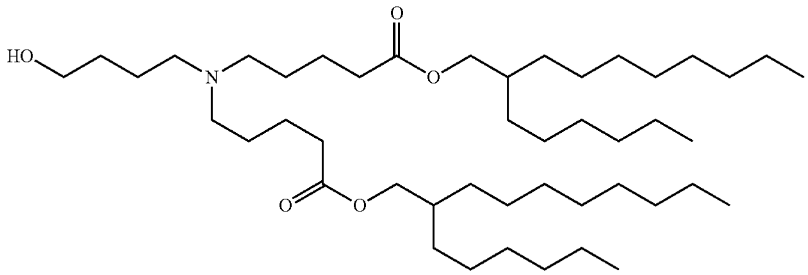 [SMILES: CCCCCCCCC(CCCCCC)COC(=O)CCCCN(CCCCO)CCCCC(=O)OCC(CCCCCC)CCCCCCCC] |
| 25 | 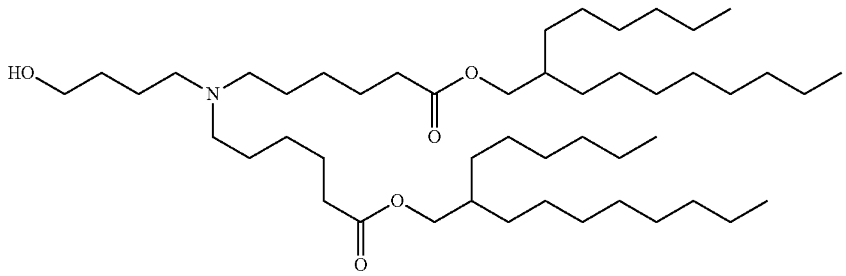 [SMILES: CCCCCCCCC(CCCCCC)COC(=O)CCCCCN(CCCCO)CCCCCC(=O)OCC(CCCCCC)CCCCCCCC] |
| 26 | 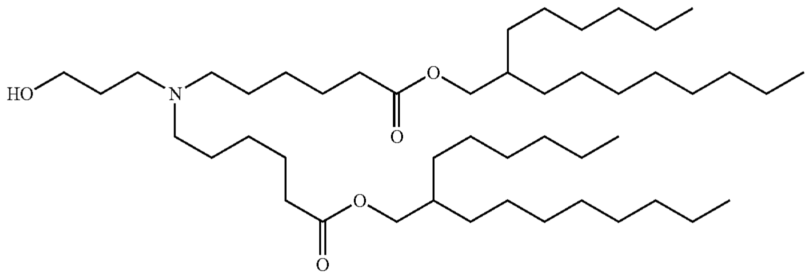 [SMILES: CCCCCCCCC(CCCCCC)COC(=O)CCCCCN(CCCO)CCCCCC(=O)OCC(CCCCCC)CCCCCCCC] |
| 27 | 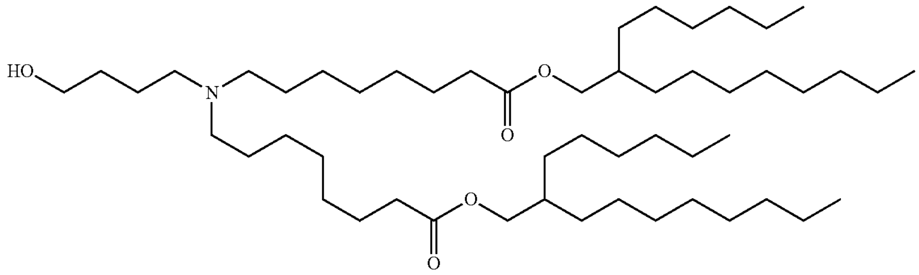 [SMILES: CCCCCCCCC(CCCCCC)COC(=O)CCCCCCCN(CCCCO)CCCCCCCC(=O)OCC(CCCCCC)CCCCCCCC] |
| 28 | 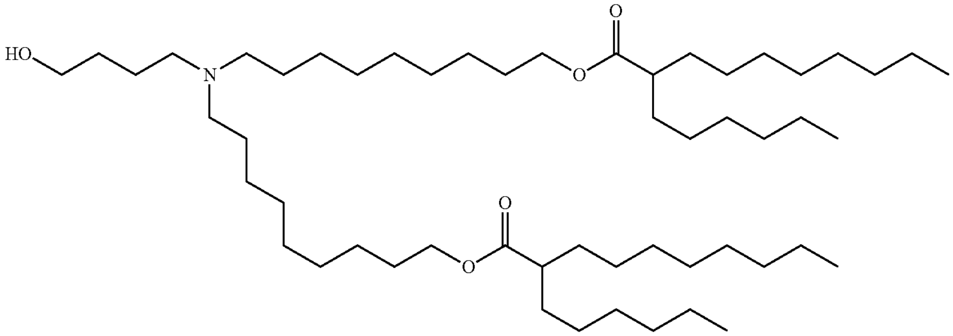 [SMILES: CCCCCCCCC(CCCCCC)C(=O)OCCCCCCCCCN(CCCCO)CCCCCCCCCOC(=O)C(CCCCCC)CCCCCCCC] |

TABLE 10b-continued
| Ionizable lipid number | Structure |
|---|---|
| 29 | 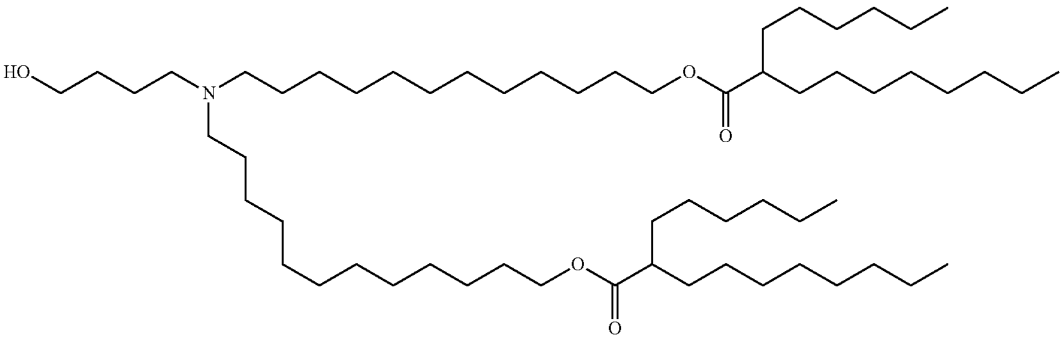 [SMILES: CCCCCCCCC(CCCCCC)C(=O)OCCCCCCCCCCCCN(CCCCO)CCCCCCCCCCCCOC(=O)C(CCCCCC)CCCCCCCC] |
| 30 | 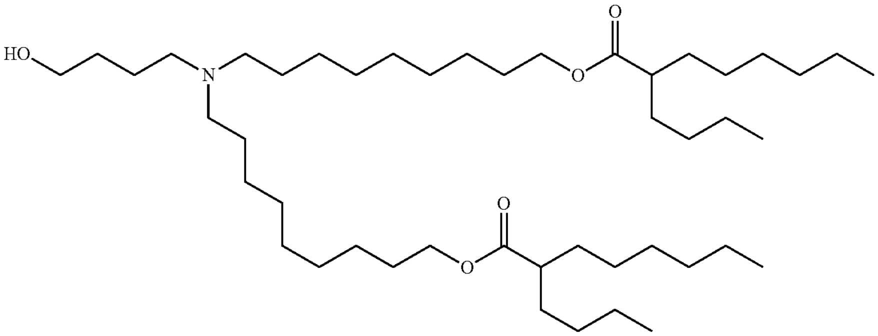 [SMILES: CCCCCCC(CCCC)C(=O)OCCCCCCCCCN(CCCCO)CCCCCCCCCOC(=O)C(CCCC)CCCCCC] |
| 31 | 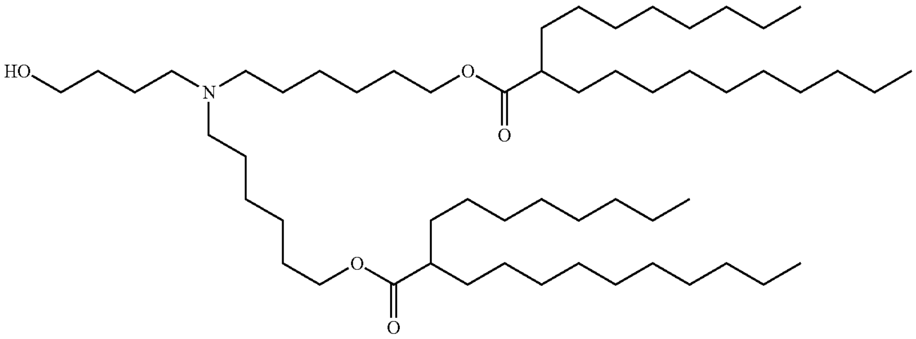 [SMILES: CCCCCCCCCCC(CCCCCCCC)C(=O)OCCCCCCN(CCCCO)CCCCCCOC(=O)C(CCCCCCCC)CCCCCCCCCC] |
| 32 | 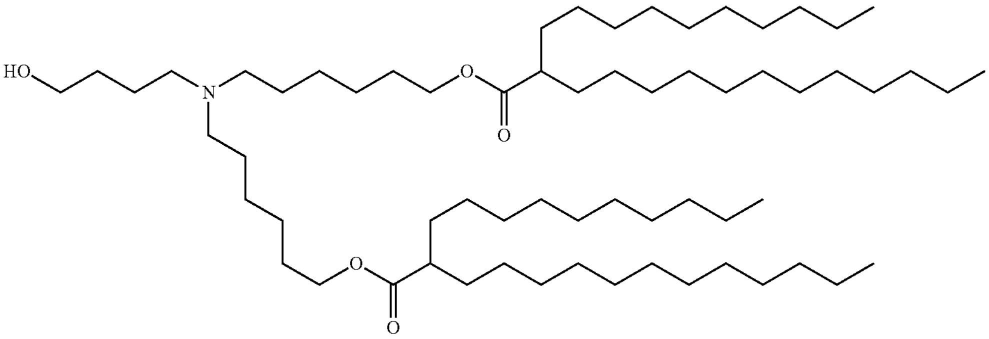 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |

TABLE 10b-continued
| Ionizable lipid number | Structure |
| --- | --- |
| 33 | 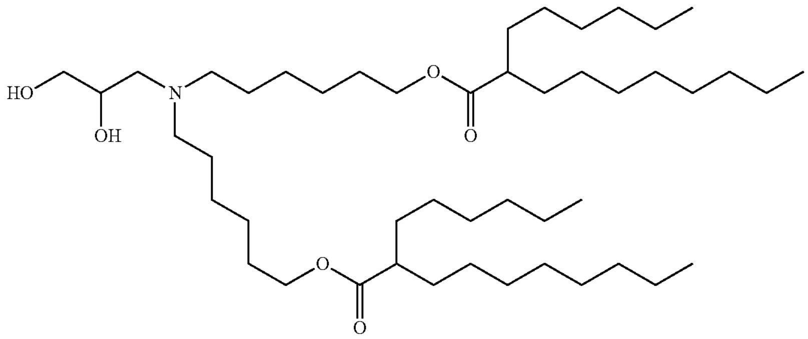 [SMILES: CCCCCCCCC(CCCCCC)C(=O)OCCCCCCN(CCCCCCOC(=O)C(CCCCCC)CCCCCCCC)CC(O)CO] |
| 34 | 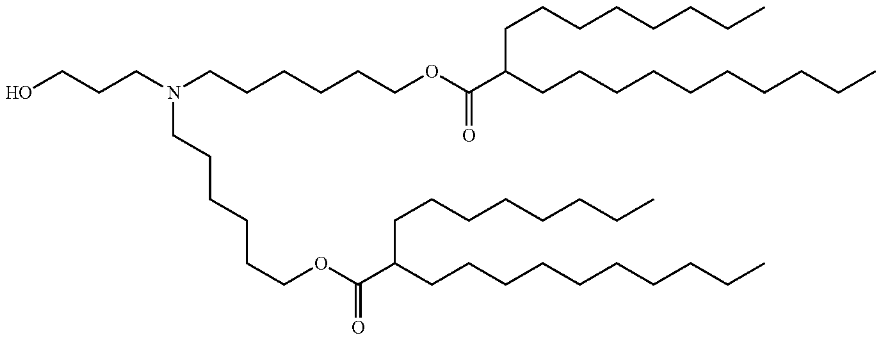 [SMILES: CCCCCCCCCCC(CCCCCCCC)C(=O)OCCCCCCN(CCCO)CCCCCCOC(=O)C(CCCCCCCC)CCCCCCCCCC] |
| 35 | 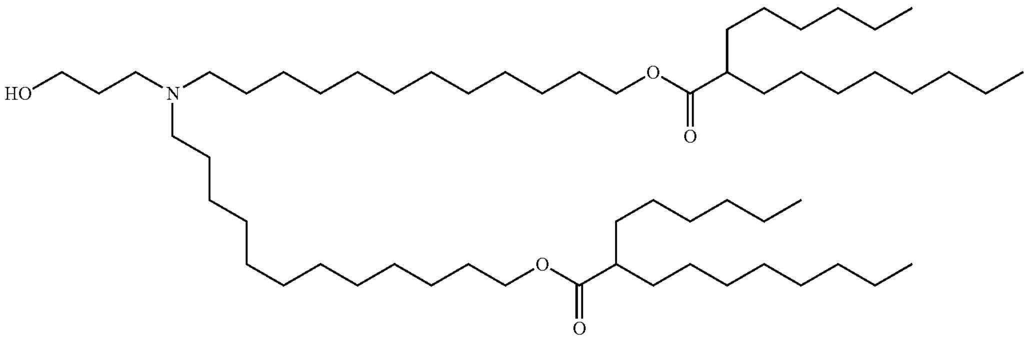 [SMILES: CCCCCCCCC(CCCCCC)C(=O)OCCCCCCCCCCCCN(CCCO)CCCCCCCCCCCCOC(=O)C(CCCCCC)CCCCCCCC] |
| 36 | 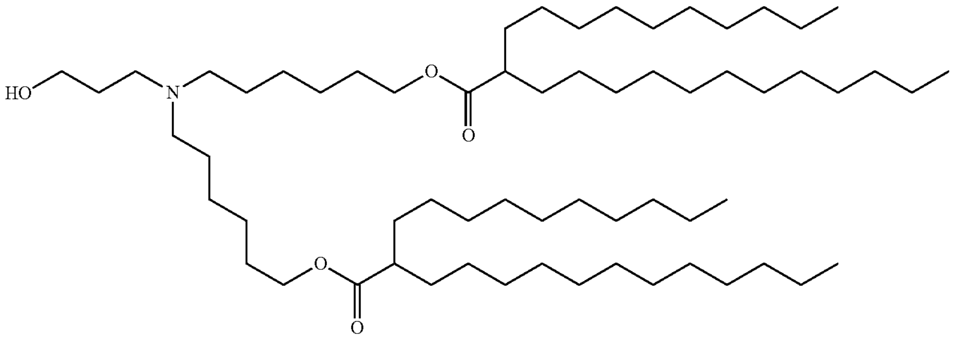 [SMILES: CCCCCCCCCCCCC(CCCCCCCCCC)C(=O)OCCCCCCN(CCCO)CCCCCCOC(=O)C(CCCCCCCCCC)CCCCCCCCCCCC] |

TABLE 10b-continued
| Ionizable lipid number | Structure |
| --- | --- |
| 37 | 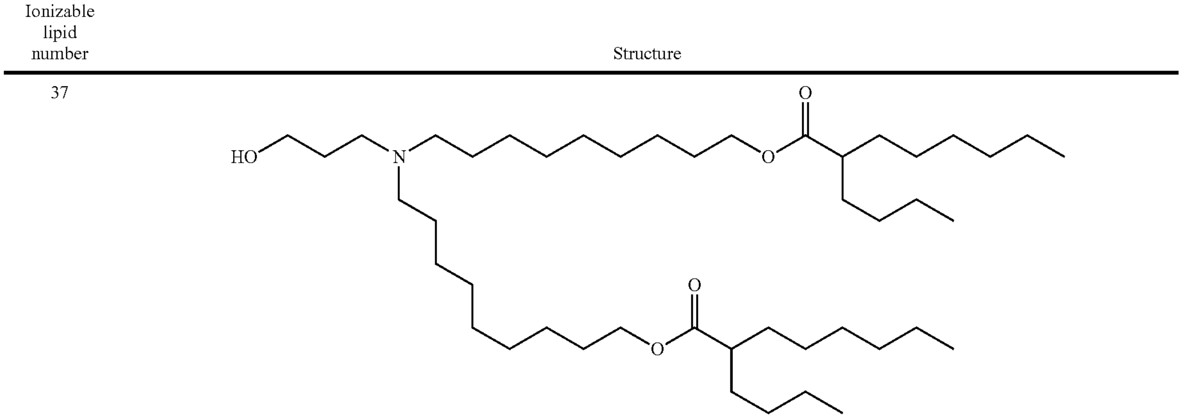 |
| 38 | 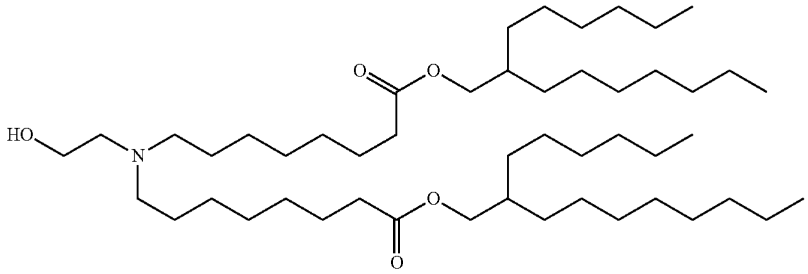 [SMILES: CCCCCCCCC(CCCCCC)COC(=O)CCCCCCCN(CCO)CCCCCCCC(=O)OCC(CCCCCC)CCCCCCC] |
In some embodiments, an ionizable lipid has one of the structures set forth in Table 10 below.
TABLE 10
| Number | Structure |
| --- | --- |
| 1 | 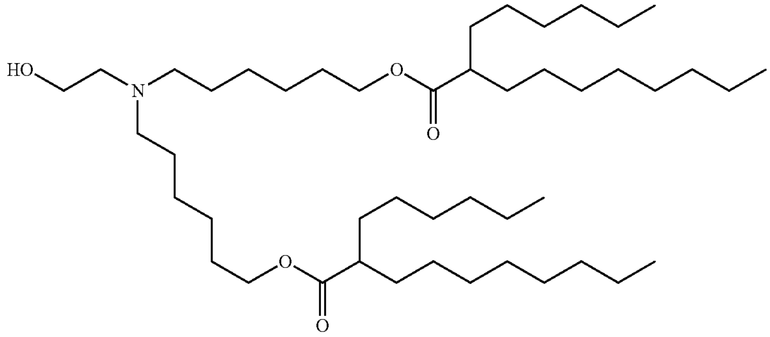 [SMILES: CCCCCCCCC(CCCCCC)C(=O)OCCCCCCN(CCO)CCCCCCOC(=O)C(CCCCCC)CCCCCCCC] |
| 2 | 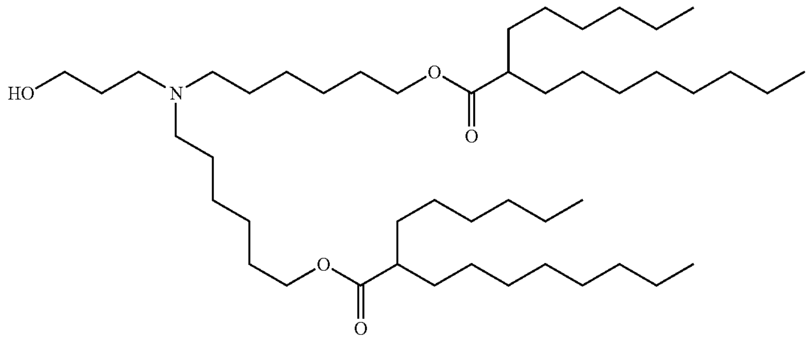 [SMILES: CCCCCCCCC(CCCCCC)C(=O)OCCCCCCN(CCCO)CCCCCCOC(=O)C(CCCCCC)CCCCCCCC] |

TABLE 10-continued
| Number | Structure |
| --- | --- |
| 3 | 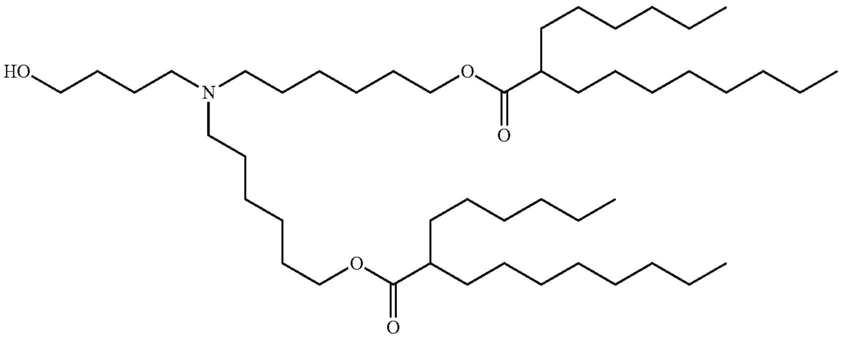 [SMILES: CCCCCCCCC(CCCCCC)C(=O)OCCCCCCN(CCCCO)CCCCCCOC(=O)C(CCCCCC)CCCCCCCC] |
| 4 | 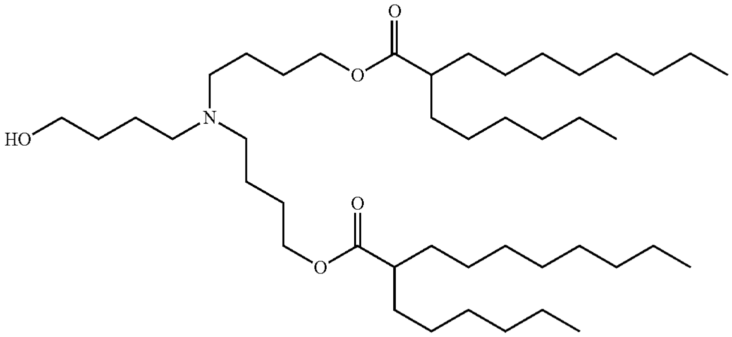 [SMILES: CCCCCCCCC(CCCCCC)C(=O)OCCCCN(CCCCO)CCCCOC(=O)C(CCCCCC)CCCCCCCC] |
| 5 | 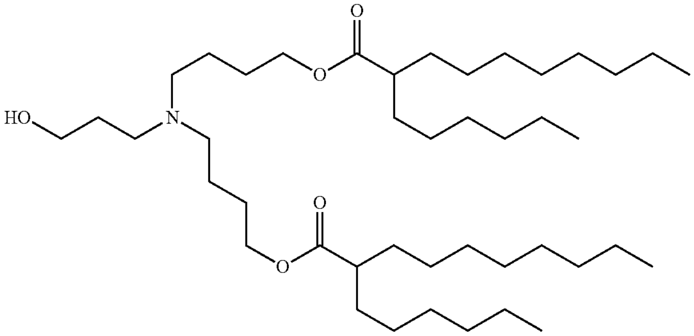 [SMILES: CCCCCCCCC(CCCCCC)C(=O)OCCCCN(CCCO)CCCCOC(=O)C(CCCCCC)CCCCCCCC] |
| 6 | 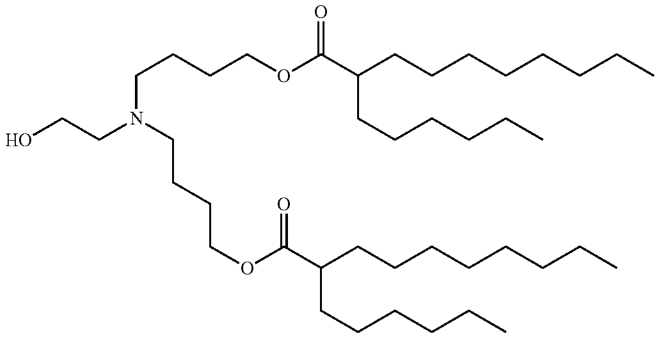 [SMILES: CCCCCCCCC(CCCCCC)C(=O)OCCCCN(CCO)CCCCOC(=O)C(CCCCCC)CCCCCCCC] |

TABLE 10-continued
| Number | Structure |
| --- | --- |
| 7 | 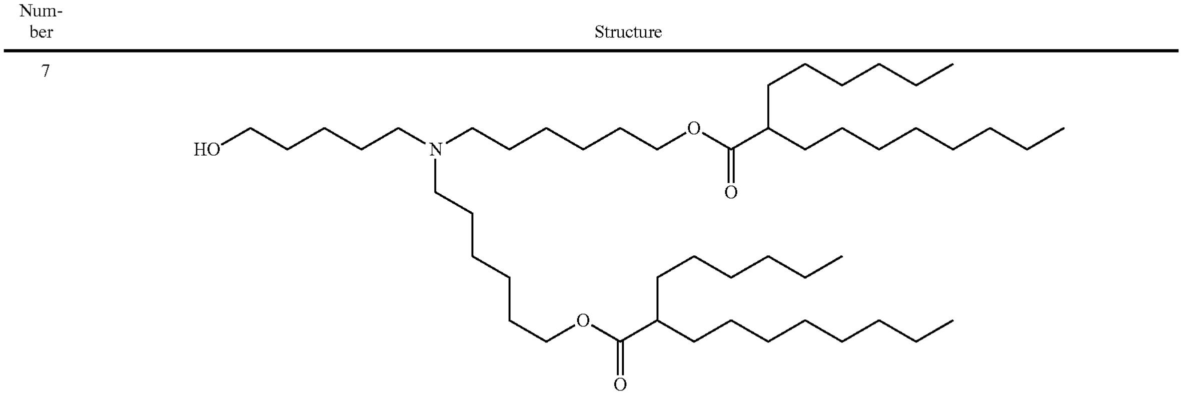 |
| 8 | 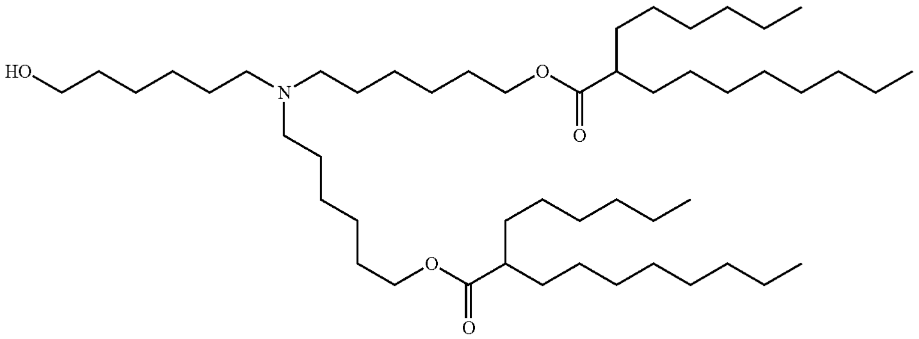 [SMILES: CCCCCCCCC(CCCCCC)C(=O)OCCCCCCN(CCCCCCO)CCCCCCOC(=O)C(CCCCCC)CCCCCCCC] |
| 9 | 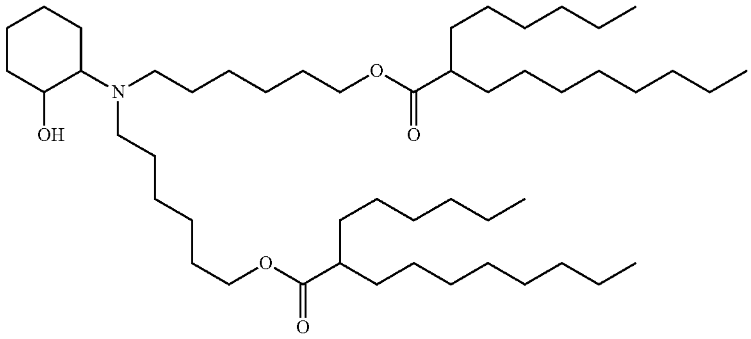 [SMILES: CCCCCCCCC(CCCCCC)C(=O)OCCCCCCN(CCCCCCOC(=O)C(CCCCCC)CCCCCCCC)C1CCCCC1O] |
| 10 | 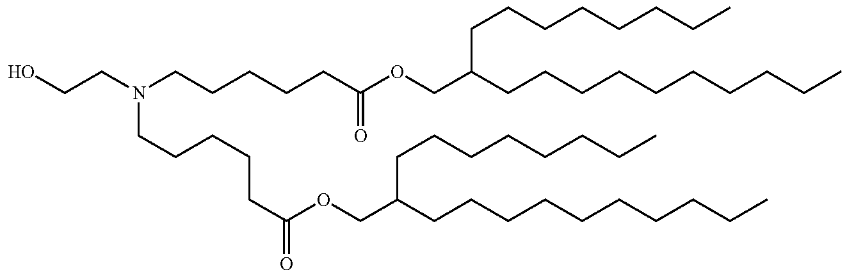 [SMILES: CCCCCCCCCCC(CCCCCCCC)COC(=O)CCCCCN(CCO)CCCCCC(=O)OCC(CCCCCCCC)CCCCCCCCCC] |
| 11 | 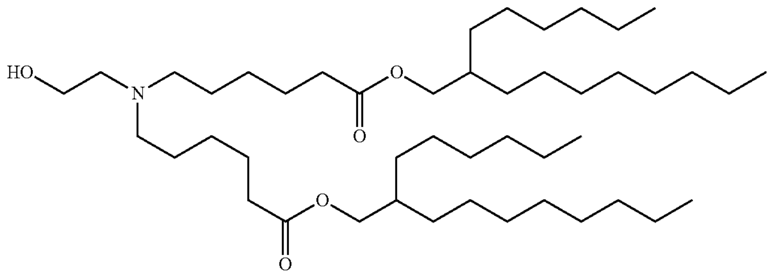 [SMILES: CCCCCCCCC(CCCCCC)COC(=O)CCCCCN(CCO)CCCCCC(=O)OCC(CCCCCC)CCCCCCCC] |

TABLE 10-continued
| Number | Structure |
|---|---|
| 12 | 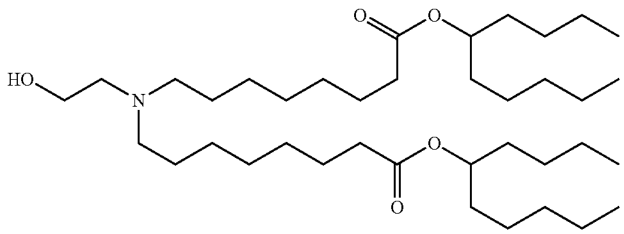 [SMILES: CCCCCC(CCCC)OC(=O)CCCCCCCN(CCO)CCCCCCCC(=O)OC(CCCC)CCCCC] |
| 13 | 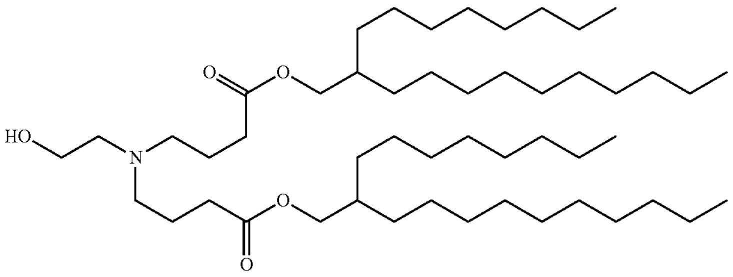 [SMILES: CCCCCCCCCCC(CCCCCCCC)COC(=O)CCCN(CCO)CCCC(=O)OCC(CCCCCCCC)CCCCCCCCCC] |
| 14 | 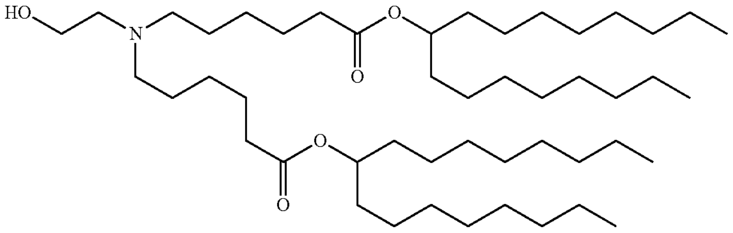 [SMILES: CCCCCCCCC(CCCCCCCC)OC(=O)CCCCCN(CCO)CCCCCC(=O)OC(CCCCCCCC)CCCCCCCC] |
| 15 | 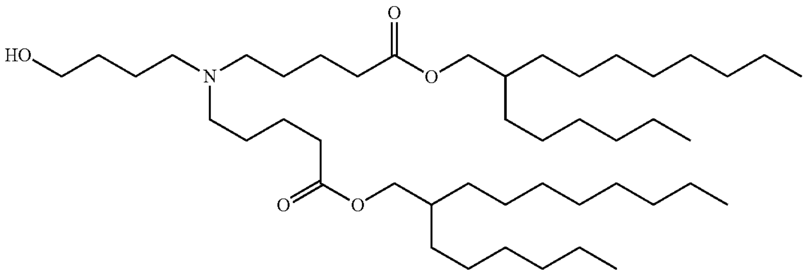 [SMILES: CCCCCCCCC(CCCCCC)COC(=O)CCCCN(CCCCO)CCCCC(=O)OCC(CCCCCC)CCCCCCCC] |
| 16 | 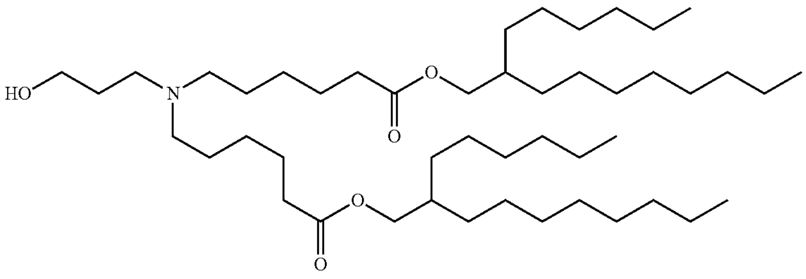 [SMILES: CCCCCCCCC(CCCCCC)COC(=O)CCCCCN(CCCO)CCCCCC(=O)OCC(CCCCCC)CCCCCCCC] |

TABLE 10-continued
| Number | Structure |
| --- | --- |
| 17 | 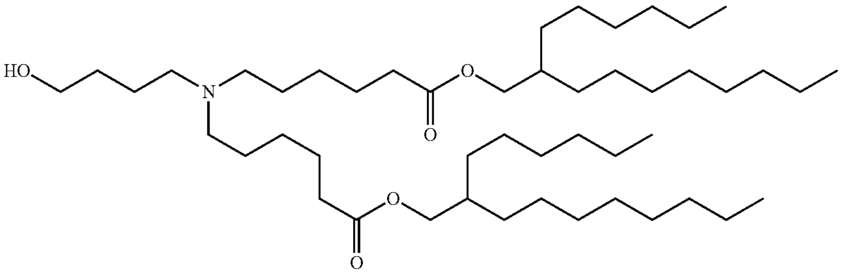 [SMILES: CCCCCCCCC(CCCCCC)COC(=O)CCCCCN(CCCCO)CCCCCC(=O)OCC(CCCCCC)CCCCCCCC] |
| 18 | 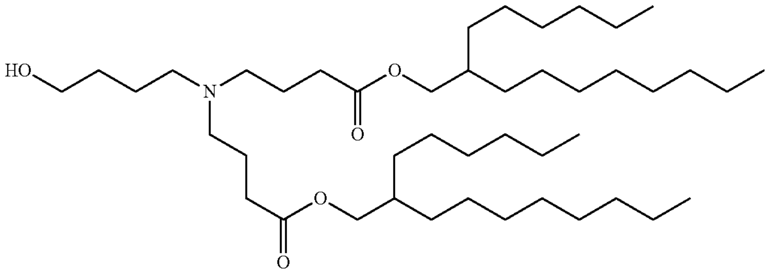 [SMILES: CCCCCCCCC(CCCCCC)COC(=O)CCCN(CCCCO)CCCC(=O)OCC(CCCCCC)CCCCCCCC] |
| 19 | 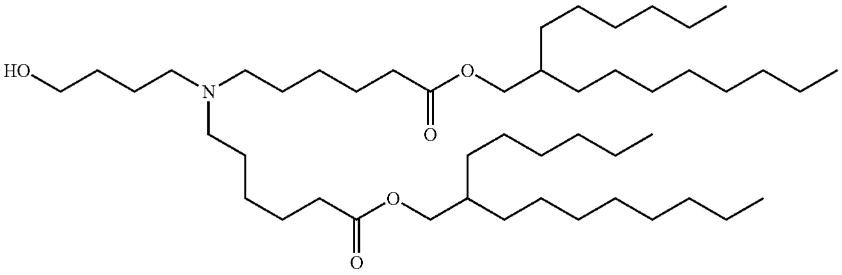 [SMILES: CCCCCCCCC(CCCCCC)COC(=O)CCCCCN(CCCCO)CCCCCC(=O)OCC(CCCCCC)CCCCCCCC] |
| 20 | 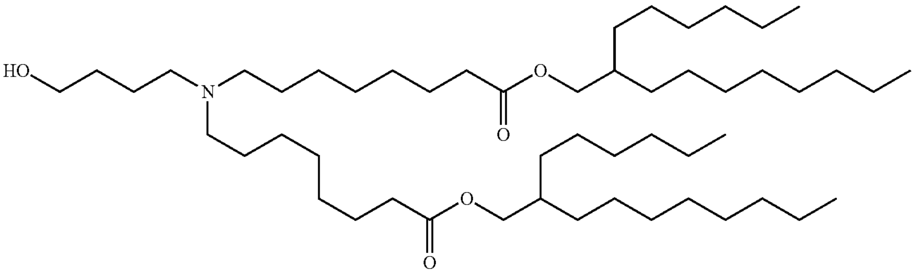 [SMILES: CCCCCCCCC(CCCCCC)COC(=O)CCCCCCCN(CCCCO)CCCCCCCC(=O)OCC(CCCCCC)CCCCCCCC] |
| 21 | 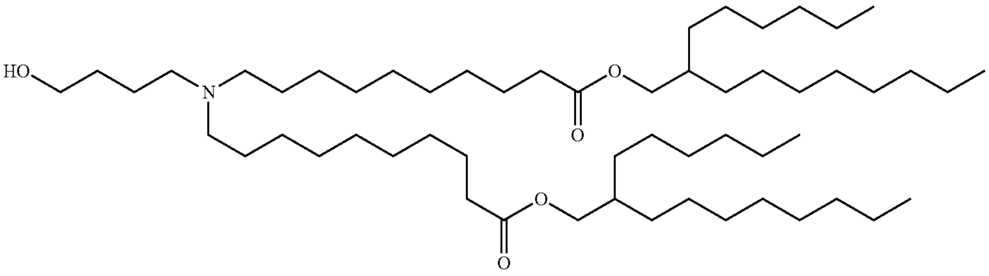 [SMILES: CCCCCCCCC(CCCCCC)COC(=O)CCCCCCCCCN(CCCCO)CCCCCCCCCC(=O)OCC(CCCCCC)CCCCCCCC] |

TABLE 10-continued
| Number | Structure |
| --- | --- |
| 22 | 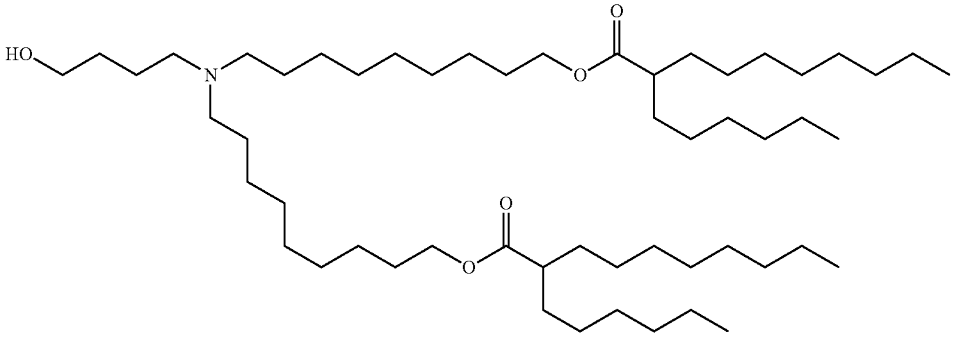 [SMILES: CCCCCCCCC(CCCCCC)C(=O)OCCCCCCCCCN(CCCCO)CCCCCCCCCOC(=O)C(CCCCCC)CCCCCCCC] |
| 23 | 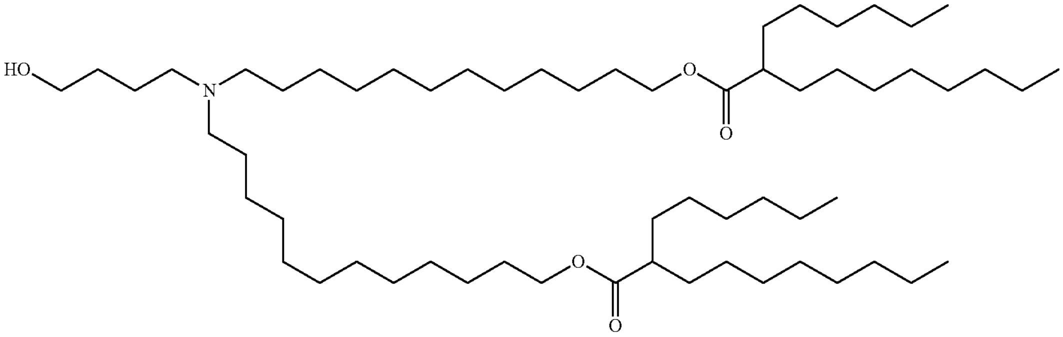 [SMILES: CCCCCCCCC(CCCCCC)C(=O)OCCCCCCCCCCCCN(CCCCO)CCCCCCCCCCCCOC(=O)C(CCCCCC)CCCCCCCC] |
| 24 | 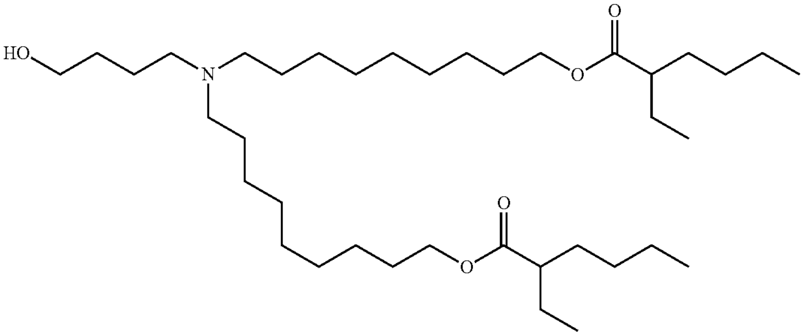 [SMILES: CCCCC(CC)C(=O)OCCCCCCCCCN(CCCCO)CCCCCCCCCOC(=O)C(CC)CCCC] |
| 25 | 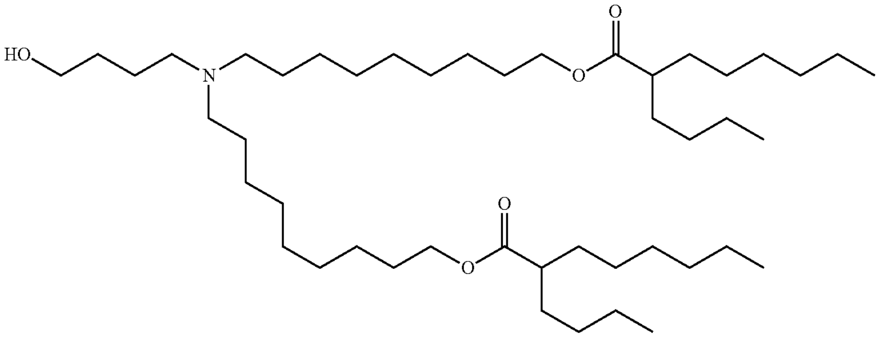 [SMILES: CCCCCCC(CCCC)C(=O)OCCCCCCCCCN(CCCCO)CCCCCCCCCOC(=O)C(CCCC)CCCCCC] |

TABLE 10-continued
| Number | Structure |
| --- | --- |
| 26 | 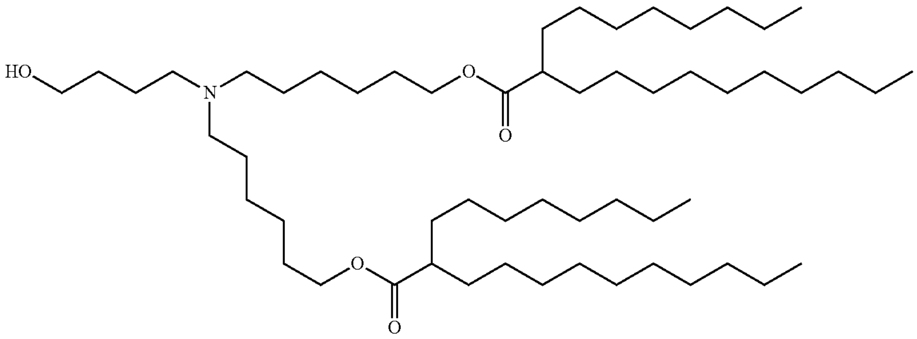 [SMILES: CCCCCCCCCCC(CCCCCCCC)C(=O)OCCCCCCN(CCCCO)CCCCCCOC(=O)C(CCCCCCCC)CCCCCCCCCC] |
| 27 | 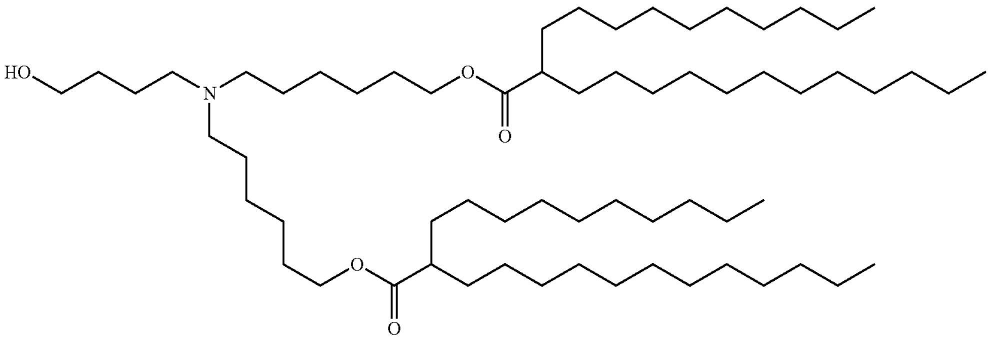 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |
| 28 | 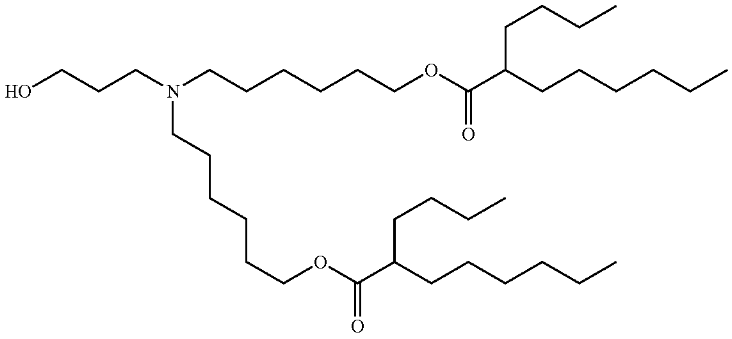 [SMILES: CCCCCCC(CCCC)C(=O)OCCCCCCN(CCCO)CCCCCCOC(=O)C(CCCC)CCCCCC] |
| 29 | 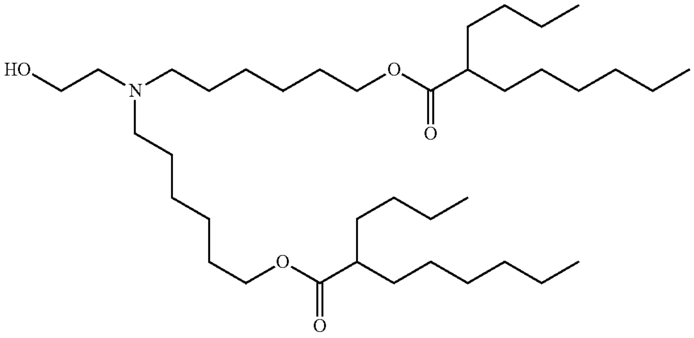 [SMILES: CCCCCCC(CCCC)C(=O)OCCCCCCN(CCO)CCCCCCOC(=O)C(CCCC)CCCCCC] |

TABLE 10-continued
| Number | Structure |
|---|---|
| 30 | 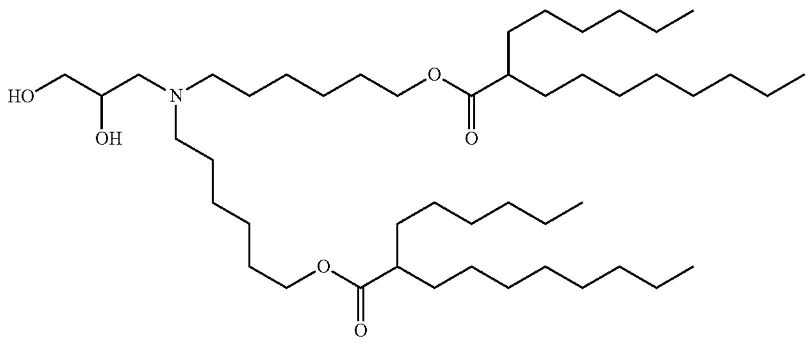 [SMILES: CCCCCCCCC(CCCCCC)C(=O)OCCCCCCN(CCCCCCOC(=O)C(CCCCCC)CCCCCCCC)CC(O)CO] |
| 31 | 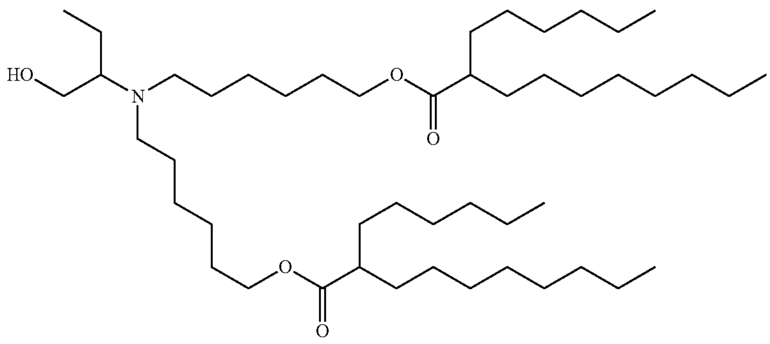 [SMILES: CCCCCCCCC(CCCCCC)C(=O)OCCCCCCN(CCCCCCOC(=O)C(CCCCCC)CCCCCCCC)C(CC)CO] |
| 32 | 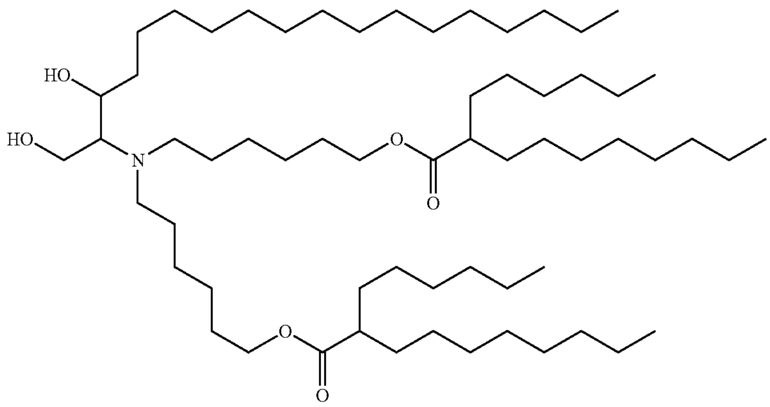 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |
| 33 | 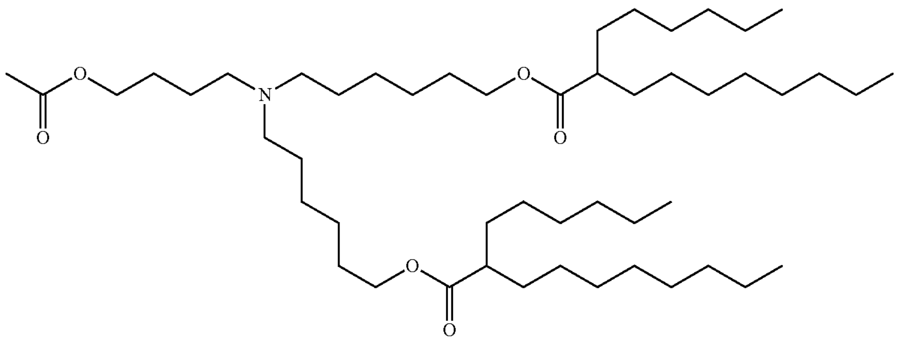 [SMILES: CCCCCCCCC(CCCCCC)C(=O)OCCCCCCN(CCCCCCOC(=O)C(CCCCCC)CCCCCCCC)CCCCOC(C)=O] |

TABLE 10-continued
| Number | Structure |
| --- | --- |
| 34 | 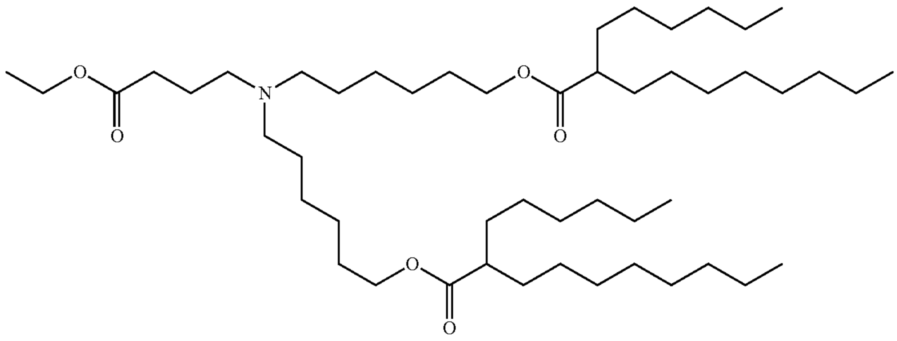 [SMILES: CCCCCCCCC(CCCCCC)C(=O)OCCCCCCN(CCCCCCOC(=O)C(CCCCCC)CCCCCCCC)CCCC(=O)OCC] |
| 35 | 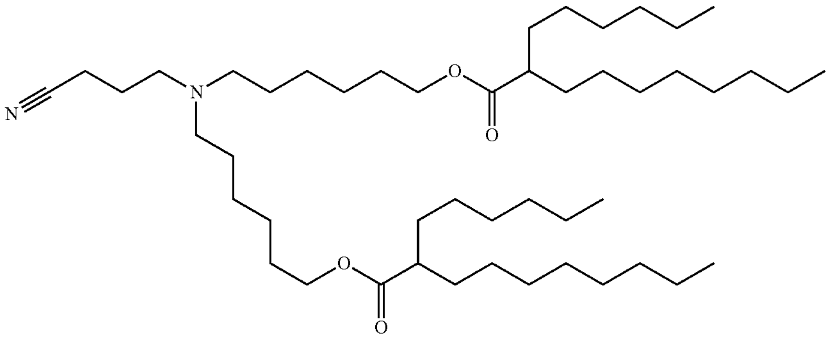 [SMILES: CCCCCCCCC(CCCCCC)C(=O)OCCCCCCN(CCCC#N)CCCCCCOC(=O)C(CCCCCC)CCCCCCCC] |
| 36 | 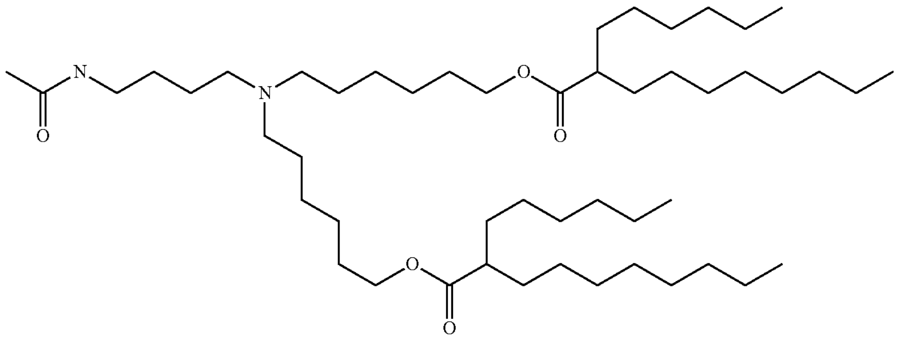 |
| 37 | 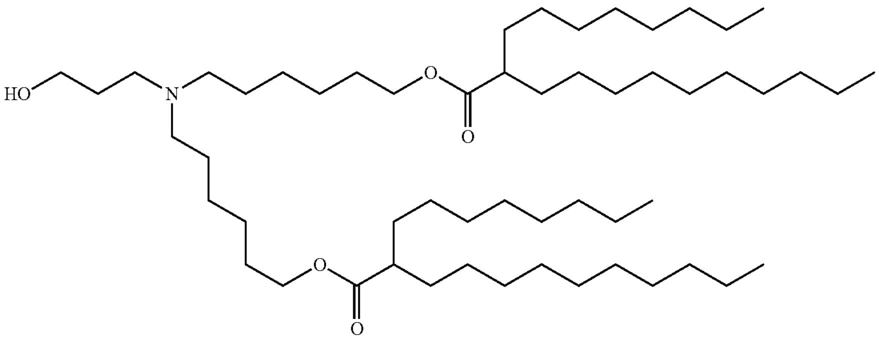 [SMILES: CCCCCCCCCCC(CCCCCCCC)C(=O)OCCCCCCN(CCCO)CCCCCCOC(=O)C(CCCCCCCC)CCCCCCCCCC] |

TABLE 10-continued
| Number | Structure |
|---|---|
| 38 | 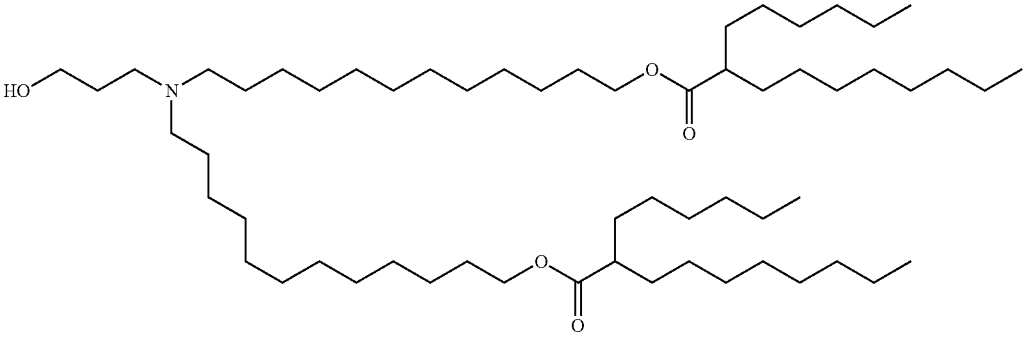 [SMILES: CCCCCCCCC(CCCCCC)C(=O)OCCCCCCCCCCCCN(CCCO)CCCCCCCCCCCCOC(=O)C(CCCCCC)CCCCCCCC] |
| 39 | 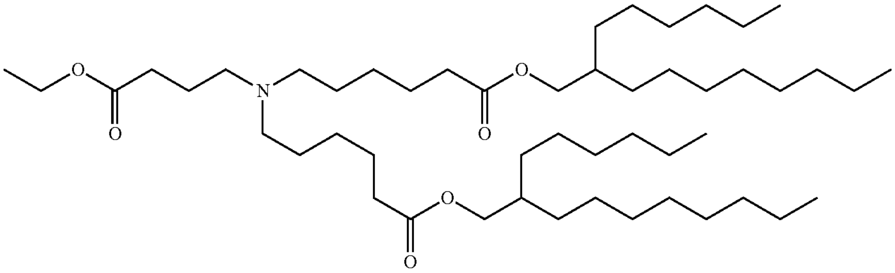 [SMILES: CCCCCCCCC(CCCCCC)COC(=O)CCCCCN(CCCCCC(=O)OCC(CCCCCC)CCCCCCCC)CCCC(=O)OCC] |
| 40 | 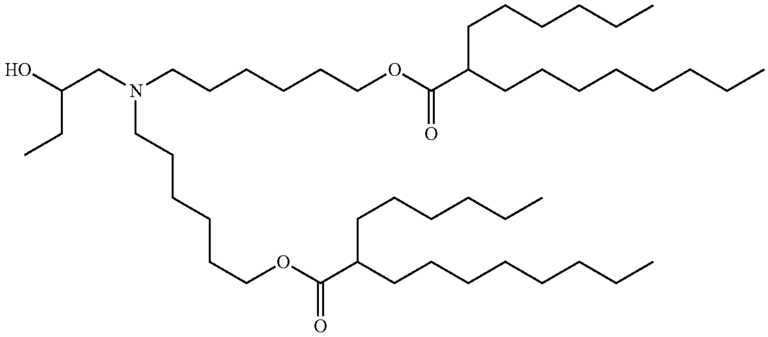 [SMILES: CCCCCCCCC(CCCCCC)C(=O)OCCCCCCN(CCCCCCOC(=O)C(CCCCCC)CCCCCCCC)CC(O)CC] |
| 41 | 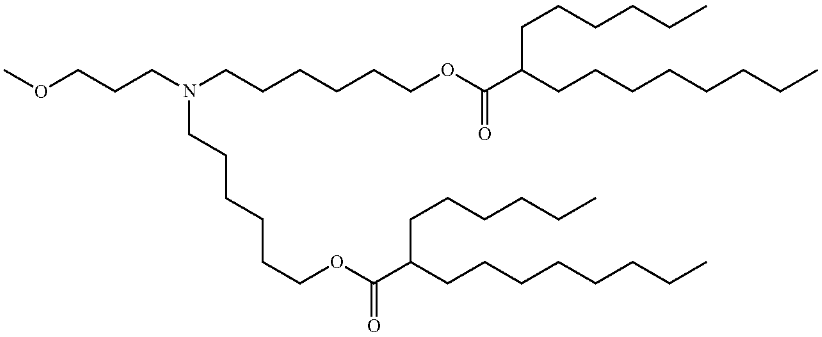 [SMILES: CCCCCCCCC(CCCCCC)C(=O)OCCCCCCN(CCCCCCOC(=O)C(CCCCCC)CCCCCCCC)CCCOC] |

TABLE 10-continued
| Number | Structure |
|---|---|
| 42 | 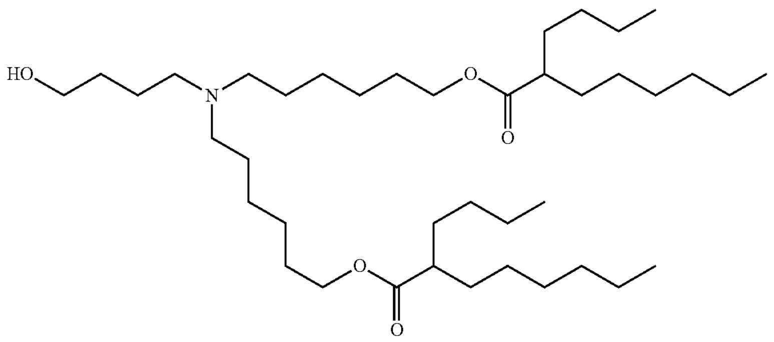 [SMILES: CCCCCCC(CCCC)C(=O)OCCCCCCN(CCCCO)CCCCCCOC(=O)C(CCCC)CCCCCC] |
| 43 | 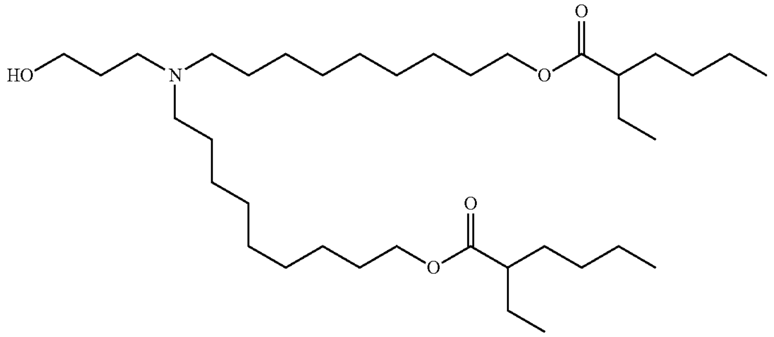 [SMILES: CCCCC(CC)C(=O)OCCCCCCCCCN(CCCO)CCCCCCCCCOC(=O)C(CC)CCCC] |
| 44 | 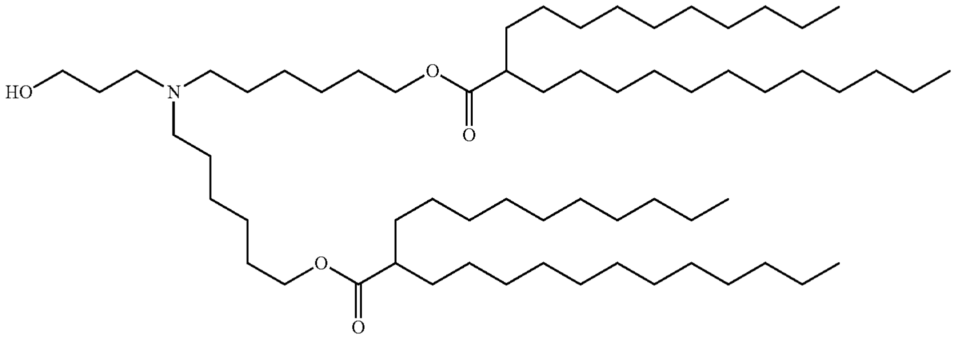 [SMILES: CCCCCCCCCCCCC(CCCCCCCCCC)C(=O)OCCCCCCN(CCCO)CCCCCCOC(=O)C(CCCCCCCCCC)CCCCCCCCCCCC] |
| 45 | 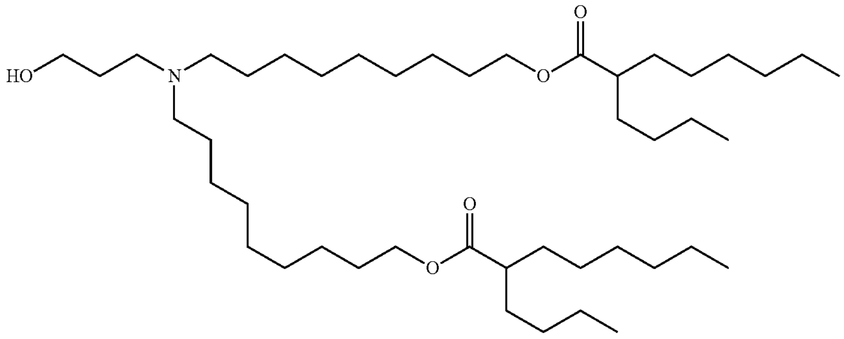 [SMILES: CCCCCCC(CCCC)C(=O)OCCCCCCCCCN(CCCO)CCCCCCCCCOC(=O)C(CCCC)CCCCCC] |

TABLE 10-continued
| Number | Structure |
| --- | --- |
| 46 | 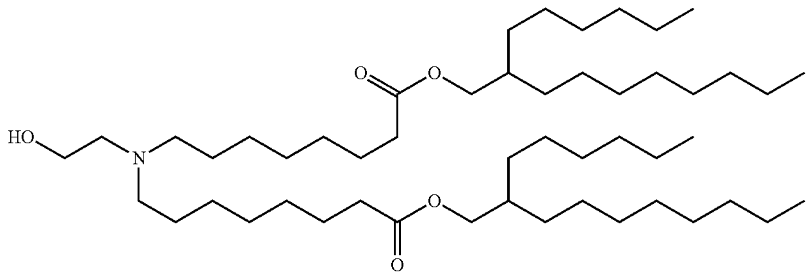 [SMILES: CCCCCCCCC(CCCCCC)COC(=O)CCCCCCCN(CCO)CCCCCCCC(=O)OCC(CCCCCC)CCCCCCCC] |
| 47 | 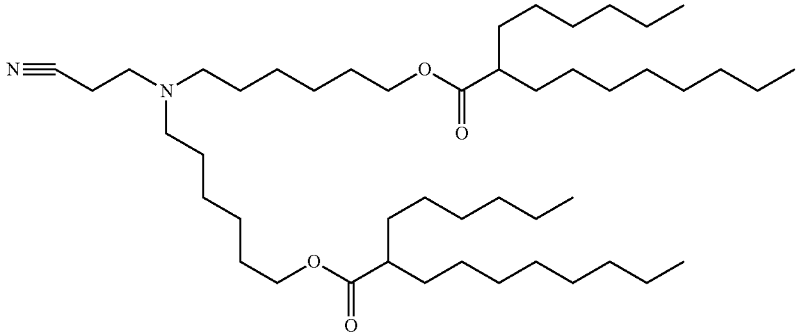 [SMILES: CCCCCCCCC(CCCCCC)C(=O)OCCCCCCN(CCC#N)CCCCCCOC(=O)C(CCCCCC)CCCCCCCC] |
| 48 | 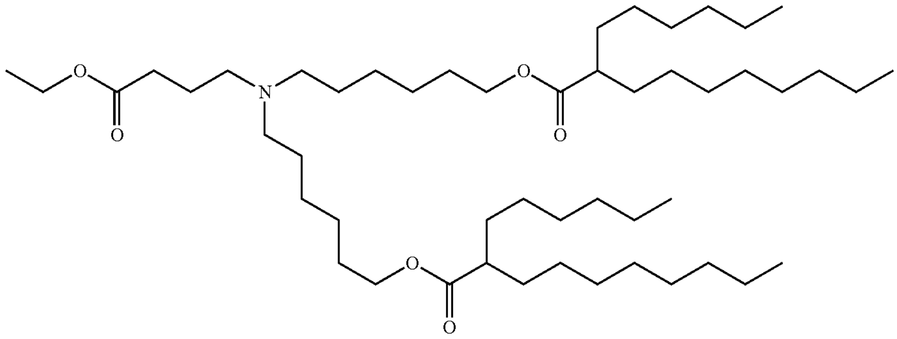 [SMILES: CCCCCCCCC(CCCCCC)C(=O)OCCCCCCN(CCCCCCOC(=O)C(CCCCCC)CCCCCCCC)CCCC(=O)OCC] |
| 49 | 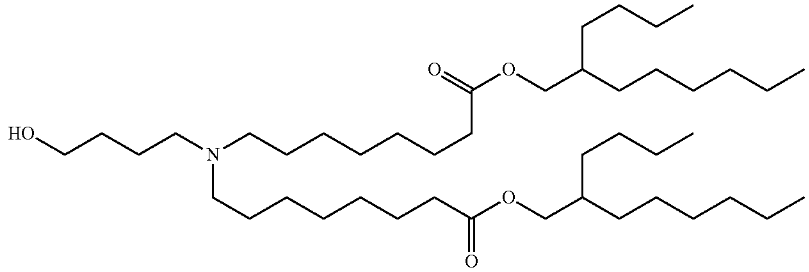 [SMILES: CCCCCCC(CCCC)COC(=O)CCCCCCCN(CCCCO)CCCCCCCC(=O)OCC(CCCC)CCCCCC] |
In some embodiments, the ionizable lipid has one of the structures set forth in Table 11 below. In some embodiments, the ionizable lipid as set forth in Table 11 is as described in international patent application PCT/US2010/061058.
TABLE 11
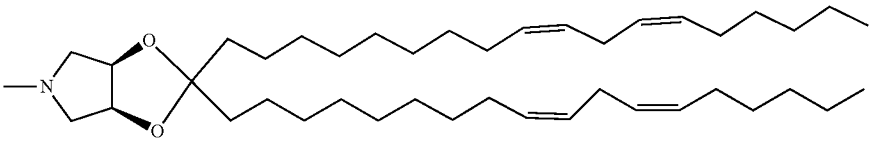
meso, cis TABLE 11-continued
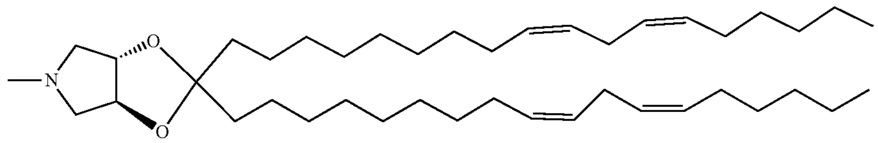 [SMILES: CCCCC/C=C\C/C=C\CCCCCCCCC1(CCCCCCCC/C=C\C/C=C\CCCCC)O[C@H]2CN(C)C[C@@H]2O1]
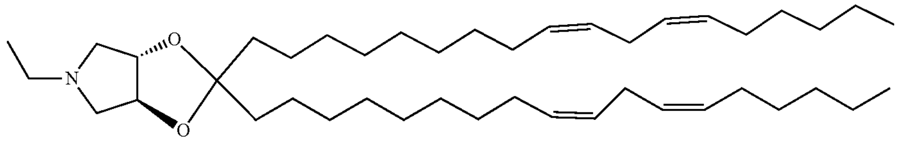 [SMILES: CCCCC/C=C\C/C=C\CCCCCCCCC1(CCCCCCCC/C=C\C/C=C\CCCCC)O[C@H]2CN(CC)C[C@@H]2O1]
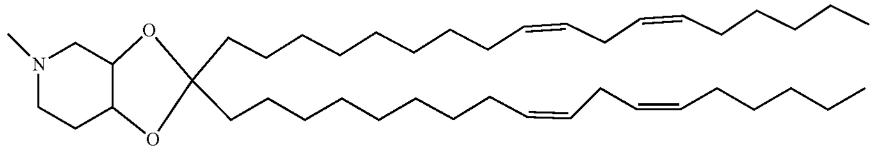
Racemic, cis
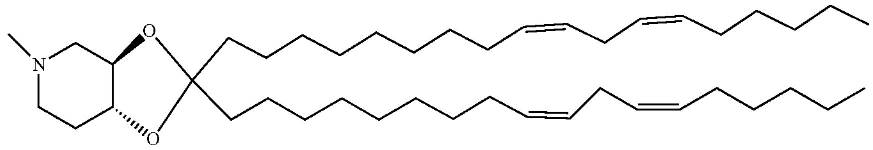
Racemic, trans
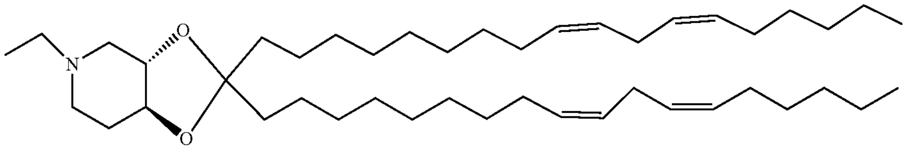 [SMILES: CCCCC/C=C\C/C=C\CCCCCCCCC1(CCCCCCCC/C=C\C/C=C\CCCCC)O[C@H]2CCN(CC)C[C@@H]2O1]
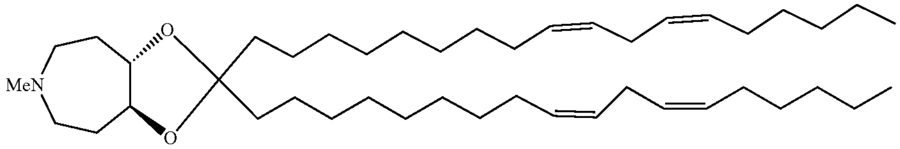 [SMILES: CCCCC/C=C\C/C=C\CCCCCCCCC1(CCCCCCCC/C=C\C/C=C\CCCCC)O[C@H]2CCN(C)CC[C@@H]2O1]
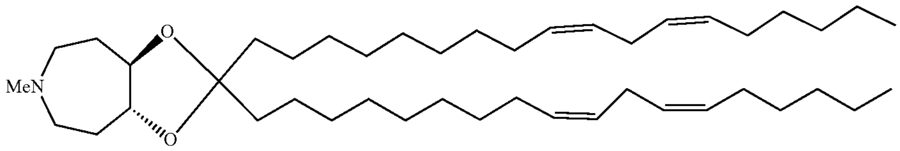 [SMILES: CCCCC/C=C\C/C=C\CCCCCCCCC1(CCCCCCCC/C=C\C/C=C\CCCCC)O[C@@H]2CCN(C)CC[C@H]2O1]
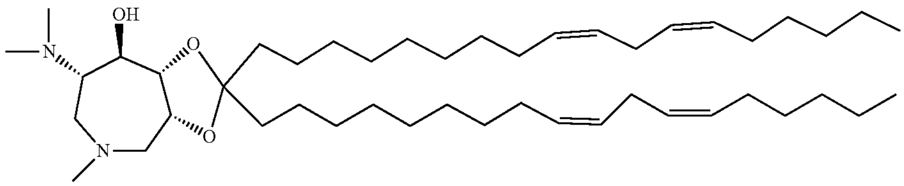 [SMILES: CCCCC/C=C\C/C=C\CCCCCCCCC1(CCCCCCCC/C=C\C/C=C\CCCCC)O[C@H]2[C@H](O)[C@@H](N(C)C)CN(C)C[C@H]2O1]
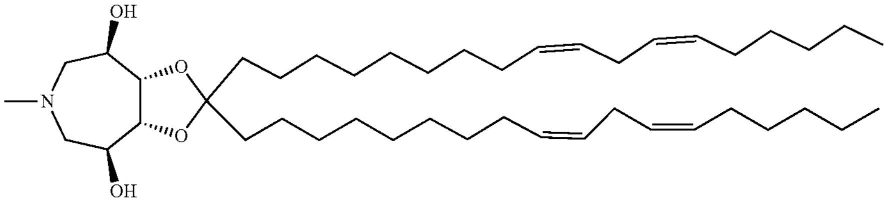 [SMILES: CCCCC/C=C\C/C=C\CCCCCCCCC1(CCCCCCCC/C=C\C/C=C\CCCCC)O[C@@H]2[C@H](O1)[C@@H](O)CN(C)C[C@H]2O]

TABLE 11-continued
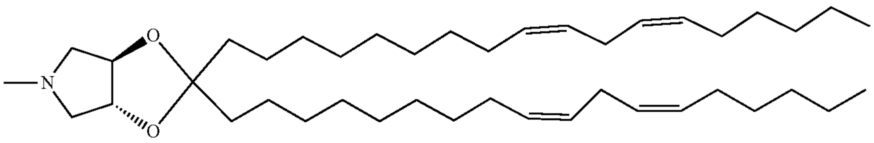
Racemic, trans
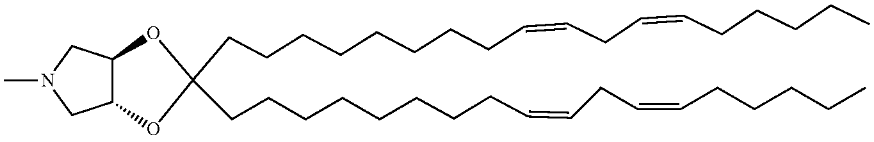 [SMILES: CCCCC/C=C\C/C=C\CCCCCCCCC1(CCCCCCCC/C=C\C/C=C\CCCCC)O[C@@H]2CN(C)C[C@H]2O1]
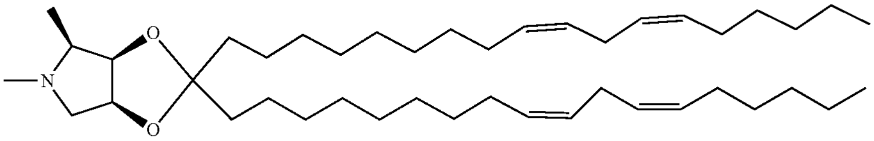 [SMILES: CCCCC/C=C\C/C=C\CCCCCCCCC1(CCCCCCCC/C=C\C/C=C\CCCCC)O[C@H]2[C@H](CN(C)[C@H]2C)O1]
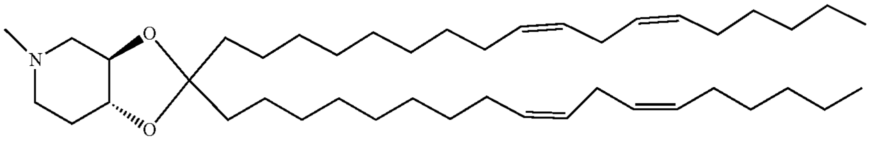 [SMILES: CCCCC/C=C\C/C=C\CCCCCCCCC1(CCCCCCCC/C=C\C/C=C\CCCCC)O[C@@H]2CCN(C)C[C@H]2O1]
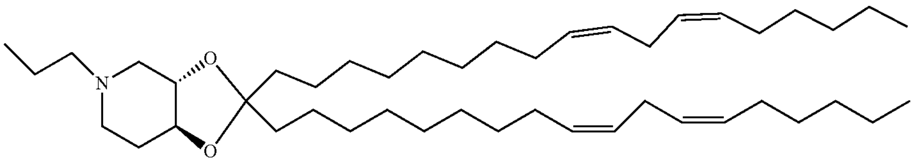 [SMILES: CCCCC/C=C\C/C=C\CCCCCCCCC1(CCCCCCCC/C=C\C/C=C\CCCCC)O[C@H]2CCN(CCC)C[C@@H]2O1]
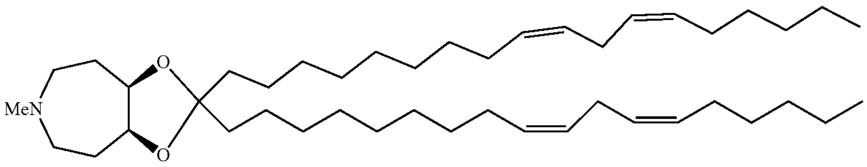 [SMILES: CCCCC/C=C\C/C=C\CCCCCCCCC1(CCCCCCCC/C=C\C/C=C\CCCCC)O[C@H]2CCN(C)CC[C@H]2O1]
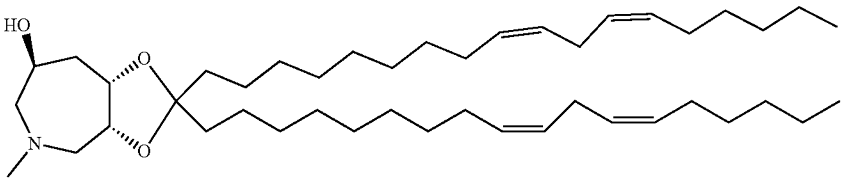 [SMILES: CCCCC/C=C\C/C=C\CCCCCCCCC1(CCCCCCCC/C=C\C/C=C\CCCCC)O[C@H]2C[C@H](O)CN(C)C[C@H]2O1]
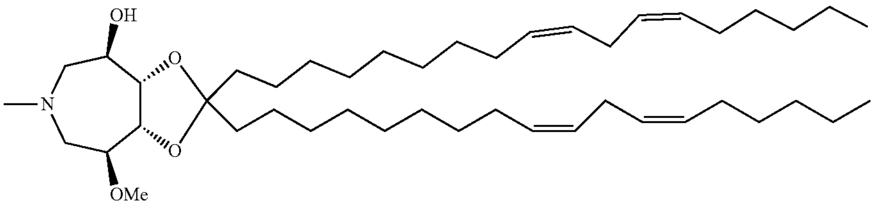 [SMILES: CCCCC/C=C\C/C=C\CCCCCCCCC1(CCCCCCCC/C=C\C/C=C\CCCCC)O[C@@H]2[C@H](O1)[C@@H](OC)CN(C)C[C@H]2O]

TABLE 11-continued
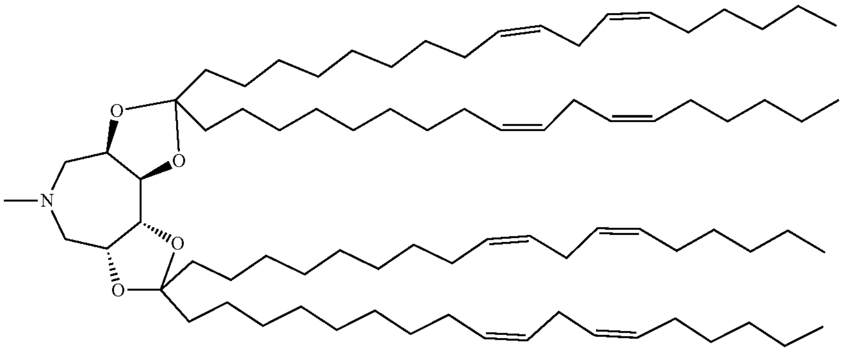 [SMILES: CCCCC/C=C\C/C=C\CCCCCCCCC1(CCCCCCCC/C=C\C/C=C\CCCCC)O[C@H]2[C@@H]3OC(CCCCCCCC/C=C\C/C=C\CCCCC)(CCCCCCCC/C=C\C/C=C\CCCCC)O[C@@H]3CN(C)C[C@H]2O1]
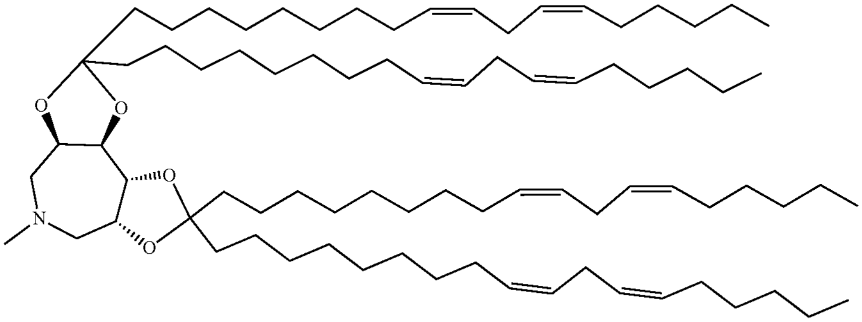 [SMILES: CCCCC/C=C\C/C=C\CCCCCCCCC1(CCCCCCCC/C=C\C/C=C\CCCCC)O[C@H]2[C@@H]3OC(CCCCCCCC/C=C\C/C=C\CCCCC)(CCCCCCCC/C=C\C/C=C\CCCCC)O[C@@H]3CN(C)C[C@H]2O1]
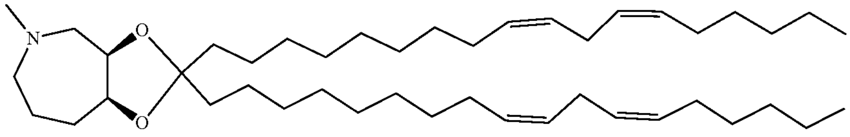 [SMILES: CCCCC/C=C\C/C=C\CCCCCCCCC1(CCCCCCCC/C=C\C/C=C\CCCCC)O[C@H]2CCCN(C)C[C@H]2O1]
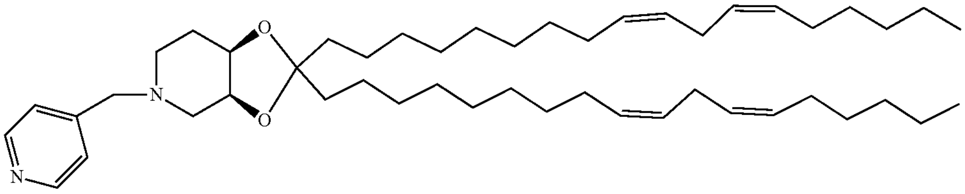 [SMILES: CCCCC/C=C\C/C=C\CCCCCCCCC1(CCCCCCCC/C=C\C/C=C\CCCCC)O[C@H]2CN(Cc3ccncc3)CC[C@H]2O1]
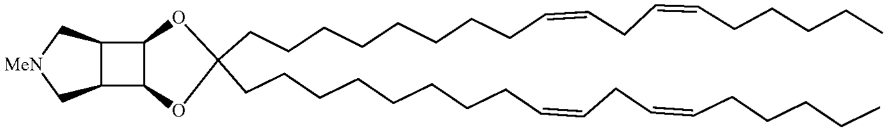 [SMILES: CCCCC/C=C\C/C=C\CCCCCCCCC1(CCCCCCCC/C=C\C/C=C\CCCCC)O[C@@H]2[C@@H]3CN(C)C[C@@H]3[C@@H]2O1]
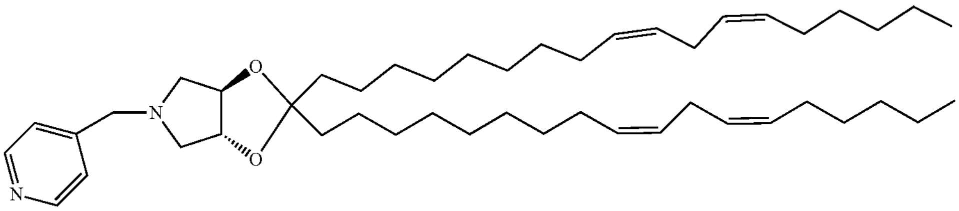 [SMILES: CCCCC/C=C\C/C=C\CCCCCCCCC1(CCCCCCCC/C=C\C/C=C\CCCCC)O[C@@H]2CN(Cc3ccncc3)C[C@H]2O1]
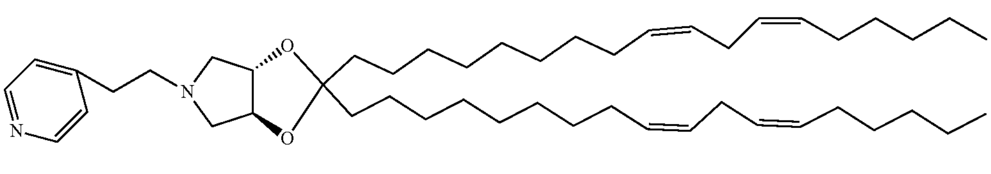 [SMILES: CCCCC/C=C\C/C=C\CCCCCCCCC1(CCCCCCCC/C=C\C/C=C\CCCCC)O[C@H]2CN(CCc3ccncc3)C[C@@H]2O1]

TABLE 11-continued
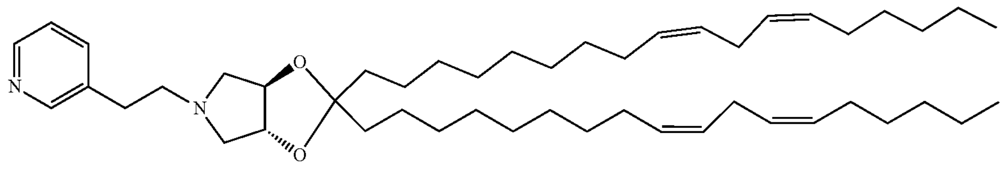 [SMILES: CCCCC/C=C\C/C=C\CCCCCCCCC1(CCCCCCCC/C=C\C/C=C\CCCCC)O[C@@H]2CN(CCc3cccnc3)C[C@H]2O1]
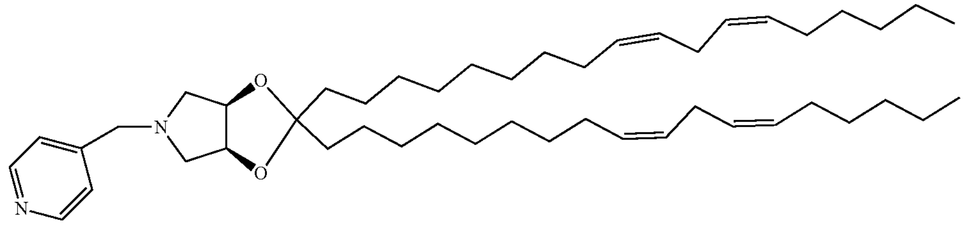 [SMILES: CCCCC/C=C\C/C=C\CCCCCCCCC1(CCCCCCCC/C=C\C/C=C\CCCCC)O[C@H]2CN(Cc3ccncc3)C[C@H]2O1]
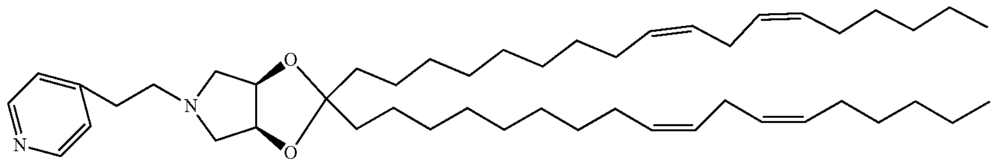 [SMILES: CCCCC/C=C\C/C=C\CCCCCCCCC1(CCCCCCCC/C=C\C/C=C\CCCCC)O[C@H]2CN(CCc3ccncc3)C[C@H]2O1]
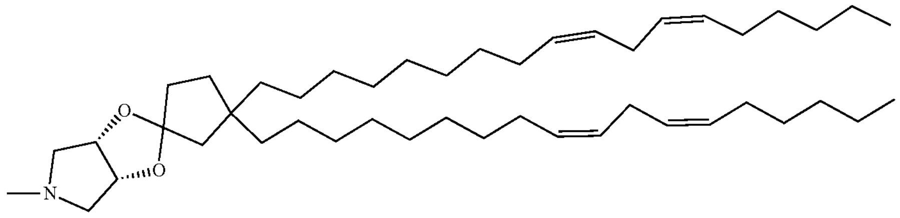
cis Racemic and optically pure
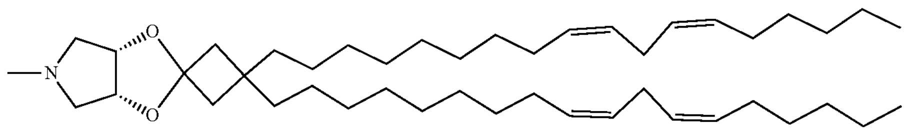
Racemic and optically pure
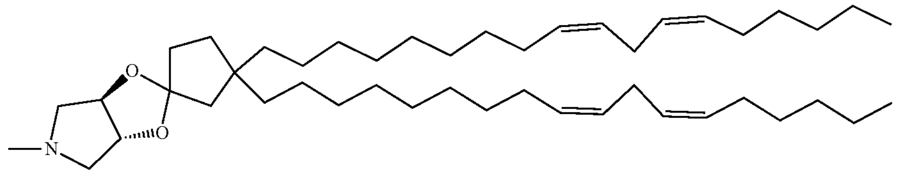 [SMILES: CCCCC/C=C\C/C=C\CCCCCCCCC1(CCCCCCCC/C=C\C/C=C\CCCCC)CCC2(C1)O[C@@H]1CN(C)C[C@H]1O2]
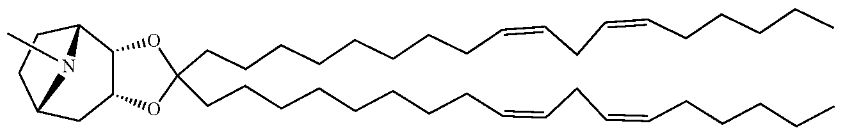 [SMILES: CCCCC/C=C\C/C=C\CCCCCCCCC1(CCCCCCCC/C=C\C/C=C\CCCCC)O[C@H]2[C@H]3CC[C@@H](C[C@H]2O1)N3C]
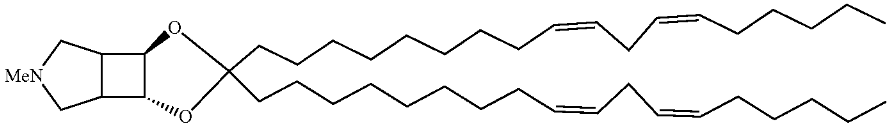 [SMILES: CCCCC/C=C\C/C=C\CCCCCCCCC1(CCCCCCCC/C=C\C/C=C\CCCCC)O[C@@H]2C3CN(C)CC3[C@H]2O1]
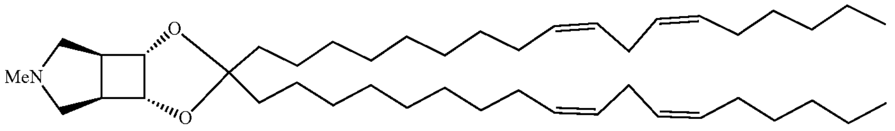 [SMILES: CCCCC/C=C\C/C=C\CCCCCCCCC1(CCCCCCCC/C=C\C/C=C\CCCCC)O[C@@H]2[C@H]3CN(C)C[C@H]3[C@@H]2O1]

TABLE 11-continued
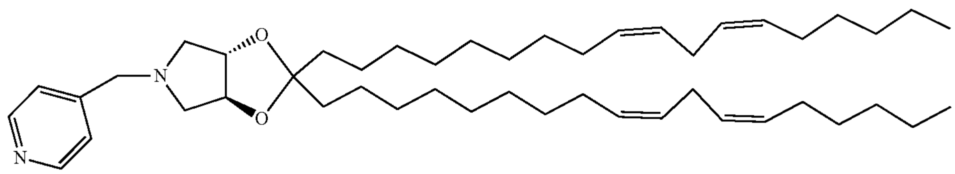 [SMILES: CCCCC/C=C\C/C=C\CCCCCCCCC1(CCCCCCCC/C=C\C/C=C\CCCCC)O[C@H]2CN(Cc3ccncc3)C[C@@H]2O1]
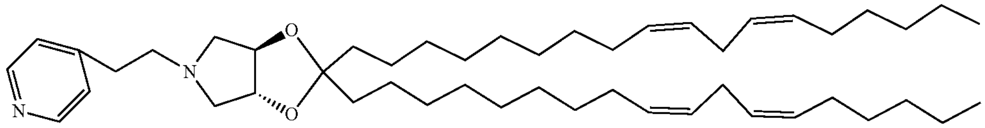 [SMILES: CCCCC/C=C\C/C=C\CCCCCCCCC1(CCCCCCCC/C=C\C/C=C\CCCCC)O[C@@H]2CN(CCc3ccncc3)C[C@H]2O1]
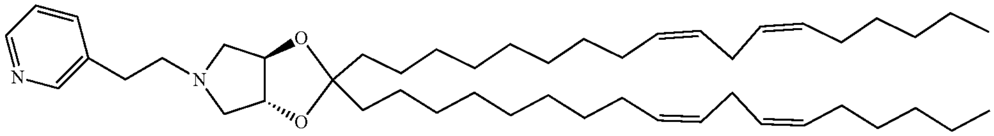 [SMILES: CCCCC/C=C\C/C=C\CCCCCCCCC1(CCCCCCCC/C=C\C/C=C\CCCCC)O[C@@H]2CN(CCc3cccnc3)C[C@H]2O1]
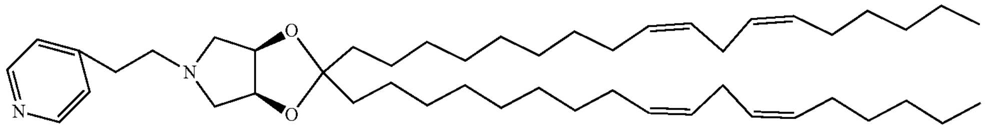 [SMILES: CCCCC/C=C\C/C=C\CCCCCCCCC1(CCCCCCCC/C=C\C/C=C\CCCCC)O[C@H]2CN(CCc3ccncc3)C[C@H]2O1]
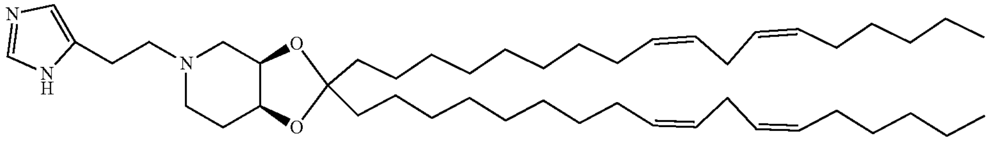 [SMILES: CCCCC/C=C\C/C=C\CCCCCCCCC1(CCCCCCCC/C=C\C/C=C\CCCCC)O[C@H]2CCN(CCc3cnc[nH]3)C[C@H]2O1]
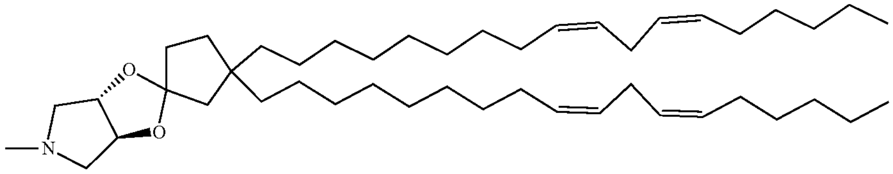 [SMILES: CCCCC/C=C\C/C=C\CCCCCCCCC1(CCCCCCCC/C=C\C/C=C\CCCCC)CCC2(C1)O[C@H]1CN(C)C[C@@H]1O2]
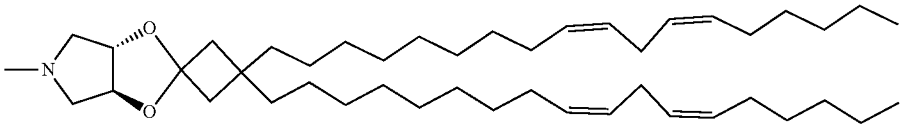 [SMILES: CCCCC/C=C\C/C=C\CCCCCCCCC1(CCCCCCCC/C=C\C/C=C\CCCCC)CC2(C1)O[C@H]1CN(C)C[C@@H]1O2]
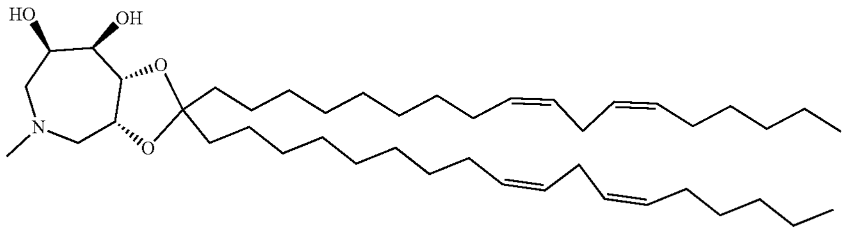 [SMILES: CCCCC/C=C\C/C=C\CCCCCCCCC1(CCCCCCCC/C=C\C/C=C\CCCCC)O[C@H]2[C@H](O)[C@H](O)CN(C)C[C@H]2O1]
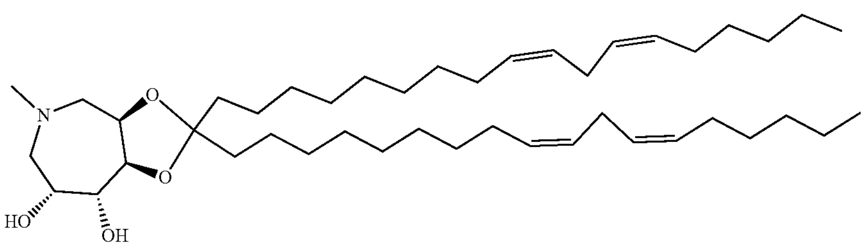 [SMILES: CCCCC/C=C\C/C=C\CCCCCCCCC1(CCCCCCCC/C=C\C/C=C\CCCCC)O[C@H]2[C@H](O)[C@H](O)CN(C)C[C@H]2O1]

TABLE 11-continued
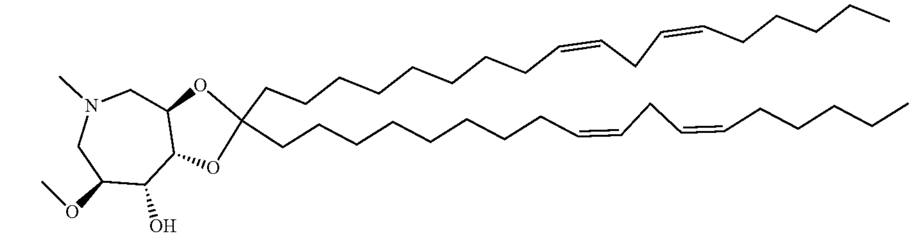 [SMILES: CCCCC/C=C\C/C=C\CCCCCCCCC1(CCCCCCCC/C=C\C/C=C\CCCCC)O[C@@H]2[C@H](O)[C@@H](OC)CN(C)C[C@H]2O1]
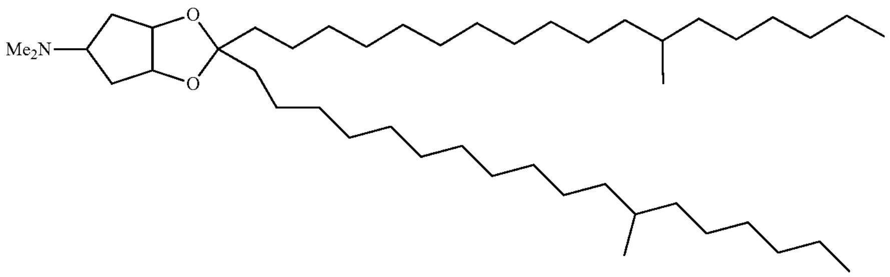 [SMILES: CCCCCCC(C)CCCCCCCCCCCC1(CCCCCCCCCCCC(C)CCCCCC)OC2CC(N(C)C)CC2O1]
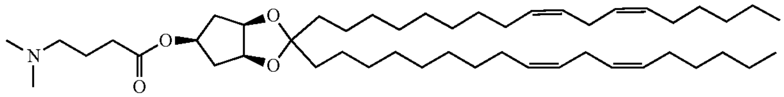 [SMILES: CCCCC/C=C\C/C=C\CCCCCCCCC1(CCCCCCCC/C=C\C/C=C\CCCCC)O[C@H]2C[C@@H](OC(=O)CCCN(C)C)C[C@H]2O1]
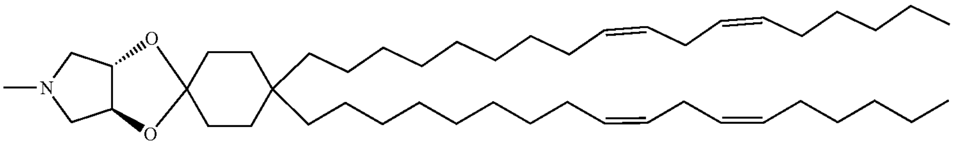 [SMILES: CCCCC/C=C\C/C=C\CCCCCCCCC1(CCCCCCCC/C=C\C/C=C\CCCCC)CCC2(CC1)O[C@H]1CN(C)C[C@@H]1O2]
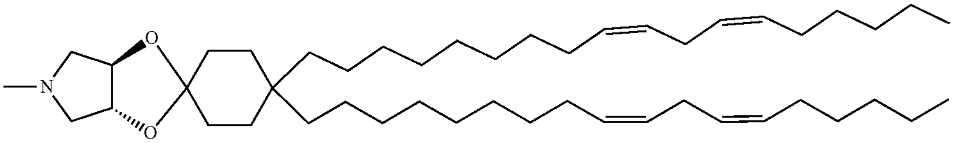 [SMILES: CCCCC/C=C\C/C=C\CCCCCCCCC1(CCCCCCCC/C=C\C/C=C\CCCCC)CCC2(CC1)O[C@@H]1CN(C)C[C@H]1O2]
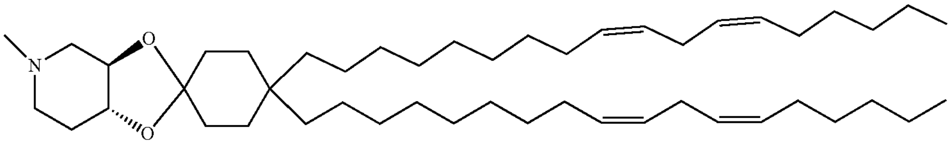 [SMILES: CCCCC/C=C\C/C=C\CCCCCCCCC1(CCCCCCCC/C=C\C/C=C\CCCCC)CCC2(CC1)O[C@@H]1CCN(C)C[C@H]1O2]
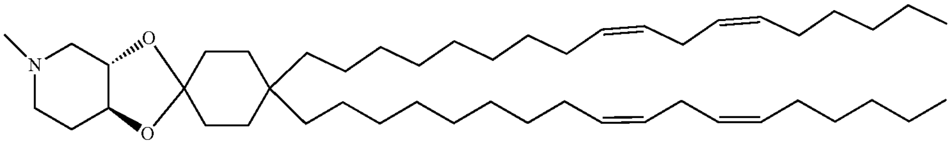 [SMILES: CCCCC/C=C\C/C=C\CCCCCCCCC1(CCCCCCCC/C=C\C/C=C\CCCCC)CCC2(CC1)O[C@H]1CCN(C)C[C@@H]1O2]
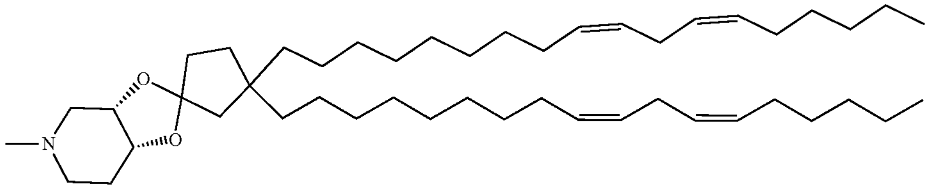
cis Racemic and optically pure TABLE 11-continued
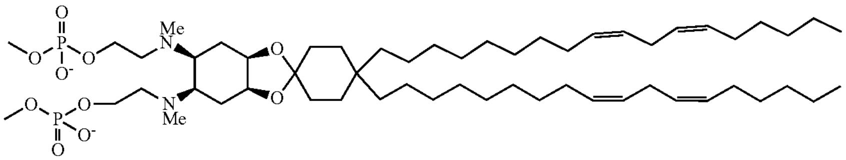 [SMILES: CCCCC/C=C\C/C=C\CCCCCCCCC1(CCCCCCCC/C=C\C/C=C\CCCCC)CCC2(CC1)O[C@H]1C[C@@H](N(C)CCOP(=O)([O-])OC)[C@@H](N(C)CCOP(=O)([O-])OC)C[C@H]1O2]
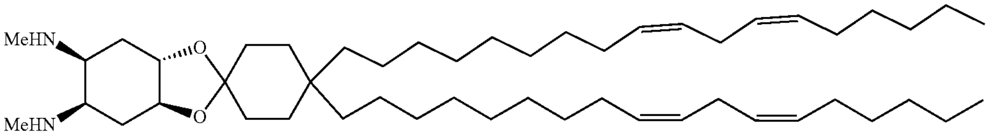 [SMILES: CCCCC/C=C\C/C=C\CCCCCCCCC1(CCCCCCCC/C=C\C/C=C\CCCCC)CCC2(CC1)O[C@H]1C[C@H](NC)[C@H](NC)C[C@@H]1O2]
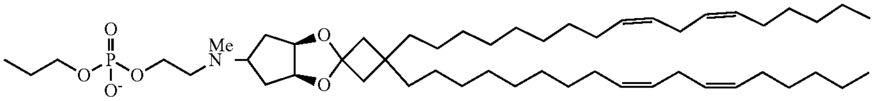 [SMILES: CCCCC/C=C\C/C=C\CCCCCCCCC1(CCCCCCCC/C=C\C/C=C\CCCCC)CC2(C1)O[C@H]1CC(N(C)CCOP(=O)([O-])OCCC)C[C@H]1O2]
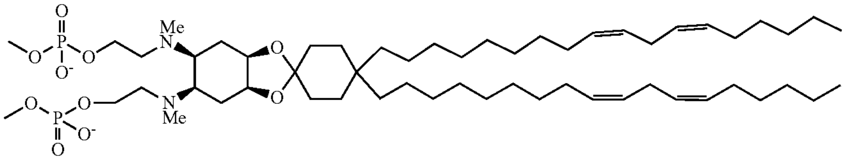 [SMILES: CCCCC/C=C\C/C=C\CCCCCCCCC1(CCCCCCCC/C=C\C/C=C\CCCCC)CCC2(CC1)O[C@H]1C[C@@H](N(C)CCOP(=O)([O-])OC)[C@@H](N(C)CCOP(=O)([O-])OC)C[C@H]1O2]
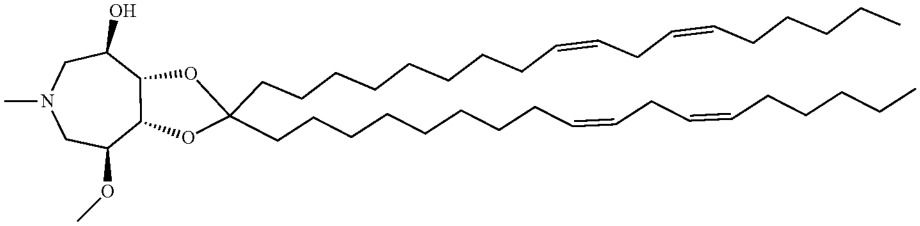 [SMILES: CCCCC/C=C\C/C=C\CCCCCCCCC1(CCCCCCCC/C=C\C/C=C\CCCCC)O[C@@H]2[C@H](O1)[C@@H](OC)CN(C)C[C@H]2O]
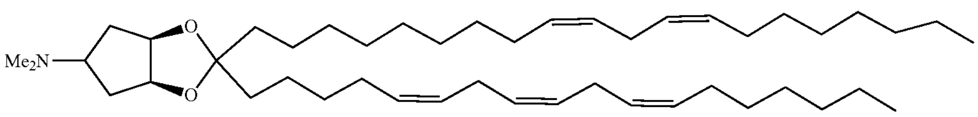
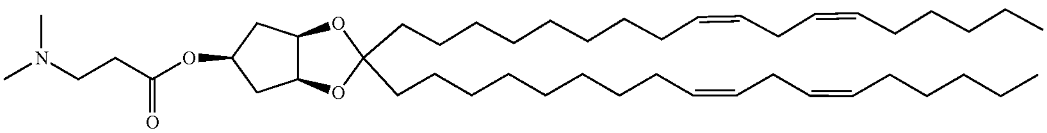 [SMILES: CCCCC/C=C\C/C=C\CCCCCCCCC1(CCCCCCCC/C=C\C/C=C\CCCCC)O[C@H]2C[C@@H](OC(=O)CCN(C)C)C[C@H]2O1]
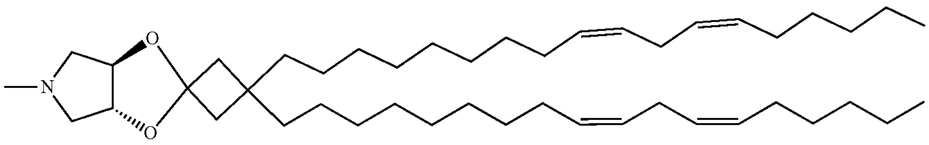 [SMILES: CCCCC/C=C\C/C=C\CCCCCCCCC1(CCCCCCCC/C=C\C/C=C\CCCCC)CC2(C1)O[C@@H]1CN(C)C[C@H]1O2]
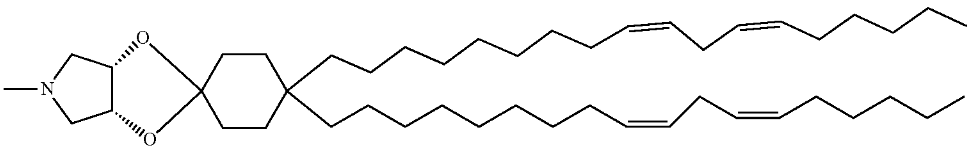
cis Racemic and optically pure TABLE 11-continued
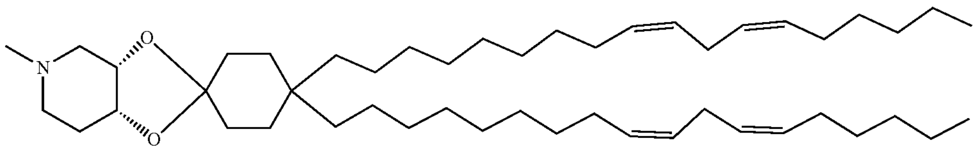
cis Racemic and optically pure
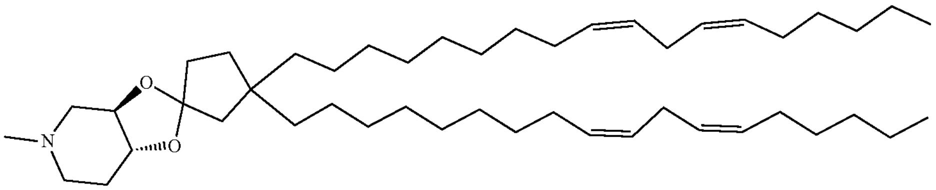
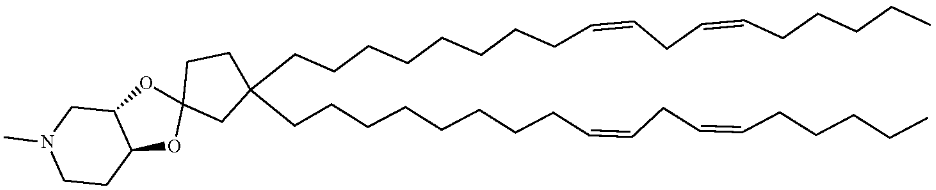
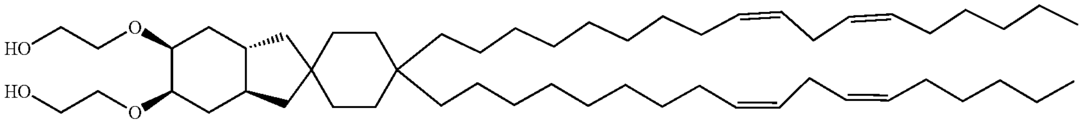 [SMILES: CCCCC/C=C\C/C=C\CCCCCCCCC1(CCCCCCCC/C=C\C/C=C\CCCCC)CCC2(CC1)C[C@H]1C[C@H](OCCO)[C@H](OCCO)C[C@@H]1C2]
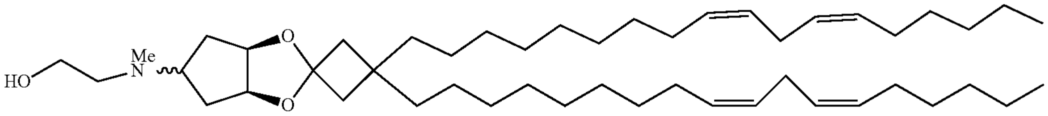 [SMILES: CCCCC/C=C\C/C=C\CCCCCCCCC1(CCCCCCCC/C=C\C/C=C\CCCCC)CC2(C1)O[C@H]1CC(N(C)CCO)C[C@H]1O2]
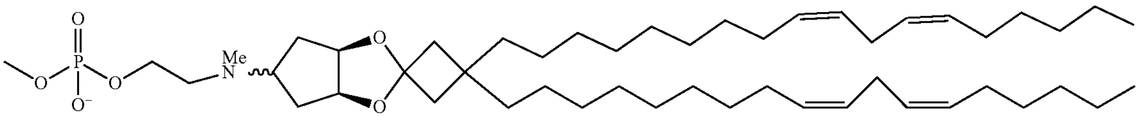 [SMILES: CCCCC/C=C\C/C=C\CCCCCCCCC1(CCCCCCCC/C=C\C/C=C\CCCCC)CC2(C1)O[C@H]1CC(N(C)CCOP(=O)([O-])OC)C[C@H]1O2]
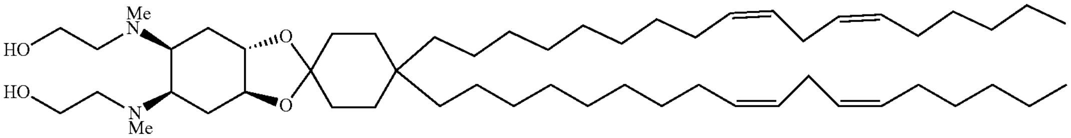
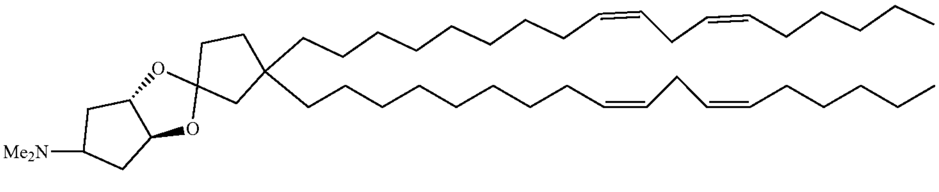 [SMILES: CCCCC/C=C\C/C=C\CCCCCCCCC1(CCCCCCCC/C=C\C/C=C\CCCCC)CCC2(C1)O[C@H]1CC(O)C[C@@H]1O2]
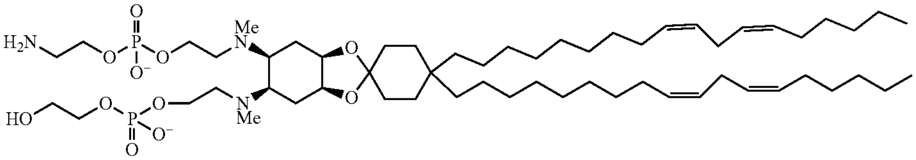 [SMILES: CCCCC/C=C\C/C=C\CCCCCCCCC1(CCCCCCCC/C=C\C/C=C\CCCCC)CCC2(CC1)O[C@H]1C[C@@H](N(C)CCOP(=O)([O-])OCCO)[C@@H](N(C)CCOP(=O)([O-])OCCN)C[C@H]1O2]

TABLE 11-continued
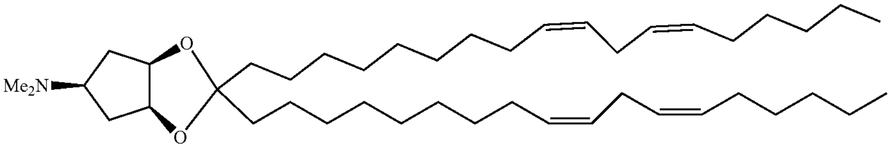
meso compound
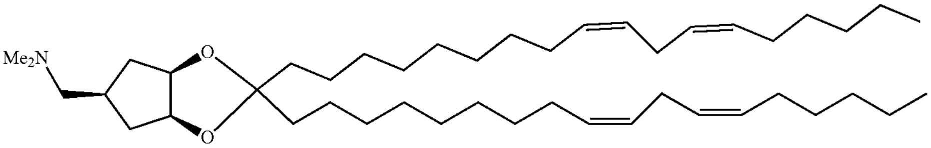 [SMILES: CCCCC/C=C\C/C=C\CCCCCCCCC1(CCCCCCCC/C=C\C/C=C\CCCCC)O[C@H]2C[C@@H](CN(C)C)C[C@H]2O1]
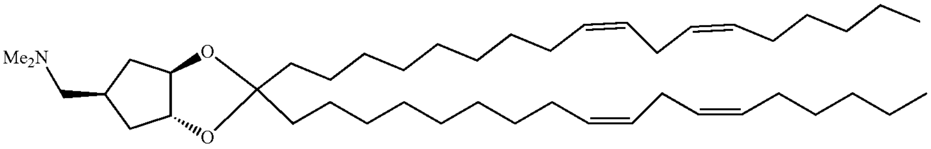
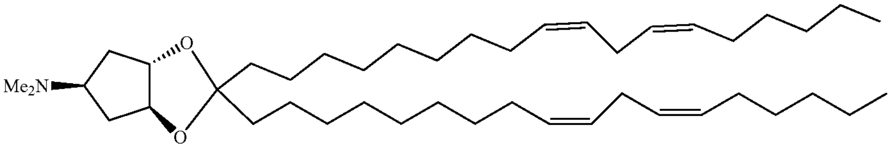
racemic compound
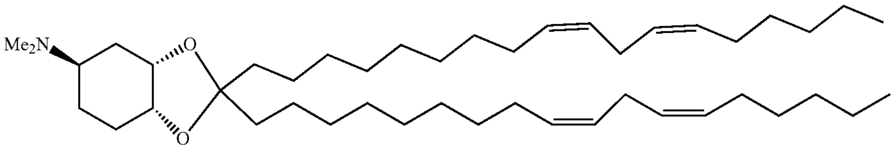
racemic compound
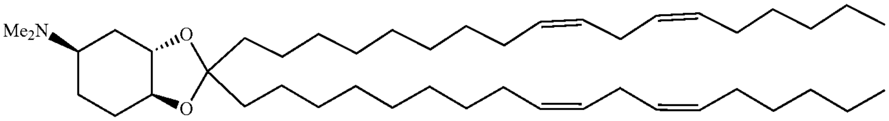
racemic compound
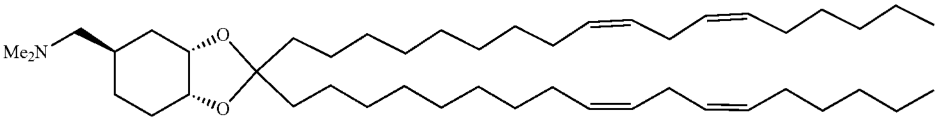 [SMILES: CCCCC/C=C\C/C=C\CCCCCCCCC1(CCCCCCCC/C=C\C/C=C\CCCCC)O[C@H]2C[C@H](CN(C)C)CC[C@H]2O1]
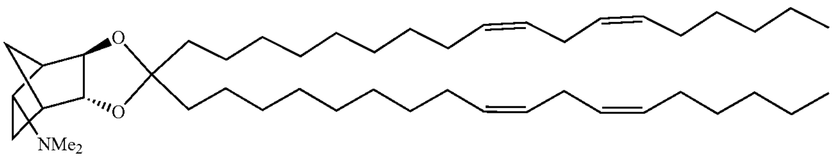 [SMILES: CCCCC/C=C\C/C=C\CCCCCCCCC1(CCCCCCCC/C=C\C/C=C\CCCCC)O[C@@H]2C3CC([C@H]2O1)C1(N(C)C)CC31]
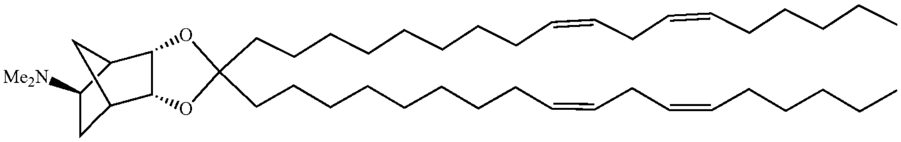 [SMILES: CCCCC/C=C\C/C=C\CCCCCCCCC1(CCCCCCCC/C=C\C/C=C\CCCCC)O[C@@H]2C3CC[C@@H](N(C)C)C(C3)[C@@H]2O1]

TABLE 11-continued
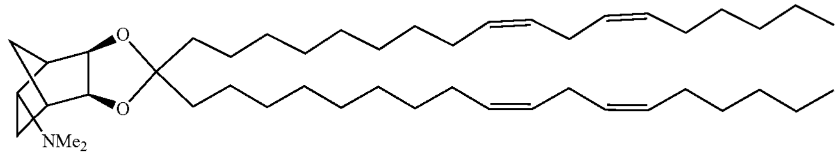 [SMILES: CCCCC/C=C\C/C=C\CCCCCCCCC1(CCCCCCCC/C=C\C/C=C\CCCCC)O[C@@H]2C3CC([C@@H]2O1)C1(N(C)C)CC31]
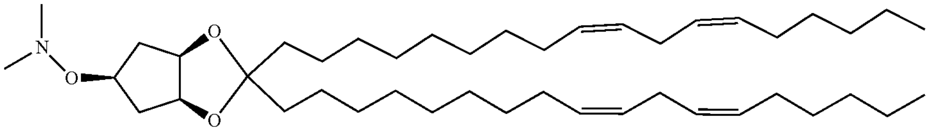 [SMILES: CCCCC/C=C\C/C=C\CCCCCCCCC1(CCCCCCCC/C=C\C/C=C\CCCCC)O[C@H]2C[C@@H](ON(C)C)C[C@H]2O1]
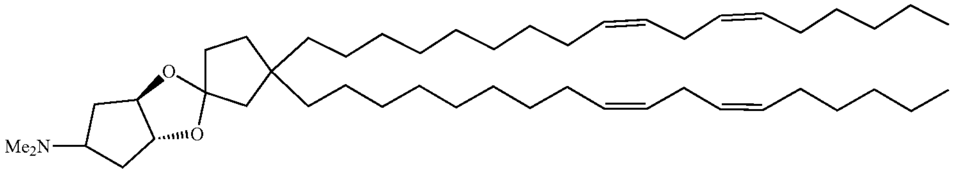 [SMILES: CCCCC/C=C\C/C=C\CCCCCCCCC1(CCCCCCCC/C=C\C/C=C\CCCCC)CCC2(C1)O[C@@H]1CC(N(C)C)C[C@H]1O2]
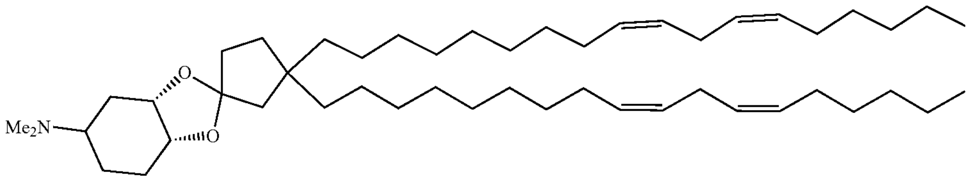
cis Racemic and optically pure
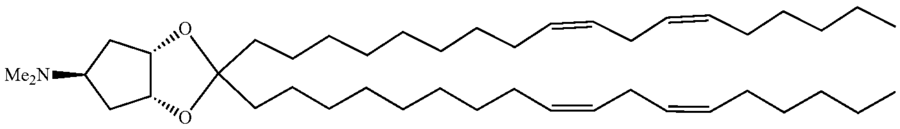
meso compound
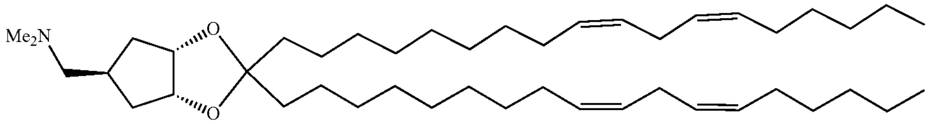 [SMILES: CCCCC/C=C\C/C=C\CCCCCCCCC1(CCCCCCCC/C=C\C/C=C\CCCCC)O[C@H]2C[C@H](CN(C)C)C[C@H]2O1]
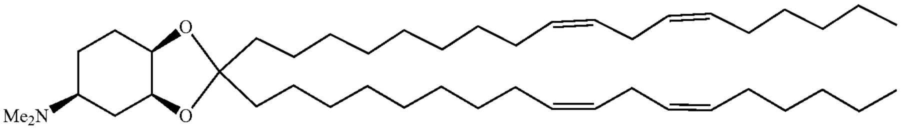 [SMILES: CCCCC/C=C\C/C=C\CCCCCCCCC1(CCCCCCCC/C=C\C/C=C\CCCCC)O[C@H]2C[C@@H](N(C)C)CC[C@H]2O1]
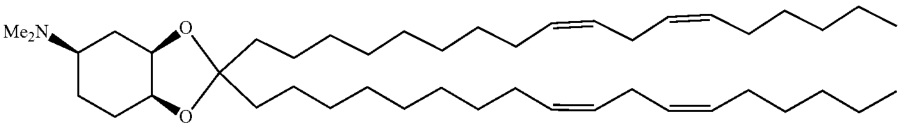
racemic compound
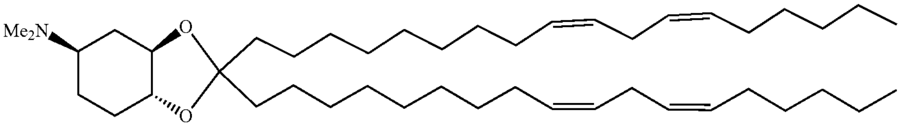
racemic compound TABLE 11-continued
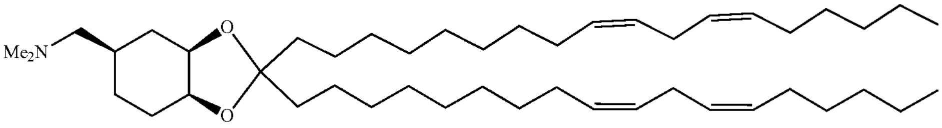 [SMILES: CCCCC/C=C\C/C=C\CCCCCCCCC1(CCCCCCCC/C=C\C/C=C\CCCCC)O[C@H]2CC[C@@H](CN(C)C)C[C@H]2O1]
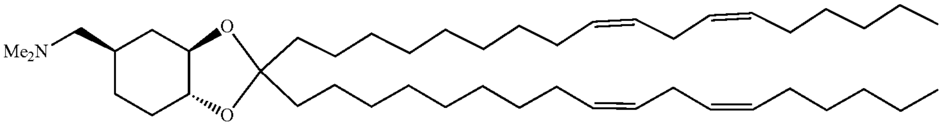 [SMILES: CCCCC/C=C\C/C=C\CCCCCCCCC1(CCCCCCCC/C=C\C/C=C\CCCCC)O[C@@H]2CC[C@@H](CN(C)C)C[C@H]2O1]
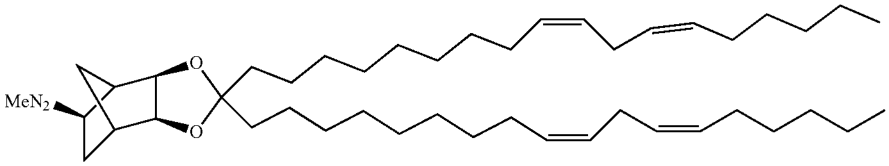
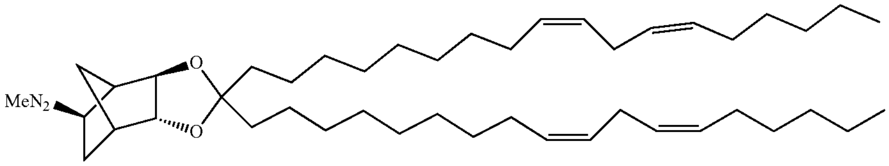
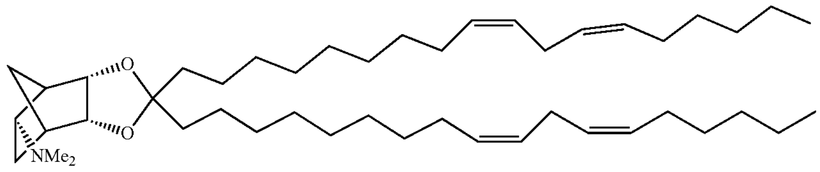 [SMILES: CCCCC/C=C\C/C=C\CCCCCCCCC1(CCCCCCCC/C=C\C/C=C\CCCCC)O[C@@H]2C3CC([C@@H]2O1)[C@@H](N(C)C)C3]
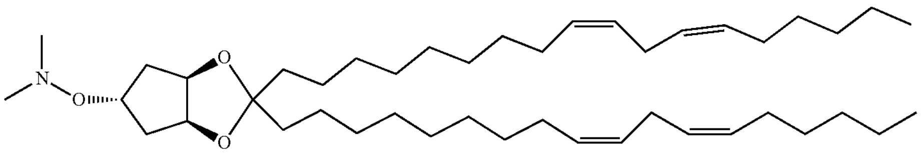 [SMILES: CCCCC/C=C\C/C=C\CCCCCCCCC1(CCCCCCCC/C=C\C/C=C\CCCCC)O[C@H]2C[C@H](ON(C)C)C[C@H]2O1]
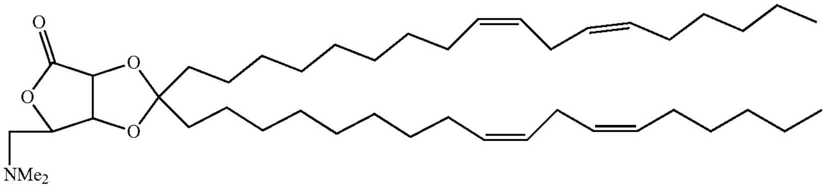
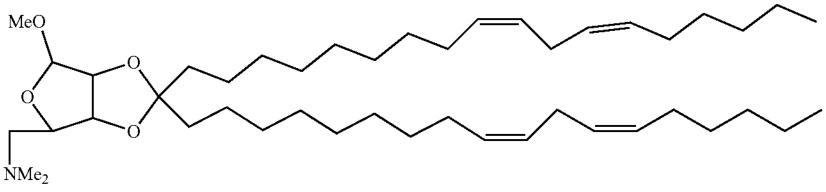 [SMILES: CCCCC/C=C\C/C=C\CCCCCCCCC1(CCCCCCCC/C=C\C/C=C\CCCCC)OC2C(CN(C)C)OC(OC)C2O1]
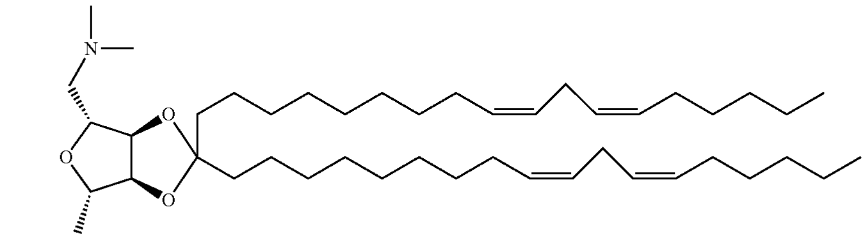 [SMILES: CCCCC/C=C\C/C=C\CCCCCCCCC1(CCCCCCCC/C=C\C/C=C\CCCCC)O[C@@H]2[C@H](O1)[C@@H](CN(C)C)O[C@H]2C]

TABLE 11-continued
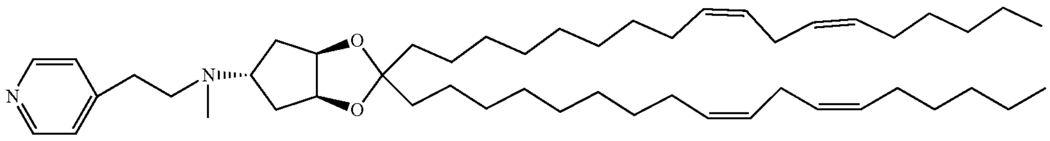 [SMILES: CCCCC/C=C\C/C=C\CCCCCCCCC1(CCCCCCCC/C=C\C/C=C\CCCCC)O[C@H]2C[C@H](N(C)CCc3ccncc3)C[C@H]2O1]
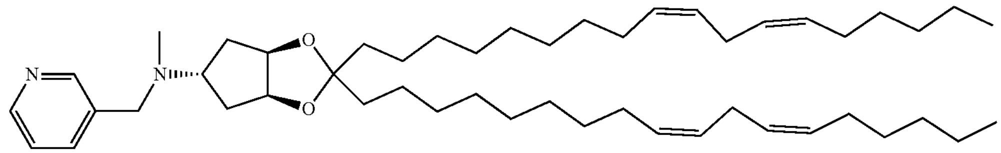 [SMILES: CCCCC/C=C\C/C=C\CCCCCCCCC1(CCCCCCCC/C=C\C/C=C\CCCCC)O[C@H]2C[C@H](N(C)Cc3cccnc3)C[C@H]2O1]
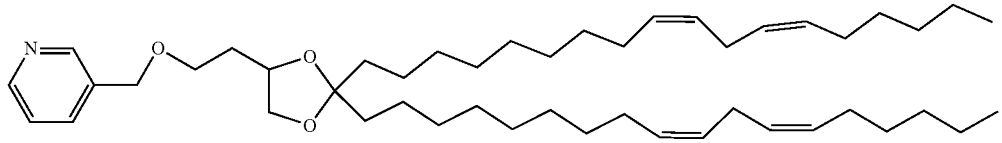 [SMILES: CCCCC/C=C\C/C=C\CCCCCCCCC1(CCCCCCCC/C=C\C/C=C\CCCCC)OCC(CCOCc2cccnc2)O1]
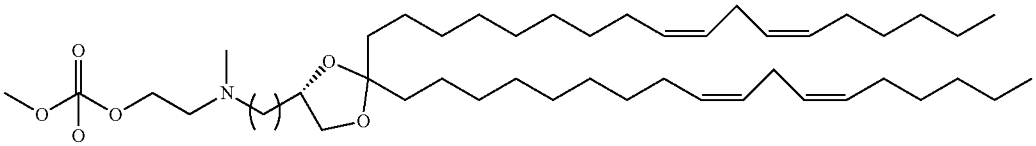
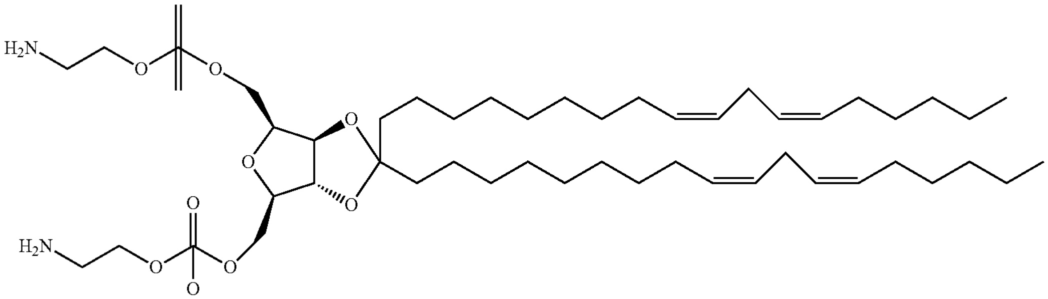
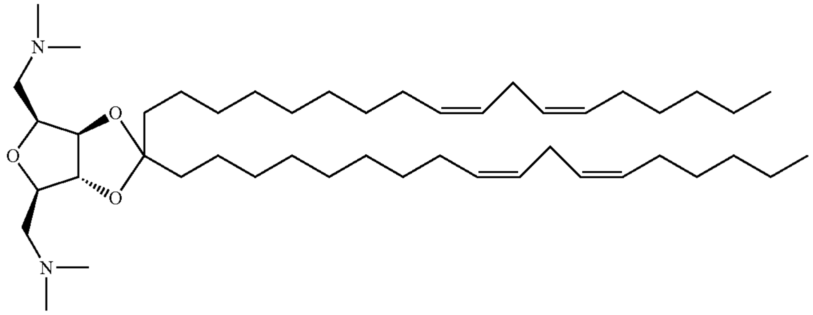 [SMILES: CCCCC/C=C\C/C=C\CCCCCCCCC1(CCCCCCCC/C=C\C/C=C\CCCCC)O[C@H]2[C@H](O1)[C@@H](CN(C)C)O[C@H]2CN(C)C]
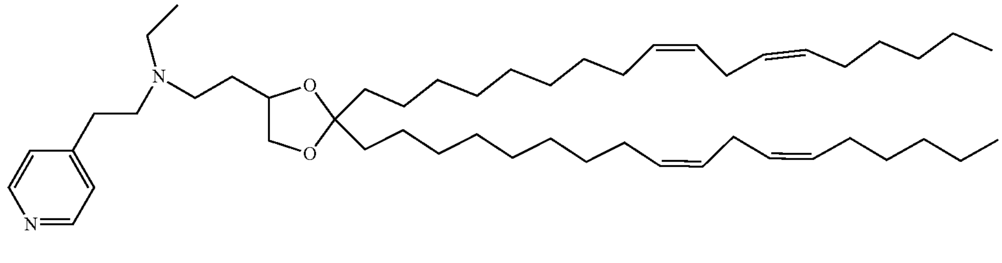 [SMILES: CCCCC/C=C\C/C=C\CCCCCCCCC1(CCCCCCCC/C=C\C/C=C\CCCCC)OCC(CCN(CC)CCc2ccncc2)O1]

TABLE 11-continued
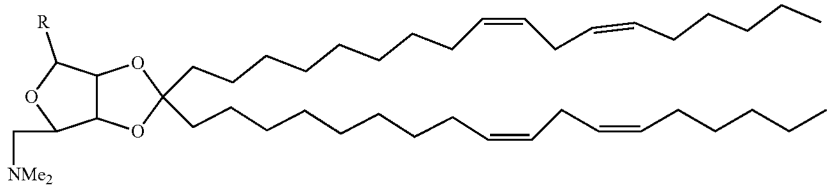
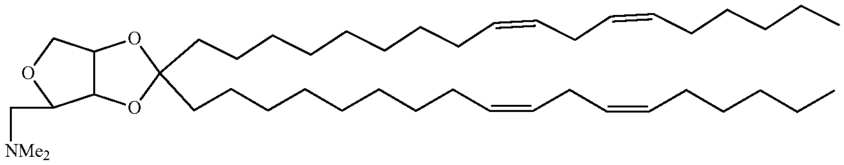 [SMILES: CCCCC/C=C\C/C=C\CCCCCCCCC1(CCCCCCCC/C=C\C/C=C\CCCCC)OC2COC(CN(C)C)C2O1]
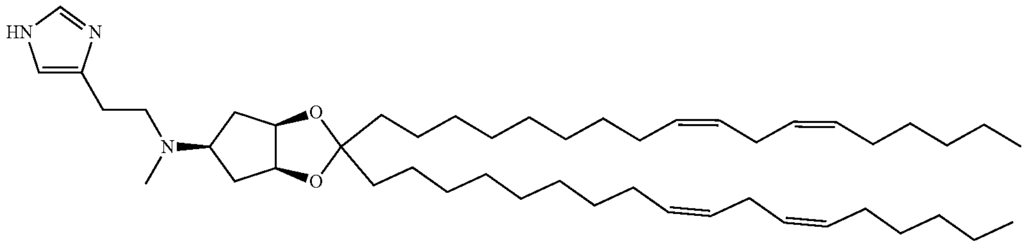 [SMILES: CCCCC/C=C\C/C=C\CCCCCCCCC1(CCCCCCCC/C=C\C/C=C\CCCCC)O[C@H]2C[C@@H](N(C)CCc3c[nH]cn3)C[C@H]2O1]
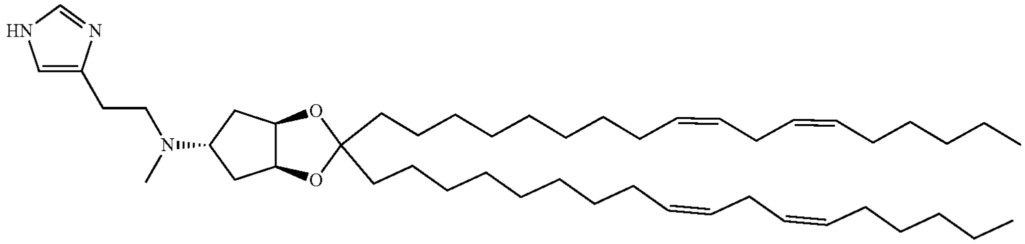 [SMILES: CCCCC/C=C\C/C=C\CCCCCCCCC1(CCCCCCCC/C=C\C/C=C\CCCCC)O[C@H]2C[C@H](N(C)CCc3c[nH]cn3)C[C@H]2O1]
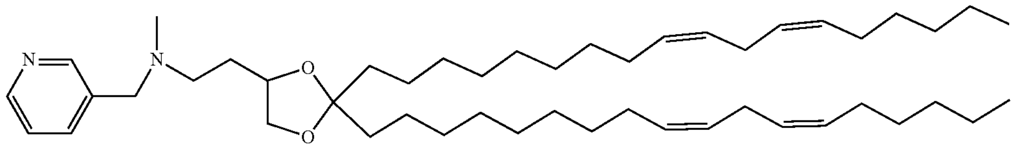 [SMILES: CCCCC/C=C\C/C=C\CCCCCCCCC1(CCCCCCCC/C=C\C/C=C\CCCCC)OCC(CCN(C)Cc2cccnc2)O1]
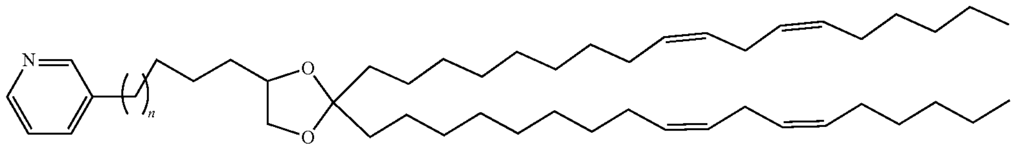
n = 1-10
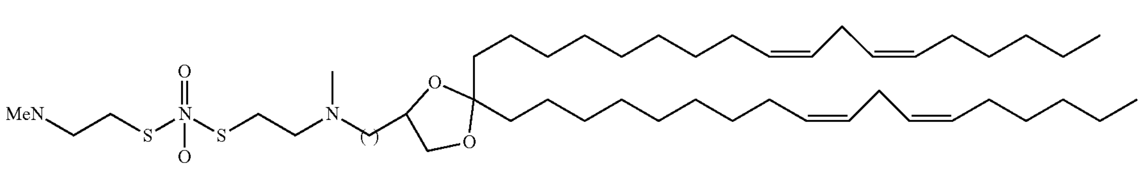
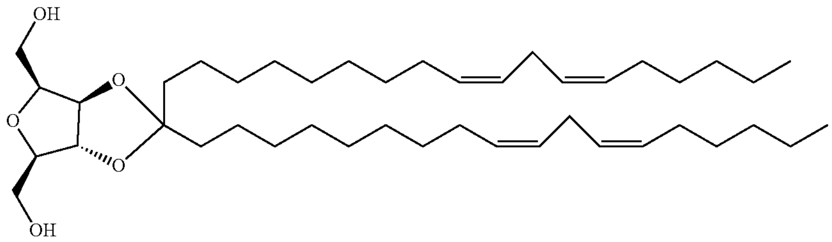 [SMILES: CCCCC/C=C\C/C=C\CCCCCCCCC1(CCCCCCCC/C=C\C/C=C\CCCCC)O[C@H]2[C@H](O1)[C@@H](CO)O[C@H]2CO]

TABLE 11-continued
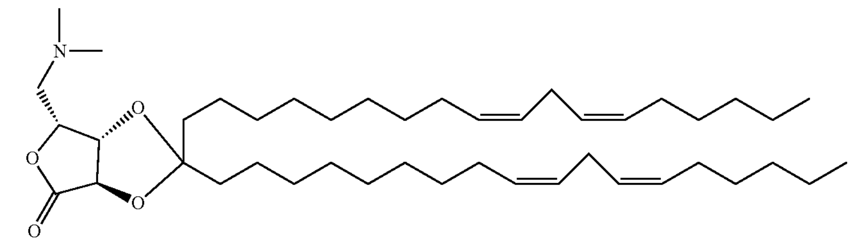 [SMILES: CCCCC/C=C\C/C=C\CCCCCCCCC1(CCCCCCCC/C=C\C/C=C\CCCCC)O[C@H]2[C@@H](CN(C)C)OC(=O)[C@@H]2O1]
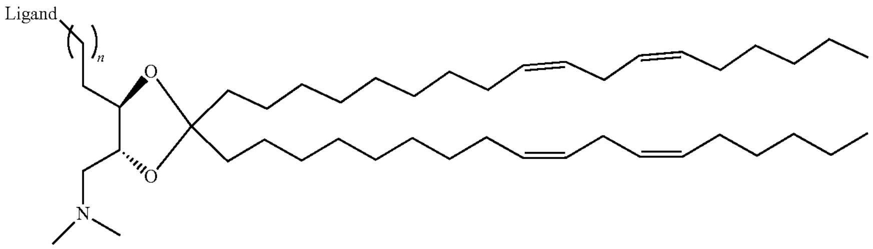
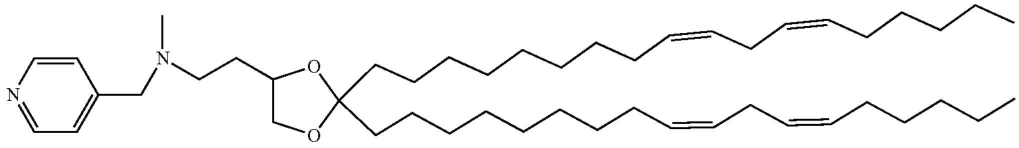 [SMILES: CCCCC/C=C\C/C=C\CCCCCCCCC1(CCCCCCCC/C=C\C/C=C\CCCCC)OCC(CCN(C)Cc2ccncc2)O1]
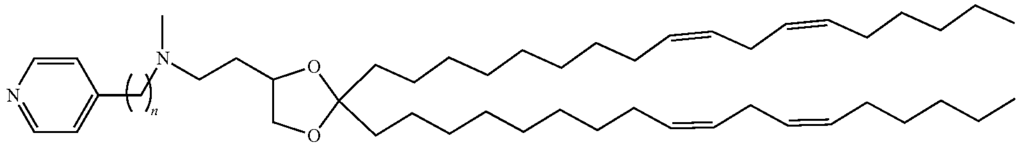
n = 0-6
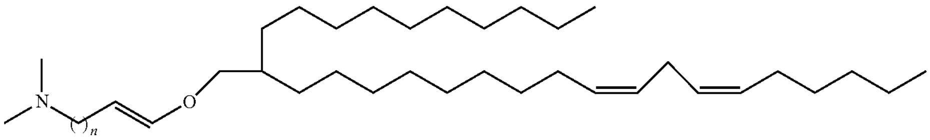
n = 0-6
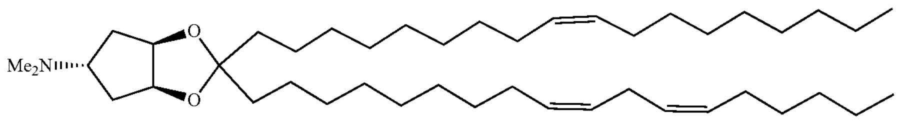
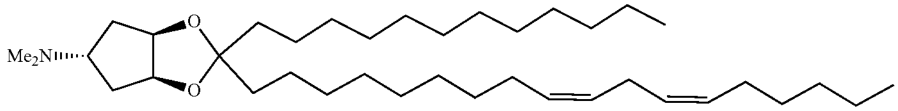
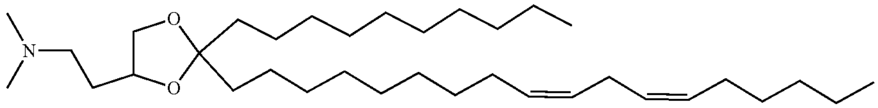 [SMILES: CCCCC/C=C\C/C=C\CCCCCCCCC1(CCCCCCCCCC)OCC(CCN(C)C)O1]
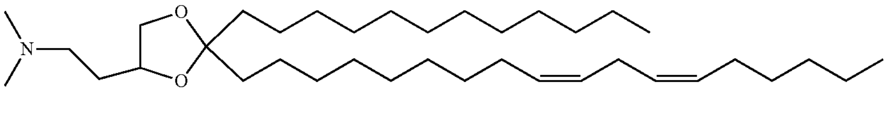 [SMILES: CCCCC/C=C\C/C=C\CCCCCCCCC1(CCCCCCCCCCCC)OCC(CCN(C)C)O1]

TABLE 11-continued
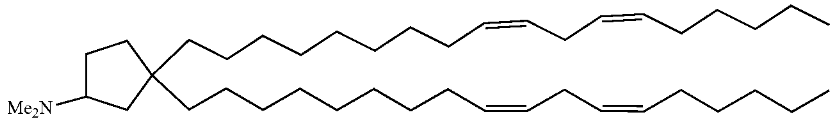
Racemic and optically pure
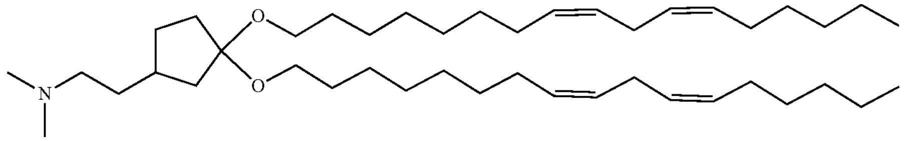 [SMILES: CCCCC/C=C\C/C=C\CCCCCCCOC1(OCCCCCCC/C=C\C/C=C\CCCCC)CCC(CCN(C)C)C1]
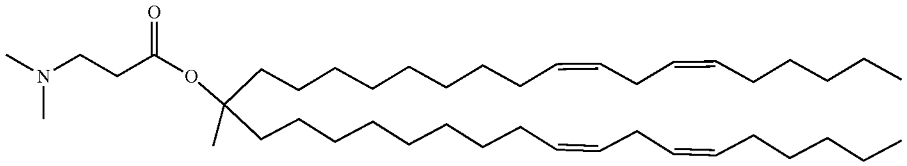 [SMILES: CCCCC/C=C\C/C=C\CCCCCCCCC(C)(CCCCCCCC/C=C\C/C=C\CCCCC)OC(=O)CCN(C)C]
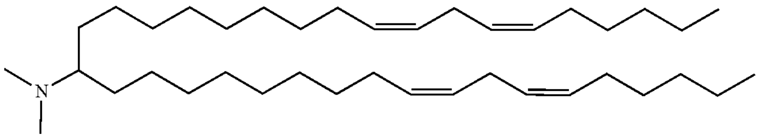 [SMILES: CCCCC/C=C\C/C=C\CCCCCCCCC(CCCCCCCC/C=C\C/C=C\CCCCC)N(C)C]
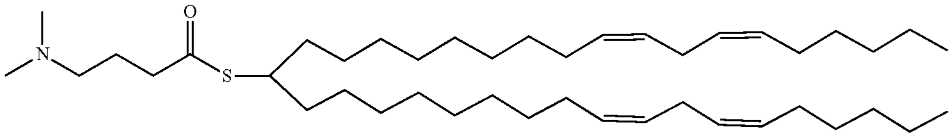 [SMILES: CCCCC/C=C\C/C=C\CCCCCCCCC(CCCCCCCC/C=C\C/C=C\CCCCC)SC(=O)CCCN(C)C]
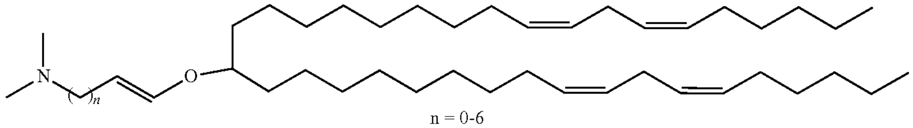
n = 0-6
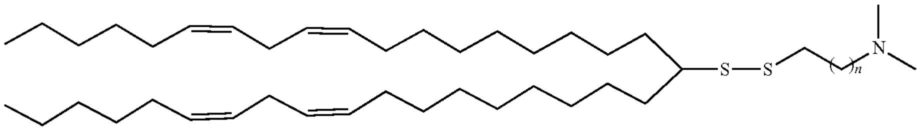
n =0-6
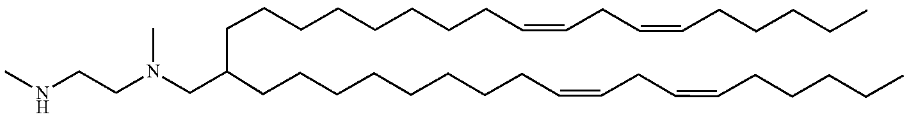 [SMILES: CCCCC/C=C\C/C=C\CCCCCCCCC(CCCCCCCC/C=C\C/C=C\CCCCC)CN(C)CCNC]
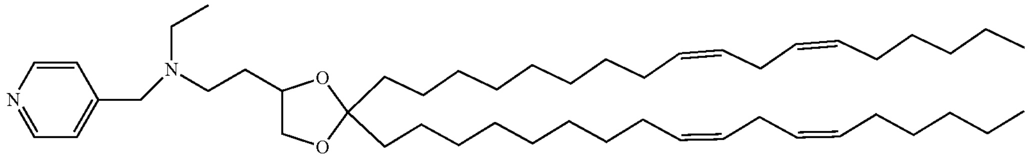 [SMILES: CCCCC/C=C\C/C=C\CCCCCCCCC1(CCCCCCCC/C=C\C/C=C\CCCCC)OCC(CCN(CC)Cc2ccncc2)O1]
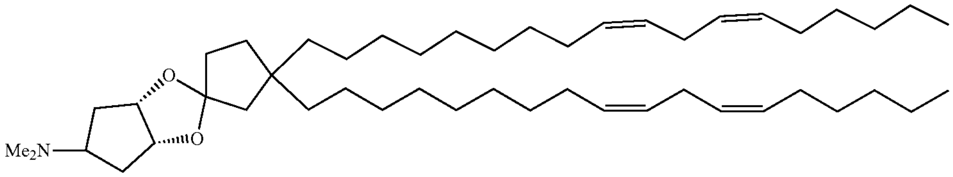
cis Racemic and optically pure TABLE 11-continued
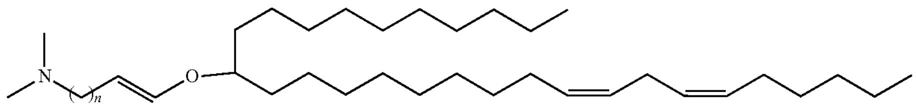
n =0-6
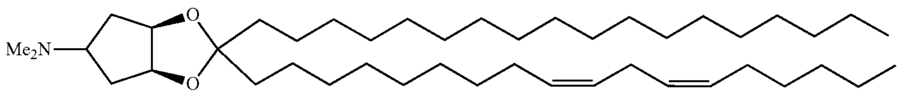
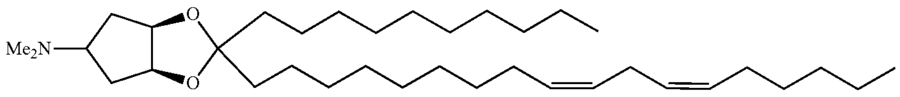
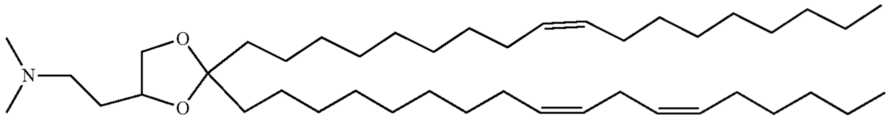 [SMILES: CCCCC/C=C\C/C=C\CCCCCCCCC1(CCCCCCCC/C=C\CCCCCCCC)OCC(CCN(C)C)O1]
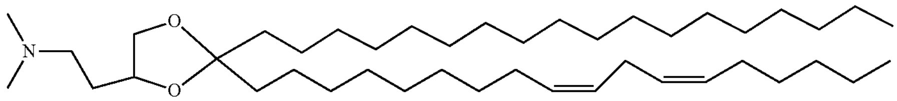 [SMILES: CCCCC/C=C\C/C=C\CCCCCCCCC1(CCCCCCCCCCCCCCCCCC)OCC(CCN(C)C)O1]
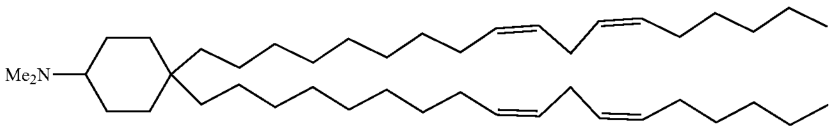
Racemic and optically pure
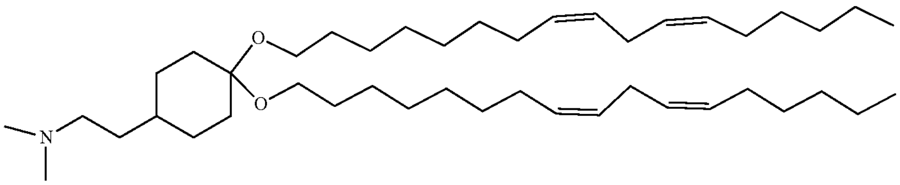 [SMILES: CCCCC/C=C\C/C=C\CCCCCCCOC1(OCCCCCCC/C=C\C/C=C\CCCCC)CCC(CCN(C)C)CC1]
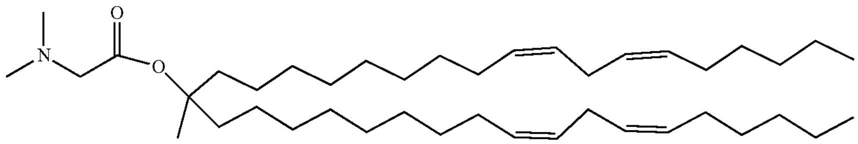 [SMILES: CCCCC/C=C\C/C=C\CCCCCCCCC(C)(CCCCCCCC/C=C\C/C=C\CCCCC)OC(=O)CN(C)C]
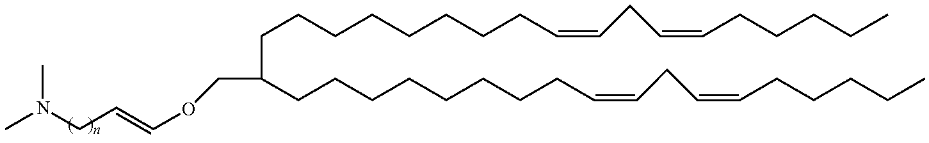
n = 0-6
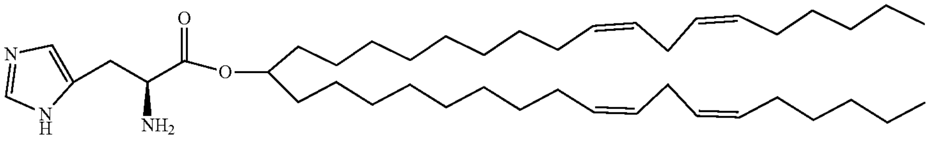 [SMILES: CCCCC/C=C\C/C=C\CCCCCCCCC(CCCCCCCC/C=C\C/C=C\CCCCC)OC(=O)[C@@H](N)Cc1cnc[nH]1]
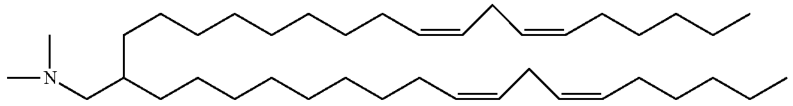 [SMILES: CCCCC/C=C\C/C=C\CCCCCCCCC(CCCCCCCC/C=C\C/C=C\CCCCC)CN(C)C]

TABLE 11-continued
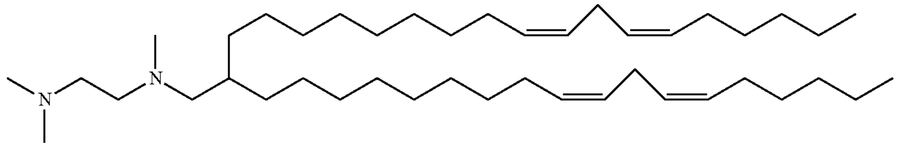
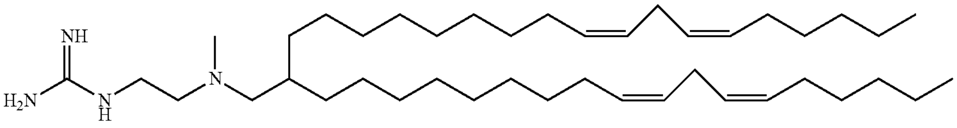 [SMILES: CCCCC/C=C\C/C=C\CCCCCCCCC(CCCCCCCC/C=C\C/C=C\CCCCC)CN(C)CCNC(=N)N]
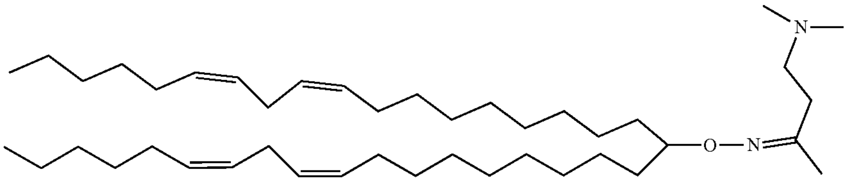 [SMILES: CCCCC/C=C\C/C=C\CCCCCCCCC(CCCCCCCC/C=C\C/C=C\CCCCC)O/N=C(/C)CCN(C)C]
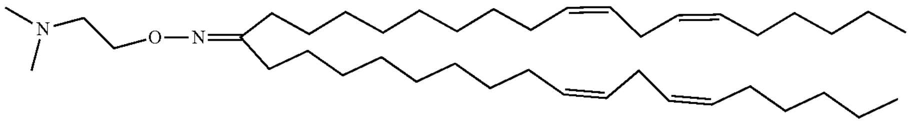 [SMILES: CCCCC/C=C\C/C=C\CCCCCCCCC(CCCCCCCC/C=C\C/C=C\CCCCC)=NOCCN(C)C]
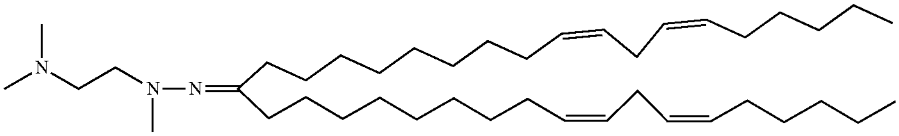 [SMILES: CCCCC/C=C\C/C=C\CCCCCCCCC(CCCCCCCC/C=C\C/C=C\CCCCC)=NN(C)CCN(C)C]
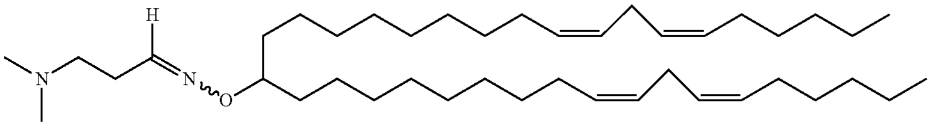 [SMILES: CCCCC/C=C\C/C=C\CCCCCCCCC(CCCCCCCC/C=C\C/C=C\CCCCC)ON=CCCN(C)C]
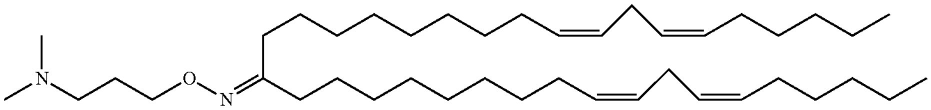 [SMILES: CCCCC/C=C\C/C=C\CCCCCCCCC(CCCCCCCC/C=C\C/C=C\CCCCC)=NOCCCN(C)C]
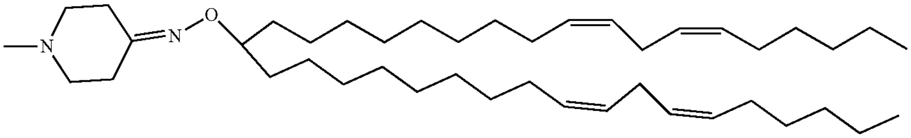 [SMILES: CCCCC/C=C\C/C=C\CCCCCCCCC(CCCCCCCC/C=C\C/C=C\CCCCC)ON=C1CCN(C)CC1]
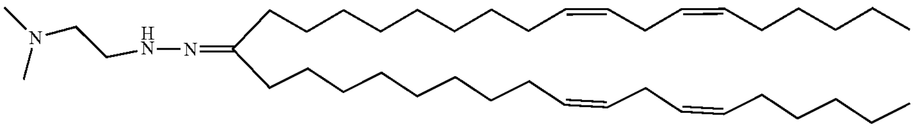 [SMILES: CCCCC/C=C\C/C=C\CCCCCCCCC(CCCCCCCC/C=C\C/C=C\CCCCC)=NNCCN(C)C]
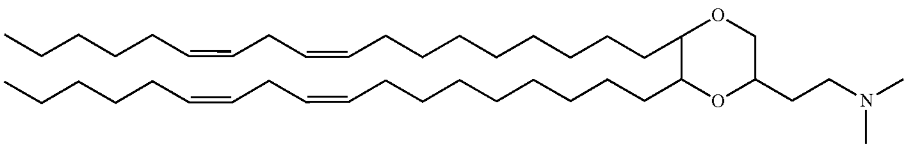 [SMILES: CCCCC/C=C\C/C=C\CCCCCCCCC1OCC(CCN(C)C)OC1CCCCCCCC/C=C\C/C=C\CCCCC]
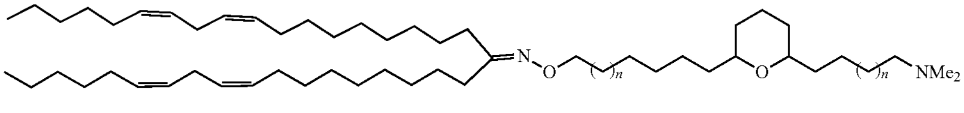

TABLE 11-continued
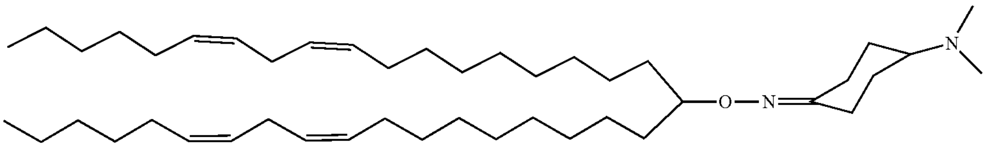 [SMILES: CCCCC/C=C\C/C=C\CCCCCCCCC(CCCCCCCC/C=C\C/C=C\CCCCC)ON=C1CCC(N(C)C)CC1]
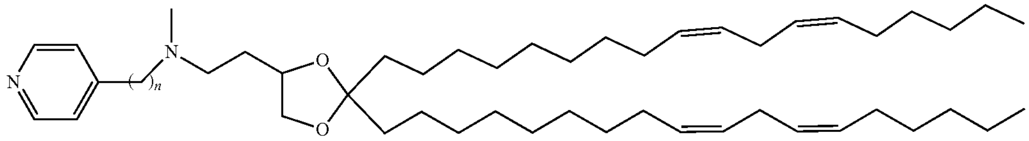
n = 0-6
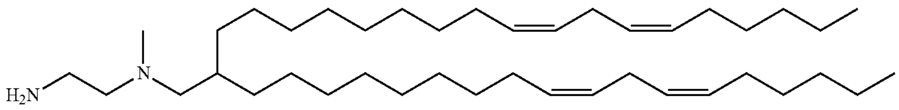
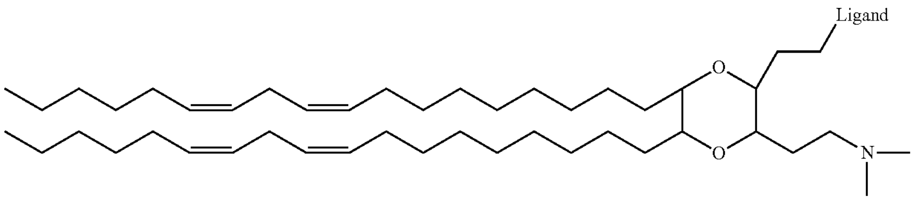
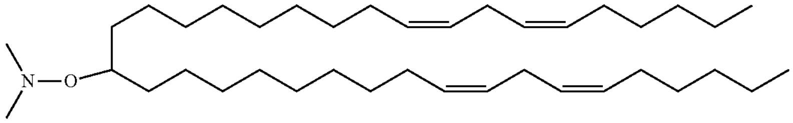 [SMILES: CCCCC/C=C\C/C=C\CCCCCCCCC(CCCCCCCC/C=C\C/C=C\CCCCC)ON(C)C]
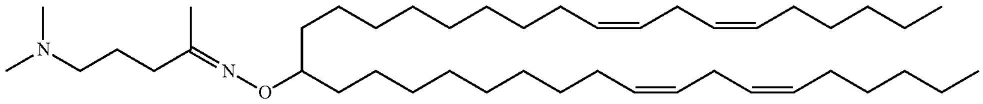 [SMILES: CCCCC/C=C\C/C=C\CCCCCCCCC(CCCCCCCC/C=C\C/C=C\CCCCC)ON=C(C)CCCN(C)C]
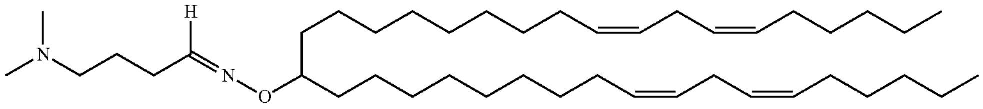 [SMILES: CCCCC/C=C\C/C=C\CCCCCCCCC(CCCCCCCC/C=C\C/C=C\CCCCC)ON=CCCCN(C)C]
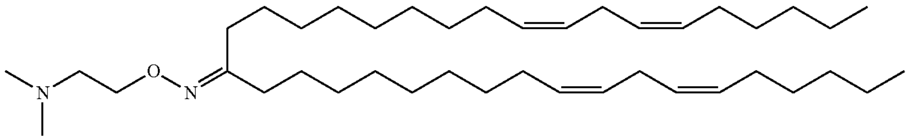 [SMILES: CCCCC/C=C\C/C=C\CCCCCCCCC(CCCCCCCC/C=C\C/C=C\CCCCC)=NOCCN(C)C]
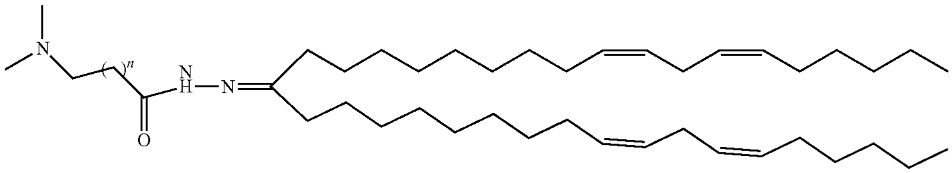
n = 0-6
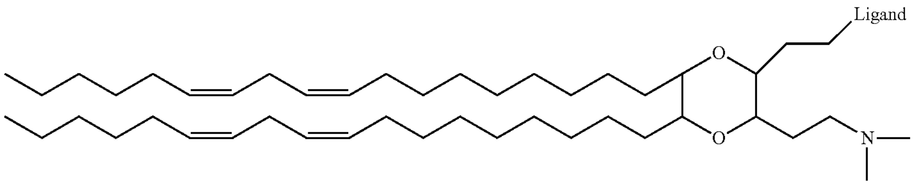

TABLE 11-continued
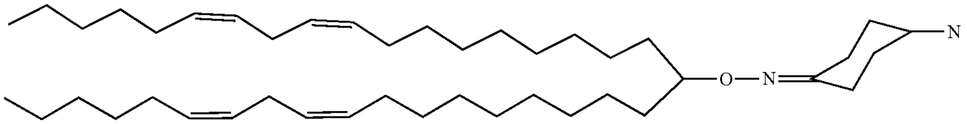 [SMILES: CCCCC/C=C\C/C=C\CCCCCCCCC(CCCCCCCC/C=C\C/C=C\CCCCC)ON=C1CCC(N)CC1]
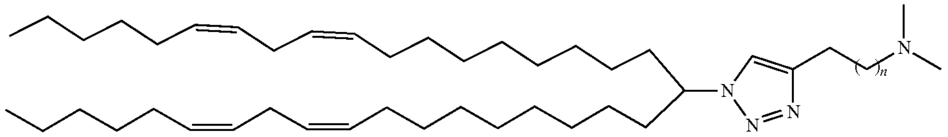
n = 0-6
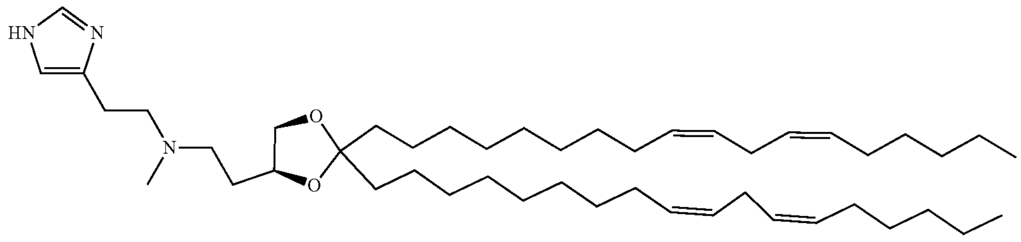
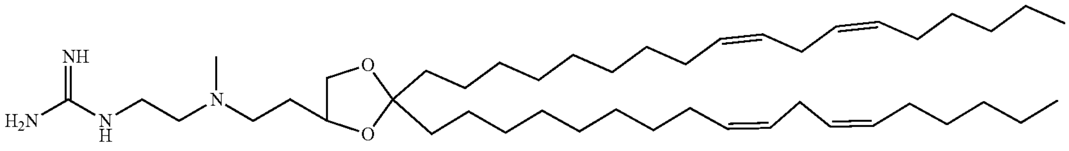 [SMILES: CCCCC/C=C\C/C=C\CCCCCCCCC1(CCCCCCCC/C=C\C/C=C\CCCCC)OCC(CCN(C)CCNC(=N)N)O1]
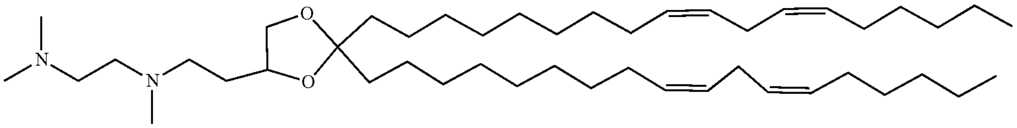 [SMILES: CCCCC/C=C\C/C=C\CCCCCCCCC1(CCCCCCCC/C=C\C/C=C\CCCCC)OCC(CCN(C)CCN(C)C)O1]
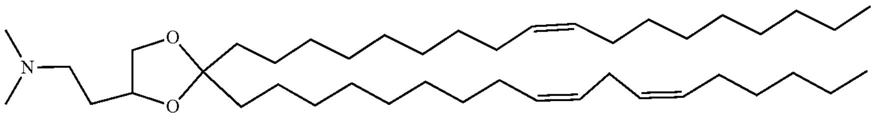 [SMILES: CCCCC/C=C\C/C=C\CCCCCCCCC1(CCCCCCCC/C=C\CCCCCCCC)OCC(CCN(C)C)O1]
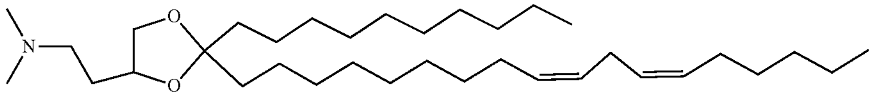 [SMILES: CCCCC/C=C\C/C=C\CCCCCCCCC1(CCCCCCCCCC)OCC(CCN(C)C)O1]
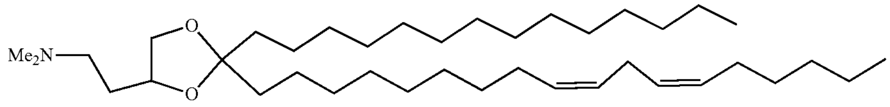 [SMILES: CCCCC/C=C\C/C=C\CCCCCCCCC1(CCCCCCCCCCCCCC)OCC(CCN(C)C)O1]
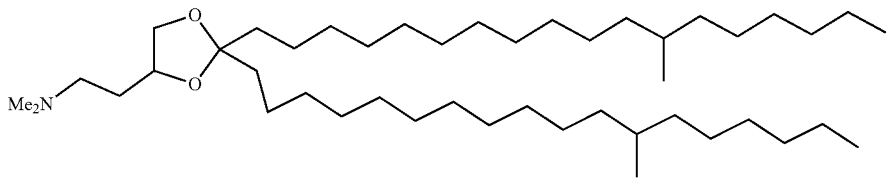 [SMILES: CCCCCCC(C)CCCCCCCCCCCC1(CCCCCCCCCCCC(C)CCCCCC)OCC(CCN(C)C)O1]
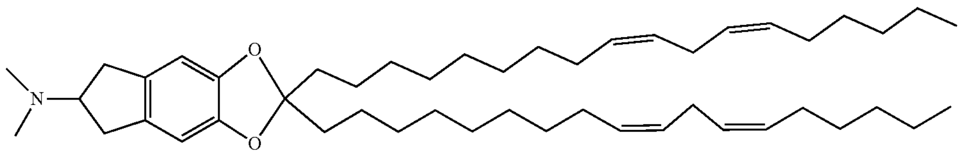 [SMILES: CCCCC/C=C\C/C=C\CCCCCCCCC1(CCCCCCCC/C=C\C/C=C\CCCCC)Oc2cc3c(cc2O1)CC(N(C)C)C3]

TABLE 11-continued
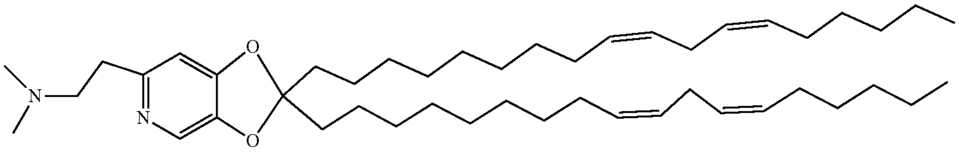 [SMILES: CCCCC/C=C\C/C=C\CCCCCCCCC1(CCCCCCCC/C=C\C/C=C\CCCCC)Oc2cnc(CCN(C)C)cc2O1]
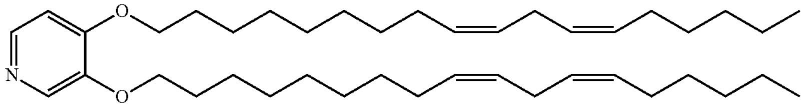 [SMILES: CCCCC/C=C\C/C=C\CCCCCCCCOc1ccncc1OCCCCCCCC/C=C\C/C=C\CCCCC]
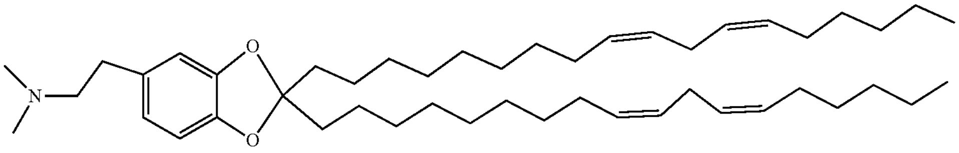 [SMILES: CCCCC/C=C\C/C=C\CCCCCCCCC1(CCCCCCCC/C=C\C/C=C\CCCCC)Oc2ccc(CCN(C)C)cc2O1]
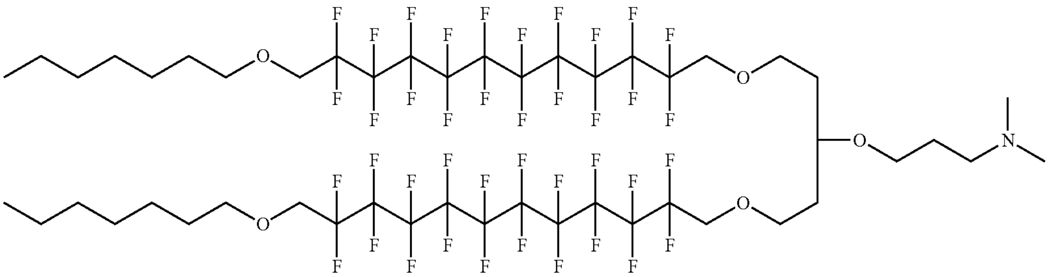 [SMILES: CCCCCCCOCC(F)(F)C(F)(F)C(F)(F)C(F)(F)C(F)(F)C(F)(F)C(F)(F)C(F)(F)C(F)(F)C(F)(F)COCCC(CCOCC(F)(F)C(F)(F)C(F)(F)C(F)(F)C(F)(F)C(F)(F)C(F)(F)C(F)(F)C(F)(F)C(F)(F)COCCCCCCC)OCCCN(C)C]
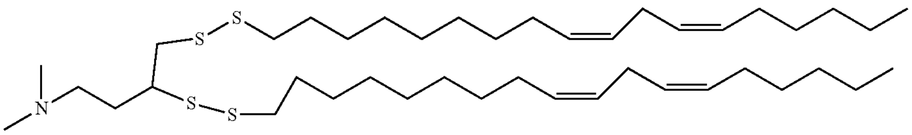 [SMILES: CCCCC/C=C\C/C=C\CCCCCCCCSSCC(CCN(C)C)SSCCCCCCCC/C=C\C/C=C\CCCCC]
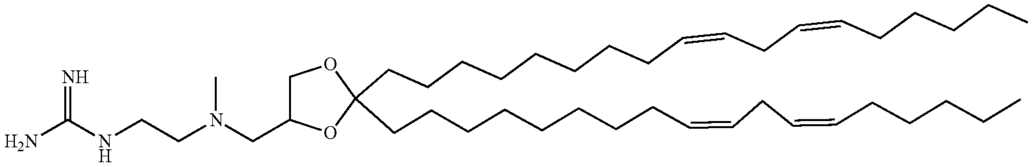 [SMILES: CCCCC/C=C\C/C=C\CCCCCCCCC1(CCCCCCCC/C=C\C/C=C\CCCCC)OCC(CN(C)CCNC(=N)N)O1]
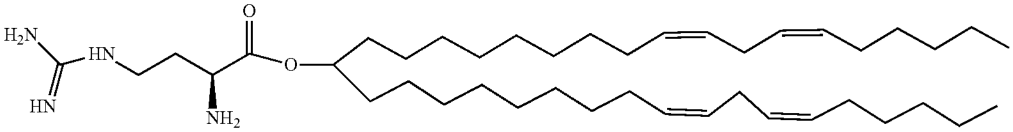 [SMILES: CCCCC/C=C\C/C=C\CCCCCCCCC(CCCCCCCC/C=C\C/C=C\CCCCC)OC(=O)[C@@H](N)CCNC(=N)N]
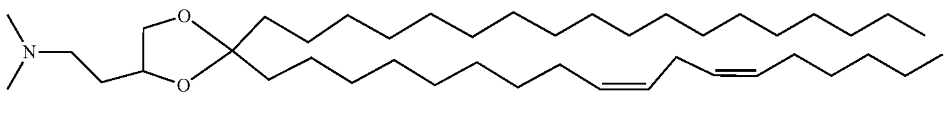 [SMILES: CCCCC/C=C\C/C=C\CCCCCCCCC1(CCCCCCCCCCCCCCCCCC)OCC(CCN(C)C)O1]
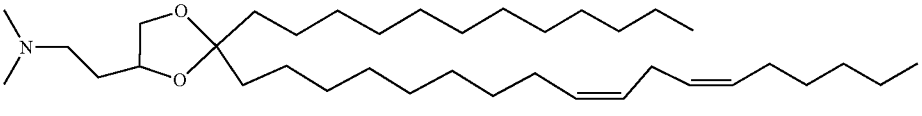 [SMILES: CCCCC/C=C\C/C=C\CCCCCCCCC1(CCCCCCCCCCCC)OCC(CCN(C)C)O1]
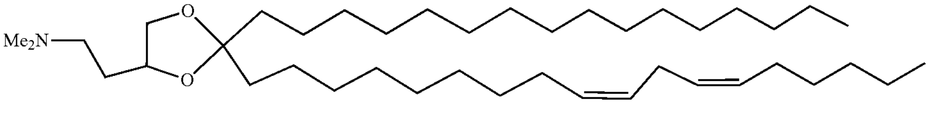 [SMILES: CCCCC/C=C\C/C=C\CCCCCCCCC1(CCCCCCCCCCCCCCCC)OCC(CCN(C)C)O1]

TABLE 11-continued
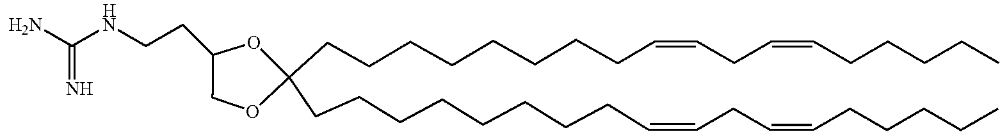 [SMILES: CCCCC/C=C\C/C=C\CCCCCCCCC1(CCCCCCCC/C=C\C/C=C\CCCCC)OCC(CCNC(=N)N)O1]
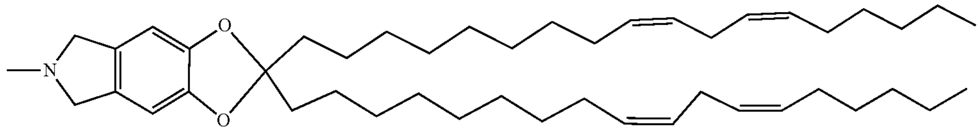 [SMILES: CCCCC/C=C\C/C=C\CCCCCCCCC1(CCCCCCCC/C=C\C/C=C\CCCCC)Oc2cc3c(cc2O1)CN(C)C3]
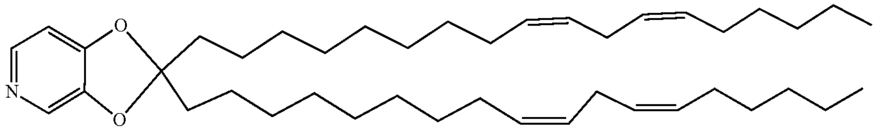 [SMILES: CCCCC/C=C\C/C=C\CCCCCCCCC1(CCCCCCCC/C=C\C/C=C\CCCCC)Oc2ccncc2O1]
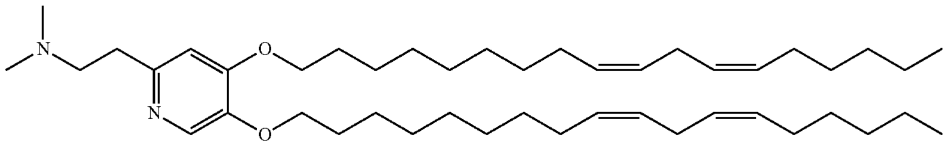 [SMILES: CCCCC/C=C\C/C=C\CCCCCCCCOc1cnc(CCN(C)C)cc1OCCCCCCCC/C=C\C/C=C\CCCCC]
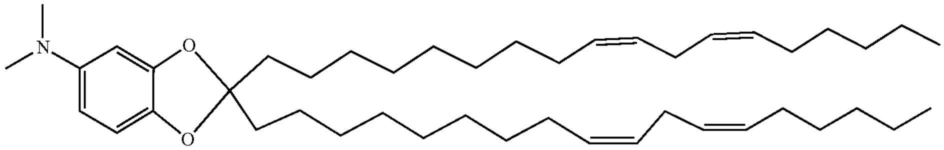 [SMILES: CCCCC/C=C\C/C=C\CCCCCCCCC1(CCCCCCCC/C=C\C/C=C\CCCCC)Oc2ccc(N(C)C)cc2O1]
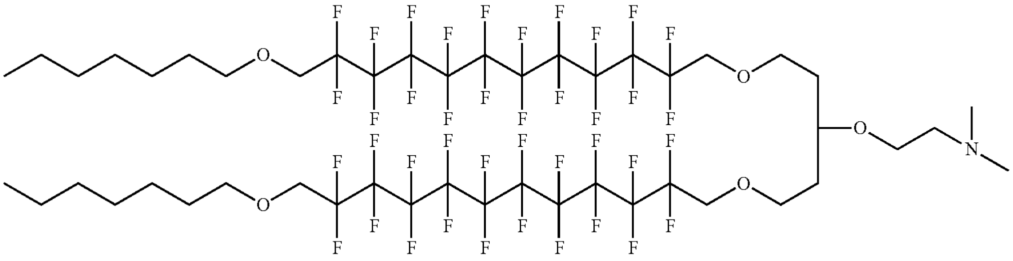 [SMILES: CCCCCCCOCC(F)(F)C(F)(F)C(F)(F)C(F)(F)C(F)(F)C(F)(F)C(F)(F)C(F)(F)C(F)(F)C(F)(F)COCCC(CCOCC(F)(F)C(F)(F)C(F)(F)C(F)(F)C(F)(F)C(F)(F)C(F)(F)C(F)(F)C(F)(F)C(F)(F)COCCCCCCC)OCCN(C)C]
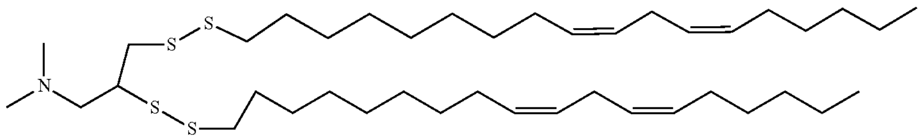 [SMILES: CCCCC/C=C\C/C=C\CCCCCCCCSSCC(CN(C)C)SSCCCCCCCC/C=C\C/C=C\CCCCC]
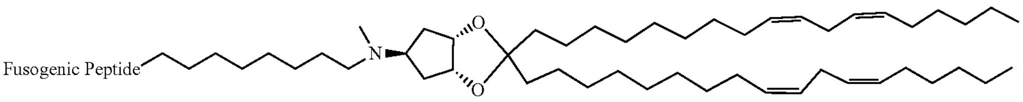
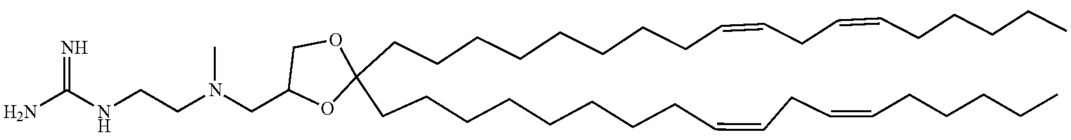 [SMILES: CCCCC/C=C\C/C=C\CCCCCCCCC1(CCCCCCCC/C=C\C/C=C\CCCCC)OCC(CN(C)CCNC(=N)N)O1]
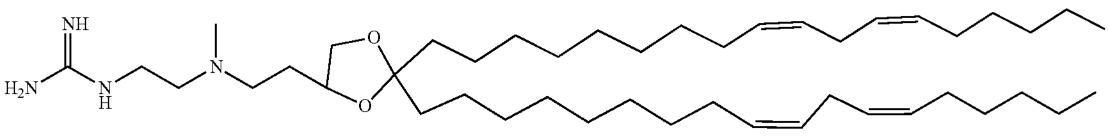 [SMILES: CCCCC/C=C\C/C=C\CCCCCCCCC1(CCCCCCCC/C=C\C/C=C\CCCCC)OCC(CCN(C)CCNC(=N)N)O1]

TABLE 11-continued
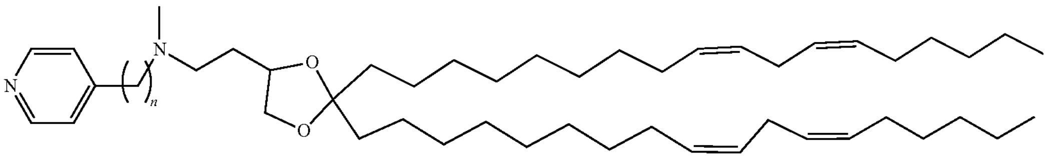
n = 0-6
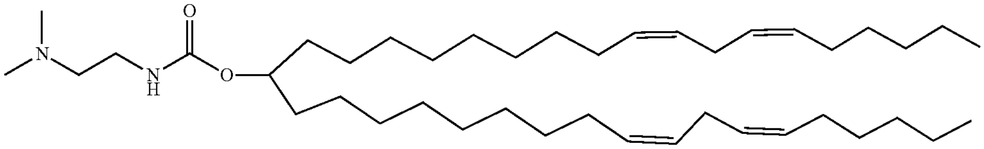 [SMILES: CCCCC/C=C\C/C=C\CCCCCCCCC(CCCCCCCC/C=C\C/C=C\CCCCC)OC(=O)NCCN(C)C]
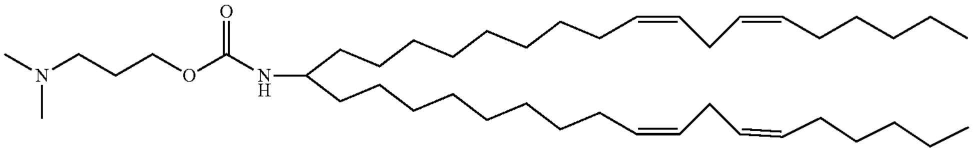 [SMILES: CCCCC/C=C\C/C=C\CCCCCCCCC(CCCCCCCC/C=C\C/C=C\CCCCC)NC(=O)OCCCN(C)C]
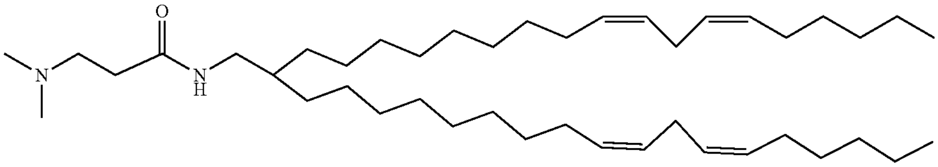 [SMILES: CCCCC/C=C\C/C=C\CCCCCCCCC(CCCCCCCC/C=C\C/C=C\CCCCC)CNC(=O)CCN(C)C]
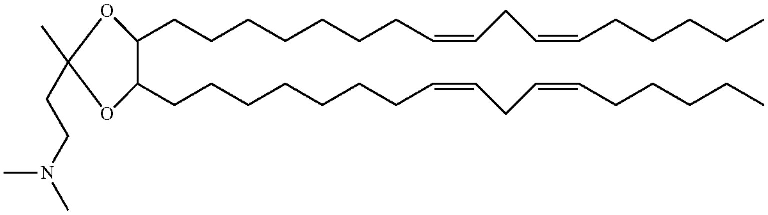
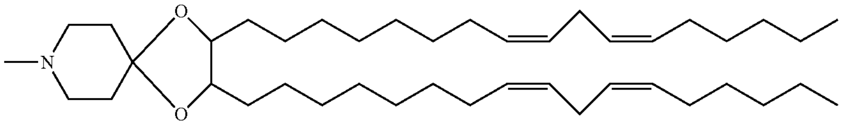 [SMILES: CCCCC/C=C\C/C=C\CCCCCCCC1OC2(CCN(C)CC2)OC1CCCCCCC/C=C\C/C=C\CCCCC]
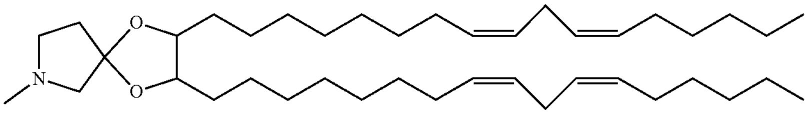 [SMILES: CCCCC/C=C\C/C=C\CCCCCCCC1OC2(CCN(C)C2)OC1CCCCCCC/C=C\C/C=C\CCCCC]
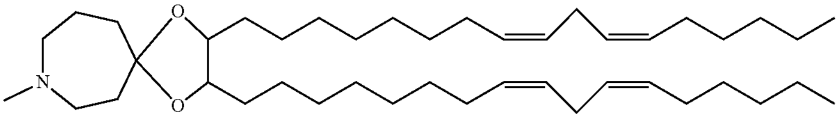 [SMILES: CCCCC/C=C\C/C=C\CCCCCCCC1OC2(CCCN(C)CC2)OC1CCCCCCC/C=C\C/C=C\CCCCC]
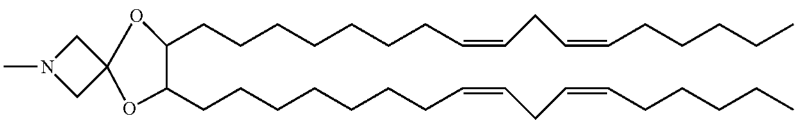 [SMILES: CCCCC/C=C\C/C=C\CCCCCCCC1OC2(CN(C)C2)OC1CCCCCCC/C=C\C/C=C\CCCCC]

TABLE 11-continued
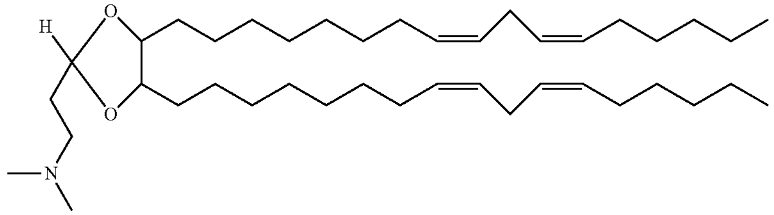 [SMILES: CCCCC/C=C\C/C=C\CCCCCCCC1OC(CCN(C)C)OC1CCCCCCC/C=C\C/C=C\CCCCC]
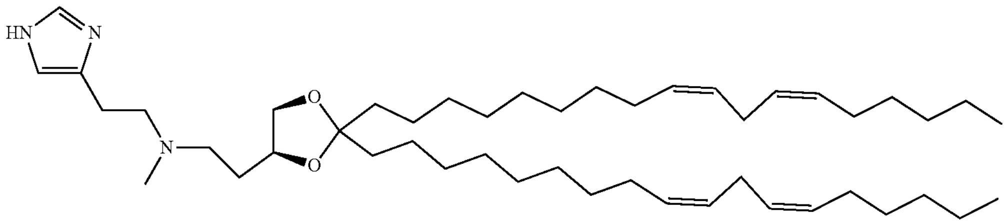
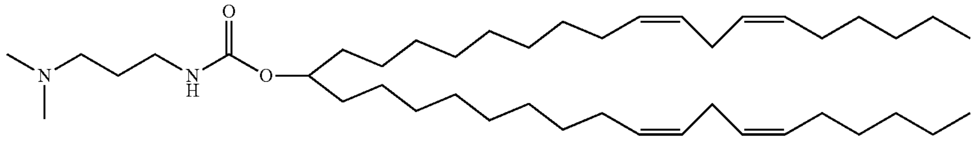 [SMILES: CCCCC/C=C\C/C=C\CCCCCCCCC(CCCCCCCC/C=C\C/C=C\CCCCC)OC(=O)NCCCN(C)C]
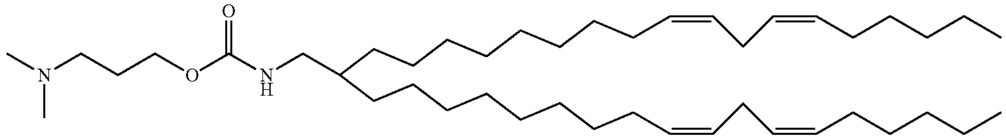 [SMILES: CCCCC/C=C\C/C=C\CCCCCCCCC(CCCCCCCC/C=C\C/C=C\CCCCC)CNC(=O)OCCCN(C)C]
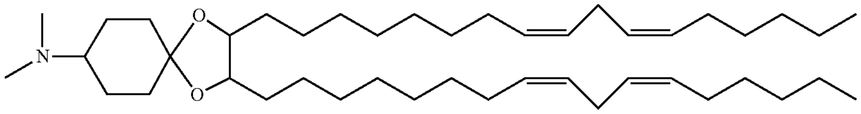 [SMILES: CCCCC/C=C\C/C=C\CCCCCCCC1OC2(CCC(N(C)C)CC2)OC1CCCCCCC/C=C\C/C=C\CCCCC]
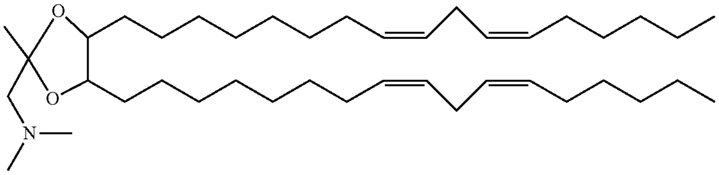 [SMILES: CCCCC/C=C\C/C=C\CCCCCCCC1OC(C)(CN(C)C)OC1CCCCCCC/C=C\C/C=C\CCCCC]
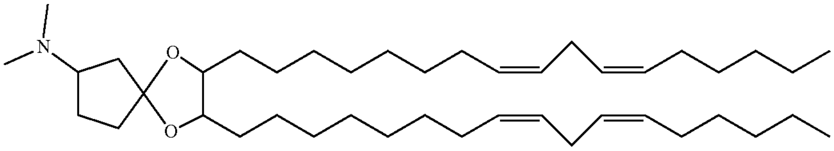 [SMILES: CCCCC/C=C\C/C=C\CCCCCCCC1OC2(CCC(N(C)C)C2)OC1CCCCCCC/C=C\C/C=C\CCCCC]
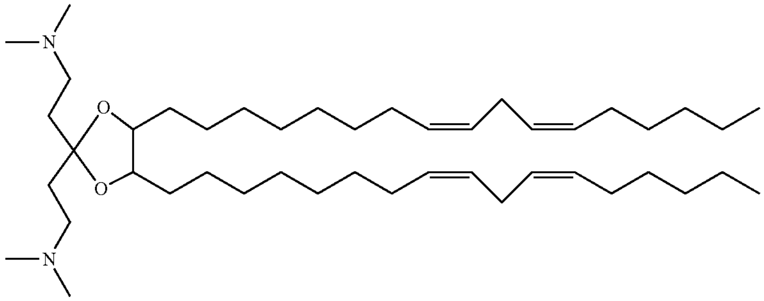 [SMILES: CCCCC/C=C\C/C=C\CCCCCCCC1OC(CCN(C)C)(CCN(C)C)OC1CCCCCCC/C=C\C/C=C\CCCCC]

TABLE 11-continued
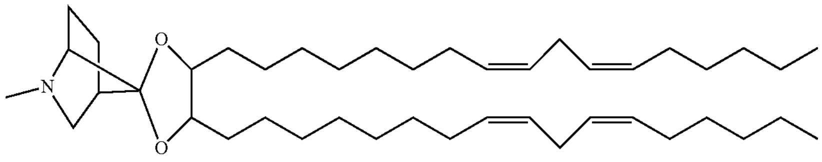 [SMILES: CCCCC/C=C\C/C=C\CCCCCCCC1OC2(OC1CCCCCCC/C=C\C/C=C\CCCCC)C1CCC2N(C)C1]
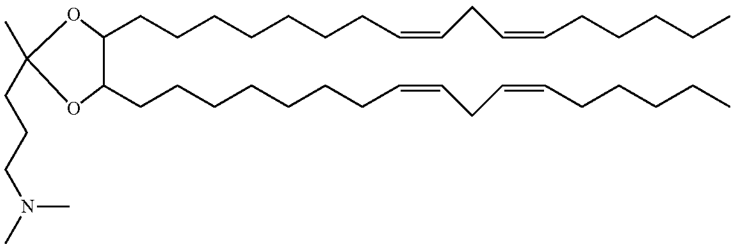 [SMILES: CCCCC/C=C\C/C=C\CCCCCCCC1OC(C)(CCCN(C)C)OC1CCCCCCC/C=C\C/C=C\CCCCC]
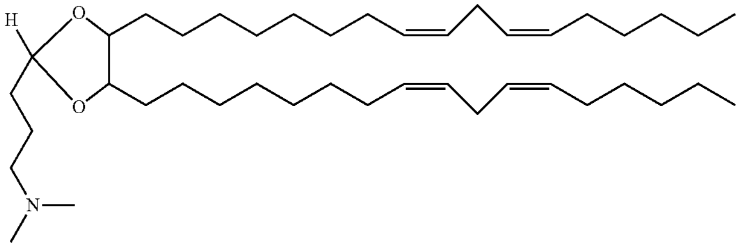 [SMILES: CCCCC/C=C\C/C=C\CCCCCCCC1OC(CCCN(C)C)OC1CCCCCCC/C=C\C/C=C\CCCCC]
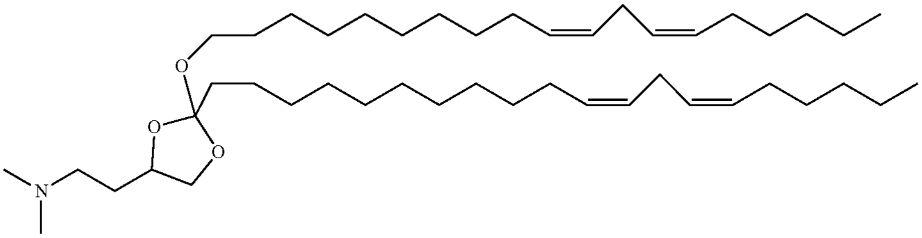 [SMILES: CCCCC/C=C\C/C=C\CCCCCCCCCCC1(OCCCCCCCCC/C=C\C/C=C\CCCCC)OCC(CCN(C)C)O1]
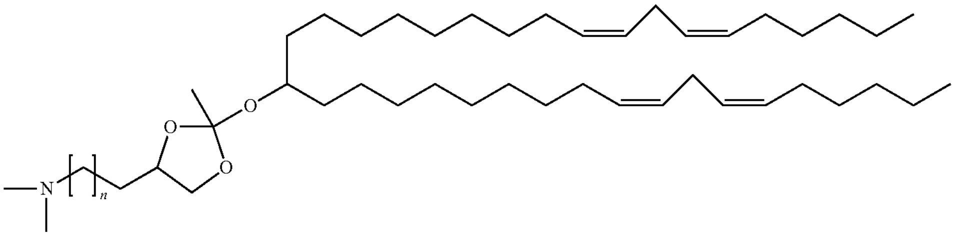
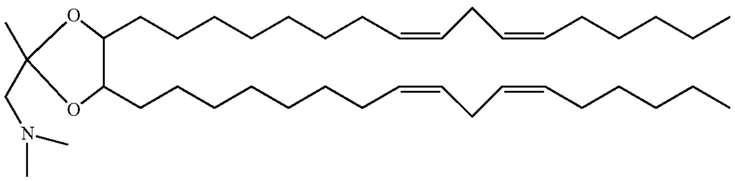 [SMILES: CCCCC/C=C\C/C=C\CCCCCCCC1OC(C)(CN(C)C)OC1CCCCCCC/C=C\C/C=C\CCCCC]
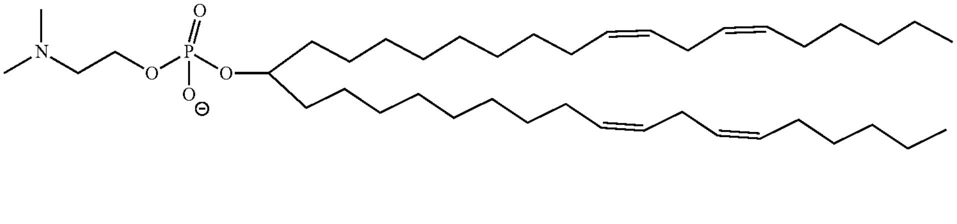 [SMILES: CCCCC/C=C\C/C=C\CCCCCCCCC(CCCCCCCC/C=C\C/C=C\CCCCC)OP(=O)([O-])OCCN(C)C]

TABLE 11-continued
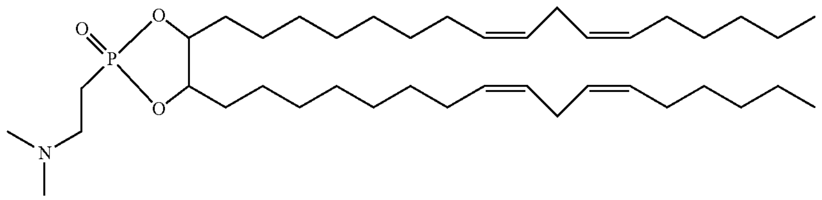
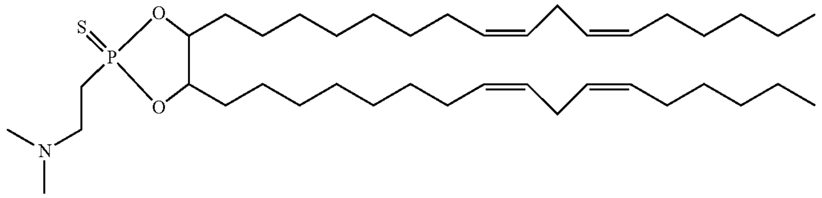 [SMILES: CCCCC/C=C\C/C=C\CCCCCCCC1OP(=O)(CCN(C)C)OC1CCCCCCC/C=C\C/C=C\CCCCC]
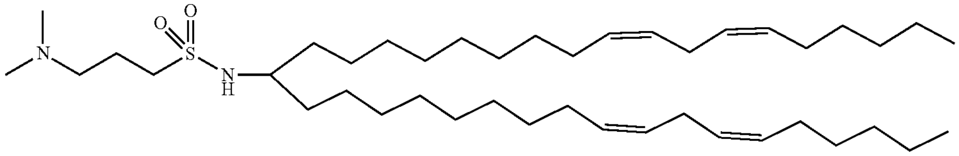 [SMILES: CCCCC/C=C\C/C=C\CCCCCCCCC(CCCCCCCC/C=C\C/C=C\CCCCC)NS(=O)(=O)CCCN(C)C]
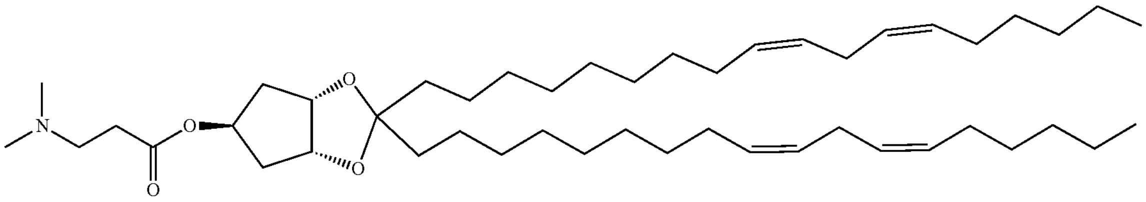
Q is O, NH, NMe
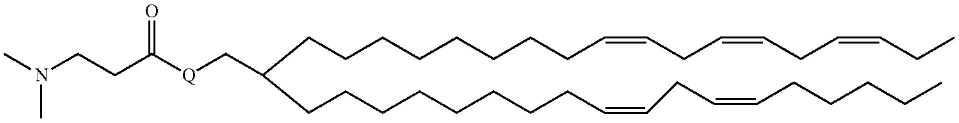
Q is O, NH, NMe
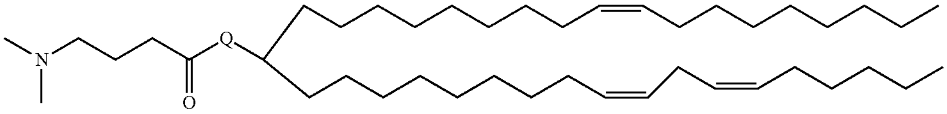
Q is O, NH, NMe
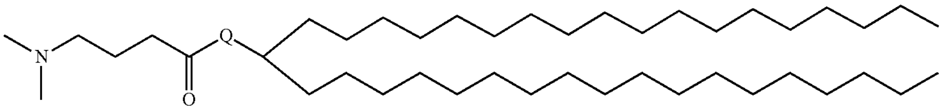
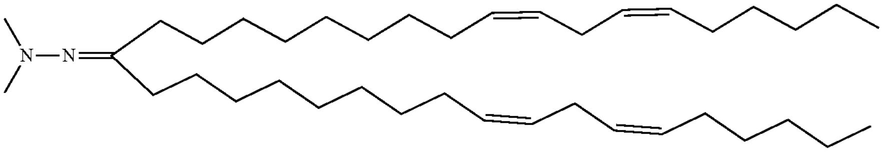 [SMILES: CCCCC/C=C\C/C=C\CCCCCCCCC(CCCCCCCC/C=C\C/C=C\CCCCC)=NN(C)C]

TABLE 11-continued
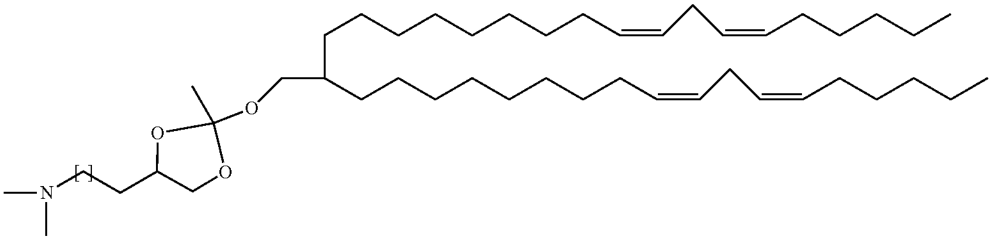
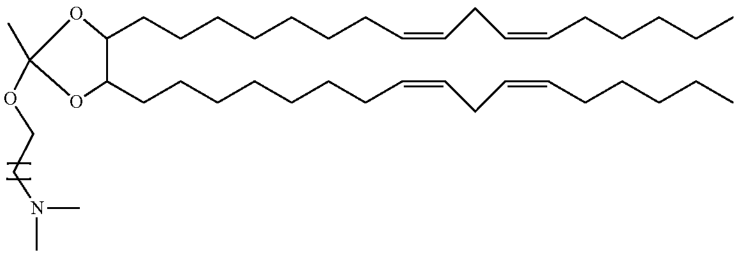
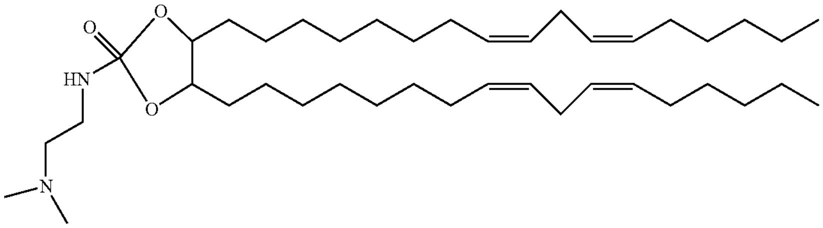
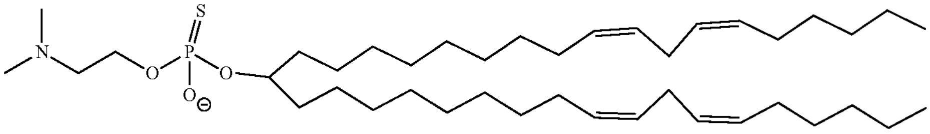 [SMILES: CCCCC/C=C\C/C=C\CCCCCCCCC(CCCCCCCC/C=C\C/C=C\CCCCC)OP([O-])(=S)OCCN(C)C]
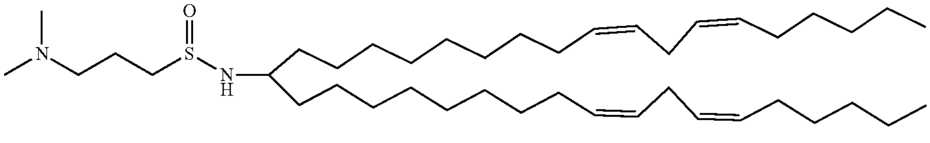 [SMILES: CCCCC/C=C\C/C=C\CCCCCCCCC(CCCCCCCC/C=C\C/C=C\CCCCC)NS(=O)CCCN(C)C]
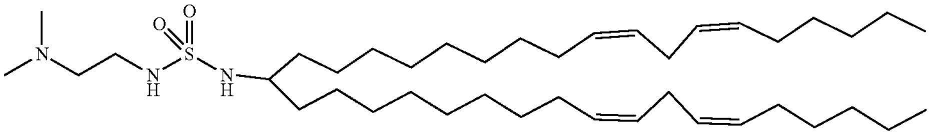 [SMILES: CCCCC/C=C\C/C=C\CCCCCCCCC(CCCCCCCC/C=C\C/C=C\CCCCC)NS(=O)(=O)NCCN(C)C]
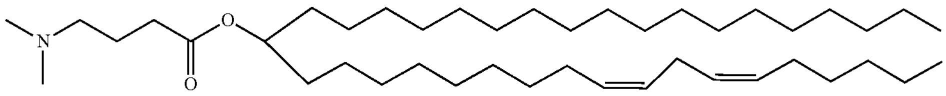
Q is O, NH, NMe
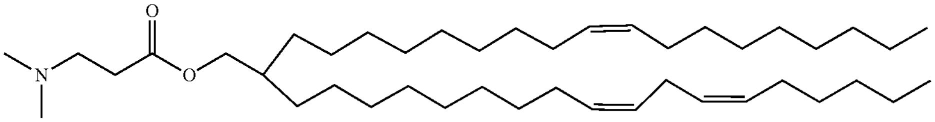
Q is O, NH, NMe
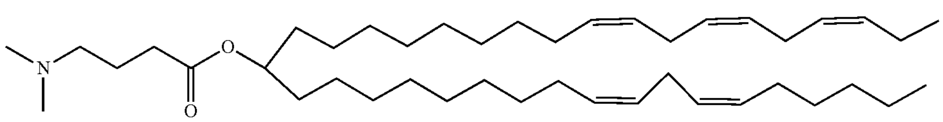
Q is O, NH, NMe TABLE 11-continued
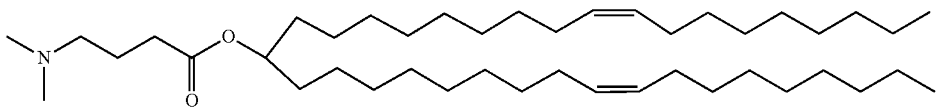 [SMILES: CCCCCCCC/C=C\CCCCCCCCC(CCCCCCCC/C=C\CCCCCCCC)OC(=O)CCCN(C)C]
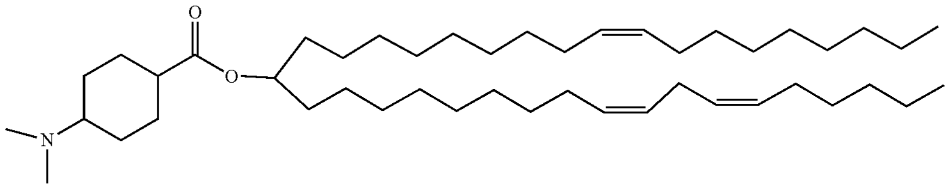 [SMILES: CCCCC/C=C\C/C=C\CCCCCCCCC(CCCCCCCC/C=C\CCCCCCCC)OC(=O)C1CCC(N(C)C)CC1]
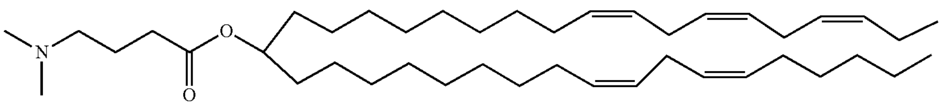 [SMILES: CC/C=C\C/C=C\C/C=C\CCCCCCCCC(CCCCCCCC/C=C\C/C=C\CCCCC)OC(=O)CCCN(C)C]
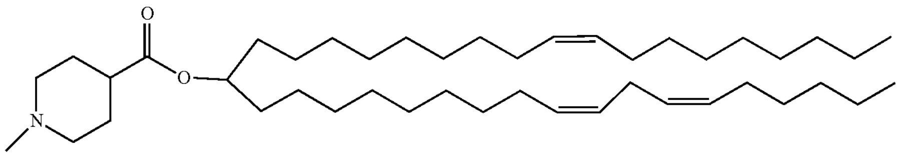 [SMILES: CCCCC/C=C\C/C=C\CCCCCCCCC(CCCCCCCC/C=C\CCCCCCCC)OC(=O)C1CCN(C)CC1]
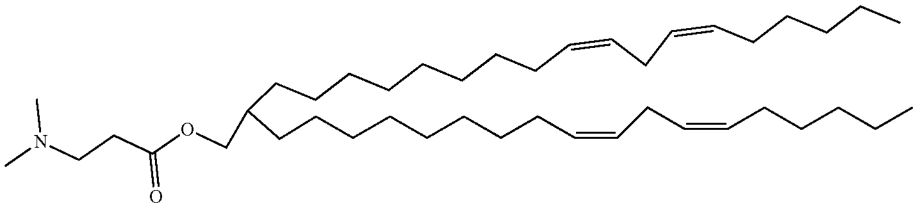
Q is O, NH, NMe
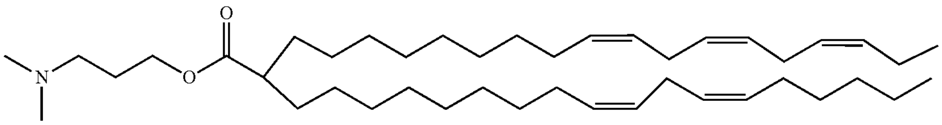
Q is O, NH, NMe
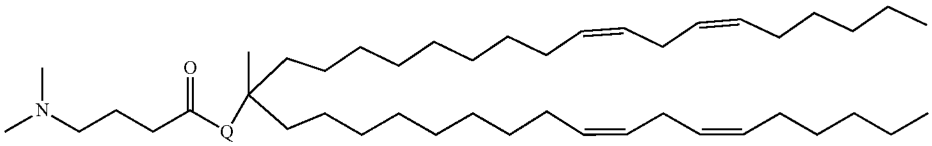
Q is O, NH, NMe
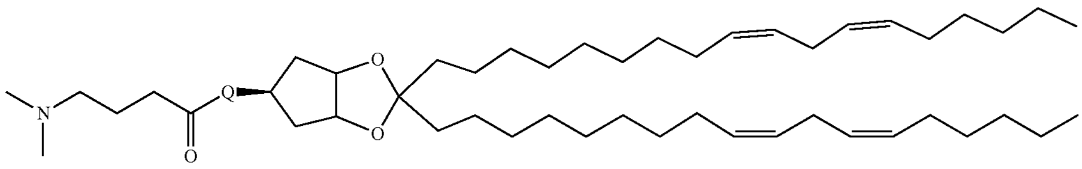
Q is O, NH, NMe TABLE 11-continued
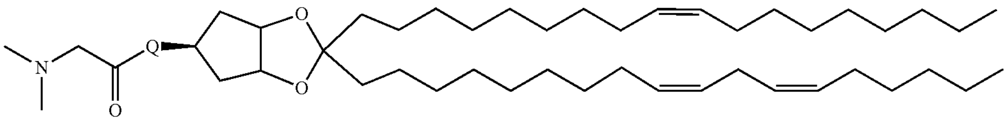
Q is O, NH, NMe
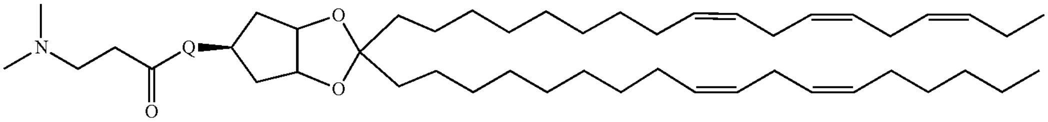
Q is O, NH, NMe
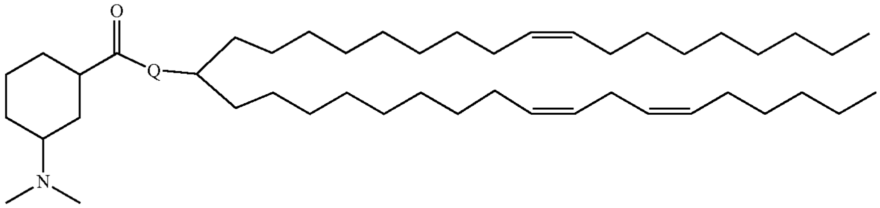
Q is O, NH, NMe
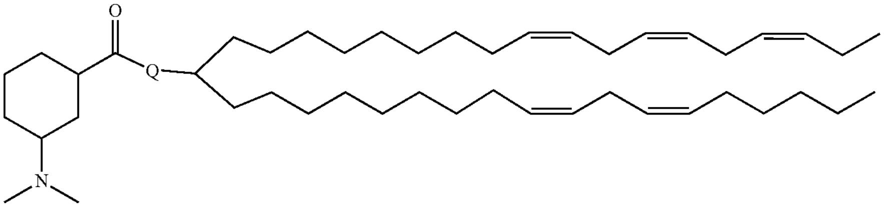
Q is O, NH, NMe
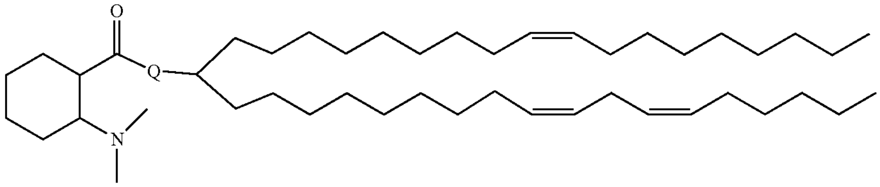
Q is O, NH, NMe
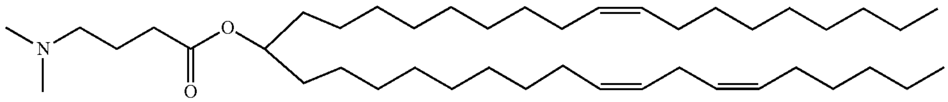 [SMILES: CCCCC/C=C\C/C=C\CCCCCCCCC(CCCCCCCC/C=C\CCCCCCCC)OC(=O)CCCN(C)C]
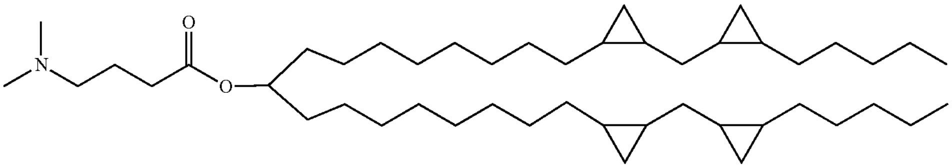 [SMILES: CCCCCC1CC1CC1CC1CCCCCCCCC(CCCCCCCCC1CC1CC1CC1CCCCC)OC(=O)CCCN(C)C]
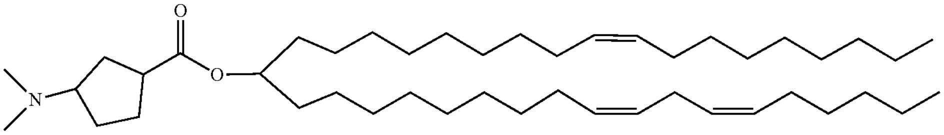 [SMILES: CCCCC/C=C\C/C=C\CCCCCCCCC(CCCCCCCC/C=C\CCCCCCCC)OC(=O)C1CCC(N(C)C)C1]

TABLE 11-continued
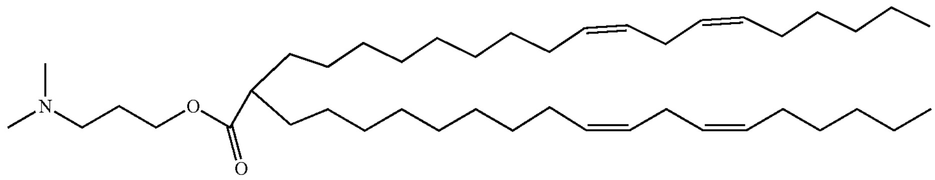
Q is O, NH, NMe
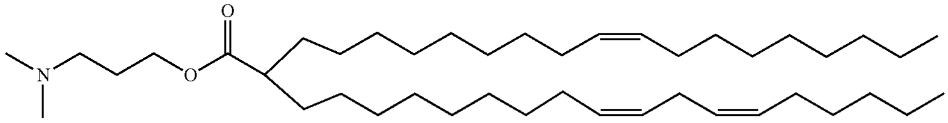
Q is O, NH, NMe
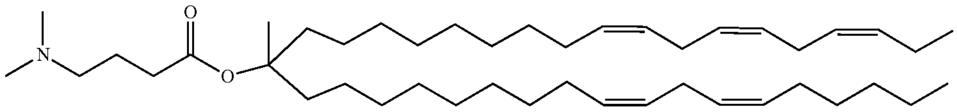
Q is O, NH, NMe
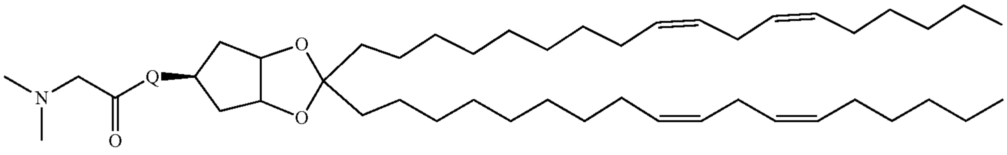
Q is O, NH, NMe
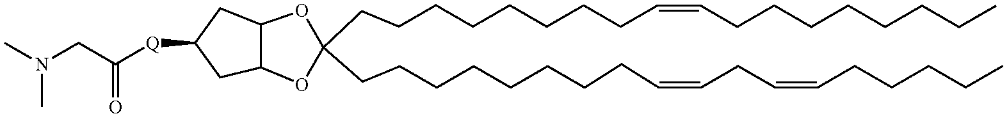
Q is O, NH, NMe
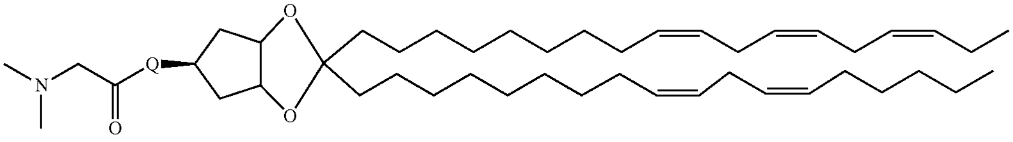
Q is O, NH, NMe
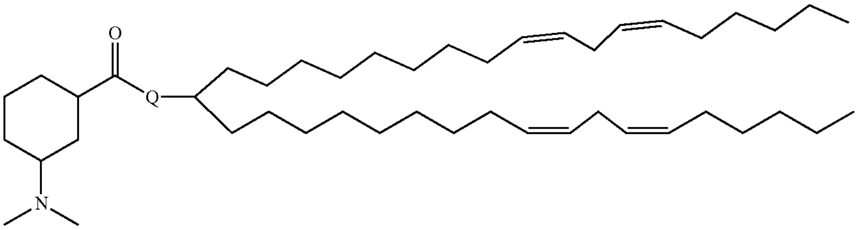
Q is O, NH, NMe TABLE 11-continued
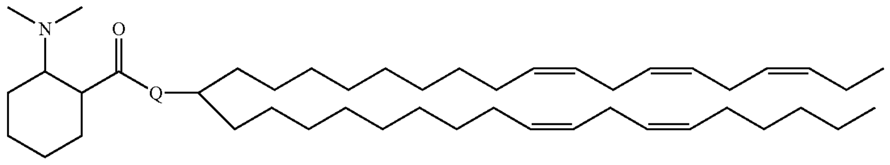
Q is O, NH, NMe
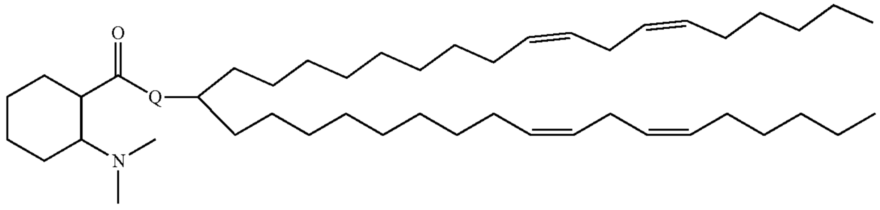
Q is O, NH, NMe
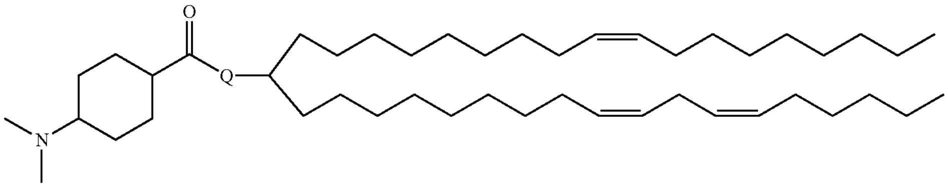
Q is O, NH, NMe
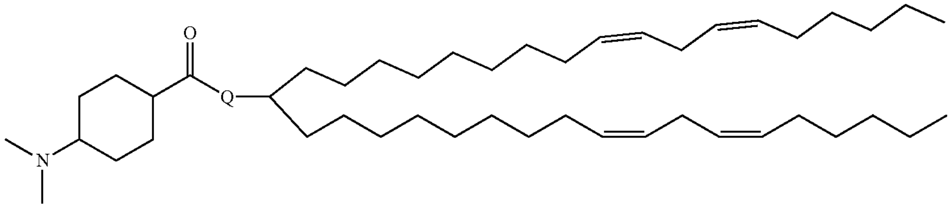
Q is O, NH, NMe
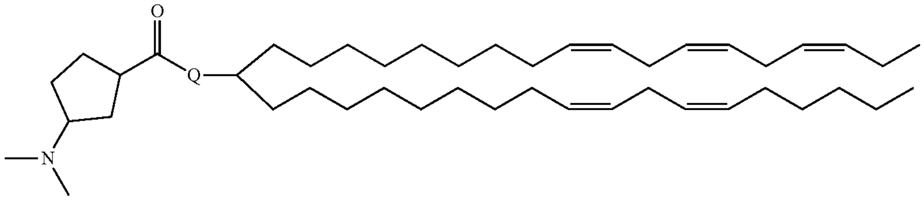
Q is O, NH, NMe
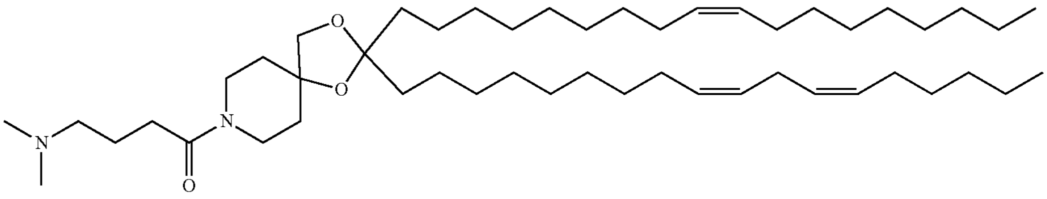 [SMILES: CCCCC/C=C\C/C=C\CCCCCCCCC1(CCCCCCCC/C=C\CCCCCCCC)OCC2(CCN(C(=O)CCCN(C)C)CC2)O1]

TABLE 11-continued
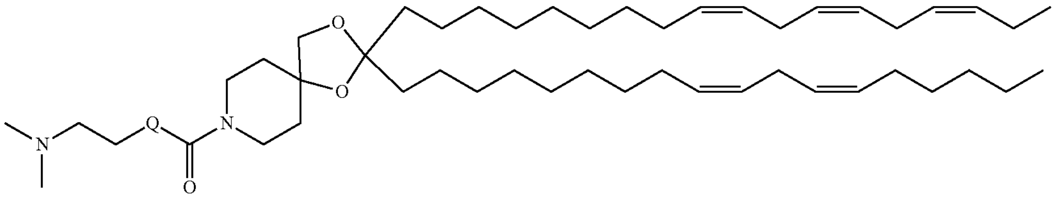
Q is O, NH, NMe
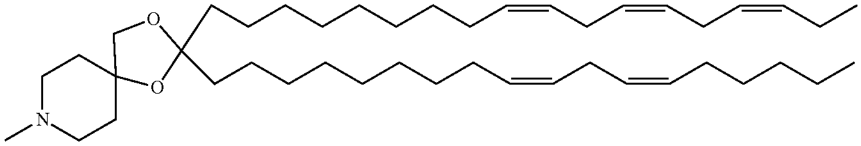 [SMILES: CC/C=C\C/C=C\C/C=C\CCCCCCCCC1(CCCCCCCC/C=C\C/C=C\CCCCC)OCC2(CCN(C)CC2)O1]
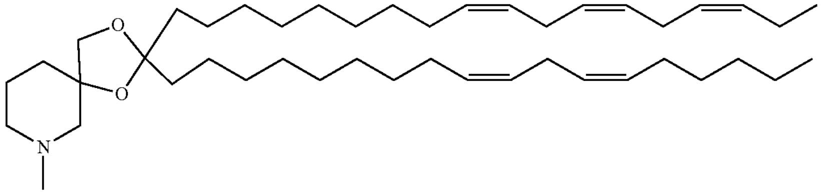 [SMILES: CC/C=C\C/C=C\C/C=C\CCCCCCCCC1(CCCCCCCC/C=C\C/C=C\CCCCC)OCC2(CCCN(C)C2)O1]
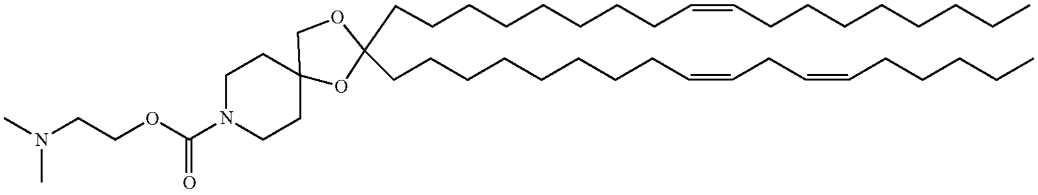 [SMILES: CCCCC/C=C\C/C=C\CCCCCCCCC1(CCCCCCCC/C=C\CCCCCCCC)OCC2(CCN(C(=O)OCCN(C)C)CC2)O1]
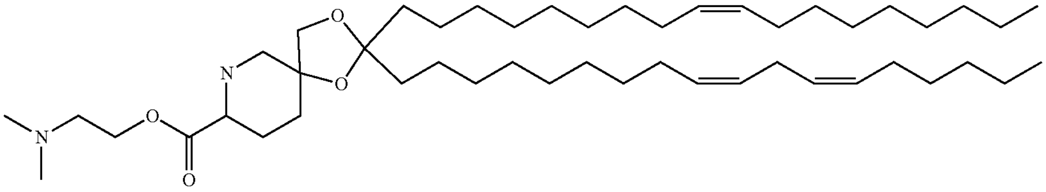 [SMILES: CCCCC/C=C\C/C=C\CCCCCCCCC1(CCCCCCCC/C=C\CCCCCCCC)OCC2(CCC(C(=O)OCCN(C)C)NC2)O1]
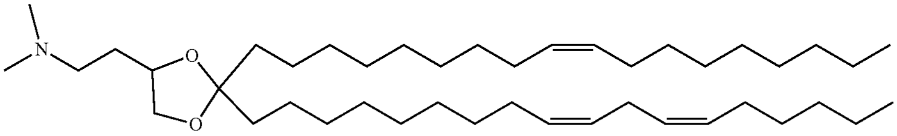 [SMILES: CCCCC/C=C\C/C=C\CCCCCCCCC1(CCCCCCCC/C=C\CCCCCCCC)OCC(CCN(C)C)O1]
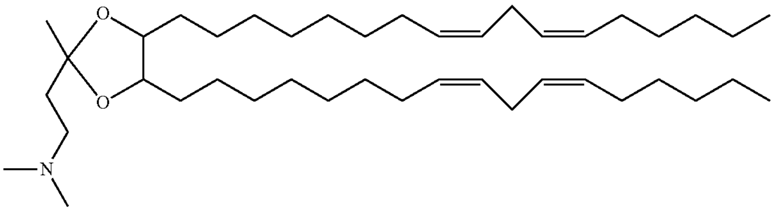 [SMILES: CCCCC/C=C\C/C=C\CCCCCCCC1OC(C)(CCN(C)C)OC1CCCCCCC/C=C\C/C=C\CCCCC]
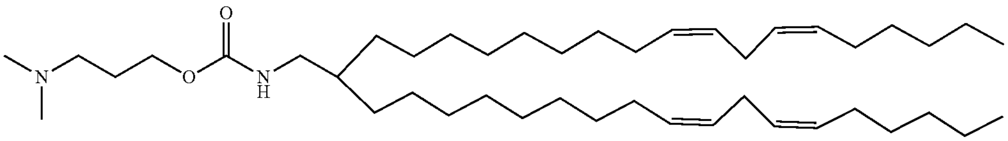 [SMILES: CCCCC/C=C\C/C=C\CCCCCCCCC(CCCCCCCC/C=C\C/C=C\CCCCC)CNC(=O)OCCCN(C)C]

TABLE 11-continued
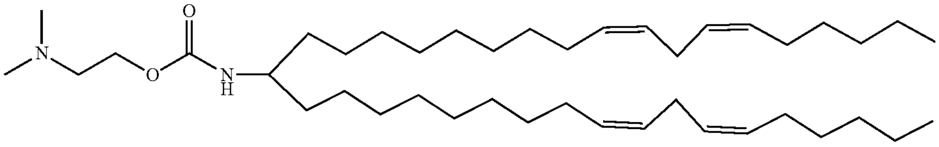 [SMILES: CCCCC/C=C\C/C=C\CCCCCCCCC(CCCCCCCC/C=C\C/C=C\CCCCC)NC(=O)OCCN(C)C]
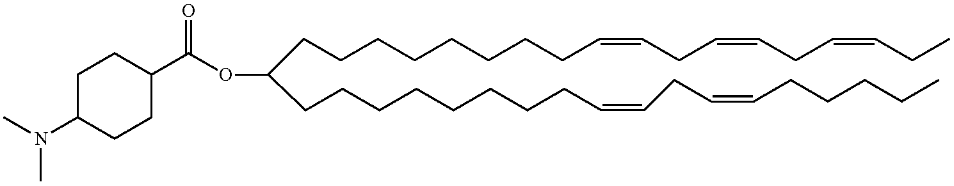
Q is O, NH, NMe
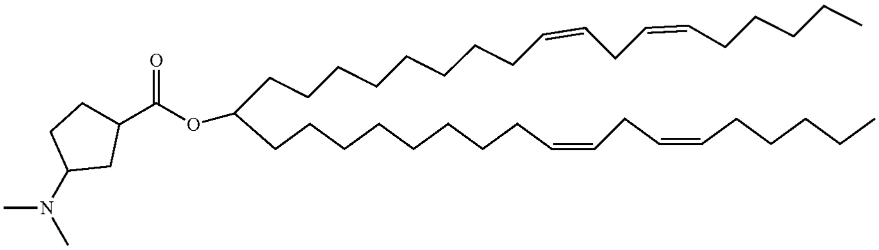
Q is O, NH, NMe
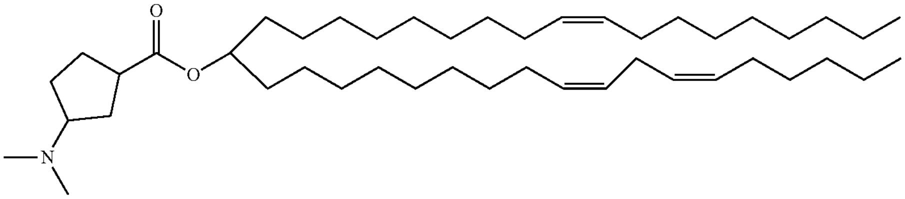
Q is O, NH, NMe
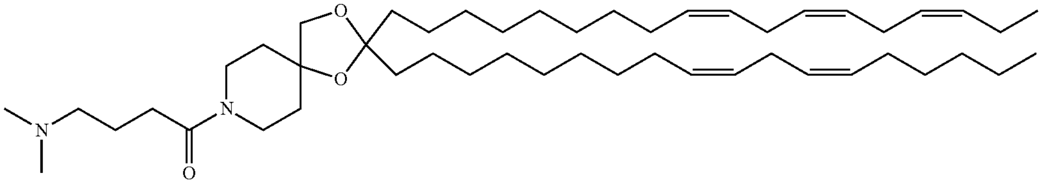 [SMILES: CC/C=C\C/C=C\C/C=C\CCCCCCCCC1(CCCCCCCC/C=C\C/C=C\CCCCC)OCC2(CCN(C(=O)CCCN(C)C)CC2)O1]
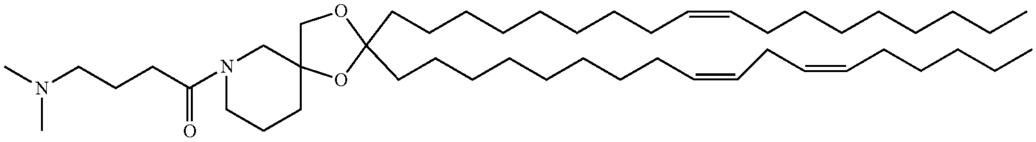 [SMILES: CCCCC/C=C\C/C=C\CCCCCCCCC1(CCCCCCCC/C=C\CCCCCCCC)OCC2(CCCN(C(=O)CCCN(C)C)C2)O1]
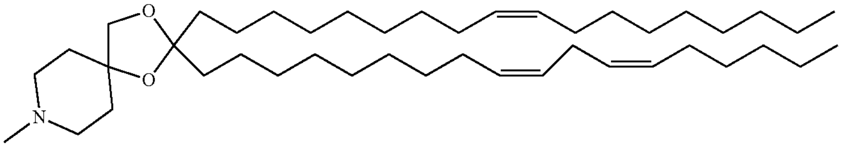 [SMILES: CCCCC/C=C\C/C=C\CCCCCCCCC1(CCCCCCCC/C=C\CCCCCCCC)OCC2(CCN(C)CC2)O1]
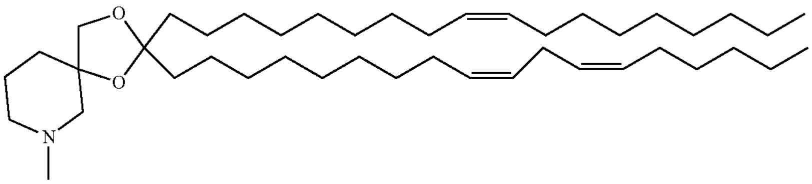 [SMILES: CCCCC/C=C\C/C=C\CCCCCCCCC1(CCCCCCCC/C=C\CCCCCCCC)OCC2(CCCN(C)C2)O1]

TABLE 11-continued
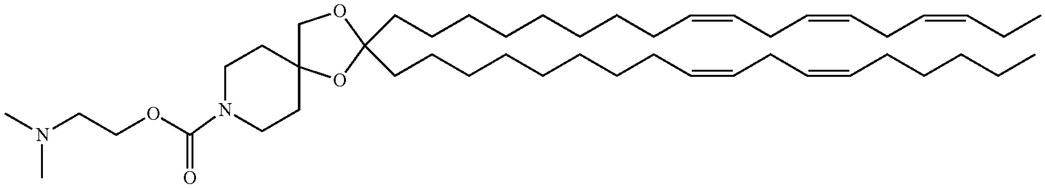 [SMILES: CC/C=C\C/C=C\C/C=C\CCCCCCCCC1(CCCCCCCC/C=C\C/C=C\CCCCC)OCC2(CCN(C(=O)OCCN(C)C)CC2)O1]
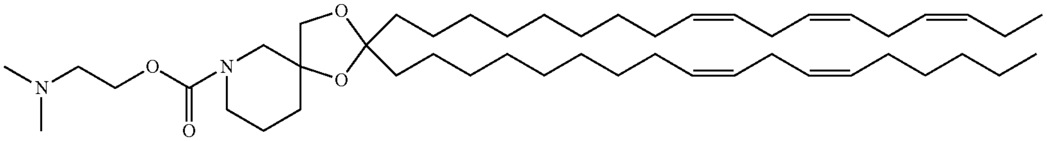 [SMILES: CC/C=C\C/C=C\C/C=C\CCCCCCCCC1(CCCCCCCC/C=C\C/C=C\CCCCC)OCC2(CCCN(C(=O)OCCN(C)C)C2)O1]
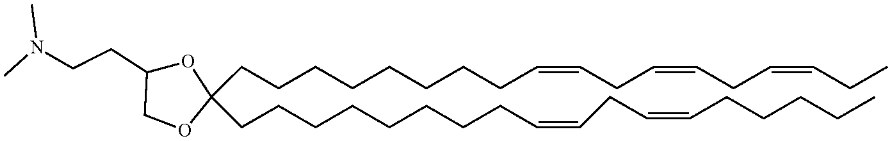 [SMILES: CC/C=C\C/C=C\C/C=C\CCCCCCCCC1(CCCCCCCC/C=C\C/C=C\CCCCC)OCC(CCN(C)C)O1]
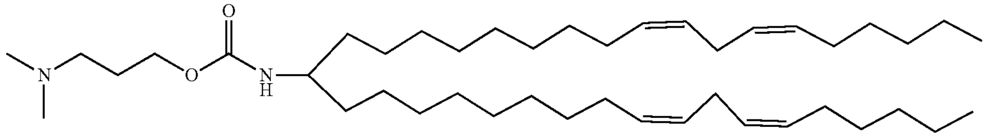 [SMILES: CCCCC/C=C\C/C=C\CCCCCCCCC(CCCCCCCC/C=C\C/C=C\CCCCC)NC(=O)OCCCN(C)C]
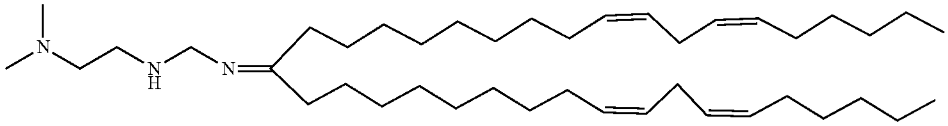 [SMILES: CCCCC/C=C\C/C=C\CCCCCCCCC(CCCCCCCC/C=C\C/C=C\CCCCC)=NCNCCN(C)C]
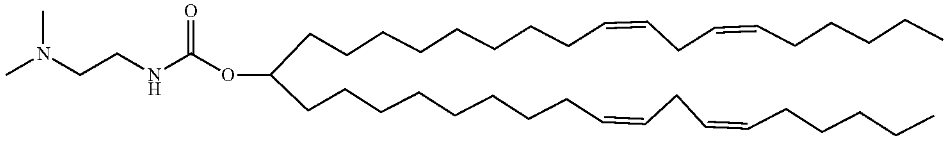 [SMILES: CCCCC/C=C\C/C=C\CCCCCCCCC(CCCCCCCC/C=C\C/C=C\CCCCC)OC(=O)NCCN(C)C]
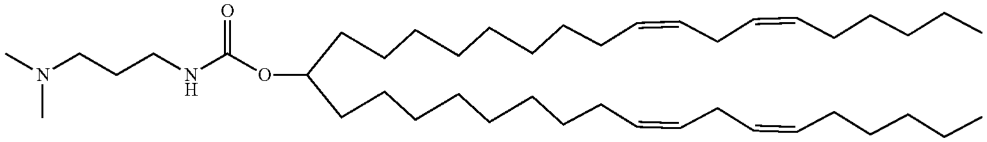 [SMILES: CCCCC/C=C\C/C=C\CCCCCCCCC(CCCCCCCC/C=C\C/C=C\CCCCC)OC(=O)NCCCN(C)C]
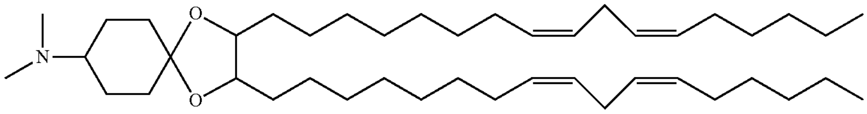 [SMILES: CCCCC/C=C\C/C=C\CCCCCCCC1OC2(CCC(N(C)C)CC2)OC1CCCCCCC/C=C\C/C=C\CCCCC]
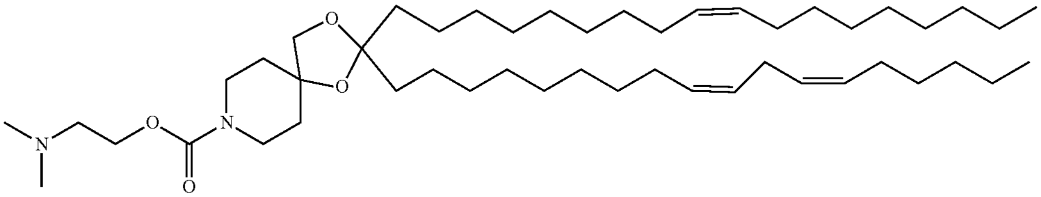 [SMILES: CCCCC/C=C\C/C=C\CCCCCCCCC1(CCCCCCCC/C=C\CCCCCCCC)OCC2(CCN(C(=O)OCCN(C)C)CC2)O1]
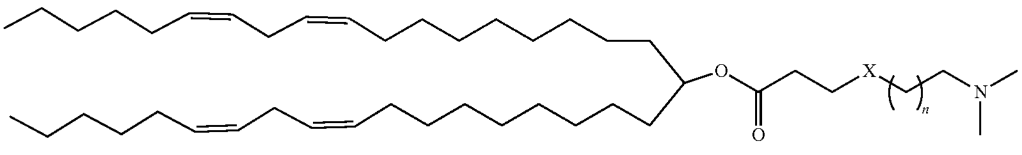
X = O, S, NH, NMe, n = 0-6

TABLE 11-continued
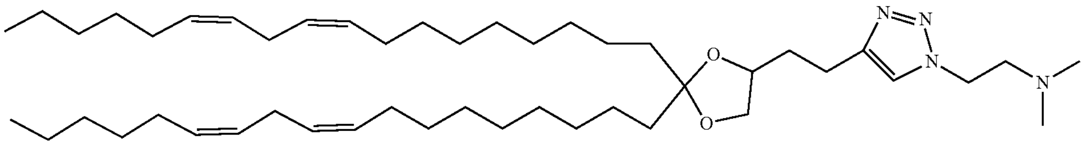 [SMILES: CCCCC/C=C\C/C=C\CCCCCCCCC1(CCCCCCCC/C=C\C/C=C\CCCCC)OCC(CCc2cn(CCN(C)C)nn2)O1]
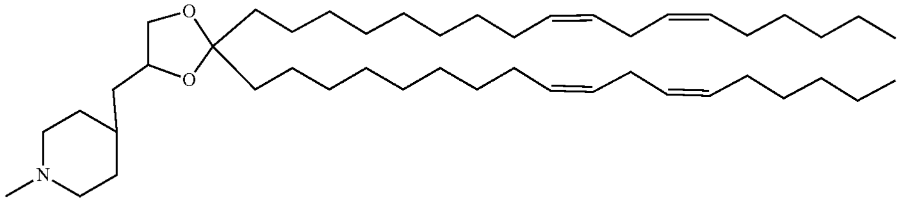 [SMILES: CCCCC/C=C\C/C=C\CCCCCCCCC1(CCCCCCCC/C=C\C/C=C\CCCCC)OCC(CC2CCN(C)CC2)O1]
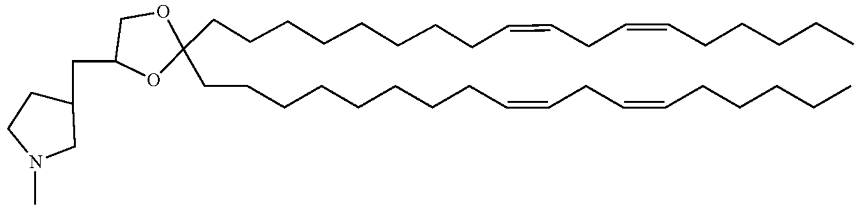 [SMILES: CCCCC/C=C\C/C=C\CCCCCCCCC1(CCCCCCCC/C=C\C/C=C\CCCCC)OCC(CC2CCN(C)C2)O1]
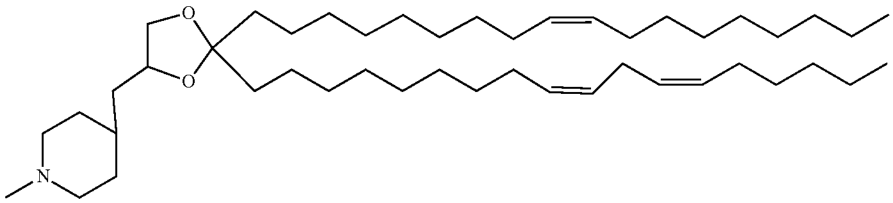 [SMILES: CCCCC/C=C\C/C=C\CCCCCCCCC1(CCCCCCCC/C=C\CCCCCCCC)OCC(CC2CCN(C)CC2)O1]
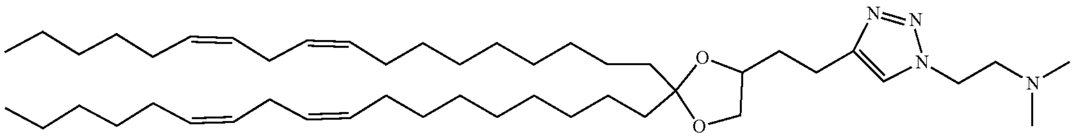 [SMILES: CCCCC/C=C\C/C=C\CCCCCCCCC1(CCCCCCCC/C=C\C/C=C\CCCCC)OCC(CCc2cn(CCN(C)C)nn2)O1]
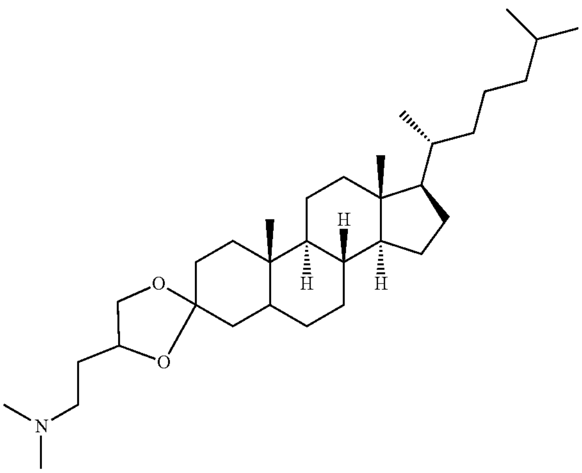

TABLE 11-continued
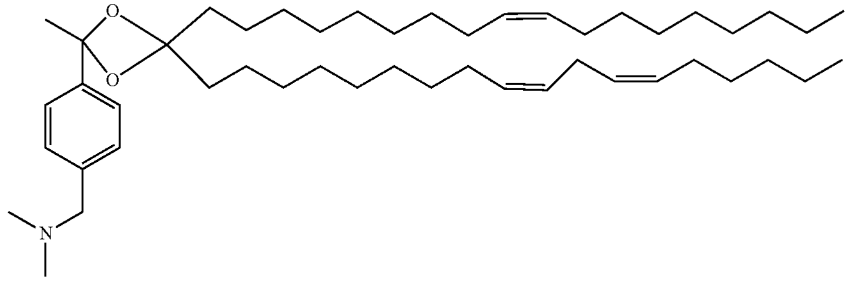 [SMILES: CCCCC/C=C\C/C=C\CCCCCCCCC1(CCCCCCCC/C=C\CCCCCCCC)OC(C)(c2ccc(CN(C)C)cc2)O1]
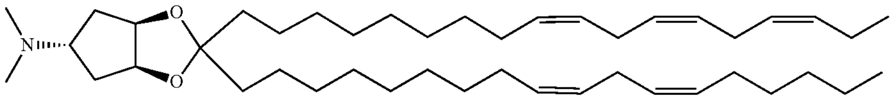
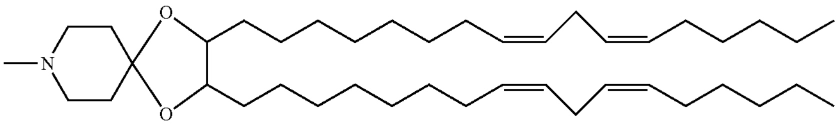 [SMILES: CCCCC/C=C\C/C=C\CCCCCCCC1OC2(CCN(C)CC2)OC1CCCCCCC/C=C\C/C=C\CCCCC]
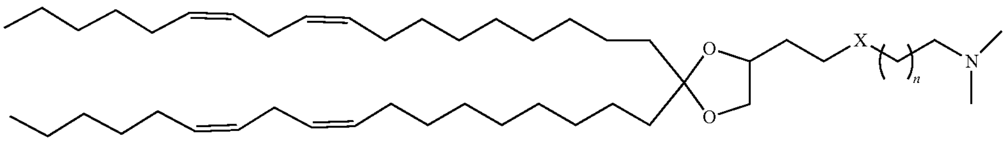
X = O, S, NH, NMe, n = 0-6
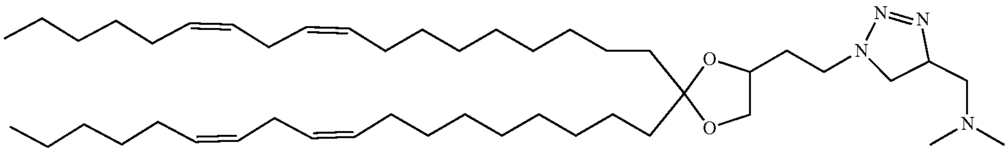 [SMILES: CCCCC/C=C\C/C=C\CCCCCCCCC1(CCCCCCCC/C=C\C/C=C\CCCCC)OCC(CCN2CC(CN(C)C)N=N2)O1]
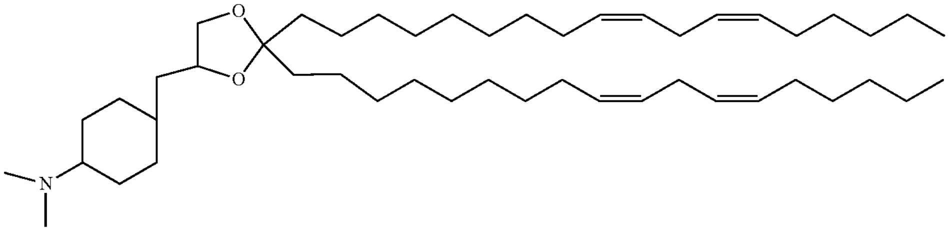 [SMILES: CCCCC/C=C\C/C=C\CCCCCCCCC1(CCCCCCCC/C=C\C/C=C\CCCCC)OCC(CC2CCC(N(C)C)CC2)O1]
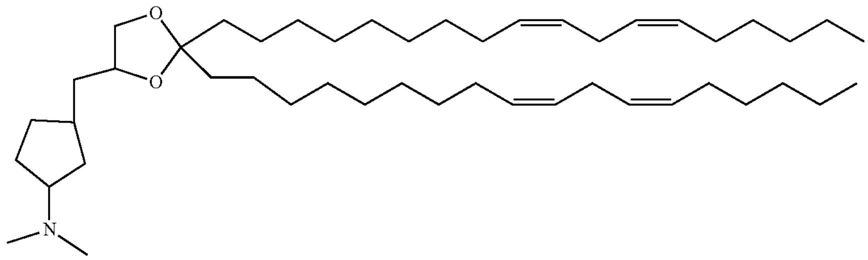 [SMILES: CCCCC/C=C\C/C=C\CCCCCCCCC1(CCCCCCCC/C=C\C/C=C\CCCCC)OCC(CC2CCC(N(C)C)C2)O1]
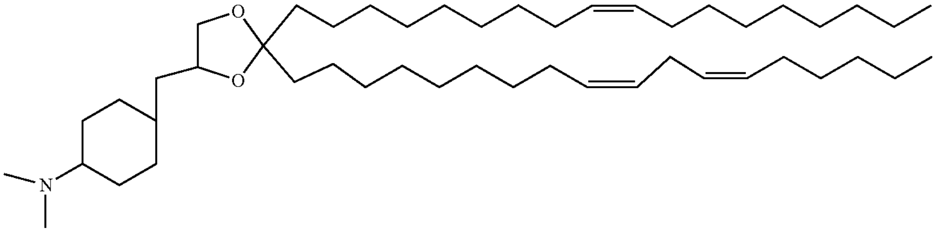 [SMILES: CCCCC/C=C\C/C=C\CCCCCCCCC1(CCCCCCCC/C=C\CCCCCCCC)OCC(CC2CCC(N(C)C)CC2)O1]

TABLE 11-continued
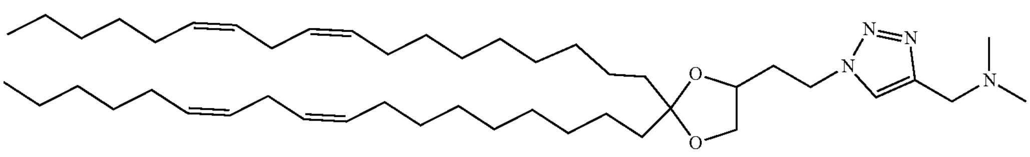 [SMILES: CCCCC/C=C\C/C=C\CCCCCCCCC1(CCCCCCCC/C=C\C/C=C\CCCCC)OCC(CCn2cc(CN(C)C)nn2)O1]
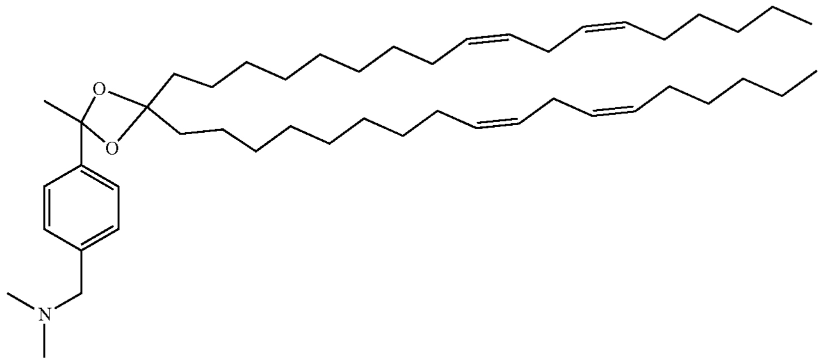 [SMILES: CCCCC/C=C\C/C=C\CCCCCCCCC1(CCCCCCCC/C=C\C/C=C\CCCCC)OC(C)(c2ccc(CN(C)C)cc2)O1]
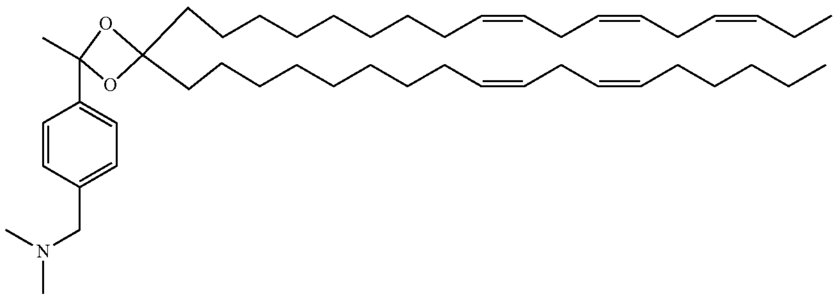 [SMILES: CC/C=C\C/C=C\C/C=C\CCCCCCCCC1(CCCCCCCC/C=C\C/C=C\CCCCC)OC(C)(c2ccc(CN(C)C)cc2)O1]
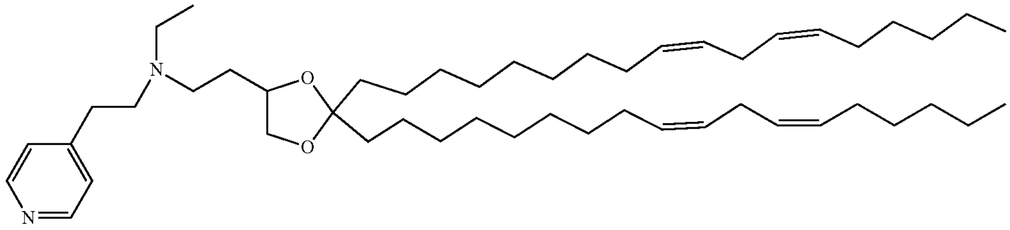 [SMILES: CCCCC/C=C\C/C=C\CCCCCCCCC1(CCCCCCCC/C=C\C/C=C\CCCCC)OCC(CCN(CC)CCc2ccncc2)O1]
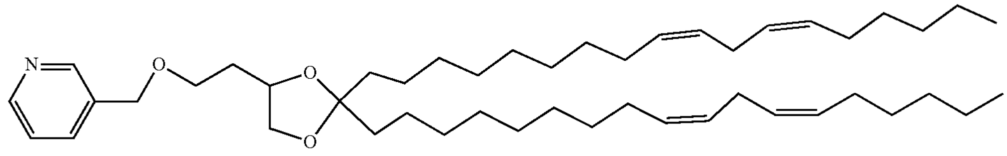 [SMILES: CCCCC/C=C\C/C=C\CCCCCCCCC1(CCCCCCCC/C=C\C/C=C\CCCCC)OCC(CCOCc2cccnc2)O1]
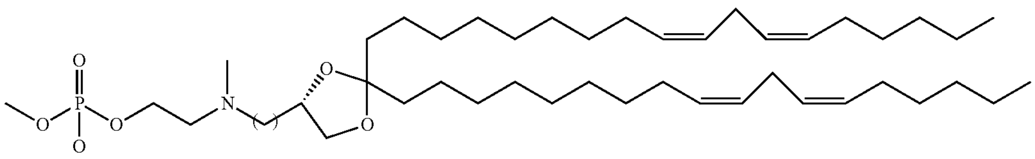
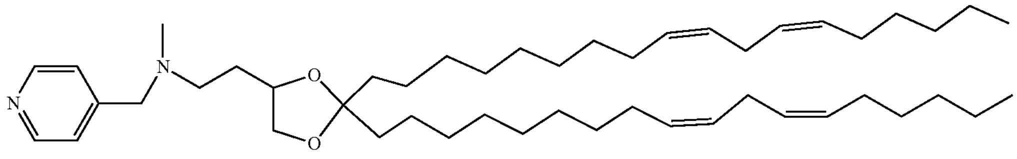 [SMILES: CCCCC/C=C\C/C=C\CCCCCCCCC1(CCCCCCCC/C=C\C/C=C\CCCCC)OCC(CCN(C)Cc2ccncc2)O1]

TABLE 11-continued
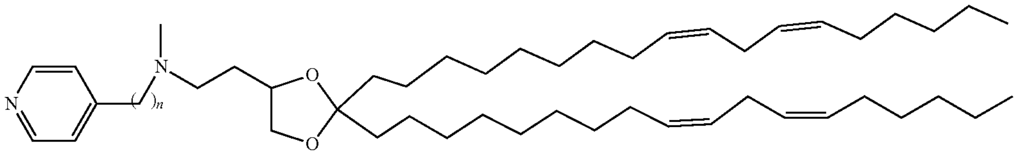
n = 0-6
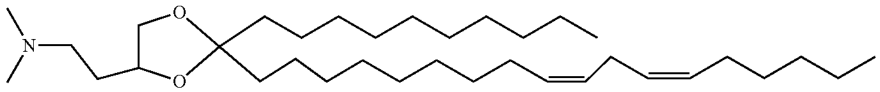 [SMILES: CCCCC/C=C\C/C=C\CCCCCCCCC1(CCCCCCCCCC)OCC(CCN(C)C)O1]
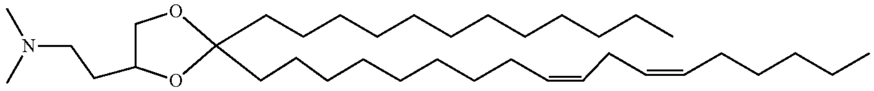 [SMILES: CCCCC/C=C\C/C=C\CCCCCCCCC1(CCCCCCCCCCCC)OCC(CCN(C)C)O1]
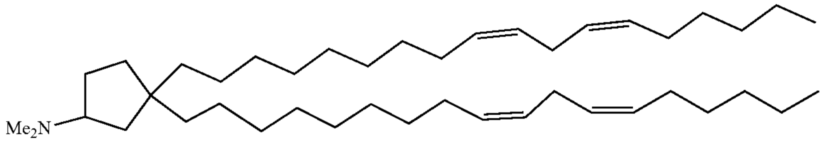
Racemic and optically pure
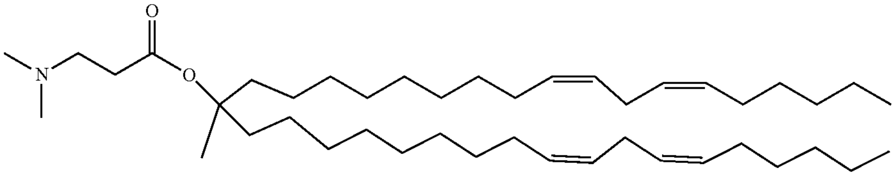 [SMILES: CCCCC/C=C\C/C=C\CCCCCCCCC(C)(CCCCCCCC/C=C\C/C=C\CCCCC)OC(=O)CCN(C)C]
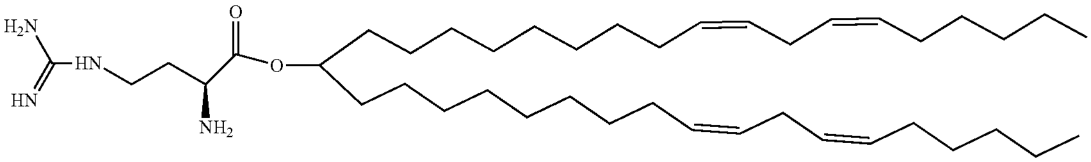 [SMILES: CCCCC/C=C\C/C=C\CCCCCCCCC(CCCCCCCC/C=C\C/C=C\CCCCC)OC(=O)[C@@H](N)CCNC(=N)N]
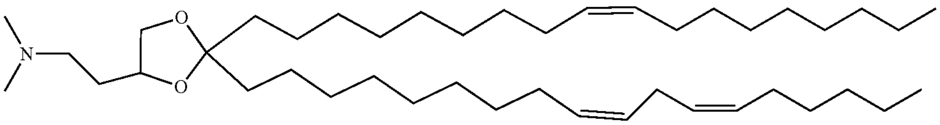 [SMILES: CCCCC/C=C\C/C=C\CCCCCCCCC1(CCCCCCCC/C=C\CCCCCCCC)OCC(CCN(C)C)O1]
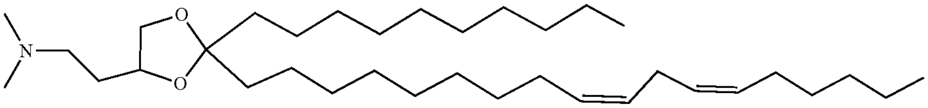 [SMILES: CCCCC/C=C\C/C=C\CCCCCCCCC1(CCCCCCCCCC)OCC(CCN(C)C)O1]
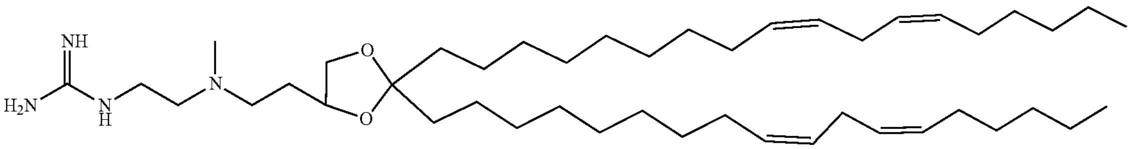 [SMILES: CCCCC/C=C\C/C=C\CCCCCCCCC1(CCCCCCCC/C=C\C/C=C\CCCCC)OCC(CCN(C)CCNC(=N)N)O1]
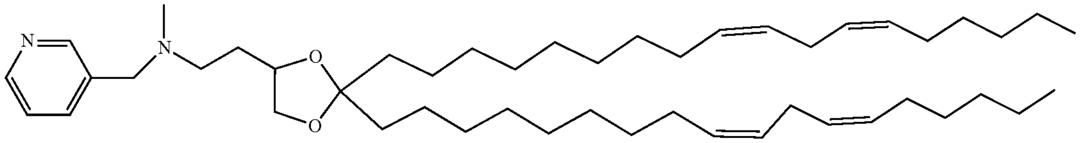 [SMILES: CCCCC/C=C\C/C=C\CCCCCCCCC1(CCCCCCCC/C=C\C/C=C\CCCCC)OCC(CCN(C)Cc2cccnc2)O1]

TABLE 11-continued
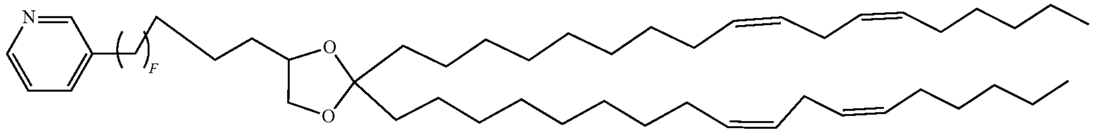
n = 1-10
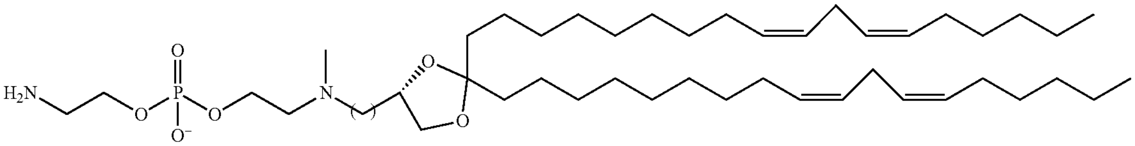
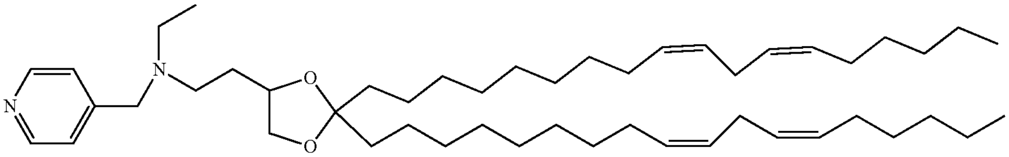 [SMILES: CCCCC/C=C\C/C=C\CCCCCCCCC1(CCCCCCCC/C=C\C/C=C\CCCCC)OCC(CCN(CC)Cc2ccncc2)O1]
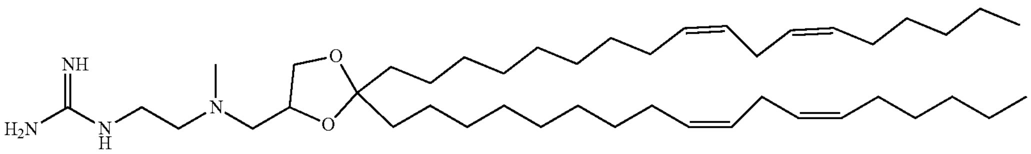 [SMILES: CCCCC/C=C\C/C=C\CCCCCCCCC1(CCCCCCCC/C=C\C/C=C\CCCCC)OCC(CN(C)CCNC(=N)N)O1]
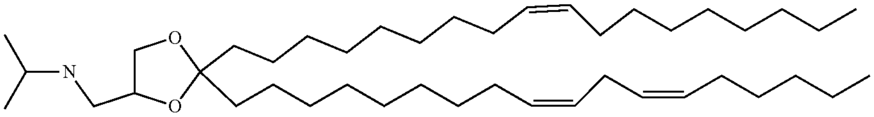 [SMILES: CCCCC/C=C\C/C=C\CCCCCCCCC1(CCCCCCCC/C=C\CCCCCCCC)OCC(CNC(C)C)O1]
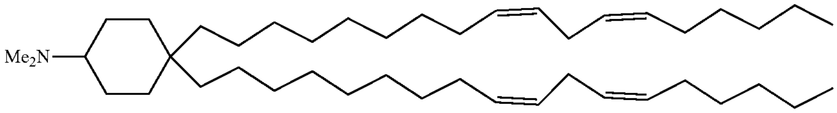
Racemic and optically pure
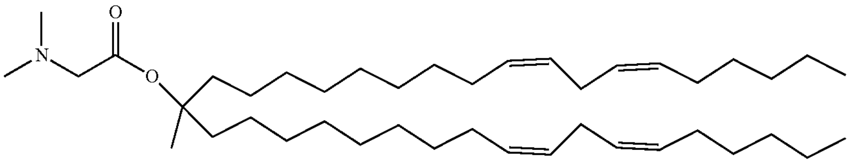 [SMILES: CCCCC/C=C\C/C=C\CCCCCCCCC(C)(CCCCCCCC/C=C\C/C=C\CCCCC)OC(=O)CN(C)C]
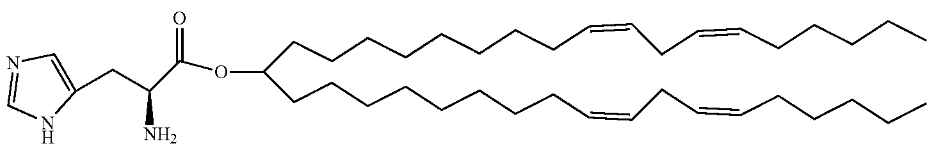 [SMILES: CCCCC/C=C\C/C=C\CCCCCCCCC(CCCCCCCC/C=C\C/C=C\CCCCC)OC(=O)[C@@H](N)Cc1cnc[nH]1]
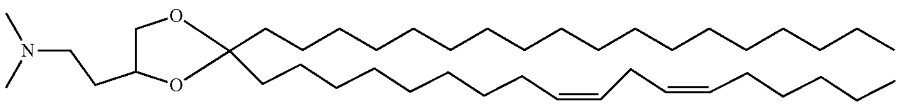 [SMILES: CCCCC/C=C\C/C=C\CCCCCCCCC1(CCCCCCCCCCCCCCCCCC)OCC(CCN(C)C)O1]
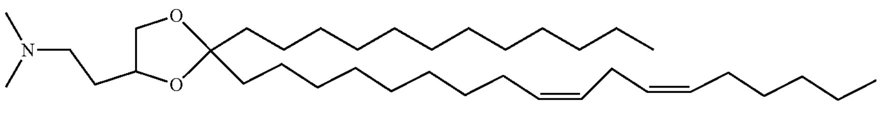 [SMILES: CCCCC/C=C\C/C=C\CCCCCCCCC1(CCCCCCCCCCCC)OCC(CCN(C)C)O1]

TABLE 11-continued
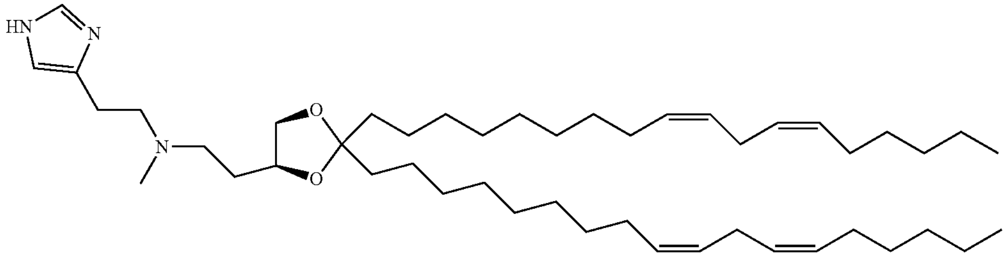
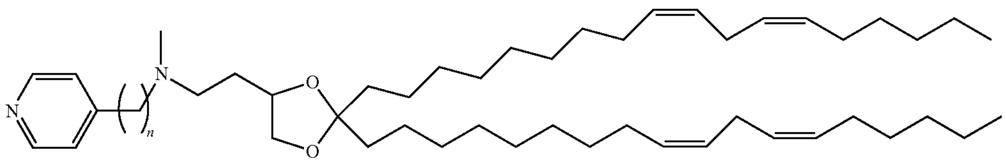
n = 0-6
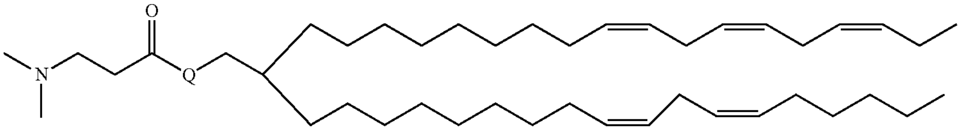
Q is O
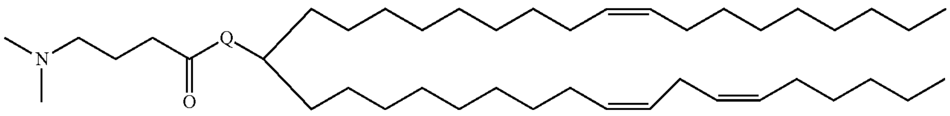
Q is O
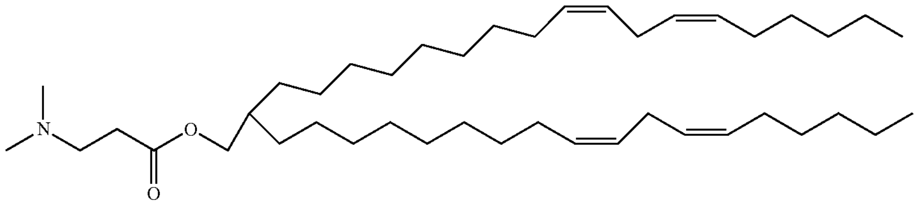
Q is O
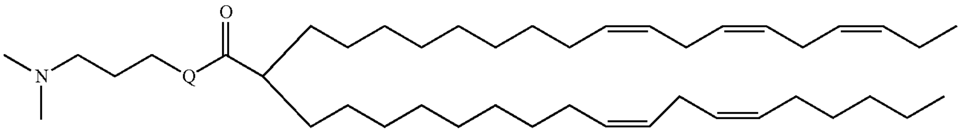
Q is O
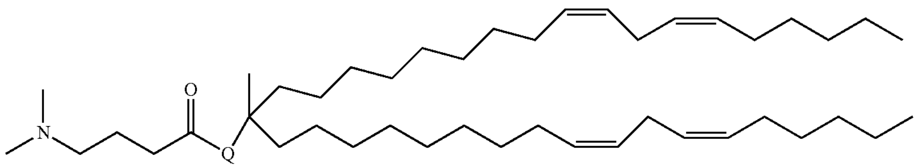
Q is O TABLE 11-continued
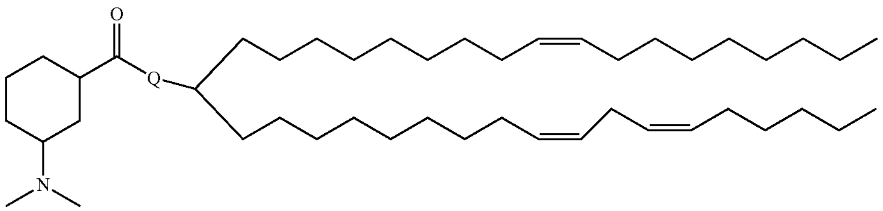
Q is O
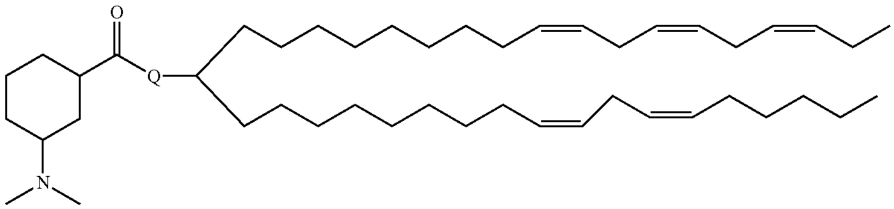
Q is O
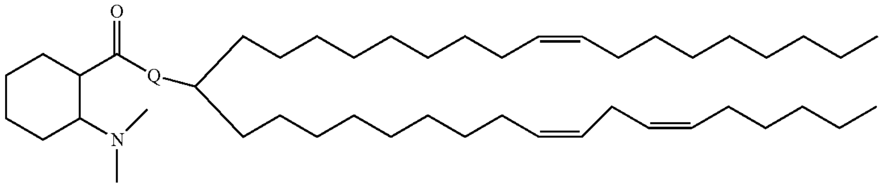
Q is O
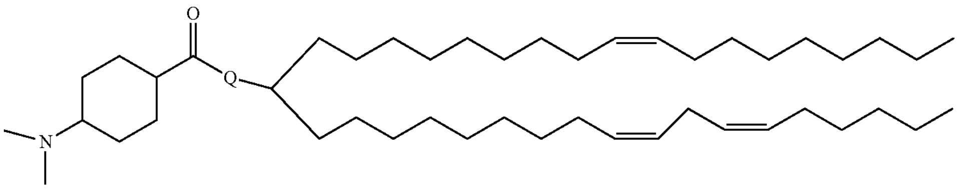
Q is O
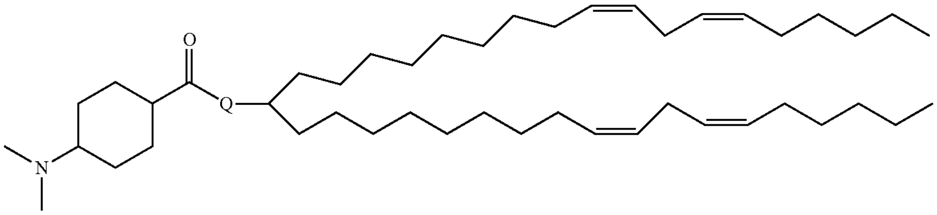
Q is O
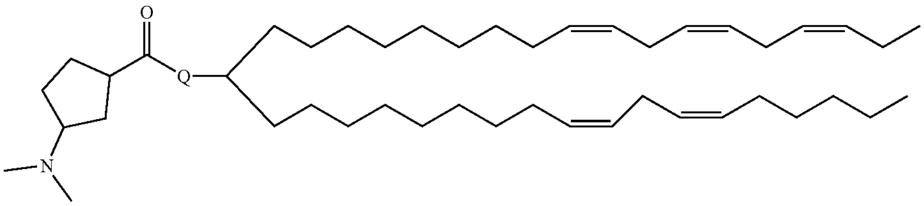
Q is O TABLE 11-continued
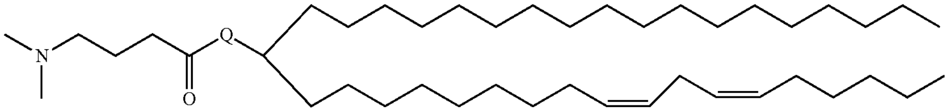
Q is O
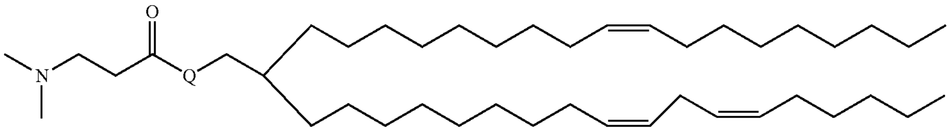
Q is O
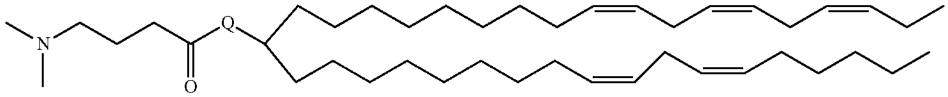
Q is O
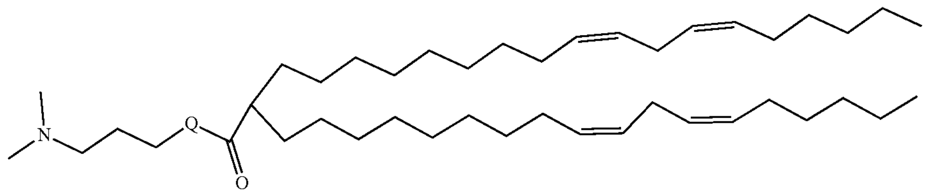
Q is O
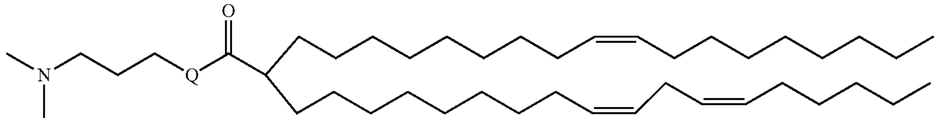
Q is O
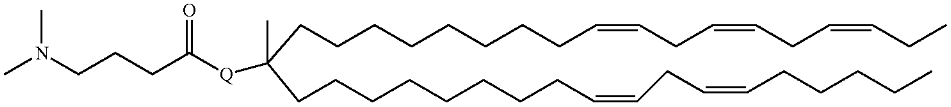
Q is O
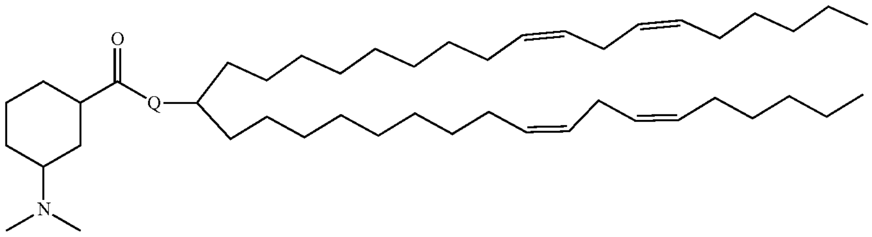
Q is O
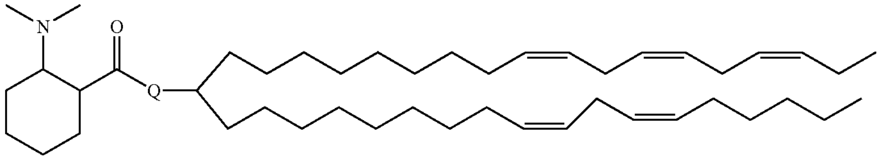
Q is O TABLE 11-continued
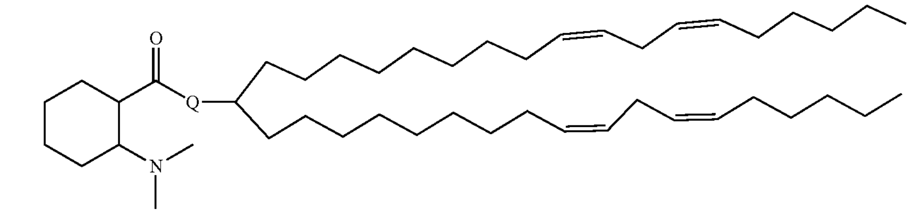
Q is O
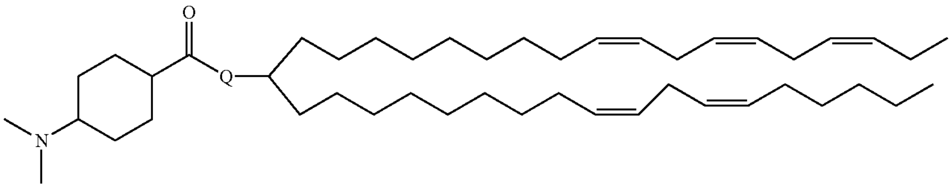
Q is O
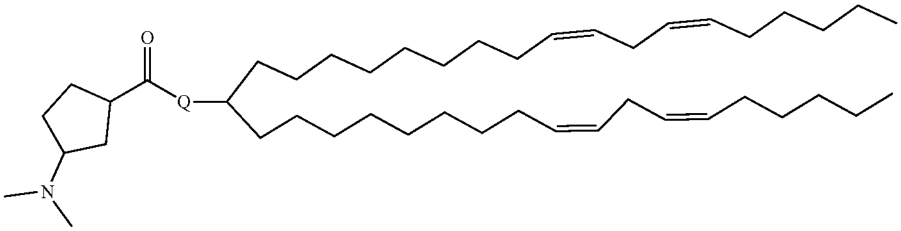
Q is O
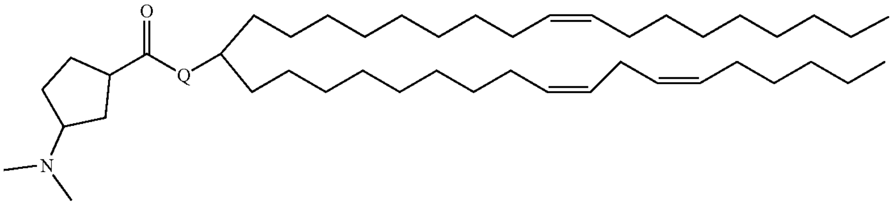
Q is O
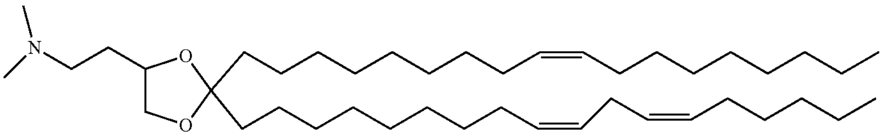 [SMILES: CCCCC/C=C\C/C=C\CCCCCCCCC1(CCCCCCCC/C=C\CCCCCCCC)OCC(CCN(C)C)O1]
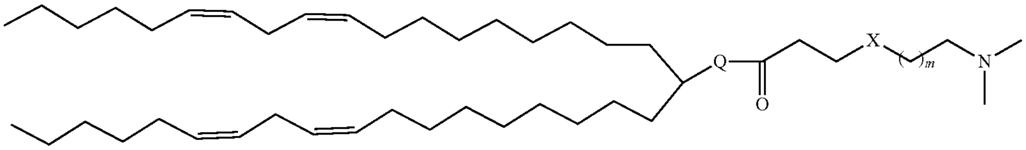
X = O, S, NH, NMe, n = 0-6
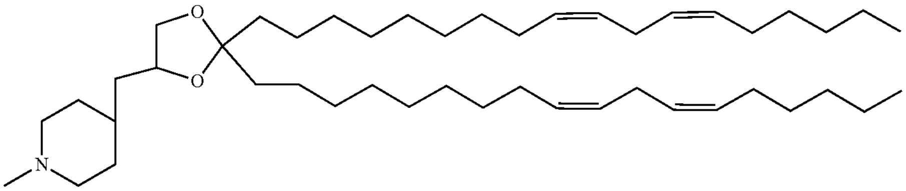 [SMILES: CCCCC/C=C\C/C=C\CCCCCCCCC1(CCCCCCCC/C=C\C/C=C\CCCCC)OCC(CC2CCN(C)CC2)O1]

TABLE 11-continued
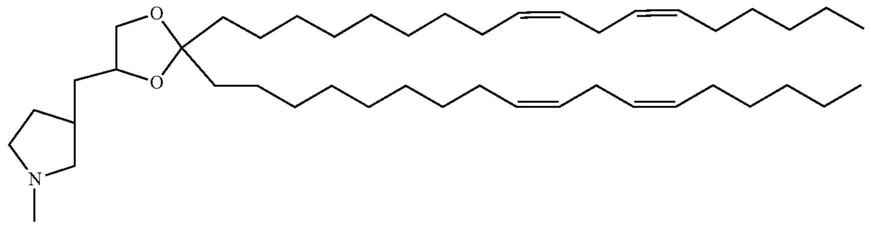 [SMILES: CCCCC/C=C\C/C=C\CCCCCCCCC1(CCCCCCCC/C=C\C/C=C\CCCCC)OCC(CC2CCN(C)C2)O1]
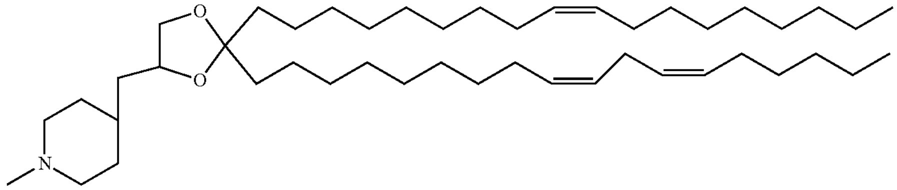 [SMILES: CCCCC/C=C\C/C=C\CCCCCCCCC1(CCCCCCCC/C=C\CCCCCCCC)OCC(CC2CCN(C)CC2)O1]
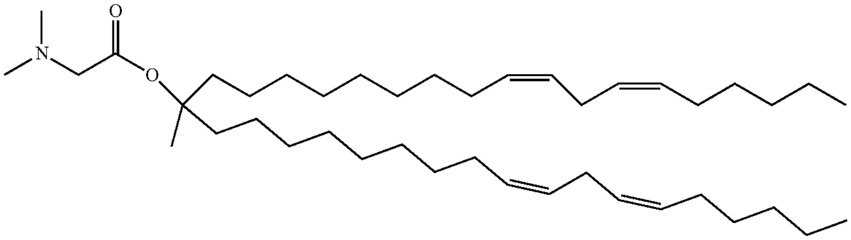 [SMILES: CCCCC/C=C\C/C=C\CCCCCCCCC(C)(CCCCCCCC/C=C\C/C=C\CCCCC)OC(=O)CN(C)C]
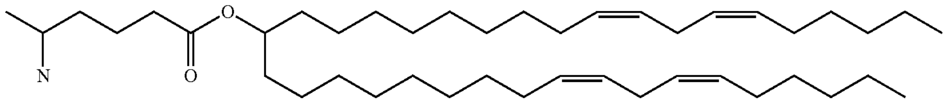
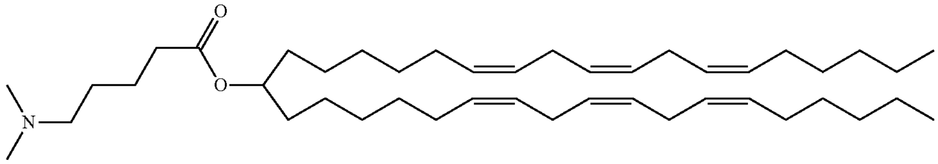 [SMILES: CCCCC/C=C\C/C=C\C/C=C\CCCCCC(CCCCC/C=C\C/C=C\C/C=C\CCCCC)OC(=O)CCCCN(C)C]
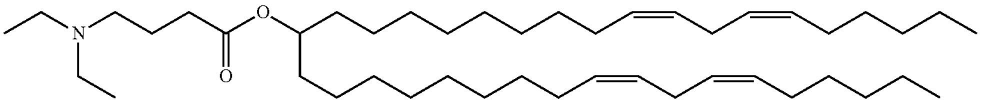 [SMILES: CCCCC/C=C\C/C=C\CCCCCCCCC(CCCCCCCC/C=C\C/C=C\CCCCC)OC(=O)CCCN(CC)CC]
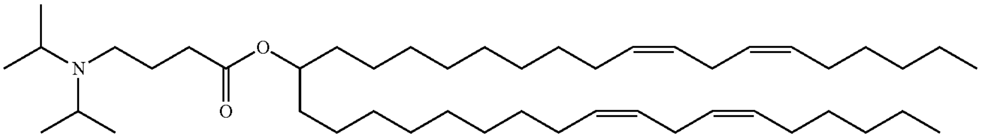 [SMILES: CCCCC/C=C\C/C=C\CCCCCCCCC(CCCCCCCC/C=C\C/C=C\CCCCC)OC(=O)CCCN(C(C)C)C(C)C]
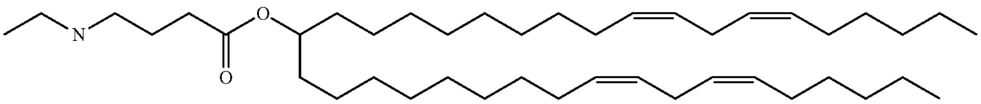
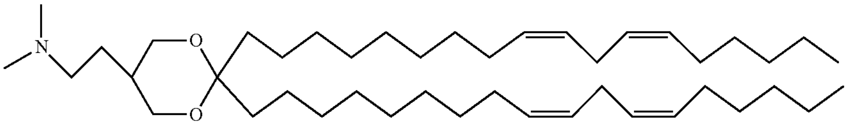

TABLE 11-continued
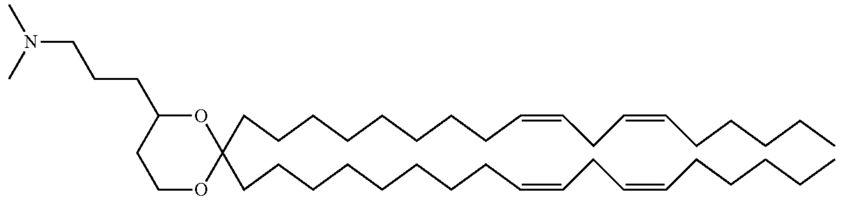 [SMILES: CCCCC/C=C\C/C=C\CCCCCCCCC1(CCCCCCCC/C=C\C/C=C\CCCCC)OCCC(CCCN(C)C)O1]
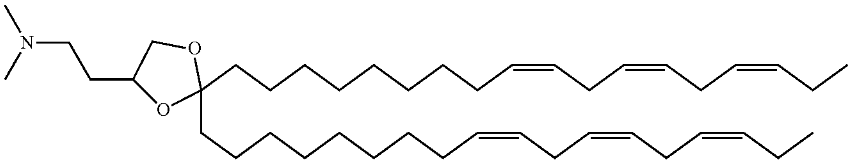 [SMILES: CC/C=C\C/C=C\C/C=C\CCCCCCCCC1(CCCCCCCC/C=C\C/C=C\C/C=C\CC)OCC(CCN(C)C)O1]
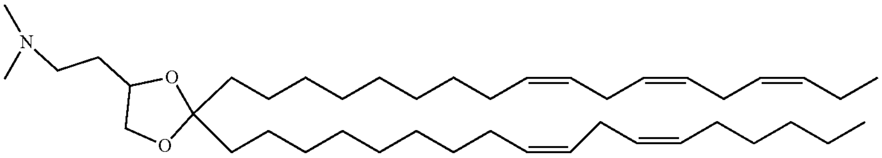 [SMILES: CC/C=C\C/C=C\C/C=C\CCCCCCCCC1(CCCCCCCC/C=C\C/C=C\CCCCC)OCC(CCN(C)C)O1]
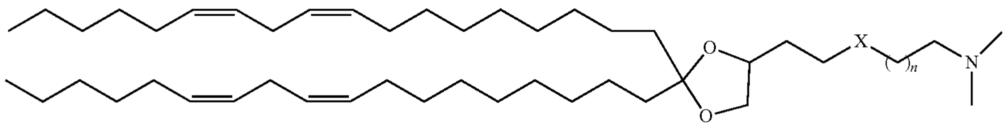
X = O, S, NH, NMe, n = 0-6
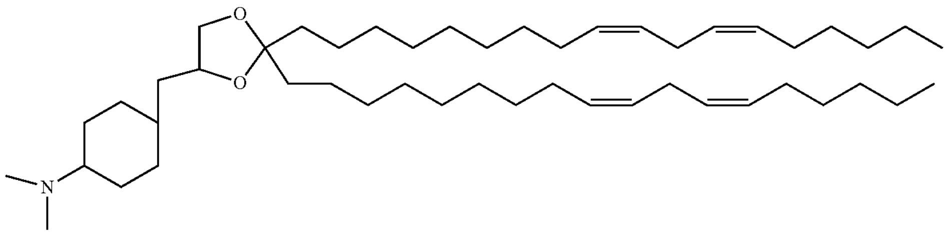 [SMILES: CCCCC/C=C\C/C=C\CCCCCCCCC1(CCCCCCCC/C=C\C/C=C\CCCCC)OCC(CC2CCC(N(C)C)CC2)O1]
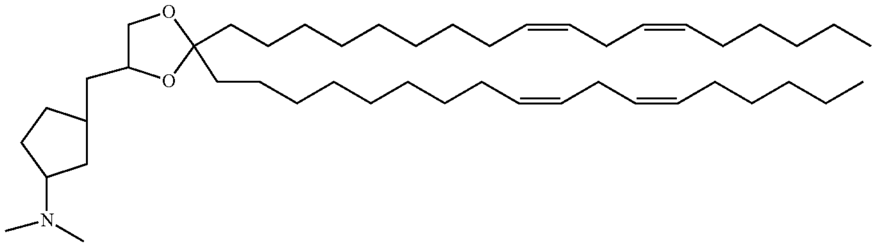 [SMILES: CCCCC/C=C\C/C=C\CCCCCCCCC1(CCCCCCCC/C=C\C/C=C\CCCCC)OCC(CC2CCC(N(C)C)C2)O1]
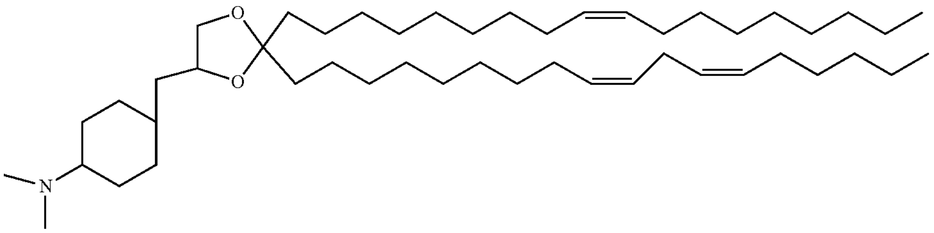 [SMILES: CCCCC/C=C\C/C=C\CCCCCCCCC1(CCCCCCCC/C=C\CCCCCCCC)OCC(CC2CCC(N(C)C)CC2)O1]

TABLE 11-continued
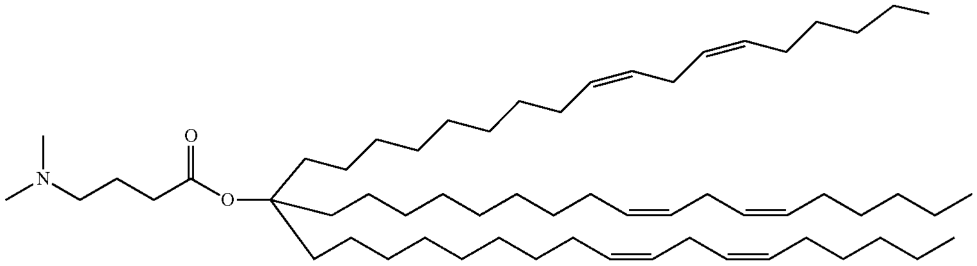
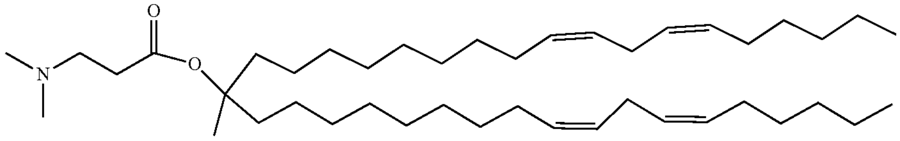 [SMILES: CCCCC/C=C\C/C=C\CCCCCCCCC(C)(CCCCCCCC/C=C\C/C=C\CCCCC)OC(=O)CCN(C)C]
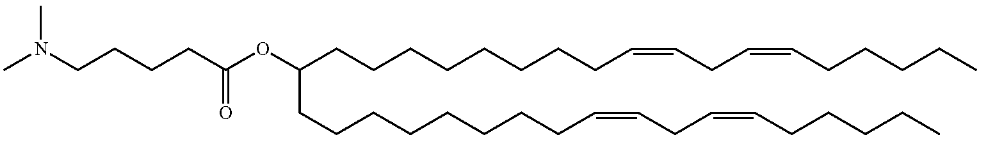 [SMILES: CCCCC/C=C\C/C=C\CCCCCCCCC(CCCCCCCC/C=C\C/C=C\CCCCC)OC(=O)CCCCN(C)C]
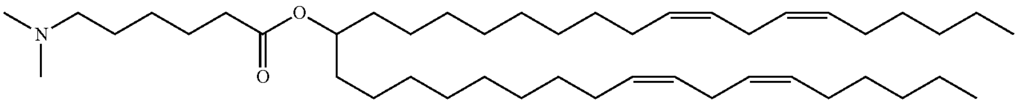 [SMILES: CCCCC/C=C\C/C=C\CCCCCCCCC(CCCCCCCC/C=C\C/C=C\CCCCC)OC(=O)CCCCCN(C)C]
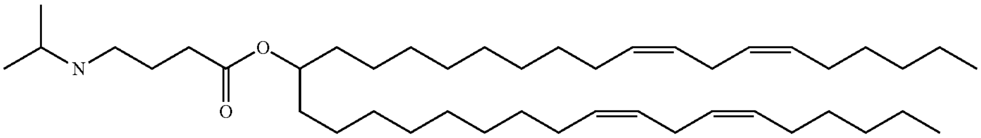 [SMILES: CCCCC/C=C\C/C=C\CCCCCCCCC(CCCCCCCC/C=C\C/C=C\CCCCC)OC(=O)CCCNC(C)C]
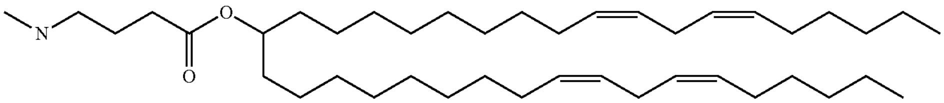 [SMILES: CCCCC/C=C\C/C=C\CCCCCCCCC(CCCCCCCC/C=C\C/C=C\CCCCC)OC(=O)CCCNC]
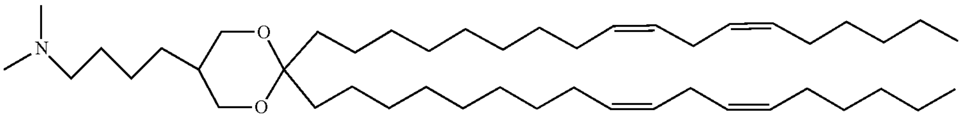 [SMILES: CCCCC/C=C\C/C=C\CCCCCCCCC1(CCCCCCCC/C=C\C/C=C\CCCCC)OCC(CCCCN(C)C)CO1]
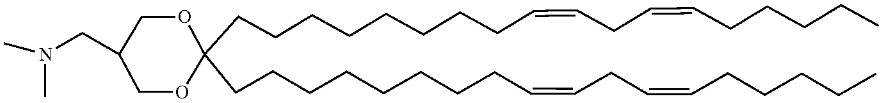 [SMILES: CCCCC/C=C\C/C=C\CCCCCCCCC1(CCCCCCCC/C=C\C/C=C\CCCCC)OCC(CN(C)C)CO1]
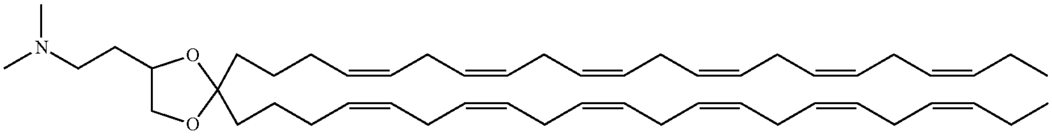 [SMILES: CC/C=C\C/C=C\C/C=C\C/C=C\C/C=C\C/C=C\CCCC1(CCC/C=C\C/C=C\C/C=C\C/C=C\C/C=C\C/C=C\CC)OCC(CCN(C)C)O1]
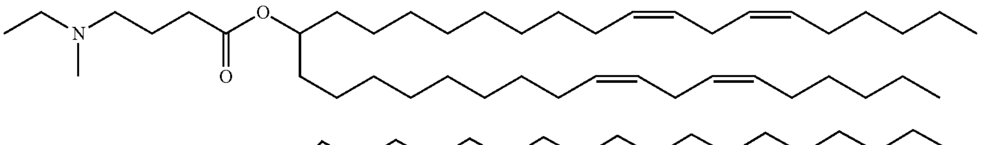
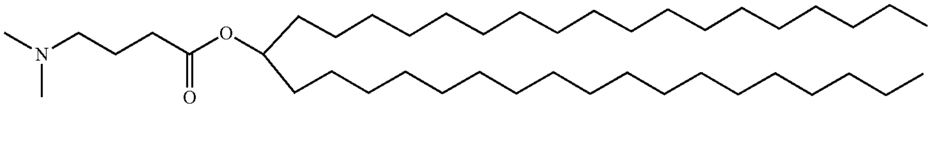 [SMILES: CCCCCCCCCCCCCCCCCCC(CCCCCCCCCCCCCCCCCC)OC(=O)CCCN(C)C]

TABLE 11-continued
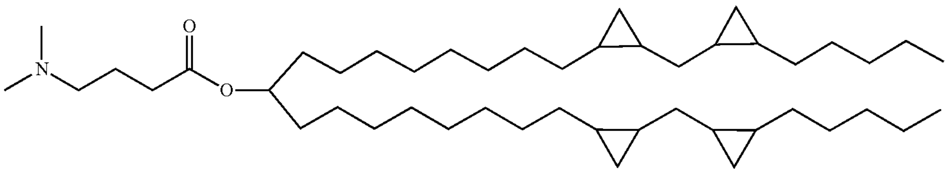 [SMILES: CCCCCC1CC1CC1CC1CCCCCCCCC(CCCCCCCCC1CC1CC1CC1CCCCC)OC(=O)CCCN(C)C]
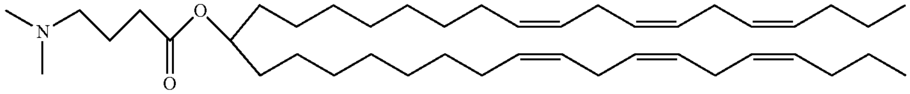 [SMILES: CCC/C=C\C/C=C\C/C=C\CCCCCCCC(CCCCCCC/C=C\C/C=C\C/C=C\CCC)OC(=O)CCCN(C)C]
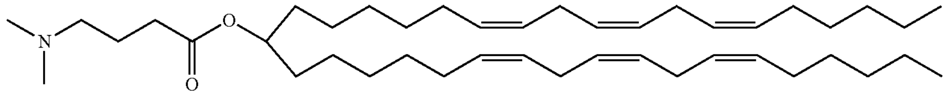 [SMILES: CCCCC/C=C\C/C=C\C/C=C\CCCCCC(CCCCC/C=C\C/C=C\C/C=C\CCCCC)OC(=O)CCCN(C)C]
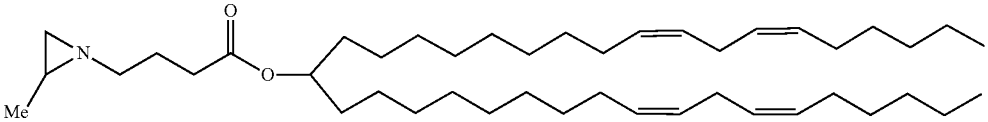 [SMILES: CCCCC/C=C\C/C=C\CCCCCCCCC(CCCCCCCC/C=C\C/C=C\CCCCC)OC(=O)CCCN1CC1C]
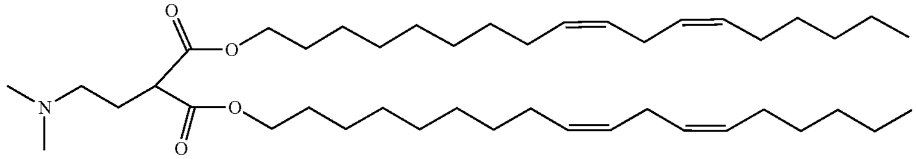 [SMILES: CCCCC/C=C\C/C=C\CCCCCCCCOC(=O)C(CCN(C)C)C(=O)OCCCCCCCC/C=C\C/C=C\CCCCC]
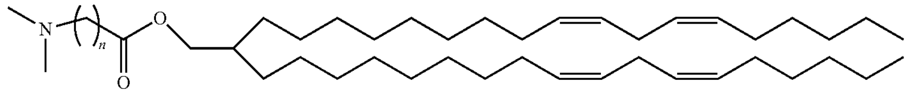
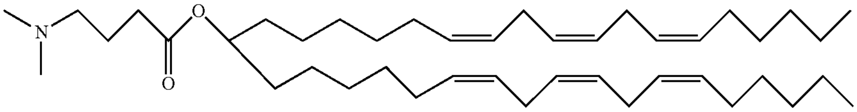 [SMILES: CCCCC/C=C\C/C=C\C/C=C\CCCCCC(CCCCC/C=C\C/C=C\C/C=C\CCCCC)OC(=O)CCCN(C)C]
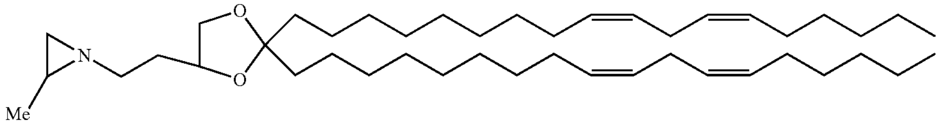 [SMILES: CCCCC/C=C\C/C=C\CCCCCCCCC1(CCCCCCCC/C=C\C/C=C\CCCCC)OCC(CCN2CC2C)O1]
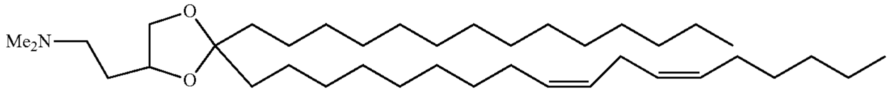 [SMILES: CCCCC/C=C\C/C=C\CCCCCCCCC1(CCCCCCCCCCCCCC)OCC(CCN(C)C)O1]
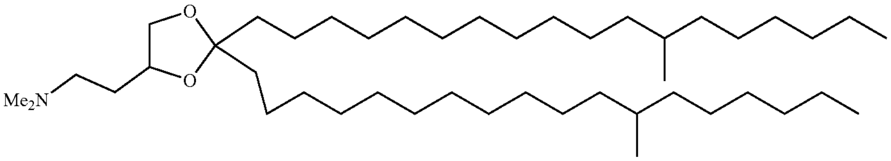 [SMILES: CCCCCCC(C)CCCCCCCCCCCC1(CCCCCCCCCCCC(C)CCCCCC)OCC(CCN(C)C)O1]
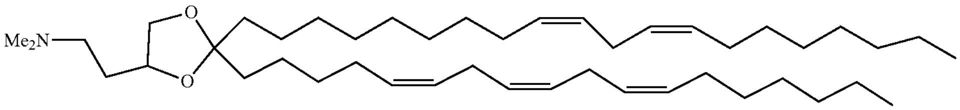 [SMILES: CCCCCC/C=C\C/C=C\C/C=C\CCCCC1(CCCCCCCC/C=C\C/C=C\CCCCCCC)OCC(CCN(C)C)O1]

TABLE 11-continued
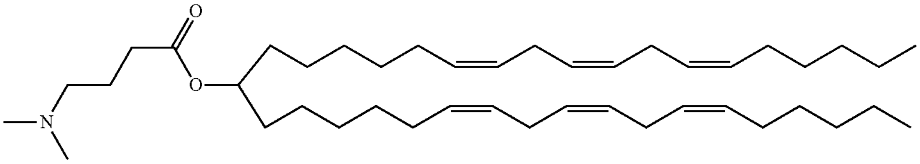 [SMILES: CCCCC/C=C\C/C=C\C/C=C\CCCCCC(CCCCC/C=C\C/C=C\C/C=C\CCCCC)OC(=O)CCCN(C)C]
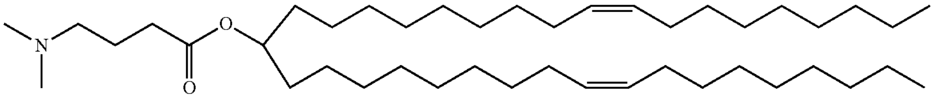 [SMILES: CCCCCCCC/C=C\CCCCCCCCC(CCCCCCCC/C=C\CCCCCCCC)OC(=O)CCCN(C)C]
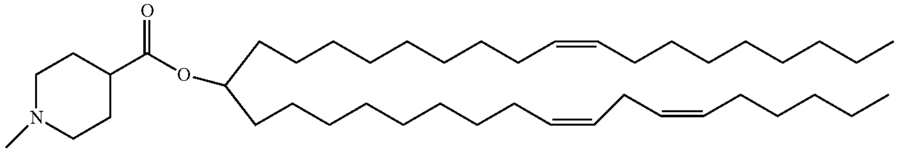 [SMILES: CCCCC/C=C\C/C=C\CCCCCCCCC(CCCCCCCC/C=C\CCCCCCCC)OC(=O)C1CCN(C)CC1]
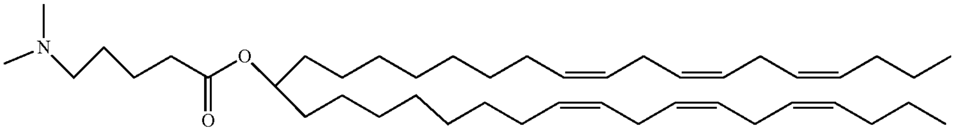 [SMILES: CCC/C=C\C/C=C\C/C=C\CCCCCCCC(CCCCCCC/C=C\C/C=C\C/C=C\CCC)OC(=O)CCCCN(C)C]
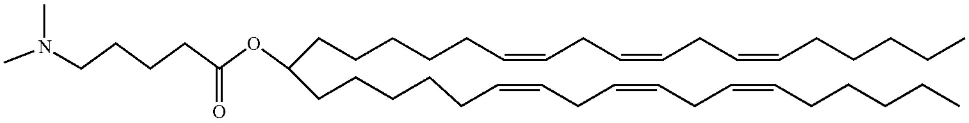 [SMILES: CCCCC/C=C\C/C=C\C/C=C\CCCCCC(CCCCC/C=C\C/C=C\C/C=C\CCCCC)OC(=O)CCCCN(C)C]
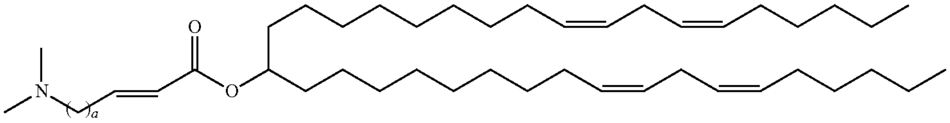
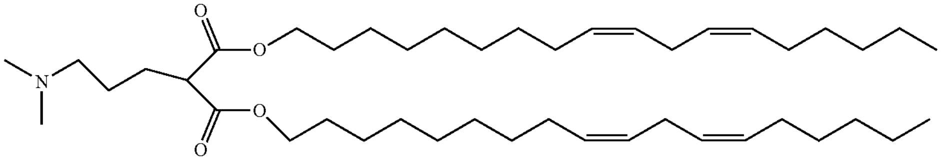 [SMILES: CCCCC/C=C\C/C=C\CCCCCCCCOC(=O)C(CCCN(C)C)C(=O)OCCCCCCCC/C=C\C/C=C\CCCCC]
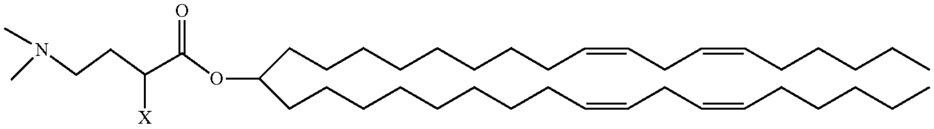
e.g., X = Me, OH, Cl, etc
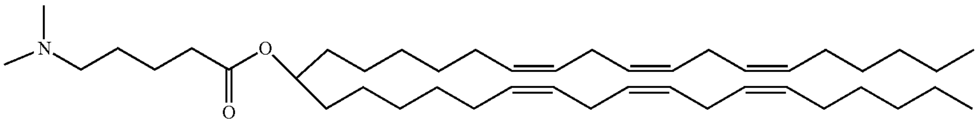 [SMILES: CCCCC/C=C\C/C=C\C/C=C\CCCCCC(CCCCC/C=C\C/C=C\C/C=C\CCCCC)OC(=O)CCCCN(C)C]
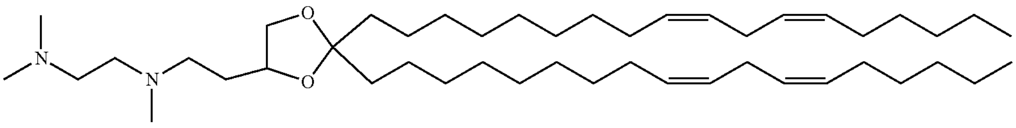 [SMILES: CCCCC/C=C\C/C=C\CCCCCCCCC1(CCCCCCCC/C=C\C/C=C\CCCCC)OCC(CCN(C)CCN(C)C)O1]
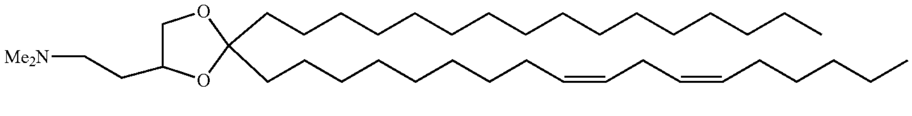 [SMILES: CCCCC/C=C\C/C=C\CCCCCCCCC1(CCCCCCCCCCCCCCCC)OCC(CCN(C)C)O1]

TABLE 11-continued
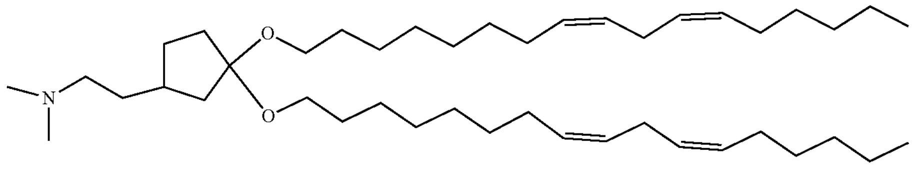 [SMILES: CCCCC/C=C\C/C=C\CCCCCCCOC1(OCCCCCCC/C=C\C/C=C\CCCCC)CCC(CCN(C)C)C1]
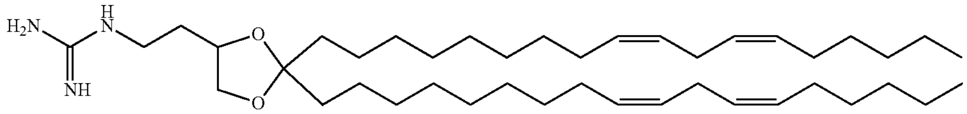 [SMILES: CCCCC/C=C\C/C=C\CCCCCCCCC1(CCCCCCCC/C=C\C/C=C\CCCCC)OCC(CCNC(=N)N)O1]
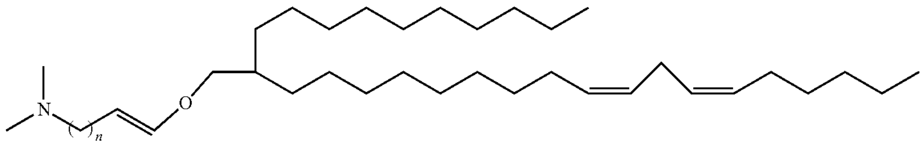
n = 0-6
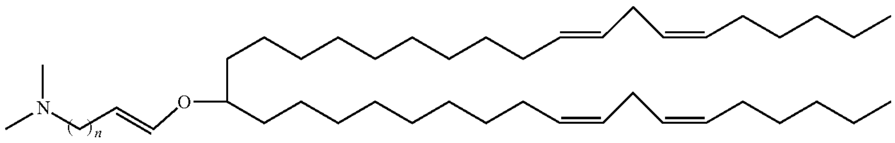
n = 0-6
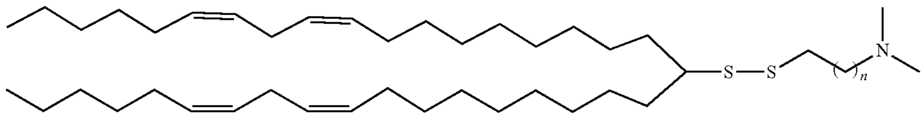
n = 0-6
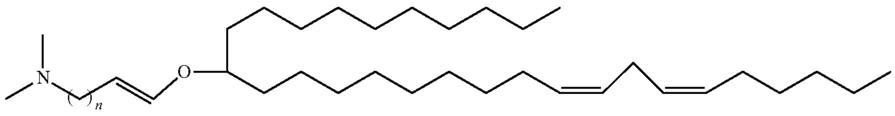
n = 0-6
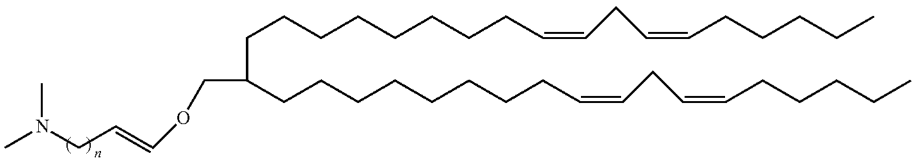
n = 0-6
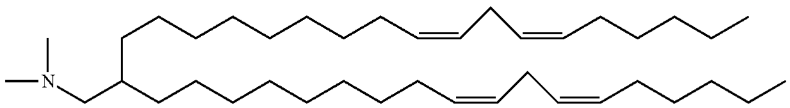 [SMILES: CCCCC/C=C\C/C=C\CCCCCCCCC(CCCCCCCC/C=C\C/C=C\CCCCC)CN(C)C]
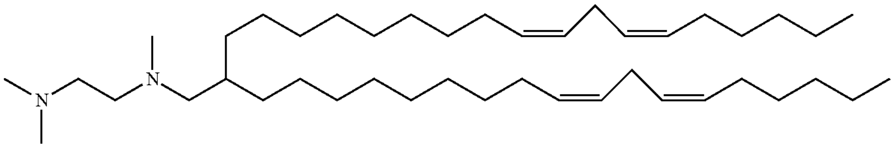 [SMILES: CCCCC/C=C\C/C=C\CCCCCCCCC(CCCCCCCC/C=C\C/C=C\CCCCC)CN(C)CCN(C)C]
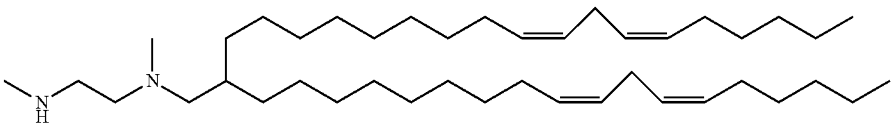 [SMILES: CCCCC/C=C\C/C=C\CCCCCCCCC(CCCCCCCC/C=C\C/C=C\CCCCC)CN(C)CCNC]

TABLE 11-continued
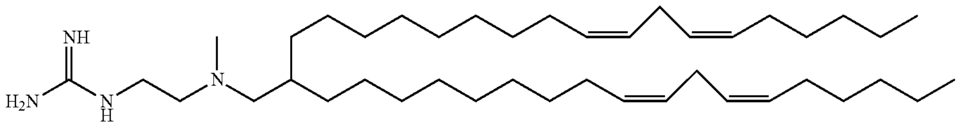
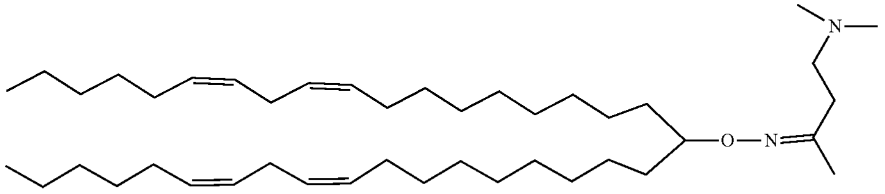 [SMILES: CCCCC/C=C\C/C=C\CCCCCCCCC(CCCCCCCC/C=C\C/C=C\CCCCC)O/N=C(/C)CCN(C)C]
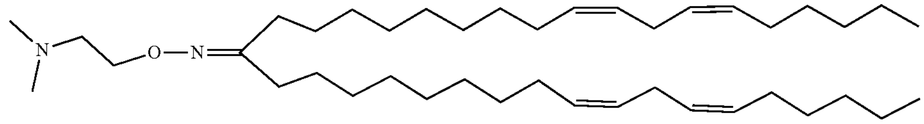 [SMILES: CCCCC/C=C\C/C=C\CCCCCCCCC(CCCCCCCC/C=C\C/C=C\CCCCC)=NOCCN(C)C]
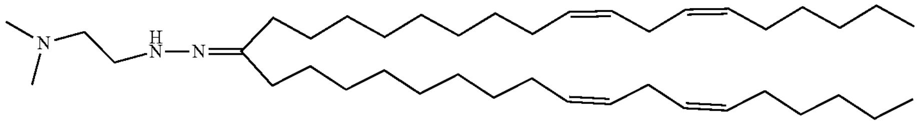 [SMILES: CCCCC/C=C\C/C=C\CCCCCCCCC(CCCCCCCC/C=C\C/C=C\CCCCC)=NNCCN(C)C]
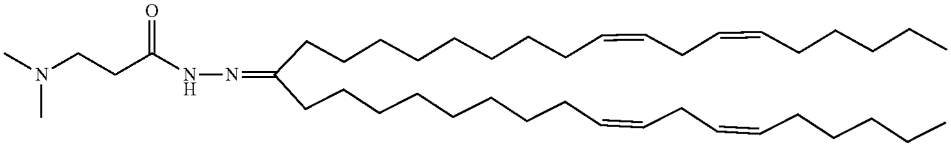 [SMILES: CCCCC/C=C\C/C=C\CCCCCCCCC(CCCCCCCC/C=C\C/C=C\CCCCC)=NNC(=O)CCN(C)C]
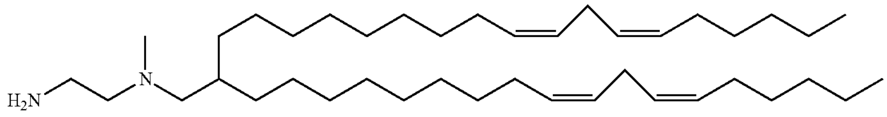
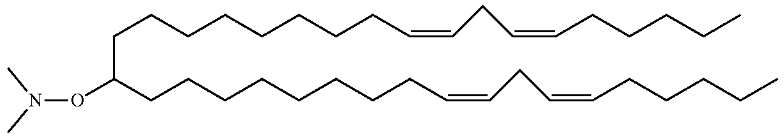 [SMILES: CCCCC/C=C\C/C=C\CCCCCCCCC(CCCCCCCC/C=C\C/C=C\CCCCC)ON(C)C]
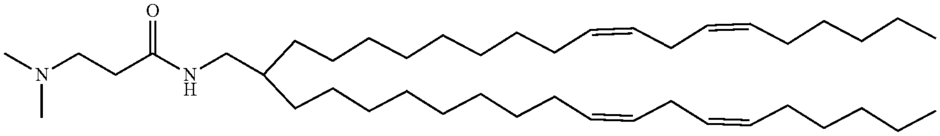 [SMILES: CCCCC/C=C\C/C=C\CCCCCCCCC(CCCCCCCC/C=C\C/C=C\CCCCC)CNC(=O)CCN(C)C]
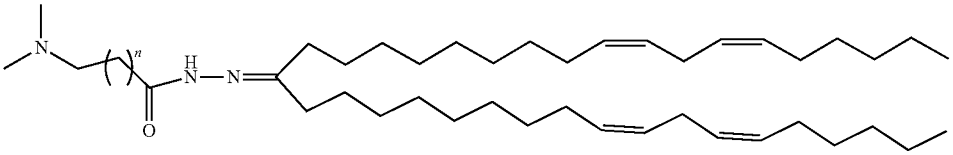
n = 0-6
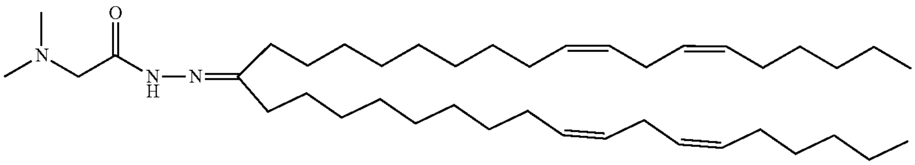 [SMILES: CCCCC/C=C\C/C=C\CCCCCCCCC(CCCCCCCC/C=C\C/C=C\CCCCC)=NNC(=O)CN(C)C]

TABLE 11-continued
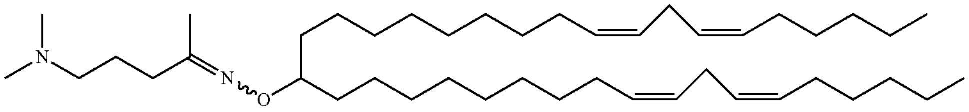
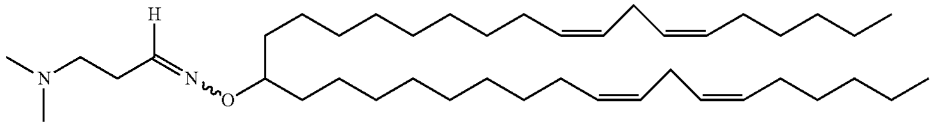 [SMILES: CCCCC/C=C\C/C=C\CCCCCCCCC(CCCCCCCC/C=C\C/C=C\CCCCC)ON=CCCN(C)C]
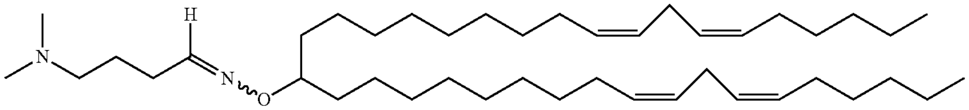 [SMILES: CCCCC/C=C\C/C=C\CCCCCCCCC(CCCCCCCC/C=C\C/C=C\CCCCC)ON=CCCCN(C)C]
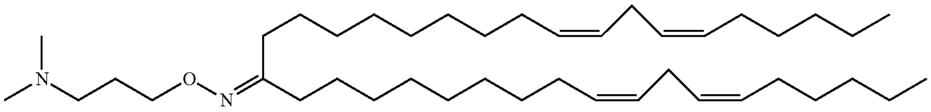 [SMILES: CCCCC/C=C\C/C=C\CCCCCCCCC(CCCCCCCC/C=C\C/C=C\CCCCC)=NOCCCN(C)C]
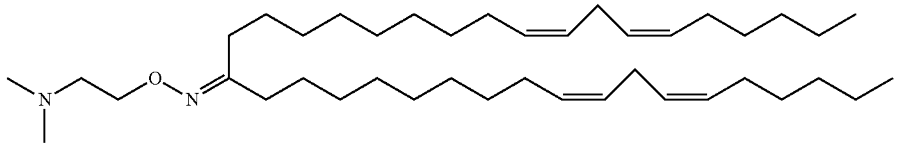 [SMILES: CCCCC/C=C\C/C=C\CCCCCCCCC(CCCCCCCC/C=C\C/C=C\CCCCC)=NOCCN(C)C]
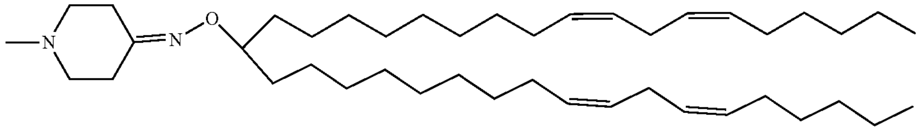 [SMILES: CCCCC/C=C\C/C=C\CCCCCCCCC(CCCCCCCC/C=C\C/C=C\CCCCC)ON=C1CCN(C)CC1]
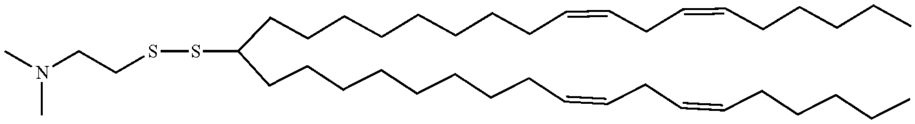 [SMILES: CCCCC/C=C\C/C=C\CCCCCCCCC(CCCCCCCC/C=C\C/C=C\CCCCC)SSCCN(C)C]
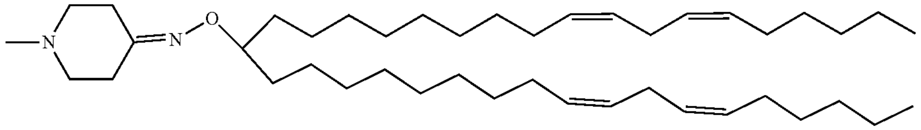 [SMILES: CCCCC/C=C\C/C=C\CCCCCCCCC(CCCCCCCC/C=C\C/C=C\CCCCC)ON=C1CCN(C)CC1]
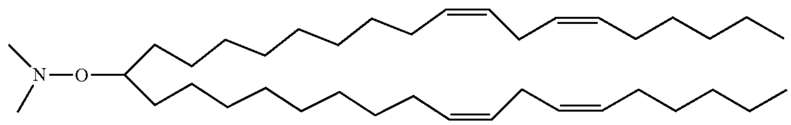 [SMILES: CCCCC/C=C\C/C=C\CCCCCCCCC(CCCCCCCC/C=C\C/C=C\CCCCC)ON(C)C]
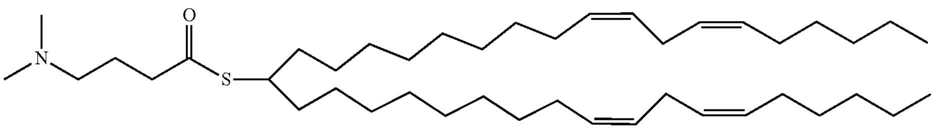 [SMILES: CCCCC/C=C\C/C=C\CCCCCCCCC(CCCCCCCC/C=C\C/C=C\CCCCC)SC(=O)CCCN(C)C]
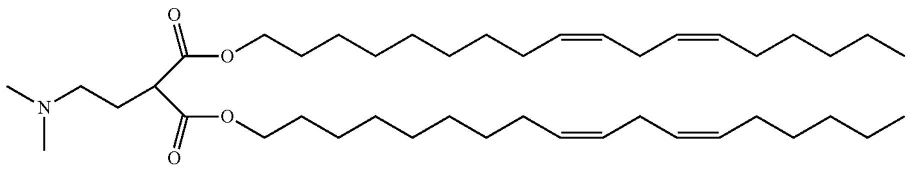 [SMILES: CCCCC/C=C\C/C=C\CCCCCCCCOC(=O)C(CCN(C)C)C(=O)OCCCCCCCC/C=C\C/C=C\CCCCC]

TABLE 11-continued
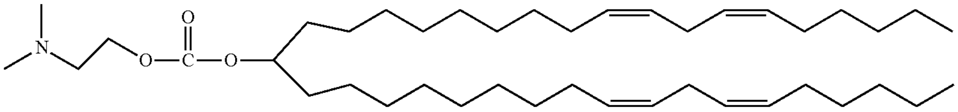 [SMILES: CCCCC/C=C\C/C=C\CCCCCCCCC(CCCCCCCC/C=C\C/C=C\CCCCC)OC(=O)OCCN(C)C]
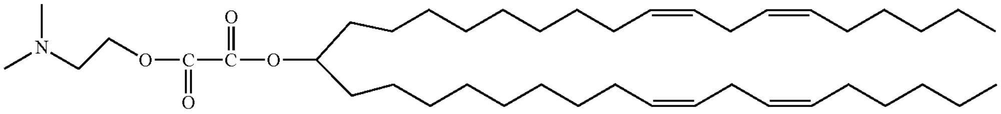 [SMILES: CCCCC/C=C\C/C=C\CCCCCCCCC(CCCCCCCC/C=C\C/C=C\CCCCC)OC(=O)C(=O)OCCN(C)C]
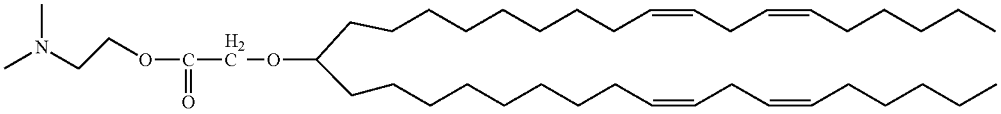
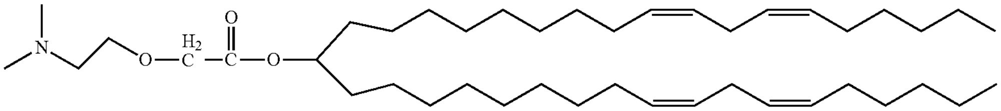 [SMILES: CCCCC/C=C\C/C=C\CCCCCCCCC(CCCCCCCC/C=C\C/C=C\CCCCC)OC(=O)COCCN(C)C]
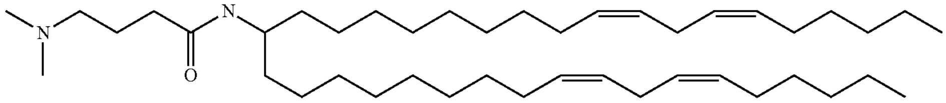
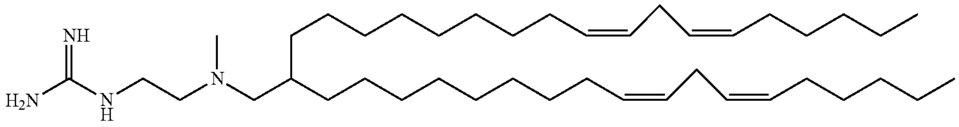 [SMILES: CCCCC/C=C\C/C=C\CCCCCCCCC(CCCCCCCC/C=C\C/C=C\CCCCC)CN(C)CCNC(=N)N]
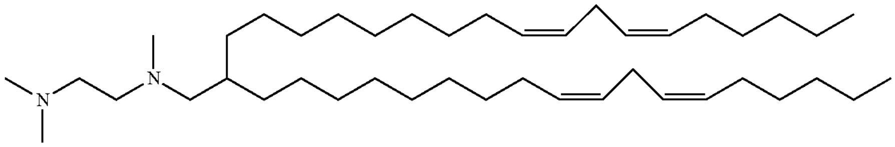
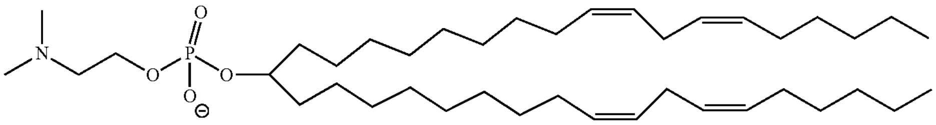 [SMILES: CCCCC/C=C\C/C=C\CCCCCCCCC(CCCCCCCC/C=C\C/C=C\CCCCC)OP(=O)([O-])OCCN(C)C]
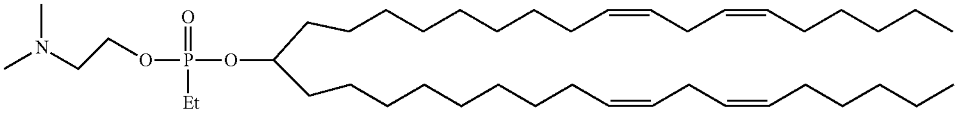
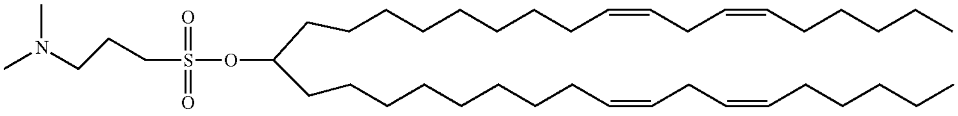 [SMILES: CCCCC/C=C\C/C=C\CCCCCCCCC(CCCCCCCC/C=C\C/C=C\CCCCC)OS(=O)(=O)CCCN(C)C]
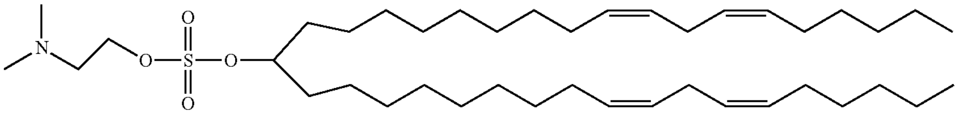 [SMILES: CCCCC/C=C\C/C=C\CCCCCCCCC(CCCCCCCC/C=C\C/C=C\CCCCC)OS(=O)(=O)OCCN(C)C]
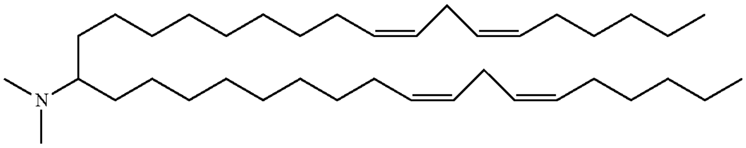 [SMILES: CCCCC/C=C\C/C=C\CCCCCCCCC(CCCCCCCC/C=C\C/C=C\CCCCC)N(C)C]

TABLE 11-continued
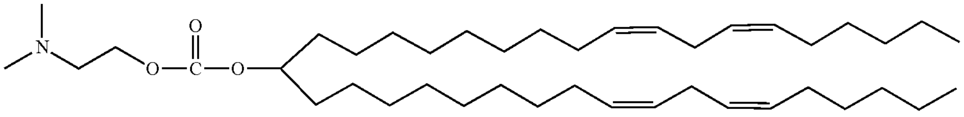 [SMILES: CCCCC/C=C\C/C=C\CCCCCCCCC(CCCCCCCC/C=C\C/C=C\CCCCC)OC(=O)OCCN(C)C]
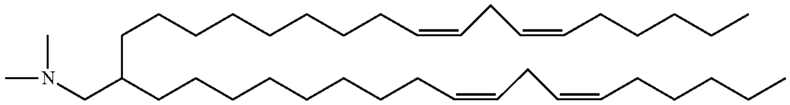
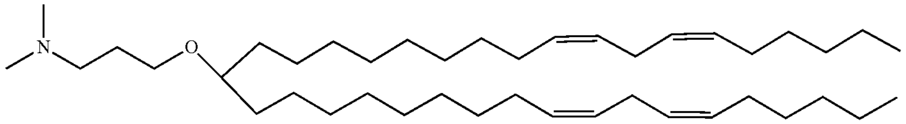 [SMILES: CCCCC/C=C\C/C=C\CCCCCCCCC(CCCCCCCC/C=C\C/C=C\CCCCC)OCCCN(C)C]
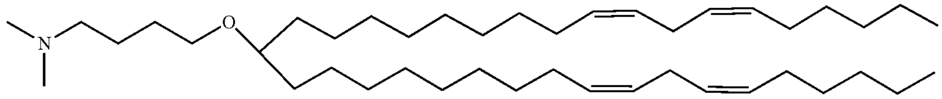 [SMILES: CCCCC/C=C\C/C=C\CCCCCCCCC(CCCCCCCC/C=C\C/C=C\CCCCC)OCCCCN(C)C]
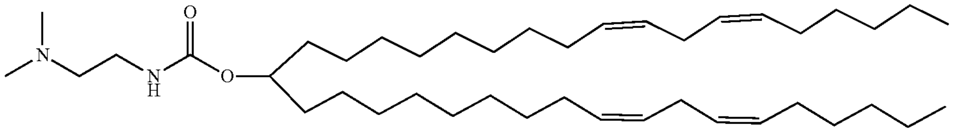 [SMILES: CCCCC/C=C\C/C=C\CCCCCCCCC(CCCCCCCC/C=C\C/C=C\CCCCC)OC(=O)NCCN(C)C]
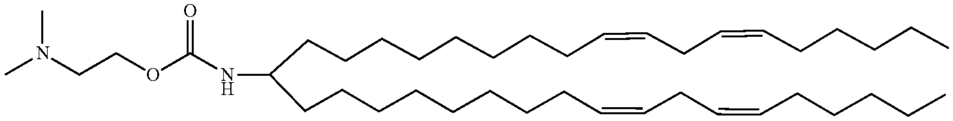 [SMILES: CCCCC/C=C\C/C=C\CCCCCCCCC(CCCCCCCC/C=C\C/C=C\CCCCC)NC(=O)OCCN(C)C]
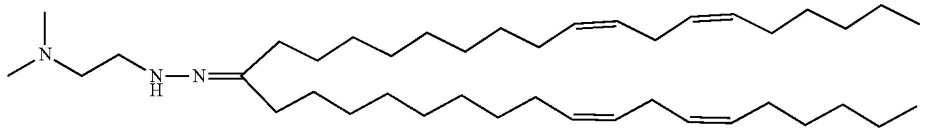 [SMILES: CCCCC/C=C\C/C=C\CCCCCCCCC(CCCCCCCC/C=C\C/C=C\CCCCC)=NNCCN(C)C]
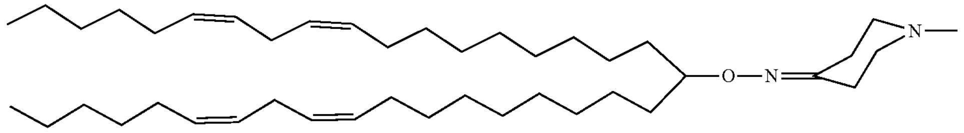 [SMILES: CCCCC/C=C\C/C=C\CCCCCCCCC(CCCCCCCC/C=C\C/C=C\CCCCC)ON=C1CCN(C)CC1]
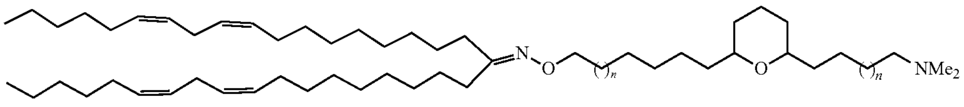
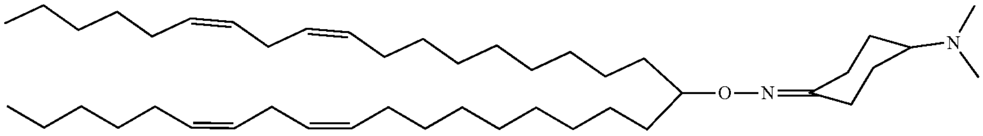 [SMILES: CCCCC/C=C\C/C=C\CCCCCCCCC(CCCCCCCC/C=C\C/C=C\CCCCC)ON=C1CCC(N(C)C)CC1]
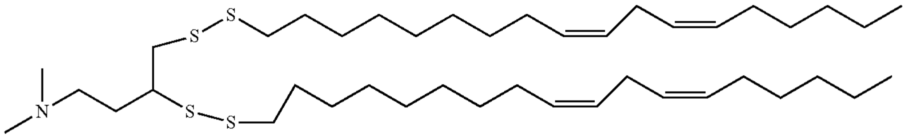 [SMILES: CCCCC/C=C\C/C=C\CCCCCCCCSSCC(CCN(C)C)SSCCCCCCCC/C=C\C/C=C\CCCCC]

TABLE 11-continued
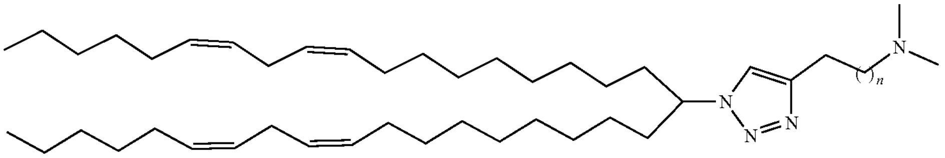
n = 0-6
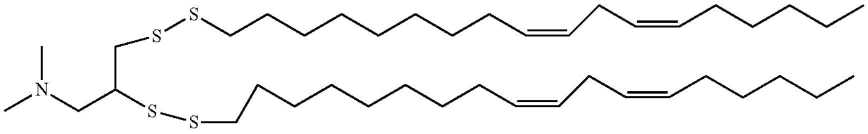 [SMILES: CCCCC/C=C\C/C=C\CCCCCCCCSSCC(CN(C)C)SSCCCCCCCC/C=C\C/C=C\CCCCC]
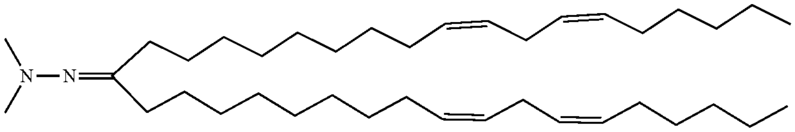 [SMILES: CCCCC/C=C\C/C=C\CCCCCCCCC(CCCCCCCC/C=C\C/C=C\CCCCC)=NN(C)C]
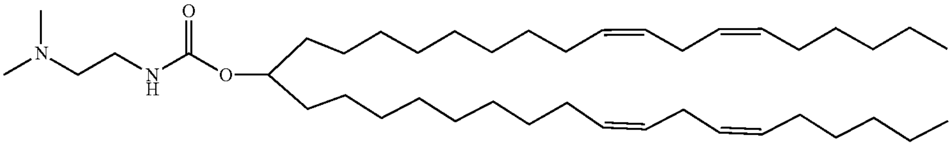 [SMILES: CCCCC/C=C\C/C=C\CCCCCCCCC(CCCCCCCC/C=C\C/C=C\CCCCC)OC(=O)NCCN(C)C]
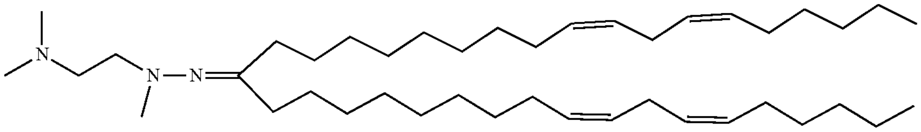 [SMILES: CCCCC/C=C\C/C=C\CCCCCCCCC(CCCCCCCC/C=C\C/C=C\CCCCC)=NN(C)CCN(C)C]
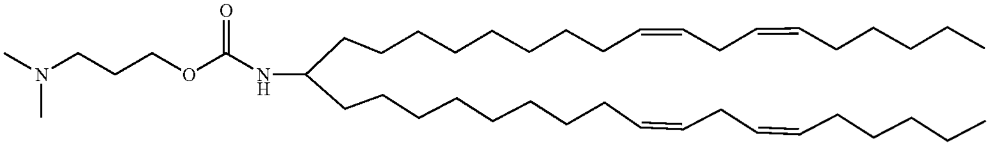 [SMILES: CCCCC/C=C\C/C=C\CCCCCCCCC(CCCCCCCC/C=C\C/C=C\CCCCC)NC(=O)OCCCN(C)C]
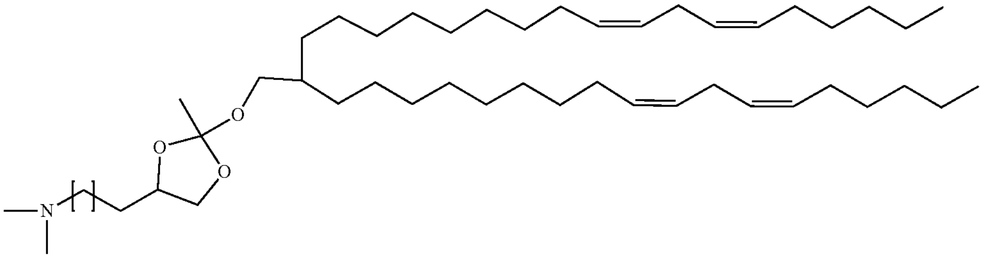
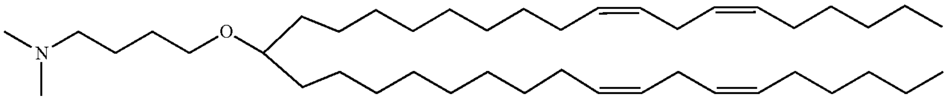 [SMILES: CCCCC/C=C\C/C=C\CCCCCCCCC(CCCCCCCC/C=C\C/C=C\CCCCC)OCCCCN(C)C]
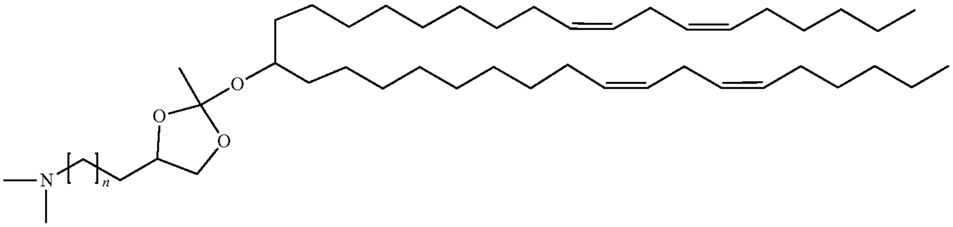

TABLE 11-continued
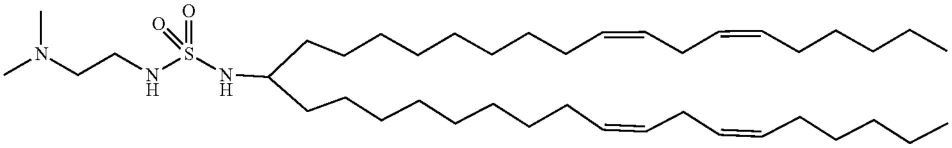 [SMILES: CCCCC/C=C\C/C=C\CCCCCCCCC(CCCCCCCC/C=C\C/C=C\CCCCC)NS(=O)(=O)NCCN(C)C]
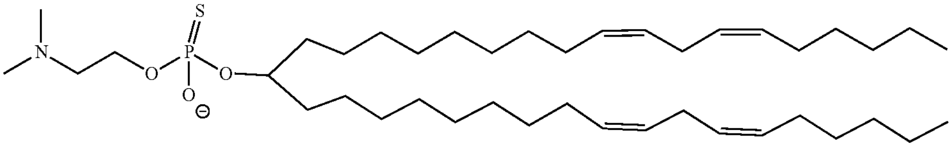 [SMILES: CCCCC/C=C\C/C=C\CCCCCCCCC(CCCCCCCC/C=C\C/C=C\CCCCC)OP([O-])(=S)OCCN(C)C]
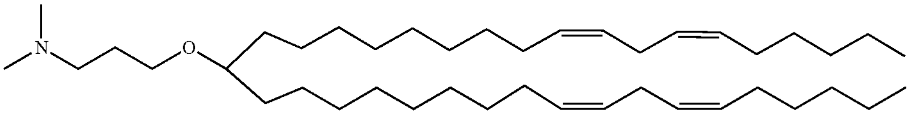 [SMILES: CCCCC/C=C\C/C=C\CCCCCCCCC(CCCCCCCC/C=C\C/C=C\CCCCC)OCCCN(C)C]
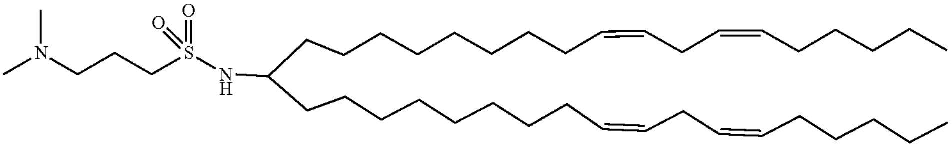 [SMILES: CCCCC/C=C\C/C=C\CCCCCCCCC(CCCCCCCC/C=C\C/C=C\CCCCC)NS(=O)(=O)CCCN(C)C]
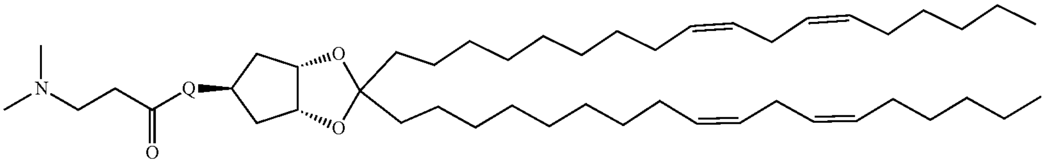
Q is NH, NMe
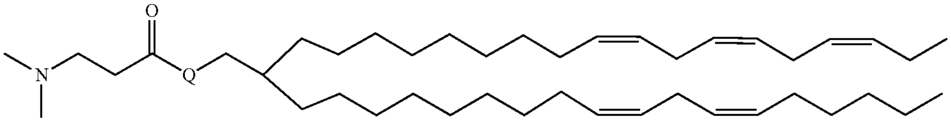
Q is NH, NMe
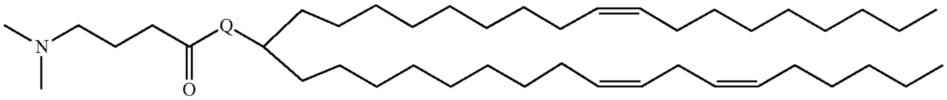
Q is NH, NMe
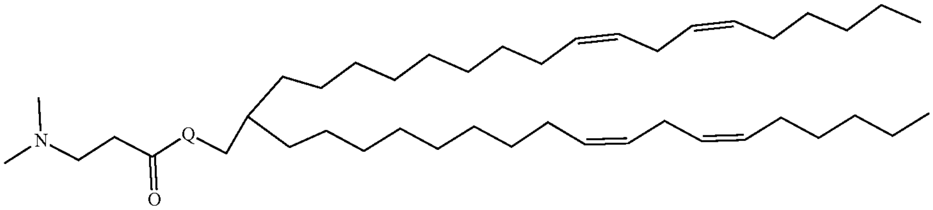
Q is NH, NMe
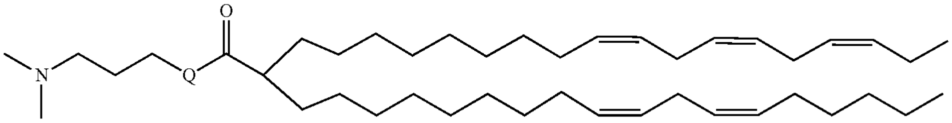
Q is NH, NMe TABLE 11-continued
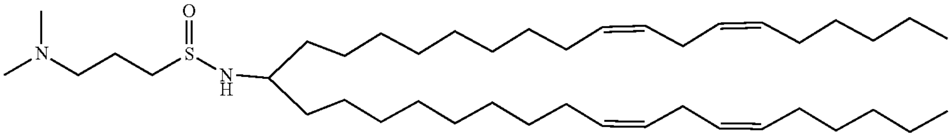 [SMILES: CCCCC/C=C\C/C=C\CCCCCCCCC(CCCCCCCC/C=C\C/C=C\CCCCC)NS(=O)CCCN(C)C]
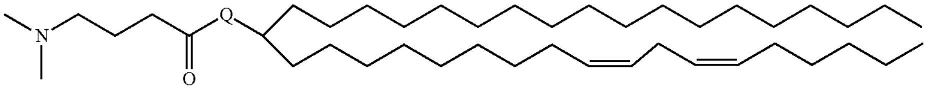
Q is NH, NMe
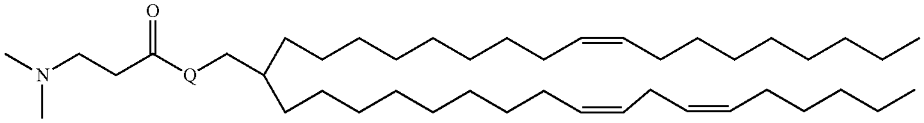
Q is NH, NMe
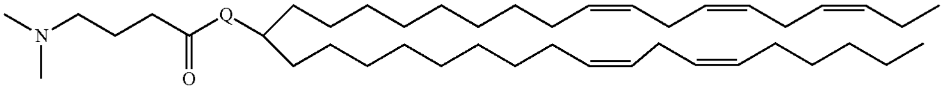
Q is NH, NMe
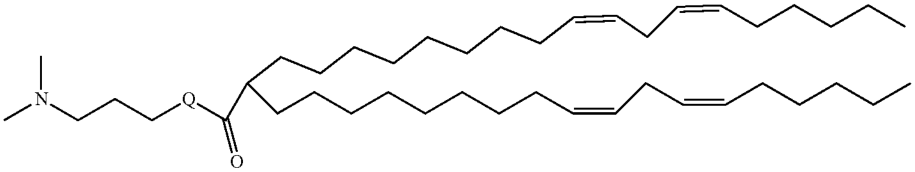
Q is NH, NMe
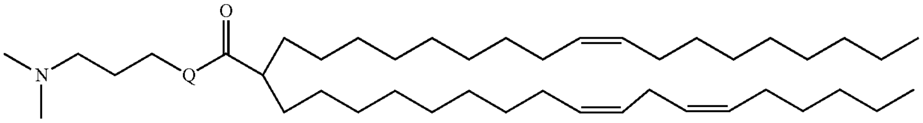
Q is NH, NMe
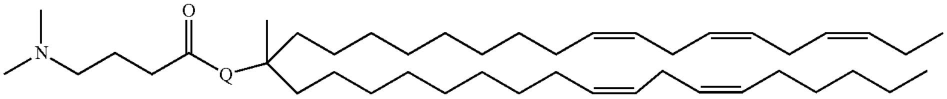
Q is NH, NMe
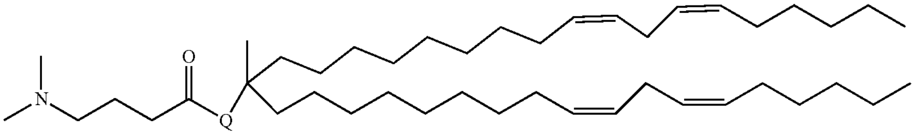
Q is NH, NMe
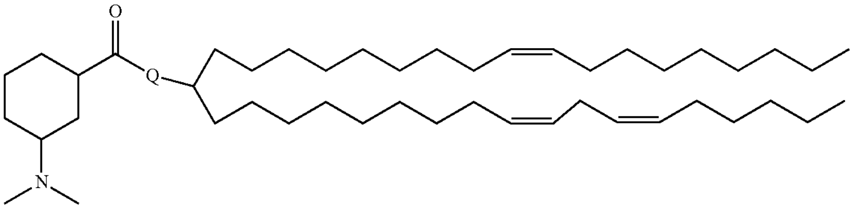
Q is NH, NMe TABLE 11-continued
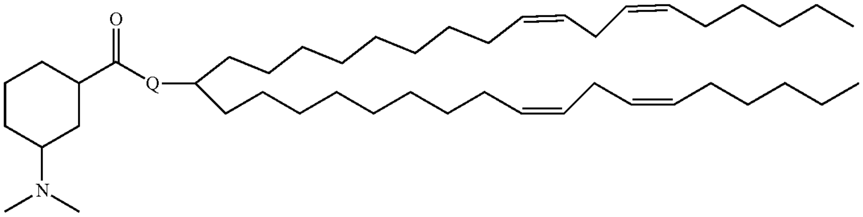
Q is NH, NMe
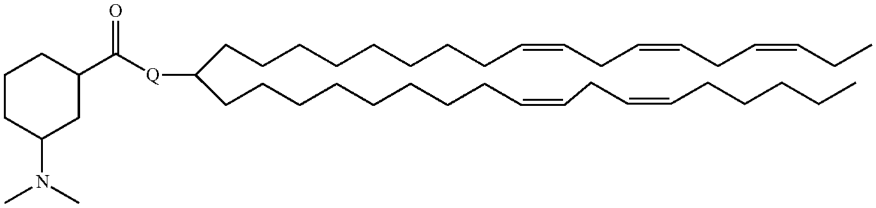
Q is NH, NMe
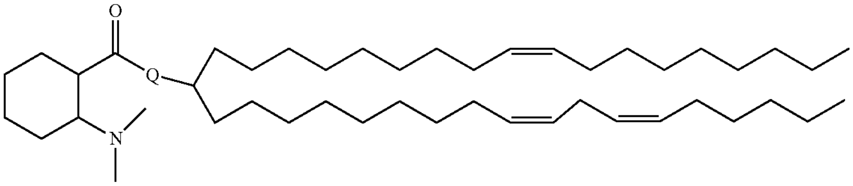
Q is NH, NMe
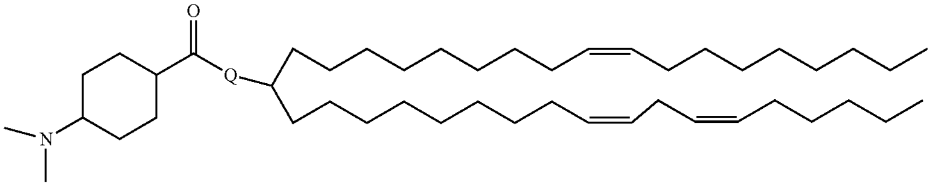
Q is NH, NMe
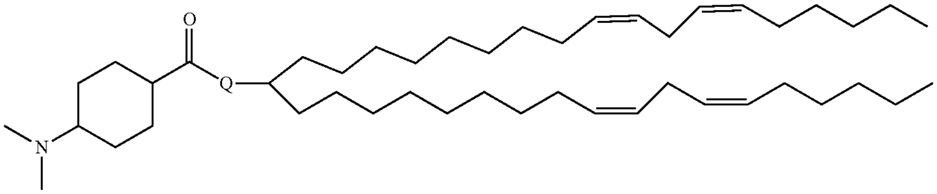
Q is NH, NMe
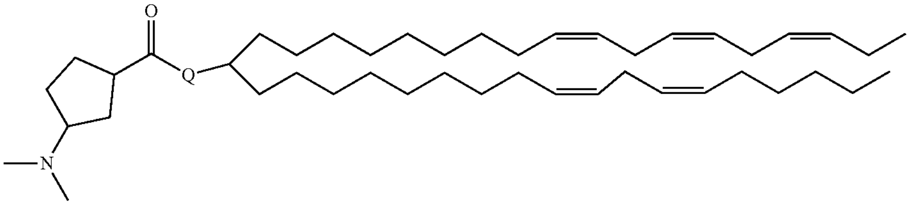
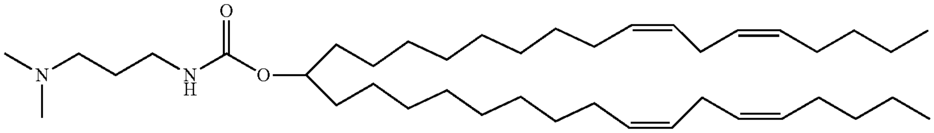 [SMILES: CCCC/C=C\C/C=C\CCCCCCCCC(CCCCCCCC/C=C\C/C=C\CCCC)OC(=O)NCCCN(C)C]

TABLE 11-continued
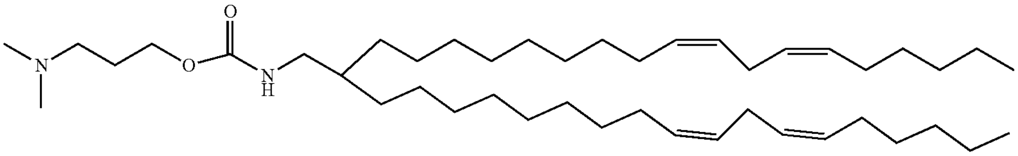 [SMILES: CCCCC/C=C\C/C=C\CCCCCCCCC(CCCCCCCC/C=C\C/C=C\CCCCC)CNC(=O)OCCCN(C)C]
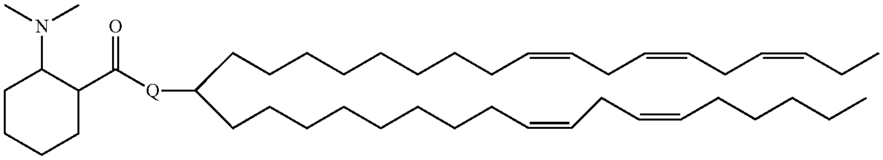
Q is NH, NMe
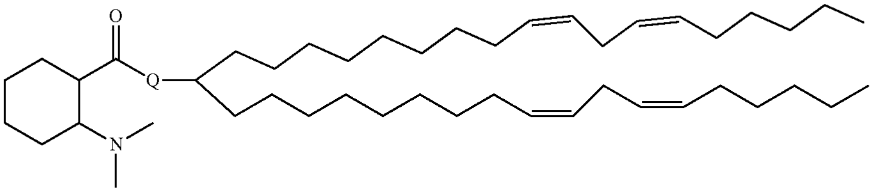
Q is NH, NMe
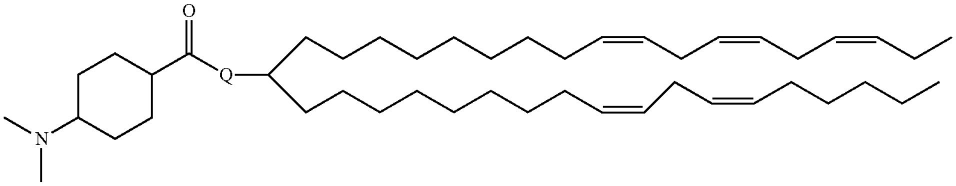
Q is NH, NMe
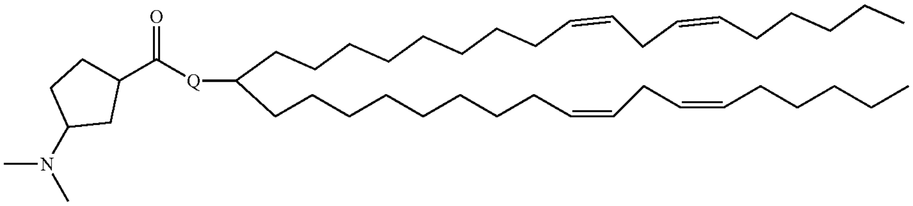
Q is NH, NMe
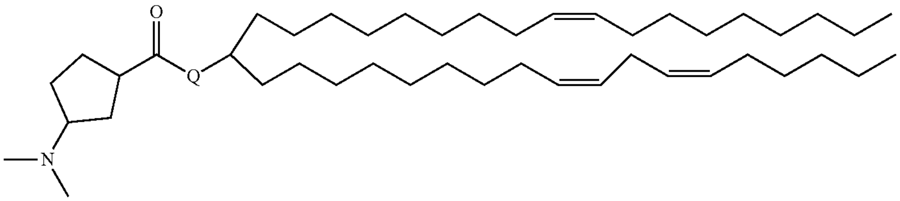
Q is NH, NMe
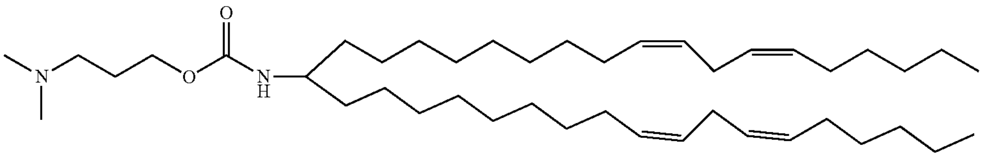 [SMILES: CCCCC/C=C\C/C=C\CCCCCCCCC(CCCCCCCC/C=C\C/C=C\CCCCC)NC(=O)OCCCN(C)C]

TABLE 11-continued
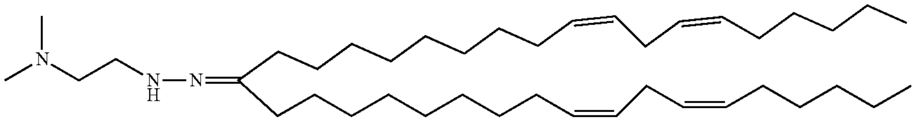 [SMILES: CCCCC/C=C\C/C=C\CCCCCCCCC(CCCCCCCC/C=C\C/C=C\CCCCC)=NNCCN(C)C]
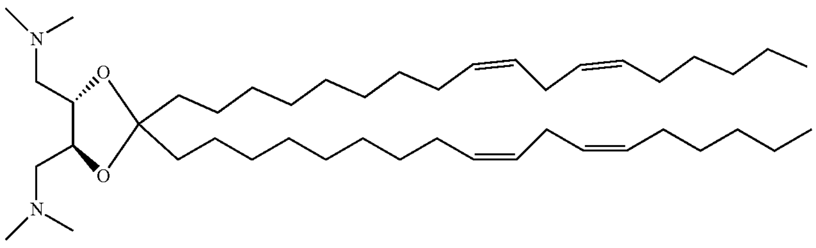 [SMILES: CCCCC/C=C\C/C=C\CCCCCCCCC1(CCCCCCCC/C=C\C/C=C\CCCCC)O[C@@H](CN(C)C)[C@H](CN(C)C)O1]
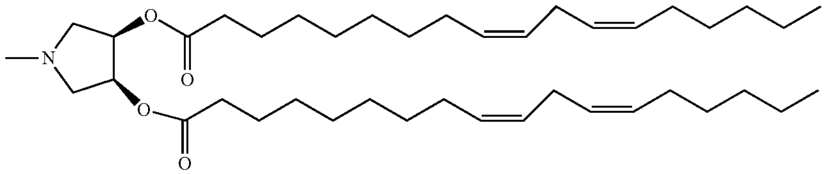 [SMILES: CCCCC/C=C\C/C=C\CCCCCCCC(=O)O[C@H]1CN(C)C[C@H]1OC(=O)CCCCCCC/C=C\C/C=C\CCCCC]
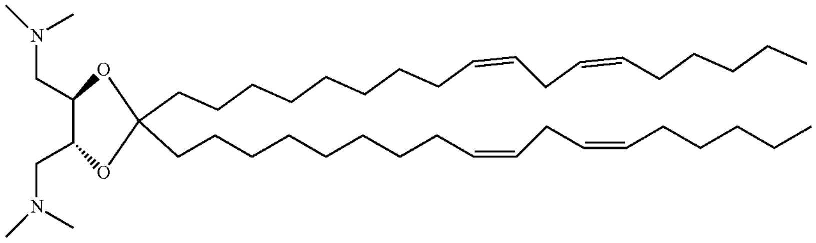 [SMILES: CCCCC/C=C\C/C=C\CCCCCCCCC1(CCCCCCCC/C=C\C/C=C\CCCCC)O[C@H](CN(C)C)[C@@H](CN(C)C)O1]
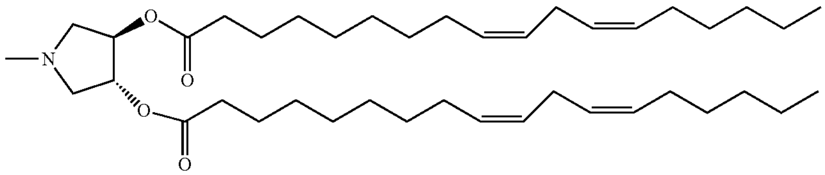 [SMILES: CCCCC/C=C\C/C=C\CCCCCCCC(=O)O[C@@H]1CN(C)C[C@H]1OC(=O)CCCCCCC/C=C\C/C=C\CCCCC]
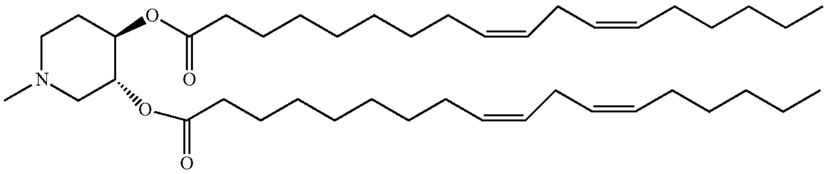 [SMILES: CCCCC/C=C\C/C=C\CCCCCCCC(=O)O[C@@H]1CCN(C)C[C@H]1OC(=O)CCCCCCC/C=C\C/C=C\CCCCC]
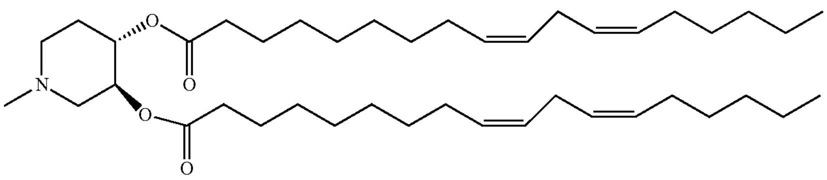 [SMILES: CCCCC/C=C\C/C=C\CCCCCCCC(=O)O[C@H]1CCN(C)C[C@@H]1OC(=O)CCCCCCC/C=C\C/C=C\CCCCC]
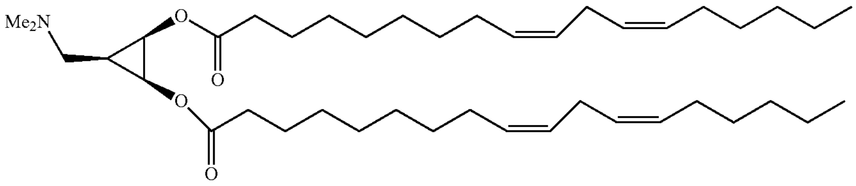 [SMILES: CCCCC/C=C\C/C=C\CCCCCCCC(=O)O[C@@H]1[C@H](CN(C)C)[C@@H]1OC(=O)CCCCCCC/C=C\C/C=C\CCCCC]

TABLE 11-continued
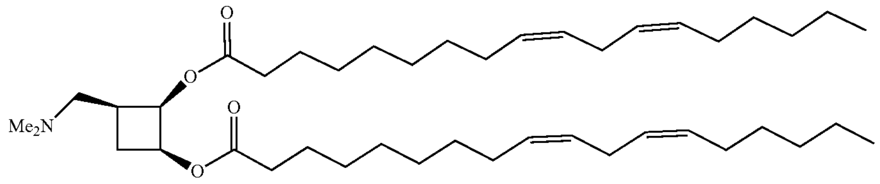 [SMILES: CCCCC/C=C\C/C=C\CCCCCCCC(=O)O[C@@H]1[C@H](CN(C)C)C[C@@H]1OC(=O)CCCCCCC/C=C\C/C=C\CCCCC]
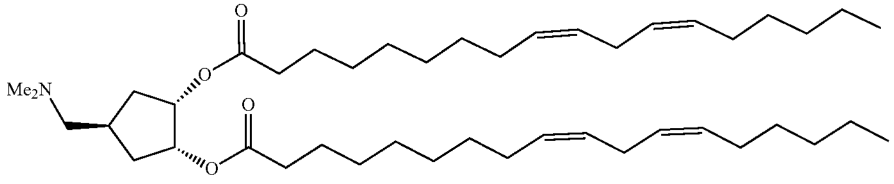 [SMILES: CCCCC/C=C\C/C=C\CCCCCCCC(=O)O[C@H]1C[C@H](CN(C)C)C[C@H]1OC(=O)CCCCCCC/C=C\C/C=C\CCCCC]
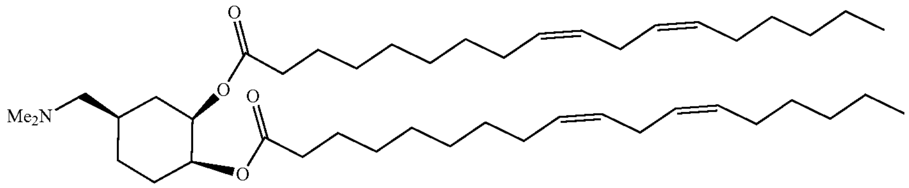 [SMILES: CCCCC/C=C\C/C=C\CCCCCCCC(=O)O[C@H]1CC[C@@H](CN(C)C)C[C@H]1OC(=O)CCCCCCC/C=C\C/C=C\CCCCC]
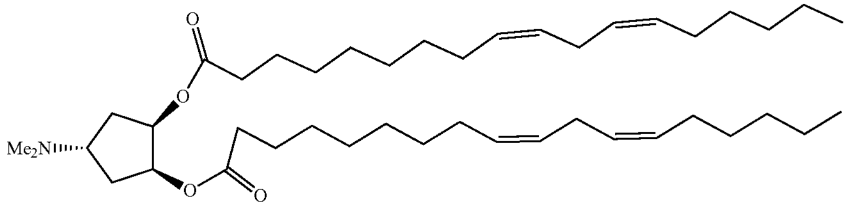 [SMILES: CCCCC/C=C\C/C=C\CCCCCCCC(=O)O[C@H]1C[C@H](N(C)C)C[C@H]1OC(=O)CCCCCCC/C=C\C/C=C\CCCCC]
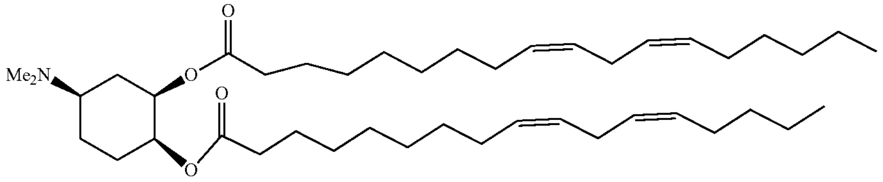 [SMILES: CCCC/C=C\C/C=C\CCCCCCCC(=O)O[C@H]1CC[C@@H](N(C)C)C[C@H]1OC(=O)CCCCCCC/C=C\C/C=C\CCCCC]
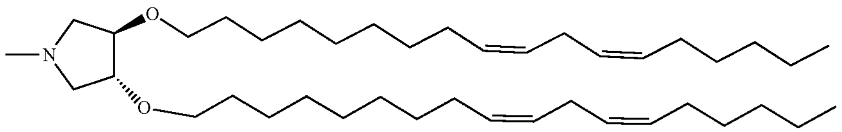 [SMILES: CCCCC/C=C\C/C=C\CCCCCCCCO[C@@H]1CN(C)C[C@H]1OCCCCCCCC/C=C\C/C=C\CCCCC]
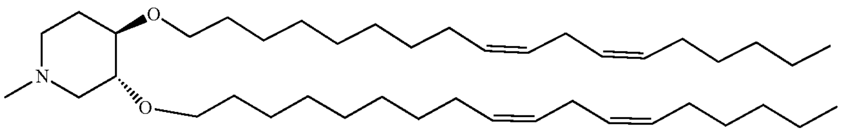 [SMILES: CCCCC/C=C\C/C=C\CCCCCCCCO[C@@H]1CCN(C)C[C@H]1OCCCCCCCC/C=C\C/C=C\CCCCC]
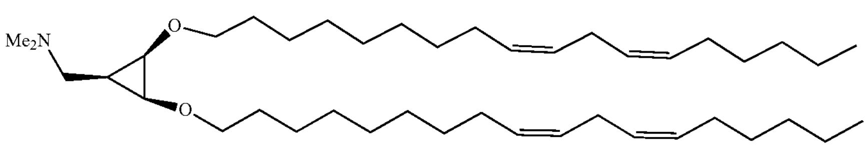 [SMILES: CCCCC/C=C\C/C=C\CCCCCCCCO[C@@H]1[C@H](CN(C)C)[C@@H]1OCCCCCCCC/C=C\C/C=C\CCCCC]
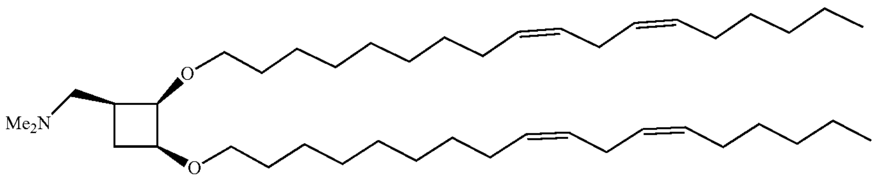 [SMILES: CCCCC/C=C\C/C=C\CCCCCCCCO[C@@H]1[C@H](CN(C)C)C[C@@H]1OCCCCCCCC/C=C\C/C=C\CCCCC]

TABLE 11-continued
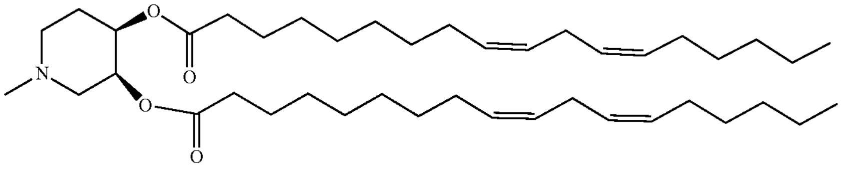 [SMILES: CCCCC/C=C\C/C=C\CCCCCCCC(=O)O[C@H]1CN(C)CC[C@H]1OC(=O)CCCCCCC/C=C\C/C=C\CCCCC]
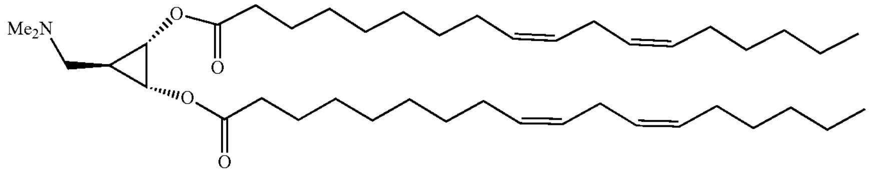 [SMILES: CCCCC/C=C\C/C=C\CCCCCCCC(=O)O[C@@H]1[C@@H](CN(C)C)[C@@H]1OC(=O)CCCCCCC/C=C\C/C=C\CCCCC]
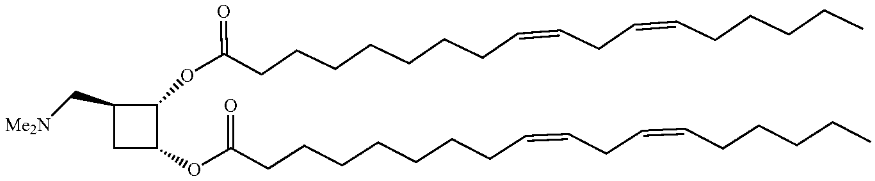 [SMILES: CCCCC/C=C\C/C=C\CCCCCCCC(=O)O[C@H]1[C@H](CN(C)C)C[C@H]1OC(=O)CCCCCCC/C=C\C/C=C\CCCCC]
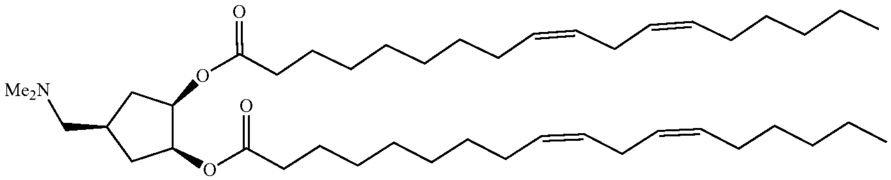 [SMILES: CCCCC/C=C\C/C=C\CCCCCCCC(=O)O[C@H]1C[C@@H](CN(C)C)C[C@H]1OC(=O)CCCCCCC/C=C\C/C=C\CCCCC]
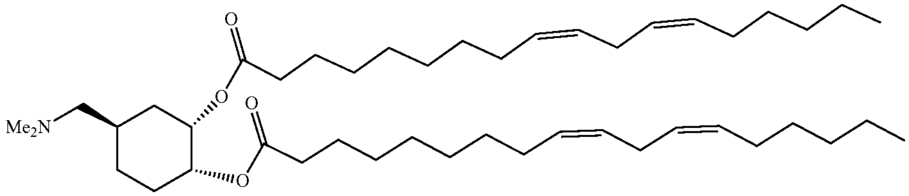 [SMILES: CCCCC/C=C\C/C=C\CCCCCCCC(=O)O[C@H]1C[C@H](CN(C)C)CC[C@H]1OC(=O)CCCCCCC/C=C\C/C=C\CCCCC]
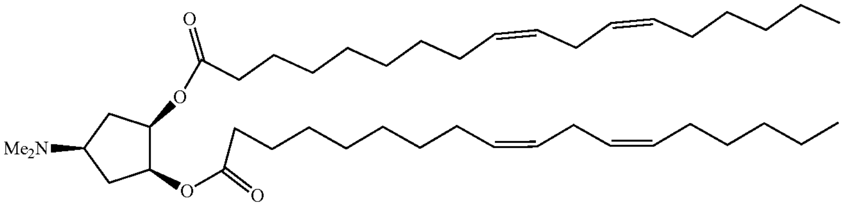 [SMILES: CCCCC/C=C\C/C=C\CCCCCCCC(=O)O[C@H]1C[C@@H](N(C)C)C[C@H]1OC(=O)CCCCCCC/C=C\C/C=C\CCCCC]
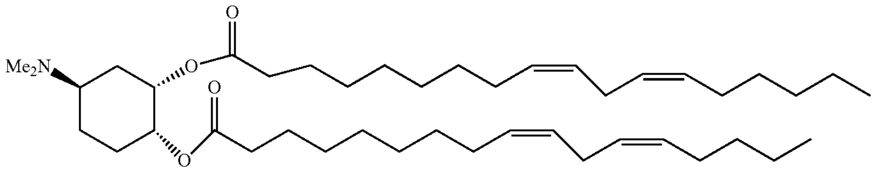 [SMILES: CCCC/C=C\C/C=C\CCCCCCCC(=O)O[C@@H]1CC[C@@H](N(C)C)C[C@@H]1OC(=O)CCCCCCC/C=C\C/C=C\CCCCC]
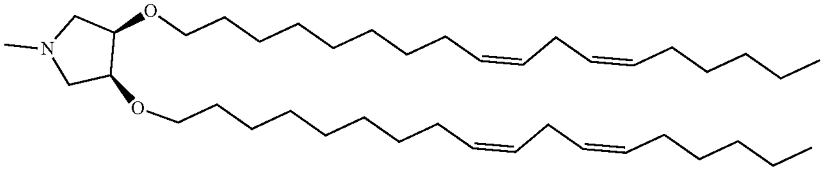 [SMILES: CCCCC/C=C\C/C=C\CCCCCCCCO[C@H]1CN(C)C[C@H]1OCCCCCCCC/C=C\C/C=C\CCCCC]

TABLE 11-continued
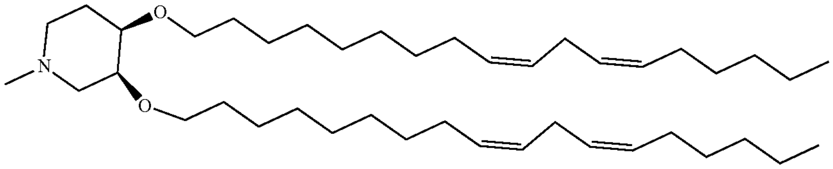 [SMILES: CCCCC/C=C\C/C=C\CCCCCCCCO[C@H]1CN(C)CC[C@H]1OCCCCCCCC/C=C\C/C=C\CCCCC]
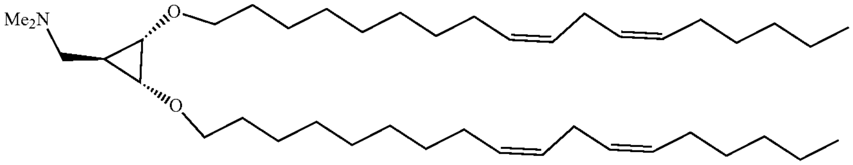 [SMILES: CCCCC/C=C\C/C=C\CCCCCCCCO[C@@H]1[C@@H](CN(C)C)[C@@H]1OCCCCCCCC/C=C\C/C=C\CCCCC]
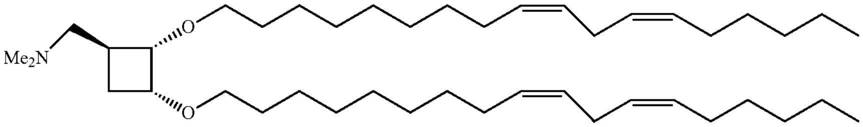 [SMILES: CCCCC/C=C\C/C=C\CCCCCCCCO[C@H]1[C@H](CN(C)C)C[C@H]1OCCCCCCCC/C=C\C/C=C\CCCCC]
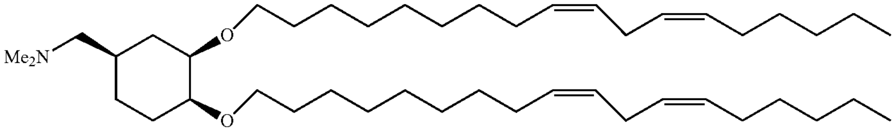 [SMILES: CCCCC/C=C\C/C=C\CCCCCCCCO[C@H]1CC[C@@H](CN(C)C)C[C@H]1OCCCCCCCC/C=C\C/C=C\CCCCC]
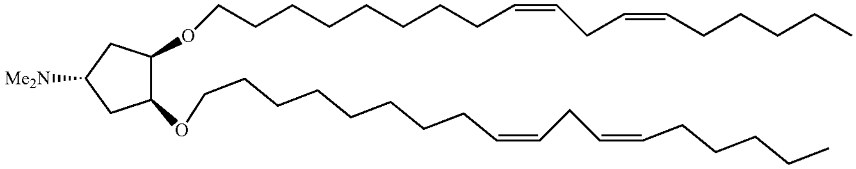 [SMILES: CCCCC/C=C\C/C=C\CCCCCCCCO[C@H]1C[C@H](N(C)C)C[C@H]1OCCCCCCCC/C=C\C/C=C\CCCCC]
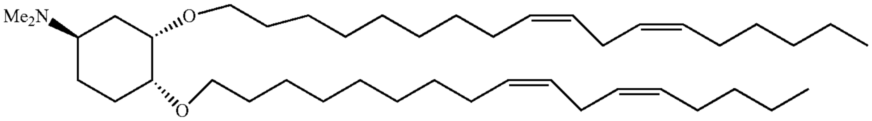 [SMILES: CCCC/C=C\C/C=C\CCCCCCCCO[C@@H]1CC[C@@H](N(C)C)C[C@@H]1OCCCCCCCC/C=C\C/C=C\CCCCC]
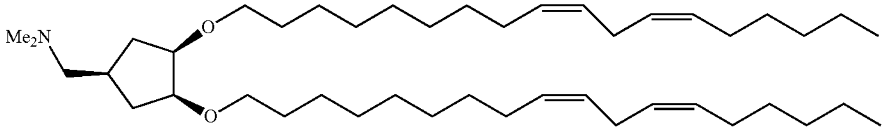 [SMILES: CCCCC/C=C\C/C=C\CCCCCCCCO[C@H]1C[C@@H](CN(C)C)C[C@H]1OCCCCCCCC/C=C\C/C=C\CCCCC]
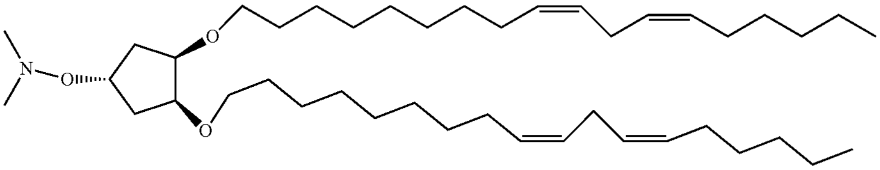 [SMILES: CCCCC/C=C\C/C=C\CCCCCCCCO[C@H]1C[C@H](ON(C)C)C[C@H]1OCCCCCCCC/C=C\C/C=C\CCCCC]
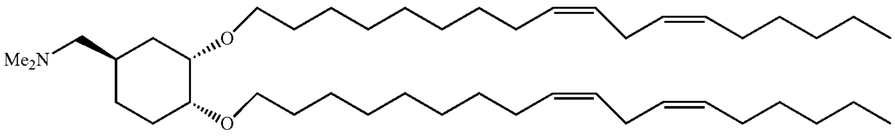 [SMILES: CCCCC/C=C\C/C=C\CCCCCCCCO[C@H]1C[C@H](CN(C)C)CC[C@H]1OCCCCCCCC/C=C\C/C=C\CCCCC]
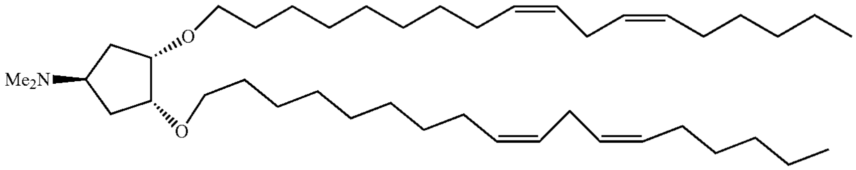 [SMILES: CCCCC/C=C\C/C=C\CCCCCCCCO[C@H]1C[C@H](N(C)C)C[C@H]1OCCCCCCCC/C=C\C/C=C\CCCCC]

TABLE 11-continued

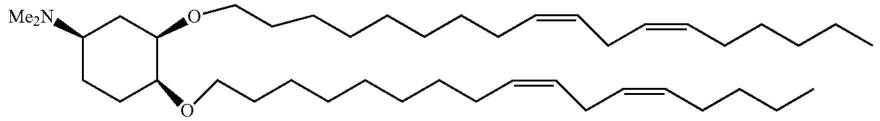 [SMILES: CCCC/C=C\C/C=C\CCCCCCCCO[C@H]1CC[C@@H](N(C)C)C[C@H]1OCCCCCCCC/C=C\C/C=C\CCCCC]

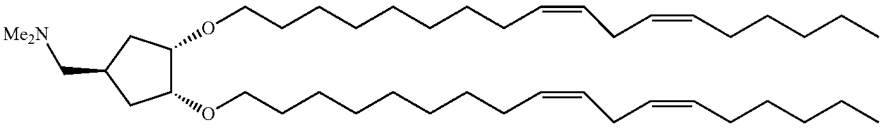 [SMILES: CCCCC/C=C\C/C=C\CCCCCCCCO[C@H]1C[C@H](CN(C)C)C[C@H]1OCCCCCCCC/C=C\C/C=C\CCCCC]

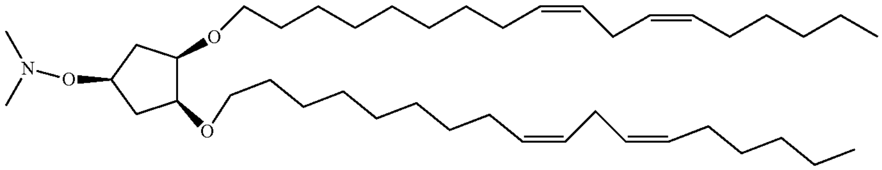 [SMILES: CCCCC/C=C\C/C=C\CCCCCCCCO[C@H]1C[C@@H](ON(C)C)C[C@H]1OCCCCCCCC/C=C\C/C=C\CCCCC]

In some embodiments, the transfer vehicle comprises Lipid A, Lipid B, Lipid C, and/or Lipid D. In some embodiments, inclusion of Lipid A, Lipid B, Lipid C, and/or Lipid D improves encapsulation and/or endosomal escape. In some embodiments, Lipid A, Lipid B, Lipid C, and/or Lipid D are described in international patent application PCT/US2017/028981.

In some embodiments, an ionizable lipid is Lipid A, which is (9Z,12Z)-3-((4,4-bis(octyloxy)butanoyl)oxy)-2-((((3-(diethylamino)propoxy)carbonyl)oxy)methyl)propyl octadeca9,12-dienoate, also called 3-((4,44bis(octyloxy)butanoyl)oxy)-2-((((3-(diethylamino)propoxy)carbonyl)oxy)methyl)propyl (9Z,12Z)-octadeca-9,12-dienoate. Lipid A can be depicted as:

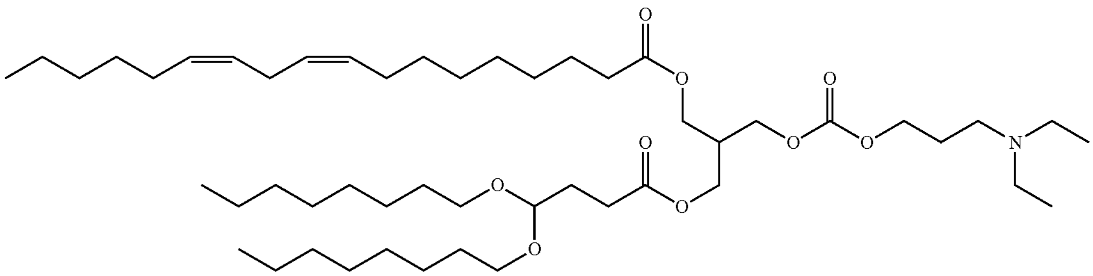 [SMILES: CCCCC/C=C\C/C=C\CCCCCCCC(=O)OCC(COC(=O)CCC(OCCCCCCCC)OCCCCCCCC)COC(=O)OCCCN(CC)CC]

Lipid A may be synthesized according to WO2015/095340 (e.g., pp. 84-86), incorporated by reference in its entirety.

In some embodiments, an ionizable lipid is Lipid B, which is ((5-((dimethylamino)methyl)-1,3-phenylene)bis(oxy))bis(octane-8,1-diyl)bis(decanoate). Lipid B can be depicted as:

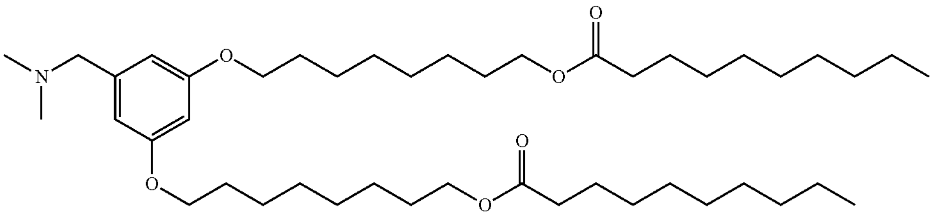 [SMILES: CCCCCCCCCC(=O)OCCCCCCCCOc1cc(CN(C)C)cc(OCCCCCCCCOC(=O)CCCCCCCCC)c1]

Lipid B may be synthesized according to WO2014/136086 (e.g., pp. 107-09), incorporated by reference in its entirety.

In some embodiments, an ionizable lipid is Lipid C, which is 2-((4-(((3-(dimethylamino)propoxy)carbonyl)oxy)hexadecanoyl)oxy)propane-1,3-diyl(9Z,9'Z,12Z,12'Z)-bis(octadeca-9,12-dienoate). Lipid C can be depicted as:

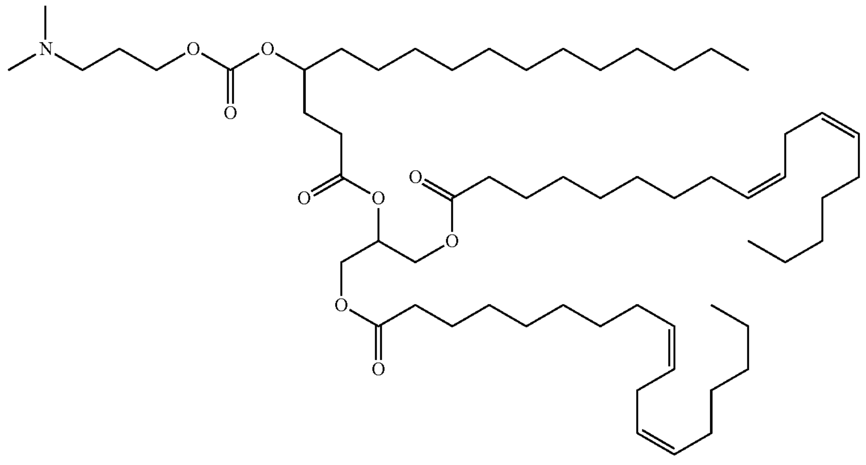 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

In some embodiments, an ionizable lipid is Lipid D, which is 3-(((3-(dimethylamino)propoxy)carbonyl)oxy)-13-(octanoyloxy)tridecyl 3-octylundecanoate. Lipid D can be depicted as:

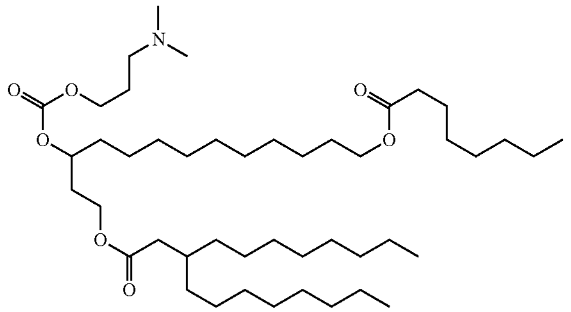 [SMILES: CCCCCCCCC(CCCCCCCC)CC(=O)OCCC(CCCCCCCCCCOC(=O)CCCCCCC)OC(=O)OCCCN(C)C]

Lipid C and Lipid D may be synthesized according to WO2015/095340, incorporated by reference in its entirety.

In some embodiments, an ionizable lipid is described in US patent publication number 20190321489. In some embodiments, an ionizable lipid is described in international patent publication WO 2010/053572, incorporated herein by reference. In some embodiments, an ionizable lipid is $C_{12}$-200, described at paragraph [00225] of WO 2010/053572.

Several ionizable lipids have been described in the literature, many of which are commercially available. In certain embodiments, such ionizable lipids are included in the transfer vehicles described herein. In some embodiments, the ionizable lipid N-[1-(2,3-dioleyloxy)propyl]-N,N,N-trimethylammonium chloride or "DOTMA" is used. (Felgner et al. Proc. Nat'l Acad. Sci. 84, 7413 (1987); U.S. Pat. No. 4,897,355). DOTMA can be formulated alone or can be combined with a neutral lipid, dioleoylphosphatidylethanolamine or "DOPE" or other cationic or non-cationic lipids into a lipid nanoparticle. Other suitable cationic lipids include, for example, ionizable cationic lipids as described in U.S. provisional patent application 61/617,468, filed Mar. 29, 2012 (incorporated herein by reference), such as, e.g., (15Z,18Z)-N,N-dimethyl-6-(9Z,12Z)-octadeca-9,12-dien-1-yl)tetracosa-15,18-dien-1-amine (HGT5000), (15Z,18Z)-N, N-dimethyl-6-((9Z,12Z)-octadeca-9,12-dien-1-yl)tetracosa-4,15,18-trien-i-amine (HGT5001), and (15Z,18Z)-N,N-dimethyl-6-((9Z,12Z)-octadeca-9,12-dien-1-yl)tetracosa-5, 15,18-trien-1-amine (HGT5002), $C_{12}$-200 (described in WO 2010/053572), 2-(2,2-di((9Z,12Z)-octadeca-9,12-dien-1-yl)-1,3-dioxolan-4-yl)-N,N-dimethylethanamine (DLinKC2-DMA)) (See, WO 2010/042877; Semple et al., Nature Biotech. 28:172-176 (2010)), 2-(2,2-di((9Z,2Z)-octadeca-9,12-dien-1-yl)-1,3-dioxolan-4-yl)-N,N-dimethylethanamine (DLin-KC2-DMA), (3S,10R,13R,17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate (ICE), (15Z,18Z)-N,N-dimethyl-6-(9Z,12Z)-octadeca-9,12-dien-1-yl)tetracosa-15,18-dien-1-amine (HGT5000), (15Z,18Z)-N, N-dimethyl-6-((9Z,12Z)-octadeca-9,12-dien-1-yl)tetr acosa-4,15,18-trien-1-amine (HGT5001), (15Z,18 Z)-N,N-dimethyl-6-((9Z,12Z)-octadeca-9,12-dien-l-yl)tetracosa-5, 15,18-trien-1-amine (HGT5002), 5-carboxyspermylglycine-dioctadecylamide (DOGS), 2,3-dioleyloxy-N-[2(spermine-carboxamido)ethyl]-N,N-dimethyl-1-propanaminium (DOSPA) (Behr et al. Proc. Nat.'l Acad. Sci. 86, 6982 (1989); U.S. Pat. Nos. 5,171,678; 5,334,761), 1,2-Dioleoyl-3-Dimethylammonium-Propane (DODAP), 1,2-Dioleoyl-3-Trimethylammonium-Propane or (DOTAP). Contemplated ionizable lipids also include 1,2-distcaryloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), N-dioleyl-N, N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9', 1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylamninopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA) or GL67, or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). The use of cholesterol-based ionizable lipids to formulate the transfer vehicles (e.g., lipid nanoparticles) is also contemplated by the present invention. Such cholesterol-based ionizable lipids can be used, either alone or in combination with other lipids. Suitable cholesterol-based ionizable lipids include, for example, DC-Cholesterol (N,N-dimethyl-N-ethylcarboxamidocholesterol), and 1,4-bis(3-N-oleylamino-propyl)piperazine (Gao, et al., Biochem. Biophys. Res. Comm. 179, 280 (1991); Wolf et al. BioTechniques 23, 139 (1997); U.S. Pat. No. 5,744,335).

Also contemplated are cationic lipids such as dialkylamino-based, imidazole-based, and guanidinium-based lipids. For example, also contemplated is the use of the ionizable lipid (3S,10R, 13R, 17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate (ICE), as disclosed in International Application No. PCT/US2010/058457, incorporated herein by reference.

Also contemplated are ionizable lipids such as the dialkylamino-based, imidazole-based, and guanidinium-based lipids. For example, certain embodiments are directed to a composition comprising one or more imidazole-based ionizable lipids, for example, the imidazole cholesterol ester or "ICE" lipid, (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (XIII) below. In an embodiment, a transfer vehicle for delivery of circRNA may comprise one or more imidazole-based ionizable lipids, for example, the imidazole cholesterol ester or "ICE" lipid (3S, 10R, 13R, 17R)-10, 13-dimethyl-17-((R)-6-methylheptan-2-yl)-2, 3, 4, 7, 9, 10, 11, 12, 13, 14, 15, 16, 17-tetradecahydro-1H-cyclopenta[a] phenanthren-3-yl 3-(1H-imidazol-4-yl)propanoate, as represented by structure (XIII).

(XIII)

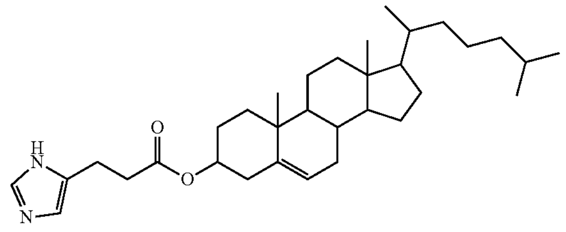

Without wishing to be bound by a particular theory, it is believed that the fusogenicity of the imidazole-based cationic lipid ICE is related to the endosomal disruption which is facilitated by the imidazole group, which has a lower pKa relative to traditional ionizable lipids. The endosomal disruption in turn promotes osmotic swelling and the disruption of the liposomal membrane, followed by the transfection or intracellular release of the nucleic acid(s) contents loaded therein into the target cell.

The imidazole-based ionizable lipids are also characterized by their reduced toxicity relative to other ionizable lipids.

In some embodiments, an ionizable lipid is described by US patent publication number 20190314284. In certain embodiments, the an ionizable lipid is described by structure 3, 4, 5, 6, 7, 8, 9, or 10 (e.g., HGT4001, HGT4002, HGT4003, HGT4004 and/or HGT4005). In certain embodiments, the one or more cleavable functional groups (e.g., a disulfide) allow, for example, a hydrophilic functional head-group to dissociate from a lipophilic functional tail-group of the compound (e.g., upon exposure to oxidative, reducing or acidic conditions), thereby facilitating a phase transition in the lipid bilayer of the one or more target cells. For example, when a transfer vehicle (e.g., a lipid nanoparticle) comprises one or more of the lipids of structures 3-10, the phase transition in the lipid bilayer of the one or more target cells facilitates the delivery of the circRNA into the one or more target cells.

In certain embodiments, the ionizable lipid is described by structure (XIV), (XIV)

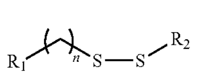

wherein:

$R_1$ is selected from the group consisting of imidazole, guanidinium, amino, imine, enamine, an optionally-substituted alkyl amino (e.g., an alkyl amino such as dimethylamino) and pyridyl;

$R_2$ is selected from the group consisting of structure XV and structure XVI;

XV

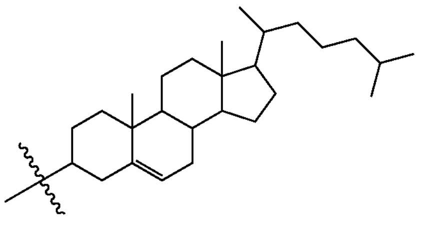

XVI

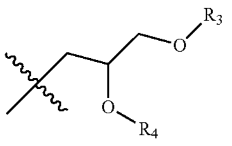

wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, $R_3$ and $R_4$ are each an optionally substituted, polyunsaturated $C_{18}$ alkyl, while in other embodiments $R_3$ and $R_4$ are each an unsubstituted, polyunsaturated $C_{18}$ alkyl. In certain embodiments, one or more of $R_3$ and $R_4$ are (9Z,12Z)-octadeca-9,12-dien.

Also disclosed herein are pharmaceutical compositions that comprise the compound of structure XIV, wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is structure XV; and wherein n is zero or any positive integer. Further disclosed herein are pharmaceutical compositions comprising the compound of structure XIV, wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is structure XVI; wherein R3 and R4 are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer. In certain embodiments. $R_3$ and $R_4$ are each an optionally substituted, polyunsaturated $C_{18}$ alkyl, while in other embodiments $R_3$ and $R_4$ are each an unsubstituted, polyunsaturated $C_{18}$ alkyl (e.g., octadeca-9,12-dien).

In certain embodiments, the $R_1$ group or head-group is a polar or hydrophilic group (e.g., one or more of the imidazole, guanidinium and amino groups) and is bound to the $R_2$ lipid group by way of the disulfide (S-S) cleavable linker group, for example as depicted in structure XIV. Other contemplated cleavable linker groups may include compositions that comprise one or more disulfide (SS) linker group bound (e.g., covalently bound) to, for example an alkyl group (e.g., $C_1$ to $C_{10}$ alkyl). In certain embodiments, the $R^1$ group is covalently bound to the cleavable linker group by way of a $C_1$-$C_{20}$ alkyl group (e.g., where n is one to twenty), or alternatively may be directly bound to the cleavable linker group (e.g., where n is zero). In certain embodiments, the disulfide linker group is cleavable in vitro and/or in vivo (e.g., enzymatically cleavable or cleavable upon exposure to acidic or reducing conditions).

In certain embodiments, the inventions relate to the compound 5-(((10,13-dimethyl-17-(6-methylheptan-2-yl)-2,3,4,7,8,9,10,11,12,13,14,15,16,17-tetradecahydro-1H-cyclopenta[a]phenanthren-3-yl)disulfanyl)methyl)-1H-imidazole, having structure XVII (referred to herein as "HGT4001").

XVII

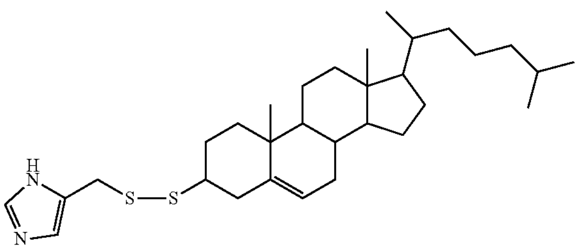

In certain embodiments, the inventions relate to the compound 1-(2-(((3S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)disulfanyl)ethyl)guanidine, having structure XVIII (referred to herein as "HGT4002").

XVIII

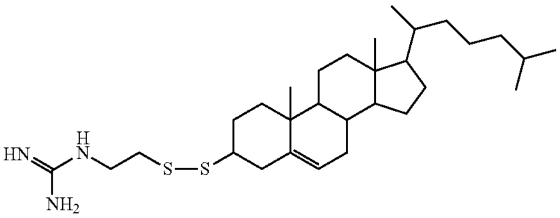

In certain embodiments, the inventions relate to the compound 2-((2,3-Bis((9Z,12Z)-octadeca-9,12-dien-1-yloxy)propyl)disulfanyl)-N N-dimethylethanamine, having structure XIX (referred to herein as "HGT4003").

XIX

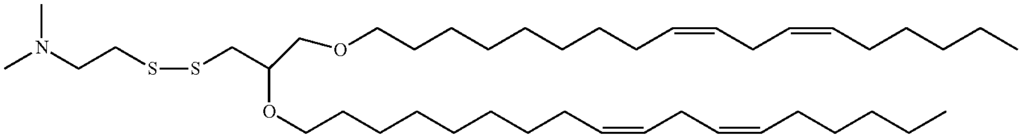

In other embodiments the inventions relate to the compound 5 (((2,3-bis((9Z,12Z)-octadeca-9,12-dien-1-yloxy)propyl)disulfanyl)methyl)-1H-imidazole having the structure of structure XX (referred to herein as "HGT4004").

XX

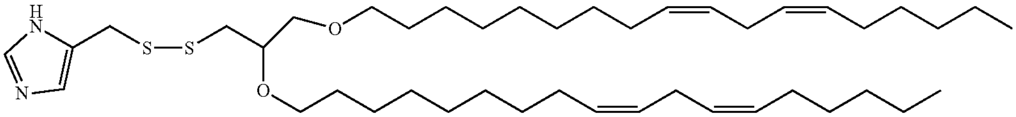

In still other embodiments, the inventions relate to the compound 1-(((2,3-bis((9Z,12Z)-octadeca-9,12-dien-1-yloxy)propyl)disulfanyl)methyl)guanidine having structure XXI (referred to herein as "HGT4005").

XXI

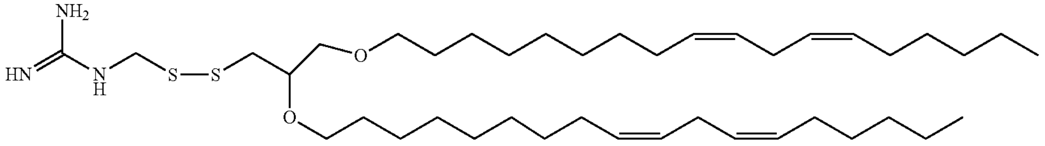

In certain embodiments, the compounds described as structures 3-10 are ionizable lipids.

The compounds, and in particular the imidazole-based compounds described as structures 3-8 (e.g., HGT4001 and HGT4004), are characterized by their reduced toxicity, in particular relative to traditional ionizable lipids. In some embodiments, the transfer vehicles described herein comprise one or more imidazole-based ionizable lipid compounds such that the relative concentration of other more toxic ionizable lipids in such pharmaceutical or liposomal composition may be reduced or otherwise eliminated.

The ionizable lipids include those disclosed in international patent application PCT/US2019/025246, and US patent publications 2017/0190661 and 2017/0114010, incorporated herein by reference in their entirety. The ionizable lipids may include a lipid selected from the following tables 12, 13, 14, or 15.

TABLE 12

| | |
|---|---|
| 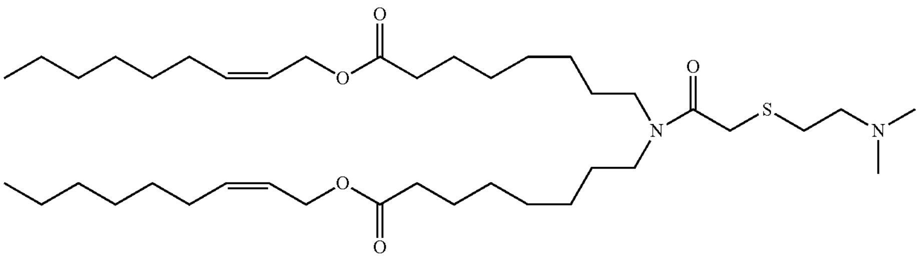 | ATX-001 |
| 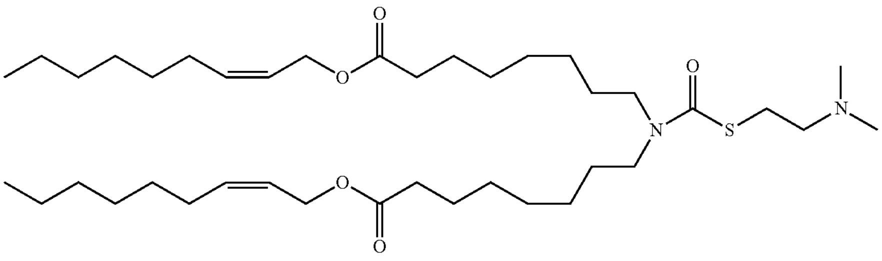 | ATX-002 |
| 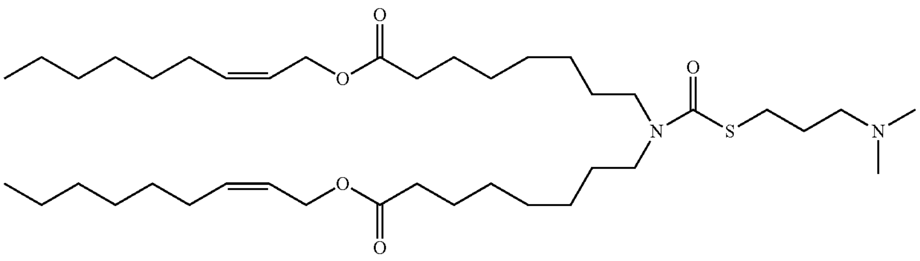 [SMILES: CCCCCC/C=C\COC(=O)CCCCCCCN(CCCCCCCC(=O)OC/C=C\CCCCCC)C(=O)SCCCN(C)C] | ATX-003 |
| 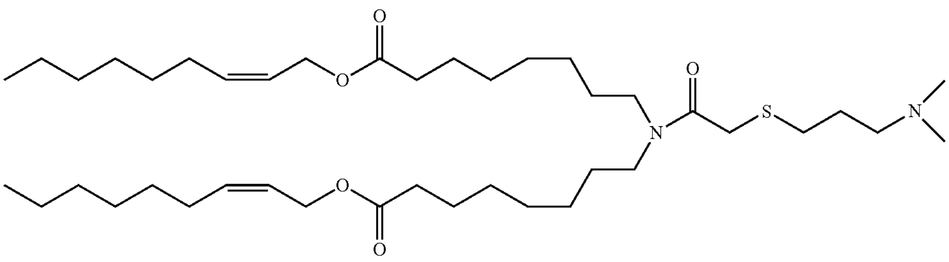 [SMILES: CCCCCC/C=C\COC(=O)CCCCCCCN(CCCCCCCC(=O)OC/C=C\CCCCCC)C(=O)CSCCCN(C)C] | ATX-004 |

TABLE 12-continued
ATX-005
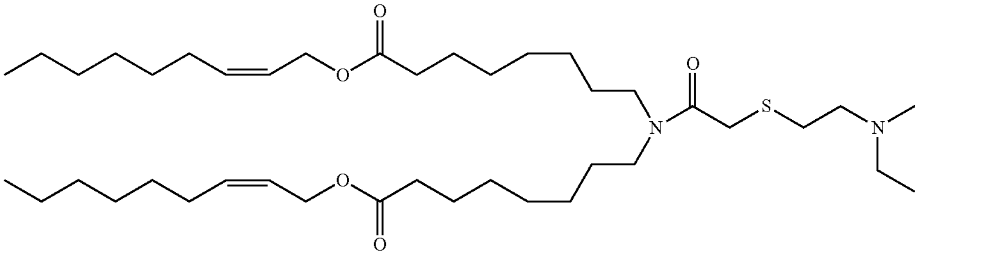 [SMILES: CCCCCC/C=C\COC(=O)CCCCCCCN(CCCCCCCC(=O)OC/C=C\CCCCCC)C(=O)CSCCN(C)CC]
ATX-006
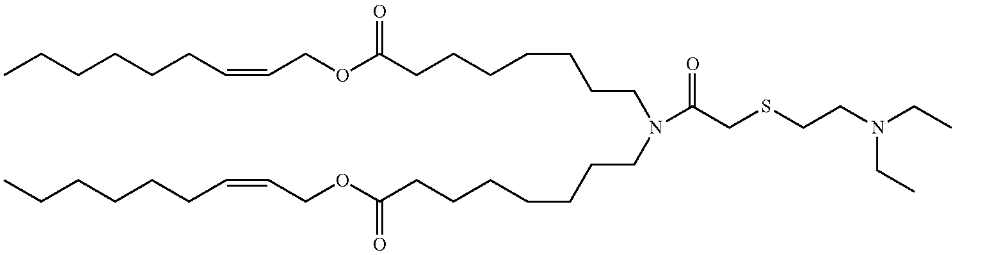 [SMILES: CCCCCC/C=C\COC(=O)CCCCCCCN(CCCCCCCC(=O)OC/C=C\CCCCCC)C(=O)CSCCN(CC)CC]
ATX-007
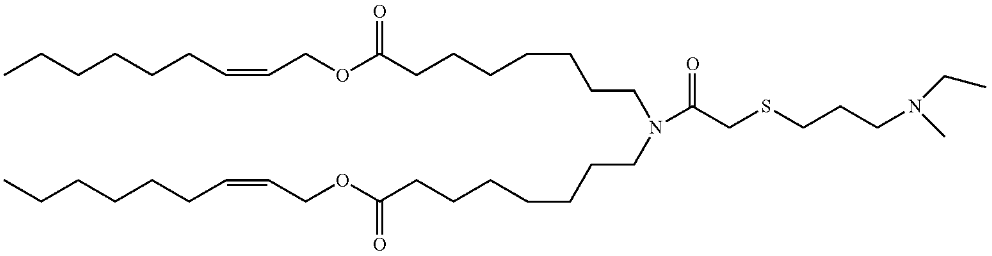 [SMILES: CCCCCC/C=C\COC(=O)CCCCCCCN(CCCCCCCC(=O)OC/C=C\CCCCCC)C(=O)CSCCCN(C)CC]
ATX-008
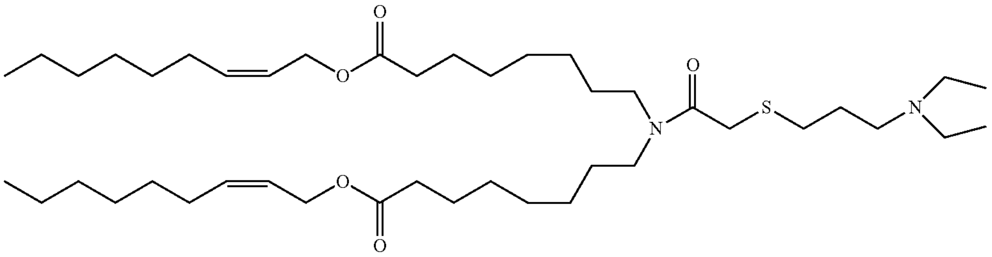 [SMILES: CCCCCC/C=C\COC(=O)CCCCCCCN(CCCCCCCC(=O)OC/C=C\CCCCCC)C(=O)CSCCCN(CC)CC]
ATX-009
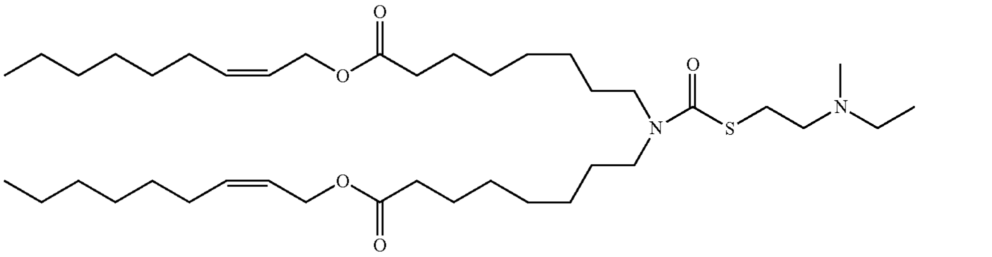 [SMILES: CCCCCC/C=C\COC(=O)CCCCCCCN(CCCCCCCC(=O)OC/C=C\CCCCCC)C(=O)SCCN(C)CC]
ATX-010
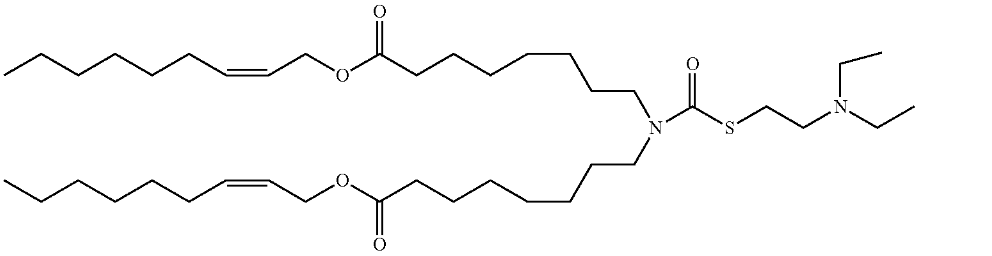 [SMILES: CCCCCC/C=C\COC(=O)CCCCCCCN(CCCCCCCC(=O)OC/C=C\CCCCCC)C(=O)SCCN(CC)CC]

TABLE 12-continued
ATX-011
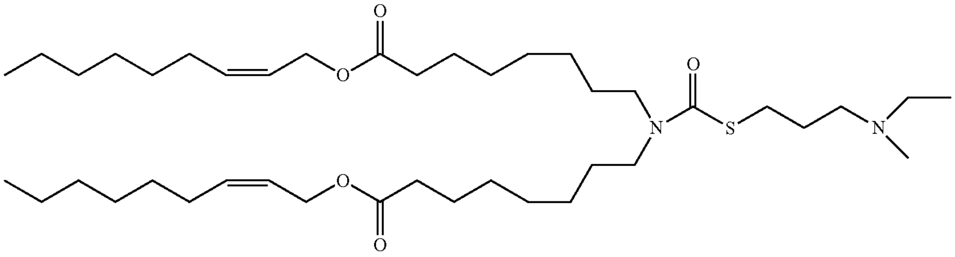 [SMILES: CCCCCC/C=C\COC(=O)CCCCCCCN(CCCCCCCC(=O)OC/C=C\CCCCCC)C(=O)SCCCN(C)CC]
ATX-012
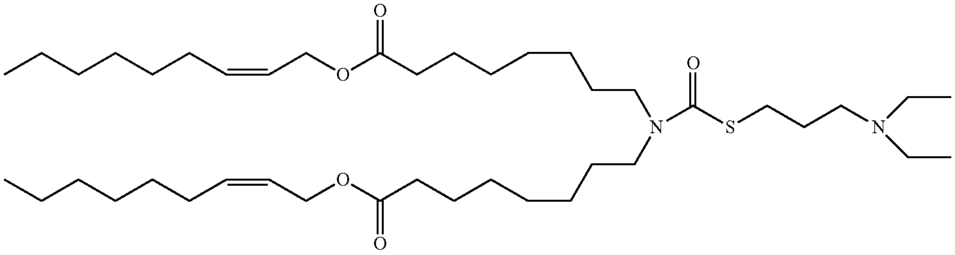 [SMILES: CCCCCC/C=C\COC(=O)CCCCCCCN(CCCCCCCC(=O)OC/C=C\CCCCCC)C(=O)SCCCN(CC)CC]
ATX-013
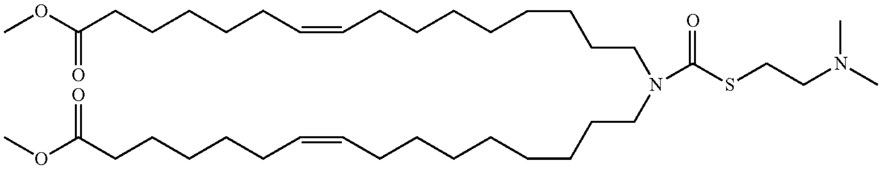
ATX-014
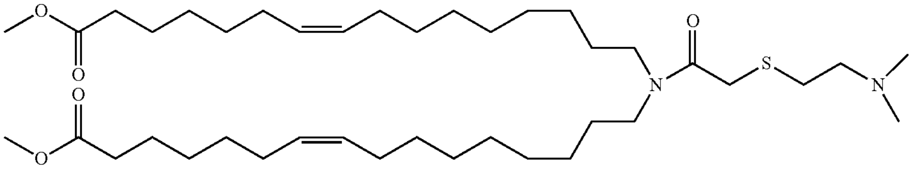
ATX-015
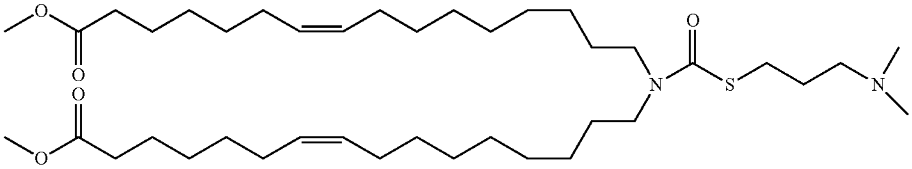
ATX-016
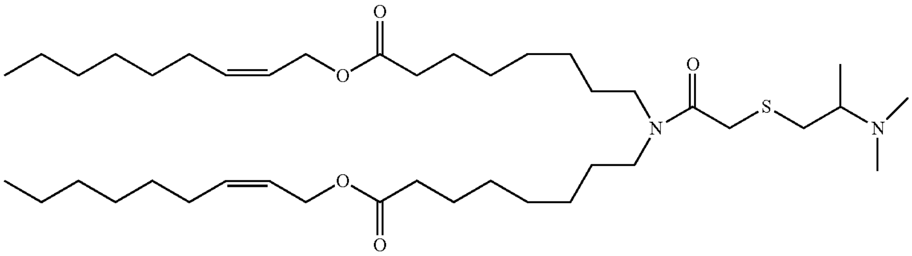 [SMILES: CCCCCC/C=C\COC(=O)CCCCCCCN(CCCCCCCC(=O)OC/C=C\CCCCCC)C(=O)CSCC(C)N(C)C]
ATX-017
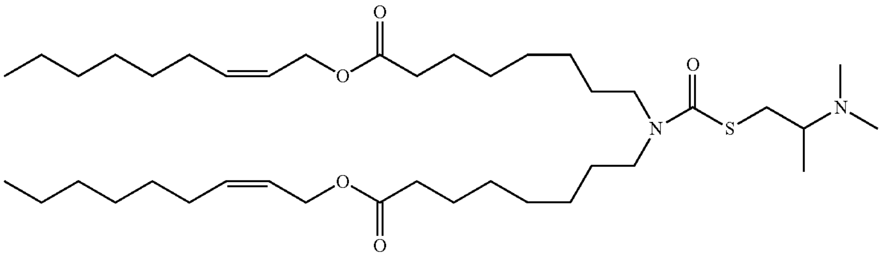 [SMILES: CCCCCC/C=C\COC(=O)CCCCCCCN(CCCCCCCC(=O)OC/C=C\CCCCCC)C(=O)SCC(C)N(C)C]

TABLE 12-continued
ATX-018
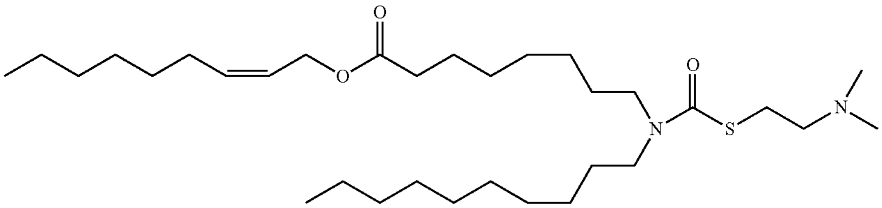 [SMILES: CCCCCC/C=C\COC(=O)CCCCCCCN(CCCCCCCCCC)C(=O)SCCN(C)C]
ATX-019
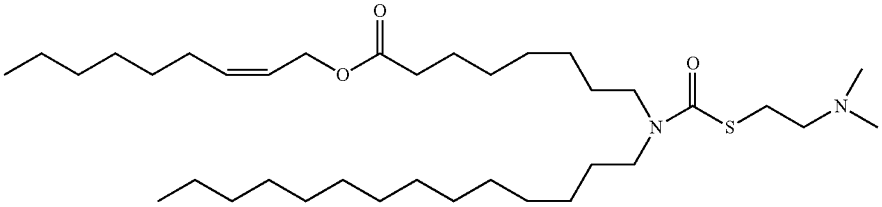 [SMILES: CCCCCC/C=C\COC(=O)CCCCCCCN(CCCCCCCCCCCCCC)C(=O)SCCN(C)C]
ATX-020
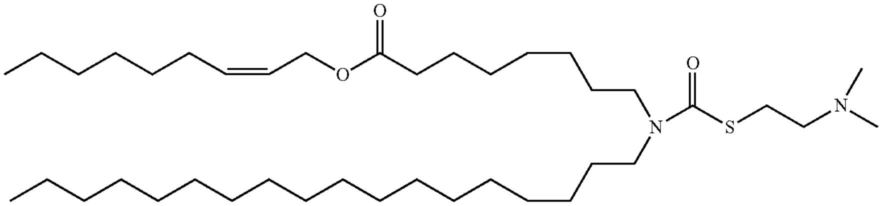 [SMILES: CCCCCC/C=C\COC(=O)CCCCCCCN(CCCCCCCCCCCCCCCCCC)C(=O)SCCN(C)C]
ATX-021
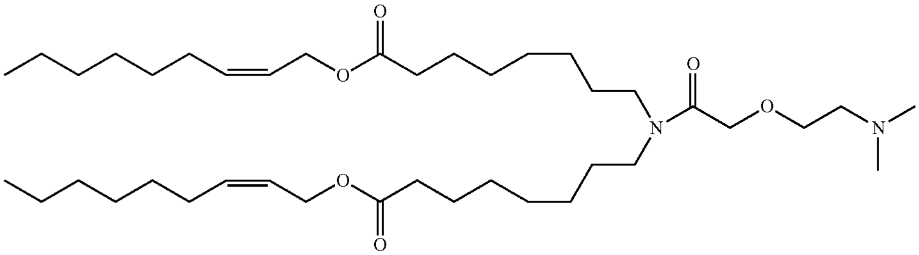
ATX-022
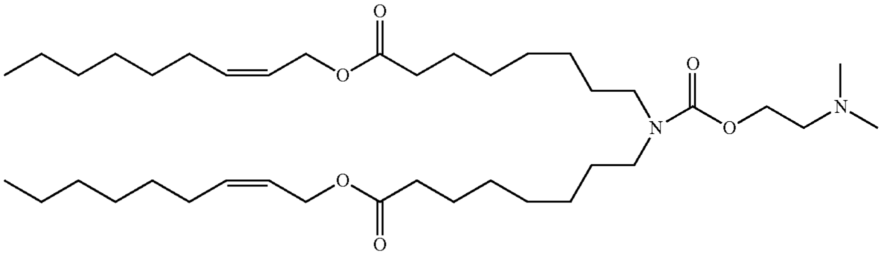
ATX-023
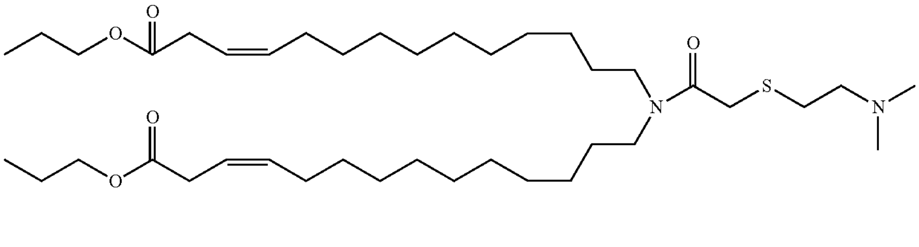 [SMILES: CCCOC(=O)C/C=C\CCCCCCCCCCN(CCCCCCCCCC/C=C\CC(=O)OCCC)C(=O)CSCCN(C)C]

TABLE 12-continued
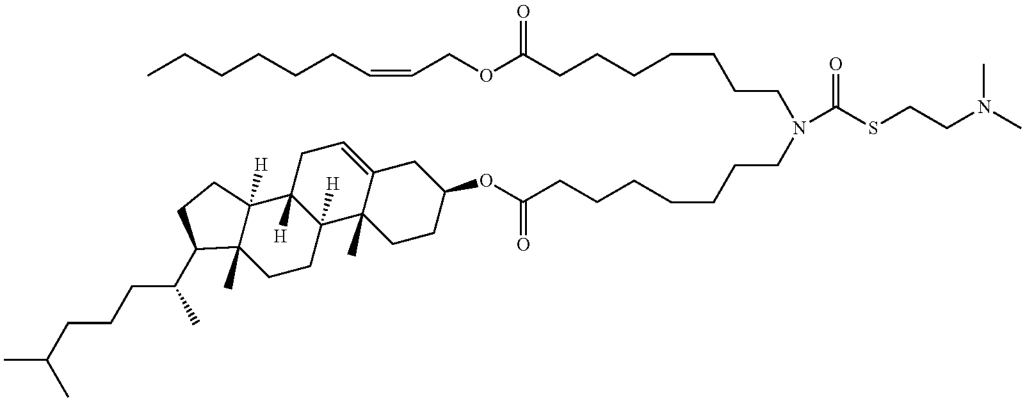
ATX-024
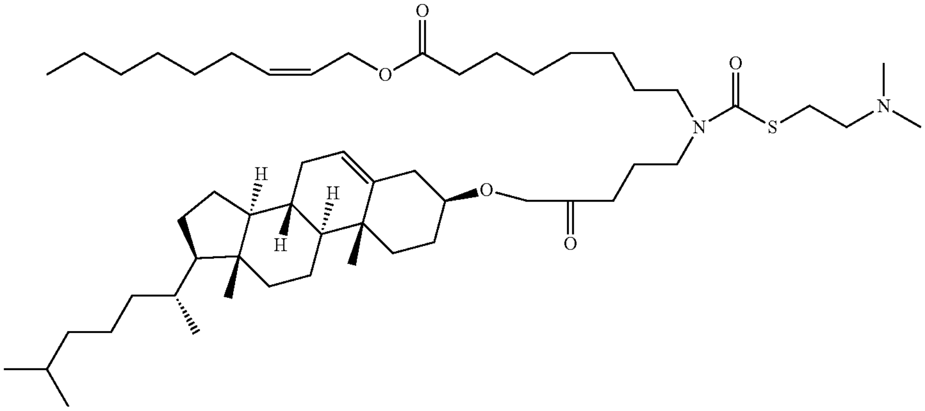
ATX-025
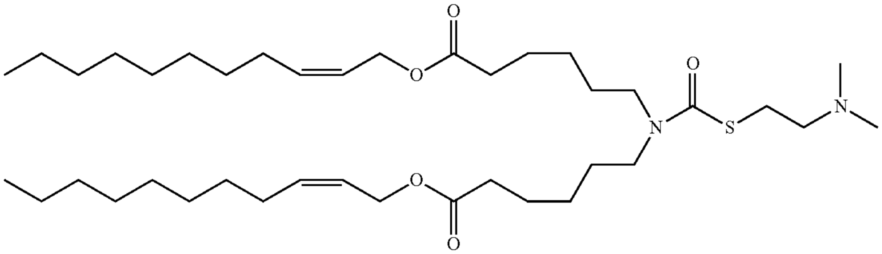 [SMILES: CCCCCCCC/C=C\COC(=O)CCCCCN(CCCCCC(=O)OC/C=C\CCCCCCCC)C(=O)SCCN(C)C]
ATX-026
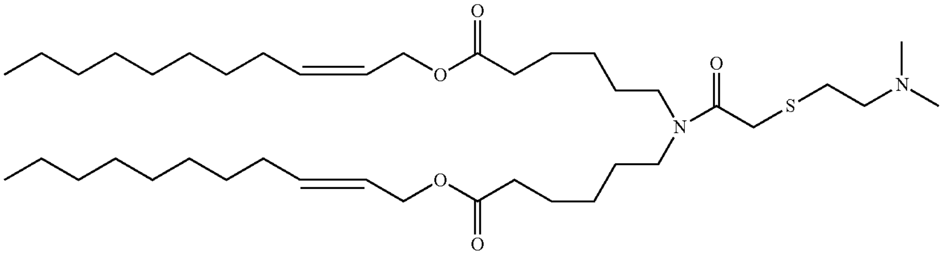 [SMILES: CCCCCCCC/C=C\COC(=O)CCCCCN(CCCCCC(=O)OC/C=C/CCCCCCCC)C(=O)CSCCN(C)C]
ATX-027
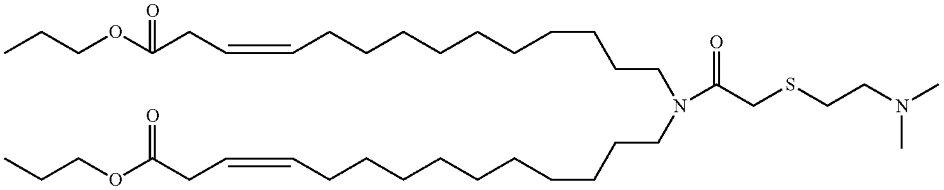 [SMILES: CCCOC(=O)C/C=C\CCCCCCCCCCN(CCCCCCCCCC/C=C\CC(=O)OCCC)C(=O)CSCCN(C)C]
ATX-028

TABLE 12-continued
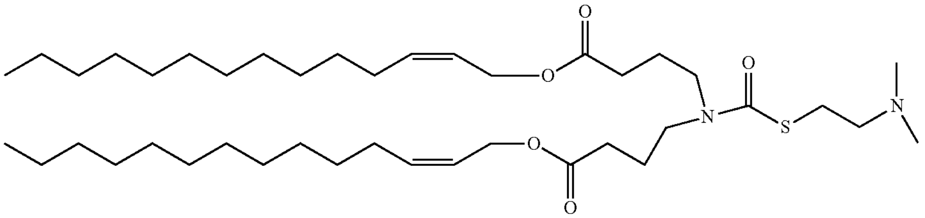 [SMILES: CCCCCCCCCCC/C=C\COC(=O)CCCN(CCCC(=O)OC/C=C\CCCCCCCCCCC)C(=O)SCCN(C)C]
ATX-029
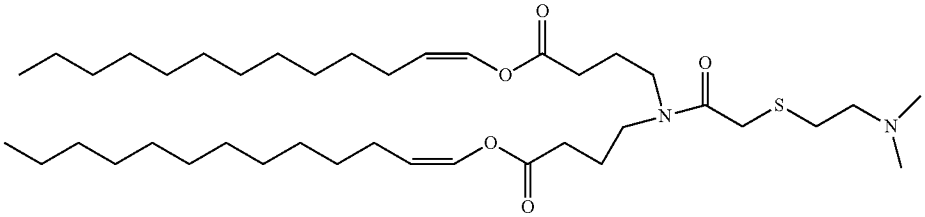 [SMILES: CCCCCCCCCCC/C=C\OC(=O)CCCN(CCCC(=O)O/C=C\CCCCCCCCCCC)C(=O)CSCCN(C)C]
ATX-030
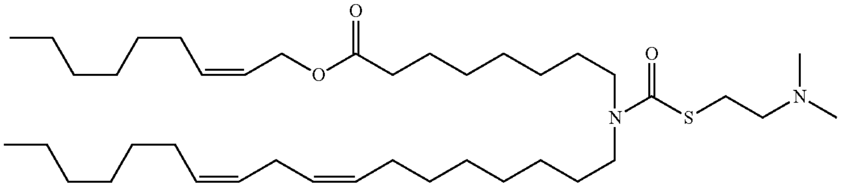 [SMILES: CCCCCC/C=C\C/C=C\CCCCCCCN(CCCCCCCC(=O)OC/C=C\CCCCCC)C(=O)SCCN(C)C]
ATX-031
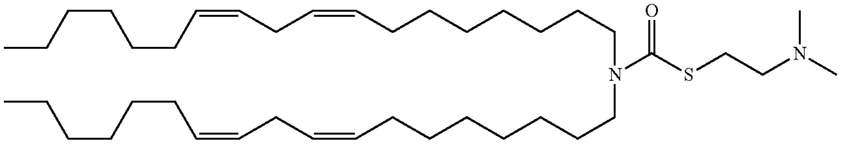 [SMILES: CCCCCC/C=C\C/C=C\CCCCCCCN(CCCCCCC/C=C\C/C=C\CCCCCC)C(=O)SCCN(C)C]
ATX-032
TABLE 13
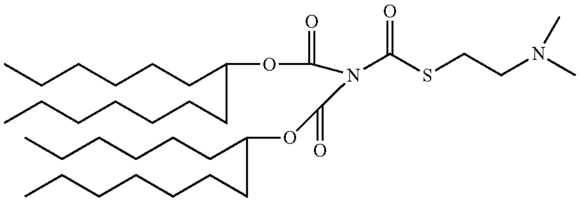 [SMILES: CCCCCCCC(CCCCCC)OC(=O)N(C(=O)OC(CCCCCC)CCCCCCC)C(=O)SCCN(C)C]
ATX-B-1
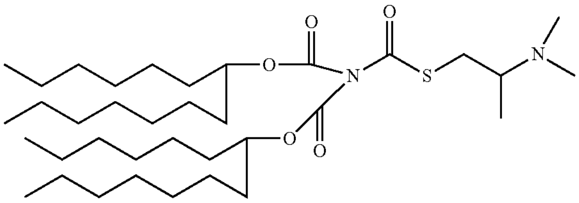 [SMILES: CCCCCCCC(CCCCCC)OC(=O)N(C(=O)OC(CCCCCC)CCCCCCC)C(=O)SCC(C)N(C)C]
ATX-B-2
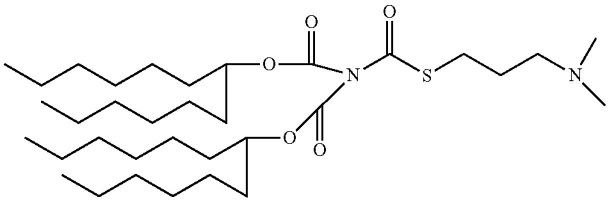 [SMILES: CCCCCCC(CCCCCC)OC(=O)N(C(=O)OC(CCCCCC)CCCCCC)C(=O)SCCCN(C)C]
ATX-B-3

TABLE 13-continued
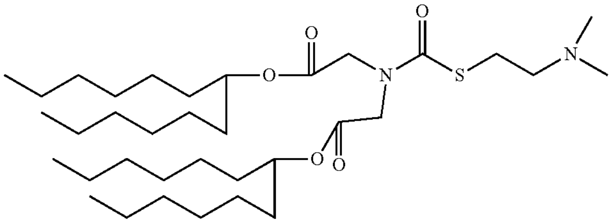 [SMILES: CCCCCCC(CCCCCC)OC(=O)CN(CC(=O)OC(CCCCCC)CCCCCC)C(=O)SCCN(C)C]
ATX-B-4
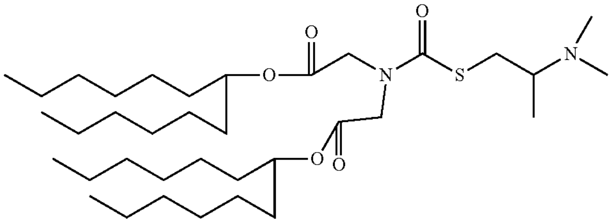 [SMILES: CCCCCCC(CCCCCC)OC(=O)CN(CC(=O)OC(CCCCCC)CCCCCC)C(=O)SCC(C)N(C)C]
ATX-B-5
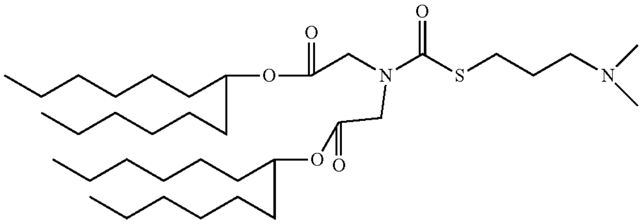 [SMILES: CCCCCCC(CCCCCC)OC(=O)CN(CC(=O)OC(CCCCCC)CCCCCC)C(=O)SCCCN(C)C]
ATX-B-6
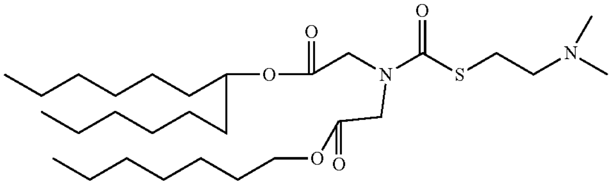 [SMILES: CCCCCCCOC(=O)CN(CC(=O)OC(CCCCCC)CCCCCC)C(=O)SCCN(C)C]
ATX-B-7
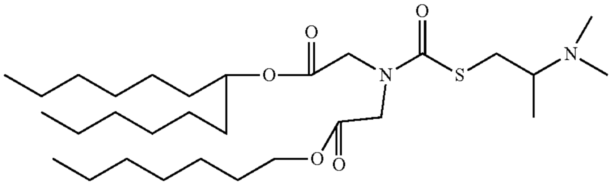 [SMILES: CCCCCCCOC(=O)CN(CC(=O)OC(CCCCCC)CCCCCC)C(=O)SCC(C)N(C)C]
ATX-B-8
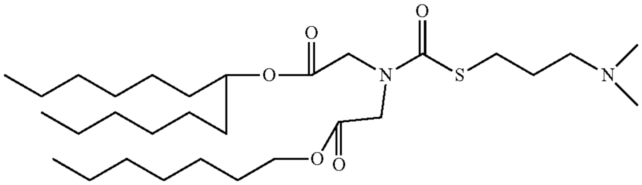 [SMILES: CCCCCCCOC(=O)CN(CC(=O)OC(CCCCCC)CCCCCC)C(=O)SCCCN(C)C]
ATX-B-9
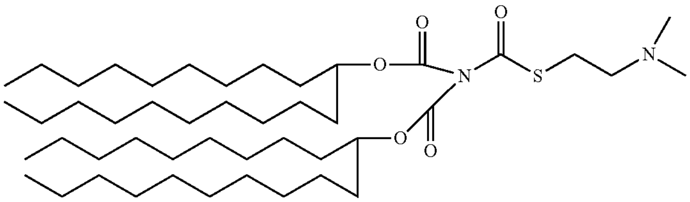 [SMILES: CCCCCCCCCCC(CCCCCCCCC)OC(=O)N(C(=O)OC(CCCCCCCCC)CCCCCCCCCC)C(=O)SCCN(C)C]
ATX-B-10

TABLE 13-continued
| | |
|---|---|
| 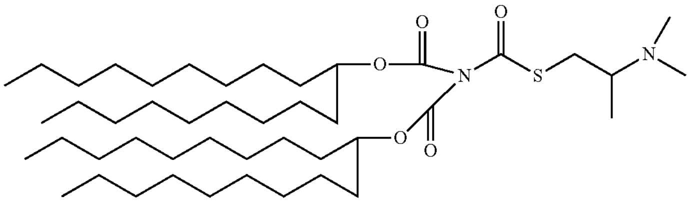 [SMILES: CCCCCCCCCC(CCCCCCCCC)OC(=O)N(C(=O)OC(CCCCCCCCC)CCCCCCCCC)C(=O)SCC(C)N(C)C] | ATX-B-11 |
| 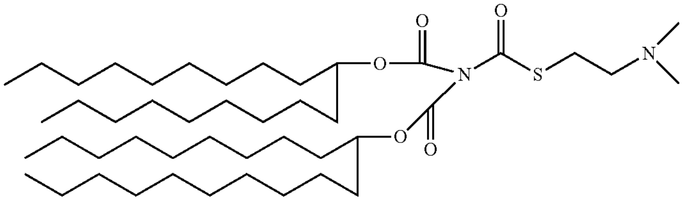 [SMILES: CCCCCCCCCCC(CCCCCCCCC)OC(=O)N(C(=O)OC(CCCCCCCCC)CCCCCCCCC)C(=O)SCCN(C)C] | ATX-B-12 |
TABLE 14
| Compound | ATX-# |
|---|---|
| 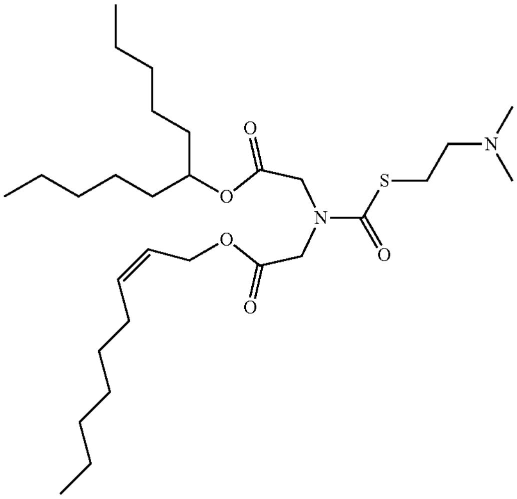 [SMILES: CCCCCC/C=C\COC(=O)CN(CC(=O)OC(CCCCC)CCCCC)C(=O)SCCN(C)C] | 0063 |
| 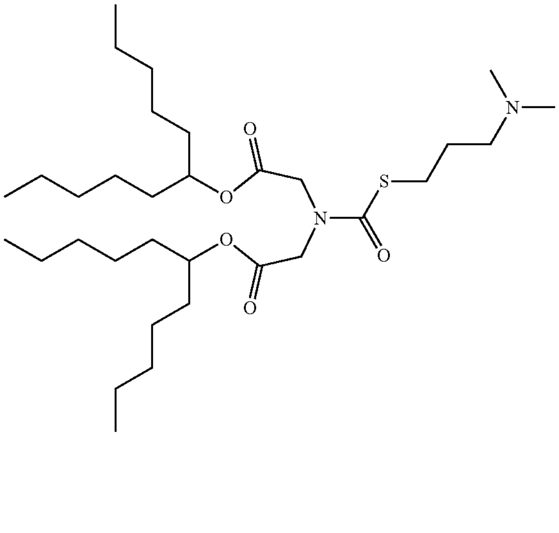 [SMILES: CCCCCC(CCCCC)OC(=O)CN(CC(=O)OC(CCCCC)CCCCC)C(=O)SCCCN(C)C] | 0130 |

TABLE 14-continued
| Compound | ATX-# |
|---|---|
| 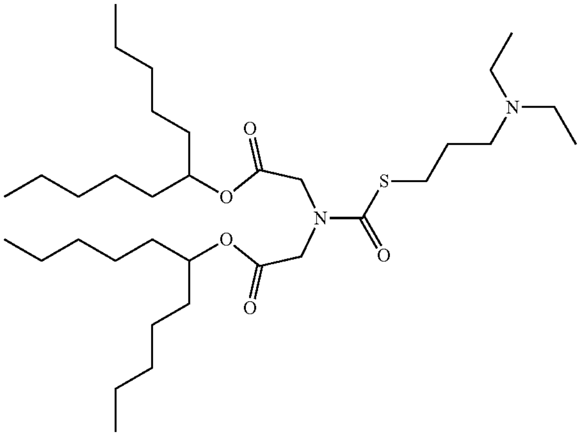 [SMILES: CCCCCC(CCCCC)OC(=O)CN(CC(=O)OC(CCCCC)CCCCC)C(=O)SCCCN(CC)CC] | 0131 |
| 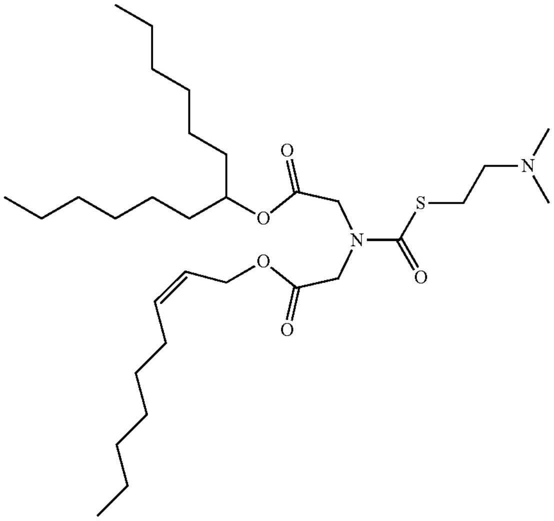 [SMILES: CCCCCC/C=C\COC(=O)CN(CC(=O)OC(CCCCCC)CCCCCC)C(=O)SCCN(C)C] | 0044 |
| 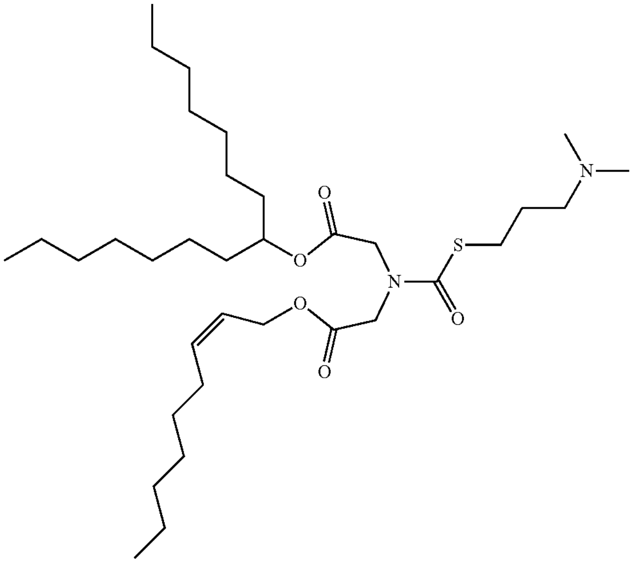 [SMILES: CCCCCC/C=C\COC(=O)CN(CC(=O)OC(CCCCCCC)CCCCCCC)C(=O)SCCCN(C)C] | 0111 |

TABLE 14-continued
| Compound | ATX-# |
| --- | --- |
| 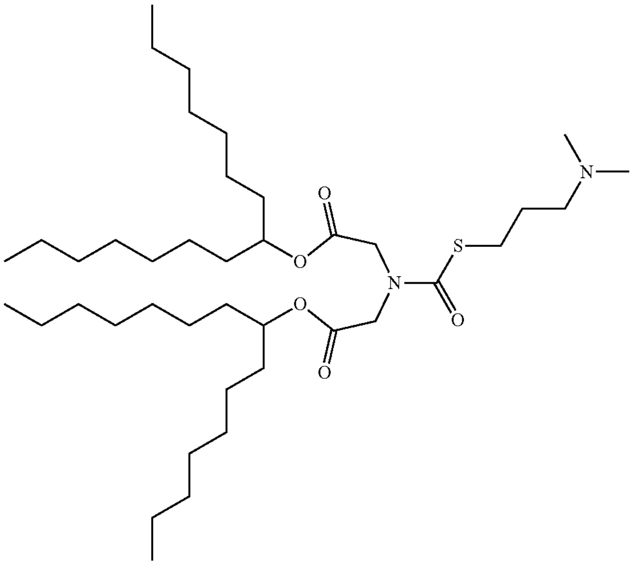 [SMILES: CCCCCCCC(CCCCCCC)OC(=O)CN(CC(=O)OC(CCCCCCC)CCCCCCC)C(=O)SCCCN(C)C] | 0132 |
| 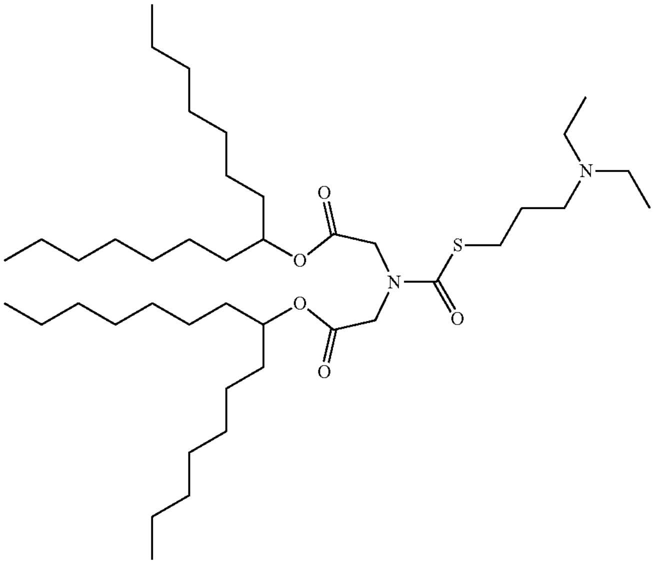 [SMILES: CCCCCCCC(CCCCCCC)OC(=O)CN(CC(=O)OC(CCCCCCC)CCCCCCC)C(=O)SCCCN(CC)CC] | 0134 |

TABLE 14-continued
| Compound | ATX-# |
|---|---|
| 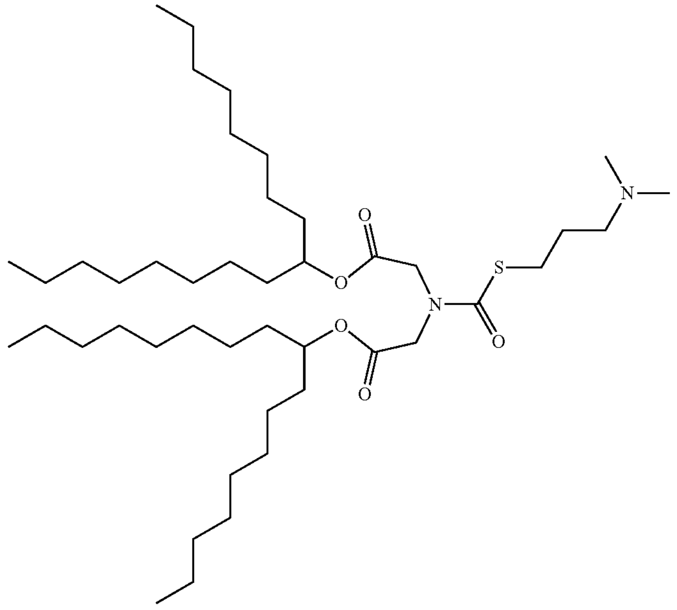 [SMILES: CCCCCCCCC(CCCCCCCC)OC(=O)CN(CC(=O)OC(CCCCCCCC)CCCCCCCC)C(=O)SCCCN(C)C] | 0133 |
| 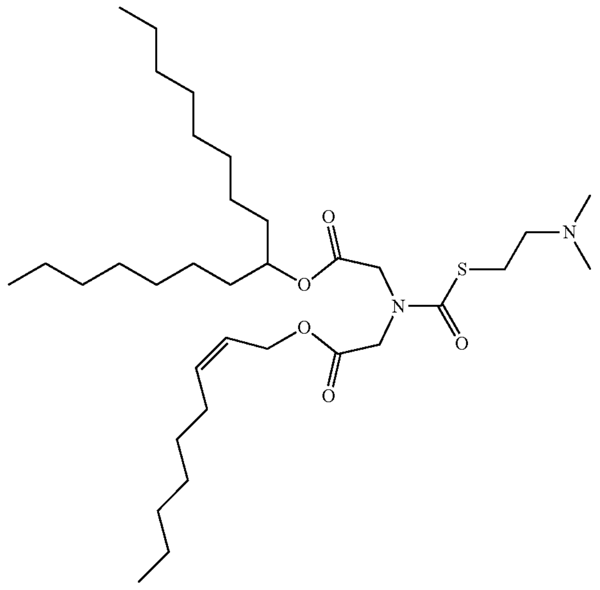 [SMILES: CCCCCC/C=C\COC(=O)CN(CC(=O)OC(CCCCCCC)CCCCCCCC)C(=O)SCCN(C)C] | 0064 |

TABLE 14-continued
| Compound | ATX-# |
|---|---|
| 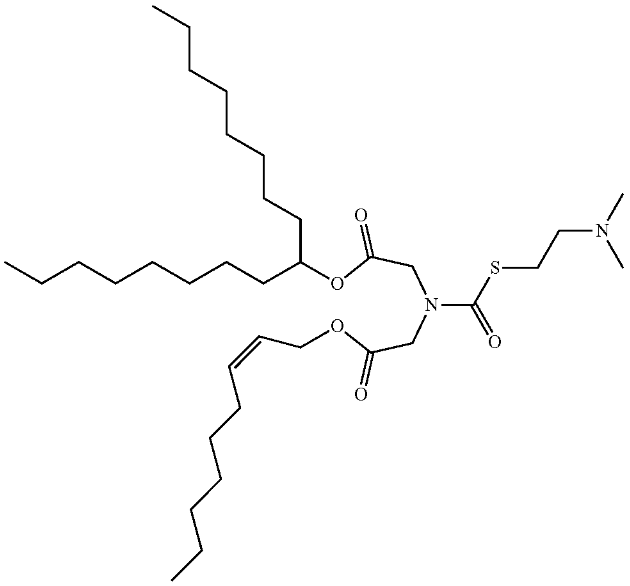 [SMILES: CCCCCC/C=C\COC(=O)CN(CC(=O)OC(CCCCCCCC)CCCCCCCC)C(=O)SCCN(C)C] | 0061 |
| 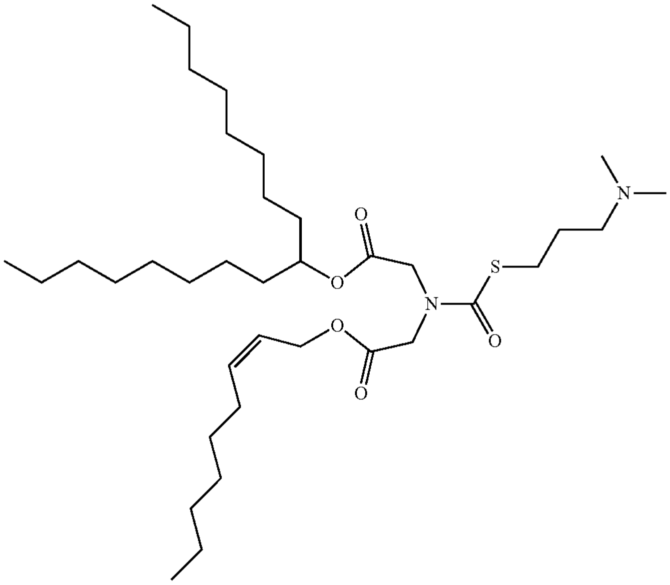 [SMILES: CCCCCC/C=C\COC(=O)CN(CC(=O)OC(CCCCCCCC)CCCCCCCC)C(=O)SCCCN(C)C] | 0100 |

TABLE 14-continued
| Compound | ATX-# |
| --- | --- |
| 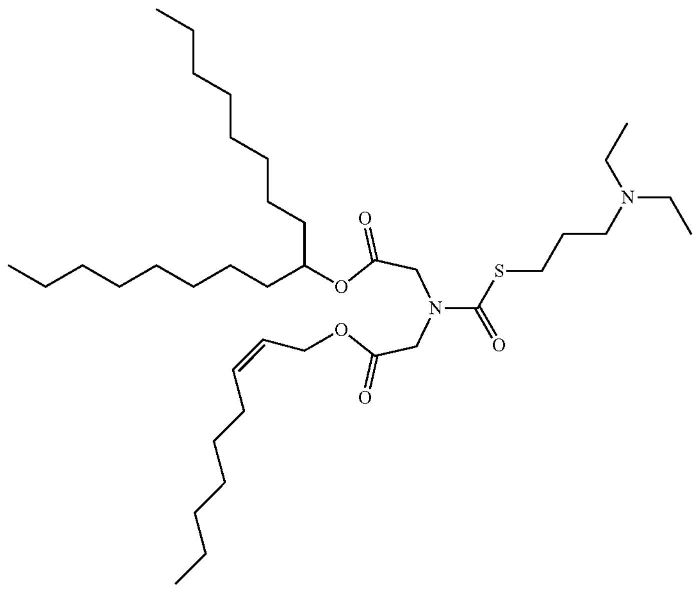 [SMILES: CCCCCC/C=C\COC(=O)CN(CC(=O)OC(CCCCCCCC)CCCCCCCC)C(=O)SCCCN(CC)CC] | 0117 |
| 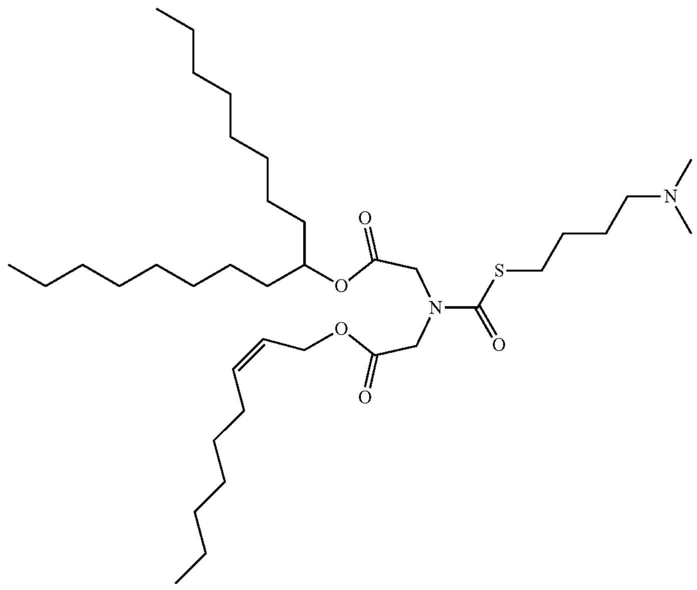 [SMILES: CCCCCC/C=C\COC(=O)CN(CC(=O)OC(CCCCCCCC)CCCCCCCC)C(=O)SCCCCN(C)C] | 0114 |

TABLE 14-continued
| Compound | ATX-# |
|---|---|
| 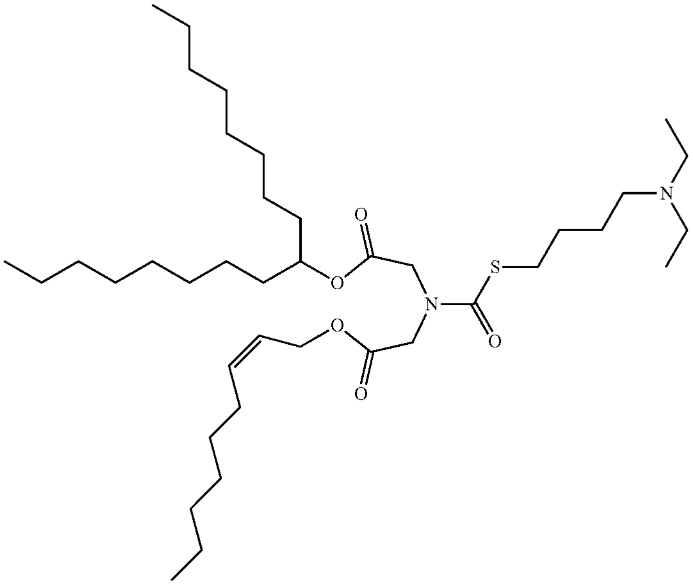 [SMILES: CCCCCC/C=C\COC(=O)CN(CC(=O)OC(CCCCCCCC)CCCCCCCC)C(=O)SCCCCN(CC)CC] | 0115 |
| 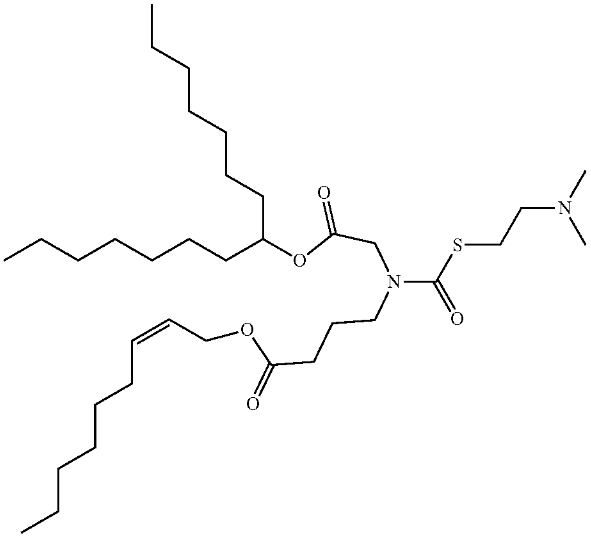 [SMILES: CCCCCC/C=C\COC(=O)CCCN(CC(=O)OC(CCCCCCC)CCCCCCC)C(=O)SCCN(C)C] | 0101 |
| 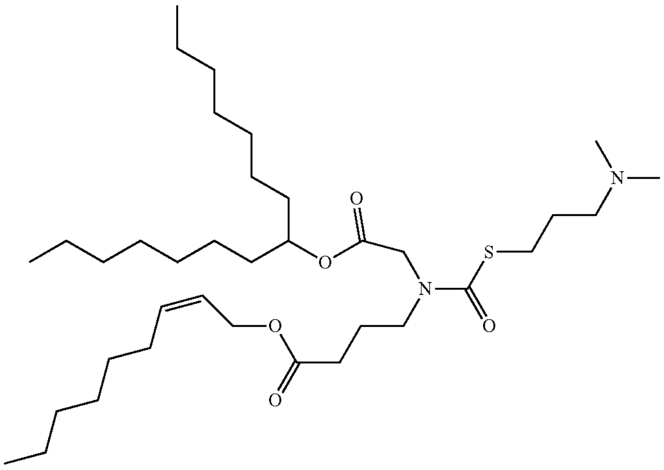 [SMILES: CCCCCC/C=C\COC(=O)CCCN(CC(=O)OC(CCCCCCC)CCCCCCC)C(=O)SCCCN(C)C] | 0106 |

TABLE 14-continued
| Compound | ATX-# |
| --- | --- |
| 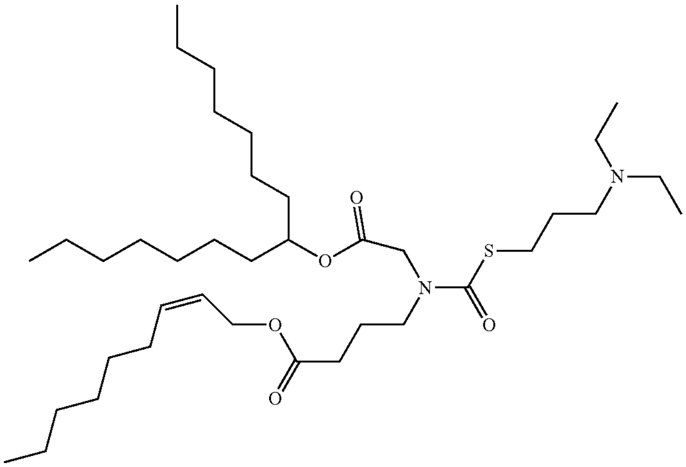 [SMILES: CCCCCC/C=C\COC(=O)CCCN(CC(=O)OC(CCCCCCC)CCCCCCC)C(=O)SCCCN(CC)CC] | 0116 |
| 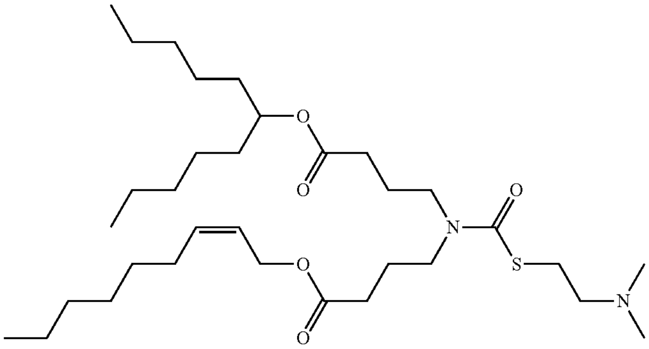 [SMILES: CCCCCC/C=C\COC(=O)CCCN(CCCC(=O)OC(CCCCC)CCCCC)C(=O)SCCN(C)C] | 0043 |
| 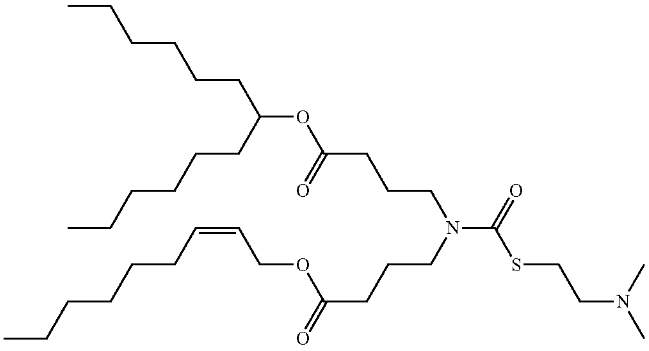 [SMILES: CCCCCC/C=C\COC(=O)CCCN(CCCC(=O)OC(CCCCCC)CCCCCC)C(=O)SCCN(C)C] | 0086 |
| 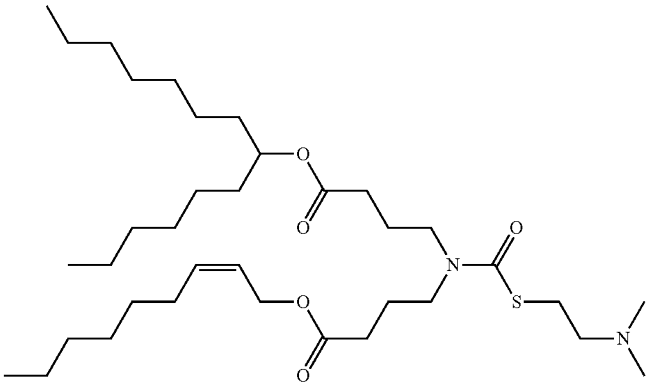 [SMILES: CCCCCC/C=C\COC(=O)CCCN(CCCC(=O)OC(CCCCCC)CCCCCCC)C(=O)SCCN(C)C] | 0058 |

TABLE 14-continued
| Compound | ATX-# |
|---|---|
| 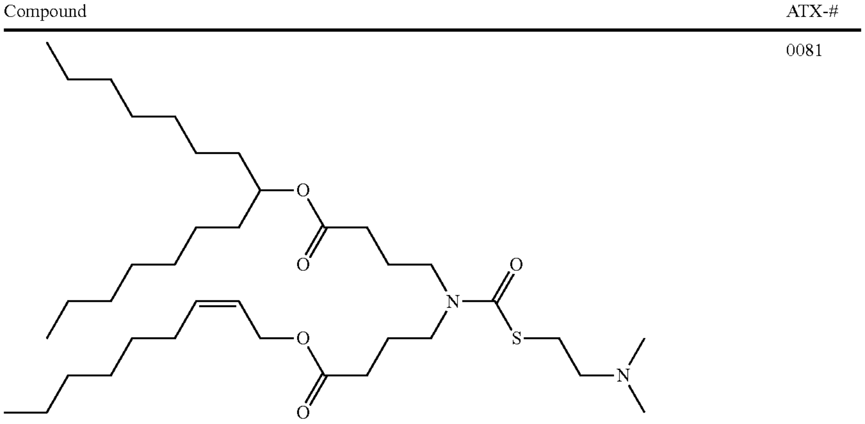 | 0081 |
| 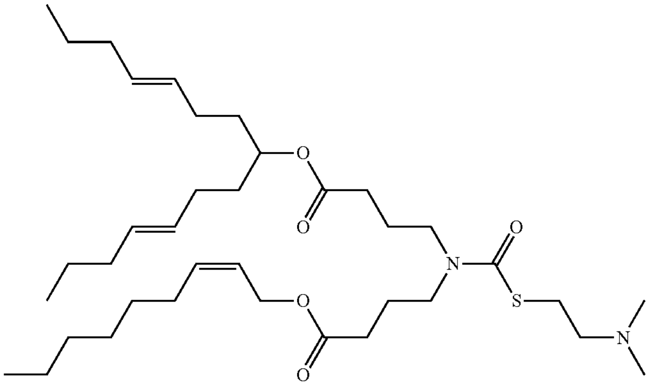 [SMILES: CCC/C=C/CCC(CC/C=C/CCC)OC(=O)CCCN(CCCC(=O)OC/C=C\CCCCCC)C(=O)SCCN(C)C] | 0123 |
| 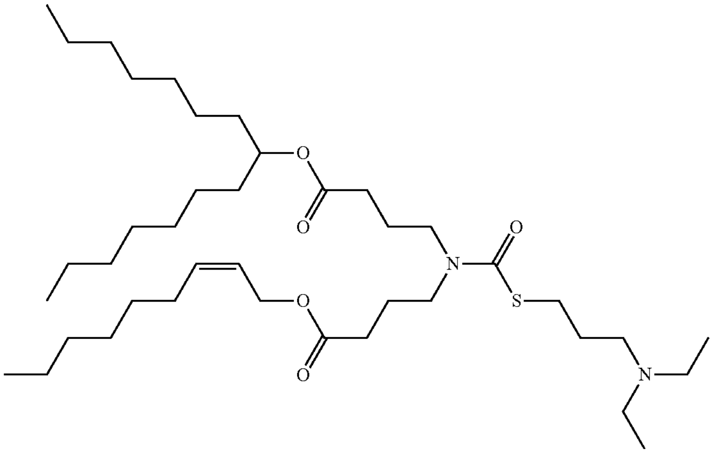 [SMILES: CCCCCC/C=C\COC(=O)CCCN(CCCC(=O)OC(CCCCCCC)CCCCCCCC)C(=O)SCCCN(CC)CC] | 0122 |
| 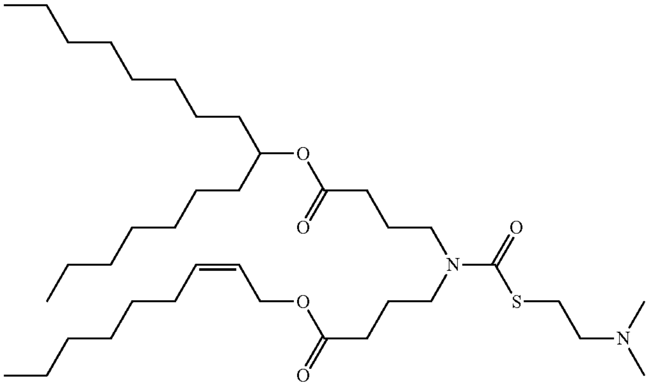 | 0057 |

TABLE 14-continued
| Compound | ATX-# |
| --- | --- |
| 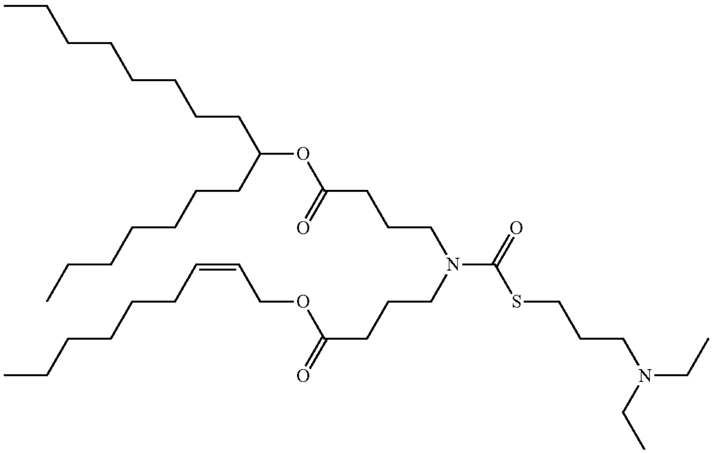 | 0088 |
| 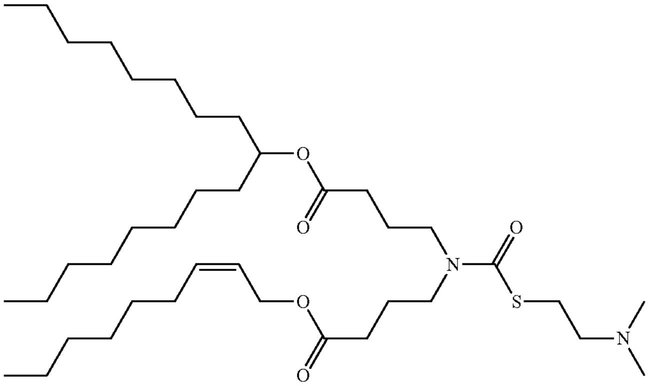 [SMILES: CCCCCC/C=C\COC(=O)CCCN(CCCC(=O)OC(CCCCCCCC)CCCCCCCC)C(=O)SCCN(C)C] | 0087 |
| 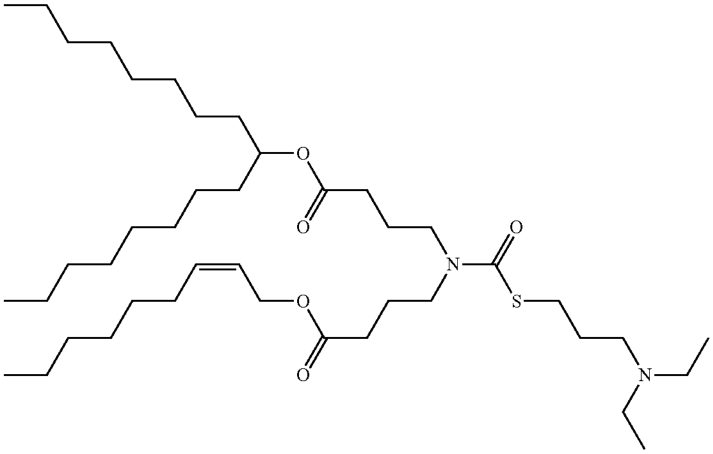 [SMILES: CCCCCC/C=C\COC(=O)CCCN(CCCC(=O)OC(CCCCCCCC)CCCCCCCC)C(=O)SCCCN(CC)CC] | 0124 |

TABLE 14-continued
| Compound | ATX-# |
| --- | --- |
| 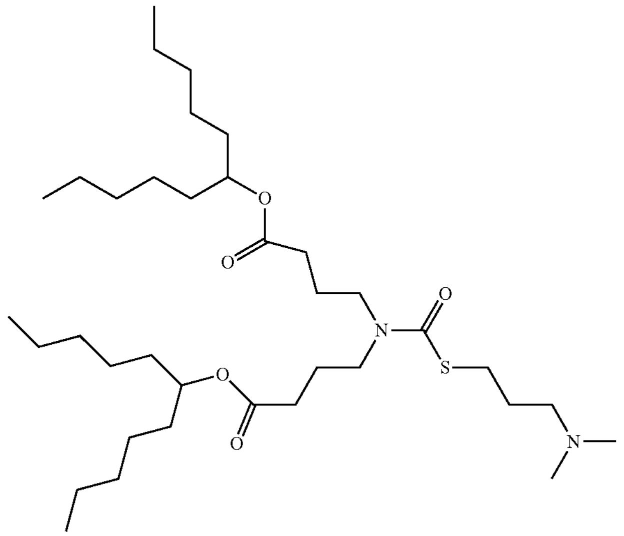 [SMILES: CCCCCC(CCCCC)OC(=O)CCCN(CCCC(=O)OC(CCCCC)CCCCC)C(=O)SCCCN(C)C] | 0128 |
| 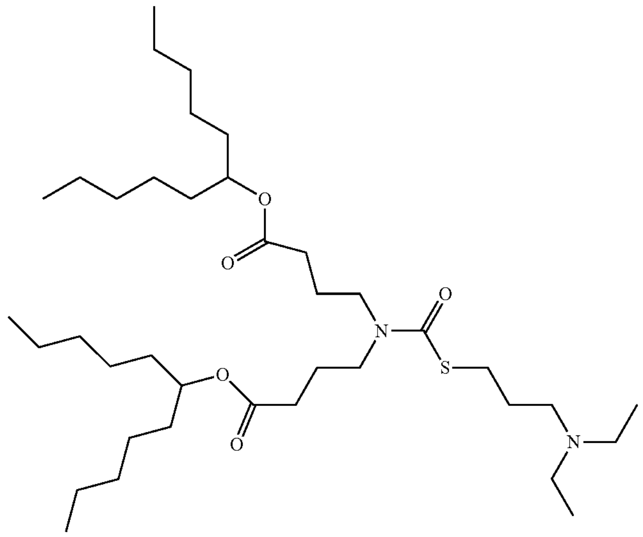 [SMILES: CCCCCC(CCCCC)OC(=O)CCCN(CCCC(=O)OC(CCCCC)CCCCC)C(=O)SCCCN(CC)CC] | 0127 |

TABLE 14-continued
| Compound | ATX-# |
| --- | --- |
| 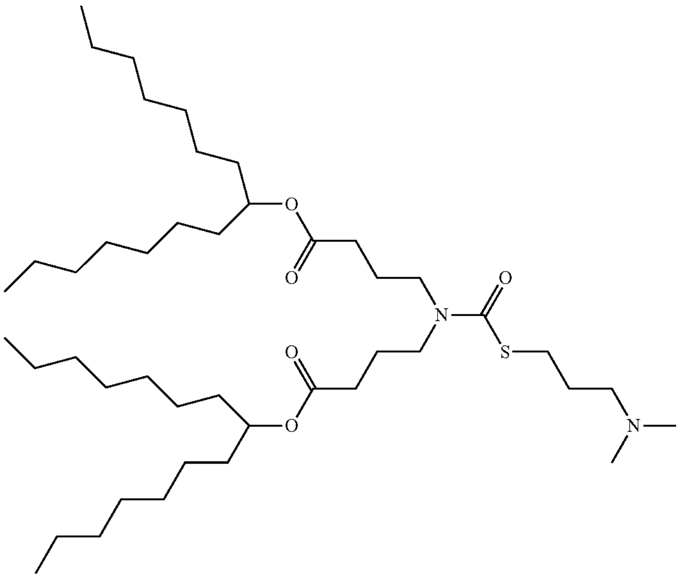 [SMILES: CCCCCCCC(CCCCCCC)OC(=O)CCCN(CCCC(=O)OC(CCCCCCC)CCCCCCC)C(=O)SCCCN(C)C] | 0126 |
| 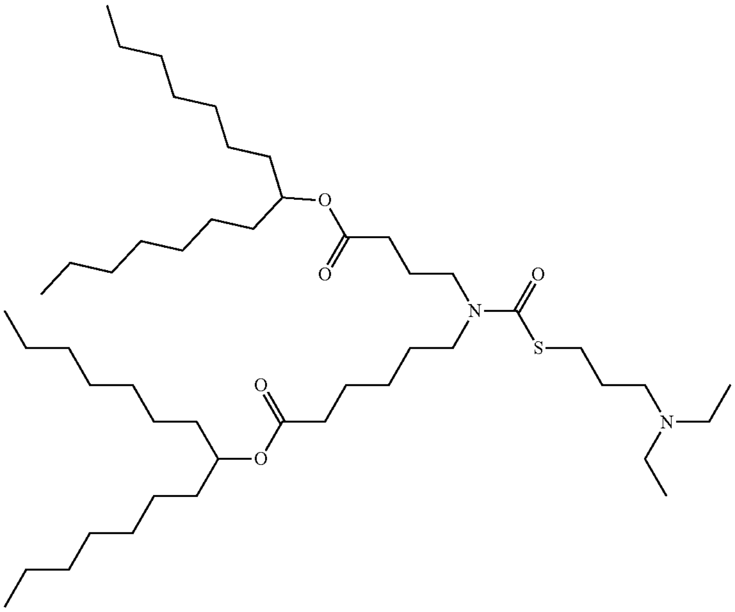 [SMILES: CCCCCCCC(CCCCCCC)OC(=O)CCCCCN(CCCC(=O)OC(CCCCCCC)CCCCCCC)C(=O)SCCCN(CC)CC] | 0129 |

TABLE 14-continued
| Compound | ATX-# |
|---|---|
| 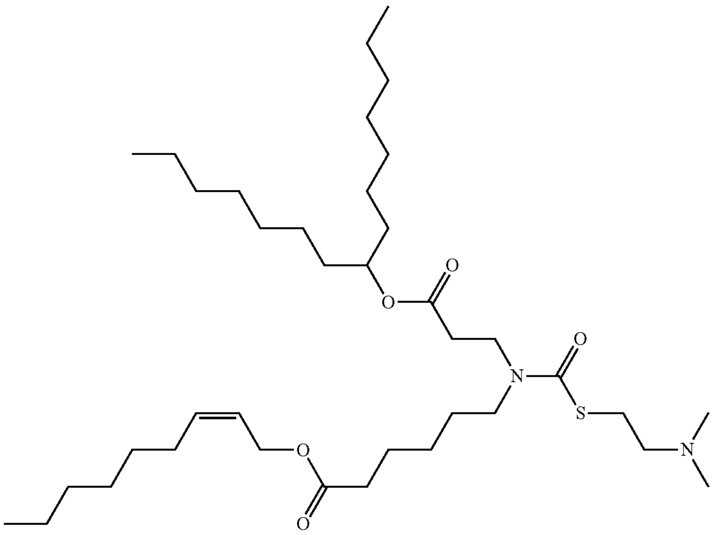 [SMILES: CCCCCC/C=C\COC(=O)CCCCCN(CCC(=O)OC(CCCCCCC)CCCCCCC)C(=O)SCCN(C)C] | 0082 |
| 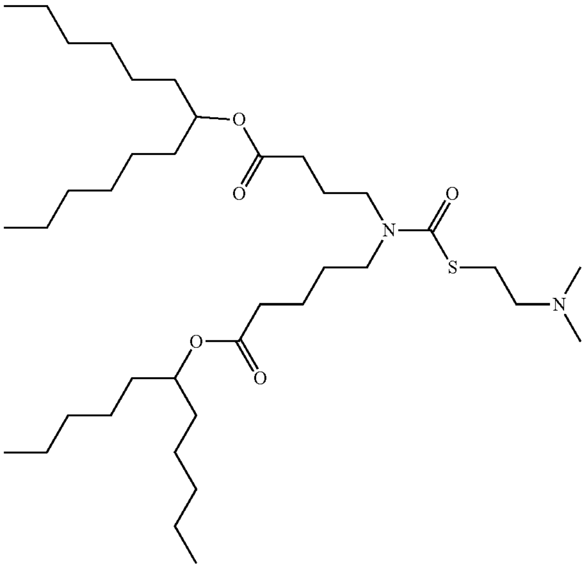 [SMILES: CCCCCCC(CCCCCC)OC(=O)CCCN(CCCCC(=O)OC(CCCCC)CCCCC)C(=O)SCCN(C)C] | 0085 |
| 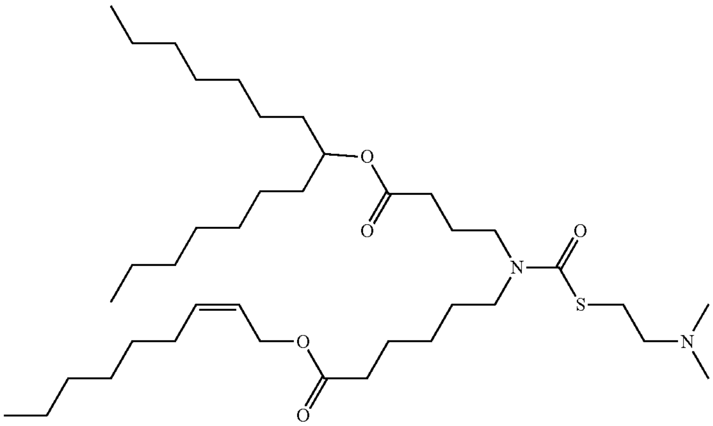 [SMILES: CCCCCC/C=C\COC(=O)CCCCCN(CCCC(=O)OC(CCCCCCC)CCCCCCC)C(=O)SCCN(C)C] | 0083 |

TABLE 14-continued
| Compound | ATX-# |
| --- | --- |
| 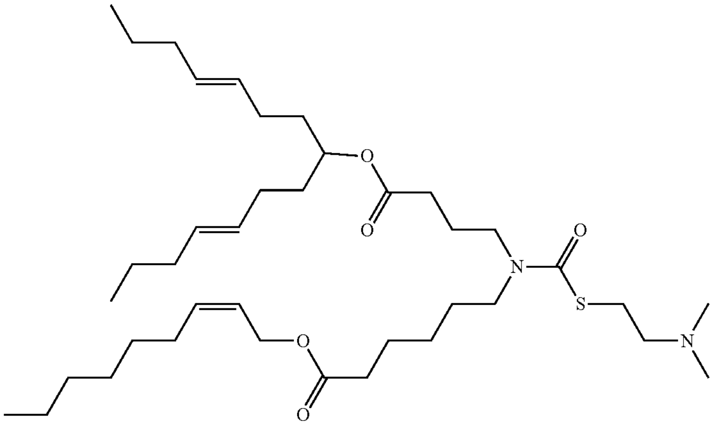 [SMILES: CCC/C=C/CCC(CC/C=C/CCC)OC(=O)CCCN(CCCCCC(=O)OC/C=C\CCCCCC)C(=O)SCCN(C)C] | 0121 |
| 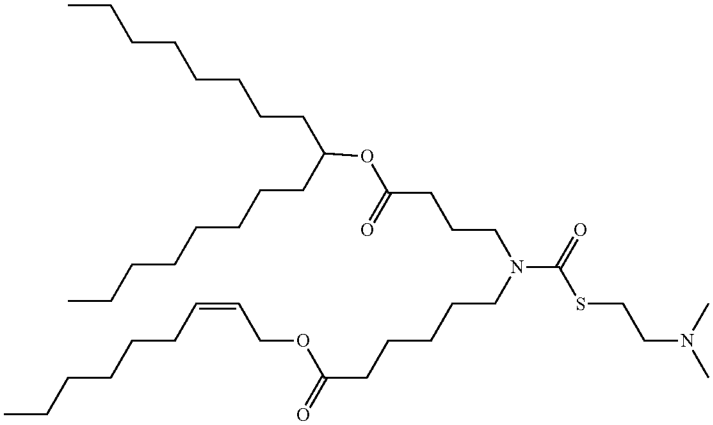 [SMILES: CCCCCC/C=C\COC(=O)CCCCCN(CCCC(=O)OC(CCCCCCCC)CCCCCCCC)C(=O)SCCN(C)C] | 0091 |
| 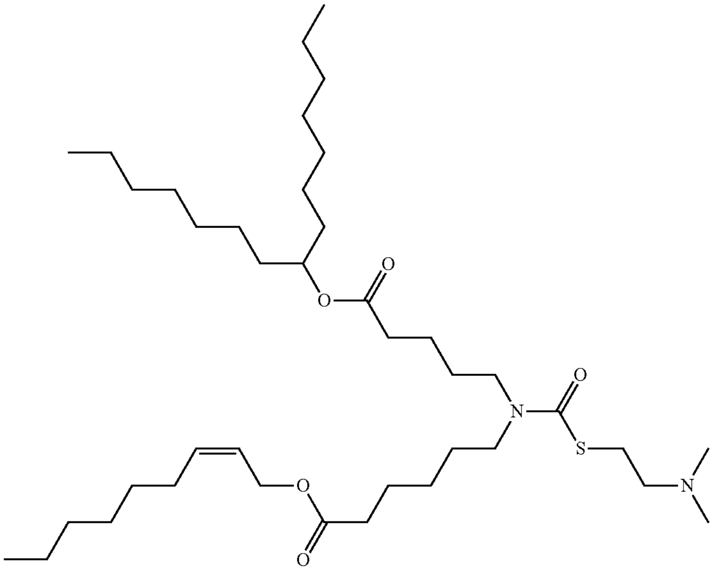 [SMILES: CCCCCC/C=C\COC(=O)CCCCCN(CCCCC(=O)OC(CCCCCCC)CCCCCCC)C(=O)SCCN(C)C] | 0102 |

TABLE 14-continued
| Compound | ATX-# |
|---|---|
| 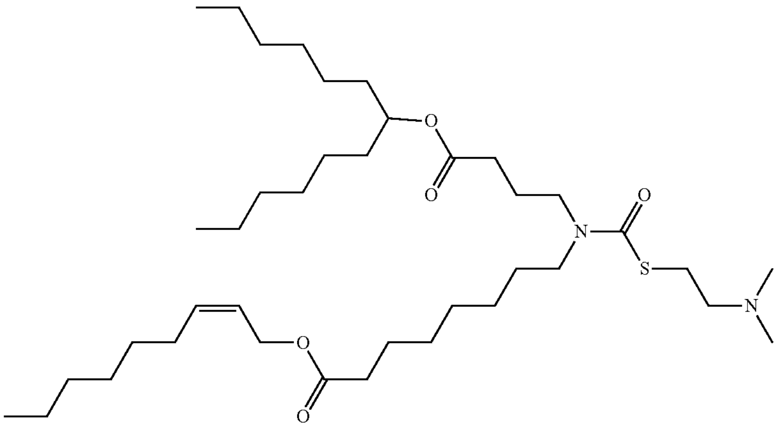 [SMILES: CCCCCC/C=C\COC(=O)CCCCCCCN(CCCC(=O)OC(CCCCCC)CCCCCC)C(=O)SCCN(C)C] | 0098 |
| 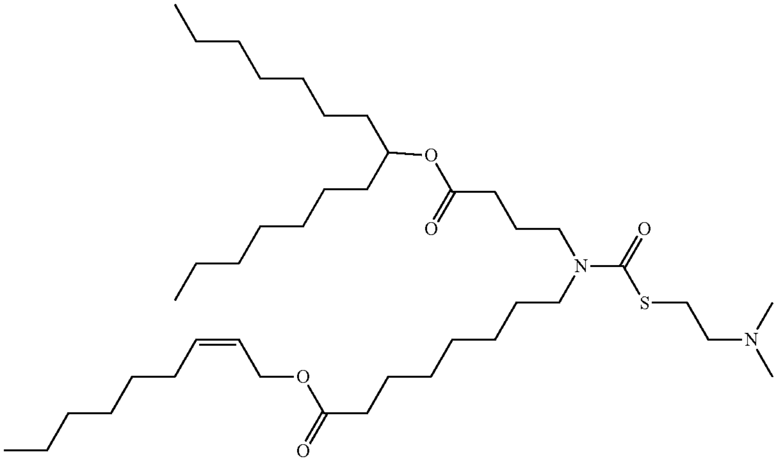 [SMILES: CCCCCC/C=C\COC(=O)CCCCCCCN(CCCC(=O)OC(CCCCCCC)CCCCCCC)C(=O)SCCN(C)C] | 0092 |
| 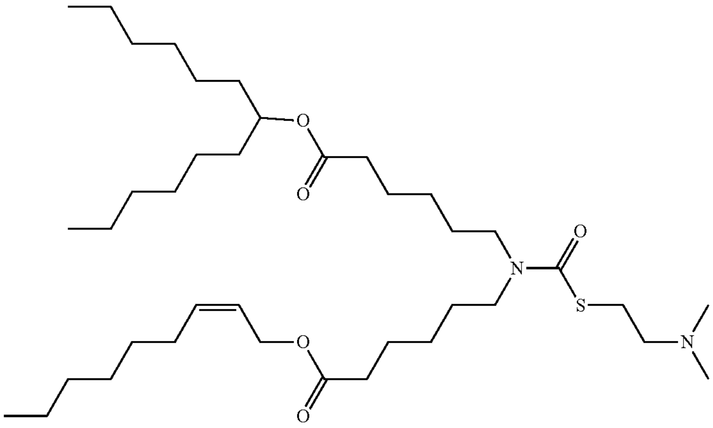 [SMILES: CCCCCC/C=C\COC(=O)CCCCCN(CCCCCC(=O)OC(CCCCCC)CCCCCC)C(=O)SCCN(C)C] | 0084 |

TABLE 14-continued
| Compound | ATX-# |
|---|---|
| 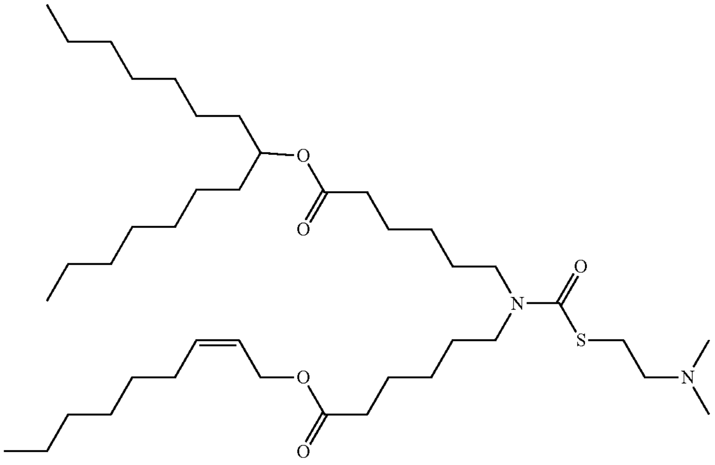 [SMILES: CCCCCC/C=C\COC(=O)CCCCCN(CCCCCC(=O)OC(CCCCCCC)CCCCCCC)C(=O)SCCN(C)C] | 0095 |
| 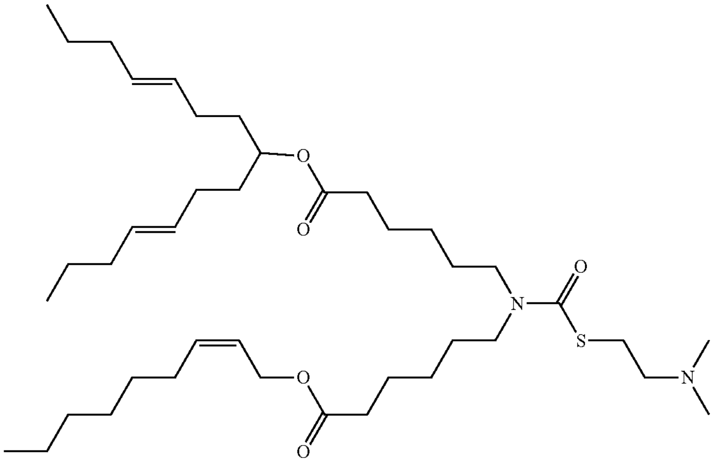 [SMILES: CCC/C=C/CCC(CC/C=C/CCC)OC(=O)CCCCCN(CCCCCC(=O)OC/C=C\CCCCCC)C(=O)SCCN(C)C] | 0125 |
| 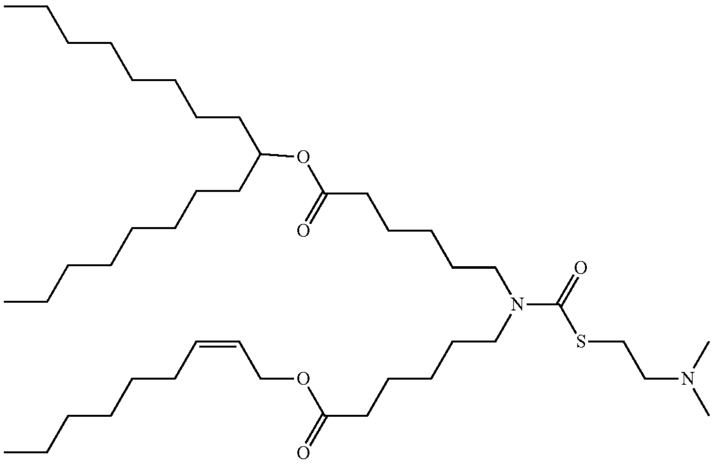 [SMILES: CCCCCC/C=C\COC(=O)CCCCCN(CCCCCC(=O)OC(CCCCCCCC)CCCCCCCC)C(=O)SCCN(C)C] | 0094 |

TABLE 14-continued
| Compound | ATX-# |
| --- | --- |
| 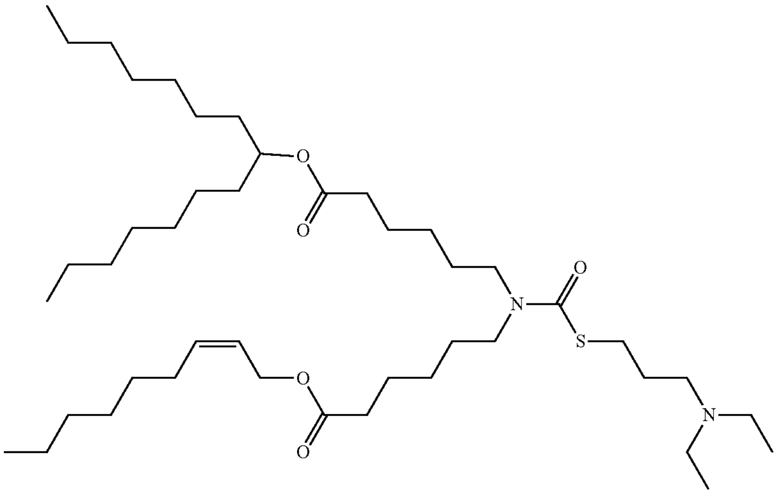 [SMILES: CCCCCC/C=C\COC(=O)CCCCCN(CCCCCC(=O)OC(CCCCCCC)CCCCCCC)C(=O)SCCCN(CC)CC] | 0109 |
| 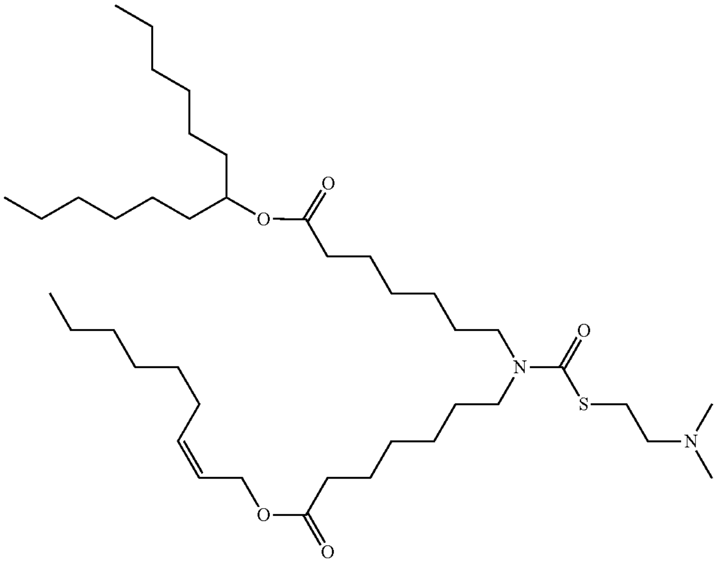 [SMILES: CCCCCC/C=C\COC(=O)CCCCCCN(CCCCCCC(=O)OC(CCCCCC)CCCCCC)C(=O)SCCN(C)C] | 0110 |

TABLE 14-continued
| Compound | ATX-# |
|---|---|
| 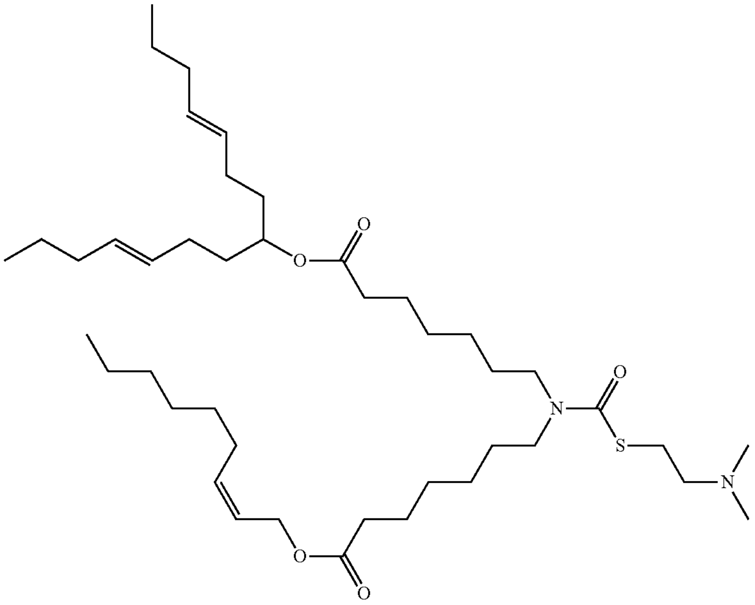 [SMILES: CCC/C=C/CCC(CC/C=C/CCC)OC(=O)CCCCCCN(CCCCCCC(=O)OC/C=C\CCCCCC)C(=O)SCCN(C)C] | 0118 |
| 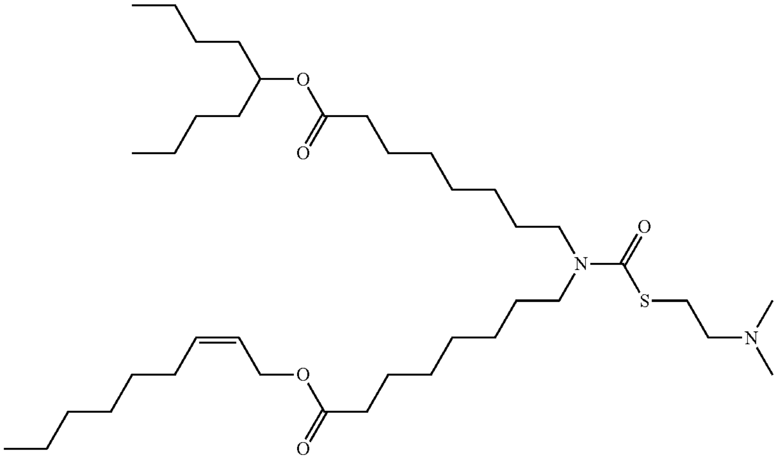 [SMILES: CCCCCC/C=C\COC(=O)CCCCCCCN(CCCCCCCC(=O)OC(CCCC)CCCC)C(=O)SCCN(C)C] | 0108 |
| 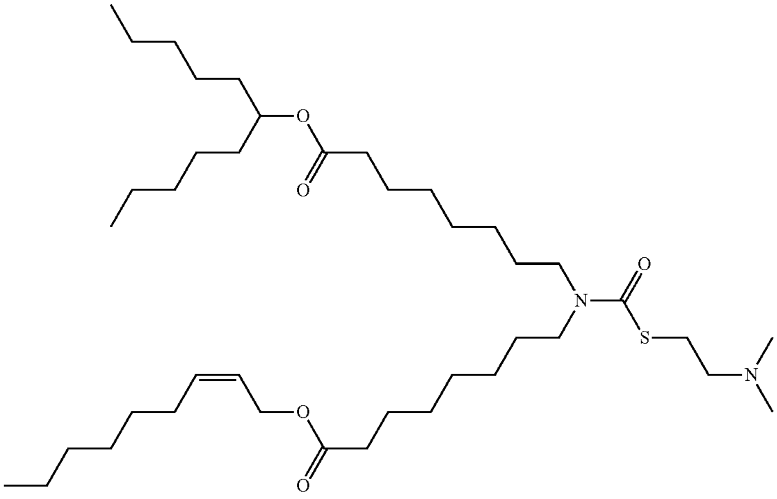 [SMILES: CCCCCC/C=C\COC(=O)CCCCCCCN(CCCCCCCC(=O)OC(CCCCC)CCCCC)C(=O)SCCN(C)C] | 0107 |

TABLE 14-continued
| Compound | ATX-# |
| --- | --- |
| 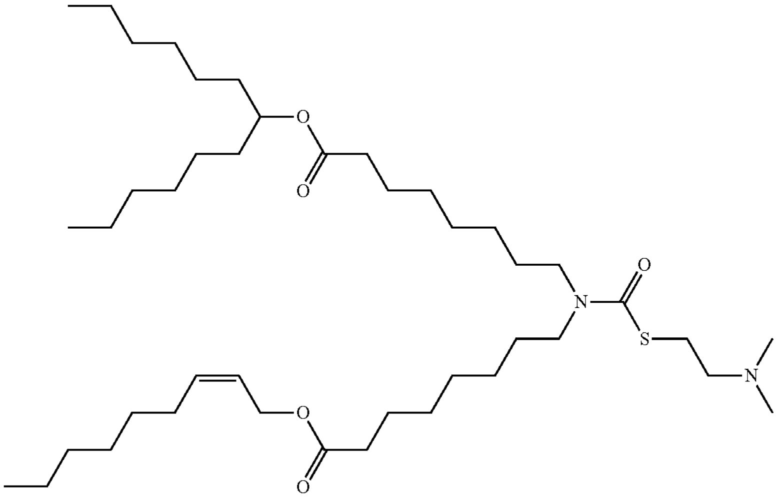 [SMILES: CCCCCC/C=C\COC(=O)CCCCCCCN(CCCCCCCC(=O)OC(CCCCCC)CCCCCC)C(=O)SCCN(C)C] | 0093 |
| 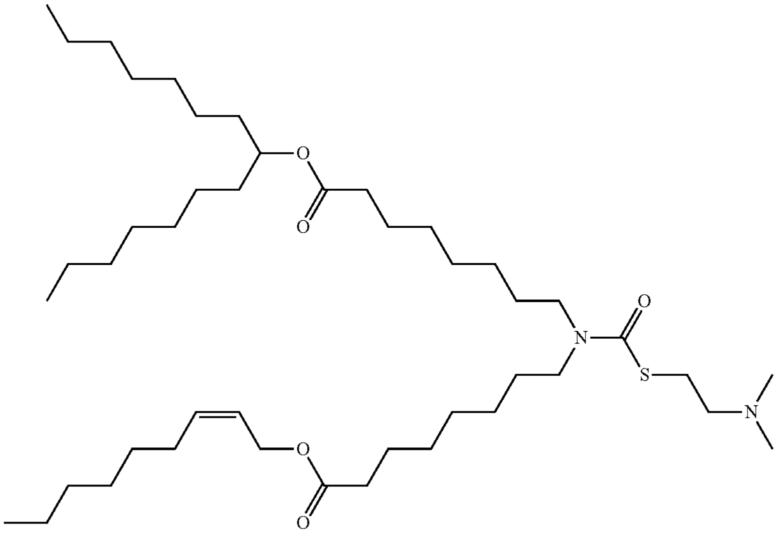 [SMILES: CCCCCC/C=C\COC(=O)CCCCCCCN(CCCCCCCC(=O)OC(CCCCCCC)CCCCCCC)C(=O)SCCN(C)C] | 0097 |
| 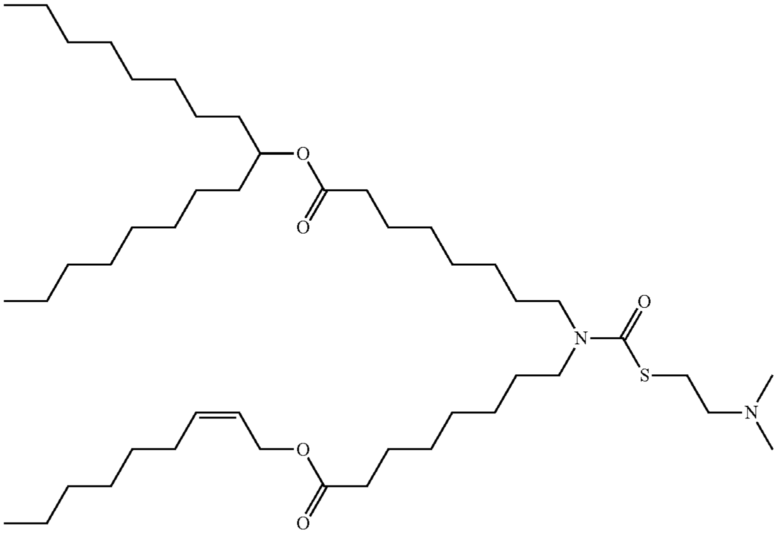 [SMILES: CCCCCC/C=C\COC(=O)CCCCCCCN(CCCCCCCC(=O)OC(CCCCCCCC)CCCCCCCC)C(=O)SCCN(C)C] | 0096 |

TABLE 15
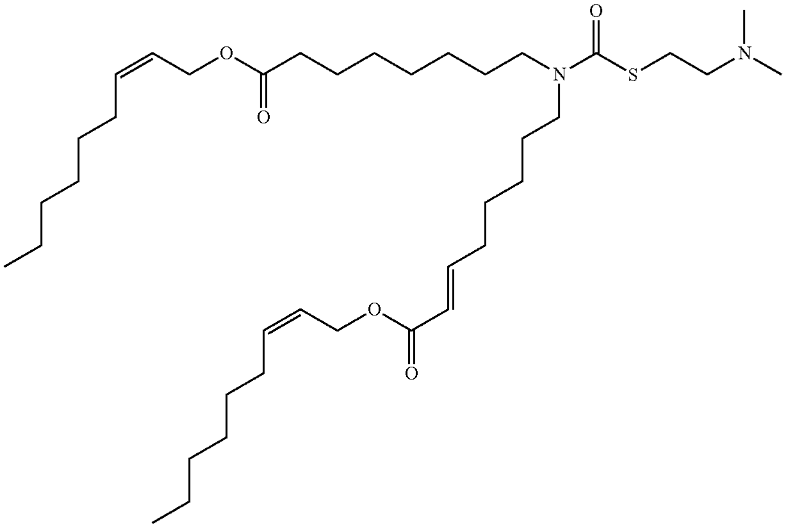 [SMILES: CCCCCC/C=C\COC(=O)/C=C/CCCCCN(CCCCCCCC(=O)OC/C=C\CCCCCC)C(=O)SCCN(C)C]
11
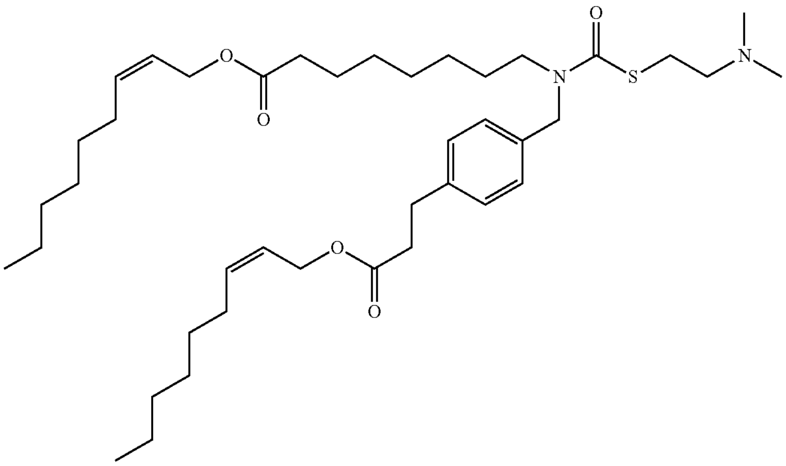 [SMILES: CCCCCC/C=C\COC(=O)CCCCCCCN(Cc1ccc(CCC(=O)OC/C=C\CCCCCC)cc1)C(=O)SCCN(C)C]
13
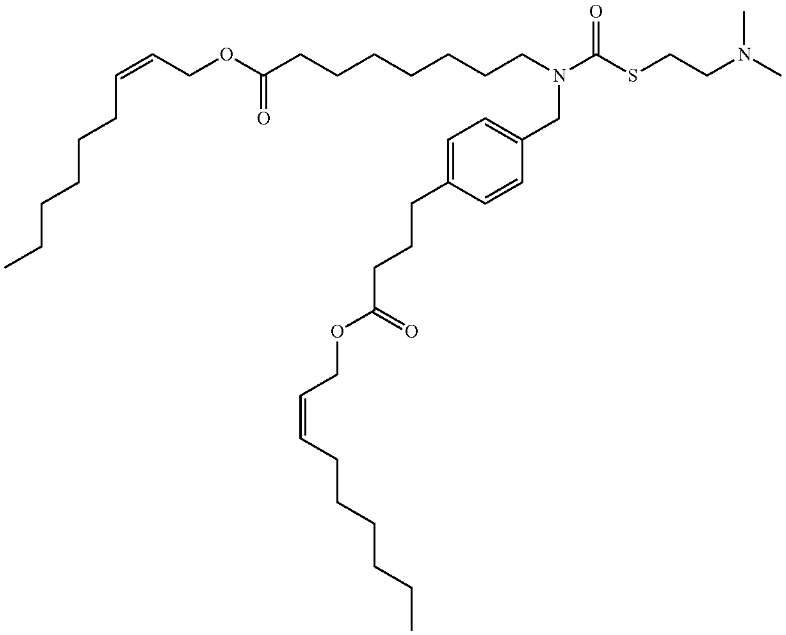 [SMILES: CCCCCC/C=C\COC(=O)CCCCCCCN(Cc1ccc(CCCC(=O)OC/C=C\CCCCCC)cc1)C(=O)SCCN(C)C]
14

TABLE 15-continued
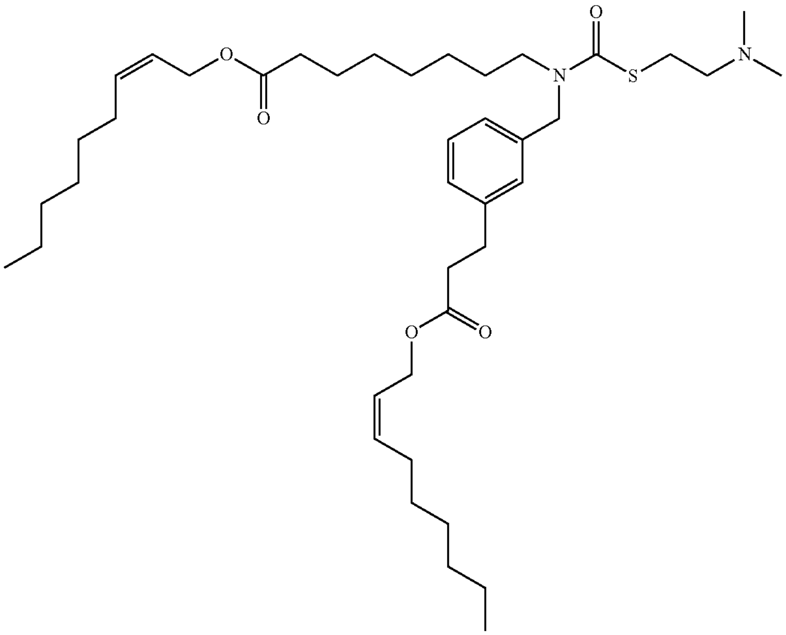 [SMILES: CCCCCC/C=C\COC(=O)CCCCCCCN(Cc1cccc(CCC(=O)OC/C=C\CCCCCC)c1)C(=O)SCCN(C)C]
15
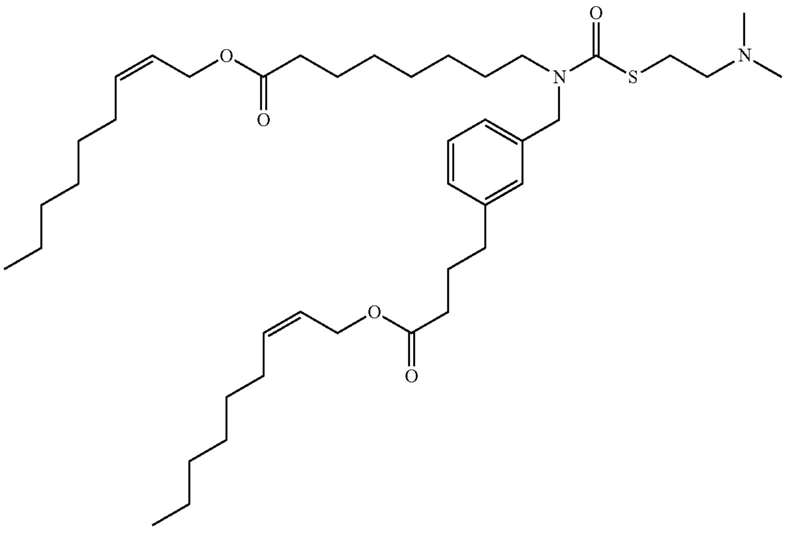 [SMILES: CCCCCC/C=C\COC(=O)CCCCCCCN(Cc1cccc(CCCC(=O)OC/C=C\CCCCCC)c1)C(=O)SCCN(C)C]
16
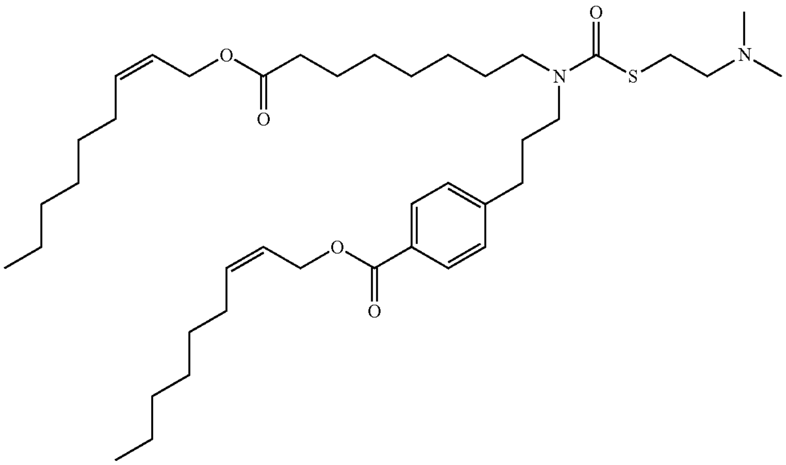 [SMILES: CCCCCC/C=C\COC(=O)CCCCCCCN(CCCc1ccc(C(=O)OC/C=C\CCCCCC)cc1)C(=O)SCCN(C)C]
17

TABLE 15-continued
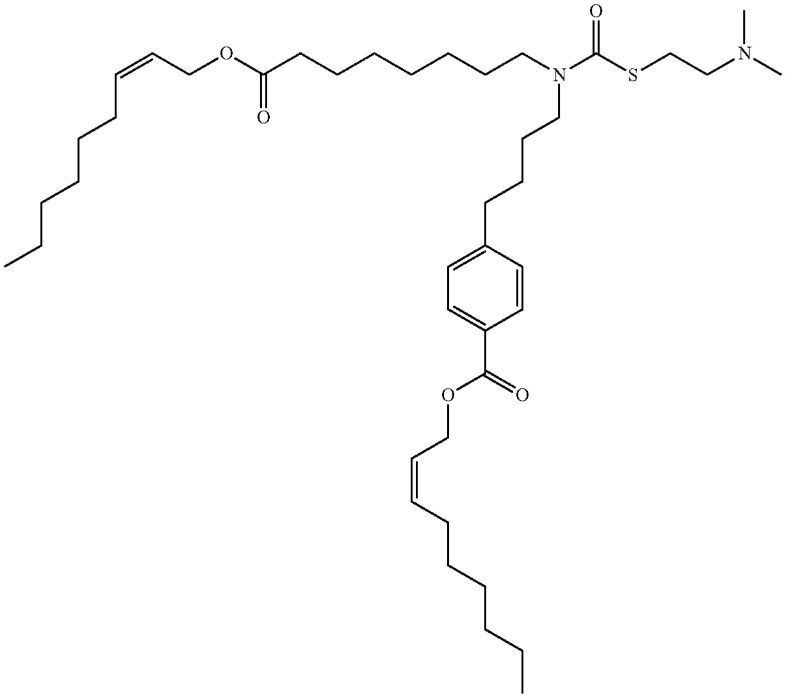 [SMILES: CCCCCC/C=C\COC(=O)CCCCCCCN(CCCCc1ccc(C(=O)OC/C=C\CCCCCC)cc1)C(=O)SCCN(C)C]
18
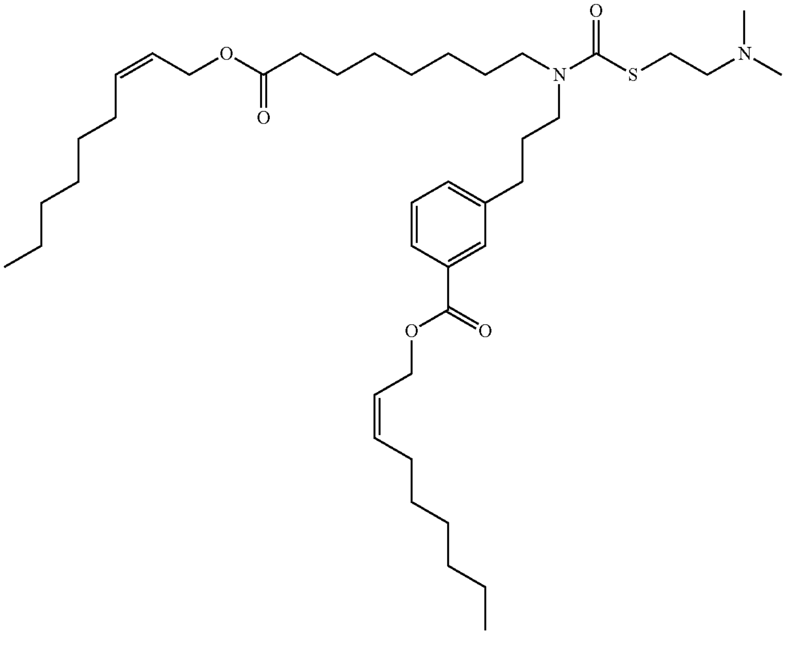 [SMILES: CCCCCC/C=C\COC(=O)CCCCCCCN(CCCc1cccc(C(=O)OC/C=C\CCCCCC)c1)C(=O)SCCN(C)C]
19

TABLE 15-continued
| |
|---|
| 20 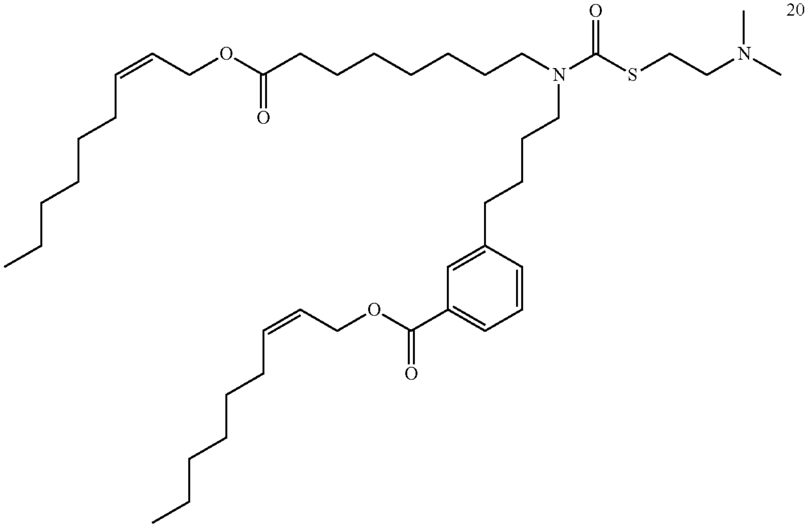 |
In some embodiments, an ionizable lipid is described in international patent application PCT/US2019/015913. In some embodiments, an ionizable lipid is chosen from the following:
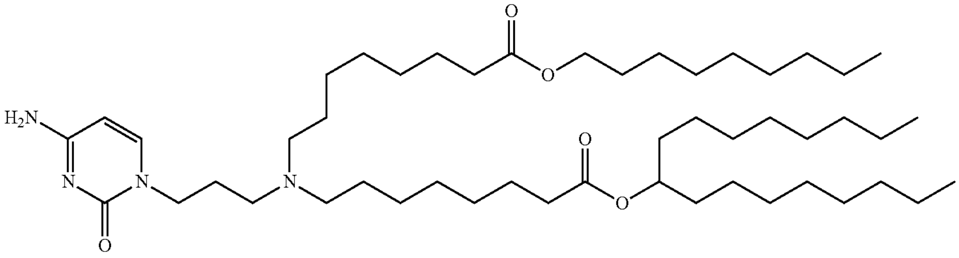
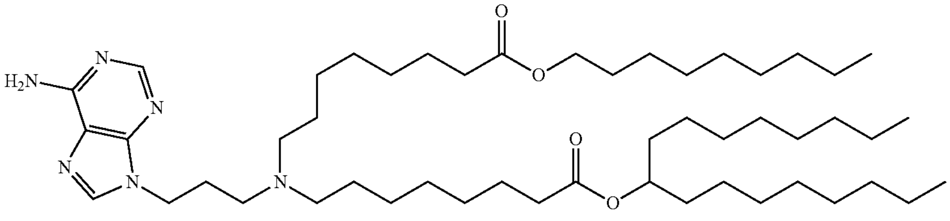
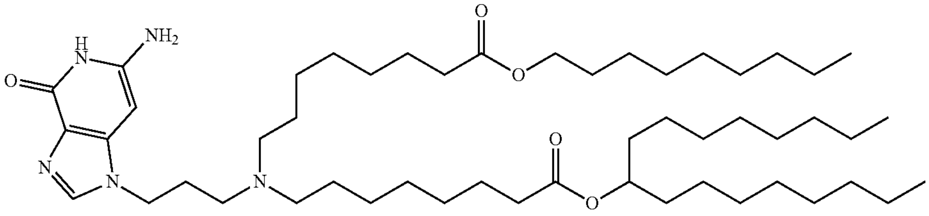
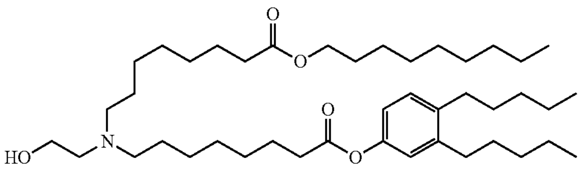
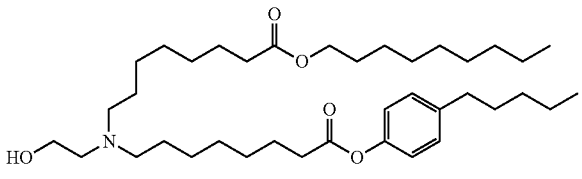

-continued
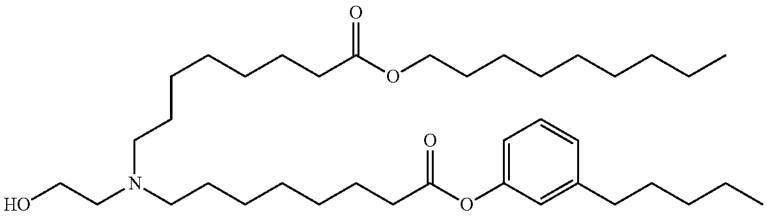
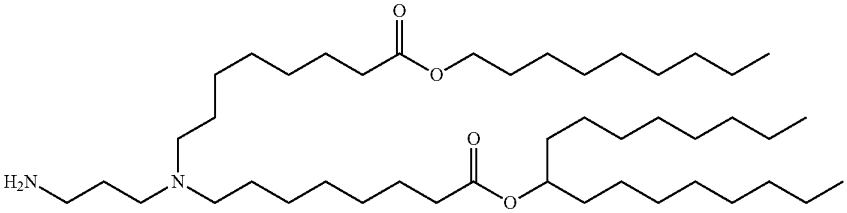
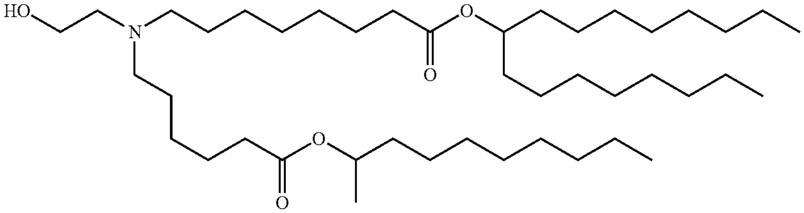
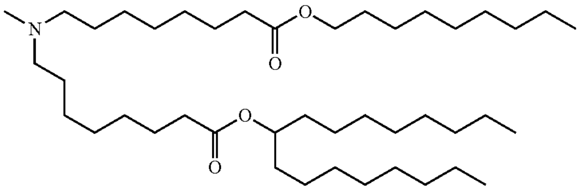
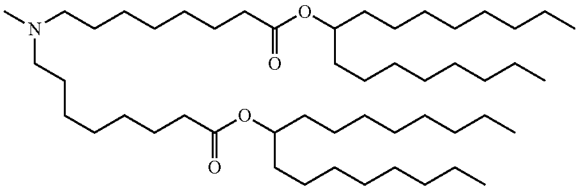
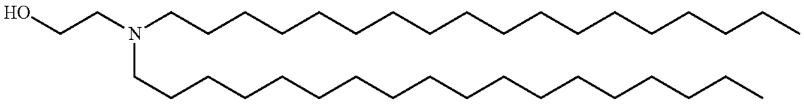
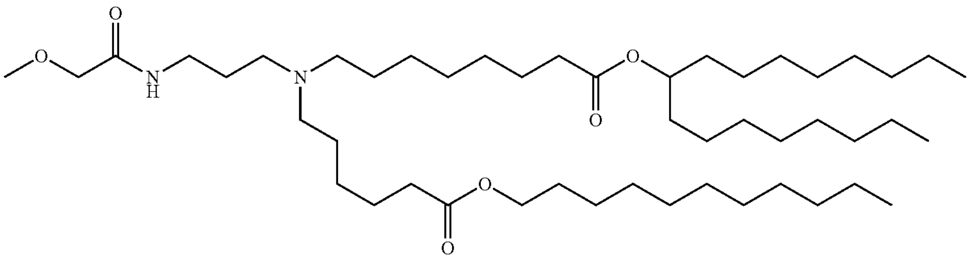
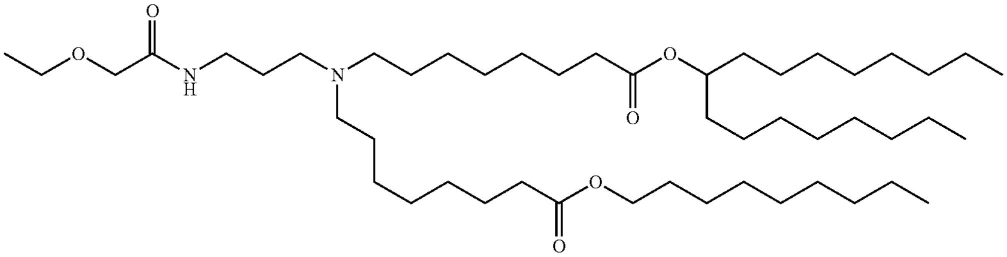

-continued
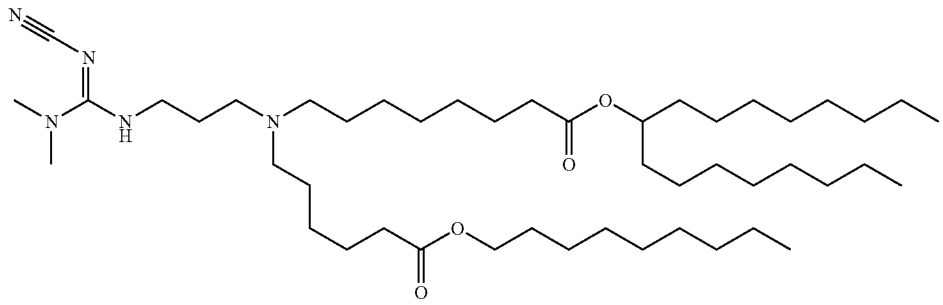
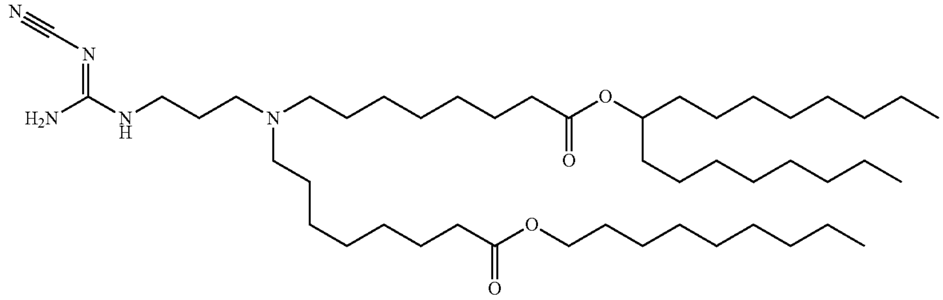
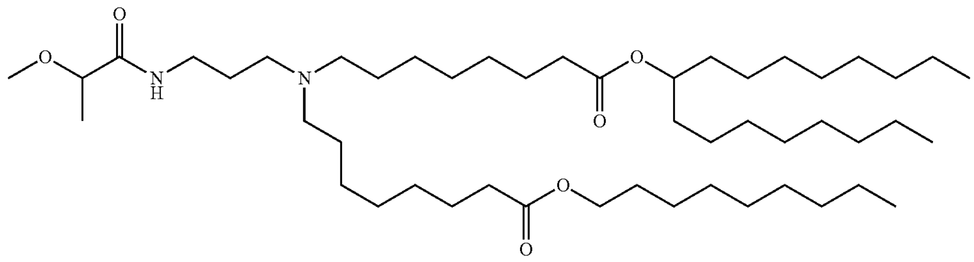
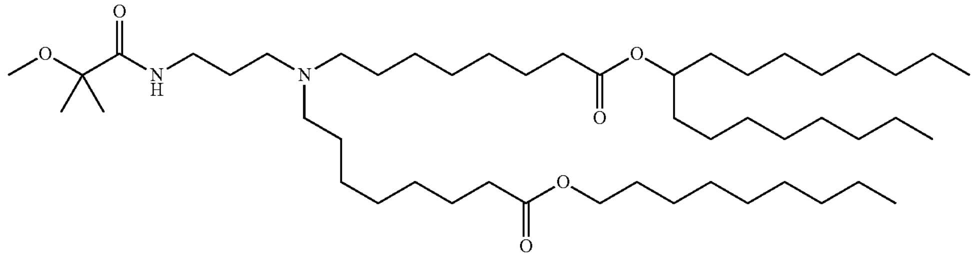
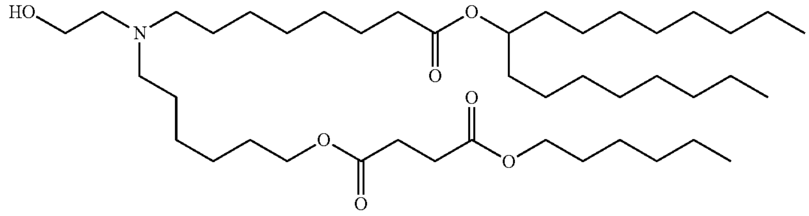
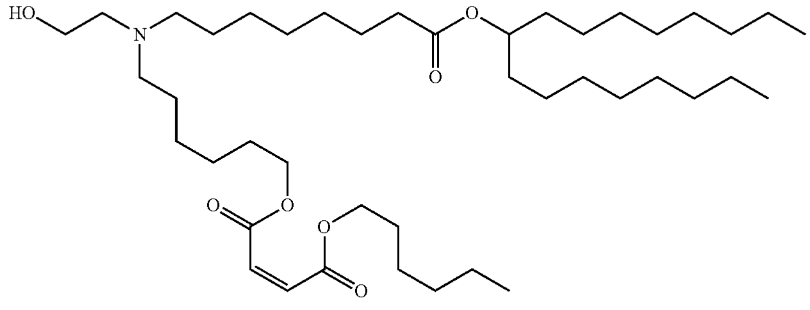

-continued
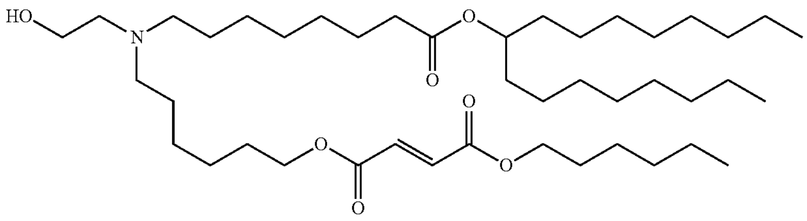
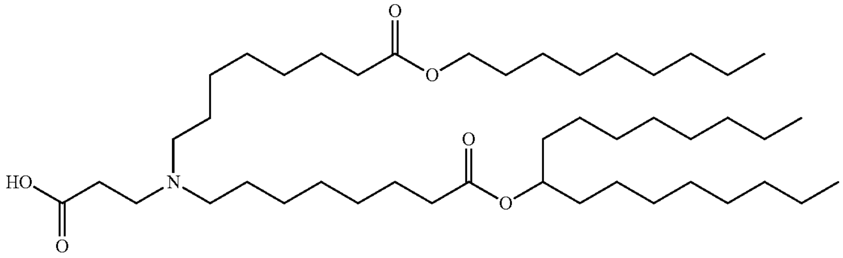
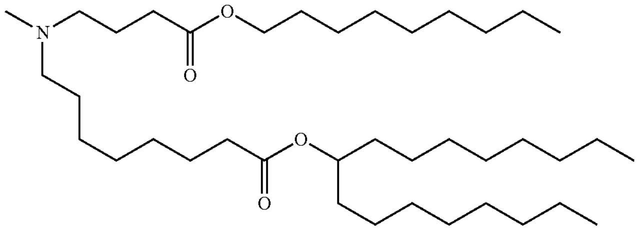
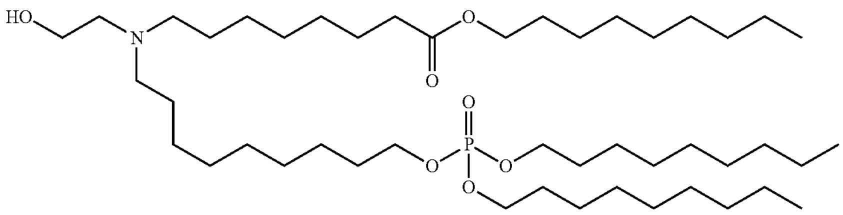
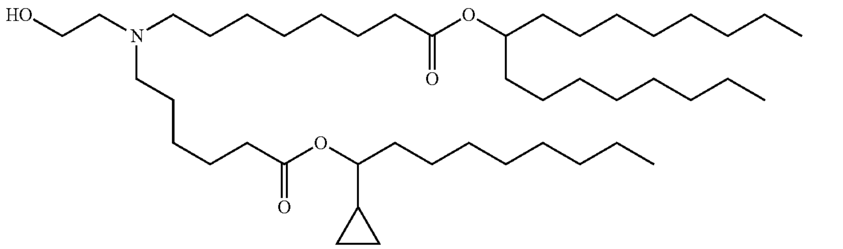
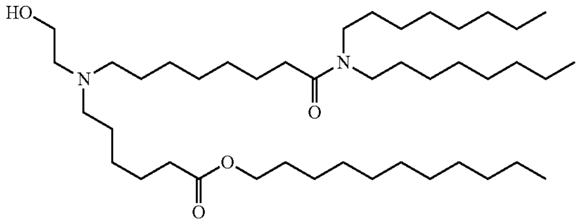
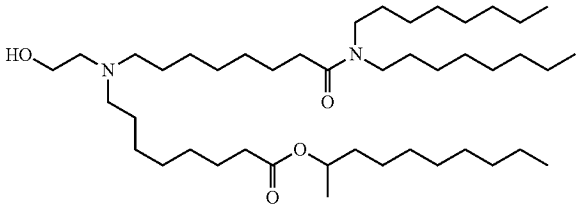
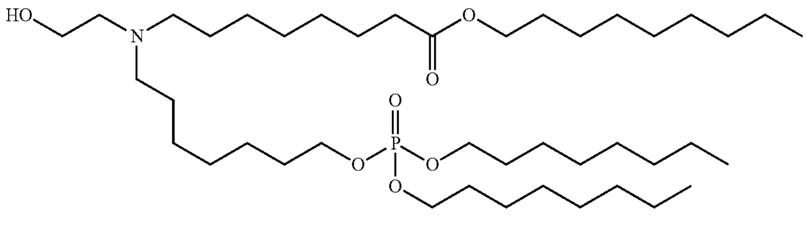

-continued
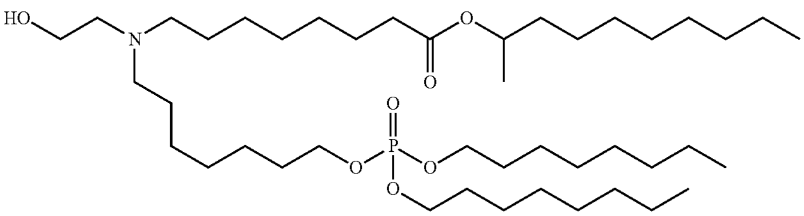
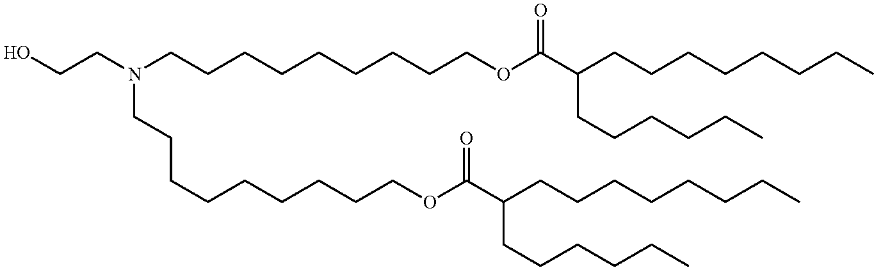
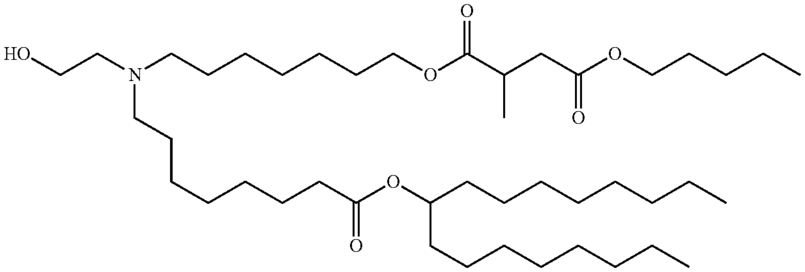
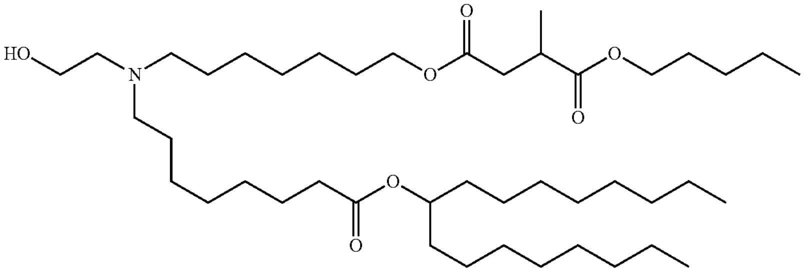
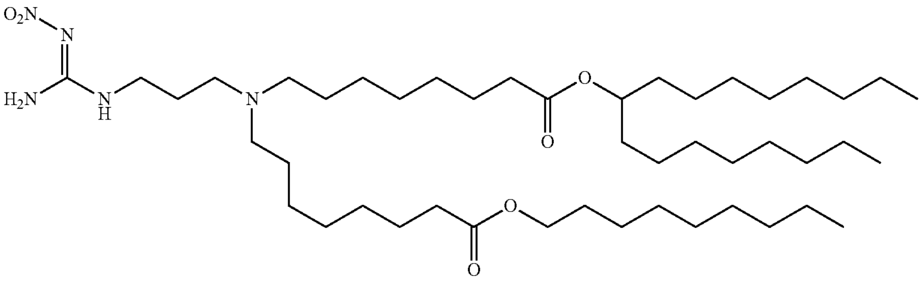
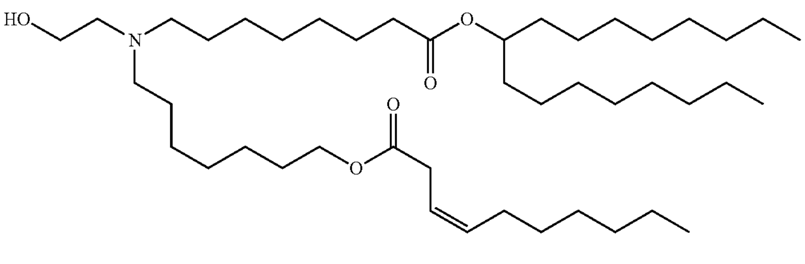

-continued
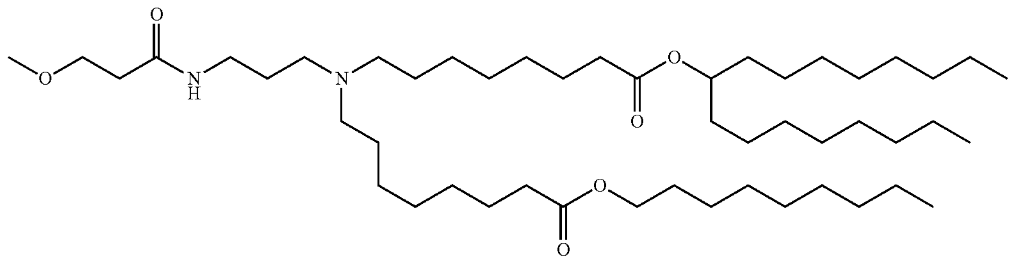
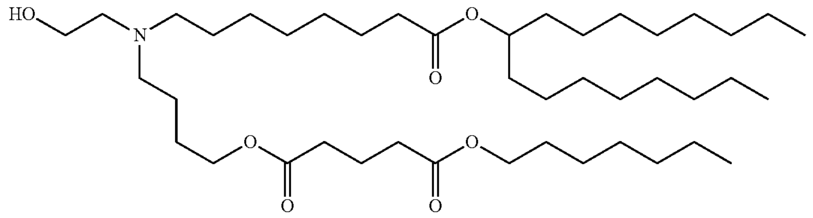
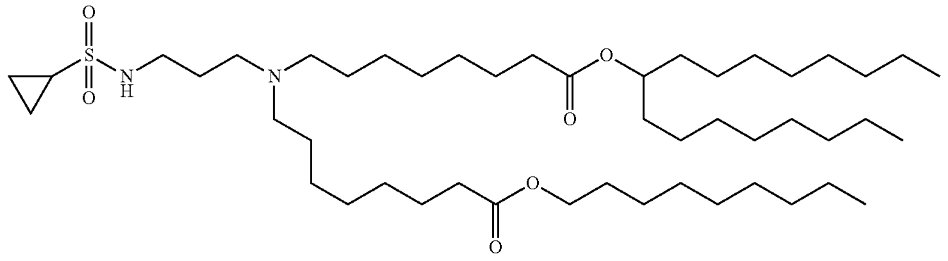
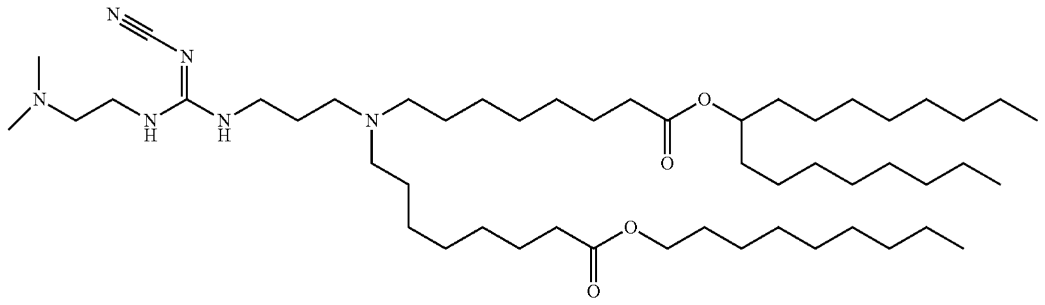
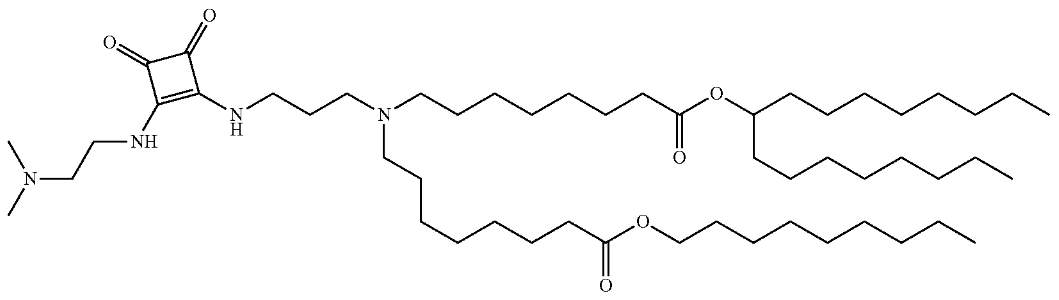
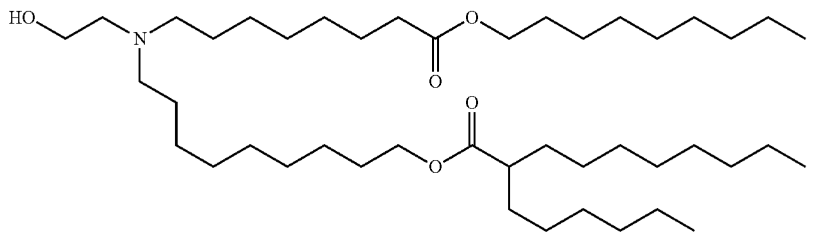

-continued
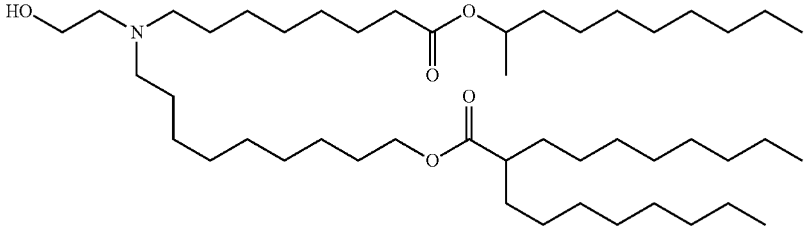
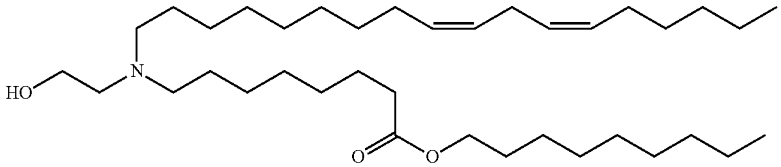
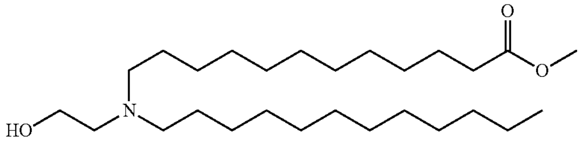
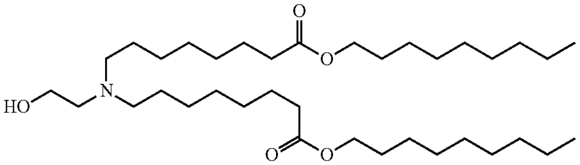
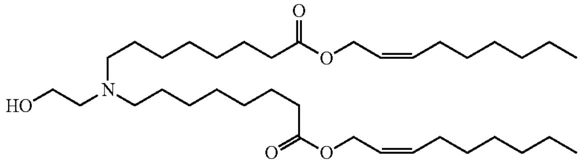
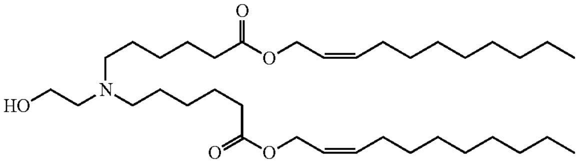
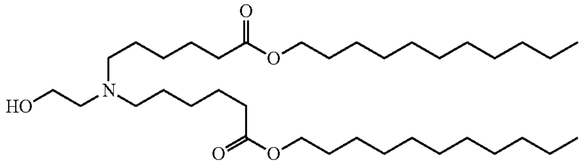
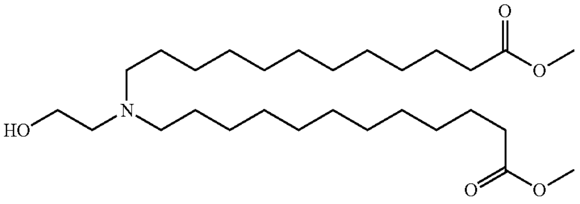
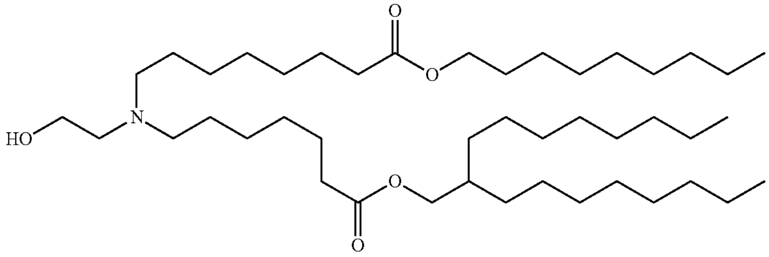
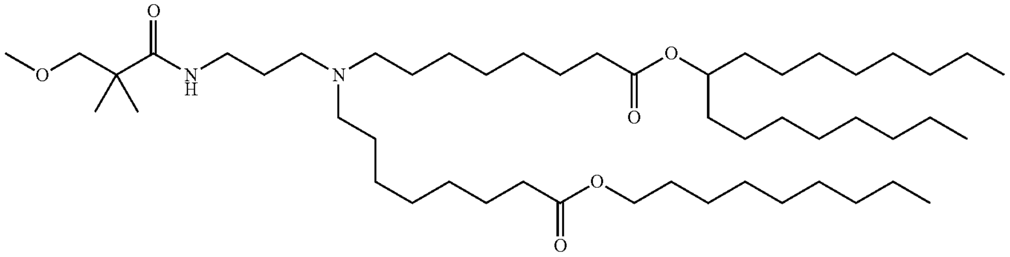
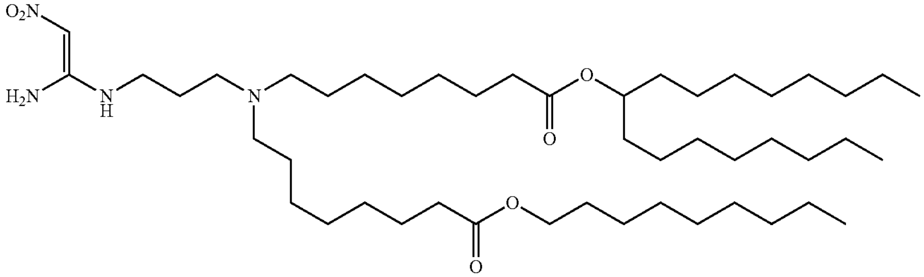

-continued
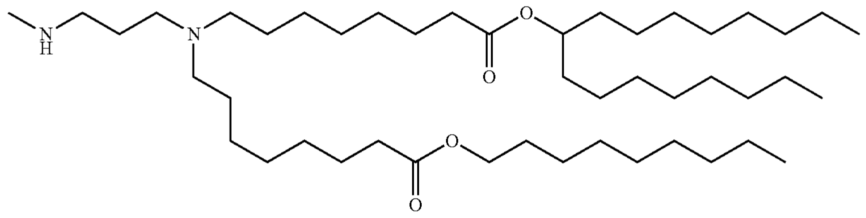
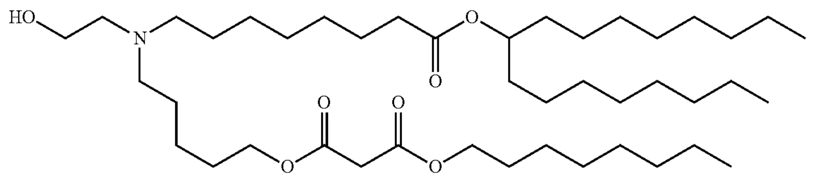
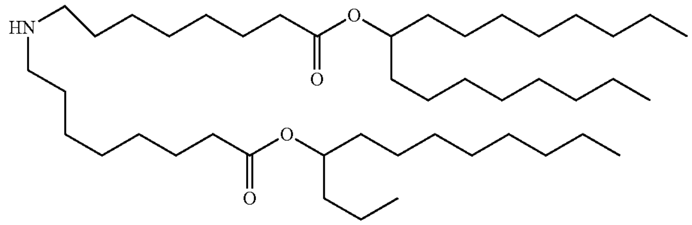
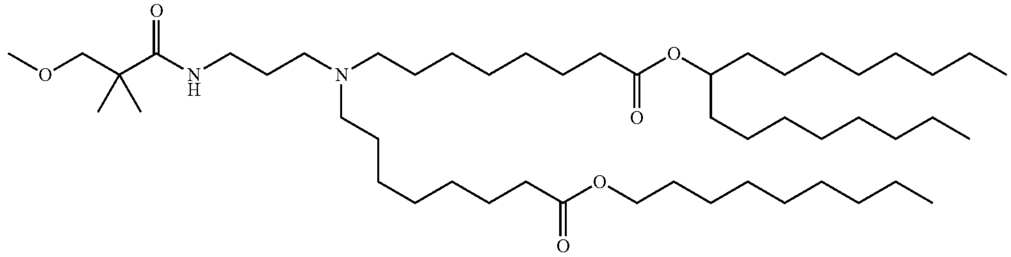
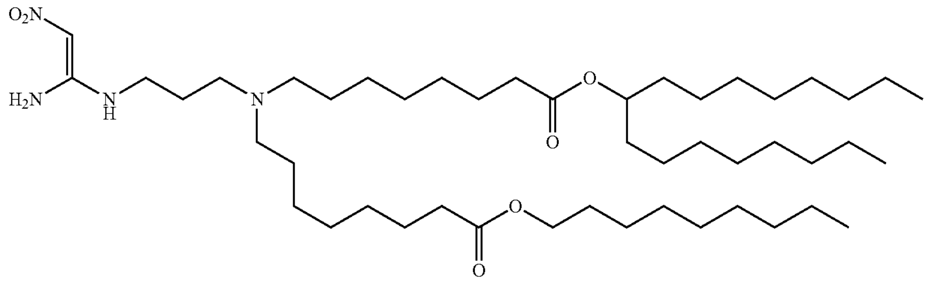
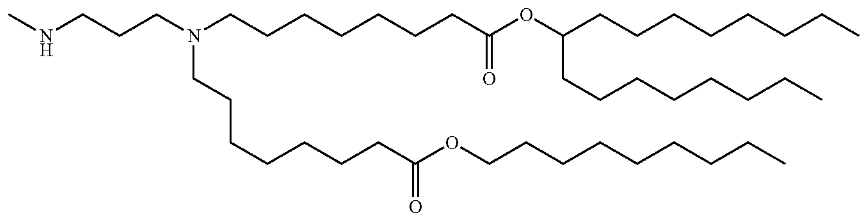
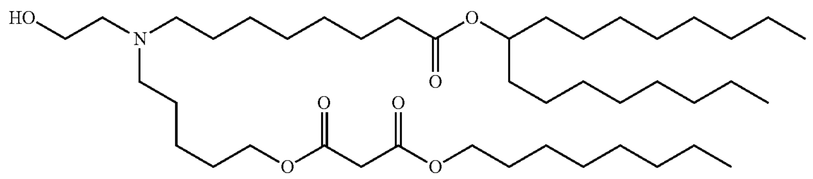

-continued
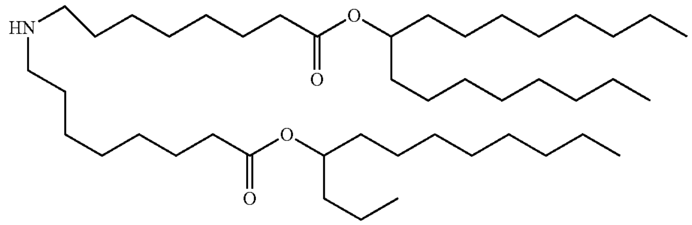
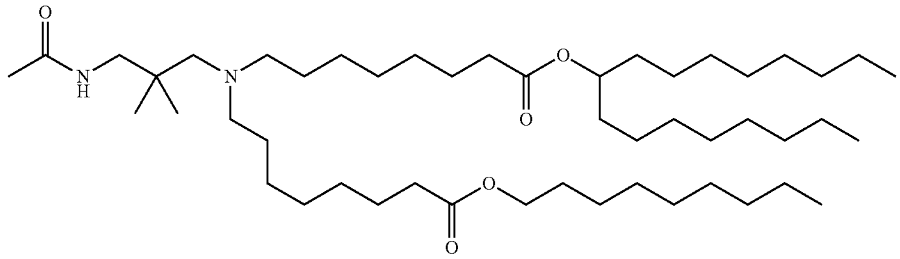
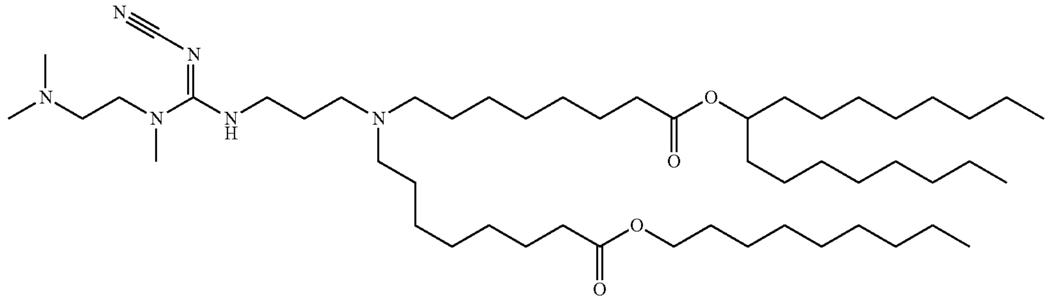
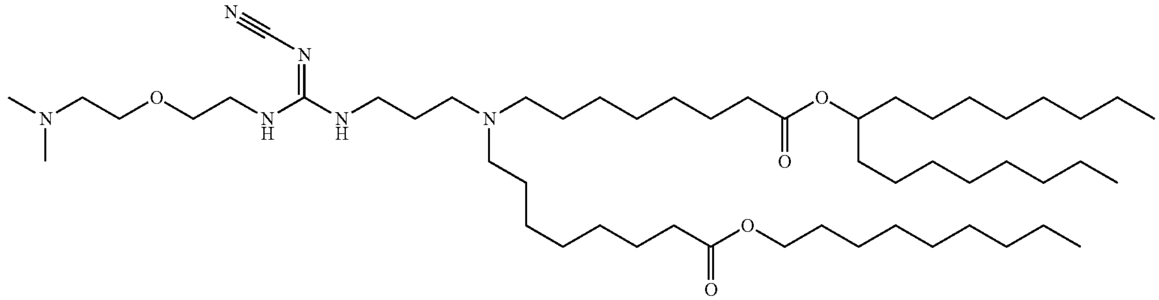
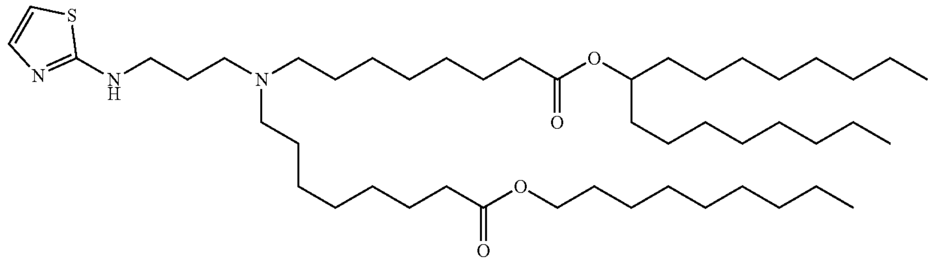
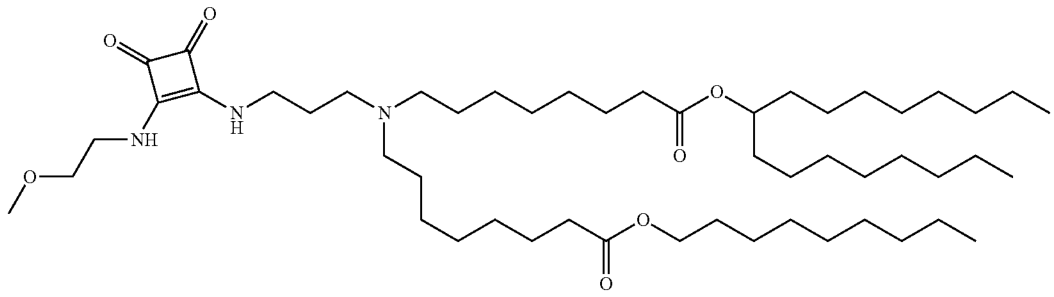

-continued
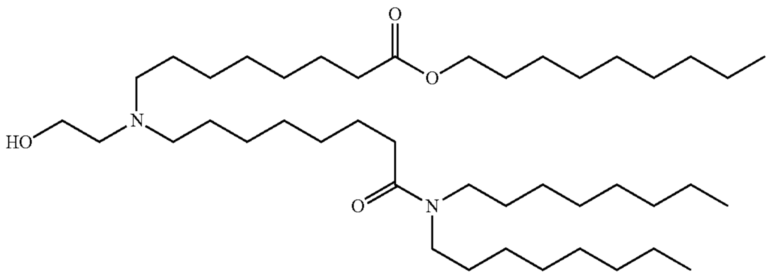
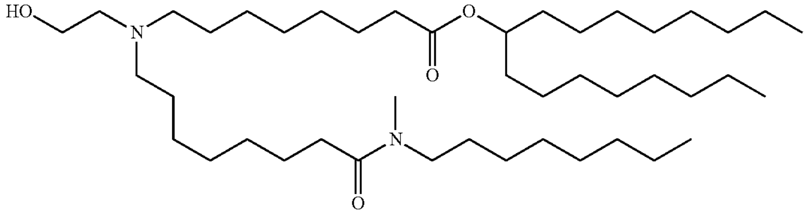
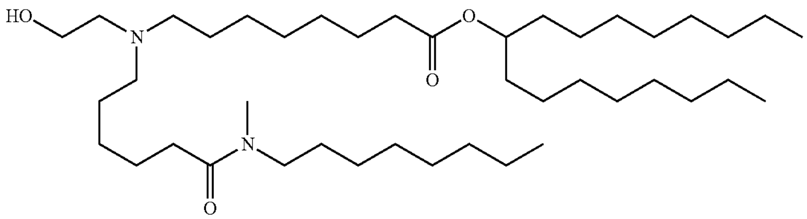
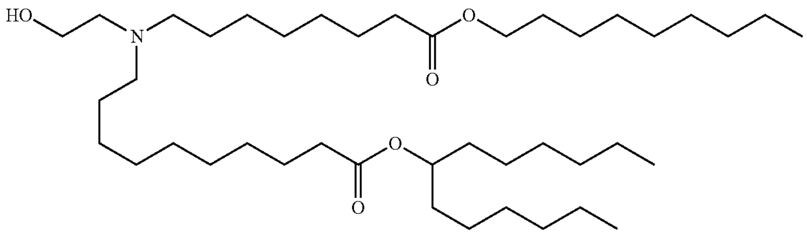
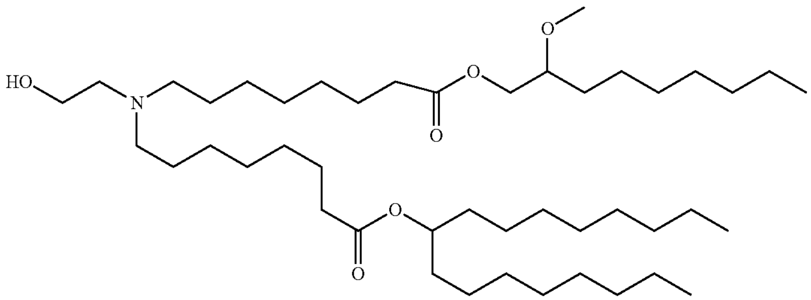
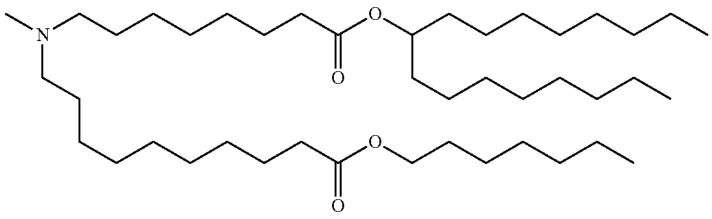
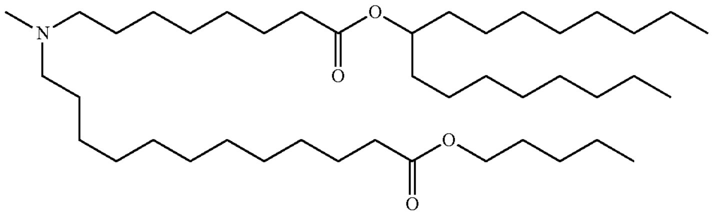

-continued
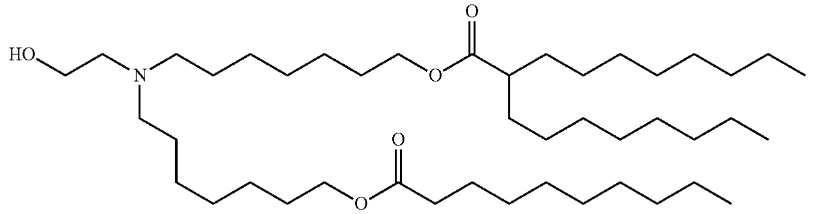
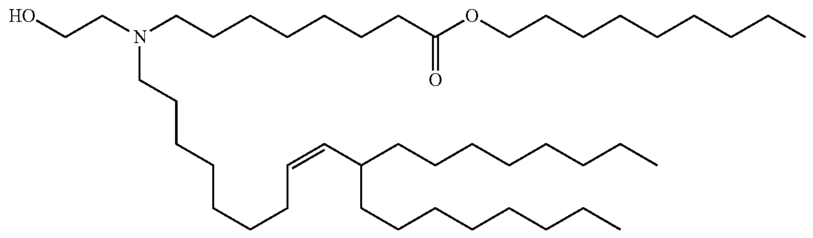
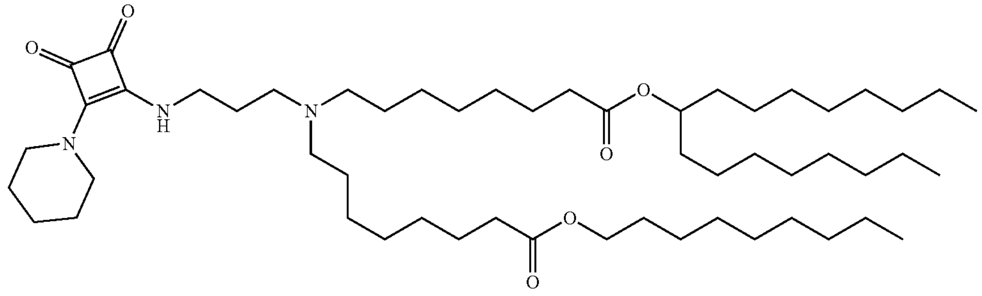
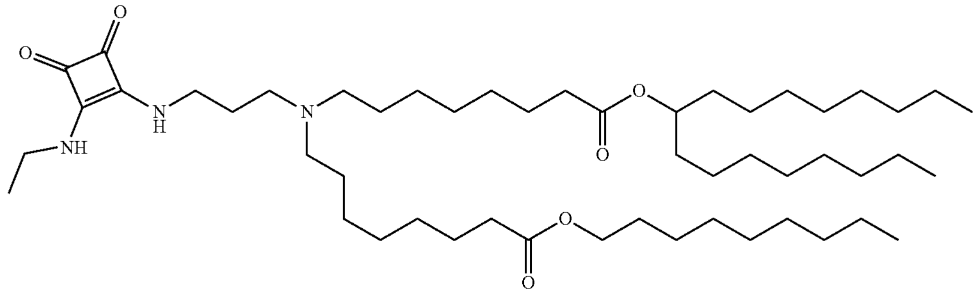
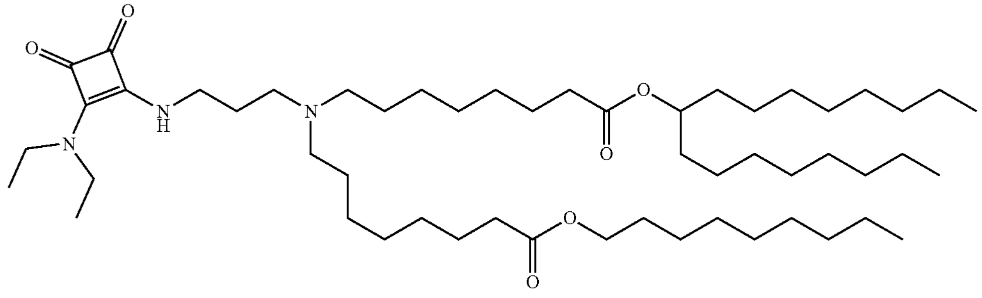
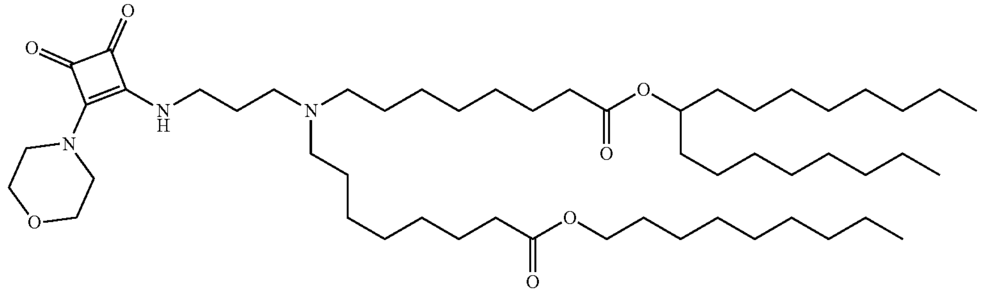

-continued
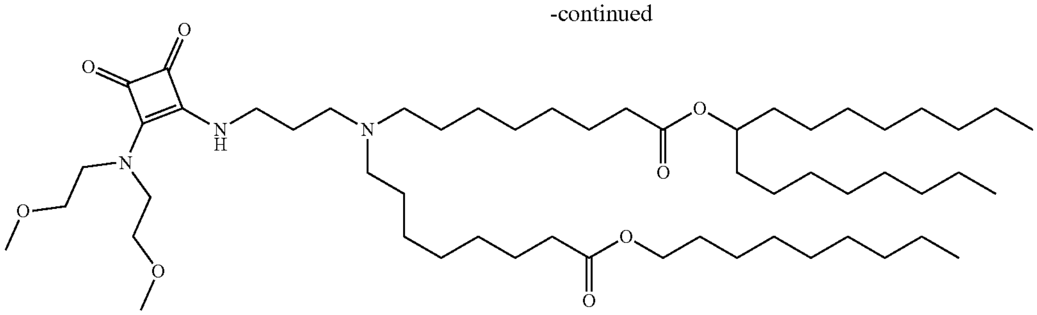
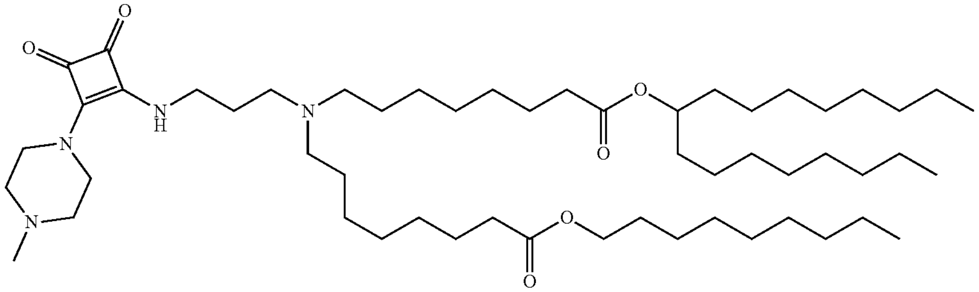
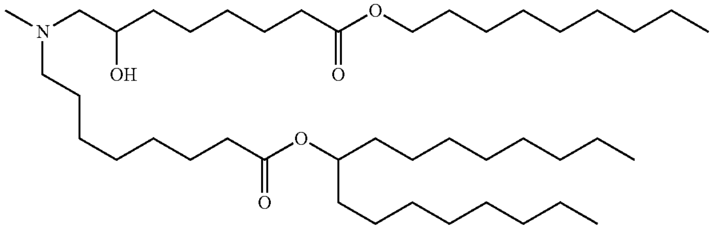
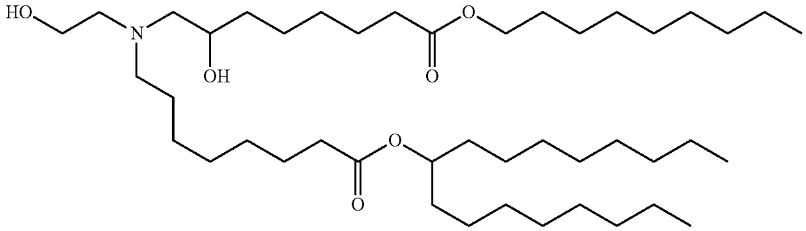
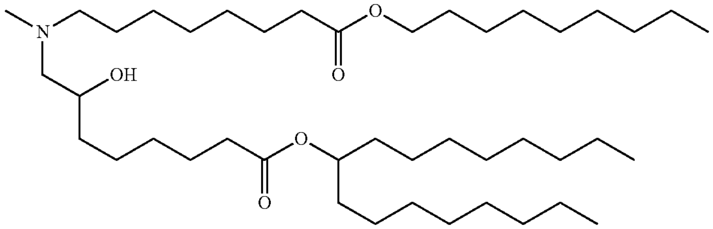
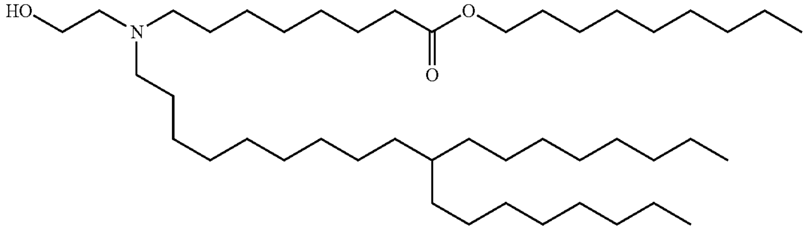
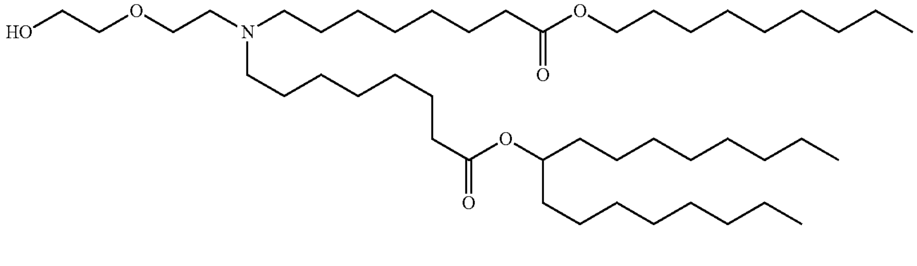

-continued
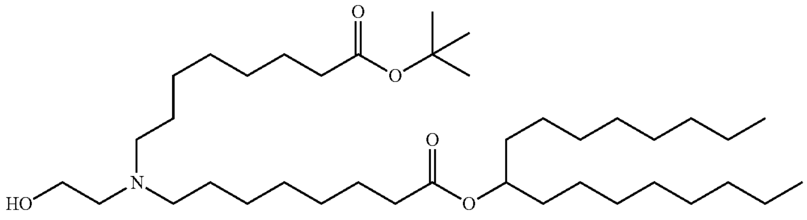
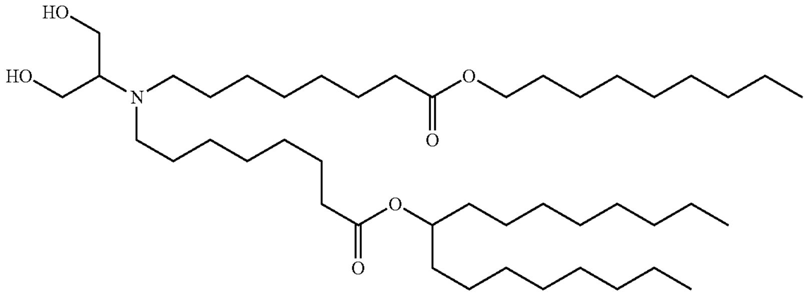
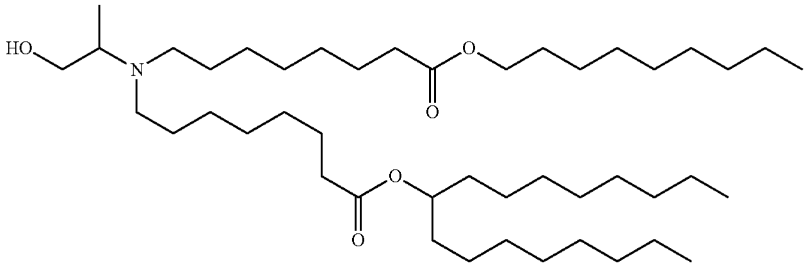
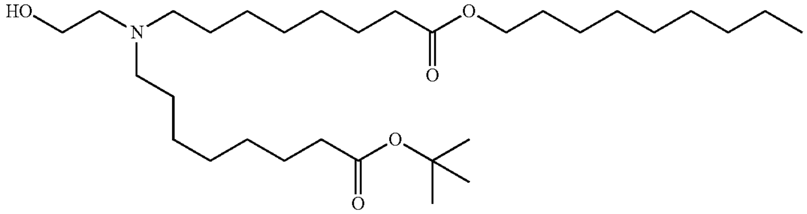
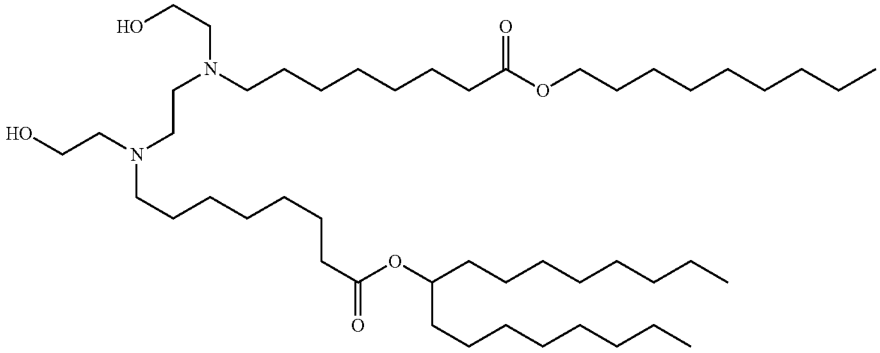

-continued
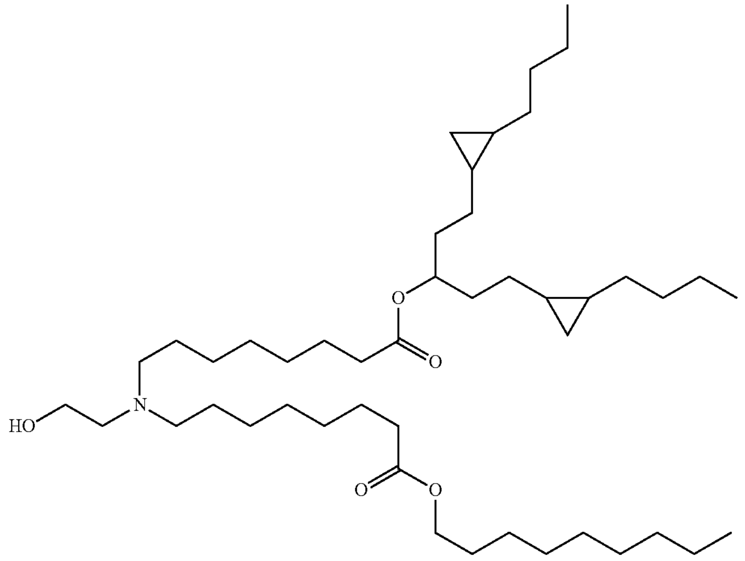
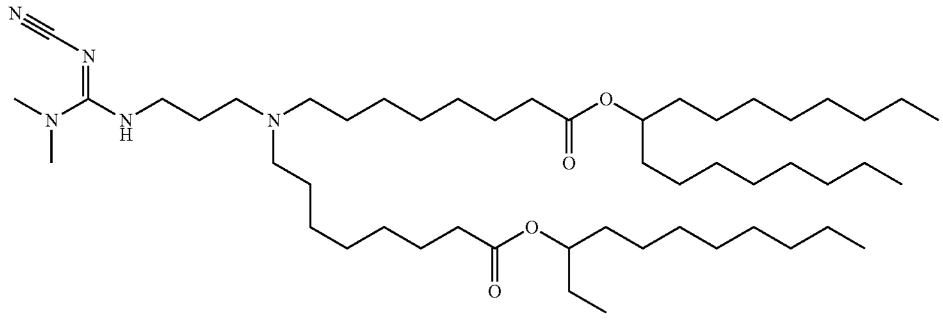
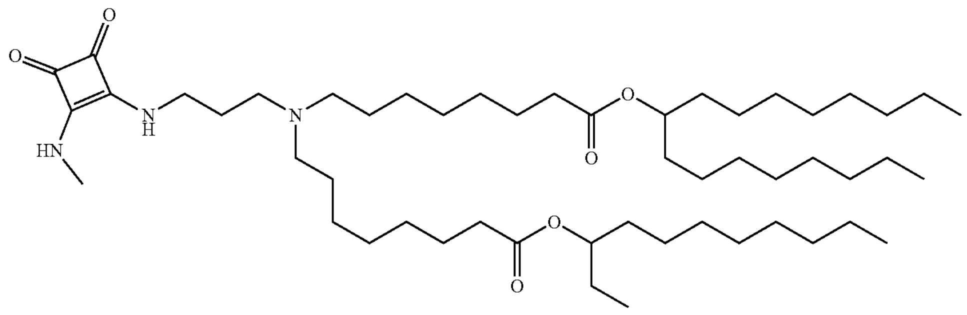
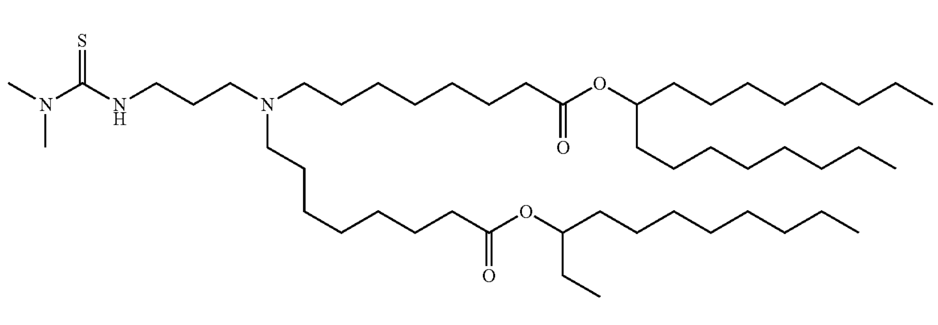

-continued
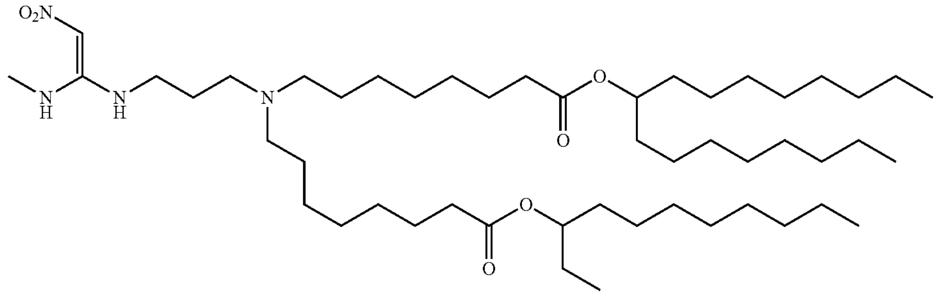
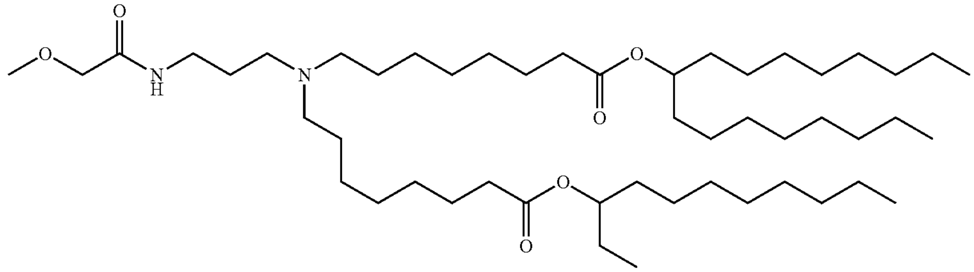
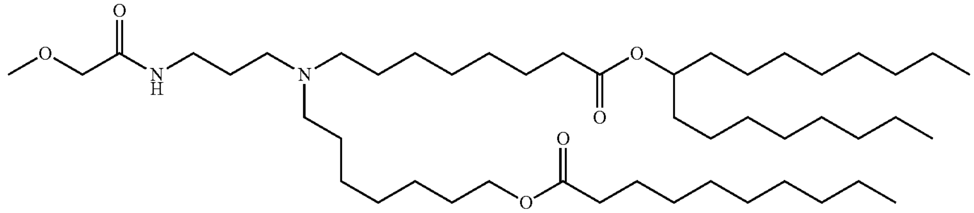
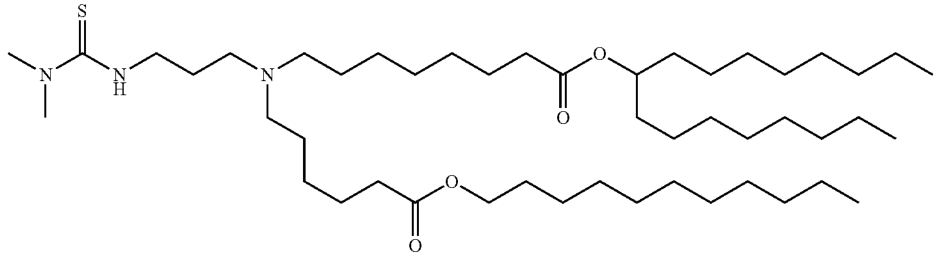
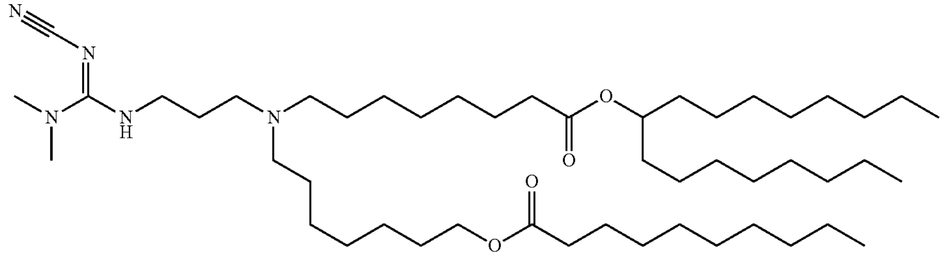
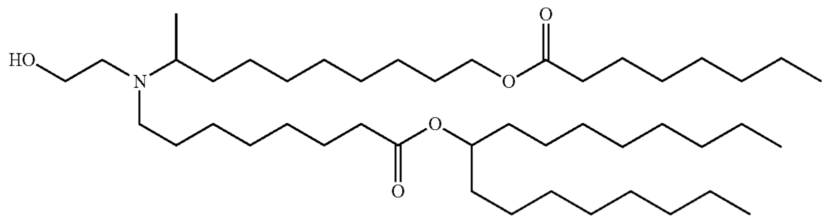
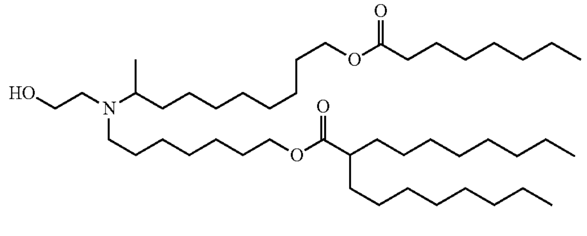
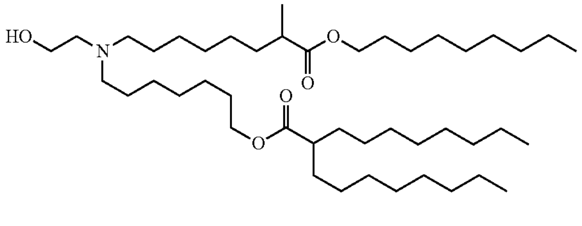

-continued
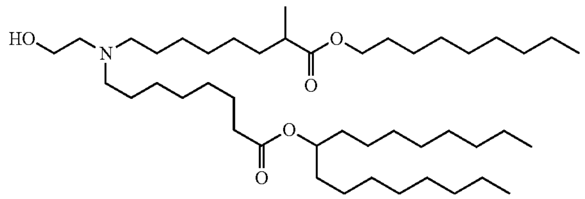
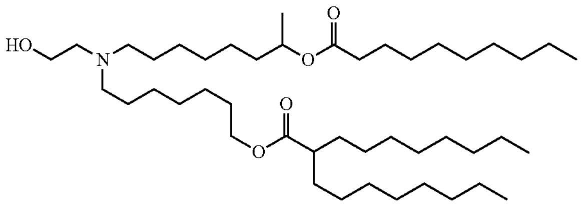
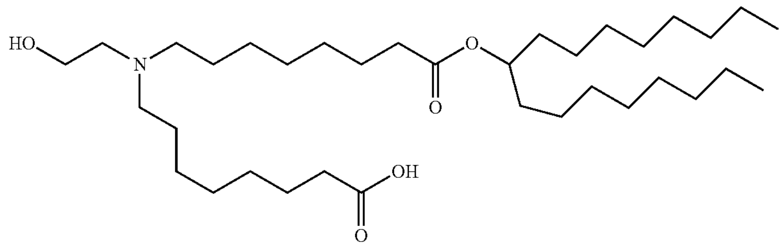
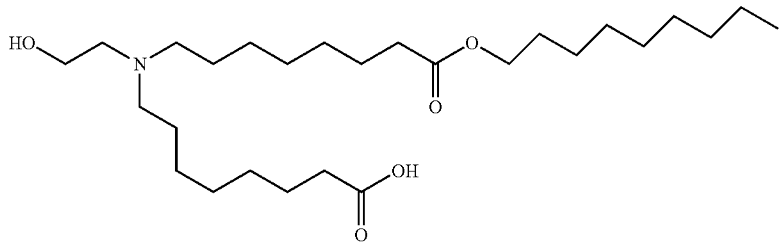
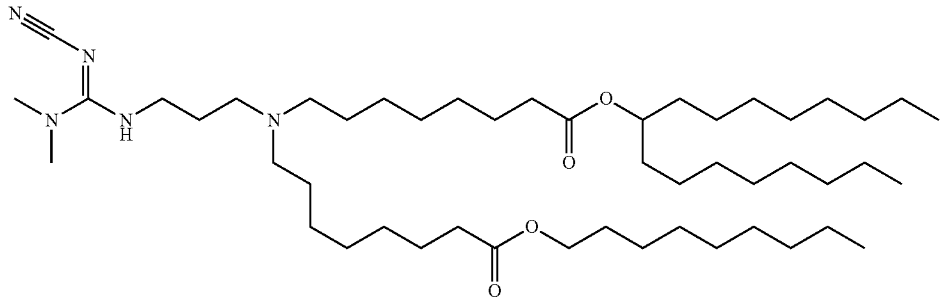
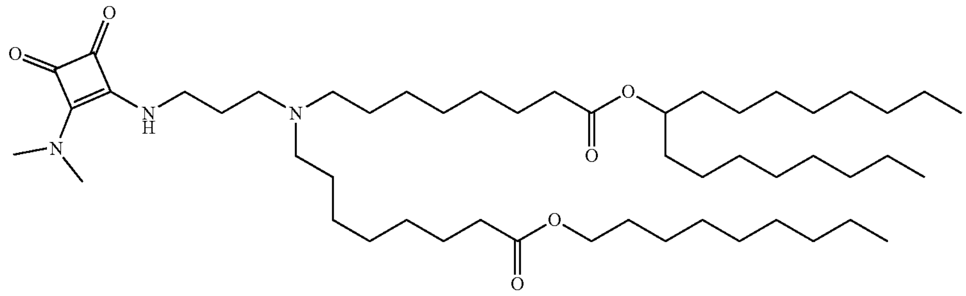
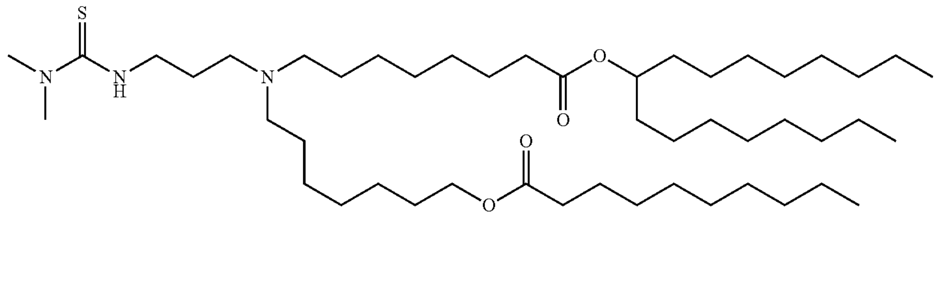

-continued
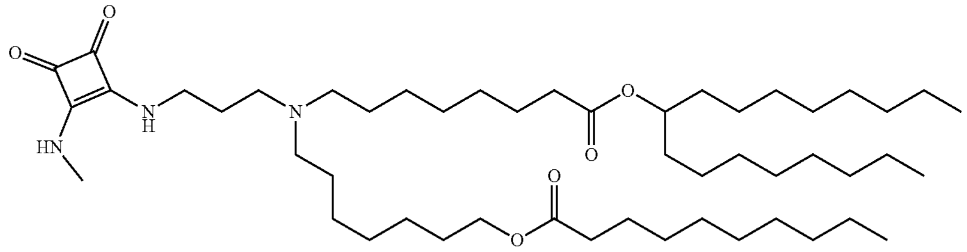
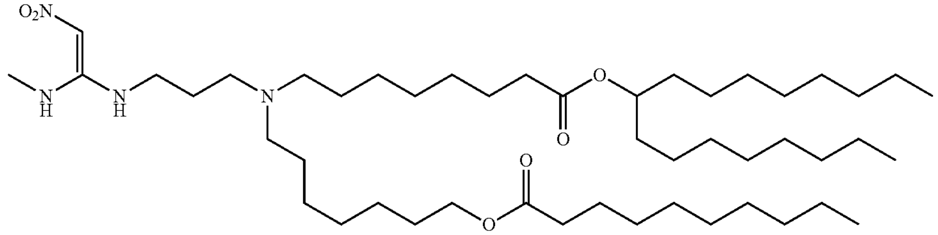
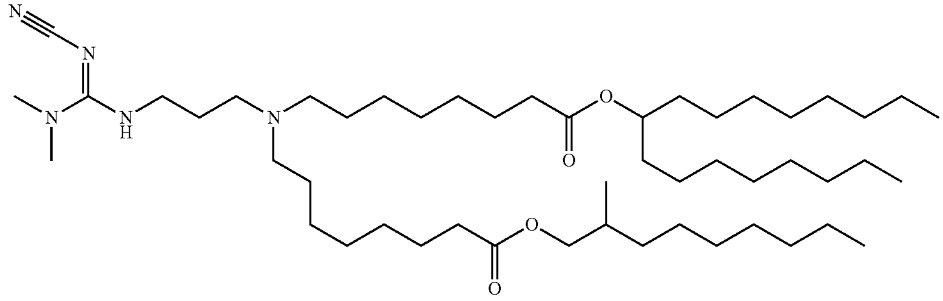
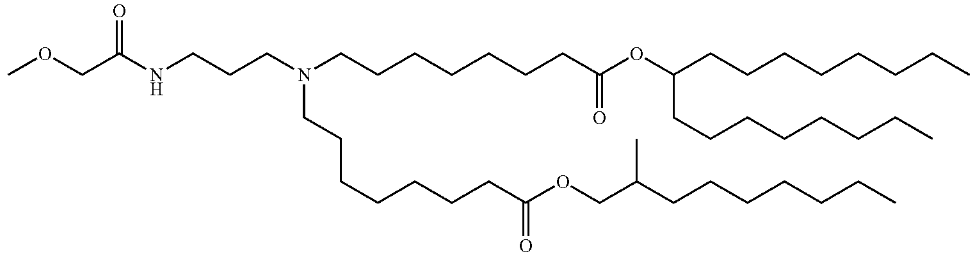
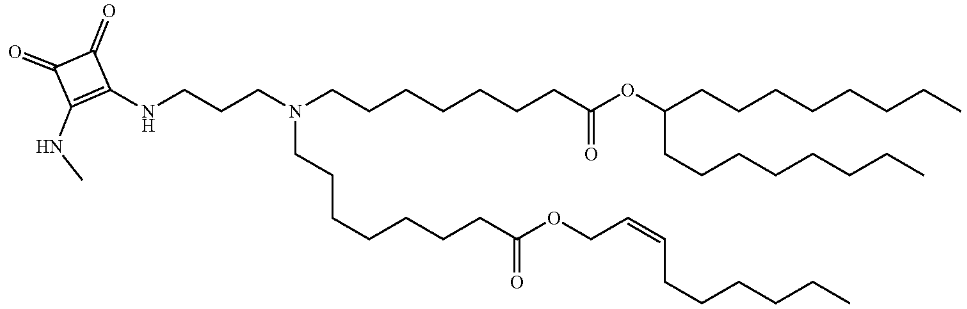
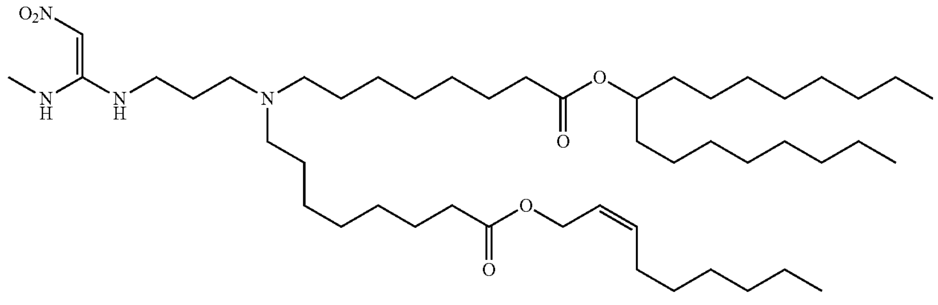

-continued
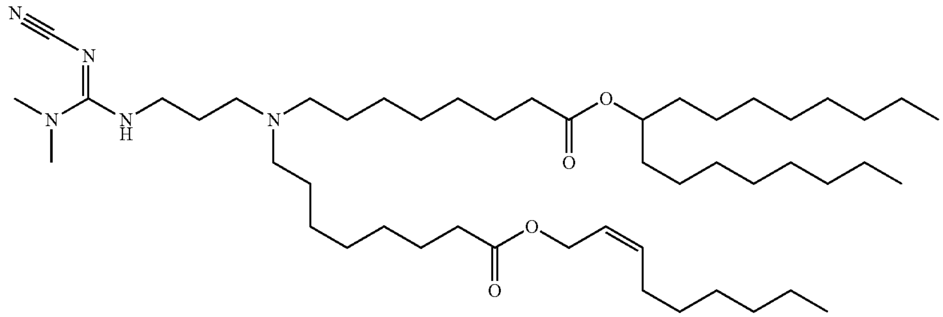
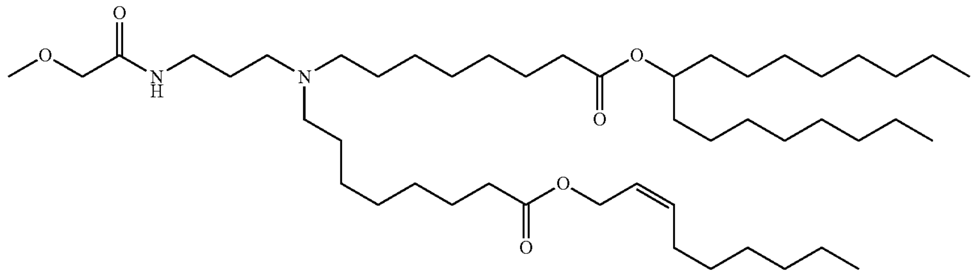
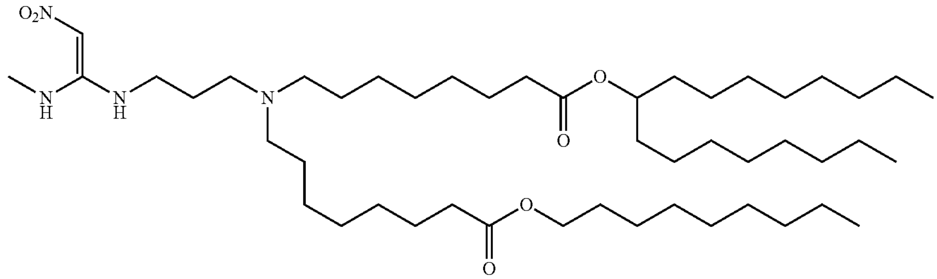
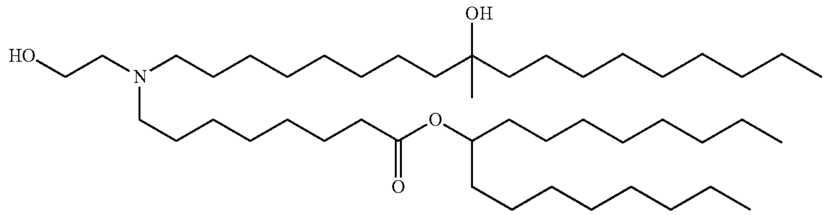
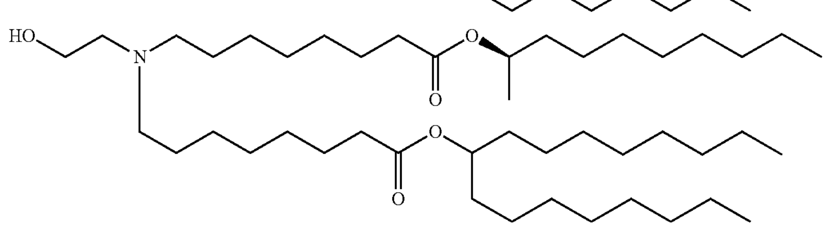
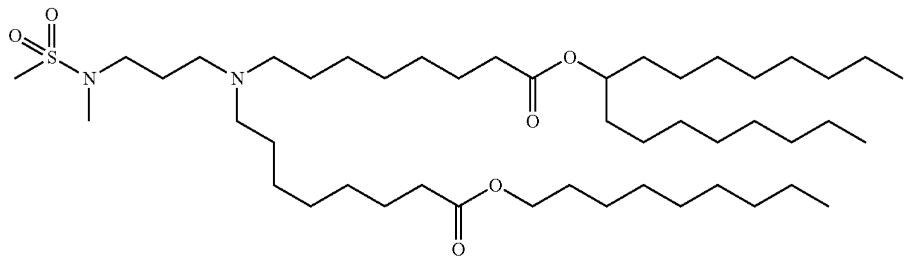

-continued
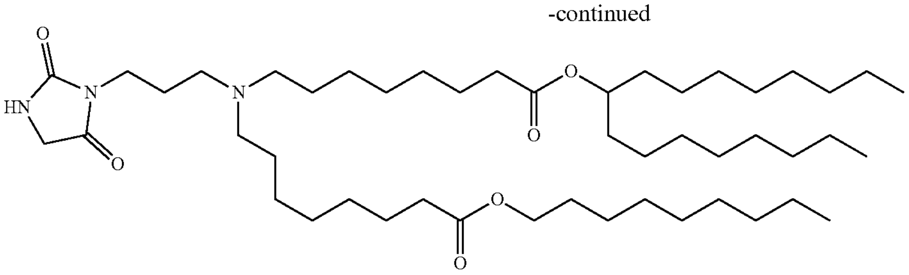
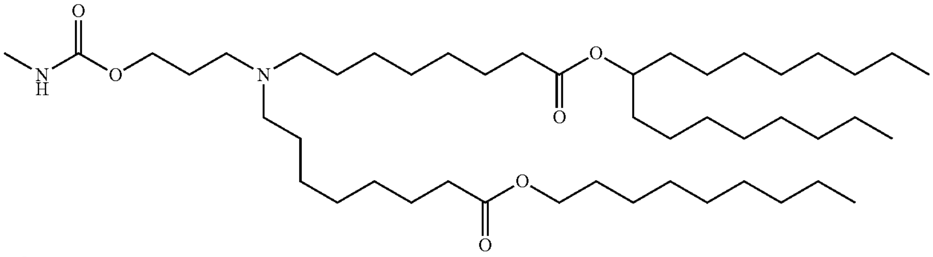
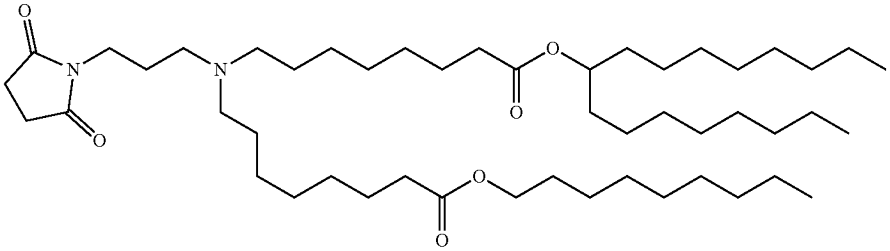
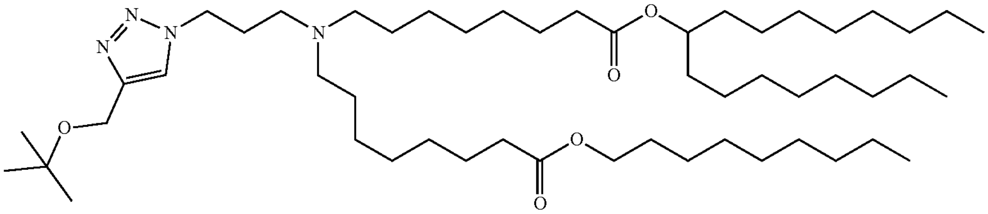
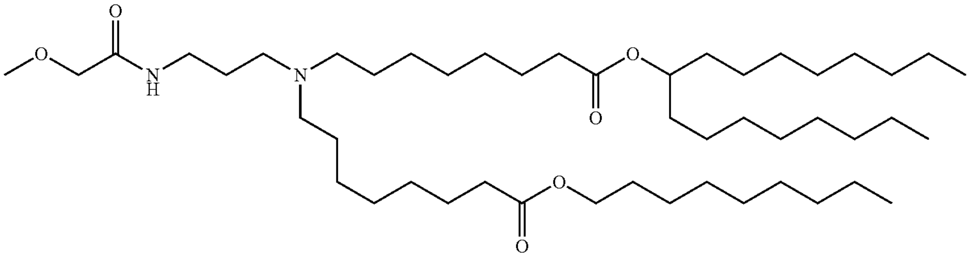
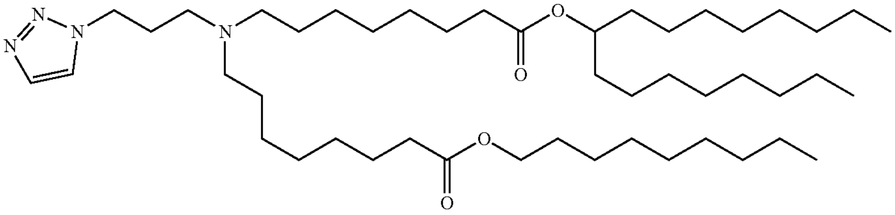
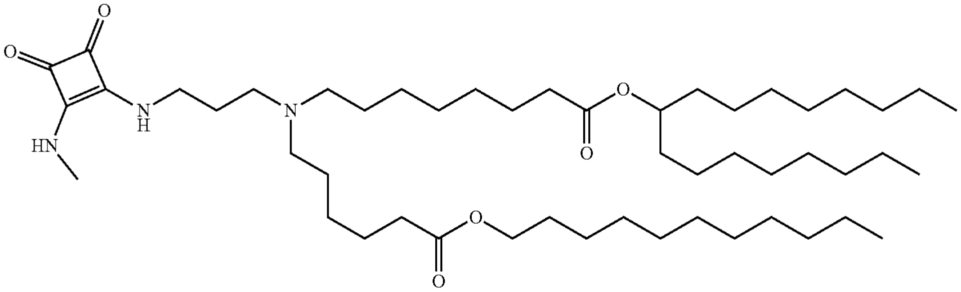

-continued
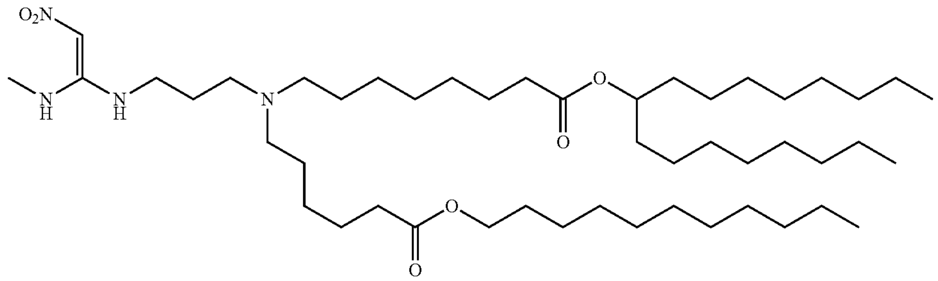
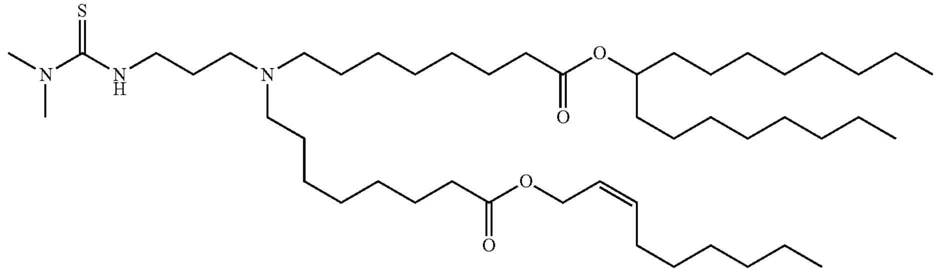
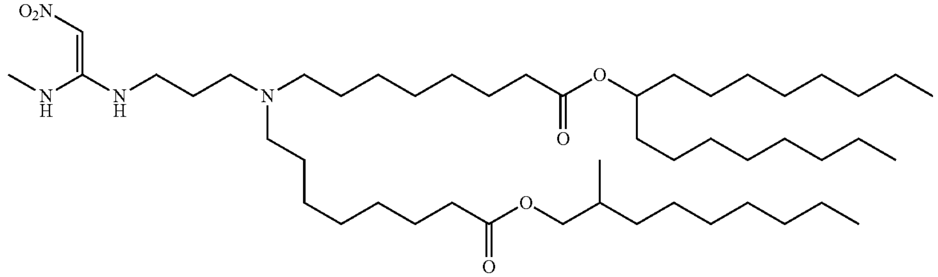
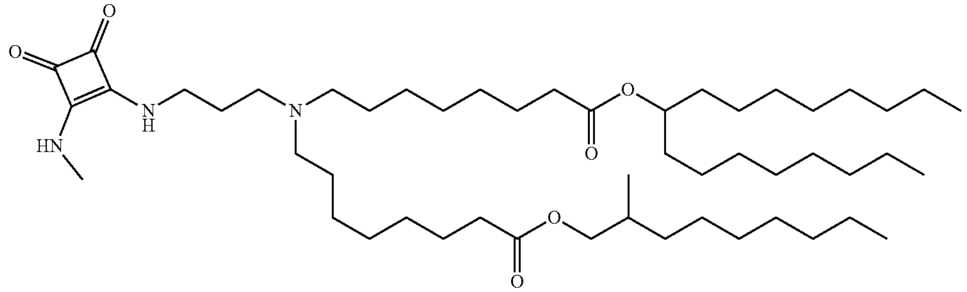
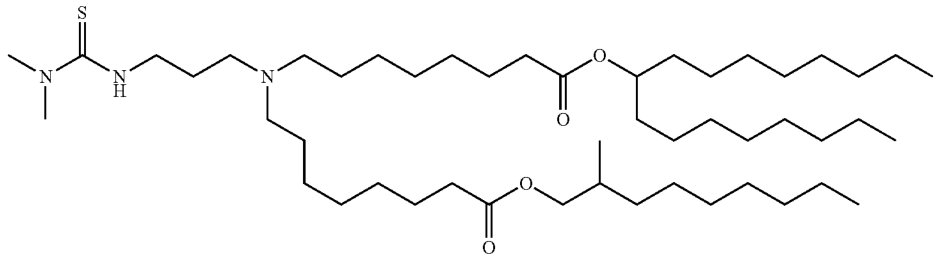
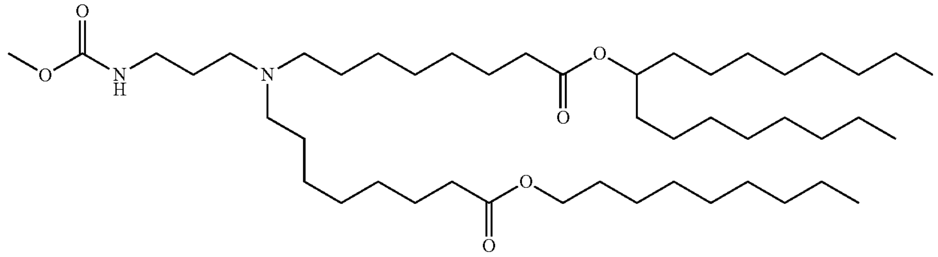

-continued
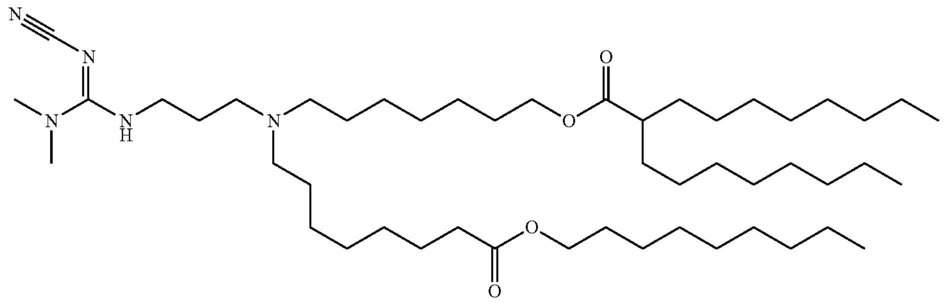
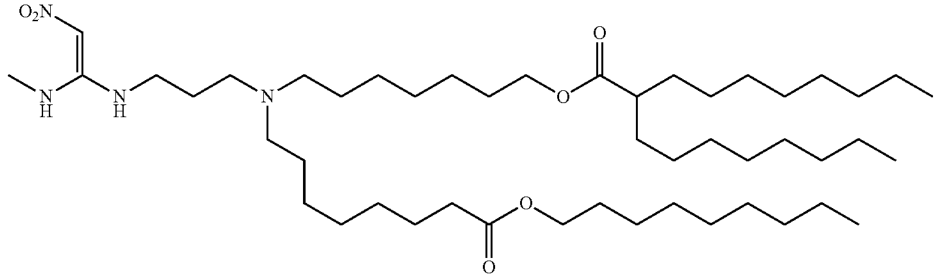
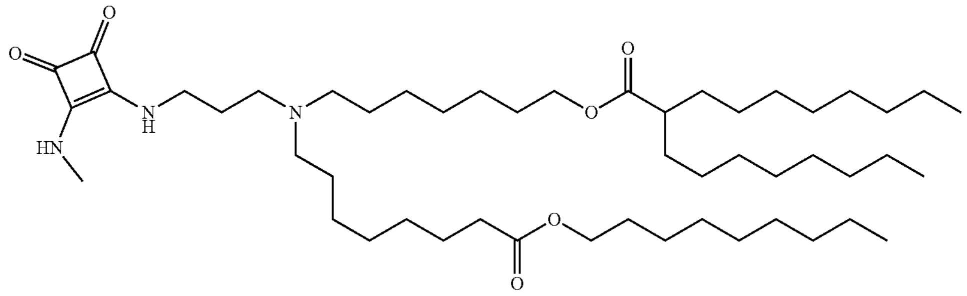
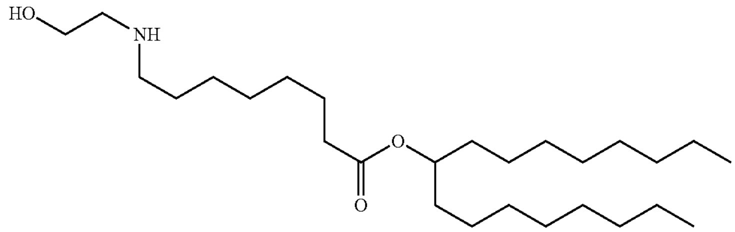
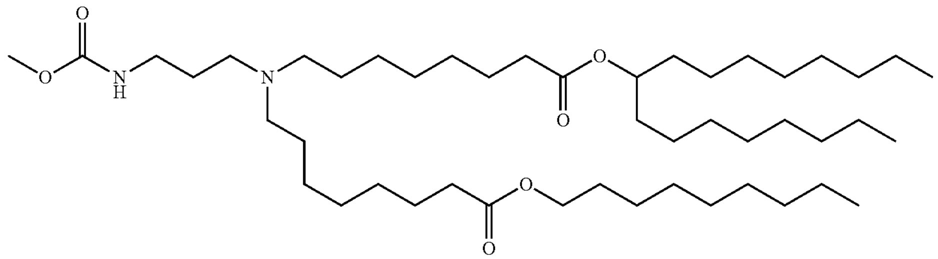
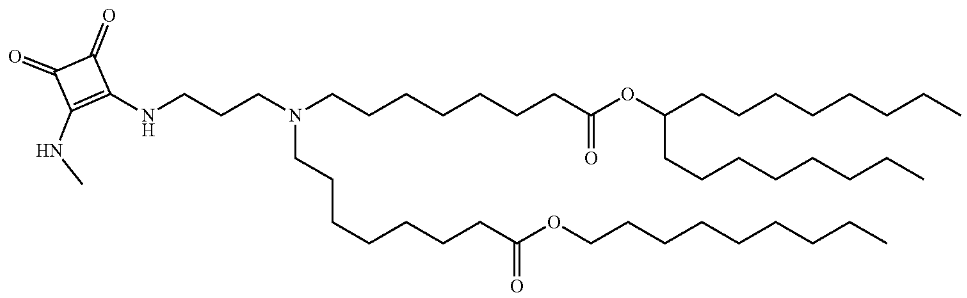

-continued
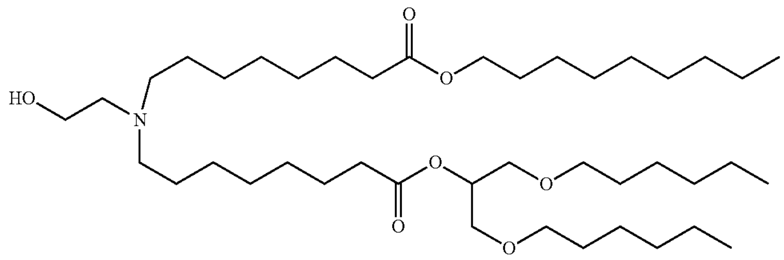
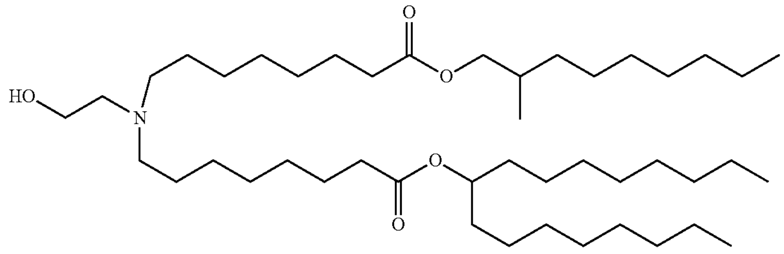
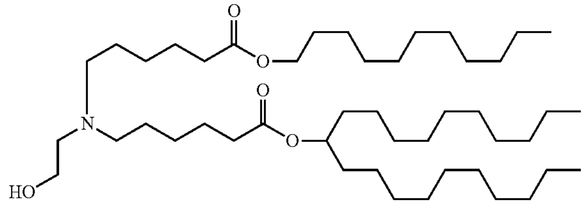
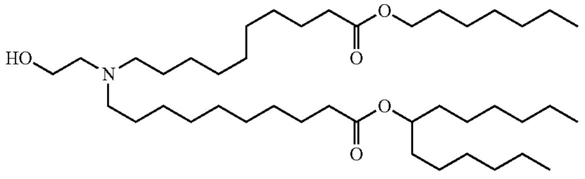
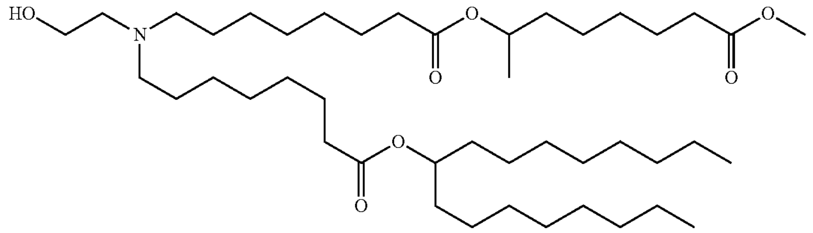
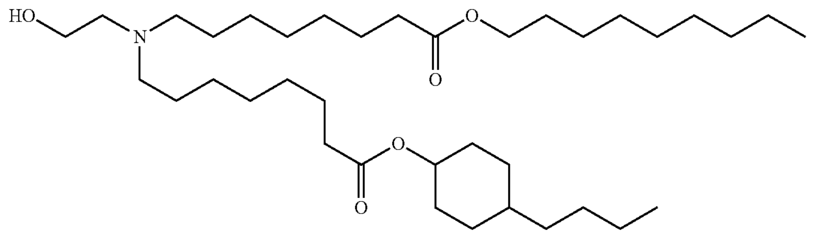
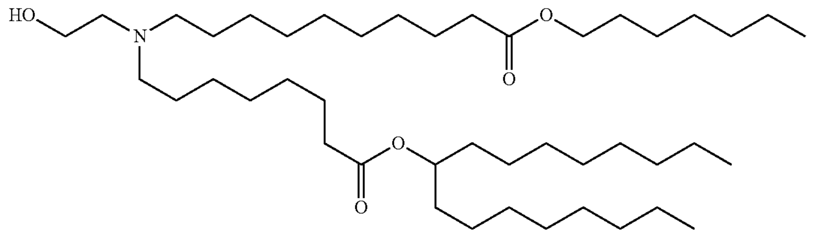
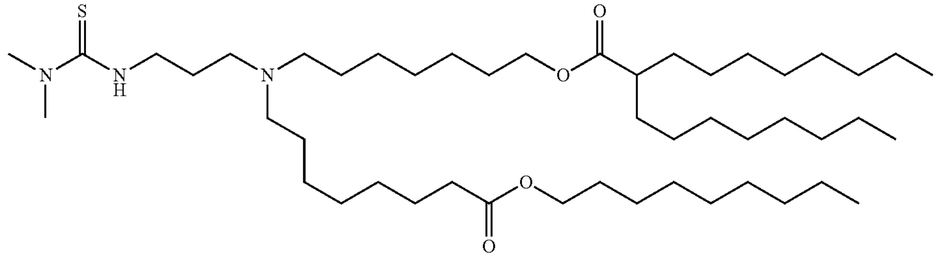

-continued
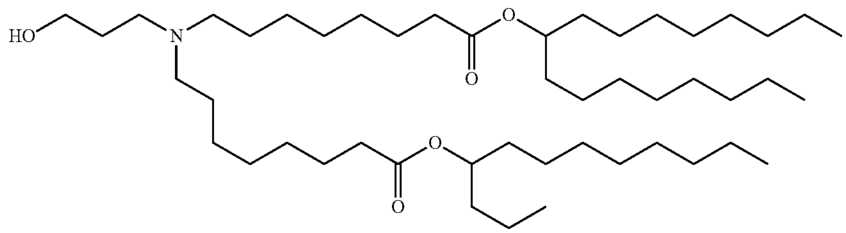
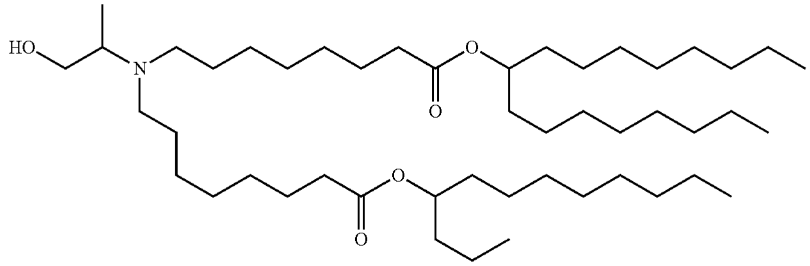
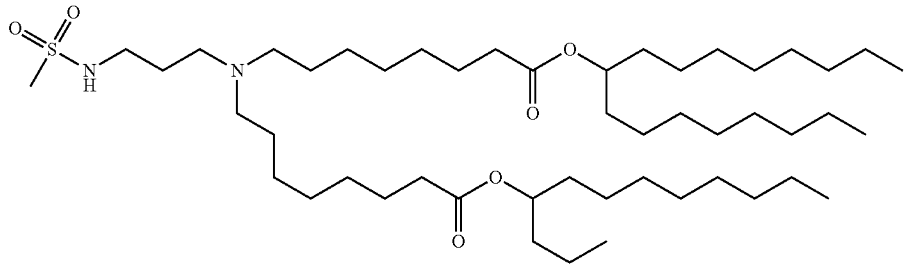
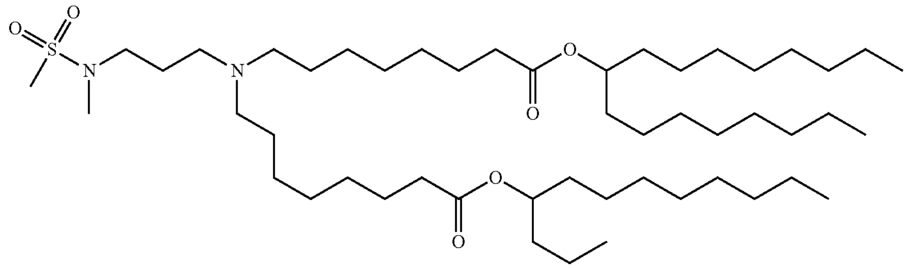
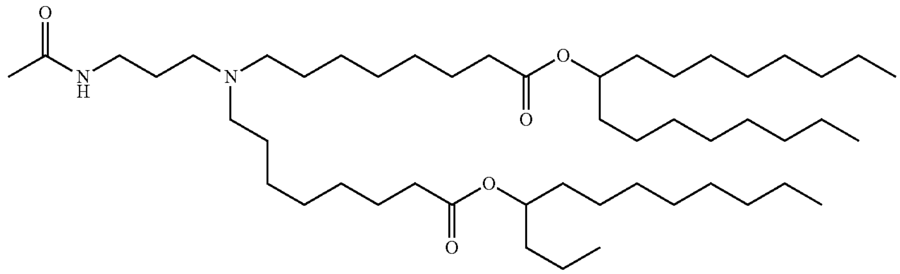
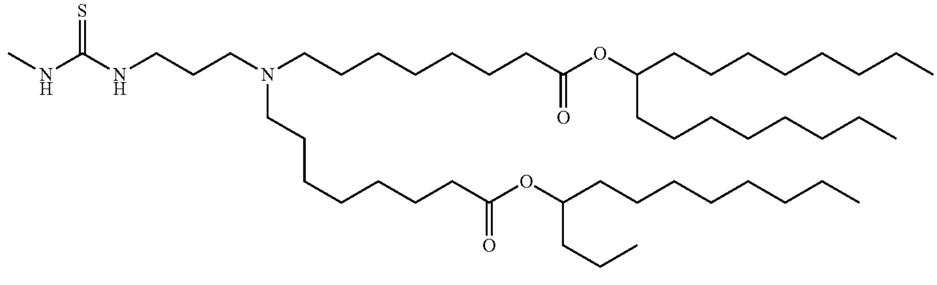

-continued
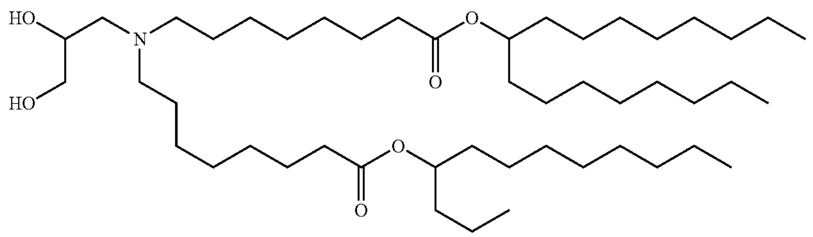
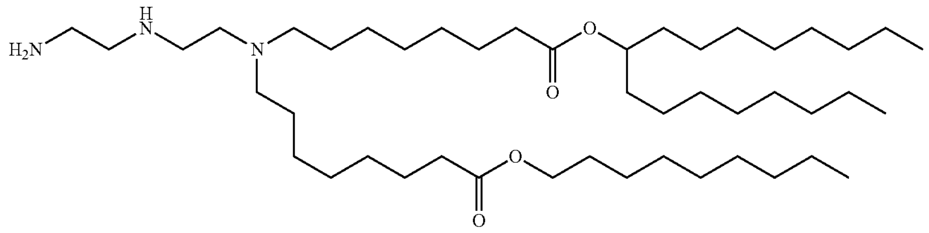
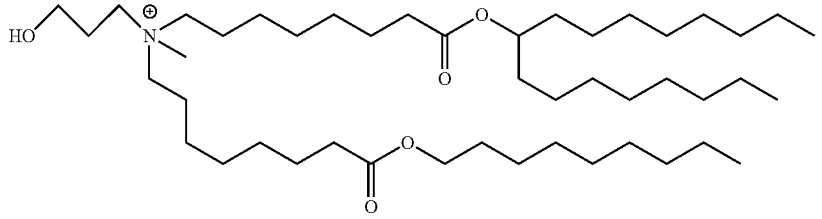
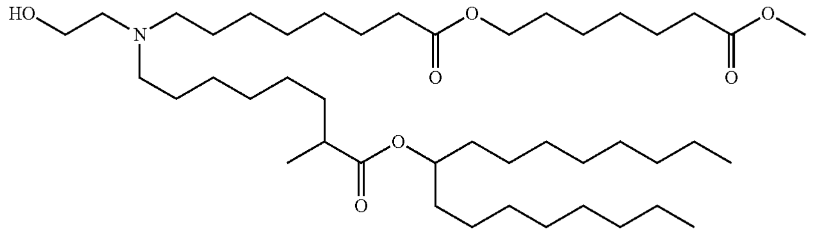
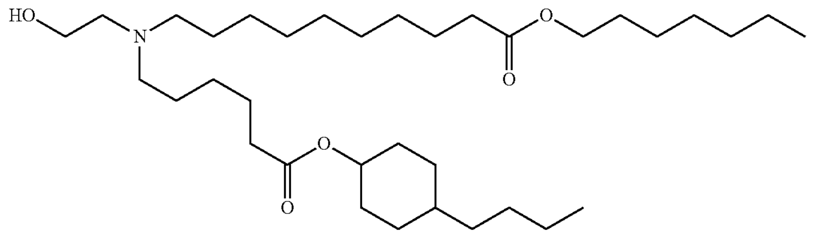
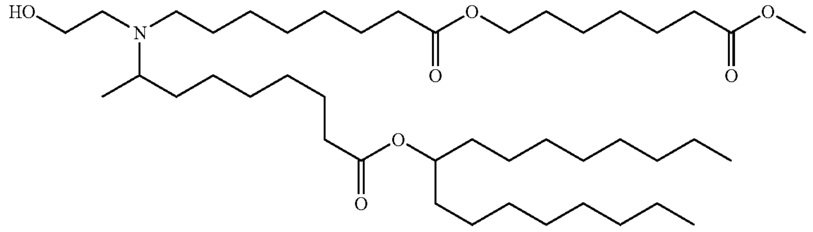
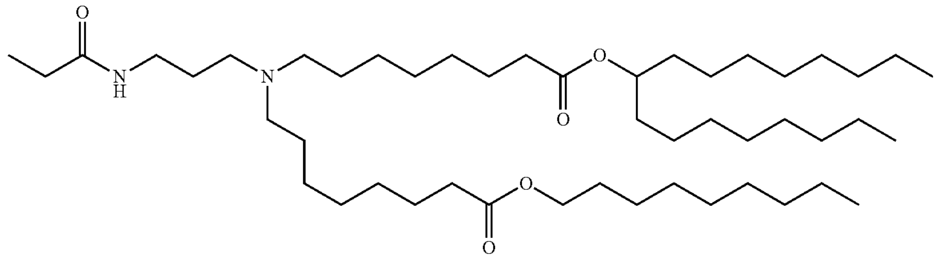

-continued
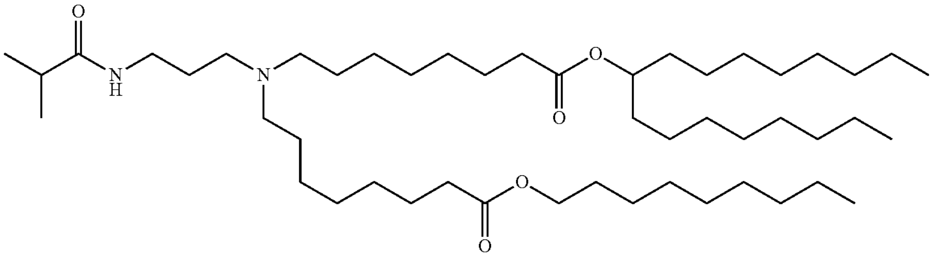
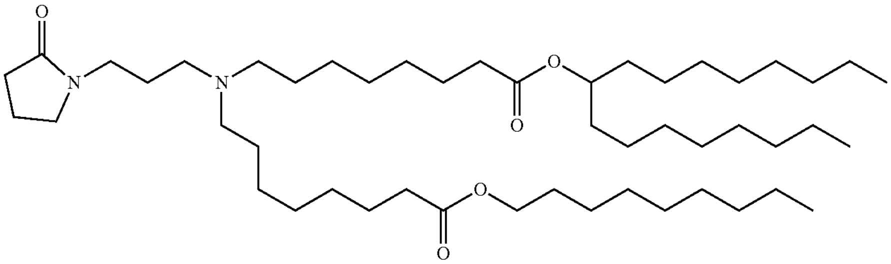
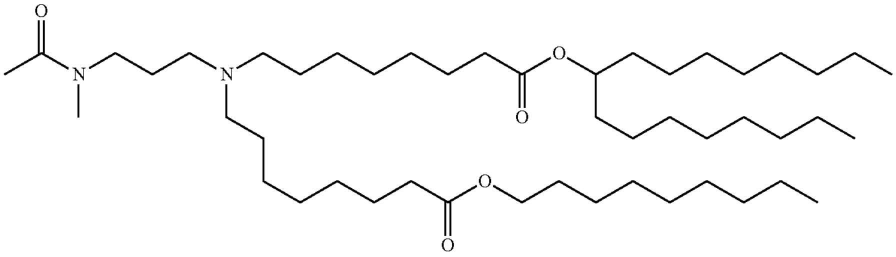
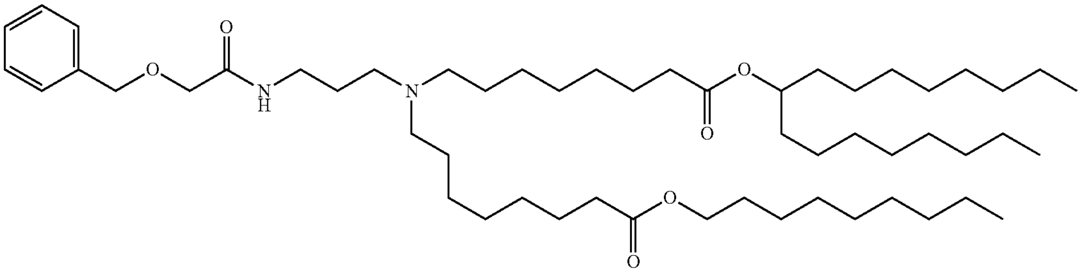
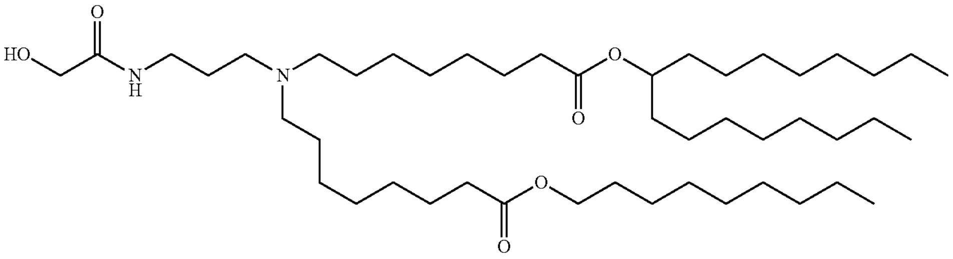
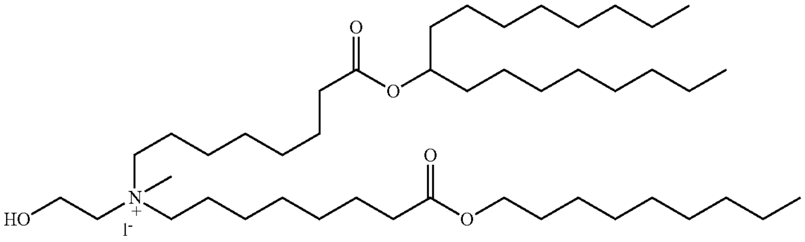

-continued
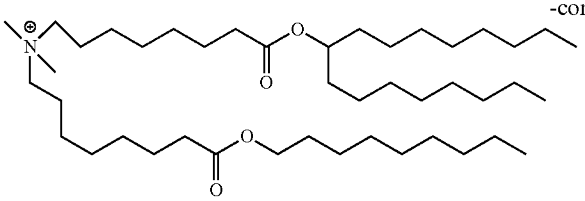
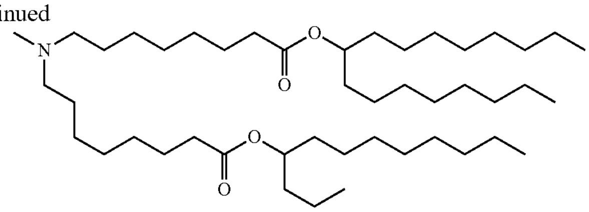
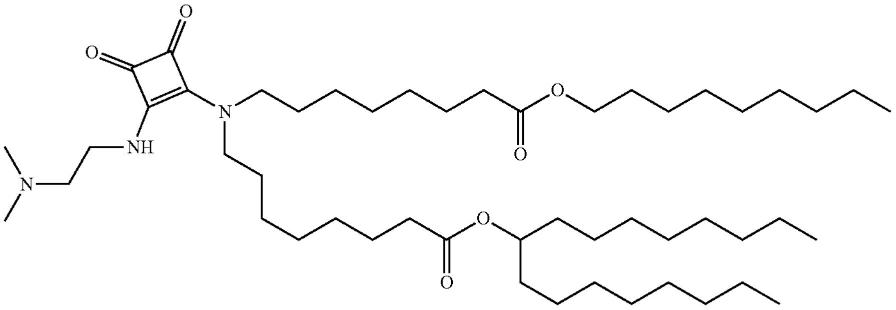
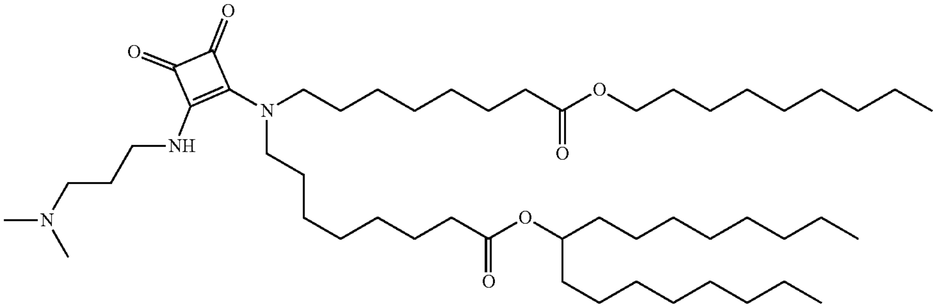
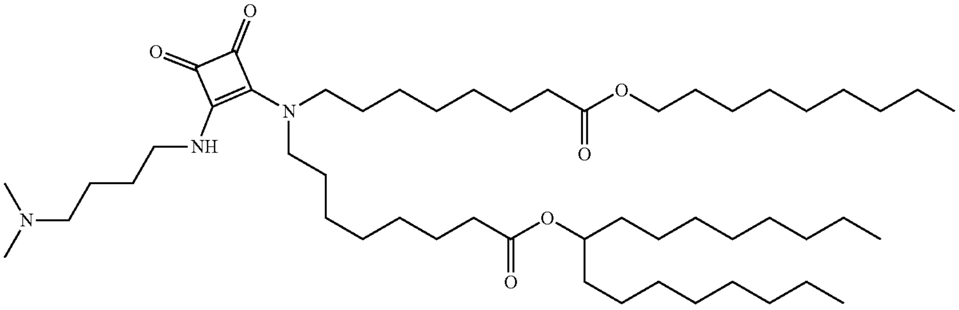
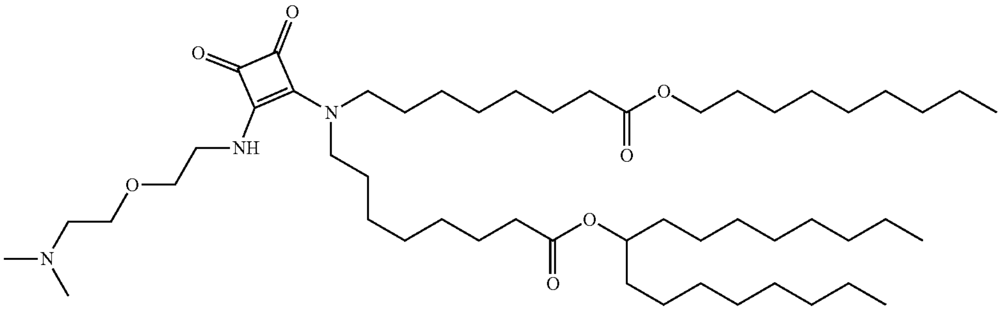
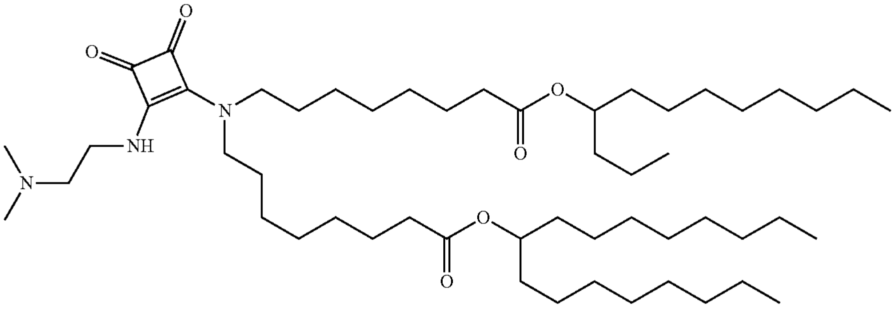

-continued
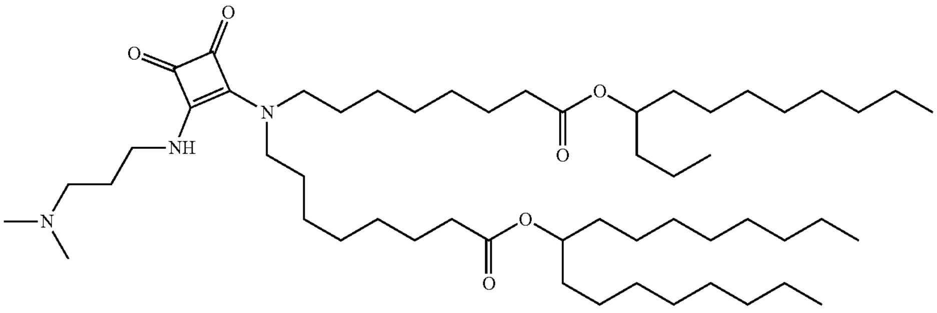
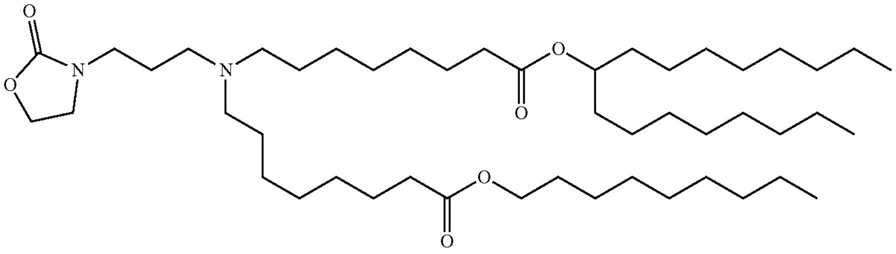
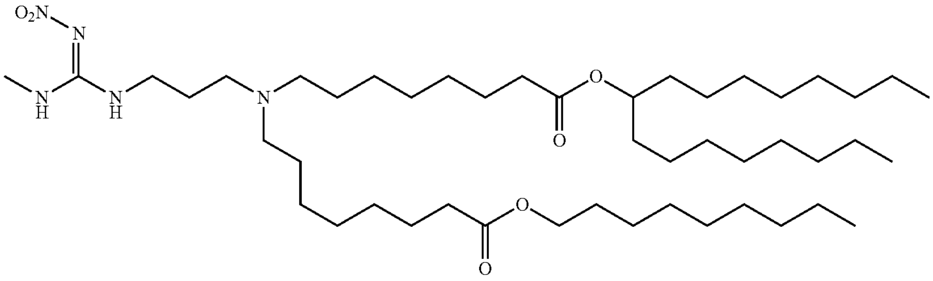
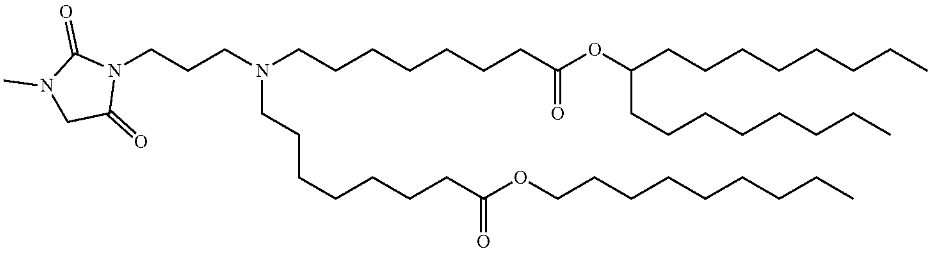
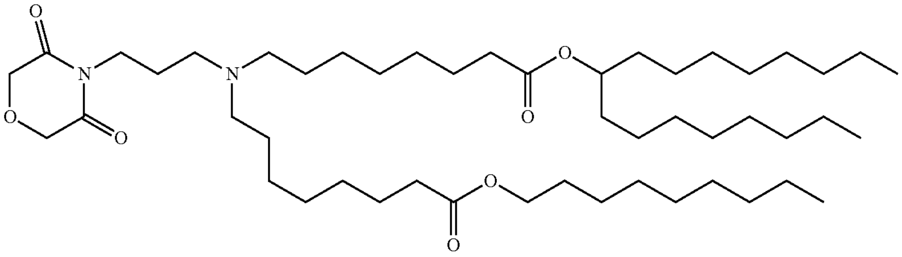
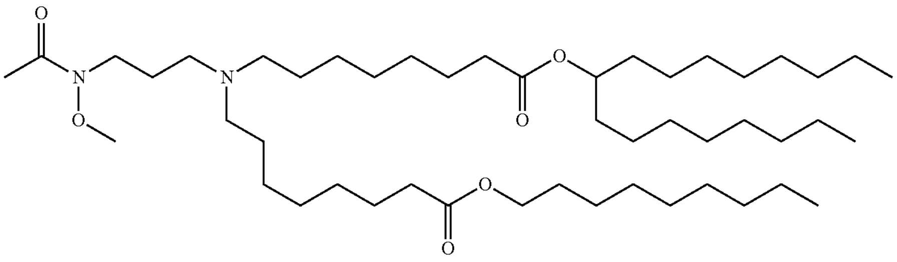

-continued
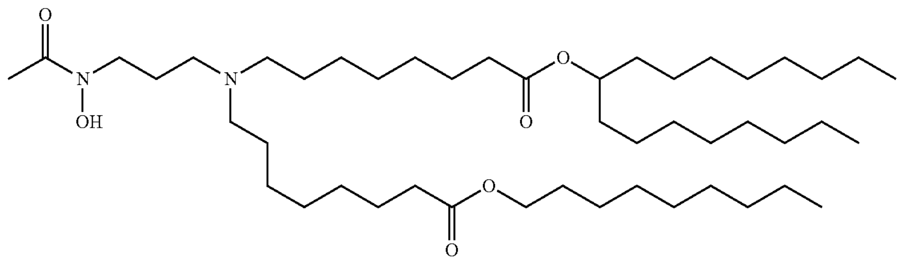
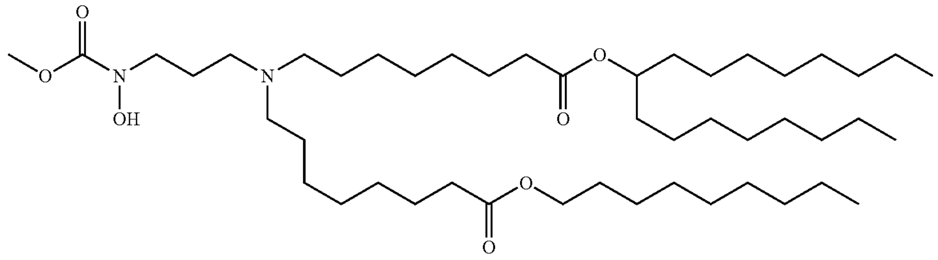
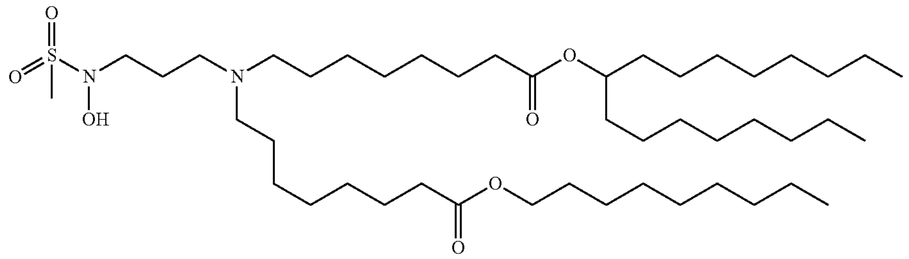
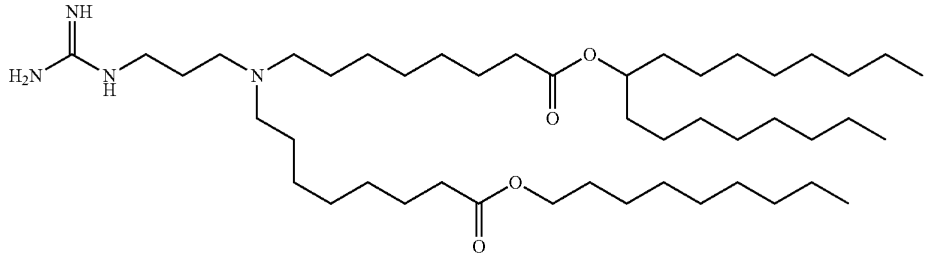
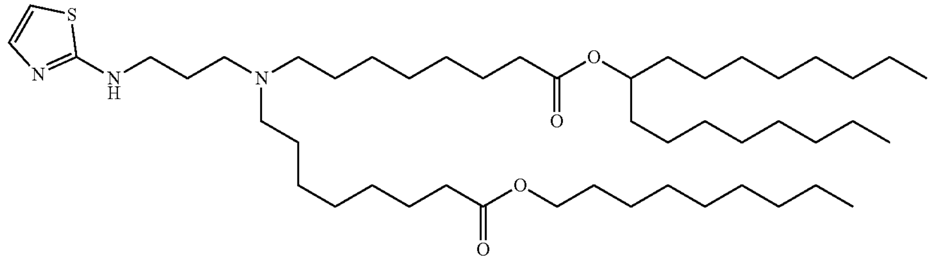
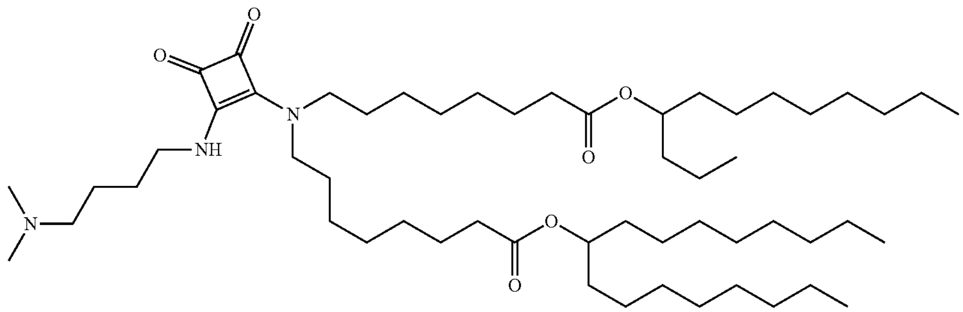

-continued
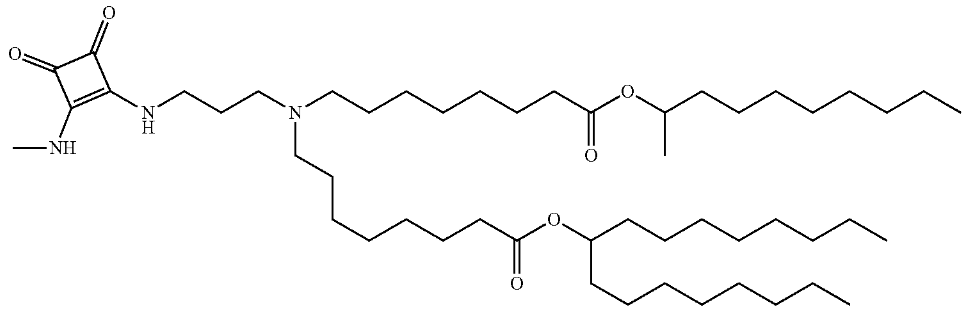
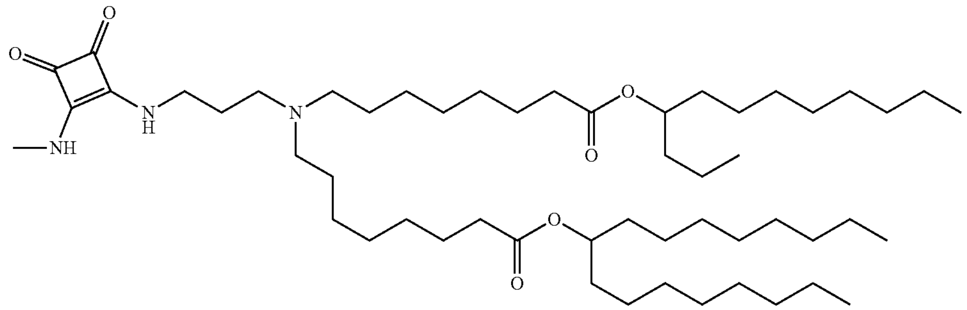
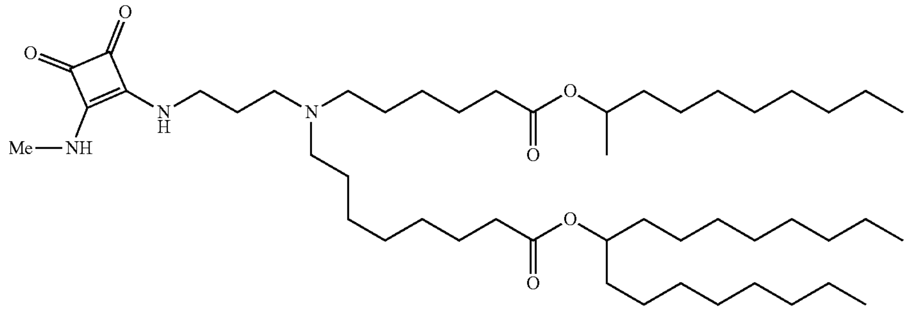
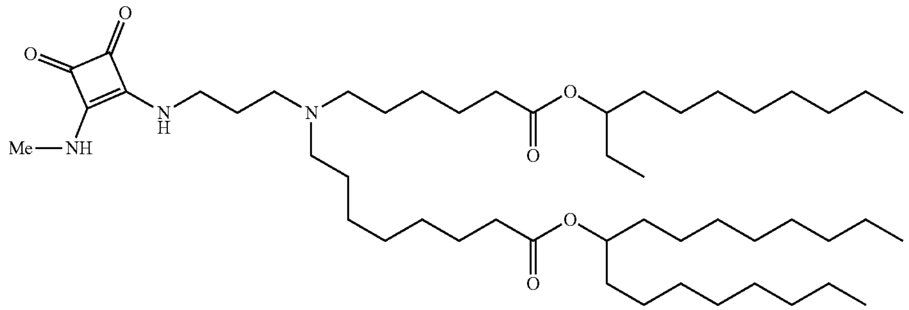
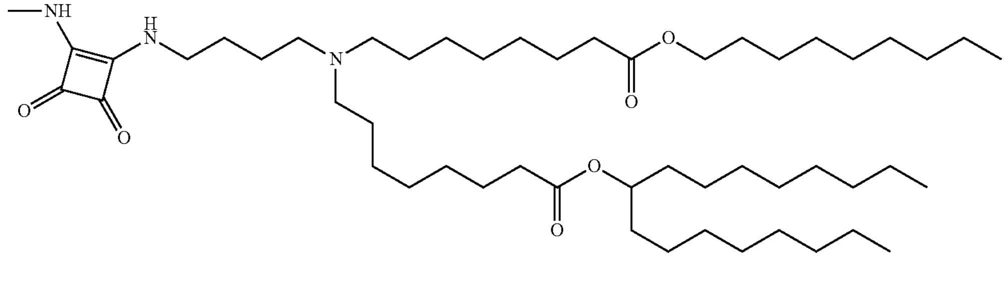

-continued
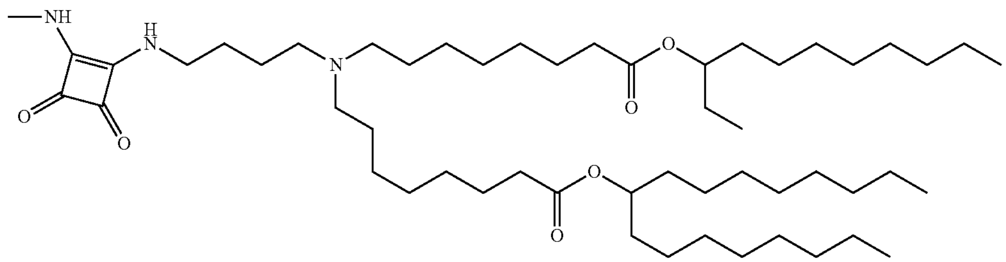
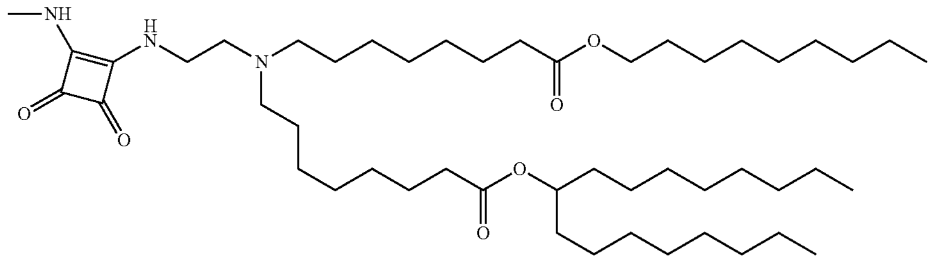
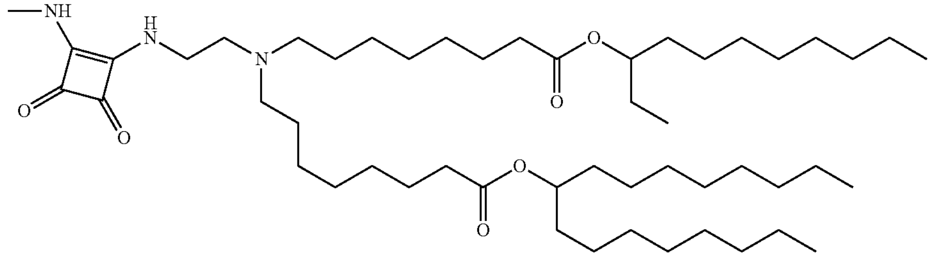
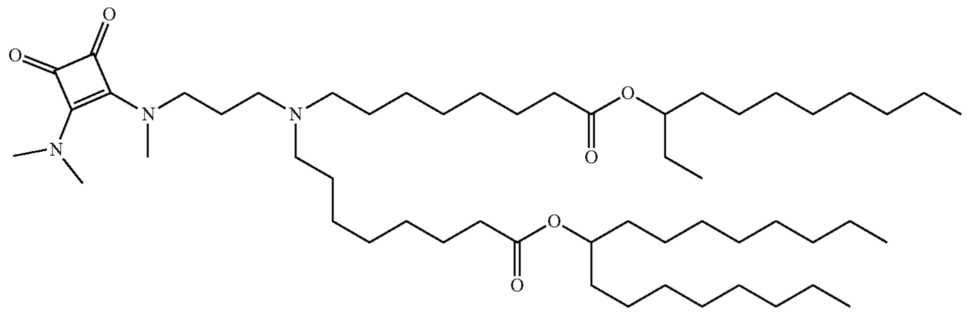
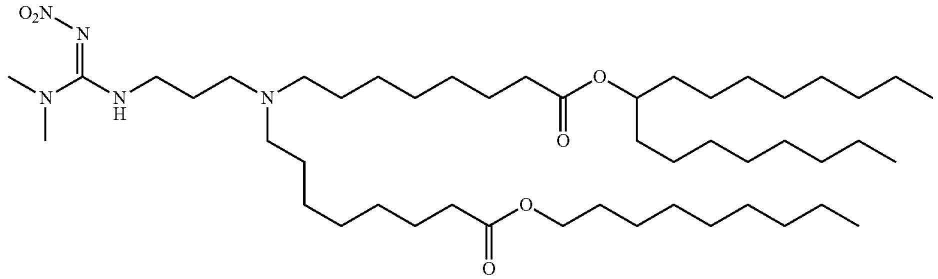
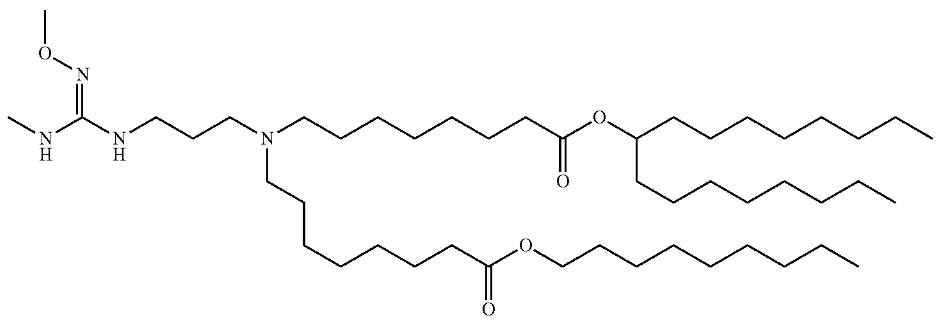

-continued
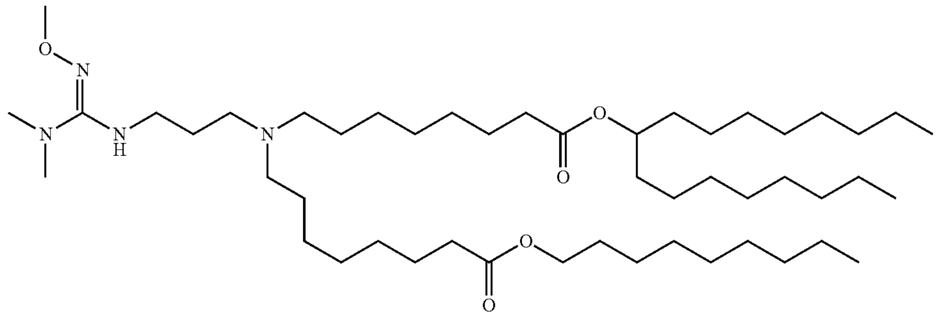
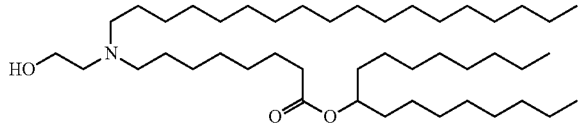
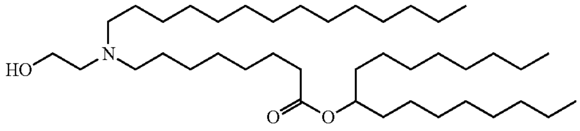
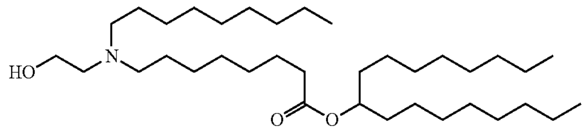
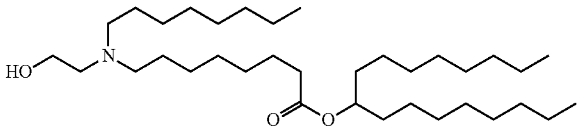
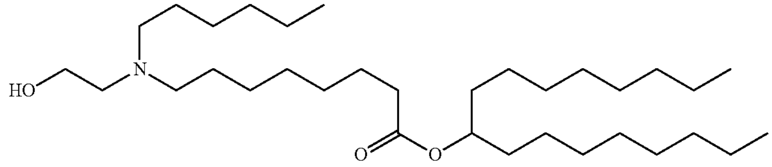
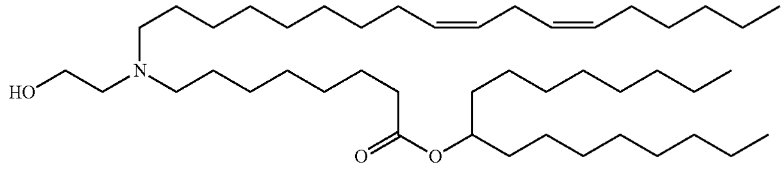
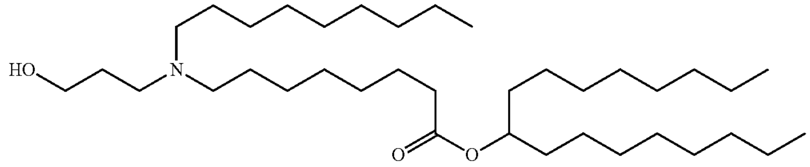
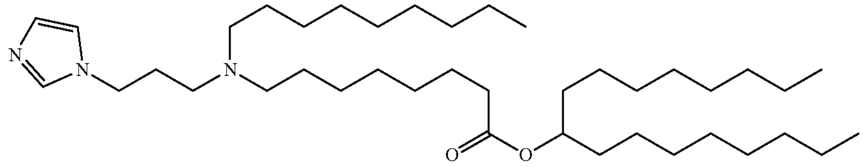
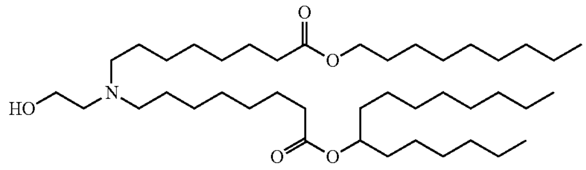
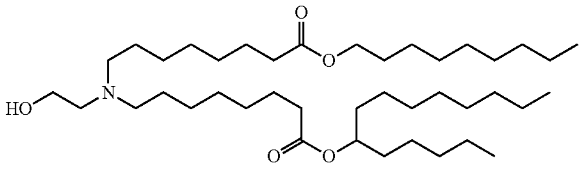
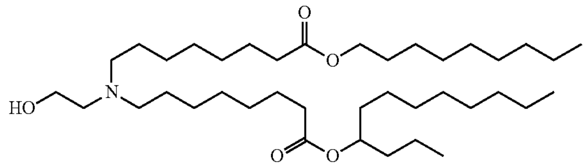
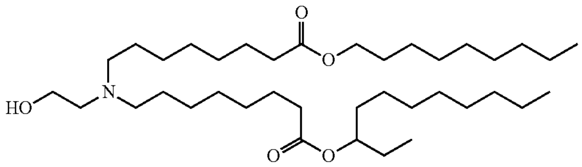

-continued
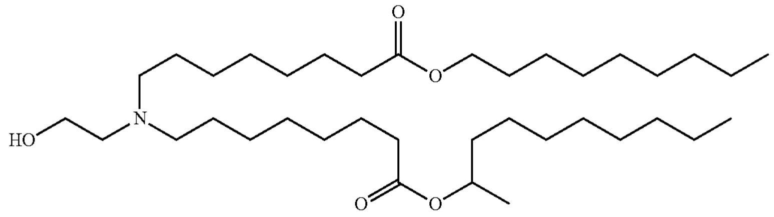
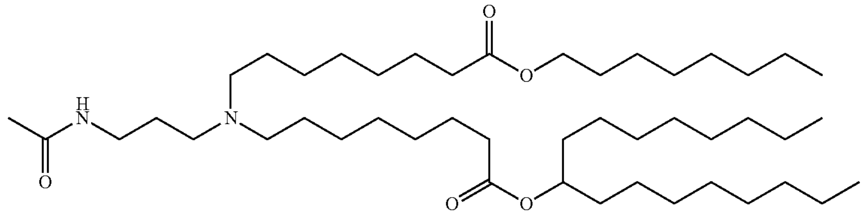
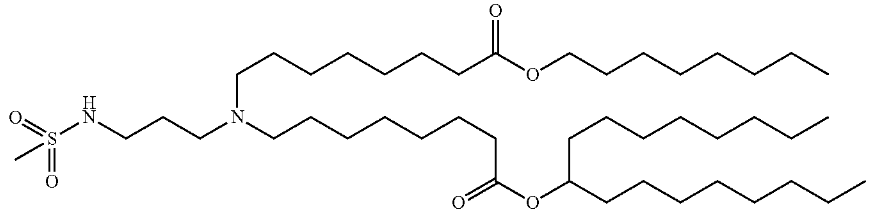
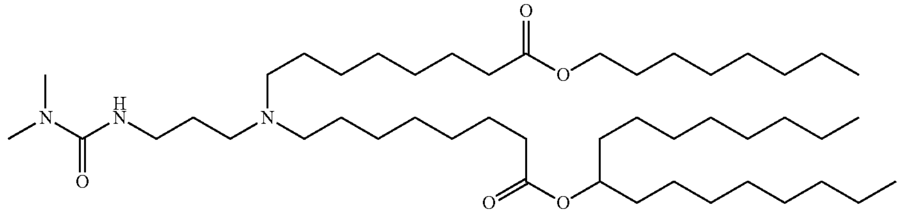
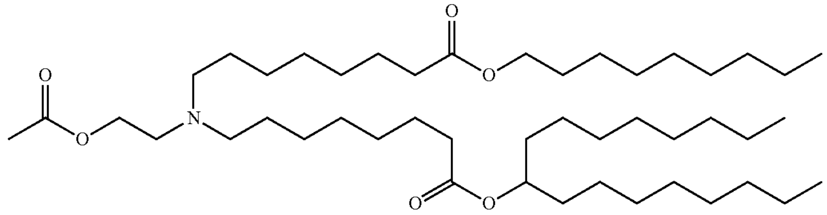
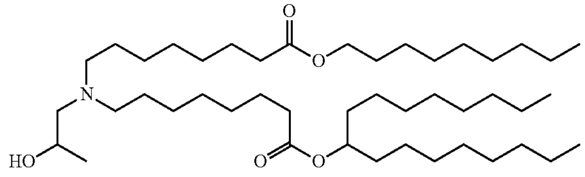
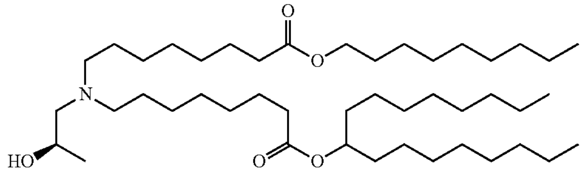
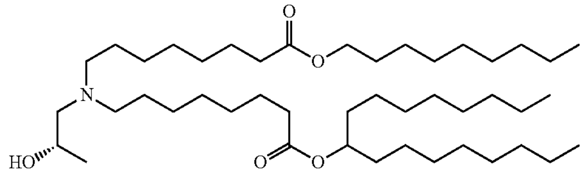
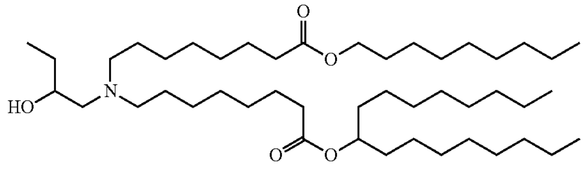
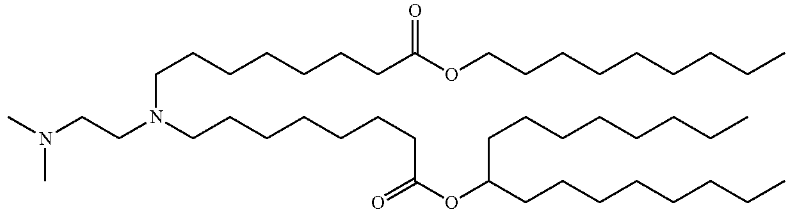

-continued
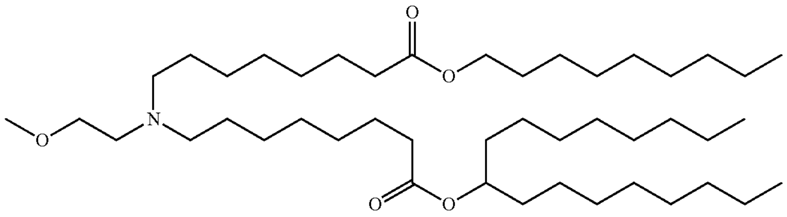
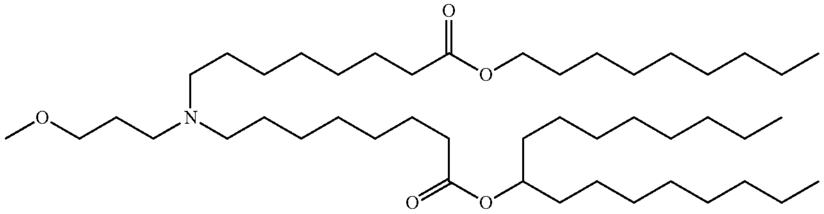
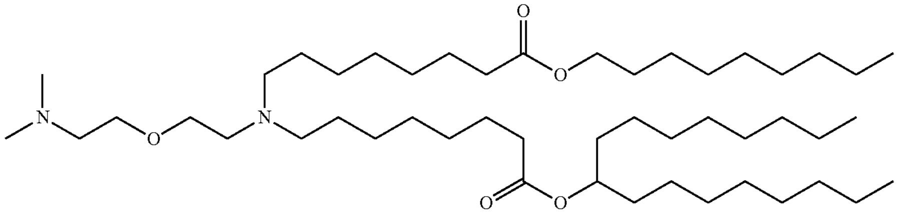
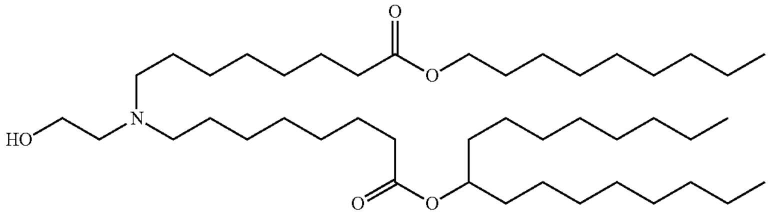
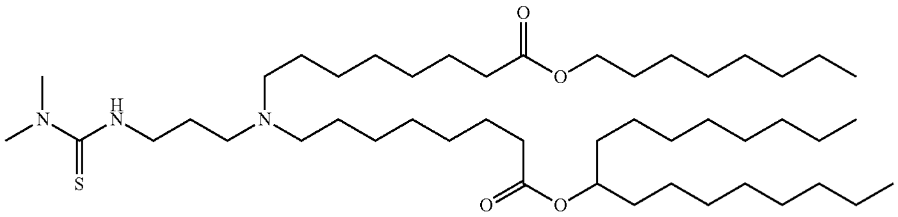
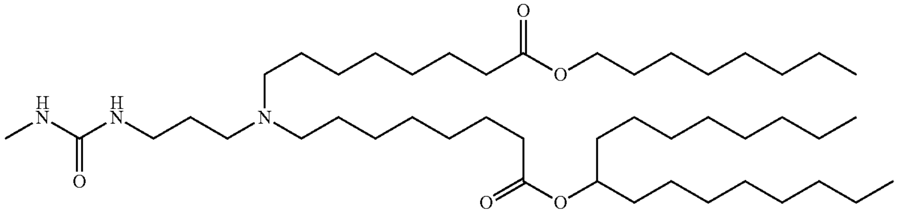
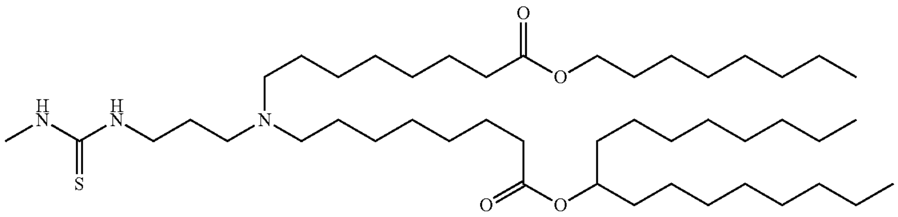
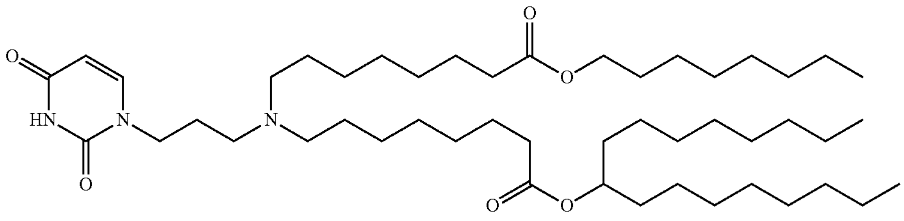

-continued
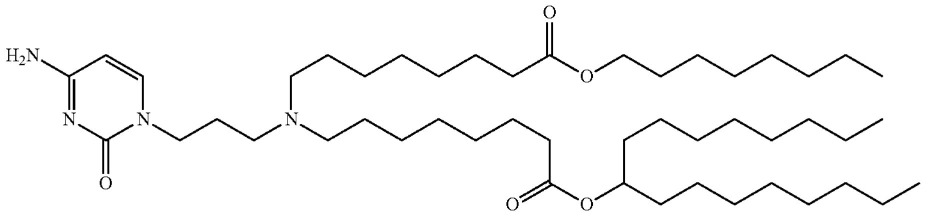
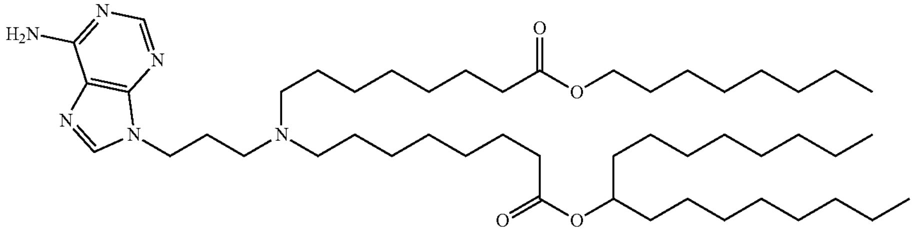
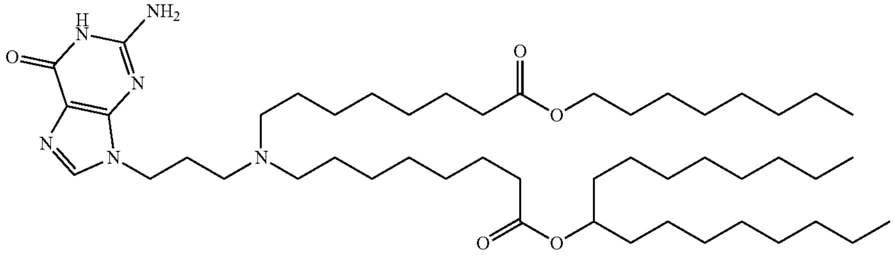
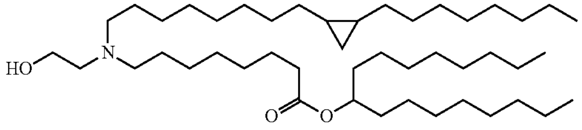
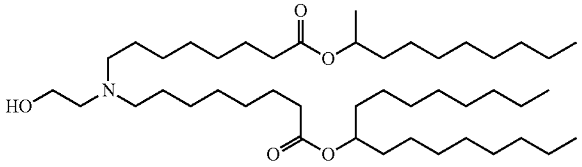
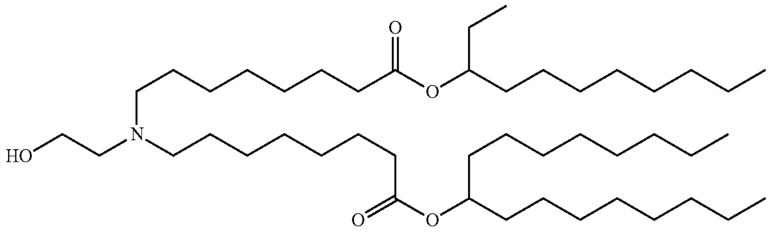
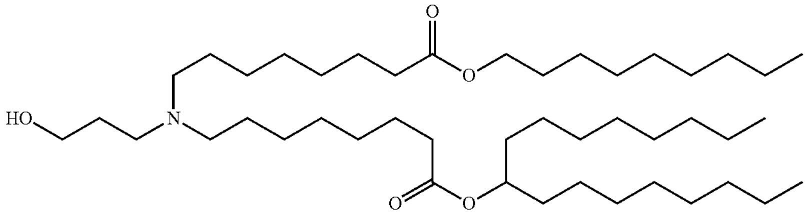
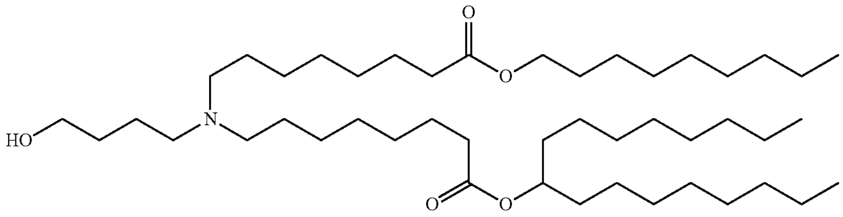
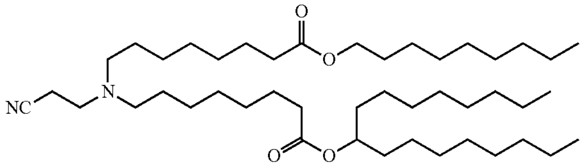
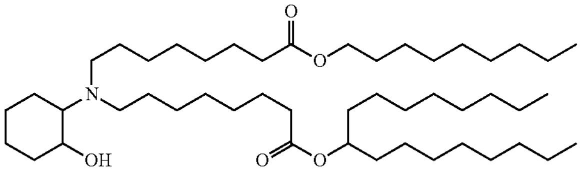

-continued
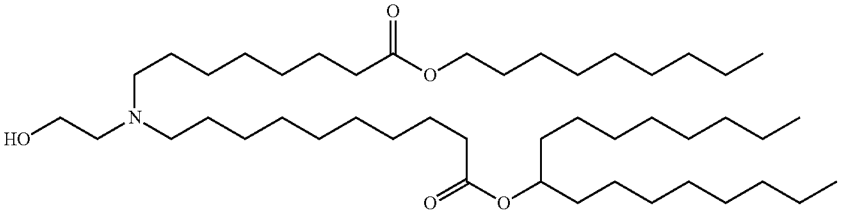
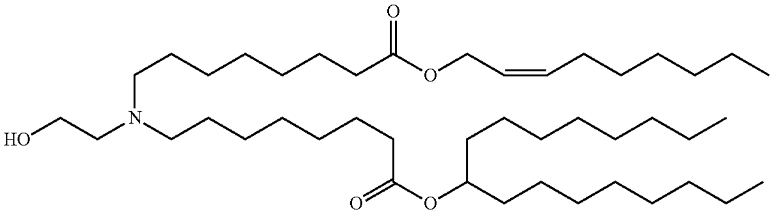
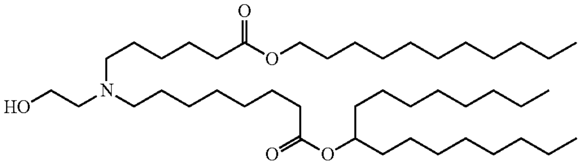
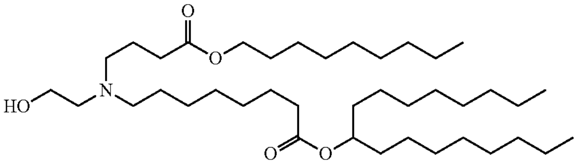
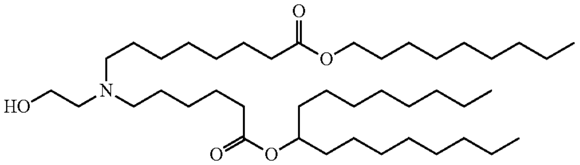
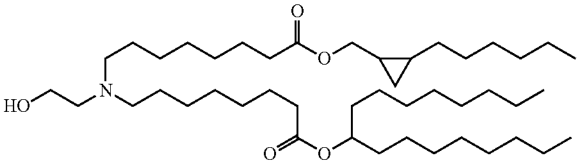
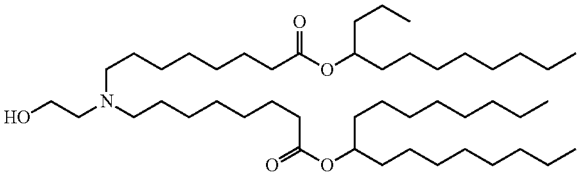
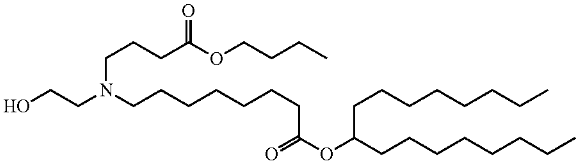
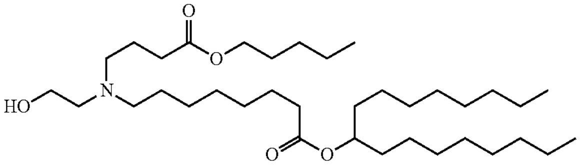
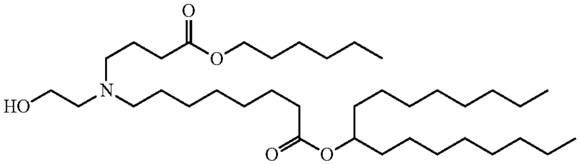
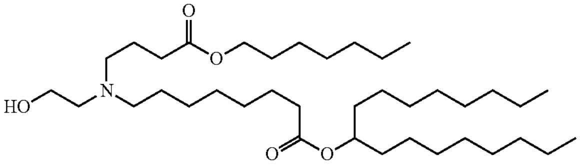
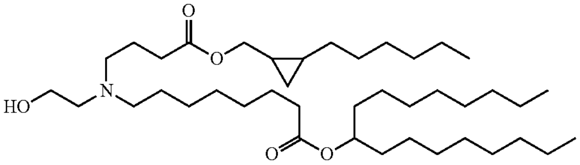
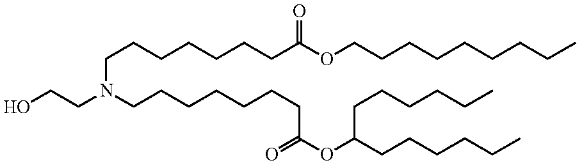
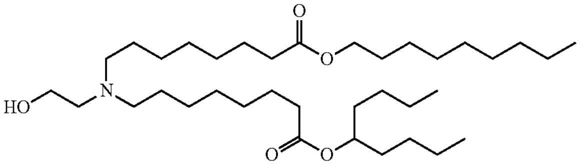
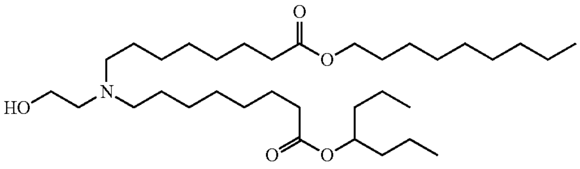
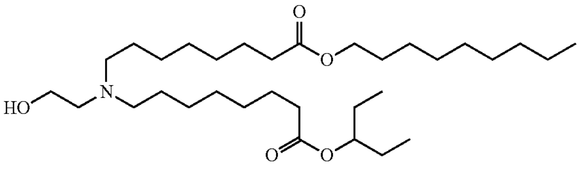

-continued
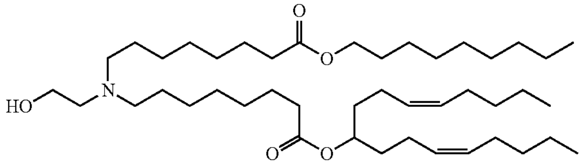
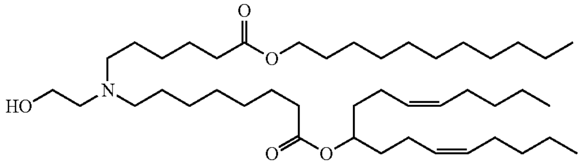
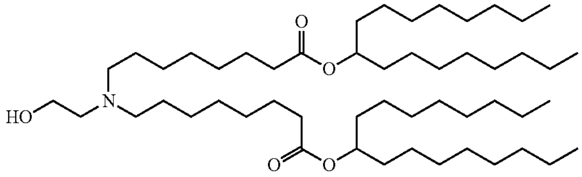
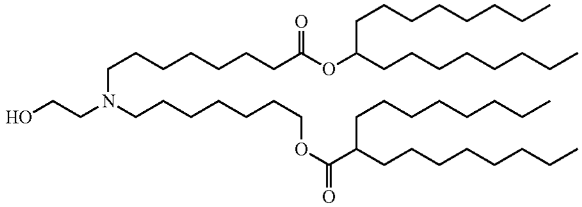
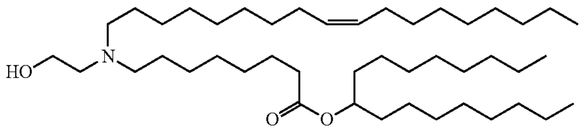
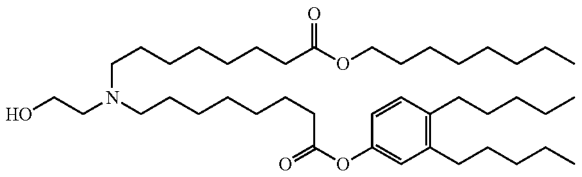
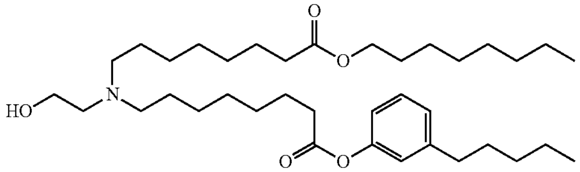
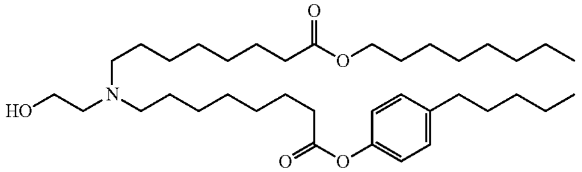
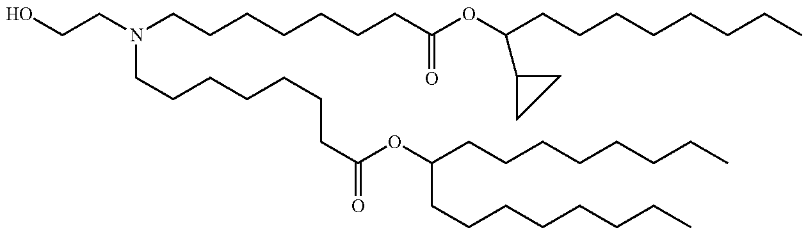
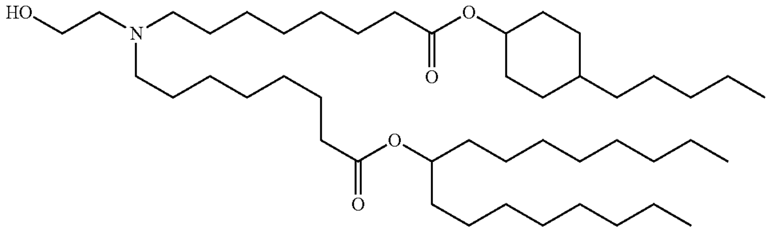
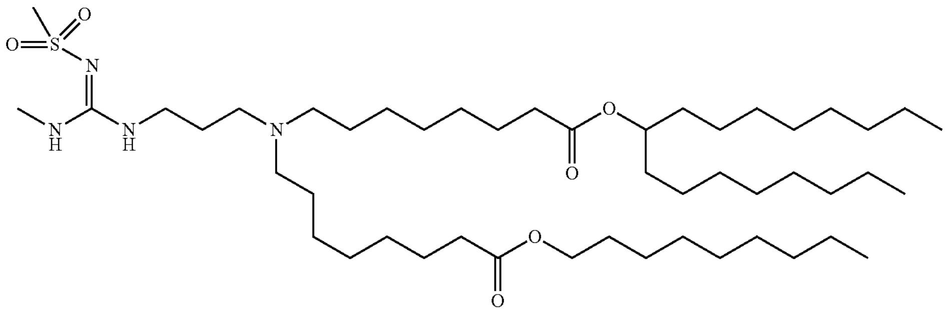

-continued
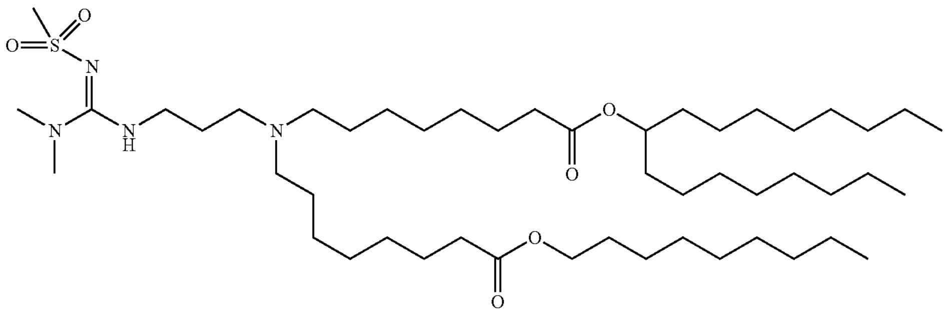
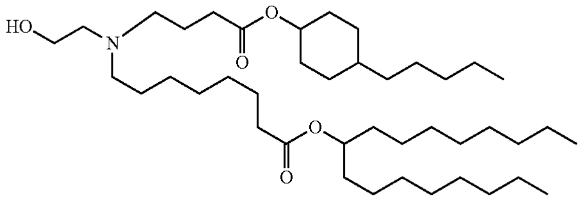
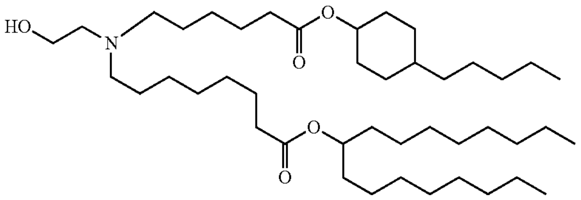
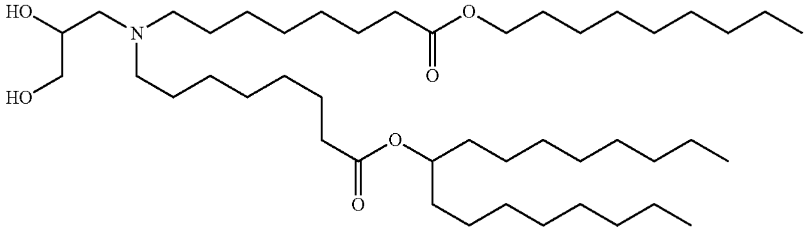
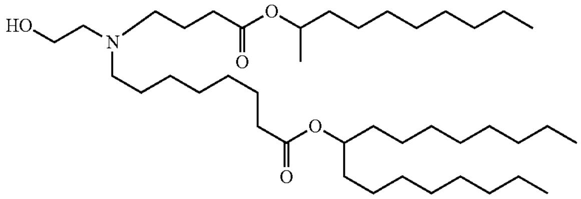
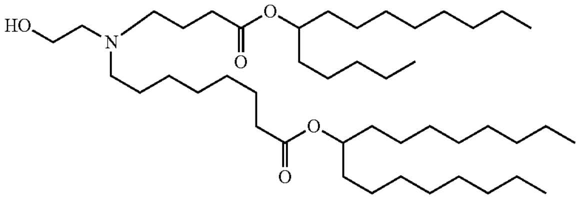
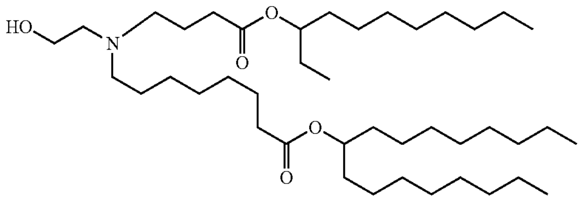
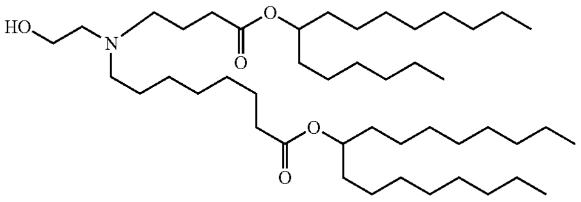
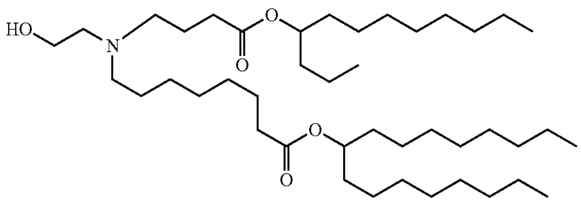
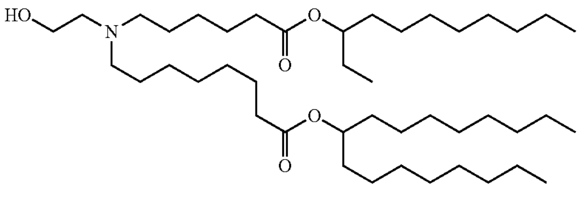
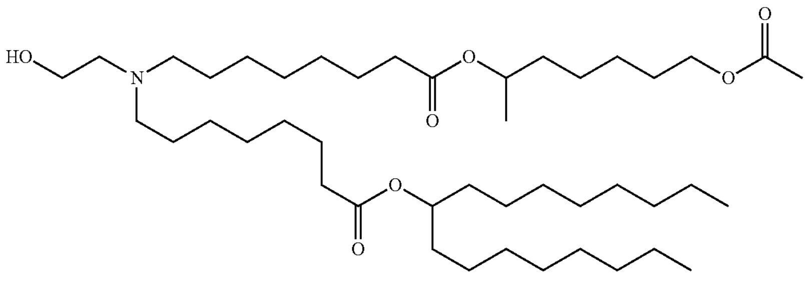

-continued
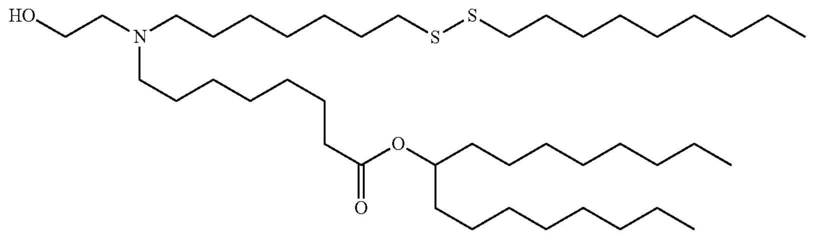
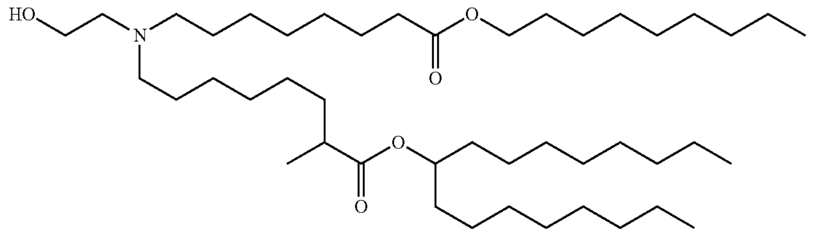
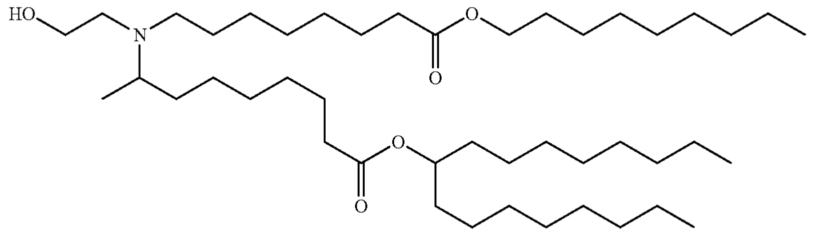
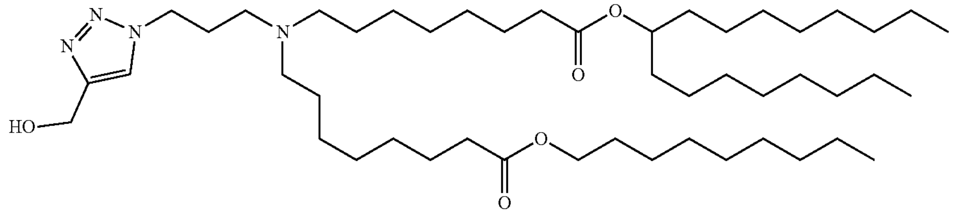
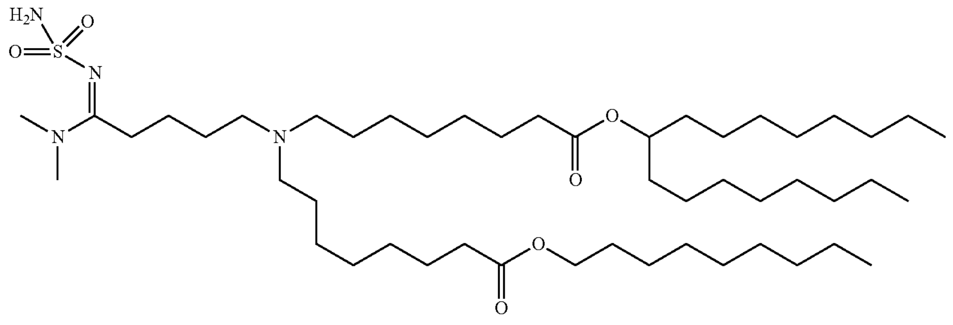
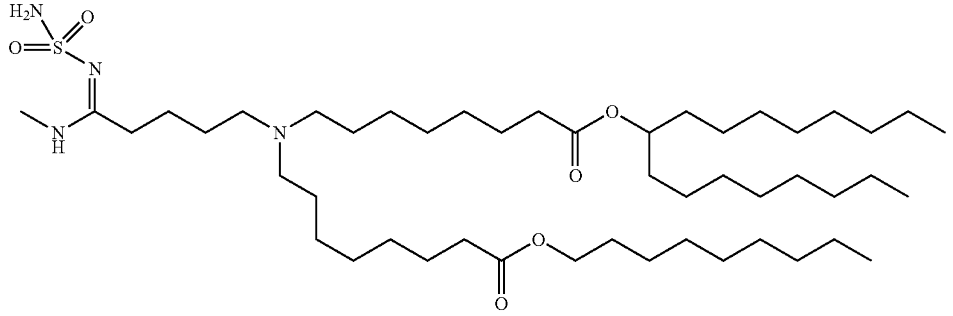

-continued
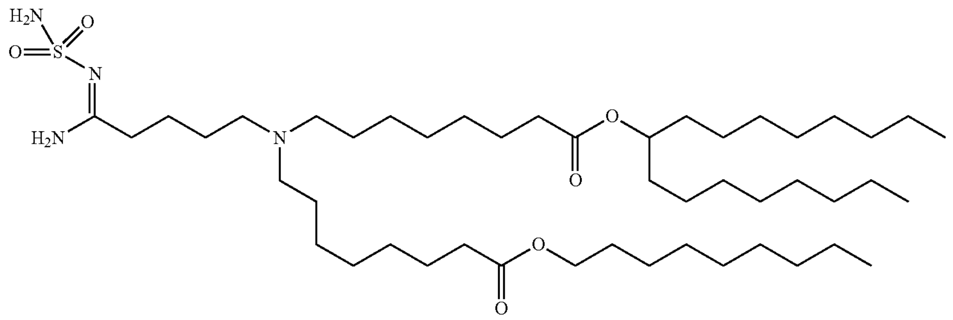
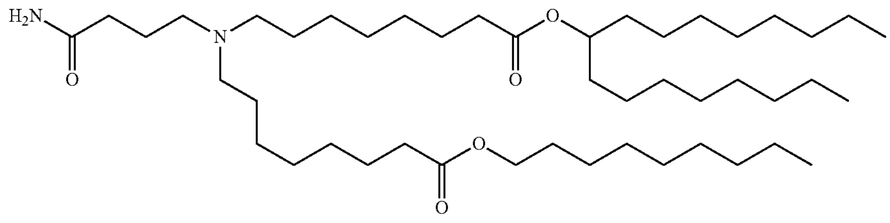
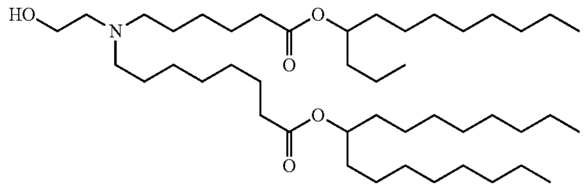
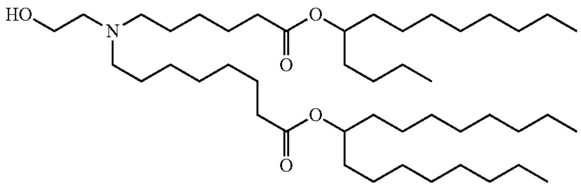
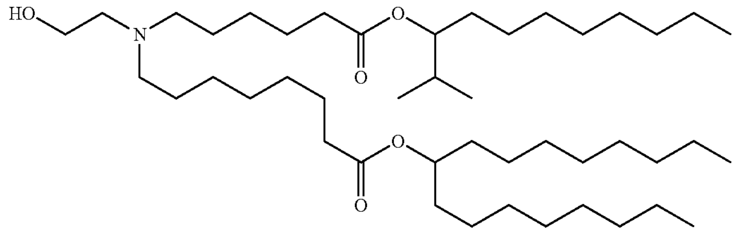
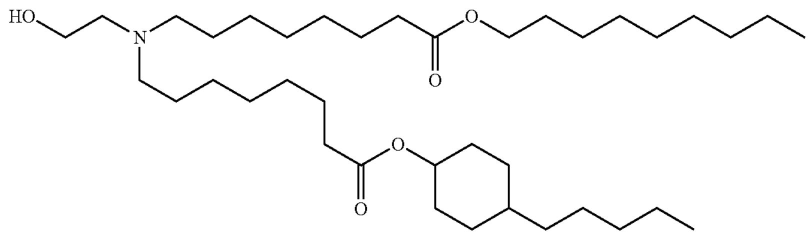
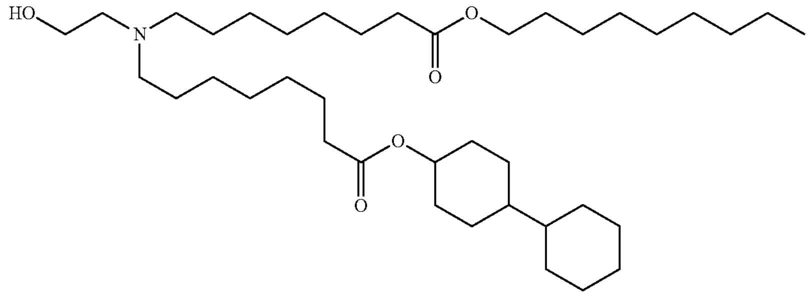

-continued
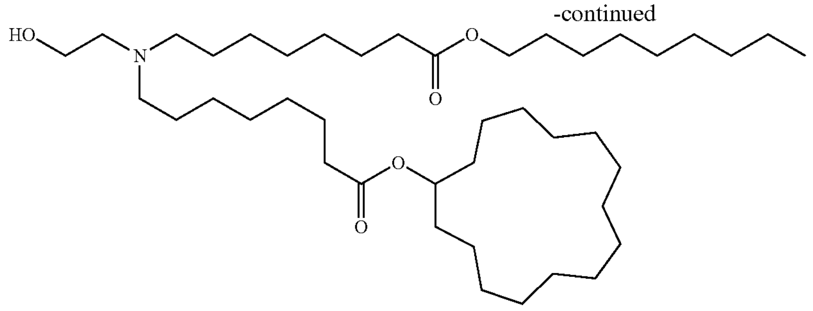
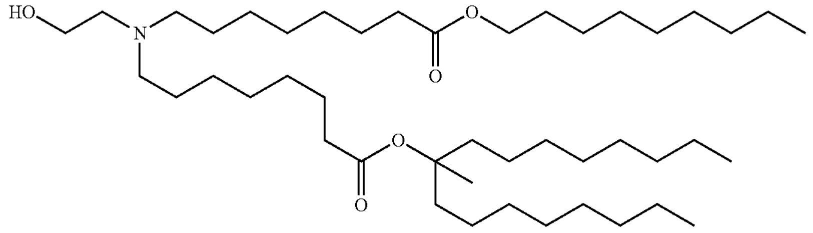
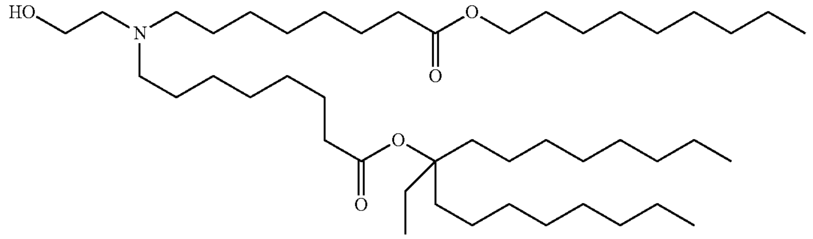
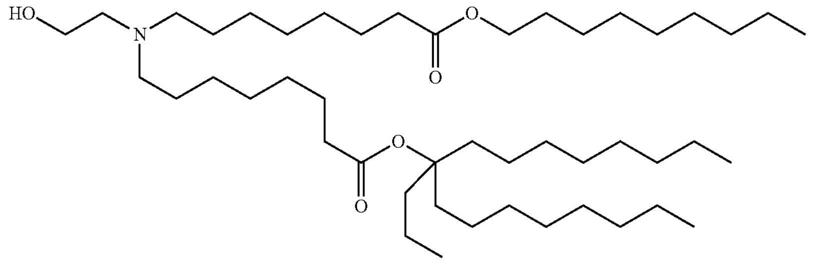
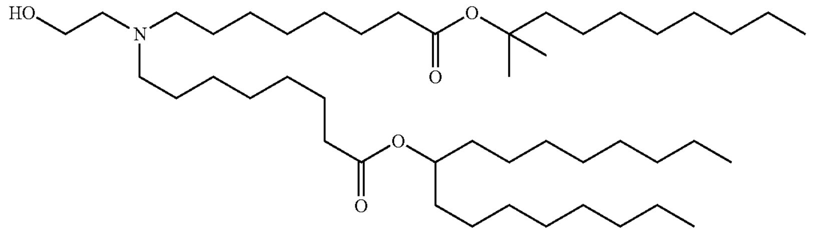
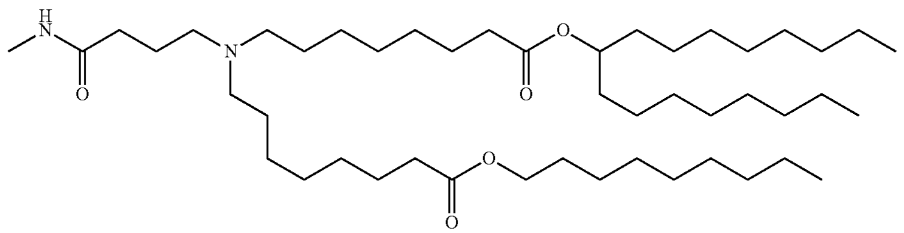
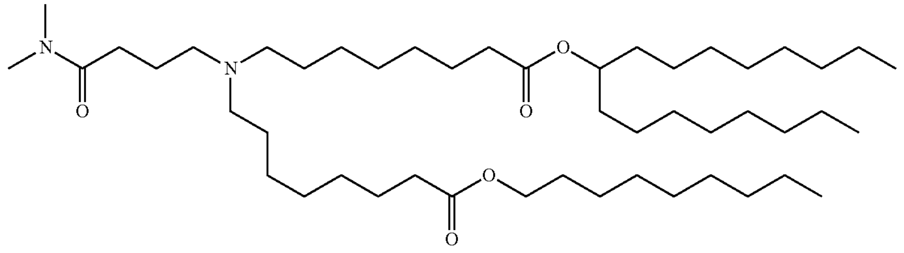

-continued
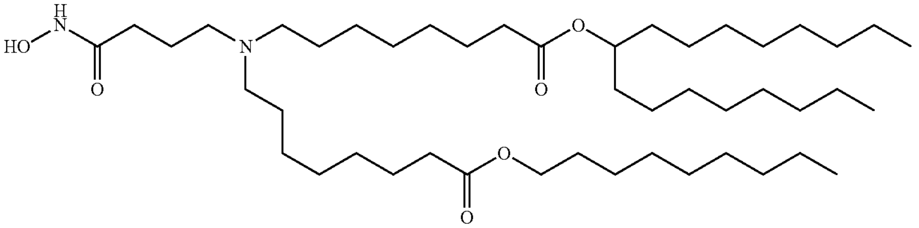
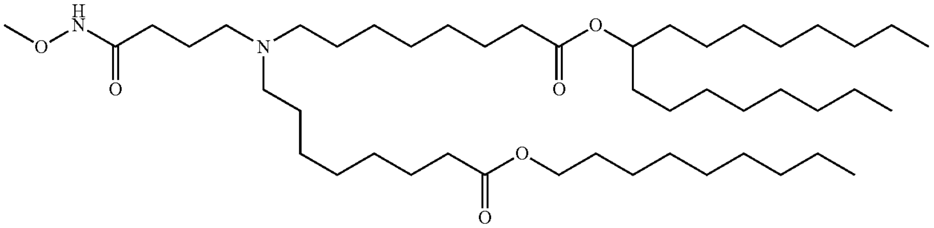
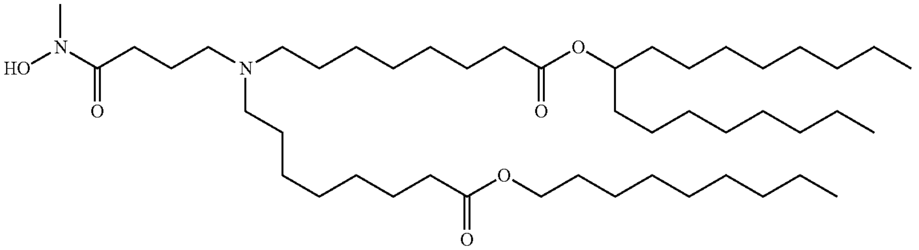
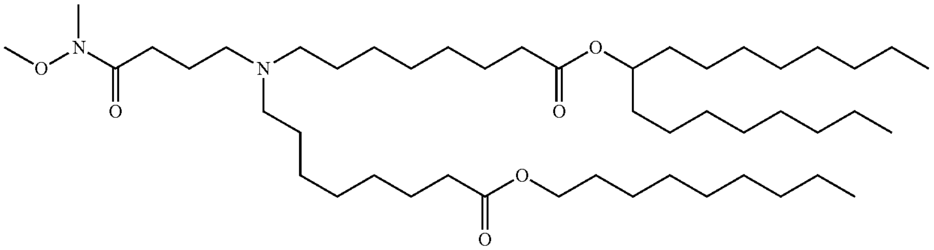
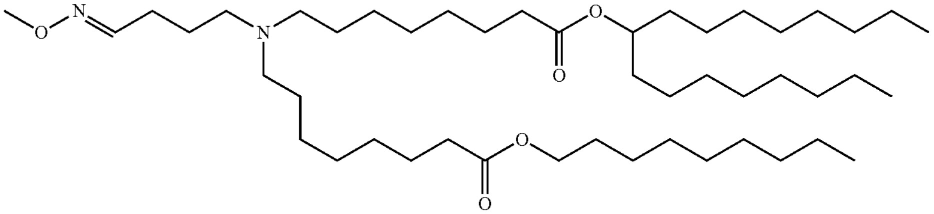
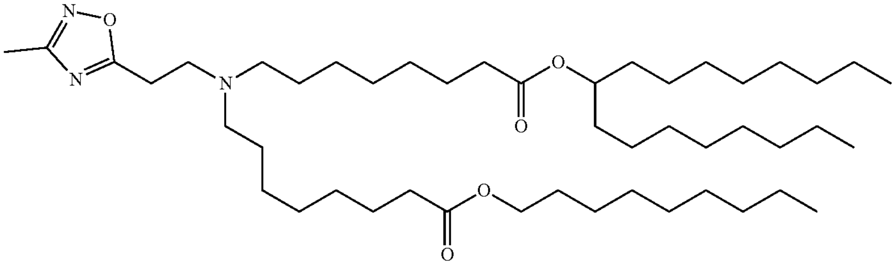
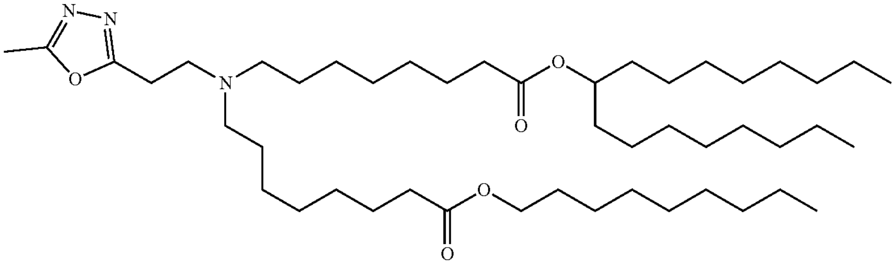

-continued
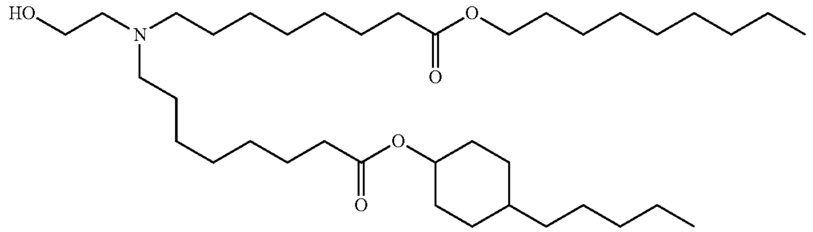
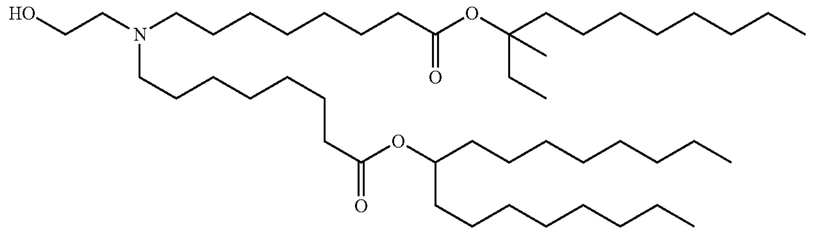
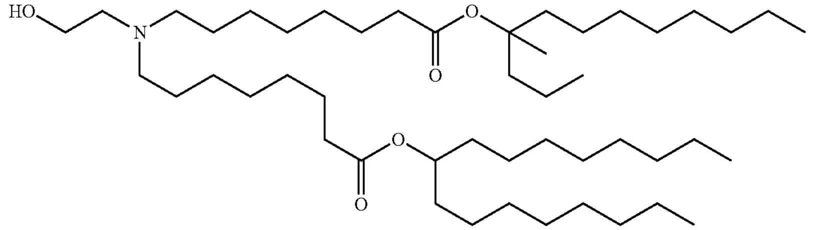
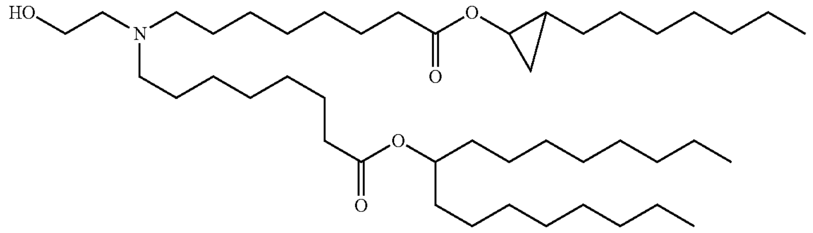
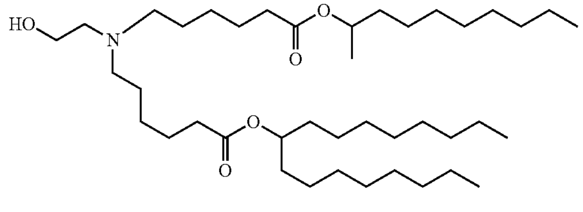
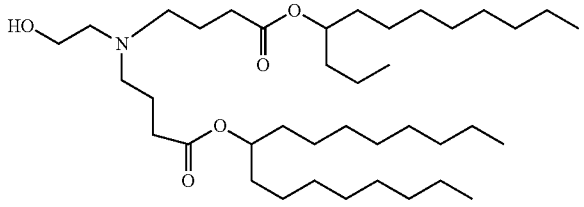
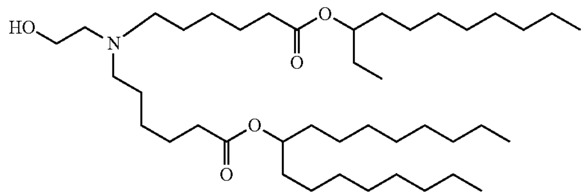
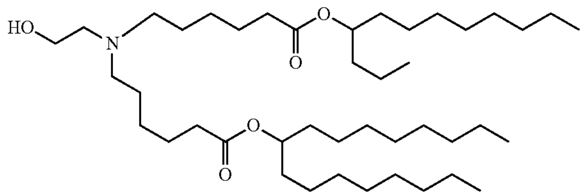
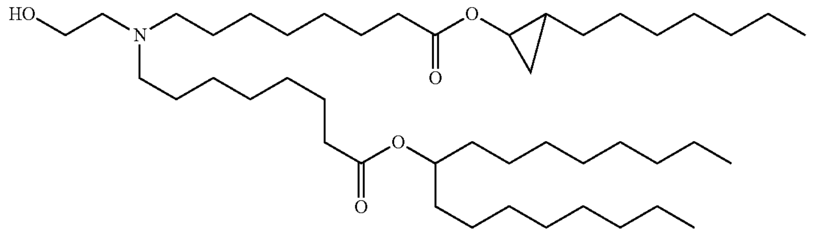

-continued
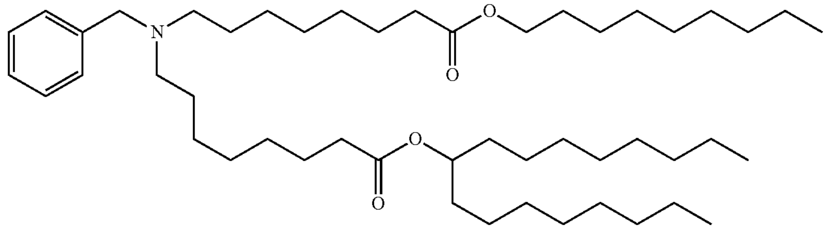
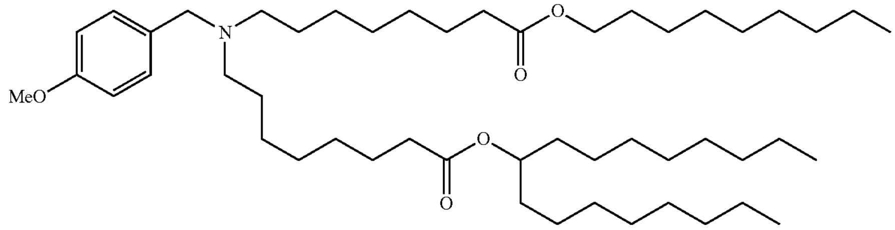
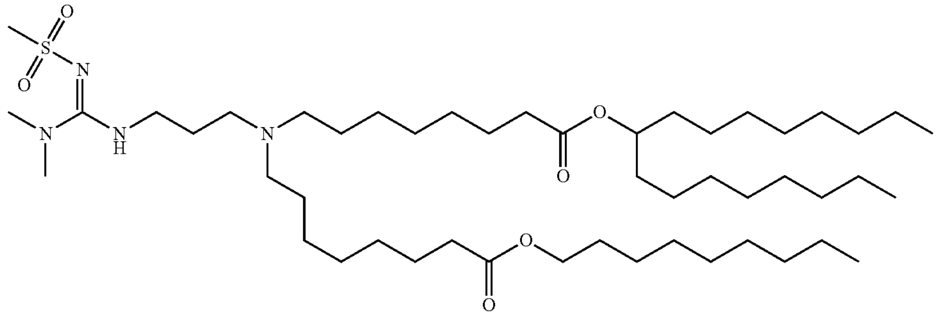
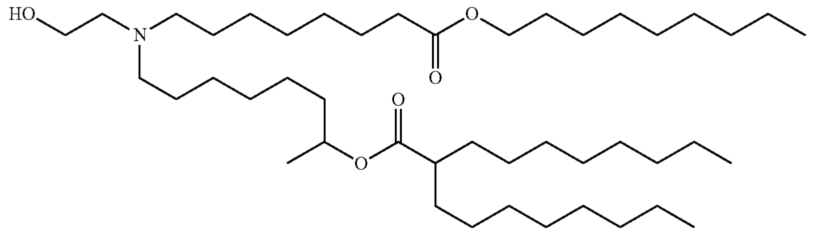
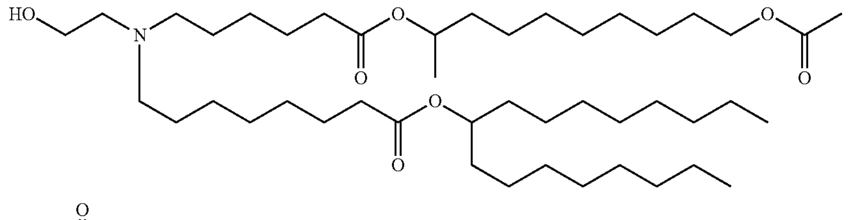
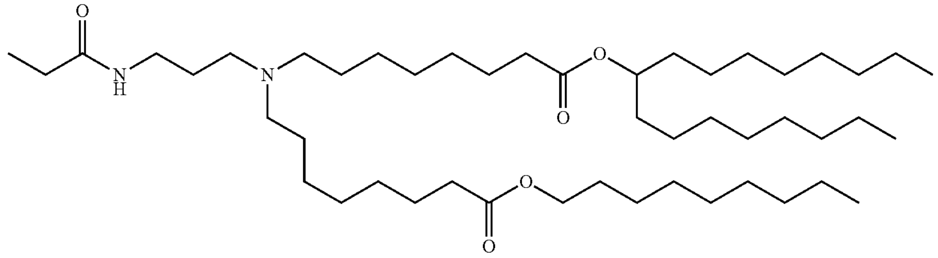
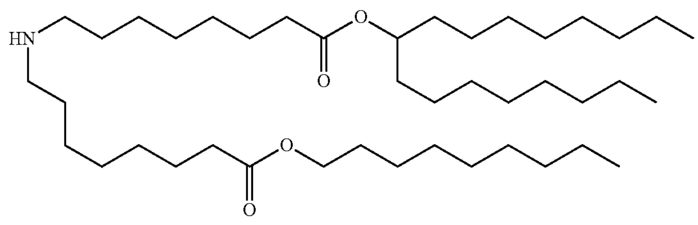

-continued
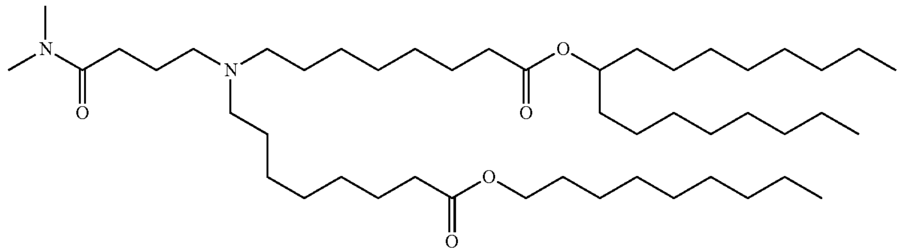
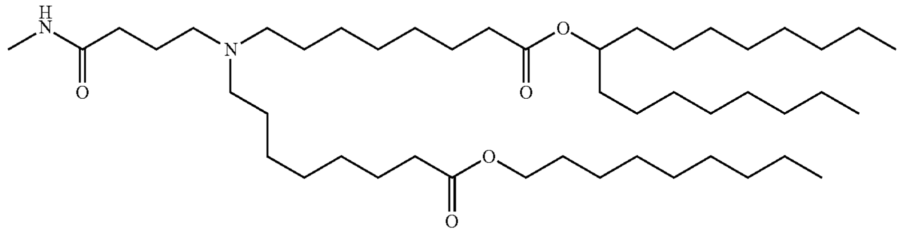
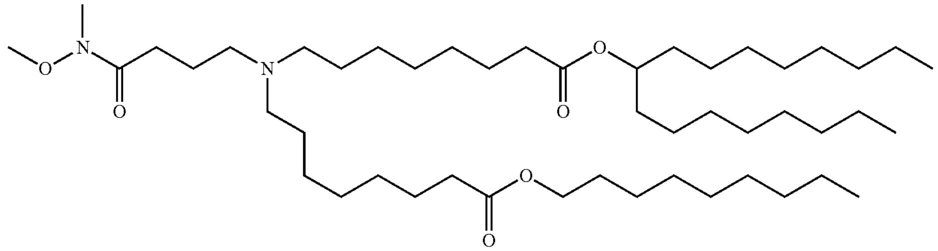
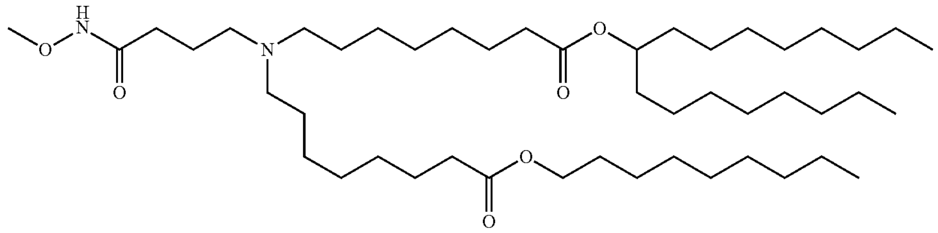
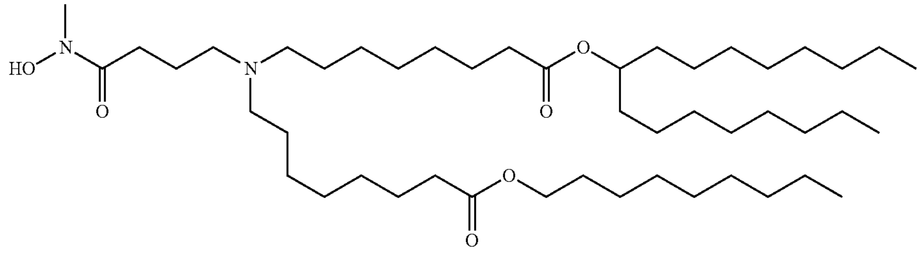
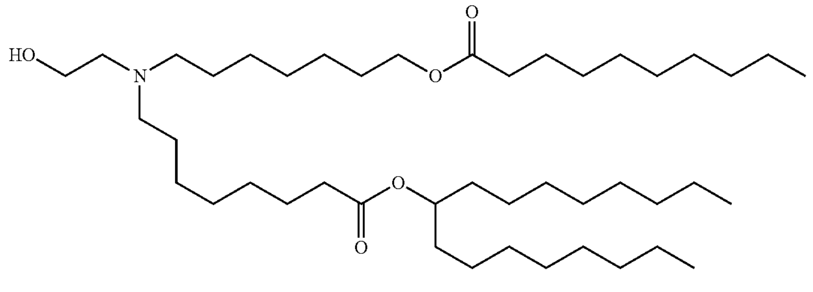

-continued
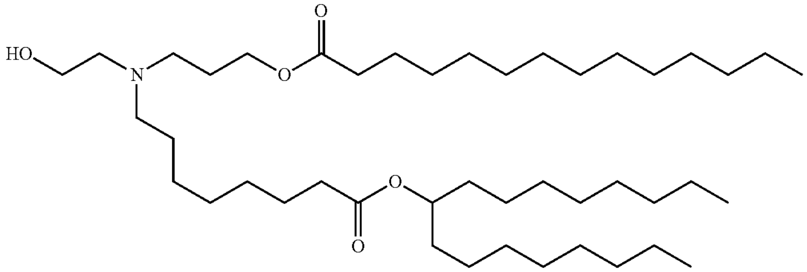
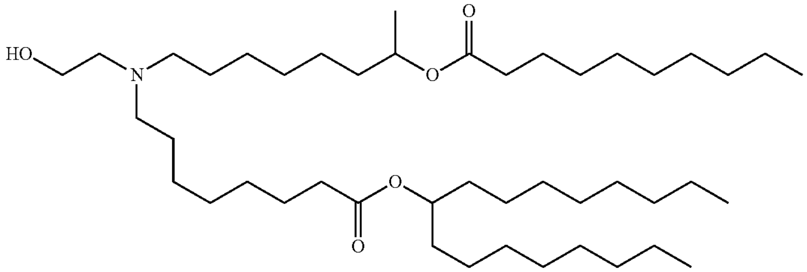
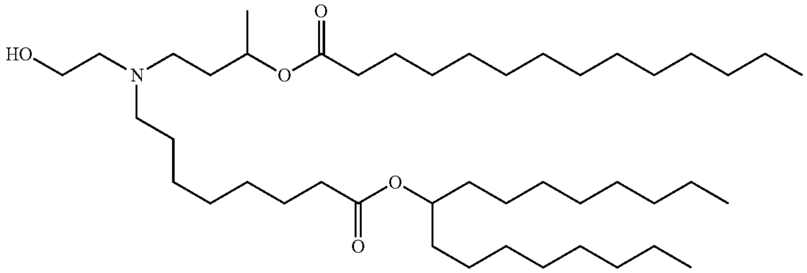
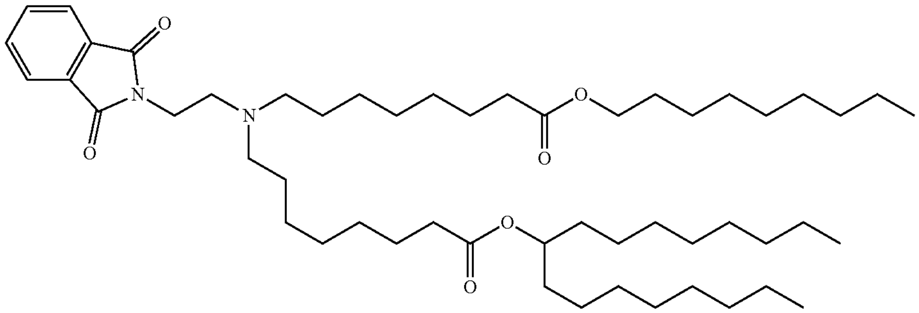
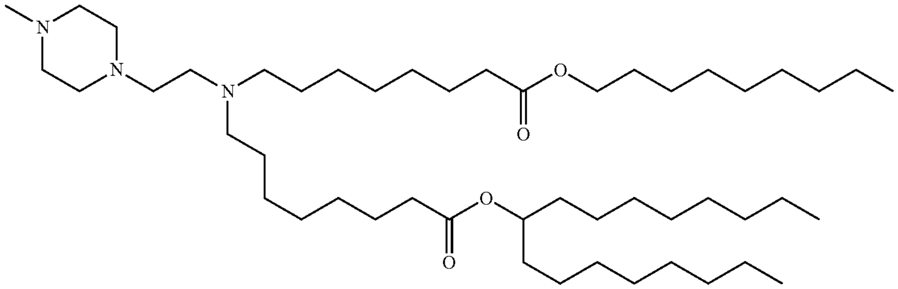
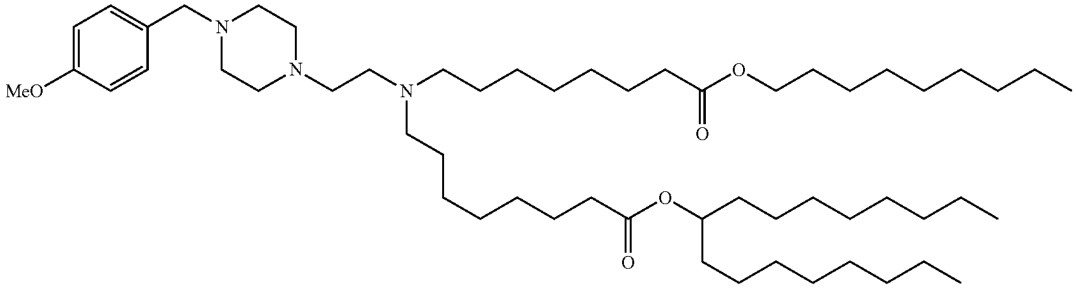

-continued
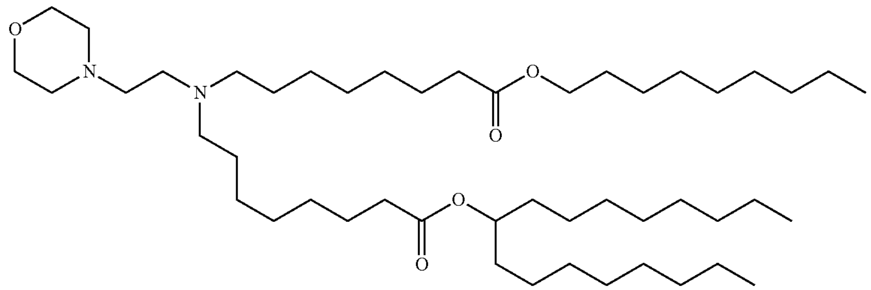
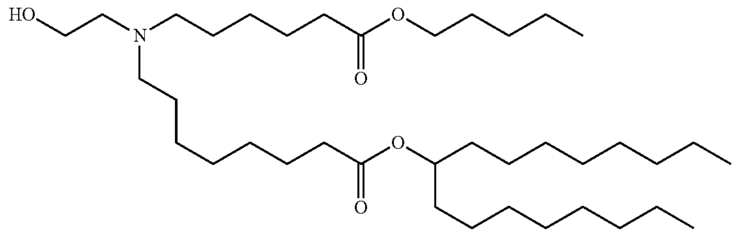
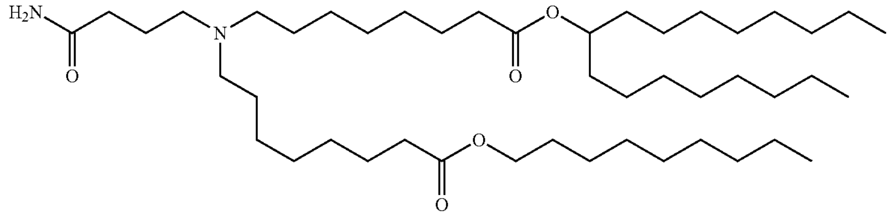
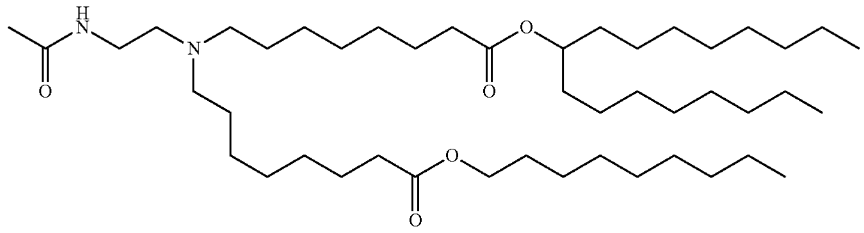
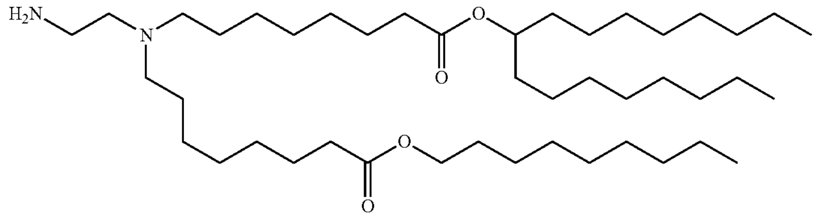
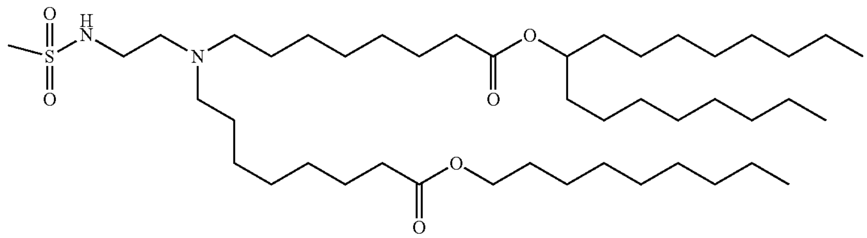
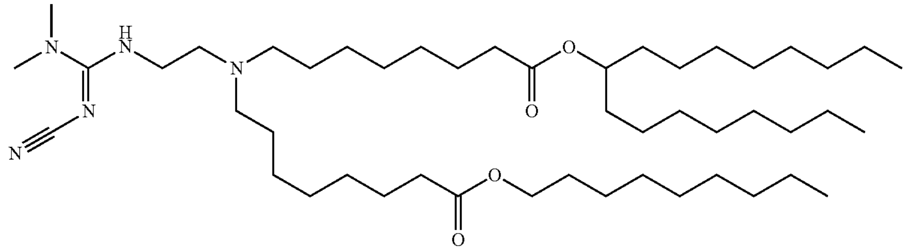

-continued
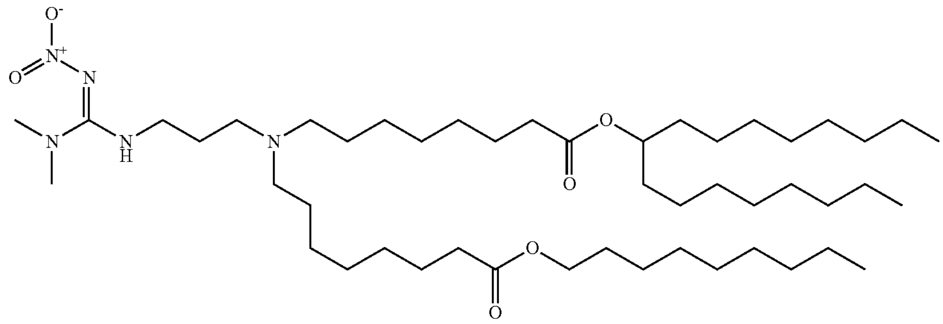
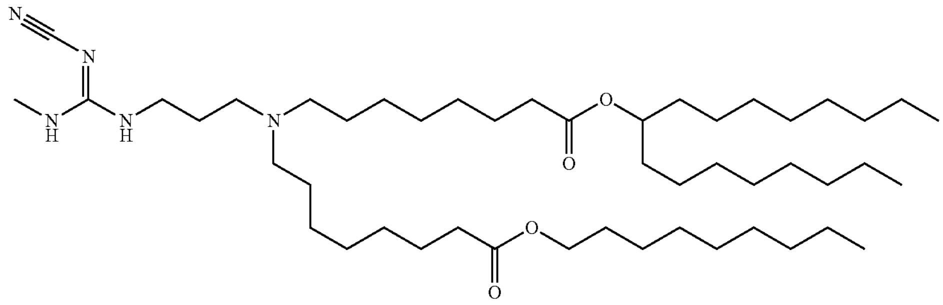
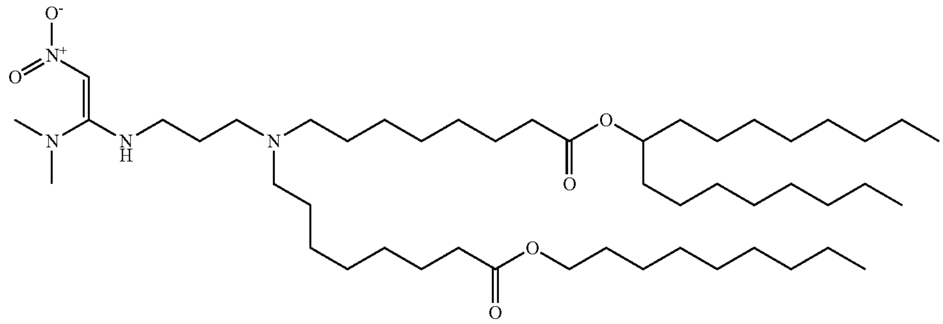
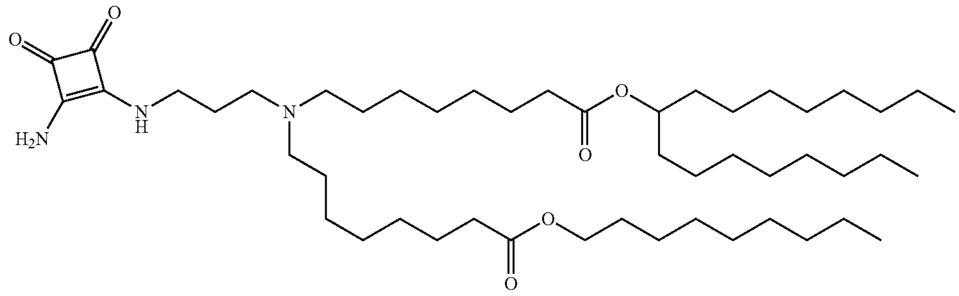
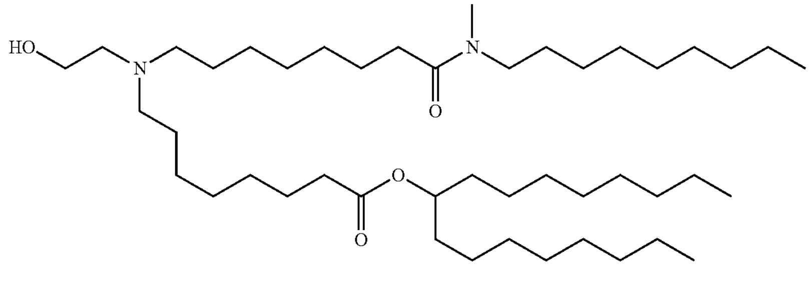

-continued
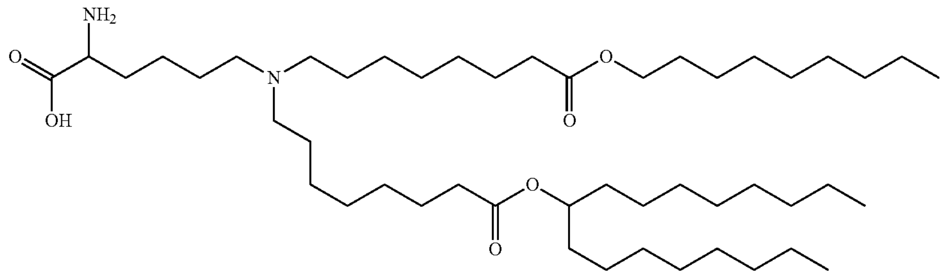
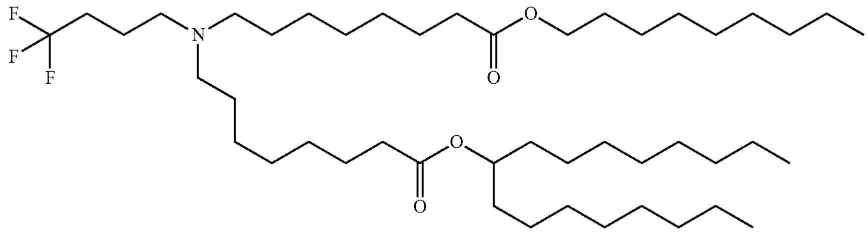
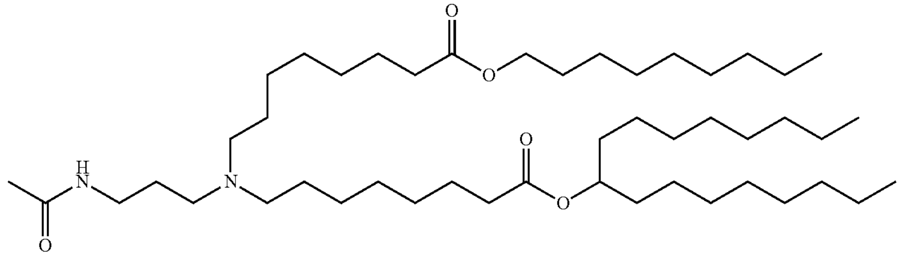
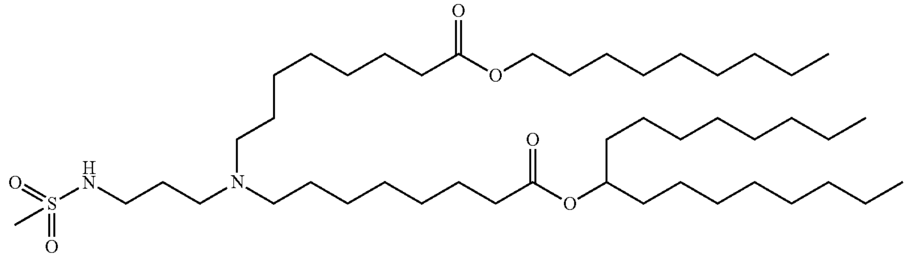
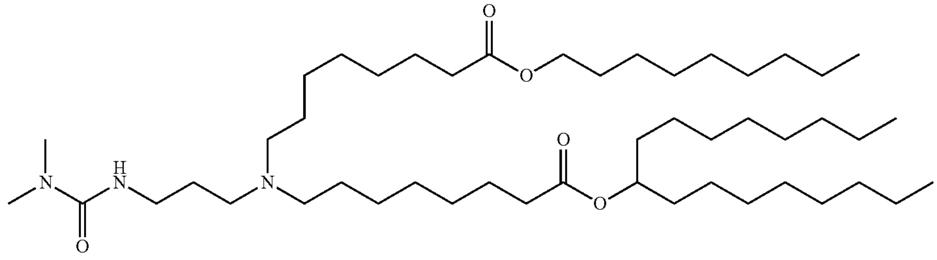
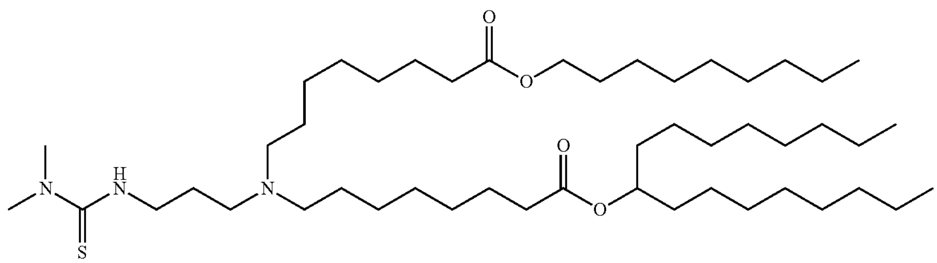

-continued
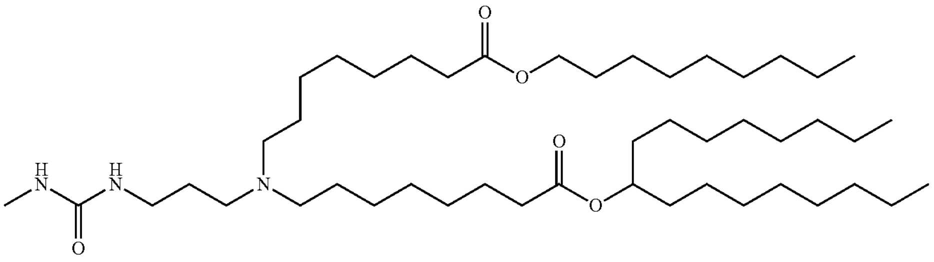
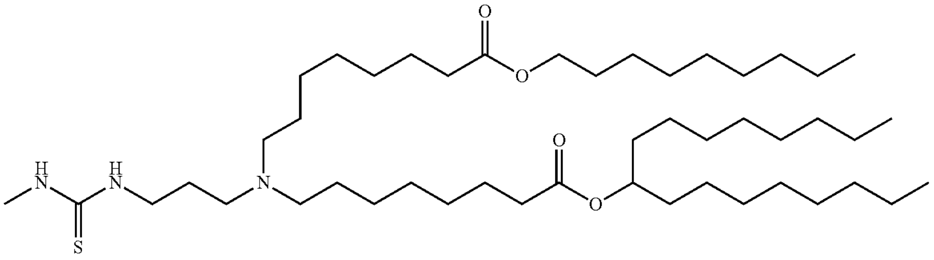
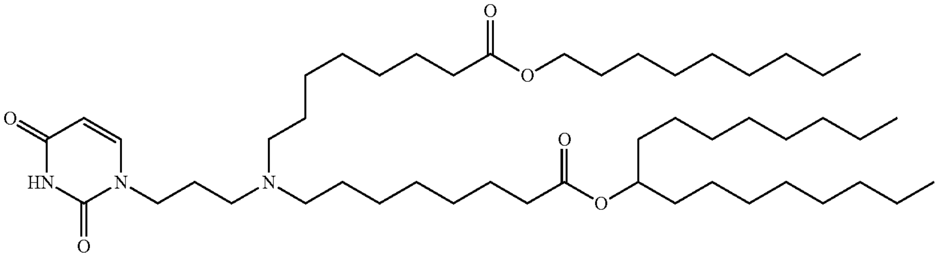
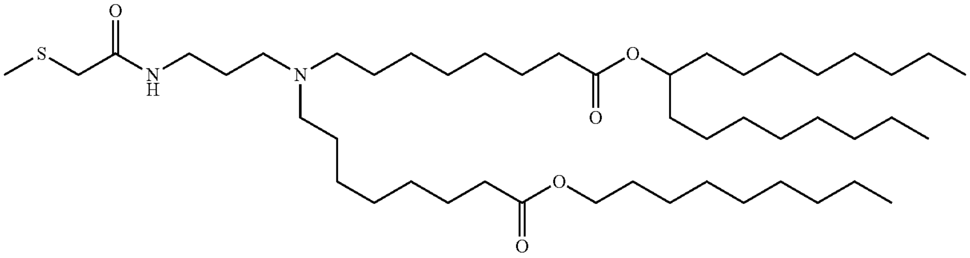
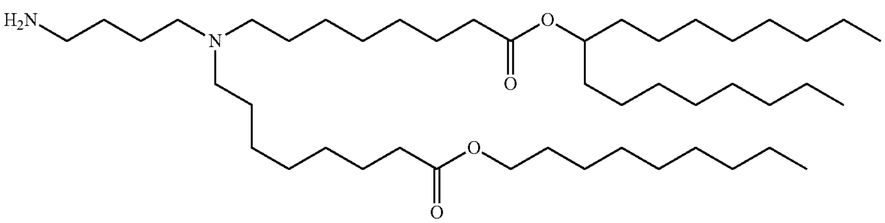
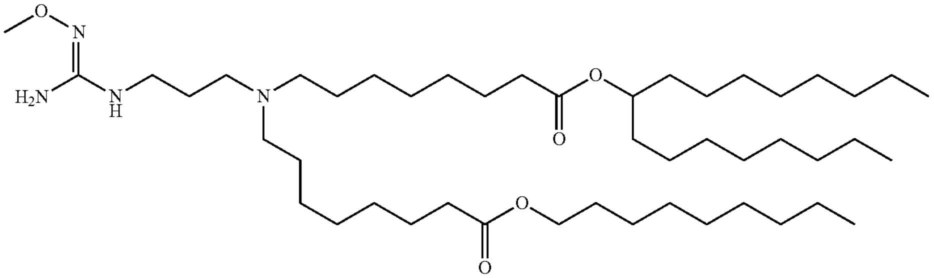

-continued
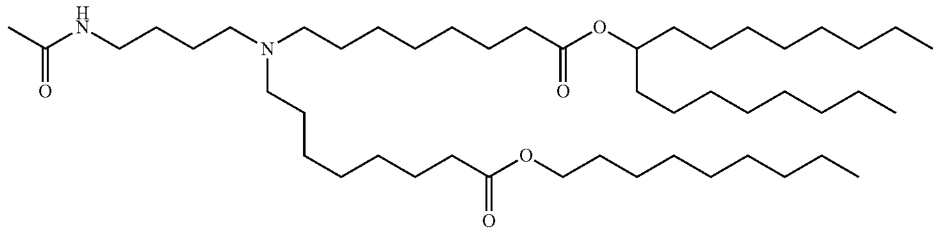
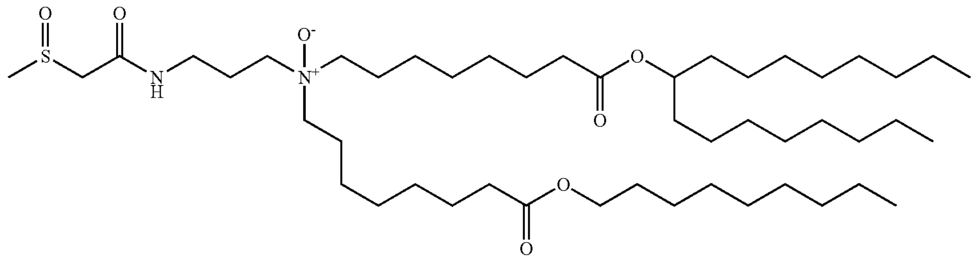
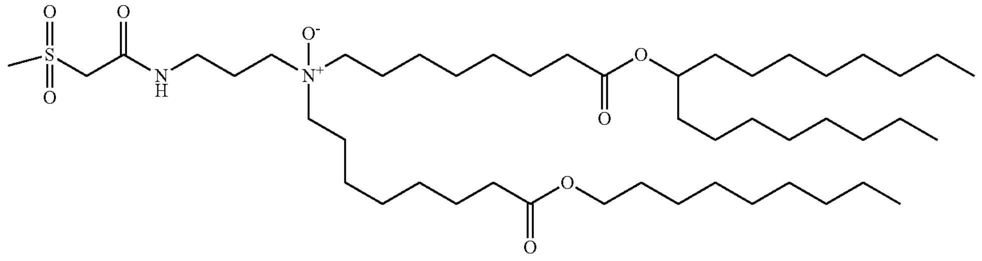
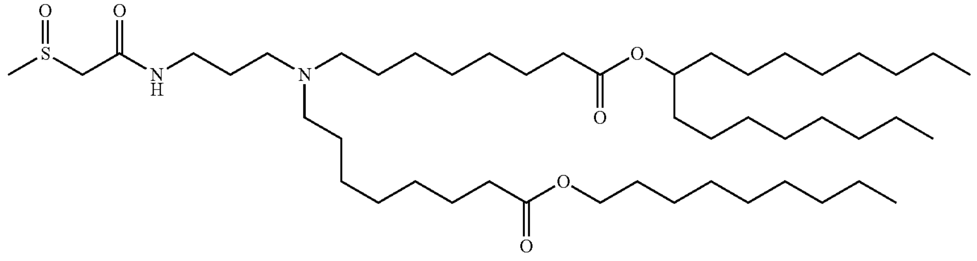
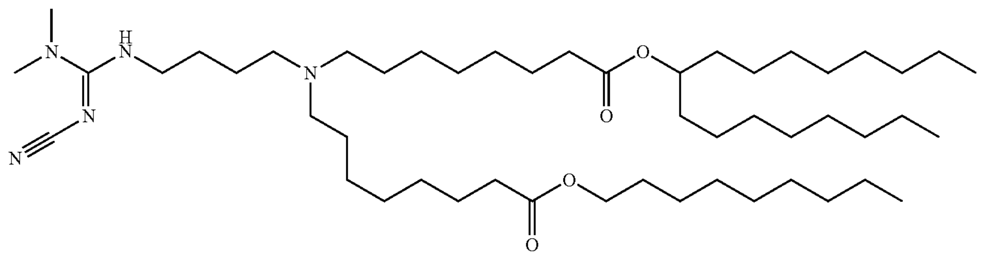
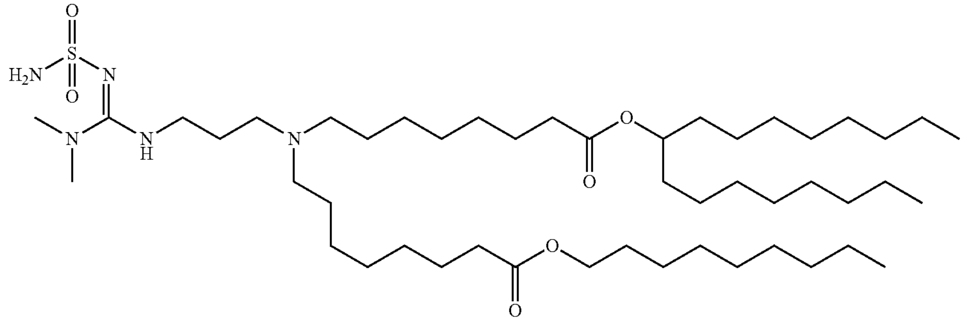

-continued

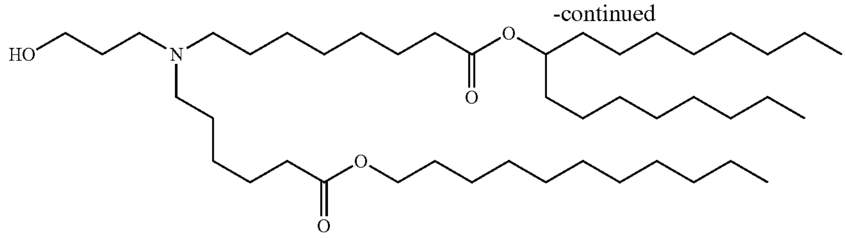

5.1 Amine lipids

In certain embodiments, transfer vehicle compositions for the delivery of circular RNA comprise an amine lipid. In certain embodiments, an ionizable lipid is an amine lipid. In some embodiments, an amine lipid is described in international patent application PCT/US2018/053569.

In some embodiments, the amine lipid is Lipid E, which is (9Z, 12Z)-3-((4,4-bis(octyloxy)butanoyl)oxy)-2-((((3-(diethylamino)propoxy)carbonyl)oxy)methyl)propyl octadeca-9, 12-dienoate.

Lipid E can be depicted as:

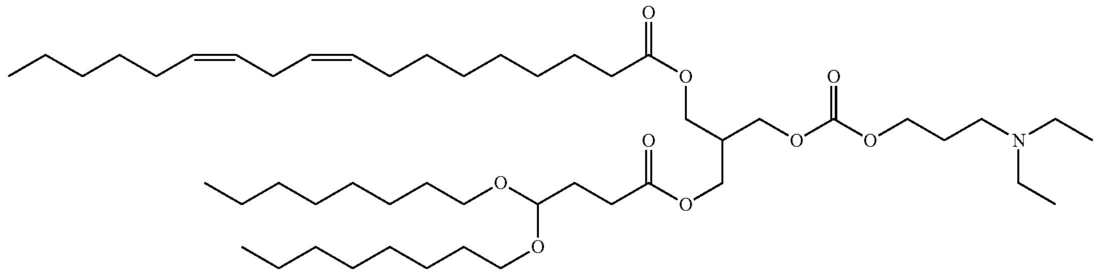 [SMILES: CCCCC/C=C\C/C=C\CCCCCCCC(=O)OCC(COC(=O)CCC(OCCCCCCCC)OCCCCCCCC)COC(=O)OCCCN(CC)CC]

Lipid E may be synthesized according to WO2015/095340 (e.g., pp. 84-86). In certain embodiments, the amine lipid is an equivalent to Lipid E.

In certain embodiments, an amine lipid is an analog of Lipid E. In certain embodiments, a Lipid E analog is an acetal analog of Lipid E. In particular transfer vehicle compositions, the acetal analog is a C4-C12 acetal analog. In some embodiments, the acetal analog is a C5C12 acetal analog. In additional embodiments, the acetal analog is a C5-C10 acetal analog. In further embodiments, the acetal analog is chosen from a C4, C5, C6, C7, C9, C10, C11 and C12 acetal analog.

Amine lipids and other biodegradable lipids suitable for use in the transfer vehicles, e.g., lipid nanoparticles, described herein are biodegradable in vivo. The amine lipids described herein have low toxicity (e.g., are tolerated in animal models without adverse effect in amounts of greater than or equal to 10 mg/kg). In certain embodiments, transfer vehicles composing an amine lipid include those where at least 75% of the amine lipid is cleared from the plasma within 8, 10, 12, 24, or 48 hours, or 3, 4, 5, 6, 7, or 10 days.

Biodegradable lipids include, for example, the biodegradable lipids of WO2017/173054, WO2015/095340, and WO2014/136086.

Lipid clearance may be measured by methods known by persons of skill in the art. See, for example, Maier, M. A., et al. Biodegradable Lipids Enabling Rapidly Eliminated Lipid Nanoparticles for Systemic Delivery of RNAi Therapeutics. *Mol. Ther.* 2013, 21(8), 1570-78.

Transfer vehicle compositions comprising an amine lipid can lead to an increased clearance rate. In some embodiments, the clearance rate is a lipid clearance rate, for example the rate at which a lipid is cleared from the blood, serum, or plasma. In some embodiments, the clearance rate is an RNA clearance rate, for example the rate at which an circRNA is cleared from the blood, serum, or plasma. In some embodiments, the clearance rate is the rate at which transfer vehicles are cleared from the blood, serum, or plasma. In some embodiments, the clearance rate is the rate at which transfer vehicles are cleared from a tissue, such as liver tissue or spleen tissue. In certain embodiments, a high rate of clearance leads to a safety profile with no substantial adverse effects. The amine lipids and biodegradable lipids may reduce transfer vehicle accumulation in circulation and in tissues. In some embodiments, a reduction in transfer vehicle accumulation in circulation and in tissues leads to a safety profile with no substantial adverse effects.

Lipids may be ionizable depending upon the pH of the medium they are in. For example, in a slightly acidic medium, the lipid, such as an amine lipid, may be protonated and thus bear a positive charge. Conversely, in a slightly basic medium, such as, for example, blood, where pH is approximately 7.35, the lipid, such as an amine lipid, may not be protonated and thus bear no charge.

The ability of a lipid to bear a charge is related to its intrinsic pKa. In some embodiments, the amine lipids of the present disclosure may each, independently, have a pKa in the range of from about 5.1 to about 7.4. In some embodiments, the bioavailable lipids of the present disclosure may each, independently, have a pKa in the range of from about 5.1 to about 7.4. For example, the amine lipids of the present disclosure may each, independently, have a pKa in the range of from about 5.8 to about 6.5. Lipids with a pKa ranging from about 5.1 to about 7.4 are effective for delivery of cargo in vivo, e.g., to the liver. Further, it has been found that lipids with a pKa ranging from about 5.3 to about 6.4 are effective for delivery in vivo, e.g., into tumors. See, e.g., WO2014/136086.

5.2 Lipids Containing a Disulfide Bond

In some embodiments, the ionizable lipid is described in U.S. Pat. No. 9,708,628.

The present invention provides a lipid represented by structure (XXII):

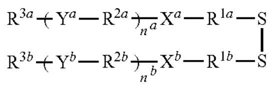

In structure (XXII), $X^a$ and $X^b$ are each independently $X^1$ or $X^2$ shown below.

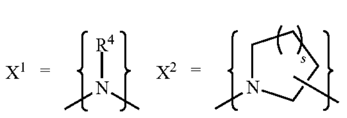

$R^4$ in $X^1$ is an alkyl group having 1-6 carbon atoms, which may be linear, branched or cyclic. The alkyl group preferably has a carbon number of 1-3. Specific examples of the alkyl group having 1-6 carbon atoms include methyl group, ethyl group, propyl group, isopropyl group, n-butyl group, sec-butyl group, isobutyl group, tert-butyl group, pentyl group, isopentyl group, neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group and the like. $R^4$ is preferably a methyl group, an ethyl group, a propyl group or an isopropyl group, most preferably a methyl group.

The s in $X^2$is 1 or 2. When s is 1, $X^2$is a pyrrolidinium group, and when s is 2, $X^2$ is a piperidinium group. s is preferably 2. While the binding direction of $X^2$is not limited, a nitrogen atom in $X^2$ preferably binds to $R^{1a}$ and $R^{1b}$.

$X^a$ may be the same as or different from $X^b$, and $X^a$ is preferably the same group as Xb.

$n^a$ and $n^b$ are each independently 0 or 1, preferably 1. When $n^a$ is 1, $R^{3a}$ binds to $X^a$ via $Y^a$ and $R^{2a}$, and when $n^a$ is 0, a structure of $R^{3a}$—$X^a$—$R^{1a}$—S is taken. Similarly, when $n^b$ is 1, $R^{3b}$ binds to $X^b$ via $Y^b$ and $R^{2b}$, and when $n^b$ is 0, a structure of $R^{3b}$—$X^b$—$R^{1b}$—S— is taken.

$n^a$ may be the same as or different from $n^b$, and $n^a$ is preferably the same as $n^b$.

$R^{1a}$ and $R^{1b}$ are each independently an alkylene group having 1-6 carbon atoms, which may be linear or branched, preferably linear. Specific examples of the alkylene group having 1-6 carbon atoms include methylene group, ethylene group, trimethylene group, isopropylene group, tetramethylene group, isobutylene group, pentamethylene group, neopentylene group and the like. $R^{1a}$ and $R^{1b}$ are each preferably a methylene group, an ethylene group, a trimethylene group, an isopropylene group or a tetramethylene group, most preferably an ethylene group.

$R^{1a}$ may be the same as or different from $R^{1b}$, and $R^{1a}$ is preferably the same group as $R^{1b}$.

$R^{2a}$ and $R^{2b}$ are each independently an alkylene group having 1-6 carbon atoms, which may be linear or branched, preferably linear. Examples of the alkylene group having 1-6 carbon atoms include those recited as the examples of the alkylene group having 1-6 carbon atoms for $R^{1a}$ or $R^{1b}$. $R^{2a}$ and $R^{2b}$ are each preferably a methylene group, an ethylene group, a trimethylene group, an isopropylene group or a tetramethylene group.

When $X^a$ and $X^b$ are each $X^1$, $R^{2a}$ and $R^{2b}$ are preferably trimethylene groups. When $X^a$ and $X^b$ are each $X^2$, $R^{2a}$ and $R^{2b}$ are preferably ethylene groups.

$R^{2a}$ may be the same as or different from $R^{2b}$, and $R^{2a}$ is preferably the same group as $R^{2b}$ $Y^a$ and $Y^b$ are each independently an ester bond, an amide bond, a carbamate bond, an ether bond or a urea bond, preferably an ester bond, an amide bond or a carbamate bond, most preferably an ester bond. While the binding direction of $Y^a$ and $Y^b$ is not limited, when $Y^a$ is an ester bond, a structure of $R^{3a}$—CO—O—$R^{2a}$— is preferable, and when $Y^b$ is an ester bond, a structure of $R^{3b}$—CO—O—$R^{2b}$— is preferable.

$Y^a$ may be the same as or different from $Y^b$, and $Y^a$ is preferably the same group as $Y^b$.

$R^{3a}$ and $R^{3b}$ are each independently a sterol residue, a liposoluble vitamin residue or an aliphatic hydrocarbon group having 12-22 carbon atoms, preferably a liposoluble vitamin residue or an aliphatic hydrocarbon group having 12-22 carbon atoms, most preferably a liposoluble vitamin residue.

Examples of the sterol residue include a cholesteryl group (cholesterol residue), a cholestaryl group (cholestanol residue), a stigmasteryl group (stigmasterol residue), a β-sitosteryl group (β-sitosterol residue), a lanosteryl group (lanosterol residue), and an ergosteryl group (ergosterol residue) and the like. The sterol residue is preferably a cholesteryl group or a cholestaryl group.

As the liposoluble vitamin residue, a residue derived from liposoluble vitamin, as well as a residue derived from a derivative obtained by appropriately converting a hydroxyl group, aldehyde or carboxylic acid, which is a functional group in liposoluble vitamin, to other reactive functional group can be used. As for liposoluble vitamin having a hydroxyl group, for example, the hydroxyl group can be converted to a carboxylic acid by reacting with succinic acid anhydride, glutaric acid anhydride and the like. Examples of the liposoluble vitamin include retinoic acid, retinol, retinal, ergosterol, 7-dehydrocholesterol, calciferol, cholecalciferol, dihydroergocalciferol, dihydrotachysterol, tocopherol, tocotrienol and the like. Preferable examples of the liposoluble vitamin include retinoic acid and tocopherol.

The aliphatic hydrocarbon group having 12-22 carbon atoms may be linear or branched, preferably linear. The aliphatic hydrocarbon group may be saturated or unsaturated. In the case of an unsaturated aliphatic hydrocarbon group, the aliphatic hydrocarbon group generally contains 1-6, preferably 1-3, more preferably 1-2 unsaturated bonds. While the unsaturated bond includes a carbon-carbon double bond and a carbon-carbon triple bond, it is preferably a carbon-carbon double bond. The aliphatic hydrocarbon group has a carbon number of preferably 12-18, most preferably 13-17. While the aliphatic hydrocarbon group includes an alkyl group, an alkenyl group, an alkynyl group and the like, it is preferably an alkyl group or an alkenyl group. Specific examples of the aliphatic hydrocarbon group having 12-22 carbon atoms include dodecyl group, tridecyl group, tetradecyl group, pentadecyl group, hexadecyl group, heptadecyl group, octadecyl group, nonadecyl group, icosyl group, henicosyl group, docosyl group, dodecenyl group, tridecenyl group, tetradecenyl group, pentadecenyl group, hexadecenyl group, heptadecenyl group, octadecenyl group, nonadecenyl group, icosenyl group, henicosenyl group, docosenyl group, decadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, octadecatrienyl group, icosatrienyl group, icosatetraenyl group, icosapentaenyl group, docosahexaenyl group, isostearyl group and the like. The aliphatic hydrocarbon group having 12-22 carbon atoms is preferably tridecyl group, tetradecyl group, heptadecyl group, octadecyl group, heptadecadienyl group or octadecadienyl group, particularly preferably tridecyl group, heptadecyl group or heptadecadienyl group.

In one embodiment, an aliphatic hydrocarbon group having 12-22 carbon atoms, which is derived from fatty acid, aliphatic alcohol, or aliphatic amine is used. When $R^{3a}$ (or $R^{3b}$) is derived from fatty acid, $Y^a$ (or $Y^b$) is an ester bond or an amide bond, and fatty acid-derived carbonyl carbon is included in $Y^a$ (or $Y^b$). For example, when linoleic acid is used, $R^{3a}$ (or $R^{3b}$) is a heptadecadienyl group.

$R^{3a}$ may be the same as or different from $R^{3b}$, and $R^{3a}$ is preferably the same group as $R^{3b}$.

In one embodiment, $X^a$ is the same as $X^b$, $n^a$ is the same as $n^b$, $R^{1a}$ is the same as $R^{1b}$, $R^{2a}$ is the same as $R^{2b}$, $R^{3a}$ is the same as $R^{3b}$, and $Y^a$ is the same as $Y^b$.

In one embodiment, $X^a$ and $X^b$ are each independently X1, $R^4$ is an alkyl group having 1-3 carbon atoms, $n^a$ and $n^b$ are each 1, $R^{1a}$ and $R^{1b}$ are each independently an alkylene group having 1-6 carbon atoms, $R^{2a}$ and $R^{2b}$ are each independently an alkylene group having 1-6 carbon atoms, $Y^a$ and $Y^b$ are each an ester bond or an amide bond, and $R^{3a}$ and $R^{3b}$ are each independently an aliphatic hydrocarbon group having 12-22 carbon atoms.

In one embodiment, $X^a$ and $X^b$ are each X1, $R^4$ is an alkyl group having 1-3 carbon atoms, $n^a$ and $n^b$ are each 1, $R^{1a}$ and $R^{1b}$ are each an alkylene group having 1-6 carbon atoms, $R^{2a}$ and $R^{2b}$ are each an alkylene group having 1-6 carbon atoms, $Y^a$ and $Y^b$ are each an ester bond or an amide bond, $R^{3a}$ and $R^{3b}$ are each an aliphatic hydrocarbon group having 12-22 carbon atoms, $X^a$ is the same as $X^b$, $R^{1a}$ is the same as $R^{1b}$, $R^{2a}$ is the same as $R^{2b}$, and $R^{3a}$ is the same as $R^{3b}$.

In one embodiment, $X^a$ and $X^b$ are each $X^1$, $R^4$ is a methyl group, $n^a$ and $n^b$ are each 1, $R^{1a}$ and $R^{1b}$ are each an ethylene group, $R^{2a}$ and $R^{2b}$ are each a trimethylene group, $Y^a$ and $Y^b$ are each —CO—O—, and $R^{3a}$ and $R^{3b}$ are each independently an alkyl group or alkenyl group having 13-17 carbon atoms.

In one embodiment, $X^a$ and $X^b$ are each $X^1$, $R^4$ is a methyl group, $n^a$ and $n^b$ are each 1, $R^{1a}$ and $R^{1b}$ are each an ethylene group, $R^{2a}$ and $R^{2b}$ are each a trimethylene group, $Y^a$ and $Y^b$ are each —CO—O—, $R^{3a}$ and $R^{3b}$ are each an alkyl group or alkenyl group having 13-17 carbon atoms, and $R^{3a}$ is the same as $R^{3b}$.

In one embodiment, $X^a$ and $X^b$ are each independently $X^1$, $R^4$ is an alkyl group having 1-3 carbon atoms, $n^a$ and $n^b$ are each 1, $R^{1a}$ and $R^{1b}$ are each independently an alkylene group having 1-6 carbon atoms, $R^{2a}$ and $R^{2b}$ are each independently an alkylene group having 1-6 carbon atoms, $Y^a$ and $Y^b$ are each an ester bond or an amide bond, and $R^{3a}$ and $R^{3b}$ are each independently a liposoluble vitamin residue (e.g., retinoic acid residue, tocopherol residue).

In one embodiment, $X^a$ and $X^b$ are each $X^1$, $R^4$ is an alkyl group having 1-3 carbon atoms, $n^a$ and $n^b$ are each 1, $R^{1a}$ and $R^{1b}$ are each an alkylene group having 1-6 carbon atoms, $R^{2a}$ and $R^{2b}$ are each an alkylene group having 1-6 carbon atoms, $Y^a$ and $Y^b$ are each an ester bond or an amide bond, $R^{3a}$ and $R^{3b}$ are each a liposoluble vitamin residue (e.g., retinoic acid residue, tocopherol residue), $X^a$ is the same as $X^b$, $R^{1a}$ is the same as $R^{1b}$, $R^{2a}$ is the same as $R^{2b}$, and $R^{3a}$ is the same as $R^{3b}$.

In one embodiment, $X^a$ and $X^b$ are each $X^1$, $R^4$ is a methyl group, $n^a$ and $n^b$ are each 1, $R^{1a}$ and $R^{1b}$ are each an ethylene group, $R^{2a}$ and $R^{2b}$ are each a trimethylene group, $Y^a$ and $Y^b$ are each —CO—O—, and $R^{3a}$ and $R^{3b}$ are each independently a liposoluble vitamin residue (e.g., retinoic acid residue, tocopherol residue).

In one embodiment, $X^a$ and $X^b$ are each $X^1$, $R^4$ is a methyl group, $n^a$ and $n^b$ are each 1, $R^{1a}$ and $R^{1b}$ are each an ethylene group, $R^{2a}$ and $R^{2b}$ are each a trimethylene group, $Y^a$ and $Y^b$ are each —CO—O—, $R^{3a}$ and $R^{3b}$ are each a liposoluble vitamin residue (e.g., retinoic acid residue, tocopherol residue), and $R^{3a}$ is the same as $R^{3b}$.

In one embodiment, $X^a$ and $X^b$ are each independently $X^2$, t is 2, $R^{1a}$ and $R^{1b}$ are each independently an alkylene group having 1-6 carbon atoms, $R^{2a}$ and $R^{2b}$ are each independently an alkylene group having 1-6 carbon atoms, $Y^a$ and $Y^b$ are each an ester bond, and $R^{3a}$ and $R^{3b}$ are each independently a liposoluble vitamin residue (e.g., retinoic acid residue, tocopherol residue) or an aliphatic hydrocarbon group having 12-22 carbon atoms (e.g., alkyl group having 12-22 carbon atoms).

In one embodiment, $X^a$ and $X^b$ are each independently $X^2$, t is 2, $R^{1a}$ and $R^{1b}$ are each independently an alkylene group having 1-6 carbon atoms, $R^{2a}$ and $R^{2b}$ are each independently an alkylene group having 1-6 carbon atoms, $Y^a$ and $Y^b$ are each an ester bond, $R^{3a}$ and $R^{3b}$ are each independently a liposoluble vitamin residue (e.g., retinoic acid residue, tocopherol residue) or an aliphatic hydrocarbon group having 12-22 carbon atoms (e.g., alkyl group having 12-22 carbon atoms), $X^a$ is the same as $X^b$, $R^{1a}$ is the same as $R^{1b}$, $R^{2a}$ is the same as $R^{2b}$, and $R^{3a}$ is the same as $R^{3b}$.

In one embodiment, $X^a$ and $X^b$ are each independently $X^2$, t is 2, $R^{1a}$ and $R^{1b}$ are each an ethylene group, $R^{2a}$ and $R^{2b}$ are each independently an alkylene group having 1-6 carbon atoms, $Y^a$ and $Y^b$ are each an ester bond, $R^{3a}$ and $R^{3b}$ are each independently a liposoluble vitamin residue (e.g., retinoic acid residue, tocopherol residue) or an aliphatic hydrocarbon group having 12-22 carbon atoms (e.g., alkyl group having 12-22 carbon atoms), $X^a$ is the same as $X^b$, $R^{2a}$ is the same as $R^{2b}$, and $R^{3a}$ is the same as $R^{3b}$.

In some embodiments, an ionizable lipid has one of the structures set forth in Table 15b below.

TABLE 15b

| Number | Structure |
|---|---|
| 1 | 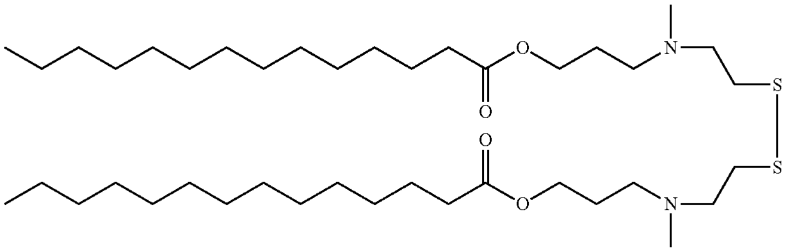 [SMILES: CCCCCCCCCCCCCC(=O)OCCCN(C)CCSSCCN(C)CCCOC(=O)CCCCCCCCCCCCC] |
| 2 | 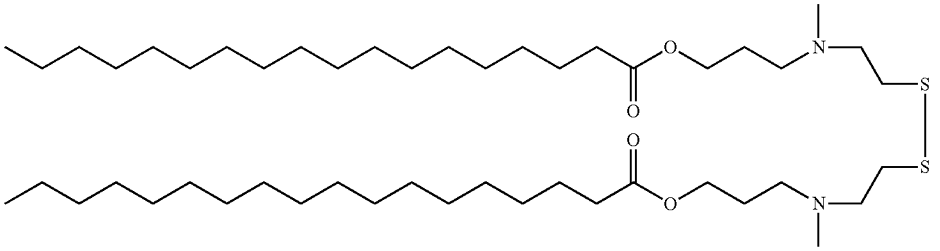 [SMILES: CCCCCCCCCCCCCCCCCC(=O)OCCCN(C)CCSSCCN(C)CCCOC(=O)CCCCCCCCCCCCCCCCC] |
| 3 | 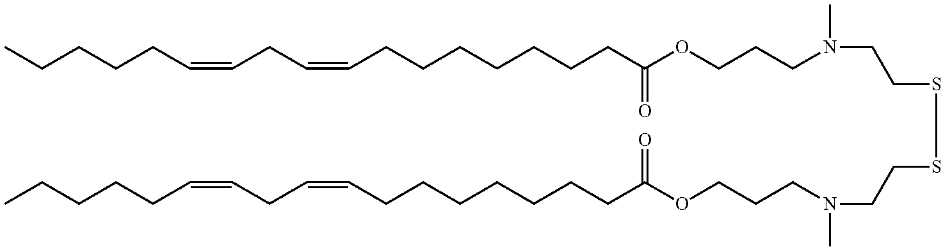 [SMILES: CCCCC/C=C\C/C=C\CCCCCCCC(=O)OCCCN(C)CCSSCCN(C)CCCOC(=O)CCCCCCC/C=C\C/C=C\CCCCC] |
| 4 | 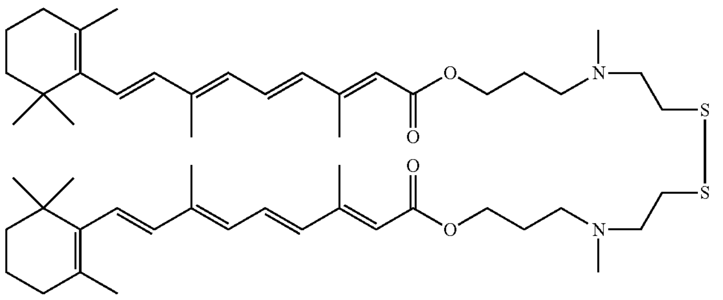 [SMILES: CC1=C(/C=C/C(C)=C/C=C/C(C)=C/C(=O)OCCCN(C)CCSSCCN(C)CCCOC(=O)/C=C(C)/C=C/C=C(C)/C=C/C2=C(C)CCCC2(C)C)C(C)(C)CCC1] |

TABLE 15b-continued
| Number | Structure |
|---|---|
| 5 | 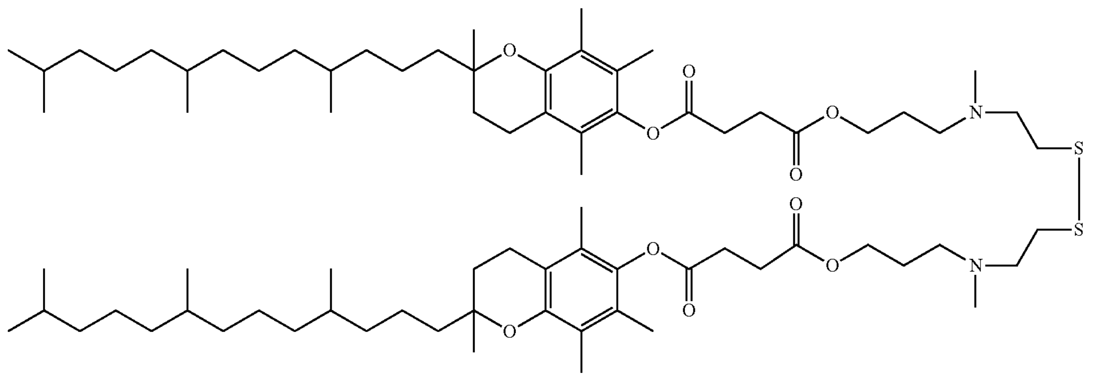 [SMILES: Cc1c(C)c2c(c(C)c1OC(=O)CCC(=O)OCCCN(C)CCSSCCN(C)CCCOC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |
| 6 | 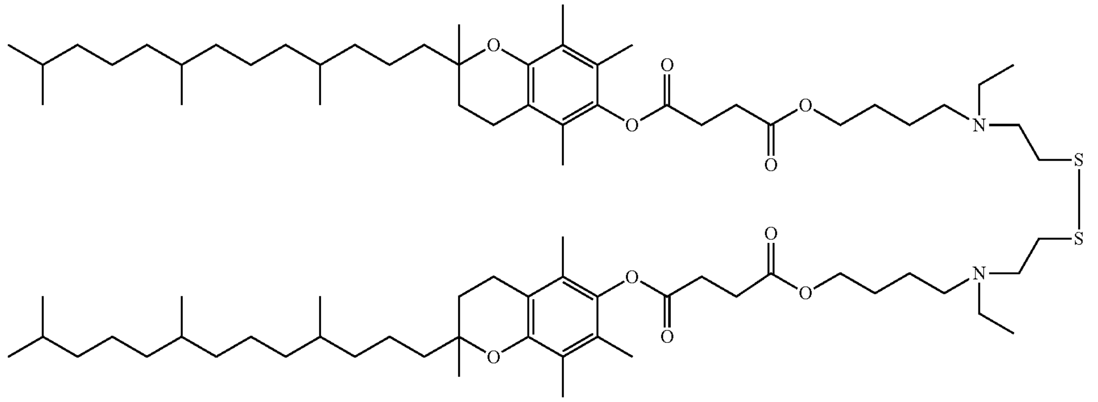 [SMILES: CCN(CCCCOC(=O)CCC(=O)Oc1c(C)c(C)c2c(c1C)CCC(C)(CCCC(C)CCCC(C)CCCC(C)C)O2)CCSSCCN(CC)CCCCOC(=O)CCC(=O)Oc1c(C)c(C)c2c(c1C)CCC(C)(CCCC(C)CCCC(C)CCCC(C)C)O2] |
| 7 | 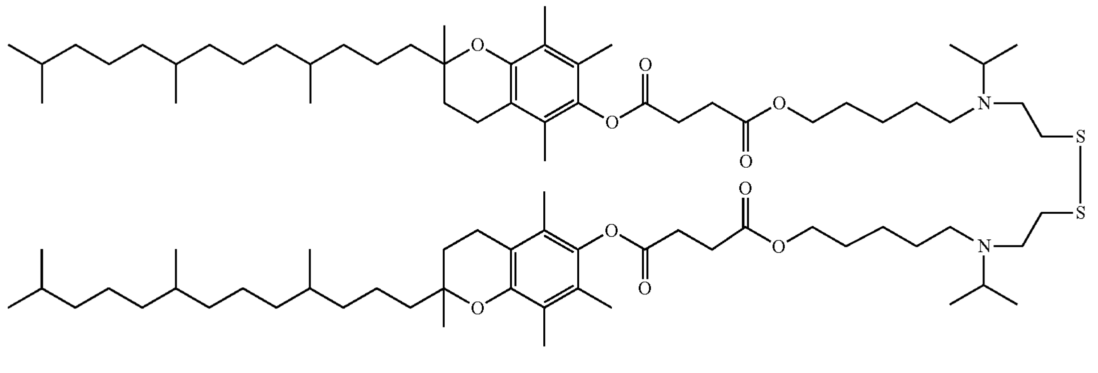 [SMILES: Cc1c(C)c2c(c(C)c1OC(=O)CCC(=O)OCCCCCN(CCSSCCN(CCCCCOC(=O)CCC(=O)Oc1c(C)c(C)c3c(c1C)CCC(C)(CCCC(C)CCCC(C)CCCC(C)C)O3)C(C)C)C(C)C)CCC(C)(CCCC(C)CCCC(C)CCCC(C)C)O2] |

TABLE 15b-continued
| Number | Structure |
|---|---|
| 8 | 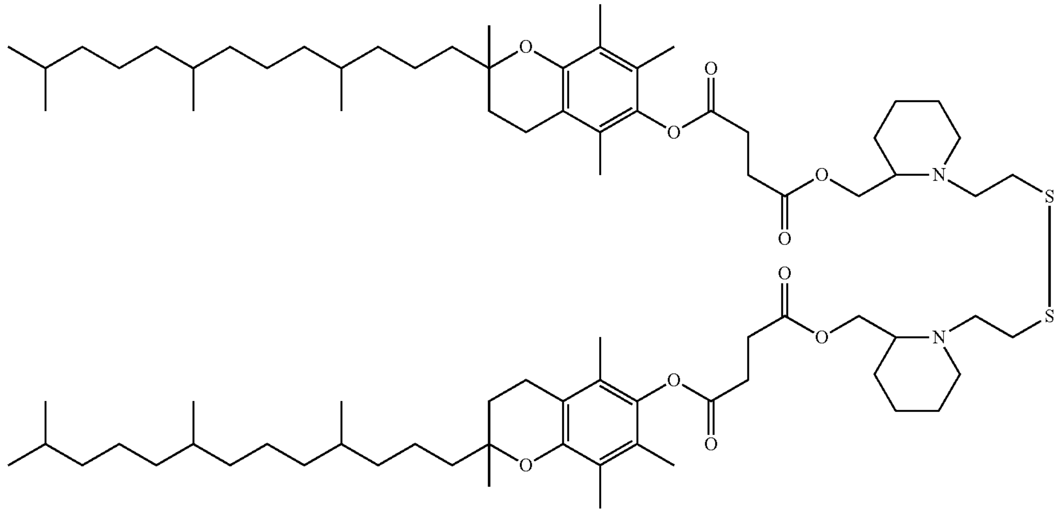 [SMILES: Cc1c(C)c2c(c(C)c1OC(=O)CCC(=O)OCC1CCCCN1CCSSCCN1CCCCC1COC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |
| 9 | 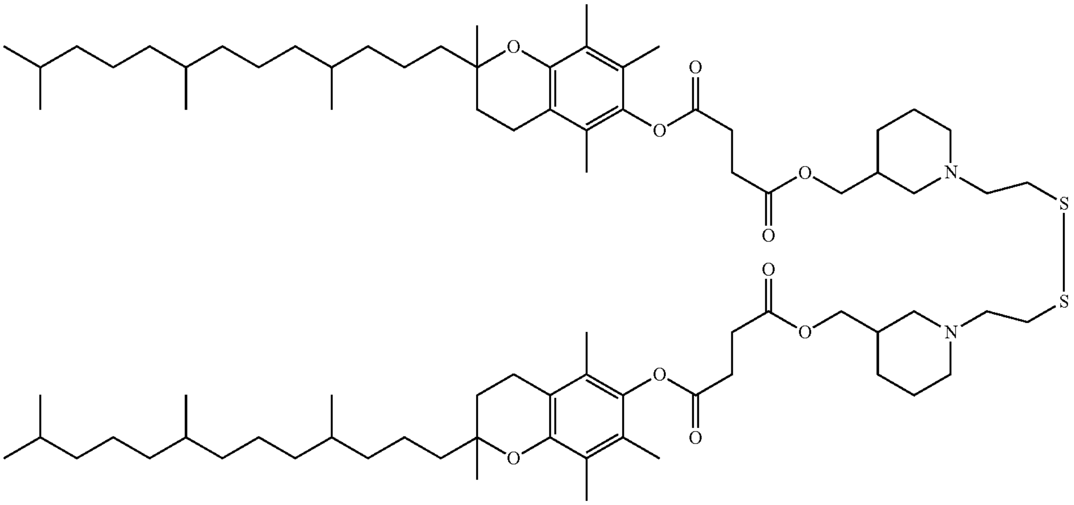 [SMILES: Cc1c(C)c2c(c(C)c1OC(=O)CCC(=O)OCC1CCCN(CCSSCCN3CCCC(COC(=O)CCC(=O)Oc4c(C)c(C)c5c(c4C)CCC(C)(CCCC(C)CCCC(C)CCCC(C)C)O5)C3)C1)CCC(C)(CCCC(C)CCCC(C)CCCC(C)C)O2] |
| 10 | 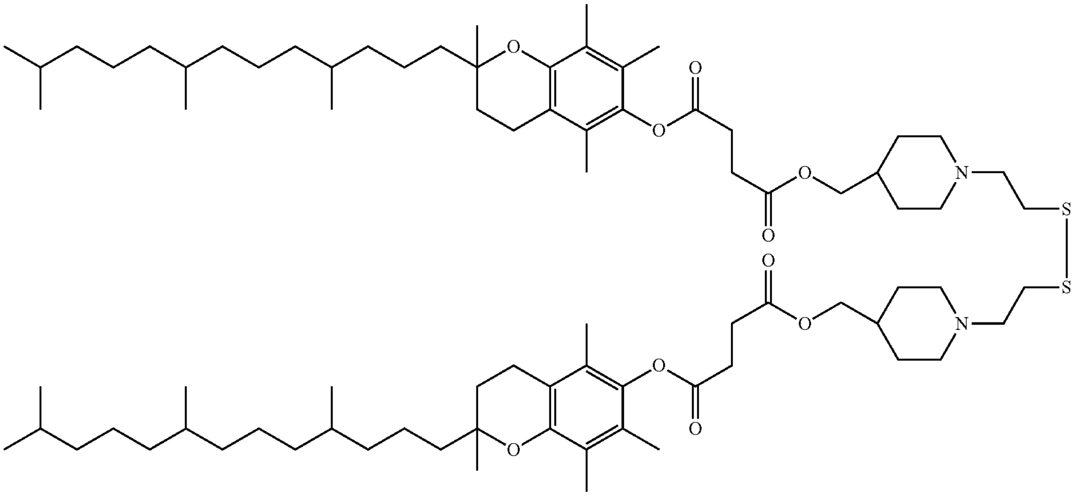 [SMILES: Cc1c(C)c2c(c(C)c1OC(=O)CCC(=O)OCC1CCN(CCSSCCN3CCC(COC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |

TABLE 15b-continued
| Number | Structure |
|---|---|
| 11 | 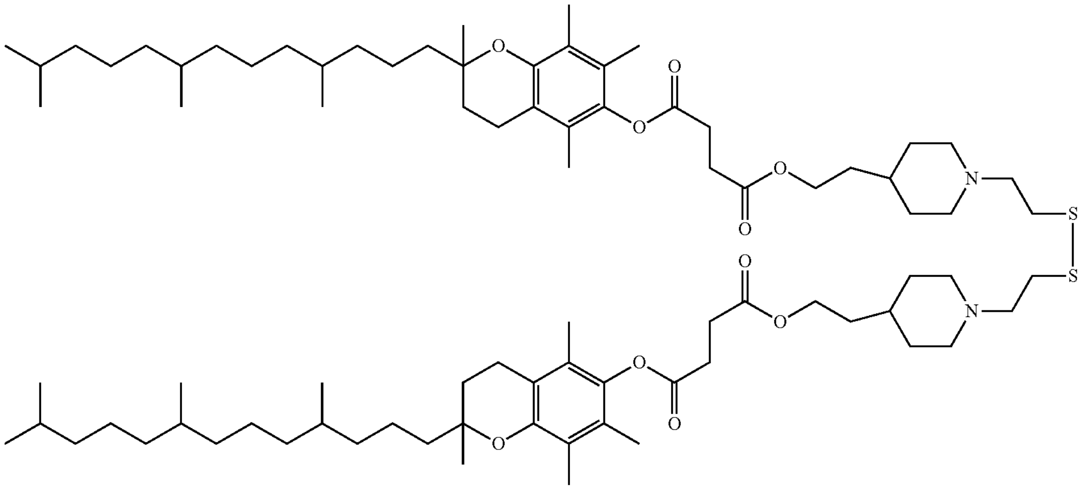 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| 12 | 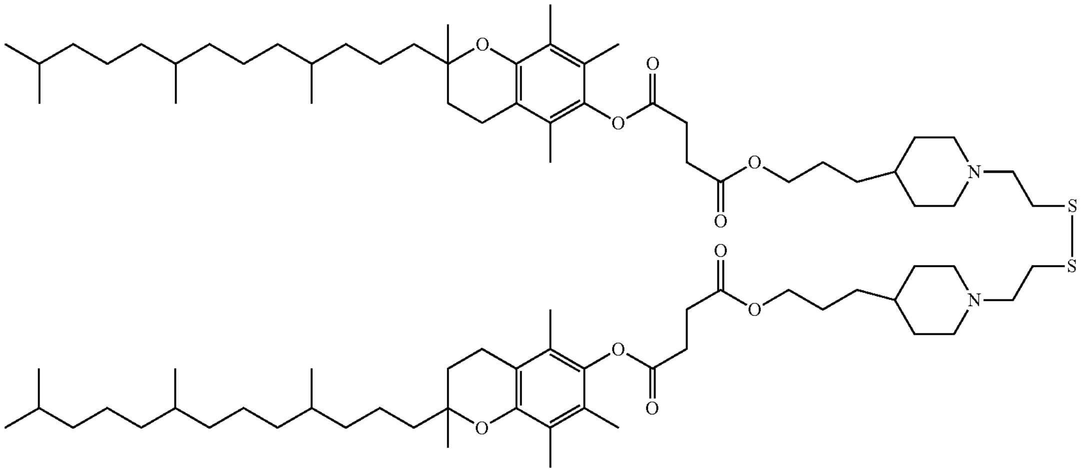 [SMILES: Cc1c(C)c2c(c(C)c1OC(=O)CCC(=O)OCCCC1CCN(CCSSCCN3CCC(CCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| 13 | 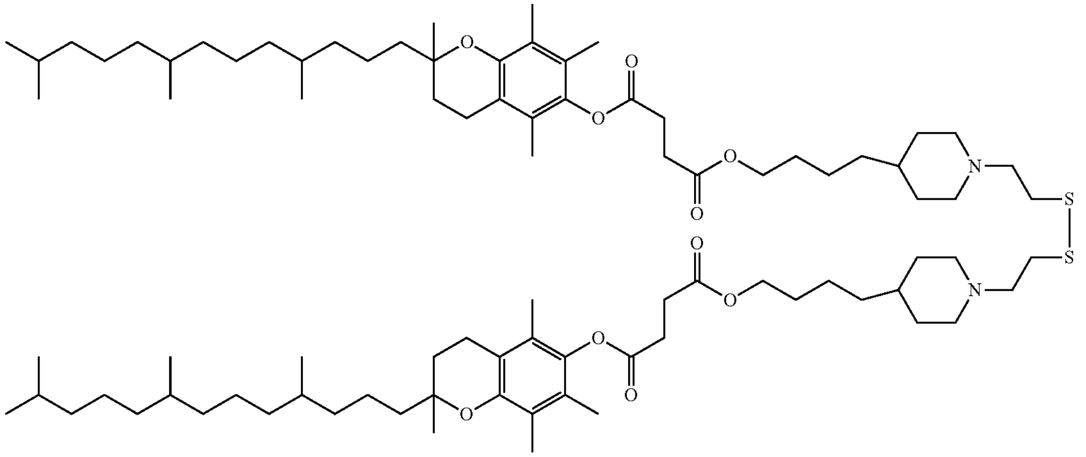 [SMILES: Cc1c(C)c2c(c(C)c1OC(=O)CCC(=O)OCCCCC1CCN(CCSSCCN3CCC(CCCCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |

TABLE 15b-continued

| Number | Structure |
| --- | --- |
| 14 | 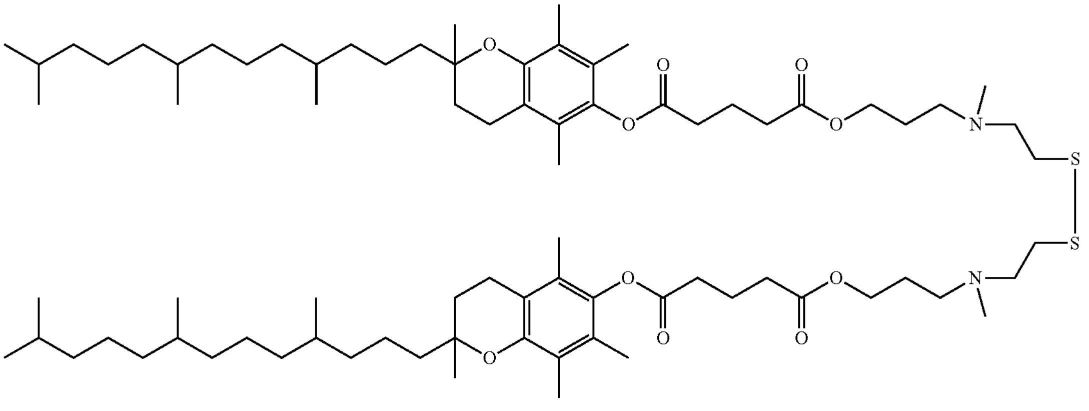 [SMILES: Cc1c(C)c2c(c(C)c1OC(=O)CCCC(=O)OCCCN(C)CCSSCCN(C)CCCOC(=O)CCCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |
| 15 | 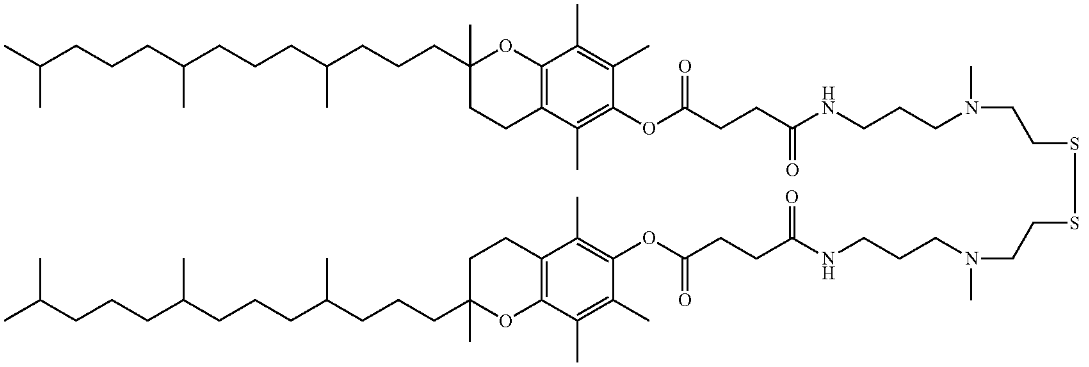 [SMILES: Cc1c(C)c2c(c(C)c1OC(=O)CCC(=O)NCCCN(C)CCSSCCN(C)CCCNC(=O)CCC(=O)Oc1c(C)c(C)c3c(c1C)CCC(C)(CCCC(C)CCCC(C)CCCC(C)C)O3)CCC(C)(CCCC(C)CCCC(C)CCCC(C)C)O2] |

A lipid of the present invention may have an S-S(disulfide) bond. The production method for such a compound includes, for example, a method including producing $R^{3a}$—($Y^a$—$R^{2a}$)$n^a$—$X^a$—$R^{1a}$—SH, and $R^{3b}$—($Y^b$—$R^{2b}$)$n^b$—$X^b$—$R^{1b}$—SH, and subjecting them to oxidation (coupling) to give a compound containing —S—S—, a method including sequentially bonding necessary parts to a compound containing an —S—S— bond to finally obtain the compound of the present invention and the like. Preferred is the latter method.

A specific example of the latter method is shown below, which is not to be construed as limiting.

Examples of the starting compound include —S—S— bond-containing two terminal carboxylic acid, two terminal carboxylate, two terminal amine, two terminal isocyanate, two terminal alcohol, two terminal alcohol having a leaving group such as MsO (mesylate group) and the like, a two terminal carbonate having a leaving group such as pNP (p-nitrophenylcarbonate group) and the like.

For example, when a compound containing $X^1$ or $X^2$for $X^a$ and $X^b$ is produced, two terminal functional groups of compound (1) containing an —S—S— bond are reacted with an NH group in compound (2) having the NH group and one functional group at the terminal, the functional group at the terminal in compound (2) which did not contribute to the reaction is reacted with a functional group in compound (3) containing $R^3$, whereby the compound of the present invention containing an —S—S— bond, $R^{1a}$ and $R^{1b}$, $X^a$ and $X^b$, $R^a$ and $R^{2b}$, $Y^a$ and $Y^b$, and $R^{3a}$ and $R^{3b}$ can be obtained.

In the reaction of compound (1) and compound (2), an alkali catalyst such as potassium carbonate, sodium carbonate, potassium t-butoxide and the like may be used as a catalyst, or the reaction may be performed without a catalyst. Preferably, potassium carbonate or sodium carbonate is used as a catalyst.

The amount of catalyst is 0.1-100 molar equivalents, preferably, 0.1-20 molar equivalents, more preferably 0.1-5 molar equivalents, relative to compound (1). The amount of compound (2) to be charged is 1-50 molar equivalents, preferably 1-10 molar equivalents, relative to compound (1).

The solvent to be used for the reaction of compound (1) and compound (2) is not particularly limited as long as it is a solvent or aqueous solution that does not inhibit the reaction. For example, ethyl acetate, dichloromethane, chloroform, benzene, toluene and the like can be mentioned. Among these, toluene and chloroform are preferable.

The reaction temperature is −20 to 200° C., preferably 0 to 80° C., more preferably 20 to 50° C., and the reaction time is 1-48 hr, preferably 2-24 hr.

When the reaction product of compound (1) and compound (2) is reacted with compound (3), an alkali catalyst such as potassium carbonate, sodium carbonate, potassium t-butoxide and the like, or an acid catalyst such as PTS (p-toluenesulfonic acid), MSA (methanesulfonic acid) and the like may be used, like the catalyst used for the reaction of compound (1) and compound (2), or the reaction may be performed without a catalyst.

In addition, the reaction product of compound (1) and compound (2) may be directly reacted with compound (3) by using a condensing agent such as DCC (dicyclohexylcarbodiimide), DIC (diisopropylcarbodiimide), EDC (1-ethyl-3-(3-dimethylaminopropyl)carbodiimide hydrochloride) and the like. Alternatively, compound (3) may be treated with a condensing agent to be once converted to an anhydride and the like, after which it is reacted with the reaction product of compound (1) and compound (2).

The amount of compound (3) to be charged is 1-50 molar equivalents, preferably 1-10 molar equivalents, relative to the reaction product of compound (1) and compound (2).

The catalyst to be used is appropriately selected according to the functional groups to be reacted.

The amount of catalyst is 0.05-100 molar equivalents, preferably 0.1-20 molar equivalents, more preferably 0.2-5 molar equivalent, relative to compound (1).

The solvent to be used for the reaction of the reaction product of compound (1) and compound (2) with compound (3) is not particularly limited as long as it is a solvent or aqueous solution that does not inhibit the reaction. For example, ethyl acetate, dichloromethane, chloroform, benzene, toluene and the like can be mentioned. Among these, toluene and chloroform are preferable.

The reaction temperature is 0 to 200° C., preferably 0 to 120° C., more preferably to 50° C., and the reaction time is 1 hr-48 hr, preferably 2-24 hr.

The reaction product obtained by the above-mentioned reaction can be appropriately purified by a general purification method, for example, washing with water, silica gel column chromatography, crystallization, recrystallization, liquid-liquid extraction, reprecipitation, ion exchange column chromatography and the like.

5.3 Structure XXIII Lipids

In some embodiments, an ionizable lipid is described in U.S. Pat. No. 9,765,022.

The present invention provides a compound represented by structure (XXIII):

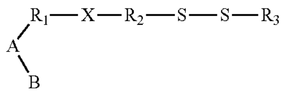

In structure XXIII, a hydrophilic and optionally positively charged head is

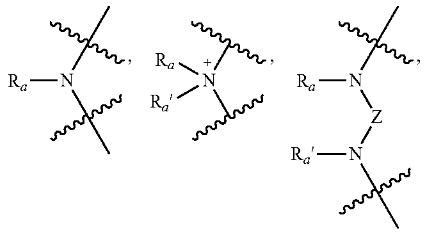

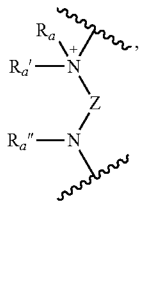

or

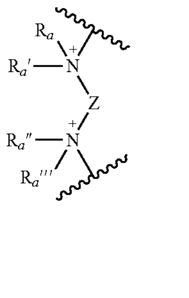

in which each of $R_a$, $R_a'$, $R_a''$, and $R_a'''$, independently, is H, a $C_1$-$C_{20}$ monovalent aliphatic radical, a $C_1$-$C_{20}$ monovalent heteroaliphatic radical, a monovalent aryl radical, or a monovalent heteroaryl radical, and Z is a $C_1$-$C_{20}$ bivalent aliphatic radical, a $C_1$-$C_{20}$ bivalent heteroaliphatic radical, a bivalent aryl radical, or a bivalent heteroaryl radical; B is a $C_1$-$C_{24}$ monovalent aliphatic radical, a $C_1$-$C_{24}$ monovalent heteroaliphatic radical, a monovalent aryl radical, a monovalent heteroaryl radical, or

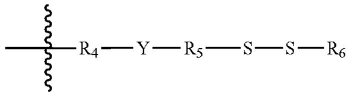

ch of $R_1$ and $R_4$, independently, is a bond, a $C_1$-$C_{10}$ bivalent aliphatic radical, a $C_1$-$C_{10}$ bivalent heteroaliphatic radical, a bivalent aryl radical, or a bivalent heteroaryl radical; each of $R_2$ and $R_5$, independently, is a bond, a $C_1$-$C_{20}$ bivalent aliphatic radical, a $C_1$-$C_{20}$ bivalent heteroaliphatic radical, a bivalent aryl radical, or a bivalent heteroaryl radical; each of $R_3$ and $R_6$, independently, is a $C_1$-$C_{20}$ monovalent aliphatic radical, a $C_1$-$C_{20}$ monovalent heteroaliphatic radical, a monovalent aryl radical, or a monovalent heteroaryl radical; each of

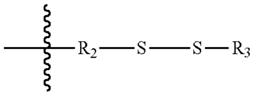

a hydrophobic tail, and

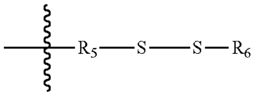

also a hydrophobic tail, has 8 to 24 carbon atoms; and each of X, a linker, and Y, also a linker, independently, is

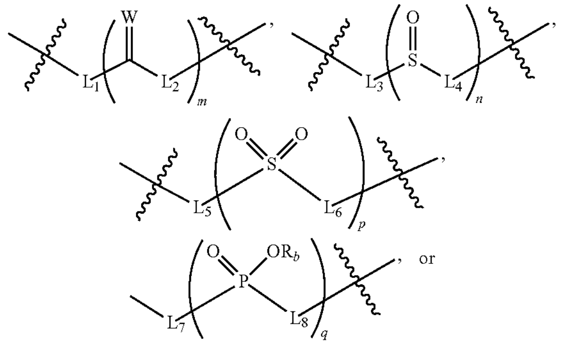

or

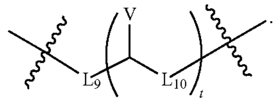

in which each of m, n, p, q, and t, independently, is 1-6; W is O, S, or $NR_c$; each of $L_1$, $L_3$, $L_5$, $L_7$, and $L_9$, directly linked to $R^1$, $R^2$, $R^4$, or $R_5$, independently, is a bond, O, S, or $NR^a$; each of $L_2$, $L_4$, $L_6$, $L_6$, and $L_{10}$, independently, is a bond, O, S, or $NR_e$; V is $OR_f$, $SR_g$, or $NR_hR_i$; and each of $R_b$, $R_c$, $R_d$, $R_e$, $R_f$, $R_g$, $R_h$, and $R_i$, independently, is H, OH, $C_{1-10}$ oxyaliphatic radical, $C_1$-$C_{10}$ monovalent aliphatic radical, $C_1$-$C_{10}$ monovalent heteroaliphatic radical, a monovalent aryl radical, or a monovalent heteroaryl radical.

A subset of the above-described lipid-like compounds include those in which A is

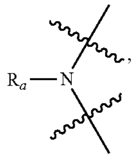

or

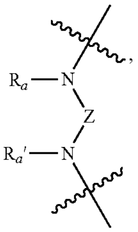

each of $R_a$ and $R_a'$, independently, being a $C_1$-$C_{10}$ monovalent aliphatic radical, a $C_1$-$C_{10}$ monovalent heteroaliphatic radical, a monovalent aryl radical, or a monovalent heteroaryl radical; and Z being a $C_1$-$C_{10}$ bivalent aliphatic radical, a $C_1$-$C_{10}$ bivalent heteroaliphatic radical, a bivalent aryl radical, or a bivalent heteroaryl radical.

Some lipid-like compounds of this invention feature each of RA and $R^4$, independently, being $C_1$-$C_6$ (e.g., $C_1$-$C_4$) bivalent aliphatic radical or a $C_1$-$C_6$ (e.g., $C_1$-$C_4$) bivalent heteroaliphatic radical, the total carbon number for $R^2$ and R3 being 12-20 (e.g., 14-18), the total carbon number of $R_5$ and $R_6$ also being 12-20 (e.g., 14-18), and each of X and Y, independently, is 4

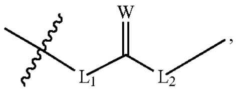

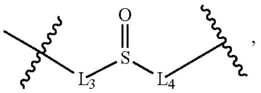

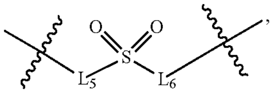

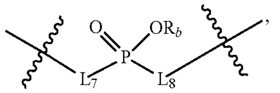

or

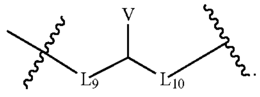

or

Specific examples of X and Y include

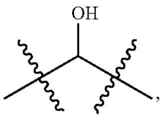

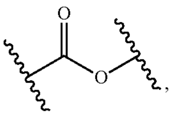

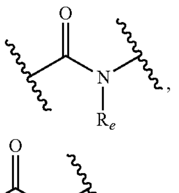

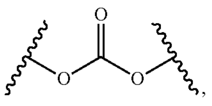

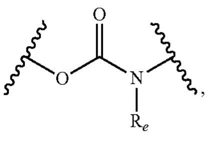

-continued

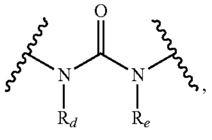

and

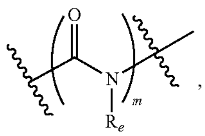

and m being 2-6.

Still within the scope of this invention is a pharmaceutical composition containing a nanocomplex that is formed of a protein and a bioreducible compound. In this pharmaceutical composition, the nanocomplex has a particle size of 50 to 500 nm; the bioreducible compound contains a disulfide hydrophobic moiety, a hydrophilic moiety, and a linker joining the disulfide hydrophobic moiety and the hydrophilic moiety; and the protein binds to the bioreducible compound via a non-covalent interaction, a covalent bond, or both.

In certain embodiments, the disulfide hydrophobic moiety is a heteroaliphatic radical containing one or more —S—S— groups and 8 to 24 carbon atoms; the hydrophilic moiety is an aliphatic or heteroaliphatic radical containing one or more hydrophilic groups and 1-20 carbon atoms, each of the hydrophilic groups being amino, alkylamino, dialkylamino, trialkylamino, tetraalkylammonium, hydroxyamino, hydroxyl, carboxyl, carboxylate, carbamate, carbamide, carbonate, phosphate, phosphite, sulfate, sulfite, or thiosulfate; and the linker is O, S, Si, $C_1$-$C_6$ alkylene,

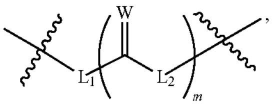

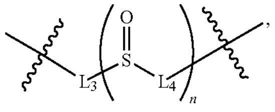

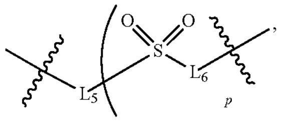

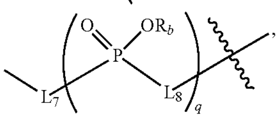

or

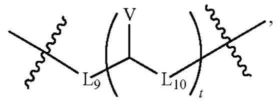

in which the variables are defined above.

Specific examples of X and Y include O, S, Si, $C_1$-$C_6$ alkylene

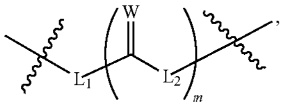

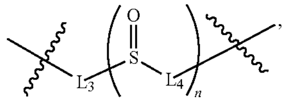

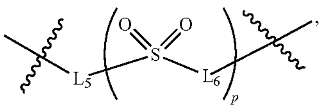

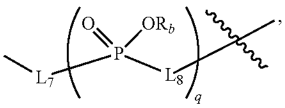

or

-continued

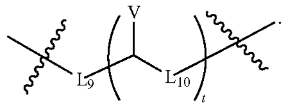

In some embodiments, a lipid-like compound of this invention, as shown in structure XXIII above, includes (i) a hydrophilic head, A; (ii) a hydrophobic tail, $R_2$—S—S—$R_3$; and (iii) a linker, X. Optionally, these compounds contain a second hydrophobic tail, $R_5$—S—S—$R_6$ and a second linker, Y.

The hydrophilic head of structure XXIII contains one or more hydrophilic functional groups, e.g., hydroxyl, carbonyl, carboxyl, amino, sulfhydryl, phosphate, amide, ester, ether, carbamate, carbonate, carbamide, and phosphodiester. These groups can form hydrogen bonds and are optionally positively or negatively charged.

Examples of the hydrophilic head include:

1

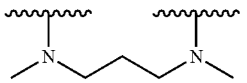

2

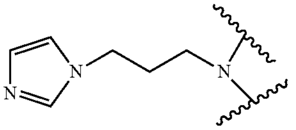

3

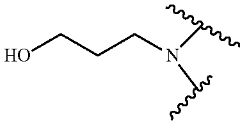

4

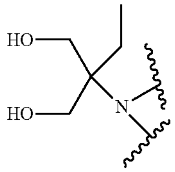

5

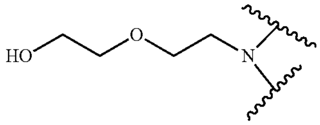

6

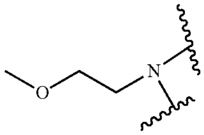

7

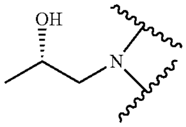

-continued

8

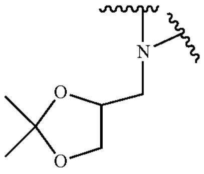

9

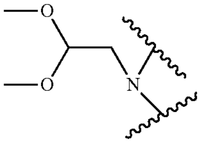

10

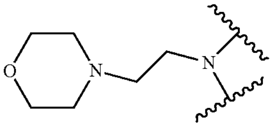

11

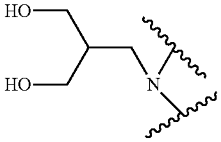

12

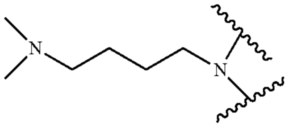

13

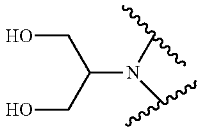

14

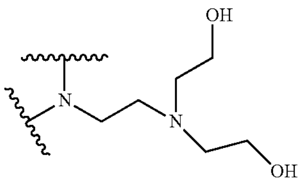

15

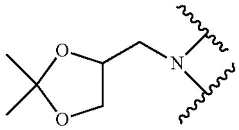

16

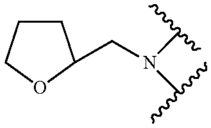

17

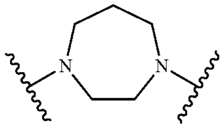

-continued

18

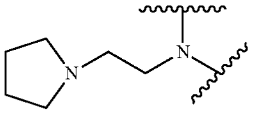

19

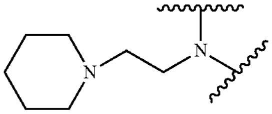

20

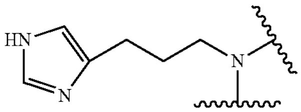

21

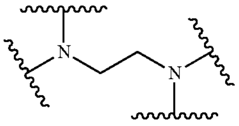

22

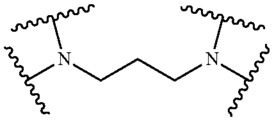

23

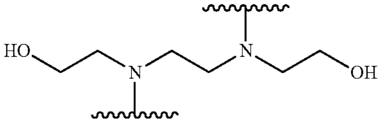

24

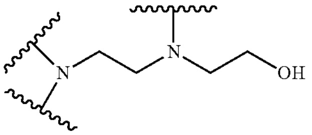

25

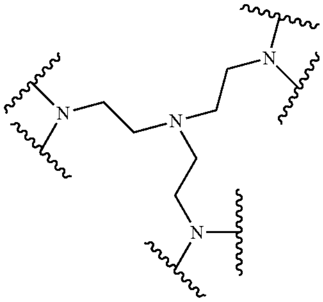

26

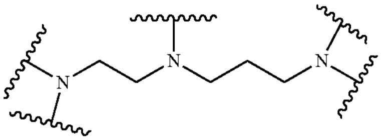

27

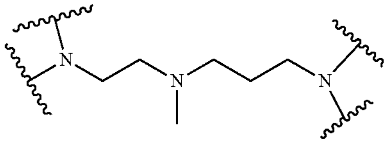

-continued

28

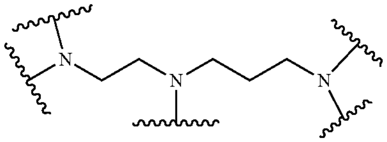

29

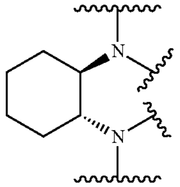

30

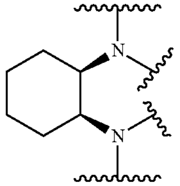

31

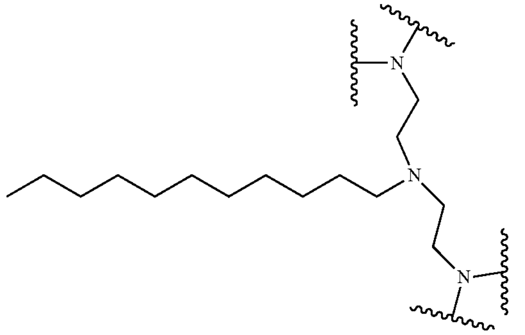

32

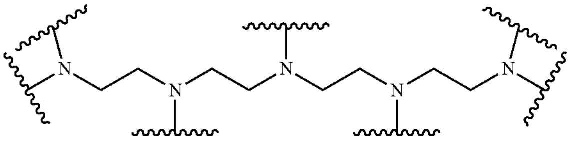

Other examples include those described in Akinc et al., Nature Biotechnology, 26, 561-69 (2008) and Mahon et al., US Patent Application Publication 2011/0293703.

The hydrophobic tail of structure XXIII is a saturated or unsaturated, linear or branched, acyclic or cyclic, aromatic or nonaromatic hydrocarbon moiety containing a disulfide bond and 8-24 carbon atoms. One or more of the carbon atoms can be replaced with a heteroatom, such as N, O, P, B, S, Si, Sb, A1, Sn, As, Se, and Ge. The tail is optionally substituted with one or more groups described above. The lipid-like compounds containing this disulfide bond can be bioreducible.

Examples include:

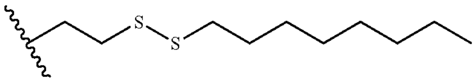

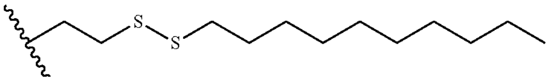

-continued

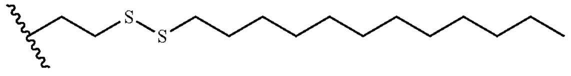
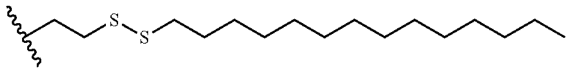
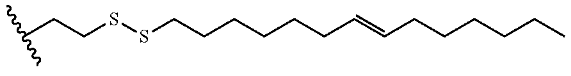
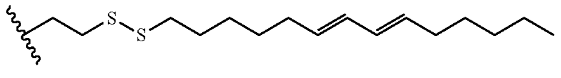
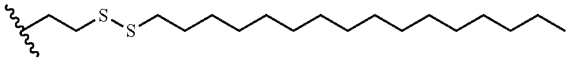

A linker of structure XXIII links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate, phosphate, phosphite, sulfate, sulfite, and thiosulfate. Examples include:

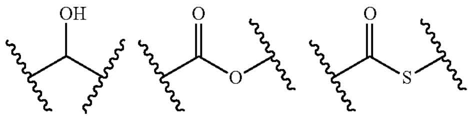
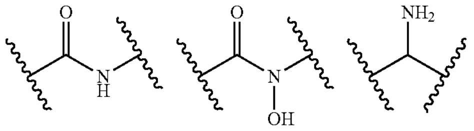
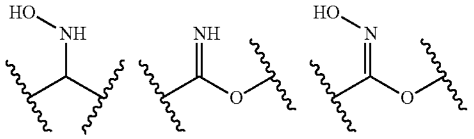
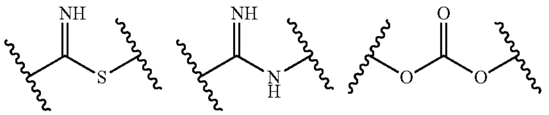
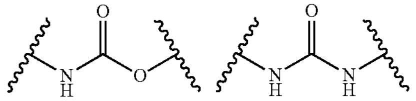
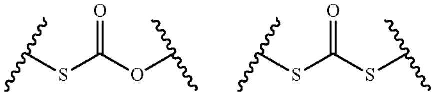
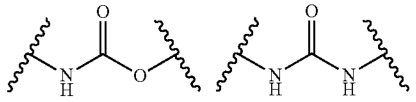
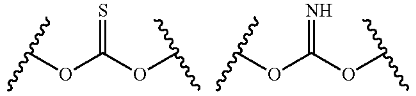
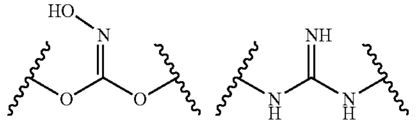

-continued

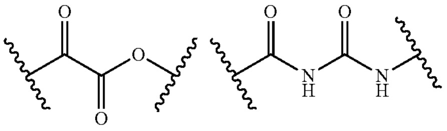

Shown below are exemplary lipid-like compounds of this invention:

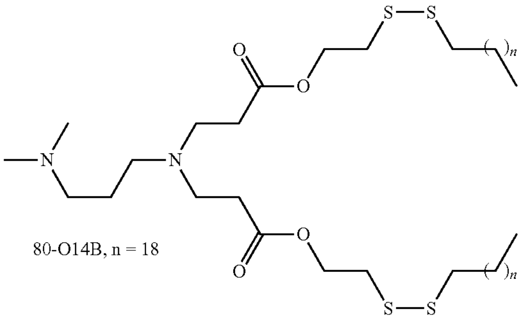

80-O14B, n = 18

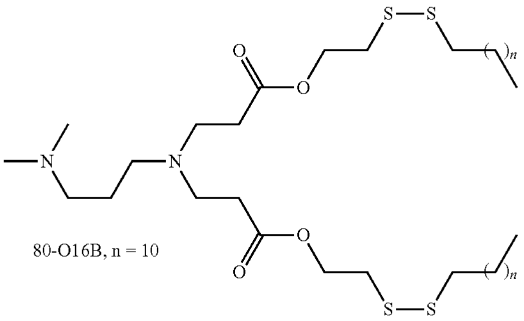

80-O16B, n = 10

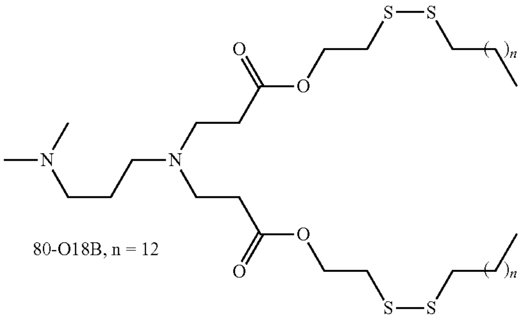

80-O18B, n = 12

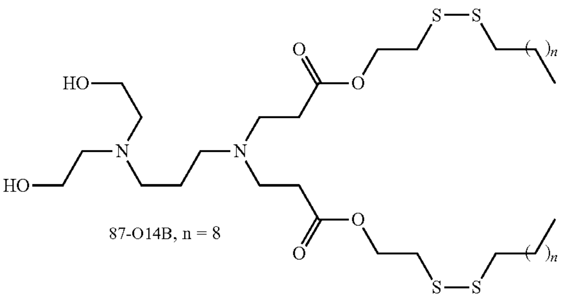

87-O14B, n = 8

-continued

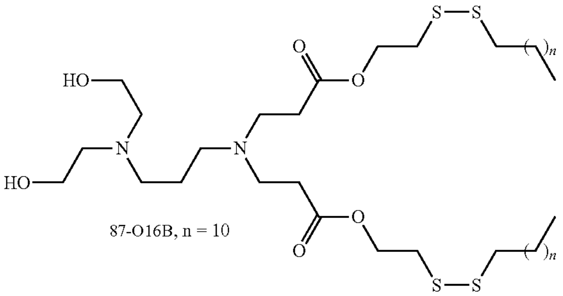

87-O16B, n = 10

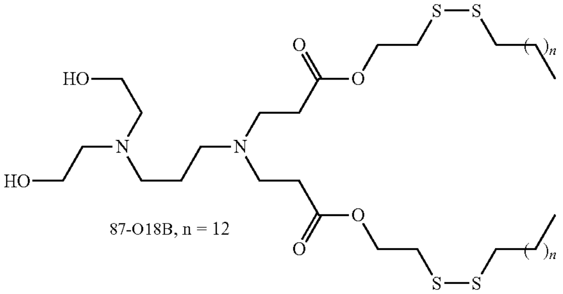

87-O18B, n = 12

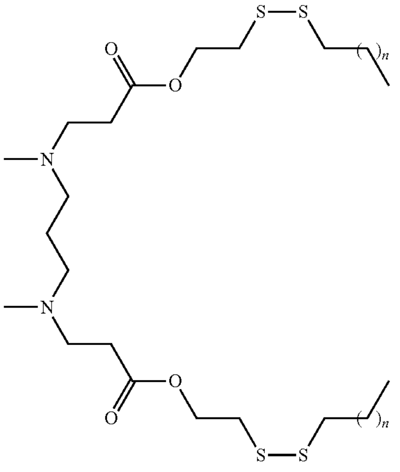

1-O16B, n = 10

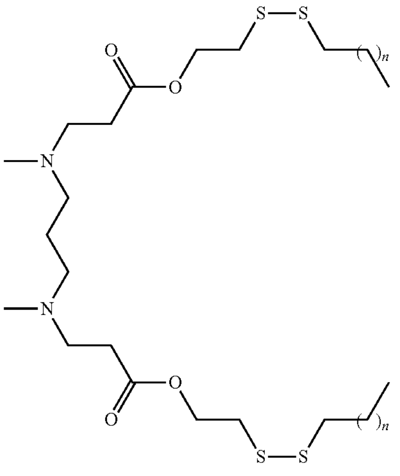

1-O18B, n = 12

The lipid-like compounds of structure XXIII can be prepared by methods well known the art. See Wang et al., ACS Synthetic Biology, 1, 403-07 (2012); Manoharan, et al., International Patent Application Publication WO 2008/042973; and Zugates et al., U.S. Pat. No. 8,071,082. The route shown below exemplifies synthesis of these lipid-like compounds:

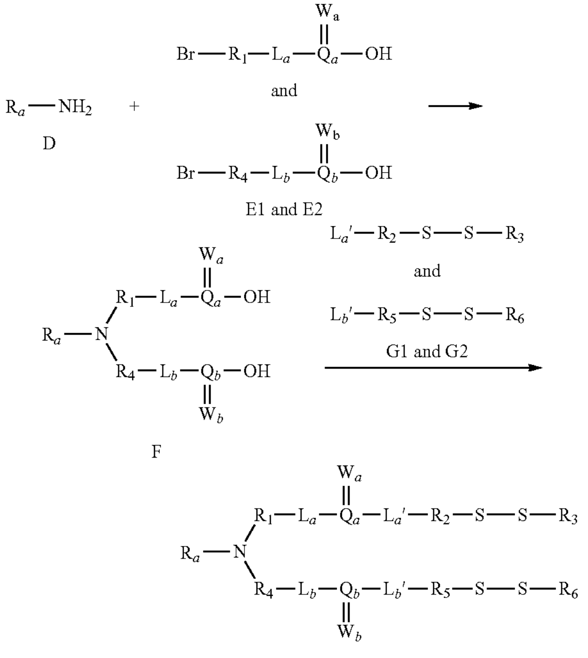

H

Each of $L_a$, $L_a'$, L, and L' can be one of $L_1$-$L_{10}$; each of $W_a$ and $W_b$, independently, is W or V; and $R_a$ and $R_1$-$R_6$ are defined above, as well as $L_1$-$L_{10}$, W, and V.

In this exemplary synthetic route, an amine compound, i.e., compound D, reacts with bromides E1 and E2 to form compound F, which is then coupled with both G1 and G2 to afford the final product, i.e., compound H. One or both of the double bonds in this compound (shown above) can be reduced to one or two single bonds to obtain different lipid-like compounds of structure XXIII.

Other lipid-like compounds of this invention can be prepared using other suitable starting materials through the above-described synthetic route and others known in the art. The method set forth above can include an additional step(s) to add or remove suitable protecting groups in order to ultimately allow synthesis of the lipid-like compounds. In addition, various synthetic steps can be performed in an alternate sequence or order to give the desired material. Synthetic chemistry transformations and protecting group methodologies (protection and deprotection) useful in synthesizing applicable lipid-like compounds are known in the art, including, for example, R. Larock, Comprehensive Organic Transformations (2nd Ed., VCH Publishers 1999); P. G. M. Wuts and T. W. Greene, Greene's Protective Groups in Organic Synthesis (4th Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis (2nd ed., John Wiley and Sons 2009) and subsequent editions thereof. Certain lipid-like compounds may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

As mentioned above, these lipid-like compounds are useful for delivery of pharmaceutical agents. They can be preliminarily screened for their efficacy in delivering pharmaceutical agents by an in vitro assay and then confirmed by animal experiments and clinic trials. Other methods will also be apparent to those of ordinary skill in the art.

Not to be bound by any theory, the lipid-like compounds of structure XXIII facilitate delivery of pharmaceutical agents by forming complexes, e.g., nanocomplexes and microparticles. The hydrophilic head of such a lipid-like compound, positively or negatively charged, binds to a moiety of a pharmaceutical agent that is oppositely charged and its hydrophobic moiety binds to a hydrophobic moiety of the pharmaceutical agent. Either binding can be covalent or non-covalent.

The above described complexes can be prepared using procedures described in publications such as Wang et al., ACS Synthetic Biology, 1, 403-07 (2012). Generally, they are obtained by incubating a lipid-like compound and a pharmaceutical agent in a buffer such as a sodium acetate buffer or a phosphate buffered saline ("PBS").

5.4 Hydrophilic Groups

In certain embodiments, the selected hydrophilic functional group or moiety may alter or otherwise impart properties to the compound or to the transfer vehicle of which such compound is a component (e.g., by improving the transfection efficiencies of a lipid nanoparticle of which the compound is a component). For example, the incorporation of guanidinium as a hydrophilic head-group in the compounds disclosed herein may promote the fusogenicity of such compounds (or of the transfer vehicle of which such compounds are a component) with the cell membrane of one or more target cells, thereby enhancing, for example, the transfection efficiencies of such compounds. It has been hypothesized that the nitrogen from the hydrophilic guanidinium moiety forms a six-membered ring transition state which grants stability to the interaction and thus allows for cellular uptake of encapsulated materials. (Wender, et al., Adv. Drug Del. Rev. (2008) 60: 452-472.) Similarly, the incorporation of one or more amino groups or moieties into the disclosed compounds (e.g., as a head-group) may further promote disruption of the endosomal/lysosomal membrane of the target cell by exploiting the fusogenicity of such amino groups. This is based not only on the pKa of the amino group of the composition, but also on the ability of the amino group to undergo a hexagonal phase transition and fuse with the target cell surface, i.e. the vesicle membrane. (Koltover, et al. Science (1998) 281: 78-81.) The result is believed to promote the disruption of the vesicle membrane and release of the lipid nanoparticle contents into the target cell.

Similarly, in certain embodiments the incorporation of, for example, imidazole as a hydrophilic head-group in the compounds disclosed herein may serve to promote endosomal or lysosomal release of, for example, contents that are encapsulated in a transfer vehicle (e.g., lipid nanoparticle) of the invention. Such enhanced release may be achieved by one or both of a proton-sponge mediated disruption mechanism and/or an enhanced fusogenicity mechanism. The proton-sponge mechanism is based on the ability of a compound, and in particular a functional moiety or group of the compound, to buffer the acidification of the endosome. This may be manipulated or otherwise controlled by the pKa of the compound or of one or more of the functional groups comprising such compound (e.g., imidazole). Accordingly, in certain embodiments the fusogenicity of, for example, the imidazole-based compounds disclosed herein (e.g., HGT4001 and HGT4004) are related to the endosomal disruption properties, which are facilitated by such imidazole groups, which have a lower pKa relative to other traditional ionizable lipids. Such endosomal disruption properties in turn promote osmotic swelling and the disruption of the liposomal membrane, followed by the transfection or intracellular release of the polynucleotide materials loaded or encapsulated therein into the target cell. This phenomenon can be applicable to a variety of compounds with desirable pKa profiles in addition to an imidazole moiety. Such embodiments also include multi-nitrogen based functionalities such as polyamines, poly-peptide (histidine), and nitrogen-based dendritic structures.

Exemplary ionizable and/or cationic lipids are described in International PCT patent publications WO2015/095340, WO2015/199952, WO2018/011633, WO2017/049245, WO2015/061467, WO2012/040184, WO2012/000104, WO2015/074085, WO2016/081029, WO2017/004 143, WO2017/075531, WO2017/117528, WO2011/022460, WO2013/148541, WO2013/116126, WO2011/153120, WO2012/044638, WO2012/054365, WO2011/090965, WO2013/016058, WO2012/162210, WO2008/042973, WO2010/129709, WO2010/144740, WO20 12/099755, WO2013/049328, WO2013/086322, WO2013/086373, WO2011/071860, WO2009/132131, WO2010/048536, WO2010/088537, WO2010/054401, WO2010/054406, WO2010/054405, WO2010/054384, WO2012/016184, WO2009/086558, WO2010/042877, WO2011/000106, WO2011/000107, WO2005/120152, WO2011/141705, WO2013/126803, WO2006/007712, WO2011/038160, WO2005/121348, WO2011/066651, WO2009/127060, WO2011/141704, WO2006/069782, WO2012/031043, WO2013/006825, WO2013/033563, WO2013/089151, WO2017/099823, WO2015/095346, and WO2013/086354, and US patent publications US2016/0311759, US2015/0376115, US2016/0151284, US2017/0210697, US2015/0140070, US2013/0178541, US2013/0303587, US2015/0141678, US2015/0239926, US2016/0376224, US2017/0119904, US2012/0149894, US2015/0057373, US2013/0090372, US2013/0274523, US2013/0274504, US2013/0274504, US2009/0023673, US2012/0128760, US2010/0324120, US2014/0200257, US2015/0203446, US2018/0005363, US2014/0308304, US2013/0338210, US2012/0101148, US2012/0027796, US2012/0058144, US2013/0323269, US2011/0117125, US2011/0256175, US2012/0202871, US2011/0076335, US2006/0083780, US2013/0123338, US2015/0064242, US2006/0051405, US2013/0065939, US2006/0008910, US2003/0022649, US2010/0130588, US2013/0116307, US2010/0062967, US2013/0202684, US2014/0141070, US2014/0255472, US2014/0039032, US2018/0028664, US2016/0317458, and US2013/0195920, the contents of all of which are incorporated herein by reference in their entirety. International patent application WO 2019/131770 is also incorporated herein by reference in its entirety.

6. PEG Lipids

The use and inclusion of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) in the liposomal and pharmaceutical compositions described herein is contemplated, preferably in combination with one or more of the compounds and lipids disclosed herein. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, the PEG-modified lipid employed in the compositions and methods of the invention is 1,2-dimyristoyl-sn-glycerol, methoxypolyethylene Glycol (2000 MW PEG) “DMG-PEG2000.” The addition of PEG-modified lipids to the lipid delivery vehicle may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., $C_{14}$ or $C_{18}$). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in a liposomal lipid nanoparticle.

In an embodiment, a PEG-modified lipid is described in International Pat. Appl. No. PCT/US2019/015913, which is incorporated herein by reference in their entirety. In an embodiment, a transfer vehicle comprises one or more PEG-modified lipids.

Non-limiting examples of PEG-modified lipids include PEG-modified phosphatidylethanolamines and phosphatidic acids, PEG-ceramide conjugates (e.g., PEG-CerC14 or PEG-CerC20), PEG-modified dialkylamines and PEG-modified 1,2-diacyloxypropan-3-amines. In some further enbodiments, a PEG-modified lipid may be, e.g., PEG-c-DOMG, PEG-DMG, PEG-DLPE, PEG-DMPE, PEG-DPPC, or a PEG-DSPE.

In some still further embodiments, the PEG-modified lipid includes, but is not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

fied ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, such as from about $C_{14}$ to about $C_{16}$. In some embodiments, a PEG moiety, for example a mPEG-$NH_2$, has a size of about 1000, about 2000, about 5000, about 10,000, about 15,000 or about 20,000 daltons. In one embodiment, the PEG-lipid is PEG2k-DMG.

In one embodiment, the lipid nanoparticles described herein can comprise a lipid modified with a non-diffusible PEG. Non-limiting examples of non-diffusible PEGs include PEG-DSG and PEG-DSPE.

PEG-lipids are known in the art, such as those described in U.S. Pat. No. 8,158,601 and International Pat. Publ. No. WO2015/130584 A2, which are incorporated herein by reference in their entirety.

In various embodiments, lipids (e.g., PEG-lipids), described herein may be synthesized as described International Pat. Publ. No. PCT/US2016/000129, which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG-DMG. PEG-DMG has the following structure:

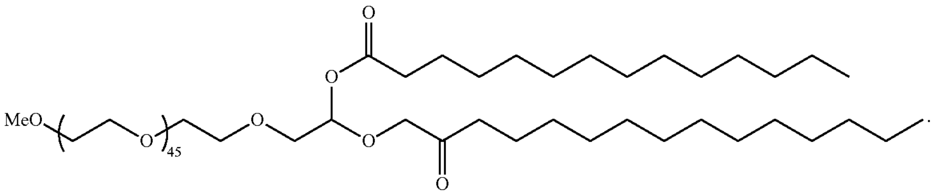

In some embodiments the PEG-modified lipids are a modified form of PEG-C18, or PEG-1. PEG-1 has the following structure

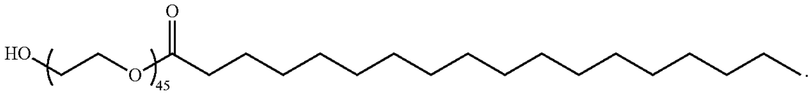

In various embodiments, a PEG-modified lipid may also be referred to as “PEGylated lipid” or “PEG-lipid.”

In one embodiment, the PEG-lipid is selected from the group consisting of a PEG-modified phosphatidylethanolamine, a PEG-modified phosphatidic acid, a PEG-modi- In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In some embodiments, the PEG lipid is a compound of Formula (P1):

(P1)

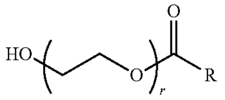

or a salt or isomer thereof, wherein:

r is an integer between 1 and 100;

R is $C_{10-40}$ alkyl, $C_{10-40}$ alkenyl, or $C_{10-40}$ alkynyl; and optionally one or more methylene groups of R are independently replaced with $C_{3-10}$ carbocyclylene, 4 to 10 membered heterocyclylene, $C_{6-10}$ arylene, 4 to 10 membered heteroarylene, —N($R^N$)—, —O—, —S—, —C(O)—, —C(O)N($R^N$)—, —$NR^N$C(O)—, —$NR^N$C(O)N($R^N$), —C(O)O—, —OC(O)—, —OC(O)O—, OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS$(O)_2$—, —S$(O)_2$O—, —OS$(O)_2$O—, —N($R^N$)S(O)—, —S(O)N($R^N$)—, —N($R^N$)S(O)N($R^N$)—, —OS(O)N($R^N$)—, —N($R^N$)S(O)O—, —S$(O)_2$—, —N($R^N$)S$(O)_2$—, —S$(O)_2$N($R^N$)—, —N($R^N$)S$(O)_2$N($R^N$)—, —OS$(O)_2$N($R^N$)—, or -N($R^N$)S$(O)_2$O—; and each instance of $R^N$ is independently hydrogen, $C_{1-6}$ alkyl, or a nitrogen protecting group.

For example, R is C17 alkyl. For example, the PEG lipid is a compound of Formula (P1-a):

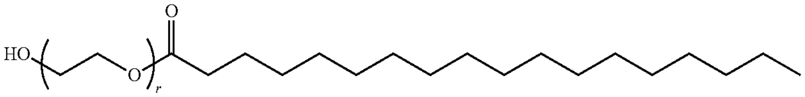

or a salt or isomer thereof, wherein r is an integer between 1 and 100.

For example, the PEG lipid is a compound of the following formula:

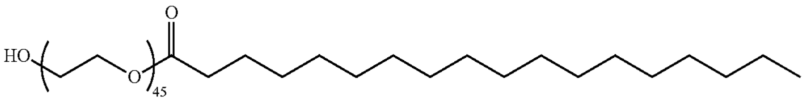

7. Helper Lipids

In some embodiments, the transfer vehicle (e.g., LNP) described herein comprises one or more non-cationic helper lipids. In some embodiments, the helper lipid is a phospholipid. In some embodiments, the helper lipid is a phospholipid substitute or replacement. In some embodiments, the phospholipid or phospholipid substitute can be, for example, one or more saturated or (poly)unsaturated phospholipids, or phospholipid substitutes, or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, the helper lipid is a 1,2-distearoyl-177-glycero-3-phosphocholine (DSPC) analog, a DSPC substitute, oleic acid, or an oleic acid analog.

In some embodiments, a helper lipid is a non-phosphatidyl choline (PC) zwitterionic lipid, a DSPC analog, oleic acid, an oleic acid analog, or a DSPC substitute.

In some embodiments, a helper lipid is described in PCT/US2018/053569. Helper lipids suitable for use in a lipid composition of the disclosure include, for example, a variety of neutral, uncharged or zwitterionic lipids. Such helper lipids are preferably used in combination with one or more of the compounds and lipids disclosed herein. Examples of helper lipids include, but are not limited to, 5-heptadecylbenzene-1,3-diol (resorcinol), dipalmitoylphosphatidylcholine (DPPC), distearoylphosphatidylcholine (DSPC), pohsphocholine (DOPC), dimyristoylphosphatidylcholine (DMPC), phosphatidylcholine (PLPC), 1,2-distearoylsn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-paimitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), paimitoyioieoyl phosphatidylcholine (POPC), lysophosphatidyl choline, dioleoyl phosphatidylethanol amine (DOPE) dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the helper lipid may be distearoylphosphatidylcholine (DSPC) or dimyristoyl phosphatidyl ethanolamine (DMPE). In another embodiment, the helper lipid may be distearoylphosphatidylcholine (DSPC). Helper lipids function to stabilize and improve processing of the transfer vehicles. Such helper lipids are preferably used in combination with other excipients, for example, one or more of the ionizable lipids disclosed herein. In some embodiments, when used in combination with an ionizable lipid, the helper lipid may comprise a molar ratio of 5% to about 90%, or about 10% to about 70% of the total lipid present in the lipid nanoparticle.

8. Structural Lipids

In an embodiment, a structural lipid is described in international patent application PCT/US2019/015913.

The transfer vehicles described herein comprise one or more structural lipids. Incorporation of structural lipids in the lipid nanoparticle may help mitigate aggregation of other lipids in the particle. Structural lipids can include, but are not limited to, cholesterol, fecosterol, ergosterol, bassicasterol, tomatidine, tomatine, ursolic, alpha-tocopherol, and mixtures thereof. In certain embodiments, the structural lipid is cholesterol. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

The transfer vehicles described herein comprise one or more structural lipids. Incorporation of structural lipids in a transfer vehicle, e.g., a lipid nanoparticle, may help mitigate aggregation of other lipids in the particle. In certain embodiments, the structural lipid includes cholesterol and a corticosteroid (such as, for example, prednisolone, dexamethasone, prednisone, and hydrocortisone), or a combination thereof.

In some embodiments, the structural lipid is a sterol. Structural lipids can include, but are not limited to, sterols (e.g., phytosterols or zoosterols).

In certain embodiments, the structural lipid is a steroid. For example, sterols can include, but are not limited to, cholesterol, β-sitosterol, fecosterol, ergosterol, sitosterol, campesterol, stigmasterol, brassicasterol, ergosterol, tomatidine, tomatine, ursolic acid, or alpha-tocopherol.

In some embodiments, a transfer vehicle includes an effective amount of an immune cell delivery potentiating lipid, e.g., a cholesterol analog or an amino lipid or combination thereof, that, when present in a transfer vehicle, e.g., an lipid nanoparticle, may function by enhancing cellular association and/or uptake, internalization, intracellular trafficking and/or processing, and/or endosomal escape and/or may enhance recognition by and/or binding to immune cells, relative to a transfer vehicle lacking the immune cell delivery potentiating lipid. Accordingly, while not intending to be bound by any particular mechanism or theory, in one embodiment, a structural lipid or other immune cell delivery potentiating lipid of the disclosure binds to C1q or promotes the binding of a transfer vehicle comprising such lipid to C1q. Thus, for in vitro use of the transfer vehicles of the disclosure for delivery of a nucleic acid molecule to an immune cell, culture conditions that include C1q are used (e.g., use of culture media that includes serum or addition of exogenous C1q to serum-free media). For in vivo use of the transfer vehicles of the disclosure, the requirement for C1q is supplied by endogenous C1q.

In certain embodiments, the structural lipid is cholesterol. In certain embodiments, the structural lipid is an analog of cholesterol. In some embodiments, the structural lipid is a lipid in Table 16:

TABLE 16

| CMPD No. S• | Structure |
|---|---|
| 1 | 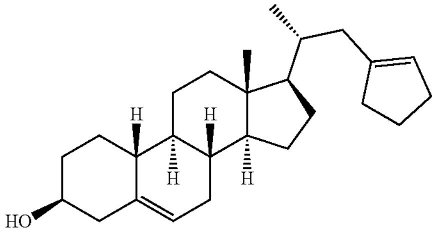 |
| 22 | 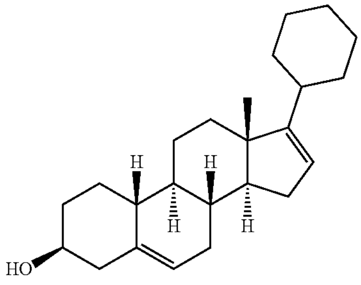 |

TABLE 16-continued
2
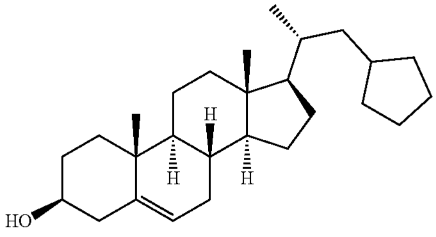
3
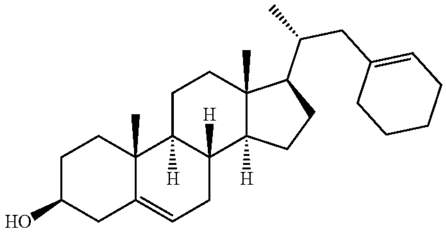
4
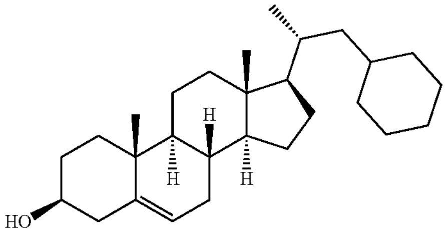
5
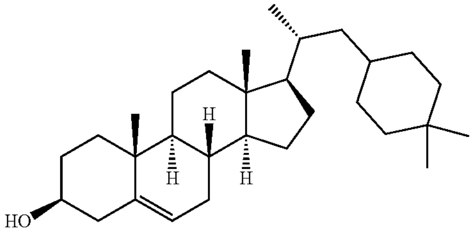
6
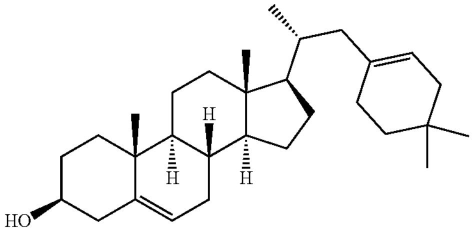
7
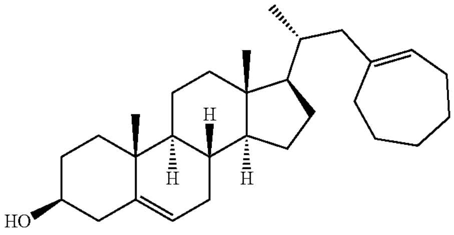

TABLE 16-continued
23
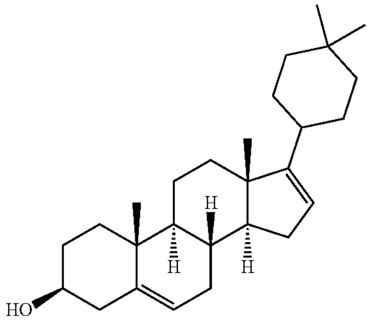
24
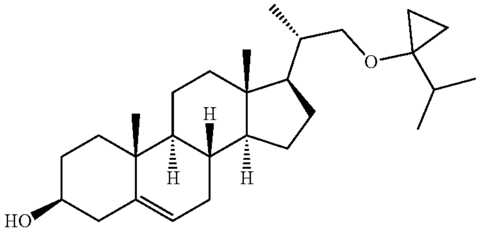
25
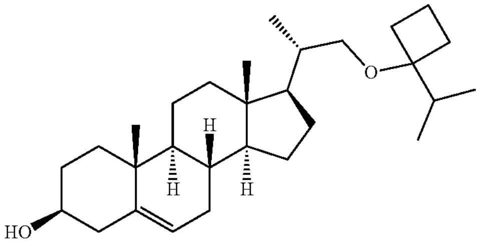
26
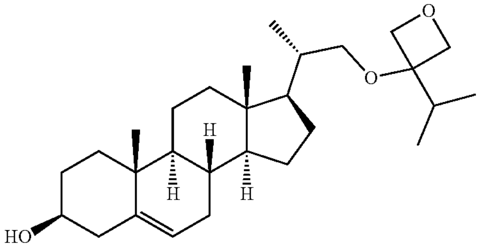
27
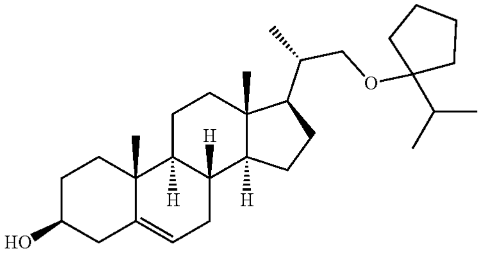
28
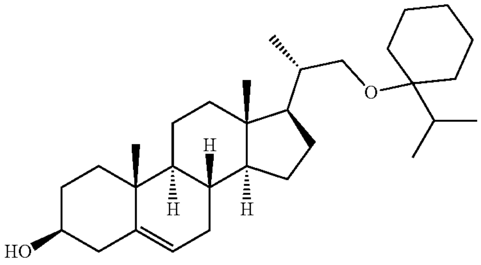

TABLE 16-continued
8
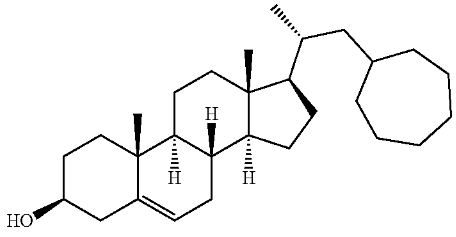
9
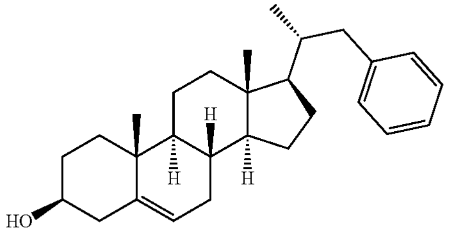
10
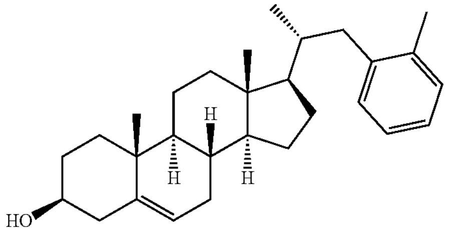
11
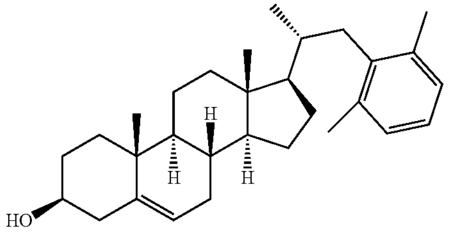
12
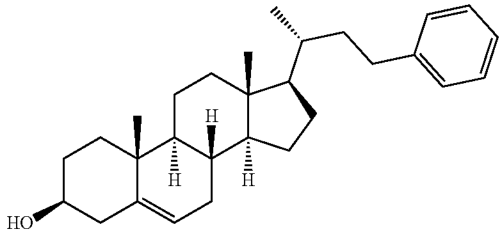
13
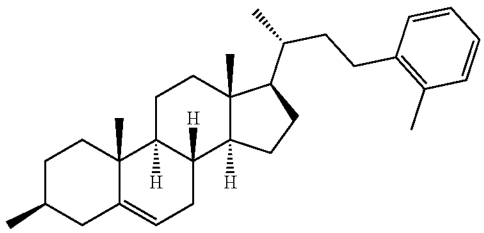

TABLE 16-continued
29
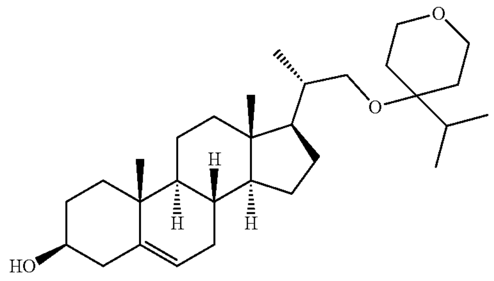
30
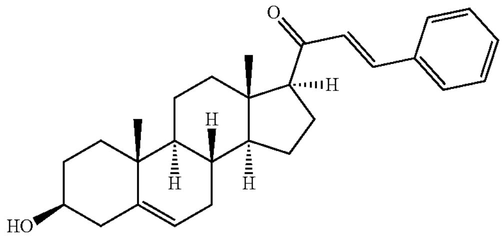
31
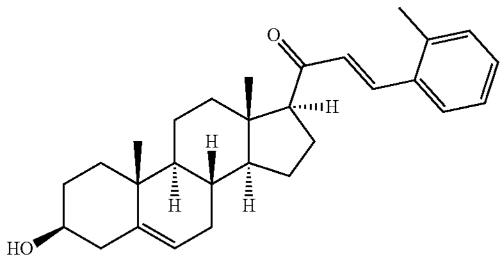
32
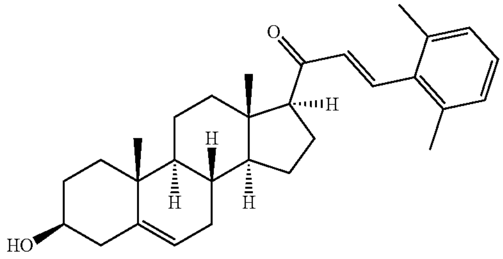
33
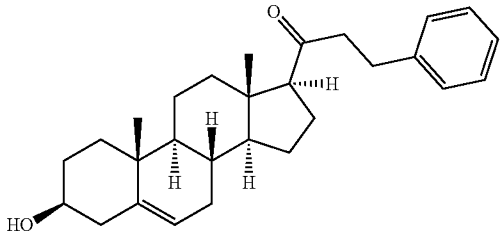
34
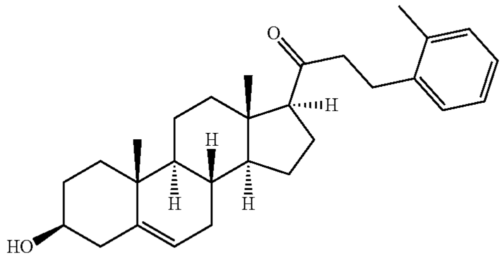

TABLE 16-continued
14
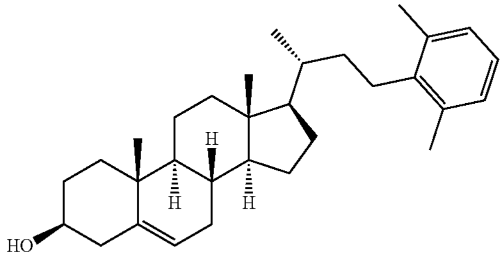
15
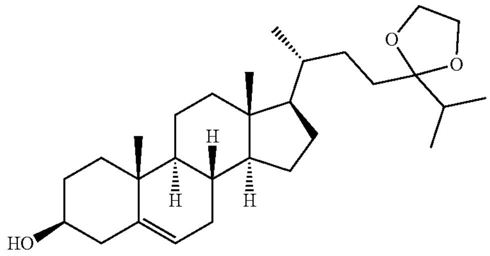
16
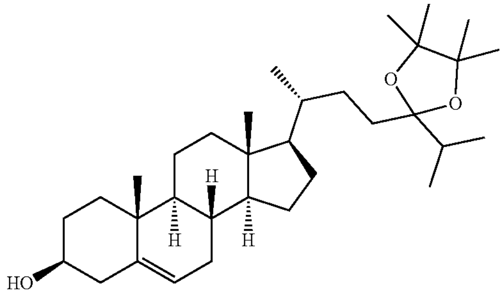
17
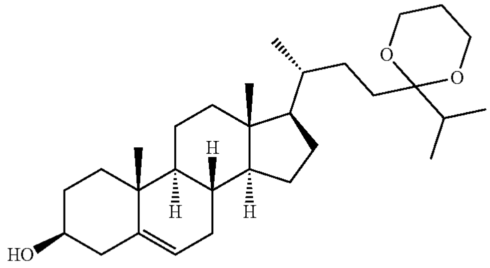
18
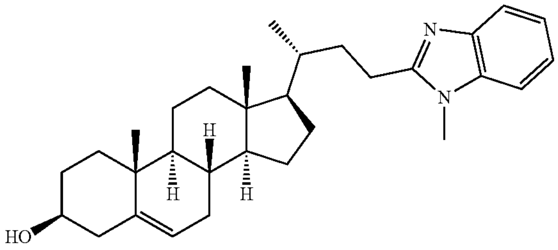
19
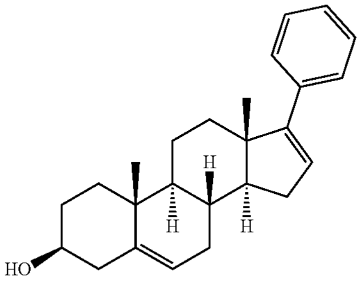

TABLE 16-continued
35
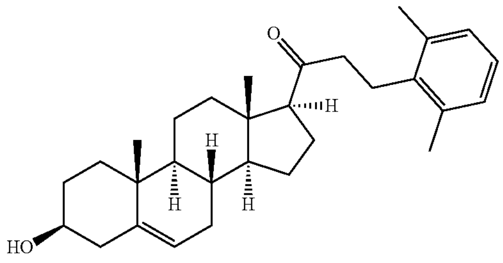
36
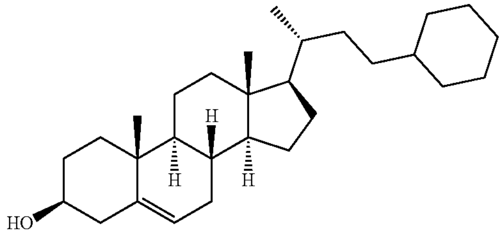
37
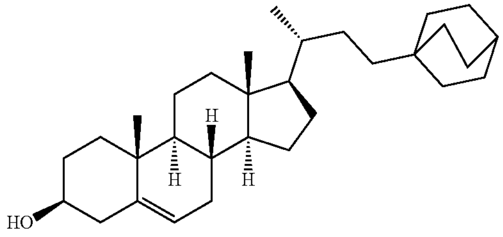
38
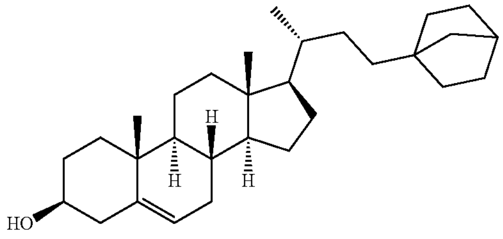
39
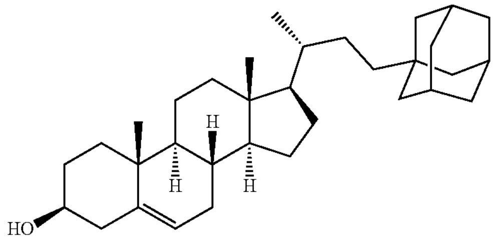
40
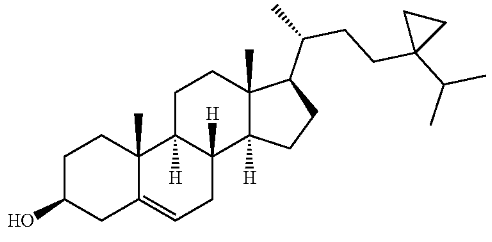

TABLE 16-continued
20
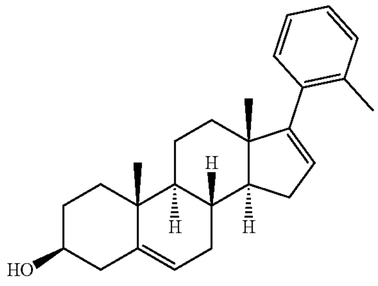
21
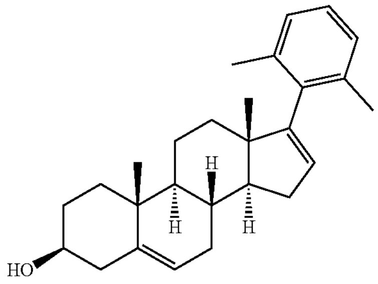
150
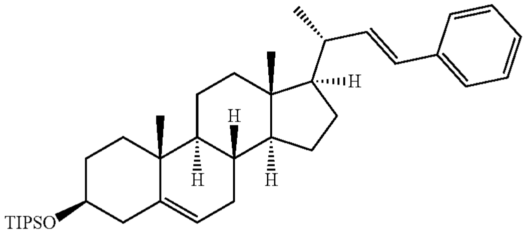
154
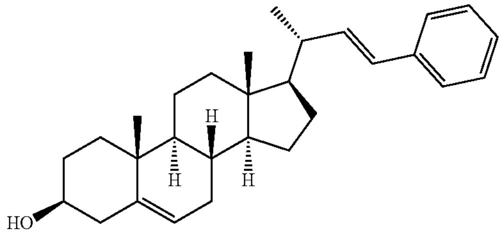
162
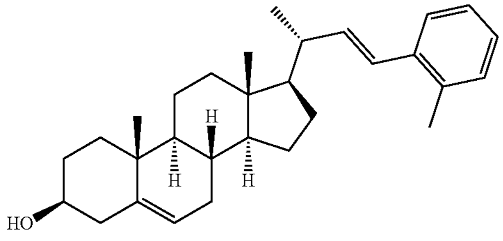
41
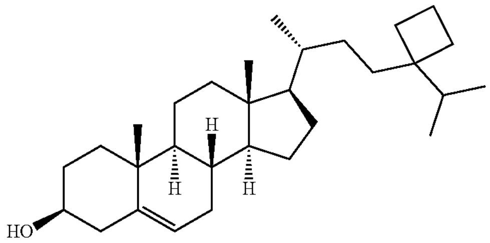

TABLE 16-continued
42
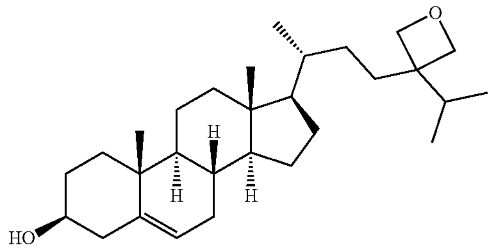
165
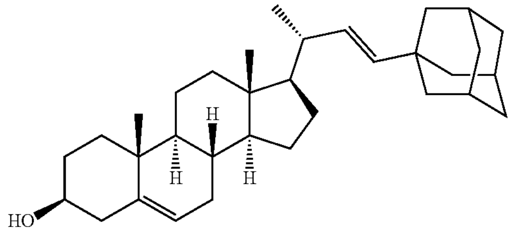
169
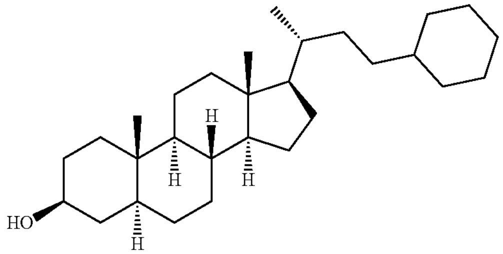
170
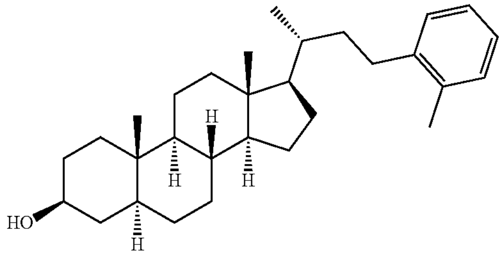
163
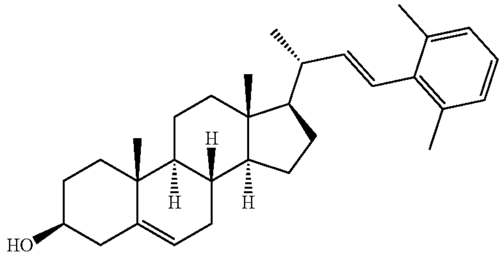
164
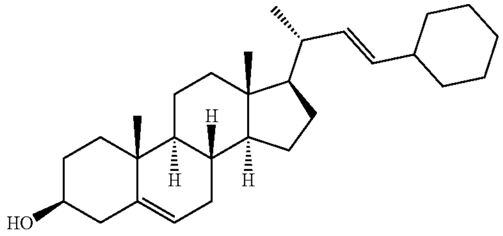

TABLE 16-continued
184
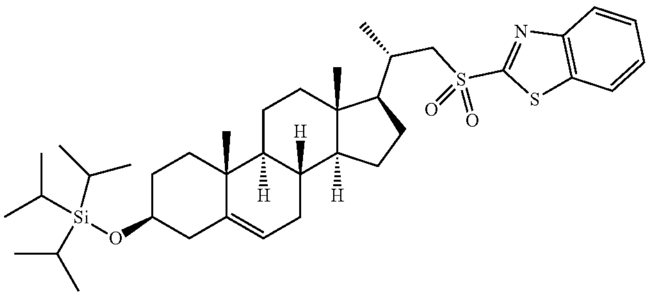
171
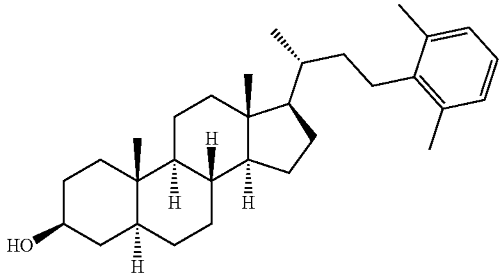
172
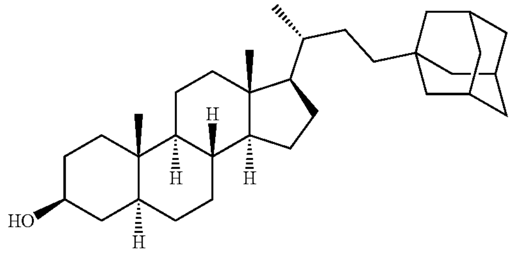
43
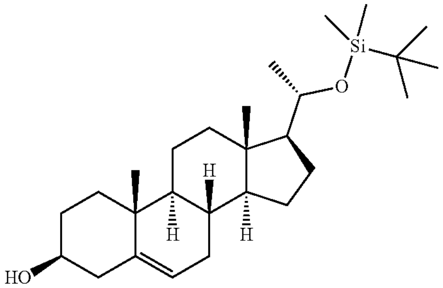
47
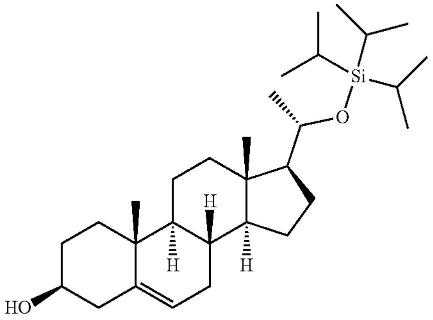

TABLE 16-continued
44
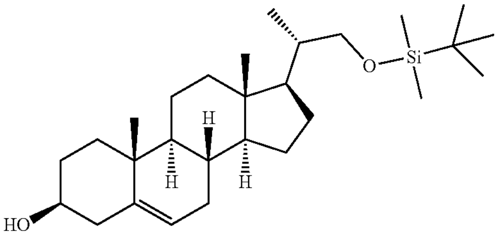
45
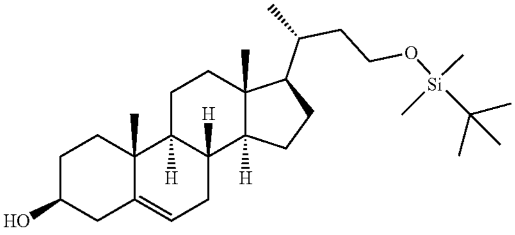
46
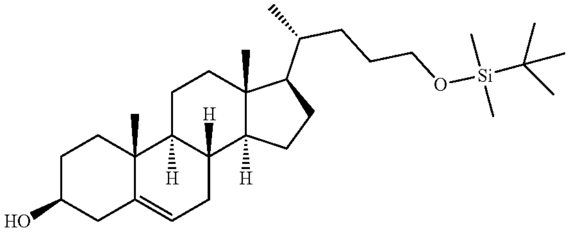
175
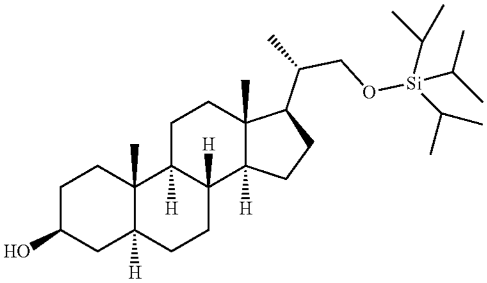
176
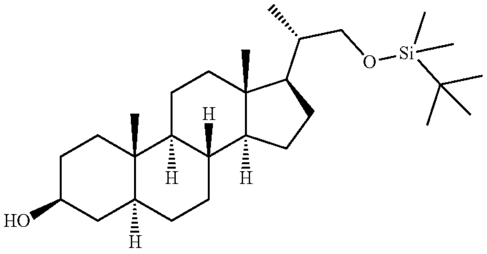
48
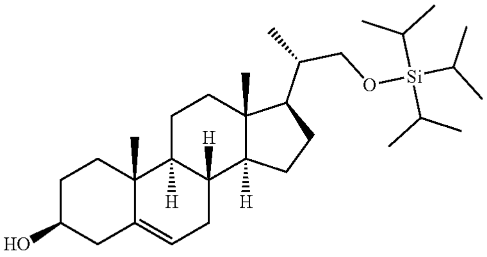

TABLE 16-continued
49
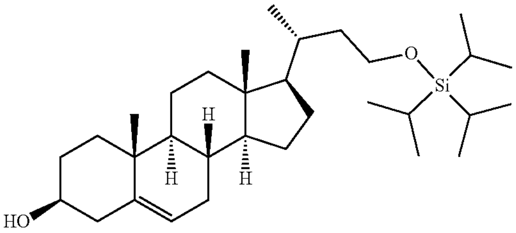
50
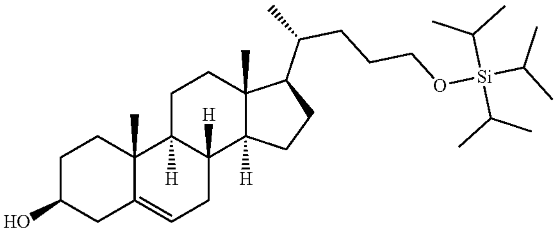
177
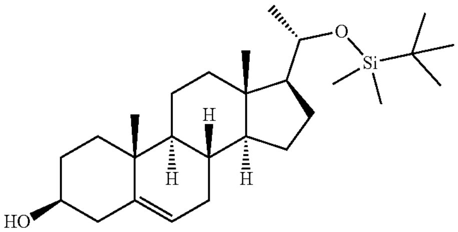
178
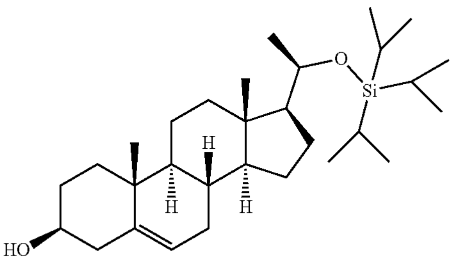
51
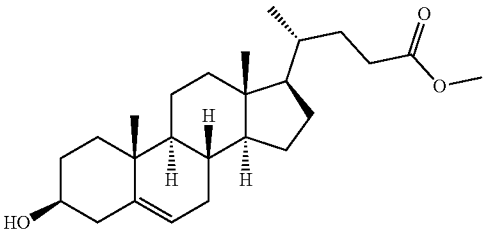
52
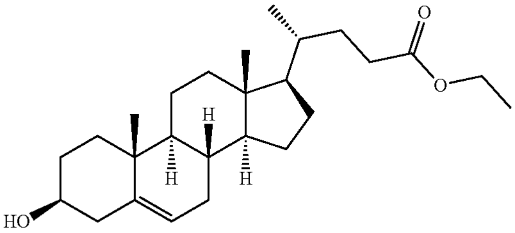

TABLE 16-continued
53
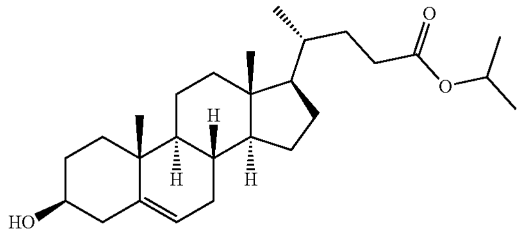
54
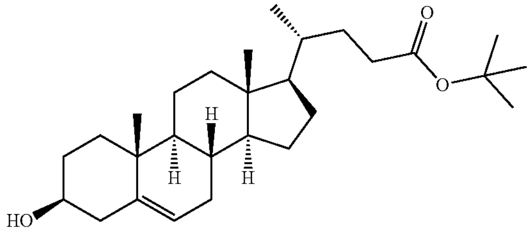
55
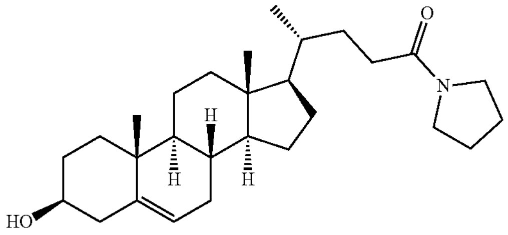
56
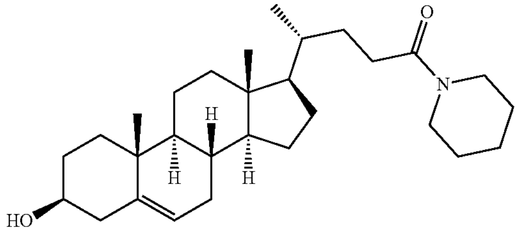
57
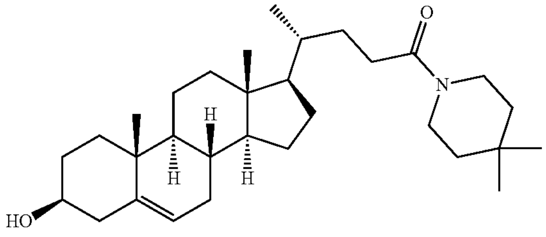
60
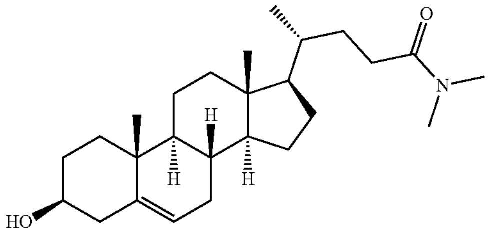

TABLE 16-continued
61
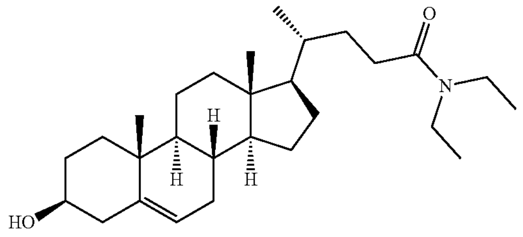
62
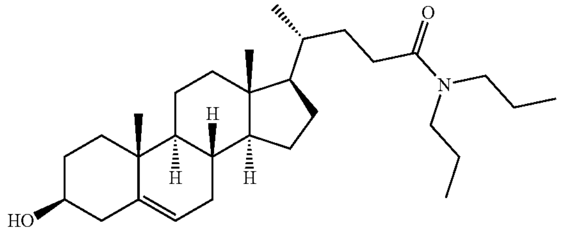
63
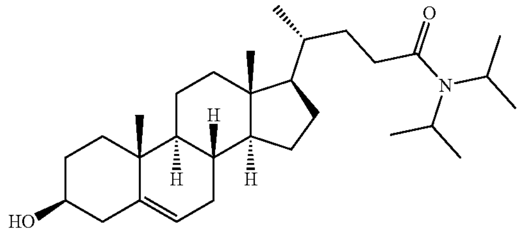
64
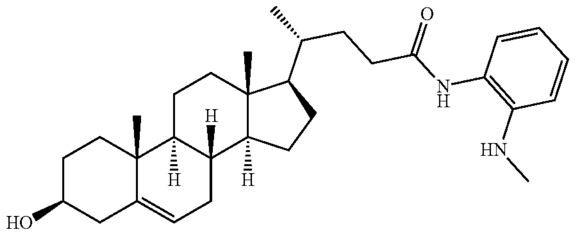
65
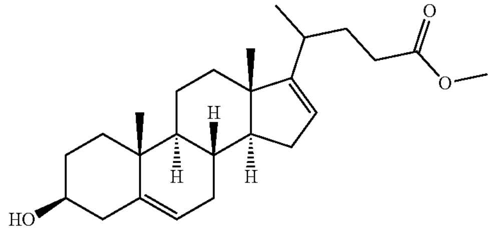
66
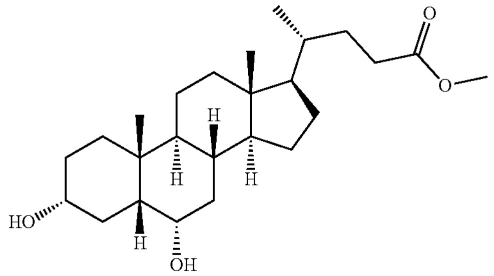

TABLE 16-continued
58
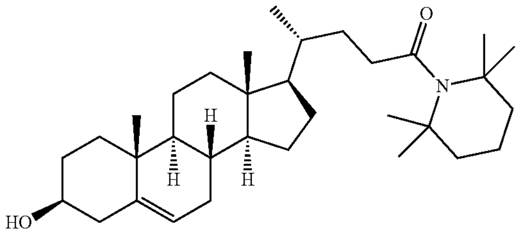
59
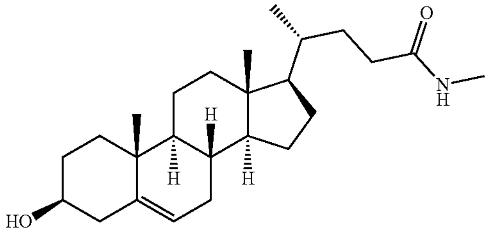
153
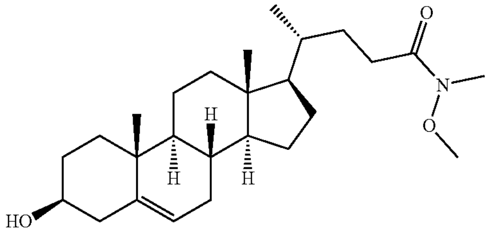
67
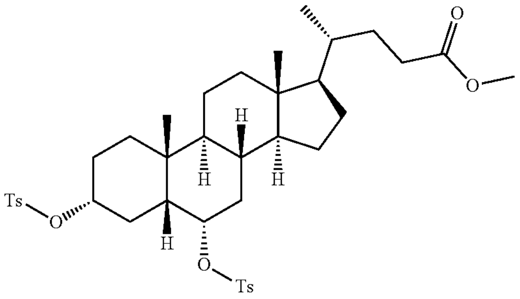
149
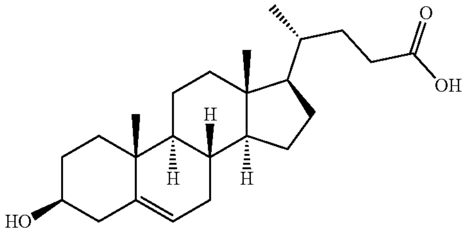
68
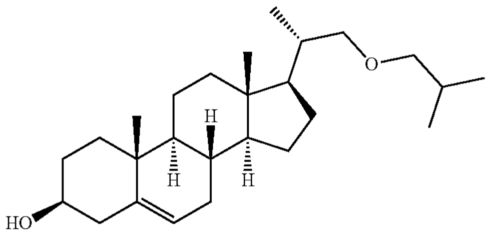

TABLE 16-continued
69
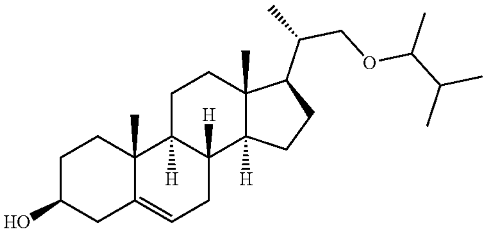
71
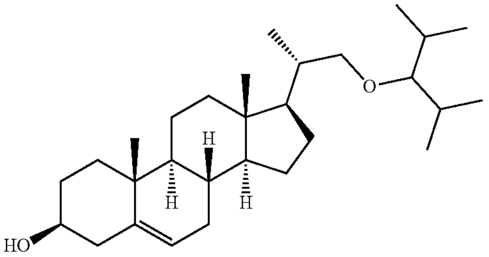
72
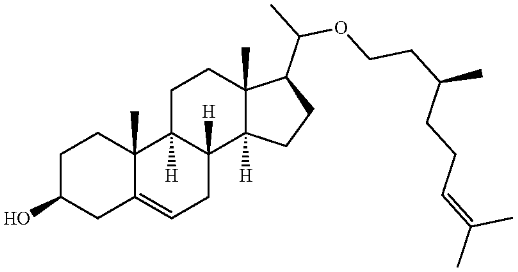
70
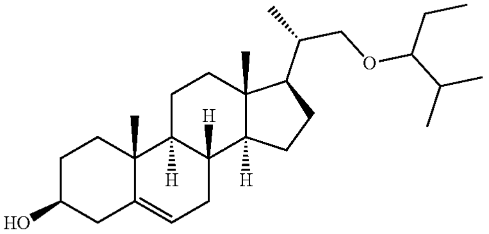
73
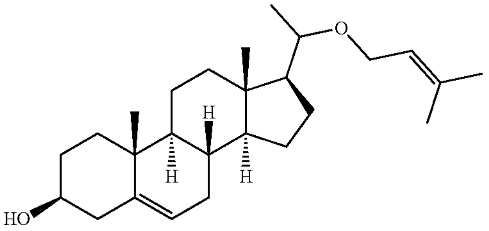
74
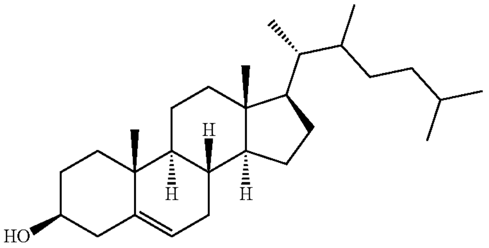

TABLE 16-continued
75
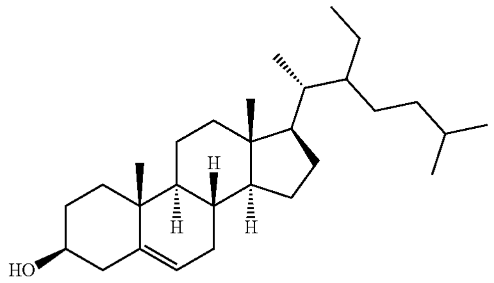
76
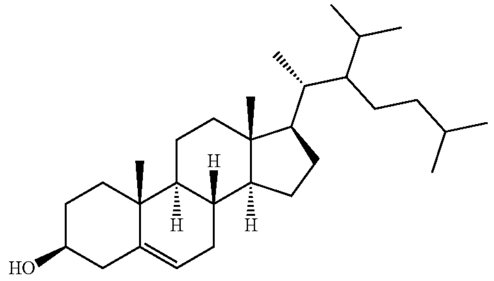
77
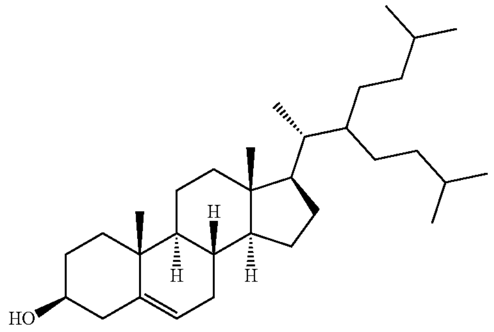
78
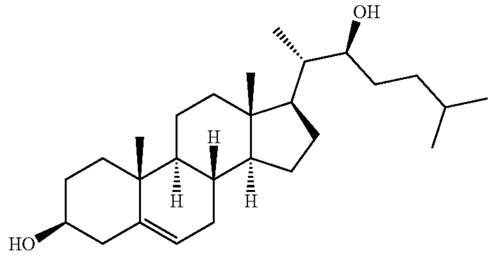
79
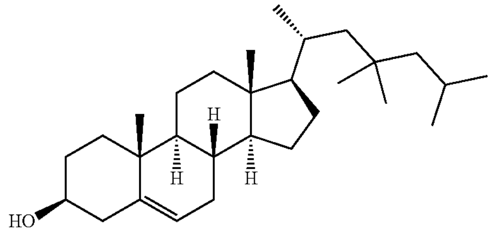

TABLE 16-continued
80
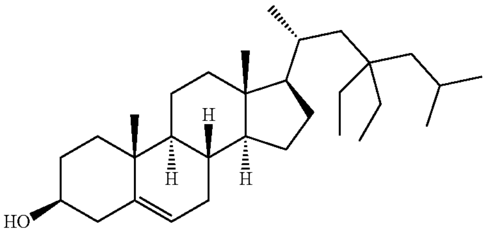
81
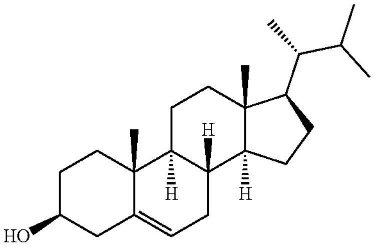
82
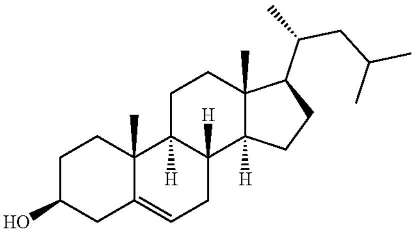
83
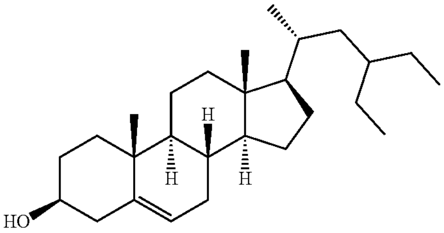
84
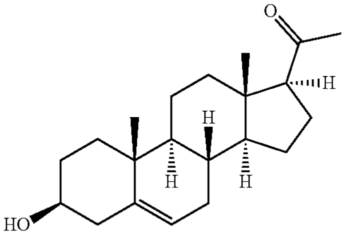
85
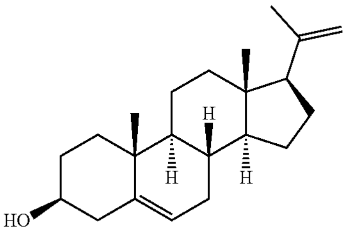

TABLE 16-continued
86
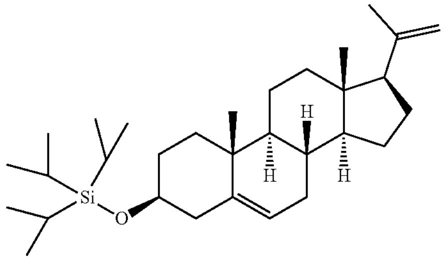
87
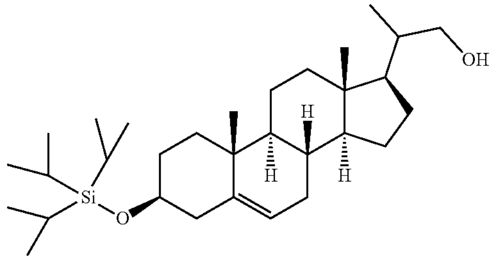
152
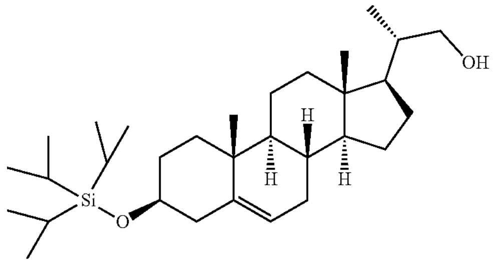
157
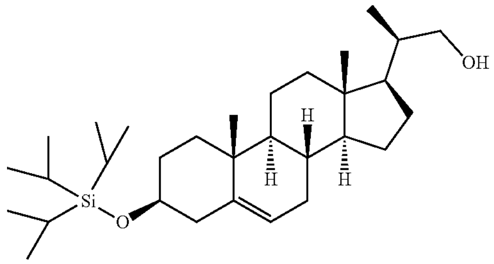
88
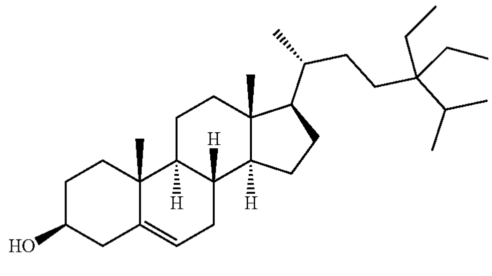
89
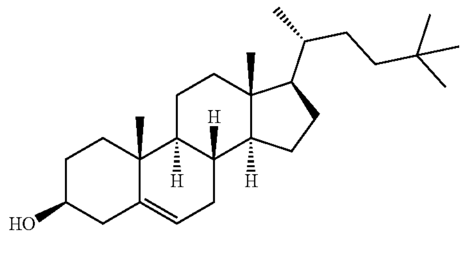

TABLE 16-continued
90
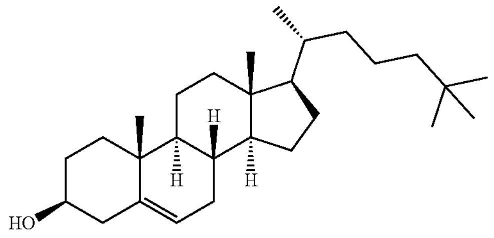
91
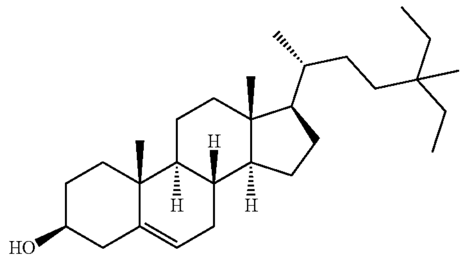
93
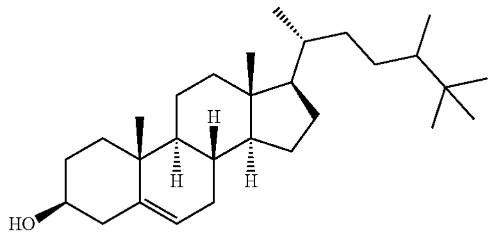
94
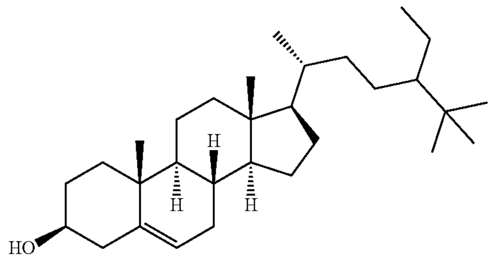
95
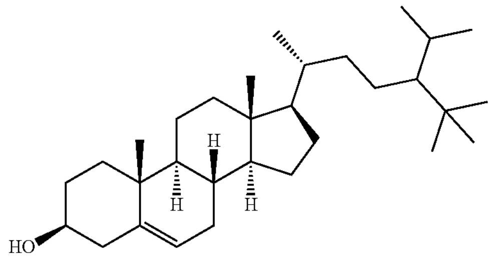
96
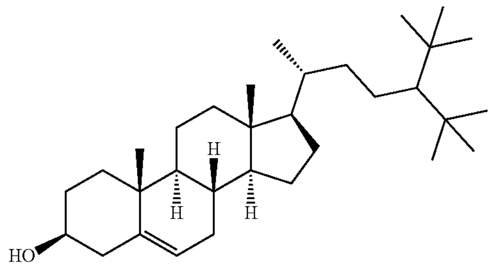

TABLE 16-continued
92
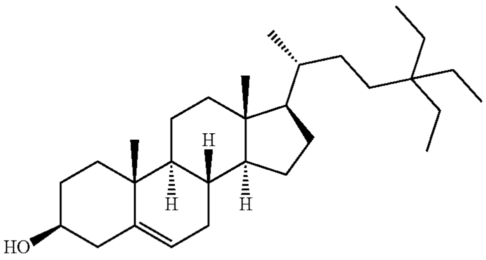
97
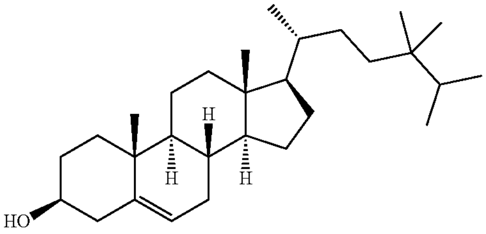
98
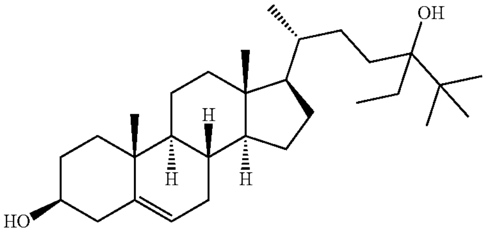
99
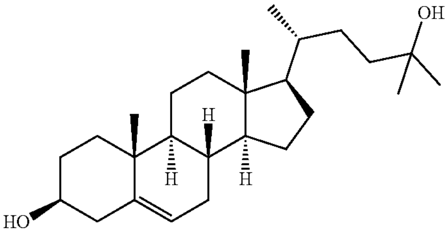
100
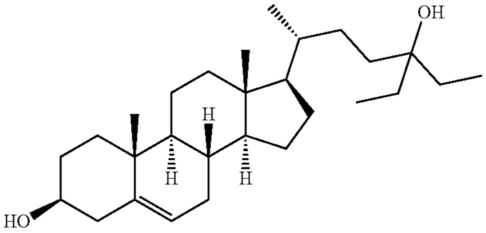
101
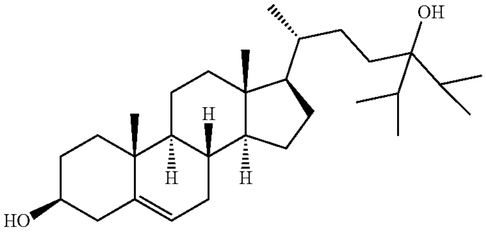

TABLE 16-continued
102
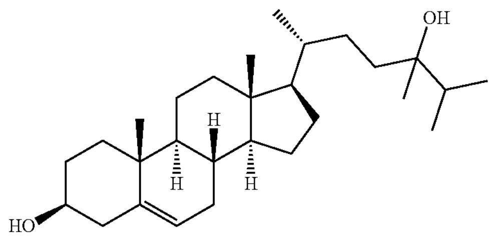
103
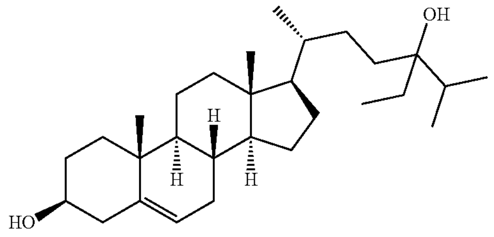
104
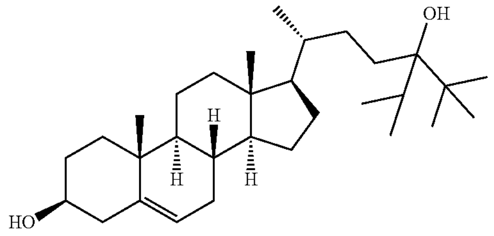
105
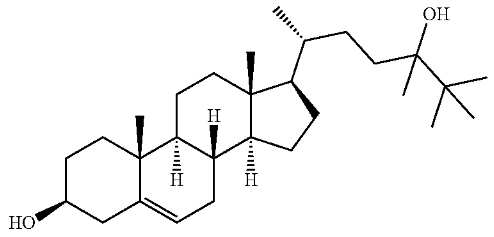
180
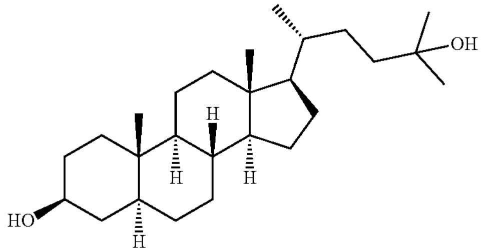
181
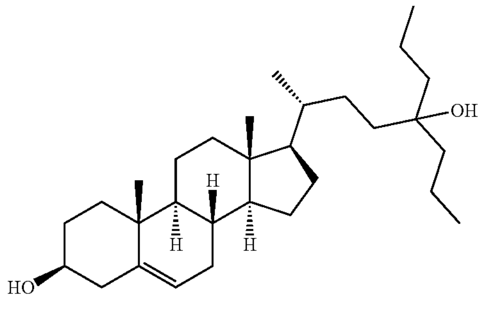

TABLE 16-continued
182
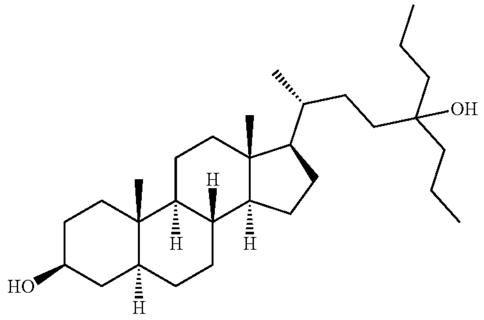
106
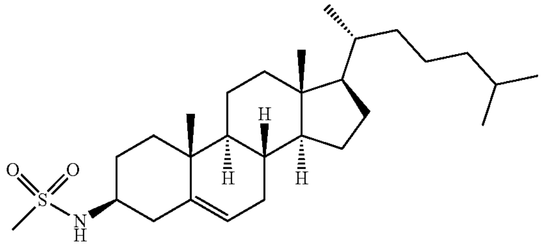
107
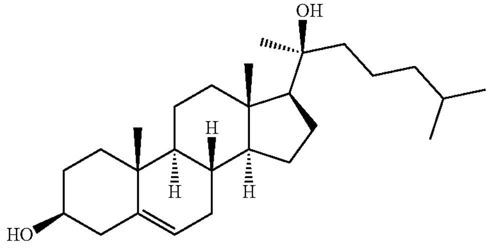
108
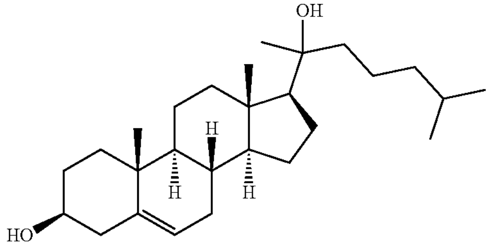
109
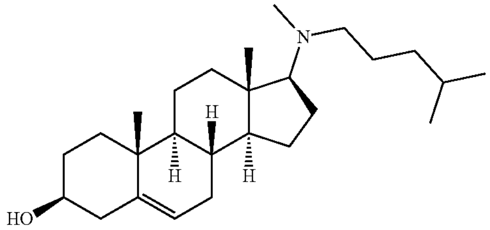
110
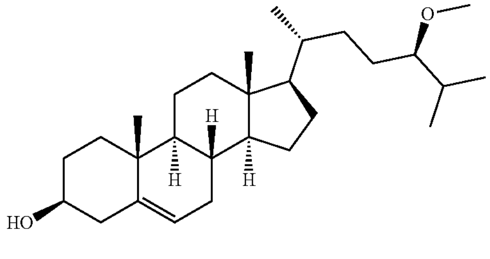

TABLE 16-continued
121 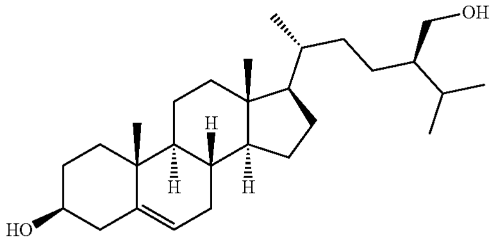
111 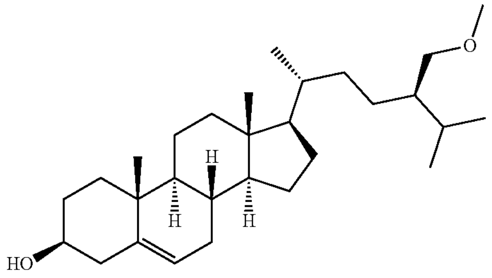
112 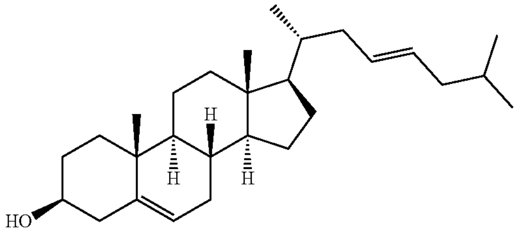
113 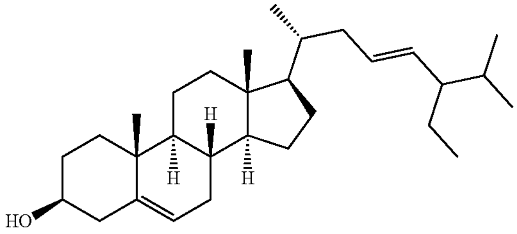
114 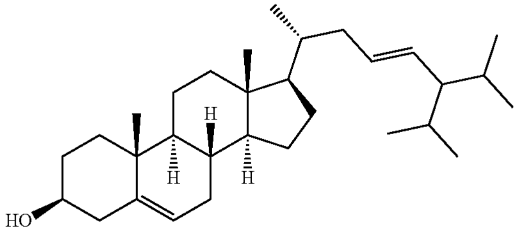
115 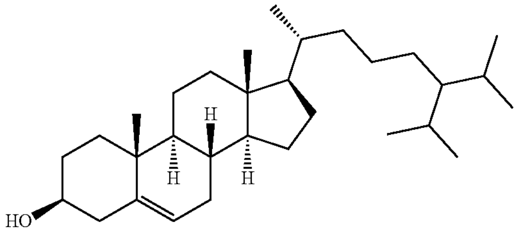

TABLE 16-continued
116
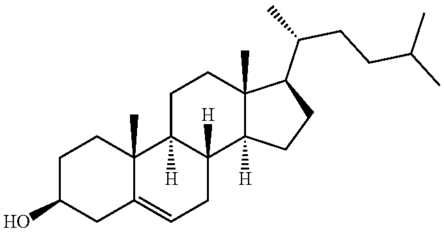
117
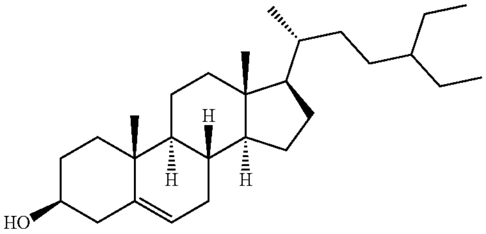
122
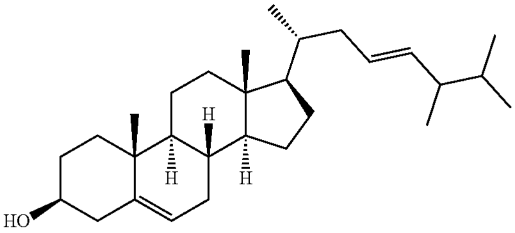
123
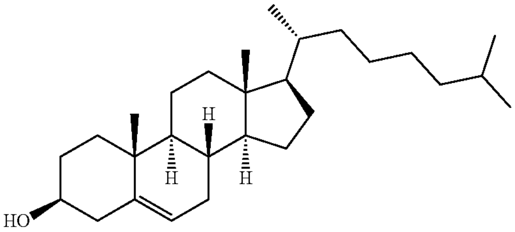
124
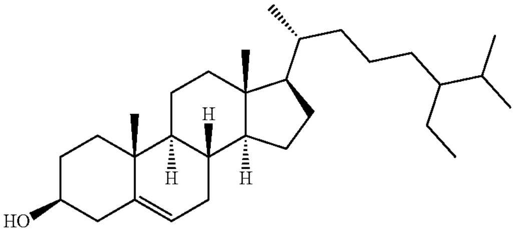
125
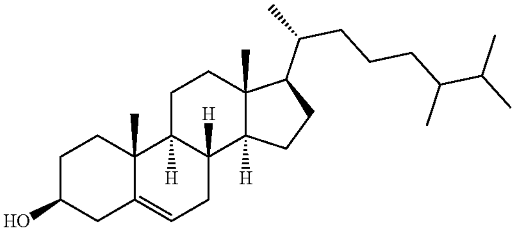

TABLE 16-continued
126
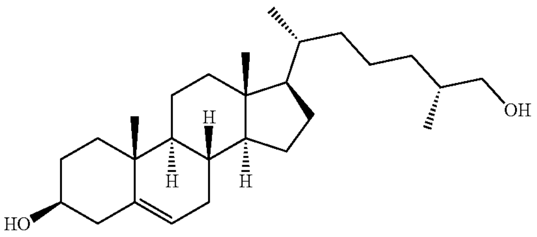
127
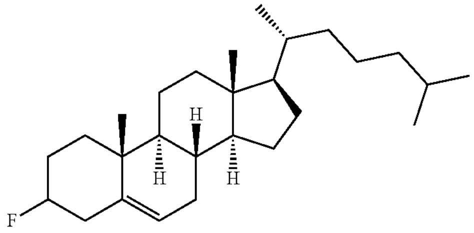
128
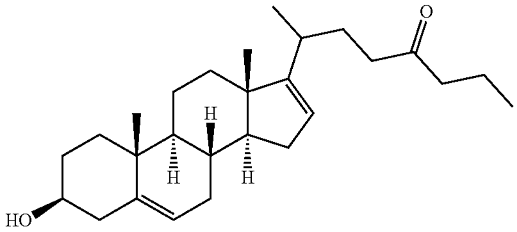
118
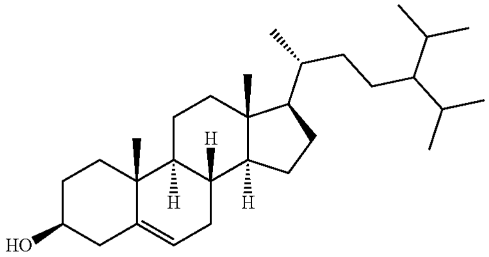
119
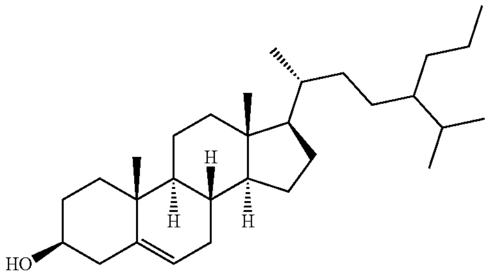
120
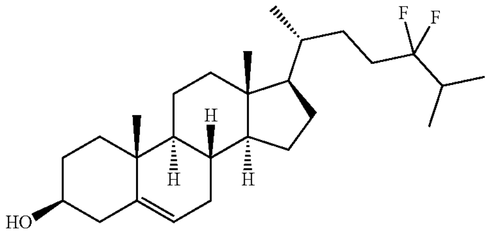

TABLE 16-continued
156
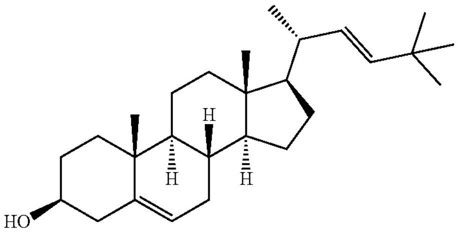
158
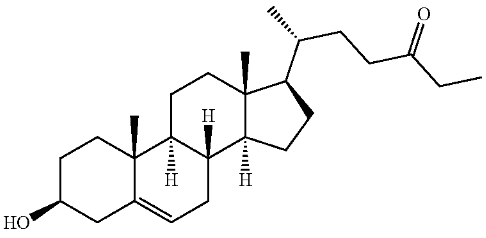
160
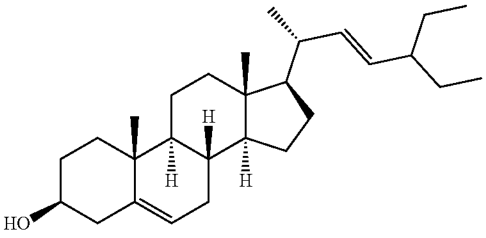
129
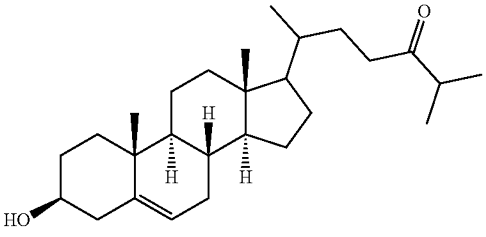
130
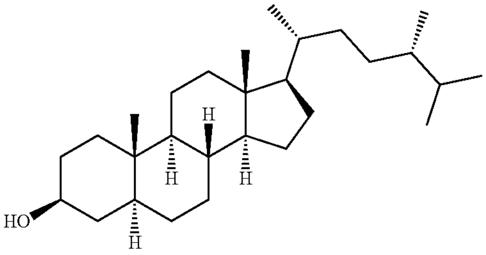
155
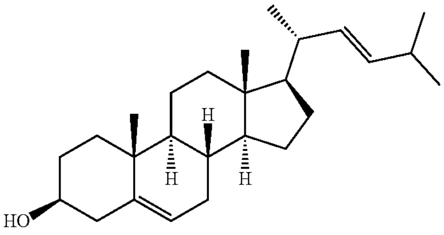

TABLE 16-continued
167
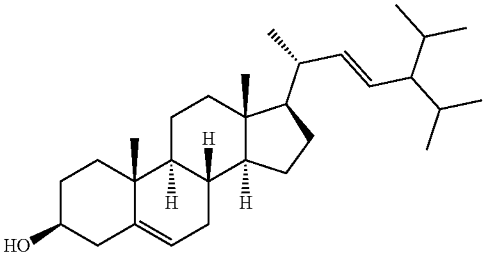
168
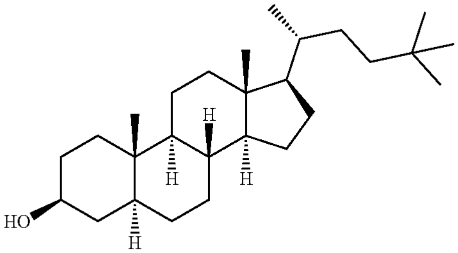
173
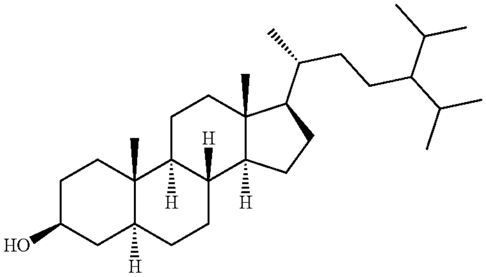
161
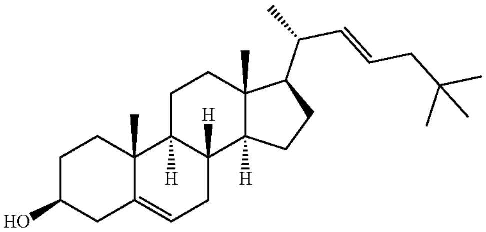
166
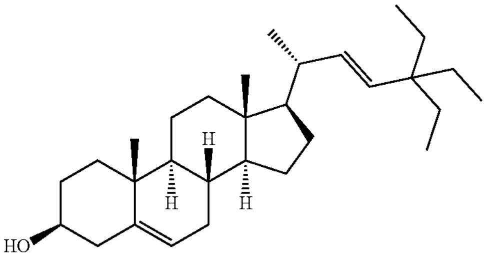
174
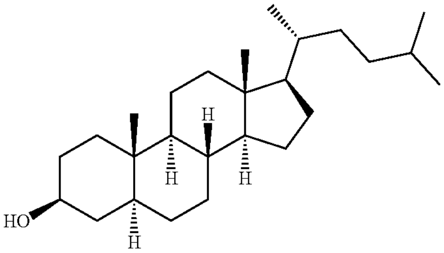

TABLE 16-continued
179
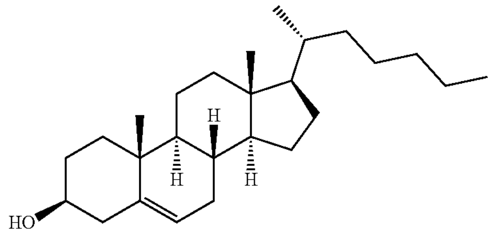
131
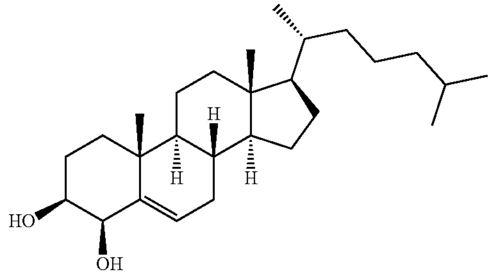
132
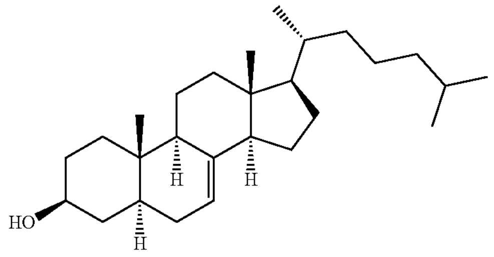
133
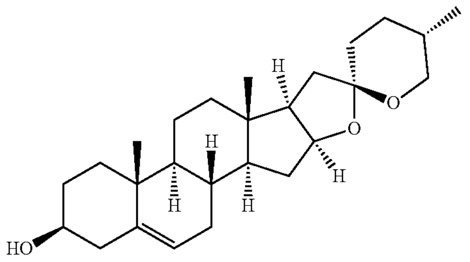
134
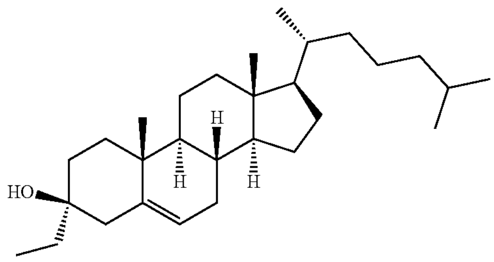
135
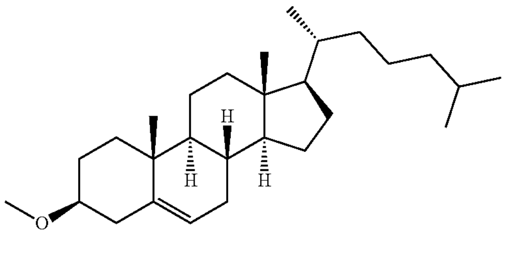

TABLE 16-continued
136 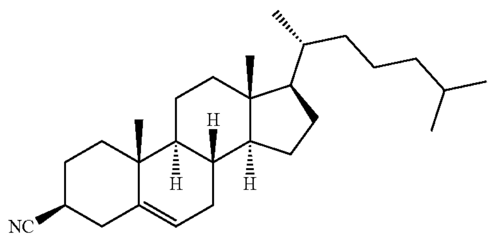
137 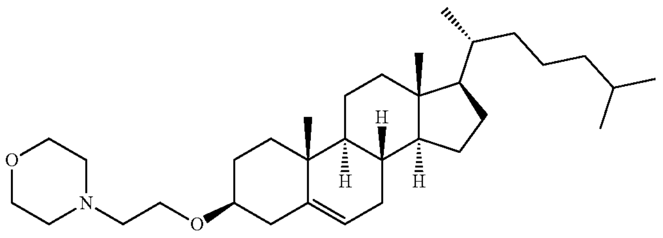
138 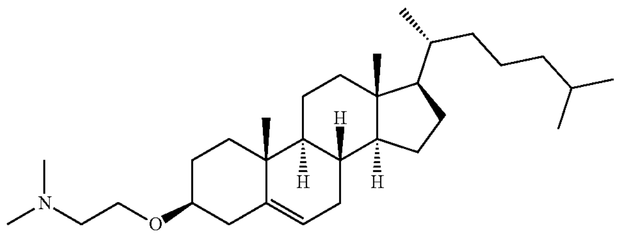
139 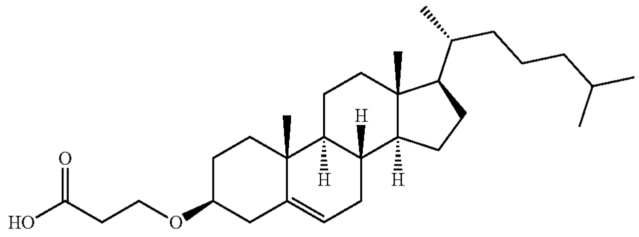
140 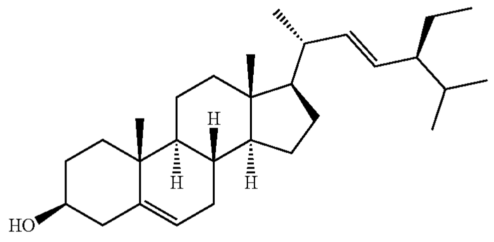
142 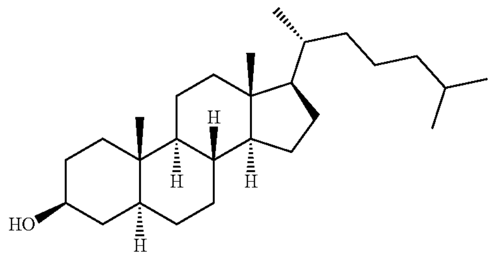

TABLE 16-continued
143
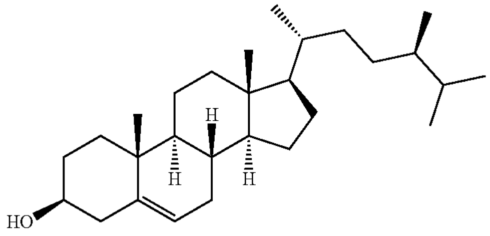
144
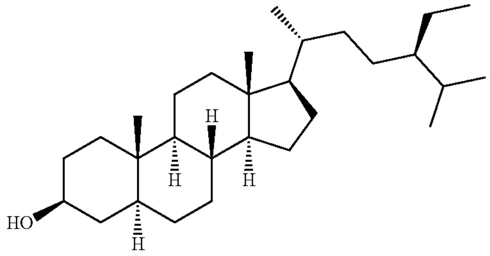
145
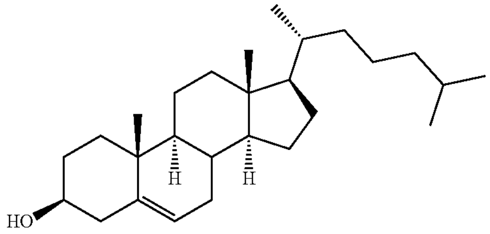
146
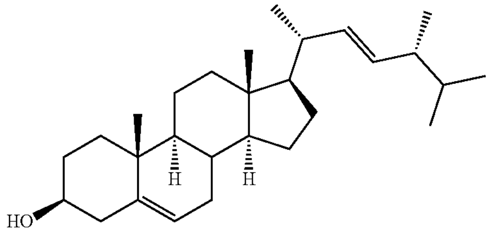
147
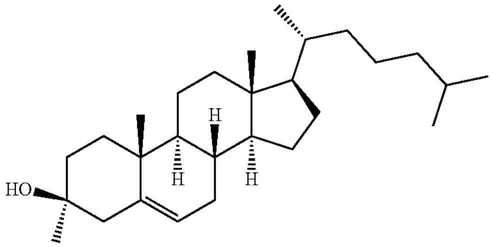
148
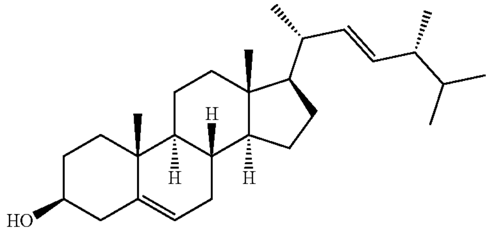

TABLE 16-continued
| | |
|---|---|
| 141 | 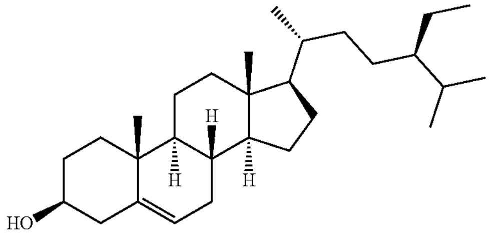 |
| 159 | 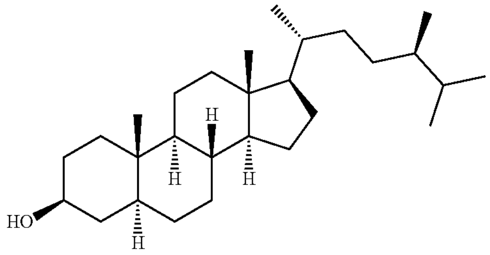 |
| 151 | 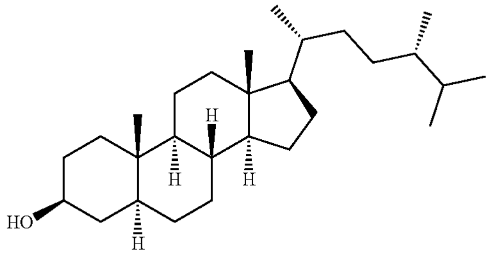 |
| Composition S• No. | Structure |
|---|---|
| 183 | 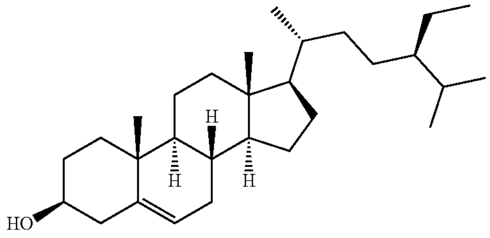<br>Compound 141<br>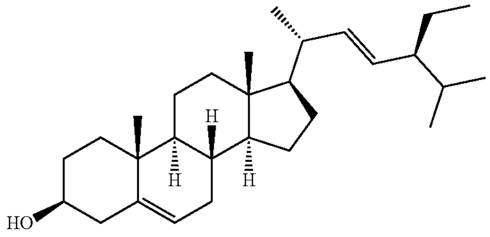<br>compound 140<br>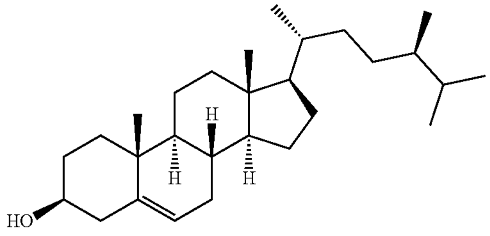<br>Compound 143 |

TABLE 16-continued

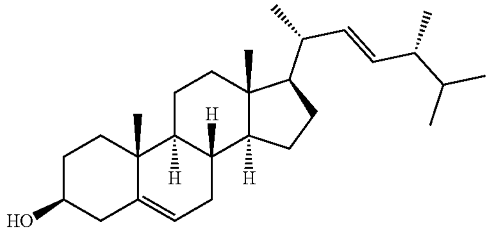

Compound 148

9. LNP Formulations

The formation of a lipid nanoparticle (LNP) described herein may be accomplished by any methods known in the art. For example, as described in U.S. Pat. Pub. No. US2012/0178702 A1, which is incorporated herein by reference in its entirety. Non-limiting examples of lipid nanoparticle compositions and methods of making them are described, for example, in Semple et al (2010) Nat. Biotechnol. 28:172-176; Jayarama et al. (2012), Angew. Chem. Int. Ed., 51:8529-8533; and Maier et al. (2013) Molecular Therapy 21, 1570-1578 (the contents of each of which are incorporated herein by reference in their entirety).

In one embodiment, the LNP formulation may be prepared by, e.g., the methods described in International Pat. Pub. No. WO 2011/127255 or WO 2008/103276, the contents of each of which are herein incorporated by reference in their entirety.

In one embodiment, LNP formulations described herein may comprise a polycationic composition. As a non-limiting example, the polycationic composition may be a composition selected from Formulae 1-60 of U.S. Pat. Pub. No. US2005/0222064 A1, the content of which is herein incorporated by reference in its entirety.

In one embodiment, the lipid nanoparticle may be formulated by the methods described in U.S. Pat. Pub. No. US2013/0156845 A1, and International Pat. Pub. No. WO2013/093648 A2 or WO2012/024526 A2, each of which is herein incorporated by reference in its entirety.

In one embodiment, the lipid nanoparticles described herein may be made in a sterile environment by the system and/or methods described in U.S. Pat. Pub. No. US2013/0164400 A1, which is incorporated herein by reference in its entirety.

In one embodiment, the LNP formulation may be formulated in a nanoparticle such as a nucleic acid-lipid particle described in U.S. Pat. No. 8,492,359, which is incorporated herein by reference in its entirety.

A nanoparticle composition may optionally comprise one or more coatings. For example, a nanoparticle composition may be formulated in a capsule, film, or tablet having a coating. A capsule, film, or tablet including a composition described herein may have any useful size, tensile strength, hardness, or density.

In some embodiments, the lipid nanoparticles described herein may be synthesized using methods comprising microfluidic mixers. Exemplary microfluidic mixers may include, but are not limited to, a slit interdigitial micromixer including, but not limited to, those manufactured by Precision Nanosystems (Vancouver, BC, Canada), Microinnova (Allerheiligen bei Wildon, Austria) and/or a staggered herringbone micromixer (SHM) (Zhigaltsev, I. V. et al. (2012) Langmuir. 28:3633-40; Belliveau, N. M. et al. Mol. Ther. Nucleic. Acids. (2012) 1:e37; Chen, D. et al. J. Am. Chem. Soc. (2012) 134(16):6948-51; each of which is herein incorporated by reference in its entirety).

In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Pat. Pub. Nos. US2004/0262223 A1 and US2012/0276209 A1, each of which is incorporated herein by reference in their entirety.

In one embodiment, the lipid nanoparticles may be formulated using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut fur Mikrotechnik Mainz GmbH, Mainz Germany). In one embodiment, the lipid nanoparticles are created using microfluidic technology (see, Whitesides (2006) Nature. 442: 368-373; and Abraham et al. (2002) Science. 295: 647-651; each of which is herein incorporated by reference in its entirety). As a non-limiting example, controlled microfluidic formulation includes a passive method for mixing streams of steady pressure-driven flows in micro channels at a low Reynolds number (see, e.g., Abraham et al. (2002) Science. 295: 647651; which is herein incorporated by reference in its entirety).

In one embodiment, the circRNA of the present invention may be formulated in lipid nanoparticles created using a micromixer chip such as, but not limited to, those from Harvard Apparatus (Holliston, Mass.), Dolomite Microfluidics (Royston, UK), or Precision Nanosystems (Van Couver, BC, Canada). A micromixer chip can be used for rapid mixing of two or more fluid streams with a split and recombine mechanism.

In one embodiment, the lipid nanoparticles may have a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm. In one embodiment, the lipid nanoparticles may have a diameter from about 10 to 500 nm. In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm. Each possibility represents a separate embodiment of the present invention.

In some embodiments, a nanoparticle (e.g., a lipid nanoparticle) has a mean diameter of 10-500 nm, 20-400 nm, 30-300 nm, or 40-200 nm. In some embodiments, a nanoparticle (e.g., a lipid nanoparticle) has a mean diameter of 50-150 nm, 50-200 nm, 80-100 nm, or 80-200 nm.

In some embodiments, the lipid nanoparticles described herein can have a diameter from below 0.1 μm to up to 1 mm such as, but not limited to, less than 0.1 μm, less than 1.0 μm, less than 5 μm, less than 10 μm, less than 15 μm, less than 20 μm, less than 25 μm, less than 30 μm, less than 35 μm, less than 40 μm, less than 50 μm, less than 55 μm, less than 60 μm, less than 65 μm, less than 70 μm, less than 75 μm, less than 80 μm, less than 85 μm, less than 90 μm, less than 95 μm, less than 100 μm, less than 125 μm, less than 150 μm, less than 175 μm, less than 200 μm, less than 225 μm, less than 250 μm, less than 275 μm, less than 300 μm, less than 325 μm, less than 350 μm, less than 375 μm, less than 400 μm, less than 425 μm, less than 450 μm, less than 475 μm, less than 500 μm, less than 525 μm, less than 550 μm, less than 575 μm, less than 600 μm, less than 625 μm, less than 650 μm, less than 675 μm, less than 700 μm, less than 725 μm, less than 750 μm, less than 775 μm, less than 800 μm, less than 825 μm, less than 850 μm, less than 875 μm, less than 900 μm, less than 925 μm, less than 950 μm, less than 975 μm.

In another embodiment, LNPs may have a diameter from about 1 nm to about 100 nm, from about 1 nm to about 10 nm, about 1 nm to about 20 nm, from about 1 nm to about nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm. Each possibility represents a separate embodiment of the present invention.

A nanoparticle composition may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20. Each possibility represents a separate embodiment of the present invention.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition may be from about −20 mV to about +20 mV, from about −20 mV to about +15 mV, from about −20 mV to about +10 mV, from about −20 mV to about +5 mV, from about −20 mV to about 0 mV, from about −20 mV to about −5 mV, from about −20 mV to about −10 mV, from about −20 mV to about −15 mV from about −20 mV to about +20 mV, from about −20 mV to about +15 mV, from about −20 mV to about +10 mV, from about −20 mV to about +5 mV, from about −20 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV. Each possibility represents a separate embodiment of the present invention.

The efficiency of encapsulation of a therapeutic agent describes the amount of therapeutic agent that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic agent in a solution containing the nanoparticle composition before and after breaking up the nanoparticle composition with one or more organic solvents or detergents. Fluorescence may be used to measure the amount of free therapeutic agent (e.g., nucleic acids) in a solution. For the nanoparticle compositions described herein, the encapsulation efficiency of a therapeutic agent may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%. Each possibility represents a separate embodiment of the present invention. In some embodiments, the lipid nanoparticle has a polydiversity value of less than 0.4. In some embodiments, the lipid nanoparticle has a net neutral charge at a neutral pH. In some embodiments, the lipid nanoparticle has a mean diameter of 50-200 nm.

The properties of a lipid nanoparticle formulation may be influenced by factors including, but not limited to, the selection of the cationic lipid component, the degree of cationic lipid saturation, the selection of the non-cationic lipid component, the degree of noncationic lipid saturation, the selection of the structural lipid component, the nature of the PEGylation, ratio of all components and biophysical parameters such as size. As described herein, the purity of a PEG lipid component is also important to an LNP's properties and performance.

10. Methods

In one embodiment, a lipid nanoparticle formulation may be prepared by the methods described in International Publication Nos. WO2011127255 or WO2008103276, each of which is herein incorporated by reference in their entirety. In some embodiments, lipid nanoparticle formulations may be as described in International Publication No. WO2019131770, which is herein incorporated by reference in its entirety.

In some embodiments, circular RNA is formulated according to a process described in U.S. patent application Ser. No. 15/809,680. In some embodiments, the present invention provides a process of encapsulating circular RNA in transfer vehicles comprising the steps of forming lipids into pre-formed transfer vehicles (i.e. formed in the absence of RNA) and then combining the pre-formed transfer vehicles with RNA. In some embodiments, the novel formulation process results in an RNA formulation with higher potency (peptide or protein expression) and higher efficacy (improvement of a biologically relevant endpoint) both in vitro and in vivo with potentially better tolerability as compared to the same RNA formulation prepared without the step of preforming the lipid nanoparticles (e.g., combining the lipids directly with the RNA).

For certain cationic lipid nanoparticle formulations of RNA, in order to achieve high encapsulation of RNA, the RNA in buffer (e.g., citrate buffer) has to be heated. In those processes or methods, the heating is required to occur before the formulation process (i.e. heating the separate components) as heating post-formulation (post-formation of nanoparticles) does not increase the encapsulation efficiency of the RNA in the lipid nanoparticles. In contrast, in some embodiments of the novel processes of the present invention, the order of heating of RNA does not appear to affect the RNA encapsulation percentage. In some embodiments, no heating (i.e. maintaining at ambient temperature) of one or more of the solutions comprising the pre-formed lipid nanoparticles, the solution comprising the RNA and the mixed solution comprising the lipid nanoparticle encapsulated RNA is required to occur before or after the formulation process.

RNA may be provided in a solution to be mixed with a lipid solution such that the RNA may be encapsulated in lipid nanoparticles. A suitable RNA solution may be any aqueous solution containing RNA to be encapsulated at various concentrations. For example, a suitable RNA solution may contain an RNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable RNA solution may contain an RNA at a concentration in a range from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml.

Typically, a suitable RNA solution may also contain a buffering agent and/or salt. Generally, buffering agents can include HEPES, Tris, ammonium sulfate, sodium bicarbonate, sodium citrate, sodium acetate, potassium phosphate or sodium phosphate. In some embodiments, suitable concentration of the buffering agent may be in a range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM.

Exemplary salts can include sodium chloride, magnesium chloride, and potassium chloride. In some embodiments, suitable concentration of salts in an RNA solution may be in a range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM.

In some embodiments, a suitable RNA solution may have a pH in a range from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5.

Various methods may be used to prepare an RNA solution suitable for the present invention. In some embodiments, RNA may be directly dissolved in a buffer solution described herein. In some embodiments, an RNA solution may be generated by mixing an RNA stock solution with a buffer solution prior to mixing with a lipid solution for encapsulation. In some embodiments, an RNA solution may be generated by mixing an RNA stock solution with a buffer solution immediately before mixing with a lipid solution for encapsulation.

According to the present invention, a lipid solution contains a mixture of lipids suitable to form transfer vehicles for encapsulation of RNA. In some embodiments, a suitable lipid solution is ethanol based. For example, a suitable lipid solution may contain a mixture of desired lipids dissolved in pure ethanol (i.e. 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. In some embodiments, a suitable lipid solution may contain a mixture of desired lipids at a total concentration in a range from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml.

11. Targeting

The present invention also contemplates the discriminatory targeting of target cells and tissues by both passive and active targeting means. The phenomenon of passive targeting exploits the natural distributions patterns of a transfer vehicle in vivo without relying upon the use of additional excipients or means to enhance recognition of the transfer vehicle by target cells. For example, transfer vehicles which are subject to phagocytosis by the cells of the reticulo-endothelial system are likely to accumulate in the liver or spleen, and accordingly may provide a means to passively direct the delivery of the compositions to such target cells.

Alternatively, the present invention contemplates active targeting, which involves the use of targeting moieties that may be bound (either covalently or non-covalently) to the transfer vehicle to encourage localization of such transfer vehicle at certain target cells or target tissues. For example, targeting may be mediated by the inclusion of one or more endogenous targeting moieties in or on the transfer vehicle to encourage distribution to the target cells or tissues. Recognition of the targeting moiety by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes). As provided herein, the composition can comprise a moiety capable of enhancing affinity of the composition to the target cell. Targeting moieties may be linked to the outer bilayer of the lipid particle during formulation or post-formulation. These methods are well known in the art. In addition, some lipid particle formulations may employ fusogenic polymers such as PEAA, hemagluttinin, other lipopeptides (see U.S. patent application Ser. No. 08/835,281, and 60/083,294, which are incorporated herein by reference) and other features useful for in vivo and/or intracellular delivery. In other some embodiments, the compositions of the present invention demonstrate improved transfection efficacies, and/or demonstrate enhanced selectivity towards target cells or tissues of interest. Contemplated therefore are compositions which comprise one or more moieties (e.g., peptides, aptamers, oligonucleotides, a vitamin or other molecules) that are capable of enhancing the affinity of the compositions and their nucleic acid contents for the target cells or tissues. Suitable moieties may optionally be bound or linked to the surface of the transfer vehicle. In some embodiments, the targeting moiety may span the surface of a transfer vehicle or be encapsulated within the transfer vehicle. Suitable moieties and are selected based upon their physical, chemical or biological properties (e.g., selective affinity and/or recognition of target cell surface markers or features). Cell-specific target sites and their corresponding targeting ligand can vary widely. Suitable targeting moieties are selected such that the unique characteristics of a target cell are exploited, thus allowing the composition to discriminate between target and non-target cells. For example, compositions of the invention may include surface markers (e.g., apolipoprotein-B or apolipoprotein-E) that selectively enhance recognition of, or affinity to hepatocytes (e.g., by receptor-mediated recognition of and binding to such surface markers). As an example, the use of galactose as a targeting moiety would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. “Drug Delivery and Targeting: For Pharmacists and Pharmaceutical Scientists” (2002) Taylor & Francis, Inc.) The presentation of such targeting moieties that have been conjugated to moieties present in the transfer vehicle (e.g., a lipid nanoparticle) therefore facilitate recognition and uptake of the compositions of the present invention in target cells and tissues. Examples of suitable targeting moieties include one or more peptides, proteins, aptamers, vitamins and oligonucleotides.

In particular embodiments, a transfer vehicle comprises a targeting moiety. In some embodiments, the targeting moiety mediates receptor-mediated endocytosis selectively into a specific population of cells. In some embodiments, the targeting moiety is capable of binding to a T cell antigen. In some embodiments, the targeting moiety is capable of binding to a NK, NKT, or macrophage antigen. In some embodiments, the targeting moiety is capable of binding to a protein selected from the group CD3, CD4, CD8, PD-1, 4-1BB, and CD2. In some embodiments, the targeting moiety is an single chain Fv (scFv) fragment, nanobody, peptide, peptide-based macrocycle, minibody, heavy chain variable region, light chain variable region or fragment thereof. In some embodiments, the targeting moiety is selected from T-cell receptor motif antibodies, T-cell α chain antibodies, T-cell β chain antibodies, T-cell 7 chain antibodies, T-cell δ chain antibodies, CCR7 antibodies, CD3 antibodies, CD4 antibodies, CD5 antibodies, CD7 antibodies, CD8 antibodies, CD1lb antibodies, CD11c antibodies, CD16 antibodies, CD19 antibodies, CD20 antibodies, CD21 antibodies, CD22 antibodies, CD25 antibodies, CD28 antibodies, CD34 antibodies, CD35 antibodies, CD40 antibodies, CD45RA antibodies, CD45RO antibodies, CD52 antibodies, CD56 antibodies, CD62L antibodies, CD68 antibodies, CD80 antibodies, CD95 antibodies, CD117 antibodies, CD127 antibodies, CD133 antibodies, CD137 (4-1BB) antibodies, CD163 antibodies, F4/80 antibodies, IL-4Rα antibodies, Sca-1 antibodies, CTLA-4 antibodies, GITR antibodies GARP antibodies, LAP antibodies, granzyme B antibodies, LFA-1 antibodies, transferrin receptor antibodies, and fragments thereof. In some embodiments, the targeting moiety is a small molecule binder of an ectoenzyme on lymphocytes. Small molecule binders of ectoenzymes include A2A inhibitors CD73 inhibitors, CD39 or adesines receptors A2aR and A2bR. Potential small molecules include AB928.

In some embodiments, transfer vehicles are formulated and/or targeted as described in Shobaki N, Sato Y, Harashima H. Mixing lipids to manipulate the ionization status of lipid nanoparticles for specific tissue targeting. Int J Nanomedicine. 2018; 13:8395-8410. Published 2018 Dec. 10. In some embodiments, a transfer vehicle is made up of 3 lipid types. In some embodiments, a transfer vehicle is made up of 4 lipid types. In some embodiments, a transfer vehicle is made up of 5 lipid types. In some embodiments, a transfer vehicle is made up of 6 lipid types.

12. Target Cells

Where it is desired to deliver a nucleic acid to an immune cell, the immune cell represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, T cells, B cells, macrophages, and dentritic cells.

In some embodiments, the target cells are deficient in a protein or enzyme of interest. For example, where it is desired to deliver a nucleic acid to a hepatocyte, the hepatocyte represents the target cell. In some embodiments, the compositions of the invention transfect the target cells on a discriminatory basis (i.e., do not transfect non-target cells). The compositions of the invention may also be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

The compositions of the invention may be prepared to preferentially distribute to target cells such as in the heart, lungs, kidneys, liver, and spleen. In some embodiments, the compositions of the invention distribute into the cells of the liver or spleen to facilitate the delivery and the subsequent expression of the circRNA comprised therein by the cells of the liver (e.g., hepatocytes) or the cells of spleen (e.g., immune cells). The targeted cells may function as a biological "reservoir" or "depot" capable of producing, and systemically excreting a functional protein or enzyme. Accordingly, in one embodiment of the invention the transfer vehicle may target hepatocytes or immune cells and/or preferentially distribute to the cells of the liver or spleen upon delivery. In an embodiment, following transfection of the target hepatocytes or immune cells, the circRNA loaded in the vehicle are translated and a functional protein product is produced, excreted and systemically distributed. In other embodiments, cells other than hepatocytes (e.g., lung, spleen, heart, ocular, or cells of the central nervous system) can serve as a depot location for protein production.

In one embodiment, the compositions of the invention facilitate a subject's endogenous production of one or more functional proteins and/or enzymes. In an embodiment of the present invention, the transfer vehicles comprise circRNA which encode a deficient protein or enzyme. Upon distribution of such compositions to the target tissues and the subsequent transfection of such target cells, the exogenous circRNA loaded into the transfer vehicle (e.g., a lipid nanoparticle) may be translated in vivo to produce a functional protein or enzyme encoded by the exogenously administered circRNA (e.g., a protein or enzyme in which the subject is deficient). Accordingly, the compositions of the present invention exploit a subject's ability to translate exogenously- or recombinantly-prepared circRNA to produce an endogenously-translated protein or enzyme, and thereby produce (and where applicable excrete) a functional protein or enzyme. The expressed or translated proteins or enzymes may also be characterized by the in vivo inclusion of native post-translational modifications which may often be absent in recombinantly-prepared proteins or enzymes, thereby further reducing the immunogenicity of the translated protein or enzyme.

The administration of circRNA encoding a deficient protein or enzyme avoids the need to deliver the nucleic acids to specific organelles within a target cell. Rather, upon transfection of a target cell and delivery of the nucleic acids to the cytoplasm of the target cell, the circRNA contents of a transfer vehicle may be translated and a functional protein or enzyme expressed.

In some embodiments, a circular RNA comprises one or more miRNA binding sites. In some embodiments, a circular RNA comprises one or more miRNA binding sites recognized by miRNA present in one or more non-target cells or non-target cell types (e.g., Kupffer cells or hepatic cells) and not present in one or more target cells or target cell types (e.g., hepatocytes or T cells). In some embodiments, a circular RNA comprises one or more miRNA binding sites recognized by miRNA present in an increased concentration in one or more non-target cells or non-target cell types (e.g., Kupffer cells or hepatic cells) compared to one or more target cells or target cell types (e.g., hepatocytes or T cells). miRNAs are thought to function by pairing with complementary sequences within RNA molecules, resulting in gene silencing.

13. Pharmaceutical Compositions

In certain embodiments, provided herein are compositions (e.g., pharmaceutical compositions) comprising a therapeutic agent provided herein. In some embodiments, the therapeutic agent is a circular RNA polynucleotide provided herein. In some embodiments the therapeutic agent is a vector provided herein. In some embodiments, the therapeutic agent is a cell comprising a circular RNA or vector provided herein (e.g., a human cell, such as a human T cell). In certain embodiments, the composition further comprises a pharmaceutically acceptable carrier. In some embodiments, the compositions provided herein comprise a therapeutic agent provided herein in combination with other pharmaceutically active agents or drugs, such as anti-inflammatory drugs or antibodies capable of targeting B cell antigens, e.g., anti-CD20 antibodies, e.g., rituximab.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the therapeutic agent(s) and one which has no detrimental side effects or toxicity under the conditions of use.

The choice of carrier will be determined in part by the particular therapeutic agent, as well as by the particular method used to administer the therapeutic agent. Accordingly, there are a variety of suitable formulations of the pharmaceutical compositions provided herein.

In certain embodiments, the pharmaceutical composition comprises a preservative. In certain embodiments, suitable preservatives may include, for example, methylparaben, propylparaben, sodium benzoate, and benzalkonium chloride. Optionally, a mixture of two or more preservatives may be used. The preservative or mixtures thereof are typically present in an amount of about 0.0001% to about 2% by weight of the total composition.

In some embodiments, the pharmaceutical composition comprises a buffering agent. In some embodiments, suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

In some embodiments, the concentration of therapeutic agent in the pharmaceutical composition can vary, e.g., less than about 1%, or at least about 1%, 2%, 3%, 4%, 5%, 6%, 7%, 8%, 9% 10%, 15%, 20%, 25%, 30%, 35%, 40%, 45%, or about 50% or more by weight, and can be selected primarily by fluid volumes, and viscosities, in accordance with the particular mode of administration selected.

The following formulations for oral, aerosol, parenteral (e.g., subcutaneous, intravenous, intraarterial, intramuscular, intradermal, intraperitoneal, and intrathecal), and topical administration are merely exemplary and are in no way limiting. More than one route can be used to administer the therapeutic agents provided herein, and in certain instances, a particular route can provide a more immediate and more effective response than another route.

Formulations suitable for oral administration can comprise or consist of (a) liquid solutions, such as an effective amount of the therapeutic agent dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the therapeutic agent with a flavorant, usually sucrose, acacia or tragacanth. Pastilles can comprise the therapeutic agent with an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In some embodiments, the therapeutic agents provided herein can be administered in a physiologically acceptable diluent in a pharmaceutical carrier, such as a sterile liquid or mixture of liquids, including water, saline, aqueous dextrose and related sugar solutions, an alcohol such as ethanol or hexadecyl alcohol, a glycol such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agents and other pharmaceutical adjuvants.

Oils, which can be used in parenteral formulations in some embodiments, include petroleum, animal oils, vegetable oils, or synthetic oils. Specific examples of oils include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in certain embodiments of parenteral formulations include fatty alkali metal, ammonium, and triethanolamme salts, and suitable detergents include (a) cationic detergents such as, for example, dimethyl dialkyl ammonium halides. and alkyl pyridinium halides, (b) anionic detergents such as, for example, alkyl, aryl, and olefin sulfonates, alky, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

In some embodiments, the parenteral formulations will contain, for example, from about 0.5% to about 25% by weight of the therapeutic agent in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and high molecular weight adducts of ethylene oxide with a hydrophobic base, formed by the condensation of propylene oxide with propylene glycol. The parenteral formulations can be presented in unit-dose or multi-dose sealed containers, such as ampoules or vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In certain embodiments, injectable formulations are provided herein. The requirements for effective pharmaceutical carriers for injectable compositions are well-known to those of ordinary skill in the art (see, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed, pages 622-630 (1986)).

In some embodiments, topical formulations are provided herein. Topical formulations, including those that are useful for transdermal drug release, are suitable in the context of certain embodiments provided herein for application to skin. In some embodiments, the therapeutic agent alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

In certain embodiments, the therapeutic agents provided herein can be formulated as inclusion complexes, such as cyclodextrin inclusion complexes, or liposomes. Liposomes can serve to target the therapeutic agents to a particular tissue. Liposomes also can be used to increase the half-life of the therapeutic agents. Many methods are available for preparing liposomes, as described in, for example, Szoka et al., Ann. Rev. Biophys. Bioeng., 9, 467 (1980) and U.S. Pat. Nos. 4,235,871, 4,501,728, 4,837,028, and 5,019,369.

In some embodiments, the therapeutic agents provided herein are formulated in time-released, delayed release, or sustained release delivery systems such that the delivery of the composition occurs prior to, and with sufficient time to cause, sensitization of the site to be treated. Such systems can avoid repeated administrations of the therapeutic agent, thereby increasing convenience to the subject and the physician, and may be particularly suitable for certain composition embodiments provided herein. In one embodiment, the compositions of the invention are formulated such that they are suitable for extended-release of the circRNA contained therein. Such extended-release compositions may be conveniently administered to a subject at extended dosing intervals. For example, in one embodiment, the compositions of the present invention are administered to a subject twice day, daily or every other day. In an embodiment, the compositions of the present invention are administered to a subject twice a week, once a week, every ten days, every two weeks, every three weeks, every four weeks, once a month, every six weeks, every eight weeks, every three months, every four months, every six months, every eight months, every nine months or annually.

In some embodiments, a protein encoded by an inventive polynucleotide is produced by a target cell for sustained amounts of time. For example, the protein may be produced for more than one hour, more than four, more than six, more than 12, more than 24, more than 48 hours, or more than 72 hours after administration. In some embodiments the polypeptide is expressed at a peak level about six hours after administration. In some embodiments the expression of the polypeptide is sustained at least at a therapeutic level. In some embodiments the polypeptide is expressed at least at a therapeutic level for more than one, more than four, more than six, more than 12, more than 24, more than 48, or more than 72 hours after administration. In some embodiments, the polypeptide is detectable at a therapeutic level in patient serum or tissue (e.g., liver or lung). In some embodiments, the level of detectable polypeptide is from continuous expression from the circRNA composition over periods of time of more than one, more than four, more than six, more than 12, more than 24, more than 48, or more than 72 hours after administration.

In certain embodiments, a protein encoded by an inventive polynucleotide is produced at levels above normal physiological levels. The level of protein may be increased as compared to a control. In some embodiments, the control is the baseline physiological level of the polypeptide in a normal individual or in a population of normal individuals. In other embodiments, the control is the baseline physiological level of the polypeptide in an individual having a deficiency in the relevant protein or polypeptide or in a population of individuals having a deficiency in the relevant protein or polypeptide. In some embodiments the control can be the normal level of the relevant protein or polypeptide in the individual to whom the composition is administered. In other embodiments the control is the expression level of the polypeptide upon other therapeutic intervention, e.g., upon direct injection of the corresponding polypeptide, at one or more comparable time points.

In certain embodiments, the levels of a protein encoded by an inventive polynucleotide are detectable at 3 days, 4 days, 5 days, or 1 week or more after administration. Increased levels of secreted protein may be observed in the serum and/or in a tissue (e.g., liver or lung).

In some embodiments, the method yields a sustained circulation half-life of a protein encoded by an inventive polynucleotide. For example, the protein may be detected for hours or days longer than the half-life observed via subcutaneous injection of the protein or mRNA encoding the protein. In some embodiments, the half-life of the protein is 1 day, 2 days, 3 days, 4 days, 5 days, or 1 week or more.

Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems: wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

In some embodiments, the therapeutic agent can be conjugated either directly or indirectly through a linking moiety to a targeting moiety. Methods for conjugating therapeutic agents to targeting moieties is known in the art. See, for instance, Wadwa et al., J, Drug Targeting 3:111 (1995) and U.S. Pat. No. 5,087,616.

In some embodiments, the therapeutic agents provided herein are formulated into a depot form, such that the manner in which the therapeutic agent is released into the body to which it is administered is controlled with respect to time and location within the body (see, for example, U.S. Pat. No. 4,450,150). Depot forms of therapeutic agents can be, for example, an implantable composition comprising the therapeutic agents and a porous or non-porous material, such as a polymer, wherein the therapeutic agents are encapsulated by or diffused throughout the material and/or degradation of the non-porous material. The depot is then implanted into the desired location within the body and the therapeutic agents are released from the implant at a predetermined rate.

14. Therapeutic Methods

In certain aspects, provided herein is a method of treating and/or preventing a condition, e.g., cancer.

In certain embodiments, the therapeutic agents provided herein are coadministered with one or more additional therapeutic agents (e.g., in the same pharmaceutical composition or in separate pharmaceutical compositions). In some embodiments, the therapeutic agent provided herein can be administered first and the one or more additional therapeutic agents can be administered second, or vice versa. Alternatively, the therapeutic agent provided herein and the one or more additional therapeutic agents can be administered simultaneously.

In some embodiments, the subject is a mammal. In some embodiments, the mammal referred to herein can be any mammal, including, but not limited to, mammals of the order Rodentia, such as mice and hamsters, or mammals of the order Logomorpha, such as rabbits. The mammals may be from the order Carnivora, including Felines (cats) and Canines (dogs). The mammals may be from the order Artiodactyla, including Bovines (cows) and Swines (pigs), or of the order Perssodactyla, including Equines (horses). The mammals may be of the order Primates, Ceboids, or Simoids (monkeys) or of the order Anthropoids (humans and apes). Preferably, the mammal is a human.

15. Sequences

TABLE 17

IRES sequences.

| SEQ ID NO | IRES | Sequence |
|---|---|---|
| 1 | EMCV-A | cccccctctccctccccccctaacgttactggccgaagccgcttggaataaggccggtgtgcgttt<br>gtctatatgttattttccaccatattgccgtcttttggcaatgtgagggcccggaaacctggccctgtct<br>tcttgacgagcattcctaggggtctttcccctctcgccaaaggaatgcaaggtctgttgaatgtcgtg<br>aaggaagcagttcctctggaagcttcttgaagacaaacaacgtctgtagcgaccctttgcaggcag<br>cggaaccccccacctggcgacaggtgcctctgcggccaaaagccacgtgtataagatacacctg<br>caaaggcggcacaaccccagtgccacgttgtgagttggatagttgtggaaagagtcaaatggctc<br>tcctcaagcgtattcaacaaggggctgaaggatgcccagaaggtaccccattgtatgggatctgat<br>ctggggcctcggtgcacatgctttacatgtgtttagtcgaggttaaaaaacgtctaggccccccgaa<br>ccacggggacgtggttttcctttgaaaaacacgatgataatatggccacaacc |
| 2 | EMCV-B | ctccccctccccccccttactatactggccgaagccacttggaataaggccggtgtgcgtttgtcta<br>catgctattttctaccgcattaccgtcttatggtaatgtgagggtccagaacctgaccctgtcttcttga<br>cgaacactcctaggggtctttcccctctcgacaaaggagtgtaaggtctgttgaatgtcgtgaagga<br>agcagttcctctggaagcttcttaaagacaaacaacgtctgtagcgaccctttgcaggcagcggaa<br>cccccacctggtgacaggtgcctctgcggccaaaagccacgtgtataagatacacctgcaaag<br>gcggcacaaccccagtgccacgttgtgagttggatagttgtggaaagagtcaaatggctctcctca<br>agcgtattcaacaaggggctgaaggatgcccagaaggtaccccattgtatgggatctgatctggg<br>gcctcggtgcacgtgctttacacgtgttgagtcgaggtgaaaaaacgtctaggccccccgaacca<br>cggggacgtggttttcctttgaaaaccacgattacaat |
| 3 | EMCV-Bf | ttgccagtctgctcgatatcgcaggctgggtccgtgactacccactcccccttcaacgtgaaggct<br>acgatagtgccagggcgggtactgccgtaagtgccaccccaaacaacaacaacaaaacaaactc<br>cccctccccccccttactatactggccgaagccacttggaataaggccggtgtgcgtttgtctacat<br>gctattttctaccgcattaccgtcttatggtaatgtgagggtccagaacctgaccctgtcttcttgacg<br>aacactcctaggggtctttcccctctcgacaaaggagtgtaaggtctgttgaatgtcgtgaaggaag<br>cagttcctctggaagcttcttaaagacaaacaacgtctgtagcgaccctttgcaggcagcggaacc<br>ccccacctggtgacaggtgcctctgcggccaaaagccacgtgtataagatacacctgcaaaggc<br>ggcacaaccccagtgccacgttgtgagttggatagttgtggaaagagtcaaatggctctcctcaag<br>cgtattcaacaaggggctgaaggatgcccagaaggtaccccattgtatgggatctgatctggggc<br>ctcggtgcacgtgctttacacgtgttgagtcgaggtgaaaaaacgtctaggccccccgaaccacg<br>gggacgtggttttcctttgaaaaccacgattacaat |
| 4 | EMCV-Cf | ttgccagtctgctcgatatcgcaggctgggtccgtgactacccactcccccttcaacgtgaaggct<br>acgatagtgccagggcgggtactgccgtaagtgccaccccaaaacaacaacaacccccccctctc<br>cctccTccccccctaacgttactggccgaagccgcttggaataaggccggtgtgcgtttgtctatat<br>gttattttccaccatattgccgtcttttggcaatgtgagggcccggaaacctggccctgtcttcttgac<br>gagcattcctaggggtctttcccctctcgccaaaggaatgcaaggtctgttgaatgtcgtgaaggaa<br>gcagttcctctggaagcttcttgaagacaaacaacgtctgtagcgaccctttgcaggcagcggaac<br>cccccacctggcgacaggtgcctctgcggccaaaagccacgtgtataagatacacctgcaaagg<br>cggcacaaccccagtgccacgttgtgagttggatagttgtggaaagagtcaaatggctctcctcaa<br>gcgtattcaacaaggggctgaaggatgcccagaaggtaccccattgtatgggatctgatctgggg<br>cctcggtgcacatgctttacatgtgtttagtcgaggttaaaaaacgtctaggccccccgaaccacgg<br>ggacgtggttttcctttgaaaaacacgatgataat |
| 5 | EMCV pEC9 | cccccccccctaacgttactggccgaagccgcttggaataaggccggtgtgcgtttgtctatatgttat<br>tttccaccatattgccgtcttttggcaatgtgagggcccggaaacctggccctgtcttcttgacgagc<br>attcctaggggtctttcccctctcgccaaaggaatgcaaggtctgttgaatgtcgtgaaggaagcag<br>ttcctctggaagcttcttgaagacaaacaacgtctgtagcgaccctttgcaggcagcggaaccccc<br>cacctggcgacaggtgcctctgcggccaaaagccacgtgtataagatacacctgcaaaggcggc<br>acaaccccagtgccacgttgtgagttggatagttgtggaaagagtcaaatggctctcctcaagcgt<br>attcaacaaggggctgaaggatgcccagaaggtaccccattgtatgggatctgatctggggcctc<br>ggtgcacatgctttacatgtgtttagtcgaggttaaaaaacgtctaggccccccgaaccacgggga<br>cgtggttttcctttgaaaaacacgatgataat |
| 6 | Picobirnavirus | gtaaattaaatgctatttacaaaatttaaacagaaaggagagatgttatgaaccggttttacaaggttt<br>catacatcgaaaatagcactacctggggcagccgacacactaacatcgtctgtttaaccagaagtg<br>ttactgaaaggaggttattta |
| 7 | HCV QC64 | acctgcccctaataggggcgacactccgccatgaatcactcccctgtgaggaactactgtcttcac<br>gcagaaagcgtctagccatggcgttagtatgagtgtcgtacagcctccaggcccccccctcccgg<br>gagagccatagtggtctgcggaaccggtgagtacaccggaattgccgggaagactgggtcctttc<br>ttggataaacccactctatgcccggacatttgggcgtgcccccgcaagactgctagccgagtagc<br>gttgggttgcgaaaggccttgtggtactgcctgatagggtgcttgcgagtgccccgggaggtctcg<br>tagaccgtgcatc |
| 8 | Human Cosavirus E/D | ctacaagctttgtgtaaacaaacttttgtttggcttttctcaagcttctctcacatcaggccccaaagat<br>gtcctgaaggtaccccgtgtatctgaggatgagcaccatcgactacccggacctgcaaaattttgc<br>aaacgcatgtggtatcccagcccccctcctctcggggagggggctttgctcactcagcacaggatct<br>gatcaggagatccacctccggtgctttacaccggggcgtggatttaaaaattgcccaaggcctggc<br>gcacaacctaggggactaggttttccttatattttaaagctgtcaat |

TABLE 17-continued

| SEQ ID NO | IRES | Sequence |
|---|---|---|
| | | IRES sequences. |
| 9 | Human Cosavirus F | gtcttaggacgacgcatgtggtatcccagcccccgcctacattggcgggggcttttgaagcacca gacactggatctgatcaggaggagggtagctgctttacagcccctcttaaaaattgcccaaggtcc ggccacccaacctaggggactaggttttccttttatttttaaattgtcatt |
| 10 | Human Cosavirus JMY | acatgggggagactgcatgtggcagtcttgaaacgtgtggtttgacgtctaccttatatggcagtgg gtggagtactgcaaagatgtcaccgtgctttacacggtttttgaaccccacaccggctgtttgacgct cgtagggcagcaggtttattttcattaaaattcttactttctagctgcatgagttctattcatgcagacgg agtgatactcccgttccttcttggacaggttgcctccacgccctttgtggatcttaaggtgaccaagtc actggtgttggaggtgaagatagagagtcctcttgggaatgtcatgtggctgtgccaggggttgta gcgatgccattcgtgtgtgcggatttcctctcgtggtgacacgagcctcacaggccaaaagccccg tccgaaaggacccgaatggtggagtgaccctgactccccctgcatagttttgtgattaggaacttg aggaatttctgtcataaatctctatcacatcaggccccaaagatgtcctgaaggtaccctgtgtatctg aggatgagcaccaccgactacccggacttgcattagcagacacatgtggttgcccagccccacct cttcagaggtggggctttgctcactcagcacaggatctgatcaggagccccgctcgtgtgctttaca ctcgacgcggggttaaaaattgcccaaggcctggcacaacaacctaggggactaggttttcctattt ttgtaaattatgtcaat |
| 11 | Rhinovirus NAT001 | gtgacaatcagccagattgttaacggtcaagcacttctgtttccccggtacccttgtatacgcttcacc cgaggcgaaaagtgaggttatcgttatccgcaaagtgcctacgagaagcctagtagcacttttgaa gcctatggctggtcgctcaactgtttacccagcagtagacctggcagatgaggctagatgttcccc accagcgatggtgatctagcctgcgtggctgcctgcacactctattgagtgtgaagccagaaagtg gacaaggtgtgaagagcctattgtgctcactttgagtcctccggcccctgaatgtggctaatcctaa ccccgtagctgttgcatgtaatccaacatgtctgcagtcgtaatgggcaactatgggatggaaccaa ctactttgggtgtccgtgtttcttgtttttctttatgcttgcttatggtgacaactgtagttattacatttgtta cc |
| 12 | HRV14 | ttaaaacagcggatgggtatcccaccattcgacccattgggtgtagtactctggtactatgtacctttg tacgcctgtttctccccaaccacccttccttaaaattcccacccatgaaacgttagaagcttgacatta aagtacaataggtggcgccatatccaatggtgtctatgtacaagcacttctgtttcccaggagcgag gtataggctgtacccactgccaaaagcctttaaccgttatccgccaaccaactacgtaacagttagt accatcttgttcttgactggacgttcgatcaggtggattttccctccactagtttggtcgatgaggcta ggaattccccacgggtgaccgtgtcctagcctgcgtggcggccaacccagcttatgctgggacgc ccttttaaggacatggtgtgaagactcgcatgtgcttggttgtgagtcctccggcccctgaatgcgg ctaaccttaaccctagagccttatgccacgatccagtggttgtaaggtcgtaatgagcaattccggg acgggaccgactactttgggtgtccgtgtttctcatttttcttcatattgtcttatggtcacagcatatata tacatatactgtgatc |
| 13 | HRV89 | ttaaaactgggagtgggttgttcccactcactccacccatgcggtgttgtactctgttattacggtaac tttgtacgccagtttttcccacccttccccataatgtaacttagaagtttgtacaatatgaccaataggt gacaatcatccagactgtcaaaggtcaagcacttctgtttccccggtcaatgaggatatgctttaccc aaggcaaaaaccttagagatcgttatccccacactgcctacacagagcccagtaccatttttgatat aattgggttggtcgctccctgcaaacccagcagtagacctggcagatgaggctggacattcccca ctggcgacagtggtccagcctgcgtggctgcctgctcacccttcttgggtgagaagcctaattattg acaaggtgtgaagagccgcgtgtgctcagtgtgcttcctccggcccctgaatgtggctaaccttaa ccctgcagccgttgcccataatccaatgggtttgcggtcgtaatgcgtaagtgcgggatgggacca actactttgggtgtccgtgtttcctgtttttcttttgattgcattttatggtgacaatttatagtgtatagattg tcatc |
| 14 | HRVC-02 | ttaaaactgggtacaggttgttcccacctgtatcacccacgtggtgtggtgctcttgtattccggtaca cttgcacgccagtttgccacccctcacccgtcgtaacttagaagctaacaactcgaccaacaggcg gtggtaaaccataccacttacggtcaagcactcctgtttccccggtatgcgaggaatagactcctac agggttgaagcctcaagtatcgttatccgcattggtactacgcaaagcttagtagtgccttgaaagtc ccttggttggtcgctccgctagtttcccctagtagacctggcagatgaggcaggacactccccact ggcgacagtggtcctgcctgcgtggctgcctgcgcacccttaggggtgcgaagccaagtgacag acaaggtgtgaagagccccgtgtgctaccaatgagtcctccggcccctgaatgcggctaatccaa ccccacagctattgcacacaagccagtgtgtatgtagtcgtaatgagcaattgtgggacggaaccg actactttgggtgtccgtgtttccttttattcttatcattctgcttatggtgacaatactgtgaaatagtgtt gttacc |
| 15 | HRV-A21 | taaaactggatccaggttgttcccacctggatctcctattgggagttgtactctattattccggtaatttt gtacgccagttttatcttcccccctccccaattgtaacttagaaggttatcaatacgaccaataggtggt agttagccaaactaccaaaggtcaagcacttctgtttccccggtcaaagttgatatgctccaacagg gcaaaaacaactgagatcgttatccgcaaagtgcctacgcaaagcctagtaacacctttgaagattt atggttggtcgttccgctatttcccatagtagacctggcagatgaggctagaaatcccccactggcg acagtgctctagcctgcgtggctgcctgcgcaccccttgggtgcgaagccatacattggacaagg tgtgaagagccccgtgtgctcactttgagtcctccggcccctgaatgtggctaaccttaaccctgca gctagtgcatgtaatccaacatgttgctagtcgtaatgagtaattgcgggacgggaccaactactttg ggtgtccgtgtttcactttttccttttaatattgcttatggtgacaatatatatagctatatatattgacacc |
| 16 | Salivirus A SH1 | ttcccctgcaaccattacgcttactcgcatgtgcattgagtggtgcatgtgttgaacaaacagctaca ctcacatgggggcgggttttcccgccctacggcttctcgcgaggcccacccctcccctttctcccat aactacagtgctttggtaggtaagcatcctgatcccccgcggaagctgctcacgtggcaactgtgg ggacccagacaggttatcaaaggcacccggtctttccgccttcaggagtatccctgctagcgaatt ctagtagggctctgcttggtgccaacctcccccaaatgcgcgctgcgggagtgctcttccccaact caccctagtatcctctcatgtgtgtgcttggtcagcatatctgagacgatgttccgctgtcccagacc |

TABLE 17-continued

IRES sequences.

| SEQ ID NO | IRES | Sequence |
|---|---|---|
| | | agtccagtaatggacgggccagtgtgcgtagtcgtcttccggcttgtccggcgcatgtttggtgaac<br>cggtggggtaaggttggtgtgcccaacgcccgtactcaggggatacctcaaggcacccaggaat<br>gccagggaggtaccccgcttcacagcgggatctgaccctggggtaaatgtctgcggggggtcttc<br>ttggcccacttctcagtacttttcagg |
| 17 | Salivirus FHB | acatgggggtctgcggacggcttcggcccacccgcgacaagaatgccgtcatctgtcctcatta<br>cccgtattccttcccttcccccgcaaccaccacgcttactcgcgcacgtgttgagtggcacgtgcgt<br>tgtccaaacagctacacccacacccttcggggcgggtttgtcccgccctcgggttcctcgcggaa<br>cccccccctccctctctctctttctatccgccctcacttcccataactacagtgctttggtaggtgagc<br>accctgaccccccgcggaagctgctaacgtggcaactgtggggatccaggcaggttatcaaagg<br>cacccggtctttccgccttcaggagtatctctgccggtgaattccggtagggctctgcttggtgcca<br>acctcccccaaatgcgcgctgcgggagtgctcttccccaactcatcttagtaacctctcatgtgtgtg<br>cttggtcagcatatctgaggcgacgttccgctgtcccagaccagtccagcaatggacgggccagt<br>gtgcgtagtcgctttccggttttccggcgcatgtttggcgaaacgctgaggtaaggttggtgtgccc<br>aacgcccgtaatttggtgatacctcaagaccacccaggaatgccagggaggtaccccacttcggt<br>gggatctgaccctgggctaattgtctacggtggttcttcttgcttccacttctctttttttctggcatg |
| 18 | Salivirus NG-J1 | tatggcaggcgggcttgtggacggcttcggcccacccacagcaagaatgccatcatctgtcctca<br>cccccaattttccctttcttcccctgcaaccattacgcttactcgcatgtgcattgagtggtgcatgtgt<br>tgaacaaacagctacactcacatgggggcgggtttcccgccctacggcctctcgcgaggcccac<br>cccttccctccccttataactacagtgctttggtaggtaagcatcctgatcccccgcggaagctgctc<br>acgtggcaactgtggggacccagacaggttatcaaaggcacccggtctttccgccttcaggagtat<br>ccctactagtgaattctagcggggctctgcttggtgccaacctcccccaaatgcgcgctgcgggag<br>tgctcttccccaactcaccctagtatcctctcatgtgtgtgcttggtcagcatatctgagacgatgttcc<br>gctgtcccagaccagtccagtaatggacgggccagtgcgtgtagtcgtcttccggcttgtccggg<br>gcatgtttggtgaaccggtggggtaaggttggtgtgcccaacgcccgtactttggtgacacctcaa<br>gaccacccaggaatgccagggaggtaccccacctcacggtgggatctgaccctgggctaattgt<br>ctacggtggttcttcttgcttccacttctttcttctgttcacg |
| 19 | Human Parechovirus 1 | tttgaaaggggtctcctagagagcttggccgtcgggccttataccccgacttgctgagtttctctagg<br>agagcccttttcccagccctgaggcggctggtcaataaaagcctcaaacgtaactaacacctaaga<br>agatcatgtaaaccctatgcctggtctccactattcgaaggcaacttgcaataagaagagtgggatc<br>aagacgcttaaagcatagagacagttttcttttctaacccacatttgtgtggggtggcagatggcgtg<br>ccataactctaatagtgagataccacgcttgtggaccttatgctcacacagccatcctctagtaagttt<br>gtgagacgtctggtgacgtgtgggaacttattggaaacaacattttgctgcaaagcatcctactgcc<br>agcggaaaaacacctggtaacaggtgcctctggggccaaaagccaaggtttaacagaccctttag<br>gattggttctaaacctgagatgttgtggaagatatttagtacctgctgatctggtagttatgcaaacact<br>agttgtaaggcccatgaaggatgcccagaaggtacccgtaggtaacaagtgacactatggatctg<br>atttggggccagatacctctatcttggtgatctggttaaaaaacatctaatgggccaaacccggggg<br>ggatccccggtttcctcttattctatcaatgccact |
| 20 | Crohivirus B | gtataagagacaggtgtttgccttgtcttcggactggcatcttgggaccaacccccctttccccagc<br>catgggttaaatggcaataaaggacgtaacaactttgtaaccattaagctttgtaattttgtaaccact<br>aagctttgtgcacataatgtaaccatcaagcttgttagtcccagcaggaggtttgcatgcttgtagcc<br>gaaatggggctcgacccccccatagtaggatacttgattttgcattccattgtggacctgcaaactcta<br>cacatagaggctttgtcttgcatctaaacacctgagtacagtgtgtacctagaccctatagtacggga<br>ggaccgtttgtttcctcaataaccctacataataggctaggtgggcatgcccaatttgcaagatccca<br>gactgggggtcggtctgggcagggttagatccctgttagctactgcctgatagggtggtgctcaac<br>catgtgtagtttaaattgagctgttcatatacc |
| 21 | Yc-3 | actgaagatcctacagtaactactgccccaatgaacgccacagatgggtctgctgatgactacctat<br>cttagtgctagttgaggtttgaagtgagccggtttttagaagaaccagtttctgaacattatcatcccc<br>agcatctattctatacgcacaagatagatagtcatcagcagacacatctgtgctactgcttgatagag<br>ttgcggctggtcaacttagattggtataaccagttgagtggcaa |
| 22 | Rosavirus M-7 | tatgcatcactggacggcctaacctcggtcgtggcttcttgccgatttcagcgctaccaggctttctg<br>gtctcgccaggcgttgattagtaggtgcactgtctaagtgaagacagcagtgctctctgtgaaaagt<br>tgatgacactcttcaggtttgtagcgatcactcaaggctagcggatttccccgtgtggtaacacacg<br>cctctaggcccagaaggcacggtgttgacagcaccccttgagtggctggtcttccccaccagcac<br>ctgatttgtggattcttcctagtaacggacaagcatggctgctcttaagcattcagtgcgtccggggc<br>tgaaggatgcccagaaggtacccgcaggtaacgataagctcactgtggatctgatctggggctgc<br>gggctgggtgtctttccacccagccaaaacccgtaaaacggtagtcgcagttaaaaaacgtctag<br>gccccacccccccagggatgggggttcccttaaaccctcacaagttcaac |
| 23 | Shanbavirus A | tgaaaaggggcgcagggtggtggtggttactaaatacccaccatcgccctgcacttccctttcc<br>cctgtggctcagggtcacttagccccctctttgggttaccagtagttttctacccctgggcacagggt<br>taactatgcaagacggaacaacaatctcttagtccccctcgccgatagtgggctcgacccccatgt<br>gtaggagtggataagggacggagtgagccgatacggggaagagtgtgcggtcacaccttaattc<br>catgagcgctgcgaagaaggaagctgtgaacaatggcgacctgaaccgtacacatggagctcca<br>caggcatggtactcgttagactacgcagcctggttgggagtgggtataccctgggtgagccgcca<br>gtgaatgggagttcactggttaacacacactgcctgatagggtcagggcctcctgtccccgccgta<br>atgaggtagaccatatgcc |
| 24 | Pasivirus A | gcggctggatattctggccgtgcaactgcttttgaccagtggctctgggtaacttagccaaagtgtc<br>cttctccctttccctattatatgttttatggctttgtctggtcttgtttagtttatatataagatcctttccgcc |

TABLE 17-continued

IRES sequences.

| SEQ ID NO | IRES | Sequence |
|---|---|---|
| | | gatatagacctcgacagtctagtgtaggaggattggtgatattaatttgccccagaagagtgaccgt<br>gacacatagaaaccatgagtacatgtgtatccgtggaggatcgcccgggactggattccatatccc<br>attgccatcccaacaagcggagggtatacccactatgtgcacgtctgcagtgggagtctgcagatt<br>tagtcatactgcctgatagggtgtgggcctgcactctggggtactcaggctgtttatataat |
| 25 | Pasivirus A2 | gctggactttctggctgcgcaactgcttttaaccagtggctctgggttacttagccaaaccccctttc<br>cccgtaccctagtttgtgtgtgtattattattttgttgttgttttgtaaatttttatataagatcctttccgccg<br>atatagacctcgacagtctagtgtaggaggattggtgatattaatatgccccagaagagtgaccgtg<br>acacatagaaaccatgagtacatgtgtatccgtggaggatcgcccgggactggattccatatccca<br>ttgccatcccaacaaacggagggtatacccgctatgtgcgcgtctacagtgggaatctgtagattta<br>gtcatactgcctgatagggtgtgggcctgcactctggggtactcaggctgtttatataat |
| 26 | Echovirus E14 | ttaaaacagcctgtgggttgttcccatccacagggcccactgggcgccagcactctggtattgcgg<br>taccttagtgcgcctgttttatatacccgtcccccaaacgtaacttagacgcatgtcaacgaagacca<br>atagtaagcgcagcacaccagctgtgttccggtcaagcacttctgttaccccggaccgagtatcaa<br>taagctactcacgtggctgaaggagaaaacgttcgttacccgaccaattacttcaagaaacctagta<br>acaccatgaaggttgcgcagtgtttcgctccgcacaaccccagtgtagatcaggtcgatgagtcac<br>cgcattccccacgggtgaccgtggcggtggctgcgctggcggcctgcccatggggaaacccat<br>gggacgcttcaatactgacatggtgcgaagagtctattgagctaattggtagtcctccggcccctga<br>atgcggctaatcctaactgcggagcagatacccacacaccagtgggcagtctgtcgtaacgggca<br>actctgcagcggaaccgactactttgggtgtccgtgtttctctttatccttatactggctgcttatggtg<br>acaattgagagattgttaccatatagctattggattggccatccggtgacaaatagagcaattgtgtat<br>ttgtttgttggtttcgtgccattaaattacaaggttctaaacacccttaatcttattatagcattcaacaca<br>acaaa |
| 27 | Human Parechovirus 5 | gtacattagatgcgtcatctgcaactttagtcaataaattacctccaatgtcattaccaacattccctac<br>cttttcactaacacctaagacaacaagtacctatgcctggtctccactattcgaaggcaacttgcaat<br>aagaagagtggaattaagacgcttaaagcatagagctagttatcttttctaacccacaaagttttgtg<br>gggtggcagatggcgtgccataactctattagtgagataccatgcttgtggatcttatgctcacaca<br>gccatcctctagtaagttgataaggtgtctggtgatatgtgggaactcacatgaaccattaatttaccg<br>taaggtatcctatagccagcggaatcacatctggtgacagatgcctctggggccgaaagccaagg<br>tttaacagaccctataggattggtttcaaaacctgaattgatgtggattgtgtatagtacctgttgatct<br>ggtaacagtgtcaacactagttgtaaggcccacgaaggatgcccagaaggtacccgtaggtaaca<br>agtgacactatggatctgatctggggccagctacctctatcatggtgagttggttaaaaaacgtctag<br>tgggccaaacccagggggggatccctggtttccttttacctaatcaaagccact |
| 28 | Aichi Virus | tttgaaaaggggggtgggggggcctcggcccccctcaccctcttttccggtggtctggtcccggacc<br>accgttactccattcagcttcttcggaacctgttcggaggaattaaacgggcacccatactcccccc<br>acccccctttttgtaactaagtatgtgtgctcgtgatcttgactcccacggaacggaccgatccgttgg<br>tgaacaaacagctaggtccacatcctcccttcccctgggagggcccccgccctcccacatcctcc<br>ccccagcctgacgtatcacaggctgtgtgaagcccccgcgaaagctgctcacgtggcaattgtgg<br>gtccccccttcatcaagacaccaggtctttcctccttaaggctagccccggcgtgtgaattcacgttg<br>ggcaactagtggtgtcactgtgcgctcccaatctcggccgcggagtgctgttccccaagccaaac<br>ccctggcccttcactatgtgcctggcaagcatatctgagaaggtgttccgctgtggctgccaacctg<br>gtgacaggtgccccagtgtgcgtaaccttcttccgtctccggacggtagtgattggttaagatttggt<br>gtaaggttcatgtgccaacgccctgtgcgggatgaaacctctactgccctaggaatgccaggcag<br>gtaccccacctccgggtgggatctgagcctgggctaattgtctacgggtagtttcatttccaatccttt<br>tatgtcggagtc |
| 29 | Hepatitis A Virus HA16 | ttcaagaggggtctccggagttttccggaacccctcttggaagtccatggtgaggggacttgatac<br>ctcaccgccgtttgcctaggctataggctaaatttccctttccctgtccttcccctatttccttttgttttgt<br>ttgtaaatattaattcctgcaggttcagggttctttaatctgtttctctataagaacactcaatttttcacgc<br>tttctgtctcctttcttccagggctctccccttgccctaggctctggccgttgcgcccggcggggtca<br>actccatgattagcatggagctgtaggagtctaaattggggacgcagatgtttggacgtcgccttg<br>cagtgttaacttggctttcatgaacctctttgatcttccacaaggggtaggctacgggtgaaacctctt<br>aggctaatacttcaatgaagagatgccttggatagggtaacagcggcggatattggtgagttgttaa<br>gacaaaaaccattcaacgccggaggactggctctcatccagtggatgcattgagggaattgattgt<br>cagggctgtctctaggtttaatctcagacctctctgtgcttagggcaaacactatttggccttaaatgg<br>gatcctgtgagaggggggtccctccattgacagctggactgttctttggggccttatgtggtgtttgcc<br>tctgaggtactcaggggcatttaggtttttcctcattcttaaataata |
| 30 | Phopivirus | gggagtaaacctcaccaccgtttgccgtggtttacggctacctattttggatgtaaatattaattcctg<br>caggttcaggtctcttgaattatgtccacgctagtggcactctcttacccataagtgacgccttagcg<br>gaacctttctacacttgatgtggttaggggttacattatttccctgggccttctttggcccttttttcccctg<br>cactatcattctttcttccgggctctcagcatgccaatgttccgaccggtgcgcccgccggggttaa<br>ctccatggttagcatggagctgtaggccctaaaagtgctgacactggaactggactattgaagcat<br>acactgttaactgaaacatgtaactccaatcgatcttctacaaggggtaggctacgggtgaaacccc<br>ttaggttaatactcatattgagagatacttctgataggttaaggttgctggataatggtgagtttaacga<br>caaaaaccattcaacagctgtgggccaacctcatcaggtagatgcttttggagccaagtgcgtagg<br>ggtgtgtgtggaaatgcttcagtggaaggtgccctcccgaaaggtcgtaggggtaatcaggggca<br>gttaggtttccacaattacaatttgaa |
| 31 | CVA10 | gctcttccgatctgggttgttcccacccacagggcccactgggcgccagcactctgattccacgga<br>atctttgtgcgcctgttttacaacccttcccaatttgtaacgtagaagcaatacacactactgatcaata<br>gtaggcatggcgcgccagtcatgtcatgatcaagcacttctgttcccccggactgagtatcaataga |

TABLE 17-continued

IRES sequences.

| SEQ ID NO | IRES | Sequence |
|---|---|---|
| | | ctgctcacgcggttgaaggagaaaacgttcgttacccggctaactacttcgagaaacctagtagca<br>ccatggaagctgcggagtgtttcgctcagcactttccccgtgtagatcaggtcgatgagtcactgca<br>atccccacgggcgaccgtggcagtggctgcgttggcggcctgcctatggggcaacccataggac<br>gctctaatgtggacatggtgcgaagagtctattgagctagttagtagtcctccggcccctgaatgcg<br>gctaatcctaactgcggagcacatgccttcaacccaggaggtggtgtgtcgtaacgggtaactctg<br>cagcggaaccgactactttgggtgtccgtgtttccttttatccttatattggctgcttatggtgacaatc<br>acggaattgttgccatatagctattggattggccatccggtgtctaacagagctattgtatacctatttg<br>ttggatttactcccctatcatacaaatctctgaacactttgtgctttatactgaacttaaacacacgaaa |
| 32 | Enterovirus C | ttaaaacagctctggggttgttcccaccccagaggcccacgtggcggccagtacaccggtaccac<br>ggtacccttgtacgcctgttttatactcccctccccgtaaactagaagcacgaaacacaagttcaata<br>gaaggggggtacagaccagtaccaccacgaacaagcacttctgttcccccggtgaggtcacatag<br>actgtccccacggtcaaaagtgactgatccgttatccgctcacgtacttcggaaagcctagtaccac<br>cttggaatctacgatgcgttgcgctcagcactcgaccccggagtgtagcttaggctgatgagtctg<br>gacgttccccactggtgacagtggtccaggctgcgttggcggcctacctgtggtccaaaaccaca<br>ggacgctagtagtgaacaaggtgtgaagagcccactgagctacctgagaatcctccggcccctg<br>aatgcggctaatcccaaccacggagcaggtaatcgcaaaccagcggtcagcctgtcgtaacgcg<br>taagtctgtggcggaaccgactactttgggtgtccgtgtttcctttttatttttatggtggctgcttatggt<br>gacaatcatagattgttatcataaagcaaattggattggccatccggagtgagctaaactatctatttc<br>tctgagtgttggattcgtttcacccacattctgaacaatcagcctcattagtgttaccctgttaataaga<br>cgatatcatcacg |
| 33 | Enterovirus D | ttaaaacagctctggggttgttcccaccccagaggcccacgtggcggctagtactccggtacccc<br>ggtacccttgtacgcctgttttatactccctttcccaagtaactttagaagaaataaactaatgttcaac<br>aggaggggggtacaaaccagtaccaccacgaacacacacttctgtttccccggtgaagttgcatag<br>actgtacccacggttgaaagcgatgaatccgttacccgcttaggtacttcgagaagcctagtatcat<br>cttggaatcttcgatgcgttgcgatcagcactctaccccgagtgtagcttgggtcgatgagtctgga<br>caccccacaccggcgacgtggtccaggctgcgttggcggcctacccatggctagcaccatggga<br>cgctagttgtgaacaaggtgcgaagagcctattgagctacctgagagtcctccggcccctgaatgc<br>ggctaatcccaaccacggagcaaatgctcacaatccagtgagtggtttgtcgtaatgcgcaagtct<br>gtggcggaaccgactactttgggtgtccgtgtttcctttttatttttattatggctgcttatggtgacaatct<br>gagattgttatcatatagctattggattagccatccggtgatatcttgaaatttgccataactttttcaca<br>aatcctacaacattacactacactttctcttgaataattgagacaactcata |
| 34 | Enterovirus J | ttaaaatagcctcagggttgttcccaccctgagggcccacgtggtgtagtactctggtattacggtac<br>ctttgtacgcctattttataccccttccccaagtaatttagaagcaagcacaaaccagttcagtagta<br>agcagtacaatccagtactgtaatgaacaagtacttctgttaccccggaagggtctatcggtaagct<br>gtacccacggctgaagaatgacctaccgttaaccggctacctacttcgagaagcctagtaatgccg<br>ttgaagttttattgacgttacgctcagcacactaccccgtgtgtagttttggctgatgagtcacggcac<br>tccccacgggcgaccgtggccgtggctgcgttggcggccaaccaaggagtgcaagctccttgga<br>cgtcatattacagacatggtgtgaagagcctattgagctaggtggtagtcctccggcccctgaatgc<br>ggctaatcctaactccggagcatatcggtgcgaaccagcacttggtgtgttgtaatacgtaagtctg<br>gagcggaaccgactactttgggtgtccgtgtttcctgttttaacttttatggctgcttatggtgacaattt<br>aacattgttaccatatagctgttgggttggccatccggattttgttataaaccatttcctcgtgccttga<br>cctttaacacatttgtgaacttctttaaatcccttttattagtccttaaatactaaga |
| 35 | Human Pegivirus 2 | aactgttgttgtagcaatgcgcatattgctacttcggtacgcctaattggtaggcgcccggccgacc<br>ggccccgcaagggcctagtaggacgtgtgacaatgccatgagggatcatgacactggggtgag<br>cggaggcagcaccgaagtcgggtgaactcgactcccagtgcgaccacctggcttggtcgttcatg<br>gagggcatgcccacgggaacgctgatcgtgcaaagggatgggtccctgcactggtgccatgcg<br>cggcaccactccgtacagcctgatagggtggcggcgggcccccccagtgtgacgtccgtggag<br>cgcaac |
| 36 | GBV-C GT110 | tgacgtggggggggttgatTTTcccccccccggcactgggtgcaagccccagaaaccgacgcct<br>atctaagtagacgcaatgactcggcgccgactcggcgaccggccaaaaggtggtggatgggtga<br>tgacagggttggtaggtcgtaaatcccggtcatcctggtagccactataggtgggtcttaagagaa<br>ggtcaagattcctcttacgcctgcggcgagaccgcgcacggtccacaggtgttggccctaccggt<br>gtgaataagggcccgacatcaggc |
| 37 | GBV-C K1737 | gacgtggggggggttgatccccccccTTTggcactgggtgcaagccccagaaaccgacgccta<br>tttaaacagacgttaagaaccggcgccgacccggcgaccggccaaaaggtggtggatgggtgat<br>gccagggttggtaggtcgtaaatcccggtcatcttggtagccactataggtgggtcttaagggttgg<br>ttaaggtccctctggcgcttgtggcgagaaagcgcacggtccacaggtgttggccctaccggtgt<br>gaataagggcccgacgtcaggctcgtcgttaaaccgagcccactacccacctgggcaaacaacg<br>cccacgtacggtccacgtcgcccttcaatgtctctcttgaccaataggcttagccggcgagttgaca<br>aggaccagtgggggctgggcggtaggggaaggacccctgccgctgcccttcccggtggagtg<br>ggaaatgc |
| 38 | GBV-C Iowa | tgacgtggggggggttgatccGcccccccccggcactCggtgcaagccccataaaccgacgccta<br>tctaagtagacgcaatgactcggcgccgactcggcgaccggccaaaaggtggtggatgggtggt<br>gacagggttggtaggtcgtaaatcccggtcatcctggtagccactataggtgggtcttaagagaag<br>gtcaagactcctcttgtgcctgcggcgagaccgcgcacggtccacaggtgctggccctaccggtg<br>tgaataagggcccgacgtcaggctcgtcgttaaaccgagcccgtcacccacctgggcaaacgac<br>gcccacgtacggtccacgtcgcccttca |

TABLE 17-continued

| IRES sequences. | | |
|---|---|---|
| SEQ ID NO | IRES | Sequence |
| 39 | Pegivirus A 1220 | tgtagcaatgcgcatattgctacttcggtacgcctaattggtaggcgcccggccgaccggccccgc aagggcctagtaggacgtgtgacaatgccatgcgggatcatgacactggggtgagcggaggca gcaccgaagtcgggtgaactcgactcccagtgcgaccacctggcttggtcgttcatggagggcat gcccacgggaacgctgatcgtgcaaagggatgggtccctgcactggtgccatgcgcggcacca ctccgtacagcctgatagggtggcggcgggcccccccagtgtgacgtccgtggagcgcaac |
| 40 | Pasivirus A 3 | attttctggccgtgtagctgcttttgaccagtggctctgggttacttagccaaatccccttccttcacc cttttaaatttgatggtctgtgttgtttgttttgtcttgtctaaataatataagatccttcccgccgataca gacctcgacagtctggtgtaggagggttggtgttattaatttgccccagaagagtgaccgtgacac atagaaaccatgagtacatgtgtatccgtggaggatcgcccgggactggattccatatcccattgcc atcccaacaagcggagggtatacccactatgtgcgcgtttgcagtgggaatctgcaaatttagtcat actgcctgatagggtgtgggcctgcactctggggtactcaggctgttcatataat |
| 41 | Sapelovirus | cccctccacccttaaggtggttgtatcccacataccccaccctcccttccaaagtggacggacaact ggattttgactaacggcaagtctgaatggtatgatttggatacgtttaaacggcagtagcgtggcga gctatggaaaaatcgcaattgtcgatagccatgttagtgacgcgcttcggcgtgctcctttggtgatt cggcgactggttacaggagagtaggcagtgagctatgggcaaacctctacagtattacttagagg gaatgtgcaattgagacttgacgagcgtctctttgagatgtggcgcatgctcttggcattaccatagt gagcttccaggttgggaaacctggactgggcctatactacctgatagggtcgcggctggccgcct gtaactagtatagtcagttgaaacccccc |
| 42 | Rosavirus B | gtctctttagtgtctatgcttcagagagcggtgaactgacaccgttgcttcttgcacagcccttcgtgc cggtctttccggttctcgacagcgttgggcatcatggctagttaggctaagatagtggatgatctagt gaacagttttggattgtttggagttttgtagcgatgctagtagtgtgtgtggacctccccacgtggtaa cacgtgccccacaggccaaaagccaaggtgttgaaagcacccctactagtcccagactcacccat ctgggaactcctctcatgaaaaatcttagtaacttttgattcggctattcatcaacctctctagtcaagg gctgaaggatgcccggaaggtacccgcaggtaacgataagctcactgtggatctgatccggggc tttggtgcgaccgtctgtccggcgtagccagagttaaaaaacgtctaggcccttccaccccaaggg attggggtttccccaatcatttgaaagttcact |
| 43 | Bakunsa Virus | ttttgaacgccacctcggagcgatatccggggacccccctccccttttccttcctaccttcttcccaaa tttccctcttcccttgttattttggtttggatttcctggacatgactcggacggatctatctcatttgctttgt gtctgctccaccagtggcatggtcgaaagatcatcaacactggacgtgtactgtaatggccaaacg tgcccacaggggaaaccatgccggtcgctgtagcggcgggtggacgtggtggacccctctccct gctcataaactttgggtaggtgaagggttcaagcgacgcttgccgtgagggcgcatccggatggt gggaaccaacaaactaggctgtaatggccgacctcaggtggatgagctagggctgctgcaccaa aagggactcgattcgatatcccggcctggtagcctagtgcagtggactcgtagttgggaatctacg actggcctagtacagggtgatagccccgtttcccacgcccacctgttgtagggacacccccccc |
| 44 | Tremovirus A | tttgaaagaggcctccggagtgtccggaggctctctttcgacccaacccatactggggggtgtgtg ggaccgtacctggagtgcacggtatatatgcattcccgcatggcaagggcgtgctaccttgcccct tgacgcatggtatgcgtcatcatttgccttggttaagccccatagaaacgaggcgtcacgtgccga aaatccctttgcgtttcacagaaccatcctaaccatgggtgtagtatgggaatcgtgtatggggatga ttaggatctctcgtagagggataggtgtgccattcaaatccagggagtactctggctctgacattgg gacatttgatgtaaccggacctggttcagtatccgggttgtcctgtattgttacggtgtatccgtcttgg cacactgaaagggtatttttgggtaatcctttcctactgcctgatagggtggcgtgcccggccacga gagattaagggtagcaatttaaac |
| 45 | Swine Pasivirus 1 | gcttttgaccagtggctctgggttacttagccaagtccctttctcttattttcactagtttatgttgtgtgtt gtctgttttgttttgtttaaattgtatacaagatccttcccgccgacacagacctcgacagtctggtgta ggagggttggtgatattaatttgccccaaaagagtgaccgtgatacgtggaaaccatgagtacatgt gtatccgtggaggatcgcccgggactggattccatatcccattgccatcccaacaaacggagggt atacccaccacgtgcgcgtttgcagtgggaatctgcaaatttagtcatactgcctgatagggtgtgg gcctgcactttggggtactcaggctgttcatataat |
| 46 | PLV-CHN | acatggggtatgttgtctgtcctgttttgttgaaacaatatataagatcctttccgccgatatagacctc gacagtctagtgtaggaggattggtgatagtaacttgccccagaagagtgaccgtgacacataga aaccatgagtacatgtgtatccgtggaggatcgcccgggactggattccatatcccattgccatccc aacaaacggagggtatacccactatgtgcgcgtttgcagtgggagcctgcaaatttagtcatactg cctgatagggtgtgggcctgcactctggggtactcaggctgtttatataat |
| 47 | Pasivirus A (longer) | tgaaaaagtggttgtgcagctggattttccggctgtgcaactgcttttgaccagtggctctgggttact tagccaaattcctttcccttatccctattggtttgtgttgtgtgttgtttgttttgttttgtcttaactatataca agatccttcccgccgatacagacctcgacagtctggtgtaggagggttggtgttattaatttgcccca aaagagtgaccgtgacacgtggaaaccatgagtacatgtgtatccgtggaggatcgcccgggact ggattccatatcccattgccatcccaacaaacggagggtatacccaccacgtgcgcgtttgcagtg ggaatctgcaaatttagtcatactgcctgatagggtgtgggcctgcactttggggtactcaggctgtt tatataat |
| 48 | Sicinivirus | gtgtcattaaggtgtgtttggaagttcgaattagctggtttgtggtgattagtagacccccctggaggta cccaattcggatctgaccagggacccgtgactataccgctccggtaattcgggtttaaaacaatga acgtcaccacacaattacttttctcattttattttcatcattgtcttcctatttaccgattacactcgatttcct tggatgttcctggagatttccctggttacctggaccctcattattgttgttgtttcacccagcgagctgt cccaattgcttattatttgcgcttacaacttcgtcctaatatttttctggttgatcgggttgattgagctcc cgggctatcctgccattcaac |

TABLE 17-continued

| IRES sequences. | | |
|---|---|---|
| SEQ ID NO | IRES | Sequence |
| 49 | Hepacivirus K | gggaacaatggtccgtccgcggaacgactctagccatgagtctagtacgagtgcgtgccacccat<br>tagcacaaaaaccactgactgagccacacccctcccggaatcctgagtacaggacattcgctcgg<br>acgacgcatgagcctccatgccgagaaaattgggtatacccacgggtaaggggtggccacccag<br>cgggaatctgggggctggtcactgactatggtacagcctgatagggtgctgccgcagcgtcagtg<br>gtatgcggctgttcatggaac |
| 50 | Hepacivirus A | acctccgtgctaggcacggtgcgttgtcagcgttttgcgcttgcatgcgctacacgcgtcgtccaac<br>gcggagggaacttcacatcaccatgtgtcactcccccctatggagggttccaccccgcttacacgga<br>aatgggttaaccatacccaaagtacgggtatgcgggtcctcctagggcccccccggcaggtcga<br>gggagctggaattcgtgaattcgtgagtacacgaaaatcgcggcttgaacgtctttgaccttcgga<br>gccgaaatttgggcgtgccccacgaaggaaggcgggggcggtgttgggccgccgcccccctttat<br>cccacggtctgatagatgcttgcgagggcacctgccggtctcgtagaccataggac |
| 51 | BVDV1 | gtatacgagaatttgcctaggacctcgtttacaatatgggcaatctaaaattataattaggcctaagg<br>gacaaatcctcctcagcgaaggccgaaaagaggctagccatgcccttagtaggactagcaaaata<br>aggggggtagcaacagtggtgagttcgttggatggctgaagccctgagtacagggtagtcgtcag<br>tggttcgacgcttcggaggacaagcctcgagataccacgtggacgagggcatgcccacagcaca<br>tcttaacctggacgggggtcgttcaggtgaaaacggtttaaccaaccgctacgaatacagcctgat<br>agggtgctgcagaggcccactgtattgctactgaaaatctctgctgtacatggcac |
| 52 | Border Disease Virus | gtatacgggagtagctcatgcccgtatacaaaattggatattccaaaactcgattgggttagggagc<br>cctcctagcgacggccgaaccgtgttaaccatacacgtagtaggactagcagacgggaggacta<br>gccatcgtggtgagatccctgagcagtctaaatcctgagtacaggatagtcgtcagtagttcaacg<br>caggcacggttctgccttgagatgctacgtggacgagggcatgcccaagacttgctttaatctcgg<br>cgggggtcgccgaggtgaaaacacctaacggtgttggggttacagcctgatagggtgctgcaga<br>ggcccacgaataggctagtataaaaatctctgctgtacatggcac |
| 53 | BVDV2 | gtatacgagattagctaaagtactcgtatatggattggacgtcaacaaatttttaattggcaacgtagg<br>gaaccttcccctcagcgaaggccgaaaagaggctagccatgccctttagtaggactagcaaaagt<br>agggggactagcggtagcagtgagttcgttggatggccgaacccctgagtacaggggagtcgtc<br>aatggttcgacactccattagtcgaggagtctcgagatgccatgtggacgagggcatgcccacgg<br>cacatcttaacccatgcgggggttgcatgggtgaaagcgctaatcgtggcgttatggacacagcct<br>gatagggtgtagcagagacctgctattccgctagtaaaaaactctgctgtacatggcac |
| 54 | CSFV-PK15C | gtatacgaggttagttcattctcgtatgcattattggacaaatcaaaatttcaatttggttcagggcctc<br>cctccagcgacggccgaactgggctagccatgcccatagtaggactagcaaacggagggacta<br>gccgtagtggcgagctccctgggtgttctaagtcctgagtacaggacagtcgtcagtagttcgacg<br>tgagcagaagcccacctcgagatgctatgtggacgagggcatgcccaagacgcaccttaaccct<br>agcgggggtcgctagggtgaaatcacaccacgtgatgggagtccgacctgatagggtgctgcag<br>aggctcactattaggctagtataaaaatctctgctgtacatggcac |
| 55 | SF573 Dicistrovirus | aaaaccgaccccagagatcagaaagtcgttgacgcgatcttttattagaggacgttgcgctggcgc<br>gagctttaattagcagacgccaaaaataaacaacaaaatgctgatcgcgagacttaattgtcagac<br>gattggccaaatccgatgtgatctttgctgctcccagattgccgaaataggagtagtag |
| 56 | Hubei Picorna-like Virus | ccccaaaacccccccccttaaactcaacactgtagtggattcattttccgttgcaaaacaaaacattac<br>tacccgcatttatgtaggctctgtgttttctatgcgaccgttacattaatctctactctgacccactagttt<br>ataaaaccgaagacctgaatgaaacgattttccttcttttcaacctctaacgaacctctgacggcttga<br>gaaacctgaagttagtaattatgtttaaaagaaaggaaagtcaaacgcgatgactcttacatccctat<br>tccataccgttgctccacaatgtgagcgatgcgaggtcgggactgcagtattaggggaacgagct<br>acatggagagttaattatctctcccctcctacgggagtctcatgtgagctgtagaaagcggttggca<br>cctctcgttacctcgcctgtacatgatcc |
| 57 | CRPV | aaaagcaaaaatgtgatcttgcttgtaaatacaattttgagaggttaataaattacaagtagtgctatttt<br>tgtatttaggttagctatttagctttacgttccaggatgcctagtggcagccccacaatatccaggaag<br>ccctctctgcggtttttcagattaggtagtcgaaaaacctaagaaatttacct |
| 58 | Salivirus A BN5 | tttcctcctttcgaccgccttacggcaggcgggtccgcggacggcttcggcctacccgcgacaag<br>aatgccgtcatctgtccttatcacccatattctttcccttcccccgcaaccatcacgcttactcgcgca<br>cgtgttgagtggcacgtgcgttgtccaaacagttacactcacacccttggggcgggtttgtcccgcc<br>ctcgggttcctcgcggaaccctccctcttctctctccctttctatccgccttcactttccataactacagt<br>gctttggtaggtaagcatcctgacccccccgcggaagctgccaacgtggcaactgtggggatccag<br>gcaggttatcaaaggcacccggtctttccgccttcaggagtatccctgccggtgaattccgacagg<br>gctctgcttggtgccaacctcccccaaatgcgcgctgcgggagtgctcttccccaactcatcttagt<br>aacctctcatgtgtgtgcttggtcagcatatctgaggcgacgttccgctgtcccagaccagtccagc<br>aatggacgggccagtgtgcgtagtcgctttccggtttcccggcgcatgtttggcgaaacgctgagg<br>taaggttggtgtgcccaatgcccgtaatttggtgacacctcaagaccacccaggaatgccaggga<br>ggtaccccacttcggtgggatctgaccctgggctaattgtctacggtggttcttcttgcttccacttctc<br>ttttttctggcatg |
| 59 | Salivirus A BN2 | tatggcaggcgggcttgtggacggcttcggcccacccacagcaagaatgccatcatctgtcctca<br>cccccatgtttcccctttctttccctgcaaccgttacgcttactcgcaggtgcatttgagtggtgcacgt<br>gttgaataaacagctacactcacatgggggcgggttttcccgccctgcggcctctcgcgaggccc<br>acccctccccttcctcccataactacagtgctttggtaggtaagcatcctgatcccccgcggaagct |

TABLE 17-continued

IRES sequences.

| SEQ ID NO | IRES | Sequence |
|---|---|---|
| | | gctcacgtggcaactgtggggacccagacaggttatcaaaggcacccggtctttccgccttcagg<br>agtatccctgctagtgaattctagtagggctctgcttggtgccaacctcccccaaatgcgcgctgcg<br>ggagtgctcttccccaactcaccctagtatcctctcatgtgtgtgcttggtcagcatatctgagacgat<br>gttccgctgtcccagaccagtccagtaatggacgggccagtgtgcgtagtcgtcttccggcttttcc<br>ggcgcatgtttggtgaaccggtggggtaaggttggtgtgcccaacgcccgtactttggtgatacct<br>caagaccacccaggaatgccagggaggtaccccgcttcacagcgggatctgaccctgggctaat<br>tgtctacggtggttcttcttgcttccacttctttctactgttc |
| 60 | Salivirus A 02394 | tttcgaccgccttatggcaggcgggcttgtggacggcttcggcccacccacagcaagaatgccat<br>catctgtcctcacccccatttctcccctccttcccctgcaaccattacgcttactcgcatgtgcattgag<br>tggtgcacgtgttgaacaaacagctacactcacgtgggggcgggttttcccgcccttcggcctctc<br>gcgaggcccacccttccccttcctcccataactacagtgctttggtaggtaagcatcctgatccccc<br>gcggaagctgctcgcgtggcaactgtggggacccagacaggttatcaaaggcacccggtctttcc<br>gcctccaggagtatccctgctagtgaattctagtggggctctgcttggtgccaacctcccccaaatg<br>cgcgctgcgggagtgctcttccccaactcaccctagtatcctctcatgtgtgtgcttggtcagcatat<br>ctgagacgatgttccgctgtcccagaccagtccagcaatggacgggccagtgtgcgtagtcgtctt<br>ccggcttgtccggcgcatgtttggtgaaccggtggggtaaggttggtgtgcccaacgcccgtactt<br>tggtgacaactcaagaccacccaggaatgccagggaggtaccccgcctcacggcgggatctga<br>ccctgggctaattgtctacggtggttcttcttgcttccatttctttcttctgttc |
| 61 | Salivirus A GUT | tatggcaggcgggcttgtggacggtttcggcccacccacagcaagaatgccatcatctgtcctcac<br>ccccaattttccctttcttcccctgcaatcatcacgcttactcgcatgtgcattgagtggtgcatgtgtt<br>gaacaaacagctacactcacatgggggcgggttttcccgccctacggcctctcgcgaggcccac<br>ccttcccctccccttataactacagtgctttggcaggtaagcatcctgatcccccgcggaagctgct<br>cacgtggcaactgtggggacccagacaggttatcaaaggcacccggtctttccgccttcaggagc<br>atccccactagtgaattctagtggggctctgcttggtgccaacctcccccaaatgcgcgctgcggg<br>agtgctcttccccaacccatcctagtatcctctcatgtgtgtgcttggtcagcatatctgagacgacgt<br>tccgctgtcccagaccagtccagtaatggacgggccagtgtgcgtagtcgtcttccggcttgtccg<br>gcgcatgtttggtgaaccggtggggtaaggttggtgtgcccaacgcccgtactttggtgacacctc<br>aagaccacccaggaatgccagggaggtaccccgcctcacggcgggatctgaccctgggctaatt<br>gtctacggtggttcttcttgcttccacttctttctt |
| 62 | Salivirus A CH | ttctcctgcaaccattacgcttaatcgcatgtgcattgagtggtgcatgtgttgaacaaacagctaca<br>atcacatgggggcgggttttcccgccccacggcttctcgcgaggcccatccctcccttttctcccat<br>aactacagtgctttggtaggtaagcatcccgatctcccgcggaagctgctcacgtggcaactgtgg<br>ggacccagacaggttatcaaaggcacccggtctttccgccttcaggagtatccctgctagcgaatt<br>ctagtagggctctgcttggtgccaacctctcccaaatgcgcgctgcgggagtgctcttccccaaatc<br>accccagtatcctctcatgtgtgtgcctggtcagcatatctgagacgatgttccgctgtcccagacca<br>gtccagtaatggacgggccagtgtgcgtagtcgtcctccggcttgtccggcgcatgtttggtgaac<br>cggtggggtaaggttggtgtgcccaacgcccgtaatcaggggatacctcaaggcacccaggaat<br>gccagggaggtatcccgcctcacagcgggatctgaccctggggtaaatgtctgcgggggggtcct<br>cttggcccaattctcagtaattttcagg |
| 63 | Salivirus A SZ1 | tctgtcctcaccccatcttcccttctttcctgcaccgttacgcttactcgcatgtgcattgagtggtgca<br>cgtgcttgaacaaacagctacactcacatgggggcgggttttcccgccctgcggcctctcgcgag<br>gcccacccctccccttcctcccataactacagtgctttggtaggtaagcatcctgatcccccgcgga<br>agctgctcacgtggcaactgtggggacccagacaggttatcaaaggcacccggtctttccgccttc<br>aggagtatccctgctagtgaattctagtagggctctgcttggtgccaacctcccccaaatgcgcgct<br>gcgggagtgctcttccccaactcaccctagtatcctctcatgtgtgtgcttggtcagcatatctgaga<br>cgatgttccgctgtcccagaccagtccagtaatggacgggccagtgtgcgtagtcgtcttccggctt<br>gtccggcgcatgtttggtgaaccggtggggtaaggttggtgtgcccaacgcccgtactttggtgat<br>acctcaagaccacccaggaatgccagggaggtaccccgcttcacagcgggatctgaccctggg<br>ctaattgtctacggtggttcttcttgcttccacttctttctactgttcatg |
| 64 | Salivirus FHB | acatggggggtctgcggacggcttcggcccacccgcgacaagaatgccgtcatctgtcctcatta<br>cccgtattccttcccttcccccgcaaccaccacgcttactcgcgcacgtgttgagtggcacgtgcgt<br>tgtccaaacagctacacccacacccttcggggcgggtttgtcccgccctcgggttcctcgcggaa<br>ccccccccctccctctctctctttctatccgccctcacttcccataactacagtgctttggtaggtgagc<br>accctgacccccccgcggaagctgctaacgtggcaactgtggggatccaggcaggttatcaaagg<br>cacccggtctttccgccttcaggagtatctctgccggtgaattccggtagggctctgcttggtgcca<br>acctcccccaaatgcgcgctgcgggagtgctcttccccaactcatcttagtaacctctcatgtgtgtg<br>cttggtcagcatatctgaggcgacgttccgctgtcccagaccagtccagcaatggacgggccagt<br>gtgcgtagtcgctttccggttttccggcgcatgtttggcgaaacgctgaggtaaggttggtgtgccc<br>aacgcccgtaatttggtgatacctcaagaccacccaggaatgccagggaggtaccccacttcggt<br>gggatctgaccctgggctaattgtctacggtggttcttcttgcttccacttctctttttttctggcatg |
| 65 | CVB3 | ttaaaacagcctgtgggttgatcccacccacaggcccattgggcgctagcactctggtatcacggt<br>acctttgtgcgcctgttttatacccccttcccccaactgtaacttagaagtaacacacaccgatcaaca<br>gtcagcgtggcacaccagccacgttttgatcaagcacttctgttaccccggactgagtatcaataga<br>ctgctcacgcggttgaaggagaaagcgttcgttatccggccaactacttcgaaaaacctagtaaca<br>ccgtggaagttgcagagtgtttcgctcagcactaccccagtgtagatcaggtcgatgagtcaccgc<br>attccccacgggcgaccgtggcggtggctgcgttggcggcctgcccatggggaaacccatggg<br>acgctctaatacagacatggtgcgaagagtctattgagctagttggtagtcctccggcccctgaatg<br>cggctaatcctaactgcggagcacacaccctcaagccagagggcagtgtgtcgtaacgggcaac<br>tctgcagcggaaccgactactttgggtgtccgtgtttcattttattcctatactggctgcttatggtgac |

TABLE 17-continued

IRES sequences.

| SEQ ID NO | IRES | Sequence |
|---|---|---|
| | | aattgagagatcgttaccatatagctattggattggccatccggtgactaatagagctattatatatcc<br>ctttgttgggtttataccacttagcttgaaagaggttaaaacattacaattcattgttaagttgaatacag<br>caaa |
| 66 | CVB1 | ttaaaacagcctgtgggttgttcccacccacaggcccattgggcgctagcactctggtatcacggta<br>cctttgtgcgcctgttttacatcccctccccaaattgtaatttagaagtttcacacaccgatcattagca<br>agcgtggcacaccagccatgttttgatcaagcacttctgttaccccggactgagtatcaatagaccg<br>ctaacgcggttgaaggagaaaacgttcgttacccggccaactacttcgaaaaacctagtaacacca<br>tggaagttgcggagtgtttcgctcagcactaccccagtgtagatcaggtcgatgagtcaccgcgttc<br>cccacgggcgaccgtggcggtggctgcgttggcggcctgcctacggggaaacccgtaggacg<br>ctctaatacagacatggtgcgaagagtctattgagctagttggtaatcctccggcccctgaatgcgg<br>ctaatcctaactgcggagcacataccctcaaaccaggggggcagtgtgtcgtaacgggcaactctg<br>cagcggaaccgactactttgggtgtccgtgtttcattttattcctatactggctgcttatggtgacaatt<br>gacaggttgttaccatatagttattggattggccatccggtgactaacagagcaattatatatctctttg<br>ttgggtttataccacttagcttgaaagaggttaaaacactacatctcatcattaaactaaatacaacaa<br>a |
| 67 | Echovirus 7 | ttaaaacagcctgtgggttgttcccacccacagggcccattgggcgtcagcaccctggtatcacgg<br>tacctttgtgcgcctgttttatatcccttcccccaattgtaacttagaagaaacacacaccgatcaaca<br>gcaagcgtggcacaccagccatgttttggtcaagcacttctgttaccccggactgagtatcaataga<br>ctgctcacgcggttgaaggagaaagcgtccgttatccggccagctacttcgagaaacctagtaac<br>accatggaagttgcggagtgtttcgctcagcactaccccagtgtagatcaggtcgatgagtcaccg<br>ctttccccacgggcgaccgtggcggtggctgcgttggcggcctgcctatgggggaacccatagg<br>acgctctaatacagacatggtgcgaagagtctattgagctagctggtattcctccggcccctgaatg<br>cggctaatcctaactgtggagcacatgcccctaatccaaggggtagtgtgtcgtaatgagcaattcc<br>gcagcggaaccgactactttgggtgtccgtgtttcctcttattcttgtactggctgcttatggtgacaat<br>tgagagattgttaccatatagctattggattggccatccggtgactaatagagctattgtgtatctcttt<br>gttggatttgtaccacttaatttgaaagaaatcaggacactacgctacattttactattgaacaccgca<br>aa |
| 68 | CVB5 | ttaaaacagcctgtgggttgtacccacccacagggcccactgggcgctagcactctggtatcacg<br>gtacctttgtgcgcctgttttatgccccccttcccccaattgaaacttagaagttacacacaccgatcaa<br>cagcgggcgtggcataccagccgcgtcttgatcaagcactcctgtttccccggaccgagtatcaat<br>agactgctcacgcggttgaaggagaaaacgttcgttacccggctaactacttcgagaaacctagta<br>gcatcatgaaagttgcgaagcgtttcgctcagcacatccccagtgtagatcaggtcgatgagtcac<br>cgcattccccacgggcgaccgtggcggtggctgcgttggcggcctgcctacggggcaacccgt<br>aggacgcttcaatacagacatggtgcgaagagtcgattgagctagttagtagtcctccggcccctg<br>aatccggctaatcctaactgcggagcacataccctcaacccaggggggcattgtgtcgtaacgggt<br>aactctgcagcggaaccgactactttgggtgtccgtgtttccttttattcttataatggctgcttatggtg<br>acaattgaaagattgttaccatatagctattggattggccatccggtgtctaacagagctattatatac<br>ctctttgttggatttgtaccacttgatctaaaggaagtcaagacactacaattcatcatacaattgaaca<br>cagcaaa |
| 69 | EVA71 | ttaaaacagcctgtgggttgcacccactcacagggcccactgggcgcaagcactctggcacttcg<br>gtacctttgtgcgcctgttttatatcccctcccccaatgaaatttagaagcagcaaaccccgatcaata<br>gcaggcataacgctccagttatgtcttgatcaagcacttctgtttccccggactgagtatcaatagac<br>tgctcacgcggttgaaggagaaaacgttcgttatccggctaactacttcggaaagcctagtaacac<br>catggaagttgcggagagtttcgttcagcacttccccagtgtagatcaggtcgatgagtcaccgcat<br>tccccacgggcgaccgtggcggtggctgcgttggcggcctgcccatggggtaacccatgggac<br>gctctaatacggacatggtgtgaagagtctactgagctagttagtagtcctccggcccctgaatgcg<br>gctaatcccaactgcggagcacacgcccacaagccagtgggtagtgtgtcgtaacgggcaactct<br>gcagcggaaccgactactttgggtgtccgtgtttccttttattcttatgttggctgcttatggtgacaatt<br>aaagagttgttaccatatagctattggattggccatccggtgtgcaacagagcgatcgtttacctattt<br>attggttttgtaccattgacactgaagtctgtgatcacccttaattttatcttaaccctcaacacagccaa<br>ac |
| 70 | CVA3 | ttaaaacagcctgtgggttgtacccacccacagggcccactgggcgctagcacactggtattacg<br>gtacctttgtgcgcctgttttataccccccccaacctcgaaacttagaagtaaagcaaacccgatca<br>atagcaggtgcggcgcaccagtcgcatcttgatcaagcacttctgtaaccccggaccgagtatcaa<br>tagactgctcacgcggttgaaggagaaaacgttcgttacccggctaactacttcgagaaacccagt<br>agcatcatgaaagttgcagagtgtttcgctcagcactacccccgtgtagatcaggccgatgagtca<br>ccgcacttccccacgggcgaccgtggcggtggctgcgttggcggcctgcctatggggcaaccca<br>taggacgctctaatacggacatggtgcgaagagtctattgagctagttagtagtcctccggcccctg<br>aatgcggctaatcctaactgcggagcacatacccttaatccaaagggcagtgtgtcgtaacgggta<br>actctgcagcggaaccgactactttgggtgtccgtgtttccttttaatttttactggctgcttatggtgac<br>aattgaggaattgttgccatatagctattggattggccatccggtgactaacagagctattgtgttcca<br>atttgttggatttaccccgctcacactcacagtcgtaagaacccttcattacgtgttatttctcaactcaa<br>gaaa |
| 71 | CVA12 | ttaaaacagcctgtgggttgtacccacccacagggcccactgggcgctagcactctggtactacg<br>gtacctttgtgtgcctgttttaagcccctaccccccactcgtaacttagaaggcttctcacactcgatc<br>aatagtaggtgtggcacgccagtcacaccgtgatcaagcacttctgttaccccggtctgagtacca<br>ataagctgctaacgcggctgaaggggaaaacgatcgttatccggctaactacttcgagaaaccca<br>gtaccaccatgaacgttgcagggtgtttcgctcggcacaaccccagtgtagatcaggtcgatgagt<br>caccgtattccccacgggcgaccgtggcggtggctgcgttggcggcctgcccatggggtgaccc |

TABLE 17-continued

IRES sequences.

| SEQ ID NO | IRES | Sequence |
|---|---|---|
| | | atgggacgctctaatactgacatggtgcgaagagtctattgagctagttagtagtcctccggcccct gaatgcggctaatcctaactgcggagcacatacccttaatccaaagggcagtgtgtcgtaacggg caactctgcagcggaaccgactactttgggtgtccgtgtttccttttattcttacattggctgcttatggt gacaattgaaaagttgttaccatatagctattggattggccatccggtgacaaatagagctattgtata tctttttgttggttacgtaccccttaattacaaagtggtttcaactttgaaatacatcctaacactaaattg tagaaa |
| 72 | EV24 | ttaaaacagcctgtgggttgcacccacccacagggcccacagggcgctagcactctggtatcacg gtacctttgtgcgcctgttttattaccccttccccaattgaaaattagaagcaatgcacaccgatcaac agcaggcgtggcgcaccagtcacgtctcgatcaagcacttctgtttccccggaccgagtatcaata gactgctcacgcggttgaaggagaaagtgttcgttatccggctaaccacttcgagaaacccagtaa caccatgaaagttgcagggtgtttcgctcagcacttccccagtgtagatcaggtcgatgagtcacc gcgttccccacgggcgaccgtggcggtggctgcgttggcggcctgcctatgggttaacccatag gacgctctaatacagacatggtgcgaagagtttattgagctggttagtatccctccggcccctgaat gcggctaatcctaactgcggagcacgtgcctccaatccaggggggttgcatgtcgtaacgggtaac tctgcagcggaaccgactactttgggtgtccgtgtttccttttattcttatactggctgcttatggtgaca atcgaggaattgttaccatatagctattggattggccatccggtgtctaacagagcgattatatacctc tttgttggatttatgcagctcaataccaccaactttaacacattgaaatatatcttaaagttaaacacag caaa |
| 348 | AP1.0 | attctcgggctacggccctggagccactccggctcctaaagatttagaagtttgagcacacccgcc cactagggcccccccatccaggggggcaacgggcaagcacttctgtttccccggtatgatctgata ggctgtaaccacggctgaaacagagattatcgttatccgcttcactacttcgagaagcctagtaatg atgggtgaaattgaatccgttgatccggtgtctcccccacaccagaaactcatgatgagggttgcca tcccggctacggcgacgtagcgggcatccctgcgctggcatgaggcctcttaggaggacggatg atatggatcttgtcgtgaagagcctattgagctagtgtcgactcctccgccccccgtgaatgcggcta atcctaaccccggagcaggtgggtccaatccagggcctggcctgtcgtaatgcgtaagtctggga cggaaccgactactttcgggaaggcgtgtttccatttgttcattatttgtgtgtttatggtgacaactctg ggtaaacgttctattgcgtttattgagagattcccaacaattgaacaaacgagaactacctgttttatta aatttacacagagaagaattaca |
| 349 | CK1.0 | gtggccacgcccgggccaccgatacttcccttcactccttcgggactgttggggaggaacacaac agggctcccctgttttcccattccttccccctttcccaaccccaaccgccgtatctggtggcggcaa gacacacgggtctttccctctaaagcacaattgtgtgtgtgtcccaggtcctcctgcgtacggtgcg ggagtgctcccacccaactgttgtaagcctgtccaacgcgtcgtcctggcaagactatgacgtcgc atgttccgctgcggatgccgaccgggtaaccggttccccagtgtgtgtagtgcgatcttccaggtc ctcctggttggcgttgtccagaaactgcttcaggtaagtggggtgtgcccaatccctacaaaggttg attctttcaccaccttaggaatgctccggaggtaccccagcaacagctgggatctgaccggaggct aattgtctacgggtggtgtttcctttttcttttcacacaactctactgctgacaactcactgactatccact tgctctgTcacG |
| 350 | PV1.0 | aacaaaaggctacaccacttgggctacggcccgcgccaccttgtggcgcaaagacattagaaga atagcataccgcccactagggccctgcagccagcagggtaacgggcaagcacttctgtctcccc ggtagaacggtataggctgtacccacggccgaaaactgaactatcgttacccgactccgtacttcg caaagcttagtaggaaactggaaagttcgagttattgacccggagtgttcccccccactccagaaac gcgtgatgagggttgccaccccgaccatggcgacatggtgggcatccctgcgctggcacgcgg cctctaagaggataactcgctcctactggtaaccgaagagccccgtgagctacggtttattcctccg cctccctgaatgcggctaatcctaacccatgagcagttgccatagatccatatggtggactgtcgta acgcgtaagttgtgggcggaaccgactactttgggatggcgtgtttccttgttttctccatttgttgttgt atggtgacaagttatagatctcgatctatagcgtttcttgagagatttccaaacatttattcaagtcgta caattcttgtgtttaagcagtacagtgtaacc |
| 351 | SV1.0 | tctgtcctcaccccatcttcccttctttcctgcaccgttacgcttactcgcatgtgcattgagtggtgca cgtgcttgaacaaacagctacactcacatgggggcgggttttcccgccctgcggcctctcgcgag gcccacccctccccttcctcccataactacagtgctttggtaggtaagcatcctgatcccccgcgga agctgctcacgtggcaactgtggggacccagacaggttatcaaaggcacccggtctttccgccttc aggagtatccctgctagtgaattctagtagggctctgcttggtgccaacctcccccaaatgcgcgct gcgggagtgctcttccccaactcaccctagtatcctctcatgtgtgtgcttggtcagcatatctgaga cgatgttccgctgtcccagaccagtccagtaatggacgggccagtgtgcgtagtcgtcttccggctt gtccggcgcatgtttggtgaaccggtggggtaaggttggtgtgcccaacgcccgtactttggtgat acctcaagaccacccaggaatgccagggaggtaccccgcttcacagcgggatctgaccctggg ctaattgtctacggtggttcttcttgcttccacttctttctactgttcgccacc |
| 352 | Caprine Kobuvirus 5Δ40 | gtggccacgcccgggccaccgatacttcccttcactccttcgggactgttggggaggaacacaac agggctcccctgttttcccattccttccccctttcccaaccccaaccgccgtatctggtggcggcaa gacacacgggtctttccctctaaagcacaattgtgtgtgtgtcccaggtcctcctgcgtacggtgcg ggagtgctcccacccaactgttgtaagcctgtccaacgcgtcgtcctggcaagactatgacgtcgc atgttccgctgcggatgccgaccgggtaaccggttccccagtgtgtgtagtgcgatcttccaggtc ctcctggttggcgttgtccagaaactgcttcaggtaagtggggtgtgcccaatccctacaaaggttg attctttcaccaccttaggaatgctccggaggtaccccagcaacagctgggatctgaccggaggct aattgtctacgggtggtgtttcctttttcttttcacacaactctactgctgacaactcactgactatccact tgctctcttgtgcctttctgctctggttcaagttccttgattgtttttgactgcttttcactgcttttcttctca caatccttgctcagttcaaagtc |

TABLE 17-continued

IRES sequences.

| SEQ ID NO | IRES | Sequence |
|---|---|---|
| 353 | Caprine Kobuvirus 5Δ40/3Δ122 | gtggccacgcccgggccaccgatacttcccttcactccttcgggactgttggggaggaacacaac agggctcccctgttttcccattccttcccccttttcccaaccccaaccgccgtatctggtggcggcaa gacacacgggtctttccctctaaagcacaattgtgtgtgtgtcccaggtcctcctgcgtacggtgcg ggagtgctcccacccaactgttgtaagcctgtccaacgcgtcgtcctggcaagactatgacgtcgc atgttccgctgcggatgccgaccgggtaaccggttccccagtgtgtgtagtgcgatcttccaggtc ctcctggttggcgttgtccagaaactgcttcaggtaagtggggtgtgcccaatccctacaaaggttg attctttcaccaccttaggaatgctccggaggtaccccagcaacagctgggatctgaccggaggct aattgtctacgggtggtgtttcctttttcttttcacacaactaaagtc |
| 354 | Caprine Kobuvirus 5Δ40/3Δ86_Distal | gtggccacgcccgggccaccgatacttcccttcactccttcgggactgttggggaggaacacaac agggctcccctgttttcccattccttcccccttttcccaaccccaaccgccgtatctggtggcggcaa gacacacgggtctttccctctaaagcacaattgtgtgtgtgtcccaggtcctcctgcgtacggtgcg ggagtgctcccacccaactgttgtaagcctgtccaacgcgtcgtcctggcaagactatgacgtcgc atgttccgctgcggatgccgaccgggtaaccggttccccagtgtgtgtagtgcgatcttccaggtc ctcctggttggcgttgtccagaaactgcttcaggtaagtggggtgtgcccaatccctacaaaggttg attctttcaccaccttaggaatgctccggaggtaccccagcaacagctgggatctgaccggaggct aattgtctacgggtggtgtttcctttttcttttcacacaactctactgctgacaactcactgactatccact tgctctaaagtc |
| 355 | Caprine Kobuvirus 5Δ40/ 3Δ122_Kozak | gtggccacgcccgggccaccgatacttcccttcactccttcgggactgttggggaggaacacaac agggctcccctgttttcccattccttcccccttttcccaaccccaaccgccgtatctggtggcggcaa gacacacgggtctttccctctaaagcacaattgtgtgtgtgtcccaggtcctcctgcgtacggtgcg ggagtgctcccacccaactgttgtaagcctgtccaacgcgtcgtcctggcaagactatgacgtcgc atgttccgctgcggatgccgaccgggtaaccggttccccagtgtgtgtagtgcgatcttccaggtc ctcctggttggcgttgtccagaaactgcttcaggtaagtggggtgtgcccaatccctacaaaggttg attctttcaccaccttaggaatgctccggaggtaccccagcaacagctgggatctgaccggaggct aattgtctacgggtggtgtttcctttttcttttcacacaactgccacc |
| 356 | Caprine Kobuvirus 5Δ40/3Δ86 Proximal | gtggccacgcccgggccaccgatacttcccttcactccttcgggactgttggggaggaacacaac agggctcccctgttttcccattccttcccccttttcccaaccccaaccgccgtatctggtggcggcaa gacacacgggtctttccctctaaagcacaattgtgtgtgtgtcccaggtcctcctgcgtacggtgcg ggagtgctcccacccaactgttgtaagcctgtccaacgcgtcgtcctggcaagactatgacgtcgc atgttccgctgcggatgccgaccgggtaaccggttccccagtgtgtgtagtgcgatcttccaggtc ctcctggttggcgttgtccagaaactgcttcaggtaagtggggtgtgcccaatccctacaaaggttg attctttcaccaccttaggaatgctccggaggtaccccagcaacagctgggatctgaccggaggct aattgtctacgggtggtgtttcctttttcttttcacacaactttcactgcttttcttctcacaatccttgctca gttcaaagtc |
| 357 | Parabovirus | tgaaccgttacgcaccactcagttggtgtttggtggcaccaatgatggaacaaaaggctacaccac ttgggctacggcccgcgccaccttgtggcgcaaagacattagaagaatagcataccgcccactag ggccctgcagccagcagggtaacgggcaagcacttctgtctccccggtagaacggtataggctgt acccacggccgaaaactgaactatcgttacccgactccgtacttcgcaaagcttagtaggaaactg gaaagttcgagttattgacccggagtgttccccccactccagaaacgcgtgatgagggttgccacc ccgaccatggcgacatggtgggcatccctgcgctggcacgcggcctctaagaggataactcgct cctactggtaaccgaagagccccgtgagctacggtttattcctccgcctccctgaatgcggctaatc ctaacccatgagcagttgccatagatccatatggtggactgtcgtaacgcgtaagttgtgggcgga accgactactttgggatggcgtgtttccttgttttctccatttgttgttgtatggtgacaagttatagatct cgatctatagcgtttcttgagagatttccaaacatttattcaagtcgtacaattcttgtgtttaagcagta cagtgtaagg |
| 358 | Parabovirus 5Δ48 | aacaaaaggctacaccacttgggctacggcccgcgccaccttgtggcgcaaagacattagaaga atagcataccgcccactagggccctgcagccagcagggtaacgggcaagcacttctgtctcccc ggtagaacggtataggctgtacccacggccgaaaactgaactatcgttacccgactccgtacttcg caaagcttagtaggaaactggaaagttcgagttattgacccggagtgttccccccactccagaaac gcgtgatgagggttgccaccccgaccatggcgacatggtgggcatccctgcgctggcacgcgg cctctaagaggataactcgctcctactggtaaccgaagagccccgtgagctacggtttattcctccg cctccctgaatgcggctaatcctaacccatgagcagttgccatagatccatatggtggactgtcgta acgcgtaagttgtgggcggaaccgactactttgggatggcgtgtttccttgttttctccatttgttgttgt atggtgacaagttatagatctcgatctatagcgtttcttgagagatttccaaacatttattcaagtcgta caattcttgtgtttaagcagtacagtgtaagg |
| 359 | Parabovirus 5Δ67 | tgggctacggcccgcgccaccttgtggcgcaaagacattagaagaatagcataccgcccactag ggccctgcagccagcagggtaacgggcaagcacttctgtctccccggtagaacggtataggctgt acccacggccgaaaactgaactatcgttacccgactccgtacttcgcaaagcttagtaggaaactg gaaagttcgagttattgacccggagtgttccccccactccagaaacgcgtgatgagggttgccacc ccgaccatggcgacatggtgggcatccctgcgctggcacgcggcctctaagaggataactcgct cctactggtaaccgaagagccccgtgagctacggtttattcctccgcctccctgaatgcggctaatc ctaacccatgagcagttgccatagatccatatggtggactgtcgtaacgcgtaagttgtgggcgga accgactactttgggatggcgtgtttccttgttttctccatttgttgttgtatggtgacaagttatagatct cgatctatagcgtttcttgagagatttccaaacatttattcaagtcgtacaattcttgtgtttaagcagta cagtgtaagg |
| 360 | Parabovirus 3Δ60 | tgaaccgttacgcaccactcagttggtgtttggtggcaccaatgatggaacaaaaggctacaccac ttgggctacggcccgcgccaccttgtggcgcaaagacattagaagaatagcataccgcccactag ggccctgcagccagcagggtaacgggcaagcacttctgtctccccggtagaacggtataggctgt |

TABLE 17-continued

IRES sequences.

| SEQ ID NO | IRES | Sequence |
|---|---|---|
| | | acccacggccgaaaactgaactatcgttacccgactccgtacttcgcaaagcttagtaggaaactg<br>gaaagttcgagttattgacccggagtgttcccccactccagaaacgcgtgatgagggttgccacc<br>ccgaccatggcgacatggtgggcatccctgcgctggcacgcggcctctaagaggataactcgct<br>cctactggtaaccgaagagccccgtgagctacggtttattcctccgcctccctgaatgcggctaatc<br>ctaacccatgagcagttgccatagatccatatggtggactgtcgtaacgcgtaagttgtgggcgga<br>accgactactttgggatggcgtgtttccttgttttctccatttgttgttgtatggtgacaagttatagatct<br>cgatctatagcgtttgtaagg |
| 361 | Apodemus Picornavirus | tttgaaaggggtgcggatatcatggcgtttctcgccatgatatccgcacattgcaaacccatattgca<br>tacccactgggtatgcattatggggaggcccctttcacccctcccccccaattaccttttcccccctct<br>agtaaccatacgctttactcagcgtaactactccgggttacgtgatgaagaagaggctacggagatt<br>ctcgggctacggccctggagccactccggctcctaaagatttagaagtttgagcacacccgccca<br>ctagggcccccatccagggggcaacgggcaagcacttctgtttccccggtatgatctgatagg<br>ctgtaaccacggctgaaacagagattatcgttatccgcttcactacttcgagaagcctagtaatgatg<br>ggtgaaattgaatccgttgatccggtgtctcccccacaccagaaactcatgatgagggttgccatcc<br>cggctacggcgacgtagcgggcatccctgcgctggcatgaggcctcttaggaggacggatgata<br>tggatcttgtcgtgaagagcctattgagctagtgtcgactcctccgcccccgtgaatgcggctaatc<br>ctaaccccggagcaggtgggtccaatccagggcctggcctgtcgtaatgcgtaagtctgggacg<br>gaaccgactactttcgggaaggcgtgtttccatttgttcattatttgtgtgtttatggtgacaactctgg<br>gtaaacgttctattgcgtttattgagagattcccaacaattgaacaaacgagaactacctgttttattaa<br>atttacacagagaagaattaca |
| 362 | Apodemus Picornavirus 5Δ105 | cccctcccccccaattaccttttcccccctctagtaaccatacgctttactcagcgtaactactccggg<br>ttacgtgatgaagaagaggctacggagattctcgggctacggccctggagccactccggctccta<br>aagatttagaagtttgagcacacccgcccactagggcccccatccagggggcaacgggcaa<br>gcacttctgtttccccggtatgatctgataggctgtaaccacggctgaaacagagattatcgttatcc<br>gcttcactacttcgagaagcctagtaatgatgggtgaaattgaatccgttgatccggtgtctcccca<br>caccagaaactcatgatgagggttgccatcccggctacggcgacgtagcgggcatccctgcgct<br>ggcatgaggcctcttaggaggacggatgatatggatcttgtcgtgaagagcctattgagctagtgtc<br>gactcctccgcccccgtgaatgcggctaatcctaaccccggagcaggtgggtccaatccagggc<br>ctggcctgtcgtaatgcgtaagtctgggacggaaccgactactttcgggaaggcgtgtttccatttgt<br>tcattatttgtgtgtttatggtgacaactctgggtaaacgttctattgcgtttattgagagattcccaaca<br>attgaacaaacgagaactacctgttttattaaatttacacagagaagaattaca |
| 363 | Apodemus Picornavirus 5Δ201 | attctcgggctacggccctggagccactccggctcctaaagatttagaagtttgagcacacccgcc<br>cactagggcccccatccagggggcaacgggcaagcacttctgtttccccggtatgatctgata<br>ggctgtaaccacggctgaaacagagattatcgttatccgcttcactacttcgagaagcctagtaatg<br>atgggtgaaattgaatccgttgatccggtgtctcccccacaccagaaactcatgatgagggttgcca<br>tcccggctacggcgacgtagcgggcatccctgcgctggcatgaggcctcttaggaggacggatg<br>atatggatcttgtcgtgaagagcctattgagctagtgtcgactcctccgcccccgtgaatgcggcta<br>atcctaaccccggagcaggtgggtccaatccagggcctggcctgtcgtaatgcgtaagtctggga<br>cggaaccgactactttcgggaaggcgtgtttccatttgttcattatttgtgtgtttatggtgacaactctg<br>ggtaaacgttctattgcgtttattgagagattcccaacaattgaacaaacgagaactacctgttttatta<br>aatttacacagagaagaattaca |
| 364 | Kobuvirus SZAL6 | tttcacaccctcttttccggtggtccggacccagaccaccgttactccattcagctacttcggtacctg<br>ttcggaggaattaaacgggcaccctacccaagggttacatgggaccatattcctcctcccctgtaac<br>tttaagttttgtgcccgtattcttgactccaggcggatgttgtgtcgcccgtcctgtgaacaaacagct<br>agacactttcctcccctccctctgggctgctccggcagtccactccctccccccagcgtaacatgcc<br>ccgctggagtgatgcacctggaagtcgtggacgtgggttagtaacttcggtgaaaacccactataa<br>tgacaactggttgacccccacactcaaaggactcgagtctttctcccttaaggctagcccggccac<br>atgaatttgcagctggcaactagtgagtccaccatgtcccgcaacctcggctgcggagtgctgttc<br>cccaagcgtatgccttccttctgtaagagtgcgcctggcaagcacatctgagaagtcgttccgctgc<br>gtcgtgccaacctggcgacaggtgacccagtgtgcgtagacttcttccggattcgtccggctcttct<br>ctaggaaacatgcgtgtaaggttcatgtgccaaagccctgcgcgcggtgttcttctactgccctagg<br>aatgtgccgcaggtacccctacttcggtagggatctgagcggtagctaattgtctacgggtagtttc<br>atttccatcttctcttcaggtcgacatc |
| 365 | Kobuvirus SZAL6 5Δ158 | ttgactccaggcggatgttgtgtcgcccgtcctgtgaacaaacagctagacactttcctcccctccct<br>ctgggctgctccggcagtccactccctccccccagcgtaacatgccccgctggagtgatgcacct<br>ggaagtcgtggacgtgggttagtaacttcggtgaaaacccactataatgacaactggttgaccccc<br>acactcaaaggactcgagtctttctcccttaaggctagcccggccacatgaatttgcagctggcaac<br>tagtgagtccaccatgtcccgcaacctcggctgcggagtgctgttccccaagcgtatgccttccttc<br>tgtaagagtgcgcctggcaagcacatctgagaagtcgttccgctgcgtcgtgccaacctggcgac<br>aggtgacccagtgtgcgtagacttcttccggattcgtccggctcttctctaggaaacatgcgtgtaa<br>ggttcatgtgccaaagccctgcgcgcggtgttcttctactgccctaggaatgtgccgcaggtaccc<br>ctacttcggtagggatctgagcggtagctaattgtctacgggtagtttcatttccatcttctcttcaggt<br>cgacatc |
| 366 | Kobuvirus SZAL6 5Δ76 | gaattaaacgggcaccctacccaagggttacatgggaccatattcctcctcccctgtaactttaagtt<br>ttgtgcccgtattcttgactccaggcggatgttgtgtcgcccgtcctgtgaacaaacagctagacact<br>ttcctcccctccctctgggctgctccggcagtccactccctccccccagcgtaacatgccccgctg<br>gagtgatgcacctggaagtcgtggacgtgggttagtaacttcggtgaaaacccactataatgacaa<br>ctggttgacccccacactcaaaggactcgagtctttctcccttaaggctagcccggccacatgaatt<br>tgcagctggcaactagtgagtccaccatgtcccgcaacctcggctgcggagtgctgttccccaag |

TABLE 17-continued

IRES sequences.

| SEQ ID NO | IRES | Sequence |
|---|---|---|
| | | cgtatgccttccttctgtaagagtgcgcctggcaagcacatctgagaagtcgttccgctgcgtcgtg<br>ccaacctggcgacaggtgacccagtgtgcgtagacttcttccggattcgtccggctcttctctagga<br>aacatgcgtgtaaggttcatgtgccaaagccctgcgcgcggtgttcttctactgccctaggaatgtg<br>ccgcaggtacccctacttcggtagggatctgagcggtagctaattgtctacgggtagtttcatttcca<br>tcttctcttcaggtcgacatc |
| 367 | Kobuvirus<br>SZAL6 3Δ37 | tttcacaccctcttttccggtggtccggacccagaccaccgttactccattcagctacttcggtacctg<br>ttcggaggaattaaacgggcaccctacccaagggttacatgggaccatattcctcctcccctgtaac<br>tttaagttttgtgcccgtattcttgactccaggcggatgttgtgtcgcccgtcctgtgaacaaacagct<br>agacactttcctcccctccctctgggctgctccggcagtccactccctccccccagcgtaacatgcc<br>ccgctggagtgatgcacctggaagtcgtggacgtgggttagtaacttcggtgaaaacccactataa<br>tgacaactggttgacccccacactcaaaggactcgagtctttctcccttaaggctagcccggccac<br>atgaatttgcagctggcaactagtgagtccaccatgtcccgcaacctcggctgcggagtgctgttc<br>cccaagcgtatgccttccttctgtaagagtgcgcctggcaagcacatctgagaagtcgttccgctgc<br>gtcgtgccaacctggcgacaggtgacccagtgtgcgtagacttcttccggattcgtccggctcttct<br>ctaggaaacatgcgtgtaaggttcatgtgccaaagccctgcgcgcggtgttcttctactgccctagg<br>aatgtgccgcaggtacccctacttcggtagggatctgagcggtagctaattggacatc |
| 368 | Salivirus SZ1 | tctgtcctcaccccatcttcccttctttcctgcaccgttacgcttactcgcatgtgcattgagtggtgca<br>cgtgcttgaacaaacagctacactcacatgggggcgggtttcccgccctgcggcctctcgcgag<br>gcccacccctccccttcctcccataactacagtgctttggtaggtaagcatcctgatcccccgcgga<br>agctgctcacgtggcaactgtggggacccagacaggttatcaaaggcacccggtctttccgccttc<br>aggagtatccctgctagtgaattctagtagggctctgcttggtgccaacctcccccaaatgcgcgct<br>gcgggagtgctcttccccaactcaccctagtatcctctcatgtgtgtgcttggtcagcatatctgaga<br>cgatgttccgctgtcccagaccagtccagtaatggacgggccagtgtgcgtagtcgtcttccggctt<br>gtccggcgcatgtttggtgaaccggtggggtaaggttggtgtgcccaacgcccgtactttggtgat<br>acctcaagaccacccaggaatgccagggaggtaccccgcttcacagcgggatctgaccctggg<br>ctaattgtctacggtggttcttcttgcttccacttctttctactgttcatg |
| 369 | Crohivirus B | gtataagagacaggtgtttgccttgtcttcggactggcatcttgggaccaacccccctttttccccagc<br>catgggttaaatggcaataaaggacgtaacaactttgtaaccattaagctttgtaattttgtaaccact<br>aagctttgtgcacataatgtaaccatcaagcttgttagtcccagcaggaggtttgcatgcttgtagcc<br>gaaatggggctcgacccccccatagtaggatacttgattttgcattccattgtggacctgcaaactcta<br>cacatagaggctttgtcttgcatctaaacacctgagtacagtgtgtacctagaccctatagtacggga<br>ggaccgtttgtttcctcaataaccctacataataggctaggtgggcatgcccaatttgcaagatccca<br>gactgggggtcggtctgggcagggttagatccctgttagctactgcctgatagggtggtgctcaac<br>catgtgtagtttaaattgagctgttcatatacc |
| 370 | Crohivirus B<br>5Δ51 | cccccctttttccccagccatgggttaaatggcaataaaggacgtaacaactttgtaaccattaagctt<br>tgtaattttgtaaccactaagctttgtgcacataatgtaaccatcaagcttgttagtcccagcaggagg<br>tttgcatgcttgtagccgaaatggggctcgacccccccatagtaggatacttgattttgcattccattgt<br>ggacctgcaaactctacacatagaggctttgtcttgcatctaaacacctgagtacagtgtgtacctag<br>accctatagtacgggaggaccgtttgtttcctcaataaccctacataataggctaggtgggcatgcc<br>caatttgcaagatcccagactgggggtcggtctgggcagggttagatccctgttagctactgcctg<br>atagggtggtgctcaaccatgtgtagtttaaattgagctgttcatatacc |
| 371 | CVB3 | ttaaaacagcctgtgggttgatcccacccacagggcccattgggcgctagcactctggtatcacgg<br>tacctttgtgcgcctgttttatacccccctcccccaactgtaacttagaagtaacacacaccgatcaac<br>agtcagcgtggcacaccagccacgttttgatcaagcacttctgttaccccggactgagtatcaatag<br>actgctcacgcggttgaaggagaaagcgttcgttatccggccaactacttcgaaaaacctagtaac<br>accgtggaagttgcagagtgtttcgctcagcactaccccagtgtagatcaggtcgatgagtcaccg<br>cattccccacgggcgaccgtggcggtggctgcgttggcggcctgcccatggggaaacccatgg<br>gacgctctaatacagacatggtgcgaagagtctattgagctagttggtagtcctccggcccctgaat<br>gcggctaatcctaactgcggagcacacaccctcaagccagagggcagtgtgtcgtaacgggcaa<br>ctctgcagcggaaccgactactttgggtgtccgtgtttcattttattcctatactggctgcttatggtga<br>caattgagagattgttaccatatagctattggattggccatccggtgaccaatagagctattatatatct<br>ctttgttgggtttataccacttagcttgaaagaggttaaaacattacaattcattgttaagttgaatacag<br>caaa |
| 372 | CVB3 3Δ91 | ttaaaacagcctgtgggttgatcccacccacagggcccattgggcgctagcactctggtatcacgg<br>tacctttgtgcgcctgttttatacccccctcccccaactgtaacttagaagtaacacacaccgatcaac<br>agtcagcgtggcacaccagccacgttttgatcaagcacttctgttaccccggactgagtatcaatag<br>actgctcacgcggttgaaggagaaagcgttcgttatccggccaactacttcgaaaaacctagtaac<br>accgtggaagttgcagagtgtttcgctcagcactaccccagtgtagatcaggtcgatgagtcaccg<br>cattccccacgggcgaccgtggcggtggctgcgttggcggcctgcccatggggaaacccatgg<br>gacgctctaatacagacatggtgcgaagagtctattgagctagttggtagtcctccggcccctgaat<br>gcggctaatcctaactgcggagcacacaccctcaagccagagggcagtgtgtcgtaacgggcaa<br>ctctgcagcggaaccgactactttgggtgtccgtgtttcattttattcctatactggctgcttatggtga<br>caattgagagattgttaccatatagctattggattggccatccggtgaagcaaa |
| 373 | SAFV | cacttatttaattcggccttttgtgacaagcccctcggtgaaagaacctctctcttttcgacgtggttgg<br>aattgccatcatttccgacgaaagtgctatcatgcctccccgattatgtgatgttttctgccctgctgg<br>gcggagcattctcgggttgagaaaccttgaatctttttctttggaaccttggttcccccggtctaagcc<br>gcttggaatatgacagggttattttcttgatcttatttctacttttgcgggttctatccgtaaaaagggtac<br>gtgctgccccttccttctctggagaattcacacggcggtctttccgtctctcaacaagtgtgaatgca |

TABLE 17-continued

IRES sequences.

| SEQ ID NO | IRES | Sequence |
|---|---|---|
| | | gcatgccggaaacggtgaagaaaacagttttctgtggaaatttagagtgcacatcgaaacagctgt<br>agcgacctcacagtagcagcggactcccctcttggcgacaagagcctctgcggccaaaagcccc<br>gtggataagatccactgctgtgagcggtgcaaccccagcaccctggttcgatgatcattctctatgg<br>aaccagaaaatggttttctcaagccctccggtagagaagccaagaatgtcctgaaggtaccccgc<br>gtgcgggatctgatcaggagaccaattggcggtgctttacactgtcactttggtttaaaaattgtcac<br>agcttctccaaaccaagtggtcttggttttccaattttgttga |
| 374 | SAFV 5Δ46 | cctctctcttttcgacgtggttggaattgccatcatttccgacgaaagtgctatcatgcctccccgatta<br>tgtgatgttttctgccctgctgggcggagcattctcgggttgagaaaccttgaatctttttctttggaac<br>cttggttcccccggtctaagccgcttggaatatgacagggttattttcttgatcttatttctacttttgcgg<br>gttctatccgtaaaaagggtacgtgctgccccttccttctctggagaattcacacggcggtctttccgt<br>ctctcaacaagtgtgaatgcagcatgccggaaacggtgaagaaaacagttttctgtggaaatttaga<br>gtgcacatcgaaacagctgtagcgacctcacagtagcagcggactcccctcttggcgacaagag<br>cctctgcggccaaaagccccgtggataagatccactgctgtgagcggtgcaaccccagcaccct<br>ggttcgatgatcattctctatggaaccagaaaatggttttctcaagccctccggtagagaagccaag<br>aatgtcctgaaggtaccccgcgtgcgggatctgatcaggagaccaattggcggtgctttacactgt<br>cactttggtttaaaaattgtcacagcttctccaaaccaagtggtcttggttttccaattttgttga |
| 375 | SAFV 5Δ93 | gtgctatcatgcctccccgattatgtgatgttttctgccctgctgggcggagcattctcgggttgaga<br>aaccttgaatctttttctttggaaccttggttcccccggtctaagccgcttggaatatgacagggttattt<br>tcttgatcttatttctacttttgcgggttctatccgtaaaaagggtacgtgctgccccttccttctctgga<br>gaattcacacggcggtctttccgtctctcaacaagtgtgaatgcagcatgccggaaacggtgaaga<br>aaacagttttctgtggaaatttagagtgcacatcgaaacagctgtagcgacctcacagtagcagcg<br>gactcccctcttggcgacaagagcctctgcggccaaaagccccgtggataagatccactgctgtg<br>agcggtgcaaccccagcaccctggttcgatgatcattctctatggaaccagaaaatggttttctcaa<br>gccctccggtagagaagccaagaatgtcctgaaggtaccccgcgtgcgggatctgatcaggaga<br>ccaattggcggtgctttacactgtcactttggtttaaaaattgtcacagcttctccaaaccaagtggtct<br>tggttttccaattttgttga |
| 376 | SAFV 3Δ47 | cacttatttaattcggccttttgtgacaagcccctcggtgaaagaacctctctcttttcgacgtggttgg<br>aattgccatcatttccgacgaaagtgctatcatgcctccccgattatgtgatgttttctgccctgctgg<br>gcggagcattctcgggttgagaaaccttgaatctttttctttggaaccttggttcccccggtctaagcc<br>gcttggaatatgacagggttattttcttgatcttatttctacttttgcgggttctatccgtaaaaagggtac<br>gtgctgccccttccttctctggagaattcacacggcggtctttccgtctctcaacaagtgtgaatgca<br>gcatgccggaaacggtgaagaaaacagttttctgtggaaatttagagtgcacatcgaaacagctgt<br>agcgacctcacagtagcagcggactcccctcttggcgacaagagcctctgcggccaaaagcccc<br>gtggataagatccactgctgtgagcggtgcaaccccagcaccctggttcgatgatcattctctatgg<br>aaccagaaaatggttttctcaagccctccggtagagaagccaagaatgtcctgaaggtaccccgc<br>gtgcgggatctgatcaggagaccaattggcggtgctttacactgtcactttggtttaatgttga |
| 377 | SAFV Kozak | cacttatttaattcggccttttgtgacaagcccctcggtgaaagaacctctctcttttcgacgtggttgg<br>aattgccatcatttccgacgaaagtgctatcatgcctccccgattatgtgatgttttctgccctgctgg<br>gcggagcattctcgggttgagaaaccttgaatctttttctttggaaccttggttcccccggtctaagcc<br>gcttggaatatgacagggttattttcttgatcttatttctacttttgcgggttctatccgtaaaaagggtac<br>gtgctgccccttccttctctggagaattcacacggcggtctttccgtctctcaacaagtgtgaatgca<br>gcatgccggaaacggtgaagaaaacagttttctgtggaaatttagagtgcacatcgaaacagctgt<br>agcgacctcacagtagcagcggactcccctcttggcgacaagagcctctgcggccaaaagcccc<br>gtggataagatccactgctgtgagcggtgcaaccccagcaccctggttcgatgatcattctctatgg<br>aaccagaaaatggttttctcaagccctccggtagagaagccaagaatgtcctgaaggtaccccgc<br>gtgcgggatctgatcaggagaccaattggcggtgctttacactgtcactttggtttaaaaattgtcac<br>agcttctccaaaccaagtggtcttggttttccaattttgttgaccgcc |
| 378 | GLuc CK dCTG1 | gtggccacgcccgggccaccgatacttcccttcactccttcgggactgttggggaggaacacaac<br>agggctcccctgttttcccattccttcccccttttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctacGTctgacaactcactgactatcca<br>cttgctctaaagtc |
| 379 | GLuc CK dCTG1_2 | gtggccacgcccgggccaccgatacttcccttcactccttcgggactgttggggaggaacacaac<br>agggctcccctgttttcccattccttcccccttttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctacGTcGTacaactcactgactatcc<br>acttgctctaaagtc |
| 380 | GLuc CK dCTG1_2_3 | gtggccacgcccgggccaccgatacttcccttcactccttcgggactgttggggaggaacacaac<br>agggctcccctgttttcccattccttcccccttttcccaaccccaaccgccgtatctggtggcggcaa<br>gacacacgggtctttccctctaaagcacaattgtgtgtgtgtcccaggtcctcctgcgtacggtgcg |

TABLE 17-continued

IRES sequences.

| SEQ ID NO | IRES | Sequence |
| --- | --- | --- |
| | | ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctacGTcGTacaactcacGTactat<br>ccacttgctctaaagtc |
| 381 | GLuc CK dAll | gtggccacgcccgggccaccgatacttcccttcactccttcgggactgttggggaggaacacaac<br>agggctcccctgttttcccattccttcccccttttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctacGTcGTacaactcacGTactaC<br>TcactGTctctaaagtc |
| 382 | CK SZ1-L1S | gggggtggggggggcctcggcccccctcaccctcttttccggtggccacgcccgggccaccgat<br>acttcccttcactccttcgggactgttggggaggaacacaacagggctcccctgttttcccattcctt<br>cccccttttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcgtcgtcctggcaagactatgacgtcgcatgttccgctgcggatgccgacc<br>gggtaaccggttccccagtgtgtgtagtgcgatcttccaggtcctcctggttggcgttgtccagaaa<br>ctgcttcaggtaagtggggtgtgcccaatccctacaaaggttgaaccacccaggaatgccaggga<br>ggtaccccgcttcacagcgggatctgaccctgggctaattgtctacggtggttcttcttgcttccactt<br>ctttctactgttcgccacc |
| 383 | CK Aichi Scan (AV-S) | gggggtggggggggcctcggcccccctcaccctcttttccggtggccacgcccgggccaccgat<br>acttcccttcactccttcgggactgttggggaggaacacaacagggctcccctgttttcccattcctt<br>cccccttttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcgtcgtcctggcaagactatgacgtcgcatgttccgctgcggatgccgacc<br>gggtaaccggttccccagtgtgtgtagtgcgatcttccaggtcctcctggttggcgttgtccagaaa<br>ctgcttcaggtaagtggggtgtgcccaatccctacaaaggttgattctttcaccaccttaggaatgct<br>ccggaggtaccccagcaacagctgggatctgaccggaggctaattgtctacgggtggtgtttcatt<br>tccaatccttttatgtcggagtc |
| 384 | CK Aichi Loop (AV-L1) | gggggtggggggggcctcggcccccctcaccctcttttccggtggccacgcccgggccaccgat<br>acttcccttcactccttcgggactgttggggaggaacacaacagggctcccctgttttcccattcctt<br>cccccttttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcgtcgtcctggcaagactatgacgtcgcatgttccgctgcggatgccgacc<br>gggtaaccggttccccagtgtgtgtagtgcgatcttccaggtcctcctggttggcgttgtccagaaa<br>ctgcttcaggtaagtggggtgtgcccaatccctacaaaggttgaactgccctaggaatgccaggca<br>ggtaccccacctccgggtgggatctgagcctgggctaattgtctacgggtagtttccttttttcttttca<br>cacaactctactgctgacaactcactgactatccacttgctctcttgtgcctttctgctctggttcaagtt<br>ccttgattgtttttgactgcttttcactgcttttcttctcacaatccttgctcagttcaaagtc |
| 385 | CK SZ1-L2 | gggggtggggggggcctcggcccccctcaccctcttttccggtggccacgcccgggccaccgat<br>acttcccttcactccttcgggactgttggggaggaacacaacagggctcccctgttttcccattcctt<br>cccccttttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcctgatccccgcggaagctgctcacgtggcaactgtggggacccagaca<br>ggttatcaaaggcacccggtctttccgccttcaggagtatccctgctagtgaattctagtagggctct<br>gcttgcgttgtccagaaactgcttcaggtaagtggggtgtgcccaatccctacaaaggttgattcttt<br>caccaccttaggaatgctccggaggtaccccagcaacagctgggatctgaccggaggctaattgt<br>ctacgggtggtgtttcctttttcttttcacacaactctactgctgacaactcactgactatccacttgctct<br>cttgtgcctttctgctctggttcaagttccttgattgtttttgactgcttttcactgcttttcttctcacaatcc<br>ttgctcagttcaaagtc |
| 386 | CK Aichi TriLoop (AV-L2) | gggggtggggggggcctcggcccccctcaccctcttttccggtggccacgcccgggccaccgat<br>acttcccttcactccttcgggactgttggggaggaacacaacagggctcccctgttttcccattcctt<br>cccccttttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt<br>aagcctgtccaacgcatgtgcctggcaagcatatctgagaaggtgttccgctgtggctgccaacct<br>ggtgacaggtgccccagtgtgcgtaaccttcttccgtctccggacggtgcgttgtccagaaactgct<br>tcaggtaagtggggtgtgcccaatccctacaaaggttgattctttcaccaccttaggaatgctccgg<br>aggtaccccagcaacagctgggatctgaccggaggctaattgtctacgggtggtgtttcctttttcttt<br>tcacacaactctactgctgacaactcactgactatccacttgctctcttgtgcctttctgctctggttcaa<br>gttccttgattgtttttgactgcttttcactgcttttcttctcacaatccttgctcagttcaaagtc |
| 387 | CK Scan Deletion (ΔS) | gggggtggggggggcctcggcccccctcaccctcttttccggtggccacgcccgggccaccgat<br>acttcccttcactccttcgggactgttggggaggaacacaacagggctcccctgttttcccattcctt<br>cccccttttcccaaccccaaccgccgtatctggtggcggcaagacacacgggtctttccctctaaa<br>gcacaattgtgtgtgtgtcccaggtcctcctgcgtacggtgcgggagtgctcccacccaactgttgt |

TABLE 17-continued

IRES sequences.

| SEQ ID NO | IRES | Sequence |
|---|---|---|
| | | aagcctgtccaacgcgtcgtcctggcaagactatgacgtcgcatgttccgctgcggatgccgacc gggtaaccggttccccagtgtgtgtagtgcgatcttccaggtcctcctggttggcgttgtccagaaa ctgcttcaggtaagtggggtgtgcccaatccctacaaaggttgattctttcaccaccttaggaatgct ccggaggtaccccagcaacagctgggatctgaccggaggctaattgtctacgggtggtg |
| 388 | CK Loop Deletion (ΔL1) | gggggtgggggggggcctcggcccccctcaccctcttttccggtggccacgcccgggccaccgat acttcccttcactccttcgggactgttggggaggaacacaacagggctcccctgttttcccattcctt ccccctttcccaaccccaaccgccgtatctggtggcggcaagacacacgggtctttccctctaaa gcacaattgtgtgtgtgtcccaggtcctcctgcgtacggtgcgggagtgctcccacccaactgttgt aagcctgtccaacgcgtcgtcctggcaagactatgacgtcgcatgttccgctgcggatgccgacc gggtaaccggttccccagtgtgtgtagtgcgatcttccaggtcctcctggttggcgttgtccagaaa ctgcttcaggtaagtggggtgtgcccaatccctacaaaggttgatttcctttttcttttcacacaactct actgctgacaactcactgactatccacttgctctcttgtgcctttctgctctggttcaagttccttgattgt tttgactgcttttcactgcttttcttctcacaatccttgctcagttcaaagtc |
| 389 | CK Triloop Deletion (ΔL2) | gggggtgggggggggcctcggcccccctcaccctcttttccggtggccacgcccgggccaccgat acttcccttcactccttcgggactgttggggaggaacacaacagggctcccctgttttcccattcctt ccccctttcccaaccccaaccgccgtatctggtggcggcaagacacacgggtctttccctctaaa gcacaattgtgtgtgtgtcccaggtcctcctgcgtacggtgcgggagtgctcccacccaactgttgt aagcctgtccaacgcgcgttgtccagaaactgcttcaggtaagtggggtgtgcccaatccctacaa aggttgattctttcaccaccttaggaatgctccggaggtaccccagcaacagctgggatctgaccg gaggctaattgtctacgggtggtgtttcctttttcttttcacacaactctactgctgacaactcactgact atccacttgctctcttgtgcctttctgctctggttcaagttccttgattgtttttgactgcttttcactgctttt cttctcacaatccttgctcagttcaaagtc |
| 413 | RhPV | gataaaagaacctataatcccttcgcacaccgcgtcacaccgcgctatatgctgctcattaggaatt acggctcctttttttgtggatacaatctcttgtatacgatatacttattgttaatttcattgacctttacgcaa tcctgcgtaaatgctggtatagggtgtacttcggatttccgagcctatattggttttgaaaggaccttta agtccctactatactacattgtactagcgtaggccacgtaggcccgtaagatattataactattttatta tattttattcaccccccacattaatcccagttaaagctttataactataagtaagccgtgccgaaacgtt aatcggtcgctagttgcgtaacaactgttagtttaattttccaaaatttatttttcacaatttttagttaaga ttttagcttgccttaagcagtctttatatcttctgtatattattttaaagtttataggagcaaagttcgcttta ctcgcaatagctattttatttattttaggaatattatcacctcgtaattatttaattataacattagctttatct atttata |
| 414 | Halastavi arva (1x mut) | cttgattctaaccttgccgtatggtgccctaacgggttcatttaatcatgcgatgagggttgctatacc gcatccattctaaggcgattcaatgcttcatttaggaattttgttgacgattaaaaggtacccccacaa aaacaaaaccaatcttacttgattttcgttttaactgaccactgcgatcccaaattttcgccttcttatca aagtatgttgtgttctttgggtgtacaacctgagaacttgtctacaactacatattactcgaggaagaa attcggtttaagccgtgccttctcacgtttagtatatctatctGgacacaccttcttcatcttctaatccc catctagtctcctgatcagagacgtcgttattaacaaataaccccccttgttaataagagacaaagta caatcaagctaagttctcttggagttcctgtaggaacttagccattgtgatagagtcataagtctatgt gcatagacagctctagctcaccatttccttcccaacccatcttttcatcagcttaactctatgaatccga tgcaaaaaccattctaacatcttatggtgctttccaagccaaatgagagctcactcttttgagccgcta tttaatggacaataaacgttttatagtgtacatcatattgtaaaaacaaa |
| 415 | Oscivirus | cctcggtccctctttccgtcgccgcccacgacgttaaatgcggtgttgtggtgcttaggtgccacac cactgctatttgggtcccccttcccctatatatgtttgtttgtttatttcaatttcttgaggattggcacctc cttatgccaaatctaaatcgtggaggatcccaggctttctggtctttaacagaactccacgtccaggt catagaaactggttggtaggctgcctgagtagtccatttgctagtagtcccttgtgaacagggtggct cccgtttactgctggtattcccggtgtaggtcgccatggtggtaacaccatcctgcattgtgtgtgaa ccagtaccgcaaggatagcaaggtatgaacacttgtggacgaaatggtaagtgatcaattcactttc atggccggaaggtcacgtggcaatcatgccacccaggtaccctcctctgggaggatctgagggt gggctaagcagaccctgccatgtggctgaacttttccctattgttttactttgtaacatttatagttgtgt tagtgatttgtgtgttgtgcccttgtgagctatatccagtataagttcgcagctagaagttaatccttcg acatcggctgtattggaa |
| 416 | Cadicivirus B | caccaacccttgacctgtaatgtcagtggacagagtgctcctctgttcccggttaccgtgttccagg acacgattgtaatcctgcgcctcaccagcgctgcgtgcacgtctgcataaggaaacgtgccttccc catgtctctatcaattctttggtgagtgaccgccctagttgctcatcctatgggattcttctctcatgggt tctttgtggcatgcgaatgtcaccttaattggaggtctttaattagatatcctttcttcatctttgatatgag tgtcggaatttgattcctagtctctgcaaaacaaccccacttgatgaattcaacttttcaaccgcacaa acataatcaggtttttaaattgaatgtttctaaattctaaatttagtttatttaagtagtttgccatcttgact cgatgtaaaattgtcatacaagtcttcttttcttttctttacactttgaagtttgcacttagcagtcgttctg cacagctttcgagttttgtttgatcgacatcgcaacttccacccacctctctttttctagtgttgaatgcg gctaatcctaacccgagagcaataaacccaggtttattgtcgtaacgcgcaagtcttggacggaac cgactatacacacacctctttaccctttagtacacccttggtacg |

TABLE 17-continued

| SEQ ID NO | IRES | Sequence |
|---|---|---|
| 417 | PSIV (2x mut for Xba1) | gcaaaatgggtacgtagttaaccactgcgtatcaggattgcaggccacgaagggtatttgcatatct ttctatgcggtattacggcttaaaacccgttgtatcttgtTgtttgactgcctgtatcactagtggccatt ttatttaggttagagacccctgatagtaggagagttacaaactctttaaaaattgttgaccccggaaa agatggtgacccctgtaagtagttgatcAagaagatctatgcgctggcatagtaatccagtgtttcc tgttttaggatgacctctgaaagtagatgaccgtggaaagtcacgtagtgccccaataagcacgttt gggcagcgtgcgctatcacaaggcttgatctccgaggagccccttgttttagctggctggaagcca atgatcttaagtagataagtgctgttgcttgtagttcaacagaaagctttgagtacgtctttcttgcgag aaagaacacatgcattcttatgctctcaattctattatttttattttgggcgaaaggaaagctctcacgc gagtacgaatagccaacccctttat |
| 418 | PSIV IGR | GCTGACTATGTGATCTTATTAAAATTAGGTTAAATTTCGAG GTTAAAAATAGTTTTAATATTGCTATAGTCTTAGAGGTCTT GTATATTTATACTTACCACACAAGATGGACCGGAGCAGCCC TCCAATATCTAGTGTACCCTCG |
| 419 | PV Mahoney | ATGAGTCTGGACATCCCTCACCGGTGACGGTGGTCCAGGCT GCGTTGGCGGCCTACCTATGGCTAACGCCATGGGACGCTAG TTGTGAACAAGGTGTGAAGAGCCTATTGAGCTACATAAGA ATCCTCCGGCCCCTGAATGCGGCTAATCCCAACCTCGGAGC AGGTGGTCACAAACCAGTGATTGGCCTGTCGTAACGCGCA AGTCCGTGGCGGAACCGACTACTTTGGGTGTCCGTGTTTCC TTTTATTTTATTGTGGCTGCTTATGGTGACAATCACAGATTG TTATCATAAAGCGAATTGGATTGGCC |
| 420 | REV A | GGGGTCGCCGTCCTACACATTGTTGTGACGTGCGGCCCAGA TTCGAATCTGTAATAAAAGCTTTTTCTTCTATATCCTCAGAT TGGCAGTGAGAGGAGATTTTGTTCGTGGTGTTGGCTGGCCT ACTGGGTGGGGTAGGGATCCGGACTGAATCCGTAGTATTTC GGTACAACATTTGGGGGCTCGTCCGGGATTCCTCCCCATCG GCAGAGGTGCCTACTGTTTCTTCGAACTCCGGCGCCGGTAA GTAAGTACTTGATTTTGGTACCTCGCGAGGGTTTGGGAGGA TCGGAGTGGCGGGACGCTGCCGGGAAGCTCCACCTCCGCT CAGCAGGGGACGCCCTGGTCTGAGCTCTGTGGTATCTGATT GTTGTTGAACCGTCTCTAAGACGGTGATACTATAAGTCGTG GtttgtGTGTTTGTTTGTTACCTTGTGTTTGTTCGTCACTTGT CGACAGCGCCCTGCGAATTGGTGTACCCACACCGCGCGGCT TGCGAATAATACTTTGGAGAGTCTTTTGCCTCCAGTGTCTTC CGTTTGTACTCGTCCTCCTCTCCCTCTCCGGCCGGGATGGG |
| 421 | Tropivirus A | tgtcgcatgttgccaacatcaaaattctgggagagtcgcgaactccttaacactgccttgcctcgac ggagccgttgttatagtgtcgacgggatacaaacattaaactaaacccacttgcctcgacggaacc ccttacctttttattttattttatagtatgaaagtgaatcttgtatgaatgttcatagaaaactgcaaatgagt accacgtctaacatgagagaatgatactggagaaatccaagtttagaagtcactacgaatcccagc ggaaacaagggaattctgagcttctaataggcgtttaagactatttgcaaaattctggtgcgtaagtg atattttcattgcgtagaacgctggtaaccactccggctagtataagcattgttagtcacttattatgaa actccacactatcctttctggagaagcacacaaacttacatggtaaagctagaccattatcttaagcg gtgagtacactgcaaccttgtaacaatgcttgtatgactactttttgtatatcttgagcaatattgttgag gtggacatgtccaaaggtaatgttgttgggaatggaggggtccattttcccgtgcacgtagtgtact agtattgggtgatagccttgcggcggatcaaccatgtattttaatccgttgactttcac |
| 422 | Symapivirus A | ttgggaaatccccaatgcttctttcaacaccgcctgactatgcggtggcgcttcggctcaaacaact agtcacttccccctcttaactactacccaagacttctaactacccttacctacttatttgtctaaatttcaa actttttattctcacgcgtcttataaacatcttttctatttgttatggtatgttttgtgatttgtgtggtgtatttc atttaatgggatctagtggaccgtgccccggttgggtatccgctccctttaaatgtttgcaagcactct tgacattataacctatcatttagtttacttgtttgtatgatcgtatttctgaatcgtaacatttatgcaattctt tctcgccgagacttgtctaggagataaagttcctgcatatttagtgttacggttgtataatggagactta gatagcttcacactgaggacgctttttcgctatccttttgacctgattcaggccagtgtggagttaatg attgtatggatgggccctacaatttgtctaagacttggtgatagcctcgcggccgctcgccatttata caactgaatagcggttgaaactctct |
| 423 | Sakobuvirus A FFUP1 (1x mut) | tcacgcgcttttccggtggtcacccaccgttagggagcgccagcgttcgcgcttccgctaccaggt gacacactcctttcccctccccattcccgttcccatcctctggactggtttctcctcacgattgacca gcagctgggagctgttaccagacgttggacagtaagtcccggatgcactatagggctggtggcta gtgcttggtaagcactcaacgccatacctaatgtgtacctcggcttgccctcctggtcgtggtgacc ggctgtttctcttcccttggctcCagacgggctggtgtcctaccaccaccgttgcatgcagacctcc ccctgcgcactcgaacgccctgtcccagcagggttagtatgtgctgtgcagatctgcatgtgacac cccatccactggtagagcaggaagttgccctagctaacgcggcaagtattactttccgctacacgt ccttgagattcctcggacctctggaactagggtgactgtgggcttgggaaaacccaccttggtcctg tactgcctgatagggtcgcggctggccgaccagtggatgtagccagttgttttgggat |
| 424 | Rosavirus C NFSM6F | cagggagatctccatgaataatcttttccaccctctttagcgtctatgctattgaggacgggttggag ccccgttgacccagcgtcagagtgtgtcggtagcaggctttctgctctcgccccatgccggccaca cctcccattagtgatgtgaaggttgtaagttacatgtgaaaaggtttctaataattgagctgaatgtag cgattacctaaggtgagcggattcccccacgtggtaacacgtgcctctcaggccaaaagccaagg tgttaaaagcaccccttaggtaggccactaccccgtggcctcagttctcttagaagattcacttagta |

TABLE 17-continued

IRES sequences.

| SEQ ID NO | IRES | Sequence |
|---|---|---|
| | | gtgtgtgcactggcaactcttaagcagagctagtgagtgggctaaggatgccctgaaggtacccg<br>caggtaacgttaagacactgtggatctgatcaggggctcgagtgctgaagctttacagaggtagct<br>cgagttaaaaaacgtctatgcccctcccccacgggagtgggggttcccccacaccaattttagatt<br>gcact |
| 425 | Rosavirus 2<br>GA7403 | ccaggcatggcgttaaacatgcattcccttcccctagtaacctcccttcgccccttccccacgttgta<br>ccccctccgagatggctgctaaggcgcttgctgctacagcagtctcgtgtttcgggtgttataagtg<br>ctttcttttccactccactccctgcctatggggagcggaacggccttgtctcggtcgttgcttcttgca<br>gatcttcacccctccaggctttctggactcgccaggggtggagtagtaggcgcactgtctaagtga<br>aggtagcagtgttgttggcgaagagttgtggacctactttgagtttgtagcgatcatccagagctag<br>cggatctccccacgcggtaacgcgtgcctctaggcccaaaaggcacggtgttcacagcaccccttt<br>ggatggcgggggtgcccccctccgcacttaaagtagaaaaacagcttagtagtcaaataacatgg<br>ctttcctcaagcattcagtgctacatgggactgaaggatgcccagaaggtacccgcaggcaacga<br>taagctcactgtggatctgatctggggccctgggccaggtgctatacacctggttaaaaccaaatct<br>ggtagtcagggttaaaaaacgtctaagtcccacccccccggggacggggggttcccttaaaccct<br>caactgacacc |
| 426 | Rhimavirus A | cgaattccggacatctcctttcgggggcgagcgtcaccgtgcccctcatggaggcaactgtgcctc<br>taatcggtgacccactgagaaaattttctttctacgtggctaaacaatgcaactttataataacacaaa<br>tttaatgcttaatcttaacaccaaagatttgaacatatgtttggaaagtggcacacttcaaacattgcat<br>agttgctaggggtgaagtccctttaaggggttgcagaggatctttcctctttatgagcggctaggagt<br>atcttcttgatattatgtggtcgtgcaactcacttcccagatgtatgacggtgtactaagcgattggaa<br>ctagtcataacctctttgaattttggtattgcgagtctagcaggggggatatttaccgctaaagggtgac<br>acactcgtgagggtggcctttggtgtgtgtatatttattccgcccatcttgcatggggtgctaaaattct<br>aatgctgtgaaataaccattttctgaatacattctctacatttggagtcaaatatgaggaatgccactca<br>ggtacccttgacatgatcttggatctgagagtgggctaattatctaattatttggcgactttctaaaatct<br>tctgtttttagtggtgacaatttatggttataaa |
| 427 | Rafivirus<br>LPXYC222841 | gtgtccgggaagcgactcaagcttttgactgagtctctacaccttcatccgtaacatctttaagtttatg<br>tgcctatggacctctagtgcactgccatcaccgggggtgtattggactggtttttccacaatccattca<br>tcctgaggaattttggctttgttactaggatggtcccaccacacgcttatctgtgcctattgtgtcaacc<br>atgttcttaagtagttgtgcccgtgggtgagtagataaccacaacaatccgataaagcatctcgcaa<br>ggatgtgagtaatggagtgtatgtgctacagagacccacaacctgaaccaagagagacacagtg<br>aggattgtaaagggggaactctttgaaagggcatgtcccgcaattcctactgactgacaccgggg<br>gttggtgtcggtggattttagcaaatcctgttactgggtgatagccttgtgcacttcacttggttcttgta<br>taagtgctgta |
| 428 | Rafivirus<br>WHWGGF74766 | tgcgaatttattcgcacagtctcttttccccatcttgtgtgtgtgatggggtaagccgcagagtaata<br>cctactctgctgcaaacacactcactctttttctatctactttatatcatgtaataataagtagggaacata<br>ttcaattcatattgttcatctcactgaacccgcatgaaggactgcattgcatatcctggacgaagtgac<br>gtggaatatttggacatttatggattggacaccattacgctttgtgcctctacggagatgtaaccataa<br>tcttaagtagtagtaccccagcacaagaggataaagtggcatacacgacaacgggtgttgctcgc<br>accttagtaatgtggatgttcaccccttggagcgtgctgaaactctgtgggtaaagacacacattagta<br>caaatgtggggggaactcactgaaagggcatgtcccgtgtactggtgtgccggaaagtgggggtc<br>gctttctggagaacttagtagttcttgttattgggtgatagccttgcggcggatcaactcacagttttaa<br>tccgttgttttgcat |
| 429 | Poecivirus<br>BCCH-449 | actacacaatcgcaacacgcgcaagtttgtagtttgattggcgtgcaaatgtcaaatcaagcatata<br>acacaatttggtggctgttggtgtttgttataggaattttggttgtgttgaaattgtggatgtgtaggaaa<br>tatgcacaattacgtcagcgtcaggagttttataacctggcgcaacaccaaaatggtcttcgcgcttt<br>aacatcaccagcgaggtgtaaacaaattgaagttgaattagatcgtgtataggccagggaaccatc<br>cctcccaacgccacatcttgtggggaagttgggataatggtgggtctatatgaattggtctgtagac<br>ccacagtgaagagtgaatagtatgcttgcggttccatttgttaatggtctagcatgggtgggggcgg<br>caaccccgtgaggggttccccactggccaaaagcccaggggttagtcatttcaaccaaggaagct<br>ggtaacctggtgacctgaacttgagtggtgagaccccttgctagagtgtgtaaaccgattgtaagc<br>attttgtttgcttagtatctgtggtataagcagtcaattttgtataggctcaaggctgtggtagttagtag<br>atgcccggaaggttattactgatccggggaccgtgactatacattaggtaaaccggtttaaaaacc |
| 430 | Megirivirus A<br>LY | ttcgggacactggatgggcgacttggtggggctgccactctatcttgacctttcgttactgactttcg<br>gatctctgactcctccttgtctcttgcgtttggtccacggacggactaattggaatgtttactggctaag<br>cctcgttctgaaataccctagccaatgggttgtagtaggatcctggtgtttccattaaacctcttccga<br>ccatagtagctagagttatggctgtgtaggatgtgggtaagaccgcttttgcgtatctcccacaaga<br>caccggattatggatgtgtccgctggataaggctcgaaacctcccaactgaaggtggtgctgaaat<br>attgcaagcctaggttgtgtagaggcaagtagatgcctgccgcgacattcgtcttccgcccttttgg<br>gttagtagtgtacctacatggacgtggggctgggaatccccaccttgcataacactggttgatagac<br>ctgcggctggtcaagttactatggtataaccagttgaaatggct |
| 431 | Megirivirus E | gcttggcaacctcatatcgttactctgccgaccagtctgggtcgtgtggccacacaatgggattcgtt<br>ctgttgtgtagagtcacatggcattactgggctgatcggtggggatccgttgccacccctaaaccct<br>tacatttactggactgcttttcttggccccggaatgattcgctcacccgcgatgaggactgttgttctta<br>ttatggcaggattacgcgtctggtccgcgtaaggactaattcctatgtttatacgttactaccttgttct<br>gaacggtgggcgccacccccgcctagtaggatcctggcttatcgtgtagacctctagggaccacatt<br>agctagagtgtaggctgctatggatggagtagtgacccctttttgggtatcactctctaagactccgg<br>aatgtgtcatagtacgctggaaatccttacttgtttttccatgagggggaggtggtgctgaaatattgc<br>aagccacccctcggttaaaacagtttggtgccgcttatgccatattaccgccccttgtagttgggctg |

TABLE 17-continued

| IRES sequences. | | |
|---|---|---|
| SEQ ID NO | IRES | Sequence |
| | | tttttgcagctccgggttagtagagtaccatagtggacgcggtgttgggaatcaccgccttggctgc acactgcttgatagagctgcggctggtcaagctaattgtggtataaccagttgatttggcat |
| 432 | Megirivirus C | ttcccgaccggtctggcaaaccggacggttatcctggttagatgtctgatggttgctggaacgtggt ggctactgctgccaccttctggcttcctttaatgggcatctagctgggttctttgccacaatccatctta ctctcttacccatttctattacccagacttgttgttaactggtaaagttgacctactggcttcgttttgag actattctggtgttggtggacactctttccacaagtagattgtatggagttcatgctcgttttgaaccgg gaatggcacaacccgtagtaggatcttgcctctgccatactaatctgcgcctgttgcttttagactatg ggctgctaaggatgacattggaacccctttttggatattccatgtcaagtcaactgtttcatctggtgta cgctggaaatccttgttccgaggtcttgtctggaggtggtgctgaaatattgcaagccacaggcagt tccttggacttggtgccgctatcagatgctacaccctctatgggcaaatgttgaaccttagtggacgc gtgagatgggaatccacgccggccatagactggctgataagctcgcggctgatcgagttgcaaca gtaatcagttgatttgccact |
| 433 | Ludopivirus | tagaccccccacctagccctttttccccgtcagtggggggcttactcactgggcatctgttaatctggc ctaactagattgacaccactcccttggaacgtaactccacgctaactcactggctctacgcacagac acacggtctttctgctatccccggggaagataccagatggcgaccggctgtcccagcggcctagt agctactcgggttgagtacccaccacggttttgacgcctgctaaaattcaagagacagaggtaggg gtgcttagtgtgtggggggaagttcccacaagcgaggcaaagcattgctccctcgcgtcaccgggt gcaaggtaaattggctggacttccgctctacccttgctactcgccctcttcggagggttcgaagtga cactaggtatacgcatggttgggaaaccatgcctggcctactactgggtgatagcctggcggcgg gtccgtctcttggcttatacccgttgatttgggat |
| 434 | Livupivirus | tatctacatggggatccaggctgtatggaatgtctgtcttaacaagcactataccagaaagatccac ccaaagtggtgggactgggactgtgaggtgagaaatcccgaaaccagccttctcaagcgtcgga cgatctttctgttttagtgaacaccttgccttttaaatggatgacaacacccctcagcaaatcgcaatc tgaaatcccaaaagactgtttagccgaactctggtaatcactccggagaagtaggatacgcagccc ctgtggactcttgatttcaggactcaaggtagctagagctggaacttcatggaatgacaaaggaata tatgcacattgtgcgctttcctggccttgtagcccgtcgtgaggatatgtcgttgggaatcgacatctt agtccagtactgcttgatagagtgtcggctggcacagttacctgagaataagtcagttgtacttaaca tgaacaaaaaaaaataactaccacaactaccacaatctaccaatacttgaattatgctgaatctcgtac agtaaaaacgttccgtggaaggacaagtattgaagtgcggttacatcatccgatacgcgctggatc cctca |
| 435 | Aichivirus A FSS693 | cacccatacaccccccacccccttttctgtaactcaagtatgtgtgctcgtaatcttgactcccacgga atggatcgatccgctggagagaacaaactgctagatccacatcctccctccccttgggaggacctcgg tcctcccacatcctccctccagcctgacgtatcacaggctgtgtgaagccccgcgaaagctgctc acgtggcaattgtgggtcccccttcatcaagacaccaggtctttcctccttaaggctagccccgat gtgtgaattcacattgggcaactagtggtgtcactgtgcgctcccaatctcggccgcggagtgctgt tccccaagccaaacccctggcccttcactatgtgcctggcaagcatatctgagaaggtgttccgct gtggctgccagcctggtaacaggtgccccagtgtgcgtaaccttcttccgtctccggacggtagtg attggttaagatttggtgtaaggttcatgtgccaacgccctgtgcgggatgaaacctctactgcccta ggaatgccaggcaggtaccccaccttcgggtgggatctgagcctgggctaattgtctacgggtag tttcatttccaattcttttatgctggagtc |
| 436 | Aichivirus KVGH | tactccattcagcttcttcggaacctgttcggaggaattaaacgggcacccatactcccccccaccc ccctttttgtaactaagtatgtgtgctcgtgaccttgactcccacggaacggaccgatccgttggtgaa caaacagctaggtccacatcctcctttcccctgggagggtccccgccctcccacatccccccccca gcctgacgtgtcacaggctgtgtgaagccccgcgaaagctgctcacgtggcaattgtgggtccc cccttcatcaagacaccaggtctttcctccttaaggctagccccggcgtgtgaactcacgttgggca actagtggtgtcactgtgcgctcccaatctcggccgcggagtgctgttccccaagccaaacccctg gcccttcactatgtgcctggcaagcacacctgagaaggtgttccgctgtggctgccagcctggtaa caggtgccccagtgtgcgtaaccttcttccgtcttcggacggtggtgattggttaagatttggtgtaa ggttcatgtgccaacgccctgtgcgggatgaaacctctactgccctaggaatgccaggcaggtac cccaccttcgggtgggatctgagcctgggctaattgtctacgggtggtttcatttccaattctttcatgt cggagtc |
| 437 | Aichivirus DV | tactccattcagcttcttcggaacctgttcggaggaattaaacgggcacccatacaccccccaccccc ttttctgcaacttaagtatgtgtgctcgtaatcttgactcccacggaacggatcgatccgctggagaa caaactgctagatccacatcctcccttccccctgggaggaccccggtcctcccacatcctcccccca gcctgacgtaacacaggctgtgtgaagtccccgcgaaagctgctcacgtggcaattgtgggtccc cccttcaccaagacaccaggtctttcctccttaaggctagccccgatgtgtgaattcacattgggca actagtggtgtcactgtgcgctcccaatctcggccgcggagtgctgttccccaagccaaacccctg gcccttcactatgtgcctggcaagcatatctgagaaggtgttccgctgtggctgccagcctggtaac aggtgccccagtgtgcgtaaccttcttccgtctccggacggtagtgattggttaagatttggtgtaag gttcatgtgccaacgccctgtgcgggatgaaacctctactgccctaggaatgccaggcaggtacc ccaccttcgggtgggatctgagcctgggctaattgtctacgggtagtttcatttccaattcttttatgtc ggagtc |
| 438 | Murine Kobuvirus 1 | gtaacttcaagtgtgtgtgctcgtaatcttgactcctgccggaatgccgcccggttcagtgaacaaa cagctaggcaagtccctcccttcccctgtggtcggttctcaccggccaccatccctcccccagcct gacgtgttacaggctgtgcaaagcccccgcgaaagctgctcacgtggcaattgtgggtcccccctt tgtcaagacaccgagtctttctcccttaaggctagcccggtcccacgaacgtggaactggcaacta gtggtgtcactacacgcctccgacctcggacgcggagtgctgttccccaagctgtaaccctgacc caagactgtgctgcctggcaagcaccgtctgggaagatgttccgctgtggctgccaaacctggta acaggtgccccagtgtgtgtagtcttcctccagtctccggactggcagtcttgtgtaaagatgcagt |

TABLE 17-continued

| IRES sequences. | | |
|---|---|---|
| SEQ ID NO | IRES | Sequence |
| | | gtaaggttcaagtgccaaatccctggaaggagtgaccctctactgccctaggaatgctgtgcaggt acccccaacttcggttggggatctgagcacaggctaattgtctacgggtagtttcatttcccatcctct ctttttggcatc |
| 439 | Porcine Kobuvirus K-30 | tttgaaaaggggggtgggggggcctcggcccccctcaccctcttttccggtggccacccgcccggg ccaccgttactccactccactccttcgggactggtttggaggaacataacagggcttcccatccctg tttacccttactccactcacccctccccttgaccaaccctatccacaccccactgactgactcctttgg atcttgacctcggaatgcctacttgacctcccacttgcctctccctttttcggattgccggtggtgcctg gcggaaaaagcacaagtgtgttgttggctaccaaactcctacccgacaaaggtgcgtgtccgcgt gctgagtaatgggataggagatgccaataacaggctcgcccatgagtagagcatggactgcggt gcatgtgacttcggtcaccaggggcatagcattgctcacccctgaatcaagtcatcgagatttctct gacctctgaagtgcactgtggttgcgtggctgggaatccacgcttgaccatgtactgcttgatagag tcgcggctggccgactcatgggttaaagtcagttgacaagacac |
| 440 | Porcine Kobuvirus XX | ccaccgttacttcactccactccctcgggactggtttggaggagcataacagggcttcccatccctg ttcaccctcaataccacccacccctttccctcaaccatccctatccacaccccactgactgattcccttg gattttgacctcagaacgcctacttgacctcccacttgcctttcccttctcggattgccggtggtgcct ggcggaaaaagcacaagtgtgttgcaggctaccaaactcctacccgacaaaggtacgtgtccgc gtgctgagtaatgggataggagatgcctacaacaggctcgcccatgagtagagcatggactgcg gtgcatgtgacttcggtcaccacgggcatagcattgctcacccgtgaatcaagtcattgagattcct ctgacctctgaagtgcactgtggttgcgtggctgggaatccacgcttgaccatgtactgcttgatag agtcgcggctggccgactcatgggttaaagtcagttgataagacac |
| 441 | Caprine Kobuvirus 12Q108 | gggggtgggggggggcctcggcccccctcaccctcttttccggtggccacgcccgggccaccgat acttcccttcactccttcgggactgttggggaggaacacaacagggctcccctgttttcccattcctt ccccctttttcccaaccccaaccgccgtatctggtggcggcaagacacacgggtctttccctctaaa gcacaattgtgtgtgtgtcccaggtcctcctgcgtacggtgcgggagtgctcccacccaactgttgt aagcctgtccaacgcgtcgtcctggcaagactatgacgtcgcatgttccgctgcggatgccgacc gggtaaccggttccccagtgtgtgtagtgcgatcttccaggtcctcctggttggcgttgtccagaaa ctgcttcaggtaagtggggtgtgcccaatccctacaaaggttgattctttcaccaccttaggaatgct ccggaggtaccccagcaacagctgggatctgaccggaggctaattgtctacgggtggtgtttcctt tttcttttcacacaactctactgctgacaactcactgactatccacttgctctcttgtgcctttctgctctg gttcaagttccttgattgtttttgactgcttttcactgcttttcttctcacaatccttgctcagttcaaagtc |
| 442 | Rabbit Kobuvirus | gggctataaatatgggcattcctcttccccccttcccctttttgaagatgagtgcgcatattcttgactccg cctggattggccgcccaaggcgtgaacaagcagctaggccaccatgacactgcggtggtgtccg aacccgcgggtgccttcacgggcacctgtggtatgtaggactcccaccgtggtcttcccctttccccc tcaatctttccccctggttcgactaacgggaccagtgctggaacctgtccggtgaacggtatagca ggcccccccggcagaaacacccggtgcttaccccttaaggctagccccccttccatgaatttggttg gggcaactagtgggtgtacagttggcgtgaaccctccggtctaggagtgctcttgcccaatcctct gtgtgtgccttgcagtagggactggcaatccttcgcgtaggtgatccgctgtgccatgccatcctgg cgacaggaggcccagtgtgcgcaacctacgtcccttctgggtgctgcattgcattacctttggagta agcttggtgtgccgaaaccccagggtttacgtaccactcgtggtgtgaggaatgtgccgcaggtac cccatccttgaggtgggatctgagcggtagctaattgtctagcaccactttcttccttttttctttgctgg tcacg |
| 443 | Aalivirus | ttgaaagggggtgctcagggtagctccctgagctcttccctccaccctctttcaacgtctggcccac gatacgggccacctttcaatcttaactaactatcccttaatctatttggatttctggtttagaataatttg gaacacataattggattatcttttaggattgtggataggatttgttcgggatatcactcccttcctgtgct aacacatattctaattccctcctttgtctattatctcttggaggtggtgctgaaatattgcaagccacttg agtgtatagatgaagtaggctcaagatgaatgttgtgttactcaaggcaagtgtagctatcactaaga tattggtaacgtgaaacggattaccggtagtagcgtgatcttccgtcttagtgctctagtgactagag gacaacgacatggcatcacatatcttaaccctccagttttggcatccgggacagaatgggctggat atccgctttctttctggggtatgtgatgggtggtattggggtaaccaccttgaccatgacgctcgata agagtgaccgcctgatcattgaaacctctagtataaaattcaggctgaaatc |
| 444 | Grusopivirus A | tgcctgagtaggattgtgaatttaggtatgagagggttagccaacccattctgaaccataatagatac gtcaatctgaatccatctaaatctatctcttaggcagtggtgctgaaatattgcaagctactagggata gacgtgatctgattcaagaacctatctaatgtggtgatgagaaggctaggtttatccatagtaatccct tgttctgaacaggcaatgcacatgctctagtaggatctcgggctctgcgattggctctaaaccgacc aatccaggtagaggcactaagtgtaggacttgccaaaatgtattacatgctggtaccgactcactag tctggaaactccacactgaaagtgactgggggggcccccatcacatttgtgctactgcttgataga gttgcggctggtcaacttggattggtataaccagttgaa |
| 445 | Grusopivirus B | gccatccgtaggttctggtaaggttccatcaactgttggggcgctagttgctatgaccgcattcacg gacggatgatttatagtatcacccaatccgggcacaacttctttagccacttcttccacattactaagg gctctcttgccgagtttcaacgtctagtccacgacacggaccttcctactttctatcttcttatttctct actaaattggtatctggtactgaagatatgcggattgtgattttgtgcctgtctaaactaaccctattcta gggttaggtgggtaccatatactaatggtgaacaggattacctatgtatccattagtccctatggatct ggcgacccacaaactcatgttcatagagaggctaagctgagtgctcgccgaataagcattgcttca ggtgccgactattgtctggaaaccactcagtgatagctataggggggggccccgtagcatctgcct tactgcctgatagggtggcggctggtccatgaacatgcagtaaccagttgacttgac |
| 446 | Yancheng osbecks grenadier | ccttagggtctggaatgcgtcctttctgggcacttccacaatcctaaggtaattttcaacgccagcga tggagcgatatccaaagaacctttatgttttagttcgtcttgtatgtttataaaatataaaattgggatta |

TABLE 17-continued

IRES sequences.

| SEQ ID NO | IRES | Sequence |
|---|---|---|
| | anchovy picornavirus | gcaacccacaaaaacatttttgttattctcaccacatgagagggtggttaaacctcttcgtaacctatc<br>ttgcttgattggctacttgggctagatttaggacaacctctttagcaagcctaaattactcctcgtactt<br>gcacctggtaacaggcgtacctggaggttacggtggcgctaacttggacttctcgttaattcgtgca<br>agtttaaatgatgcctattttgaatacaagaaagtatgatagtaacttagggcgtgaagttccgcttaa<br>cataaggcagtataagtactaagataaggtgtaagacctaccttaataactgttgtcttttctcatggtc<br>tttccgtgggagcccttgctaggggtaaagttaagtattctcaaataatttttcattcaaactctttctctc<br>tgtttt |
| 447 | Turkey Gallivirus M176 | ccactcgcacttcctggatagtgcgttagatatgcccgacatatcgcttccaggaccaaagccccc<br>cttttctctttcccaaccagcttcgccactcaagctgtaattccatgtccggtctttccggccttagtatc<br>atggaaatgtggtcgtgctcaaatgaaattgagttgacattgatcaatgaaagttgcactgaactttg<br>ctaaactggctagcgccacctggtgtgtgccgttggtctcctcacatggtaacatgtgccaacggg<br>cccgaaaggctagtgggcaattaccgctccaagggaggggtacccaccccgacctgaacagcg<br>gtaatgaagctcacctcccaggctctgaccccgagaagtttagttatttagtaggtgtaattagtactt<br>gtgattggtcaatttgatagtagtttgaaacgttatggatgaatgagtagacccccctgaaggtacccc<br>attacatgggatctgatcagggccacattctgcgtgtctccccgcacttgtggttaaaaccatgaaa<br>gttcatcccaaacaatcttttcctcttctttttcttttagtggtgacaacctactggattggtgattaccaat<br>ctgtactagtgttgtattaagacttgttgtgtggagaaaatggactctttcaagaagatttttg |
| 448 | Falcovirus A1 | taaaaggggacgcggtgtggcagctttggctgtcatgccgtgttctccttttaccccaaggactagc<br>cttggggttttccaaattcctttccctgtaggctttacttctctttatctatcttttctgtaactaagttttgc<br>ctattctaaaaatatttagaatgtgtttggatgtaactaagtttgtgcctgccctaaaaatattttagggc<br>ttgtttggataacctcgtcccttgtgttcagtgccgcacaatttgctaggcactgttcacttcctttgtttg<br>tccattatgtatgctaaggtatgaattccatcatatgcttagcctctacatgcataatcttattccctccct<br>ggtgcaaactacgcccccaacatatgtgaatcttttaagcatattcctgaccccacacatatatatgtg<br>ttctcgtgaattcccccaccgtgaggtggtcacttggacgtggtgtgtgtcacacagcatatatatga<br>tgcaggatgttgtttttaagataagcatatgtccttagtgctttgcatcatttcctccacaccccgtgaat<br>gcggctaatcttaaccctgttgggtccgtgggtaaaccaacccattaaccacaggacggaaccga<br>ctactttcgggagtgtgtgtttctttttcttcttttgtcact |
| 449 | Tremovirus B | ttcaaatggcccctgggttgatacccagtggtcatttggacactttggtaaggaggtgtaattatcctt<br>cccatgtggaacctagtgcttaggtttactttatatgttctttgtttgtcctttgtactttctatcgggcaat<br>cttgttgttcaatacaatatgtatttgaactgcctaagataaattcagttttcaaccaacccctctcttgg<br>ggttgtgtctttctttctttcttatatcctcttaagctgacttacttgctaatccgactcctcgtcaacggg<br>agggtaaagcagtatcactagggtattgtgatgtaggagaaaaagtaagtagagatagtgcatgta<br>acgaaagtgacttggtactttaaactctcttaatcccaaagtgtggtattggtcatgttggagtaggct<br>acgggtgaaactccttcacatttagtaatgtgttcacacgctaacgctacggtagatgacagactag<br>gtcttattctcaacgtaggggggacgggtgtatgttcatgattagccacatattaaggttttgaggggct<br>gagtcatataagtatgtgcattaatttctggtactggtccctggggactggcccttttctaggttgatttt<br>agtttccccaatttttaaaaactaatgagatttacgac |
| 450 | Didelphis aurita HAV | tctttggtctggggaactaaaataccagacccgcgtttgcctagcgatataggctttaattgttgtttgt<br>cattgtgcgtttgatatgtgttttaatgtaaataataattctagcaggttctagttcttgatcatgtcctcttt<br>aaggcactcatttcaacttgctatctttcttttcttccttggttctccctacaccaaatgcactggccgct<br>gcgcccggcggggtcaaccacatgattagcatgtggctgtaggtgttgaaggctgggacatgaac<br>atcaatggaatagtgcgcatgcttactggggtccattgaagtagtgggatctttctattggggtaggc<br>tacgggtgaaacccccttaggttaatactcatattgagagataccttggataggttaactgtgctggat<br>atggttgagtttaacgacaaaaagccatcaacagctgtggacagaacctcatccttagattgctcac<br>tatggatatgtgctctgggcgtgtttcttgcatgatggccattggtcaattcatgcctgggccaatgta<br>ggattagccttaaattacttttttaaaagtagcctcatttagctggactaatggtggggcgtatgatcctg<br>catttggcctctggggtaatcaggggcatttaggtttccacataatagcaaat |
| 451 | Hepatovirus G1 | gcaaggggtggttttaaccttgcacgcgtttaccgtgcgttaacggttttccatgtttgtatgtcttgttt<br>gtattatgtgttttgtaaatattaattcctgcaggttcagggttctttaatcatgttgggctgtacccacac<br>tcaacttttggccataagtgagtttcttaacgaaccttttaacacaggatgttattagggcccaatatttt<br>ccctgaggccttctttggcctctatttttttcccctttttctatctccttgtattccgggctcacgtgatgcca<br>atggactgacccatgcgcccgtgggggttaactactggagtagccagtagctgtaggtgctaaaa<br>gtcacgtacgtgtaagactggacgagacctctcagctataactgaaagtagtaagtatgtctgaact<br>tcttgaaggggtaggctacgggtgaaacccccttaggttaatactcatattgagagatacctctgatag<br>gtgaaggtttccggtagaggtgagtttaacgacaaagcctctcaacggatgtgggcccacctcatc<br>agcaagatgctttcatacccaataccgtaggggctgggttgttgagttcagtcccaagcgtccctcc<br>cgcaaggttgtaggggtactcaggggcatttaggtttccacaattaaacaaataca |
| 452 | Hepatovirus D | ctttggatgcccatagtgcgggggtataaataccgcactccctttagctgttccgagggtatcggaa<br>cctatatgtttgttttctgtctgtctgtcagctttatgtgtgctcgtcccctttagggcactcatttcagctt<br>gctttcattcttttcttccccggttctcaccttaccggaggcactggccgttgcgcccggcggggtca<br>acctagtgattagcactaggctgtaggtgtctaaagtggtgacattaagacttggtaactgatttcag<br>cactgttaactgatgttggggatgacttgattgatcttctggaaggggtaggctacgggtgaaaccc<br>cttatcttaataccactatgtagagatagattcagtaggttaagggcagtggataaggttgagttcattt<br>tggacaataaaccttcaacactggtggacccaatctcactgaccagatgctttcttgactgatccttc<br>agaggggtgattcttctgaataggttgccttgacactgatgcctgagacccattgggtcgggcctta<br>aatcatggaactccactggactttcatggcctagcttctgccttagacagactctggggccccacga<br>ccctctgggcccttcggggtactcaggggcatttaggtttttccacaattaaaagagtta |

TABLE 17-continued

IRES sequences.

| SEQ ID NO | IRES | Sequence |
|---|---|---|
| 453 | Hepatovirus H2 | gtcatgtttctctttaagaacactcaattttggccataagtgagactcttgtcgaacctttcatgtcagg<br>accatgttagggccattatccttttccctggggcattcttcttgcccctgtttcatctttctatcatctttctt<br>ccgggctctcacaatgccaatggagcgaccgatgcgcacgtcggggttaacccatggattagcc<br>atgggctgtagctgctaaaagttgtgactcctgaagcatactatcaatggtagtagatgtaactgaaa<br>cactgaagcttctctgatcttgaaagaagggtaggctacgggtgaaacccttcaggttaatactcat<br>attgagagatacctttggtaggttaacgttggcggataatgttgagtttaacgacaataaacattcaac<br>gcctgtgggcgaacctcaccaatttcatgctttgaagtgaatgtgcgtagggtctctatcggagatg<br>ctatgtggatggtgccctccctggaaacaggttgtaggggtactcaggtgcacttaggtttccacatt<br>ttaaagatttttc |
| 454 | Hepatovirus I | ggctgcctgtgtctcaggggtaagtactggggccgcgttgaccgtgcggtacggttatgcttttaga<br>ttaggatgtccgtctgtccggcactctcttttgcttaaaatggccttaaatccatgggaggcgtaacca<br>tgggccctttgttacctagacatgattgcattgggggccgtccttggggcttaggccccagccatttc<br>tcttgactcgtctaagagtttacttcatccttttctttactttattttccaggctctcagcatgccgacggct<br>ctgaccactgcgcccggtggggttaactgcatgattagcatgcagctgtaggagttaaaagtgctg<br>acaggccaattctgacgtaagtccactctatattaacttgatcaagtaaggttgattgatctttgtgaga<br>gggtaggctacgggtgaaaccctctaggttaatactcatattgagagatacctccagaaggtgaag<br>gttggcggatattggtgagttcttttaggacaaaaacctttcaacgcctgtgggcccacctcactggc<br>acaatgctttcatccccaattgtgatgggtagtttggactgaaatcaggagtaacctgccctacgagt<br>ttaggggtagttcaggggtatttaggcttccacatttgatagagtttatgagagtgagcc |
| 455 | Hepatovirus C | ttcaaaagccccagcggggtttcattaccccgctgtggcttttggacttccctaggatggggaagta<br>aattaccatcctcgcgtttgccgtgcgttaacggctactttcttctagctgtagaagtaaaattcagca<br>tgttttatgtttgtttgtcttgtttgttatatacattttacactcctacaaatgcacatgaagaacagtttgt<br>agagattaacaaacgcttagctgaacctaggtggtgaatctagtagtaagataagtagaggaagct<br>ataccttaagttggttgggccctcgtgtttgctctataaacaaaaccaagtgagtagagtggatgaac<br>agtactaaatccctgagtacagggaacctcacaggtgtgatacacttatgtctatgtgacctggttgg<br>aggttgggcgtgccctatgatactggagtgggagatcttttggggaacccacgttttcacactgcct<br>gatagggtcttgccgagagactcacttgtttcggctgtacttgtaac |
| 456 | Fipivirus A | tgcgggtaaactcccgcatgtgtgaatgaggcgatgtcccaggaactaactgccgatcctggtttta<br>actacgatccgtatttgttactaatgcgatatcccccattgtttgcctccatgttgttttcaacgcttttg<br>gccttgagtgttatcaagtgttttagcgacatagtgggaagctacggctgcgtccccatttttgagtg<br>gcgacccagttttagtggccactctgtccctgaactgcgctataatgtgaatttatgttcacaaaaac<br>ggactgatgtaactgttaatgactaaggaatagtacctcactgaagtatcaagaccccgttcgagcg<br>gtgtacatatatggatggaaaccttgtctgagtcatctcgaatactaatcaatgagggatgtcgagta<br>agcatatcatgaaccacatagaatagtggggtttcggggttagaggctctctgcagcaatgtatctct<br>aacaccatggccgaaatgagagatagagaccacgatgtttgtgtgtaagtaatgatgtgtggaaag<br>aaaattctgaatgttggtatgatatcagtctaaggggagtggctcacctaagagctacccaaacattt<br>cacagcagacaacataacgtactgagagtagttggaaggttccagaaatcagt |
| 457 | Fipivirus C | cgcggttaaacccgcgcaaccttctttcagccgcgtctgagtagcgcggttagtcctgatacacagt<br>ttcctgttgggtactgtgtcttcgggtgaatgctcttgtgtgaatgttttaggctgtttaagggaagcgtt<br>tccccgtgcgctgtgagggtttctcacgctctttcggggtgcagtctcttctgttgttcattaagatgta<br>tggatgcactgttgtgaaggatttgtgaactggggatcgacaccccgtgaggggtgccccagtgtc<br>cataggagtttgctggagaggtgtgttgctgtagtgactatccgtgacctggcattctaaggtgttga<br>ccccaacctgtgagggtctggatcgcagtgttgaagtgctttggagggttcaatggggtttctgtagt<br>ggatattatgtgcttgacgactactggtacgagtgtattgggggtctacatgtgtga |
| 458 | Fipivirus E | ctcttccgatcttgggggttcgcccccatgtctcatttcaactagccgtgtgtctagttaacgcaccgc<br>ctcaccctggtcgttatcgggtcggttcttgcgaccgttagatcgtgagcgtttctgaggatcagttc<br>gtataagttctccggtgtggcgaccgtaaaatcgtcacgtcccatgcaatagatgacgttaaactcg<br>tttgccagttacataaaggaatgttgttacttttaaattgtctgttacatttaacatcttgccagtatgatg<br>ctactgtacactacgggtgtaggaaccttgtagtgtgacgtatcactcatatgtggatgggtgctcca<br>gacctttatggaagctctcagttagtagtgatccttgacttcattgagccctggtaacagtggaagtc<br>aagatgtatatgttgctcaacacacttcggtgctacgaagctgtttgtggaagtactggcgaggttca<br>ttctgaatcatatgtttgtcacatagtcagggagtgccgtcgcttacgacggacccttttttctttataatt<br>acaaatctgtgtctcaagtgttgttggctggttttcttcttctgttttcattgttcatatatatacgtcagagt<br>gaaagactcggtatatacaaaactgatccaga |
| 459 | Aquamavirus | ttcaaaggtggcgggagagttggcctcacgctgtttagcgtgagagctggctctcctgccccttcc<br>cctgagccggggatcttggctcattcccctcttttctatcctccctcattggactttacggatgacccg<br>gcataaacttgacaaccgatgttggatttcccttgtggctgtgatggaggacataccctcgggtgta<br>gttgtgtgcgtgtcgctctgcgactcgagcttcaaagtggtgctgaaatattgcaagcgtcgttgctc<br>gattaacggagtggtacaatcctatgaacccaagtgcattcatgcgaaagccccggaggggtgag<br>tagcatggactcgaatcagaagagctggagctcgcttggtacggcacgtagcattgctttgcctaa<br>agaccaaggggggtatggctataggtgggggcctatagcttgtccagtgctggttgacagactcgtg<br>ctacgcgtctggttcgagtataagtagctgcaactcact |
| 460 | Avisivirus A | ttcactcgctttccccccctctctataggggcggtcttttaattcttattaatttcctactttactatcaaatt<br>tcttctaagtagggactgaggtcacttagccctccctctcctgggctttccagggttatagaggttcta<br>aagctaagccatgtgtcttgagctacacttagtacaaaggtttagtaatgattgtacatgccagtaac<br>cttctagtgcccatggattaaagagtggtaacactctccatggggcccgaaaggctagtgggcata<br>gttggcatcaaggaaggggtccccaccccaacctgaattgctggctagaagctcaccttagaaga<br>agtgctgggtgacaacgtgtccaatcgtgaacgactgatggaaacgtgtggagatggatatgtgg |

TABLE 17-continued

| IRES sequences. | | |
|---|---|---|
| SEQ ID NO | IRES | Sequence |
| | | gggttcactgagtagatgccctgaaggagaaatctgatcaggggcccgtgactatacgctaggta<br>aaccgggtataaaaaccatgaaaggtggcccaaaatctcttcctttttatttatttctatgttggtgaca<br>gtcaag |
| 461 | Avisivirus B | cacccccctactgccctaacccccaaagttagttatagggtggctccctacccttactccacggggta<br>agccctaacccggttgaatctcaagatcagccttagcgaggactattagtaccgctcaaaccctttg<br>cctgtagtgcccaggggtcacagaggggtgaccctctccctggggcccaaaaggctaggtggca<br>agacagggtccaagtgaggggctactctaagtagccccaagctgaacatcctgtctgaagccacc<br>cttgcagggccaggtttgattggggaaactagacaccagctttgtcctgggattgggggggatatcg<br>agttagtccaggaggtgcgagtagatgcccccgaaggtaccccaggcacatctgggatctgatcg<br>ggggcccgtgactatacaataggtaaaccgggttaaaaaacatgaaagcgcctctctctttcctact<br>tctttttattgactggtgacaaaaatagcagt |
| 462 | Crohivirus A | gttgaagtccatttcttgcttgcccccgatgaatcctgttaaggcctcacggccctaagggtgaaact<br>cggttatcccctcctgtacttcgagaagattagtacaacactatgaaatctacatcttgtgatccggga<br>taaccccaatcccagaaacctgtgatgggcgtcaccacccctcttatggtaacataagggtgtcgc<br>cgcgttggcacaggaccctttgggctggatgtttttagtaatggtgtcgaaggtcctattgagctaca<br>ggagtttcctccgccctggtgaatgcggctaatcttatccctgagcctaaggttgcgatccagcaac<br>ttgatggtcgtaatgcgtaagttgggggcggaaccgactactttccagaaggcgtgtttctttgttttg<br>tctgttactatggtgcatgatatagatattgaatatttgatctttttgagctgtttcttatcttattgctacatc<br>ctttcaggtgttggatttacattttggttaataag |
| 463 | Kunsagivirus B | gattttctggttatccctttttggacttggtaggggcccacgtgcccacccacctctgtgtgtgttgattt<br>ctaatcgatgcctggcagtggcggccacctctccttactggtaaacctccggtgagtgaagttgtca<br>agctacaggtaccgtgcaggatgaaatgcgcacatgtgaacaaactaggagtcatacaccgggtc<br>aaactctggaaacggagtccgggactctgaccttggttgggtgagctcgaggcatcacattgatgg<br>acgcgattcgctatccttccctagtaggaccttgtggtgtacccctggttgggaatccagggctggt<br>cgggtgcagggtgacagcctgttctccacctcaaccattgtaggagaaatcaacccct |
| 464 | Limnipivirus A | ttctttggatatccatttaacgtgtaccctatacgataattggggtggattctggatgcctagttccagt<br>gattggttaagaactcgtttactacgtatagtatgattagcaaagtgctcgattgatcacgtaatgatct<br>atgtggttaaaaacccagtagtatggtatatactcagtagtgtacactgtgagtacaactcttggcgta<br>gagagaacaattcacccgaatccgtggcgtatccatggaaataagtttacctaattgtatgttacaag<br>gcatatgagacatttatgagatatggtttattttgactaaacgagtgtagaggtggtggagtctatcca<br>acttcaagccatgcaattgttgtgttgattgatatcattgaccatttttgtggattgtgtacacatacaatt<br>tgaaaattaacccccctcaagaataagacatgggaccattcgtggtagataccgtgctcggatgcttg<br>agattagatgggttagactagttttggaatgagattgccgagaaagtcccgctagacatgttttacaa<br>gtcgtggtattccgctagactttttcgcagacacatggaagggtccatgtgttgtgcaattgcagggt<br>gacagcccaactgcagagttttccttactagaataaaaatctgttgtcaatttt |
| 465 | Limnipivirus C | gtttctgagcactggtaagagcttagacaaacgtttttaaaatttattttctctgcaacttttgtttgtgttt<br>atttttatttgttaattttgcgcctaagcatttgttgcgaagtatttgattcattagtaatattacttattgttta<br>tttagatggtattcaaagtggtgggagtatcgaacccaagcgtcgtatgctatctccttgaacaattttt<br>aatcattgcgaagtgatcattgaaaaggataggtgtttaagaactcaaagagtgttaataatgttggg<br>tgacaggtgtccccatagaatttattaacatgatttggactggttatctagtaagaagaaccatcgaa<br>cgcacgagcgagcattgcttgcggggcagttaccctgcgtcgatgtaagtgtgtaccggggggtg<br>cacatgttgattctttatggcctgatagggtgcgtcattcgcgcctagataattagtataatgcgaatg<br>gaataaatttac |
| 466 | Orivirus | ggtcccaggccaatattcttcgtaaggcttggttccaattttccaccactcgtgtttgggttctggccta<br>tggtacccagaggggcggtttgggggaattaactccccctcccctgtggtcctataccaccccaca<br>cctctgtgggctttctttactatcttcttgttttccgacttttaaacactaggcaggcgcgcctagtcata<br>caccgcccggctggtctttccagctcttgtgggcggtgcgcgctggtccatcgtgcccagcgacat<br>agcaccttgtggacacctccgaacgccctcccctgtatggggtggtgcccaggggtttcagtgtgg<br>tgacacactccctggggcccgaaaggctagtgtgcaacaggtgaggtacagccagctgcccccg<br>tggctggagggaccaagcttgtgaagcacacctcaccttcttgggggtgggctagtaagtggtga<br>aagcatagtgtccgtgtcgctggccaacactttgggtcaagtccagccactcagtgagtagatgcc<br>caggaggtacccctagtggatctgacttggggcctgttacttaatgcaggttaaaaactatgaaagc<br>tgagtagtgtagcccggctggtggcttctcttccttattcattctattttatggtgacaaacgcaactga<br>agcc |
| 467 | HAV FH1 | cttgatacctcaccgccgtttgcctaggctataggctaaatttccctttccctgtcctttccctatttcctt<br>ttgttttgtttgtaaatattaattcctgcaggttcagggttctttaatctgtttctctataagaacactcaatt<br>ttcacgctttctgtctcctttcttccagggctctccccttgccctaggctctggccgttgcgcccggcg<br>gggtcaactccatgattagcatggagctgtaggagtctaaattggggacgcagatgtttgggacgt<br>cgccttgcagtgttaacttggctttcatgaacctctttgatcttccacaaggggtaggctacgggtga<br>aacctcttaggctaatacttctatgaagagatgccttggatagggtaacagcggcggatattggtga<br>gttgttaagacaaaaaccattcaacgccgaaggactggctctcatccagtggatgcattgagggaa<br>ttgattgtcagggctgtctctaggtttaatctcagacctctctgtgcttagggcaaacactatttggcct<br>taaatgggatcctgtgagaggggtccctccattgacagctggactgttctttggggccttatgtggt<br>gtttgcctctgaggtactcaggggcatttaggtttttcctcattcttaaacaata |
| 468 | HAV HM175 | cgccgtttgcctaggctataggctaaattttccctttcccttttccctttcctattccctttgttttgcttgta<br>aatattgatttgtaaatattgattcctgcaggttcagggttcttaaatctgtttctctataagaacactcatt<br>tcacgctttctgtcttctttcttccagggctctccccttgccctaggctctggccgttgcgcccggcgg |

TABLE 17-continued

IRES sequences.

| SEQ ID NO | IRES | Sequence |
|---|---|---|
| | | ggtcaactccatgattagcatggagctgtaggagtctaaattggggacacagatgtttggaacgtca<br>ccttgcagtgttaacttggctttcatgaatctctttgatcttccacaaggggtaggctacgggtgaaac<br>ctcttaggctaatacttctatgaagagatgccttggatagggtaacagcggcggatattggtgagttg<br>ttaagacaaaaaccattcaacgccggaggactgactctcatccagtggatgcattgagtggattga<br>ctgtcggggctgtctttaggcttaattccagacctctctgtgcttggggcaaacatcatttggccttaa<br>atgggattctgtgagaggggatccctccattgccagctggactgttctttggggccttatgtggtgttt<br>gccgctgaggtactcaggggcatttaggtttttcctcattcttaaataata |
| 469 | Parechovirus F | ggtcggggagatgtgttcatgatcggttaacaccatcatggatcatctctccccgacctctttttgacc<br>cagctatgggttaaatagtacttttcttttctcttttgctttcttttgtgttttgtttgttttgcaacatataaca<br>agcattttatcagtattagtgtctgcaactgtataacaagcaaggtggagcaatcatgcgagtatatct<br>caattgaattgtgacacacaagtgtgcactatgtggaataaatgccattttggccaaacctggttagc<br>cagaccagtagtaggacaatttggcacccttagtgggcgcgacctagatgctagggatgagcaaa<br>cctatttcccctgagtacaggggctctccttcacctctacattttggacctctttttgagtatcctcgata<br>gaaggtgaagtgacggtgtaccggatggttaattgatctcattgctgggtgacagcccgctaggac<br>caggcagcatctttgtatggacctgtacatgtaac |
| 470 | Parechovirus D | acatggggcaggtgtgctgtgccaagagcaacactacggtggccgagccgatggttcgtcacca<br>cgtagtaggactccgtagtgcttggttacggcggacgtaagtcagttgagtgatgtctaagtggcaa<br>accatgagtacatggtaaccttgtgtggactcgcgggacggaatttcctatcccattgactccttgta<br>gcaaggtgggtatacccaaccacaatggcagcaccctgggtgggaacccaggggcctggatta<br>gtatccagtcacacagcctgatagggtggcggctcagccactgaccagcgtctctaaataattgtg<br>agctgttcatgcacc |
| 471 | Parechovirus C | cggtcatccccctttccccacagccggtgtgggttctaatcggctcctactaaacacctaagcatca<br>ctgcgcctctatctctcctatccacaggtctaagacgcttggaataagacatgtgggtgcaatagga<br>agattagctagtccaatctctccttccagctacgcttctcccttcgatgagcgtagggggggccccc<br>acctccctcatctctggatagggctcttgctacggggctttcccgtctggaccagcaggcccactg<br>gtgcgcttccattcaagtttagtgtgcattactgtctgaaatattgctttgctaggatctagtgtagcga<br>cctgcatattgccagcggacttccccacatggtaacatgtgcctctgggcccaaaaggcatgtcttt<br>gaccgtatgcagtacaaccccagtataggtcctttctatggcagtatggatctcagtgatgagtctat<br>acagaatatggaagtggttcggatatgtcagcccgaaggatgcccagaaggtacccgcagataa<br>ccttaagagactgtggatctgatctggggcccaccaccttcgggtgggtagaagctaaccatgcct<br>tgggttaaaaaacgtctaagggctgaccagacccgggggatccgggttttccctatcttgacctact<br>ctaatc |
| 472 | Ljungan Virus 87-012 | ctcattgcccacacctggttggttcccaggttcatacaataaccatcaataaacttttaacatctaagat<br>agtattatcccatactagactggacgaagccgcttggaataagtctagtcttatcttgtatgtgtcctg<br>cactgaacttgtttctgtctctggagtgctctacacttcagtaggggctgtacccgggcggtcccact<br>cttcacaggaatctgcacaggtggctttcacctctggacagtgcattccacacccgctccacggta<br>gaagatgatgtgtgtctttgcttgtgaaaagcttgtgaaaatcgtgtgtaggcgtagcggctacttga<br>gtgccagcggattaccccctagtggtaacactagcctctgggcccaaaaggcatgtcatttgaccac<br>tcaggtacacaaccccagtgatgcacacgcttagtaatggcttagtaacaaacattgattgatcattt<br>gaaagctgttaggaggtttaggtatgacgggctgaaggatgccctgaaggtacccataggtaacct<br>taagcgactatggatctgatcaggggcccaccatgtaacacatgggtagaagtcttcggaccttgg<br>gttaaaaaacgtctaggcccgccccccacagggatgtggggtttcccttataaccccaatattgtat<br>a |
| 473 | Parechovirus A2 | gccgtcgggccttacaccccgacttgctgagtttctctaggagagtccctttcccagccagaggtg<br>gctggtcaaacaataccaaacgtaactaaacatctaagataacatagccctatgcctggtctccacc<br>agttgaaggcatcttgcaataaaatgggtggattaagacgcttaaagcatggagtcaattatcttttct<br>aactagtgatcttcactgggtggcagatggcgtgccataactctattagtgggataccacgctcgtg<br>gatcttatgcccacacagccatcctctagtaagtttgcaaggtgtctgatgaggcgtgggaacttatt<br>ggaaataattacttgctgcgaagcatcctactgccagcggatcaacacctggtaacaggtgcccct<br>ggggccaaaagccacggtttaacagaccctttaggattggttaaaacctgagtaattatggaagata<br>cttagtacctaccaacttggtaacagtgcaaacactagttgtaaggcccacgaaggatgcccagaa<br>ggtacccgcaggtaacaagagacactgtggatctgatctggggccacctacctctatcctggtgag<br>gtggttaaaaaacgtctagtgggccaaacccagggggggatccctggtttccttattttagtgtaaatg<br>tcatt |
| 474 | Parechovirus A3 | agagtccttttcccagccagaggtggctggttaaataatacctactgtaacaaaacatctaagatgta<br>acaaccacacacctggtctccactggccgaaggcaactagcaataaggcaggtgggttcagacg<br>cttaaagtgtgttgtacatattcttttctaacctgtgttttacacagggtggcagatggcgtgccataac<br>tctaacagtgagataccacgcttgtggaccttatgctcacacagccatcctctagtaagtttgtaagat<br>gtctgatgacgtgtgggaacctgttggagataacagtttgctgcaaagcatcccactgccagcgga<br>tctacatctggtaacagatgcctctggggccaaaagccaaggtttaacagaccctttgggattggtt<br>caaacctgaactgttatggaagacatttagtacctgctgatttggtagtaatgcaaacactagttgtaa<br>ggcccacgaaggatgcccagaaggtacccgtaggtaacaagtggcactatggatctgatctggg<br>gccagctacctctatcttggtgagttggttaaaaaacgtctagtgggccaaacccagggggggatcc<br>tggtttctttttaatttaagtaatcact |
| 475 | Parechovirus A8 | gggccttataccccgacttgctgagtttctctaggagagtccctttcccagccctgaggcggctgga<br>taataaaggcctcacatgtaacaaacatctaagacaaaataatttgccttgcacctggtccccactag<br>ttgaaggcatctagcaataagatgagtggaacaaggacgcttaaagtgcaatgatagttatcttttct<br>aacccactatttatagtggggtggtggatggcgcaccataattctaatagtgagataccacgcttgtg |

TABLE 17-continued

IRES sequences.

| SEQ ID NO | IRES | Sequence |
|---|---|---|
| | | gaccttatgctcacacagccatcctctagtaagtttgtgagacgtctggtgacgtgtgggaacttact<br>ggaaacaatgctttgccgtaaggctttcattagccagcggaccaccacctggtaacaggtgcctct<br>ggggccaaaagccaaggtttaatagaccctaatggaatggttcaaacctggagcattgtggaaagt<br>acttagtacctgctgatctggtagtaatgcaaacactagttgtacggcccacgaaggatgcccaga<br>aggtacccgtaggtaacaagtgacactatggatctgatctggggccaactacctctatcttggtgag<br>ttggttaaaaaacgtctagtgggccaaacccagggggggatccctggtttccttttattttactttgtcaa<br>t |
| 476 | Parechovirus A17 | ctctattagtgagataccacgcttgtggaccttatgctcacacagccatcctctagtaagtttgtaaga<br>cgtctggtgacgtgtgggaacttgtgggaatcaatattttgctttaaagcatccattagccagcggat<br>aaaacacctggtaacaggtgcctctggggccaaaagccaaggtttaacagaccctagtggattgg<br>tttcaaaacctgaaatattgtggaacacactcagtacctactgatctggtagtaatgcaagcactagtt<br>gtaaggcccacgaaggatgcccagaaggtacctgtagggaacaagagacactatagatctgatct<br>ggggctggctacctctattttggtgagtcagttaaaaaacgtctagtgggccaaacccagggggga<br>ccctggtttccatttattttacaaaggcact |
| 477 | Potamipivirus A | cacatggaaagcttttcgcttccatgtttacgcacacactctctttgacaccctgttgtatggtgttaaa<br>ctacaacatttgtctgtctataatcgtttattttgtttaccctatatgtacccaagtatttgattgcttgactc<br>acataagcatcggtaacccatactgttttatgagctactacctctgctgtctacatacattttatatgaat<br>ggtttgagctctgcctcaggatcaaacatggtaacatgttcctttggtcagttagaatcttattgtataat<br>ctaaggtgtctattagtacgtagaaagttgtaacacatatggggcctgatagccgctatctctgatgg<br>atgtaaggtaaccttctttaggtctgatacattctgcacaggatccaattttcggtgccctgtacgagt<br>gcactcttatgcacgaggacgagatatgctacaacccactgcaaatttaaacccaaactttaaca |
| 478 | Potamipivirus B | tttcaacgtcgtggctgacgttaaaaagccacaattccacttaccttttaccttttatgtttaatgtttgtta<br>gttttgtgatctttaacaaatagatctaaataatttgttggtaaccaatctcggatgtttcggctgcattgt<br>agtttatttatttcattttagttgtaggtggccactacgtcctggaatcatacatggtaacatgtacctcg<br>gcggttatccactattacgctaatctaagaatatttaaatgaaaatgtaagtgttacggctgactttgg<br>gcctgatagttaaatgctcgcactgacagatagtaccctcctttaggatcgattctgttacatgggatc<br>cattttggtgccccactgattcaacctctttgttgaaaaagagttagcatactacaaattttccaaacaa<br>aaacccttttttaatgactacaacttatgattttatgaattttactgctcttgaaaaagatattttgacattga<br>tcgctgtactgtttcagacattcattgcatccattttttgttggctactcctcacaaactcaaaacttttcca<br>cacgagaaaccttgtttattgaattttgcctttatatttggaacttgttgttggatttattgtttgcttaatta<br>ttgacctcacacctgttttaaacactacaat |
| 479 | Beihai Conger Picornavirus | gggacaaccccacagctggtacaaccattgtgggttggtctccaccctttttcaaccgtggcaactt<br>cggttaaagttgcaaatccccccctctccctattccacctcccttactttcactccccatatatggtccca<br>gattttattctacctctttatatttttatttagtacagtggtggtgaattactcccagcataaactttgctgg<br>atcagtgttcatcaagcatactaattactaatgtactgagctatactattatctggcatctcacctggat<br>aaccggtgtgaccatatttcctaggttgcctccctatgtattttgtagcacctgtgcatctgcacgttgg<br>ggcgacaaattgtaggtttcctggcacgggtaagaattgtggaaagctagtatgcagttaatgcaa<br>gggcgcgtttttcgctaccccgacactgctaaagtttttgggaggggtcccttaaacatttctagtatt<br>gagtgatagctttgcggcaggtcaccacaaccttactataaataaacctgttgaatctcac |
| 480 | Porcine Sapelovirus JD2011 | tacgcatgtattccacactcatttccccccctccaccccttaaggtggttgtatccccataccttaccctcc<br>cttccacaatggacggacaaatggatttgacctcacggcaaacacatatggtatgatttcggataca<br>ccttaacggcagtagcgtggcgagctatggaaaaatcgcaattgtcgatagccatgttagtgacgc<br>gcttcggcgtgctcctttggtgattcggcgactggttacaggagagtaggcagtgagctatgggca<br>aacctctacagtattacttagagggaatgtgcaattgagacttgacgagcgtctcctcggagatgtg<br>gcgcatgctcttggcattaccatagtgagcttccaggttgggaaacctggactgggcctatactacc<br>tgatagggtcgcggctggccgcctgtaactagtatagtcagttgaaaccccccc |
| 481 | Porcine Sapelovirus A2 | ttgaaatgggtgtggggtacatgcgtattacggtacgcatatattccacactcatttcccccccctcca<br>cccttaaggtggttgtatccccataccttaccctcccttctaaaacagatggacaaatggatttgaact<br>tatggcaagtgaatatggtatgactttggatacactttaacggcagtagcgtggcgagctatggaaa<br>aatcgcaattgtcgatagccatgttagtgacgcgcttcggcgtgctcctttggtgattcggcgactgg<br>ttacaggagagtaggcagtgagctatgggcaaacctctacagtattacttagagggaatgtgcaatt<br>gagacttgacgagcgtctcttagagatgtggcgcatgctcttggcattaccatagtgagcttccagg<br>ttgggaaacctggactgggcctatactacctgatagggtcgcggctggccgcctgtaactagtata<br>gtcagttgaaaccccccc |
| 482 | Simian Sapelovirus 1 | ccaaggatctgttgcataggcgttgtatcccctaaccttttacctacccatcccaataggactggtatt<br>tcggttttgattgagtaatggatactgattctatacctgttacccattcaggggaaaaatggagtttcttt<br>catggatctgacttgatatgaccaagagtcaacactttgcgtgttggccgtatggaatgctttaaggtt<br>tattctttggattatgacttcagggttggccgcccaggataaaaggcaattgtggtaagtgatgttagt<br>cattggtggttgaaacctgcctaagacgtcctaggtctacgctgtgcgggccgaagtaagcttagg<br>aataacagggagtatgccattttctgctttcacccaacacgaccgtacacgaaagagctagaggca<br>ctttggggcaaagggaaaagctttgcttagcccgaatgttcatttgagtccttgacgaatgcgtccc<br>gtctgtcccgacggtgaggcgtatggcgcatgctcatggcattacccaatggtgtatctgtgaggg<br>gggggctcctcacacttagtctagtgctacctgacagggccgcggctggtcgtttgtgtatggtata<br>accagtagtaatcccccatggattgctttaacttcccctcctcccttaccaagacattctctaag |
| 483 | Simian Sapelovirus 2 | ttttaacttgttatgacattcaaggaaaaaatgtctttttcattatgggactgacctgtttatgaacatgag<br>cagcggcactgctccacgggctatccgtgtaagaaatattgattattcttatggatcatgatttcagg<br>gttggccgcccagtctaaaaggcaattgtggtaagctatgtaagtagttggctgttgaaaggagcc |

TABLE 17-continued

IRES sequences.

| SEQ ID NO | IRES | Sequence |
|---|---|---|
| | | aagtacatcctaggtctacgctgtgcgggccgaagtaagacttggaacaactctgagtaggcagtt tttctctttagcccaacacgaccgcatactgaagagctagaggcactttggggcaaaggtaaaagc attgcttagaccgaatgttcaatgagaccttgacgagtgctgtcacagtgtcccctgatggcagtatg gcgcatgctcttggcattacccatatgtgtatctatagggggggggcccccctatacttagtctagtgc tacctgacagggccgcggctggtcgtcggtgtgtggtataaccagtagtaatcccccatggattgc tttaactccccctcctccctcaacaaaactttctctaag |
| 484 | Rabovirus C | ccgggtataacccggagttttggggcaggtccaagccccacataggaacatacgatccacggatc gtgtgttcttttatgctttctaaccttaccctttgtaaccattacgctttacgccgcatggtgtttggcggc accatgacgtggacaagaggttacgccattacgatatgtaccctccccttttggggagagaccgac caattatggtacagtatccaactgtattgtggtcaagtacttctgtttccccggtgatgcgggataggc tgtacccacggccaaaacctgctgatccgttacccgactcacatctacgaggaggctagtaaaag gcatgaagttcaagagtatgatccaaccagatccccactggtaaactagtgatgagggttcccgttc cgaacatggcaacatgtgggttccctgcgttggcactaggccccttccgaggggtgctctgaagat ggattgttgatgaagaccaatttgtgcatgtgtttatcctccggccctctga |
| 485 | Rabovirus A NYC-B10 | ccgaccccactggtcgaaggccacttggcaataagactggtggaacaaggtcgcctgtagttgatt ggaaccttctttctaatgacttatgtcagcggtgctactcacaccgtaactctcctaccctatccccac gcttgtggaactaggaggggatgagtgattcaagtaagtactgtcagaatggtgaaaataatctgat tctgaaacgctatggatccatcgaaagatggggctacacgcctgcggaacaacacatggtaacat gtgccccaggggccgaaagccacggtgataggatcacccgtgtagtttgagatcatatcaatgttc atagtctagtaagatgatttgaaatctaactggtctgatggctaactgcttgtcttattgcggcctaagg atgtcctgcaggtacctttagagaaccttaagagactattgatctgagcaggagccaaggtggtcttt cccagccttggttaaaaagcgtctaagccgcggcagggggcgggaggccccctttcctcccaaa ctataatatagattgt |
| 486 | Parabovirus C | gatgtatccccatcccccagtgtgtatgccatactgcatagctcgcctatgccctatggattcacaac cctttcatataccctccctacccaaccccgtaaccacatgctttactccgcttggggttttgcggcccc atgttgtgacgaaatggctacgcaatcaatgcggctaatggggcctgccgcttttaagtggcccca gttagaagtttatgcacacccgcccattaggaggccaccagccaggtggtcagagggcaagcac ttctgtttccccggtgaagtttgataagctgtgcccacggctgaagcagacagatccgttacccgcc tcactactacgagacggctagtagtgtgtaatatccgaatttcattgatccgggtgttccccccaccc agaaacgtgtgatgaggagcggcacccctcctatggcaacatagggcctctcctgcgctggcac acgggctctatgagcatgaaatcaggagaaagtcacacgaagaccttattgtgctagtgttgattcc tccgccccccctgaatgcggctaatcccaactccggagcgcccgctggcaaacccgccagaaga gcgtcgtaatgcgtaagtctggagcggaaccgactactttgggtgtggcgtgtttcctttatttccttt gtatttgtat |
| 487 | Parabovirus B | aacccataatccattgtccatcaatgttttatgggggggaccctttctcccctccccctccaaatacct tttacccctctgtaaccaagagtgtgcaaaatctatttactagcccagaattgcggcttctggggagg tttattcctcatgcctaacaagatgttacgcaaactccgggctacggccctgggcttttgccctaaag atttagaagtttacactatcgtccaacaggaggacaacaaaccagttgttctaaggacaagcacttct gtttccccggtgagactggatagactgtacccacggttgaaactggttgatccgttacccgactcac tacttcgagaagattagtaggaaactgtgaaactgattccattgatccggatactttccccgtatcca gaaactactgatgagggttgacttcccgactacggcgacgtagtgtcatccctgcgctggcagtag gcctctttgaggatggaagatgtggatcggtaaccgaaggtcctattgagctagtgtttatacctccg gcctcctgaatgcggctaatcctaacccatgatctagtgctcacaaaccagtgagtagctagtcgta acgcgtaagtcgtgggcggaaccgactactttggagtgaccgtgtttcctattttacttttgtttg |
| 488 | Parabovirus A3 | accgttacgcaccactcagttggtgtttggtggcaccaatgatggaacaaaaggctacaccacttg ggctacggcccgcgccaccttgtggcgcaaagacattagaagaatagcataccgcccactaggg ccctgcagccagcagggtaacgggcaagcacttctgtctccccggtagaacggtataggctgtac ccacggccgaaaactgaactatcgttacccgactccgtacttcgcaaagcttagtaggaaactgga aagttcgagttattgacccggagtgttcccccactccagaaacgcgtgatgagggttgccacccc gaccatggcgacatggtgggcatccctgcgctggcacgcggcctctaagaggataactcgctcct actggtaaccgaagagccccgtgagctacggtttattcctccgcctccctgaatgcggctaatccta acccatgagcagttgccatagatccatatggtggactgtcgtaacgcgtaagttgtgggcggaacc gactactttgggatggcgtgtttccttgttttctccatttgttgttgtatggtgacaagttatagatctcga tctatagcgtttcttgagagatttccaaacatttattcaagtcgtacaattcttgtgtttaagcagtacagt gtaagg |
| 489 | Felipivirus 127F | gatgtcggatgacggctggccaccggggaaaaacggcaaatgtgcaccacctctgcaacccac gccgaccacgtttaaccatggcgttagtaggagtggaccactgcagtgggctctggtgtgcgaca gtcagtggtagagtagacagtcctgactgggcaatgggaccgcgttgcgtatccctaggtggcat cgagattcctctgctacccaccagcgtggactcctatgggggggccccataggctaggtctatac tgcctgatagggtcgcggctggtcgaccactgactgtataaccagttgtaactcact |
| 490 | Boosepivirus A | ttgaaagacctcggcatatatcgttgtcacaacggtatatgtcgagatctttctccccacccccctcca attccctttttccccctcttgcaacttagaagtttgtacacacagggcaataggatacgtgatccagcc aggacacgtgagctcaagcacttctgtttccccgtccccttcacgtactacgggaatgttagtaattt gtgtgcactttagtaaggttgatccgggattaaccccaaatcccagaaactggtgatgagcgttacc acccccgccgggcgaccggaaggtttcgctgcgttggcaccagggcttcggcaccagaaaaag |

TABLE 17-continued

IRES sequences.

| SEQ ID NO | IRES | Sequence |
|---|---|---|
| | | gtaaagcaaatgaaggcgctactgtgctacgagaagtttcctccaggcccctgaatgcggctaatc<br>ctaaccagtgatccaccggtgcaaaaccatgtactaggtggtcgtaacgcgcaagtcgctggcgg<br>aaccgactactttgggtgtcctgtgtttccatattttattttattcaattttatggtgacaagagtaaagag<br>atacagatttgcagcc |
| 491 | Boosepivirus B | ttttctcccctcccccctccaactaccttttccccctcttgtaacgctagaagtttgtgcaaaccgcctgt<br>agggtactgcaatccagcagtgcataggctaagcttttcttgttaccccaccccacattatactgagg<br>aggattgtgaaattgtgttagtatgggttagtagcggtgacccgggtaaccccaacccagaaactc<br>acggatgagatgaacaggaccccacatggtaacgtgtgtgttcgtctgccccgcaaggtgaggcc<br>gtgagagctttgcacgcgaaaaccttgaaaacccaaaagtaccttgagctcttcgctattttgtgtttc<br>ctccaggaccctgaatgcggctaaacctaacccgcgatccgcacgtagcaacccagctagagtgt<br>ggtcgtaatgcgcaagttgcgggcggtaccgactactttggtgttcctgtgtttcctttattttattttga<br>atttttatggtgacaacagctagaaaataagagtgaac |
| 492 | Phacovirus Pf-CHK1 | gtgtgtcatttctcccctcccccctcccaaaccttttcccccctctaatcggattgattaacccggttaaag<br>atgattaatggtttgtgagttgatatgatggcccggcattgaatccgggaattcttaagtaatggaatt<br>gcatccaatatgaaagtgagtgtggcaagctcacaagtagtacttggctctgcccattatttgagga<br>ccaactcttcttgactacaatgtgtttaaagtaaactggaccacattgtgtatccagacaactccatttg<br>ataatgtacgctggaaacgttttcagtgcatagggtcctaaagtggtgctgaaatattgcaagctcaa<br>tgggatactgaacgctgaaaaccgccgctgttatcatatgggcccctagtgggtaaatgttggcttt<br>aggcatatactgcttgggaatgcagtactggttgtagacagggtgatagcctaccggctggcgtag<br>ttgagttggtatagccagttgattgccat |
| 493 | HRVC3 QPM | ttaaagctggatcatggttgttcccaccatgattacccacgcggtgcagtggtcttgtattacggtac<br>atttccataccagttttatacaccccaccccgaaactcatagaagtttgtacacaatgaccaataggt<br>ggtggccatccaggtcgctaatggtcaagcacttctgtttccccggcacccttgtatacgcttcaccc<br>gaggcgaaaaatgaggttgtcgttatccgcaaagtgcctacgaaaagcctagtaacactttgaaaa<br>cccatggttggtcgctcagctgtttacccaacagtagacctggcagatgaggctagacattcccca<br>ccagcgatggtggtctagcctgcgtggctgcctgcacaccctgccgggtgtgaagccagaaagt<br>ggacaaggtgtgaagagcctattgtgctcactttgagtcctccggcccctgaatgtggctaaccta<br>accccgtagctgttgcatgtaacccaacatgtatgcagtcgtaatgggcaactatgggatgggacc<br>aactactttgggtgtccgtgtttcctgttttactttttcattgcttatggtgacaattgtatctgatacacttg<br>ttacc |
| 494 | HRVB27 | ttaaaacagcggatgggtatcccaccatccgacccacagggtgtagtgctctggtattttgtaccttt<br>gcacgcctgtttccccattgtacccctccttaaatttcctccccaagtaacgttagaagtttaaggaaa<br>caaatgtacaataggaagcatcacatccagtggtgttatgtacaagcacttctgtttccccggagcg<br>aggtataagtggtacccaccgccgaaagcctttaaccgttatccgccaatcaactacgtaatggcta<br>gtattaccatgtttgtgacttggtgttcgatcaggtggttccccccactagtttggtcgatgaggctag<br>gaactccccacgggtgaccgtgtcctagcctgcgtggcggccaacccagcttttgctgggacgcc<br>tttttacagacatggtgtgaagacctgcatgtgcttgattgtgagtcctccggcccctgaatgcggct<br>aaccttaaccccggagccttgcaacataatccaatgttgttgaggtcgtaatgagtaattctgggatg<br>ggaccgactactttgggtgtccgtgtttccttttattctttatattgtcttatggtcacagcatatatagcat<br>atatactgtgatc |
| 495 | HRVA73 | ttaaaactgggtttgggttgttcccacccaaaccacccacgcggtgttgtacactgttattccggtaa<br>ccttgtacgccagttttatatcccttccccccccttgtaacttagaagacatgcgaatcgaccaatagca<br>ggcaatcaaccagattgtcaccggtcaagcacttctgtttccccggctctcgttgatatgctccaaca<br>gggcaaaaacaattggagtcgttacccgcaagatgcctacgcaaaacctagtagcatcttcgaag<br>atttttggttggtcgctcagttgctaccccagcaatagacctggcagatgaggctagaaataccccca<br>ctggtgacagtgttctagcctgcgtggctgcctgcacacccacacgggtgtgaagccaaagattg<br>gacaaggtgtgaagagtcacgtgtgctcatcttgagtcctccggcccctgaatgcggctaacctta<br>accccgtagccattgctcgcaatccagcgagtatatggtcgtaatgagtaattacgggatgggacc<br>gactactttgggtgtccgtgtttcactttttacttatcaatttgcttatggtgacaatatatatagatatatat<br>tgacacc |
| 496 | EV L | acatgggccagcccaccacacccactgggtgtagtagtctggttctatggaacctttctacgcctctt<br>ttgcttccctcccccatttctccttcgattgctccacctgtgatctttgcaacttagaagaaataatgaac<br>ccgcacaatagcgggcgctgagccacagcgtcaatgtgcaagcacttctgtttccccggaatggg<br>cccataggctgtacccacggctgaaagggaccggcccgttacccgccttggtactgcgagaatgt<br>tagtaactccctcgatagctttaggcgttacgctcagccctttgagcccgaagggtagttcgggtcg<br>atgaggctcgtcattccccactggcgacagtgtgacttgcctgcgttggcggcccggggtggggg<br>gcaacccccatccacgcctactgaaggacagggtgtgaaggcgctattgcgctactaaggagtcc<br>tccggcccctgaatgcggctaacccgaaccccgagcccacggtggtaaacccgccacaagtgg<br>gtcgtaatgagtaatttggggcagggaccgactactttgggtgtccgtgtttcctgtttttccatacgat<br>ggctgcttatggtgacaaccataagcaattggattggccatccggtgttcatattgcgaat |
| 497 | EV K | tcagcctgacgcaagtgcctccattggagtctctccaagccctccggggcttggagggcgccgac<br>cccctgcctagggggagcccacgacacggctggagtccattggcacaccgcagccacgattca<br>agccagaattgaaagcgggaagcacttctgtctccccggtgtggatcatacgctgtacccacggc<br>gaaaagtgaagcatcgttacccgactcggtacttcgagaagcccagtacagttgtggatctctgca<br>gggtatacgctcagcgtgacccctacgtagttccttgagatggctgagagaacaccccacgggcg<br>accgtgtctctcggcgcgtggctcaaggccgggccttcagtggctcggtgccttgcagagtgaag<br>cctccgaacagcctattgagctaccgtttagcctccgccctcttgaatgcggctaatcctaaccatg<br>gagcgcccgcccacagtccagtgggtagagcgtcgtaacgcgcaagtccgtggcggaaccgac |

TABLE 17-continued

IRES sequences.

| SEQ ID NO | IRES | Sequence |
|---|---|---|
| | | tactttagagtggcgtgtttccaatttatcctttataaagttgcttatggtgacaccacaagagatccac<br>gatttcttgtttcttatcactgagacacaagtcatattcatcaatctttattgcggaattaacttggtgcgt<br>ccaaacacatcagc |
| 498 | EV J 1631 | caccctgagggcccacgtggcgtagtactctggtatcaaggtacctttgtacgcctattttatttccct<br>tcccccacagtaacttagaagcttatctcatagttcaacagtagggtcactaaccaagtggctcagc<br>gaacaagcacttctgtttccccggtcctagtacctgtgaagctgtacccacggcggaaggggaaa<br>aagatcgttatccggcccccctacttcggaaagcctagtaacaccattgaagcaatcgagtgttgcg<br>ctcagcacagtaacccctgtgtagctttggttgatgagtctgggcactccccactggcgacagcgg<br>cccaggctgcgttggcggccaaccgactcgggcaacccgggtcggacgctcgtttgtggacatgg<br>tgtgaagagcctactgagctagagggtagtcctccggcccctgaatgcggataatcctaacccccg<br>gagcacccacactcaatccagagtgcaggatgtcgtaacgcgtaagtctgggacggaaccgact<br>actttgggtgtccgtgtttcctgttttacttactttggctgcttatggtgacaatctagtgttgttaccatat<br>agctattggattggccatccggtgttttgaattgtgtgtttatactaattcttttacatatcacagacaacc<br>aaat |
| 499 | EV J N125 | cggtacctttgtacgcctatttaccccccttccccttgtaacttagaagcaaagcaaaccagttcaata<br>gtaagcaacacaacccagtgttgtgacgaacaagtacttctgtttccccgggagggtctgacggta<br>agctgtacccacggctgaagtatgacctaccgttaaccggctacctacttcgagaagtctagtaata<br>ccattgaagttttgttggcgttacgctcaacacactaccccgtgtgtagttttggctgatgagtcacgg<br>cattccccacgggcgaccgtggccgtggctgcgttgcggccaaccaaggggcgcaagctccttg<br>gacgtcacttaacagacatggtgtgaagaacctattgagctaggtagtagtcctccggcccctgaat<br>gcggctaatcctaactccggagcacatcagtgcaacccagcatttggtgtgttgtaatacgcaagtc<br>tggagcggaaccgactactttgggtgtccgtgtttcctgttttaccttatttggctgcttatggtgacaa<br>tttgatattgttaccatatagctgttggattggccatccggattttttgaaagagacccaaaactttcttct<br>ctacttcagattcaagtgcgaagttttcctttttcatatattacttactaatttgaagtaccaaag |
| 500 | EV I | ttagtactttctcacggggatagtggtatccctccctagtaatttagaagacttgaaaaaccgaccaat<br>aggcacctcgcatccagcggggtaaaggtcaagcacttctgtttccccgggtcgagtagcgatag<br>actgtgcccacggtcgaaggtgaaacaacccgttatccgactttgtacttcgggaagcctagtacc<br>accaaagattatgcttggggtttcgctcagcacgaccctggtgtagatcaggccgatggatcaccg<br>cattcctcacaggcgactgtggcggtggtcgcgtggcagcctgccgatggggcaacccatcgga<br>cgccaagcatatgacagggtgtgaagagcctactgagctacaaagtattcctccggcccctgaat<br>gcggctaatcccaaccacggagcatttgctaccaaaccaggtagtggaatgtcgtaacgggtaac<br>tctgtggcggaaccgactactttgggtgtccgtgtttccttttaatttatcattctgtatatggtgacaact<br>atagtgctatctcgatttgcattactattgttgagattaaaacttttattacattgttgcatttttaccctttgag<br>tgagttttcacctgaacagattaatttactcatcctgtttatatattacaagcagaaatacttgcaaag |
| 501 | EV F1 BEV 261 | gcaatgctgcaccagtgcactggtacgctagtaccttttcacggagtagatggtatcccttaccccg<br>gaacctagaagattgcacacaaaccgaccaataggcgcaccgcatccagccgtgcagcggtca<br>agcacttctgtctccccggtctgtaaagatcgttatccgcccgacccactacgaaaagcctagtaac<br>tggccaagtgaacgcgaagttgcgctccgccacaaccccagtggtagctctggaagatggggct<br>cgcaccaccccccgtggtaacacggttgcctgcccgcgtgtgcttccgggttcggtctcgtgccgtt<br>cacttcaacttcacgcaaccagccaagagcctattgtgctgggacggttttcctccggggccgtga<br>atgctgctaatcccaacctccgagcgtgtgcgcacaatccagtgttgctacgtcgtaacgcgtaagt<br>tggaggcggaacagactactttcggtaccccgtgtttcctctcattttatttaatattttatggtgacaat<br>tgttgagatttgcgctcttgcaacgttgccattgaatattggcttatactatttggttgccttttacaaaac<br>ctctgatatacccagttcttacattgatctgcttgtttttctcaatttgaagtatagactacaaatagcaaa |
| 502 | EV D94 | cgtggcggccagtactctggtatcacggtacctttgtacgcctgttttatatccccttcccccgcaact<br>tagaagaaaacaaatcaagttcactaggaggggtacaaaccagtaccaccacgaacaagcact<br>tctgtttccccggtgatgtcgtatagactgtaaccacggttgaaaacgattgatccgttatccgctctt<br>gtacttcgaaaagcccagtatcaccttggaatcttcgatgcgttgcgctcagcactcaaccccagag<br>tgtagcttaggtcgatgagtctggacactcctcaccggcgacggtggtccaggctgcgttggcgg<br>cctacctgtggtccaaagccacaggacgctagttgtgaacaaggtgtgaagagcctattgagctac<br>aagagaatcctccggcccctgaatgcggctaatcctaaccacggagcaagggtacacaaaccag<br>tgtatatcttgtcgtaacgcgcaagtctgtggcggaaccgactactttgggtgtccgtgtttccttttgt<br>ttttatcatggctgcttatggtgacaatctaagattgttatcatatagctgttggattggccatccggtaa<br>tttattgagatttgagcatttgcttgtttcttcaacaatttcacctattcattgcatttcagcagtcaaa |
| 503 | PV3 | tacctttgtacgcctgttttatactccctcccccgcaacttagaagcatacaattcaagctcaatagga<br>gggggtgcaagccagcgcctccgtgggcaagcactactgtttccccggtgaggccgcatagact<br>gttcccacggttgaaagtggccgatccgttatccgctcatgtacttcgagaagcctagtatcgctctg<br>gaatcttcgacgcgttgcgctcagcactcaaccccggagtgtagcttgggccgatgagtctggac<br>agtccccactggcgacagtggtccaggctgcgctggcggcccacctgtggcccaaagccacgg<br>gacgctagttgtgaacagggtgtgaagagcctattgagctacatgagagtcctccggcccctgaat<br>gcggctaatcctaaccatggagcaggcagctgcaacccagcagccagcctgtcgtaacgcgcaa<br>gtccgtggcggaaccgactactttgggtgtccgtgtttccttttattcttgaatggctgcttatggtgac<br>aatcatagattgttatcataaagcgagttggattggccatccagtgtgaatcagattaattactcccttg<br>tttgttggatccactcccgaaacgttttactccttaacttattgaaattgtttgaagacaggatttcagtgt<br>caca |
| 504 | EV C102 | ctttgtacgcctgttttacatcccctcccccacgtaactttagaagcaattcaacaagttcaatagagg<br>gggtacaaaccagtatcaccacgaacaagcacttctgtttccccggtgattttacataagctgtgcc<br>cacggctgaaagtgaatgatccgttacccgctcgagtacttcgaaaagcctagtatcgctttgggat |

TABLE 17-continued

| IRES sequences. | | |
|---|---|---|
| SEQ ID NO | IRES | Sequence |
| | | cttcgacgcgttgcgctcagcactctaccccgagtgtagcttaggctgatgagtctgggcattcccc atcggcgacgatggcccaggctgcgttggcggcctacccatggctaacgccatgggacgctagt tgtgaacaaggtgtgaagagcctattgagctactcgagagtcctccggcccctgaatgcggctaat cccaaccacggatcaggtgcctccaacccaggaggtggcctgtcgtaacgcgcaagtctgtggc ggaaccgactactttgggtgtccgtgtttccttttatcttttaaatggctgcttatggtgacaatcataga ttgttatcataaagcgaattggattggccatccggtgaaatacaaacacattatttacttgtttgttggat ttactccgctcacacagcttactcctaagataatatttattgtattgctggtaaggagacactattata |
| 505 | EV 30 | aagcaaggcaaacctgaccaatagtaggtgtggcacaccagccgcattttggtcaagcacttctgt ttccccggaccgagtatcaataagctgctcacgcggctgaaggagaaaccgttcgttacccgacc agctacttcgagaaacctagtaacactatgaacgttgcggagtgtttcgttcagcacttccccgtgt agatcaggtcgatgagtcaccgcattcctcacgggtgaccgtggcggtggctgcgttggcggcct gcctacgggttcgcccgtaggacgctctaataccgacatggtgtgaagagtccattgagctagctg gtagtcctccggcccctgaatgcggctaatcctaactgcggagcaggtgctcacagaccagtgag tagcctgtcgtaacgggcaactctgcagcggaaccgactactttgggtgtttttcctttttttcttctctta tattggctgcttatggtgacaattaaagaattgttaccatatagctattggattggccatccggtgacg agcagagccattgtttacctctttgttggatttgtacctttgaaccacaaagtcttgaataccattcatct cattttaaagttcaactcagctaaaagaaa |
| 506 | SA5 | agtacttggtattccggtacctttgtacacctatttacaaaccctaccccttgtaaccttagaagcaatt atttaaccgctcactagggggtgtgctatccaagcacatcaagagcaagcacttctgtctccccgg gaggggctaatggtacgctgtgcccacggcggaaatgagccctaccgttaaccggcagtctactt cgggaagcccagtaactacattgaaactttgaggcgttacactcagcacataaccccaatgtgtagt tctggtcgatgagccttggcatcccccacaggcgactgtggccaaggctgcgttggcggccagc ctgcggaccaaaagtccgtaggacgcctaattgtggacatggtgtgaagagcctactgagctaga ctgtagtcctccggcccctgaatgcggctaatcctaaccctggagcatccgcgtgcaacccagtac gtagggtgtcgtaatgcgtaagtctgggatggaaccgactactttgggtgtccgtgtttcttgtttttca tactgggtcgcttatggttacaactaattgttgtaatcattggcagtgcgcgctgaccacgcgattatt gatatttccatttgttggatactccaatagtgtcaactcatatacacaacttttaccactgatcaagataa aa |
| 507 | EV A114 | tgtgcgcctgttttgaaacccctcccccaactcgaaacgtagaagtaatgtacactactgatcagta gcaggcgtggcgcaccagccatgtctcgatcaagcacttctgtttccccggactgagtatcaatag actgctcacgcggttgaaggtgaaaacgtccgttacccggctaactacttcgagaaacctagtagc accatagaaactgcagagtgtttcgctcagcacttccccgtgtagatcaggtcgatgagtcactgc aatccccacgggtgaccgtggcagtggctgcgttggcggcctgcctatggggcaacccatagga cgctctaaggtggacatggtgtgaagagtctattgagctagttagtagtcctccggcccctgaatgc ggctaatcctaactgtggagcgcatactcccaaaccagggagcagtgcgtcgtaacgggcaactc cgcagcggaaccgactactttgggtgtccgtgtttccttttattcctatactggctgcttatggtgacaa ttgagagattgttaccatatagctattggattggccatccagtgtgtaatagagcaatcatttaccaatt tgttggatttactccattaacccacacgtctctcaacacactacatttcatcttactactgaacactaga aa |
| 508 | Mobovirus A | tattctcccacaaaccttcttgtaactctgttaagccttttacatccatgtaatttaattttctccacctaaa aggatttcccccatggtcctttttggctcgaacaaatgctacatagggtcttgttttctcccccctggctc tcttgccagggttccataccccaattcctctatttccatgattttcatcatggtttatttttactgtcttctta ttttctgaggtgaccaactcctaagccgactgggtcgcggaagcccggactcctcgcatcactagg gtgcgtagcgatgtaggcgaaaatattggttgctagatgcatacatatagtgaattgatactacacca aactctgttctttttgaaactagctattttctaagtaaggtaggctacgggtgaaaccttaccattgcag gtacgtgaaccgcaacggacatttggccgaagactggtgtacccacgtcagttataggacctcttc aacgttggtggacggcatgtcactgattagttaggctagtgaatttaagttcaggggggtatcttttagc ttaagcgtgtattctagtaggacttgcagagcctccccacctaggaggatctctgtttatagcccctttt tccttgttccgttagttttccacacttttacaatatttgatgatttgtt |
| 509 | Burpengary Virus | ctcccccccttccccttcccgagtaggagattggcatgtatgctctacatgcccgattctctcttgct cactctcttaaatcctggtggcggtctcggattaaacatttatgtcgtatctgggatcgtcttacttggt ggtaattcctctgttgcctagggacctccggactgccggattaaaggtctcaacagagggcaatgt acaaggaagtcattatacgctaattaagtatttgatgaatgactagtgtgacagggctgaggaactc cccccgggtaaccggtgcctcagcgtccgaaagacacgtggataggatccaccctgttataccca gcacgatgtaatagtcaaatacctctgatttgtgtaggatgtataaattgtgcattgtaaattttgggcg tagagatgctccgaaggtaccccgttttacgggatctgatcggaggctaattacccaatgcgcccta aataacttcatataatttctttttctttattcaaa |
| 510 | Hunnivirus A1 | taacgtttggcaagaaccctcacctgtcaattgggaccaccactttcagtgaccccatgcgaagtag tgagagagaataagctttcttacccttcatttgtgaacccttcagtcgaagccgcttggaataagata ggaggaaaagttcattctaaatggagtgaaacatgtacttcagaatttctagcacgcgctgggctttc ttgcgtgtgacggcactgtcttgccggagctctccacactgacaccccacgcttgtggaccttggtg gcagatgacaacactgcagctggaattgagtgtctggtacactctgtgtaacagtgaaaacaatgt gatcacttcggtgagctagtagcctgtggaccaacaactggtaacagttgcctcaggggccaaaa gccacggtgtttacagcaccctactggtttgattggagcaatccaagatgtcacagagttagtaattg ccaagcagtccgtactggtatcttgacataccgtgcagttttggatagtgaaggatgccctgacggt acccataggtaacaagtgacactatggatctaagcaggggctcactctacgctgctttacagctgg ctgtgagttaaaaaacgtctagctatccacaacctaggggactaggttttccttttatttagattacaatt at |

TABLE 17-continued

IRES sequences.

| SEQ ID NO | IRES | Sequence |
|---|---|---|
| 511 | Hunnivirus A2 | acagtttttgacaaggaccctcacctgtcaatcgggaccaccactttcagtgaccccgtgcgaagt gttgagagaaagtgagctttcttacccttcatttgtgaacccttcagtcgaagccgcttggaataagat ggaaggaaatgttcattctaaatggagtgaaacatatacttaatttccagtgtttagtggtctttccact agacaacggcactgtcttgccggaactctacacaccaacattccacgcttgtgggactcaaatgttg gatgacacagttgtagctggaactgagtgtttagtgcactctgtgtaacagtgaaaacaatgtgatca cttcggtgggctagtagcctgtggactaacaactggtaacagttgcctcaggggccaaaagccac ggtgttaacagcaccctactagtttgattggagcaatccatgatgttacagagttagtaactgccaaa cagattgtactggtatcttggcataccgtgcaacttaggatagtgaaggatgccctggcggtaccca taggtaacaagtgacactatggatctaaacaggggctcactctacgttgctttacaactagctgtga gttaaaaaacgtctaactatccacaacctaggggactaggttttccttttttattttttatacacaacta |
| 512 | Ia Io | ggtgtccgggtgtgtgggatagacccagatgtgcagtggatgcgagcatttgagtcagagtagga gcaagcccaggggcaaagggaccacattgtgtatcccgaatgaaggatcgagatttctctcctcat tacccggtgtcttgtcactgttggggggggcccaacagtcttagtcctatactgcctgatagggtcgc ggctggccggactcaagtgctatagtcagttgattttcactc |
| 513 | Taura Syndrome Virus | ctttaaaagtcgtgcgtggcttcaccacgcacgatcagtactatcagttaaccactcttgaatatgctc aatgaccctattcaacactggtgtctcttagtacattattttagcacttaacgtgcatgagttttgcccat ttctttcaaaaaaatgagtattcgaggagacgtcccgctccccgtcttatttcaaccgtagactcgac atctattggtggacatttaattccagtcgccgtaagttgcttctgccccgcgctatatttcttatacttat ggttctataggtctggtttaaaacgtaaatagacggcccacaaactatagaacgcgtacccggaac gccaatcccggataagtccctggatatatagatgcaccgcaatataagcctgcagactgtctcatat act |
| 514 | ABPV | cccgtcaaaataacaacttataacacgatgttacccgaagaaaccattttagtgtaacatttaagatta gaagtagttcatctaatagagataggcactattagaaggaggccttttctaaaggagccgttagtca gcccagacaagcgcagtactttagaagagagaagttccccgatagcgaccgaaaagacgcgtttt ccgtgctaactaatttaaatgtgggaacgaatattattattgaaattatgtgagccacgtagcaatcaa gtcatgtttttgtcactacgtttactcatctaatgtagataattttgtttaagtacctatttaggtgtcatccc accagagaagaaataatacgtaccggaacccagagtacaccccttattttaagccttactgggcttc tctgttagttagtaatctggcccacgttttgcgttgagtggggtcccaacagtaggaattcgacggac aagtagcaagcgagtcggtaccaattggtttagccttcgaaattactctgggcaggaagttactaaa cgagaactttctgcttaaatcccaacgcacaaacaaatagagtaaataaataattata |
| 515 | BRAV-2 | tttgttttgcggctttgccgttgttcgggttttacctgttttcacacagcaaaacaggccttctagtttcgt gcttaaacgagatcatgctcgaactagaactacatagctggtcactggactcataccacaccttgtg gagctttatgggaaaggtggctagtgggctgtggaagtgactctgaccacatgcctctcaagtgtg ggaaatcacggatcggtgtagcgacgacaacaggccttgggacaccctctccagtaatggagac ccaaggggccaaaagccacgcctcgtgccctgttgttcacaaccccagtgcgacccgtgttagta cctatttgcgagaactgtgtctggacagctaaacacaaccctagtgggagagactaaggatgcccag gaggtacccggaggtaacaagtgacactctggatctgacctggggagagagggcttgctttacag gcgcctctctttaaaaagcttctatgtctcatcaggcaccggaggccgggccttttccttttaaaatta cactta |
| 516 | BRBV-1 | ccccccctacttaaagatgtacggttttgctgctttcacagagtaaagcagatagaggttctgaactg gcaaactttacctcgaaacacgcccgtttttctgctgtgtctcacagactgtcctgtcacacttgtggc ggcttgtgacactgtgaacatagtgagaccgaccaagacaacagtttcaagtgatgaacatcgaac gtctaaactggatccgtaactggacatgttagggcaaggacttccccccctggtaacaggagcctgg ctggccaaaagccccgctcattgagcctagcatgttgtcgaccctggactgttcagtttagttagtac atggaattcacttgtcacggttcttctgaactcggtctctagtatgacagcctaaggatgccctccag gtaccccggggtaacaagtgacacccgggatctgaggaggggactactttacgtagtttaaaaaa cgtctaagctgttatggtgaccagaggctggcacctttcacttttaaaattacactactgactacaatt gaagtgataacggttttacaggctttcaaactagttacacaagcactgttttcctgacacacacacttt |
| 517 | ERAV-1 U188 | aatattggcgcgcgcatttgcgcgccccccccccatttcagccccctgtcattgactggtcgaaggc gttcgcaataagactggtcgtcacttggctgttctatcgtttcaggctttagcgcgccctcgcgcggc gggccgtcaagcccgtgcgctgtatagcgccaggtaaccggacagcggcttgctggattttcccg gtgccattgctctggatggtgtcaccaagctgacaaatgcggactgaacctcacaaagcgacaca cctgtggtagcgctgcccaaaagggagcggaactcccccgccgcgaggcggtcctctctggcc aaaagcccagcgttaatagcgccttttgggatgcaggagccccacctgccaggtgtgaagtggag tgagtggatctccaatttggtctgttctgaactacaccatctactgctgtgaagaatgccctggaggc aagctggttacagccctgaccaggggccctgcccgtgactctcgatcggcgcaggtcaaaaatt gtctaagcagcagcaggaacgcgggagcgtttcttttccctttgtatcgac |
| 518 | GFTV | atggggaagggtatgacgtgccccttccttcttcggagaactcgctctagtggtctttccacttctgg aaaagagtgagtgcacgtgatcaggaccgtcgaagacgacaaatacctggtgctctatctcatag acgtttcacagctgtagcgacccctcagtagcagcggaagccccctcctggtgacaggagcctct gcggccaaaagccacgtggataagatccactgctgagggcggtgcgaccctagcaccctgtgat gcatactagttgtagcgtgccggactattggtctgtcataagacacctgatagagagaccaagaat gtcctggaggtaccccgcgtgcgggatctgaccaggagaccattgcccaatgctttacaacgggt ctatggtttaaaaactgtcgcagtctctccaaaccaagtggtcttggttttcaattactttgaatatttca ct |
| 519 | SAFV V13C | ttttcgacgtggttggaattgccatcatttccgacgaaagtgctatcatgcctccccgattatgtgatgt tttctgccctgctgggcggagcattctcgggttgagaaaccttgaatctttttctttggaaccttggttc |

TABLE 17-continued

IRES sequences.

| SEQ ID NO | IRES | Sequence |
| --- | --- | --- |
| | | ccccggtctaagccgcttggaatatgacagggttattttcttgatcttatttctacttttgcgggttctatc<br>cgtaaaaagggtacgtgctgccccttccttctctggagaattcacacggcggtctttccgtctctcaa<br>caagtgtgaatgcagcatgccggaaacggtgaagaaaacagttttctgtggaaatttagagtgcac<br>atcgaaacagctgtagcgacctcacagtagcagcggactcccctcttggcgacaagagcctctgc<br>ggccaaaagccccgtggataagatccactgctgtgagcggtgcaaccccagcaccctggttcgat<br>gatcattctctatggaaccagaaaatggttttctcaagccctccggtagagaagccaagaatgtcct<br>gaaggtaccccgcgtgcgggatctgatcaggagaccaattggcggtgctttacactgtcactttgg<br>tttaaaaattgtcacagcttctccaaaccaagtggtcttggttttccaattttgttgaatggcaat |
| 520 | SAV P-113 | ggagatctaagtcaaccgactccgacgaaactaccatcatgcctccccgattatgtgatgctttctg<br>ccctgctgggtggagcatcctcgggttgagaaaaccttcttcctttttccttggaccccggtcccccg<br>gtctaagccgcttggaataagacagggttatcttcacctcttccttcttctacttcatagtgttctatact<br>atgaaagggtatgtgtcgccccttccttctttggagaacacgcgcggcggtctttccgtctctcgaaa<br>agcgcgtgtgcgacatgcagagaaccgtgaagaaagcagtttgcggactagctttagtgcccaca<br>agaaaacagctgtagcgaccacacaaaggcagcggaccccccctcctggcaacaggagcctct<br>gcggccaaaagccacgtggataagatccacctttgtgtgcggcacaaccccagtgccctggtttct<br>tggtgacacttcagtgaaaacgcaaatggcgatctgaagcgcctctgtaggaaagccaagaatgt<br>ccaggaggtaccccttccctcgggaaggatctgacctggagacacatcacatgtgctttacacct<br>gtgcttgtgtttaaaaattgtcacagctttcccaaaccaagtggtcttggttttcactctttaaactgattt<br>cact |
| 521 | VHEV | aattccttcttcctttctccttggacctcggtcccccggtctaagccgctcggaatatgacagggttatt<br>ttcacctcttctctcttctacttcatagtgttctatactatgaaagggtatgtgtcgccccttccttcttgga<br>gaacgtgcgtggcggtctttccgtctctcgaaaaacgtgcgtgcgacatgcagagtaacgcaaag<br>aaagcagttcttggtctagctctggtgcccacaagaaaacagctgtagcgaccacacaaaggcag<br>cggaaaccccctcctggtaacaggagcctctgcggccaaaagccacgtggataagatccaccttt<br>gtgtgcggtgcaaccccagcaccctggtttcttggtgacaccttagtgaaccctcgaatggcaatct<br>caagcgcctctgtaggaaagccaagaatgtccaggaggtaccccttcctcatggagggatctgac<br>ctggagacacatcacacgtgctatacacttgtgcttgtgtttaaaaattgtcacagctttcccaaacca<br>agtggtcttggttttcccttaacttcgaaaagtcactatggcctgcaaacatggatacccagacgtgt<br>gccct |
| 522 | TRV NGS910 | atgcgacgtggttggagattaaaccgactccgacgaaagtgctatcatgcctccccgattatgtgat<br>gttttctgccctgctgggcggagcattcctcgggttgatacaccttgaatccttcatccttggacctcag<br>gtcccccggtctaagccgcttggaatacgacagggttattttccaatcttctcctttctactttcatgag<br>tcctattcatgaaaagggtctgtgctgccccttccttcttggagaatctgcgcggcggtctttccgtct<br>ctcgaaaagcgcagatgcagcatgctggaaccggtgaagaaaacagttctttgtggaaacttaga<br>gcagacatcgaaacagctgtagtgacctcacagtagcagcggaaccccctcctggtaacaggag<br>cctctgcggccaaaagccccgtggataagatccactgctgtgagcggtgcaaccccagcaccct<br>ggttcgatggttgttctctgtggaaccagagaatggtctttctcaagccctccagtagagaagccaa<br>gaatgtcctgaaggtaccccgcatgcgggatctgatcaggagaccaatcgtcagtgctttacactg<br>gcgctttggtttaaaaactgtcacagcttctccaaaccaagtggtcttggttttcacttttatcaaactgt<br>ttc |
| 523 | EMCV2 RD1338 | aaatactggtcgaaaccgcttgggataagaccggggtttgttaatgtctcaatgttattctccaccca<br>attgacgtcttttgtcaattggagggcagtgaaaccttgcccttgcttcttgcagaggattcccagtgg<br>tctttccgctctcgacaagggaattcatgatccaccaaaagttgtgaagagagcaggtcccatgga<br>agctttctgacgactgatgatgactgtagcgaccctttgcaggcagcggacccccccacctggtga<br>caggtgcctctgcggccaaaagccacgtgtttaacagacacctgcaaaggcggcacaaccccag<br>tgcctcatcaaaagtctgatgactgtggaaatagtcaaccggcttttcttaagcaaatttggtgtcgg<br>ggctgaaggatgcccggaaggtaccacactggttgtgatctgatccggggccacagtacatgtgc<br>tttacacatgtagctgcggttaaaaaacgtctaggcccccgaaccacggggacgtggttttccttt<br>gaaaaccacgattacaat |
| 524 | EMCV1 JZ1203 | gtctgctcgatatcgcaggctgggtccgtgactacccactccccctttcaacgtgaaggctacgata<br>gtgccagggcgggtactgccgtaagtgccaccccaaaacaacaacaaaccccccctaacattact<br>ggccgacgccgcttggaataaggccggtgtgcgtttgtctatatgttatttcccaccacattgccgtc<br>ttttggcaatgtgtgggcccggaaacctggccctgtcttcttgacgagcattcctaggggtctttccc<br>ctctcgccaaaggaatgcaaggtctgttgaatgtcgtgaaggaagcagttcctctggaagcttcttg<br>aagacaaacaacgtctgtagcggccctttgcaggcagcggaaccccccacctggcgacaggtg<br>cctctgcggccaaaagccacgtgtataagatacacctgcaaaggcggcacaaccccagtgccac<br>gttgtgagttggatagttgtggaaagagtcaaatggctctcctcaagcgtattcaacaaggggctga<br>aggatgcccagaaggtaccccattgtatgggatctgatctggggcctcggtgcacatgctttacatg<br>tgtttagtcgaggttaaaaaacgtctaggcccccgaaccacggggacgtggttttcctttgaaaaa<br>cacgatgataat |
| 525 | EMCV1 AnrB-<br>3741 | atgtggtcgaagccacttggaataagaccggcgtgcgcttgtctatatgttacttccaccacattgcc<br>gtcttttggcaatgtgagggcccggaacctggccctgtcttcttgacgaacattcctaggggactttc<br>ccctctcgccaaaggaatgtaaggtctgttgaatgtcgtgaaggaagcagttcctctggaagcttctt<br>gaagacaaacagcgtctgtagcgaccctttgcaggcagcggaacccccacctggtaacaggtg<br>cctctgcggccgaaagccacgtgtataagatacacctgcaaaggcggcacaaccccagtgccac<br>gttgtgcgttggatagttgtggaaagagtcaaatggctttccccaagcgtattcaacaaggggctga<br>aggatgcccagaaggtaccccactggttgggatctgatctggggcctcggtgcaggtgctttacac<br>ctgttgagtcgaggttaaaaaacgtctaggcccccgaaccacggggacgtggttttcctagaaaa<br>ccactatgacaat |

TABLE 17-continued

IRES sequences.

| SEQ ID NO | IRES | Sequence |
|---|---|---|
| 526 | Cosavirus D1 | cgtgctttacacggtttttgaaccccacaccggctgtttggcgcttgcaggacagtaggtatattttctt tcatttctcttttctagccgcgtaggttctatctacgcgggcggagtgatactcccgctccttcttggac aggcggcctccacgctctttgtggatcttaaggctgccaagtcactggtgtttgaagtgaagaatgg agagacactagggcgtttcatgtggctttgccagggattgtagcgatgctgtgtgtgtgtgcggattt cccctcgtggcgacacgagcctcacaggccaaaagccctgtccgaaaggacccacacagtggg gttgccccgacccctcccttcaaagctttgtgtaaacaaacttttgtttagactttcttaagcttctctca catcaggccccaaagatgtcctgaaggtaccctgtgtatctgaggatgagcaccaccaactaccc ggacttgtgggacgtgtcccacagacgcatgtggtattccagcccccttccttttgaggagggggct tttgctcgctcagcacaggatctgatcaggagattcatctctggtgctttacaccagagcatggattta aaaattgcccaaggcctggcaaacaacctaggggactaggttttctctattttaaaagatgtcaat |
| 527 | Cosavirus B1 | cgtgctttacacggtttttgaaccccacaccggctgtttggcgcttgcaggacagcaggtttattttctt ttaactctctctttctagccacacacgatctatgtgtgtgggcggagtgatactcccgttccttcttgga caggcggcctccacgccctttgtggatcttaaggctaccaagtcactggtgttggaaagtgaagag aaaggagttccttgggaactacatgtggcattgacagaggttgtagcgatgctgtgtgtgtgtgcgg attacccccgtggcgacacggaccccacaggccaaaagccctgtccgaaaggacccacacagt ggagcaaccccagctccccctcttcaatgttttgtgttagcaaccttggtattattttctctcaagcttcca atacaccgggccccaaagatgtcctgaaggtaccccgtgtatctgaggatgagcaccatcaacta cccggacttgttctttcgagaacagacgcatgtggtaacccagccccgatcctaaggggtcgggg cttttgctcactcagcacaggatctgatcaggagacctcccccccctgctttacagggggcggggg tttaaaaattgcccaaggcctggcaaataacctaggggactaggttttccttttttattttaaagttgtca at |
| 528 | Cosavirus A SH1 | ccgtgctttacacggtttttgaaccccacaccggctgtttggcgcttgcaggacagcaggtttattttc ttatgctctttatttctagccaacagggttctatcctgttgggcggagtgatactcccgttccttcttgga cagattgcctccacgatctttgtggatctcaaggtgatcaagtcactggtaaatagagcgaaggttg aggaaacctgaggaatttccatgtggttttgccaggagttgtagcgatgctgtgtgtgtgtgcggatt tcccctcatggcaacatgagcctcacaggccaaaagccctgtccgaaaggacccacacagtgga gcaatcccagctccctcctacaaagctttgtgagaatgaactcacgttattcttctctttattctctgtttac atcaggccccaaagatgtcctgaaggtaccttgtgtatctgggcatgagcaccatcaactacccgg acttgcatttcggtgcagacacatgtggttacccagcccctctgctttggcagaggggcttttgctcg ctcagcacgagatctgatcaggagcccttcccagtgtgctttacacctggcgggggggttaaaaatt gcccaaggcctggcaaaataacctaggggactaggttttccttttattaacaatgtctgtcatt |
| 529 | Malagasivirus B | ctttatttcttatgtaactcttcttttaagttttattttgcctacttgtgagcttatgcgggaccactgtctta gacaaccccacatttgtcatgagtaagtacacgcaaccattacgattacttttaaccgtctgaccttt gataacaactgaagttaggcgtgaaacatgcatttataccaaagtagccccgcatttccccactacg gtggggggggctaccctactggctttggaactgtagccattatgtgttgcctggctttcaggatctcac aacacaacagttctctcacaatggaatatgggtgagattgcagtgacatgaacaagtatctagtagt acatagactcaagcctagttgcctgcggaacaacatgtggtaacacatgccccagggtccaaaag acaagggttaacagccccttctaggtgtctgtgtgtgaagaatactttagtagtgttgttatgatctcac ctgttagtacagaatgagtatggcttggtgaaggatgtcctacaggtacccattatatggatctgagt aggagaccactagtggtggctttaccgccaggtgagtggtttaaaaagcgtctagccaagccaac agcactagggatagtgctttctatattttatattttcagtgtat |
| 530 | Mosavirus A2 SZAL6 | ccccccccctcaaattgcaacgatatagctaatggcgagattgagatgctatatcacctcttctaagtt atagacctcatctgattgataaggacgtaatttggtcgaaaccgcttggaataagaccgatgcgcgt agtcatgatgatgatgtaagatctaggaacttatccaatctgcttatgtctatgtaagtagaggggca ggcctcattgccctaattctttctaccgagtatctgctagggtttctagcggcttgaatacttggattga gggatacaagatactactgatcgattgtcgattgggaaacttgtagatacttcaaagctaccagtag cgtggactcacagccagcggactacccctcatggtaacatgagcctctgggcccacaaggcacg tcgcaagacctgtgagacggcaaccccagcctagctttgttgaggaaacaagcgataacatgaca tgagagaccggaaggattcttgtattgtgagccgaaggatggcctctaggtacctcattttatgagat ctgaggaggtgctcttgagttggtgctttacactgacaacacagagttaaaaagcgtctaagctcac ccggaaattgggaaatttccgttatttccattttgtttgcaaagtcgttc |
| 531 | SVV | ctgggccctcatgcccagtccttcctttccccttccgggggg taaaccggctgtgtttgctagaggc acagaggagcaacatccaacctgcttttgtggggaacggtgcggctccaattcctgcgtcgccaa aggtgttagcgcacccaaacggcgcatctaccaatgctattggtgtggtctgcgagttctagcctac tcgtttctcccctatccactcactcacgcacaaaaagtgtgctgtaattacaagatttagccctcgcac gagatgtgcgataaccgcaagattgactcaagcgcggaaagcgctgtaaccacatgctgttagtc ccttcatggctgcgagatggctatccacctcggatcactgaactggagctcgaccctccttagtaag ggaaccgagaggccttcttgcaacaagctccgacacagagtccacgtgattgctaccaccatgag tacatggttctcccctctcgacccaggacttctttttgaatatccacggctcgatccagagggtgggg catgatcccccctagcatagcgagctacagcgggaactgtagctaggccttagcgtgccttggatac tgcctgatagggcgacggcctagtcgtgtcggttctataggtagcacatacaaat |
| 532 | PTV A | actagtccttggactttgttgtgtttaaacacagaaatttaattacctggccatgaattcattggattaa cccttctgaaagacttgctctggcgcgagctaaagcgcaattgtcaccaggtattgcaccagtggt ggcgacagggtacagaagagcaagtactcctgaccgggcaatgggactgcattgcatatcccta ggcacctattgagatttctctggggcccaccggcgtggagttcctgtatgggaatgcaggactgga cttgtgctgcctgacagggtcgcggctggccgtctgtactttgtatagtcagttgaaactcacc |

TABLE 17-continued

| SEQ ID NO | IRES | Sequence |
|---|---|---|
| 533 | PTV B | cttccttttaattcgtaactgataagtgatagtccttggaagctaggtatttgttacgctagttttggatta<br>tcttgtgcccaacatttgttttcgaacatatgttgtgtttaaacacagaaatctagtttctttggttatgagt<br>ttaatggaatatccttttgaaagacttgccttggcgcgggctagagcgcaattgtcaccaggtattgc<br>accaatggtggcgacagggtacagaagagcaagtactcctgactgggtaatgggactgcattgca<br>tatccctaggcatctattgagatttctctggagcccaccagcatggagttcctgtatgggaatgcagg<br>actggacttgtgctgcctgacagggtcgcggctggccgtctgtactttgtatagtcagttgaaactca<br>tt |
| 534 | Tottorivirus | cccctttacgtaactgcaacttaaagagtaccctactgcattggatgtgtggtaaacttttacgcacac<br>atttgtagtagtgttagttatgttctacctaatgagtatgcatgcacccgtcgaaacacgcttgtgataa<br>gataggtgagtccatgtgactaatctcattaagataaataagcaccctacaacgcacggcacgctc<br>gtgtcttccgtgcggggccgggacaacagcggcctaaatcttctaggtgaccaccatgcttttggg<br>actatggcaccactgtggacgtgagtacctggcagtaagtctgtgaaaagatggaaggtgtccca<br>agctatggggcgtatgcatatagcctgcggaacaaacaacggcgacgttgtccccagggcccaa<br>aaggcacgtggataagatccacctatatgtttaccccatagtgtaagtcactggaagtcctagtaatg<br>gatgtctggagtaaggctcacggggtagggcgaaggatgcccagaaggtacccgtaggtaacct<br>taagagactatggatctgatctggggaccggatggcgccatcaccatgacgtggaggccggttta<br>aaaaacgtctaagcccgaccaacaacctaggggactaggttttcctttttttattcatgtatgacgtt |
| 535 | Posavirus 1 | acatttccttgcgtgcgcacccgaaaatttattgaacttggcttgaatcataagtaatgcttcttatagc<br>ggacactttgagaatataatgcttgtatggattaatgtatactgttttaaataacaaacctagacacgc<br>agttgcgttgatggttgtatcaatcacatataagtgttgaactcgtgttaatcctcgatcgctatatgttt<br>gccgcctacttccaataaaatagattacatgcgcgtcatgcctttgtgggttacctattggcctctgac<br>aaaaacaagtcgtaagatttgtagcttcccggtgtaaaaagctgggcgcggtctggctctcgtagg<br>gtggaaaggtccaccaatggctggttgagtgtaagctccggtgtcctggttgtcgcaattccaggc<br>gtcgtaataacctatattgcatctgactctaactcttgtggctctactgtatctagttcttgttctactaact<br>ctaataatactactggctctaatactgaaaaacttacatatgttaatatagataatatccttgatcctgat<br>atccctcacgtcactgaagttcgccgaaaacgaatttcagatcatatcattgaatctcaaggatgtac<br>ttgctctgaacctactataactcctcatgcgttttcattttctactcttggc |
| 536 | A105-675 | ccacccacagcaagaatgccatcatctgtcctcacccccatttctcccctccttcccctgcaaccatt<br>acgcttactcgcatgtgcattgagtggtgcacgtgttgaacaaacagctacactcacgtgggggcg<br>ggttttcccgcccttcggcctctcgcgaggcccacccttccccttcctcccataactacagtgctttg<br>gtaggtaagcatcctgatcccccgcggaagctgctcgcgtggcaactgtggggacccagacagg<br>ttatcaaaggcacccggtctttccgcctccaggagtatccctgctagtgaattctagtggggctctgc<br>ttggtgccaacctcccccaaatgcgcgctgcgggagtgctcttccccaactcaccctagtatcctct<br>catgtgtgtgcttggtcagcatatctgagacgatgttccgctgtcccagaccagtccagcaatggac<br>gggccagtgtgcgtagtcgtcttccggcttgtccggcgcatgtttggtgaaccggtggggtaaggt<br>tggtgtgcccaacgcccgtactttggtgacaactcaagaccacccaggaatgccagggaggtacc<br>ccgcctcacggcgggatctgaccctgggctaattgtctacggtggttcttcttgcttccatttctttctt<br>ctgttc |
| 537 | A110-675 | acctttgtgcgcctgttttatacccccctcccccaactgtaacttagaagtaacacacaccgatcaaca<br>gtcagcgtggcacaccagccacgttttgatcaagcacttctgttaccccggactgagtatcaataga<br>ctgctcacgcggttgaaggagaaagcgttcgttatccggccaactacttcgaaaaacctagtaaca<br>ccgtggaagttgcagagtgtttcgctcagcactaccccagtgtagatcaggtcgatgagtcaccgc<br>attccccacgggcgaccgtggcggtggctgcgttggcggcctgcccatggggaaacccatggg<br>acgctctaatacagacatggtgcgaagagtctattgagctagttggtagtcctccggcccctgaatg<br>cggctaatcctaactgcggagcacacaccctcaagccagagggcagtgtgtcgtaacgggcaac<br>tctgcagcggaaccgactactttgggtgtccgtgtttcattttattcctatactggctgcttatggtgac<br>aattgagagatcgttaccatatagctattggattggccatccggtgactaatagagctattatatatcc<br>ctttgttgggtttataccacttagcttgaaagaggttaaaacattacaattcattgttaagttgaatacag<br>caaa |
| 538 | 18-675 | cccacagcaagaatgccatcatctgtcctcacccccaatttcccttttcttcccctgcaaccattacg<br>cttactcgcatgtgcattgagtggtgcatgtgttgaacaaacagctacactcacatgggggcgggtt<br>ttcccgccctacggcctctcgcgaggcccaccccttccctccccttataactacagtgctttggtag<br>gtaagcatcctgatcccccgcggaagctgctcacgtggcaactgtggggacccagacaggttatc<br>aaaggcacccggtctttccgccttcaggagtatccctactagtgaattctagcggggctctgcttggt<br>gccaacctcccccaaatgcgcgctgcgggagtgctcttccccaactcaccctagtatcctctcatgt<br>gtgtgcttggtcagcatatctgagacgatgttccgctgtcccagaccagtccagtaatggacgggc<br>cagtgcgtgtagtcgtcttccggcttgtccggggcatgtttggtgaaccggtggggtaaggttggtg<br>tgcccaacgcccgtactttggtgacacctcaagaccacccaggaatgccagggaggtaccccac<br>ctcacggtgggatctgaccctgggctaattgtctacggtggttcttcttgcttccacttctttcttctgttc<br>acg |
| 539 | A115-675 | acctttgtgcgcctgttttatacccccccccaacctcgaaacttagaagtaaagcaaacccgatcaata<br>gcaggtgcggcgcaccagtcgcatcttgatcaagcacttctgtaaccccggaccgagtatcaata<br>gactgctcacgcggttgaaggagaaaacgttcgttacccggctaactacttcgagaaacccagta<br>gcatcatgaaagttgcagagtgtttcgctcagcactacccccgtgtagatcaggccgatgagtcac<br>cgcacttccccacgggcgaccgtggcggtggctgcgttggcggcctgcctatggggcaacccat<br>aggacgctctaatacggacatggtgcgaagagtctattgagctagttagtagtcctccggcccctg<br>aatgcggctaatcctaactgcggagcacataccctta atccaaagggcagtgtgtcgtaacgggta |

TABLE 17-continued

IRES sequences.

| SEQ ID NO | IRES | Sequence |
|---|---|---|
| | | actctgcagcggaaccgactactttgggtgtccgtgtttccttttaatttttactggctgcttatggtgac aattgaggaattgttgccatatagctattggattggccatccggtgactaacagagctattgtgttcca atttgttggatttaccccgctcacactcacagtcgtaagaacccttcattacgtgttatttctcaactcaa gaaa |
| 540 | A73-675 | ttactccattcagcttcttcggaacctgttcggaggaattaaacgggcacccatactccccccaccc ccctttttgtaactaagtatgtgtgctcgtgatcttgactcccacggaacggaccgatccgttggtgaa caaacagctaggtccacatcctcccttcccctgggagggcccccgccctcccacatcctcccccc agcctgacgtatcacaggctgtgtgaagcccccgcgaaagctgctcacgtggcaattgtgggtcc ccccttcatcaagacaccaggtctttcctccttaaggctagccccggcgtgtgaattcacgttgggc aactagtggtgtcactgtgcgctcccaatctcggccgcggagtgctgttccccaagccaaacccct ggcccttcactatgtgcctggcaagcatatctgagaaggtgttccgctgtggctgccaacctggtga caggtgccccagtgtgcgtaaccttcttccgtctccggacggtagtgattggttaagatttggtgtaa ggttcatgtgccaacgccctgtgcgggatgaaacctctactgccctaggaatgccaggcaggtac cccacctccgggtgggatctgagcctgggctaattgtctacgggtagtttcatttccaatccttttatgt cggagtc |
| 541 | Kobuvirus 16317 | ttactccattcagcttcttcggaacctgttcggaggaattaaacgggcacccatacaccccccatccc ctttctgcaacttaagtatgtgtgctcgtgatcttgactcccacggaatggatcgatccgctggagaa caaactgctagatccacatcctcccttcccctgggaggaccttggtcctcccacatcctccccccag cctgacgtaccacaggctgtgtgaagcccccgcgaaagctgctcacgtggcaattgtgggtcccc ccttcatcaagacaccaggtctttcctccttaaggctagccccgatgtgtgaattcacattgggcaac tagtggtgtcactgtgcgctcccaatctcggccgcggagtgctgttccccaagccaaacccctggc ccttcactatgtgcctggcaagcatacctgagaaggtgttccgctgtggctgccagcctggtaaca ggtgccccagtgtgcgtaaccttcttccgtcttcggacggtagtgattggttaagatttggtgtaaggt ccatgtgccaacgccctgtgcgggatgaaacctctactgccctaggaatgccaggcaggtacccc acccccgggtgggatctgagcctgggctaattgtctacgggtagtttcatttccaattcttttatgtcg gagtc |
| 542 | Aichivirus Chshc7 | ttactccattcagcttcttcggaacctgttcggaggaattaaacgggcacccatacatccccatcccc tttctgtaacttaagtatgtgtgcttgtaatcttgactcccacggaatggatcgatccgctggagaaca aactgctagatccacatcctcccttcccctgggaggaccttggtcctcccacatcctcccccccagcc tgacgtaccacaggctgtgtgaagcccccgcgaaagctgctcacgtggcaattgtgggtcccccc ttcatcaagacaccaggtctttcctccttaaggctagccccgatgtgtgaattcacattgggcaacta gtggtgtcactgtgcgctcccaatctcggccgcggagtgctgttccccaagccaaacccctggcc cttcactatgtgcctggcaagcatatctgagaaggtgttccgctgtggctgccagcctggtaacagg tgccccagtgtgcgtaaccttcttccgtctccggacggtagtgattggttaagatttggtgtaaggttc atgtgccaacgccctgtgcgggatgaaatctctactgccctaggaatgccaggcaggtaccccac cctcgggtgggatctgagcctgggctaattgtctacgggtagtttcatttccaatccttttatgtcgga gtc |
| 543 | Aichivirus Goiania | actccattcagcttcttcggaacctgttcggaggaattaaacgggcacccatacaccccccatcccct tttttgcaacttaagtatgtgtgctcgtaatcttgactcccacggaatggatcgatccgctggagaaca aactgctagatccacatcctccctccccccctgggaggacctcggtcctcccacatcctccccccag cctgacgtatcacaggctgtgtgaagcccccgcgaaagctgctcacgtggcaattgtgggtcccc ccttcatcaagacaccaggtctttcctccttaaggctagtcccgatgtgtgaattcacatcgggcaac tagtggtgtcactgtgcgctcccaatctcggccgcggagtgctgttccccaagccaaacccctggc ccttcactatgtgcctggcaagcatatctgagaaggcgttccgctgtggctgccagcctggtaaca ggtgccccagtgtgcgtaaccttcttccgtccccggacggtagtgattggttaagacttggcgtaag gttcatgtgccaacgccctgtgcgggatgaaacctctactgccctaggaatgccaggcaggtacc ccaccttcgggtgggatctgagcctgggctaattgtctacgggtagtttcatttctaattctttcatgtc ggagtc |
| 544 | Aichivirus ETHP4 | ttactccattcagcttcttcggaacctgttcggaggaattaaacgggcacccatacaccccccacccc ctttttgcaacttaagtatgtgtgctcgtgatcttgactcccacggaatggatcgatccgctggagaa caaactgctagatccacatcctcccttcccttgggaggacctcggtcctcccacatcctccccccag cctgacgtaccacaggctgtgtgaagcccccgcgaaagccgctcacgtggcaattgtgggtccc cccttcattaagacaccaggtctttcctccttaaggctagtcccgatgtgtgaattcacattgggcaac tagtggtgtcactgtgcgctcccaatctcggccgcggagtgctgttccccaagccaaacccctggc ccttcactatgtgcctggcaagcatatctgagaaggtgttccgctgtggctgccagcctggtaacag gtgccccagtgtgcgtaaccttcttccgtcttcggacggtagtgattggttaagatttggcgtaaggtt catgtgccaacgccctgtgcgggatgaaacctctactaccctaggaatgccaggcaggtacccca ccctcgggtgggatctgagcctgggctaattgtctacgggtagtttcatttccaattcttctatgtcgg agtc |
| 545 | Aichivirus DVI2169 | tactccattcagcttcttcggaacctgttcggaggaattaaacgggcacccatacaccccccaccccc ttttctgcaacttaagtatgtgtgctcgtaatcttgactcccacggaatggatcgatccgctggagaac aaactgctagatccacatcctcccttcccctgggaggaccccggtcctcccacatcctccccccag cctgacgtatcacaggctgtgtgaagtccccgcgaaagctgctcacgtggcaattgtgggtccccc cttcatcaagacaccaggtctttcctccttaaggctagccccgatgtgtgaattcacattgggcaact agtggtgtcactgtgcgctcccaatctcggccgcggagtgctgttccccaagccaaacccctggc |

TABLE 17-continued

IRES sequences.

| SEQ ID NO | IRES | Sequence |
|---|---|---|
| | | ccttcactatgtgcctggcaagcatatctgagaaggtgttccgctgtggctgccagcctggtaacag<br>gtgccccagtgtgcgtaaccttcttccgtctccggacggtagtgattggttaagatttggtgtaaggtt<br>catgtgccaacgccctgtgcgggatgaaacctctactgccctaggaatgccaggcaggtacccca<br>ccttcgggtgggatctgagcctgggctaattgtctacgggtagtttcatttccaattcttttatgtcgga<br>gtc |
| 546 | Aichivirus DVI2321 | gcttcttcggaacctgttcggaggaattaaacgggcacccatacacccccacccccttttctgcaac<br>ttaagtatgtgtgctcgtaatcttgactcccacggaatggatcgatccgctggagaacaaactgcta<br>gatccacatcctcccttcccctgggaggaccccggtcctcccacatcctcccccagcctgacgta<br>tcacaggctgtgtgaagtccccgcgaaagctgctcacgtggcaattgtgggtccccccttcatcaa<br>gacaccaggtctttcctccttaaggctagccccgatgtgtgaattcacattgggcaactagtggtgtc<br>actgtgcgctcccaatctcggccgcggagtgctgttccccaagccaaaccccctggcccttcactat<br>gtgcctggcaagcatatctgagaaggtgttccgctgtggctgccagcctggtaacaggtgcccca<br>gtgtgcgtaaccttcttccgtctccggacggtagtgattggttaagatttggtgtaaggttcatgtgcc<br>aacgccctgtgcgggatgaaacctctactgccctaggaatgccaggcaggtaccccaccttcggg<br>tgggatctgagcctgggctaattgtctacgggtagtttcatttccaattcttttatgtcggagtc |
| 547 | Aichivirus rat08 | tactccattcagcttcttcggaacctgttcggaggaattaaacgggcacccactttcctgtcctctccc<br>cttttctgtaactccaagtgtgtgctcgtaatcttgactcccgcggattgaccgctccgctggtgaaca<br>aactgctaggtcatctcctccccacccttgggcgtccttccgggcgtccacaccctcccccagcc<br>tgacgtgtcacaggctgtacaaagaccccgcgaaagctgctaacgtggcaattgtgggtcccccc<br>tttgtaaaggaaccgagtctttctcccttaaggctagacccctgtgtgaattcacaggtggcaactag<br>tggttccactgcatgctcccgacctcggccgcggagtgctgttccccaagtcgtaacactgaccttc<br>acttatgtgcctggcaagcatatctgagaagatgttccgctgtggctgccaaacctggtaacaggtg<br>ccccagtgtgcgtagtcttcttccgtcttcggacggtaggtgttaggtaaagatgcggcgtaaggtt<br>caagtgccaacgccctggaagggatgacccttctactgccctaggaatgccgcgcaggtacccc<br>aggttcgcctgggatctgagcgcgggctaattgtctacgggtagtttcatttccctcttcttccactgg<br>catc |
| 548 | Aichivirus Rt386 | actccattcagcttcttcggaacctgttcggaggaattaaacgggcacccactttcctgtcctctccc<br>cctttctgcaactcaagtgtgtgctcgtaatcctgactcccacgggttgaccgccccgttggtgaac<br>aaacagctaggtcattccctccctacccctgggcgccatttcagtggcgttcatatcctcccccag<br>cctgacgtgtcacaggctgtgcaaagtccccgcgaaagctgctcacgtggcaattgtgggtcccc<br>cctttgtgaaggaaccgagtctttctcccttaaggctagacccctgtgtgaactcacaggtggcaac<br>tagtggttccactgcatgctcccgacctcggccgcggagtgctgttccccaagtcgtgacactgac<br>ctccacttatgtgcctggcaagcatatctgagaagatgttccgctgtggctgccaaacctggtaaca<br>ggtgccccagtgcgtgtagtcttcttccgtctccggacggtaagtgtgtggtaaagatgcggcgtaa<br>ggttcaagtgccaacgccctggaagggatgacccttctactgccctaggaatgccgcgcaggtac<br>cccaggttcgcctgggatctgagcgcgggctaattgtctacgggtagtttcatttccctctcttttcact<br>ggcatc |
| 549 | Norway Rat Pestivirus | gtataagggttgggaaccttgtaccaagctacctctgccattcagtatttgggagtagaagtagatgt<br>gtttacaaactcacacgtgtgggggcggggatagactgtgccagcggtcgtgtaccagcacctac<br>gcatacgtgtggactgcgaaccaggagagcacctaggtctgacaagctgtgagaacacagtagt<br>cgtcagtgagtcagctggtaaggatcacccacctggatactcacgtggacgagggagtttcccag<br>tcagaaacctacaccagaggaggggtcctctggagacatggatggtctgagtaacagactatcta<br>ctggggtgtgctgcctgacagggtctcggctgatagcctggctagcagtataaaaatcagttgaatt<br>ggcatatgagttgtgaacatctagtaaacaatgaaagacaaaaacaaaaaatgagcataataaaaa<br>aattgtacaatccactactcaggtgtggctgcagactt |
| 550 | Porcine Kobuvirus GS2 | tttgaaaaggggggtggggggcctcggccccctcaccctcttttccggtggccattcgcccgggc<br>caccgttactccactccactccttcgggactggtttggaggaacacaacagggcttcccatccctgt<br>ttaccctttattccatcatcctttccccaagtttaccctatccacaccccactgactgactcctttggattt<br>tgacctcagaatgcctatttgacctcccactcgcctctcccttttcggattgccggtggtgcctggcg<br>gaaaaagcacaagtgtgttgcaggctaccaaactcctacccgacaaaggtgcgtgtccgcgtgct<br>gagtaatgggataggagatgcctacaacaggctcgcccatgagtagagcatggactgcggtgca<br>tgtgacttcggtcaccacgggcatagcattgctcacccgtgaatcaagtcatcgagatttctctgacc<br>tctgaagtgcactgtggttgcgtggctgggaatccacgcttgaccatgtactgcttgatagagtcgc<br>ggctggccgactcatgggttaaagtcagttgacaagacac |
| 551 | Kobuvirus SZAL6 | cctacccaagggttacatgggaccatattcctcctcccctgtaactttaagttttgtgcccgtattcttg<br>actccaggcggatgttgtgtcgcccgtcctgtgaacaaacagctagacactttcctcccctccctct<br>gggctgctccggcagtccactccctcccccccagcgtaacatgccccgctggagtgatgcacctgg<br>aagtcgtggacgtgggttagtaacttcggtgaaaacccactataatgacaactggttgacccccac<br>actcaaaggactcgagtctttctcccttaaggctagcccggccacatgaatttgcagctggcaacta<br>gtgagtccaccatgtcccgcaacctcggctgcggagtgctgttccccaagcgtatgccttccttctg<br>taagagtgcgcctggcaagcacatctgagaagtcgttccgctgcgtcgtgccaacctggcgacag<br>gtgacccagtgtgcgtagacttcttccggattcgtccggctcttctctaggaaacatgcgtgtaaggt<br>tcatgtgccaaagccctgcgcgcggtgttcttctactgccctaggaatgtgccgcaggtacccctac<br>ttcggtagggatctgagcggtagctaattgtctacgggtagtttcatttccatcttctcttcaggtcgac<br>atc |
| 552 | Kobuvirus sheep TB3 | gaccttctggtacttcttcgcctgggtcacaaaagcgaagaacctgcctctctaacgccagacgag<br>cggcattaaacttgaacttctggcactctccactctcccttttccctgtccctttccccactgcgctctc<br>aaggtcgcgcaatcctgggactagcccagttttaaaagttcctggcaccctttgcccctctaggccc |

TABLE 17-continued

IRES sequences.

| SEQ ID NO | IRES | Sequence |
|---|---|---|
| | | ttaaggtaggaactgaccttgtgctgtgatctcggtgcgggagtgctaccacgtagtcatcgtaagc<br>ctcgtttctggttctgccctggcaaggctacagagtaccgtgttccgctgtggatgccatccgggta<br>accggacccccagtgtgtgtagcggtatgttcacggtccgccgtgttcaccagattcctgacctgg<br>ctttgctagaaatggtgtgtgcccaatccctgtgaccagtatcaattacatcacctaggaatgctagg<br>aaggtaccccagtcctgagctgggatctgatcctaggctaattgtctacggtgatgctccttttattttc<br>ttacaactgctattgactgtctgattgctgattctgctcttgtgctcttctgctctggctcattctcaaggg<br>ttctctttgtccaagatcctttggttctctccttgttccacttgccactgccaacgcttgtc |
| 553 | Pronghorn antelope pestivirus | gtatacgcagttagttcatcctgtgtatacagattggagactctaaaaacaacgattcggaataggg<br>gcccgcggcgaagaccgaagacaggctaaccatgccgttagtagggctagcaccaaaacgcg<br>ggaactagacacttaggagagtggtctggctactctaagaggtgagtacaccttaaccgtcaagg<br>gttctactcctcagttgaggactagagatgccctgtggacgggggcatgcccaagagttagcttag<br>ccggggcgggggttgttccggtgaaagtagcaatattgaccacactgcctgatagggcggagca<br>ggccccctaggtagtctagtataaaatgtctgctgtacatggcac |
| 554 | Porcine pestivirus isolate Bungowannah | tacgcggggtataacgacagtagttcaagtgtcgttatgcatcattggccataacaaattatctaattt<br>ggaatagggacctgcgacctgtacgaaggccgagcgtcggtagccattccgactagtaggacta<br>gtacaaataggtcaactggttgagcaggtgagtgtgctgcagcggctaagcggtgagtacaccgt<br>attcgtcaacaggtgctactggaaaggatcacccactagcgatgcctgtgtggacgaggacatgtc<br>caagccaatgttatcagtagcgggggtcgttactgagaaagctgcccagaatgggtagttgcacat<br>acagtctgataggatgccggcggatgccctgtattttgaccagtataaatattatccgttgtaaagcat |
| 555 | Porcine pestivirus 1 | gcagatatcggtggtggacctggggggttgggctcaccgtgccccttcatggggtagacctcactg<br>cttgatagagtgccggcggatgcctcaggtaagagtataaaatccgttgttcactaac |
| 556 | Pestivirus giraffe-1 | gtatacgagtttagctcaatcctcgtatacaatattgggcgtcaccaaatatagatttggcataggca<br>acaccccgatgcgaaggccgaaaagggctaaccatgcccttagtaggactagcaaaaaatcggg<br>gactagcccaggtggtgagcttcctggatgaccgaagccctgagtacagggcagtcgtcaacagt<br>tcaacacgcagaataggtttgcgtcttgatatgctgtgtggacgagggcatgcccacggtacatctt<br>aacctatccgggggtcggataggcgaaagtccagtattggactgggagtacagcctgatagggtg<br>ttgcagagacccatctgataggctagtataaaaaactctgctgtacatggcac |
| 557 | Classical swine fever virus | gtatacgaggttagttcattctcgtatgcatgattggacaaattaaaatttcaatttggatcagggcctc<br>cctccagcgacggccgaactgggctagccatgcccacagtaggactagcaaacggagggacta<br>gccgtagtggcgagctccctgggtggtctaagtcctgagtacaggacagtcgtcagtagttcgac<br>gtgagcagaagcccacctcgatatgctatgtggacgagggcatgcccaagacacaccttaaccct<br>agcgggggtcgctagggtgaaatcacaccacgtgatgggagtacgacctgatagggtgctgcag<br>aggcccactattaggctagtataaaaatctctgctgtacatggcac |
| 558 | Human pegivirus isolate JD2B1I | tcagggttggtaggtcgtaaatcccggtcaccttggtagccactataggtgggtcttaagagaaggt<br>taagattcctcttgtgcctgcggcgagaccgcgcacggtccacaggtgttggccctaccggtggg<br>aataagggcccgacgtcaggctcgtcgttaaaccgagcccgtcacccacctgggcaaacgacgc<br>ccacgtacggtccacgtcgcccttca |
| 559 | Human pegivirus isolate GBV-C-ZJ | cccggcactgggtgcaagccccagaaaccgacgcctatttaaacagacgttatgaaccggcgcc<br>gacccggcgaccggccaaaaggtggtggatgggtgatgccagggttggtaggtcgtaaatcccg<br>gtcatcttggtagccactataggtgggtcttaagggttggtcaaggtccctctggcgcttgtggcga<br>gaaagcgcacggtccacaggtgttggccctaccggtgtgaataagggcccgacgtcaggctcgt<br>cgttaaaccgagcccattacccacctgggcaaacaacgcccacgtacggtccacgtcgccctaca<br>atgtctctcttgaccaataggctttgccggcgagttgacaaggaccagtgggggctgggcgacgg<br>gggtcgtataggaagaaaaatgccacccgccctcacccgaaggttcttgggctaccccggctgca<br>ggccgccgcggagctggggtagcccaagaaccttcgggtgagggcgggtggcatttttcttccta<br>taccgatc |
| 560 | Human pegivirus isolate JD2B8C | tggtcaccttggtagccactataggtgggtcttaagagaaggttaagattcctcttgtgcctgcggcg<br>agaccgcgcacggtccacaggtgttggccctaccggtgtgaataagggcccgacgtcaggctcg<br>tcgttaaaccgagcccatttcccgcctgggcaaacgacgcccacgtacggtccacgtcgcccttttt<br>aatgtctctcttgaccaataggttcatccggcgagttgacaaggaccagtgggggccgggggtca<br>cagggatggaccctgggccctgcccttcccggcggggtggggaaagcatggggccacccagct<br>ccgcggcggcctgcagccggggtagcccaagaaccttcgggtgagggcgggtggcatttttctt<br>cctataccgatc |
| 561 | Hepatitis GB virus A | gccgggtggaaggcccggaaccgccccaccacctcaactaggtggtaagggtacgtctatcggt<br>ccggctggcccgaaaggcggtggatcctgtgtgttagggttcgtaggtggtaaatcccagcacag<br>gtggtaatcgctatagggcaggcttatcccggtgaccgcttccctggatcctggagcgggtcgtgg<br>cggcacggtccacaggagtggggcctccggtgtgaataagccctcgtctggagcatcagacgtt<br>aaactgagacgtcccgaagagatcggaacgacgccccacgtatggcaacgccgcttaaaaccct<br>tcggggacagctatgcgggttgacaatgccagtgggggccgggcccactattgttgtgggctcc<br>gagttcctctagggatggccgaaaggcagccatggggccacccaggcggcgccgtgctacagg<br>cggcaaggggaaaaatccttcgggtgaccccgggtggcattccctcccttagcagcatgagtgtg<br>gtggtagctgcaacc |
| 562 | Simian pegivirus | ggggaatctcacccccccgtccggttccggaagaatcggaaaccgacaccctgaccaatcattctt<br>gatcatagagtggatgttagtgaaagccagacgaaagccggcggatgggtggtgacagggttgg<br>taggtcgtaaatcccggccaccctggtacccggtataagttgggcggaagctgactgaagctccg |

TABLE 17-continued

IRES sequences.

| SEQ ID NO | IRES | Sequence |
|---|---|---|
| | | tgctcttttctgtgcgttcttggtgcacggtccacaggtgacgcctataccggtgtgaataataggcc<br>gactcgagcggagtcgttaaactgagaacctccatacggatggcaacttggcttgcgtacgggga<br>cgccgctaaagtcacagtgggttaagtccggcgggttgacaaccccagcaaggcgagggggtc<br>ctattgttggactctgccagttcccggtggaggtaggcatggggtggcccagctccgcggcgcgc<br>tacagccggggtagcccaaaatccgaaaggtgagggcgggccacatgtccgaaatttagtcaag<br>c |
| 563 | Pegivirus 1 | agaatggtctaagtggttgccaccgtggtccgaaggggaggaggacctacgctgccagggttgg<br>caggtcgtaaatcccgggtgtaggagatccctccttgttaggactgctggtagctgggggtcggt<br>gaccccctgggcaaccgccaaacccggacgaccgggtggcggctccatgttggcacggtccac<br>aggtgtgaaccctaccggtgtgaataagggttggtggttgcggtccaccttaaacgtagtatgcatt<br>gggcttggtaaaacaccgctcgtagtacggaacgccgcctttaaagacacagtaggcgtagccg<br>gcgggttgacaatccatacgggggtggggtgtggtcatggatctgtccacaccaccttcatgcg<br>gccctctaagcaagccataccgggggggaggcgcgcggcaccgcactgccgggcaaggggaa<br>gaaccttcgggtgaccccccccaaccaccgtccgatcaatgctaatgttgcgtttaggcgtgaca<br>ccggcaca |
| 564 | Pegivirus K | agaatggtgtgatccgtcgccgctccagcggaaagcgggcgggatctagtggttagggttgttcg<br>cgtaaatcccacactagtggtacgctcgtataacgtgggagcagccggTggggtcgaccccccc<br>Acctggcggctgctgagcaccggacgaagcgcgggggggtgaacgctaacccgcggcccggg<br>ctgccaacgttaggcacgtcttggctggaagacgttaaacacagggccccccctcaaccctgatc<br>cgaggccagagaccaaggtacgccgccctttttaaaggcgttactcgtccaataggatctctccgg<br>cgggttgtcaaaccttgctggccctggtgatggttacgggagggggtggggcggggagtagaag<br>ccccgcccggcatgggggtaccaagctcggcacgcccagcacgcgtggcgtaggggaaaaat<br>ccttcgggtgacccctggtaccataaagtaattaacatgagcatgccgctagggtgtgctttttcttcc<br>ttccttgggaaggcggtggcacc |
| 565 | Theiler's disease-associated virus | tgataccgtgtcccggtacgacctcgcgcgtccccaagctcgccctgagggggggagcgtaaggg<br>cgcgtagtggggtagccccccaaaccgagccaccctagtgagtgactttagaatggttagggaga<br>ctaccgccttcgctgtttggggacctaatgatccgcgtgccagggttcttcgggtaaatcccggcgc<br>ggtgttttgggttcagggcagtaggggcagacgggccagcagtcgctggttcctggtaccaccac<br>cctatccggacgacctccctcacgaaaggtcgccacggtctgtggctcgacgacgcctataattca<br>gtccgagggggcgcagccctcgttaaacttaggcaaggttcctcgccattgatttggccaggggttt<br>aagtgaacgccgcccttttaatgtttaatagggttctttcccggcgggttgacaaacacttccctggg<br>ctcttcgttggcctcggttccttgatgcttcggcacccatgagcgcacagggggggggaccctgcga<br>cagtccgccaagaggaaaatccttcgggtgacctcgtgcgcaacccaatcccttcttcttccacatg<br>gcgtgtctgtggtgcatgctgtg |
| 566 | Rodent pegivirus | ggacttcggtccccctgttactctgcgagccaccgcagagccagggttggtacgcccgaggtgtt<br>agaccccggccgaaagctcctaaccatggggttagtaggacgtggtaaatgccactgaggggtt<br>ggagagctggtagagcgagtaagtcggcgtaaggcccgagtacgggcctcccagcccgggtca<br>gcctaaacctggctgtgatacccggtgcatggagggcgtgtcccaacgctcgatcgctgtagggt<br>gggtccctgcagttgggtgtggctaccctgctcgtactgcttgatagagtcccggcggacggacc<br>agctctcgtcagtccgtggagttgcac |
| 567 | Human pegivirus 2 | aactgttgttgtagcaatgcgcatattgctacttcggtacgcctaattggtaggcgcccggccgacc<br>ggccccgcaagggcctagtaggacgtgtgacaatgccatgagggatcatgacactggggtgag<br>cggaggcagcaccgaagtcgggtgaactcgactcccagtgcgaccacctggcttggtcgttcatg<br>gagggcatgcccacgggaacgctgatcgtgcaaagggatgggtccctgcactggtgccatgcg<br>cggcaccactccgtacagcctgatagggtggcggcgggcccccccagtgtgacgtccgtggag<br>cgcaac |
| 568 | GB virus C/Hepatitis G virus | cccccggcactgggtgcaagccccagaaaccgacgcctatctaagtagacgcaatgactcggcg<br>ccgactcggcgaccggccaaaaggtggtggatgggtgatgacagggttggtaggtcgtaaatcc<br>cggtcaccttggtagccactataggtgggtcttaagagaaggttaagattcctcttgtgcctgcggc<br>gagaccgcgcacggtccacaggtgttggccctaccggtgggaataagggcccgacgtcaggct<br>cgtcgttaaaccgagcccgttacccacctgggcaaacgacgcccacgtacggtccacgtcgccct<br>tcaatgtctctcttgaccaataggcgtagccggcgagttgacaaggaccagtgggggccggggg<br>cttggagagggactccaagtcccgcccttcccggtgggccgggaaatgc |
| 569 | Equine Pegivirus 1 | agaatggggagttaactcctggcactggcccgaagcatgaactgatcgcggtggcagggttcttc<br>gggtaaatcccggccgcgtgttgtgattgtgttagggcaggtgacagtcggcagggtcgaccccc<br>tgcttcaggaccactgtcttcctggacgaccgttgctgaaaaagggccgccacggtctgtagctcg<br>ccgacgcttctaattcaggccggaggaccacgctccgtaatcgagcccaagtactcaaaccccag<br>cacccctgggtcacgccctacgccgcccttttaacgcttcggctaatagggtctatccggcgggtt<br>gacaaagggcgcagggttacctggtactacgagcttgggtgtccctgggagtaatcccagggtgc<br>c |
| 570 | Culex theileri flavivirus | atataaatcccagtttggttaaacctatttcaaggcttaagttgtttattattttatcgccgctcgtgactat<br>aaagttgcctagcggagagagataaagaagaaggagttcaaggctcagggcagggcgcaagtt<br>ccctggtccctaggccgctcgcaggaaggaggagtgaagaagaagaaagagaaggagaggac<br>caccgccgaaagaaggcaggtgcctcacaagagggccaaccagcgtgttggaccagtggcca<br>acgccggacggcgtggtggcctgctgggacgcctggggattggatggagtgccttcctacagga<br>agacatcgttcaagccatc |

TABLE 17-continued

IRES sequences.

| SEQ ID NO | IRES | Sequence |
|---|---|---|
| 571 | Bussuquara virus | agtatttcttctgcgtgagaccattgcgacagttcgtaccggtgagttttgacttaacgcagtgagaa aagttttcgaggaaagacgagaagcgaattctctga |
| 572 | Zika Virus | agttgttgatctgtgtgagtcagactgcgacagttcgagtctgaagcgagagctaacaacagtatca acaggtttaatttggatttggaaacgagagtttctggtc |
| 573 | Yokose virus | agtaaattttgcgtgctagtcgctgagcgtcagaccgcaaagtgagtttttagtgatctaaagtgagg agttattcttactgtcatcaaacactacaaataaacacgttgaaattatttccggaagaacaactgtcc ggaatcaaagacg |
| 574 | Wesselsbron virus | agtatattctgcgtgctaatcgttcgacgttagtccgtggagtgagcttctattagagtcgttaacacg tttgaataatttctactgaaaggagtagaagaaaggagattcattccca |
| 575 | Equine hepacivirus | acctccgtgctatgcacggtgcgttgtcagcgttttgcgcttgcatgcgctacacgcgtcgtccaac gcggagggattcttccacattaccatgtgtcactccccctatggagggttccaccccgcccacacg gaaataggttaaccatacctatagtacgggtgagcgggtcctcctagggcccccccggcaggtcg agggagctgaaattcgtgaatccgtgagtacacggaaatcgcggcttgaacgtcatacgtgacctt cggagccgaaatttgggcgtgccccacgaaggaaggcgggggcggtgttgggccgccgcccc ctttatcccacggtctgataggatgcttgcgagggcacctgccggtctcgtagaccataggac |
| 576 | Hepacivirus B | accacaaacactccagtttgttacactccgctaggaatgctcctggagcaccccccctagcagggc gtgggggatttcccctgcccgtctgcagaagggtggagccaaccaccttagtatgtaggcggcgg gactcatgacgctcgcgtgatgacaagcgccaagcttgacttggatggccctgatgggcgttcatg ggttcggtggtggtggcgctttaggcagcctccacgcccaccacctcccagatagagcggcggc actgtagggaagaccggggaccggtcactaccaaggacgcagacctctttttgagtatcacgcct ccggaagtagttgggcaagcccacctatatgtgttgggatggttggggttagccatccataccgta ctgcctgatagggtccttgcgaggggatctgggagtctcgtagaccgtagcac |
| 577 | Hepacivirus I | cagggtttcgaccctggcccggatacctatcgccttacgccgaaaggtaacgagtaggagtcggg tccccaggcccttaccgccaccaagccaggtggggaggtatgggagccgggggtgcagctg gtagctccatgggggacgccccgtgagcggatgctgcatcgataccgggttagctctctgggaga gcggcacttgacaccacgaatccgggaaccggacaatcgccggcgtgggacgcgttgcctccg tggccgagcaatttggcatgcccgtggtgaagagtgatggtgggggggggcccccttccagta ccgtactgcctgatagggtcttgcctcaagcccagagagtcgaggctgaaaaccgccatc |
| 578 | Hepacivirus J | gccgctcccgaaagggagtccggcgcgtcatcccactccgaggagtggggtggcgtccccgtg tgccggggaaccatgaagcctaagggcatccacattttagaatgaacttgaagcttcgtttcgctgg ccggaaagtcctgggttcccatggccagggttccgcaggtgggtaaatcccggtggggttccatc caggatatacggcaggcgggcgtagtccggcggttcggacgacgtgtgggtcgcctacggtgg attgttcacaggatgggcactccggtgtgaataggccccgtcagggtgcgctgacgttaaactcag gccttgcctggtgttcggggaggattgcagggccacgccgcctctaagggccgtatggcacagta cttcttcgggcgggttgtcaaggccctccaacgcgacaccagtgcctcggcaggcatggggcca cccagctcggcgtcccgcacacagacggcgtaggggaaaatcagcaatgtgaccccgggtggc attttccttctctctacttccatgcatgatcaaccgcaatc |
| 579 | Hepacivirus K | gggaacaatggtccgtccgcggaacgactctagccatgagtctagtacgagtgcgtgccacccat tagcacaaaaaccactgactgagccacacccctcccggaatcctgagtacaggacattcgctcgg acgacgcatgagcctccatgccgagaaaattgggtatacccacgggtaaggggtggccacccag cgggaatctgggggctggtcactgactatggtacagcctgatagggtgctgccgcagcgtcagtg gtatgcggctgttcatggaac |
| 580 | Icavirus | cgaagtttaagctaagcaccctcgggcgttcccggattatgtgatcacatcaatttgatggctggtca ccacgcaacgcctggagagatactcttacttttctcttaagatccccggtcatttgacgcttgtaggat gatagggttattttccactataaatactttcatactcttggatgttctatatccaagacgggaggaccta ccccgtaccccttagaggtgagatgccaagaacaggccctttctgttctctcgacaatggcatcata ggcaacaagcatcacaccaagattgctaagttttgttaagagttcttcaagctatagggtggctgtag cgaccttctgatgcctgcggatttccccacggagcgatccgtgccacaggggccaaaagccacg gctaacgcccatcaggagcggcacttaccccgtgccccacccttgaaacttgaatgttcacactgg cttctctcggctttctgaactgtctgcttgttggggccccgaaggatgccctggaggtaccccattta tgggatctgaccaggggacacctcagctctctaagttgctggtgtttaaaaaacgtctaagggccc ccaccccttaggtggagggatccacctttcctttatttttaaaactcttttatggtcacaattgttt |
| 581 | Antarctic penguin virus A | ctaggagactacgcagtgggataagatgactatgatgtcgtacgggcagaagccagtacagtcga agtcgagaccgacgtcgaggatttgactctgcctgacctagtgccatc |
| 582 | Forest pouched giant rat arterivirus | tattggatccgcctccgggcaaaggttactttcttgtacctcggcttagccacagggtgaccccttgt acgtaggggccccgacgtagcactggtctgacaacaccttctcggcatttcaccttctgcccgctct tccgggcggtggtgtcaagaagcagcagtgctcttctcttttcttcctgcagttcaccgagccctacg gggggtaggtg |
| 583 | Avisivirus Pf-CHK1 | cattcccctttccccagccatgggttaaatggcccctcaccaggttcggtgctgtctaggcttccagt aaagaagtcaaccgagcattgaacaaaacctcagtgggtatggtagttaaccccgtccactggac aactttgtcctcttaaaagtggatcaatccaccccaactccccccctagccacctgagccatggtgg atagcagtgacgaaactagggaccccaatacctctagtgccaagagaattccccccctcgcgagag gtgctcttgggcccgaaaggctagttggcagggtgaagtgaaggaagctgctagcgtggcaacc |

TABLE 17-continued

| IRES sequences. | | |
|---|---|---|
| SEQ ID NO | IRES | Sequence |
| | | ttaagcgtagcccgaagctgaccttagaggttaaccctagtggaccactggatgaagctgtggag<br>gtggtggataggaaagttggccacttgtgagtagatgcccagaaggcataaggctgatctggggc<br>cagtgactataccgttccggtaaacctggtataaaaaccatgaaagcaagtgggtttaaaatttcttct<br>aattccttcatttcagtagtgataactggcaga |
| 584 | Avian paramyxovirus penguin | accaaacaaggactagataacccacgtgaccgttaactggaaaataagatgttgtaggggcgacc<br>tagttggaattcgaccccggctccgaaacctctaattgtggttattggcagtctagtctacttctaacg |
| 585 | Newcastle disease virus | accaaacagagaatctgtgaggtacgataaaaggcgaagaagcaatcgagatcgtacgggtaga<br>aggtgtgaaccccgagcgcgaggccgaagctcgaacctgagggaaccttctaccgat |
| 586 | Bat Hp-betacoronavirus | ttaagcttcggcttgttgcataggaccggaaaggtactatctaccctaactcttgtagttagactctcta<br>aacgaactttaaaactggttgtgtccttcagtagtctgtatggccattggaggcacaccggtaattatc<br>aaatactaagaagattcatagtacatccttgtctagcttttggttggcagtgagcctacggtttcgtcc<br>gtgtcgctcacaattatccacacagtaggtttcgtccgctgtggttgagttgctagtccgttgctgtttc<br>gtcagccatctacaactcgacacc |
| 587 | Basella alba endornavirus | ggaatatggctaatcggcttattctaatcaaacgcaaaagacttatgacacagaccggacctgaac<br>gaggtgataaaacacctcgttcaggttcaaaacgtagaagattcattcctccgattagaaatacaact<br>acgtctaagcacgatagagatggtatcaagatcggttttagaccacgagaaaatcggcaaatgaaa<br>gtacaagttgggtggtttaaattaccaagaacagtaacattcaagaacaacggcaacccgtttgtta<br>cctcatttcgtaaattgtttagaagtaacaaagataaattatttaatggtgggaagaacctaagtacag<br>taccagccagaagtagtgaaatgacagaaatgtttatgttcatgtccacgctagagggccaattgtc<br>aatccaagatcgagatccaaaaataatcaataagtctatatacatgatagaggta |
| 588 | Ball python nidovirus | ccccttcacccataggcactaggagaacaggataacccctaacggggcatcctgcctgtgaccttt<br>cagattcgctagttagatatcttcacagactctgctaggcttctgacccagtccgttcccaaagtccgt<br>taccgcccgagtagcgcttaggcgcgaaagggacggaagtacctccagtaagcgaaagctgaa<br>gtaagggaaatacggcaagactaacttgttagtcttacagtgtggataacctggtagttatccccga<br>caagagacctgactcgatgtgaaaacatccaactaggttggcttcaaactagctacaggcaggata<br>tcccccaacggggcctccaaggaatcgagaaccaaccctcattccacgtctgtagtaagcaaaaa<br>caggggcgatcttcaccgacacctctcaccacagagcacaccaacctctgtgaagccaatttcctc<br>gtccaaggacaggttattgagggtcaactttcttccgaccagaagaagggatttcctaccaaaaga<br>aaaaccaaatccaccaacaccacaaggtaaaacaacaacttgtgaagccaatacttagtcaaaga<br>ctaactattgagggtcaactttctcttcaatagagaagggatttcctggtaaaacaaataacaacaac<br>taacatcagcaact |
| 589 | Bat sapelovirus | gacaggtgttttggagggcggatgacgatatctggctggccaccagggaataacggcaaatgtct<br>gatcatacggttcacaagtctaccggcgatagtggttcaacaccatgtgtagcagggattcttgcgt<br>atgtgaaggcgacagtgc |
| 590 | Bat Picornavirus 3 | taagcggaaagcattcttgtcccccggtcagtaacctataggctgttcccacggctgaaagggtga<br>acatccgttacccgcctcagtacttcgagaaacctagtacgcctgatgattccaaattggtatgatcc<br>ggtcaaccccagaccagaaactgtggatgggggtcaccattcctagtatggcaacatacaggtgt<br>ccccgcgtgtgtcacaggcccttacgggtgccatttcggatgagtctggccgaagagtctattgag<br>ctactgttgatacctccggcccccctgaatgcggctaatctcaaccccggagccactgggtggtgaa<br>ccaaccacttggtggtcgtaatgagcaattctgggacggaaccgactactttggggtgtccgtgttt<br>cttttgttcatattaaactgttttatggtcacaacacaacttggtacgatttgtgattattcactgctcactt<br>gtcacagtaaatatacacaatcatc |
| 591 | Bat Picornavirus 2 | gggttttacgaaacccgtatacaccagaccttttctcccctcccccctccacctaccttttccccctcttt<br>ggaccgaaacaaggacacgtaagtggaaacgcgattttatatgtggttggccaccacggaataac<br>ggcaattgtctacatgtgggaagtgcaacctccctagccgataacccctgaccgggtgtgtaggat<br>aggaaaggtgcccactgtgggcgacaggttatggtagagtggatacctagccaggggcaatggg<br>actgctttgcatatccctaatgaagtattgagatttctctgctcattacccggtgatggttgtgtggggg<br>gggccccatacactagatccatactgcctgatagggtcgcggctggccgaccataacctgtatagt<br>cagttgaattcagccaag |
| 592 | Bat Picornavirus 1 | gaaacccgtatacaccggaccttttctcccctccctctccacttacctttttcccctcttcggcatgaaa<br>caaggattattcaagtggaaacgcgatttaatatgcggctggccaccgcggaataacggcaattgt<br>gtatctgctggaagccaagcctgcctagccgatagcccttgaccgggtgtgtaggatagcccagg<br>aaccagcaatacgcgacaggttatggtagagtagatacctagccaggggcaatgggactgcattg<br>catatccctaatgaaccattgagatttctctggtcattacccggtgatggttactagagggggggcctc<br>tagtactagatctatactgcctgatagggtcgcggctggccgaccatgacctgtatagtcagttgatt<br>tgagcaat |
| 593 | Bat Iflavirus | acgaatcggtatacgcttcggtacctattgttgcaagttcgttccctattttcgatttgcctgcccgaatt<br>tgactcaaacaattgtgacatactatgtctctgtttgaaagcactacacgagtttgcgcccagcatgta<br>tgttttcaagtcttttgtataagtctgcctctatagtggttttctttgaccttaaagccttgtcaaccatcct<br>atatgctgcatcgagacttgatgtcaatctgcctctactacgcaaatgtctagtaattagttataaggtt<br>ttactattttccctcatttccaattttagtttgtagtgtatgtgagtatcattcttactccgactgttaagaga<br>aaccaatttatagtcgttaaatatgataaatggaatgaatgatggtgtcattttaaaaacactcttctcta<br>taggcgtaagcattctcgctcttagagtcgtaaagaagaaatgccgtgtctatcagtatgttatgcga<br>tttattttctgccacgcgcttctagtgcaatctagttgacatacagacattgcctaccactcgcgaggg |

TABLE 17-continued

IRES sequences.

| SEQ ID NO | IRES | Sequence |
|---|---|---|
| | | tcgaccggtagtgtaaggagtaagtgatgatttccgcttattctgtaccctttgcctggtgaggacag<br>atcctgactaattttaaatataaatgaacactagcttccaag |
| 594 | Bat dicibavirus | gtatagcaccggaatggtattttactactccaagtatacgtactaggagttaaaccctgtaatttacag<br>gggatttagtgacttttatccgtaaaagtcgattggacgttaatcggtaacgaggccaagtaccgtg<br>aaccaatttaaaaacgtattttctcatgtggtagaaccaacttggaaatagcatggcatataggttgttt<br>aggg |
| 595 | Betacoronavirus HKU24 | gataaagtgtgaatcgcttccgtagcatcgcaccctcgatctcttgttagatctaatctaatctaaactt<br>tataaaaacactaggtccctgctagcctatgcctgagggtttaggcgttgcatactagtgtcttagga<br>atttgactgataacacttccctgctaacggcgtgttgcactctcagtctaagcctcccacccatagga<br>ggtatc |
| 596 | Betacoronavirus England 1 | atttaagtgaatagcttggctatctcacttcccctcgttctcttgcagaactttgattttaacgaacttaaa<br>taaaagccctgttgtttagcgtattgttgcacttgtctggtgggattgtggcattaatttgcctgctcatc<br>taggcagtggacatatgctcaacactgggtataattctaattgaatactatttttcagttagagcgtcgt<br>gtctcttgtacgtctcggtcacaatacacggtttcgtccggtgcgtggcaattcggggcacatc |
| 597 | Boone cardiovirus 1 | tacgatcgctgtacattccactactgccaattagctccccttcccgttgctcccctctataaggaga<br>gccttctcttgcaaaggtgaagccttcacccccggtcgaagccgcttggaataagacagggttattt<br>tctcctctcctcggcgcttgcctcttctaagctgaataggttctatctattcaggcggatggtctggtcc<br>gttccttcttggacagagtgtgtatctgggttttccggatctcgaccacacactcaccagagctcagg<br>agtgattaagtcaaggcccgatctgcggcgaaaaggaaatgaagtattttgcagctgtagcgacct<br>ctcaaggccagcggatttccccacctggtgacaggtgcctctggggccaaaagccacgtgttaat<br>agcacccttgagagcggtggtaccccaccaccctgcaaattatggatttgacttagtaactaaaaga<br>ttgacttggcatacctcaacctgagcggcggctaaggatgccctgaaggtacccgtgttgaaatcg<br>cttcggcgaccatggatctgatcaggggccctgcctggagtggttctatcccacacagcgtagggt<br>taaaaaacgtctaaccgccccacaaagaccccggcagggatgccggtttccttttaccaattcttg<br>acact |
| 598 | Breda virus | atcacctagtacttacaagcgggtcaaaccgccctccggaacggtcataacccccctcccgaacgt<br>gcgcttgacgtgactggtctttcagtctagctttctgagaaatactccggggttgtaacccaccatttt<br>gacctttggtcagtttggtaacactccaaccaaacagcatctgacccacctccagcttgctgcaggc<br>catttggacCaaacgggttcagatatcttgtggctaaacctctgacccacctccagtttactgcagg<br>ccttttggactaaacgggtAcagactctttgtggttagttttaactacccactgtttagccgccaacc<br>tgatttttattgttacaaaattttgtgtttacacattattttcttacggttggcagtttgtttggttgtttgcaca<br>gtttttgctgataccaattttactgtgcttttggtgttttcggctaaggctgtttttcacatacttagtttgct<br>tgaagtaaccttcacaacatctgttttgtttttggtttctaaggtaaagagtttcaggaaaaaacatagg<br>cgcccatcttgtggtgtctagttttaattaatctggcaaacaagtatcaagtcatcgactccctttggag<br>tgagacttacgagtaccaattcgcctattttggccatccatataaaa |
| 599 | Bovine viral diarrhea virus 3 | gtatacgcccagttagttcaggtggacgtgtacgattgggtatcccaaattaataatttggtttaggga<br>ctaaatcccctggcgaaggccgaaacaggttaaccatacctttagtaggacgagcataatggggg<br>actagtggtggcagtgagctccctggatcaccgaagccccgagtacggggtagtcgtcaatggtt<br>cgacgcatcaaggaatgcctcgagatgccatgtggacgagggcgtgcccacggtgtatcttaacc<br>caggcgggggccgcttgggtgaaatagggttgttatacaagcctttgggagtacagcctgatagg<br>gtgttgcagagacctgctacaccactagtataaaaactctgctgtacatggcac |
| 600 | Bovine rhinitis A virus | ttttgcggctctgccgccgttcgggttttacctgttttcacagagcaaaacaggacctctagtttcgtg<br>cttaaacgagatcatgctcgaactagaactataacgctggtcactggacccgtgccgcgccttgcg<br>gatctttgcgggaatggtggctagtgggctgtggaagtgactctaaccacacgcccctcaagtgtg<br>ggaaaacacgaactggtgtagcgacgacgataggccttgggacaccctctccagtgatggagac<br>ccaaggggccaaaagccacgccttgtgccctgtcgttcacaaccccagtgcagttcgtgccagta<br>cctgcttttgggaagtgtgctttggacagctgaaaacagtcctagtgggagactaaggatgcccag<br>gaggtacccggaggtaacaagtgacactctggatctgacttggggagagcgggtctgctttacag<br>acgccactctttaaaaaacttctatgtctcgtcaggcaccggaggccgggccttttcctttaaaacaa<br>tacacttt |
| 601 | Bovine picornavirus isolate TCH6 | ttggatctgagcaggggccccctttgggttgctttacaactcaactgggggttaaaaaacgtctaac<br>ccgacacgccagagggatctggtttccttttatttcttttactcaccactggatgcagattgacgataa<br>acgttgttgtttgtgactattgacttgatctgcttctacgggtttactttcactgttatacttcttgctttgttt<br>ggtgttcactgtactttgtctccttctacatttcaca |
| 602 | Bovine nidovirus TCH5 | caccaatagattagtcaagctgtctataggcataaactaaccccaaccccattaccccggggcca<br>ggtgggccgccgccttcgggcaaacccgtgcgctggtataatcaaggttcacagccagattcact<br>gccggttagctagtggggcggtagcctggcaaaacccgaagaggttggaaagggaacttcagg<br>gtagtttatcctaggctagcgtagctacagttcggtcaagataaccgtcctggtgctagggctagta<br>gagacagtggtaacttggacaagggtccagggccactttagggaataccctacggaaggctagg<br>tccgtaaggaagacccccgcagttgtccgcggttgagcagagctcctgcgtagacaaaaggcaa<br>aaagtggattacattcgcctgcaggaaaaggcaaacgtcgttggagtcggagctaaagtactgga<br>cgattgataccacgcctgctgcggtagataaa |
| 603 | Bovine hepacivirus | ccatcgacactccaggctcacggattaagttaggttccgccgaagcgggctaaccaggcccctag<br>taggaggcgcctatcccgtgagccctttccccacggattgagtggagctggagctgggaaggac<br>cgagtacggtccaatcgagaagaaccctgatgaacattccaggcctcttcggtagatttggatatat |

TABLE 17-continued

IRES sequences.

| SEQ ID NO | IRES | Sequence |
| --- | --- | --- |
| | | ccaccagtgaaggcggggtcgtgggtacaggccccctagtccacacagcctgatagggtcctgc<br>cgcaggatccgtgggtgcggctgtacatgtacc |
| 604 | Botrytis cinerea mitovirus 4 RdRp | gccccgccgaccttcctatttatttctaaataggaaggtcccgactagtcggataattcggtttaacg<br>aattatggttagatctattaaagttaaaatagattgaatttctttctcatcctccttattcctatactttggga<br>gtaaatgacaaatgtctatcctcaaaccgaaatggcttaagtgatgaatttgaaagaaaggtaggttt<br>taagaatataaggcatcaatatattatacccttgaatgttaagtgaccacggcgtgacgattagggct<br>atcttaggatagacagccatctaacgcgacagcagtggaaatcagcttagcatctcaagatcatgta<br>taatatatacataaccttacaattataaaaccaaaccaaaacacactataattttatataaattatagaa<br>gtatcggacctggacggtacctactattaactgatagtagccaaatgcaggaagctc |
| 605 | Botrytis cinerea mitovirus 2 RdRp | ggaacttttcagttccagaagtggctttattaagccttcaaagtttacactttgaacctgcgattaattcc<br>ccatagtgactcttgttactgtgaattaggaatagttgtagttcaacttctaatgaggtgaacaatataa<br>taactcatcttattaaccctatacgtagacaattgtccaaagagacagttggaattctgccaatctgga<br>atgtttggtacgcgtagaagataataagagaccctctattcccctgcctcatgactaagtcatggccc<br>ggggtgtaatagagatacttttatatattatacaatc |
| 606 | Canine picodicistrovirus strain 209 | cgctctttatacaaatctgtcaaccctttgtataactctaagccgaacaattatagctaggcttttttattat<br>ataacattaattaggcattagcgttgtcgccaatctcttggtaatcctaaggatacctttcctgttgacta<br>agatgaagcgccttcggttaccgatgcccggtgtccacgaagccatcgtggtcggccgcgtcccc<br>cacctctcccaacttggactccatgttttcagtaggtgtaatgattagtattattgattctgctcgttcaat<br>gtgtttatcttcacgatctgggacccaacacatgcttcactcatgtttaaatgttggttccctcattttga<br>agacacccaaaccatagagtgcgagaatgaggatttctacttccattctggtaacagaaatgaattc<br>ctgcgtgtgtctcgtaaatggaatctttaagaacttcagataaatcgaacaatacactaatacaagttg<br>ttttctaccaacatgttcaatgcggctaatctgaccgtggagctgtgaagcgctcaaacccgagtgtt<br>gtatacagtcgtaatgcgtaagtccatgaggaaccgactactgttacctctgttggtgtgtttctccttt<br>CCtctcttttattattatttgttattgcaaatactacaactttgatcaac |
| 607 | Canine distemper virus | accagacaaagttggctaaggatagttaaattattgaatattttattaaaaacttagggtcaatgatcct<br>accttaaagaacaaggctagggttcagacctaccaat |
| 608 | Canine kobuvirus | tttaagtgttgtgcccaatctcttgactcctgctggaaccaccgaccagtagtgtccaaaatgccagg<br>tggaaaatcctcccttcccctctgggcttcatgcccggcatcctccccccagcctgacgtgccaca<br>ggctgtgcaaagaccccgcgaaagctgccaaaagtggcaattgtgggtcccccctttgtcaaggc<br>stcgagtctttctcccttaaggctagtcctgtcagtgaactctgtcgggcaactagtgacgccactgc<br>atgcctccgacctcggccgcggagtgctgcccccccaagtcatgcccctgaccacaagttgtgctg<br>tctggcaaacattgtctgtgagaatgttccgctgtggctgccaagcctggtaacaggctgccccagt<br>gtgcgtaattctcatccagacttcggtctggcaacttgctgttaagacatggcgtaaggggcgtgtg<br>ccaacgccctggaacgagtgtccactctaataccccgaggaatgctacgcaggtacccctggctc<br>gccagggatctgagcgtaggctaattgtctaagggtattttcatttcccaccctcttcttcttgttcata |
| 609 | Camel alphacoronavirus | cttaagtgtcttatctatctatagatagaaaagtcgctttttagactttgtgtctactcttctcaactaaac<br>gaaatttttgctacggccggcatctctgatgctggagtcgtggcgtaattgaaatttcatttgggttgc<br>aacagtttggaaataagtgctgtgcgtcctagtctaagggttctgtgttctgtcacgggattccattct<br>acaaacgccttactcgaggttctgtctcgtgtttgtgtggaagcaaagttctgtctttgtggaaaccag<br>taactgttccta |
| 610 | Cripavirus | gcaaaatcggtagtacgttaaacgtacgaccaccgatgagactgaaatgacactagttgagattatt<br>tcaatatcctagtgttataaagtcaatatttgttggttgatcgtttcgtcaatcgatggcgctgacagcc<br>ggaaagacggcaataataaaaaccaagatttagtttttaagttttgattgaattgcaaaagctatcttg<br>aatagacaatcaaaatattaagtaaagcaaaagcttcttaaagaagacaatatttaattagttagtaac<br>caaacctcatcgtgcccctaagggttaaccggttacgtaaaagcgtagaggtattaaggtcactgc<br>ggagacctaaaatccgcaatttttatgttttgtaatgttttagttatagacttagatgtaactataagagttt<br>ataaatacttgtttcaagatttatagacaagatctgatcctatggattttagataaccttcatgttagtgg<br>atagtgtgtgtacctatctaaacgcataaggctcttatttcatatttaaagtaggactatgtattacggc<br>gcatctaacggtaacgttagtcaagaccggagaatctcggaatgaattttagtaattcccaaatttata |
| 611 | Human coxsackievirus A2 | acctttgtgcgcctgttttatatccccaccccgagtaaacgttagaagttacgcaaccccgatcaata<br>gtaggtgtagcactccagctgcatcgagatcaagcacttctgtctccccggaccgagtatcaatag<br>actgctaacgcggttgaaggagaaaacgttcgttacccggccaattacttcgagaagcccagtagt<br>gccgtgaaagttgcggagtgtttcgctcagcacttcccccgtgtagatcaggctgatgagtcaccg<br>cgatccccacaggtgactgtggcggtggctgcgttggcggcctgcctatggggcaacccatagg<br>acgctctaatacagacatggtgcgaagagcctattgagctaattggtagtcctccggcccctgaatg<br>cggctaatcctaactgcggagcacatgccctcaaaccagggggtggtgtgtcgtaacgggtaact<br>ctgcagcggaaccgactactttgggtgtccgtgtttcttttttattcttataatggctgcttatggtgacaa<br>ttaaagaattgttaccatatagctattggattggccatccggtgactaacaaatcgctcatataccagt<br>ttgttggttttgttcccttatcacatacagctcataacaccctcttatatttactacaattgaatagcaaga<br>a |

TABLE 17-continued

| IRES sequences. | | |
|---|---|---|
| SEQ ID NO | IRES | Sequence |
| 612 | Coronavirus AcCoV-JC34 | agaaacaagtagtgttttaaaaaccttcaaattagtgcctgtaacatctttgcaatgaaagtagcgctc actagcctctatgcaaagaatgttaaaagaaatacgaagcatttaaagaatacaatctatctaggata ggtacaattctcctccccctcttgacttcggtcaactcaactcaactaaacgaaatccccccttgcatg gttccgacccgtgtaaggttgtgtatttcgtgcagtcgttgcccttactagtgtaagcgtaacggcatc taggtttgcacgtcttggaggaaacggtgtgtacgtttctagtgtttacgccgtatcggttccggccc gataggtattgcattagacgtcctgggtggttctgcctgcccttgtgtgattcggctgttccgtcagttt ggtcacctcacacgtccttaagac |
| 613 | Chicken picornavirus 3 | gggtatggtggttaaccccgtccactgggcatctttgccctctcagaagtggatcaatccaccccaa ctcccccctggttacctgagccacagtggactccggtgacgaagctagggaccccaatacctca agtgccaagagagtcccccctcgcgagaggtgctcttgggcccaaaaggctagttggcagagt gaagtgaaggaagctgctaacgtggtgaccttaagcgtaattcgaagctgacctttgaggttaacc ctagtggaccactggaggaatctgtggaggtggtggttaggaaagttggccacttgtgagtagatg cccagaaggcataaggctgatctggggccagtgactataccgttccggtaaacctggtataaaaa ccatgaaagcaagtgggtgaaattttctctttttatccttcattcagcagttgatattggcaaa |
| 614 | Chicken picornavirus 1 | gtggccgacttgcagaacttcctaccgaaccaccacctcacccccataactccttccctctacacct tccgctatggtggttaccactgctttattgccttgactgagaatggccacccccctcgacacctgcccc ctactgccccaccgcgcaaccttttgcttgtccactcggttggagaggcatgggggccccgttcat atccccagtccagttggtgaccttccccctccccgtccggtagatggtccagagggctttgccgac gccctctatgatgcttgcttgtctttcctccgtcagcgcgagcatgcacttgtcgagcccacggaaa cacagcctagcttttgcttctctcaccctgcgtaccctgggcgccttccgctcgagattcgctttgttc gacaccctggcgtccccccaccgctacgtgattttactcgtggcatacaccgccctggcgttcagt acattccactgcctaatttgggtggcctccctcaatctcccgcaccccccattgcgcacgtcatcac cgccgccgctaacgcgatccggcgcggttctcactggcactgtcccctcgtccgccgggtttcca ctcatggttggcttttcacttattctggttactggtgttccatcctacttcatgatggtcgccatgaccat gac |
| 615 | Chicken orivirus 1 | aaaccctcacgagtgcttgtggtaggtcccaggccaatattcttcgtaaggcttggttccaattttcca ccactcgtgtttgggttctggcctatggtacccagaggggcggtttgggggaattaactcccccctcc cctgtggtcctataccaccccacacctctgtgggctttctttactatcttcttgttttccgacttttaaaca ctaggcaggcgcgcctagtcatacaccgcccggctggtctttccagctcttgtgggcggtgcgcg ctggtccatcgtgcccagcgacatagcaccttgtggacacctccgaacgccctcccctgtatggg gtggtgcccaggggtttcagtgtggtgacacactccctggggcccgaaaggctagtgtgcaacag gtgaggtacagccagctgcccccgtggctggagggaccaagcttgtgaagcacacctcaccttct tgggggtgggctagtaagtggtgaaagcatagtgtccgtgtcgctggccaacactttgggtcaagt ccagccactcagtgagtagatgcccaggaggtacccctagtggatctgacttggggcctgttactt aatgcaggttaaaaactatgaaagctgagtagtgtagcccggctggtggcttctcttccttattcattc tatttt |
| 616 | Chicken gallivirus 1 | ggttaacttgtttaaccaaggcttccgtgcagggcttgcacgttaggagttcatgttgattcatgctcc aatgcccaaaactttgtgtgtttgtttatgtctttcccaaagtttcccccaaggtttcggtactcaaacct taattcctagtcccatcttttgggccttagtatctaggaaatgtacccgtgccttgacgaacgtaagaa agctgtcttttattgaacggttctaatgaactaagtataactggctcgcgccacctggtgtgtgccgtt ggaattcccccatggtaacatggtccaacgggcccgaaaggctagtgggcaatcggtcctccaa ggaaggggttcccaccccgacctgaacaggatttgatgaagctcacctcccaggctcctaacccc aaggaagtttacttatagtaattagaatttagtatgtaattgctggcaatcttgctagtagtcaggaacg ttatgaccaaatgagtagacccccagaaggtaccccattatatgggatctgatctgggcctcatact gtgtgtctccccacatatgaggttaaaaccatgaaagtttggtccaaaatattcttttcctttttatcttttct ttagtggtgacgccattatatcagcagtttgctg |
| 617 | Chicken calicivirus | ggtgcatcatcactgaacaccctcgggcagagatgcaagggtggaagtcactcctgccccctgg caacatgcaggtgcccgatcccaagcttagttctgacttcctctcctgggtggtgcaacactccaag gttgatgaacaaacctggagggacctctgggcaacctggtctctcgaggatctccggcgcatctcc acagactacctcatgctcccggaacctgagaagaacactgatgcctatgatggctggctgatggtc ggcgagatgttgacctttgccggtctcattggctgggagg |
| 618 | Carp picornavirus 1 | agctacaggaaagagagagataatcacagcacataaatacaactacagaagagagcctttccctg agcactatttacagcaaaccacgctgggaaaagtggtagcatgacccacttacgggttacttagtat aggattttaatatcttcgattctttattttcttttcttaactaagttcgcccggactttatccgtgttttatttta gtttaagcaaaattgagtaactaagtttttaacctgccaaatggtgagaagtaactctgtgaaaatacc atttgtgcatgaaattgtcttgaaaactcttaggcttttggggggtcccactgctgtttggaggactatt gacagactctattgtagttgagtagtgactaatgataacgatttgcgtattacgcaatgggctgtacc cgttagatttagtatgccggggggaggggtcccactggattgcactatgtaacctgacagggcgtc tgccgacgcactacaatgaggataagatcggctgtttttattt |

TABLE 17-continued

IRES sequences.

| SEQ ID NO | IRES | Sequence |
|---|---|---|
| 619 | Falcon picornavirus | cgcttggaataagttgagaggaattatgcatgctagttgtgtttgtttacaactaattgttctaatccaa<br>gtgaagctcttcgcttggggcggcacgacacttgccgtaattcttctaccgtccctccacaccttgtg<br>gatgaagggccggatgtgtggcctctggctaacccctctctctggggtgatgctactggatgtttta<br>ctcctagaccaaatcacatgaactcctcttgatccacttcggtggggctatgagcctgcggattaata<br>gctggcgacagctaccccaggggccaaaagccacggtgttagcagcaccctcatagtctgatgc<br>ccaagggctgatgttgggagctagtagtgtgtgtctggcctatgtttaggacttctggccaagcgca<br>gaggagtggggctgaaggatgcccagaaggtacccgtaggtaaccttaagagactatggatctg<br>atctggggcccccctcacgtggctttaccacgtgttgggggttaaaaaacgtctaggccccaccagc<br>ccacgggagtgggctttcccttaaaaagcccaacaatatttatggtgacaattcactgtttcttctttgc<br>aatttttgtattcttggactccttatttttgtttgcttgattttagtggacattcagattcaaatacaaa |
| 620 | Equine rhinitis B virus 1 | cgacaggcacaggtcgctccgagttctagtagtgtgggaacttgttactactgatgaaacgaggta<br>gtgacactcagtacctgcgaacgaggtcggggccctcccttcttccttcacccaactttcacttttcgt<br>tccactttagcaggggtcttctttctatccccctggcggcattggaactagccgtcgcgtcttaacgc<br>gcagccctgaaggccccacaccttgtggatcttgccgtgggtatgtttctggcatgtgtttctcaagc<br>ctgcaaccgaagccgaacagccacatgaacagtttgagcgtggtagcgctgtgtgagttggcggt<br>ggatccccctcgtggtaacacgagcccccgtggccaaaagcccagtgtttacagcacctctcaca<br>tccaggacgaccccatcctggcgctcactcttagtagtatggcttagtacgcattaggtggtaagcc<br>gagctctccctcggccttgttctgaatgcacacatgtctaggggctaaggatgtcctacaggtaccc<br>gcacgtaaccttcagagagtgcggatctgagtaggagaccgtggtgcactgctttacagatgcag<br>cccggtttaaaaagcgtctatgcccctacagggtagcggtgggccgcgccctttccttttaaaacta<br>cttgttct |
| 621 | Equine rhinitis A virus | aagggttactgctcgtaatgagagcacatgacattttgccaagatttcctggcaattgtcacgggag<br>agaggagcccgttctcgggcacttttctctcaaacaatgttggcgcgcctcggcgcgcccccccttt<br>ttcagccccctgtcattgactggtcgaaggcgctcgcaataagactggtcgttgcttggcttttctatt<br>gtttcaggctttagcgcgcccttgcgcggcgggccgtcaagcccgtgtgctgtacagcaccaggt<br>aaccggacagcggcttgctggattttcccggtgccattgctctggatggtgtcaccaagctggcag<br>atgcggagtgaaccttacgaagcgacacacctgtggtagcgctgcccagaagggagcggagct<br>cccccgccgcgaggcggtcctctctggccaaaagcccagcgttaatagcgccttctgggatgca<br>ggaaccccacctgccaggtgtgaagtggactaagtggatctccaatttggcctgttctgaactacac<br>catctactgctgtgaagaatgtcctgaaggcaagctggttacagccctgatcaggagccccgctcg<br>tgactctcgatcgacgcggggtcaaaaactgtctaagcagcagcagaaacgcgggagcgtttcttt<br>ttcctcatttgtttc |
| 622 | Equine arteritis virus | gctcgaagtgtgtatggtgccatatacggctcaccaccatatacactgcaagaattactattcttgtg<br>ggcccctctcggtaaatcctagagggctttcctctcgttattgcgagattcgtcgttagataacggca<br>agttccctttcttactatcctattttcatcttgtggcttgacgggtcactgccatcgtcgtcgatctctatc<br>aactacccttgcgact |
| 623 | Enterovirus sp. isolate CPML | actctggtatcacggtacctttgcacgcctattttataccccttccccatcgtaacttagaagcaacaa<br>acaaactgcccaatagcagcacaacacccagttgtgttaggggcaagcacttctgtttccccggaa<br>gggtctgacggtatgctgtacccacggcagaagtatgacctaccgttaaccggccatgtacttcga<br>gaagcctagtaccattatgaaggttgattgatgttacgctccccagcaaccccagctggtagttctg<br>gtcgatgagtctcggcattccccacgggcgaccgtggccgaggctgcgttggcggccagcctac<br>accatacggtgtaggacgtcaagatactgacatggtgtgaagagcctattgagctacgtggtagtc<br>ctccggcccctgaatgcggctaatcctaactccggagcatccgccagtaagcccactggaagggt<br>gtcgtaatgcgaaagtctggagcggaaccgactactttgggtgtccgtgtttcctgttttacttattgtt<br>tggctgcttatggtgacaacttatagttatcatcataagctacttggtcttgccaaccggagaattattt<br>ggttatttgttggtttcataaacctacagtcgtattttcctgtcttattaattgttctcaaaattaacaaca |
| 624 | Enterovirus AN12 | taccgctgcaccagtgagctggtacgctagtaccttcgcacggagtagatggcatcccccacccc<br>gtaacttagaagcaaagtacacatctggccaatagtggcgctgcatccagccgcgcaacggtcaa<br>gcacttctgtttccccggtccgcaagggtcgttatccgcccagtccactacggaaagcctactaacc<br>attgaagctatcgagaggttgcgctcggccacgaccccggtggtagctctgagtgatggggctcg<br>caaacacccccgtggtaacacggatgcttgcccgcgcgtgcactcgggttcagcctattggttgtt<br>cacctcaacatagtgtaaatggccaagagcctactgtgctggattggttttcctccggagccgtgaa<br>tgctgctaatcccaacctccgagcgtgtgcgcacaatccagtgttgctacgtcgtaacgcgtaagtt<br>ggaggcggaacagactactttcggtactccgtgtttcttttgttttattttgaattttatggtgacaattgc<br>tgagatttgcgaattagcgactctaccgctgaacattgccctgtactacctaatcgcatttcacaaaa<br>cctcagagataccaagctcttacattgatctgcttgttttcctgaatctcaaatataaattggaacaagc<br>aaa |
| 625 | Dolphin morbillivirus | accagacaaagctggctaggggtagaataacagataatgataaattatcatacttaggattaatgat<br>cctatcaattggcacaggatttggataaaggttcacagtc |
| 626 | Dianke virus | tgttttcaaccataatactactactacaagtataaaaccccgtccgtctgtcggagacgctaaactctg<br>accaccaatctagccacatcagttgcttaaagaacctcttgagacactctcccacttaacatcttttag<br>gaatcttcgatgctacaacaacttggctagtgaacaataaatccgtacaattcacagttgtaagagg<br>ccataggtccagactttgaaaggtttgtttctattgttacaaatacttagattaacagaggctatttaata<br>gtgctcatcacgttaacagagtaaccttgtgcaatagtatgagcttgttgtaaaacgtcttgatacgac<br>acc |
| 627 | Guereza hepacivirus | cactcaatactacactccgcatttggggagaagcgctggcgttcgcggaaccgcgttaaccatac<br>gcgtagtacgagtgcgacagaccccggtgctactggtggtagcgagacacgagccgaagtctgt |

TABLE 17-continued

IRES sequences.

| SEQ ID NO | IRES | Sequence |
|---|---|---|
| | | ggggggaactccacttagagggcatgcccgggcgtaggcttctgagttgggatgggccccaact<br>tggcccctgagtggggggtgttacgacctgatagggtgcgggctggcgcctaccactttccagt<br>cgtacatgagtc |
| 628 | Grapevine associated narnavirus-1 | gcccgggggtgcagtcctgtgaaagggtctgcaccatactatatatgtatatgattacatcccaaa<br>aggcgacttcgttcaggttttaaatctgacgtaggtccagtaaataagcatgtcaaaacatgtaagttt<br>atcctgtaatctactctcataagatgagataagatgatattgcagttcccatgtaaataaatccattatg<br>aattcattcatataaggtagaagtggtaactatggttgaaacattaatataaaacggtcattttgcatga<br>acgtcattaaggaactggcataccaatgtctatttagtgactatgatatttagagtatcccttatattaat<br>taacaattattccttttagcatatcatccgacaacaaattttaaaagaagaaatattactcattaaaa |
| 629 | Goat torovirus | gtacttacaagcgggttaaaccgccctccggaacggttacaacccccctcccgaacgtgcgcttga<br>cgtgactggttctcagtctggctttctgagaaatactccagggttgtatcccaccatcttgacctctgg<br>tcattttggtaacaccataaccaaacaaactctacacacctaacccacctccagcttgctgcaggcc<br>ttttggactaaacgggtttaggtgttttgtgaccaactcgtctacccacctccagttttactgcaggcct<br>ttttggactaaacggCtttagacttttgtggttagtttttaactacccactgtttagccgccaacctgatt<br>ttcattgttgtaaaattttgtgtttatacactattttcatacggttggcagtttgtttggttgtttgcacagttt<br>ttgttgataccaattttttactgtgcttttagtgtattctgctaaggctgtattttacatacttagtttggttga<br>agcaattttttacaacatttatattgtttttgatttctaaggtaaagagtcttaggaaacaccatagacgcc<br>attcttgtggtgtctagttccaactaatctggcaaacaagtaccaagtcattgactcactttggagtga<br>gacttacgagtaccaatttgcctatttcggacatccatataaag |
| 630 | Foot-and-mouth disease virus 0 isolate | acaagcttgacaccgcctgtcccggcgttaaagggaagtaaccacaagcttacaaccgcctaccc<br>cggtgttaatgggatgtaaccacaagatacaccttcacccggaagtaaaacggcaaattcacaca<br>gttttgcccgtttttcatgagaaacgggacgtctgcgcacgaaacgcgccgtcgcttgaggaggac<br>ttgtacaaacacgatctaaacaggtttccccaactgacatacaccgtgcaatttgaaactccgcctg<br>gtctttccaggtctagaggggtaacactttgtactgtgcttgactccacgctcggtccactggcgagt<br>gttagtaacagcactggtgcttcgtagcggagcatggtggccgtgggaactcctccttggtaacaa<br>ggacccacggggccgaaagccacgtcctgacggacccaccatgtgtgcaaccccagcacggc<br>aacttttctgtgaaactcactctaaggtgacactgatactggtattcaagtactggtgacaggctaag<br>gatgcccttcaggtaccccgaggtaacacgcgacactcgggatctgagaaggggactggggctt<br>ctgtaaaagcgcccagtttaaaaagcttctatgcctggataggtgaccggaggccggcgcctttcc<br>attataactactgacttt |
| 631 | Feline infectious peritonitis virus | acttttaaagtaaagtgagtgtagcgtggctataactcttcttttactttaactagccttgtgctagatttg<br>tcttcggacaccaactcgaactaaacgaaatatttgtctctctatgaaaccatagaagacaagcgttg<br>attatttcaccagtttggcaatcactcctaggaacggggttgagagaacggcgcaccagggttccg<br>tccctgtttggtaagtcgtctagtattagctgcggcggttccgcccgtcgtagttgggtagaccgggt<br>tccgtcctgtgatctccctcgccggccgccaggaga |
| 632 | Farmington virus | acgacgcataagcagagaaacataagagactatgttcatagtcaccctgtattcattattgacttttat<br>gacctattattagacccttcacgggtaaatccttctccttgcagttctcgccaagtacctccaaagtca<br>gaacg |
| 633 | Avian infectious bronchitis virus | acttaagatagatattaatatatatctattacactagccttgcgctagattttaacttaacaaaacggac<br>ttaaatacctacagctggtcctcataggtgttccattgcagtgcactttagtgccctggatggcacctg<br>gccacctgtcaggtttttgttattaaaatcttattgttgctggtatcactgcttgttttgccgtgtctcacttt<br>atacatctgttgcttgggctacctagtgtccagcgtcctacgggcgtcgtggctggttcgagtgcga<br>ggaacctctggttcatctagcggtaggcgggtgtgtggaagtagcacttcagacgtaccggttctgt<br>tgtgtgaaatacggggtcacctccccccacatacctctaagggcttttgagcctagcgttgggctac<br>gttctcgcataaggtcggctatacgacgtttgtaggggggtagtgccaaacaacccctgaggtgaca<br>ggttctggtggtgtttagtgagcagacatacaatagacagtgacaac |
| 634 | Human rhinovirus 1 | ttaaaactgggtgtgggttgttcccacccacaccacccaatgggtgttgtactctgttattccggtaac<br>tttgtacgccagttttccctcccctccccatcctttacgtaacttagaagttttaaatacaagaccaat<br>agtaggcaactctccaggttgtctaaggtcaagcacttctgtttccccggttgatgttgatatgctcca<br>acagggcaaaaacaacagataccgttatccgcaaagtgcctacacagagcttagtaggattctga<br>aagatctttggttggtcgttcagctgcatacccagcagtagaccttgcagatgaggctggacattcc<br>ccactggtaacagtggtccagcctgcgtggctgcctgcgcacctctcatgaggtgtgaagccaaa<br>gatcggacagggtgtgaagagccgcgtgtgctcactttgagtcctccggcccctgaatgcggcta<br>accttaaacctgcagccatggctcataagccaatgagtttatggtcgtaacgagtaattgcgggatg<br>ggaccgactactttgggtgtccgtgtttcactttttcctttattaattgcttatggtgacaatatatatattg<br>atatatattggcatc |
| 635 | EV22 | ccttataacccgacttgctgagcttctataggaaaaaaccctttcccagccttggggtggctggtcaa<br>taaaaaccccccatagtaaccaacacctaagacaatttgatcaaccctatgcctggtccccactattc<br>gaaggcaacttgcaataagaagagtggaacaaggatgcttaaagcatagtgtaaatgatcttttcta<br>acctgtattatgtacagggtggcagatggcgtgccataaatctattagtgggataccacgcttgtgg<br>accttatgcccacacagccatcctctagtaagtttgtaaaatgtctggtgagatgtgggaacttattgg<br>aaacaacaatttgcttaatagcatcctagtgccagcggaacaacatctggtaacagatgcctctggg<br>gccaaaagccaaggtttgacagacccattaggattggtttcaaaacctgaattgttgtggaagatatt<br>cagtacctatcaatctggtagtggtgcaaacactagttgtaaggcccacgaaggatgcccagaag<br>gtacccgcaggtaacaagagacactgtggatctgatctggggccaactacctctatcaggtgagtt<br>agttaaaaaacgtctagtgggccaaacccaggggggatccctggtttccttttattgttaatattgaca<br>tt |

TABLE 17-continued

| IRES sequences. | | |
|---|---|---|
| SEQ ID NO | IRES | Sequence |
| 636 | Human TMEV-like cardiovirus | tccgacgtggttggaattaacatcttttccgacgaaagtgctattatgcctccccgattgtgtgatgctt tctgccctgctgggcggagcgtcctcgggttgagaaaccttgaatcttttcctttggagccttggctc ccccggtctaagccgcttggaatatgacagggttattttccaaactctttatttctactttcatgggttct atccatgaaaagggtatgtgttgccccttccttctttggagaatctgcgcggcggtctttccgtctctc aacaggcgtggatgcaacatgccggaaacggtgaagaaaacagttttctgtggaaatttagagtg gacatcgaaacagctgtagcgacctcacagtagcagcggattcccctcttggcgacaagagcctc tgcggccaaaagccccgtggataagatccactgctgtgagcggtgcaaccccagcaccctggttc gatggccattctctatggaaccagaaaatggttttctcaagccctccggtagagaagccaagaatgt cctgaaggtaccccgcgcgcgggatctgatcaggagaccaattggcagtgctttacgctgccactt tggtttaaaaactgtcacagcttctccaaaccaagtggtcttggttttccaattttgttgactgacaat |
| 637 | Human coronavirus 229E | acttaagtaccttatctatctacagatagaaaagttgcttttagactttgtgtctacttttctcaactaaac gaaatttttgctatggccggcatctttgatgctggagtcgtagtgtaattgaaatttcatttgggttgca acagtttggaagcaagtgctgtgtgtcctagtctaagggtttcgtgttccgtcacgagattccattcta caaacgccttactcgaggttccgtctcgtgtttgtgtggaagcaaagttctgtctttgtggaaaccagt aactgttccta |
| 638 | Hubei zhaovirus-like virus 1 | gtgcaggatggcctttcccatcttaagtggtttgtaggatttcgtgggtccataccccccgatttcttg gtacgtattccatgcacggagaatacgaccaaaactcttatttcaaaaaatattatttttttactcttgtgg gctgagtgcgacccaccagttccagcttagcaacctggaagttgttggagatttatggaaccaaatt acacatgcgtggagtgccgccactccgtatctgttcactcattacgcgattaagttctgcgacgaga cgagcgaa |
| 639 | Hubei tombus-like virus 9 | ggaccatccaggcaggtgtaggctagtaccctcacctgacctgtcgcgatgtttggctttgtgagg cttgtgggaggatcccttggcccatgcattgctgctgtcatcgtgaaaaatgttgtatgctcgcacct ggcgtggaggaaacggcatttgacggatgctaaggaggatttgaaggtcctcaactcccatgcctt attacaagtccccttttccttcaagcttcgagcccacgtctgtgacgagcagaggtgaggttggagtc aagaggagtcctattcaagctgttcgcagcaagaaccataaaactttcattgctcaatgggcaaga gcggctaaggctcggttctcgtttgcacgacagtgtgagcggagccctgtaaatgtcgcggccctt catcggtggtttgcatcggagtttaagaaaattggcatgaacttgctccaggtttcgtacgtgatcgat gaggttgttgaacttagtttggaaccaacgtatgagcgtatggtgtccgaaactaagaagcaattcc gtcatcgggcacgtatggaatactacaacgagaaaaaatgccttgaaaagatccactaggaacgc |
| 640 | Hubei tombus-like virus 32 | ttcgggtttacccgcgtaagcggccacactgactggttgtcggtgttgaatttgtataccagatgagg agacgttaccaccgtctcggcagtgctacgtctgggaaaggactgtgatagtggacagtcctacc gtctttagatacattgcgttgtgtatagcccgggagggattaactaatagcaacgcaatgcacacgg cggttcggatttgcttgactgatggaaagacatctaagttctaattgaacc |
| 641 | Hubei sobemo-like virus 3 | gagatgtttgcgtgggccgttgcgctgcgggcggcccacctccctacggggaccgtgagacacc gctggggaaggccccccaccccggccaaggggatcctgccgagaggcaggagaaagaggcc cagccctctggggcgccctttaggggTgcctgggagggaagtacccgagccgggcggccggtc gggtgcggctgtgcagttcgaggctaaccgtaaggaaggcctgagctgcctcggcttgtcggaa aggaagacgaaggcacttatcaaggctttcaggaagcaggagcgcaattacagcgcgcgccgt gcggcctggattaaccgcatttggccg |
| 642 | Hubei picorna-like virus 2 | agcaacttctttctgaaaactagctagagttcgacgatctctctggctaatgacaaataaccaatcaa aaagtcaaatgttcatgtatatatatatttagtagtgacctttatttagaaaaactttagatgatttatcgtc aagttgccctttgtgaagcgatcagctttttatatcgtttcatttttgtatacgtcttaattgacgttgtaag tacgttttgcatacctcacattgaggatagtatcgtttcctgactaagaagttaaactagtctaccaata gcaaccatataggatatagctttgtttttaacaaggtttaatctgatcttatgctcttgcttacggtgtttta tgtatagaaaaGtttttataaaaactacataattgtcaaaagaaaaagcgttacgtactgacgcattta tgttcacagtgtgacacaaaccttctatattttgattgtaaaataggctttgcctgaccatttatcaaata caaactgtttcaaacgcctctccgagccatattggccgacgcgaatcgacataacagggtgagttt acagctgcagttgcagccgaggatccacttatttgagagagaattactcttaacgaaattttgaagtc acttctacacagttaagtctgagtaggcgttatccaaacgtaaa |
| 643 | Hepacivirus P | acatggggggggggctgacagtgagtacactgtgccaagcaggtgctacgctatgcctaggtgct gctgtaggccaaggacatgtcccagtcatcccaggtgaggggggggggttcccctcaccgctgcc actgcctgatagggtcctgccggagggtctcggtgtccggctgtac |
| 644 | Harrier picornavirus 1 | gatgtgtgacggtgtaattactttccggatcccactttcctattataactctttcatcccaaggttaggg aaagaacctggctcggtaccaccagaccctccgccacgctagtggactctccggagataacggt accccctttgtagtcacctgtgctggtgaagaaccacctagtattgcttgggtgcgtgccgcctagct tccatttcttctggagcactgtgcaatgaggtttccccacttggtaacaagtgcctcaggtcccgcaa ggatactgtggggtggtgtgaccgcagggagctgtctccacggctcctctaatgttacgccgctat ccacaggccagtgcgtgtcatcgatcccggatgacagagctagtattgcgaaccccccaagtaaga aaagtggctagtaacctgatagctggtgaagagggtgggtcagttgagtagatgccctagaggta cccgaaaggatctgactagggacccgtgactatacattaggtaaaccgggtataaaaaccatgaa aaactgaccacttttcttttaacctcttctttcttttttatgtgtgttaagtgttttgagtttggactgtaccttg cccgcctttcttggattttctctatcgctcttcttacacctactgttatcaaggcactctttagagata |
| 645 | Kunsagivirus 1 | tttcaaatcggactccggtagttataccggagcccggtttggacgcttgggccgcgttaacagccc cccacccctttcccactgactgatttctcggattggactcatttgcattgctaactctgattctggatttc cccgtttatgtcgtcgcggtcggaagtgcacgtacttcgacgttgatctgatggcgtttgtttccagg |

TABLE 17-continued

IRES sequences.

| SEQ ID NO | IRES | Sequence |
|---|---|---|
| | | ggggaggtggcggcagaaacgcccccgccgtaaacttcggcgggccacgcctgtcaagccact ccctggggccgagcgcctgaggtgatacagagagataagcacactgggcgctgacaacgcccg ggacctcagtgagaagagcagtagggccgtgtttatgggactccattggatatcccccgcttgtcg gaactcacggctactccgggttgggaagcccgcgactggtactgtactgggtgatagcctggtgc cttccctctcactgttgtatgaaggctgaaaacccccct |
| 646 | Kagoshima-2-24-KoV | tatagtttgcctgtttctcgcaccgttaccgctcgttcgggaatgtgaaactggcacccctcctctccc ctaccaccctttctccttcgcccccattcataatttacaacgccgcacacagcggcggccgccaag ggctagcctggcggttataaaaggaacctgggtctttccctcttcaagccaaaaggtaggttccctg tgtccctgaatgctcggtgaggaatgctgcaccgtaacgctttgtgaagtgtttgcaagttctggccc ggcaagcctacagagtgctgtgatccgctgcggacgccatcctggtaacaggacccccagtgtg cgcaacagtatgttcagacttcggtttgttcacttgctttcatggaccattgcgcgaaagtgcgtgcg ccatatccctgtacttcaggtgtgcttctctggaccctaggaatgctgcgaaggtaccccgtttcggc gggatctgatcgcaggctaattgtctatgggttcagtttccttttttctttactccacaattgactgcttaa ctgactctggatcttgtgcttccactgctctttctgctctcaaaacggcttcacttaccaactctcacctt tcgaccaacaccatttacacactaactttttttcgactcttctgactcctggcttggtgaagac |
| 647 | Kashmir bee virus | tacgtacaattttgacgcttcgttcatgcaacaatgaactcacatgtggcgctcggtagtaaccagag gggcgtcattcccccgtatggagtggagaatataagctaccgactcgagctgtagaataattcagc aacttataacgaacacgaattttagtcgacgaaaccattttagcctttaattctatgatttgattataatg ataaacagctcatgtaactgtctaaactacataaatacaactggattacgaacctttaagtaactatctt agatgaagtctagtagtctcccaatatttccgtgaaaagaatgagggacgagatagctctatttaaa gacgtgaggctttaaattctgataaatacattacctgagaattcctcctttaggagttagaatttgaaaa gattagtacctatacttaatagaatttaaatatgttaataatgctgaagacaagtatttcgattattaacct ctatatttctatataaagtatctgtgagtctcagtggacatcacagtaaggtcgcagttaacttgtaatc ttttcattcctgtgtcggagcagtggtaatggagccggacgatttcgccaaaac |
| 648 | Jingmen picorna-like virus | tgtgtttttgtcaagataattgttctgtgattaacagtgattgtggttcgtgtaatgcgacgcagtcaaat gctagttttgatgaagtgtatgagagagtggaaaacttatctcataagaagattgaagagtgtgtaga tcaggctattgatcgagcttctaagcttcgtgattacaagcttaatgttcacaatggctcccgacggg aatcatctgatcctctctttatttcgccccattcgttgttatcgcttggggtatctaagtttgttgcgtttga gcagcatcacagtttcgcttcagttgagtctctgaagttgcttgctctgtct |
| 649 | Mumps virus | accaaggggaaaatgaagatgggatgttggtagaacaaatagtgtaagaaacagtaagcccgga agtggtgttttgcgatttcgaggccgggctcgatcctcacctttcattgtcgataggggacattttgac actacctggaaa |
| 650 | Mouse Mosavirus | gaagttgatcatgaacttggttattggtggaacgcacatgaactcccaacaatgatcttgaagacac agcgtggtaacaattaccatgcccttgtggctgcccaagacattgatggctattgggtgatttatgat gac |
| 651 | Miniopterus schreibersii picornavirus 1 | gttgtcgacccgttgcttggtttaagcatgaggtggattcccccgattatgtctacccgttactatggc gggcggtcgtttcagggtgtttctactgaggactgcaccaagtctttatcttttattctcagatctccgg ctgtttgacgcttgtaggacagcaggactattttctcttaatctttttctacccactagggtcctatccta gtggagggagggtgccaccccttctctctttagagagtgcgcctggcggtctttccgtctctggaaa aaggagcacatggcatgctacaattggcacaagaaaacaagctttgcggattctttctttgtactaga ggaagctgtagcgaccctgtatggcgagcggactcccctctcggcgacgagagcctctcgggcc aaaagccaagtgttaatagcacccatacaggcggcagtaccccactgccctttctcaacatacaat gactgatgaaccactgttggtttttctgacacctttgtagtaggattccaaggaatgtcctgaaggtac cctgttagcttacgcgcaggatctgatcaggagtctctttacagtgctgtacactgtgcaagggatta aaaattgtttgaggaatccccgagatagtggtctatctcttcctattttgttttacagacacg |
| 652 | Linda virus | gtatagcagcagtagctcaaggctgctatacgattggacataccaaattccaattggtgttagggac cacctaggtgaaggccgacgacaggtagccattcctgttagtaggacgaaccgttatggtggact ggttgctcaggtgagcaggctgcaatgcgtaagtggtgagtacaccacagccgtcaaaggtgcc actggtaaggatcacccactggcgatgccttgtggacgggggcgtgcccaacgcaatgttagcg gtggcgggggctgccatcgtgaaagctaggtcttgatggaccttgttgcctgtacagtctgatagg atgccggcggatgccctgtgacagccagtataaagaatatccgttgtgattgcac |
| 653 | Lesavirus 2 | tctttctttatttcttatgtaactcttctttttaagttttatttgcctacttgtgagcttatgcgggaccactg tcttagacaaccccacatttgtcatgagtaagtacacgcaaccattacgattactttttaaccgtctga ccttttgataacaactgaagttaggcgtgaaacatgcatttataccaaagtagccccgcatttcccca ctacggtgggggggctaccctactggctttggaactgtagccattatgtgttgcctggctttcaggat ctcacaacacaacagttctctcacaatggaatatgggtgagattgcagtgacatgaacaagtatcta gtagtacatagactcaagcctagttgcctgcggaacaacatgtggtaacacatgccccagggtcca aaagacaagggttaacagccccttctaggtgtctgtgtgtgaagaatactttagtagtgttgttatgat ctcacctgttagtacagaatgagtatggcttggtgaaggatgtcctacaggtacccattatatggatc tgagtaggagaccactagtggtggctttaccgccaggtgagtggtttaaaaagcgtctagccaagc caacagcactagggatagtgctttctatattttatattttcagtgtatatggtgacaa |
| 654 | Lesavirus 1 | gtaactaataagcaagttttactgcctgcaaactgcttcaatgggaccaccgcttcggcgaccccttt gttgagtttgtatgtttttaagtaatctttgcaaccatacgattattttagccgcctctctataatgatcttgt tatagtgggacgtgaaacattggtttttctcacacacgtccggtcacccgggcgtgtgttcttccgta agtcctatccacataccatcgtgggtaggccagcatgtttgcacaggctgtgacagtgtgggtggg ctttccacctctcaacaacacactgaattgcaatgcactcacggaggaaatgacaatttggttatagt |

TABLE 17-continued

IRES sequences.

| SEQ ID NO | IRES | Sequence |
|---|---|---|
| | | tttgaactgtgctagtaatttctttcacattaagccatgttgcctgcggaatcacatgtggtaacacatg<br>cctcagggcccaaaaggcacgggttagcagccccttcatggtgtgttagaagtgaaaacacatag<br>tatgagctataatatctttgttgtcttctctgtagtgtaccccgccaaatgtaaggatgcccagcaggt<br>acccattttatggatctgagctggggattgatagtgtatctataaatgcactgatcaatttaaaaagcg<br>tctaagtttggcacaaacactggggacagtgtttttcctttattcttttatttgatta |
| 655 | Phopivirus strain NewEngland | gggagtaaacctcaccaccgtttgccgtggtttacggctacctatttttggatgtaaatattaattcctg<br>caggttcaggtctcttgaattatgtccacgctagtggcactctcttacccataagtgacgccttagcg<br>gaacctttctacacttgatgtggttaggggttacattatttccctgggccttctttggcccttttttcccctg<br>cactatcattctttcttccgggctctcagcatgccaatgttccgaccggtgcgcccgccggggttaa<br>ctccatggttagcatggagctgtaggccctaaaagtgctgacactggaactggactattgaagcat<br>acactgttaactgaaacatgtaactccaatcgatcttctacaaggggtaggctacgggtgaaacccc<br>ttaggttaatactcatattgagagatacttctgataggttaaggttgctggataatggtgagtttaacga<br>caaaaaccattcaacagctgtgggccaacctcatcaggtagatgcttttggagccaagtgcgtagg<br>ggtgtgtgtggaaatgcttcagtggaaggtgccctcccgaaaggtcgtaggggtaatcaggggca<br>gttaggtttccacaattacaatttgaa |
| 656 | Pestivirus strain Aydin | gtatacgagattagctcatactcgtgtacaaattggacgtagcaaatttaaaaattcggatagggtcc<br>ccatccagcgacggccgaacggggttaaccatacctctagtaggactagcagacggatggacta<br>gccacagtggtgagctccctgggaggtctaagttctgagtacagaacagtcgtcagtagttcaacg<br>ctggtaaaccccagccttgagatgctacgtggacgagggcatgcccaagacacaccttaacctgg<br>acgggggtcgtccaggtgaaagtacccatctttgggtgctgggagtacagcctgatagggcgctg<br>cagaggcccactgacaggctagtataaaaatctctgctgtacatggaac |
| 657 | Quail picornavirus QPV1 | tttgcatcagttcgcccctcccctcaccataccttttttcccctctttaggactgatacttggttatgatga<br>gcagaggatttcgcaagttatgcttcttgataaaaagtaattcacgaatcatgggattatagcctgga<br>agtgaacactcatgtggcaagtgggttagtagctctccatgttcccatgtgcagtggactgacaaca<br>gtgagttcggggttgtgtagtaaagggaaagtattacttacccgcacctgctatacgtggtgtacgta<br>ggatacgagttagtagtgcttagcaactttaaactggtgctgaaatattgcaaggtcactgaagttgt<br>gaacgcgaacgctccgccactgccatgtatagcgtgcaatgcataaatggtgcactacatgatacg<br>agggaatgggaaaccctccatggccgaatgcagggtgacagcctgccggcggatgcctgttgtt<br>agtataatccgttgtttgccac |
| 658 | Porcine sapelo virus 1 | acactcatttccccccctccacccttaaggtggttgtatcccctacaccctaccctcccttccacatagg<br>acgaataaacggacttgagattaaggcaagtacataaggtatggtttttggatacacttaaatggca<br>gtagcgtggcgagctatggaaaaatcgcaattgtcgatagccatgttagcgacgcgcttcggcgtg<br>ctcctttggtgattcggcgactggttacaggagagtagacagtgagctatgggcaaacccctacag<br>tattacttaggggaatgtgcaattgagacttgacgagcgtctctttgagatgtggcgcatgctcttgg<br>cattaccatagtgagcttccaggttgggaaacctggactgggtctatactgcctgatagggtcgcg<br>gctggccgcctgtaactagtatagtcagttgaaaaccccccc |
| 659 | Porcine reproductive and respiratory syndrome virus 2 | atgacgtataggtgttggctctatgccttggcatttgtattgtcaggagctgtgaccattggcacagc<br>ccaaaacttgctgcacagaaacacccttctgtgatagcctccttcaggggagcttagggtttgtccct<br>agcaccttgcttccggagttgcactgctttacggtctctccacccctttaacc |
| 660 | Porcine enterovirus 9 | Gaaccttagaagtttacacaaacaaagaccaataggagtccaacacccagttggattgcggtcaa<br>gcacttctgtttccccggacctagtagtgataggctgtacccacggccgaagatgaacccgtccgtt<br>atccggctacctacttcgggaagcctagtaacattctgaagtctctgaggcgtttcgctcagcacga<br>ccccggtgtagatcgggctgatgggtctccgcataccccacgggcgaccgtggcggaggccgc<br>gttggcggcccgcctatggcgaaagccataggacgcctcttagatgacagggtgtgaagagcct<br>actgagctgggtagtagtcctccggcccctgaatgcggctaatcctaaccacggagcgtccacca<br>gcaatccagctggcagggcgtcgtaacgggcaactctgtggcggaaccgactactttgggtgtcc<br>gtgtttccttttgatcctattttggctgcttatggtgacaacgataagttgttatcataaagctcttgggtt<br>ggccacctggaaaaagttatcagtgtttgatattgttcggctctcacgcctaccaataagacaagcc<br>ctatatttacttgttgcattttactcgtcagaagaaatcacagagtatcatttggatttgttactcacatta<br>aggacaag |
| 661 | Pigeon picornavirus B | tttatttagctgttaagttttatttgtgccgagAccccatagtaggatcttggtgttccacattaagctct<br>Cccgaccacacatccaaacgataggcggtgtaagggctccctggctaagtgtttactcattgctag<br>ggaagtgttgcgacccgttaccagtaggaatacaggaggtcttagttgcctaaccagataaagtgg<br>tgctgaaatattgcaagctcaatgtctggcgaacgacggactaccgttgaactattgttaacgcccg<br>cgtgtgtaggcaacacacgggttagtaggtcacttacattgacatccgtgccgggaaagcggatct<br>gagctatcgattgcctgatagggtgccggcgggcgcggtacgtgtggtatagtccgctgtcttggg<br>gtatggcgtctactcggttttgttgtcgttttggaatgtcccatgtcggagatgtcgttaccggtgtttg<br>ctttacttgtgcacgaataagaaaacagagtttggagttttggaagttaatggataacatcaagtttcc<br>attgcgttcctcgtgcattttaggccagaaaatcgaccacaaaatcgaga |
| 662 | Picornavirus HK21 | aaacgggaggatcggctttggcttatcctcttaatagtctacaaaactgggctgactggtgggga<br>gctactagatccgggagaggactagttaccccgcgtaacttccctttttgtcactccctccacctacc<br>ccttccctgtcccttagactcttaagtaggtgtgcaggcctggcccccccggaaatgggcaaatcgg<br>acgtttgcgtgtagggtcgttctgaaaggtggggcccactccaccgtagtaggatcttcctgtttcac<br>gtttaaacctctccgggcaggtatcgctagacactaggctgtataggatggcacgcacttaggtttc<br>gcaccttcctagtgcgccaagatcccgcttttgagctcaagtacatggttctttgtaagatgtctaacc<br>agaggaggtggtgctgaaatattgcaagccactctggcgaacgtccactgcattgcctggaacag |

TABLE 17-continued

IRES sequences.

| SEQ ID NO | IRES | Sequence |
|---|---|---|
| | | gctctctagcgccctccactggtagcgcggtggtgggttagtaggatacctatatggacaggggat<br>gcgggaataccccctcactagctagtgactggttgatcgactggcggcggatccagtgatacttgca<br>taatccgcagacttgggag |
| 663 | Picornavirales Tottori-HG1 | agccatgaactagtgtgcgattcccacagtgttggtcgaaagccccgcactgtctactcgcatattt<br>gactccagtccttccgcagccagcggttaggttctggttaaagtgcattatgtgcacggcgccacg<br>cagaactgccagaaatggtaagctgcgcccaacgccaacggtttgtgtatcccgttagtcacacgt<br>ttacagctgttcgttaacagtagggttttgtcgacccggacccccttaatgcgcgcgaattcaaccgc<br>gcctagtcggcaatggtatcatttaatcccatgcactacgggagaaatttgagaccaaagaattcct<br>gagggccactgcttgctctaagtgcaatgcctcgggagacttctgtcaggagcctagcggctttca<br>accgcgacagctaactcctgcgggatgtttggtgtccatacttactggcgtcctcacaacgctaagt<br>ggatgttgtccacaggtaggcaaacaccgagccccacattcaggagacctgtatgaacgatcctat<br>cagcattagagttggaattgggtgtgctaacgtccgcataagtgcaccccgtggtaacgctgggaa<br>actatccagcgcaacgtactgtcctcaatgtctagggaaggaccgccctaagcgtacaaccgggc<br>catgtgtcgagc |
| 664 | Rodent hepatovirus | ttcaaagaggggtccgggattttcctggtccccctctttgggcacccttggctcgggggtgtgaata<br>ccgtgctcgcgtttgccgtgcgttaacggcttcatttatgtttgtttgtctgttttattatgttGgtttgtct<br>gtttgttatgttggtattgttcgtgtttaatgttatgaccacattacactccagccaatgaagaacagatg<br>gtgcggttattgctggcggaattcctaacgtcctggatccgttggtacgcatcacaaaacaatttgca<br>gagagagtggtgaaacggcttgggaatccctgagtacagggaaatcacactgatagctcatcttg<br>gctgttttcagtcatggaccttatgcagtgtaatttgggtgtacccccccatagcttaggaggaatgttc<br>tgtcttggcactagagtgggacgctgatgcctccgtgtctaggatggtctaagggacagaatgggg<br>tgcctctgatgccatactacctgatagggtgctctcacggcctctgcatcttagtgagaagttcaattt<br>t |
| 665 | Rinderpest virus | accaaacaaagttgggtaaggatcggtctatcaatgattatgatttagcacacttaggattcaagatc<br>ctatcgactggagcaggcttaaggtaaaggttctttaaa |
| 666 | Rabovirus A | ctacggatatttgcatgacccgctttctatcgccccaacaatcccctttgtaaccacaagctttactca<br>ggctagcagcccgactagctgtttggaagaaaaggctagggcacacaccaacaacaccgaccc<br>cactggtcgaaggccgcttggcaataagactggtggaacagggtcgcctgtagttgtttggaacat<br>tctttctaatgactttgtcagcggtgctactcacaccgtaactcttctaccctatccccacgcttgtgga<br>actaggaggggatgagtgattcaagtaagtactgtcagaatggtgaaaatgatctgattctgaaacg<br>ctatggatccatcgaaagatggggctacacgcctgcggaacaacacatggtaacatgtgccccag<br>gggccgaaagccacggtgataggatcacccgtgtagtttgagatcatatcaatgttcatagtctagt<br>aagatgatttgaaatctaactgagctgatggctaactgcttgtcttattgcggcctaaggatgtcctgc<br>aggtacctttagataaccttaagagactattgatctgagcaggagccaaagtggtctttcccagcttt<br>ggttaaaaaacgtctaagccgcggcaggggggcgggaggccccctttcctcccaaaacttaatatt<br>gattgt |
| 667 | Shingleback nidovirus 1 | ctgtgagtaccgacaggctcgaagtctattatgaggcgtcgaaacagaaaacctgtaacaactccg<br>gtttcatctatcactgccgtcaagaggcagaagaggacgaccacgtgtcaccagatcacttgtatct<br>gtttcagtcaggaagtcaacttttcgacgaagttcgaccattcatcgacccgctgaaaagcgtagaa<br>gtcgatgaagatgagctccaaagagccatcgccgatttcgacaaccaaagtgactgtttccactcct<br>tcgagctcgtgaatttcgagctgaaacaacaaatcaacgagaacgagtggtacggttattataatta<br>cgacaaccaaaactgcaaagttcagttgccagtcacatgtcgaatcgaggacgtaacctgggatc<br>aggtttacgtg |
| 668 | Seneca valley virus | tttgaaatggggggctgggccctgatgcccagtccttcctttccccttccgggggggttaaccggctg<br>tgtttgctagaggcacagaggggcaacatccaacctgcttttgcggggaacggtgcggctccgatt<br>cctgcgtcgccaaaggtgttagcgcacccaaacggcgcacctaccaatgttattggtgtggtctgc<br>gagttctagcctactcgtttctcccccgaccattcactcacccacgaaaagtgtgttgtaaccataag<br>atttaaccccccgcacgggatgtgcgataaccgtaagactggctcaagcgcggaaagcgctgtaac<br>cacatgctgttagtccctttatggctgcaagatggctacccacctcggatcactgaactggagctcg<br>accctccttagtaagggaaccgagaggccttcgtgcaacaagctccgacacagagtccacgtga<br>ctgctaccaccatgagtacatggttctcccctctcgacccaggacttctttttgaatatccacggctcg<br>atccagagggtggggcatgacccctagcatagcgagctacagcgggaactgtagctaggcctta<br>gcgtgccttggatactgcctgatagggcgacggcctagtcgtgtcggttctataggtagcacatac<br>aaat |
| 669 | Sclerotinia sclerotiorum dsRNA mycovirus-L | ttgaattaatcttttacgtttacgcgcataaaatcaggacacatctcttgtatactttagtatatcaatgat<br>gtttttgttttatgcgattaatcgtaagagaacttctttccatccgcctgtatgggcgggataataagttc<br>accgccttggtcgaggcgcaaacttgtatgtgcaaaggtgagctatatgctcgaaatagtcgtaact<br>aacacacagccactacctgtagagctctattgatccggaatcctttagtgggaatgcagagctcaca<br>ccggacctgcgggtatcttcggcgttagggacttctgtttcagccttgaatcatttacctttataccttct<br>ctgaggcgcctgggccgggcgcgatattaagtacaagtcaaggacatcgcgggtagtggtctaat<br>cagccgctagtcctgctggagagttccaacttagttgggtgtggtgcatactagctggatagagtag<br>gtatgtattgctaacgtatgccggaggctatccgtcctcggtagaacgtgccgaggagtagtctctg<br>cagacccccgaacgcgtggggtctttacttaaatgtaggcggagggagcgctcgtaggtggaac<br>gactgcctcccagtcgaatgcaagattttgcacgcggaccagtctgcccggcaattcccgggtg |
| 670 | Yak enterovirus | ctccggcacagccgcaccagtgcactggtacgctagtaccttttcacggggtagtcggtatccccc<br>cccgtaacttagaagcatgtaacaaaccgaccaataggtgcgcggcagccagctgcgttgcggtc<br>aagcacttctgtctccccggtccgcaaggatcgttacccgcccactccactacgaggagcctagta |

TABLE 17-continued

| IRES sequences. | | |
|---|---|---|
| SEQ ID NO | IRES | Sequence |
| | | actggccaagtgattgcggagttgcgttcagccacaaccccagtggtagctctggaagatggggc<br>tcgcacatcccccgtggtaacacggttgcttgcccgcgtgtgcttccgggttcagtctccgactgttc<br>acttcaacatcacgcaaccagccaagagccgattgtgctggagtggtcttcctccggggccgtga<br>atgctgctaatcctaacctccgagcgtgtgcgcacaatccagtgttgctacgtcgtaacgcgtaagt<br>tggaggcggaacagactactttcggcaccccgtgtttcctttattttattcttattttatggtgacaattg<br>cagagatttgtgatattgcgactttaccgttaaacatagcactgcattacctggttgcattccacaaaa<br>cttcagagattcctagttcctacattgacctacttgtttatttgaatcttaaatacaaacttgagcaagtg<br>aa |
| 671 | Wobbly possum disease virus | cggctgtgagtgcttagcatatgctagagtactacagccgggtgttggagtcatatgcactggttgc<br>ctgtataatagtcgggatctgtctgacctacattatctttgggagttgcttatcacgacaattctcgaag<br>tgtctgtcgacagcttacccccgattcgacaaggccccttgtccaccgcagacctatcgattttcaac<br>gagaacactatcagaggtttaaatttaaaactcaccaaca |
| 672 | Avian orthoreo virus segment S1 | gctttttcaatcccttgtgtcgatgttcccgtatgtcatctggttcatgtaacggtgcaacttctatttttg<br>gtaacgttcactgtcaggcagcgcaaaactcggcgggtggtgatcttcaagcgacttcctctcttgtt<br>gcttattggccctacttggctgcgggcggtggtctgctcgttgttattattataattgttggcgctgtttg<br>ttgttgcaaggctaaggttaaagcggacgcagcccgaaacgttttctaccgagagctgttcgcactt<br>aattcgggtaaaagtgatgcaggacctccgatttaccaggtttagtgtacgacgatttgagttttcac<br>ctttcgtcttagaggagtgcactactccatctttcacgactataactaataccgatccggctctctactt<br>taacattgagtttccgtcaagtcatcgtctctccccccttcattccagaactgttgtctcagccttgtacc<br>gttcacgtttcattgattcggagattcgctctctgtgcaaccttatctagtatttgtgaatacgactgtgc<br>gctactgccatccatcaacgctattacgacgatccctacaccaggtgcgtcatcatctctgattgttc<br>attggg |
| 673 | Caprine Kobuvirus d10 | ggggcctcggcccccctcaccctcttttccggtggccacgcccgggccaccgatacttcccttcact<br>ccttcgggactgttggggaggaacacaacagggctcccctgttttcccattccttcccccttttccca<br>accccaaccgccgtatctggtggcggcaagacacacgggtctttccctctaaagcacaattgtgtg<br>tgtgtcccaggtcctcctgcgtacggtgcgggagtgctcccacccaactgttgtaagcctgtccaa<br>cgcgtcgtcctggcaagactatgacgtcgcatgttccgctgcggatgccgaccgggtaaccggtt<br>ccccagtgtgtgtagtgcgatcttccaggtcctcctggttggcgttgtccagaaactgcttcaggtaa<br>gtggggtgtgcccaatccctacaaaggttgattctttcaccaccttaggaatgctccggaggtaccc<br>cagcaacagctgggatctgaccggaggctaattgtctacgggtggtgtttcctttttcttttcacacaa<br>ctctactgctgacaactcactgactatccacttgctctcttgtgcctttctgctctggttcaagttccttg<br>attgtttttgactgcttttcactgcttttcttctcacaatccttgctcagttcaaagtc |
| 674 | Caprine Kobuvirus d20 | ccccctcaccctcttttccggtggccacgcccgggccaccgatacttcccttcactccttcgggact<br>gttggggaggaacacaacagggctcccctgttttcccattccttcccccttttcccaaccccaaccg<br>ccgtatctggtggcggcaagacacacgggtctttccctctaaagcacaattgtgtgtgtgtcccagg<br>tcctcctgcgtacggtgcgggagtgctcccacccaactgttgtaagcctgtccaacgcgtcgtcct<br>ggcaagactatgacgtcgcatgttccgctgcggatgccgaccgggtaaccggttccccagtgtgt<br>gtagtgcgatcttccaggtcctcctggttggcgttgtccagaaactgcttcaggtaagtggggtgtg<br>cccaatccctacaaaggttgattctttcaccaccttaggaatgctccggaggtaccccagcaacag<br>ctgggatctgaccggaggctaattgtctacgggtggtgtttcctttttcttttcacacaactctactgct<br>gacaactcactgactatccacttgctctcttgtgcctttctgctctggttcaagttccttgattgtttttga<br>ctgcttttcactgcttttcttctcacaatccttgctcagttcaaagtc |
| 675 | Caprine Kobuvirus d30 | ctcttttccggtggccacgcccgggccaccgatacttcccttcactccttcgggactgttggggagg<br>aacacaacagggctcccctgttttcccattccttcccccttttcccaaccccaaccgccgtatctggt<br>ggcggcaagacacacgggtctttccctctaaagcacaattgtgtgtgtgtcccaggtcctcctgcgt<br>acggtgcgggagtgctcccacccaactgttgtaagcctgtccaacgcgtcgtcctggcaagactat<br>gacgtcgcatgttccgctgcggatgccgaccgggtaaccggttccccagtgtgtgtagtgcgatct<br>tccaggtcctcctggttggcgttgtccagaaactgcttcaggtaagtggggtgtgcccaatccctac<br>aaaggttgattctttcaccaccttaggaatgctccggaggtaccccagcaacagctgggatctgac<br>cggaggctaattgtctacgggtggtgtttcctttttcttttcacacaactctactgctgacaactcactg<br>actatccacttgctctcttgtgcctttctgctctggttcaagttccttgattgtttttgactgcttttcactgc<br>ttttcttctcacaatccttgctcagttcaaagtc |
| 676 | Caprine Kobuvirus d40 | gtggccacgcccgggccaccgatacttcccttcactccttcgggactgttggggaggaacacaac<br>agggctcccctgttttcccattccttcccccttttcccaaccccaaccgccgtatctggtggcggcaa<br>gacacacgggtctttccctctaaagcacaattgtgtgtgtgtcccaggtcctcctgcgtacggtgcg<br>ggagtgctcccacccaactgttgtaagcctgtccaacgcgtcgtcctggcaagactatgacgtcgc<br>atgttccgctgcggatgccgaccgggtaaccggttccccagtgtgtgtagtgcgatcttccaggtc<br>ctcctggttggcgttgtccagaaactgcttcaggtaagtggggtgtgcccaatccctacaaaggttg<br>attctttcaccaccttaggaatgctccggaggtaccccagcaacagctgggatctgaccggaggct<br>aattgtctacgggtggtgtttcctttttcttttcacacaactctactgctgacaactcactgactatccact<br>tgctctcttgtgcctttctgctctggttcaagttccttgattgtttttgactgcttttcactgcttttcttctca<br>caatccttgctcagttcaaagtc |
| 677 | Caprine Kobuvirus d50 | ccgggccaccgatacttcccttcactccttcgggactgttggggaggaacacaacagggctcccc<br>tgttttcccattccttcccccttttcccaaccccaaccgccgtatctggtggcggcaagacacacgg<br>gtctttccctctaaagcacaattgtgtgtgtgtcccaggtcctcctgcgtacggtgcgggagtgctcc<br>cacccaactgttgtaagcctgtccaacgcgtcgtcctggcaagactatgacgtcgcatgttccgctg<br>cggatgccgaccgggtaaccggttccccagtgtgtgtagtgcgatcttccaggtcctcctggttgg<br>cgttgtccagaaactgcttcaggtaagtggggtgtgcccaatccctacaaaggttgattctttcacca |

TABLE 17-continued

| SEQ ID NO | IRES | Sequence |
|---|---|---|
| | IRES sequences. | |
| | | ccttaggaatgctccggaggtaccccagcaacagctgggatctgaccggaggctaattgtctacg ggtggtgtttccttttctttcacacaactctactgctgacaactcactgactatccacttgctctcttgt gcctttctgctctggttcaagttccttgattgtttttgactgcttttcactgcttttcttctcacaatccttgct cagttcaaagtc |
| 678 | Picornavirales sp. isolate RtMruf-PicoV | tttgctcagcgtaacttctccgggttacgtggagaccaaaaggctacggagactcgggctacggc cctggagcacctaggtgctcctaaagacgttagaagttgtacaaactcgcccaatagggcccccc aaccaggggggtagcgggcaagcacttctgtttccccggtatgatctcataggctgtacccacgg ctgaaagagagattatcgttacccgcctcactacttcgagaagcccagtaatggttcatgaagttgat ctcgttgacccggtgtttcccccacaccagaaacctgtgatgggggtggtcatcccggtcatggcg acatgacggacctccccgcgccggcacagggcctcttcggaggacgagtgacatggattcaacc gtgaagagcctattgagctagtgttgattcctccgcccccgtgaatgcggctaatcccaactccgga gcaggcgggcccaaaccagggtctggcctgtcgtaacgcgaaagtctggagcggaaccgacta ctttcgggaaggcgtgtttccttttgttccttttatcaagttttatggtgacaactcctggtagacgttttat tgcgtttattgagagatttccaacaattgaacagactagaaccacttgttttatcaaaccctcacagaa taagataaca |
| 679 | Apodemus agrarius picornavirus strain Longquan-Aa118 | ttactcagcgtaactactccgggttacgtgatgaagaagaggctacggagattctcgggctacggc cctggagccactccggctcctaaagatttagaagtttgagcacacccgcccactagggcccccca tccaggggggcaacgggcaagcacttctgtttccccggtatgatctgataggctgtaaccacggct gaaacagagattatcgttatccgcttcactacttcgagaagcctagtaatgatgggtgaaattgaatc cgttgatccggtgtctcccccacaccagaaactcatgatgagggttgccatcccggctacggcga cgtagcgggcatccctgcgctggcatgaggcctcttaggaggacggatgatatggatcttgtcgtg aagagcctattgagctagtgtcgactcctccgcccccgtgaatgcggctaatcctaaccccggagc aggtgggtccaatccagggcctggcctgtcgtaatgcgtaagtctgggacggaaccgactactttc gggaaggcgtgtttccatttgttcattatttgtgtgtttatggtgacaactctgggtaaacgttctattgc gtttattgagagattcccaacaattgaacaaacgagaactacctgttttattaaatttacacagagaag aattaca |
| 680 | Niviventer confucianus picornavirus | ccctttcataacccccccctttttaacccaacccttcgtaaccgtacgcttcactcgcctttgggtatag cggcccaatgtgctgaagaaaaggatacgctataaggggccaacgggtggtggcccttaagacc acccaacctagaagcttgtacactcgggcaatagtgaggcccacatccagtgggtcaagcccaaa gcattcttgttccccggtatgatctcataagctgtacccacggctgaaagagtgattatcgttatccca ctcagtacttcggagagcctagtacaccacttggaaatggaagtctgtgatccggggttgaccctg aaccccagaaactcatgatgaggctaaccttcccgaacacggcgacgtgtggttagcctgcgctg gcatgaggcctctttgtaggcagactgaaatggaagggtgacgaagagccgactgagctactgttt tattcctccggccccctgaatgcggctaatcctaactcctggtccagtacttgtaacccaacaggtg gctggtcgtaatgcgtaagccgggagcggaaccgactactttggggcgtccgtgtttctcaatatta ttcatttctagcttatggtgacaatttatgattgcagagattgtgctgtatttgtgtctgagagaagaagt aacaat |
| 681 | Bat picornavirus isolate BtRs-PicoV | tttcaaaaggccctgggcatacggcgttattcgtaacgtcgtatgtccagggcggtagcatcaggc caaggcctgatgctaccacgtgtggactaaaccacacactcttcttgtgacacgttgtgtcacctatc cctttcttggtaacttagaagcttgtacacttacgcacgtaggtgccccacatccagtggggtttgtg caaagcaatcttgttccccggtaaaccctgataggctgtaaccacggccgaaacaaggtttgtcgtt acccgactcactactacacaaagcctagtaaagttcaatgaaagtgcgcagcgtgatccggtcaaa accccttgaccagaaacacatgatgagggtcaccaaccccactggcgacagtgtggtgtccct gcgttggcatgtggcctcgtagaggcgttgcaatctggatttgctccgaagagccccgtgtgctagt gtttatacctccggccccttgaatgcggctaatcctaacccccgagcatgtacacacaagccagtgt gtagcatgtcgtaatgagcaatttggggatggaaccgactactttagggtgtccgtgtttctcattatt ctttgtttgatgtttt |
| 682 | Rhinolophus picornavirus strain Guizhou-Rr100 | tttttttctcaggcggtagcatccagccaaggcctgatgctaccaacgtgtgactaaaccacactct ctttttgtgatacattgtgtcacctatccctttcttggtaacttagaagcttgtacacccacgcacgtag gtaccccacatccagtggggtttgtgcaaagcattcttgttccccggtaaaccctgataggctgtaa ccacggctgaaacaaggtttgtcgttacccgactcactactacgcaaagcctagtaaagttcaatga aagtgcgcagcgtgatccggtcaaaaccccccttgaccagaaacacatgatgagggtcaccaacc cccactggcgacagtgtggtgtccctgcgttggcatgtggcctcatagaggcgttgcaatctggatt tgctccgaagagccccgtgtgctagtgtttatacctccggccccttgaatgcggctaatcctaaccc ccgagcatgtacacacacgccagtgtgcagcatgtcgtaatgagcaatttggggatggaaccgac tactttagggtgtccgtgtttctcattattctttgtttgatgttttatggtgacaaca |
| 683 | Rhinolophus picornavirus strain Henan-Rf265 | cggaacgttgtatgctcagggcgtaggcaccacccacgggtggtgcctacacgtgtggactaaac cacacactcttttcagcacttagtgctgctatctctttttgtaacttagaagtttgtacacaatgcgttag ggccacacatccagtgtggtatcgcaaagcacttctgtttccccggtgctagtaggagggtggctg ctccacggccacttgccgaacccatcgttacccgactcattacttcgcaaagcctagtaacccagtt gaagcaagcccggcgtgttccggtcaggaaaaacccccctggccagaaacatgtgatgagggt gggctatccccactggtgacagtgagccctccctgcgttggcacatggcccgatctgggcgtggtt cttgtggatgctgccgaagagccccgtgagctagtgtttataccgccggcctcgtgaatgcggcta accctaaccccggagcagaggctactgaagccacagtagtcgctgtcgtaacgagtaattctggg atgggaccgactactttcgagtgtccgtgtttcctttattcttttattgttgtttatggtgacaaac |
| 684 | Human enterovirus C105 | cccctaggatccactggatgtcagtacactggtatcgtggtacctttgtacgcctgttttatacccccctt ccccgcaactttagaagcatcaaaagcaccgctcaatagtcaccacacccccagtgtggtttcgag caagcacttctgttttcccggttgcgtcccatatgctgtgcaaacggcaaaaagggacaatatcgtta |

TABLE 17-continued

| IRES sequences. | | |
|---|---|---|
| SEQ ID NO | IRES | Sequence |
| | | cccgcttgtatactacgggaaacctagtaccaccattgattgtgttgagagttgcgctcatcacctttc cccggtgtagctcaggccgatgaggctcagaatcccccacaggtgactgtgtctgagcctgcgtt ggcggcctgccctcgccttatggcgtgggacgcttgatacatgacatggtgcgaagagtctactgt gctatgcaagagtcctccggcccctgaatgtggctaatcctaaccactgatcccacgcacgcaaac cagtgtgtagtgggtcgtaacgcgcaagtcggtggcggaaccaactactttgggtgaccgtgtttc ctttattacttattgaatgtttatggtgacaattgtttgattcagttgttgccattctctacattcatttaccca gcatcaaaccaattgaactgttaca |
| 685 | Human poliovirus 1 strain NIEI116623 | agtctggacatccctcaccggcgacggtggtccaggctgcgctggcggcctacctgtggtccaaa gccacgggacgctacatgtgaacaaggtgtgaagagcctattgagctacaaaagagtcctccgg cccctgaatgcggctaatcccaaccacggatcaagggtgcacaaaccagtgtacaccttgtcgta acgcgcaagtctgtggcggaaccgactactttgggtgtccgtgtttcctttttaattttgatggctgctt atggtgacaatcatagattgttatcataaagctaattggattggccatccggtgagagtgaaatatatt gtttacctccctgttgggtttactctaactaacttctccatttataaacttgtcatcacagttttaataatta gaagtgcagtttaca |
| 686 | Human enterovirus 109 | tttaaaacagcctggggttgttcccacccccagggcccactgggcgttagtactctggtatcgcg gtaccttagtatgcctgttttatgtctcctttcccccgcaactttagaagtaatcaagttatggctcaaca gtcgccacacccccagtgtggttccgagcaagcacttctgttccccggttgcgtcttatatgctgtgt gaacggcagaaagggacaatatcgttatccgctcaactactacgggaagcctagtaccaccatgg attgacctgaaagttgcgttcagcgcacccccagcgcagctcaggccgatgaggctccgaatacc ccacgggcgaccgtgtcggagcctgcgttggcggcctgcccacgttgcaaaacgtgggacgctc atttcatgacatggtgcgaagagcctactgtgctagttgagagtcctccggcccctgaatgtggata atcctaaccactgaacctacgggcgcaaaccagcgtctggtaggccgtaacgcgcaagtcggtg gcggaaccaactactttgggtgtccgtgtttccttttatctttttgaatgtttatggtgacaattgttgtgta cagttgttaccatagtttgcattcagaaataaacctaacactttccaattatttgttaca |
| 687 | Human poliovirus 2 strain NIE0811460 | ttgtgcgcctgttttatattcccccccccgcaacttagaagcacgaaaccaagttcaatagaaggggg tacaaaccagtaccaccacgaacaagcacttctgtttccccggtgacattgcatagactgctcacgc ggttgaaagtgatcgatccgttacccgcttgtgtacttcgaaaagcctagtattgccttggaatcttcg acgcgttgcgctcagcacccgaccccggggtgtagcttaggctgatgagtctggacattcctcacc ggtgacggtggtccaggctgcgttggcggcctacctatggctaatgccataggacgctagatgtg aacaaggtgtgaagagcctattgagctacataagagtcctccggcccctgaatgcggctaatccta accacggagcaggcggtcgcaaaccagtgactagcttgtcgtaacgcgcaagtctgtggcggaa ccgactactttgggtgtccgtgtttcctgttatttttattatggctgcttatggtgacaatcagagattgtt atcataaagcgaattggattggccatccggtgagtgttgtgtcaggtatacaactgtttgttggaacc actgtgttagtttaacctctctttcaaccaattagtcaaaaacaatacgaagatagaacaacaatacta ca |
| 688 | Bovine picornavirus | ttttctcccctcccccctccaactaccttttccccctcttgtaacgctagaagtttgtgcaaaccgcctgt agggtactgcaatccagcagtgcataggctaagcttttcttgttaccccaccccacattatactgagg aggattgtgaaattgtgttagtatgggttagtagcggtgacccgggtaaccccaacccagaaactc acggatgagatgaacaggaccccacatggtaacgtgtgtgttcgtctgccccgcaaggtgaggcc gtgagagctttgcacgcgaaaaccttgaaaacccaaaagtaccttgagctcttcgctattttgtgtttc ctccaggaccctgaatgcggctaaacctaacccgcgatccgcacgtagcaacccagctagagtgt ggtcgtaatgcgcaagttgcgggcggtaccgactactttggtgttcctgtgtttcctttattttattttga atttttatggtgacaacagctagaaaataagagtgaac |
| 689 | Human poliovirus 1 strain EQG1419328 | acccttgtacgcctgttttatactcccctccccgtaacttagaagaaacaaaataagttcaataggag ggggtacaaaccagtaccaccacgaacaagcacttctgtctccccggtgacattgcatagactgtc cccacggttgaaagcaattgatccgttacccgctcttgtacttcgagaagcctagtaccatcttggaa tcatcgatgcgttgcgctccacactcagtcccagagtgtagcttaggctgatgagtctggacattcct caccggcgacggtggtccaggctgcgttggcggcctacctgtggcccaaagccacaggacgct agatgtgaacaaggtgtgaagagcctattgagctataagagagtcctccggcccctgaatgcggc taatcccaaccacggatcaagggtgcacgaaccagtgtataccttgtcgtaacgcgcaagtccgtg gcggaaccgactactttgggtgaccgtgtttccttttattatttcaatggctgcttatggtgacaatcatt gattgttatcataaagcgaattggactggccatccggtgaaagtgaaacatattgtttgcctcctcgtt gggtctacttcaaccaatctttacttacaatcttaccactacagttttgctggttagaagtgtgtttcacg |
| 690 | Human poliovirus 2 isolate IS_061 | ttgtgcgcctgttttatactcccctcccgcaacttagaagcacgaaaccaagttcaatagaaggggg tacaaaccagtaccactacgaacaagcacttctgtttccccggtgacattgcatagactgctcacgc ggttgaaagtgatcgatccgttacccgcttgtgtacttcgaaaagcctagtatcgccttggaatcttc gacgcgttgcgctcagcacccgaccccggggtgtagcttaggccgatgagtctggacattcctca ccggtgacggtggtccaggctgcgttggcggcctacctatggctaacgccataggacgttagatg tgaacaaggtgtgaagagcctattgagctacataagagtcctccggcccctgaatgcggctaatcc taaccacggagcaggcggtcgcgaaccagtgactggcttgtcgtaacgcgcaagtctgtggcgg aaccgactactttgggtgtccgtgtttcctgttatttttatcatggctgcttatggtgacaatcagagatt gttatcataaagcgaattggattggccatccggtgagtgttgtgtcaggtatacaactgtttgttggaa ccactgtgttagctttgcttctcatttaaccaattaatcaaaaacaatacgaggataaaacaacaatac taca |
| 691 | Coxsackievirus B5 | cctttgtgcgcctgttttatgccccccttcccccaattgaaacttagaagttacacacaccgatcaacag cgggcgtggcataccagccgcgtcttgatcaagcactcctgtttccccggaccgagtatcaataga ctgctcacgcggttgaaggagaaaacgttcgttacccggctaactacttcgagaaacctagtagca tcatgaaagttgcgaagcgtttcgctcagcacatccccagtgtagatcaggtcgatgagtcaccgc |

TABLE 17-continued

| IRES sequences. | | |
|---|---|---|
| SEQ ID NO | IRES | Sequence |
| | | attccccacgggcgaccgtggcggtggctgcgttggcggcctgcctacggggcaacccgtagg<br>acgcttcaatacagacatggtgcgaagagtcgattgagctagttagtagtcctccggcccctgaatc<br>cggctaatcctaactgcggagcacataccctcaacccaggggcattgtgtcgtaacgggtaact<br>ctgcagcggaaccgactactttgggtgtccgtgtttccttttattcttataatggctgcttatggtgaca<br>attgaaagattgttaccatatagctattggattggccatccggtgtctaacagagctattatatacctct<br>ttgttggatttgtaccacttgatctaaaggaagtcaagacactacaattcatcatacaattgaacacag<br>caaa |
| 692 | Coxsackievirus A10 | tttgtgcgcctgttttacaacccttccccaacttgtaacgtagaagtaatacacactactgatcaatag<br>caggcatggcgcgccagtcatgtctcgatcaagcacttctgttcccccggactgagtatcaataga<br>ctgctcacgcggttgaaggagaaaacgttcgttacccggctaactacttcgagaaacctagtagca<br>ccatagaagctgcagagtgtttcgctcagcacttccccgtgtagatcaggctgatgagtcactgca<br>atccccacgggtgaccgtggcagtggctgcgttggcggcctgcctatggggcaacccataggac<br>gctctaatgtggacatggtgcgaagagtctattgagctagttagtagtcctccggcccctgaatgcg<br>gctaatcctaactgcggagcacatgccttcaacccagaaggtagtgtgtcgtaacgggcaactctg<br>cagcggaaccgactactttgggtgtccgtgtttctttttattcctatattggctgcttatggtgacaatca<br>cggaattgttgccatatagctattggattggccatccggtgtctaatagagctattgtgtacctatttgtt<br>ggatttactccgctatcacataaatctctgaacactttgtgctttatattgaacttaaacacccgaaa |

In some embodiments, an IRES of the invention is an IRES having a sequence as listed in Table 17 (SEQ ID NOs: 1-72 and 348-389). In some embodiments, an IRES is a Salivirus IRES. In some embodiments, an IRES is a Salivirus SZ1 IRES. In some embodiments, an IRES is a AP1.0 (SEQ ID NO:348). In some embodiments, an IRES is a CK1.0 (SEQ ID NO:349). In some embodiments, an IRES is a PV1.0 (SEQ ID NO:350). In some embodiments, an IRES is a SV 1.0 (SEQ ID NO:351).

TABLE 18

| Anabaena permutation site 5′ intron fragment sequences. | | |
|---|---|---|
| SEQ ID NO | Permutation site | Sequence |
| 73 | L2-1 | GAAGAAATTCTTTAAGTGGATGCTCTCAAACTCAGGGAAACC<br>TAAATCTAGTTATAGACAAGGCAATCCTGAGCCAAGCCGAAG<br>TAGTAATTAGTAAGTTAACAATAGATGACTTACAACTAATCG<br>GAAGGTGCAGAGACTCGACGGGAGCTACCCTAACGTCAAGAC<br>GAGGGTAAAGAGAGAGTCCAATTCTCAAAGCCAATAGGCAGT<br>AGCGAAAGCTGCAAGAGAATGAAAATCCGT |
| 74 | L2-2 | AAGAAATTCTTTAAGTGGATGCTCTCAAACTCAGGGAAACCT<br>AAATCTAGTTATAGACAAGGCAATCCTGAGCCAAGCCGAAGT<br>AGTAATTAGTAAGTTAACAATAGATGACTTACAACTAATCGG<br>AAGGTGCAGAGACTCGACGGGAGCTACCCTAACGTCAAGACG<br>AGGGTAAAGAGAGAGTCCAATTCTCAAAGCCAATAGGCAGTA<br>GCGAAAGCTGCAAGAGAATGAAAATCCGT |
| 75 | L2-3 | AGAAATTCTTTAAGTGGATGCTCTCAAACTCAGGGAAACCTA<br>AATCTAGTTATAGACAAGGCAATCCTGAGCCAAGCCGAAGTA<br>GTAATTAGTAAGTTAACAATAGATGACTTACAACTAATCGGA<br>AGGTGCAGAGACTCGACGGGAGCTACCCTAACGTCAAGACGA<br>GGGTAAAGAGAGAGTCCAATTCTCAAAGCCAATAGGCAGTAG<br>CGAAAGCTGCAAGAGAATGAAAATCCGT |
| 76 | L5-1 | GTTATAGACAAGGCAATCCTGAGCCAAGCCGAAGTAGTAATT<br>AGTAAGTTAACAATAGATGACTTACAACTAATCGGAAGGTGC<br>AGAGACTCGACGGGAGCTACCCTAACGTCAAGACGAGGGTAA<br>AGAGAGAGTCCAATTCTCAAAGCCAATAGGCAGTAGCGAAAG<br>CTGCAAGAGAATGAAAATCCGT |
| 77 | L5-2 | TTATAGACAAGGCAATCCTGAGCCAAGCCGAAGTAGTAATTA<br>GTAAGTTAACAATAGATGACTTACAACTAATCGGAAGGTGCA<br>GAGACTCGACGGGAGCTACCCTAACGTCAAGACGAGGGTAAA<br>GAGAGAGTCCAATTCTCAAAGCCAATAGGCAGTAGCGAAAGC<br>TGCAAGAGAATGAAAATCCGT |
| 78 | L5-3 | TATAGACAAGGCAATCCTGAGCCAAGCCGAAGTAGTAATTAG<br>TAAGTTAACAATAGATGACTTACAACTAATCGGAAGGTGCAG<br>AGACTCGACGGGAGCTACCCTAACGTCAAGACGAGGGTAAAG<br>AGAGAGTCCAATTCTCAAAGCCAATAGGCAGTAGCGAAAGCT<br>GCAAGAGAATGAAAATCCGT |

TABLE 18-continued

Anabaena permutation site 5' intron fragment sequences.

| SEQ ID NO | Permutation site | Sequence |
|---|---|---|
| 79 | L5-4 | ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAGGCAGTAGCGAAAGCTG CAAGAGAATGAAAATCCGT |
| 80 | L5-5 | TAGACAAGGCAATCCTGAGCCAAGCCGAAGTAGTAATTAGTA AGTTAACAATAGATGACTTACAACTAATCGGAAGGTGCAGAG ACTCGACGGGAGCTACCCTAACGTCAAGACGAGGGTAAAGAG AGAGTCCAATTCTCAAAGCCAATAGGCAGTAGCGAAAGCTGC AAGAGAATGAAAATCCGT |
| 81 | L6-1 | ACAATAGATGACTTACAACTAATCGGAAGGTGCAGAGACTCG ACGGGAGCTACCCTAACGTCAAGACGAGGGTAAAGAGAGAG TCCAATTCTCAAAGCCAATAGGCAGTAGCGAAAGCTGCAAGA GAATGAAAATCCGT |
| 82 | L6-2 | CAATAGATGACTTACAACTAATCGGAAGGTGCAGAGACTCGA CGGGAGCTACCCTAACGTCAAGACGAGGGTAAAGAGAGAGTC CAATTCTCAAAGCCAATAGGCAGTAGCGAAAGCTGCAAGAGA ATGAAAATCCGT |
| 83 | L6-3 | AATAGATGACTTACAACTAATCGGAAGGTGCAGAGACTCGAC GGGAGCTACCCTAACGTCAAGACGAGGGTAAAGAGAGAGTCC AATTCTCAAAGCCAATAGGCAGTAGCGAAAGCTGCAAGAGAA TGAAAATCCGT |
| 84 | L6-4 | ATAGATGACTTACAACTAATCGGAAGGTGCAGAGACTCGACG GGAGCTACCCTAACGTCAAGACGAGGGTAAAGAGAGAGTCCA ATTCTCAAAGCCAATAGGCAGTAGCGAAAGCTGCAAGAGAAT GAAAATCCGT |
| 85 | L6-5 | TAGATGACTTACAACTAATCGGAAGGTGCAGAGACTCGACGG GAGCTACCCTAACGTCAAGACGAGGGTAAAGAGAGAGTCCAA TTCTCAAAGCCAATAGGCAGTAGCGAAAGCTGCAAGAGAATG AAAATCCGT |
| 86 | L6-6 | AGATGACTTACAACTAATCGGAAGGTGCAGAGACTCGACGGG AGCTACCCTAACGTCAAGACGAGGGTAAAGAGAGAGTCCAAT TCTCAAAGCCAATAGGCAGTAGCGAAAGCTGCAAGAGAATGA AAATCCGT |
| 87 | L6-7 | GATGACTTACAACTAATCGGAAGGTGCAGAGACTCGACGGGA GCTACCCTAACGTCAAGACGAGGGTAAAGAGAGAGTCCAATT CTCAAAGCCAATAGGCAGTAGCGAAAGCTGCAAGAGAATGA AAATCCGT |
| 88 | L6-8 | ATGACTTACAACTAATCGGAAGGTGCAGAGACTCGACGGGAG CTACCCTAACGTCAAGACGAGGGTAAAGAGAGAGTCCAATTC TCAAAGCCAATAGGCAGTAGCGAAAGCTGCAAGAGAATGAA AATCCGT |
| 89 | L6-9 | TGACTTACAACTAATCGGAAGGTGCAGAGACTCGACGGGAGC TACCCTAACGTCAAGACGAGGGTAAAGAGAGAGTCCAATTCT CAAAGCCAATAGGCAGTAGCGAAAGCTGCAAGAGAATGAAA ATCCGT |
| 90 | L8-1 | CAAGACGAGGGTAAAGAGAGAGTCCAATTCTCAAAGCCAATA GGCAGTAGCGAAAGCTGCAAGAGAATGAAAATCCGT |
| 91 | L8-2 | AAGACGAGGGTAAAGAGAGAGTCCAATTCTCAAAGCCAATAG GCAGTAGCGAAAGCTGCAAGAGAATGAAAATCCGT |
| 92 | L8-3 | AGACGAGGGTAAAGAGAGAGTCCAATTCTCAAAGCCAATAGG CAGTAGCGAAAGCTGCAAGAGAATGAAAATCCGT |
| 93 | L8-4 | GACGAGGGTAAAGAGAGAGTCCAATTCTCAAAGCCAATAGGC AGTAGCGAAAGCTGCAAGAGAATGAAAATCCGT |
| 94 | L8-5 | ACGAGGGTAAAGAGAGAGTCCAATTCTCAAAGCCAATAGGCA GTAGCGAAAGCTGCAAGAGAATGAAAATCCGT |
| 95 | L9a-1 | AATAGGCAGTAGCGAAAGCTGCAAGAGAATGAAAATCCGT |
| 96 | L9a-2 | ATAGGCAGTAGCGAAAGCTGCAAGAGAATGAAAATCCGT |

TABLE 18-continued

Anabaena permutation site 5′ intron fragment sequences.

| SEQ ID NO | Permutation site | Sequence |
|---|---|---|
| 97 | L9a-3 | TAGGCAGTAGCGAAAGCTGCAAGAGAATGAAAATCCGT |
| 98 | L9a-4 | AGGCAGTAGCGAAAGCTGCAAGAGAATGAAAATCCGT |
| 99 | L9a-5 | GGCAGTAGCGAAAGCTGCAAGAGAATGAAAATCCGT |
| 100 | L9-1 | GAAAGCTGCAAGAGAATGAAAATCCGT |
| 101 | L9-2 | AAAGCTGCAAGAGAATGAAAATCCGT |
| 102 | L9-3 | AAGCTGCAAGAGAATGAAAATCCGT |
| 103 | L9-4 | AGCTGCAAGAGAATGAAAATCCGT |
| 104 | L9-5 | GCTGCAAGAGAATGAAAATCCGT |
| 105 | L9-6 | CTGCAAGAGAATGAAAATCCGT |
| 106 | L9-7 | AAGAGAATGAAAATCCGT |
| 107 | L9-8 | AGAGAATGAAAATCCGT |
| 108 | L9-9 | GAGAATGAAAATCCGT |
| 109 | L9a-6 | GCAGTAGCGAAAGCTGCAAGAGAATGAAAATCCGT |
| 110 | L9a-7 | AGTAGCGAAAGCTGCAAGAGAATGAAAATCCGT |
| 111 | L9a-8 | GTAGCGAAAGCTGCAAGAGAATGAAAATCCGT |

In some embodiments, a 5' intron fragment is a fragment having a sequence listed in Table 18. Typically, a construct containing a 5' intron fragment listed in Table 18 will contain a corresponding 3' intron fragment as listed in Table 19 (e.g., both representing fragments with the L9a-8 permutation site).

TABLE 19

Anabaena permutation site 3′ intron fragment sequences.

| SEQ ID NO | Permutation site | Sequence |
|---|---|---|
| 112 | L2-1 | ACGGACTTAAATAATTGAGCCTTAAA |
| 113 | L2-2 | ACGGACTTAAATAATTGAGCCTTAAAG |
| 114 | L2-3 | ACGGACTTAAATAATTGAGCCTTAAAGA |
| 115 | L5-1 | ACGGACTTAAATAATTGAGCCTTAAAGAAGAAATTCTTTAAG TGGATGCTCTCAAACTCAGGGAAACCTAAATCTA |
| 116 | L5-2 | ACGGACTTAAATAATTGAGCCTTAAAGAAGAAATTCTTTAAG TGGATGCTCTCAAACTCAGGGAAACCTAAATCTAG |
| 117 | L5-3 | ACGGACTTAAATAATTGAGCCTTAAAGAAGAAATTCTTTAAG TGGATGCTCTCAAACTCAGGGAAACCTAAATCTAGT |
| 118 | L5-4 | ACGGACTTAAATAATTGAGCCTTAAAGAAGAAATTCTTTAAG TGGATGCTCTCAAACTCAGGGAAACCTAAATCTAGTT |
| 119 | L5-5 | ACGGACTTAAATAATTGAGCCTTAAAGAAGAAATTCTTTAAG TGGATGCTCTCAAACTCAGGGAAACCTAAATCTAGTTA |
| 120 | L6-1 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT A |
| 121 | L6-2 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AA |

TABLE 19-continued

Anabaena permutation site 3' intron fragment sequences.

| SEQ ID NO | Permutation site | Sequence |
|---|---|---|
| 122 | L6-3 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AAC |
| 123 | L6-4 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACA |
| 124 | L6-5 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAA |
| 125 | L6-6 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAAT |
| 126 | L6-7 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATA |
| 127 | L6-8 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAG |
| 128 | L6-9 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGA |
| 129 | L8-1 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGT |
| 130 | L8-2 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTC |
| 131 | L8-3 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCA |
| 132 | L8-4 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAA |
| 133 | L8-5 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAG |
| 134 | L9a-1 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCC |
| 135 | L9a-2 | ACGGACTTAAATAATTGAGCCTTAAAGAAGAAATTCTTTAAG TGGATGCTCTCAAACTCAGGGAAACCTAAATCTAGTTATAGA |

TABLE 19-continued

Anabaena permutation site 3′ intron fragment sequences.

| SEQ ID NO | Permutation site | Sequence |
|---|---|---|
| | | CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCA |
| 136 | L9a-3 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAA |
| 137 | L9a-4 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAAT |
| 138 | L9a-5 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATA |
| 139 | L9-1 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGC |
| 140 | L9-2 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCG |
| 141 | L9-3 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGA |
| 142 | L9-4 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAA |
| 143 | L9-5 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAA |
| 144 | L9-6 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAAG |
| 145 | L9-7 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAAGCTGC |

TABLE 19-continued

Anabaena permutation site 3′ intron fragment sequences.

| SEQ ID NO | Permutation site | Sequence |
|---|---|---|
| 146 | L9-8 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAAGCTGCA |
| 147 | L9-9 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCAGTAGCGAAAGCTGCA A |
| 148 | L9a-6 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAG |
| 149 | L9a-7 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGC |
| 150 | L9a-8 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACT CGACGGGAGCTACCCTAACGTCAAGACGAGGGTAAAGAGAG AGTCCAATTCTCAAAGCCAATAGGCA |

In some embodiments, a 3' intron fragment is a fragment having a sequence listed in Table 19. In some embodiments, a construct containing a 3' intron fragment listed in Table 19 will contain a corresponding 5' intron fragment as listed in Table 18 (e.g., both representing fragments with the L9a-8 permutation site).

TABLE 20

Non-anabaena permutation site 5′ intron fragment sequences.

| SEQ ID NO | Intron | Sequence |
|---|---|---|
| 151 | Azop1 | tgcgccgatgaaggtgtagagactagacggcacccacctaaggcaaacgctatggtgaaggcatagtcca gggagtggcgaaagtcacacaaaccggaatccgt |
| 152 | Azop2 | ccgggcgtatggcaacgccgagccaagcttcggcgcctgcgcc gatgaaggtgta gagactagac ggc acccacctaaggcaaacgctatggtgaaggcatagtccagggagtggcgaaagtcacacaaaccggaat ccgt |
| 153 | Azop3 | acggcacccacctaaggcaaacgctatggtgaaggcatagtccagggagtggcgaaagtcacacaaacc ggaatccgt |
| 154 | Azop4 | acgctatggtgaaggcatagtccagggagtggcgaaagtcacacaaaccggaatccgt |
| 155 | S795p1 | attaaagttatagaattatcagagaatgatatagtccaagccttatggtaacatgagggcacttgaccctggta g |
| 156 | Twortp1 | aagatgtaggcaatcctgagctaagctcttagtaataagagaaagtgcaacgactattccgataggaagtag ggtcaagtgactcgaaatggggattacccttctagggtagtgatatagtctgaacatatatggaaacatatag aaggataggagtaacgaacctattcgtaacataattgaacttttagttat |
| 157 | Twortp2 | taataagagaaagtgcaacgactattccgataggaagtagggtcaagtgactcgaaatggggattacccttc tagggtagtgatatagtctgaacatatatggaaacatatagaaggataggagtaacgaacctattcgtaacat aattgaacttttagttat |
| 158 | Twortp3 | taggaagtagggtcaagtgactcgaaatggggattacccttctagggtagtgatatagtctgaacatatatgg aaacatatagaaggataggagtaacgaacctattcgtaacataattgaacttttagttat |

TABLE 20-continued

Non-anabaena permutation site 5′ intron fragment sequences.

| SEQ ID NO | Intron | Sequence |
|---|---|---|
| 159 | Twortp4 | ctagggtagtgatatagtctgaacatatatggaaacatatagaaggataggagtaacgaacctattcgtaaca taattgaacttttagttat |
| 160 | LSUp1 | agttaataaagatgatgaaatagtctgaaccattttgagaaaagtggaaataaaagaaaatcttttatgataac ataaattgaacaggctaa |
| 161 | Phip1 | caaagactgatgatatagtccgacactcctagtaataggagaatacagaaaggatgaaatcc |
| 162 | Nostoc | agtcgagggtaaagggagagtccaattctcaaagcctattggcagtagcgaaagctgcgggagaatgaaa atccgt |
| 163 | Nostoc | agccgagggtaaagggagagtccaattctcaaagccaataggcagtagcgaaagctgcgggagaatgaa aatccgt |
| 164 | Nodularia | agccgagggtaaagggagagtccaattctcaaagccgaaggttattaaaacctggcagcagtgaaagctg cgggagaatgaaaatccgt |
| 165 | Pleurocapsa | agctgagggtaaagagagagtccaattctcaaagccagcagatggcagtagcgaaagctgcgggagaat gaaaatccgt |
| 166 | Planktothrix | agccgagggtaaagagagagtccaattctcaaagccaattggtagtagcgaaagctacgggagaatgaaa atccgt |

In some embodiments, a 5' intron fragment is a fragment having a sequence listed in Table 20. A construct containing a 5' intron fragment listed in Table 20 will contain a corresponding 3' intron fragment in Table 21 (e.g., both representing fragments with the Azop1 intron).

TABLE 21

Non-anabaena permutation site 3′ intron fragment sequences.

| SEQ ID NO | Intron | Sequence |
|---|---|---|
| 167 | Azop1 | gcggactcatatttcgatgtgccttgcgccgggaaaccacgcaagggatggtgtcaaattcggcgaaac ctaagcgcccgcccgggcgtatggcaacgccgagccaagcttcggcgcc |
| 168 | Azop2 | gcggactcatatttcgatgtgccttgcgccgggaaaccacgcaagggatggtgtcaaattcggcgaaac ctaagcgcccgc |
| 169 | Azop3 | gcggactcatatttcgatgtgccttgcgccgggaaaccacgcaagggatggtgtcaaattcggcgaaac ctaagcgcccgcccgggcgtatggcaacgccgagccaagcttcggcgcctgcgccgatgaaggtgta gagactag |
| 170 | Azop4 | gcggactcatatttcgatgtgccttgcgccgggaaaccacgcaagggatggtgtcaaattcggcgaaac ctaagcgcccgcccgggcgtatggcaacgccgagccaagcttcggcgcctgcgccgatgaaggtgta gagactagacggcacccacctaaggcaa |
| 171 | S795p1 | aggattagatactacactaagtgtcccccagactggtgacagtctggtgtgcatccagctatatcggtgaa accccattggggtaataccgagggaagctatattatatatatattaataaatagccccgtagagactatgta ggtaaggagatagaagatgataaaatcaaaatcatc |
| 172 | Twortp1 | actactgaaagcataaataattgtgcctttatacagtaatgtatatcgaaaaatcctctaattcagggaacac ctaaacaaact |
| 173 | Twortp2 | actactgaaagcataaataattgtgcctttatacagtaatgtatatcgaaaaatcctctaattcagggaacac ctaaacaaactaagatgtaggcaatcctgagctaagctcttag |
| 174 | Twortp3 | actactgaaagcataaataattgtgcctttatacagtaatgtatatcgaaaaatcctctaattcagggaacac ctaaacaaactaagatgtaggcaatcctgagctaagctcttagtaataagagaaagtgcaacgactattcc ga |
| 175 | Twortp4 | actactgaaagcataaataattgtgcctttatacagtaatgtatatcgaaaaatcctctaattcagggaacac ctaaacaaactaagatgtaggcaatcctgagctaagctcttagtaataagagaaagtgcaacgactattcc gataggaagtagggtcaagtgactcgaaatggggattaccctt |
| 176 | LSUp1 | cgctagggatttataactgtgagtcctccaatattataaaatgttggtaatatattgggtaaatttcaaagaca acttttctccacgtcaggatatagtgtatttgaagcgaaacttattttagcagtgaaaaagcaaataaggac gttcaacgactaaaaggtgagtattgctaacaataatcctttttttttaatgcccaacatctttattaact |

TABLE 21-continued

Non-anabaena permutation site 3' intron fragment sequences.

| SEQ ID NO | Intron | Sequence |
|---|---|---|
| 177 | Phip1 | gtgggtgcataaactatttcattgtgcacattaaatctggtgaactcggtgaaaccctaatggggcaatacc gagccaagccatagggaggatatatgagaggcaagaagttaattcttgaggccactgagactggctgta tcatccctacgtcacacaaacttaatgccgatggttatttcagaaagaaaaccaatggcgtcttagagatgt atcacagaacggtgtggaaggagcataacggagacatacctgatggcttcgagatagaccataagtgtc gcaatagggcttgctgtaatatagagcatttacagatgcttgagggtacagcccacactgttaagaccaat cgtgaacgctacgcagacagaaaggaaacagctagggaatactggctggagactggatgtaccggcc tagcactcggtgagaagtttggtgtgtcgttctcttctgcttgtaagtggattagagaatggaaggcgtaga gactatccgaaaggagtagggccgagggtgagactccctcgtaacccgaagcgccagacagtcaact |
| 178 | Nostoc | acggacttaagtaattgagccttaaagaagaaattctttaagtggcagctctcaaactcagggaaacctaa atctgttcacagacaaggcaatcctgagccaagccgaaagagtcatgagtgctgagtagtgagtaaaat aaaagctcacaactcagaggttgtaactctaagctagtcggaaggtgcagagactcgacgggagctac cctaacgtaa |
| 179 | Nostoc | acggacttaaactgaattgagccttagagaagaaattctttaagtgtcagctctcaaactcagggaaacct aaatctgttgacagacaaggcaatcctgagccaagccgagaactctaagttattcggaaggtgcagaga ctcgacgggagctaccctaacgtca |
| 180 | Nodularia | acggacttagaaaactgagccttgatcgagaaatctttcaagtggaagctctcaaattcagggaaacctaa atctgtttacagatatggcaatcctgagccaagccgaaacaagtcctgagtgttaaagctcataactcatc ggaaggtgcagagactcgacgggagctaccctaacgtta |
| 181 | Pleurocapsa | acggacttaaaaaaattgagccttggcagagaaatctgtcatgcgaacgctctcaaattcagggaaacct aagtctggcaacagatatggcaatcctgagccaagccttaatcaaggaaaaaaacatttttaccttttacctt gaaaggaaggtgcagagactcaacgggagctaccctaacaggtca |
| 182 | Planktothrix | acggacttaaagataaattgagccttgaggcgagaaatctctcaagtgtaagctgtcaaattcagggaaa cctaaatctgtaaattcagacaaggcaatcctgagccaagcctaggggtattagaaatgagggagtttcc ccaatctaagatcaatacctaggaaggtgcagagactcgacgggagctaccctaacgtta |

In some embodiments, a 3' intron fragment is a fragment having a sequence listed in Table 21. A construct containing a 3' intron fragment listed in Table 21 will contain the corresponding 5' intron fragment as listed in Table 20 (e.g., both representing fragments with the Azop1 intron).

TABLE 22

Spacer and Anabaena 5' intron fragment sequences.

| SEQ ID NO | Spacer | Sequence |
|---|---|---|
| 183 | T25 L10 | agtatataagaaacaaaccacTAGATGACTTACAACTAATCGGAAGGTGC AGAGACTCGACGGGAGCTACCCTAACGTCAAGACGAGGGTAA AGAGAGAGTCCAATTCTCAAAGCCAATAGGCAGTAGCGAAAG CTGCAAGAGAATGAAAATCCGTggctcgcagc |
| 184 | T25 L20 | ctgaaattatacttatactcaaacaaaccacTAGATGACTTACAACTAATCGGAA GGTGCAGAGACTCGACGGGAGCTACCCTAACGTCAAGACGAG GGTAAAGAGAGAGTCCAATTCTCAAAGCCAATAGGCAGTAGC GAAAGCTGCAAGAGAATGAAAATCCGTggctcgcagc |
| 185 | T25 L30 (180-10) [Control] | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagc |
| 186 | T25 L40 | catcaacaatatgaaattatacttatactcagtatatgacaaacaaaccacTAGATGACTTAC AACTAATCGGAAGGTGCAGAGACTCGACGGGAGCTACCCTAA CGTCAAGACGAGGGTAAAGAGAGAGTCCAATTCTCAAAGCCA ATAGGCAGTAGCGAAAGCTGCAAGAGAATGAAAATCCGTggct cgcagc |
| 187 | T25 L50 | catcaacaatatgaaactatacttatactcagtatatgaagcattatcgcaaacaaaccacTAGATG ACTTACAACTAATCGGAAGGTGCAGAGACTCGACGGGAGCTA CCCTAACGTCAAGACGAGGGTAAAGAGAGAGTCCAATTCTCA AAGCCAATAGGCAGTAGCGAAAGCTGCAAGAGAATGAAAAT CCGTggctcgcagc |

TABLE 22-continued

Spacer and Anabaena 5′ intron fragment sequences.

| SEQ ID NO | Spacer | Sequence |
|---|---|---|
| 188 | T50 L10 | tagcgtcagcaaacaaacaaaTAGATGACTTACAACTAATCGGAAGGTGC AGAGACTCGACGGGAGCTACCCTAACGTCAAGACGAGGGTAA AGAGAGAGTCCAATTCTCAAAGCCAATAGGCAGTAGCGAAAG CTGCAAGAGAATGAAAATCCGTggctcgcagc |
| 189 | T50 L20 | atactcatactagcgtcagcaaacaaacaaaTAGATGACTTACAACTAATCGGA AGGTGCAGAGACTCGACGGGAGCTACCCTAACGTCAAGACGA GGGTAAAGAGAGAGTCCAATTCTCAAAGCCAATAGGCAGTAG CGAAAGCTGCAAGAGAATGAAAATCCGTggctcgcagc |
| 190 | T50 L30 | gtgtgaagctatactcatactagcgtcagcaaacaaacaaaTAGATGACTTACAACTA ATCGGAAGGTGCAGAGACTCGACGGGAGCTACCCTAACGTCA AGACGAGGGTAAAGAGAGAGTCCAATTCTCAAAGCCAATAGG CAGTAGCGAAAGCTGCAAGAGAATGAAAATCCGTggctcgcagc |
| 191 | T50 L40 | cctcacctgagtgtgaagctatactcatactagcgtcagcaaacaaacaaaTAGATGACTTA CAACTAATCGGAAGGTGCAGAGACTCGACGGGAGCTACCCTA ACGTCAAGACGAGGGTAAAGAGAGAGTCCAATTCTCAAAGCC AATAGGCAGTAGCGAAAGCTGCAAGAGAATGAAAATCCGTgg ctcgcagc |
| 192 | T50 L50 | ccgaatgatgcctcacctgagtgtgaagctatactcatactagcgtcagcaaacaaacaaaTAGAT GACTTACAACTAATCGGAAGGTGCAGAGACTCGACGGGAGCT ACCCTAACGTCAAGACGAGGGTAAAGAGAGAGTCCAATTCTC AAAGCCAATAGGCAGTAGCGAAAGCTGCAAGAGAATGAAAA TCCGTggctcgcagc |
| 193 | T75 L10 | cggtgcgagcaaacaaacaaaTAGATGACTTACAACTAATCGGAAGGTG CAGAGACTCGACGGGAGCTACCCTAACGTCAAGACGAGGGTA AAGAGAGAGTCCAATTCTCAAAGCCAATAGGCAGTAGCGAAA GCTGCAAGAGAATGAAAATCCGTggctcgcagc |
| 194 | T75 L20 | cgctccgacccagtgcgagcaaacaaacaaaTAGATGACTTACAACTAATCGG AAGGTGCAGAGACTCGACGGGAGCTACCCTAACGTCAAGACG AGGGTAAAGAGAGAGTCCAATTCTCAAAGCCAATAGGCAGTA GCGAAAGCTGCAAGAGAATGAAAATCCGTggctcgcagc |
| 195 | T25 L30 1MM | ctgaaattatactAatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagc |
| 196 | T25 L30 3MM | ctgaaaAtatactAatactcaCtatatgacaaacaaaccacT AGATGACTT ACAACT A ATCGGAAGGTGCAGAGACTCGACGGGAGCTACCCTAACGTCA AGACGAGGGTAAAGAGAGAGTCCAATTCTCAAAGCCAATAGG CAGTAGCGAAAGCTGCAAGAGAATGAAAATCCGTggctcgcagc |
| 197 | T25 L30 5MM | ctgaTaAtataGtAatactcaCtatatgacaaacaaaccacTAGATGACTTACAACT AATCGGAAGGTGCAGAGACTCGACGGGAGCTACCCTAACGTC AAGACGAGGGTAAAGAGAGAGTCCAATTCTCAAAGCCAATAG GCAGTAGCGAAAGCTGCAAGAGAATGAAAATCCGTggctcgcagc |
| 198 | T25 L30 8MM | ctgaTaAtaAaGtAatacAcaCtataAgacaaacaaaccacTAGATGACTTACAA CTAATCGGAAGGTGCAGAGACTCGACGGGAGCTACCCTAACG TCAAGACGAGGGTAAAGAGAGAGTCCAATTCTCAAAGCCAAT AGGCAGTAGCGAAAGCTGCAAGAGAATGAAAATCCGTggctcgc agc |
| 199 | T25 L30 OffTarget 10 | ctgaaattatacttatactctctaagttacaaacaaaccacTAGATGACTTACAACTAAT CGGAAGGTGCAGAGACTCGACGGGAGCTACCCTAACGTCAAG ACGAGGGTAAAGAGAGAGTCCAATTCTCAAAGCCAATAGGCA GTAGCGAAAGCTGCAAGAGAATGAAAATCCGTggctcgcagc |
| 200 | T25 L30 OffTarget 20 | ctgaaattatgtgtgttacAtctaagttacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagc |
| 201 | T25 L30 OffTarget 30 | gttgatcggtgtgtgttacAtctaagttacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagc |
| 202 | T25 L30I25-10 | ctgaaattatacttatactcagtatatgacaaacaaaccacTAGATGACTTACAACTAA TCGGAAGGTGCAGAGACTCGACGGGAGCTACCCTAACGTCAA |

TABLE 22-continued

Spacer and Anabaena 5′ intron fragment sequences.

| SEQ ID NO | Spacer | Sequence |
|---|---|---|
| | | GACGAGGGTAAAGAGAGAGTCCAATTCTCAAAGCCAATAGGC AGTAGCGAAAGCTGCAAGAGAATGAAAATCCGTgattaaacag |
| 203 | T25 L30I25-20 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTgattcacaatataaa ttacg |
| 204 | T25 L30I50-10 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggatcatagc |
| 205 | T25 L30I50-20 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggatcgcagcataa tatccg |
| 206 | T25 L30I80-20 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagcgcg cctaccg |
| 207 | T25 L30I80-20x2 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggctcgcagcgcg cctaccgaaagccggcgtcgacgttagcgc |
| 208 | T25 L30I50-20x2 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTggatcgcagcataa tatccgaaacgaggatacaagtgacatgc |
| 209 | T25 L30I25-20x2 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGTgattcacaatctaaa ttacgaaacgataaatgataactctaac |
| 210 | T0 L0 | aaacaaaccacTAGATGACTTACAACTAATCGGAAGGTGCAGAGAC TCGACGGGAGCTACCCTAACGTCAAGACGAGGGTAAAGAGAG AGTCCAATTCTCAAAGCCAATAGGCAGTAGCGAAAGCTGCAA GAGAATGAAAATCCGTggctcgcagc |
| 211 | T100 L5 | cgggcaaacaaacaaaTAGATGACTTACAACTAATCGGAAGGTGCAG AGACTCGACGGGAGCTACCCTAACGTCAAGACGAGGGTAAAG AGAGAGTCCAATTCTCAAAGCCAATAGGCAGTAGCGAAAGCT GCAAGAGAATGAAAATCCGTggctcgcagc |
| 212 | T75 L30 | cgctccgacgagcttccggccagtgcgagcaaacaaacaaaTAGATGACTTACAACT AATCGGAAGGTGCAGAGACTCGACGGGAGCTACCCTAACGTC AAGACGAGGGTAAAGAGAGAGTCCAATTCTCAAAGCCAATAG GCAGTAGCGAAAGCTGCAAGAGAATGAAAATCCGTggctcgcagc |
| 213 | T0 L0a | aaacaaaccacGGCAGTAGCGAAAGCTGCAAGAGAATGAAAATCC GTggctcgcagc |
| 214 | T25 L10a | agtatataagaaacaaaccacGGCAGTAGCGAAAGCTGCAAGAGAATGA AAATCCGT ggctcgcagc |
| 215 | T25 L20a | ctgaaattatacttatactcaaacaaaccacGGCAGTAGCGAAAGCTGCAAGAG AATGAAAATCCGTggctcgcagc |
| 216 | T25 L30a (180-10) [Control] | ctgaaattatacttatactcagtatatgacaaacaaaccacGGCAGTAGCGAAAGCTGC AAGAGAATGAAAATCCGTggctcgcagc |
| 217 | T50 L10a | tagcgtcagcaaacaaacaaaGGCAGTAGCGAAAGCTGCAAGAGAATGA AAATCCGT ggctcgcagc |

TABLE 22-continued

| Spacer and Anabaena 5′ intron fragment sequences. | | |
|---|---|---|
| SEQ ID NO | Spacer | Sequence |
| 218 | T50 L20a | atactcatactagcgtcagcaaacaaacaaaGGCAGTAGCGAAAGCTGCAAGAG AATGAAAATCCGTggctcgcagc |
| 219 | T50 L30a | gtgtgaagctatactcatactagcgtcagcaaacaaacaaaGGCAGTAGCGAAAGCTG CAAGAGAATGAAAATCCGTggctcgcagc |
| 220 | T75 L10a | cggtgcgagcaaacaaacaaaGGCAGTAGCGAAAGCTGCAAGAGAATGA AAATCCGTggctcgcagc |
| 221 | T75 L20a | cgctccgacccagtgcgagcaaacaaacaaaGGCAGTAGCGAAAGCTGCAAGA GAATGAAAATCCGTggctcgcagc |
| 222 | T75 L30a | cgctccgacgagcttccggccagtgcgagcaaacaaacaaaGGCAGTAGCGAAAGCT GCAAGAGAATGAAAATCCGTggctcgcagc |
| 223 | T0 L0b | aaacaaaccacAAGACGAGGGTAAAGAGAGAGTCCAATTCTCAAA GCCAATAGGCAGTAGCGAAAGCTGCAAGAGAATGAAAATCC GTggctcgcagc |
| 224 | T25L10b | agtatataagaaacaaaccacAAGACGAGGGTAAAGAGAGAGTCCAATTC TCAAAGCCAATAGGCAGTAGCGAAAGCTGCAAGAGAATGAA AATCCGTggctcgcagc |
| 225 | T25 L20b | ctgaaattatacttatactcaaacaaaccacAAGACGAGGGTAAAGAGAGAGTC CAATTCTCAAAGCCAATAGGCAGTAGCGAAAGCTGCAAGAGA ATGAAAATCCGTggctcgcagc |
| 226 | T25 L30b (180-10) [Control] | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTggctcgcagc |
| 227 | T50 L10b | tagcgtcagcaaacaaacaaaAAGACGAGGGTAAAGAGAGAGTCCAATT CTCAAAGCCAATAGGCAGTAGCGAAAGCTGCAAGAGAATGA AAATCCGTggctcgcagc |
| 228 | T50 L20b | atactcatactagcgtcagcaaacaaacaaaAAGACGAGGGTAAAGAGAGAGT CCAATTCTCAAAGCCAATAGGCAGTAGCGAAAGCTGCAAGAG AATGAAAATCCGTggctcgcagc |
| 229 | T50 L30b | gtgtgaagctatactcatactagcgtcagcaaacaaacaaaAAGACGAGGGTAAAGA GAGAGTCCAATTCTCAAAGCCAATAGGCAGTAGCGAAAGCTG CAAGAGAATGAAAATCCGTggctcgcagc |
| 230 | T75 L10b | cggtgcgagcaaacaaacaaaAAGACGAGGGTAAAGAGAGAGTCCAATT CTCAAAGCCAATAGGCAGTAGCGAAAGCTGCAAGAGAATGA AAATCCGTggctcgcagc |
| 231 | T75 L20b | cgctccgacccagtgcgagcaaacaaacaaaAAGACGAGGGTAAAGAGAGAG TCCAATTCTCAAAGCCAATAGGCAGTAGCGAAAGCTGCAAGA GAATGAAAATCCGTggctcgcagc |
| 232 | T75 L30b | cgctccgacgagcttccggccagtgcgagcaaacaaacaaaAAGACGAGGGTAAAG AGAGAGTCCAATTCTCAAAGCCAATAGGCAGTAGCGAAAGCT GCAAGAGAATGAAAATCCGTggctcgcagc |
| 233 | T25 L30I0-0 | ctgaaattatacttatactcagtatatgacaaacaaaccacTAGATGACTTACAACTAA TCGGAAGGTGCAGAGACTCGACGGGAGCTACCCTAACGTCAA GACGAGGGTAAAGAGAGAGTCCAATTCTCAAAGCCAATAGGC AGTAGCGAAAGCTGCAAGAGAATGAAAATCCGT |
| 234 | T25 L30 aI0-0 | ctgaaattatacttatactcagtatatgacaaacaaaccacGGCAGTAGCGAAAGCTGC AAGAGAATGAAAATCCGT |
| 235 | T25 L30a 125-10 | ctgaaattatacttatactcagtatatgacaaacaaaccacGGCAGTAGCGAAAGCTGC AAGAGAATGAAAATCCGTgattaaacag |
| 236 | T25 L30a 125-20 | ctgaaattatacttatactcagtatatgacaaacaaaccacGGCAGTAGCGAAAGCTGC AAGAGAATGAAAATCCGTgattcacaatataaattacg |
| 237 | T25 L30a 150-10 | ctgaaattatacttatactcagtatatgacaaacaaaccacGGCAGTAGCGAAAGCTGC AAGAGAATGAAAATCCGTggatcatagc |
| 238 | T25 L30a 150-20 | ctgaaattatacttatactcagtatatgacaaacaaaccacGGCAGTAGCGAAAGCTGC AAGAGAATGAAAATCCGTggatcgcagcataatatccg |

TABLE 22-continued

| Spacer and Anabaena 5′ intron fragment sequences. | | |
|---|---|---|
| SEQ ID NO | Spacer | Sequence |
| 239 | T25 L30a 180-20 | ctgaaattatacttatactcagtatatgacaaacaaaccacGGCAGTAGCGAAAGCTGC AAGAGAATGAAAATCCGT ggctcgcagcgcgcctaccg |
| 240 | T25 L30b 10-0 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGT |
| 241 | T25 L30b 125-10 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTgattaaacag |
| 242 | T25 L30b 125-20 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTgattcacaatataaattacg |
| 243 | T25 L30b 150-10 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTggatcatagc |
| 244 | T25 L30b 150-20 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTggatcgcagcataatatccg |
| 245 | T25 L30b 180-20 | ctgaaattatacttatactcagtatatgacaaacaaaccacAAGACGAGGGTAAAGAG AGAGTCCAATTCTCAAAGCCAATAGGCAGTAGCGAAAGCTGC AAGAGAATGAAAATCCGTggctcgcagcgcgcctaccg |

In some embodiments, a spacer and 5' intron fragment are spacers and fragments having sequences as listed in Table 22.

TABLE 23

| Spacer and Anabaena 3' intron fragment sequences. | | |
|---|---|---|
| SEQ ID NO | Spacer | Sequence |
| 246 | T25 L10 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaacttatatact |
| 247 | T25 L20 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagagtataagtataatttcag |
| 248 | T25 L30 (I80-10) [Control] | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 249 | T25 L40 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcatattgttgatg |
| 250 | T25 L50 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagcgataatgcttcatatactgagtataagtatagtttcatattg ttgatg |
| 251 | T50 L10 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgcta |

TABLE 23-continued

Spacer and Anabaena 3' intron fragment sequences.

| SEQ ID NO | Spacer | Sequence |
|---|---|---|
| 252 | T50 L20 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgctagtatgagtat |
| 253 | T50 L30 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgctagtatgagtatagcttcacac |
| 254 | T50 L40 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgctagtatgagtatagcttcacactcaggtgagg |
| 255 | T50 L50 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctgacgctagtatgagtatagcttcacactcaggtgaggc atcattcgg |
| 256 | T75 L10 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctcgcaccg |
| 257 | T75 L20 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAaacaaaaacaagctcgcactgggtcggagcg |
| 258 | T25 L30 1 MM | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 259 | T25 L30 3 MM | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 260 | T25 L30 5 MM | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 261 | T25 L30 8 MM | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 262 | T25 L30 OffTarget 10 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtaacttagagagtataagtataatttcag |
| 263 | T25 L30 OffTarget 20 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtaacttagaTgtaacacacataatttcag |
| 264 | T25 L30 OffTarget 30 | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtaacttagaTgtaacacacaccgatcaac |
| 265 | T25 L30 I25-10 | ctgtttaatcACGGACTTAAATAATTGAGCCTTAAAGAAGAAATTCT TTAAGTGGATGCTCTCAAACTCAGGGAAACCTAAATCTAGTT ATAGACAAGGCAATCCTGAGCCAAGCCGAAGTAGTAATTAGT AAGTTAACAAcacaaacacaagtcatatactgagtataagtataatttcag |
| 266 | T25 L30 I25-20 | cgtaatttatattgtgaatcACGGACTTAAATAATTGAGCCTTAAAGAAGA AATTCTTTAAGTGGATGCTCTCAAACTCAGGGAAACCTAAATC TAGTTATAGACAAGGCAATCCTGAGCCAAGCCGAAGTAGTAA TTAGTAAGTTAACAAcacaaacacaagtcatatactgagtataagtataatttcag |

TABLE 23-continued

Spacer and Anabaena 3' intron fragment sequences.

| SEQ ID NO | Spacer | Sequence |
|---|---|---|
| 267 | T25 L30 I50-10 | gctatgatccACGGACTTAAATAATTGAGCCTTAAAGAAGAAATTC<br>TTTAAGTGGATGCTCTCAAACTCAGGGAAACCTAAATCTAGTT<br>ATAGACAAGGCAATCCTGAGCCAAGCCGAAGTAGTAATTAGT<br>AAGTTAACAAcacaaacacaagtcatatactgagtataagtataatttcag |
| 268 | T25 L30 I50-20 | cggatattatgctgcgatccACGGACTTAAATAATTGAGCCTTAAAGAAG<br>AAATTCTTTAAGTGGATGCTCTCAAACTCAGGGAAACCTAAA<br>TCTAGTTATAGACAAGGCAATCCTGAGCCAAGCCGAAGTAGT<br>AATTAGTAAGTTAACAAcacaaacacaagtcatatactgagtataagtataatttcag |
| 269 | T25 L30 I80-20 | cggtaggcgcgctgcgagccACGGACTTAAATAATTGAGCCTTAAAGAA<br>GAAATTCTTTAAGTGGATGCTCTCAAACTCAGGGAAACCTAA<br>ATCTAGTTATAGACAAGGCAATCCTGAGCCAAGCCGAAGTAG<br>TAATTAGTAAGTTAACAAcacaaacacaagtcatatactgagtataagtataatttcag |
| 270 | T25 L30 I80-20x2 | gcgctaacgtcgacgccggcaaacggtaggcgcgctgcgagccACGGACTTAAATAA<br>TTGAGCCTTAAAGAAGAAATTCTTTAAGTGGATGCTCTCAAAC<br>TCAGGGAAACCTAAATCTAGTTATAGACAAGGCAATCCTGAG<br>CCAAGCCGAAGTAGTAATTAGTAAGTTAACAAcacaaacacaagtcat<br>atactgagtataagtataatttcag |
| 271 | T25 L30 I50-20x2 | gcatgtcacttgtatcctcgaaacggatattatgctgcgatccACGGACTTAAATAATTG<br>AGCCTTAAAGAAGAAATTCTTTAAGTGGATGCTCTCAAACTC<br>AGGGAAACCTAAATCTAGTTATAGACAAGGCAATCCTGAGCC<br>AAGCCGAAGTAGTAATTAGTAAGTTAACAAcacaaacacaagtcatatac<br>tgagtataagtataatttcag |
| 272 | T25 L30 I25-20x2 | gttagagttatcatttatcgaaacgtaatttagattgtgaatcACGGACTTAAATAATTGA<br>GCCTTAAAGAAGAAATTCTTTAAGTGGATGCTCTCAAACTCA<br>GGGAAACCTAAATCTAGTTATAGACAAGGCAATCCTGAGCCA<br>AGCCGAAGTAGTAATTAGTAAGTTAACAAcacaaacacaagtcatatactg<br>agtataagtataatttcag |
| 273 | T0 L0 | gctgcgagccACGGACTTAAATAATTGAGCCTTAAAGAAGAAATTC<br>TTTAAGTGGATGCTCTCAAACTCAGGGAAACCTAAATCTAGTT<br>ATAGACAAGGCAATCCTGAGCCAAGCCGAAGTAGTAATTAGT<br>AAGTTAACAAcacaaacacaa |
| 274 | T100 L5 | gctgcgagccACGGACTTAAATAATTGAGCCTTAAAGAAGAAATTC<br>TTTAAGTGGATGCTCTCAAACTCAGGGAAACCTAAATCTAGTT<br>ATAGACAAGGCAATCCTGAGCCAAGCCGAAGTAGTAATTAGT<br>AAGTTAACAAaacaaaaacaagcccg |
| 275 | T75 L30 | gctgcgagccACGGACTTAAATAATTGAGCCTTAAAGAAGAAATTC<br>TTTAAGTGGATGCTCTCAAACTCAGGGAAACCTAAATCTAGTT<br>ATAGACAAGGCAATCCTGAGCCAAGCCGAAGTAGTAATTAGT<br>AAGTTAACAAaacaaaaacaagctcgcactggccggaagctcgtcggagcg |
| 276 | T0 L0a | gctgcgagccACGGACTTAAATAATTGAGCCTTAAAGAAGAAATTC<br>TTTAAGTGGATGCTCTCAAACTCAGGGAAACCTAAATCTAGTT<br>ATAGACAAGGCAATCCTGAGCCAAGCCGAAGTAGTAATTAGT<br>AAGTTAACAATAGATGACTTACAACTAATCGGAAGGTGCAGA<br>GACTCGACGGGAGCTACCCTAACGTCAAGACGAGGGTAAAGA<br>GAGAGTCCAATTCTCAAAGCCAATAcacaaacacaa |
| 277 | T25 L10a | gctgcgagccACGGACTTAAATAATTGAGCCTTAAAGAAGAAATTC<br>TTTAAGTGGATGCTCTCAAACTCAGGGAAACCTAAATCTAGTT<br>ATAGACAAGGCAATCCTGAGCCAAGCCGAAGTAGTAATTAGT<br>AAGTTAACAATAGATGACTTACAACTAATCGGAAGGTGCAGA<br>GACTCGACGGGAGCTACCCTAACGTCAAGACGAGGGTAAAGA<br>GAGAGTCCAATTCTCAAAGCCAATAcacaaacacaacttatatact |
| 278 | T25 L20a | gctgcgagccACGGACTTAAATAATTGAGCCTTAAAGAAGAAATTC<br>TTTAAGTGGATGCTCTCAAACTCAGGGAAACCTAAATCTAGTT<br>ATAGACAAGGCAATCCTGAGCCAAGCCGAAGTAGTAATTAGT<br>AAGTTAACAATAGATGACTTACAACTAATCGGAAGGTGCAGA<br>GACTCGACGGGAGCTACCCTAACGTCAAGACGAGGGTAAAGA<br>GAGAGTCCAATTCTCAAAGCCAATAcacaaacacaagagtataagtataatttc<br>ag |
| 279 | T25 L30a (I80-10) [Control] | gctgcgagccACGGACTTAAATAATTGAGCCTTAAAGAAGAAATTC<br>TTTAAGTGGATGCTCTCAAACTCAGGGAAACCTAAATCTAGTT<br>ATAGACAAGGCAATCCTGAGCCAAGCCGAAGTAGTAATTAGT<br>AAGTTAACAATAGATGACTTACAACTAATCGGAAGGTGCAGA |

TABLE 23-continued

Spacer and Anabaena 3' intron fragment sequences.

| SEQ ID NO | Spacer | Sequence |
|---|---|---|
| | | GACTCGACGGGAGCTACCCTAACGTCAAGACGAGGGTAAAGA GAGAGTCCAATTCTCAAAGCCAATAcacaaacacaagtcatatactgagtataa gtataatttcag |
| 280 | T50 L10a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctgacgcta |
| 281 | T50 L20a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctgacgctagtatga gtat |
| 282 | T50 L30a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctgacgctagtatga gtatagcttcacac |
| 283 | T75 L10a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctcgcaccg |
| 284 | T75 L20a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctcgcactgggtcgg agcg |
| 285 | T75 L30a | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAaacaaaaacaagctcgcactggccgga agctcgtcggagcg |
| 286 | T0 L0b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaa |
| 287 | T25 L10b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaacttatatact |
| 288 | T25 L20b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaagagtataagtataatt tcag |
| 289 | T25 L30b (I80-10) [Control] | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaagtcatatactgagtat aagtataatttcag |

TABLE 23-continued

Spacer and Anabaena 3' intron fragment sequences.

| SEQ ID NO | Spacer | Sequence |
|---|---|---|
| 290 | T50 L10b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctgacgcta |
| 291 | T50 L20b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctgacgctagtatg agtat |
| 292 | T50 L30b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctgacgctagtatg agtatagcttcacac |
| 293 | T75 L10b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctcgcaccg |
| 294 | T75 L20b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctcgcactgggtcg gagcg |
| 295 | T75 L30b | gctgcgagccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCaacaaaaacaagctcgcactggccg gaagctcgtcggagcg |
| 296 | T25 L30 I0-0 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAAcacaaacacaagtcatatactgagtataagtataatttcag |
| 297 | T25 L30a I0-0 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACTC GACGGGAGCTACCCTAACGTCAAGACGAGGGTAAAGAGAGA GTCCAATTCTCAAAGCCAATAcacaaacacaagtcatatactgagtataagtataat ttcag |
| 298 | T25 L30a I25-10 | ctgtttaatcACGGACTTAAATAATTGAGCCTTAAAGAAGAAATTCT TTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA GAGAGTCCAATTCTCAAAGCCAATAcacaaacacaagtcatatactgagtataa gtataatttcag |
| 299 | T25 L30a I25-20 | cgtaatttatattgtgaatcACGGACTTAAATAATTGAGCCTTAAAGAAGA AATTCTTTAAGTGGATGCTCTCAAACTCAGGGAAACCTAAATC TAGTTATAGACAAGGCAATCCTGAGCCAAGCCGAAGTAGTAA TTAGTAAGTTAACAATAGATGACTTACAACTAATCGGAAGGT GCAGAGACTCGACGGGAGCTACCCTAACGTCAAGACGAGGGT AAAGAGAGAGTCCAATTCTCAAAGCCAATAcacaaacacaagtcatatac tgagtataagtataatttcag |
| 300 | T25 L30a I50-10 | gctatgatccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCAAGACGAGGGTAAAGA |

TABLE 23-continued

Spacer and Anabaena 3' intron fragment sequences.

| SEQ ID NO | Spacer | Sequence |
|---|---|---|
| | | GAGAGTCCAATTCTCAAAGCCAATAcacaaacacaagtcatatactgagtataa gtataatttcag |
| 301 | T25 L30a I50-20 | cggatattatgctgcgatccACGGACTTAAATAATTGAGCCTTAAAGAAG AAATTCTTTAAGTGGATGCTCTCAAACTCAGGGAAACCTAAA TCTAGTTATAGACAAGGCAATCCTGAGCCAAGCCGAAGTAGT AATTAGTAAGTTAACAATAGATGACTTACAACTAATCGGAAG GTGCAGAGACTCGACGGGAGCTACCCTAACGTCAAGACGAGG GTAAAGAGAGAGTCCAATTCTCAAAGCCAATAcacaaacacaagtcat atactgagtataagtataatttcag |
| 302 | T25 L30a I80-20 | cggtaggcgcgctgcgagccACGGACTTAAATAATTGAGCCTTAAAGAA GAAATTCTTTAAGTGGATGCTCTCAAACTCAGGGAAACCTAA ATCTAGTTATAGACAAGGCAATCCTGAGCCAAGCCGAAGTAG TAATTAGTAAGTTAACAATAGATGACTTACAACTAATCGGAA GGTGCAGAGACTCGACGGGAGCTACCCTAACGTCAAGACGAG GGTAAAGAGAGAGTCCAATTCTCAAAGCCAATAcacaaacacaagtc atatactgagtataagtataatttcag |
| 303 | T25 L30b I0-0 | ACGGACTTAAATAATTGAGCCTTAAAGAAGAAATTCTTTAAG TGGATGCTCTCAAACTCAGGGAAACCTAAATCTAGTTATAGA CAAGGCAATCCTGAGCCAAGCCGAAGTAGTAATTAGTAAGTT AACAATAGATGACTTACAACTAATCGGAAGGTGCAGAGACTC GACGGGAGCTACCCTAACGTCcacaaacacaagtcatatactgagtataagtataat ttcag |
| 304 | T25 L30b I25-10 | ctgtttaatcACGGACTTAAATAATTGAGCCTTAAAGAAGAAATTCT TTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaagtcatatactgagtat aagtataatttcag |
| 305 | T25 L30b I25-20 | cgtaatttatattgtgaatcACGGACTTAAATAATTGAGCCTTAAAGAAGA AATTCTTTAAGTGGATGCTCTCAAACTCAGGGAAACCTAAATC TAGTTATAGACAAGGCAATCCTGAGCCAAGCCGAAGTAGTAA TTAGTAAGTTAACAATAGATGACTTACAACTAATCGGAAGGT GCAGAGACTCGACGGGAGCTACCCTAACGTCcacaaacacaagtcatat actgagtataagtataatttcag |
| 306 | T25 L30b I50-10 | gctatgatccACGGACTTAAATAATTGAGCCTTAAAGAAGAAATTC TTTAAGTGGATGCTCTCAAACTCAGGGAAACCTAAATCTAGTT ATAGACAAGGCAATCCTGAGCCAAGCCGAAGTAGTAATTAGT AAGTTAACAATAGATGACTTACAACTAATCGGAAGGTGCAGA GACTCGACGGGAGCTACCCTAACGTCcacaaacacaagtcatatactgagtat aagtataatttcag |
| 307 | T25 L30b I50-20 | cggatattatgctgcgatccACGGACTTAAATAATTGAGCCTTAAAGAAG AAATTCTTTAAGTGGATGCTCTCAAACTCAGGGAAACCTAAA TCTAGTTATAGACAAGGCAATCCTGAGCCAAGCCGAAGTAGT AATTAGTAAGTTAACAATAGATGACTTACAACTAATCGGAAG GTGCAGAGACTCGACGGGAGCTACCCTAACGTCcacaaacacaagtc atatactgagtataagtataatttcag |
| 308 | T25 L30b I80-20 | cggtaggcgcgctgcgagccACGGACTTAAATAATTGAGCCTTAAAGAA GAAATTCTTTAAGTGGATGCTCTCAAACTCAGGGAAACCTAA ATCTAGTTATAGACAAGGCAATCCTGAGCCAAGCCGAAGTAG TAATTAGTAAGTTAACAATAGATGACTTACAACTAATCGGAA GGTGCAGAGACTCGACGGGAGCTACCCTAACGTCcacaaacacaagt catatactgagtataagtataatttcag |

In some embodiments, a spacer and 3' intron fragment is a spacer and intron fragment having sequences as listed in Table 23.

TABLE 24

CAR sequences

| SEQ ID NO | CAR | Sequence |
|---|---|---|
| 309 | FMC63-4-1BB | ATGCTGCTGCTGGTCACATCTCTGCTGCTGTGCGAGCTGCCCC ATCCTGCCTTTCTGCTGATCCCCGACATCCAGATGACCCAGAC CACAAGCAGCCTGTCTGCCAGCCTGGGCGATAGAGTGACCAT CAGCTGTAGAGCCAGCCAGGACATCAGCAAGTACCTGAACTG GTATCAGCAAAAGCCCGACGGCACCGTGAAGCTGCTGATCTA CCACACCAGCAGACTGCACAGCGGCGTGCCAAGCAGATTTTC TGGCAGCGGCTCTGGCACCGACTACAGCCTGACAATCAGCAA CCTGGAACAAGAGGATATCGCTACCTACTTCTGCCAGCAAGG CAACACCCTGCCTTACACCTTTGGCGGAGGCACCAAGCTGGA AATCACCGGCTCTACAAGCGGCAGCGGCAAACCTGGATCTGG CGAGGGATCTACCAAGGGCGAAGTGAAACTGCAAGAGTCTG GCCCTGGACTGGTGGCCCCATCTCAGTCTCTGAGCGTGACCTG TACAGTCAGCGGAGTGTCCCTGCCTGATTACGGCGTGTCCTG GATCAGACAGCCTCCTCGGAAAGGCCTGGAATGGCTGGGAGT GATCTGGGGCAGCGAGACAACCTACTACAACAGCGCCCTGAA GTCCCGGCTGACCATCATCAAGGACAACTCCAAGAGCCAGGT GTTCCTGAAGATGAACAGCCTGCAGACCGACGACACCGCCAT CTACTATTGCGCCAAGCACTACTACTACGGCGGCAGCTACGC CATGGATTATTGGGGCCAGGGCACCAGCGTGACCGTTTCTTCT GCCGCCGCTATCGAAGTGATGTACCCTCCTCCTTACCTGGACA ACGAGAAGTCCAACGGCACCATCATCCACGTGAAGGGCAAG CACCTGTGTCCTTCTCCACTGTTCCCCGGACCTAGCAAGCCTT TCTGGGTGCTCGTTGTTGTTGGCGGCGTGCTGGCCTGTTACAG CCTGCTGGTTACCGTGGCCTTCATCATCTTTTGGGTCAAGAGA GGCCGGAAGAAACTTCTTTATATATTCAAGCAGCCCTTTATGC GACCCGTTCAGACTACCCAAGAGGAAGATGGATGCAGTTGCC GCTTTCCAGAAGAGGAGGAGGGCGGGTGCGAACTGtaa |
| 310 | FMC63-CD28 | ATGCTGCTGCTGGTCACATCTCTGCTGCTGTGCGAGCTGCCCC ATCCTGCCTTTCTGCTGATCCCCGACATCCAGATGACCCAGAC CACAAGCAGCCTGTCTGCCAGCCTGGGCGATAGAGTGACCAT CAGCTGTAGAGCCAGCCAGGACATCAGCAAGTACCTGAACTG GTATCAGCAAAAGCCCGACGGCACCGTGAAGCTGCTGATCTA CCACACCAGCAGACTGCACAGCGGCGTGCCAAGCAGATTTTC TGGCAGCGGCTCTGGCACCGACTACAGCCTGACAATCAGCAA CCTGGAACAAGAGGATATCGCTACCTACTTCTGCCAGCAAGG CAACACCCTGCCTTACACCTTTGGCGGAGGCACCAAGCTGGA AATCACCGGCTCTACAAGCGGCAGCGGCAAACCTGGATCTGG CGAGGGATCTACCAAGGGCGAAGTGAAACTGCAAGAGTCTG GCCCTGGACTGGTGGCCCCATCTCAGTCTCTGAGCGTGACCTG TACAGTCAGCGGAGTGTCCCTGCCTGATTACGGCGTGTCCTG GATCAGACAGCCTCCTCGGAAAGGCCTGGAATGGCTGGGAGT GATCTGGGGCAGCGAGACAACCTACTACAACAGCGCCCTGAA GTCCCGGCTGACCATCATCAAGGACAACTCCAAGAGCCAGGT GTTCCTGAAGATGAACAGCCTGCAGACCGACGACACCGCCAT CTACTATTGCGCCAAGCACTACTACTACGGCGGCAGCTACGC CATGGATTATTGGGGCCAGGGCACCAGCGTGACCGTTTCTTCT GCCGCCGCTATCGAAGTGATGTACCCTCCTCCTTACCTGGACA ACGAGAAGTCCAACGGCACCATCATCCACGTGAAGGGCAAG CACCTGTGTCCTTCTCCACTGTTCCCCGGACCTAGCAAGCCTT TCTGGGTGCTCGTTGTTGTTGGCGGCGTGCTGGCCTGTTACAG CCTGCTGGTTACCGTGGCCTTCATCATCTTTTGGGTCCGAAGC AAGCGGAGCCGGCTGCTGCACTCCGACTACATGAACATGACC CCTAGACGGCCCGGACCAACCAGAAAGCACTACCAGCCTTAC GCTCCTCCTAGAGACTTCGCCGCCTACCGGTCCtaa |
| 311 | FMC63-CD28-zeta | ATGCTGCTGCTGGTCACATCTCTGCTGCTGTGCGAGCTGCCCC ATCCTGCCTTTCTGCTGATCCCCGACATCCAGATGACCCAGAC CACAAGCAGCCTGTCTGCCAGCCTGGGCGATAGAGTGACCAT CAGCTGTAGAGCCAGCCAGGACATCAGCAAGTACCTGAACTG GTATCAGCAAAAGCCCGACGGCACCGTGAAGCTGCTGATCTA CCACACCAGCAGACTGCACAGCGGCGTGCCAAGCAGATTTTC TGGCAGCGGCTCTGGCACCGACTACAGCCTGACAATCAGCAA CCTGGAACAAGAGGATATCGCTACCTACTTCTGCCAGCAAGG CAACACCCTGCCTTACACCTTTGGCGGAGGCACCAAGCTGGA AATCACCGGCTCTACAAGCGGCAGCGGCAAACCTGGATCTGG CGAGGGATCTACCAAGGGCGAAGTGAAACTGCAAGAGTCTG GCCCTGGACTGGTGGCCCCATCTCAGTCTCTGAGCGTGACCTG TACAGTCAGCGGAGTGTCCCTGCCTGATTACGGCGTGTCCTG GATCAGACAGCCTCCTCGGAAAGGCCTGGAATGGCTGGGAGT |

TABLE 24-continued

| CAR sequences | | |
|---|---|---|
| SEQ ID NO | CAR | Sequence |
| | | GATCTGGGGCAGCGAGACAACCTACTACAACAGCGCCCTGAA<br>GTCCCGGCTGACCATCATCAAGGACAACTCCAAGAGCCAGGT<br>GTTCCTGAAGATGAACAGCCTGCAGACCGACGACACCGCCAT<br>CTACTATTGCGCCAAGCACTACTACTACGGCGGCAGCTACGC<br>CATGGATTATTGGGGCCAGGGCACCAGCGTGACCGTTTCTTCT<br>GCCGCCGCTATCGAAGTGATGTACCCTCCTCCTTACCTGGACA<br>ACGAGAAGTCCAACGGCACCATCATCCACGTGAAGGGCAAG<br>CACCTGTGTCCTTCTCCACTGTTCCCCGGACCTAGCAAGCCTT<br>TCTGGGTGCTCGTTGTTGTTGGCGGCGTGCTGGCCTGTTACAG<br>CCTGCTGGTTACCGTGGCCTTCATCATCTTTTGGGTCCGAAGC<br>AAGCGGAGCCGGCTGCTGCACTCCGACTACATGAACATGACC<br>CCTAGACGGCCCGGACCAACCAGAAAGCACTACCAGCCTTAC<br>GCTCCTCCTAGAGACTTCGCCGCCTACCGGTCCAGAGTGAAG<br>TTCAGCAGATCCGCCGATGCTCCCGCCTATCAGCAGGGCCAA<br>AACCAGCTGTACAACGAGCTGAACCTGGGGAGAAGAGAAGA<br>GTACGACGTGCTGGACAAGCGGAGAGGCAGAGATCCTGAAA<br>TGGGCGGCAAGCCCAGACGGAAGAATCCTCAAGAGGGCCTG<br>TATAATGAGCTGCAGAAAGACAAGATGGCCGAGGCCTACAG<br>CGAGATCGGAATGAAGGGCGAGCGCAGAAGAGGCAAGGGAC<br>ACGATGGACTGTACCAGGGACTGAGCACCGCCACCAAGGATA<br>CCTATGACGCCCTGCACATGCAGGCCCTGCCTCCAAGAtaa |
| 312 | FMC63-zeta | ATGCTGCTGCTGGTCACATCTCTGCTGCTGTGCGAGCTGCCCC<br>ATCCTGCCTTTCTGCTGATCCCCGACATCCAGATGACCCAGAC<br>CACAAGCAGCCTGTCTGCCAGCCTGGGCGATAGAGTGACCAT<br>CAGCTGTAGAGCCAGCCAGGACATCAGCAAGTACCTGAACTG<br>GTATCAGCAAAAGCCCGACGGCACCGTGAAGCTGCTGATCTA<br>CCACACCAGCAGACTGCACAGCGGCGTGCCAAGCAGATTTTC<br>TGGCAGCGGCTCTGGCACCGACTACAGCCTGACAATCAGCAA<br>CCTGGAACAAGAGGATATCGCTACCTACTTCTGCCAGCAAGG<br>CAACACCCTGCCTTACACCTTTGGCGGAGGCACCAAGCTGGA<br>AATCACCGGCTCTACAAGCGGCAGCGGCAAACCTGGATCTGG<br>CGAGGGATCTACCAAGGGCGAAGTGAAACTGCAAGAGTCTG<br>GCCCTGGACTGGTGGCCCCATCTCAGTCTCTGAGCGTGACCTG<br>TACAGTCAGCGGAGTGTCCCTGCCTGATTACGGCGTGTCCTG<br>GATCAGACAGCCTCCTCGGAAAGGCCTGGAATGGCTGGGAGT<br>GATCTGGGGCAGCGAGACAACCTACTACAACAGCGCCCTGAA<br>GTCCCGGCTGACCATCATCAAGGACAACTCCAAGAGCCAGGT<br>GTTCCTGAAGATGAACAGCCTGCAGACCGACGACACCGCCAT<br>CTACTATTGCGCCAAGCACTACTACTACGGCGGCAGCTACGC<br>CATGGATTATTGGGGCCAGGGCACCAGCGTGACCGTTTCTTCT<br>GCCGCCGCTATCGAAGTGATGTACCCTCCTCCTTACCTGGACA<br>ACGAGAAGTCCAACGGCACCATCATCCACGTGAAGGGCAAG<br>CACCTGTGTCCTTCTCCACTGTTCCCCGGACCTAGCAAGCCTT<br>TCTGGGTGCTCGTTGTTGTTGGCGGCGTGCTGGCCTGTTACAG<br>CCTGCTGGTTACCGTGGCCTTCATCATCTTTTGGGTCAGAGTG<br>AAGTTCAGCAGATCCGCCGATGCTCCCGCCTATCAGCAGGGC<br>CAAAACCAGCTGTACAACGAGCTGAACCTGGGGAGAAGAGA<br>AGAGTACGACGTGCTGGACAAGCGGAGAGGCAGAGATCCTG<br>AAATGGGCGGCAAGCCCAGACGGAAGAATCCTCAAGAGGGC<br>CTGTATAATGAGCTGCAGAAAGACAAGATGGCCGAGGCCTAC<br>AGCGAGATCGGAATGAAGGGCGAGCGCAGAAGAGGCAAGGG<br>ACACGATGGACTGTACCAGGGACTGAGCACCGCCACCAAGG<br>ATACCTATGACGCCCTGCACATGCAGGCCCTGCCTCCAAGAtaa |
| 313 | CircKymriah - Q388 | ATGGCTCTCCCGGTCACAGCCCTTCTCCTGCCCCTGGCACTCT<br>TGCTGCATGCGGCACGACCCGACATCCAGATGACCCAGACCA<br>CAAGCAGCCTGTCTGCCAGCCTGGGCGATAGAGTGACCATCA<br>GCTGTAGAGCCAGCCAGGACATCAGCAAGTACCTGAACTGGT<br>ATCAGCAAAAGCCCGACGGCACCGTGAAGCTGCTGATCTACC<br>ACACCAGCAGACTGCACAGCGGCGTGCCAAGCAGATTTTCTG<br>GCAGCGGCTCTGGCACCGACTACAGCCTGACAATCAGCAACC<br>TGGAACAAGAGGATATCGCTACCTACTTCTGCCAGCAAGGCA<br>ACACCCTGCCTTACACCTTTGGCGGAGGCACCAAGCTGGAAA<br>TCACCGGTGGAGGTGGTTCTGGCGGAGGGGGATCTGGTGGAG<br>GCGGTTCAGAAGTGAAACTGCAAGAGTCTGGCCCTGGACTGG<br>TGGCCCCATCTCAGTCTCTGAGCGTGACCTGTACAGTCAGCG<br>GAGTGTCCCTGCCTGATTACGGCGTGTCCTGGATCAGACAGC<br>CTCCTCGGAAAGGCCTGGAATGGCTGGGAGTGATCTGGGGCA<br>GCGAGACAACCTACTACAACAGCGCCCTGAAGTCCCGGCTGA<br>CCATCATCAAGGACAACTCCAAGAGCCAGGTGTTCCTGAAGA<br>TGAACAGCCTGCAGACCGACGACACCGCCATCTACTATTGCG<br>CCAAGCACTACTACTACGGCGGCAGCTACGCCATGGATTATT<br>GGGGCCAGGGCACCAGCGTGACCGTTTCTTCTACCACAACGC<br>CCGCCCCGCGACCGCCTACTCCCGCTCCCACAATTGCATCACA |

TABLE 24-continued

CAR sequences

| SEQ ID NO | CAR | Sequence |
|---|---|---|
| | | ACCCCTGTCTTTGAGACCCGAAGCTTGTCGACCAGCTGCCGGT<br>GGCGCGGTTCACACGCGGGGGCTCGATTTCGCCTGTGATATA<br>TATATATGGGCCCCATTGGCTGGAACATGCGGAGTATTGCTTC<br>TGAGCCTGGTGATTACCCTCTACTGTAAGAGAGGCCGGAAGA<br>AACTTCTTTATATATTCAAGCAGCCCTTTATGCGACCCGTTCA<br>GACTACCCAAGAGGAAGATGGATGCAGTTGCCGCTTTCCAGA<br>AGAGGAGGAGGGCGGGTGCGAACTGAGAGTGAAGTTCAGCA<br>GATCCGCCGATGCTCCCGCCTATCAGCAGGGCCAAAACCAGC<br>TGTACAACGAGCTGAACCTGGGGAGAAGAGAAGAGTACGAC<br>GTGCTGGACAAGCGGAGAGGCAGAGATCCTGAAATGGGCGG<br>CAAGCCCAGACGGAAGAATCCTCAAGAGGGCCTGTATAATGA<br>GCTGCAGAAAGACAAGATGGCCGAGGCCTACAGCGAGATCG<br>GAATGAAGGGCGAGCGCAGAAGAGGCAAGGGACACGATGGA<br>CTGTACCAGGGACTGAGCACCGCCACCAAGGATACCTATGAC<br>GCCCTGCACATGCAGGCCCTGCCTCCAAGAtaa |
| 314 | CircKymriah - K388 | ATGGCTCTCCCGGTCACAGCCCTTCTCCTGCCCCTGGCACTCT<br>TGCTGCATGCGGCACGACCCGACATCCAGATGACCCAGACCA<br>CAAGCAGCCTGTCTGCCAGCCTGGGCGATAGAGTGACCATCA<br>GCTGTAGAGCCAGCCAGGACATCAGCAAGTACCTGAACTGGT<br>ATCAGCAAAAGCCCGACGGCACCGTGAAGCTGCTGATCTACC<br>ACACCAGCAGACTGCACAGCGGCGTGCCAAGCAGATTTTCTG<br>GCAGCGGCTCTGGCACCGACTACAGCCTGACAATCAGCAACC<br>TGGAACAAGAGGATATCGCTACCTACTTCTGCCAGCAAGGCA<br>ACACCCTGCCTTACACCTTTGGCGGAGGCACCAAGCTGGAAA<br>TCACCGGTGGAGGTGGTTCTGGCGGAGGGGGATCTGGTGGAG<br>GCGGTTCAGAAGTGAAACTGCAAGAGTCTGGCCCTGGACTGG<br>TGGCCCCATCTCAGTCTCTGAGCGTGACCTGTACAGTCAGCG<br>GAGTGTCCCTGCCTGATTACGGCGTGTCCTGGATCAGACAGC<br>CTCCTCGGAAAGGCCTGGAATGGCTGGGAGTGATCTGGGGCA<br>GCGAGACAACCTACTACAACAGCGCCCTGAAGTCCCGGCTGA<br>CCATCATCAAGGACAACTCCAAGAGCCAGGTGTTCCTGAAGA<br>TGAACAGCCTGCAGACCGACGACACCGCCATCTACTATTGCG<br>CCAAGCACTACTACTACGGCGGCAGCTACGCCATGGATTATT<br>GGGGCCAGGGCACCAGCGTGACCGTTTCTTCTACCACAACGC<br>CCGCCCCGCGACCGCCTACTCCCGCTCCCACAATTGCATCACA<br>ACCCCTGTCTTTGAGACCCGAAGCTTGTCGACCAGCTGCCGGT<br>GGCGCGGTTCACACGCGGGGGCTCGATTTCGCCTGTGATATA<br>TATATATGGGCCCCATTGGCTGGAACATGCGGAGTATTGCTTC<br>TGAGCCTGGTGATTACCCTCTACTGTAAGAGAGGCCGGAAGA<br>AACTTCTTTATATATTCAAGCAGCCCTTTATGCGACCCGTTCA<br>GACTACCCAAGAGGAAGATGGATGCAGTTGCCGCTTTCCAGA<br>AGAGGAGGAGGGCGGGTGCGAACTGAGAGTGAAGTTCAGCA<br>GATCCGCCGATGCTCCCGCCTATAAGCAGGGCCAAAACCAGC<br>TGTACAACGAGCTGAACCTGGGGAGAAGAGAAGAGTACGAC<br>GTGCTGGACAAGCGGAGAGGCAGAGATCCTGAAATGGGCGG<br>CAAGCCCAGACGGAAGAATCCTCAAGAGGGCCTGTATAATGA<br>GCTGCAGAAAGACAAGATGGCCGAGGCCTACAGCGAGATCG<br>GAATGAAGGGCGAGCGCAGAAGAGGCAAGGGACACGATGGA<br>CTGTACCAGGGACTGAGCACCGCCACCAAGGATACCTATGAC<br>GCCCTGCACATGCAGGCCCTGCCTCCAAGAtaa |
| 315 | CircM971 - CD22 | ATGCTGCTGCTGGTCACATCTCTGCTGCTGTGCGAGCTGCCCC<br>ATCCTGCCTTTCTGCTGATCCCCCAGGTTCAACTCCAGCAGTC<br>TGGTCCCGGCCTCGTTAAACCAAGCCAGACTTTGTCTCTTACC<br>TGTGCTATCAGTGGCGATAGCGTGTCTAGTAATTCAGCCGCAT<br>GGAACTGGATCCGACAATCACCGAGTAGGGGACTTGAATGGC<br>TGGGTAGAACCTATTACCGGTCCAAATGGTACAATGACTATG<br>CAGTGTCTGTAAAAAGCAGGATCACGATCAACCCTGATACGT<br>CTAAAAACCAGTTTTCTCTGCAACTTAATAGTGTGACCCCTGA<br>AGACACCGCTGTGTATTACTGTGCACGGGAGGTTACCGGTGA<br>TCTTGAAGATGCTTTTGATATATGGGGCCAAGGTACGATGGT<br>CACGGTGTCTAGTgggggaggcggcagcGACATACAGATGACGCAG<br>AGCCCATCCAGTCTCTCCGCGTCTGTTGGTGACAGAGTGACTA<br>TTACATGTAGGGCGTCTCAGACCATTTGGTCTTACCTCAATTG<br>GTATCAACAGCGACCAGGCAAAGCACCGAACTTGCTCATTTA<br>CGCTGCCAGCTCACTCCAAAGTGGTGTGCCGTCCAGATTTAGT<br>GGTAGGGGCAGTGGCACTGATTTCACTCTGACTATTTCAAGTC<br>TTCAAGCTGAGGATTTTGCCACATACTACTGCCAGCAAAGTT<br>ACTCAATACCTCAGACTTTTGGACAGGGGACAAAATTGGAGA<br>TTAAAtccggaACCACAACGCCCGCCCCGCGACCGCCTACTCCC<br>GCTCCCACAATTGCATCACAACCCCTGTCTTTGAGACCCGAA<br>GCTTGTCGACCAGCTGCCGGTGGCGCGGTTCACACGCGGGGG<br>CTCGATTTCGCCTGTGATATATATATATGGGCCCCATTGGCTG<br>GAACATGCGGAGTATTGCTTCTGAGCCTGGTGATTACCCTCTA |

TABLE 24-continued

| CAR sequences | | |
|---|---|---|
| SEQ ID NO | CAR | Sequence |
| | | CTGTAAGAGAGGCCGGAAGAAACTTCTTTATATATTCAAGCA GCCCTTTATGCGACCCGTTCAGACTACCCAAGAGGAAGATGG ATGCAGTTGCCGCTTTCCAGAAGAGGAGGAGGGCGGGTGCGA ACTGAGAGTGAAGTTCAGCAGATCCGCCGATGCTCCCGCCTA TAAGCAGGGCCAAAACCAGCTGTACAACGAGCTGAACCTGG GGAGAAGAGAAGAGTACGACGTGCTGGACAAGCGGAGAGGC AGAGATCCTGAAATGGGCGGCAAGCCCAGACGGAAGAATCC TCAAGAGGGCCTGTATAATGAGCTGCAGAAAGACAAGATGG CCGAGGCCTACAGCGAGATCGGAATGAAGGGCGAGCGCAGA AGAGGCAAGGGACACGATGGACTGTACCAGGGACTGAGCAC CGCCACCAAGGATACCTATGACGCCCTGCACATGCAGGCCCT GCCTCCAAGAtaa |
| 316 | CircCD19_22 Bispecific 29 | ATGCTGCTGCTGGTCACATCTCTGCTGCTGTGCGAGCTGCCCC ATCCTGCCTTTCTGCTGATCCCCGACATCCAGATGACCCAGAC CACAAGCAGCCTGTCTGCCAGCCTGGGCGATAGAGTGACCAT CAGCTGTAGAGCCAGCCAGGACATCAGCAAGTACCTGAACTG GTATCAGCAAAAGCCCGACGGCACCGTGAAGCTGCTGATCTA CCACACCAGCAGACTGCACAGCGGCGTGCCAAGCAGATTTTC TGGCAGCGGCTCTGGCACCGACTACAGCCTGACAATCAGCAA CCTGGAACAAGAGGATATCGCTACCTACTTCTGCCAGCAAGG CAACACCCTGCCTTACACCTTTGGCGGAGGCACCAAGCTGGA AATCACCggcggcggaggatccCAGGTTCAACTCCAGCAGTCTGGTC CCGGCCTCGTTAAACCAAGCCAGACTTTGTCTCTTACCTGTGC TATCAGTGGCGATAGCGTGTCTAGTAATTCAGCCGCATGGAA CTGGATCCGACAATCACCGAGTAGGGGACTTGAATGGCTGGG TAGAACCTATTACCGGTCCAAATGGTACAATGACTATGCAGT GTCTGTAAAAAGCAGGATCACGATCAACCCTGATACGTCTAA AAACCAGTTTTCTCTGCAACTTAATAGTGTGACCCCTGAAGAC ACCGCTGTGTATTACTGTGCACGGGAGGTTACCGGTGATCTTG AAGATGCTTTTGATATATGGGGCCAAGGTACGATGGTCACGG TGTCTAGTGGCTCTACAAGCGGCAGCGGCAAACCTGGATCTG GCGAGGGATCTACCAAGGGCGACATACAGATGACGCAGAGC CCATCCAGTCTCTCCGCGTCTGTTGGTGACAGAGTGACTATTA CATGTAGGGCGTCTCAGACCATTTGGTCTTACCTCAATTGGTA TCAACAGCGACCAGGCAAAGCACCGAACTTGCTCATTTACGC TGCCAGCTCACTCCAAAGTGGTGTGCCGTCCAGATTTAGTGGT AGGGGCAGTGGCACTGATTTCACTCTGACTATTTCAAGTCTTC AAGCTGAGGATTTTGCCACATACTACTGCCAGCAAAGTTACT CAATACCTCAGACTTTTGGACAGGGGACAAAATTGGAGATTA AAgggggaggcggcagcGAAGTGAAACTGCAAGAGTCTGGCCCTGG ACTGGTGGCCCCATCTCAGTCTCTGAGCGTGACCTGTACAGTC AGCGGAGTGTCCCTGCCTGATTACGGCGTGTCCTGGATCAGA CAGCCTCCTCGGAAAGGCCTGGAATGGCTGGGAGTGATCTGG GGCAGCGAGACAACCTACTACAACAGCGCCCTGAAGTCCCGG CTGACCATCATCAAGGACAACTCCAAGAGCCAGGTGTTCCTG AAGATGAACAGCCTGCAGACCGACGACACCGCCATCTACTAT TGCGCCAAGCACTACTACTACGGCGGCAGCTACGCCATGGAT TATTGGGGCCAGGGCACCAGCGTGACCGTTTCTTCTtccggaACC ACAACGCCCGCCCCGCGACCGCCTACTCCCGCTCCCACAATT GCATCACAACCCCTGTCTTTGAGACCCGAAGCTTGTCGACCA GCTGCCGGTGGCGCGGTTCACACGCGGGGGCTCGATTTCGCC TGTGATATATATATATATGGGCCCCATTGGCTGGAACATGCGGA GTATTGCTTCTGAGCCTGGTGATTACCCTCTACTGTAAGAGAG GCCGGAAGAAACTTCTTTATATATTCAAGCAGCCCTTTATGCG ACCCGTTCAGACTACCCAAGAGGAAGATGGATGCAGTTGCCG CTTTCCAGAAGAGGAGGAGGGCGGGTGCGAACTGAGAGTGA AGTTCAGCAGATCCGCCGATGCTCCCGCCTATAAGCAGGGCC AAAACCAGCTGTACAACGAGCTGAACCTGGGGAGAAGAGAA GAGTACGACGTGCTGGACAAGCGGAGAGGCAGAGATCCTGA AATGGGCGGCAAGCCCAGACGGAAGAATCCTCAAGAGGGCC TGTATAATGAGCTGCAGAAAGACAAGATGGCCGAGGCCTACA GCGAGATCGGAATGAAGGGCGAGCGCAGAAGAGGCAAGGGA CACGATGGACTGTACCAGGGACTGAGCACCGCCACCAAGGAT ACCTATGACGCCCTGCACATGCAGGCCCTGCCTCCAAGAtaa |
| 317 | CircCD19_22 Bispecific 30 | ATGCTGCTGCTGGTCACATCTCTGCTGCTGTGCGAGCTGCCCC ATCCTGCCTTTCTGCTGATCCCCCAGGTTCAACTCCAGCAGTC TGGTCCCGGCCTCGTTAAACCAAGCCAGACTTTGTCTCTTACC TGTGCTATCAGTGGCGATAGCGTGTCTAGTAATTCAGCCGCAT GGAACTGGATCCGACAATCACCGAGTAGGGGACTTGAATGGC TGGGTAGAACCTATTACCGGTCCAAATGGTACAATGACTATG CAGTGTCTGTAAAAAGCAGGATCACGATCAACCCTGATACGT CTAAAAACCAGTTTTCTCTGCAACTTAATAGTGTGACCCCTGA AGACACCGCTGTGTATTACTGTGCACGGGAGGTTACCGGTGA |

TABLE 24-continued

CAR sequences

| SEQ ID NO | CAR | Sequence |
|---|---|---|
| | | TCTTGAAGATGCTTTTGATATATGGGGCCAAGGTACGATGGT<br>CACGGTGTCTAGTgggggaggcggcagcGACATACAGATGACGCAG<br>AGCCCATCCAGTCTCTCCGCGTCTGTTGGTGACAGAGTGACTA<br>TTACATGTAGGGCGTCTCAGACCATTTGGTCTTACCTCAATTG<br>GTATCAACAGCGACCAGGCAAAGCACCGAACTTGCTCATTTA<br>CGCTGCCAGCTCACTCCAAAGTGGTGTGCCGTCCAGATTTAGT<br>GGTAGGGGCAGTGGCACTGATTTCACTCTGACTATTTCAAGTC<br>TTCAAGCTGAGGATTTTGCCACATACTACTGCCAGCAAAGTT<br>ACTCAATACCTCAGACTTTTGGACAGGGGACAAAATTGGAGA<br>TTAAAGGGGGAGGCGGATCCGGCGGTGGTGGCTCCGGCGGTG<br>GTGGTTCTGGAGGCGGCGGAAGCGGTGGGGGTGGTAGCGAC<br>ATCCAGATGACCCAGACCACAAGCAGCCTGTCTGCCAGCCTG<br>GGCGATAGAGTGACCATCAGCTGTAGAGCCAGCCAGGACATC<br>AGCAAGTACCTGAACTGGTATCAGCAAAAGCCCGACGGCACC<br>GTGAAGCTGCTGATCTACCACACCAGCAGACTGCACAGCGGC<br>GTGCCAAGCAGATTTTCTGGCAGCGGCTCTGGCACCGACTAC<br>AGCCTGACAATCAGCAACCTGGAACAAGAGGATATCGCTACC<br>TACTTCTGCCAGCAAGGCAACACCCTGCCTTACACCTTTGGCG<br>GAGGCACCAAGCTGGAAATCACCGGCTCTACAAGCGGCAGC<br>GGCAAACCTGGATCTGGCGAGGGATCTACCAAGGGCGAAGT<br>GAAACTGCAAGAGTCTGGCCCTGGACTGGTGGCCCCATCTCA<br>GTCTCTGAGCGTGACCTGTACAGTCAGCGGAGTGTCCCTGCCT<br>GATTACGGCGTGTCCTGGATCAGACAGCCTCCTCGGAAAGGC<br>CTGGAATGGCTGGGAGTGATCTGGGGCAGCGAGACAACCTAC<br>TACAACAGCGCCCTGAAGTCCCGGCTGACCATCATCAAGGAC<br>AACTCCAAGAGCCAGGTGTTCCTGAAGATGAACAGCCTGCAG<br>ACCGACGACACCGCCATCTACTATTGCGCCAAGCACTACTAC<br>TACGGCGGCAGCTACGCCATGGATTATTGGGGCCAGGGCACC<br>AGCGTGACCGTTTCTTCTtccggaACCACAACGCCCGCCCCGCGA<br>CCGCCTACTCCCGCTCCCACAATTGCATCACAACCCCTGTCTT<br>TGAGACCCGAAGCTTGTCGACCAGCTGCCGGTGGCGCGGTTC<br>ACACGCGGGGGCTCGATTTCGCCTGTGATATATATATATGGG<br>CCCCATTGGCTGGAACATGCGGAGTATTGCTTCTGAGCCTGGT<br>GATTACCCTCTACTGTAAGAGAGGCCGGAAGAAACTTCTTTA<br>TATATTCAAGCAGCCCTTTATGCGACCCGTTCAGACTACCCAA<br>GAGGAAGATGGATGCAGTTGCCGCTTTCCAGAAGAGGAGGA<br>GGGCGGGTGCGAACTGAGAGTGAAGTTCAGCAGATCCGCCG<br>ATGCTCCCGCCTATAAGCAGGGCCAAAACCAGCTGTACAACG<br>AGCTGAACCTGGGGAGAAGAGAAGAGTACGACGTGCTGGAC<br>AAGCGGAGAGGCAGAGATCCTGAAATGGGCGGCAAGCCCAG<br>ACGGAAGAATCCTCAAGAGGGCCTGTATAATGAGCTGCAGAA<br>AGACAAGATGGCCGAGGCCTACAGCGAGATCGGAATGAAGG<br>GCGAGCGCAGAAGAGGCAAGGGACACGATGGACTGTACCAG<br>GGACTGAGCACCGCCACCAAGGATACCTATGACGCCCTGCAC<br>ATGCAGGCCCTGCCTCCAAGAtaa |

In some embodiments, a CAR is encoded by a nucleotide sequence as listed in Table 24.

TABLE 25

CAR domain sequences.

| SEQ ID NO | Protein | Sequence |
|---|---|---|
| 318 | 4-1BB | KRGRKKLLYIFKQPFMRPVQTTQEEDGCSCRFPEEEEGGCEL |
| 319 | CD3ζ intracellular domain | RVKFSRSADAPAYKQGQNQLYNELNLGRREEYDVLDKRRGRDPE<br>MGGKPRRKNPQEGLYNELQKDKMAEAYSEIGMKGERRRGKGHD<br>GLYQGLSTATKDTYDALHMQALPPR |
| 320 | CD28 intracellular signaling domain | QVQLVQSGAEVEKPGASVKVSCKASGYTFTDYYMHWVRQAPGQ<br>GLEWMGWINPNSGGTNYAQKFQGRVTMTRDTSISTAYMELSRLR<br>SDDTAVYYCASGWDFDYWGQGTLVTVSSGGGGSGGGGSGGGGS<br>GGGGSDIVMTQSPSSLSASVGDRVTITCRASQSIRYYLSWYQQKP<br>GKAPKLLIYTASILQNGVPSRFSGSGSGTDFTLTISSLQPEDFATYY<br>CLQTYTTPDFGPGTKVEIK |
| 321 | FMC63 VH | EVKLQESGPGLVAPSQSLSVTCTVSGVSLPDYGVSWIRQPPRKGLE<br>WLGVIWGSETTYYNSALKSRLTIIKDNSKSQVFLKMNSLQTDDTA<br>IYYCAKHYYYGGSYAMDYWGQGTSVTVSS |

TABLE 25-continued

| CAR domain sequences. | | |
|---|---|---|
| SEQ ID NO | Protein | Sequence |
| 322 | FMC63 VL | DIQMTQTTSSLSASLGDRVTISCRASQDISKYLNWYQQKPDGTVK LLIYHTSRLHSGVPSRFSGSGSGTDYSLTISNLEQEDIATYFCQQGN TLPYTFGGGTKLEIT |

In some embodiments, a CAR domain encoded by an inventive polynucleotide has a sequence as listed in Table 25.

TABLE 26

| PD-1 or PD-L1 sequences. | | |
|---|---|---|
| SEQ ID NO | Description | Sequence |
| 323 | Pembrolizumab heavy chain | QVQLVQSGVEVKKPGASVKVSCKASGYTFTNYYMYWV RQAPGQGLEWMGGINPSNGGTNFNEKFKNRVTLTTDSST TTAYMELKSLQFDDTAVYYCARRDYRFDMGFDYWGQG TTVTVSSASTKGPSVFPLAPCSRSTSESTAALGCLVKDYFP EPVTVSWNSGALTSGVHTFPAVLQSSGLYSLSSVVTVPSS SLGTKTYTCNVDHKPSNTKVDKRVESKYGPPCPPCPAPE FLGGPSVFLFPPKPKDTLMISRTPEVTCVVVDVSQEDPEV QFNWYVDGVEVHNAKTKPREEQFNSTYRVVSVLTVLHQ DWLNGKEYKCKVSNKGLPSSIEKTISKAKGQPREPQVYT LPPSQEEMTKNQVSLTCLVKGFYPSDIAVEWESNGQPEN NYKTTPPVLDSDGSFFLYSRLTVDKSRWQEGNVFSCSVM HEALHNHYTQKSLSLSLGK |
| 324 | Pembrolizumab light chain | EIVLTQSPATLSLSPGERATLSCRASKGVSTSGYSYLHWY QQKPGQAPRLLIYLASYLESGVPARFSGSGSGTDFTLTISS LEPEDFAVYYCQHSRDLPLTFGGGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| 325 | Nivolumab heavy chain | QVQLVESGGGVVQPGRSLRLDCKASGITFSNSGMHWVR QAPGKGLEWVAVIWYDGSKRYYADSVKGRFTISRDNSK NTLFLQMNSLRAEDTAVYYCATNDDYWGQGTLVTVSSA STKGPSVFPLAPCSRSTSESTAALGCLVKDYFPEPVTVSW NSGALTSGVHTFPAVLQSSGLYSLSSVVTVPSSSLGTKTY TCNVDHKPSNTKVDKRVESKYGPPCPPCPAPEFLGGPSVF LFPPKPKDTLMISRTPEVTCVVVDVSQEDPEVQFNWYVD GVEVHNAKTKPREEQFNSTYRVVSVLTVLHQDWLNGKE YKCKVSNKGLPSSIEKTISKAKGQPREPQVYTLPPSQEEM TKNQVSLTCLVKGFYPSDIAVEWESNGQPENNYKTTPPV LDSDGSFFLYSRLTVDKSRWQEGNVFSCSVMHEALHNH YTQKSLSLSLGK |
| 326 | Nivolumab light chain | EIVLTQSPATLSLSPGERATLSCRASQSVSSYLAWYQQKP GQAPRLLIYDASNRATGIPARFSGSGSGTDFTLTISSLEPE DFAVYYCQQSSNWPRTFGQGTKVEIKRTVAAPSVFIFPPS DEQLKSGTASVVCLLNNFYPREAKVQWKVDNALQSGNS QESVTEQDSKDSTYSLSSTLTLSKADYEKHKVYACEVTH QGLSSPVTKSFNRGEC |
| 327 | Atezolizumab heavy chain | EVQLVESGGGLVQPGGSLRLSCAASGFTFSDSWIHWVRQ APGKGLEWVAWISPYGGSTYYADSVKGRFTISADTSKNT AYLQMNSLRAEDTAVYYCARRHWPGGFDYWGQGTLVT VSSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKKVEPKSCDKTHTCPPCPAPE LLGGPSVFLFPPKPKDTLMISRTPEVTCVVVDVSHEDPEV KFNWYVDGVEVHNAKTKPREEQYASTYRVVSVLTVLHQ DWLNGKEYKCKVSNKALPAPIEKTISKAKGQPREPQVYT LPPSREEMTKNQVSLTCLVKGFYPSDIAVEWESNGQPEN NYKTTPPVLDSDGSFFLYSKLTVDKSRWQQGNVFSCSVM HEALHNHYTQKSLSLSPGK |
| 328 | Atezolizumab light chain | DIQMTQSPSSLSASVGDRVTITCRASQDVSTAVAWYQQK PGKAPKLLIYSASFLYSGVPSRFSGSGSGTDFTLTISSLQPE DFATYYCQQYLYHPATFGQGTKVEIKRTVAAPSVFIFPPS |

TABLE 26-continued

PD-1 or PD-L1 sequences.

| SEQ ID NO | Description | Sequence |
|---|---|---|
| | | DEQLKSGTASVVCLLNNFYPREAKVQWKVDNALQSGNS QESVTEQDSKDSTYSLSSTLTLSKADYEKHKVYACEVTH QGLSSPVTKSFNRGEC |
| 329 | Avelumab heavy chain | EVQLLESGGGLVQPGGSLRLSCAASGFTFSSYIMMWVRQ APGKGLEWVSSIYPSGGITFYADTVKGRFTISRDNSKNTL YLQMNSLRAEDTAVYYCARIKLGTVTTVDYWGQGTLVT VSSASTKGPSVFPLAPSSKSTSGGTAALGCLVKDYFPEPV TVSWNSGALTSGVHTFPAVLQSSGLYSLSSVVTVPSSSLG TQTYICNVNHKPSNTKVDKKVEPKSCDKTHTCPPCPAPE LLGGPSVFLFPPKPKDTLMISRTPEVTCVVVDVSHEDPEV KFNWYVDGVEVHNAKTKPREEQYNSTYRVVSVLTVLHQ DWLNGKEYKCKVSNKALPAPIEKTISKAKGQPREPQVYT LPPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 330 | Avelumab light chain | QSALTQPASVSGSPGQSITISCTGTSSDVGGYNYVSWYQQ HPGKAPKLMIYDVSNRPSGVSNRFSGSKSGNTASLTISGL QAEDEADYYCSSYTSSSTRVFGTGTKVTVLGQPKANPTV TLFPPSSEELQANKATLVCLISDFYPGAVTVAWKADGSPV KAGVETTKPSKQSNNKYAASSYLSLTPEQWKSHRSYSCQ VTHEGSTVEKTVAPTECS |
| 331 | Durvalumab heavy chain | EVQLVESGGGLVQPGGSLRLSCAASGFTFSRYWMSWVR QAPGKGLEWVANIKQDGSEKYYVDSVKGRFTISRDNAK NSLYLQMNSLRAEDTAVYYCAREGGWFGELAFDYWGQ GTLVTVSSASTKGPSVFPLAPSSKSTSGGTAALGCLVKDY FPEPVTVSWNSGALTSGVHTFPAVLQSSGLYSLSSVVTVP SSSLGTQTYICNVNHKPSNTKVDKRVEPKSCDKTHTCPPC PAPEFEGGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPASIEKTISKAKGQPREP QVYTLPPSREEMTKNQVSLTCLVKGFYPSDIAVEWESNG QPENNYKTTPPVLDSDGSFFLYSKLTVDKSRWQQGNVFS CSVMHEALHNHYTQKSLSLSPGK |
| 332 | Durvalumab light chain | EIVLTQSPGTLSLSPGERATLSCRASQRVSSSYLAWYQQK PGQAPRLLIYDASSRATGIPDRFSGSGSGTDFTLTISRLEPE DFAVYYCQQYGSLPWTFGQGTKVEIKRTVAAPSVFIFPPS DEQLKSGTASVVCLLNNFYPREAKVQWKVDNALQSGNS QESVTEQDSKDSTYSLSSTLTLSKADYEKHKVYACEVTH QGLSSPVTKSFNRGEC |

In some embodiments, a cleavage site separating expression sequences encoded by an inventive polynucleotide has a sequence listed in Table 26.

TABLE 27

Cytokine sequences.

| SEQ ID NO | Cytokine | Sequence |
|---|---|---|
| 333 | IL-2 | APTSSSTKKTQLQLEHLLLDLQMILNGINNYKNPKLTRMLTFKFY MPKKATELKHLQCLEEELKPLEEVLNLAQSKNFHLRPRDLISNINV IVLELKGSETTFMCEYADETATIVEFLNRWITFCQSIISTLT |
| 334 | IL-12A | RNLPVATPDPGMFPCLHHSQNLLRAVSNMLQKARQTLEFYPCTSE EIDHEDITKDKTSTVEACLPLELTKNESCLNSRETSFITNGSCLASR KTSFMMALCLSSIYEDLKMYQVEFKTMNAKLLMDPKRQIFLDQN MLAVIDELMQALNFNSETVPQKSSLEEPDFYKTKIKLCILLHAFRIR AVTIDRVMSYLNAS |
| 335 | IL-12B | IWELKKDVYVVELDWYPDAPGEMVVLTCDTPEEDGITWTLDQSS EVLGSGKTLTIQVKEFGDAGQYTCHKGGEVLSHSLLLLHKKEDGI WSTDILKDQKEPKNKTFLRCEAKNYSGRFTCWWLTTISTDLTFSV KSSRGSSDPQGVTCGAATLSAERVRGDNKEYEYSVECQEDSACPA AEESLPIEVMVDAVHKLKYENYTSSFFIRDIIKPDPPKNLQLKPLKN SRQVEVSWEYPDTWSTPHSYFSLTFCVQVQGKSKREKKDRVFTD KTSATVICRKNASISVRAQDRYYSSSWSEWASVPCS |

TABLE 27-continued

| Cytokine sequences. | | |
|---|---|---|
| SEQ ID NO | Cytokine | Sequence |
| 336 | IL-7 | DCDIEGKDGKQYESVLMVSIDQLLDSMKEIGSNCLNNEFNFFKRHI CDANKEGMFLFRAARKLRQFLKMNSTGDFDLHLLKVSEGTTILLN CTGQVKGRKPAALGEAQPTKSLEENKSLKEQKKLNDLCFLKRLL QEIKTCWNKILMGTKEH |
| 337 | IL-10 | SPGQGTQSENSCTHFPGNLPNMLRDLRDAFSRVKTFFQMKDQLD NLLLKESLLEDFKGYLGCQALSEMIQFYLEEVMPQAENQDPDIKA HVNSLGENLKTLRLRLRRCHRFLPCENKSKAVEQVKNAFNKLQE KGIYKAMSEFDIFINYIEAYMTMKIRN |
| 338 | IL-15 | NWVNVISDLKKIEDLIQSMHIDATLYTESDVHPSCKVTAMKCFLL ELQVISLESGDASIHDTVENLIILANNSLSSNGNVTESGCKECEELE EKNIKEFLQSFVHIVQMFINTS |
| 339 | IL-18 | YFGKLESKLSVIRNLNDQVLFIDQGNRPLFEDMTDSDCRDNAPRTI FIISMYKDSQPRGMAVTISVKCEKISTLSCENKIISFKEMNPPDNIKD TKSDIIFFQRSVPGHDNKMQFESSSYEGYFLACEKERDLFKLILKK EDELGDRSIMFTVQNED |
| 340 | IL-27beta | RKGPPAALTLPRVQCRASRYPIAVDCSWTLPPAPNSTSPVSFIATY RLGMAARGHSWPCLQQTPTSTSCTITDVQLFSMAPYVLNVTAVH PWGSSSSFVPFITEHIIKPDPPEGVRLSPLAERQLQVQWEPPGSWPF PEIFSLKYWIRYKRQGAARFHRVGPIEATSFILRAVRPRARYYVQV AAQDLTDYGELSDWSLPATATMSLGK |
| 341 | IFNgamma | QDPYVKEAENLKKYFNAGHSDVADNGTLFLGILKNWKEESDRKI MQSQIVSFYFKLFKNFKDDQSIQKSVETIKEDMNVKFFNSNKKKR DDFEKLTNYSVTDLNVQRKAIHELIQVMAELSPAAKTGKRKRSQ MLFRG |
| 342 | TGFbeta1 | ALDTNYCFSSTEKNCCVRQLYIDFRKDLGWKWIHEPKGYHANFC LGPCPYIWSLDTQYSKVLALYNQHNPGASAAPCCVPQALEPLPIV YYVGRKPKVEQLSNMIVRSCKCS |

In some embodiments, a cytokine encoded by an inventive polynucleotide has a sequence as listed in Table 27.

TABLE 28

| Transcription factor sequences. | | |
|---|---|---|
| SEQ ID NO | Transcription factor | Sequence |
| 343 | FOXP3 | MPNPRPGKPSAPSLALGPSPGASPSWRAAPKASDLLGARGPGGT FQGRDLRGGAHASSSSLNPMPPSQLQLPTLPLVMVAPSGARLGP LPHLQALLQDRPHFMHQLSTVDAHARTPVLQVHPLESPAMISLT PPTTATGVFSLKARPGLPPGINVASLEWVSREPALLCTFPNPSAPR KDSTLSAVPQSSYPLLANGVCKWPGCEKVFEEPEDFLKHCQADH LLDEKGRAQCLLQREMVQSLEQQLVLEKEKLSAMQAHLAGKM ALTKASSVASSDKGSCCIVAAGSQGPVVPAWSGPREAPDSLFAV RRHLWGSHGNSTFPEFLHNMDYFKFHNMRPPFTYATLIRWAILE APEKQRTLNEIYHWFTRMFAFFRNHPATWKNAIRHNLSLHKCFV RVESEKGAVWTVDELEFRKKRSQRPSRCSNPTPGP |
| 344 | FOXP3 | MPNPRPGKPSAPSLALGPSPGASPSWRAAPKASDLLGARGPGGT FQGRDLRGGAHASSSSLNPMPPSQLQLPTLPLVMVAPSGARLGP LPHLQALLQDRPHFMHQLSTVDAHARTPVLQVHPLESPAMISLT PPTTATGVFSLKARPGLPPGINVASLEWVSREPALLCTFPNPSAPR KDSTLSAVPQSSYPLLANGVCKWPGCEKVFEEPEDFLKHCQADH LLDEKGRAQCLLQREMVQSLEQQLVLEKEKLSAMQAHLAGKM ALTKASSVASSDKGSCCIVAAGSQGPVVPAWSGPREAPDSLFAV RRHLWGSHGNSTFPEFLHNMDYFKFHNMRPPFTYATLIRWAILE APEKQRTLNEIYHWFTRMFAFFRNHPATWKNAIRHNLSLHKCFV RVESEKGAVWTVDELEFRKKR |
| 345 | FOXP3 | GGAHASSSSLNPMPPSQLQLPTLPLVMVAPSGARLGPLPHLQAL LQDRPHFMHQLSTVDAHARTPVLQVHPLESPAMISLTPPTTATG VFSLKARPGLPPGINVASLEWVSREPALLCTFPNPSAPRKDSTLS AVPQSSYPLLANGVCKWPGCEKVFEEPEDFLKHCQADHLLDEK GRAQCLLQREMVQSLEQQLVLEKEKLSAMQAHLAGKMALTKA |

TABLE 28-continued

| Transcription factor sequences. | | |
|---|---|---|
| SEQ ID NO | Transcription factor | Sequence |
| | | SSVASSDKGSCCIVAAGSQGPVVPAWSGPREAPDSLFAVRRHLW GSHGNSTFPEFLHNMDYFKFHNMRPPFTYATLIRWAILEAPEKQ RTLNEIYHWFTRMFAFFRNHPATWKNAIRHNLSLHKCFVRVESE KGAVWTVDELEFRKKR |
| 346 | STAT5B | MAVWIQAQQLQGEALHQMQALYGQHFPIEVRHYLSQWIESQA WDSVDLDNPQENIKATQLLEGLVQELQKKAEHQVGEDGFLLKI KLGHYATQLQNTYDRCPMELVRCIRHILYNEQRLVREANNGSSP AGSLADAMSQKHLQINQTFEELRLVTQDTENELKKLQQTQEYFII QYQESLRIQAQFGPLAQLSPQERLSRETALQQKQVSLEAWLQRE AQTLQQYRVELAEKHQKTLQLLRKQQTIILDDELIQWKRRQQLA GNGGPPEGSLDVLQSWCEKLAEIIWQNRQQIRRAEHLCQQLPIPG PVEEMLAEVNATITDIISALVTSTFIIEKQPPQVLKTQTKFAATVR LLVGGKLNVHMNPPQVKATIISEQQAKSLLKNENTRNDYSGEIL NNCCVMEYHQATGTLSAHFRNMSLKRIKRSDRRGAESVTEEKF TILFESQFSVGGNELVFQVKTLSLPVVVIVHGSQDNNATATVLW DNAFAEPGRVPFAVPDKVLWPQLCEALNMKFKAEVQSNRGLTK ENLVFLAQKLFNNSSSHLEDYSGLSVSWSQFNRENLPGRNYTFW QWFDGVMEVLKKHLKPHWNDGAILGFVNKQQAHDLLINKPDG TFLLRFSDSEIGGITIAWKFDSQERMFWNLMPFTTRDFSIRSLADR LGDLNYLIYVFPDRPKDEVYSKYYTPVPCESATAKAVDGYVKPQ IKQVVPEFVNASADAGGGSATYMDQAPSPAVCPQAHYNMYPQ NPDSVLDTDGDFDLEDTMDVARRVEELLGRPMDSQWIPHAQS |
| 347 | HELIOS | METEAIDGYITCDNELSPEREHSNMAIDLTSSTPNGQHASPSHMT STNSVKLEMQSDEECDRKPLSREDEIRGHDEGSSLEEPLIESSEVA DNRKVQELQGEGGIRLPNGKLKCDVCGMVCIGPNVLMVHKRSH TGERPFHCNQCGASFTQKGNLLRHIKLHSGEKPFKCPFCSYACRR RDALTGHLRTHSVGKPHKCNYCGRSYKQRSSLEEHKERCHNYL QNVSMEAAGQVMSHHVPPMEDCKEQEPIMDNNISLVPFERPAVI EKLTGNMGKRKSSTPQKFVGEKLMRFSYPDIHFDMNLTYEKEA ELMQSHMMDQAINNAITYLGAEALHPLMQHPPSTIAEVAPVISS AYSQVYHPNRIERPISRETADSHENNMDGPISLIRPKSRPQEREAS PSNSCLDSTDSESSHDDHQSYQGHPALNPKRKQSPAYMKEDVK ALDTTKAPKGSLKDIYKVFNGEGEQIRAFKCEHCRVLFLDHVMY TIHMGCHGYRDPLECNICGYRSQDRYEFSSHIVRGEHTFH |

In some embodiments, a transcription factor encoded by an inventive polynucleotide has a sequence as listed in Table 28.

TABLE 29

| Additional Accessory Sequences | | |
|---|---|---|
| SEQ ID NO | IRES | Sequence |
| 390 | CK 3'UTR Scr | ccctgcagccgtcaccgtaagtttgaagttaccgcatatcagcctctgcttcccagcgcgtccaatt cctgttcttattgtttcccctccaggcgttacgcgtgacgacgaactgtgtcgcagctaccacattatt ccggagccttcattctcgcggctctgatcgt |
| 391 | CK 3'UTR S2M | ggagaccgcggccacgccgagtaggatcgagggtacagtctcc |
| 392 | CK 3'UTR | gacaccaggatcactcttgctctgacccgccctgtgtagaatagactcatgcttccctaagacctgg atttcttcccaggcactttcacccgcctgccctgctccttcagtggactgcacccagggaggcggtc tctgactgtcctttactttctattctggattgc |
| 393 | CK 5'UTR 1 | AAACCCCCCTAAGCCGCCGCCGCCGCCACC |
| 394 | CK 5'UTR 2 | CCCCCCCAACCCGTCACG |
| 395 | CK 5'UTR 3 | GTCACG |
| 396 | SZ1 3'UTR Scr | tctgcgcactcgtaatcagtactaaccccccctttgtcggacactatgcgataatcgatccgccttttttc accgccttcggaattttatttacctcaactgatcctggagtctctcttggttttcacggaggcctccgcc ca |
| 397 | SZ1 S2M | ggagaccgcggccacgccgagtaggatcgagggtacagtctcc |

TABLE 29-continued

Additional Accessory Sequences

| SEQ ID NO | IRES | Sequence |
|---|---|---|
| 398 | SZ1 3'UTR | ccccttgaaacccccgccccaggttcagtctctcttcatccctctgtcctgcatggtgatacaaagac cctttgtggaccctaagccatgtagttgctgctccctccttccagttgtgaatattggtttctgttaatca ca |
| 399 | SZ1 5'UTR 1 | AAACCCCCCTAAGCCGCCGCCGCCGCCACC |
| 400 | SZ1 5'UTR 2 | CCCCCCCAACCCGTCACG |
| 401 | SZ1 5'UTR 3 | GTCACG |
| 402 | UTR1 | gTcacG |
| 403 | UTR2 | AATAAGAGAGAAAAGAAGAGTAAGAAGAAATATAAGAGC CACC |
| 404 | UTR3 | cgaactagtattcttctggtccccacagactcagagagaacccgccacc |
| 405 | UTR4 | Agccacc |
| 406 | STOP1 | tgatAGctAaCtaG |
| 407 | STOP2 | tagtAGctAaCtaG |
| 408 | STOP3 | tGatGActGaGtGA |
| 409 | STOP4 | tagtagctagGtag |
| 410 | STOP5 | taa |
| 411 | STOP6 | taatagCtaaCtag |
| 412 | STOP7 | taaCtagCtaaCtag |

In some embodiments, a circular RNA or a precursor RNA (e.g., linear precursor RNA) disclosed herein comprises a sequence as listed in Table 29.

In some embodiments, a polynucleotide or a protein encoded by a polynucleotide contains a sequence with at least about 70%, 75%, 80%, 85%, 90%, 91%, 92%, 93%, 94%, 95%, 96%, 97%, 98%, 99%, or 99.5% similarity to one or more sequences disclosed herein. In some embodiments, a polynucleotide or a protein encoded by a polynucleotide contains a sequence that is identical to one or more sequences disclosed herein.

Preferred embodiments are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Wesselhoeft et al. (2019) RNA Circularization Diminishes Immunogenicity and Can Extend Translation Duration In Vivo. Molecular Cell. 74(3), 508-520 and Wesselhoeft et al. (2018) Engineering circular RNA for Potent and Stable Translation in Eukaryotic Cells. Nature Communications. 9, 2629 are incorporated by reference in their entirety.

The invention is further described in detail by reference to the following examples but are not intended to be limited to the following examples. These examples encompass any and all variations of the illustrations with the intention of providing those of ordinary skill in the art with complete disclosure and description of how to make and use the subject invention and are not intended to limit the scope of what is regarded as the invention.

Example 1

Example 1A: External Homology Regions Allow for Circularization of Long Precursor RNA Using the Permuted Intron Exon (PIE) Circularization Strategy A 1,100 nt sequence containing a full-length encephalomyocarditis virus (EMCV) IRES, a *Gaussia* luciferase (GLuc) expression sequence, and two short exon fragments of the permuted intron-exon (PIE) construct were inserted between the 3' and 5' introns of the permuted group I catalytic intron in the thymidylate synthase (Td) gene of the T4 phage. Precursor RNA was synthesized by run-off transcription. Circularization was attempted by heating the precursor RNA in the presence of magnesium ions and GTP, but splicing products were not obtained.

Perfectly complementary 9 nucleotide and 19 nucleotide long homology regions were designed and added at the 5' and 3' ends of the precursor RNA. Addition of these homology arms increased splicing efficiency from 0 to 16% for 9 nucleotide homology regions and to 48% for 19 nucleotide homology regions as assessed by disappearance of the precursor RNA band.

The splicing product was treated with RNase R. Sequencing across the putative splice junction of RNase R-treated splicing reactions revealed ligated exons, and digestion of the RNase R-treated splicing reaction with oligonucleotide-targeted RNase H produced a single band in contrast to two bands yielded by RNase H-digested linear precursor. This shows that circular RNA is a major product of the splicing reactions of precursor RNA containing the 9 or 19 nucleotide long external homology regions.

Example 1B: Spacers that Conserve Secondary Structures of IRES and PIE Splice Sites Increase Circularization Efficiency A series of spacers was designed and inserted between the 3' PIE splice site and the IRES. These spacers were designed to either conserve or disrupt secondary structures within intron sequences in the IRES, 3' PIE splice site, and/or 5' splice site. The addition of spacer sequences designed to conserve secondary structures resulted in 87% splicing efficiency, while the addition of a disruptive spacer sequences resulted in no detectable splicing.

Example 2

Example 2A: Internal Homology Regions in Addition to External Homology Regions Creates a Splicing Bubble and Allows for Translation of Several Expression Sequences Spacers were designed to be unstructured, non-homologous to the intron and IRES sequences, and to contain spacer-spacer homology regions. These were inserted between the 5' exon and IRES and between the 3' exon and expression sequence in constructs containing external homology regions, EMCV IRES, and expression sequences for *Gaussia* luciferase (total length: 1289 nt), Firefly luciferase (2384 nt), eGFP (1451 nt), human erythropoietin (1313 nt), and Cas9 endonuclease (4934 nt). Circularization of all 5 constructs was achieved. Circularization of constructs utilizing T4 phage and *Anabaena* introns were roughly equal. Circularization efficiency was higher for shorter sequences. To measure translation, each construct was transfected into HEK293 cells. *Gaussia* and Firefly luciferase transfected cells produced a robust response as measured by luminescence, human erythropoietin was detectable in the media of cells transfected with erythropoietin circRNA, and EGFP fluorescence was observed from cells transfected with EGFP circRNA. Co-transfection of Cas9 circRNA with sgRNA directed against GFP into cells constitutively expressing GFP resulted in ablated fluorescence in up to 97% of cells in comparison to an sgRNA-only control.

Example 2B: Use of CVB3 IRES Increases Protein Production

Constructs with internal and external homology regions and differing IRES containing either *Gaussia* luciferase or Firefly luciferase expression sequences were made. Protein production was measured by luminescence in the supernatant of HEK293 cells 24 hours after transfection. The Coxsackievirus B3 (CVB3) IRES construct produced the most protein in both cases.

Example 2C: Use of polyA or polyAC Spacers Increases Protein Production

Thirty nucleotide long polyA or polyAC spacers were added between the IRES and splice junction in a construct with each IRES that produced protein in example 2B. *Gaussia* luciferase activity was measured by luminescence in the supernatant of HEK293 cells 24 hours after transfection. Both spacers improved expression in every construct over control constructs without spacers.

Example 3

HEK293 or HeLa Cells Transfected with Circular RNA Produce More Protein than Those Transfected with Comparable Unmodified or Modified Linear RNA.

HPLC-purified *Gaussia* luciferase-coding circRNA (CVB3-GLuc-pAC) was compared with a canonical unmodified 5' methylguanosine-capped and 3' polyA-tailed linear GLuc mRNA, and a commercially available nucleoside-modified (pseudouridine, 5-methylcytosine) linear GLuc mRNA (from Trilink). Luminescence was measured 24 h post-transfection, revealing that circRNA produced 811.2% more protein than the unmodified linear mRNA in HEK293 cells and 54.5% more protein than the modified mRNA. Similar results were obtained in HeLa cells and a comparison of optimized circRNA coding for human erythropoietin with linear mRNA modified with 5-methoxyuridine.

Luminescence data was collected over 6 days. In HEK293 cells, circRNA transfection resulted in a protein production half-life of 80 hours, in comparison with the 43 hours of unmodified linear mRNA and 45 hours of modified linear mRNA. In HeLa cells, circRNA transfection resulted in a protein production half-life of 116 hours, in comparison with the 44 hours of unmodified linear mRNA and 49 hours of modified linear mRNA. CircRNA produced substantially more protein than both the unmodified and modified linear mRNAs over its lifetime in both cell types.

Example 4

Example 4A: Purification of circRNA by RNase Digestion, HPLC Purification, and Phosphatase Treatment Decreases Immunogenicity. Completely Purified Circular RNA is Significantly Less Immunogenic than Unpurified or Partially Purified Circular RNA. Protein Expression Stability and Cell Viability are Dependent on Cell Type and Circular RNA Purity Human embryonic kidney 293 (HEK293) and human lung carcinoma A549 cells were transfected with:

- products of an unpurified GLuc circular RNA splicing reaction,
- products of RNase R digestion of the splicing reaction,
- products of RNase R digestion and HPLC purification of the splicing reaction, or
- products of RNase digestion, HPLC purification, and phosphatase treatment of the splicing reaction.

RNase R digestion of splicing reactions was insufficient to prevent cytokine release in A549 cells in comparison to untransfected controls.

The addition of HPLC purification was also insufficient to prevent cytokine release, although there was a significant reduction in interleukin-6 (IL-6) and a significant increase in interferon-α1 (IFN-α1) compared to the unpurified splicing reaction.

The addition of a phosphatase treatment after HPLC purification and before RNase R digestion dramatically reduced the expression of all upregulated cytokines assessed in A549 cells. Secreted monocyte chemoattractant protein 1

(MCP1), IL-6, IFN-α1, tumor necrosis factor α (TNFα), and IFNγ inducible protein-10 (IP-10) fell to undetectable or un-transfected baseline levels.

There was no substantial cytokine release in HEK293 cells. A549 cells had increased GLuc expression stability and cell viability when transfected with higher purity circular RNA. Completely purified circular RNA had a stability phenotype similar to that of transfected 293 cells.

Example 4B: Circular RNA does not Cause Significant Immunogenicity and is not a RIG-I Ligand A549 cells were transfected with the products of a splicing reaction:

A549 cells were transfected with:

unpurified circular RNA, high molecular weight (linear and circular concatenations) RNA, circular (nicked) RNA, an early fraction of purified circular RNA (more overlap with nicked RNA peak), a late fraction of purified circular RNA (less overlap with nicked RNA peak), introns excised during circularization, or vehicle (i.e. untransfected control).

Precursor RNA was separately synthesized and purified in the form of the splice site deletion mutant (DS) due to difficulties in obtaining suitably pure linear precursor RNA from the splicing reaction. Cytokine release and cell viability was measured in each case.

Robust IL-6, RANTES, and IP-10 release was observed in response to most of the species present within the splicing reaction, as well as precursor RNA. Early circRNA fractions elicited cytokine responses comparable to other non-circRNA fractions, indicating that even relatively small quantities of linear RNA contaminants are able to induce a substantial cellular immune response in A549 cells. Late circRNA fractions elicited no cytokine response in excess of that from untransfected controls. A549 cell viability 36 hours post-transfection was significantly greater for late circRNA fractions compared with all of the other fractions.

RIG-I and IFN-β1 transcript induction upon transfection of A549 cells with late circRNA HPLC fractions, precursor RNA or unpurified splicing reactions were analyzed. Induction of both RIG-I and IFN-β1 transcripts were weaker for late circRNA fractions than precursor RNA and unpurified splicing reactions. RNase R treatment of splicing reactions alone was not sufficient to ablate this effect. Addition of very small quantities of the RIG-I ligand 3p-hpRNA to circular RNA induced substantial RIG-I transcription. In HeLa cells, transfection of RNase R-digested splicing reactions induced RIG-I and IFN-β1, but purified circRNA did not. Overall, HeLa cells were less sensitive to contaminating RNA species than A549 cells.

A time course experiment monitoring RIG-I, IFN-β1, IL-6, and RANTES transcript induction within the first 8 hours after transfection of A549 cells with splicing reactions or fully purified circRNA did not reveal a transient response to circRNA. Purified circRNA similarly failed to induce pro-inflammatory transcripts in RAW264.7 murine macrophages.

A549 cells were transfected with purified circRNA containing an EMCV IRES and EGFP expression sequence. This failed to produce substantial induction of pro-inflammatory transcripts. These data demonstrate that non-circular components of the splicing reaction are responsible for the immunogenicity observed in previous studies and that circRNA is not a natural ligand for RIG-I.

Example 5

Circular RNA Avoids Detection by TLRs.

TLR 3, 7, and 8 reporter cell lines were transfected with multiple linear or circular RNA constructs and secreted embryonic alkaline phosphatase (SEAP) was measured.

Linearized RNA was constructed by deleting the intron and homology arm sequences. The linear RNA constructs were then treated with phosphatase (in the case of capped RNAs, after capping) and purified by HPLC.

None of the attempted transfections produced a response in TLR7 reporter cells. TLR3 and TLR8 reporter cells were activated by capped linearized RNA, polyadenylated linearized RNA, the nicked circRNA HPLC fraction, and the early circRNA fraction. The late circRNA fraction and m1ψ-mRNA did not provoke TLR-mediated response in any cell line.

In a second experiment, circRNA was linearized using two methods: treatment of circRNA with heat in the presence of magnesium ions and DNA oligonucleotide-guided RNase H digestion. Both methods yielded a majority of full-length linear RNA with small amounts of intact circRNA. TLR3, 7, and 8 reporter cells were transfected with circular RNA, circular RNA degraded by heat, or circular RNA degraded by RNase H, and SEAP secretion was measured 36 hours after transfection. TLR8 reporter cells secreted SEAP in response to both forms of degraded circular RNA, but did not produce a greater response to circular RNA transfection than mock transfection. No activation was observed in TLR3 and TLR7 reporter cells for degraded or intact conditions, despite the activation of TLR3 by in vitro transcribed linearized RNA.

Example 6

Unmodified Circular RNA Produces Increased Sustained In Vivo Protein Expression than Linear RNA.

Mice were injected and HEK293 cells were transfected with unmodified and m1ψ-modified human erythropoietin (hEpo) linear mRNAs and circRNAs. Equimolar transfection of m1ψf-mRNA and unmodified circRNA resulted in robust protein expression in HEK293 cells. hEpo linear mRNA and circRNA displayed similar relative protein expression patterns and cell viabilities in comparison to GLuc linear mRNA and circRNA upon equal weight transfection of HEK293 and A549 cells.

In mice, hEpo was detected in serum after the injection of hEpo circRNA or linear mRNA into visceral adipose. hEpo detected after the injection of unmodified circRNA decayed more slowly than that from unmodified or m1ψ-mRNA and was still present 42 hours post-injection. Serum hEpo rapidly declined upon the injection of unpurified circRNA splicing reactions or unmodified linear mRNA. Injection of unpurified splicing reactions produced a cytokine response detectable in serum that was not observed for the other RNAs, including purified circRNA.

Example 7

Circular RNA can be Effectively Delivered In Vivo or In Vitro Via Lipid Nanoparticles.

Purified circular RNA was formulated into lipid nanoparticles (LNPs) with the ionizable lipidoid cKK-E12 (Dong et al., 2014; Kauffman et al., 2015). The particles formed uniform multilamellar structures with an average size, polydispersity index, and encapsulation efficiency similar to that of particles containing commercially available control linear mRNA modified with 5moU.

Purified hEpo circRNA displayed greater expression than 5moU-mRNA when encapsulated in LNPs and added to HEK293 cells. Expression stability from LNP-RNA in HEK293 cells was similar to that of RNA delivered by transfection reagent, with the exception of a slight delay in decay for both 5moU-mRNA and circRNA. Both unmodified circRNA and 5moU-mRNA failed to activate RIG-I/IFN-β1 in vitro.

In mice, LNP-RNA was delivered by local injection into visceral adipose tissue or intravenous delivery to the liver. Serum hEpo expression from circRNA was lower but comparable with that from 5moU-mRNA 6 hours after delivery in both cases. Serum hEpo detected after adipose injection of unmodified LNP-circRNA decayed more slowly than that from LNP-5moU-mRNA, with a delay in expression decay present in serum that was similar to that noted in vitro, but serum hEpo after intravenous injection of LNP-circRNA or LNP-5moU-mRNA decayed at approximately the same rate. There was no increase in serum cytokines or local RIG-I, TNFα, or IL-6 transcript induction in any of these cases.

Example 8

Figure 1B:
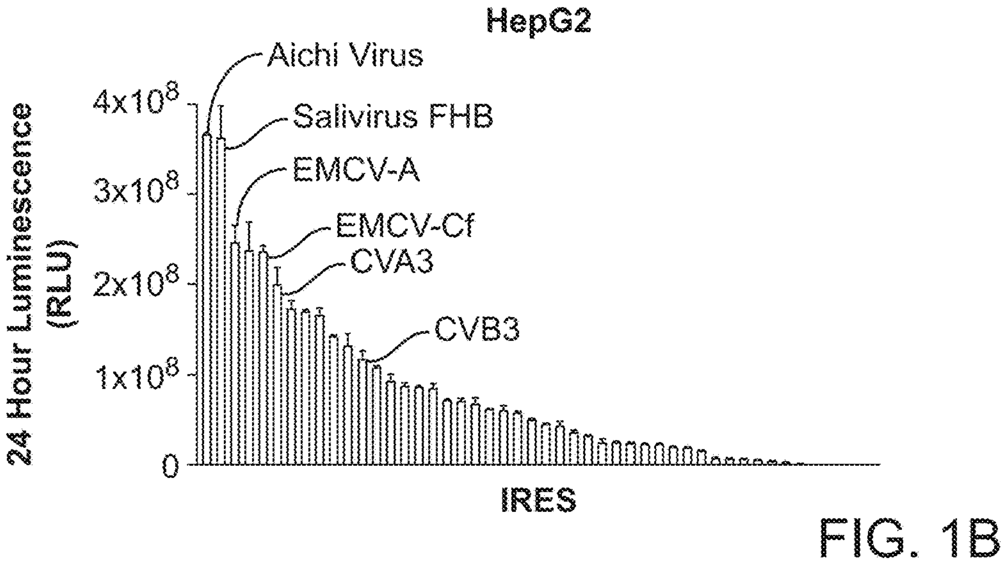
Figure 1C:
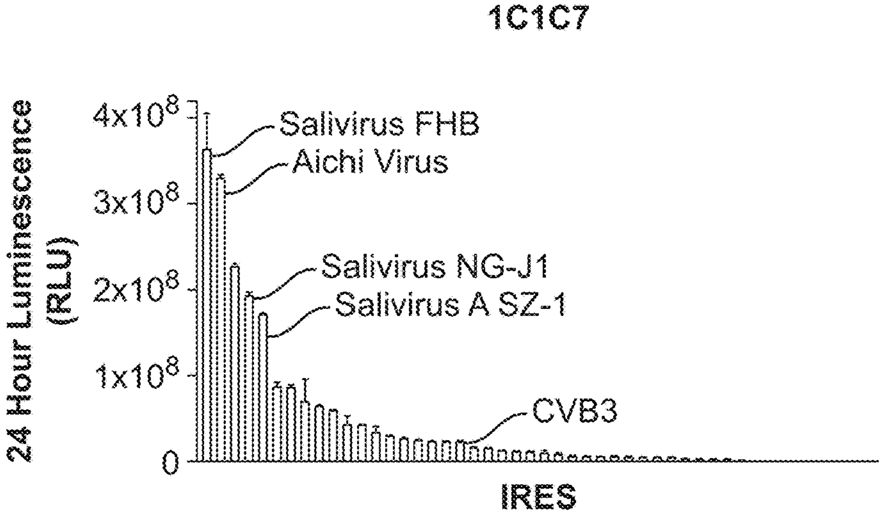

Example 8A: Expression and Functional Stability by IRES in HEK293, HepG2, and 1C1C7 Cells Constructs including anabaena intron/exon regions, a *Gaussia* luciferase expression sequence, and varying IRES were circularized. 100 ng of each circularization reaction was separately transfected into 20,000 HEK293 cells, HepG2 cells, and 1C1C7 cells using Lipofectamine MessengerMax. Luminescence in each supernatant was assessed after 24 hours as a measure of protein expression. In HEK293 cells, constructs including Crohivirus B, Salivirus FHB, Aichi Virus, Salivirus HG-J1, and Enterovirus J IRES produced the most luminescence at 24 hours (FIG. 1A). In HepG2 cells, constructs including Aichi Virus, Salivirus FHB, EMCV-Cf, and CVA3 IRES produced high luminescence at 24 hours (FIG. 1B). In 1C1C7 cells, constructs including Salivirus FHB, Aichi Virus, Salivirus NG-J1, and Salivirus A SZ-1 IRES produced high luminescence at 24 hours (FIG. 1C).

Figure 2A:
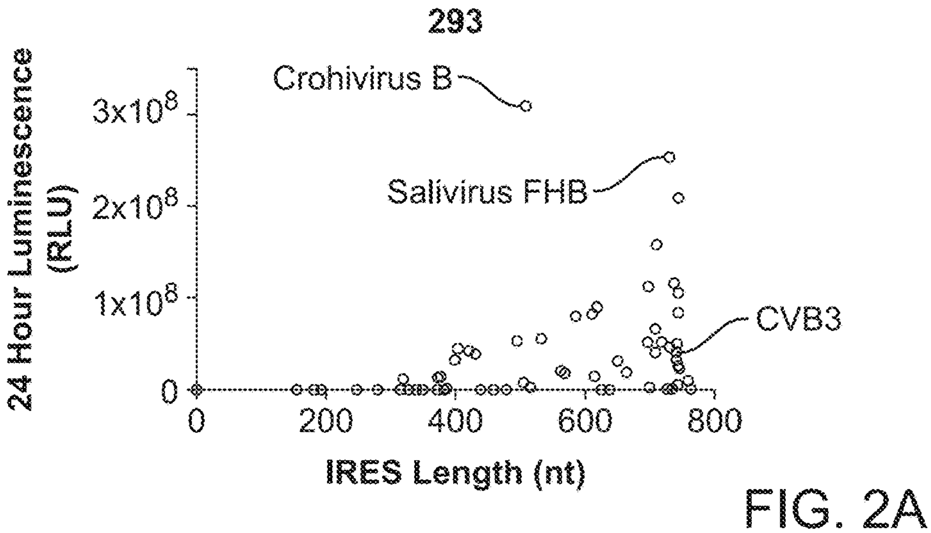
FIG. 2A, 2B and 2C depicts luminescence in supernatants of HEK293 (FIG. 2A), HepG2 (FIG. 2B), or 1C1C7 (FIG. 2C) cells 24 hours after transfection with circular RNA comprising a *Gaussia* luciferase expression sequence and various IRES sequences having different lengths.
Figure 2B:
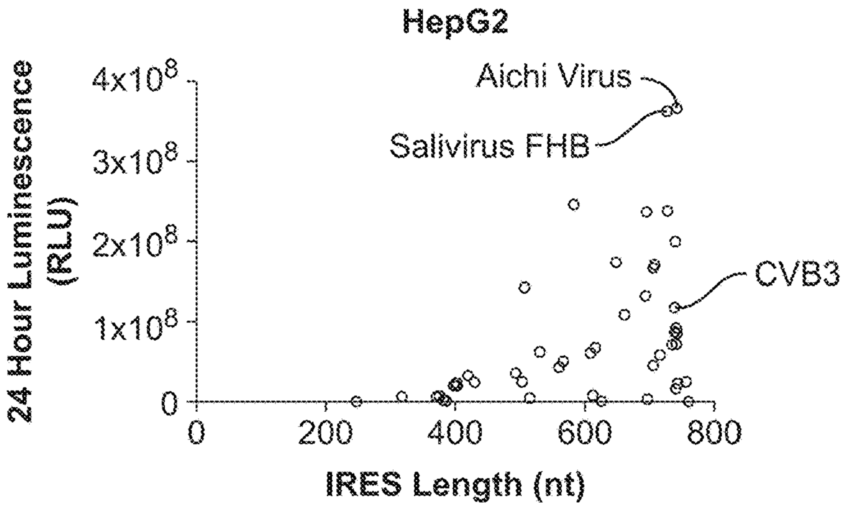
Figure 2C:
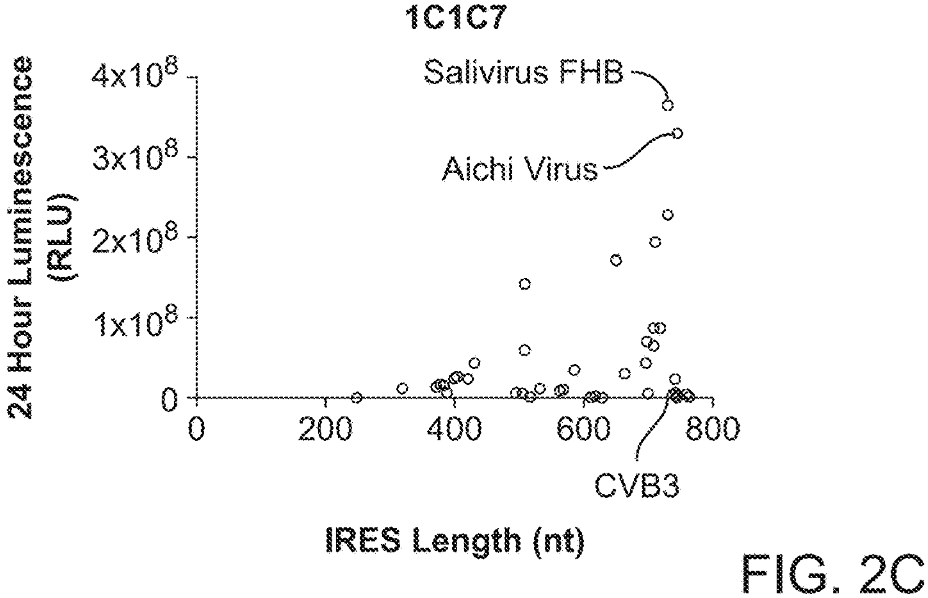

A trend of larger IRES producing greater luminescence at 24 hours was observed. Shorter total sequence length tends to increase circularization efficiency, so selecting a high expression and relatively short IRES may result in an improved construct. In HEK293 cells, a construct using the Crohivirus B IRES produced the highest luminescence, especially in comparison to other IRES of similar length (FIG. 2A). Expression from IRES constructs in HepG2 and 1C1C7 cells plotted against IRES size are in FIGS. 2B and 2C.

Figure 3A:
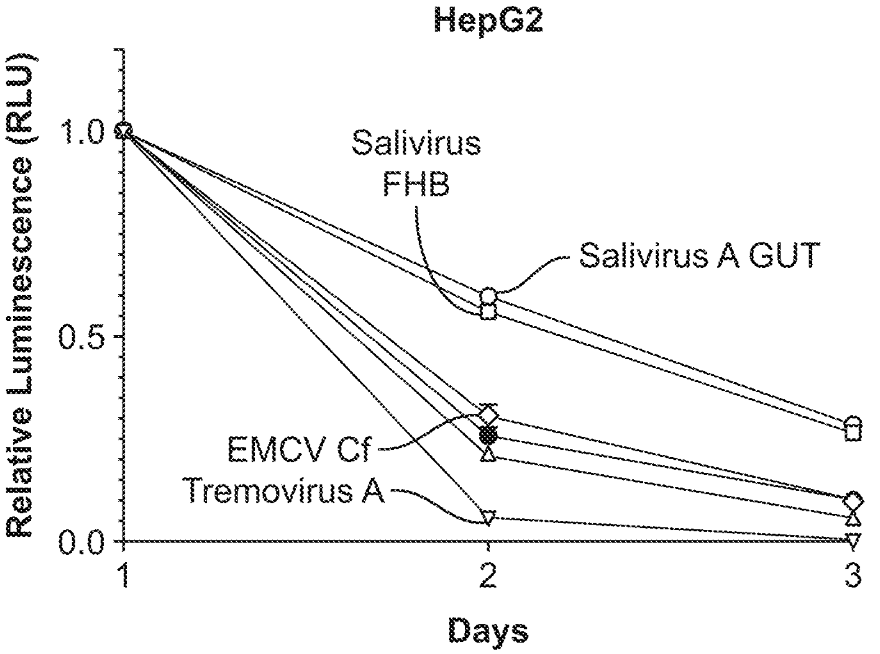
FIGS. 3A and 3B depicts stability of select IRES constructs in HepG2 (FIG. 3A) or 1C1C7 (FIG. 3B) cells over 3 days as measured by luminescence.
Figure 3B:
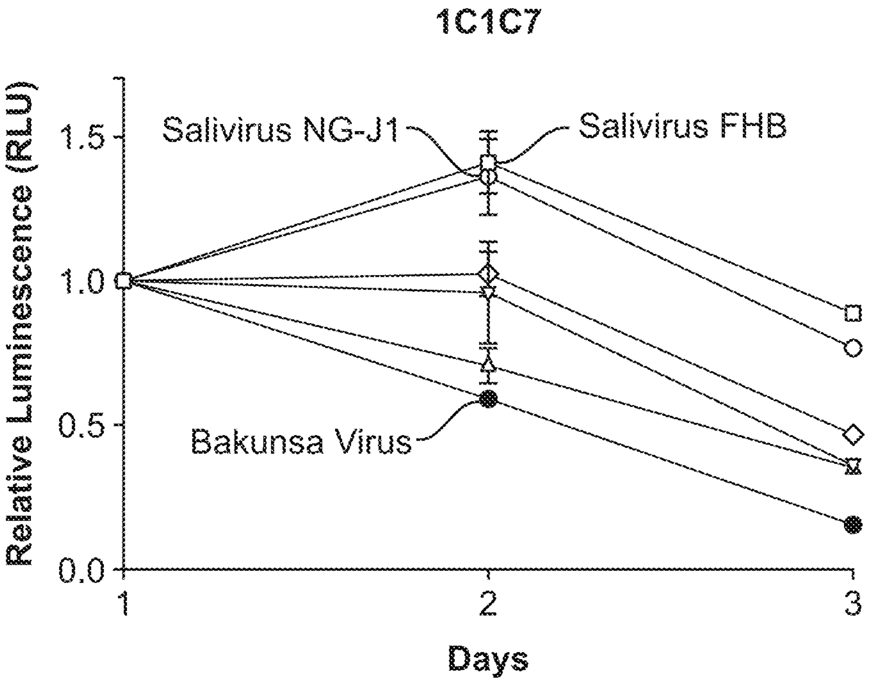

Functional stability of select IRES constructs in HepG2 and 1C1C7 cells were measured over 3 days. Luminescence from secreted *Gaussia* luciferase in supernatant was measured every 24 hours after transfection of 20,000 cells with 100 ng of each circularization reaction, followed by complete media replacement. Salivirus A GUT and Salivirus FHB exhibited the highest functional stability in HepG2cells, and Salivirus N-J1 and Salivirus FHB produced the most stable expression in 1C1C7 cells (FIGS. 3A and 3B).

Example 8B: Screening of Additional IRES

Figure 1D:
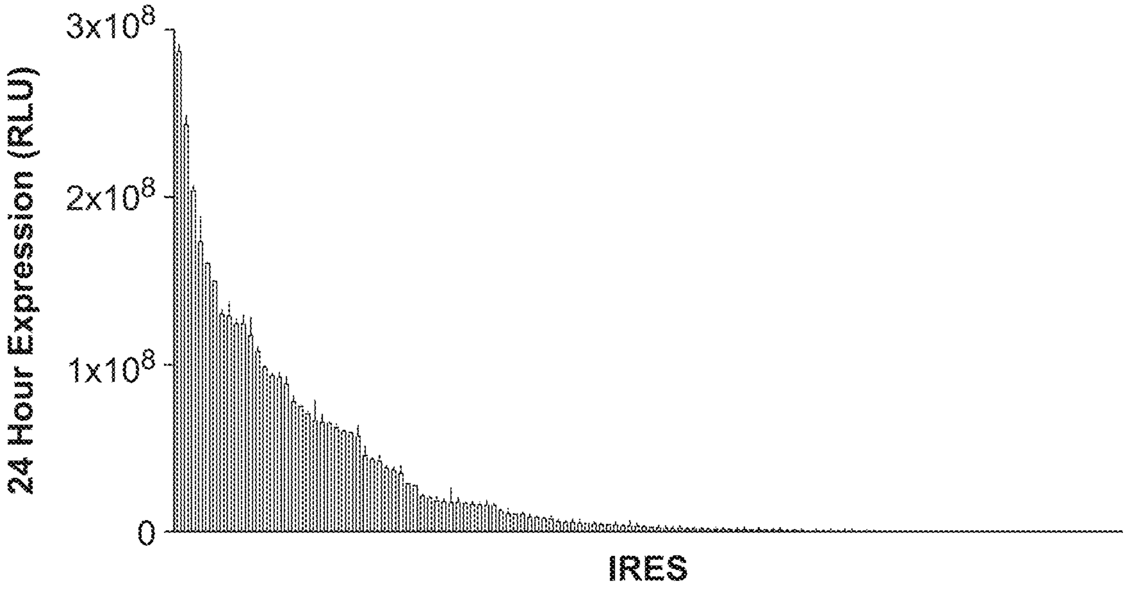
Figure 1E:
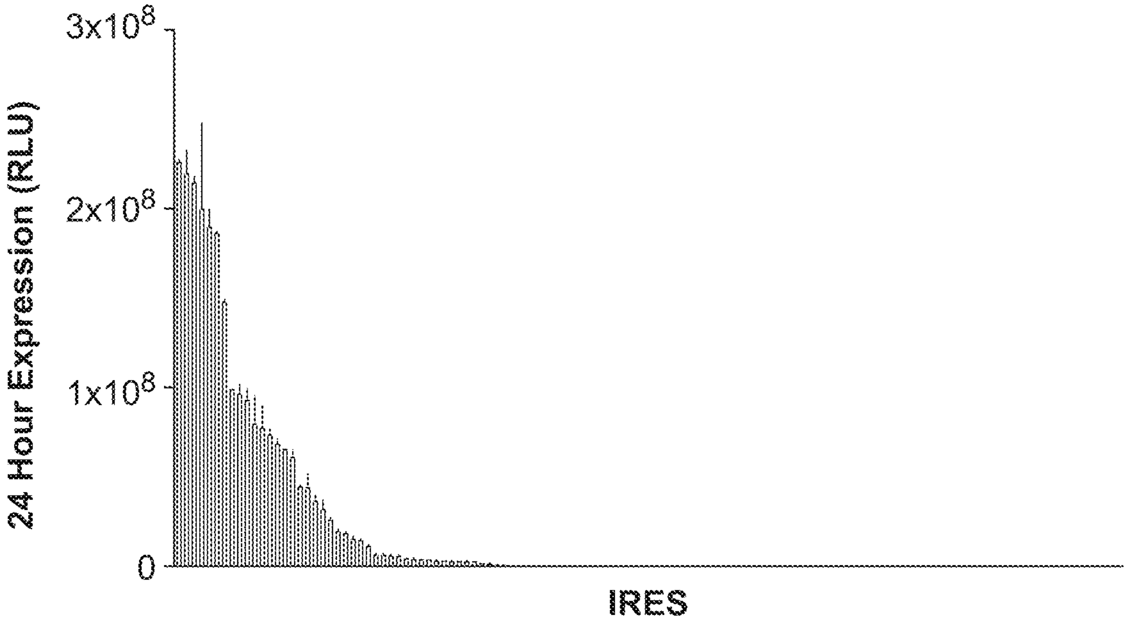

Functional stability of additional IRES constructs in HEK293 cells were measured. Briefly, 5' untranslated regions (UTRs) of interest were identified from GenBank. Selected UTRs UTRs were truncated to 675 nt from the 5' end and inserted into a circular RNA backbone construct encoding *Gaussia* Luciferase (Gluc) and in front of the Gluc coding region. The circular RNAs were transfected into HEK293 cells. After 24 hours, the supernatants were collected and the luminescence from secreted Gluc protein was measured using commercially available reagents. The results are depicted in FIGS. 1D and 1E and Table 30, suggesting that many natural IRES sequences enhance the protein expression in a circular RNA context.

TABLE 30

| SEQ ID NO | IRES | Expression |
|---|---|---|
| 413 | RhPV | 1.10E+05 |
| 414 | Halastavi arva (1 × mut) | 9.46E+04 |
| 415 | Oscivirus | 4.55E+07 |
| 416 | Cadicivirus B | 2.10E+05 |
| 417 | PSIV (2 × mut for Xbal) | 9.70E+04 |
| 418 | PSIV IGR | 1.01E+05 |
| 419 | PV Mahoney | 1.09E+05 |
| 420 | REV A | 9.44E+04 |
| 421 | Tropivirus A | 9.52E+04 |
| 422 | Symapivirus A | 1.27E+05 |
| 423 | Sakobuvirus A FFUPI (1 × mut) | 8.82E+06 |
| 424 | Rosavirus C NFSM6F | 6.84E+05 |
| 425 | Rosavirus 2 GA7403 | 5.05E+06 |
| 426 | Rhimavirus A | 8.42E+05 |
| 427 | Rafivirus LPXYC222841 | 2.22E+05 |
| 428 | Rafivirus WHWGGF74766 | 4.53E+06 |
| 429 | Poecivirus BCCH-449 | 3.43E+05 |
| 430 | Megirivirus A LY | 1.80E+06 |
| 431 | Megirivirus E | 1.10E+07 |
| 432 | Megirivirus C | 1.24E+05 |
| 433 | Ludopivirus | 1.05E+05 |
| 434 | Livupivirus | 2.10E+05 |
| 435 | Aichivirus A FSS693 | 6.25E+07 |
| 436 | Aichivirus KVGH | 1.72E+07 |
| 437 | Aichivirus DV | 7.79E+07 |
| 438 | Murine Kobuvirus 1 | 1.60E+07 |
| 439 | Porcine Kobuvirus K-30 | N/A |
| 440 | Porcine Kobuvirus XX | 1.32E+07 |
| 441 | Caprine Kobuvirus 12Q108 | 2.87E+08 |
| 442 | Rabbit Kobuvirus | 3.73E+07 |
| 443 | Aalivirus | 2.65E+05 |
| 444 | Grusopivirus A | 1.09E+05 |
| 445 | Grusopivirus B | 2.12E+05 |
| 446 | Yanchengosbecks grenadier anchovy picornavirus | 1.57E+06 |
| 447 | Turkey Gallivirus M176 | 4.37E+05 |
| 448 | Falco virus A1 | 1.48E+05 |
| 449 | Tremovirus B | 1.31E+05 |
| 450 | Didelphis aurita HAV | 1.38E+05 |
| 451 | Hepatovirus G1 | 1.41E+05 |
| 452 | Hepatovirus D | 1.47E+06 |
| 453 | Hepatovirus H2 | 1.08E+05 |
| 454 | Hepatovirus I | 8.79E+05 |
| 455 | Hepatovirus C | 5.08E+05 |
| 456 | Fipivirus A | 2.69E+05 |
| 457 | Fipivirus C | 1.09E+05 |
| 458 | Fipivirus E | 1.10E+05 |
| 459 | Aquamavirus | 4.51E+06 |
| 460 | Avisivirus A | 1.91E+05 |

TABLE 30-continued

| SEQ ID NO | IRES | Expression |
|---|---|---|
| 461 | Avisivirus B | 8.68E+04 |
| 462 | Crohivirus A | 9.96E+04 |
| 463 | Kunsagivirus B | 8.01E+04 |
| 464 | Limnipivirus A | 8.30E+04 |
| 465 | Limnipivirus C | 1.35E+05 |
| 466 | Orivirus | 6.09E+05 |
| 467 | HAV FH1 | 1.24E+05 |
| 468 | HAV HM175 | 4.96E+05 |
| 469 | Parechovirus F | 6.56E+05 |
| 470 | Parechovirus D | 3.10E+05 |
| 471 | Parechovirus C | 1.24E+06 |
| 472 | Ljungan Virus 87-012 | 2.00E+06 |
| 473 | Parechovirus A2 | 1.80E+07 |
| 474 | Parechovirus A3 | 3.58E+06 |
| 475 | Parechovirus A8 | 1.61E+07 |
| 476 | Parechovirus A17 | 1.20E+06 |
| 477 | Potamipivirus A | 8.43E+05 |
| 478 | Potamipivirus B | 7.20E+05 |
| 479 | Beihai Conger Picornavirus | 1.15E+06 |
| 480 | Porcine Sapelovirus JD2011 | N/A |
| 481 | Porcine Sapelovirus A2 | 4.34E+06 |
| 482 | Simian Sapelovirus 1 | 6.55E+07 |
| 483 | Simian Sapelovirus 2 | 4.24E+07 |
| 484 | Rabovirus C | 2.49E+06 |
| 485 | Rabovirus A NYC-B10 | 1.24E+06 |
| 486 | Parabovirus C | 1.83E+07 |
| 487 | Parabovirus B | 7.85E+06 |
| 488 | Parabovirus A3 | 2.44E+08 |
| 489 | Felipivirus 127F | 8.92E+06 |
| 490 | Boosepivirus A | 7.07E+07 |
| 491 | Boosepivirus B | 1.17E+08 |
| 492 | Phacovirus Pf-CHK1 | 5.87E+06 |
| 493 | HRVC3 QPM | 1.64E+07 |
| 494 | HRVB27 | 2.04E+08 |
| 495 | HRVA73 | 1.08E+08 |
| 496 | EV L | 6.49E+07 |
| 497 | EV K | 7.52E+07 |
| 498 | EV J 1631 | 9.88E+07 |
| 499 | EV J N125 | 2.90E+07 |
| 500 | EV I | 1.31E+08 |
| 501 | EV F1 BEV 261 | 1.12E+07 |
| 502 | EV D94 | 9.25E+07 |
| 503 | PV3 | 1.25E+08 |
| 504 | EV C102 | 8.85E+07 |
| 505 | EV 30 | 5.48E+06 |
| 506 | SA5 | 1.61E+08 |
| 507 | EV A114 | 1.50E+08 |
| 508 | Mobovirus A | 3.44E+06 |
| 509 | Burpengary Virus | 1.09E+07 |
| 510 | Hunnivirus A1 | 1.61E+06 |
| 511 | Hunnivirus A2 | 6.38E+06 |
| 512 | Ia Io | 1.35E+06 |
| 513 | Taura Syndrome Virus | 8.30E+05 |
| 514 | ABPV | 6.48E+05 |
| 515 | BRAV-2 | 3.98E+06 |
| 516 | BRBV-1 | 3.34E+06 |
| 517 | ERAV-1 U188 | N/A |
| 518 | GFTV | 1.23E+06 |
| 519 | SAFV V13C | 9.32E+07 |
| 520 | SAV P-113 | 4.37E+07 |
| 521 | VHEV | 1.74E+08 |
| 522 | TRV NGS910 | 3.84E+07 |
| 523 | EMCV2 RD1338 | 1.97E+06 |
| 524 | EMCV1 JZ1203 | N/A |
| 525 | EMCV1 AnrB-3741 | 2.55E+06 |
| 526 | Cosavirus D1 | 2.11E+06 |
| 527 | Cosavirus B1 | 1.91E+06 |
| 528 | Cosavirus A SH1 | 2.16E+06 |
| 529 | Malagasivirus B | 5.05E+06 |
| 530 | Mosavirus A2 SZAL6 | 8.27E+06 |
| 531 | SVV | 1.06E+06 |
| 532 | PTV A | 7.29E+05 |
| 533 | PTV B | 6.02E+06 |
| 534 | Tottorivirus | 2.76E+07 |

TABLE 30-continued

| SEQ ID NO | IRES | Expression |
|---|---|---|
| 535 | Posavirus 1 | 1.55E+06 |
| 536 | A105-675 | 2.18E+07 |
| 537 | A110-675 | 1.24E+08 |
| 538 | 18-675 | 6.04E+07 |
| 539 | A115-675 | 5.93E+07 |
| 540 | A73-675 | 1.30E+08 |
| 541 | Kobuvirus 16317 | 2.03E+07 |
| 542 | Aichivirus Chshc7 | 1.87E+07 |
| 543 | Aichivirus Goiania | 1.66E+07 |
| 544 | Aichivirus ETHP4 | 1.78E+07 |
| 545 | Aichivirus DVI2169 | 2.98E+06 |
| 546 | Aichivirus DVI2321 | 6.63E+07 |
| 547 | Aichivirus rat08 | 3.51E+07 |
| 548 | Aichivirus Rt386 | 5.71E+07 |
| 549 | Norway Rat Pestivirus | N/A |
| 550 | Porcine Kobuvirus GS2 | 44200000 |
| 551 | Kobuvirus SZAL6 | 98850000 |
| 552 | Kobuvirus sheep TB3 | N/A |
| 553 | Pronghorn antelope pestivirus | 1.35E+06 |
| 554 | Porcine pestivirus isolate Bungowannah | 1.10E+07 |
| 555 | Porcine pestivirus 1 | 9.46E+04 |
| 556 | Pestivirus giraffe-1 | 4.72E+05 |
| 557 | Classical swine fever virus | 3.16E+05 |
| 558 | Human pegivirus isolate JD2B1I | 6.85E+05 |
| 559 | Human pegivirus isolate GBV-C-ZJ | N/A |
| 560 | Human pegivirus isolate JD2B8C | 5.36E+05 |
| 561 | Hepatitis GB virus A | N/A |
| 562 | Simian pegivirus | 8.56E+04 |
| 563 | Pegivirus I | 8.02E+04 |
| 564 | Pegivirus K | 8.07E+04 |
| 565 | Theiler's disease-associated virus | 7.84E+04 |
| 566 | Rodent pegivirus | 1.79E+05 |
| 567 | Human pegivirus 2 | 3.14E+05 |
| 568 | GB virus C/Hepatitis G virus | 1.36E+05 |
| 569 | Equine Pegivirus 1 | 8.80E+04 |
| 570 | Culex theileri flavivirus | 8.52E+04 |
| 571 | Bussuquara virus | 8.20E+04 |
| 572 | Zika Virus | 8.61E+04 |
| 573 | Yokose virus | 8.55E+04 |
| 574 | Wesselsbron virus | N/A |
| 575 | Equine hepacivirus | 8.40E+04 |
| 576 | Hepacivirus B | 8.84E+04 |
| 577 | Hepacivirus I | 7.50E+04 |
| 578 | Hepacivirus J | 7.65E+04 |
| 579 | Hepacivirus K | 8.91E+04 |
| 580 | Icavirus | 4.41E+06 |
| 581 | Antarctic penguin virus A | 8.42E+04 |
| 582 | Forest pouched giant rat arterivirus | N/A |
| 583 | Avisivirus Pf-CHK1 | 1.19E+05 |
| 584 | Avian paramyxovirus penguin | 9.91E+04 |
| 585 | Newcastle disease virus | 8.86E+04 |
| 586 | Bat Hp-betacoronavirus | 8.47E+04 |
| 587 | Basella alba endornavirus | 7.65E+04 |
| 588 | Ball python nidovirus | 8.25E+04 |
| 589 | Bat sapelovirus | 8.05E+04 |
| 590 | Bat Picornavirus 3 | N/A |
| 591 | Bat Picornavirus 2 | 7.99E+07 |
| 592 | Bat Picornavirus 1 | 1.85E+07 |
| 593 | Bat Iflavirus | 9.76E+04 |
| 594 | Bat dicibavirus | 7.43E+04 |
| 595 | Betacoronavirus | 8.96E+04 |

TABLE 30-continued

| SEQ ID NO | IRES | Expression |
|---|---|---|
| | HKU24 | |
| 596 | Betacoronavirus England 1 | 8.74E+04 |
| 597 | Boone cardiovirus 1 | 2.62E+06 |
| 598 | Breda virus | 1.16E+05 |
| 599 | Bovine viral diarrhea virus 3 | 2.70E+06 |
| 600 | Bovine rhinitis A virus | 3.62E+06 |
| 601 | Bovine picornavirus isolate TCH6 | 1.21E+05 |
| 602 | Bovine nidovirus TCH5 | 1.17E+05 |
| 603 | Bovine hepacivirus | 1.89E+05 |
| 604 | Botrytis cinerea mitovirus 4 RdRp | 9.68E+04 |
| 605 | Botrytis cinerea mitovirus 2 RdRp | 8.73E+04 |
| 606 | Canine picodicistrovirus strain 209 | 2.79E+06 |
| 607 | Canine distemper virus | 3.02E+05 |
| 608 | Canine kobuvirus | 1.48E+08 |
| 609 | Camel alphacoronavirus | 2.48E+05 |
| 610 | Cripavirus | 1.95E+05 |
| 611 | Human coxsackievirus A2 | 7.75E+07 |
| 612 | Coronavirus AcCoV-JC34 | 1.82E+05 |
| 613 | Chicken picornavirus 3 | 9.13E+04 |
| 614 | Chicken picornavirus 1 | 1.21E+05 |
| 615 | Chicken orivirus 1 | 3.16E+05 |
| 616 | Chicken gallivirus 1 | 1.51E+07 |
| 617 | Chicken calicivirus | 1.28E+05 |
| 618 | Carp picornavirus 1 | 1.13E+05 |
| 619 | Falcon picornavirus | 3.08E+06 |
| 620 | Equine rhinitis B virus 1 | 1.01E+05 |
| 621 | Equine rhinitis A virus | 3.73E+05 |
| 622 | Equine arteritis virus | 1.89E+05 |
| 623 | Enterovirus sp. isolate CPML | 6.83E+07 |
| 624 | Enterovirus AN12 | 3.87E+06 |
| 625 | Dolphin morbillivirus | 1.22E+05 |
| 626 | Dianke virus | 1.35E+05 |
| 627 | Guereza hepacivirus | 1.38E+05 |
| 628 | Grapevine associated narnavirus-1 | 1.30E+05 |
| 629 | Goat torovirus | 1.19E+05 |
| 630 | Foot-and-mouth disease virus O isolate | 1.12E+05 |
| 631 | Feline infectious peritonitis virus | 1.35E+05 |
| 632 | Farmington virus | 1.22E+05 |
| 633 | Avian infectious bronchitis virus | 2.84E+05 |
| 634 | Human rhinovirus 1 | 7.40E+07 |
| 635 | EV22 | 1.95E+07 |
| 636 | Human TMEV-like cardiovirus | 4.48E+07 |
| 637 | Human coronavirus 229E | N/A |
| 638 | Hubei zhaovirus-like virus 1 | 1.03E+05 |
| 639 | Hubei tombus-like virus 9 | 9.28E+04 |
| 640 | Hubei tombus-like virus 32 | 9.23E+04 |
| 641 | Hubei sobemo-like virus 3 | 1.17E+05 |
| 642 | Hubei picorna-like virus 2 | 1.95E+05 |
| 643 | Hepacivirus P | 6.04E+05 |
| 644 | Harrier picornavirus 1 | 1.47E+05 |
| 645 | Kunsagivirus 1 | 4.15E+05 |
| 646 | Kagoshima-2-24-KoV | 9.30E+07 |
| 647 | Kashmir bee virus | 1.65E+05 |
| 648 | Jingmen picorna-like virus | 9.32E+04 |
| 649 | Mumps virus | 1.47E+05 |
| 650 | Mouse Mosavirus | 9.00E+04 |
| 651 | Miniopterus schreibersii picornavirus 1 | 6.05E+06 |
| 652 | Linda virus | 7.37E+05 |
| 653 | Lesavirus 2 | 3.67E+07 |
| 654 | Lesavirus 1 | 6.37E+06 |
| 655 | Phopivirus strain NewEngland | 1.06E+05 |
| 656 | Pestivirus strain Aydin | 3.11E+06 |
| 657 | Quail picornavirus QPV1 | 6.55E+07 |
| 658 | Porcine sapelovirus 1 | N/A |
| 659 | Porcine reproductive and respiratory syndrome virus 2 | 1.29E+05 |
| 660 | Porcine enterovirus 9 | 3.20E+07 |
| 661 | Pigeon picornavirus B | 1.24E+05 |
| 662 | Picornavirus HK21 | 4.09E+05 |
| 663 | Picornavirales Tottori-HG1 | 9.54E+04 |
| 664 | Rodent hepatovirus | 1.39E+05 |
| 665 | Rinderpest virus | 4.26E+05 |
| 666 | Rabovirus A | 2.88E+06 |
| 667 | Shingleback nidovirus 1 | 2.62E+05 |
| 668 | Seneca valley virus | 1.46E+07 |
| 669 | Sclerotinia sclerotiorum dsRNA mycovirus-L | 1.69E+05 |
| 670 | Yak enterovirus | 6.19E+06 |
| 671 | Wobbly possum disease virus | 2.60E+05 |
| 672 | Avian orthoreovirus segment S1 | 4.37E+05 |
| 673 | Caprine Kobuvirus d10 | 2.20E+08 |
| 674 | Caprine Kobuvirus d20 | 2.00E+08 |
| 675 | Caprine Kobuvirus d30 | 1.87E+08 |
| 676 | Caprine Kobuvirus d40 | 2.15E+08 |
| 677 | Caprine Kobuvirus d50 | 9.65E+07 |
| 678 | Picornavirales sp. isolate RtMruf-PicoV | 2.26E+08 |
| 679 | Apodemus agrarius picornavirus strain Longquan-Aal 18 | 1.90E+08 |
| 680 | Niviventer confucianus picornavirus | 6.10E+07 |
| 681 | Bat picornavirus isolate BtRs-PicoV | 1.13E+06 |
| 682 | Rhinolophus picornavirus strain Guizhou-Rr 100 | N/A |
| 683 | Rhinolophus picornavirus strain Henan-Rf265 | 3.85E+05 |
| 684 | Human enterovirus C105 | 5.49E+05 |
| 685 | Human poliovirus 1 strain NIEI116623 | 3.94E+05 |
| 686 | Human enterovirus 109 | 4.92E+05 |
| 687 | Human poliovirus 2 strain NIE0811460 | 2.59E+07 |
| 688 | Bovine picornavirus | 3.82E+06 |
| 689 | Human poliovirus 1 strain EQG1419328 | 2.44E+05 |
| 690 | Human poliovirus 2 isolate IS_061 | 5.84E+06 |
| 691 | Coxsackievirus B5 | N/A |
| 692 | Coxsackievirus A10 | N/A |

Example 9

Expression and Functional Stability by IRES in Jurkat Cells.

Figure 4A:
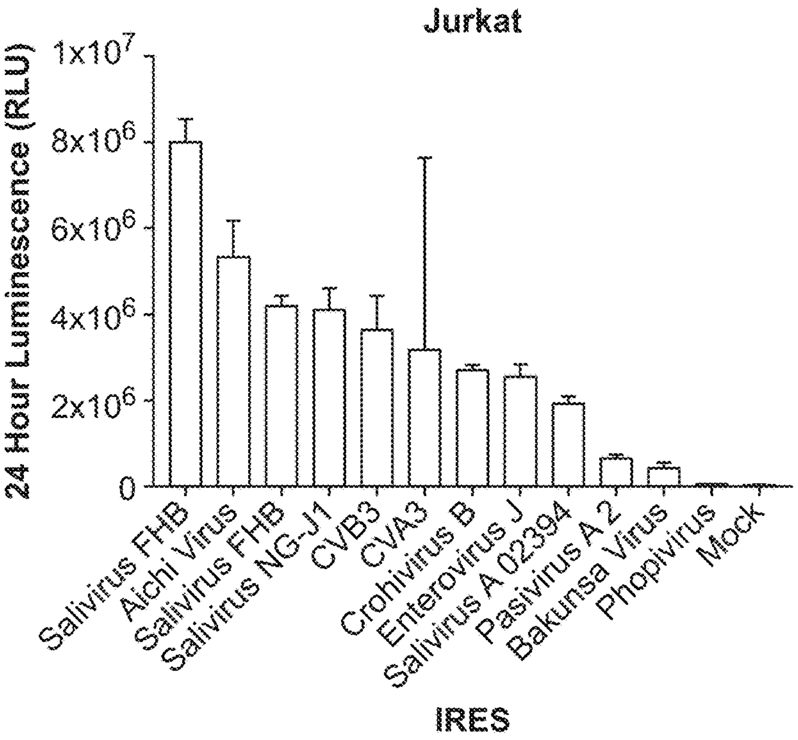
FIGS. 4A and 4B depict protein expression from select IRES constructs in Jurkat cells, as measured by luminescence from secreted *Gaussia* luciferase in cell supernatants.
Figure 4B:
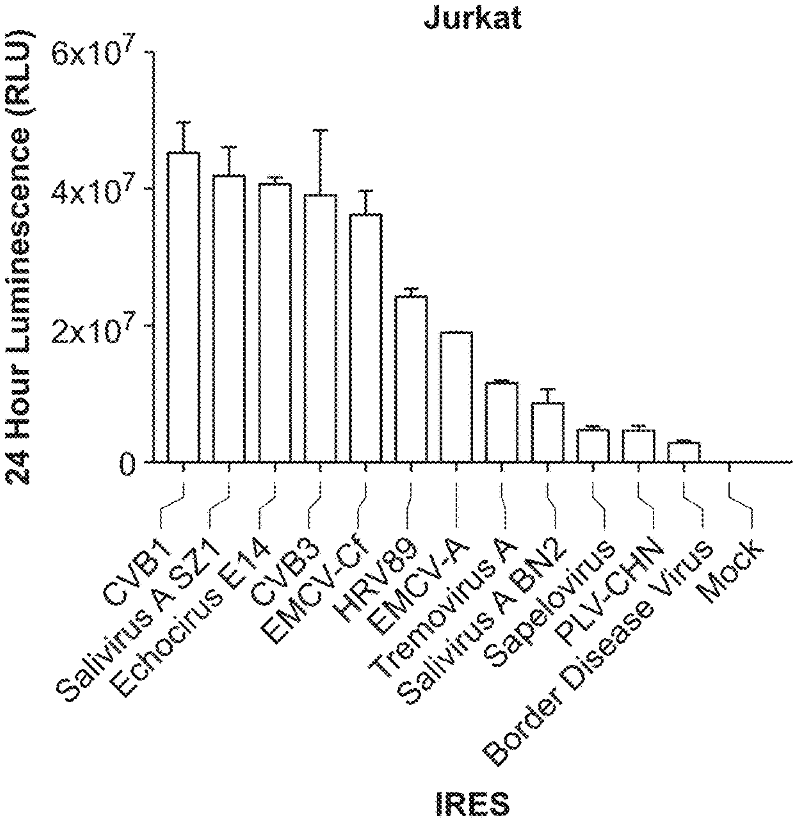

2 sets of constructs including anabaena intron/exon regions, a *Gaussia* luciferase expression sequence, and a subset of previously tested IRES were circularized. 60,000 Jurkat cells were electroporated with 1 μg of each circularization reaction. Luminescence from secreted *Gaussia* luciferase in supernatant was measured 24 hours after electroporation. A CVB3 IRES construct was included in both sets for comparison between sets and to previously defined IRES efficacy. CVB1 and Salivirus A SZ1 IRES constructs produced the most expression at 24h. Data can be found in FIGS. 4A and 4B.

Figure 5A:
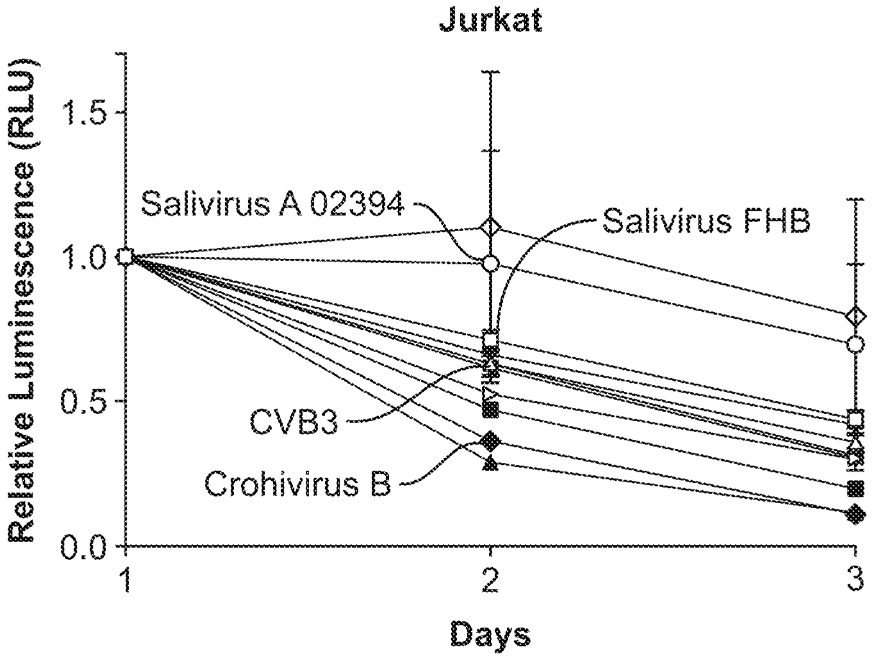
FIGS. 5A and 5B depict stability of select IRES constructs in Jurkat cells over 3 days as measured by luminescence.
Figure 5B:
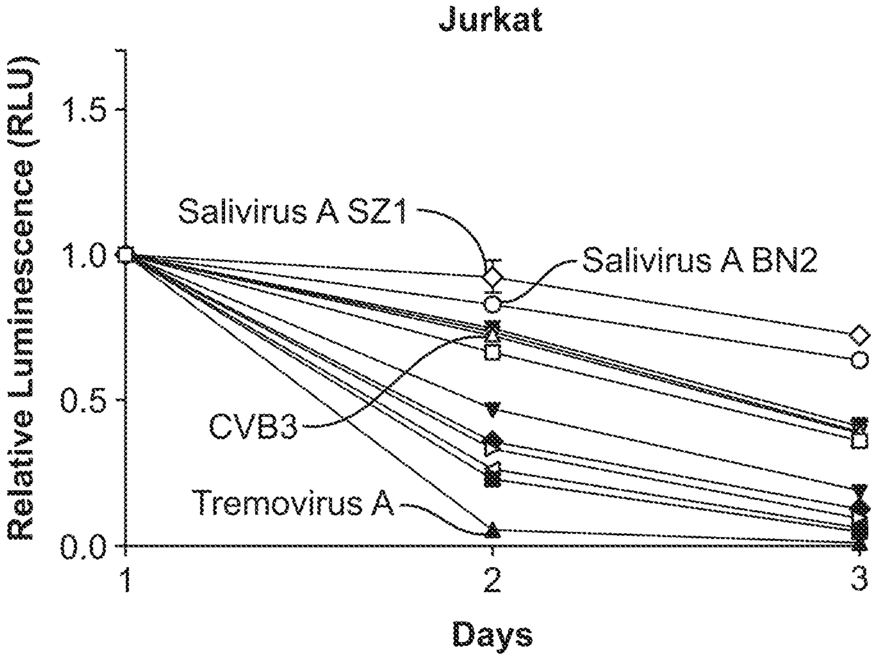

Functional stability of the IRES constructs in each round of electroporated Jurkat cells was measured over 3 days. Luminescence from secreted *Gaussia* luciferase in supernatant was measured every 24 hours after electroporation of 60,000 cells with 1 μg of each circularization reaction, followed by complete media replacement (FIGS. 5A and 5B).

Salivirus A SZ1 and Salivirus A BN2 IRES constructs had high functional stability compared to other constructs.

Example 10

Expression, Functional Stability, and Cytokine Release of Circular and Linear RNA in Jurkat Cells.

Figure 6A:
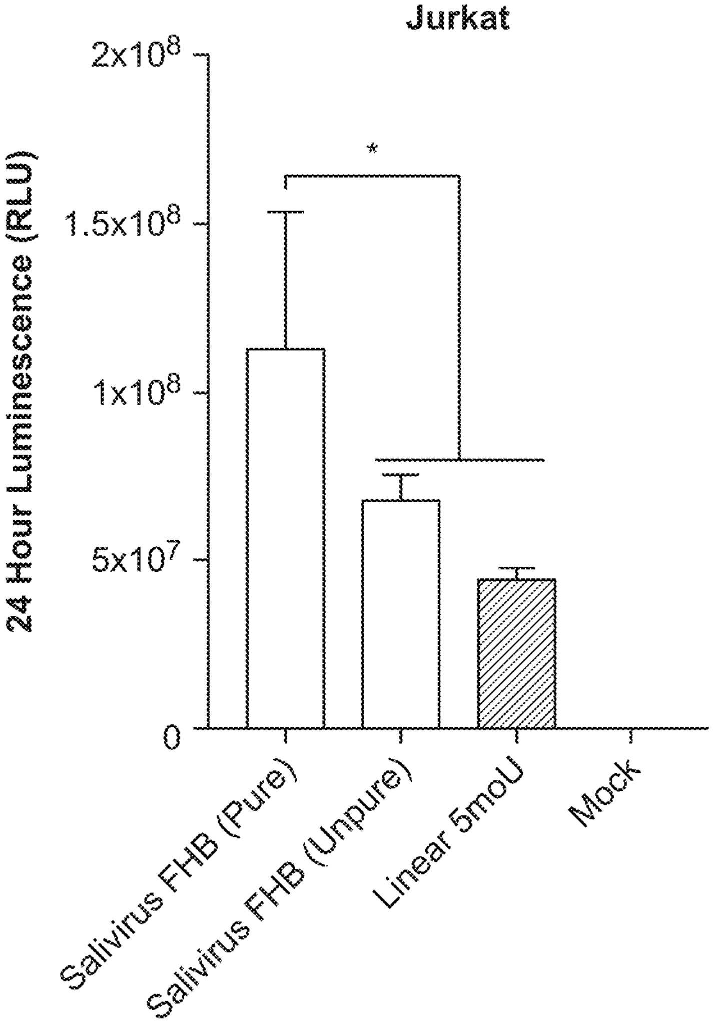
FIGS. 6A and 6B depicts comparisons of 24 hour luminescence (FIG. 6A) or relative luminescence over 3 days (FIG. 6B) of modified linear, unpurified circular, or purified circular RNA encoding *Gaussia* luciferase.

A construct including anabaena intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) is commercially available and was purchased from Trilink. 5moU nucleotide modifications have been shown to improve mRNA stability and expression (Bioconjug Chem. 2016 Mar. 16; 27(3):849-53). Expression of modified mRNA, circularization reactions (unpure), and circRNA purified by size exclusion HPLC (pure) in Jurkat cells were measured and compared (FIG. 6A). Luminescence from secreted *Gaussia* luciferase in supernatant was measured 24 hours after electroporation of 60,000 cells with 1 μg of each RNA species.

Figure 6B:
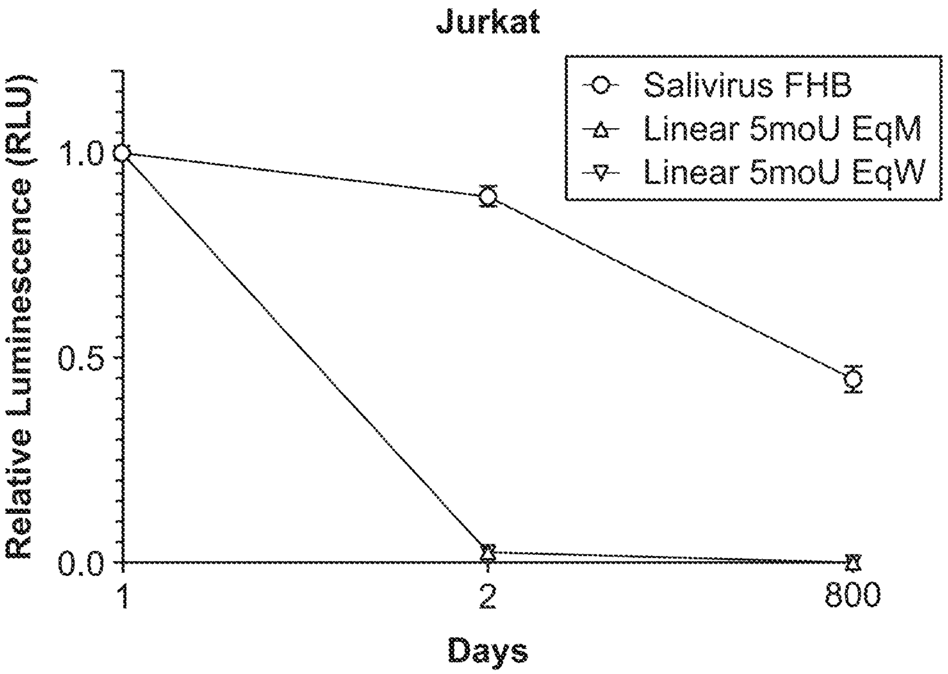

Luminescence from secreted *Gaussia* luciferase in supernatant was measured every 24 hours after electroporation of 60,000 cells with 1 ug of each RNA species, followed by complete media replacement. A comparison of functional stability data of modified mRNA and circRNA in Jurkat cells over 3 days is in FIG. 6B.

Figure 7A:
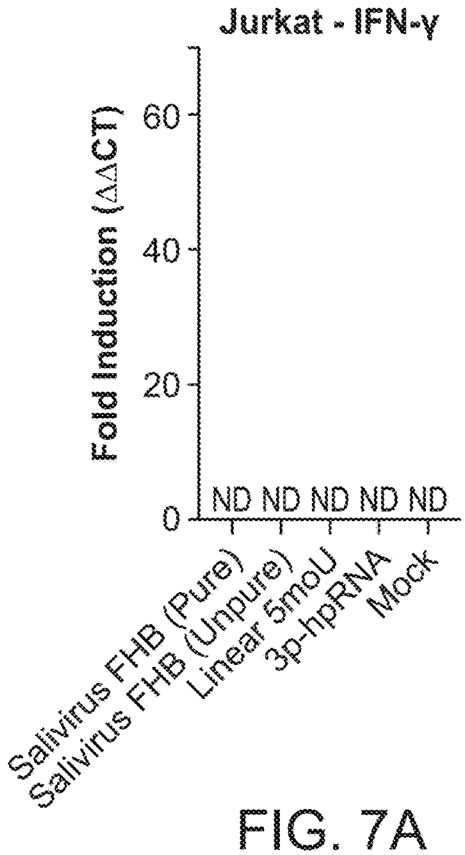
FIGS. 7A, 7B, 7C, 7D, 7E and 7F depicts transcript induction of IFNγ (FIG. 7A), IL-6 (FIG. 7B), IL-2 (FIG. 7C), RIG-I (FIG. 7D), IFN-β1 (FIG. 7E), and TNFα (FIG. 7F) after electroporation of Jurkat cells with modified linear, unpurified circular, or purified circular RNA.
Figure 7B:
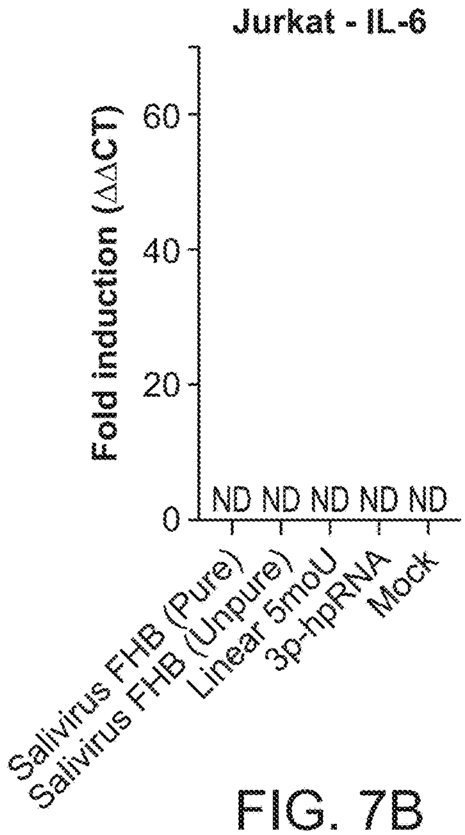
Figure 7C:
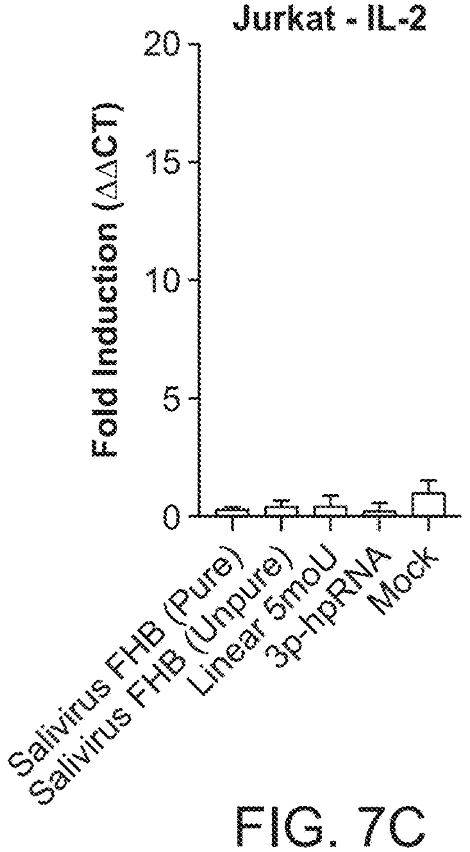
Figure 7D:
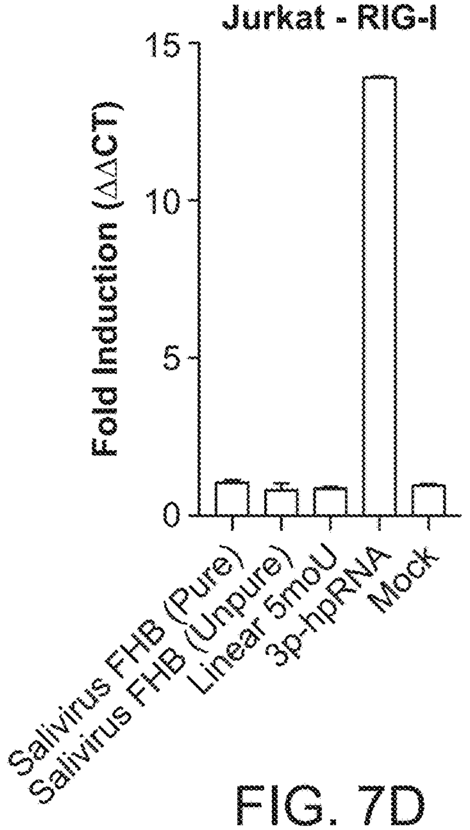
Figure 7E:
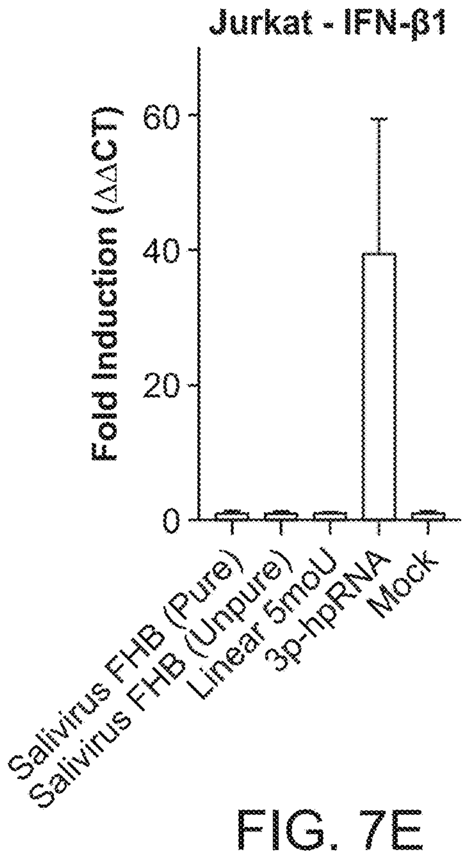
Figure 7F:
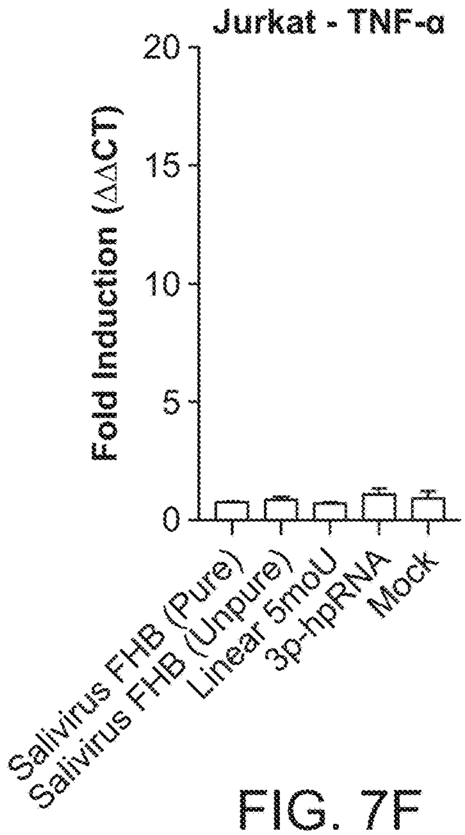

IFNγ (FIG. 7A), IL-6 (FIG. 7B), IL-2 (FIG. 7C), RIG-I (FIG. 7D), IFN-β1 (FIG. 7E), and TNFα (FIG. 7F) transcript induction was measured 18 hours after electroporation of 60,000 Jurkat cells with 1 μg of each RNA species described above and 3p-hpRNA (5' triphosphate hairpin RNA, which is a known RIG-I agonist).

Example 11

Expression of Circular and Linear RNA in Monocytes and Macrophages.

Figure 8A:
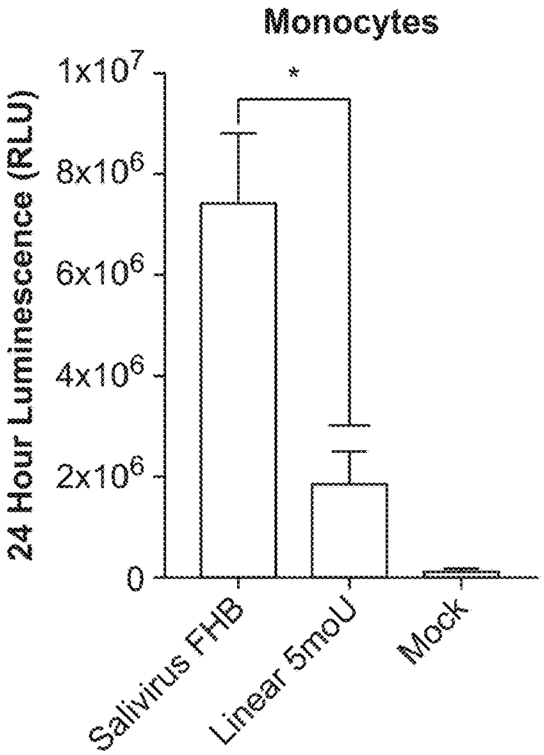
FIGS. 8A, 8B and 8C depicts a comparison of luminescence of circular RNA and modified linear RNA encoding *Gaussia* luciferase in human primary monocytes (FIG. 8A) and macrophages (FIG. 8B and FIG. 8C).
Figure 8B:
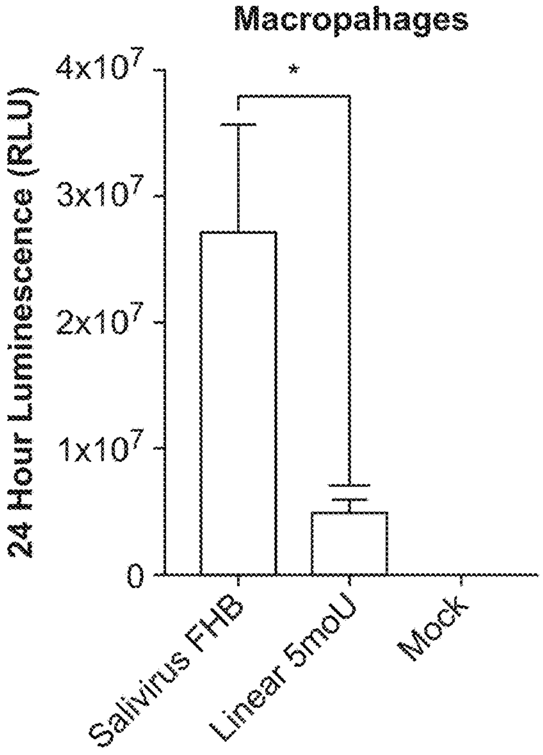
Figure 8C:
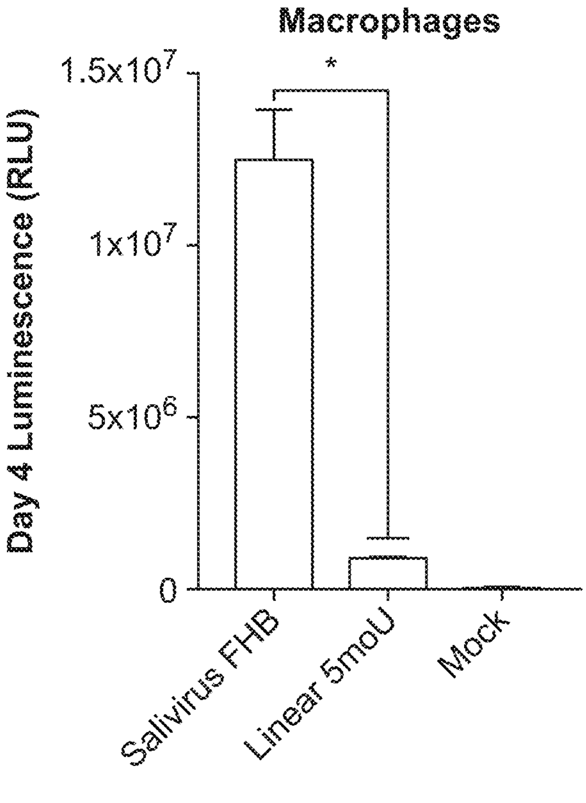

A construct including anabaena intron/exon regions, a *Gaussia* luciferase expression sequence, and a Salivirus FHB IRES was circularized. mRNA including a *Gaussia* luciferase expression sequence and a ~150 nt polyA tail, and modified to replace 100% of uridine with 5-methoxy uridine (5moU) was purchased from Trilink. Expression of circular and modified mRNA was measured in human primary monocytes (FIG. 8A) and human primary macrophages (FIG. 8B). Luminescence from secreted *Gaussia* luciferase in supernatant was measured 24 hours after electroporation of 60,000 cells with 1 μg of each RNA species. Luminescence was also measured 4 days after electroporation of human primary macrophages with media changes every 24 hours (FIG. 8C). The results can be found in FIG. 8. The difference in luminescence was statistically significant in each case ($p<0.05$).

Example 12

Expression and Functional Stability by IRES in Primary T Cells.

Figure 9A:
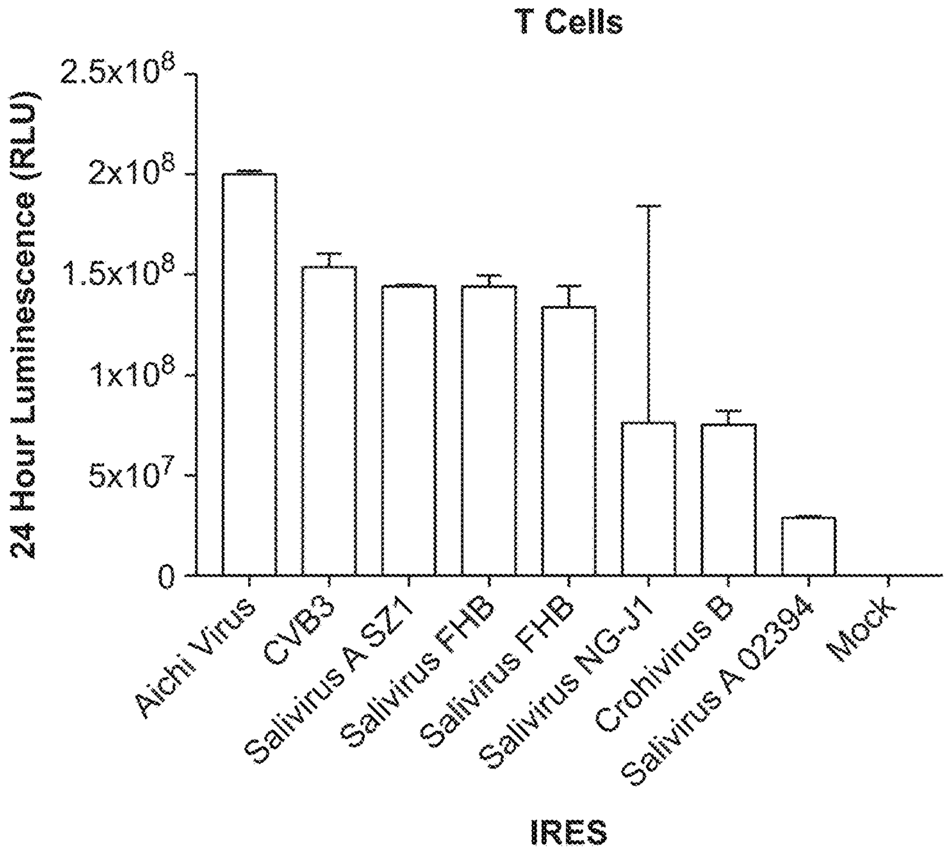
FIGS. 9A and 9B depicts relative luminescence over 3 days (FIG. 9A) in supernatant of primary T cells after transduction with circular RNA comprising a *Gaussia* luciferase expression sequence and varying IRES sequences or 24 hour luminescence (FIG. 9B).

Constructs including anabaena intron/exon regions, a *Gaussia* luciferase expression sequence, and a subset of previously tested IRES were circularized and reaction products were purified by size exclusion HPLC. 150,000 primary human CD3+ T cells were electroporated with 1 μg of each circRNA. Luminescence from secreted *Gaussia* luciferase in supernatant was measured 24 hours after electroporation (FIG. 9A). Aichi Virus and CVB3 IRES constructs had the most expression at 24 hours.

Figure 9B:
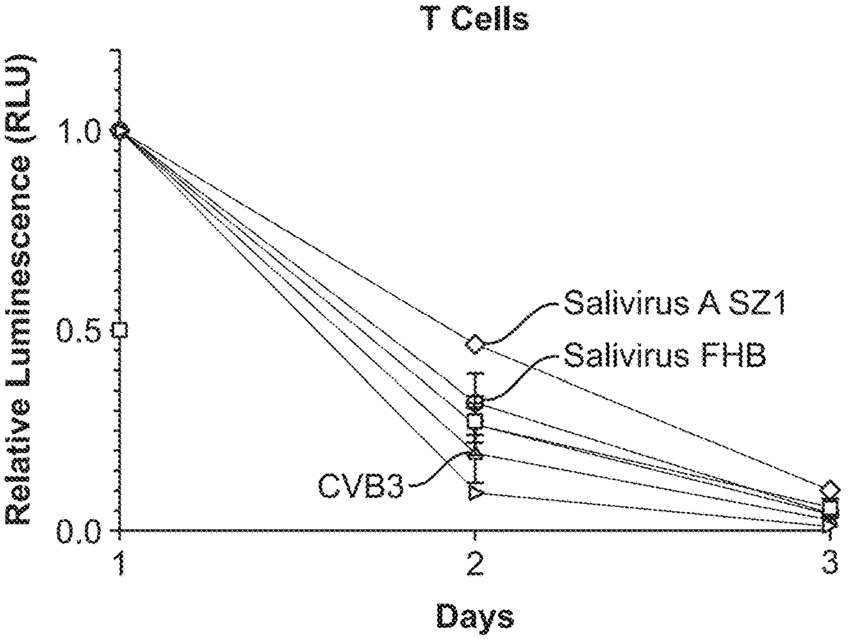

Luminescence was also measured every 24 hours after electroporation for 3 days in order to compare functional stability of each construct (FIG. 9B). The construct with a Salivirus A SZ1 IRES was the most stable.

Example 13

Expression and Functional Stability of Circular and Linear RNA in Primary T Cells and PBMCs.

Figure 10A:
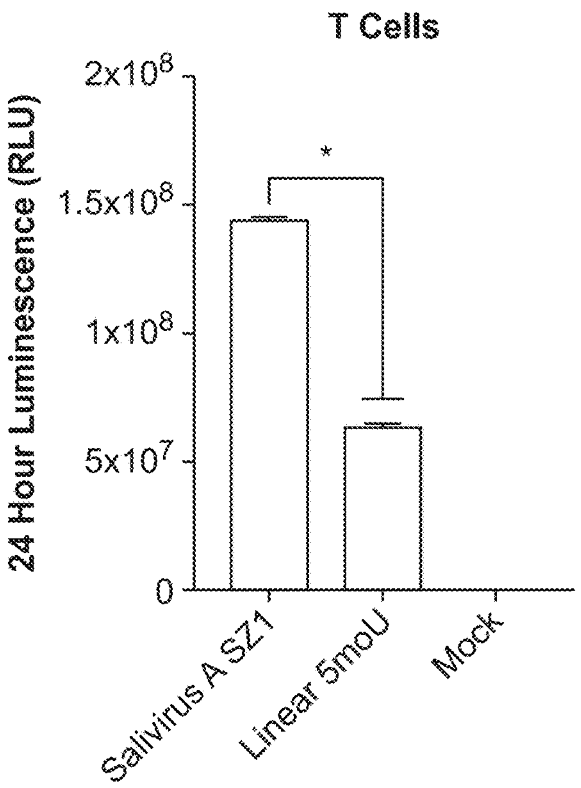
FIGS. 10A, 10B and 10C depicts 24 hour luminescence in supernatant of primary T cells (FIG. 10A) after transduction with circular RNA or modified linear RNA comprising a *gaussia* luciferase expression sequence, or relative luminescence over 3 days (FIG. 10B), and 24 hour luminescence in PBMCs (FIG. 10C).
Figure 10B:
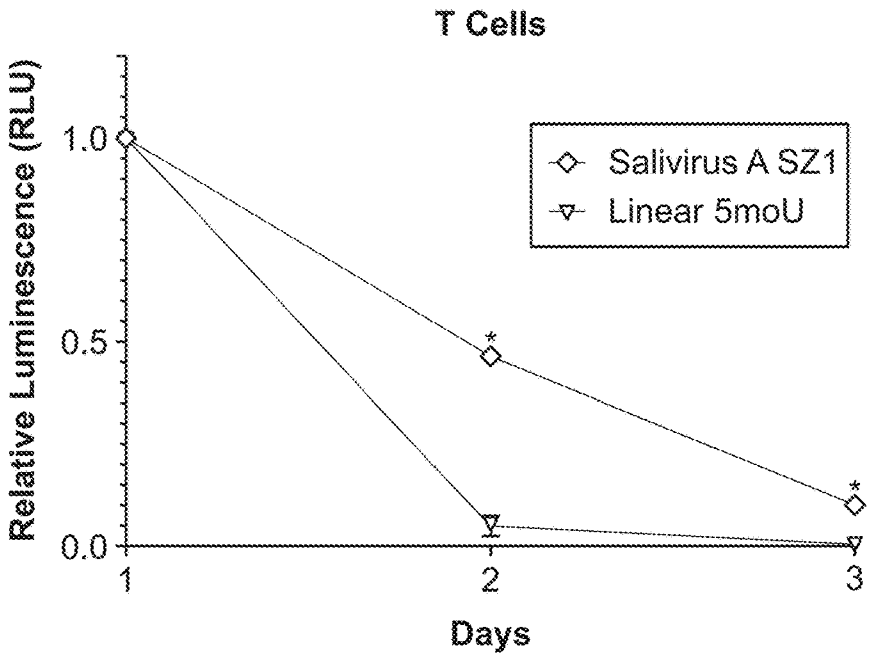
Figure 10C:
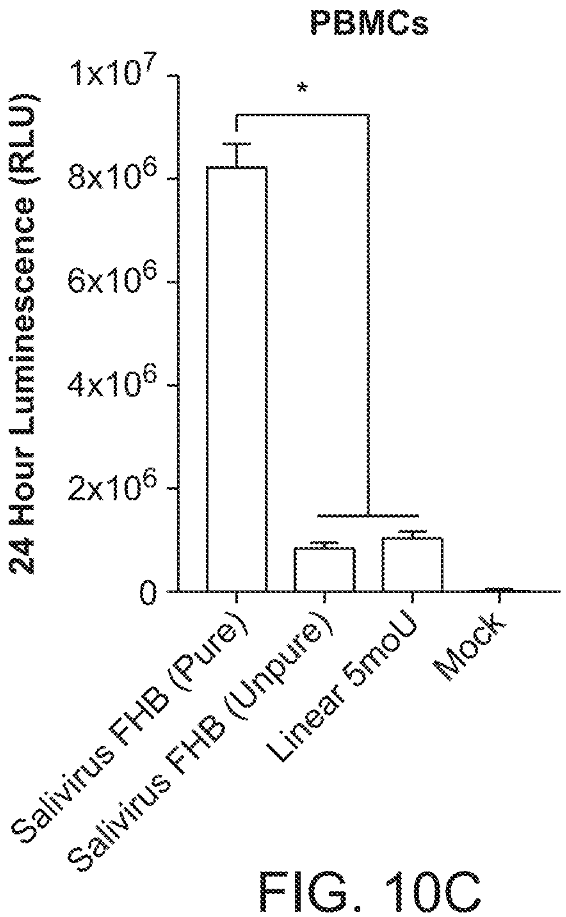

Constructs including anabaena intron/exon regions, a *Gaussia* luciferase expression sequence, and a Salivirus A SZ1 IRES or Salivirus FHB IRES were circularized. mRNA including a *Gaussia* luciferase expression sequence and a ~150 nt polyA tail, and modified to replace 100% of uridine with 5-methoxy uridine (5moU) and was purchased from Trilink. Expression of Salivirus A SZ1 IRES HPLC purified circular and modified mRNA was measured in human primary CD3+ T cells. Expression of Salivirus FHB HPLC purified circular, unpurified circular and modified mRNA was measured in human PBMCs. Luminescence from secreted *Gaussia* luciferase in supernatant was measured 24 hours after electroporation of 150,000 cells with 1 μg of each RNA species. Data for primary human T cells is shown in FIGS. 10A and 10B, and data for PBMCs is shown in FIG. 10C. The difference in expression between the purified circular RNA and unpurified circular RNA or linear RNA was significant in each case ($p<0.05$).

Luminescence from secreted *Gaussia* luciferase in primary T cell supernatant was measured every 24 hours after electroporation over 3 days in order to compare construct functional stability. Data is shown in FIG. 10B. The difference in relative luminescence from the day 1 measurement between purified circular RNA and linear RNA was significant at both day 2 and day 3 for primary T cells.

Example 14

Circularization Efficiency by Permutation Site in *Anabaena* Intron.

Figure 11A:
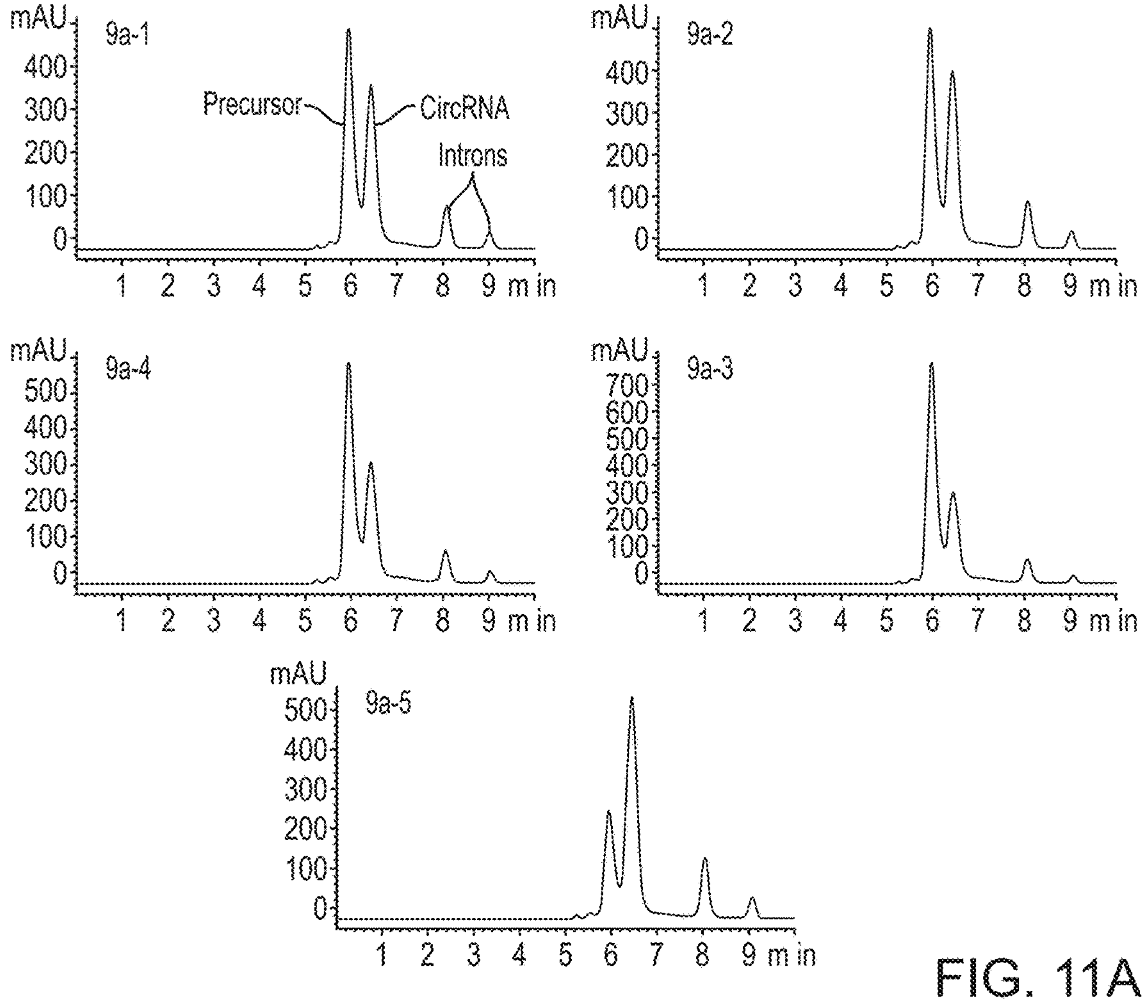
FIGS. 11A and 11B depicts HPLC chromatograms (FIG. 11A) and circularization efficiencies (FIG. 11B) of RNA constructs having different permutation sites.

RNA constructs including a CVB3 IRES, a *Gaussia* luciferase expression sequence, anabaena intron/exon regions, spacers, internal homology regions, and homology arms were produced. Circularization efficiency of constructs using the traditional anabaena intron permutation site and 5 consecutive permutations sites in P9 was measured by HPLC. HPLC chromatograms for the 5 consecutive permutation sites in P9 are shown in FIG. 11A.

Figure 11B:
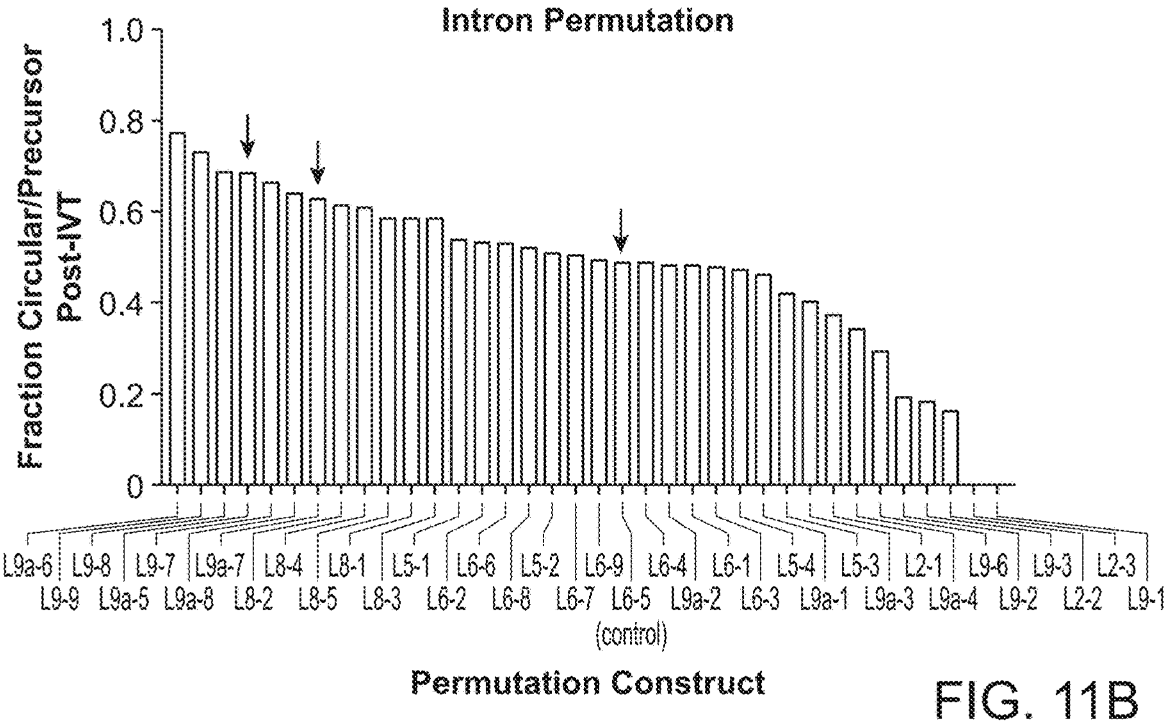

Circularization efficiency was measured at a variety of permutation sites. Circularization efficiency is defined as the area under the HPLC chromatogram curve for each of: circRNA/(circRNA+precursor RNA). Ranked quantification of circularization efficiency at each permutation site is in FIG. 11B. 3 permutation sites (indicated in FIG. 11B) were selected for further investigation.

Circular RNA in this example was circularized by in vitro transcription (IVT) then purified via spin column. Circularization efficiency for all constructs would likely be higher if the additional step of incubation with Mg2+ and guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

Example 15

Circularization Efficiency of Alternative Introns.

Figure 12A:
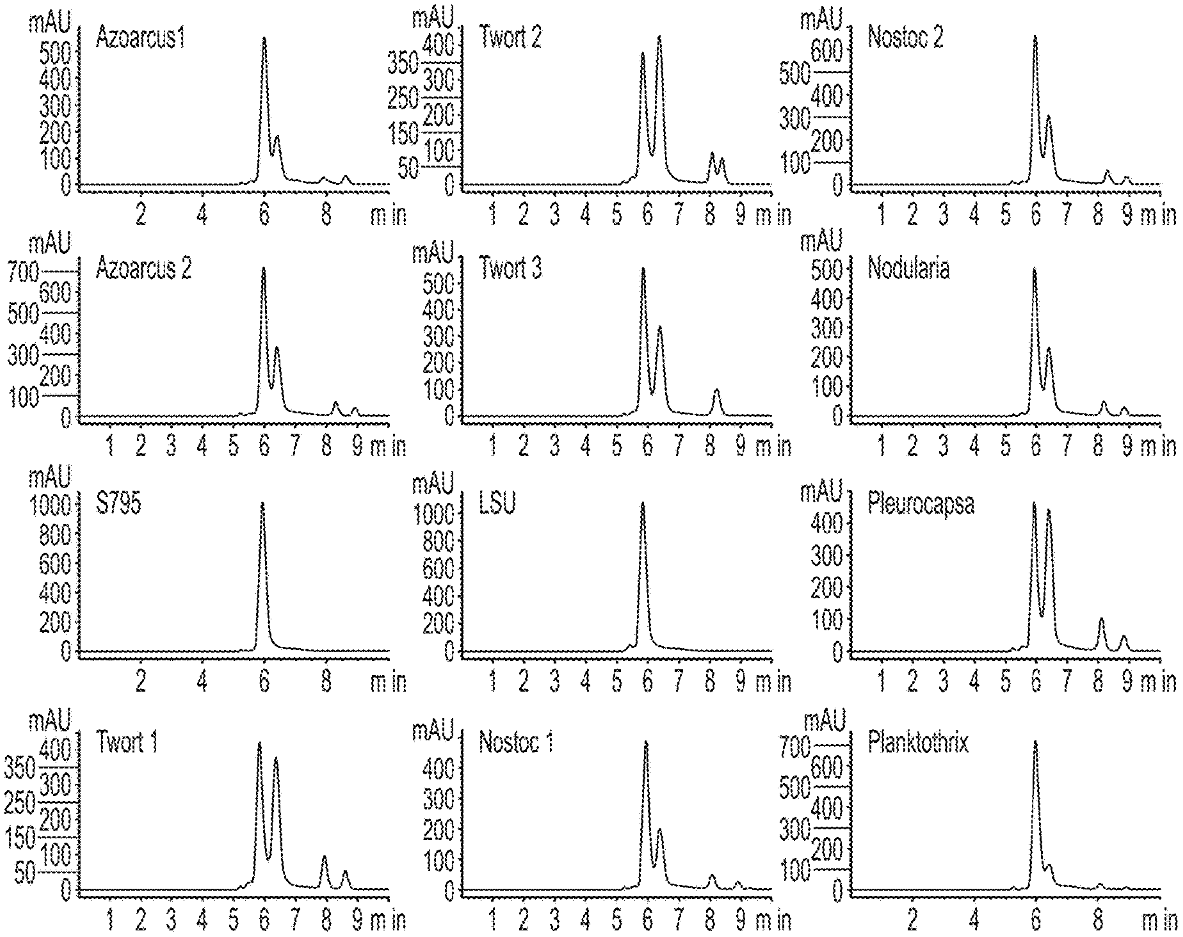
FIGS. 12A and 12B depicts HPLC chromatograms (FIG. 12A) and circularization efficiencies (FIG. 12B) of RNA constructs having different introns and/or permutation sites.
Figure 12B:
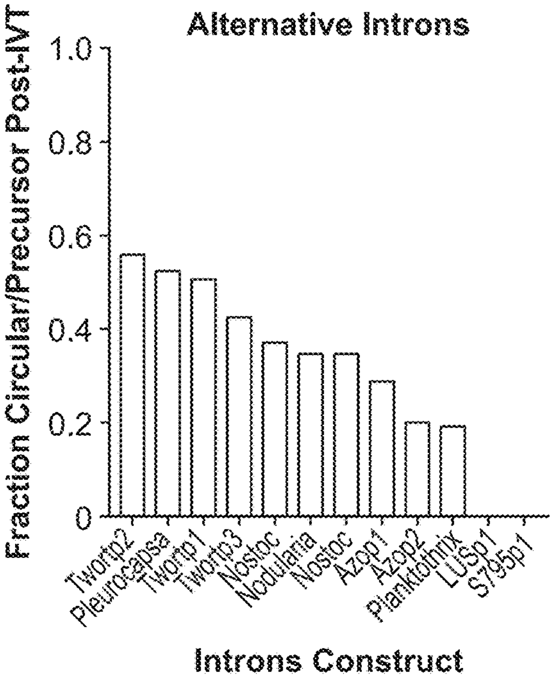

Precursor RNA containing a permuted group 1 intron of variable species origin or permutation site and several constant elements including: a CVB3 IRES, a *Gaussia* luciferase expression sequence, spacers, internal homology regions, and homology arms were created. Circularization data can be found in FIG. 12. FIG. 12A shows chromatograms resolving precursor, CircRNA and introns. FIG. 12B provides ranked quantification of circularization efficiency, based on the chromatograms shown in FIG. 12A, as a function of intron construct.

Circular RNA in this example was circularized by in vitro transcription (IVT) then spin column purification. Circularization efficiency for all constructs would likely be higher if the additional step of incubation with Mg2+ and guanosine nucleotide were included; however, removing this step allows for comparison between, and optimization of, circular RNA constructs. This level of optimization is especially useful for maintaining high circularization efficiency with large RNA constructs, such as those encoding chimeric antigen receptors.

Example 16

Circularization Efficiency by Homology Arm Presence or Length.

Figure 13A:
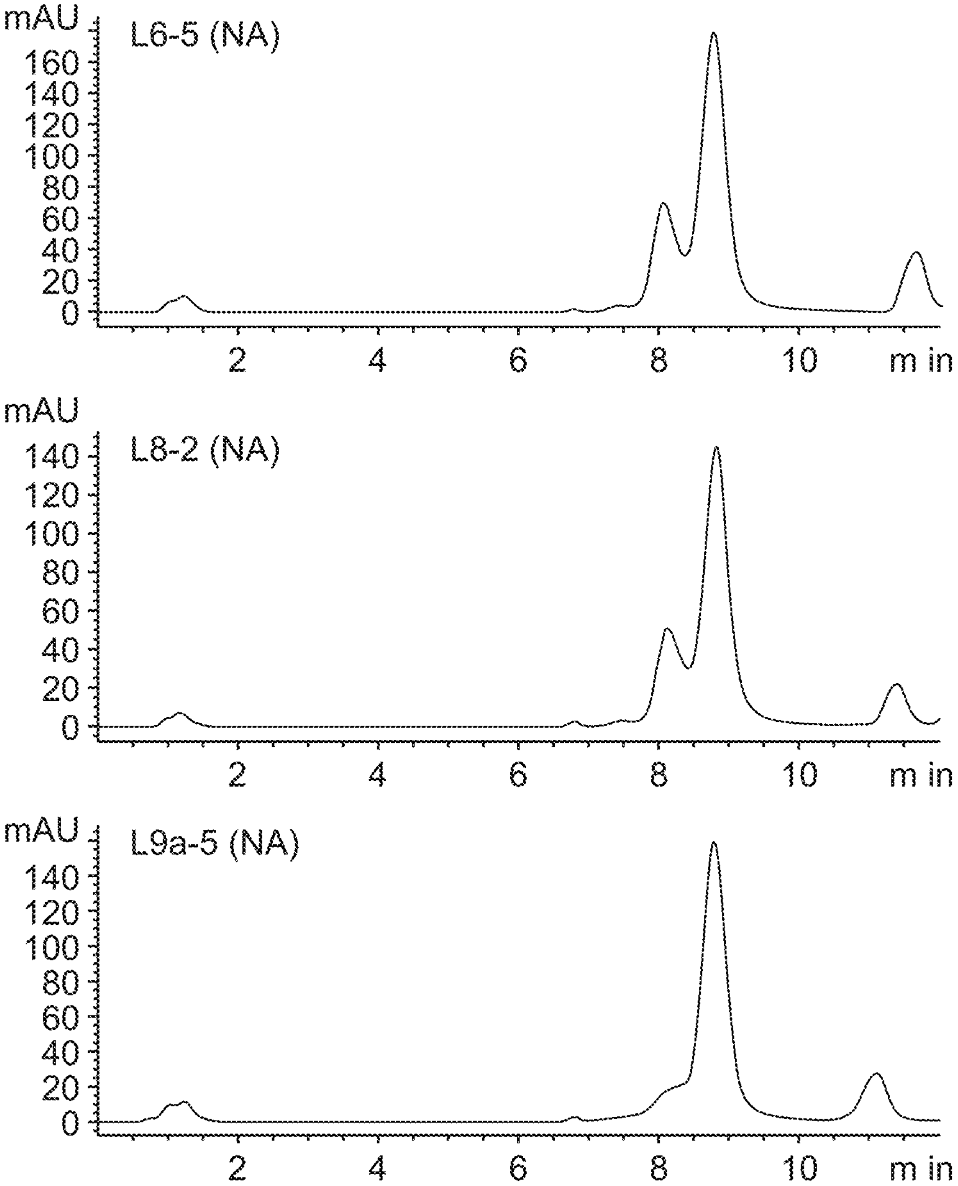
Figure 13B:
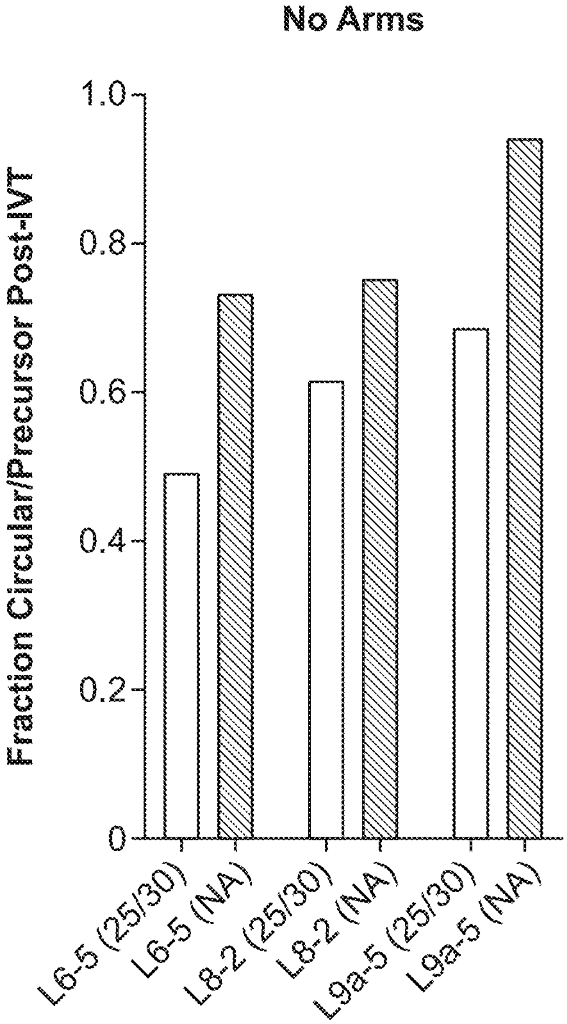

RNA constructs including a CVB3 IRES, a *Gaussia* luciferase expression sequence, anabaena intron/exon regions, spacers, and internal homology regions were produced. Constructs representing 3 anabaena intron permutation sites were tested with 30 nt, 25% GC homology arms or without homology arms ("NA"). These constructs were allowed to circularize without an $Mg^{2+}$ incubation step. Circularization efficiency was measured and compared. Data can be found in FIGS. 13A and 13B. Circularization efficiency was higher for each construct lacking homology arms. FIG. 13A provides ranked quantification of circularization efficiency; FIG. 13B provides chromatograms resolving precursor, circRNA and introns.

Figure 14:
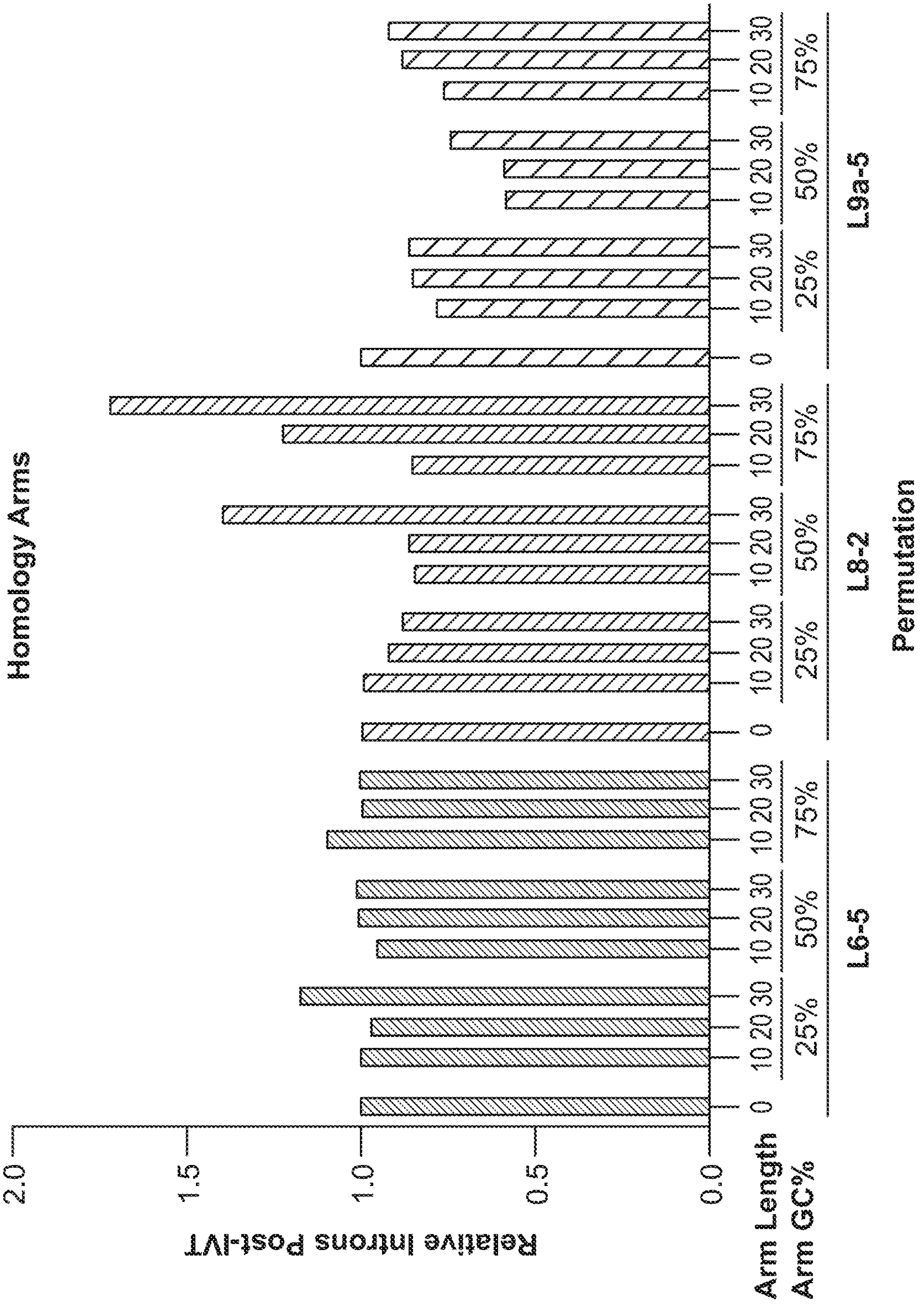
FIG. 14 depicts circularization efficiencies of 3 RNA constructs without homology arms or with homology arms having various lengths and GC content.

For each of the 3 permutation sites, constructs were created with 10 nt, 20 nt, and nt arm lengths and 25%, 50%, and 75% GC content. Splicing efficiency of these constructs was measured and compared to constructs without homology arms (FIG. 14). Splicing efficiency is defined as the proportion of free introns relative to the total RNA in the splicing reaction.

Figure 15A:
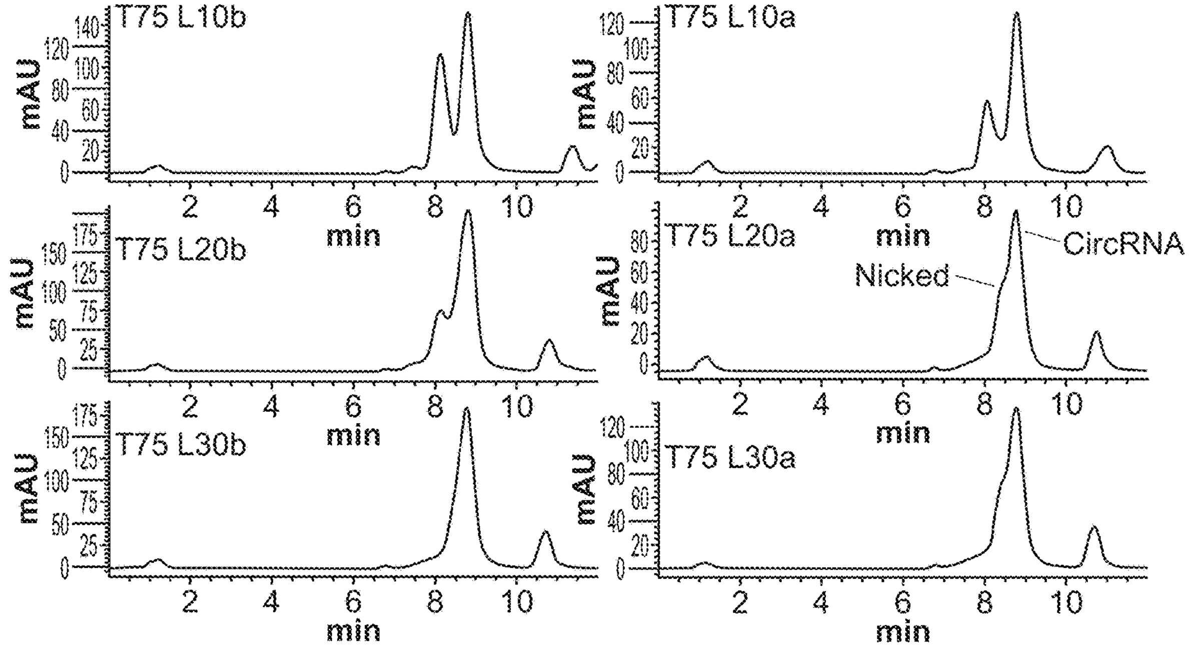
FIGS. 15A and 15B depict HPLC HPLC chromatograms showing the contribution of strong homology arms to improved splicing efficiency, the relationship between circularization efficiency and nicking in select constructs, and combinations of permutations sites and homology arms hypothesized to demonstrate improved circularization efficiency.
Figure 15B:
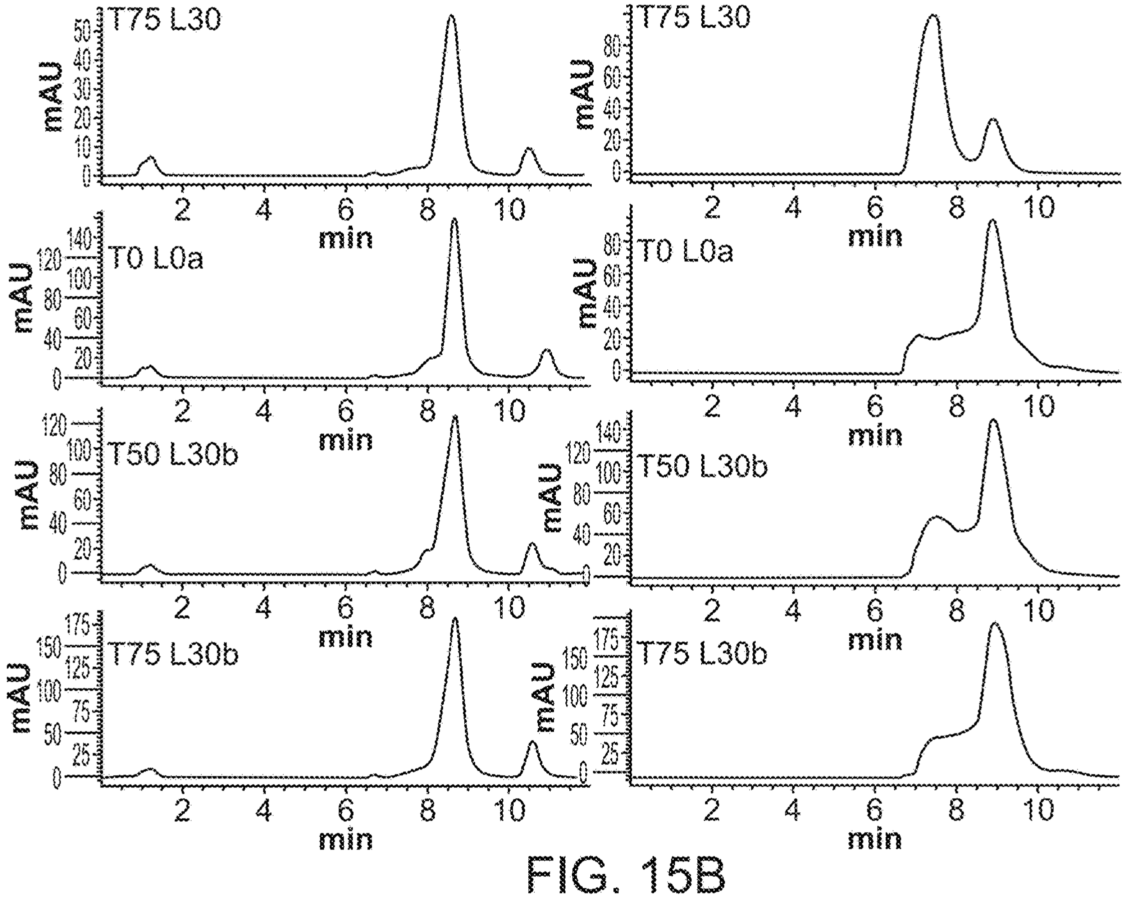

FIG. 15 A (left) shows HPLC chromatograms indicating the contribution of strong homology arms to improved splicing efficiency. Top left: 75% GC content, 10 nt homology arms. Center left: 75% GC content, 20 nt homology arms. Bottom left: 75% GC content, 30 nt homology arms.

FIG. 15 A (right) shows HPLC chromatograms showing increased splicing efficiency paired with increased nicking, appearing as a shoulder on the circRNA peak. Top right: 75% GC content, 10 nt homology arms. Center right: 75% GC content, 20 nt homology arms. Bottom right: 75% GC content, 30 nt homology arms.

FIG. 15 B (left) shows select combinations of permutation sites and homology arms hypothesized to demonstrate improved circularization efficiency.

FIG. 15 B (right) shows select combinations of permutation sites and homology arms hypothesized to demonstrate improved circularization efficiency, treated with *E. coli* polyA polymerase.

Circular RNA in this example was circularized by in vitro transcription (IVT) then spin-column purified. Circularization efficiency for all constructs would likely be higher if an additional Mg2+ incubation step with guanosine nucleotide were included; however, removing this step allowed for comparison between, and optimization of, circular RNA constructs. This level of optimization is especially useful for maintaining high circularization efficiency with large RNA constructs, such as those encoding chimeric antigen receptors.

Example 17

Circular RNA Encoding Chimeric Antigen Receptors

Figure 16:
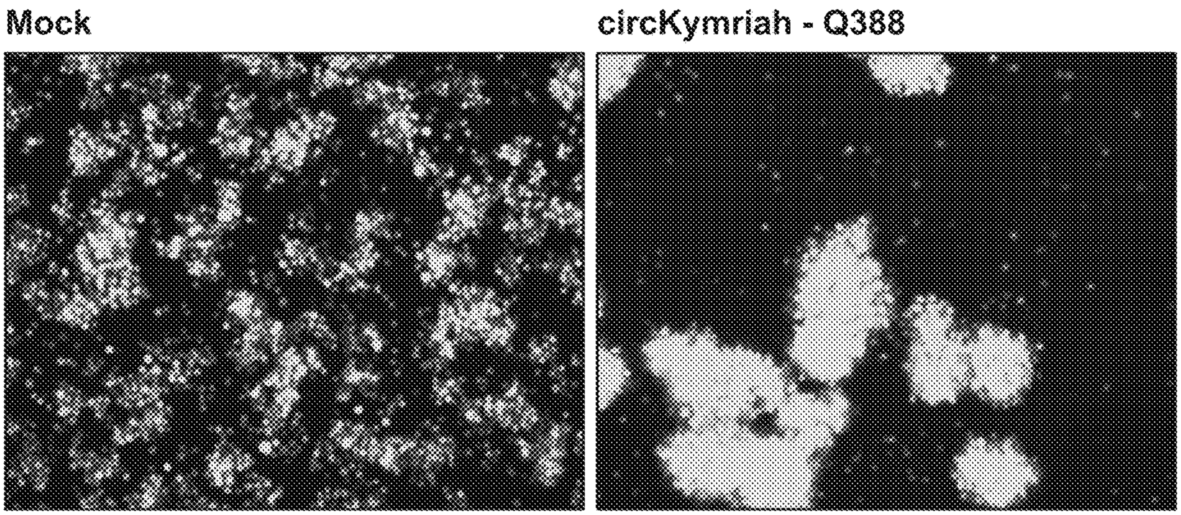
FIG. 16 shows fluorescent images of T cells mock electroporated (left) or electroporated with circular RNA encoding a CAR (right) and co-cultured with Raji cells expressing GFP and firefly luciferase.

Constructs including anabaena intron/exon regions, a Kymriah chimeric antigen receptors (CAR) expression sequence, and a CVB3 IRES were circularized. 100,000 human primary CD3+ T cells were electroporated with 500ng of circRNA and co-cultured for 24 hours with Raji cells stably expressing GFP and firefly luciferase. Effector to target ratio (E:T ratio) 0.75:1. 100,000 human primary CD3+ T cells were mock electroporated and co-cultured as a control (FIG. 16).

Figure 17:
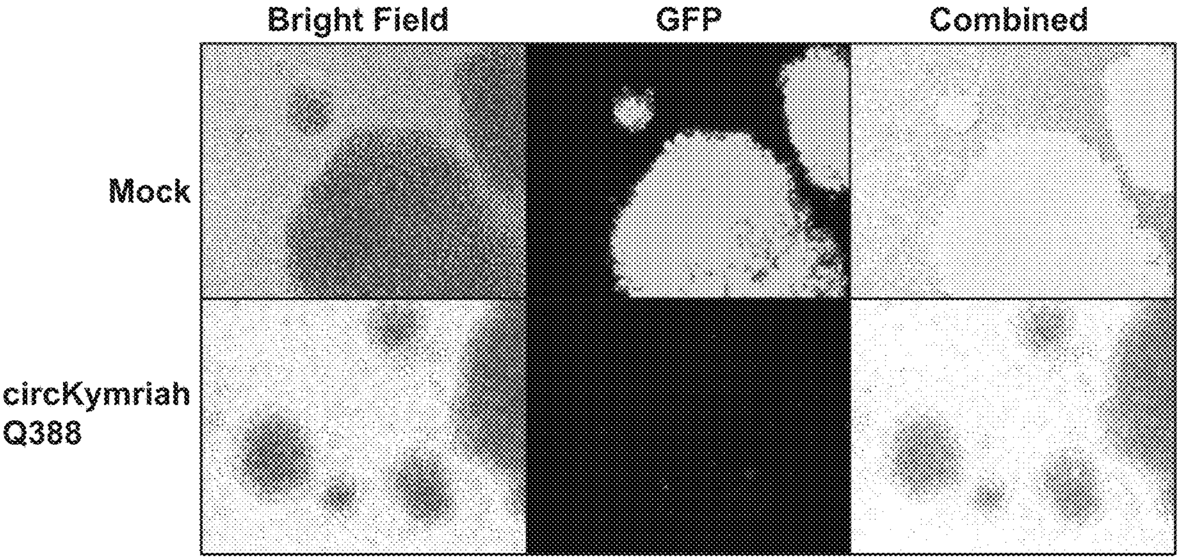
FIG. 17 shows bright field (left), fluorescent (center), and overlay (right) images of T cells mock electroporated (top) or electroporated with circular RNA encoding a CAR (bottom) and co-cultured with Raji cells expressing GFP and firefly luciferase.

Sets of 100,000 human primary CD3+ T cells were mock electroporated or electroporated with 1 μg of circRNA then co-cultured for 48 hours with Raji cells stably expressing GFP and firefly luciferase E:T ratio 10:1 (FIG. 17).

Figure 18:
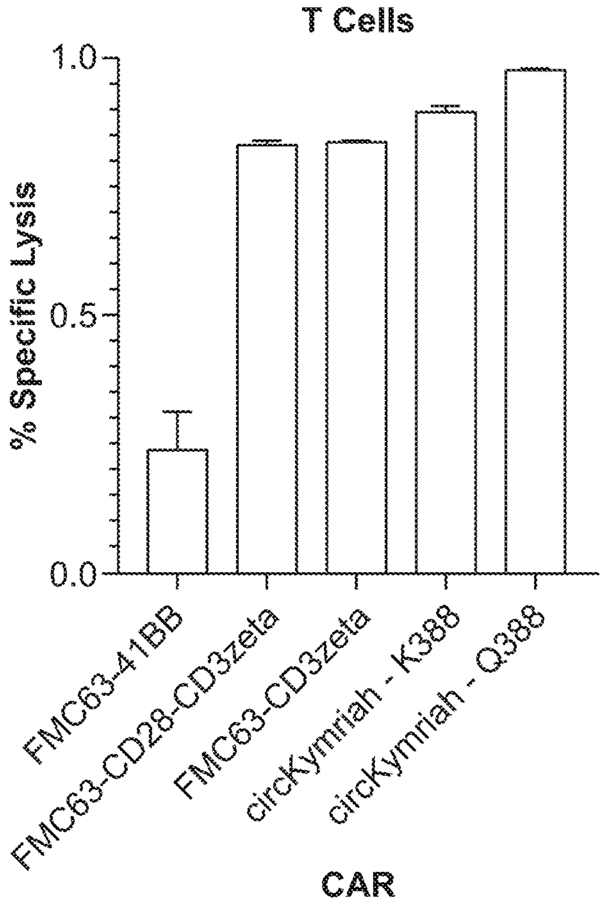
FIG. 18 depicts specific lysis of Raji target cells by T cells mock electroporated or electroporated with circular RNA encoding different CAR sequences.

Quantification of specific lysis of Raji target cells was determined by detection of firefly luminescence (FIG. 18). 100,000 human primary CD3+ T cells either mock electroporated or electroporated with circRNA encoding different CAR sequences were co-cultured for 48 hours with Raji cells stably expressing GFP and firefly luciferase. % Specific lysis defined as 1-[CAR condition luminescence]/[mock condition luminescence]. E:T ratio 10:1.

Example 18

Expression and Functional Stability of Circular and Linear RNA in Jurkat Cells and Resting Human T Cells.

Figure 19A:
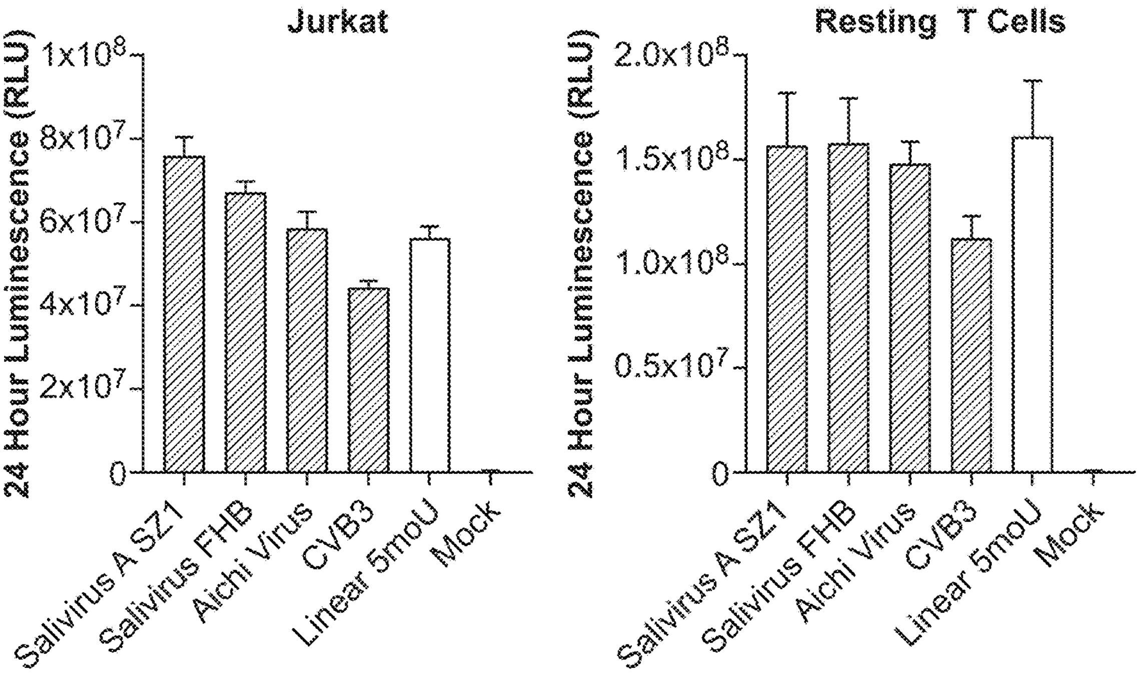
FIGS. 19A and 19B depicts luminescence in supernatants of Jurkat cells (left) or resting primary human CD3+ T cells (right) 24 hours after transduction with linear or circular RNA comprising a *Gaussia* luciferase expression sequence and varying IRES sequences (FIG. 19A), and relative luminescence over 3 days (FIG. 19B).

Constructs including anabaena intron/exon regions, a *Gaussia* luciferase expression sequence, and a subset of previously tested IRES were circularized and reaction products were purified by size exclusion HPLC. 150,000 Jurkat cells were electroporated with 1 μg of circular RNA or 5moU-mRNA. Luminescence from secreted *Gaussia* luciferase in supernatant was measured 24 hours after electroporation (FIG. 19A left). 150,000 resting primary human CD3+ T cells (10 days post-stimulation) were electroporated with 1 μg of circular RNA or 5moU-mRNA. Luminescence from secreted *Gaussia* luciferase in supernatant was measured 24 hours after electroporation (FIG. 19A right).

Figure 19B:
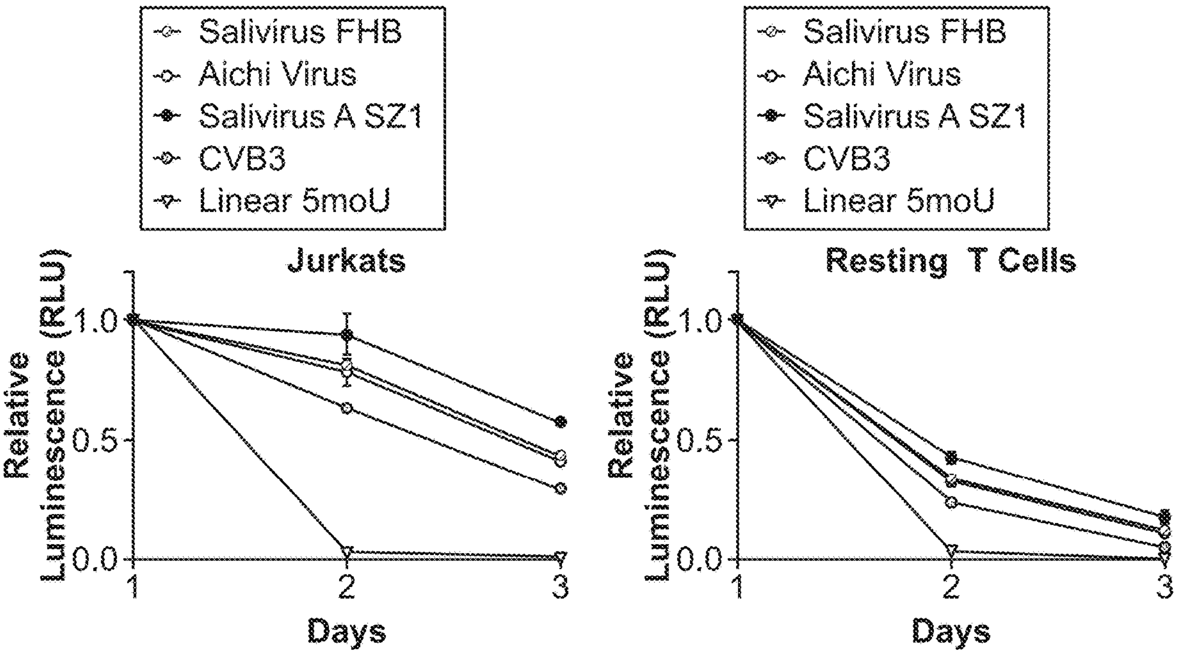

Luminescence from secreted *Gaussia* luciferase in supernatant was measured every 24 hours after electroporation, followed by complete media replacement. Functional stability data shown in FIG. 19B. Circular RNA had more functional stability than linear RNA in each case, with a more pronounced difference in Jurkat cells.

Example 19

IFN-β1, RIG-1, IL-2, IL-6, IFNγ, and TNFα Transcript Induction of Cells Electroporated with Linear RNA or Varying Circular RNA Constructs.

Figure 20A:
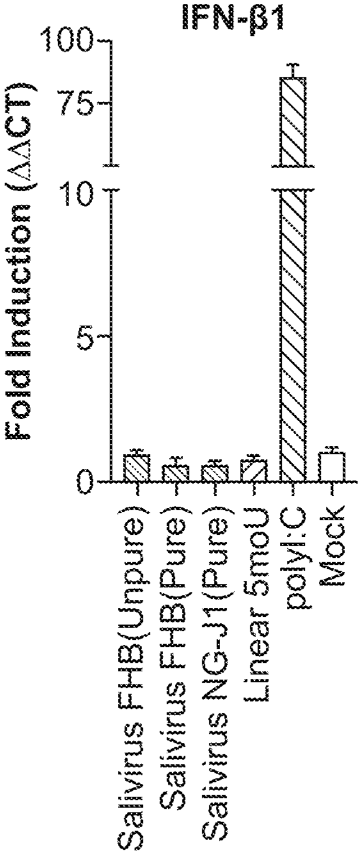
FIGS. 20A, 20B, 20C, 20D, 20E and 20F depicts transcript induction of IFN-R 1 (FIG. 20A), RIG-I (FIG. 20B), IL-2 (FIG. 20C), IL-6 (FIG. 20D), IFNγ (FIG. 20E), and TNFα (FIG. 20F) after electroporation of human CD3+ T cells with modified linear, unpurified circular, or purified circular RNA.
Figure 20B:
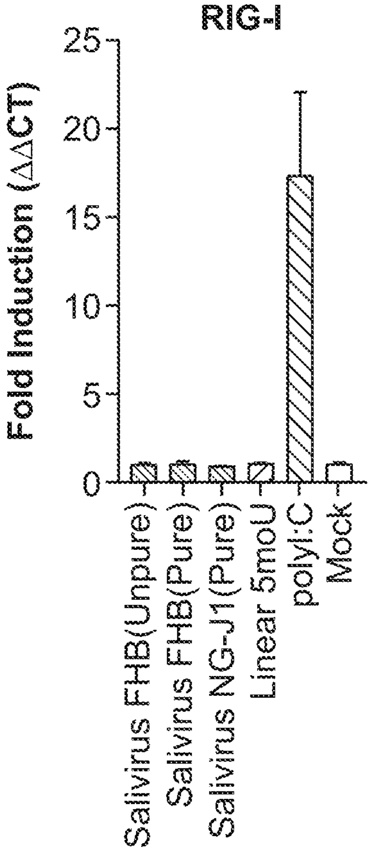
Figure 20C:
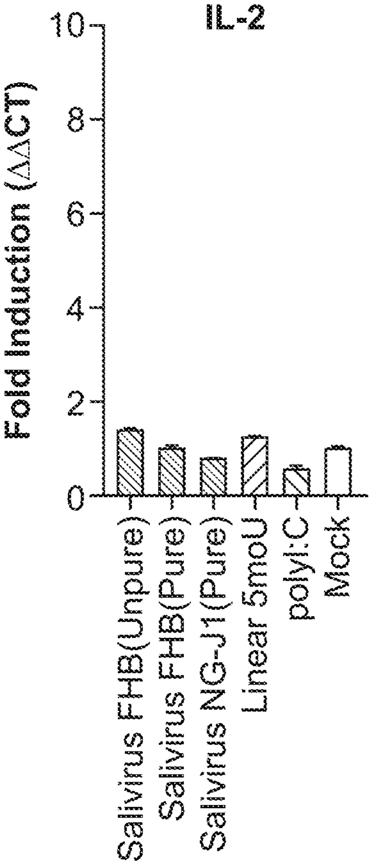
Figure 20D:
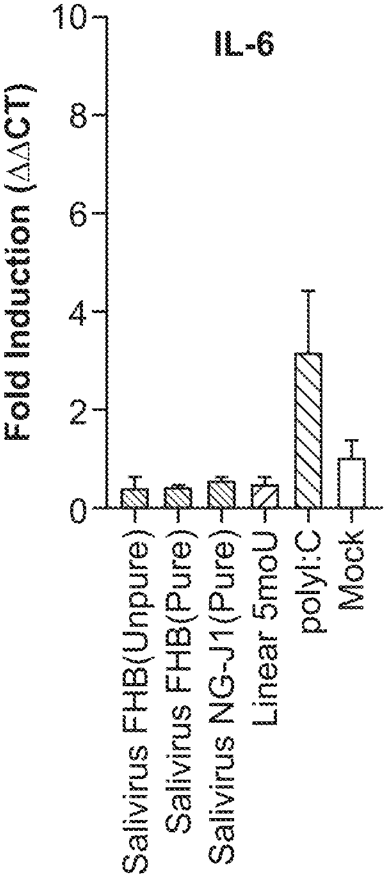
Figure 20E:
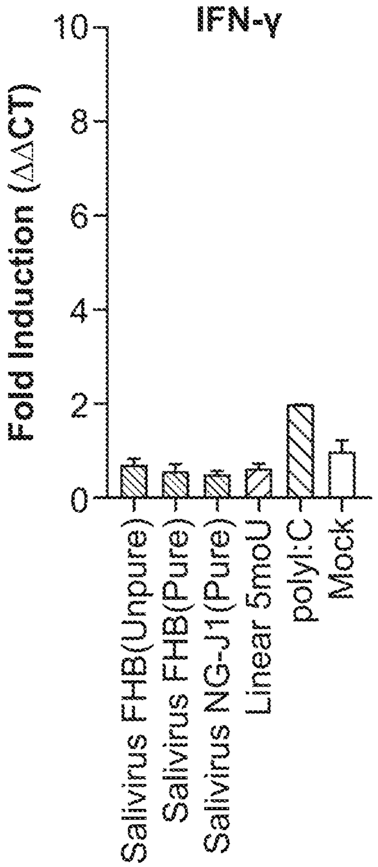
Figure 20F:
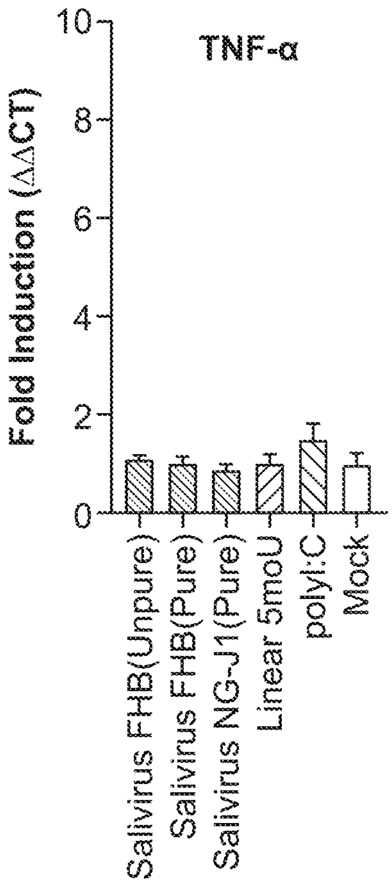

Constructs including anabaena intron/exon regions, a *Gaussia* luciferase expression sequence, and a subset of previously tested IRES were circularized and reaction products were purified by size exclusion HPLC. 150,000 CD3+ human T cells were electroporated with 1 μg of circular RNA, 5moU-mRNA, or immunostimulatory positive control poly inosine:cytosine. IFN-β1 (FIG. 20A), RIG-I (FIG. 20B), IL-2 (FIG. 20C), IL-6 (FIG. 20D), IFNγ (FIG. 20E), and TNFα (FIG. 20F) transcript induction was measured 18 hours after electroporation.

Example 20

Specific Lysis of Target Cells and IFNγ Transcript Induction by CAR Expressing Cells Electroporated with Different Amounts of Circular or Linear RNA; Specific Lysis of Target and Non-Target Cells by CAR Expressing Cells at Different E:T Ratios.

Figure 21A:
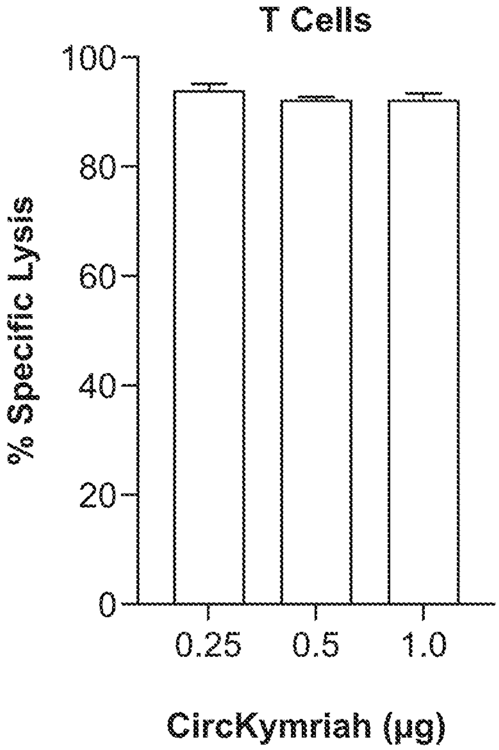
FIGS. 21A and 21B depicts specific lysis of Raji target cells by human primary CD3+ T cells electroporated with circRNA encoding a CAR as determined by detection of firefly luminescence (FIG. 21A), and IFNγ transcript induction 24 hours after electroporation with different quantities of circular or linear RNA encoding a CAR sequence (FIG. 21B).
Figure 21B:
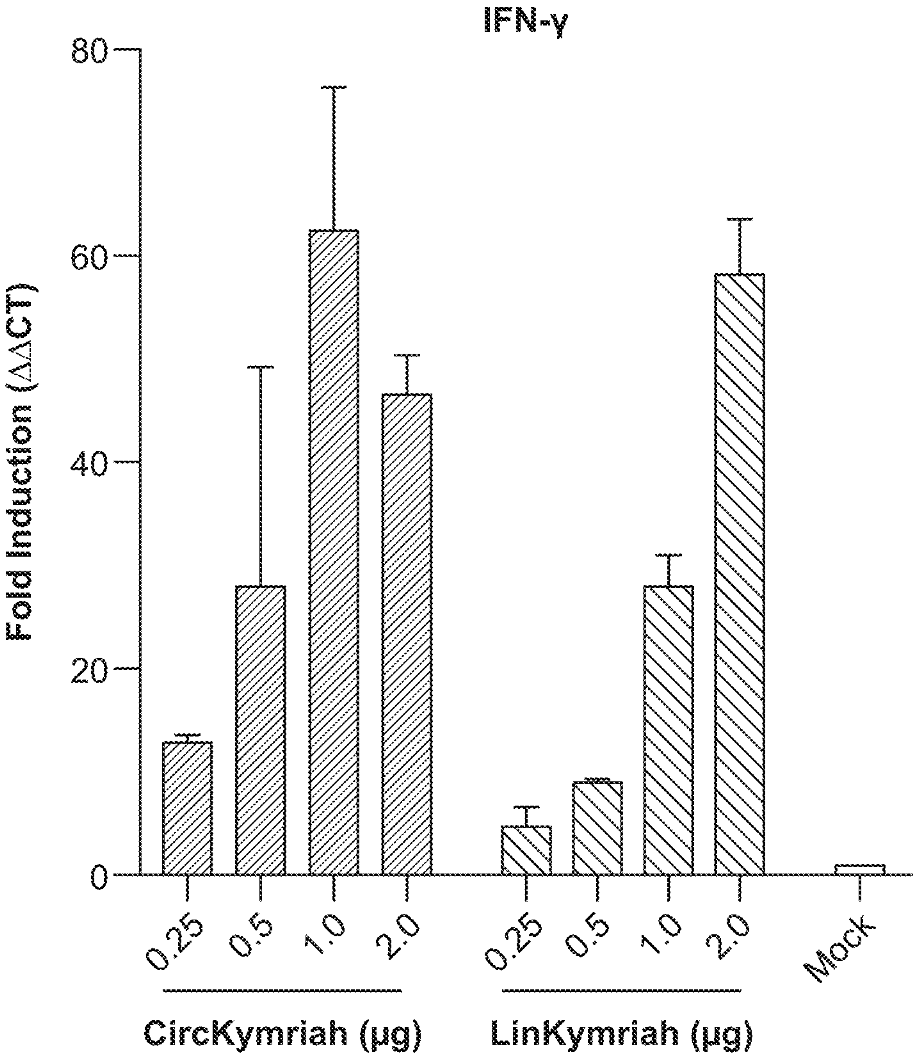

Constructs including anabaena intron/exon regions, an anti-CD19 CAR expression sequence, and a CVB3 IRES were circularized and reaction products were purified by size exclusion HPLC. 150,000 human primary CD3+ T cells either mock electroporated or electroporated with different quantities of circRNA encoding an anti-CD19 CAR sequence were co-cultured for 12 hours with Raji cells stably expressing GFP and firefly luciferase at an E:T ratio of 2:1. Specific lysis of Raji target cells was determined by detection of firefly luminescence (FIG. 21A). % Specific lysis was defined as 1-[CAR condition luminescence]/[mock condition luminescence]. IFNγ transcript induction was measured 24 hours after electroporation (FIG. 21B).

Figure 22A:
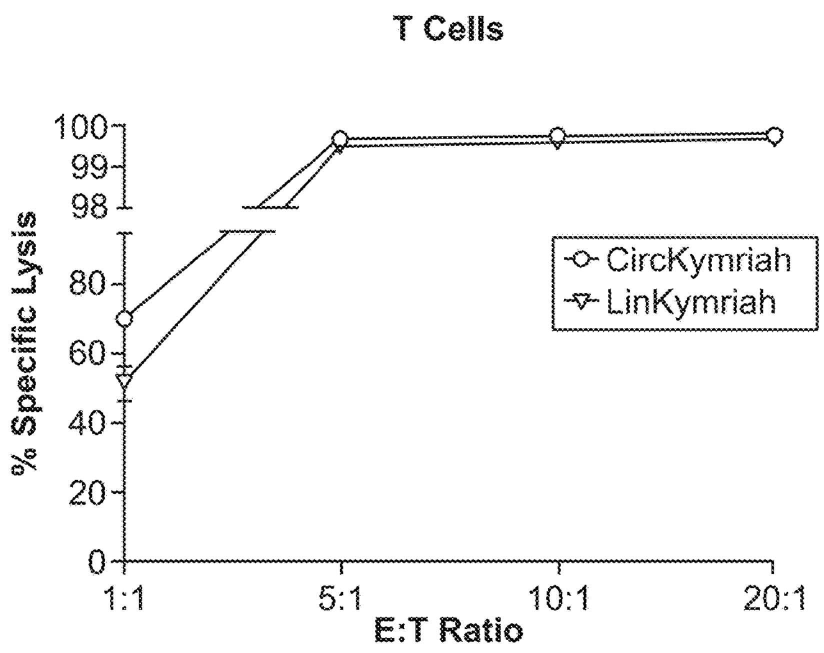
FIGS. 22A and 22B depicts specific lysis of target or non-target cells by human primary CD3+ T cells electroporated with circular or linear RNA encoding a CAR at different E:T ratios (FIG. 22A and FIG. 22B) as determined by detection of firefly luminescence.

150,000 human primary CD3+ T cells were either mock electroporated or electroporated with 500ng circRNA or m1ψ-mRNA encoding an anti-CD19 CAR sequence, then co-cultured for 24 hours with Raji cells stably expressing firefly luciferase at different E:T ratios. % Specific lysis of Raji target cells was determined by detection of firefly luminescence (FIG. 22A). % Specific lysis was defined as 1−[CAR condition luminescence]/[mock condition luminescence].

Figure 22B:
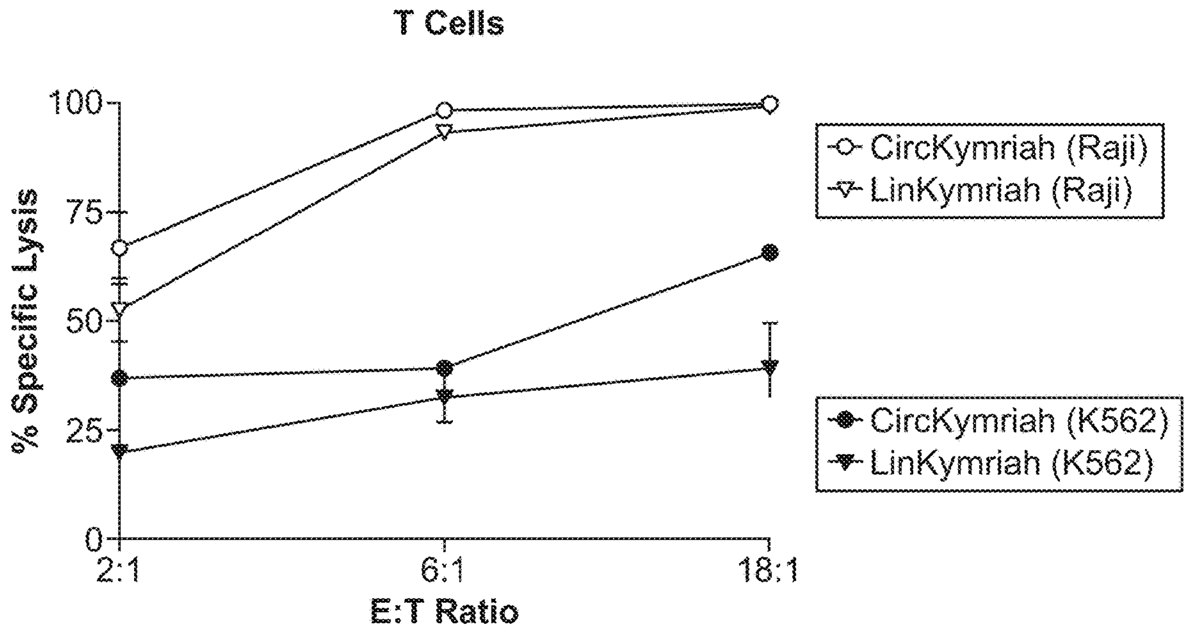

CAR expressing T cells were also co-cultured for 24 hours with Raji or K562 cells stably expressing firefly luciferase at different E:T ratios. Specific lysis of Raji target cells or K562 non-target cells was determined by detection of firefly luminescence (FIG. 22B). % Specific lysis is defined as 1−[CAR condition luminescence]/[mock condition luminescence].

Example 21

Specific Lysis of Target Cells by T Cells Electroporated with Circular RNA or Linear RNA Encoding a CAR.

Figure 23:
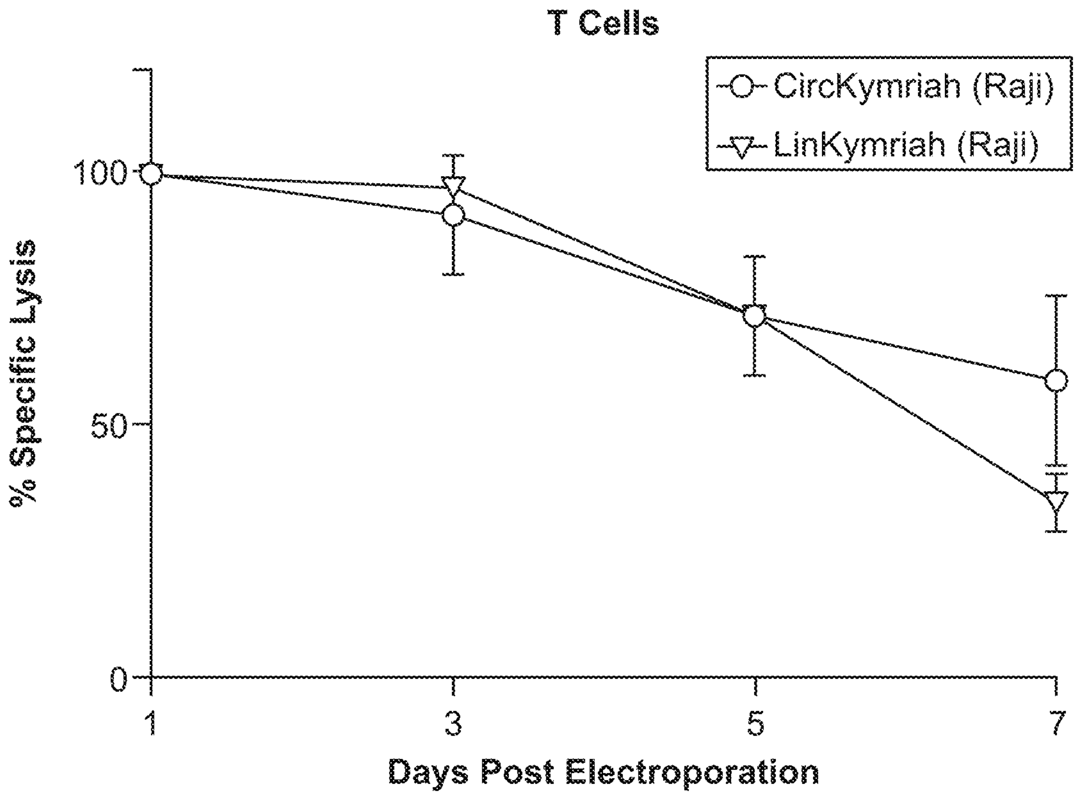
FIG. 23 depicts specific lysis of target cells by human CD3+ T cells electroporated with RNA encoding a CAR at 1, 3, 5, and 7 days post electroporation.

Constructs including anabaena intron/exon regions, an anti-CD19 CAR expression sequence, and a CVB3 IRES were circularized and reaction products were purified by size exclusion HPLC. Human primary CD3+ T cells were electroporated with 500 ng of circular RNA or an equimolar quantity of m1ψ-mRNA, each encoding a CD19-targeted CAR. Raji cells were added to CAR-T cell cultures over 7 days at an E:T ratio of 10:1. % Specific lysis was measured for both constructs at 1, 3, 5, and 7 days (FIG. 23).

Example 22

Specific Lysis of Raji Cells by T Cells Expressing an Anti-CD19 CAR or an Anti-BCMA CAR.

Figure 24:
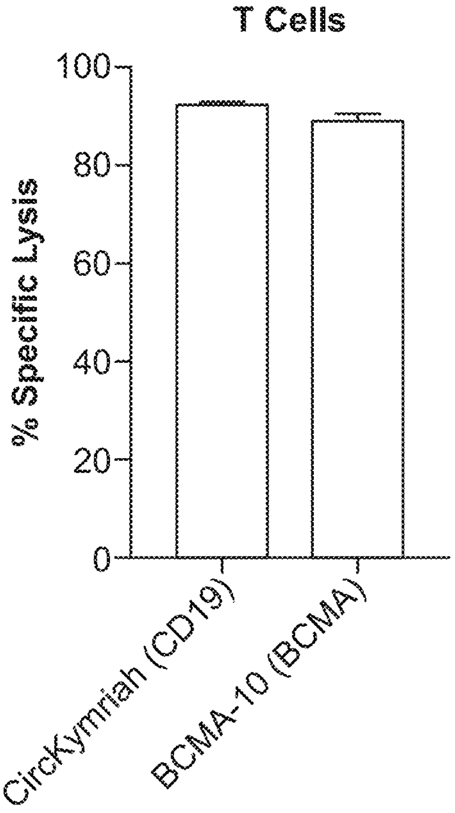
FIG. 24 depicts specific lysis of target cells by human CD3+ T cells electroporated with circular RNA encoding a CD19 or BCMA targeted CAR.

Constructs including anabaena intron/exon regions, anti-CD19 or anti-BCMA CAR expression sequence, and a CVB3 IRES were circularized and reaction products were purified by size exclusion HPLC. 150,000 primary human CD3+ T cells were electroporated with 500ng of circRNA, then were co-cultured with Raji cells at an E:T ratio of 2:1. % Specific lysis was measured 12 hours after electroporation (FIG. 24).

Example 23

Example 23A: Synthesis of Compounds

Synthesis of representative ionizable lipids of the invention are described in PCT applications PCT/US2016/052352, PCT/US2016/068300, PCT/US2010/061058, PCT/US2018/058555, PCT/US2018/053569, PCT/US2017/028981, PCT/US2019/025246, PCT/US2018/035419, PCT/US2019/015913, and US applications with publication numbers 20190314524, 20190321489, and 20190314284, the contents of each of which are incorporated herein by reference in their entireties.

Example 23B: Synthesis of Compounds

Synthesis of representative ionizable lipids of the invention are described in US patent publication number US20170210697A1, the contents of of which is incorporated herein by reference in its entirety.

Example 24

Protein Expression by Organ

Figure 25:
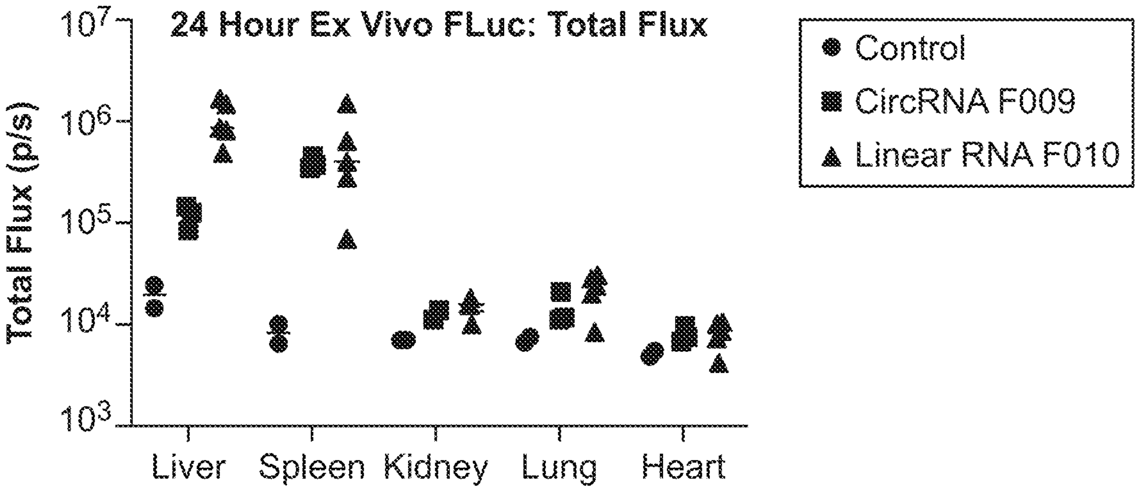
FIG. 25 depicts total Flux of organs harvested from CD-1 mice dosed with circular RNA encoding FLuc and formulated with 50% Lipid 15 (Table 10b), 10% DSPC, 1.5% PEG-DMG, and 38.5% cholesterol.
Figure 26:
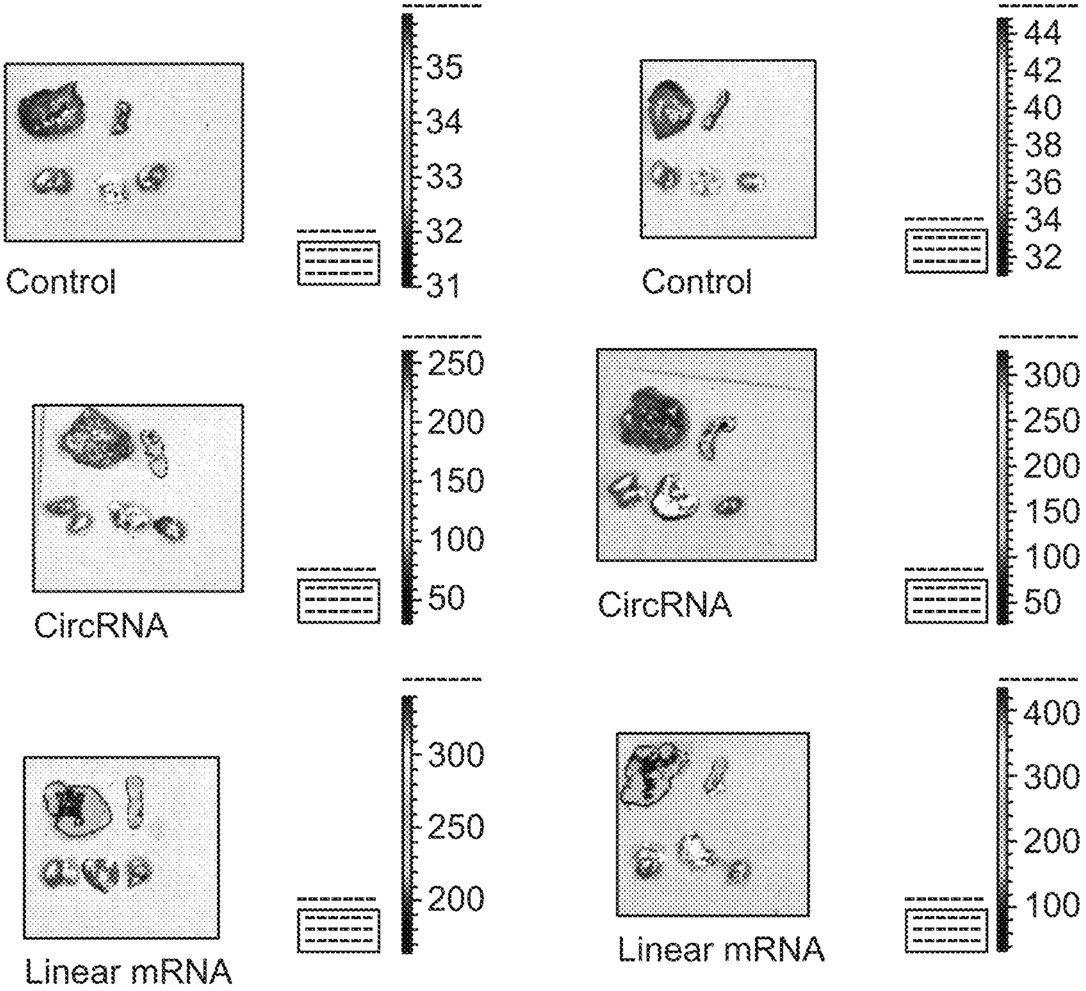
FIG. 26 shows images highlighting the luminescence of organs harvested from CD-1 mice dosed with circular RNA encoding FLuc and formulated with 50% Lipid 15 (Table 10b), 10% DSPC, 1.5% PEG-DMG, and 38.5% cholesterol.

Circular or linear RNA encoding FLuc was generated and loaded into transfer vehicles with the following formulation: 50% ionizable lipid 15 in Table 10b, 10% DSPC, 1.5% PEG-DMG, 38.5% cholesterol. CD-1 mice were dosed at 0.2 mg/kg and luminescence was measured at 6 hours (live IVIS) and 24 hours (live IVIS and ex vivo IVIS). Total Flux (photons/second over a region of interest) of the liver, spleen, kidney, lung, and heart was measured (FIGS. 25 and 26).

Example 25

Distribution of Expression in the Spleen

Circular or linear RNA encoding GFP is generated and loaded into transfer vehicles with the following formulation: 50% ionizable lipid 15 in Table 10b, 10% DSPC, 1.5% PEG-DMG, 38.5% cholesterol. The formulation is administered to CD-1 mice. Flow cytometry is run on spleen cells to determine the distribution of expression across cell types.

Example 26

Production of Nanoparticle Compositions

In order to investigate safe and efficacious nanoparticle compositions for use in the delivery of circular RNA to cells, a range of formulations are prepared and tested. Specifically, the particular elements and ratios thereof in the lipid component of nanoparticle compositions are optimized.

Nanoparticles can be made in a 1 fluid stream or with mixing processes such as microfluidics and T-junction mixing of two fluid streams, one of which contains the circular RNA and the other has the lipid components.

Lipid compositions are prepared by combining an ionizable lipid, optionally a helper lipid (such as DOPE, DSPC, or oleic acid obtainable from Avanti Polar Lipids, Alabaster, Ala.), a PEG lipid (such as 1,2-dimyristoyl-sn-glycerol methoxypolyethylene glycol, also known as PEG-DMG, obtainable from Avanti Polar Lipids, Alabaster, Ala.), and a structural lipid such as cholesterol at concentrations of about, e.g., 40 or 50 mM in a solvent, e.g., ethanol. Solutions should be refrigerated for storage at, for example, −20° C. Lipids are combined to yield desired molar ratios (see, for example, Tables 31a and 31b below) and diluted with water and ethanol to a final lipid concentration of e.g., between about 5.5 mM and about 25 mM.

TABLE 31a

| Formulation number | Description |
|---|---|
| 1 | Aliquots of 50 mg/mL ethanolic solutions of C12-200, DOPE, Chol and DMG-PEG2K (40:30:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 2 | Aliquots of 50 mg/mL ethanolic solutions of DODAP, DOPE, cholesterol and DMG-PEG2K (18:56:20:6) are mixed anddiluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.35 mg/mL EPO circRNA (encapsulated). Zave = 75.9nm (Dv(50) = 57.3 nm; Dv(90) = 92.1 nm). |
| 3 | Aliquots of 50 mg/mL ethanolic solutions of HGT4003, DOPE, cholesterol and DMG-PEG2K (50:25:20:5) are mixed and diluted with ethanol to 3 mL final volume. Separately, an aqueous buffered solution (10 mM citrate/150 mM NaCl, pH 4.5) of circRNA is prepared froma 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 4 | Aliquots of 50 mg/mL ethanolic solutions of ICE, DOPE and DMG-PEG2K (70:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 5 | Aliquots of 50 mg/mL ethanolic solutions of HGT5000, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.82 mg/mL EPO mRNA (encapsulated). Zave = 105.6 nm (Dv(50) = 53.7 nm; Dv(90) = 157 nm). |
| 6 | Aliquots of 50 mg/mL ethanolic solutions of HGT5001, DOPE, cholesterol and DMG-PEG2K (40:20:35:5) are mixed anddiluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (DH 7.4), concentrated and stored at 2-8° C. |

In some embodiments, transfer vehicle has a formulation as described in Table 31a.

TABLE 31b

| Cempesition (mol %) | Components |
|---|---|
| 40:20:38.5:1.5 | Compound:Phospholipid:Phytosterol*:PEG-DMG |
| 45:15:38.5:1.5 | Compound:Phospholipid:Phytosterol*:PEG-DMG |
| 50:10:38.5:1.5 | Compound:Phospholipid:Phytosterol*:PEG-DMG |
| 55:5:38.5:1.5 | Compound:Phospholipid:Phytosterol*:PEG-DMG |
| 60:5:33.5:1.5 | Compound:Phospholipid:Phytosterol*:PEG-DMG |
| 45:20:33.5:1.5 | Compound:Phospholipid:Phytosterol*:PEG-DMG |
| 50:20:28.5:1.5 | Compound:Phospholipid:Phytosterol*:PEG-DMG |

TABLE 31b-continued

| Cempesition (mol %) | Components |
|---|---|
| 55:20:23.5:1.5 | Compound:Phospholipid:Phytosterol*:PEG-DMG |
| 60:20:18.5:1.5 | Compound:Phospholipid:Phytosterol*:PEG-DMG |
| 40:15:43.5:1.5 | Compound:Phospholipid:Phytosterol*:PEG-DMG |
| 50:15:33.5:1.5 | Compound:Phospholipid:Phytosterol*:PEG-DMG |
| 55:15:28.5:1.5 | Compound:Phospholipid:Phytosterol*:PEG-DMG |
| 60:15:23.5:1.5 | Compound:Phospholipid:Phytosterol*:PEG-DMG |
| 40:10:48.5:1.5 | Compound:Phospholipid:Phytosterol*:PEG-DMG |
| 45:10:43.5:1.5 | Compound:Phospholipid:Phytosterol*:PEG-DMG |
| 55:10:33.5:1.5 | Compound:Phospholipid:Phytosterol*:PEG-DMG |
| 60:10:28.5:1.5 | Compound:Phospholipid:Phytosterol*:PEG-DMG |
| 40:5:53.5:1.5 | Compound:Phospholipid:Phytosterol*:PEG-DMG |
| 45:5:48.5:1.5 | Compound:Phospholipid:Phytosterol*:PEG-DMG |
| 50:5:43.5:1.5 | Compound:Phospholipid:Phytosterol*:PEG-DMG |
| 40:20:40:0 | Compound:Phospholipid:Phytosterol*:PEG-DMG |
| 45:20:35:0 | Compound:Phospholipid:Phytosterol*:PEG-DMG |
| 50:20:30:0 | Compound:Phospholipid:Phytosterol*:PEG-DMG |
| 55:20:25:0 | Compound:Phospholipid:Phytosterol*:PEG-DMG |
| 60:20:20:0 | Compound:Phospholipid:Phytosterol*:PEG-DMG |
| 40:15:45:0 | Compound:Phospholipid:Phytosterol*:PEG-DMG |

In some embodiments, transfer vehicle has a formulation as described in Table 31b.

For nanoparticle compositions including circRNA, solutions of the circRNA at concentrations of 0.1 mg/ml in deionized water are diluted in a buffer, e.g., 50 mM sodium citrate buffer at a pH between 3 and 4 to form a stock solution. Alternatively, solutions of the circRNA at concentrations of 0.15 mg/ml in deionized water are diluted in a buffer, e.g., 6.25 mM sodium acetate buffer at a pH between 3 and 4.5 to form a stock solution.

Nanoparticle compositions including a circular RNA and a lipid component are prepared by combining the lipid solution with a solution including the circular RNA at lipid component to circRNA wt:wt ratios between about 5:1 and about 50:1. The lipid solution is rapidly injected using, e.g., a NanoAssemblr microfluidic based system at flow rates between about 10 ml/min and about 18 ml/min or between about 5 ml/min and about 18 ml/min into the circRNA solution, to produce a suspension with a water to ethanol ratio between about 1:1 and about 4:1.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, Ill.) with a molecular weight cutoff of 10 kDa or 20 kDa. The formulations are then dialyzed overnight at 4° C. The resulting nanoparticle suspension is filtered through 0.2 m sterile filters (Sarstedt, Nümbrecht, Germany) into glass vials and sealed with crimp closures. Nanoparticle composition solutions of 0.01 mg/ml to 0.15 mg/ml are generally obtained.

The method described above induces nano-precipitation and particle formation.

Alternative processes including, but not limited to, T-junction and direct injection, may be used to achieve the same nano-precipitation. B. Characterization of nanoparticle compositions A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of circRNA in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, Calif.). The concentration of circRNA in the nanoparticle composition can be calculated based on the extinction coefficient of the circRNA used in the composition and on the difference between the absorbance at a wavelength of, for example, 260 nm and the baseline value at a wavelength of, for example, 330 nm.

A QUANT-IT™ RIBOGREEN® RNA assay (Invitrogen Corporation Carlsbad, Calif.) can be used to evaluate the encapsulation of circRNA by the nanoparticle composition. The samples are diluted to a concentration of approximately 5 μg/mL or 1 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2-4% Triton X-100 solution is added to the wells. The plate is incubated at a temperature of 37° C. for 15 minutes. The RIBOGREEN® reagent is diluted 1:100 or 1:200 in TE buffer, and 100 μL of this solution is added to each well. The fluorescence intensity can be measured using a fluorescence plate reader (Wallac Victor 1420 Multilabel Counter; Perkin Elmer, Waltham, Mass.) at an excitation wavelength of, for example, about 480 nm and an emission wavelength of, for example, about 520 nm. The fluorescence values of the reagent blank are subtracted from that of each of the samples and the percentage of free circRNA is determined by dividing the fluorescence intensity of the intact sample (without addition of Triton X-100) by the fluorescence value of the disrupted sample (caused by the addition of Triton X-100). C.

In Vivo Formulation Studies:

In order to monitor how effectively various nanoparticle compositions deliver circRNA to targeted cells, different nanoparticle compositions including circRNA are prepared and administered to rodent populations. Mice are intravenously, intramuscularly, intraarterially, or intratumorally administered a single dose including a nanoparticle composition with a lipid nanoparticle formulation. In some instances, mice may be made to inhale doses. Dose sizes may range from 0.001 mg/kg to 10 mg/kg, where 10 mg/kg describes a dose including 10 mg of a circRNA in a nanoparticle composition for each 1 kg of body mass of the mouse. A control composition including PBS may also be employed.

Upon administration of nanoparticle compositions to mice, dose delivery profiles, dose responses, and toxicity of particular formulations and doses thereof can be measured by enzyme-linked immunosorbent assays (ELISA), bioluminescent imaging, or other methods. Time courses of protein expression can also be evaluated. Samples collected from the rodents for evaluation may include blood and tissue (for example, muscle tissue from the site of an intramuscular injection and internal tissue); sample collection may involve sacrifice of the animals.

Higher levels of protein expression induced by administration of a composition including a circRNA will be indicative of higher circRNA translation and/or nanoparticle composition circRNA delivery efficiencies. As the non-RNA components are not thought to affect translational machineries themselves, a higher level of protein expression is likely indicative of a higher efficiency of delivery of the circRNA by a given nanoparticle composition relative to other nanoparticle compositions or the absence thereof.

Example 27

Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the transfer vehicle compositions in 1×PBS in determining particle size and 15 mM PBS in determining zeta potential.

Ultraviolet-visible spectroscopy can be used to determine the concentration of a therapeutic and/or prophylactic (e.g., RNA) in transfer vehicle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, Calif.). The concentration of therapeutic and/or prophylactic in the transfer vehicle composition can be calculated based on the extinction coefficient of the therapeutic and/or prophylactic used in the composition and on the difference between the absorbance at a wavelength of, for example, 260 nm and the baseline value at a wavelength of, for example, 330 nm.

For transfer vehicle compositions including RNA, a QUANT-IT™ RIBOGREEN® RNA assay (Invitrogen Corporation Carlsbad, Calif.) can be used to evaluate the encapsulation of RNA by the transfer vehicle composition. The samples are diluted to a concentration of approximately 5 μg/mL or 1 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2-4% Triton X-100 solution is added to the wells. The plate is incubated at a temperature of 37° C. for 15 minutes. The RIBOGREEN® reagent is diluted 1:100 or 1:200 in TE buffer, and 100 μL of this solution is added to each well. The fluorescence intensity can be measured using a fluorescence plate reader (Wallac Victor 1420 Multilablel Counter; Perkin Elmer, Waltham, Mass.) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Example 28

T Cell Targeting

To target transfer vehicles to T-cells, T cell antigen binders, e.g., anti-CD8 antibodies, are coupled to the surface of the transfer vehicle. Anti-T cell antigen antibodies are mildly reduced with an excess of DTT in the presence of EDTA in PBS to expose free hinge region thiols. To remove DTT, antibodies are passed through a desalting column. The heterobifunctional cross-linker SM(PEG)24 is used to anchor antibodies to the surface of circRNA-loaded transfer vehicles (Amine groups are present in the head groups of PEG lipids, free thiol groups on antibodies were created by DTT, SM(PEG)24 cross-links between amines and thiol groups). Transfer vehicles are first incubated with an excess of SM(PEG)24 and centrifuged to remove unreacted cross-linker. Activated transfer vehicles are then incubated with an excess of reduced anti-T cell antigen antibody. Unbound antibody is removed using a centrifugal filtration device.

Example 29

RNA Containing Transfer Vehicle Using RV88.

In this example RNA containing transfer vehicles are synthesized using the 2-D vortex microfluidic chip with the cationic lipid RV88 for delivery of circRNA.

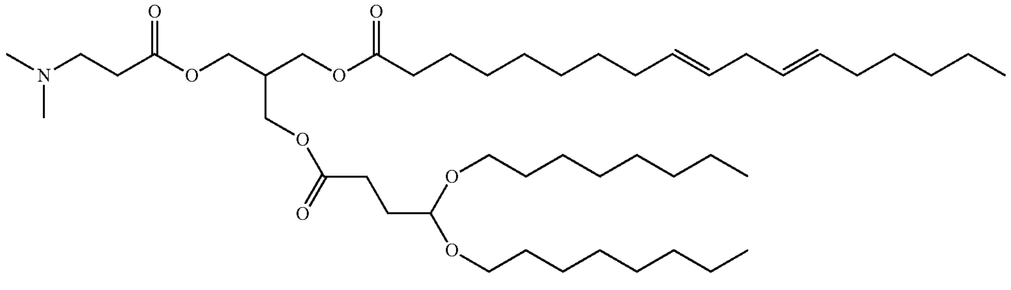

RV88

TABLE 32a

| Material and Insturment | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787-100ML |
| RV88 | GVK bio | |
| DSPC | Lipoid | 558500 |
| Cholesterol | Sigma | C3045-5G |
| PEG2K | Avanti Polar Lipids | 880150 |
| Ethanol | Acros Organic | 615090010 |
| 5 mL Borosilicate glass vials | Thermo Scientific | ST5-20 |

TABLE 32a-continued

| Material and Insturment | Vendor | Cat # |
|---|---|---|
| PD MiniTrap G-25 Desalting Columns | GE Healthcare | VWR Cat. #95055-984 |
| Quant-iT RiboGreen RNA Assay kit | Molecular Probes/Life Technologies | R11490 |
| Black 96-well microplates | Greiner | 655900 |

RV88, DSPC, and cholesterol all being prepared in ethanol at a concentration of 10 mg/ml in borosilica vials. The lipid 14:0-PEG2K PE is prepared at a concentration of 4 mg/ml also in a borosilica glass vial. Dissolution of lipids at stock concentrations is attained by sonication of the lipids in ethanol for 2 min. The solutions are then heated on an orbital tilting shaker set at 170 rpm at 37° C. for 10 min. Vials are then equilibrated at 26° C. for a minimum of 45 min. The lipids are then mixed by adding volumes of stock lipid as shown in Table 32b. The solution is then adjusted with ethanol such that the final lipid concentration was 7.92 mg/ml.

TABLE 32b

| Composition | MW | % | nmoles | mg | Stock (mg/ml) | ul | Ethanol (ul) |
|---|---|---|---|---|---|---|---|
| RV88 | 794.2 | 40% | 7200 | 5.72 | 10 | 571.8 | 155.3 |
| DSPC | 790.15 | 10% | 1800 | 1.42 | 10 | 142.2 | |
| Cholesterol | 386.67 | 48% | 8640 | 3.34 | 10 | 334.1 | |
| PEG2K | 2693.3 | 2% | 380 | 0.97 | 4 | 242.4 | |

RNA is prepared as a stock solution with 75 mM Citrate buffer at pH 6.0 and a concentration of RNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the ethanolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the RNA-liposomes is exchanged by using G-25 mini desalting columns to 10 mM Tris-HCl, 1 mM EDTA, at pH 7.5. Following buffer exchange, the materials are characterized for size, and RNA entrapment through DLS analysis and Ribogreen assays, respectively.

Example 30

RNA Containing Transfer Vehicle Using RV94.

In this example, RNA containing liposome are synthesized using the 2-D vortex microfluidic chip with the cationic lipid RV94 for delivery of circRNA.

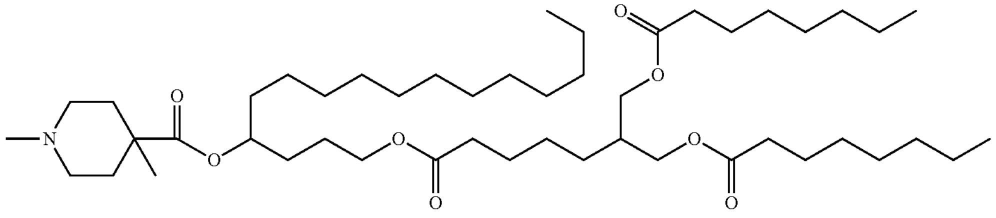

RV94

TABLE 33

| Material and Insturment | Vendor | Cat # |
|---|---|---|
| 1M Tris-HCl, pH 8.0, Sterile | Teknova | T1080 |
| 5M Sodium Chloride solution | Teknova | S0250 |
| QB Citrate buffer, pH 6.0 (100 mM) | Teknova | Q2446 |
| Nuclease-free water | Ambion | AM9937 |
| Triton X-100 | Sigma-Aldrich | T8787-100ML |
| RV94 | GVKbio | |
| DSPC | Lipoid | 556500 |
| Cholesterol | Sigma | C3045-5G |
| PEG2K | Avanti Polar Lipids | 880150 |
| Ethanol | Acros Organic | 615090010 |
| 5 mL Borosilicate glass vials | Thermo Scientific | ST5-20 |
| PD MiniTrap G-25 Desalting Columns | GE Healthcare | VWR Cat. #95055-984 |
| Quant-iT RiboGreen RNA Assay kit | Molecular Probes/Life Technologies | R11490 |
| Black 96-well microplates | Greiner | 655900 |

The lipids were prepared as in Example 29 using the material amounts named in Table 34 to a final lipid concentration of 7.92 mg/ml.

TABLE 34

| Composition | MW | % | nmoles | mg | Stack (mg/ml) | ul | Ethanol (ul) |
|---|---|---|---|---|---|---|---|
| RV94 | 808.22 | 40% | 2880 | 2.33 | 10 | 232.8 | 155.3 |
| DSPC | 790.15 | 10% | 720 | 0.57 | 10 | 56.9 | |
| Cholesterol | 386.67 | 48% | 3456 | 1.34 | 10 | 133.6 | |
| PEG2K | 2693.3 | 2% | 144 | 0.39 | 4 | 97.0 | |

The aqueous solution of circRNA is prepared as a stock solution with 75 mM Citrate buffer at pH 6.0 the circRNA at 1.250 mg/ml. The concentration of the RNA is then adjusted to 0.1037 mg/ml with 75 mM citrate buffer at pH 6.0, equilibrated to 26° C. The solution is then incubated at 26° C. for a minimum of 25 min.

The microfluidic chamber is cleaned with ethanol and neMYSIS syringe pumps are prepared by loading a syringe with the RNA solution and another syringe with the ethanolic lipid. Both syringes are loaded and under the control of neMESYS software. The solutions are then applied to the mixing chip at an aqueous to organic phase ratio of 2 and a total flow rate of 22 ml/min (14.67 ml/min for RNA and 7.33 ml/min for the lipid solution. Both pumps are started synchronously. The mixer solution that flowed from the microfluidic chip is collected in 4×1 ml fractions with the first fraction being discarded as waste. The remaining solution containing the circRNA-transfer vehicles is exchanged by using G-25 mini desalting columns to 10 mM Tris-HCl, 1 mM EDTA, at pH 7.5, as described above. Following buffer exchange, the materials are characterized for size, and RNA entrapment through DLS analysis and Ribogreen assays, respectively. The biophysical analysis of the liposomes is shown in Table 35.

TABLE 35

| Sample Name | N:P Ratio | TFR ml/min | Ratio (aqueous/ org phase) | RNA encapsulation amount (μg/ml) | RNA encapsulation yield % | size d.nm | size PDI |
|---|---|---|---|---|---|---|---|
| SAM-RV94 | 8 | 22 | 2 | 31.46 | 86.9 | 113.1 | 0.12 |

Example 31

General Protocol for in Line Mixing.

Individual and separate stock solutions are prepared—one containing lipid and the other circRNA. Lipid stock containing a desired lipid or lipid mixture, DSPC, cholesterol and PEG lipid is prepared by solubilized in 90% ethanol. The remaining 10% is low pH citrate buffer. The concentration of the lipid stock is 4 mg/mL. The pH of this citrate buffer can range between pH 3 and pH 5, depending on the type of lipid employed. The circRNA is also solubilized in citrate buffer at a concentration of 4 mg/mL. 5 mL of each stock solution is prepared.

Stock solutions are completely clear and lipids are ensured to be completely solubilized before combining with circRNA. Stock solutions may be heated to completely solubilize the lipids. The circRNAs used in the process may be unmodified or modified oligonucleotides and may be conjugated with lipophilic moieties such as cholesterol.

The individual stocks are combined by pumping each solution to a T-junction. A dual-head Watson-Marlow pump was used to simultaneously control the start and stop of the two streams. A 1.6 mm polypropylene tubing is further downsized to 0.8 mm tubing in order to increase the linear flow rate. The polypropylene line (ID=0.8 mm) are attached to either side of a T-junction. The polypropylene T has a linear edge of 1.6 mm for a resultant volume of 4.1 $mm^3$. Each of the large ends (1.6 mm) of polypropylene line is placed into test tubes containing either solubilized lipid stock or solubilized circRNA. After the T-junction, a single tubing is placed where the combined stream exited. The tubing is then extended into a container with 2× volume of PBS, which is rapidly stirred. The flow rate for the pump is at a setting of 300 rpm or 110 mL/min. Ethanol is removed and exchanged for PBS by dialysis. The lipid formulations are then concentrated using centrifugation or diafiltration to an appropriate working concentration.

C57BL/6 mice (Charles River Labs, MA) receive either saline or formulated circRNA via tail vein injection. At various time points after administration, serum samples are collected by retroorbital bleed. Serum levels of Factor VII protein are determined in samples using a chromogenic assay (Biophen FVTI, Aniara Corporation, OH). To determine liver RNA levels of Factor VII, animals are sacrificed and livers are harvested and snap frozen in liquid nitrogen. Tissue lysates are prepared from the frozen tissues and liver RNA levels of Factor VII are quantified using a branched DNA assay (QuantiGene Assay, Panomics, CA).

FVII activity is evaluated in FVTI siRNA-treated animals at 48 hours after intravenous (bolus) injection in C57BL/6 mice. FVII is measured using a commercially available kit for determining protein levels in serum or tissue, following the manufacturer's instructions at a microplate scale. FVII reduction is determined against untreated control mice, and the results are expressed as % Residual FVII. Two dose levels (0.05 and 0.005 mg/kg FVII siRNA) are used in the screen of each novel liposome composition.

Example 32 circRNA Formulation Using Preformed Vesicles.

Cationic lipid containing transfer vehicles are made using the preformed vesicle method. Cationic lipid, DSPC, cholesterol and PEG-lipid are solubilized in ethanol at a molar ratio of 40/10/40/10, respectively. The lipid mixture is added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids are extruded through two stacked 80 nm pore-sized filters (Nuclepore) at 22° C. using a Lipex Extruder (Northern Lipids, Vancouver, BC) until a vesicle diameter of 70-90 nm, as determined by Nicomp analysis, is obtained. For cationic lipid mixtures which do not form small vesicles, hydrating the lipid mixture with a lower pH buffer (50 mM citrate, pH 3) to protonate the phosphate group on the DSPC headgroup helps form stable 70-90 nm vesicles.

The FVII circRNA (solubilised in a 50 mM citrate, pH 4 aqueous solution containing 30% ethanol) is added to the vesicles, pre-equilibrated to 35° C., at a rate of μ5 mL/min with mixing. After a final target circRNA/lipid ratio of 0.06 (wt wt) is achieved, the mixture is incubated for a further 30 min at 35° C. to allow vesicle re-organization and encapsulation of the FVII RNA. The ethanol is then removed and the external buffer replaced with PBS (155 mM NaCl, 3 mM Na2HP04, 1 mM KH2PO4, pH 7.5) by either dialysis or tangential flow diafiltration. The final encapsulated circRNA-to-lipid ratio is determined after removal of unencapsulated RNA using size-exclusion spin columns or ion exchange spin columns.

Example 33

Expression of Trispecific Antigen Binding Proteins from Engineered Circular RNA

Circular RNAs are designed to include: (1) a 3' post splicing group I intron fragment; (2) an Internal Ribosome Entry Site (IRES); (3) a trispecific antigen-binding protein coding region; and (4) a 3' homology region. The trispecific antigen-binding protein regions are constructed to produce an exemplary trispecific antigen-binding protein that will bind to a target antigen, e.g., GPC3.

Generation of a scFv CD3 Binding Domain

The human CD3epsilon chain canonical sequence is Uniprot Accession No. P07766. The human CD3gamma chain canonical sequence is Uniprot Accession No. P09693. The human CD3delta chain canonical sequence is Uniprot Accession No. P043234. Antibodies against CD3epsilon, CD3gamma or CD3delta are generated via known technologies such as affinity maturation. Where murine anti-CD3 antibodies are used as a starting material, humanization of murine anti-CD3 antibodies is desired for the clinical setting, where the mouse-specific residues may induce a human-anti-mouse antigen (HAMA) response in subjects who receive treatment of a trispecific antigen-binding protein described herein. Humanization is accomplished by grafting CDR regions from murine anti-CD3 antibody onto appropriate human germline acceptor frameworks, optionally including other modifications to CDR and/or framework regions.

Human or humanized anti-CD3 antibodies are therefore used to generate scFv sequences for CD3 binding domains of a trispecific antigen-binding protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e. VL-VH, or VH-VL orientation), and three copies of the "G4S" or "$G_4S$" subunit $(G_4S)_3$ connect the variable domains to create the scFv domain. Anti-CD3 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD3-expressing cells.

Generation of a scFv Glypican-3 (GPC3) Binding Domain

Glypican-3 (GPC3) is one of the cell surface proteins present on Hepatocellular Carcinoma but not on healthy normal liver tissue. It is frequently observed to be elevated in hepatocellular carcinoma and is associated with poor prognosis for HCC patients. It is known to activate Wnt signalling. GPC3 antibodies have been generated including MDX-1414, HN3, GC33, and YP7.

A scFv binding to GPC-3 or another target antigen is generated similarly to the above method for generation of a scFv binding domain to CD3.

Expression of Trispecific Antigen-Binding Proteins In Vitro

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted trispecific antigen-binding proteins are generated by transfection of suspension-adapted cells. During selection with the antibiotic Hygromycin B viable cell densities are measured twice a week, and cells are centrifuged and resuspended in fresh selection medium at a maximal density of $0.1\times10^6$viable cells/mL. Cell pools stably expressing trispecific antigen-binding proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Trispecific antigen-binding proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Trispecific Antigen-Binding Proteins

Trispecific antigen-binding proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL Purity and homogeneity (typically >90%) of final samples are assessed by SDS PAGE under reducing and non-reducing conditions, followed by immunoblotting using an anti-(half-life extension domain) or anti idiotype antibody as well as by analytical SEC, respectively. Purified proteins are stored at aliquots at −80° C. until use.

Example 34

Expression of Engineered Circular RNA with a Half-Life Extension Domain has Improved Pharmacokinetic Parameters than without a Half-Life Extension Domain The trispecific antigen-binding protein encoded on a circRNA molecule of example 23 is administered to cynomolgus monkeys as a 0.5 mg/kg bolus injection intramuscularly. Another cynomolgus monkey group receives a comparable protein encoded on a circRNA molecule in size with binding domains to CD3 and GPC-3, but lacking a half-life extension domain. A third and fourth group receive a protein encoded on a circRNA molecule with CD3 and half-life extension domain binding domains and a protein with GPC-3 and half-life extension domains, respectively. Both proteins encoded by circRNA are comparable in size to the trispecific antigen-binding protein. Each test group consists of 5 monkeys. Serum samples are taken at indicated time points, serially diluted, and the concentration of the proteins is determined using a binding ELISA to CD3 and/or GPC-3.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-at}+Be^{-\rho t}$, where c(t) is the plasma concentration at time t, A and B are intercepts on the Y-axis, and a and β are the apparent first-order rate constants for the distribution and elimination phases, respectively. The a-phase is the initial phase of the clearance and reflects distribution of the protein into all extracellular fluid of the animal, whereas the second or 0-phase portion of the decay curve represents true plasma clearance. Methods for fitting such equations are well known in the art. For example, A=D/V(a−k21)/(a−p), B=D/V(p−k21)/(a−p), and α and β (for α>β) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, EST: Handbook Of Basic Pharmacokinetics Including Clinical Applications, 5th edition, American Pharmaceutical Assoc., Washington, D C.

It is expected that the trispecific antigen-binding protein encoded on a circRNA molecule of Example 23 has improved pharmacokinetic parameters such as an increase in elimination half-time as compared to proteins lacking a half-life extension domain.

Example 35

Cytotoxicity of the Trispecific Antigen-Binding Protein

The trispecific antigen-binding protein encoded on a circRNA molecule of Example 23 is evaluated in vitro on its mediation of T cell dependent cytotoxicity to GPC-3+ target cells.

Fluorescence labeled GPC3 target cells are incubated with isolated PBMC of random donors or T-cells as effector cells in the presence of the trispecific antigen-binding protein of Example 23. After incubation for 4 h at 37° C. in a humidified incubator, the release of the fluorescent dye from the target cells into the supernatant is determined in a spectrofluorimeter. Target cells incubated without the trispecific antigen-binding protein of Example 23 and target cells totally lysed by the addition of saponin at the end of the incubation serve as negative and positive controls, respectively.

Based on the measured remaining living target cells, the percentage of specific cell lysis is calculated according to the following formula: [1−(number of living targets(sample)/number of living targets(spontaneous))]×100%. Sigmoidal dose response curves and EC50 values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 36

Synthesis of Ionizable Lipids

38.1 Synthesis of((3-(2-methyl-1H-imidazol-I-yl)propyl)azanediyl)bis(hexane-6,1-diyl) bis(2-hexyldecanoate)(Lipid 27, Table 10a) and ((3-(1H-imidazol-1-yl)propyl)azanediyl)bis(hexane-6,1-diyl) bis(2-hexyldecanoate))(Lipid 26, Table 10a)

In a 100 mL round bottom flask connected with condenser, 3-(1H-imidazol-1-yl)propan-1-amine (100 mg, 0.799 mmol) or 3-(2-methyl-1H-imidazol-1-yl)propan-1-amine (0.799 mmol), 6-bromohexyl 2-hexyldecanoate (737.2 mg, 1.757 mmol), potassium carbonate (485 mg, 3.515 mmol) and potassium iodide (13 mg, 0.08 mmol) were mixed in acetonitrile (30 mL), and the reaction mixture was heated to 80° C. for 48 h. The mixture was cooled to room temperature and was filtered through a pad of Celite. The filtrate was diluted with ethyl acetate. After washing with water, brine and dried over anhydrous sodium sulfate. The solvent was evaporated and the crude residue was purified by flash chromatography ($SiO_2$: $CH_2Cl_2$=100% to 10% of methanol in $CH_2Cl_2$) and colorless oil product was obtained (92 mg, 15%). Molecular formula of ((3-(1H-imidazol-1-yl)propyl)azanediyl)bis(hexane-6,1-diyl) bis(2-hexyldecanoate)) is $C_{50}H_{95}N_3O_4$ and molecular weight ($M_w$) is 801.7.

Reaction scheme for synthesis of ((3-(JH-imidazol-1-yl)propyl)azanediyl)bis(hexane-6,1-diyl) bis(2-hexyldecanoate)) (Lipid 26, Table 10a)

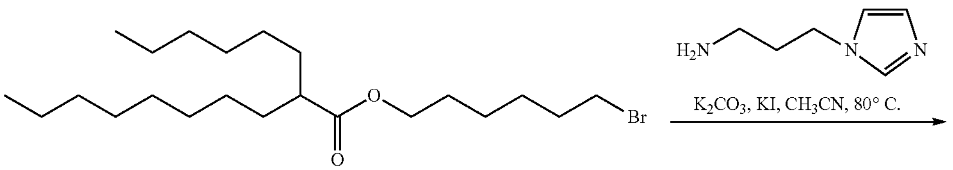

-continued

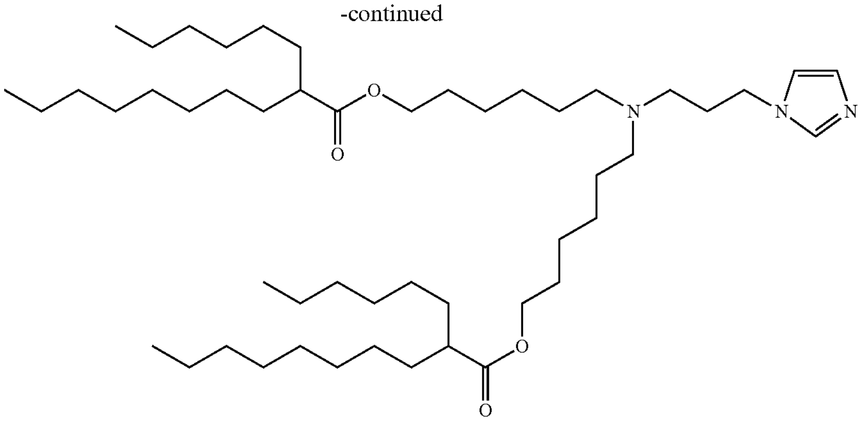

Figure 27A:
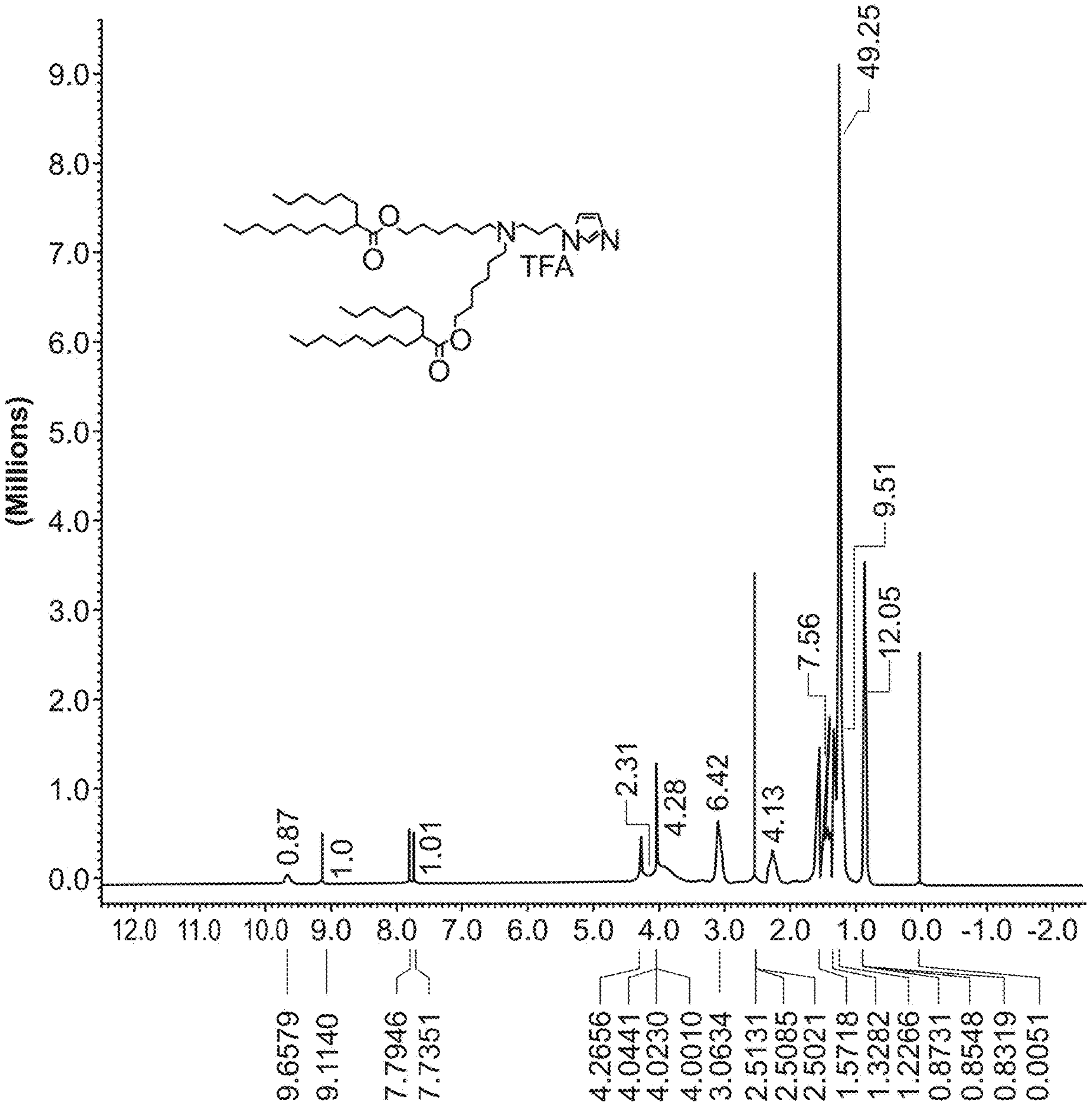
Figure 27B:
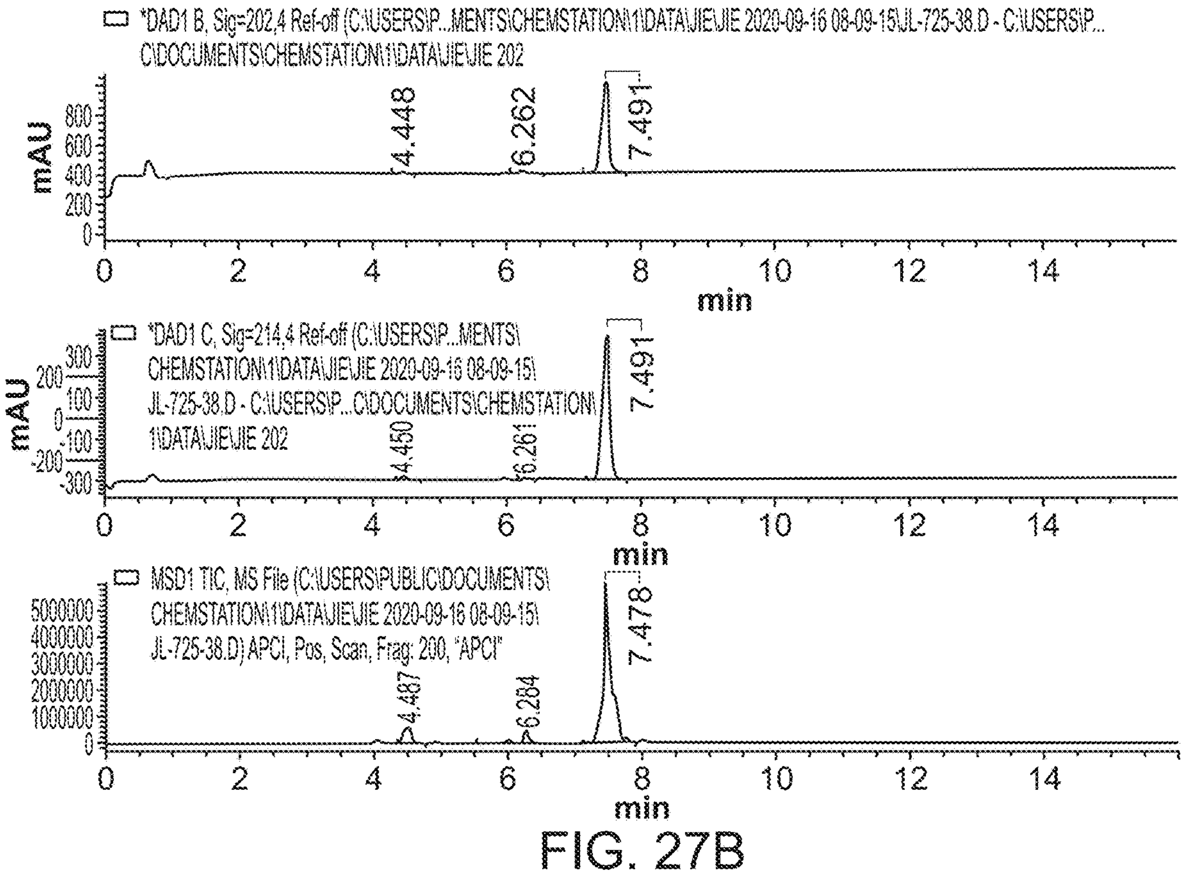
Figure 27C:
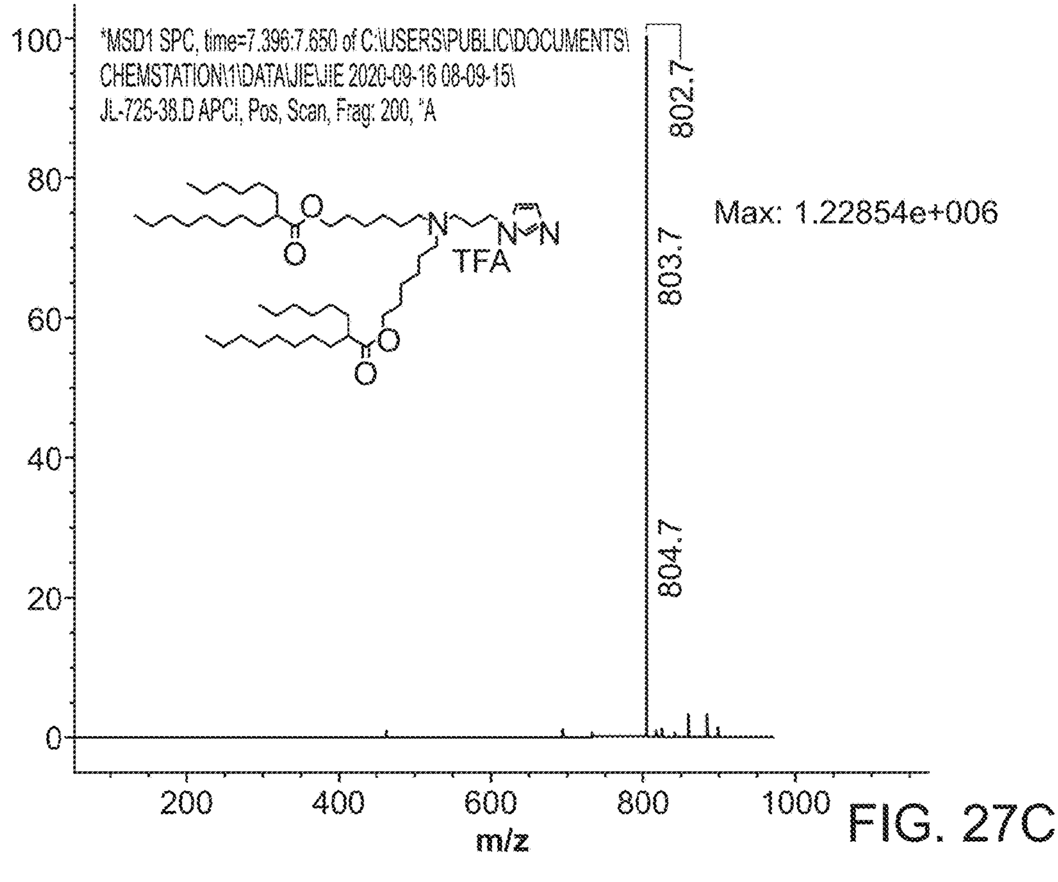
Figure 27D:
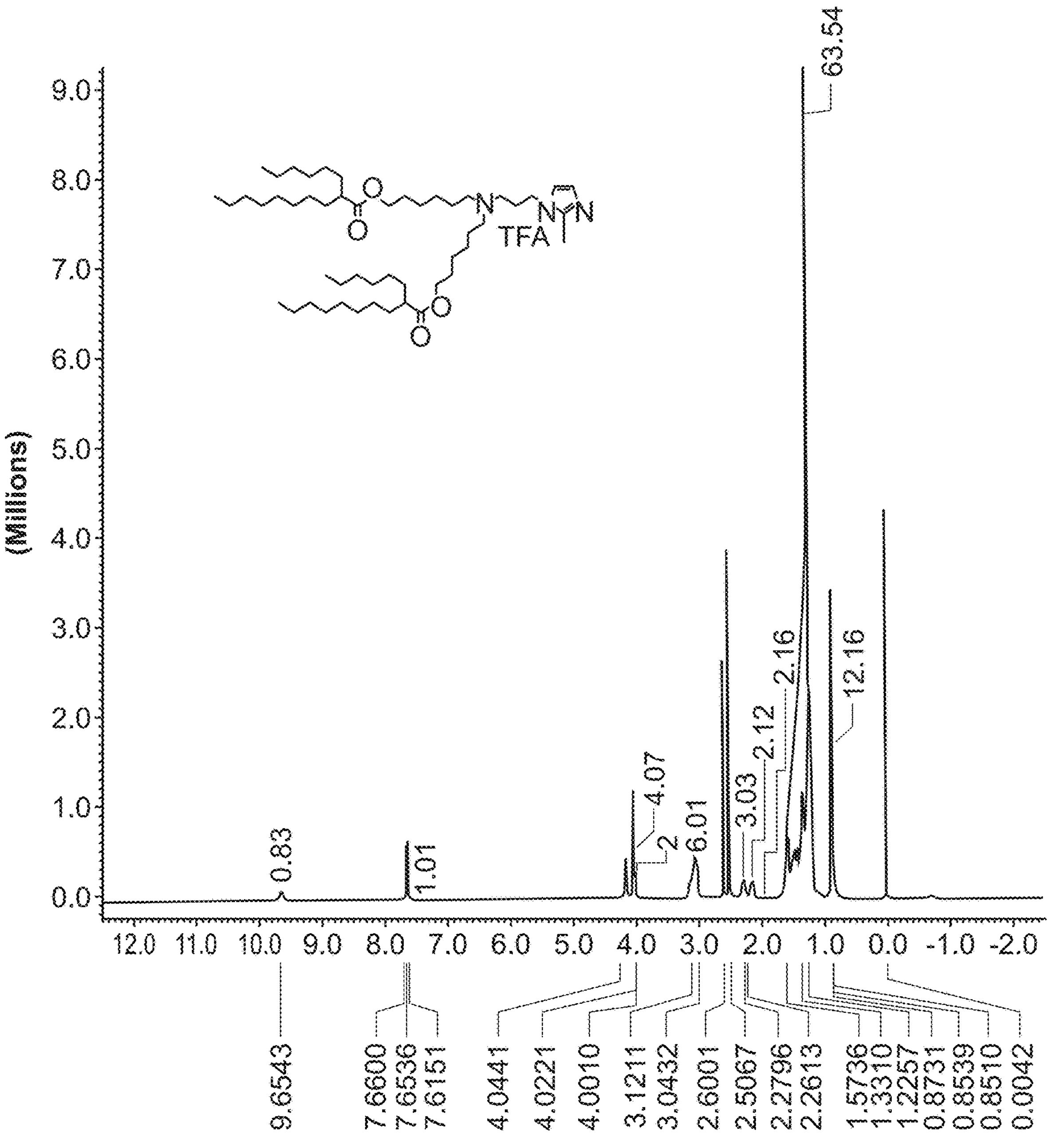
Figure 27E:
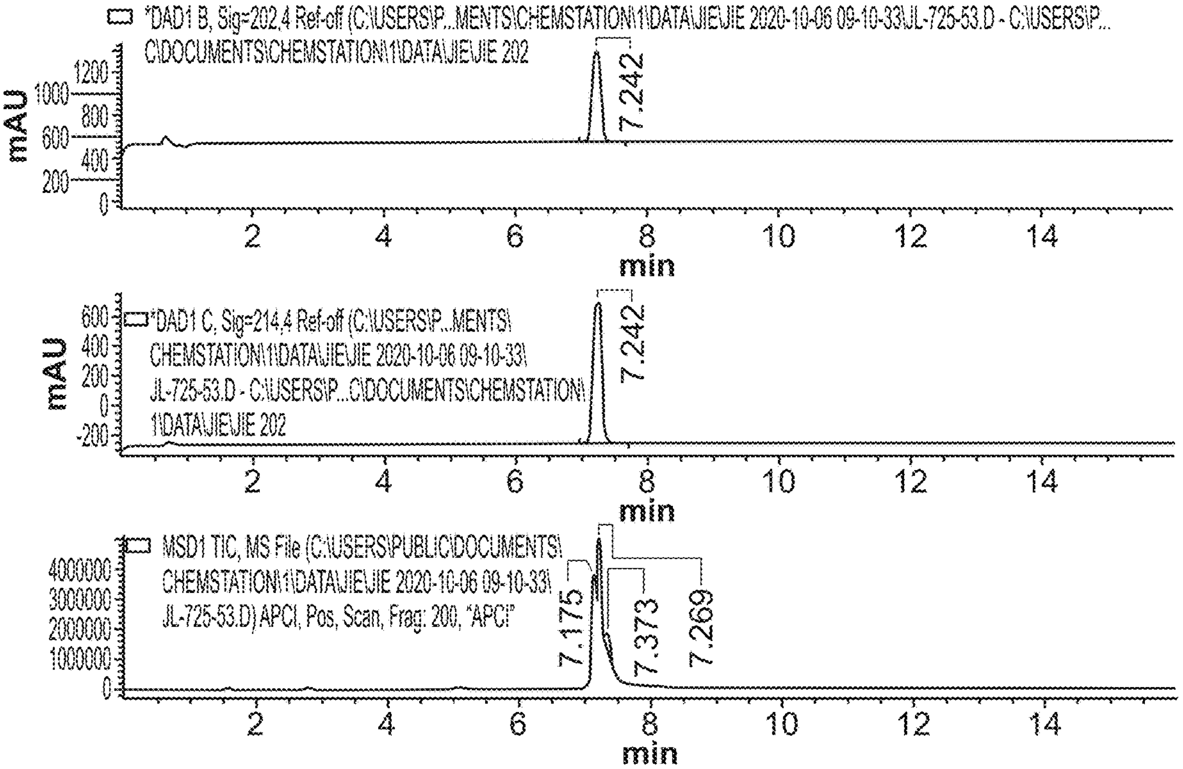
Figure 27F:
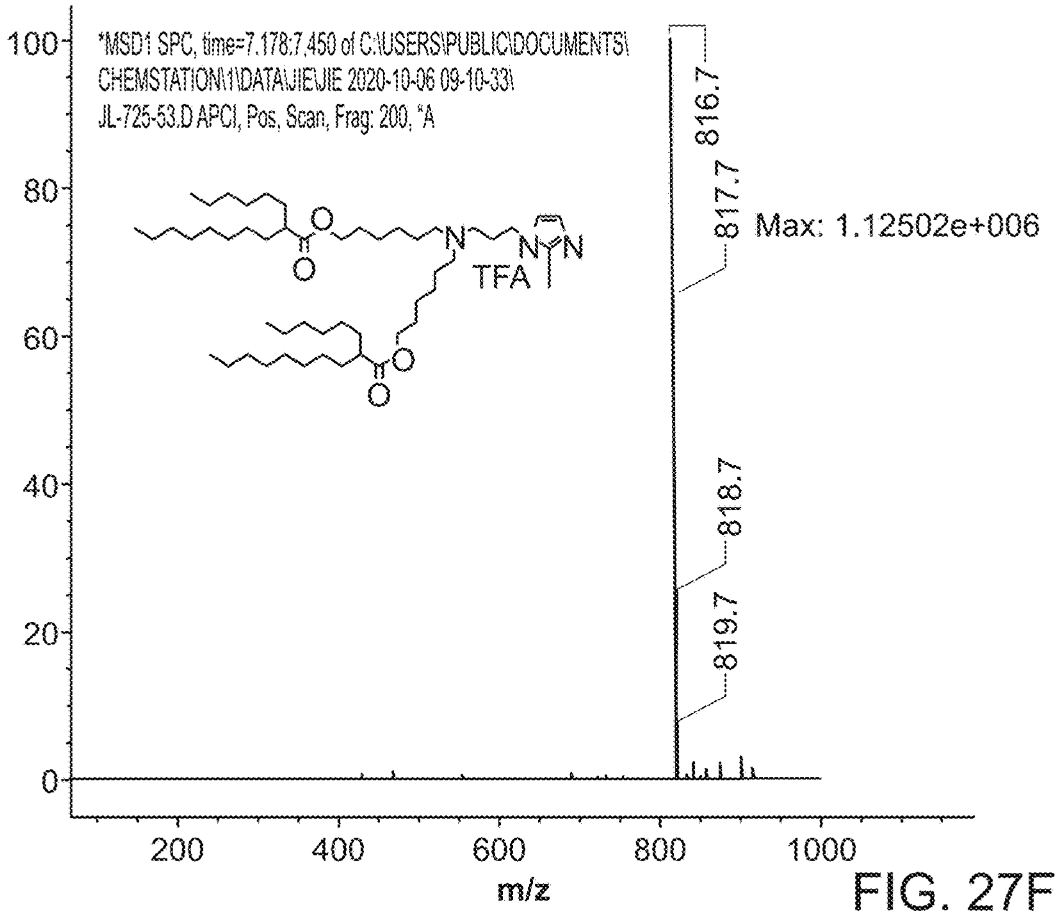

Characterization of Lipid 26 was performed by LC-MS. FIG. 27A-C shows characterization of Lipid 26. FIG. 27A shows the proton NMR observed for Lipid 26. FIG. 27B is a representative LC/MS trace for Lipid 26 with total ion and UV chromatograms shown.

38.2 Synthesis of Lipid 22-S14

38.2.1 Synthesis of 2-(tetradecylthio)ethan-1-ol

To a mixture of 2-sulfanylethanol (5.40 g, 69.11 mmol, 4.82 mL, 0.871 eq) in acetonitrile (200 mL) was added 1-Bromotetradecane(22 g, 79.34 mmol, 23.66 mL, 1 eq) and potassium carbonate (17.55 g, 126.95 mmol, 1.6 eq) at 25° C. The reaction mixture was warmed to 40° C. and stirred for 12 hr. TL C (ethyl acetate/petroleum ether=25/1, $R^c$=0.3, stained by 12) showed the starting material was consumed completely and a new main spot was generated. The reaction mixture was filtered and the filter cake was washed with acetonitrile (50 mL) and then the filtrate was concentrated under vacuum to get a residue which was purified by column on silica gel (ethyl acetate/petroleum ether=1/100 to 1/25) to afford 2-(tetradecylthio)ethan-1-ol (14 g, yield 64.28%) as a white solid.

Figure 28A:
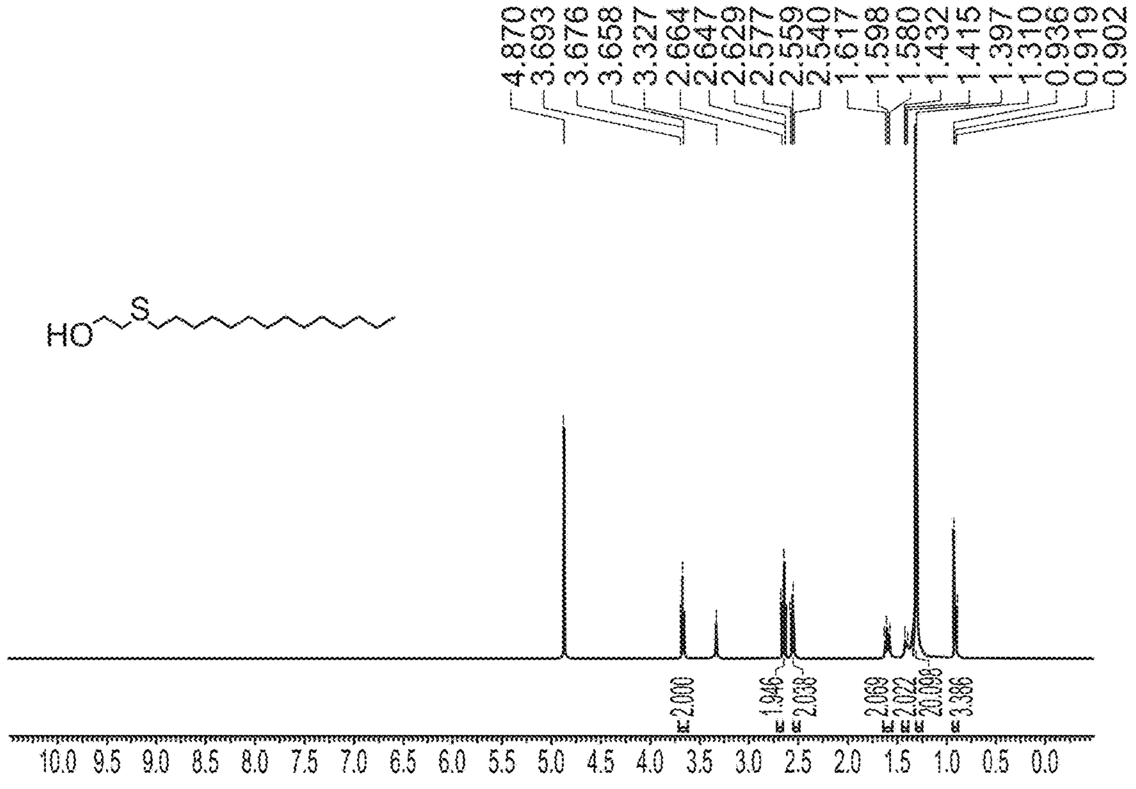
FIGS. 28A, 28B and 28C depicts molecular characterization of Lipid 22-S14 and its synthetic intermediates.
Figure 28B:
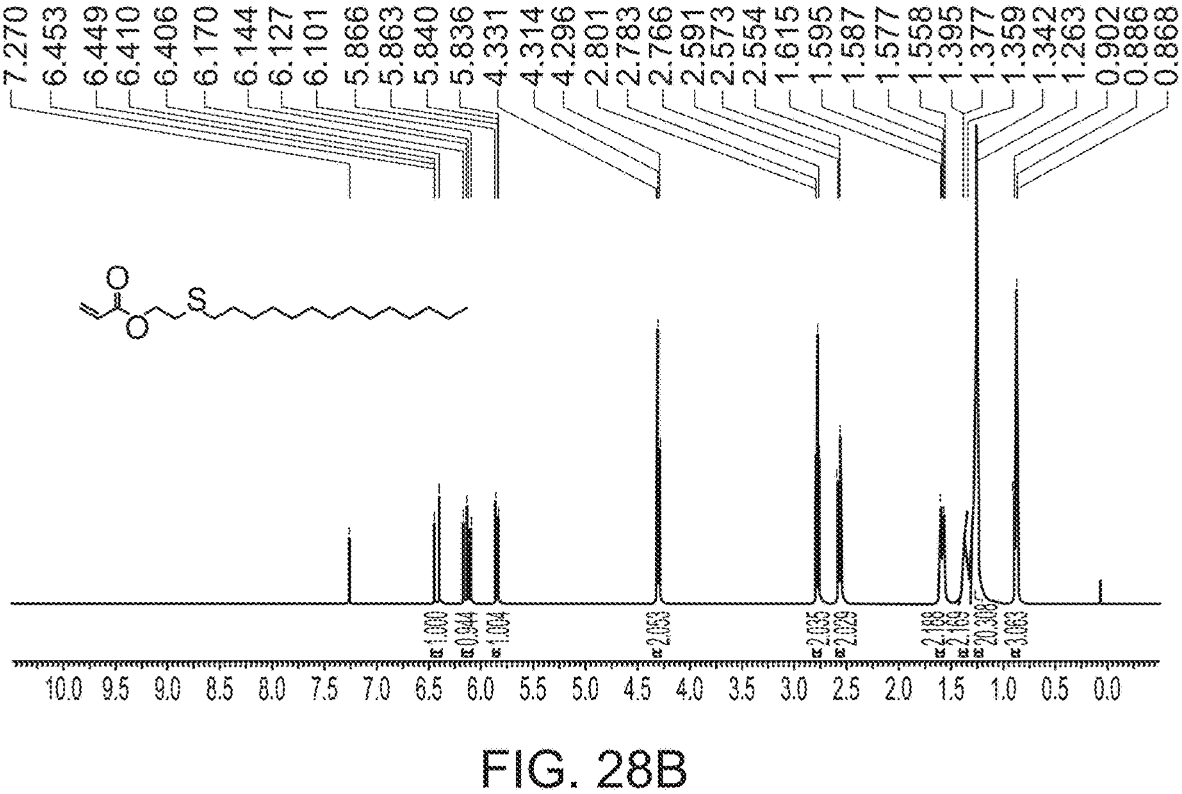
Figure 28C:
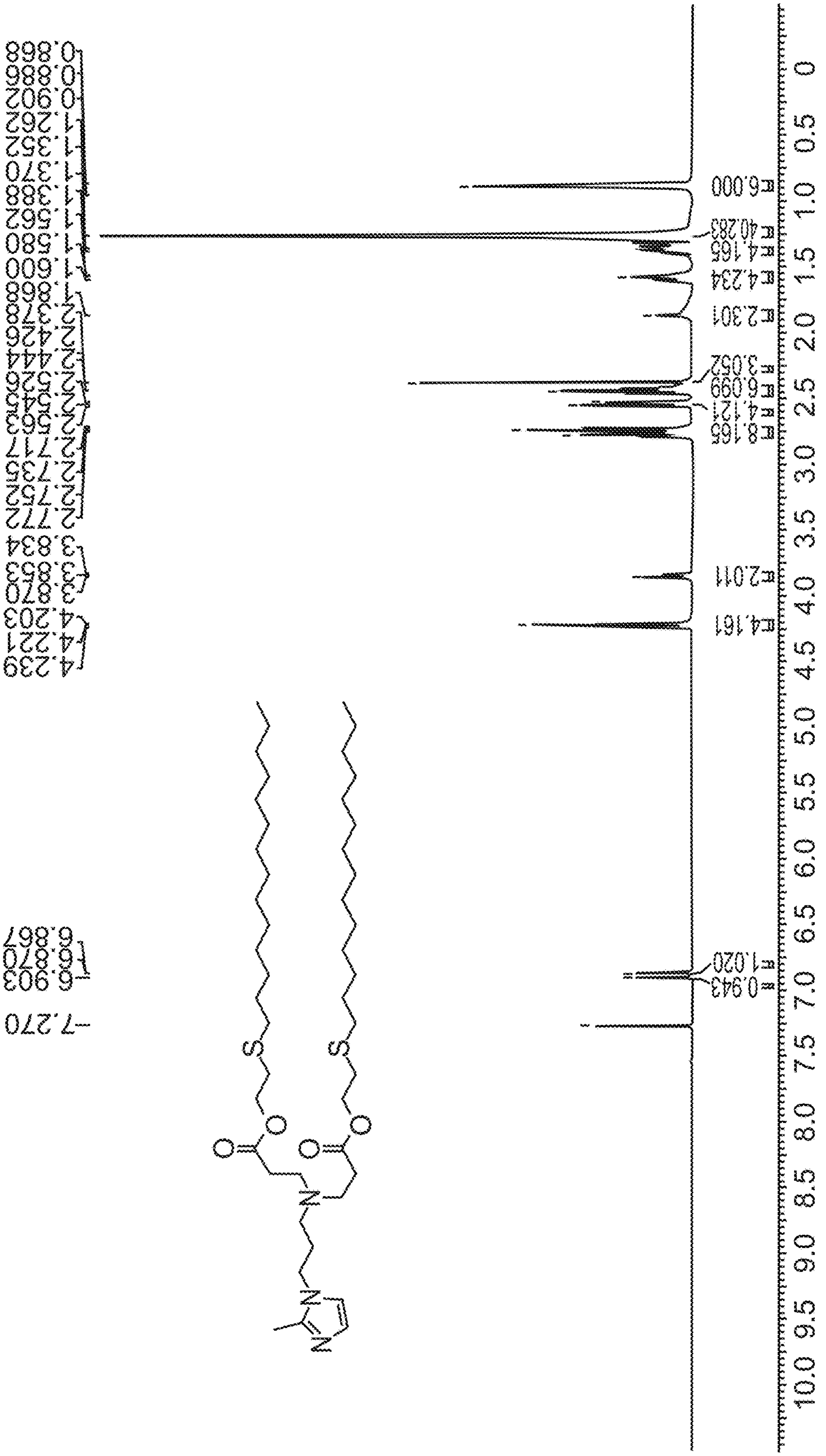

$^1$H NMR (ET363 87-45-P1IA, 400 MHz, CHLOROFORM-d) δ 0.87-0.91 (m, 3H) 1.27 (s, 20H) 1.35-1.43 (m, 2H) 1.53-1.64 (m, 2H) 2.16 (br s, 1H) 2.49-2.56 (m, 2H) 2.74 (t, J=5.93 Hz, 2H) 3.72 (br d, J=4.89 Hz, 2H). FIG. 28 shows corresponding
Nuclear Magnetic Resonance (NMR) Spectrum.

38.2.2 Synthesis of 2-(tetradecylthio)ethyl acrylate

To a solution of 2-(tetradecylthio)ethan-1-ol (14 g, 51.00 mmol, 1 eq) in dichloromethane (240 mL) was added triethylamine (7.74 g, 76.50 mmol, 10.65 mL, 1.5 eq) and prop-2-enoyl chloride (5.54 g, 61.20 mmol, 4.99 mL, 1.2 eq) dropwise at 0° C. under nitrogen. The reaction mixture was warmed to 25° C. and stirred for 12 hr. TLC (ethyl acetate/petroleum ether=25/1, $R^f$=0.5, stained by 12) showed the starting material was consumed completely and a new main spot was generated. The reaction solution was concentrated under vacuum to get crude which was purified by column on silica gel (ethyl acetate/petroleum ether=1/100 to 1/25) to afford 2-(tetradecylthio)ethyl acrylate (12 g, yield 71.61%) as a colorless oil.

Figure 29:
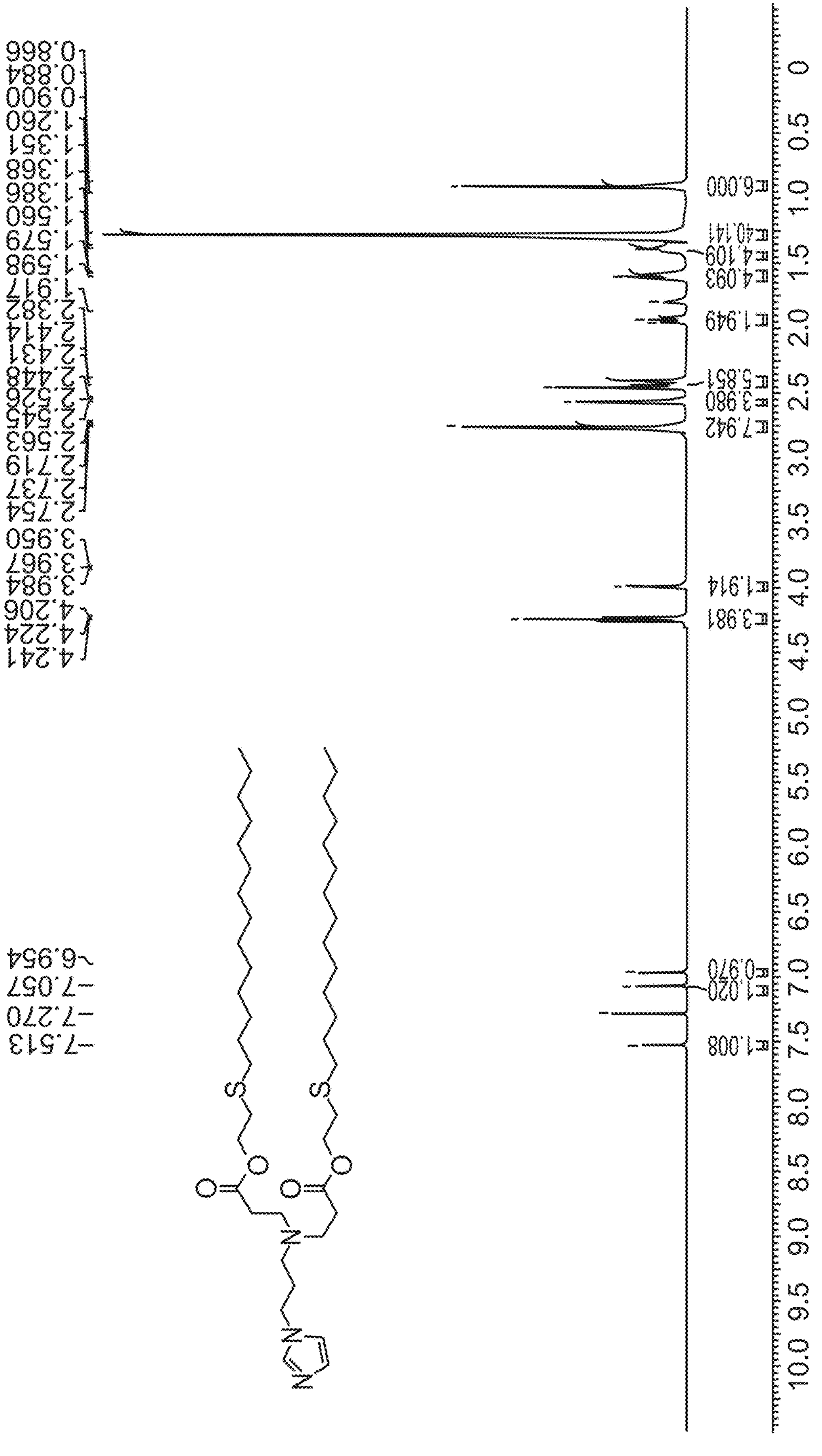
FIG. 29 depicts the NMR spectrum of bis(2-(tetradecylthio)ethyl) 3,3'-((3-(1H-imidazol-1-yl)propyl)azanediyl)dipropionate (Lipid 93-S14).

$^1$H NMR (ET36387-49-P1A, 400 MHz, CHLOROFORM-d) δ 0.85-0.93 (m, 3H) 1.26 (s, 19H) 1.35-1.43 (m, 2H) 1.53-1.65 (m, 2H) 2.53-2.62 (m, 2H) 2.79 (t, J=7.03 Hz, 2H) 4.32 (t, J=7.03 Hz, 2H) 5.86 (dd, J=10.39, 1.47 Hz, 1H) 6.09-6.19 (m, 1H) 6.43 (dd, J=17.30, 1.41 Hz, 1H). FIG. 29 shows corresponding Nuclear Magnetic Resonance (NMR) spectrum.

38.2.3 Synthesis of bis(2-(tetradecylthio)ethyl) 3,3'-((3-(2-methyl-1H-imidazol-1 -yl)propyl)azanediyl) dipropionate (Lipid 22-S14)

A flask was charged with 3-(2-methyl-1H-imidazol-1-yl) propan-1-amine (300 mg, 2.16 mmol) and 2-(tetradecylthio) ethyl acrylate (1.70 g, 5.17 mmol). The neat reaction mixture was heated to 80° C. and stirred for 48 hr. TLC (ethyl acetate, $R^f$=0.3, stained by 12, one drop ammonium hydroxide added) showed the starting material was consumed completely and a new main spot was formed. The reaction mixture was diluted with dichloromethane (4 mL) and purified by column on silica gel (petroleum ether/ethyl acetate=3/1 to 0/1, 0.1% ammonium hydroxide added) to get bis(2-(tetradecylthio)ethyl) 3,3'-((3-(2-methyl-1H-imidazol-1-yl)propyl)azanediyl)dipropionate (501 mg, yield 29.1%) as colorless oil.

Figure 30A:
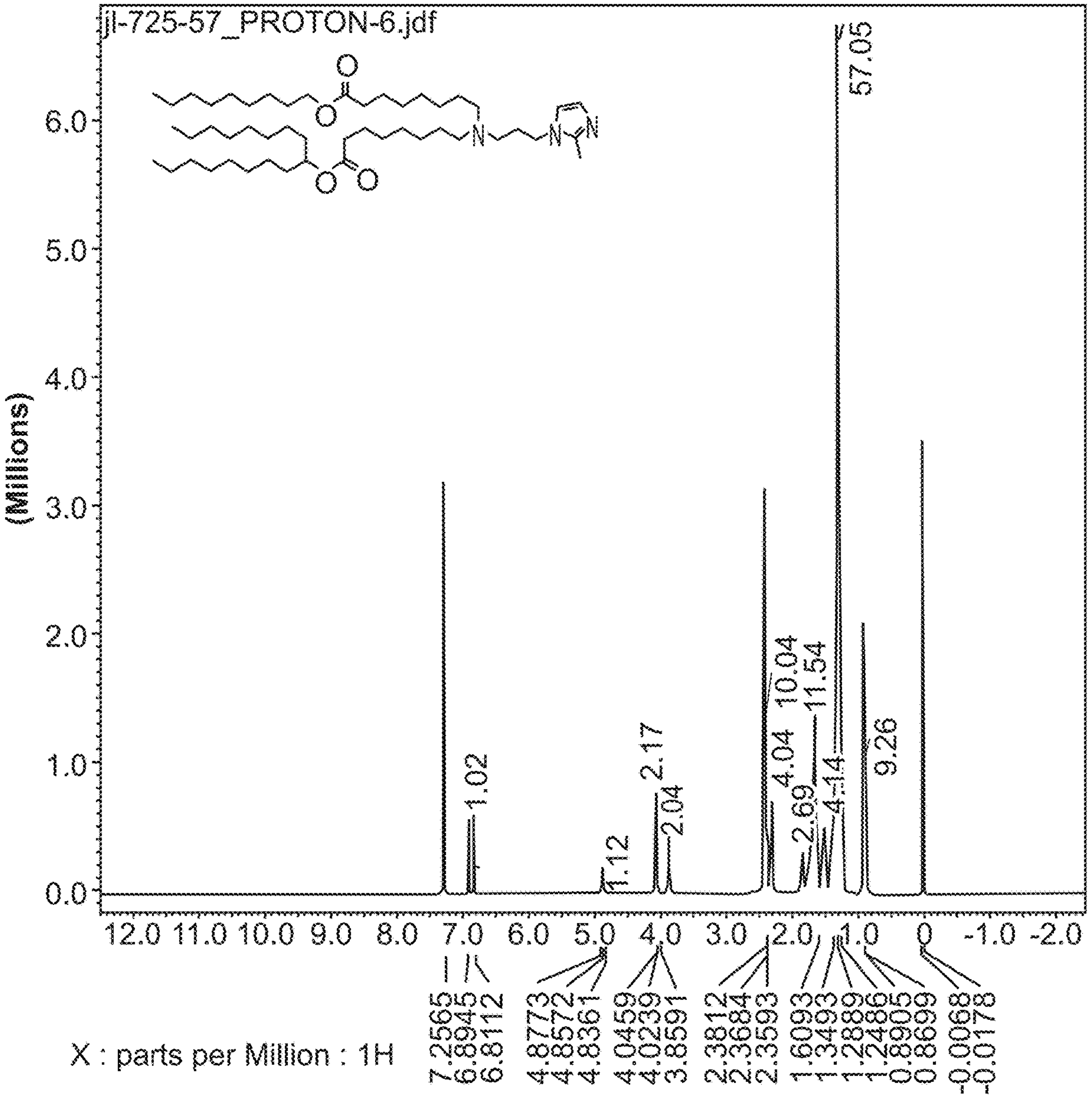
FIGS. 30A, 30B and 30C depicts molecular characterization of heptadecan-9-yl 8-((3-(2-methyl-1H-imidazol-1-yl)propyl)(8-(nonyloxy)-8-oxooctyl)amino)octanoate (Lipid 54 from Table 10a).
Figure 30B:
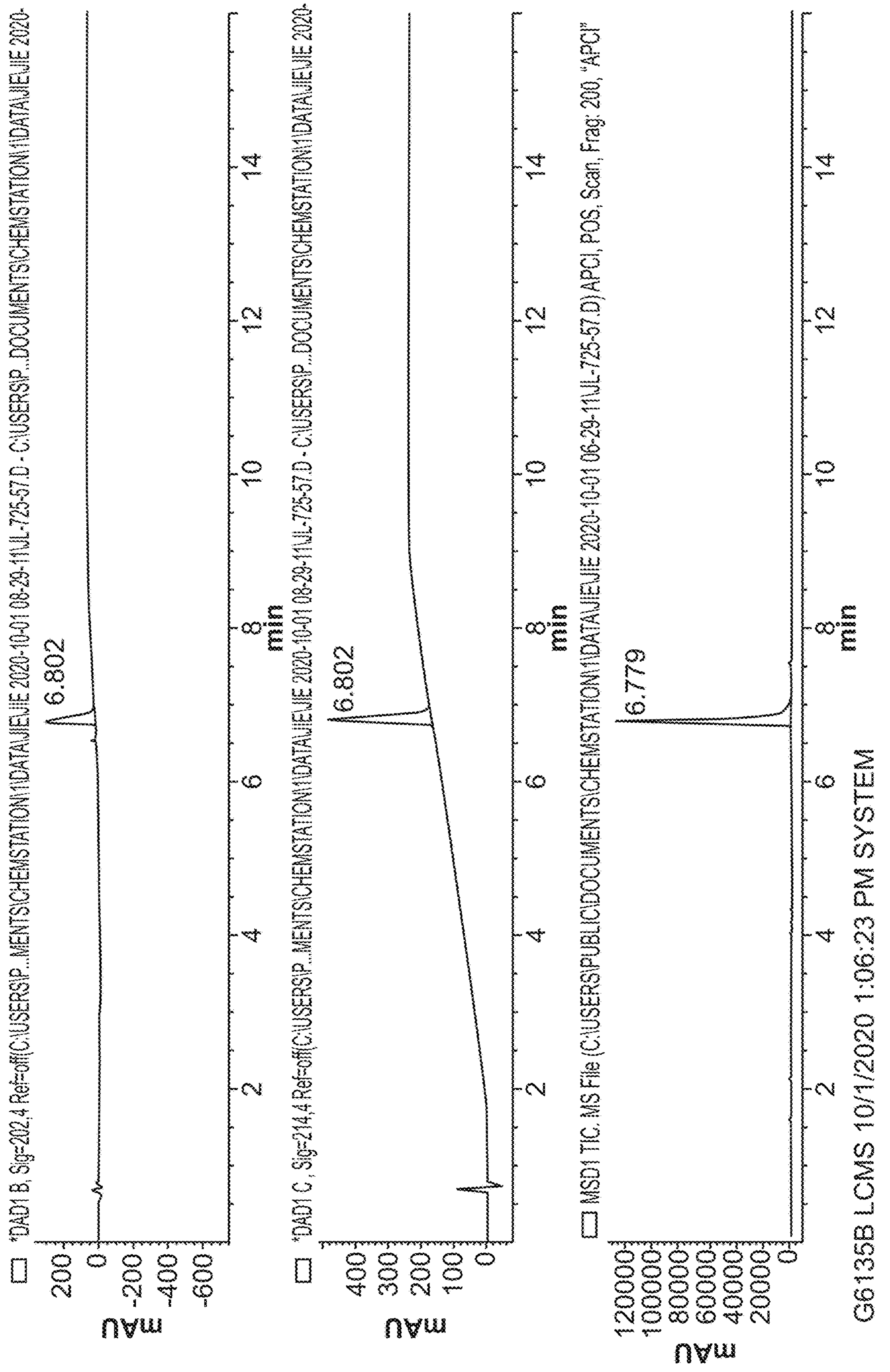
Figure 30C:
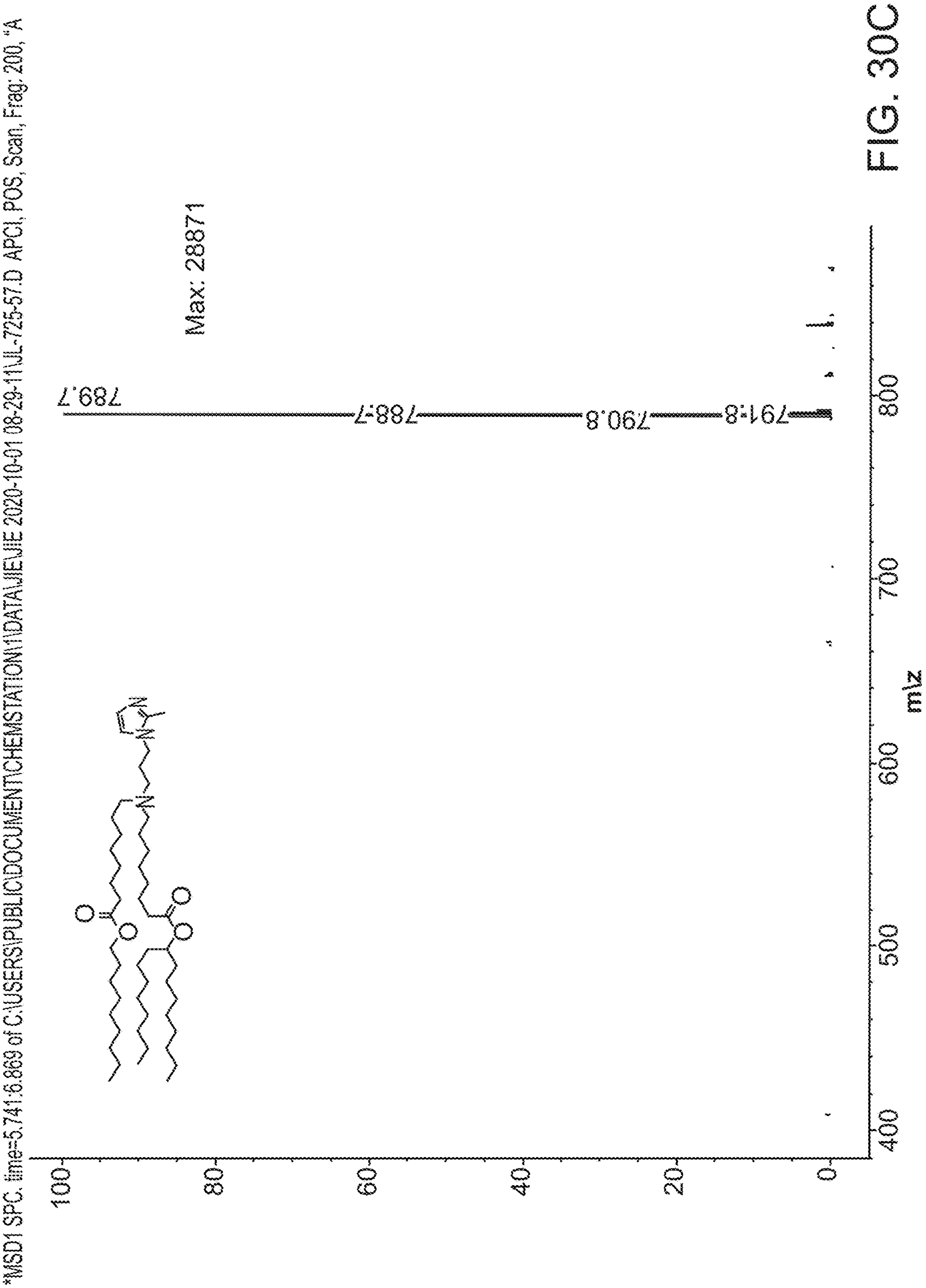

$^1$H NMR (ET36387-51-P1A, 400 MHz, CHLOROFORM-d) δ0.87 (t, J=6.73 Hz, 6H) 1.25 (s, 40H) 1.33-1.40 (m, 4H) 1.52-1.61 (m, 4H) 1.81-1.90 (m, 2H) 2.36 (s, 3H) 2.39-2.46 (m, 6H) 2.53 (t, J=7.39 Hz, 4H) 2.70-2.78 (m, 8H) 3.84 (t, J=7.17 Hz, 2H) 4.21 (t, J=6.95 Hz, 4H) 6.85 (s, 1H) 6.89 (s, 1H). FIG. 30 shows corresponding Nuclear Magnetic Resonance (NMR) spectrum.

38.3 Synthesis of bis(2-(tetradecylthio)ethyl) 3,3'-((3-(1H-imidazol-1-yl)propyl)azanediyl)dipropionate (Lipid 93-S14)

A flask was charged with 3-(1H-imidazol-1-yl)propan-1-amine (300 mg, 2.40 mmol, 1 eq) and 2-(tetradecylthio)ethyl acrylate (1.89 g, 5.75 mmol, 2.4 eq). The neat reaction mixture was heated to 80° C. and stirred for 48 hr. TLC (ethyl acetate, $R^f$=0.3, stained by $\mathbf{1}_2$, one drop ammonium hydroxide added) showed the starting material was consumed completely and a new main spot was formed. The reaction mixture was diluted with dichloromethane (4 mL) and purified by column on silica gel (petroleum ether/ethyl acetate=1/20-0/100, 0.1% ammonium hydroxide added) to get bis(2-(tetradecylthio)ethyl) 3,3'-((3-(1H-imidazol-1-yl) propyl)azanediyl)dipropionate (512 mg, yield 27.22%) as colorless oil.

Figure 31A:
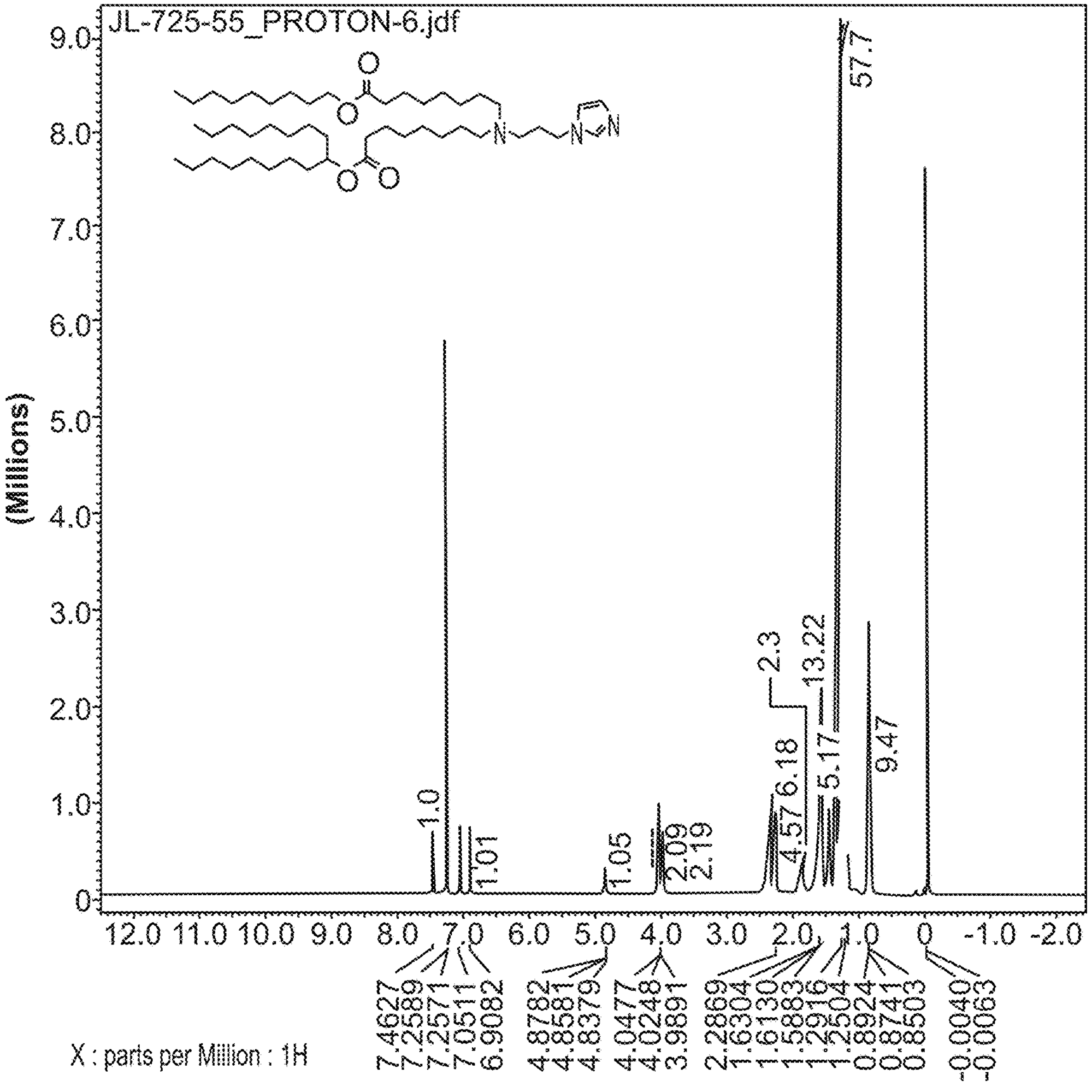
FIGS. 31A, 31B and 31C depicts molecular characterization of heptadecan-9-yl 8-((3-(1H-imidazol-1-yl)propyl)(8-(nonyloxy)-8-oxooctyl)amino)octanoate (Lipid 53 from Table 10a).
Figure 31B:
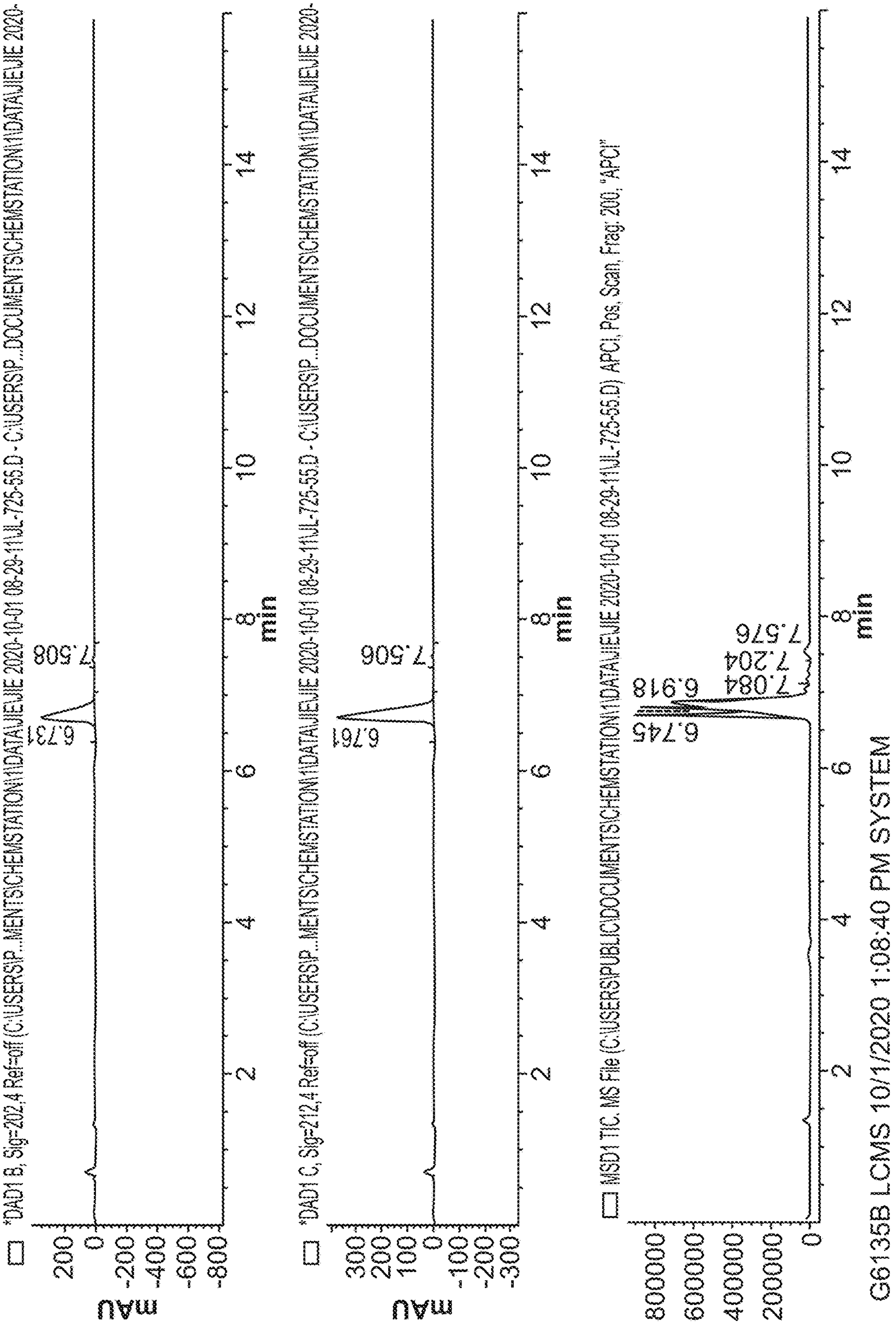
Figure 31C:
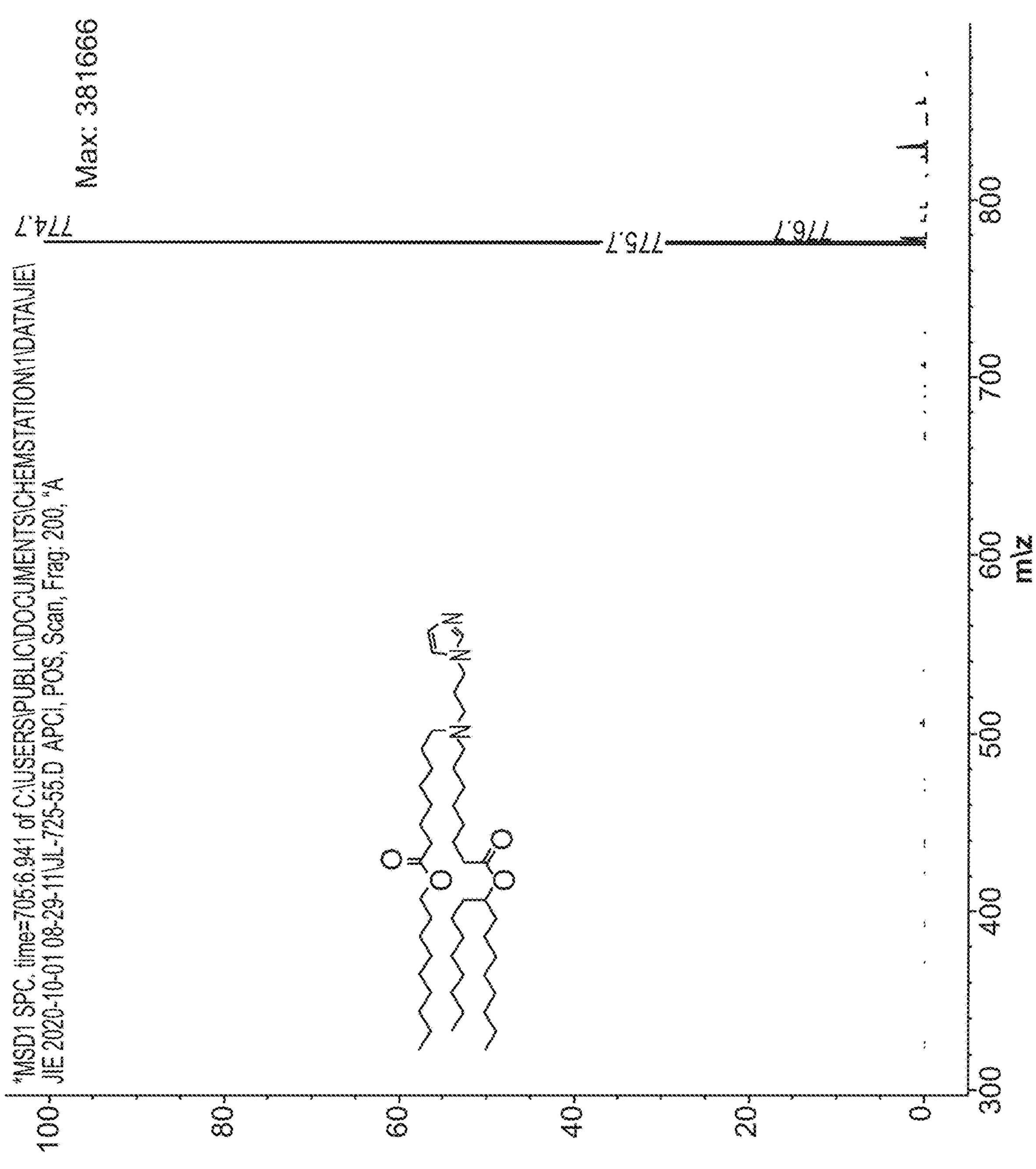

$^1$H NMR (ET36387-54-P1A, 400 MHz, CHLOROFORM-d) δ 0.89 (t, J=6.84 Hz, 6H) 1.26 (s, 40H) 1.34-1.41 (m, 4H) 1.58 (br t, J=7.50 Hz, 4H) 1.92 (t, J=6.62 Hz, 2H) 2.36-2.46 (m, 6H) 2.55 (t, J=7.50 Hz, 4H) 2.75 (q, J=6.84 Hz, 8H) 3.97 (t, J=6.95 Hz, 2H) 4.23 (t, J=6.95 Hz, 4H) 6.95 (s, 1H) 7.06 (s, 1H) 7.51 (s, 1H). FIG. 31 shows corresponding Nuclear Magnetic Resonance (NMR) spectrum.

38.4 Synthesis of heptadecan-9-yl 8-((3-(2-methyl-1H-imidazol-1-yl)propyl)(8-(nonyloxy)-8-oxooctyl)amino)octanoate (Lipid 54, Table 10a)

38.4.1 Synthesis of nonyl 8-bromooctanoate (3)

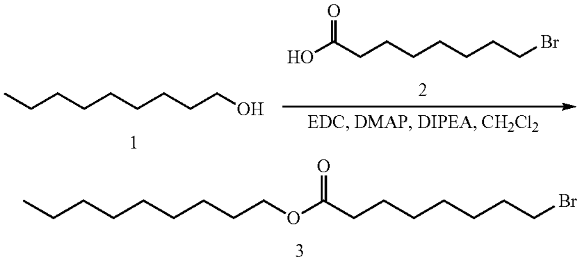

To a mixture of 8-bromooctanoic acid (2) (18.6 g, 83.18 mmol) and nonan-1-ol (1) (10 g, 69.32 mmol) in $CH_2Cl_2$ (500 mL) was added DMAP (1.7 g, 13.86 mmol), DIPEA (48 mL, 277.3 mmol) and EDC (16 g, 83.18 mmol). The reaction was stirred at room temperature overnight. After concentration of the reaction mixture, the crude residue was dissolved in ethyl acetate (500 mL), washed with 1N HCl, sat. $NaHCO_3$, water and Brine. The organic layer was dried over anhydrous $Na_2SO_4$. The solvent was evaporated and the crude residue was purified by flash chromatography ($SiO_2$: Hexane=100% to 30% of EtOAc in Hexane) and colorless oil product 3 was obtained (9 g, 37%). 38.4.2 Synthesis of heptadecan-9-yl 8-bromooctanoate (5)

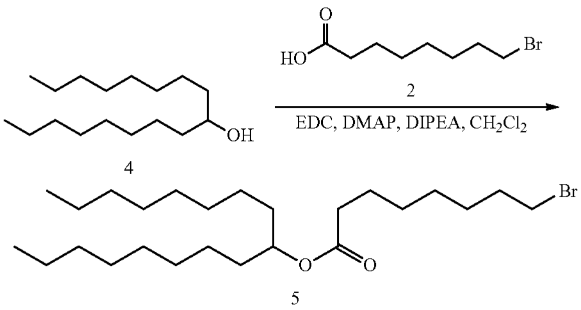

To a mixture of 8-bromooctanoic acid (2) (10 g, 44.82 mmol) and heptadecan-9-ol (4) (9.6 g, 37.35 mmol) in $CH_2Cl_2$ (300 mL) was added DMAP (900 mg, 7.48 mmol), DIPEA (26 mL, 149.7 mmol) and EDC (10.7 g, 56.03 mmol). The reaction was stirred at room temperature overnight. After concentration of the reaction mixture, the crude residue was dissolved in ethyl acetate (300 mL), washed with 1N HCl, sat. $NaHCO_3$, water and Brine. The organic layer was dried over anhydrous $Na_2SO_4$. The solvent was evaporated and the crude residue was purified by flash chromatography ($SiO_2$: Hexane=100% to 30% of EtOAc in Hexane) and colorless oil product 5 was obtained (5 g, 29%).

38.4.3 Synthesis of heptadecan-9-yl 8-((3-(2-methyl-1H-imidazol-1-yl)propyl)amino)octanoate (7)

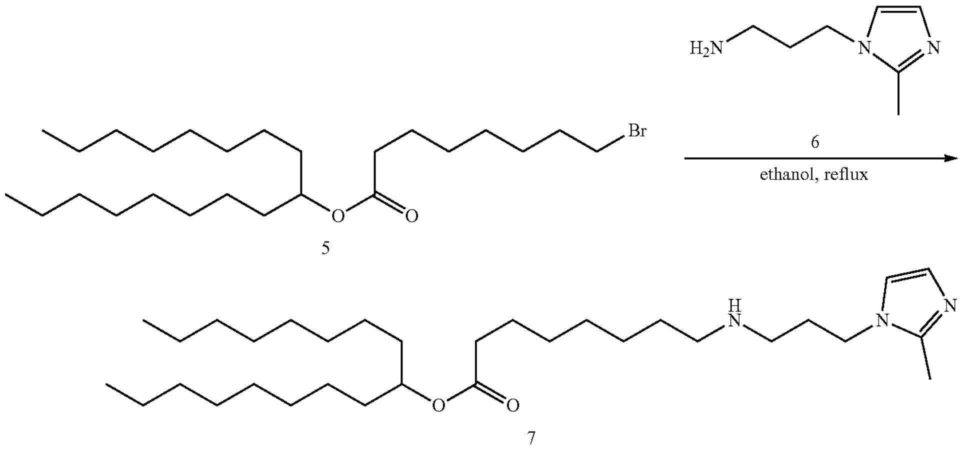

In a 100 mL round bottom flask connected with condenser, heptadecan-9-yl 8-bromooctanoate (5) (860 mg, 1.868 mmol) and 3-(2-methyl-1H-imidazol-1-yl)propan-1-amine (6) (1.3 g, 9.339 mmol) were mixed in ethanol (10 mL). The reaction mixture was heated to reflux overnight. MS (APCI) showed the expected product. The mixture was cooled to room temperature and concentrated. The crude residue was purified by flash chromatography ($SiO_2$: $CH_2Cl_2$=100% to 10% of methanol+1% $NH_4OH$ in $CH_2Cl_2$) and colorless oil product 7 was obtained (665 mg, 69%).

38.4.4 Synthesis of heptadecan-9-yl 8-((3-(2-methyl-1H-imidazol-1-yl)propyl)(8-(nonyloxy)-8-oxooctyl)amino)octanoate (Lipid 54, Table 10a)

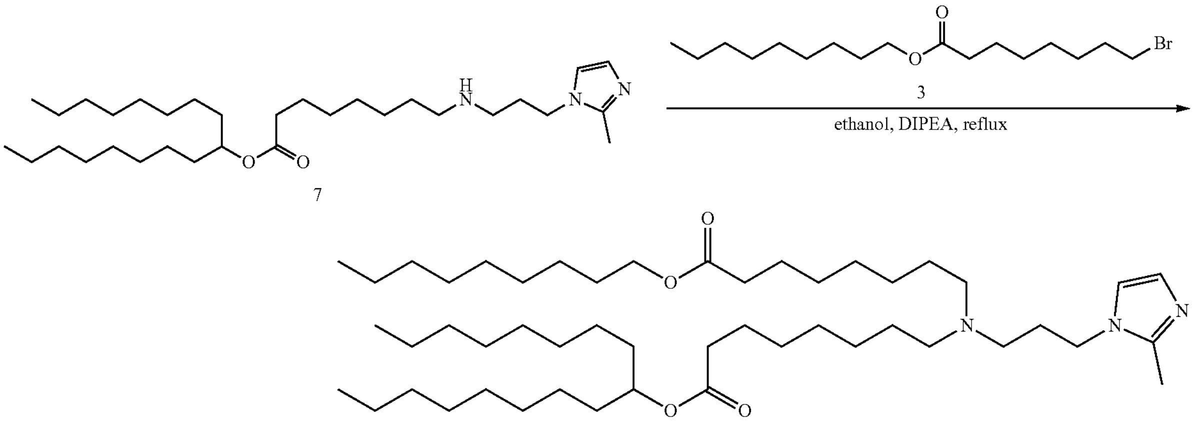

In a 100 mL round bottom flask connected with condenser, heptadecan-9-yl 8-((3-(2-methyl-1H-imidazol-1-yl)propyl)amino)octanoate (7) (665 mg, 1.279 mmol) and nonyl 8-bromooctanoate (3) (536 mg, 1.535 mmol) were mixed in ethanol (10 mL), then DIPEA (0.55 mL, 3.198 mmol) was added. The reaction mixture was heated to reflux overnight. Both MS (APCI) and TLC (10% MeOH+1% $NH_4OH$ in $CH_2Cl_2$) showed the product and some unreacted starting material. The mixture was cooled to room temperature and concentrated. The crude residue was purified by flash chromatography ($SiO_2$: $CH_2Cl_2$=100% to 10% of methanol+1% $NH_4OH$ in $CH_2Cl_2$) and colorless oil was obtained (170 mg, 17%).

38.5 Synthesis of heptadecan-9-yl 8-((3-(1H-imidazol-1-yl)propyl)(8-(nonyloxy)-8-oxooctyl)amino)octanoate (Lipid 53, Table 10a)

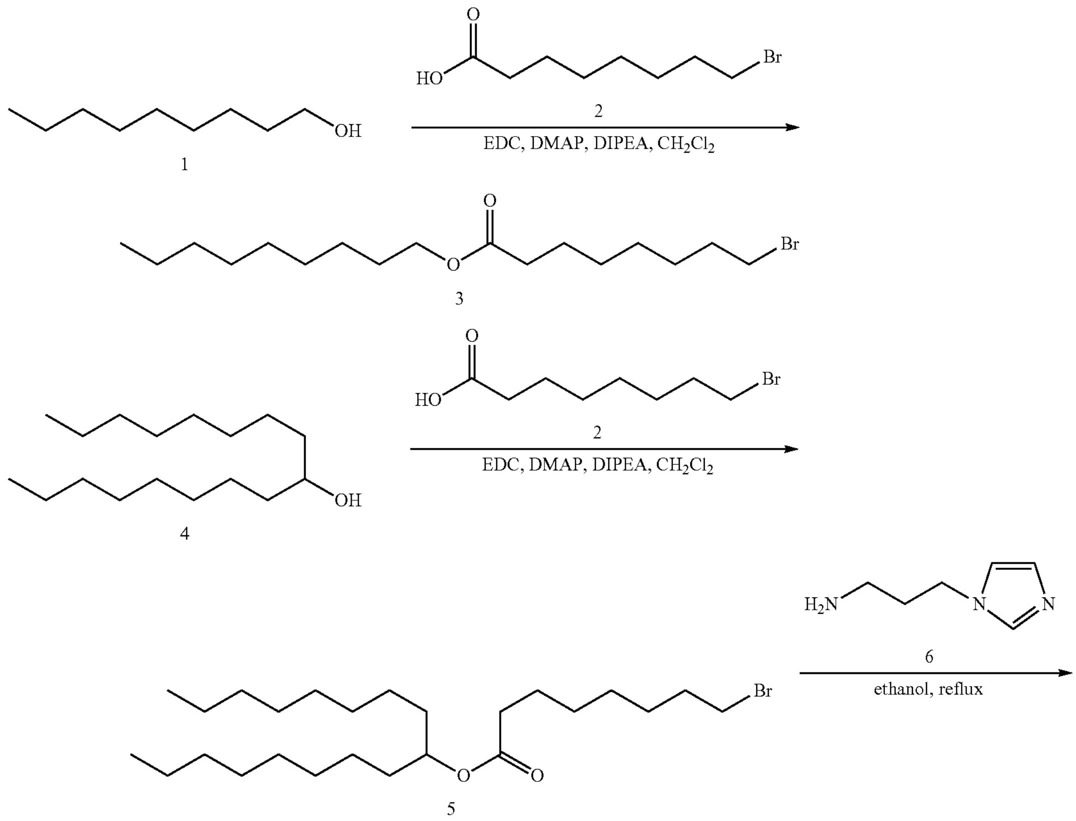

-continued

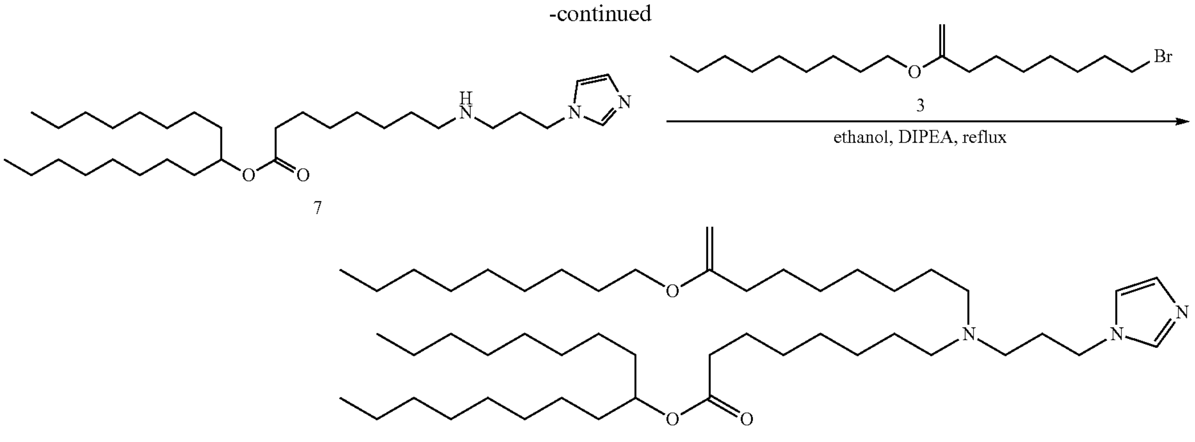

Lipid 53 from Table 10a is synthesized according to the scheme above. Reaction conditions are identical to Lipid 54 with the exception of 3-(1H-imidazol-1-yl)propan-1-amine as the imidazole amine.

Example 37

Lipid Nanoparticle Formulation with Circular RNA

Lipid Nanoparticles (LNPs) were formed using a Precision Nanosystems Ignite instrument with a ‘NextGen’ mixing chamber. Ethanol phase contained ionizable Lipid 26 from Table 10a, DSPC, Cholesterol, and DSPE-PEG 2000 (Avanti Polar Lipids Inc.) at a weight ratio of 16:1:4:1 or 62:4:33:1 molar ratio was combined with an aqueous phase containing circular RNA and 25 mM sodium acetate buffer at pH 5.2. A 3:1 aqueous to ethanol mixing ratio was used. The formulated LNP then were dialyzed in 1L of water and exchanged 2 times over 18 hours. Dialyzed LNPs were filtered using 0.2 μm filter. Prior to in vivo dosing, LNPs were diluted in PBS. LNP sizes were determined by dynamic light scattering. A cuvette with 1 mL of 20 μg/mL LNPs in PBS (pH 7.4) was measured for Z-average using the Malvern Panalytical Zetasizer Pro. The Z-average and polydispersity index were recorded.

39.1 Formulation of Lipids 26 and 27 from Table 10a

Lipid Nanoparticles (LNPs) were formed using a Precision Nanosystems Ignite instrument with a ‘NextGen’ mixing chamber. Ethanol phase contained ionizable Lipid 26 or Lipid 27 from Table 10a, DOPE, Cholesterol, and DSPE-PEG 2000 (Avanti Polar Lipids Inc.) at a weight ratio of 16:1:4:1 or 62:4:33:1 molar ratio was combined with an aqueous phase containing circular RNA and 25 mM sodium acetate buffer at pH 5.2. A 3:1 aqueous to ethanol mixing ratio was used. The formulated LNPs were then dialyzed in 1L of water and exchanged 2 times over 18 hours. Dialyzed LNPs were filtered using 0.2 μm filter. Prior to in vivo dosing, LNPs were diluted in PBS. LNP sizes were determined by dynamic light scattering. A cuvette with 1 mL of 20 μg/mL LNPs in PBS (pH 7.4) was measured for Z-average using the Malvern Panalytical Zetasizer Pro. The Z-average and polydispersity index were recorded.

39.2 Formulation of Lipids 53 and 54 from Table 10a

Lipid Nanoparticles (LNPs) were formed using a Precision Nanosystems Ignite instrument with a ‘NextGen’ mixing chamber. Ethanol phase contained ionizable Lipid 53 or 54 of Table 10a, DOPE, Cholesterol, and DSPE-PEG 2000 (Avanti Polar Lipids Inc.) at a molar ratio of 50:10:38.5:1.5 was combined with an aqueous phase containing circular RNA and 25 mM sodium acetate buffer at pH 5.2. A 3:1 aqueous to ethanol mixing ratio was used. The formulated LNPs were then dialyzed in 1L of lx PBS and exchanged 2 times over 18 hours. Dialyzed LNPs were filtered using 0.2 μm filter. Prior to in vivo dosing, LNPs were diluted in PBS. LNP sizes were determined by dynamic light scattering. A cuvette with 1 mL of 20 μg/mL LNPs in PBS (pH 7.4) was measured for Z-average using the Malvern Panalytical Zetasizer Pro. The Z-average and polydispersity index were recorded.

LNP zeta potential was measured using the Malvern Panalytical Zetasizer Pro. A mixture containing 200 μL of the particle solution in water and 800 μL of distilled RNAse-free water with a final particle concentration of 400 μg/mL was loaded into a zetasizer capillary cell for analysis.

RNA encapsulation was determined using a Ribogreen assay. Nanoparticle solutions were diluted in tris-ethylene-diaminetetraacetic acid (TE) buffer at a theoretical oRNA concentration of 2 μg/mL. Standard oRNA solutions diluted in TE buffer were made ranging from 2 μg/mL to 0.125 μg/mL. The particles and standards were added to all wells and a second incubation was performed (37° C. at 350 rpm for 3 minutes). Fluorescence was measured using a SPECTRAmax® GEMINI XS microplate spectrofluorometer. The concentration of circular RNA in each particle solution was calculated using the standard curve. The encapsulation efficiency was calculated from the ratio of oRNA detected between lysed and unlysed particles.

TABLE 36a

Characterization of LNPs

| Ionizable Lipid | Size (nm) | PDI | Encapsulation Efficiency (%) | Zeta Data Potential (mV) |
|---|---|---|---|---|
| 22-S14 | 88 | 0.09 | 96 | 3.968 |
| 93-S14 | 119 | 0.02 | 96 | −6.071 |
| Lipid 26, Table 10a | 86 | 0.08 | 92 | −15.24 |

TABLE 36b

| Characterization of LNPs | | | |
|---|---|---|---|
| Ionizable Lipid | Z-Average (nm) | PDI | RNA Entrapment (%) |
| 22-S14 | 64 | 0.05 | 97 |
| 93-S14 | 74 | 0.04 | 95 |
| Lipid 26, Table 10a | 84 | 0.04 | 96 |

Example 38

In Vivo Analysis

Female CD-1 or female c57BL/6J_mice ranging from 22-25 g were dosed at 0.5 mg/kg RNA intravenously. Six hours after injection, mice were injected intraperitoneally with 200 μL of D-luciferin at 15 mg/mL concentration. 5 minutes after injection, mice were anesthetized using isoflurane, and placed inside the IVIS Spectrum In Vivo Imaging System (Perkin Elmer) with dorsal side up. Whole body total IVIS flux of Lipids 22-S14, 93-S14, Lipid 26 (Table 10a) is presented in FIG. 32A. Post 10 minutes injection, mice were scanned for luminescence. Mice were euthanized and organs were extracted within 25 minutes of luciferin injection to scan for luminescence in liver, spleen, kidneys, lungs, and heart. Images (FIGS. 33A-B, 34A-B, 35A-B) were analyzed using Living Images (Perkin Elmer) software. Regions of interest were drawn to obtain flux and average radiance and analyzed for biodistribution of protein expression (FIG. 32A-B).

Figure 32A:
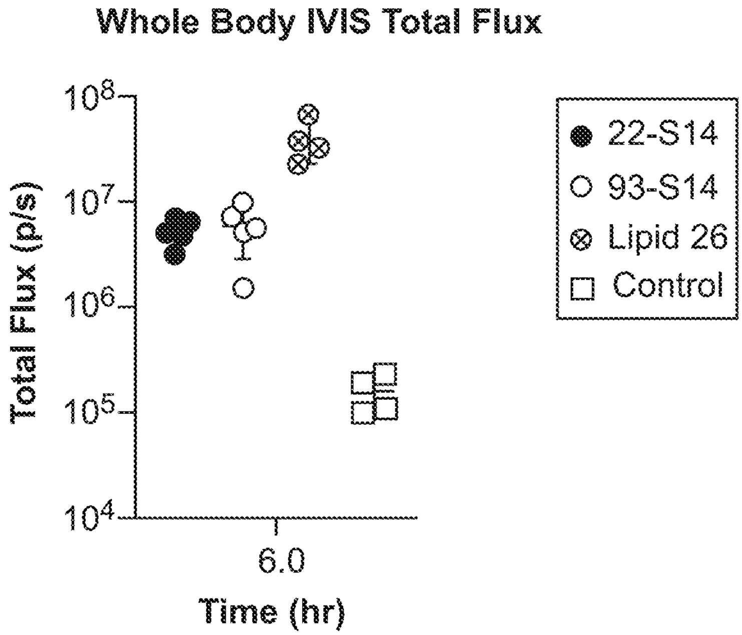
FIG. 32A depicts total flux of spleen and liver harvested from CD-1 mice dosed with circular RNA encoding firefly luciferase (FLuc) and formulated with ionizable lipid of interest, DSPC, cholesterol, and DSPE-PEG 2000 (Avanti Polar Lipids Inc.) at a weight ratio of 16:1:4:1 or 62:4:33:1 molar ratio.
Figure 32B:
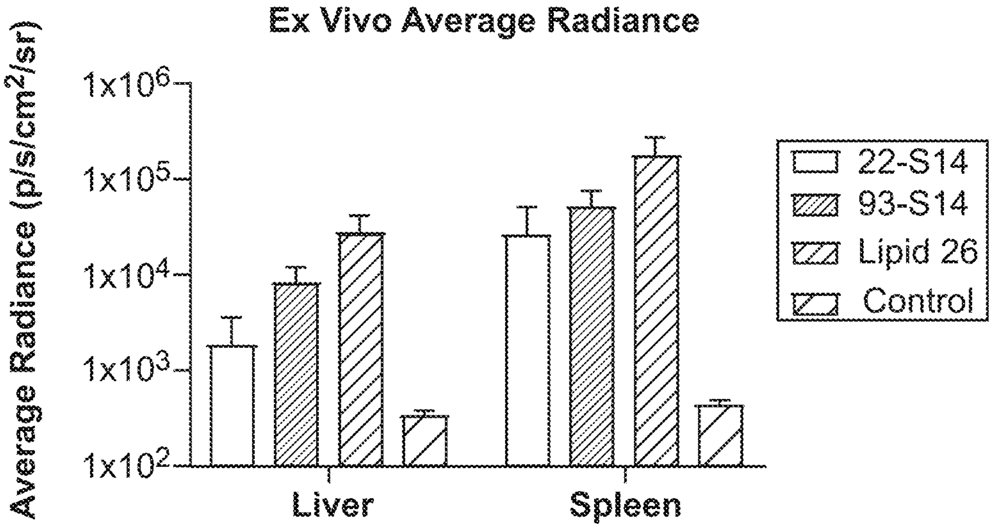
FIG. 32B depicts average radiance for biodistribution of protein expression.
Figure 33A:
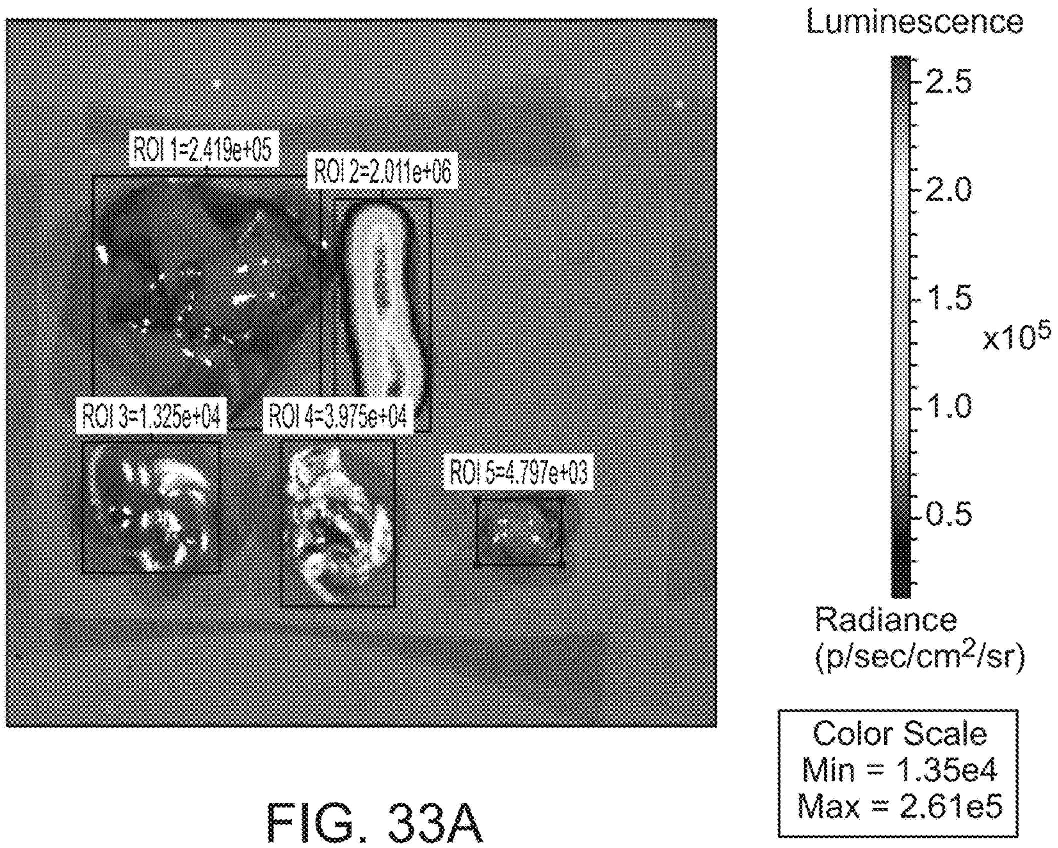
FIG. 33A depicts images highlighting the luminescence of organs harvested from CD-1 mice dosed with circular RNA encoding FLuc and formulated with ionizable Lipid 22-S14, DSPC, cholesterol, and DSPE-PEG 2000 (Avanti Polar Lipids Inc.) at a weight ratio of 16:1:4:1 or 62:4:33:1 molar ratio.
Figure 33B:
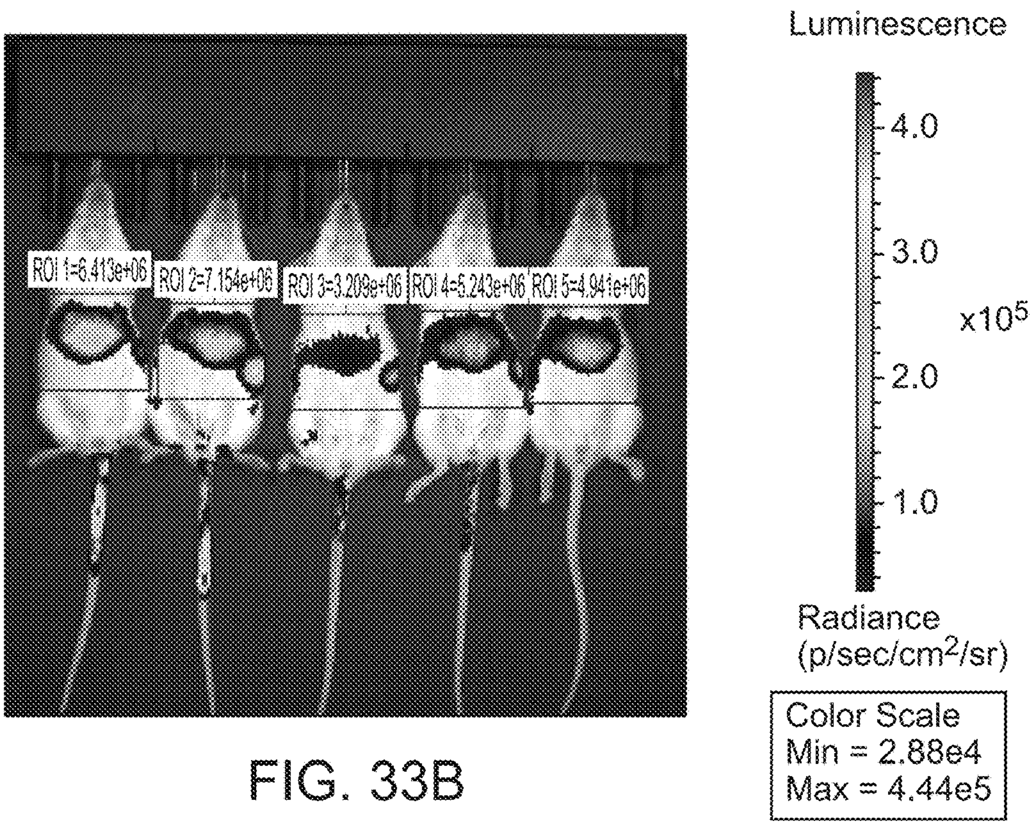
FIG. 33B depicts whole body IVIS images of CD-1 mice dosed with circular RNA encoding FLuc and formulated with ionizable Lipid 22-S14, DSPC, cholesterol, and DSPE-PEG 2000 (Avanti Polar Lipids Inc.) at a weight ratio of 16:1:4:1 or 62:4:33:1 molar ratio.
Figure 34A:
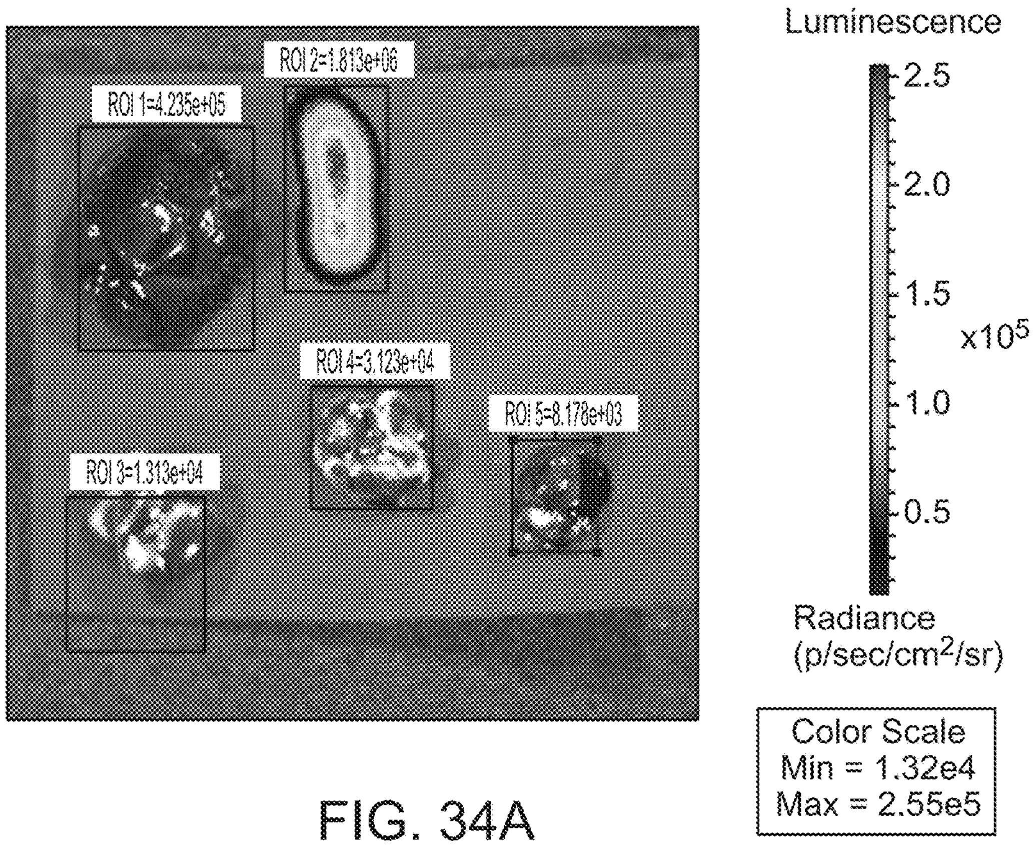
FIG. 34A depicts images highlighting the luminescence of organs harvested from CD-1 mice dosed with circular RNA encoding FLuc and formulated with ionizable Lipid 93-S14, DSPC, cholesterol, and DSPE-PEG 2000 (Avanti Polar Lipids Inc.) at a weight ratio of 16:1:4:1 or 62:4:33:1 molar ratio.
Figure 34B:
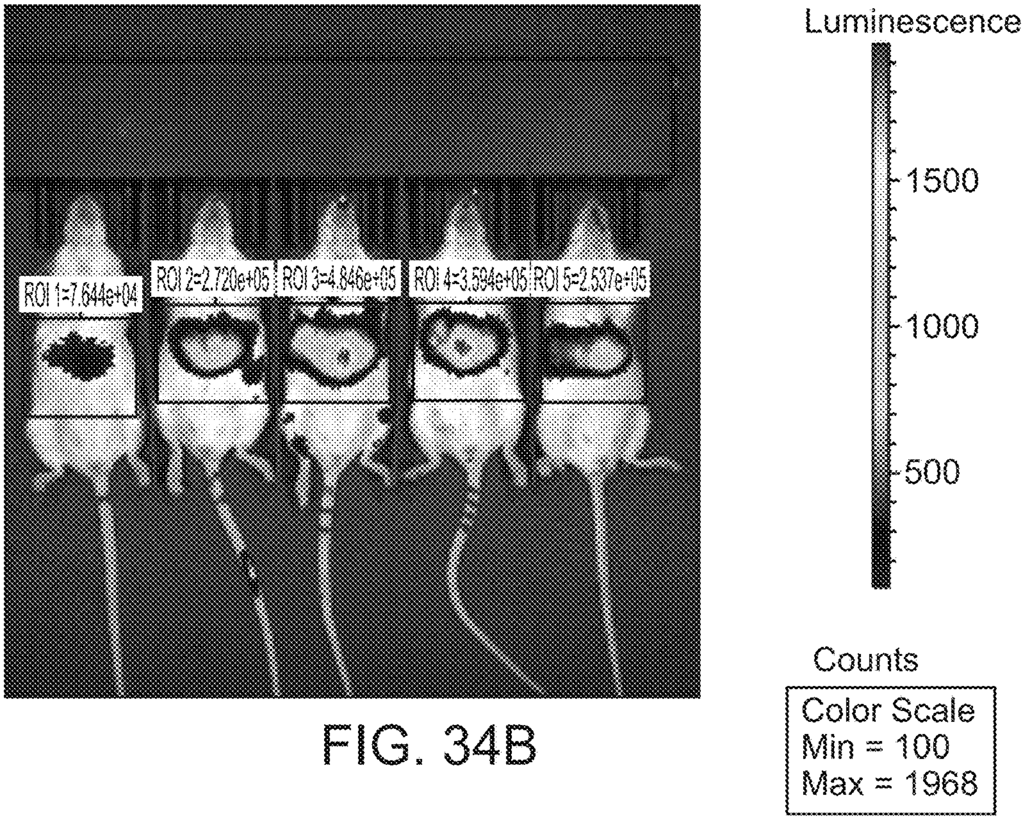
FIG. 34B depicts whole body IVIS images of CD-1 mice dosed with circular RNA encoding FLuc and formulated with ionizable Lipid 93-S14, DSPC, cholesterol, and DSPE-PEG 2000 (Avanti Polar Lipids Inc.) at a weight ratio of 16:1:4:1 or 62:4:33:1 molar ratio.
Figure 35A:
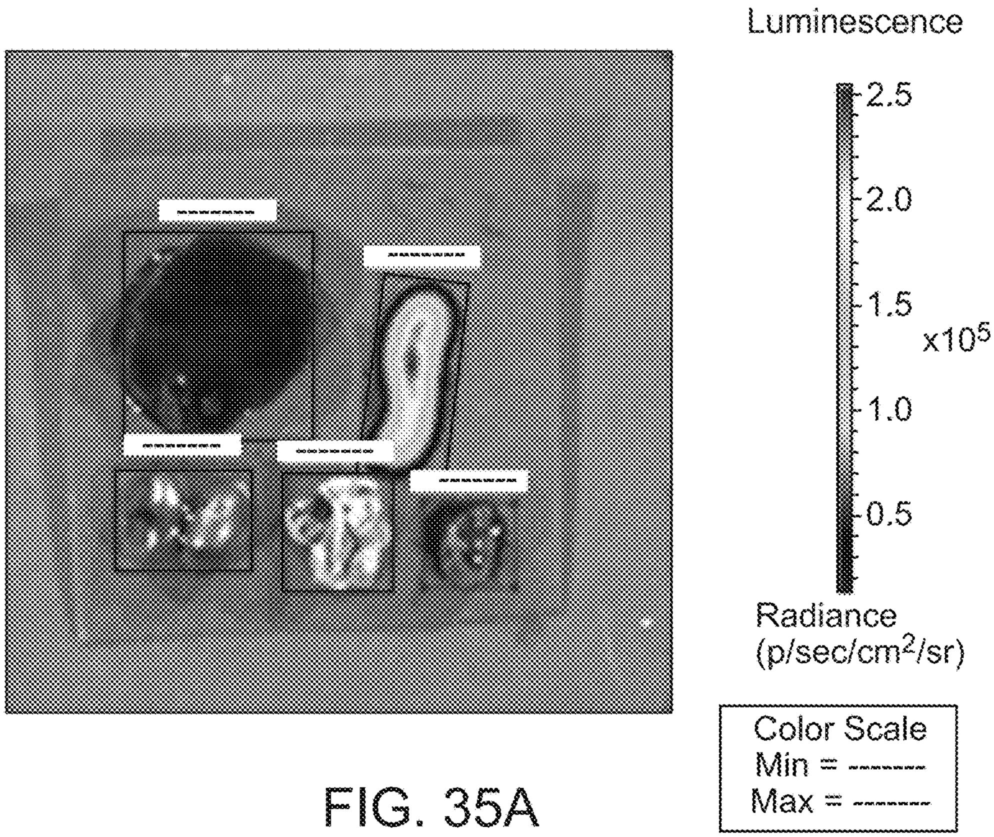
FIG. 35A depicts images highlighting the luminescence of organs harvested from CD-1 mice dosed with circular RNA encoding FLuc and formulated with ionizable Lipid 26 from Table 10a, DSPC, cholesterol, and DSPE-PEG 2000 (Avanti Polar Lipids Inc.) at a weight ratio of 16:1:4:1 or 62:4:33:1 molar ratio.
Figure 35B:
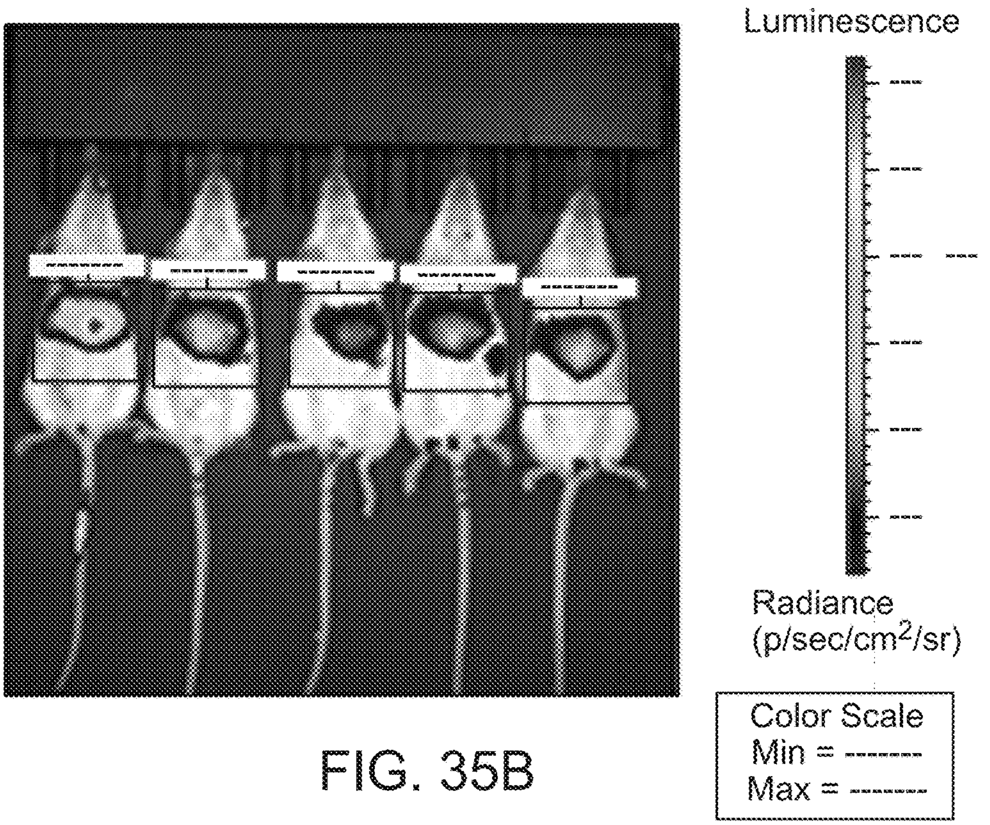
FIG. 35B depicts whole body IVIS images of CD-1 mice dosed with circular RNA encoding FLuc and formulated with ionizable Lipid 26, DSPC, cholesterol, and DSPE-PEG 2000 (Avanti Polar Lipids Inc.) at a weight ratio of 16:1:4:1 or 62:4:33:1 molar ratio.

FIG. 32A illustrates the increased whole-body total flux observed from luciferase oRNA with Lipid 26 (Table 10a) LNPs compared to LNPs made with lipids 22-S14 and 93-S14. FIG. 32B shows the ex vivo IVIS analysis of tissues further highlighting the increased overall expression with Lipid 26 (Table 10a) while maintaining the desired spleen to liver ratios observed with lipids 22-S14 and 93-S14 despite the significant structural changes designed to improve expression. These data highlight the improvements afforded by Lipid 26 (Table 10a) compared to previously reported lipids.

Figure 36A:
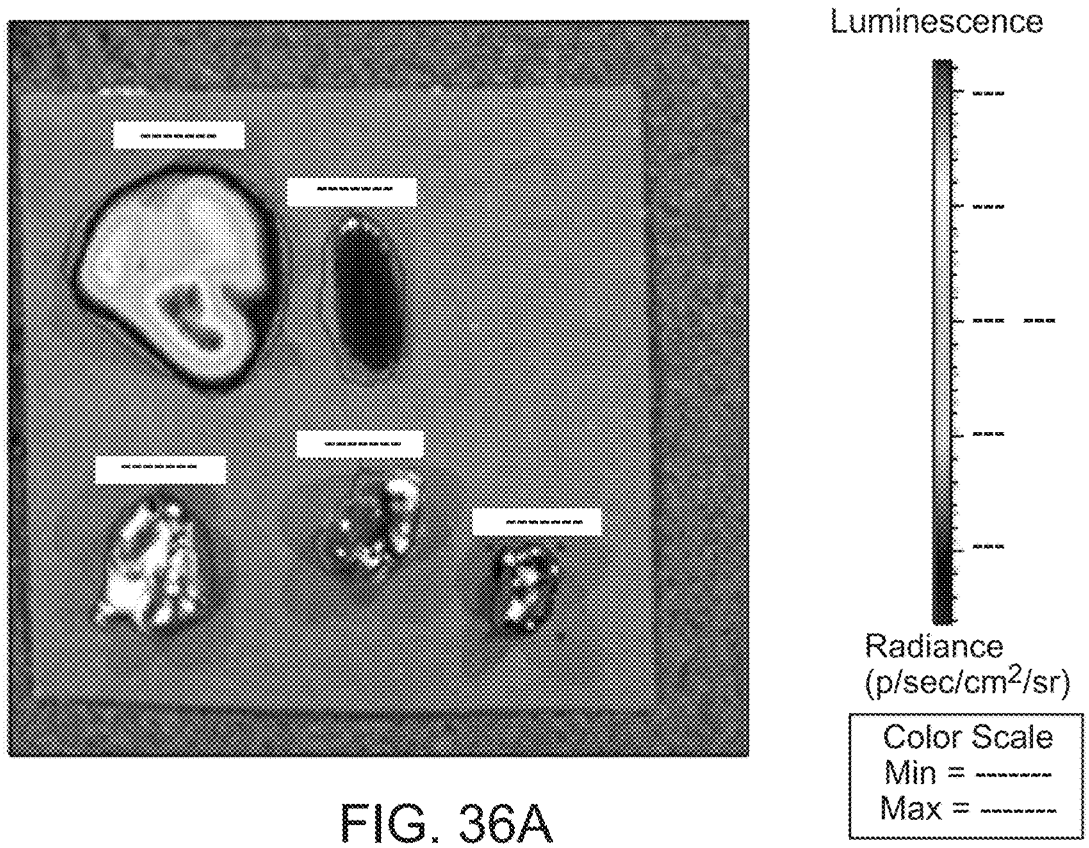
FIGS. 36A, 36B, 36C and 36D depicts images highlighting the luminescence of organs harvested from c57BL/6J mice dosed with circular RNA encoding FLuc and encapsulated in lipid nanoparticles formed with Lipid 15 from Table 10b (FIG. 36A), Lipid 53 from Table 10a (FIG. 36B), or Lipid 54 from Table 10a (FIG. 36C). PBS was used as control (FIG. 36D).
Figure 36B:
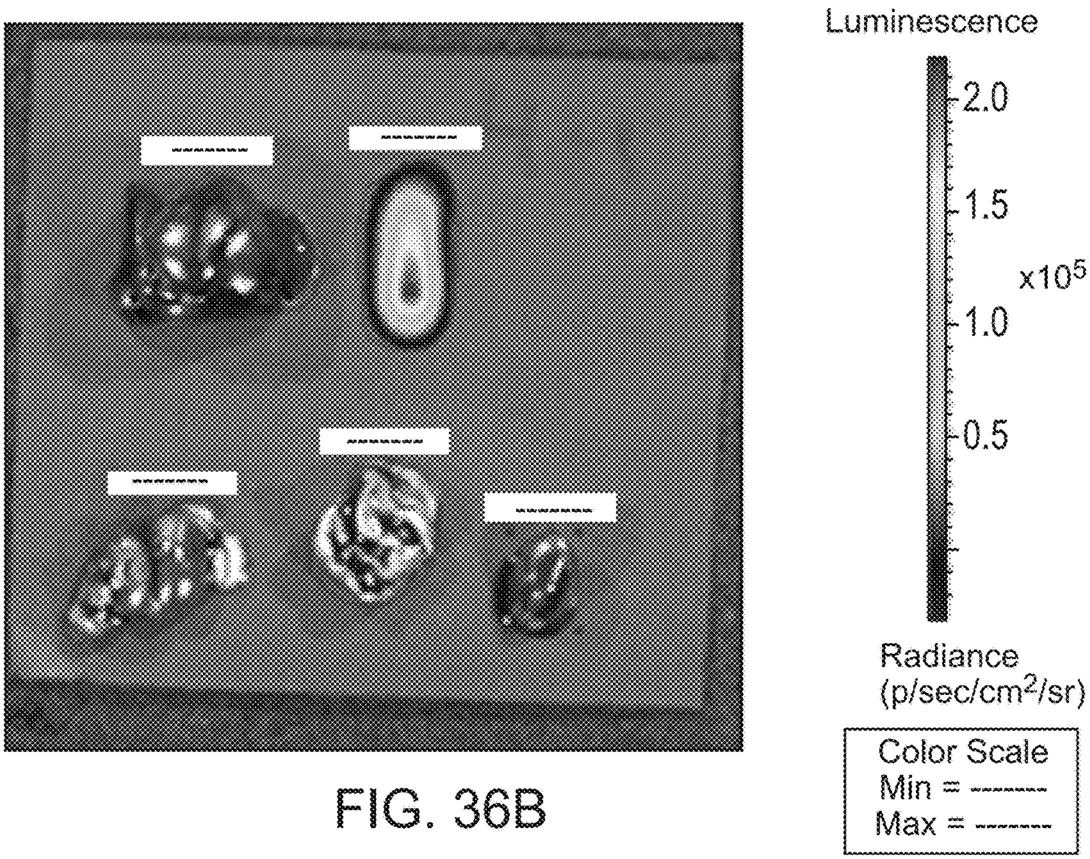
Figure 36C:
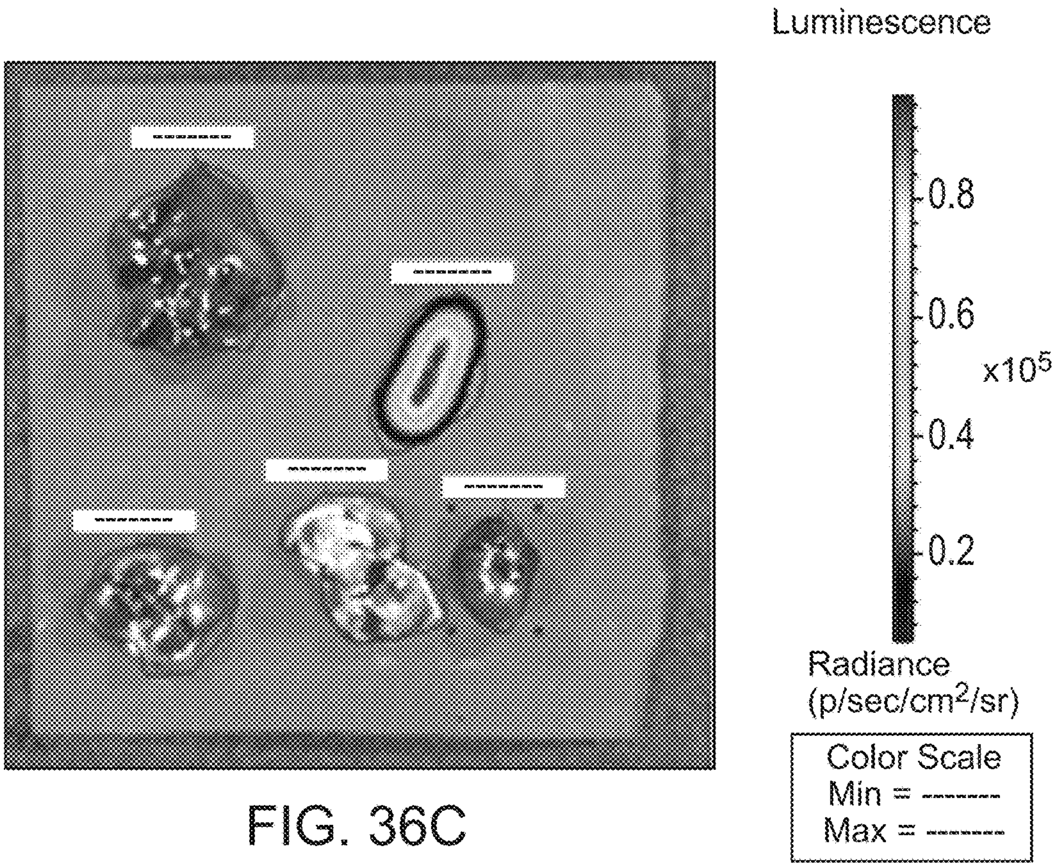
Figure 36D:
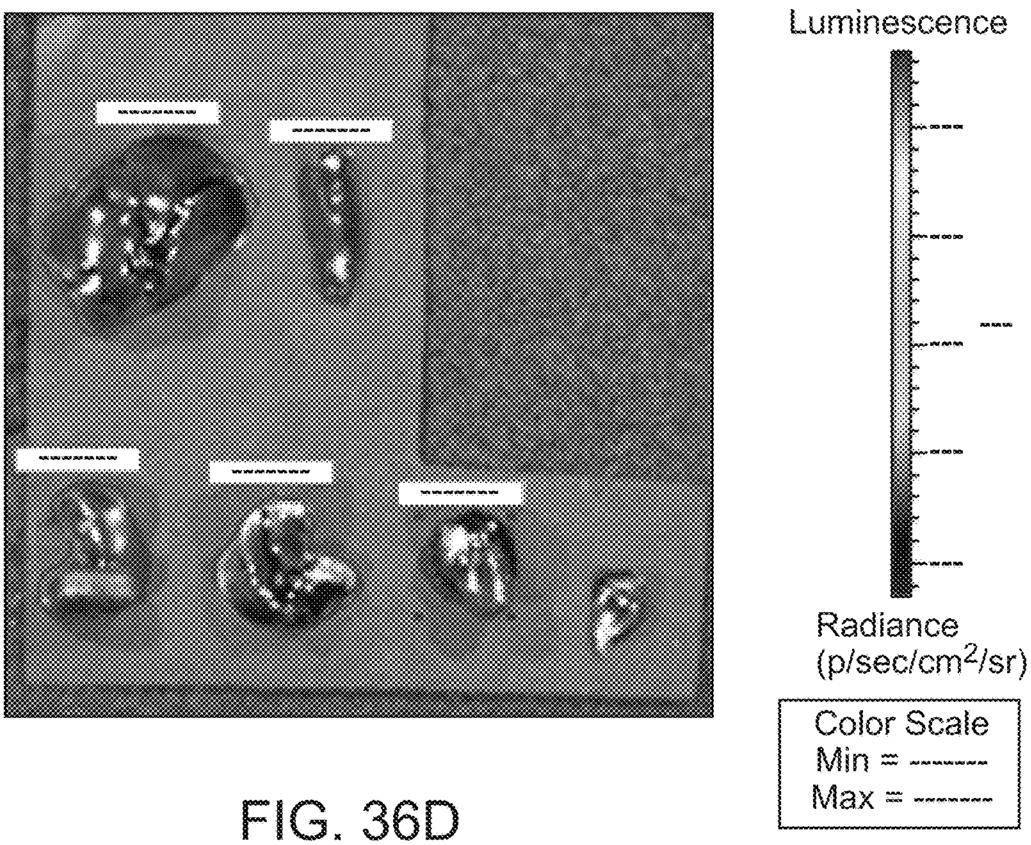

Similar analysis as described above was also performed with oRNA encapsulated in LNPs formed with Lipid 15 from Table 10b or Lipid 53 or 54 from Table 10a. FIGS. 36A-C show the ex vivo IVIS analysis of tissues, respectively highlighting the overall expression with Lipid 15, 53, and 54 while maintaining the desired spleen to liver ratios despite the significant structural changes designed to improve expression. FIG. 36D shows the results for PBS control. These data demonstrates the improvements afforded by Lipids 15, 53, and 54 from Table 10a compared to previously reported lipids such as 93-S14 and 22-S14.

Example 39

Delivery of Luciferase

Human peripheral blood mononuclear cells (PBMCs) (Stemcell Technologies) were transfected with lipid nanoparticles (LNP) encapsulating firefly luciferase (f.luc) circular RNA and examined for luciferase expression. PBMCs from two different donors were incubated in vitro with five different LNP compositions, containing circular RNA encoding for firefly luciferase (200 ng), at 37° C. in RPMI, 2% human serum, IL-2 (10 ng/mL), and 50 uM BME. PBMCs incubated without LNP were used as a negative control. After 24 hours, the cells were lysed and analyzed for firefly luciferase expression based on bioluminescence (Promega BrightGlo).

Figure 37A:
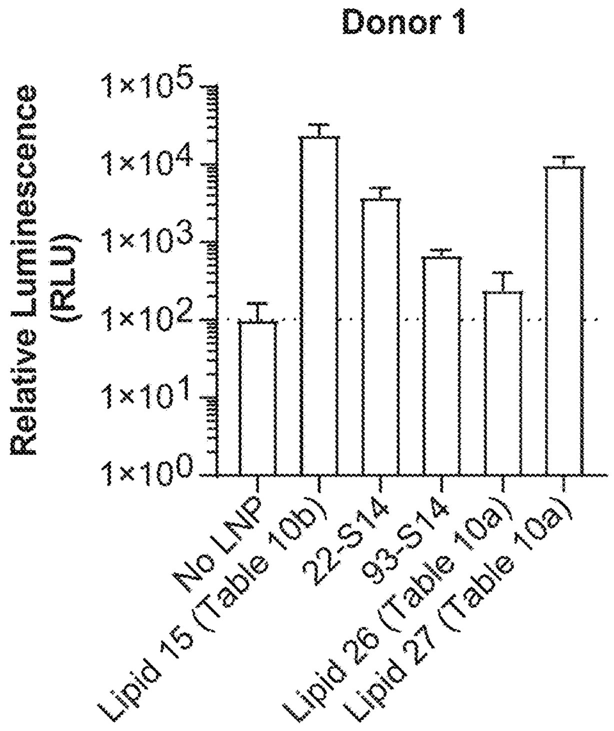
FIGS. 37A and 37B depict relative luminescence in the lysates of human PBMCs after 24-hour incubation with testing lipid nanoparticles containing circular RNA encoding firefly luciferase.
Figure 37B:
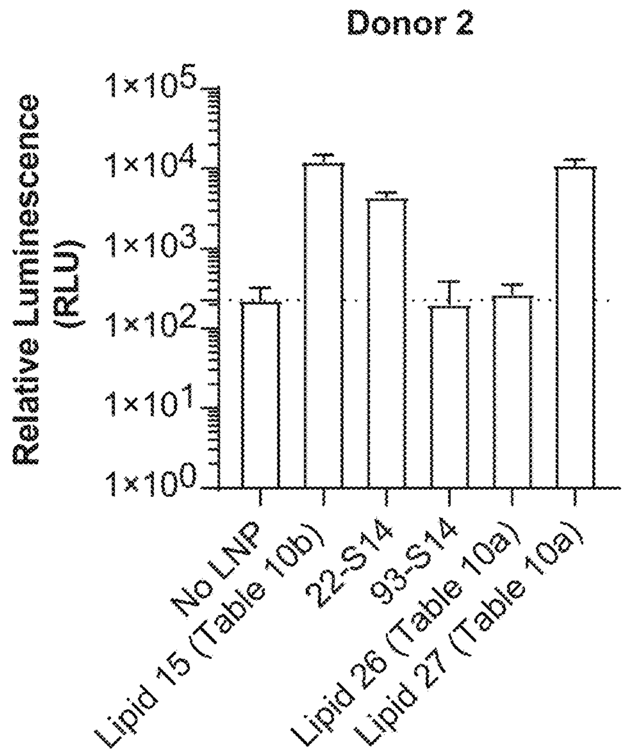

Representative data are presented in FIGS. 37A and 37B, showing that that the tested LNPs are capable of delivering circular RNA into primary human immune cells resulting in protein expression.

Example 40

In Vitro Delivery of Green Fluorescent Protein (GFP) or Chimeric Antigen Receptor (CAR)

Human PBMCs (Stemcell Technologies) were transfected with LNP encapsulating GFP and examined by flow cytometry. PBMCs from five different donors (PBMC A-E) were incubated in vitro with one LNP composition, containing circular RNA encoding either GFP or CD19-CAR (200 ng), at 37° C. in RPMI, 2% human serum, IL-2 (10 ng/mL), and 50 uM BME. PBMCs incubated without LNP were used as a negative control. After 24, 48, or 72 hours post-LNP incubation, cells were analyzed for CD3, CD19, CD56, CD14, CD11b, CD45, fixable live dead, and payload (GFP or CD19-CAR).

Figure 38A:
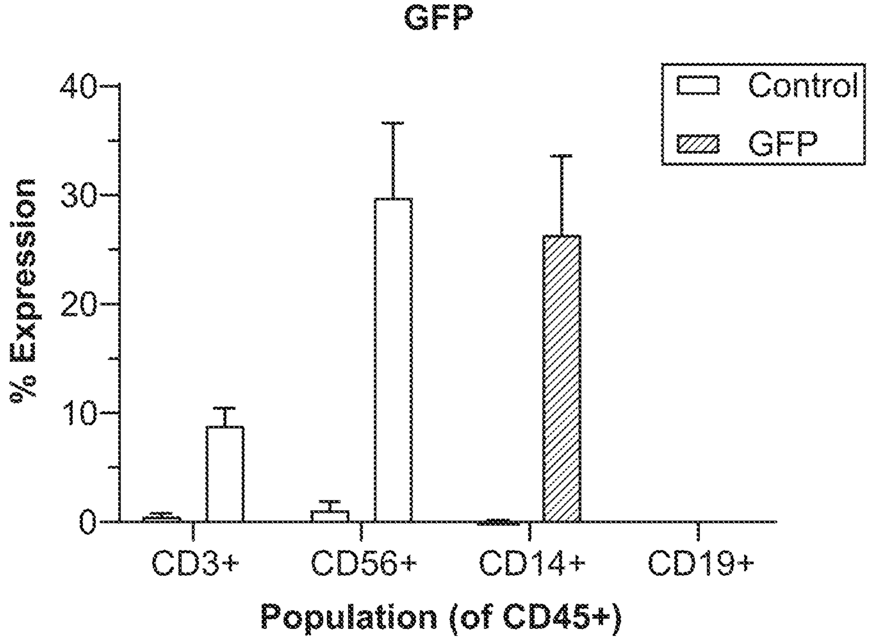
FIGS. 38A and 38B show the expression of GFP (FIG. 38A) and CD19 CAR (FIG. 38B) in human PBMCs after incubating with testing lipid nanoparticle containing circular RNA encoding either GFP or CD19 CAR.
Figure 38B:
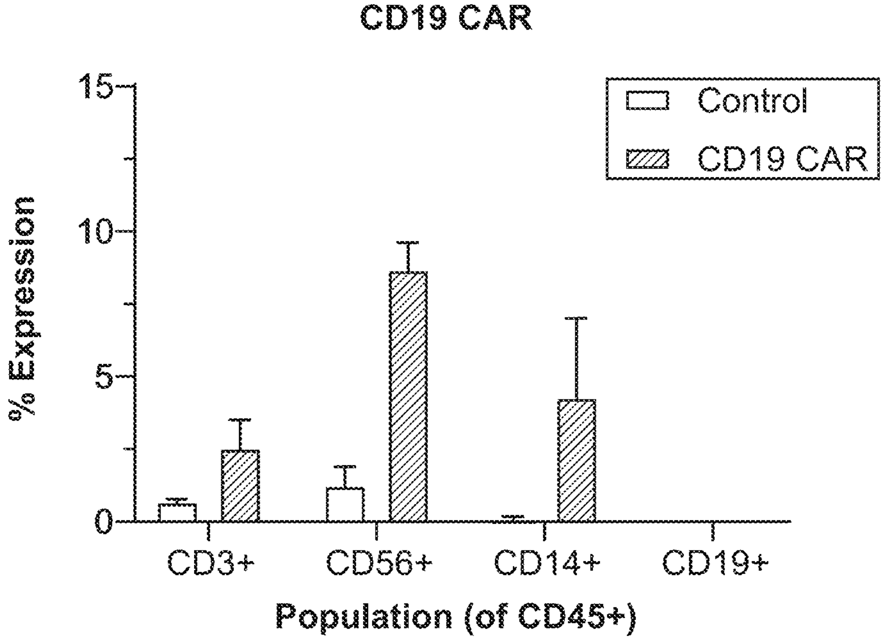

Representative data are presented in FIGS. 38A and 38B, showing that the tested LNP is capable of delivering circular RNA into primary human immune cells resulting in protein expression.

Example 41

Multiple IRES Variants can Mediate Expression of Murine CD19 CAR In Vitro

Multiple circular RNA constructs, encoding anti-murine CD19 CAR, contains unique IRES sequences and were lipotransfected into 1C1C7 cell lines. Prior to lipotransfection, 1C1C7 cells are expanded for several days in complete RPMI Once the cells expanded to appropriate numbers, 1C1C7 cells were lipotransfected (Invitrogen RNAiMAX) with four different circular RNA constructs. After 24 hours, 1C1C7 cells were incubated with His-tagged recombinant murine CD19 (Sino Biological) protein, then stained with a secondary anti-His antibody. Afterwards, the cells were analyzed via flow cytometry.

Figure 39:
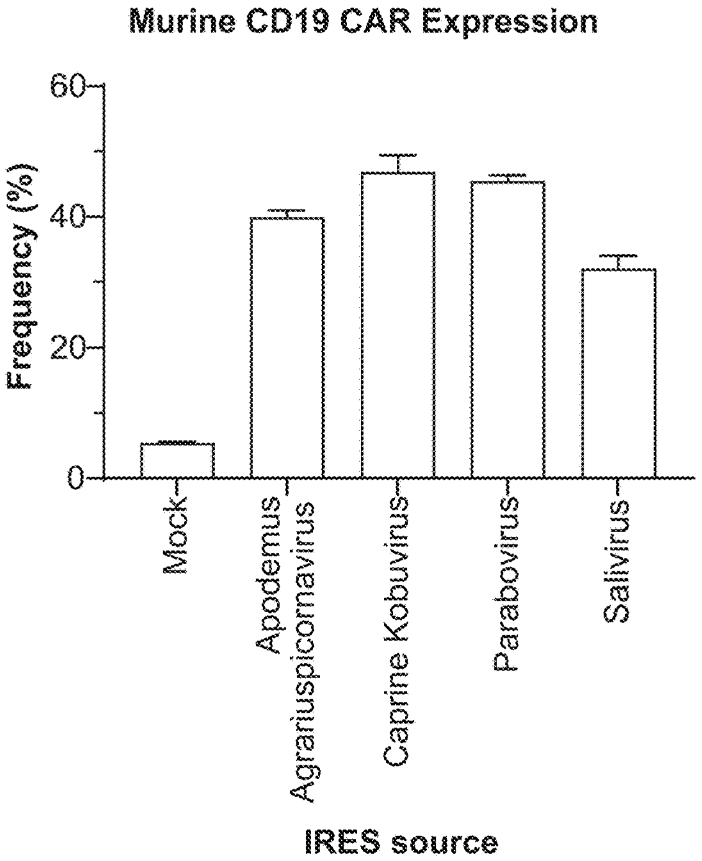
FIG. 39 depicts the expression of an anti-murine CD19 CAR in 1C1C7 cells lipotransfected with circular RNA comprising an anti-murine CD19 CAR expression sequence and varying IRES sequences.

Representative data are presented in FIGS. 39, showing that IRES sourced from the indicated virus (apodemus agrarius picornavirus, caprine kobuvirus, parabovirus, and salivirus) are capable of driving expression of an anti-mouse CD19 CAR in murine T cells.

Example 42

Murine CD19 CAR Mediates Tumor Cell Killing In Vitro

Circular RNA encoding anti-mouse CD19 CAR were electroporated into murine T cells to evaluate CAR-mediated cytotoxicity. For electroporation, T cells were electroporated with circular RNA encoding anti-mouse CD19 CAR using ThermoFisher's Neon Transfection System then rested overnight. For the cytotoxicity assay, electroporated T cells were co-cultured with Fluc+ target and non-target cells at 1:1 ratio in complete RPMI containing 10% FBS, IL-2 (10 ng/mL), and 50 uM BME and incubated overnight at 37° C. Cytotoxicity was measured using a luciferase assay system 24 hours post-co-culture (Promega Brightglo Luciferase System) to detect lysis of Fluc+ target and non-target cells. Values shown are calculated relative to the untransfected mock signal.

Figure 40:
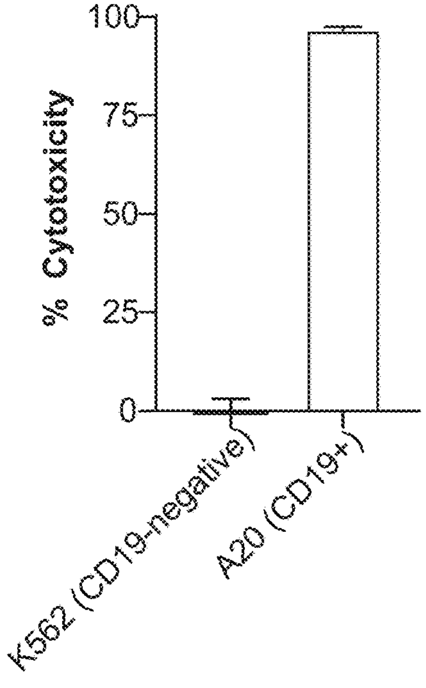
FIG. 40 shows the cytotoxicity of an anti-murine CD19 CAR to murine T cells. The CD19 CAR is encoded by and expressed from a circular RNA, which is electroporated into the murine T cells.

Representative data are presented in FIG. 40, showing that an anti-mouse CD19 CAR expressed from circular RNA is functional in murine T cells in vitro.

Example 43

Functional Depletion of B Cells with a Lipid Encapsulated Circular RNA Encoding Murine CD19 CAR C57BL/6J mice were injected with LNP formed with Lipid 15 in Table 10b, encapsulating circular RNA encoding anti-murine CD19 CAR. As a control, Lipid 15 in Table 10b encapsulating circular RNA encoding firefly luciferase (f Luc) were injected in different group of mice. Female C57BL.6J, ranging from 20-25 g, were injected intravenously with 5 doses of 0.5 mg/kg of LNP, every other day. Between injections, blood draws were analyzed via flow cytometry for fixable live/dead, CD45, TCRvb, B220, CD11b, and anti-murine CAR. Two days after the last injection, spleens were harvested and processed for flow cytometry analysis. Splenocytes were stained with fixable live/dead, CD45, TCRvb, B220, CD11b, NK1.1, F4/80, CD11c, and anti-murine CAR. Data from mice injected with anti-murine CD19 CAR LNP were normalized to mice that received fLuc LNP.

Figure 41A:
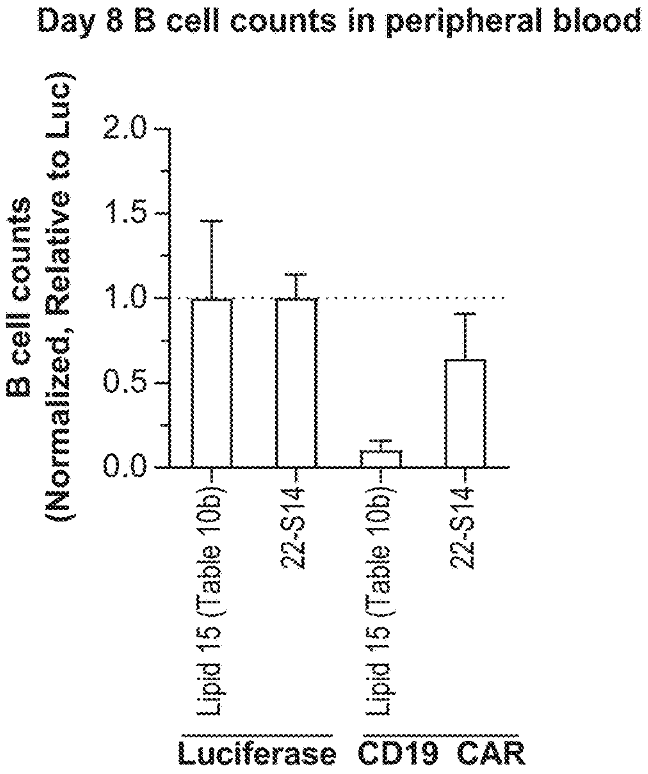
FIGS. 41A, 41B and 41C depict the B cell counts in peripheral blood (FIGS. 41A and 41B) or spleen (FIG. 41C) in C57BL/6J mice injected every other day with testing lipid nanoparticles encapsulating a circular RNA encoding an anti-murine CD19 CAR.
Figure 41B:
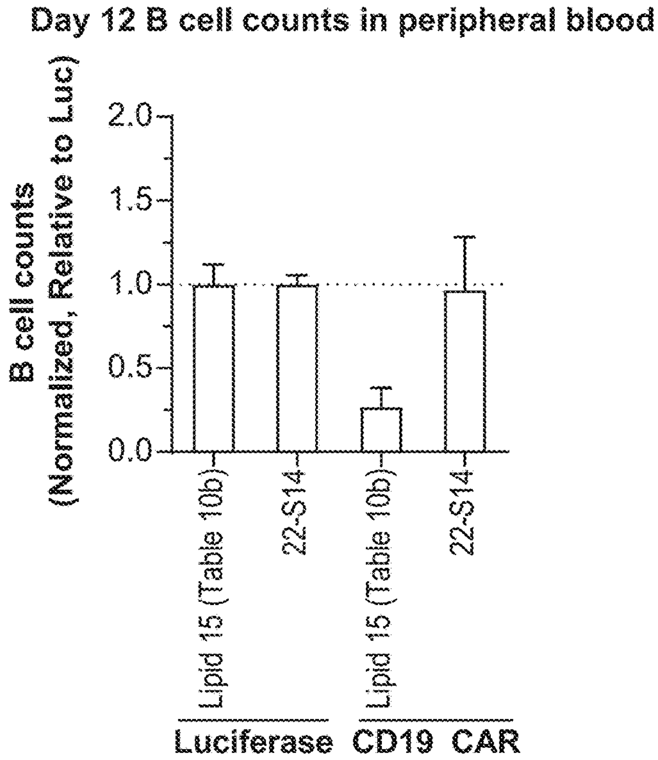
Figure 41C:
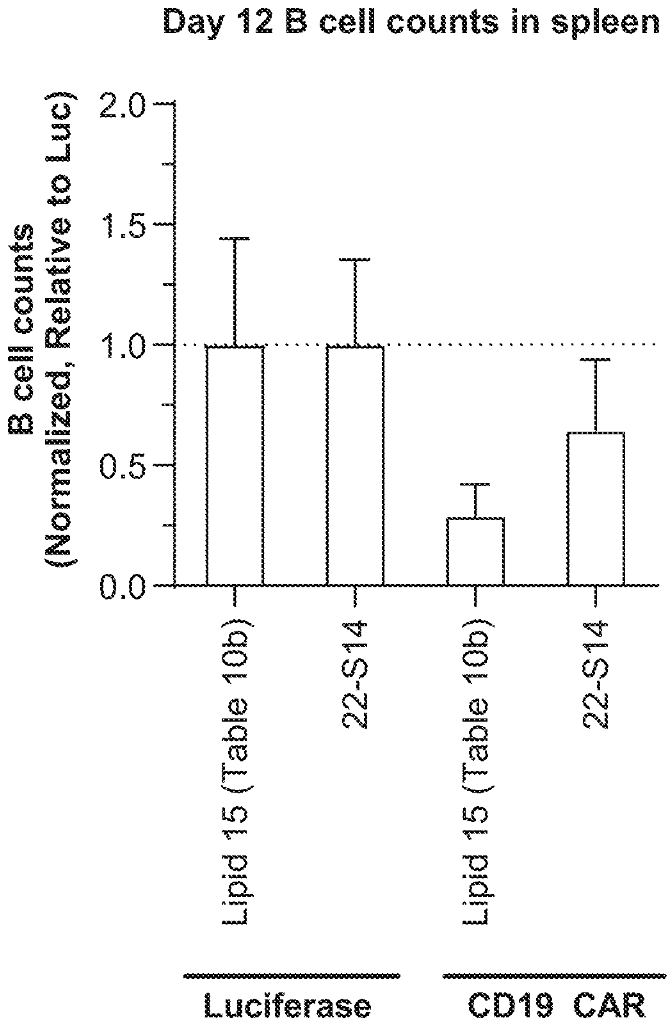

Representative data are presented in FIGS. 41A, 41B, and 41C, showing that an anti-mouse CD19 CAR expressed from circular oRNA delivered in vivo with LNPs is functional in murine T cells in vivo.

Example 44

CD19 CAR Expressed from Circular RNA has Higher Yield and Greate Cytotoxic Effect Compared to that Expressed from mRNA Circular RNA encoding encoding anti-CD19 chimeric antigen antigen receptor, which includes, from N-terminus to C-terminus, a FMC63-derived scFv, a CD8 transmembrane domain, a4-1BB costimulatory domain, and a CD3ζ intracellular domain, were electroporated into human peripheral T cells to evaluate surface expression and CAR-mediated cytotoxicity. For comparison, circular RNA-electroporated T cells were compared to mRNA-electroporated T cells in this experiment. For electroporation, CD3+ T cells were isolated from human PBMCs using commercially available T cell isolation kits (Miltenyi Biotec) from donor human PBMCs. After isolation, T cells were stimulated with anti-CD3/anti-CD28 (Stemcell Technologies) and expanded over 5 days at 37° C. in complete RPMI containing 10% FBS, IL-2 (10 ng/mL), and 50 uM BME. Five days post stimulation, T cells were electroporated with circular RNA encoding anti-human CD19 CAR using ThermoFisher's Neon Transfection System and then rested overnight. For the cytotoxicity assay, electroporated T cells were co-cultured with Fluc+ target and non-target cells at 1:1 ratio in complete RPMI containing 10% FBS, IL-2 (10 ng/mL), and 50 uM BME and incubated overnight at 37° C. Cytotoxicity was measured using a luciferase assay system 24 hours post-co-culture (Promega Brightglo Luciferase System) to detect lysis of Fluc+ target and non-target cells. Furthermore, an aliquot of electroporated T cells were taken and stained for live dead fixable staining, CD3, CD45, and chimeric antigen receptors (FMC63) at the day of analysis.

Figure 42A:
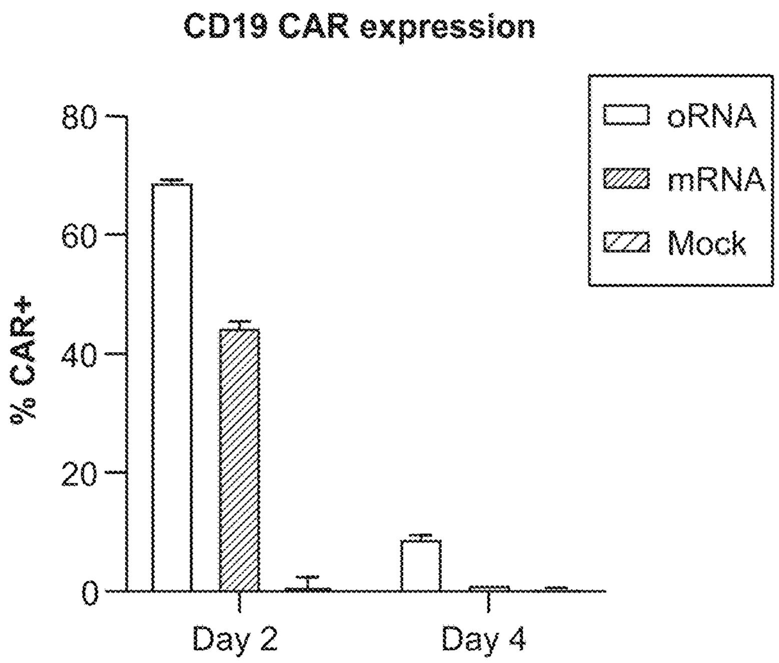
FIGS. 42A and 42B compares the expression level of an anti-human CD19 CAR expressed from a circular RNA with that expressed from a linear mRNA.
Figure 42B:
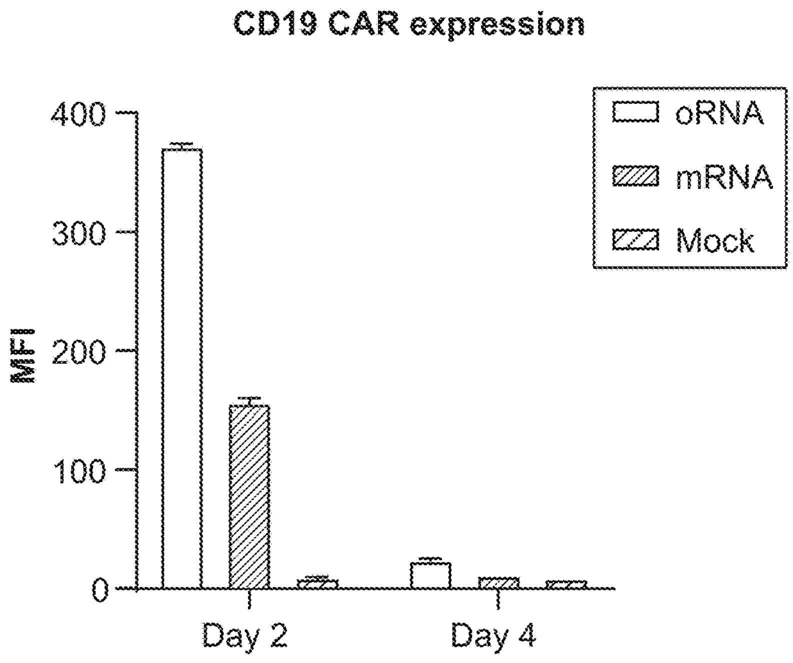
Figure 43A:
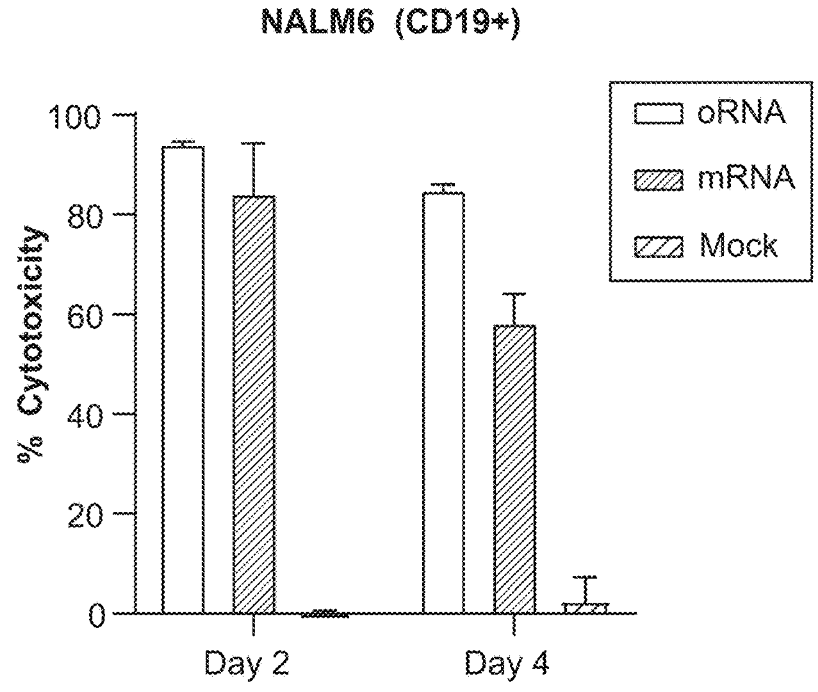
FIGS. 43A and 43B compares the cytotoxic effect of an anti-human CD19 CAR expressed from a circular RNA with that expressed from a linear mRNA
Figure 43B:
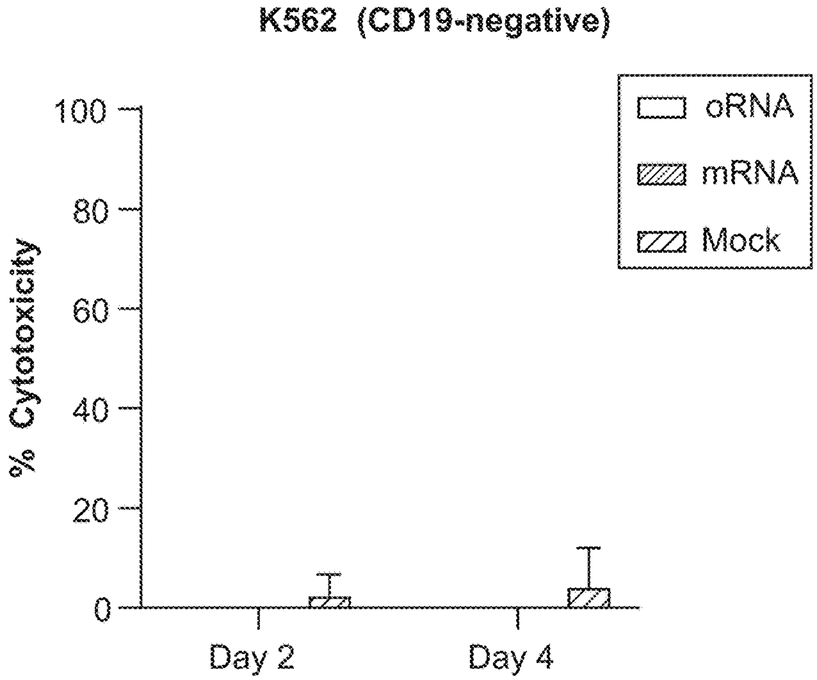

Representative data are presented in FIGS. 42 and 43. FIGS. 42A and 42B show that an anti-human CD19 CAR expressed from circular RNA is expressed at higher levels and longer than an anti-human CD19 CAR expressed from linear mRNA. FIGS. 43A and 43B show that an anti-human CD19 CAR expressed from circular RNA is exerts a greater cytotoxic effect relative to anti-human CD19 CAR expressed from linear mRNA.

Example 45

Functional Expression of Two CARs from a Single Circular RNA

Circular RNA encoding chimeric antigen receptors were electroporated into human peripheral T cells to evaluate surface expression and CAR-mediated cytotoxicity. The purpose of this study is to evaluate if circular RNA encoding for two CARs can be stochastically expressed with a 2A (P2A) or an IRES sequence. For electroporation, CD3+ T cells were commercially purchased (Cellero) and stimulated with anti-CD3/anti-CD28 (Stemcell Technologies) and expanded over 5 days at 37° C. in complete RPMI containing 10% FBS, IL-2 (10 ng/mL), and 50 uM BME. Four days post stimulation, T cells were electroporated with circular RNA encoding anti-human CD19 CAR, anti-human CD19 CAR-2A-anti-human BCMA CAR, and anti-human CD19 CAR-IRES-anti-human BCMA CAR using ThermoFisher's Neon Transfection System then rested overnight. For the cytotoxicity assay, electroporated T cells were co-cultured with Fluc+K562 cells expressing human CD19 or BCMA antigens at 1:1 ratio in complete RPMI containing 10% FBS, IL-2 (10 ng/mL), and 50 uM BME and incubated overnight at 37° C. Cytotoxicity was measured using a luciferase assay system 24 hours post-co-culture (Promega BrightGlo Luciferase System) to detect lysis of Fluc+ target cells.

Figure 44:
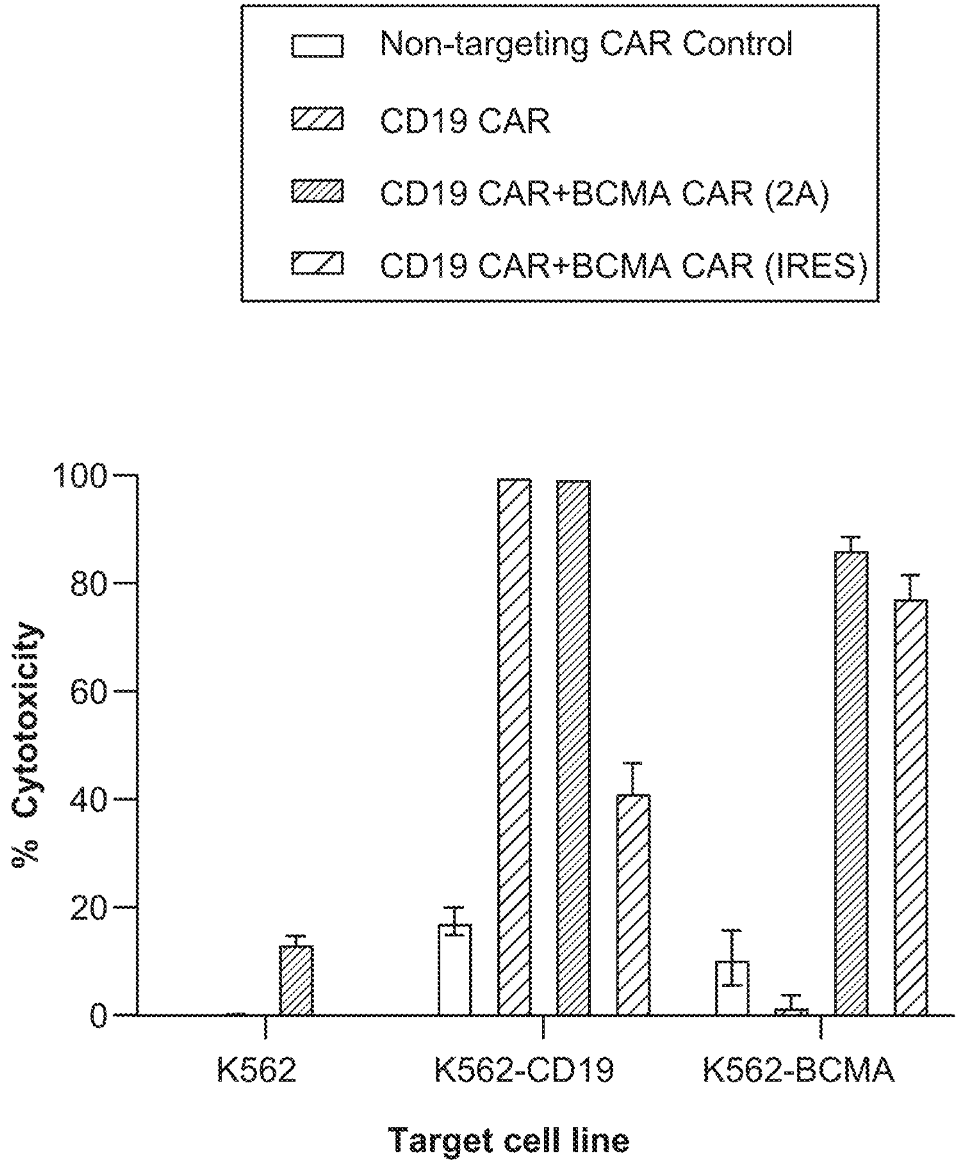
FIG. 44 depicts the cytotoxicity of two CARs (anti-human CD19 CAR and anti-human BCMA CAR) expressed from a single circular RNA in T cells.

Representative data are presented in FIG. 44, showing that two CARs can be functionally expressed from the same circular RNA construct and exert cytotoxic effector function.

Example 46

In Vivo Circular RNA Transfection Using Cre Reporter Mice

Circular RNAs encoding Cre recombinase (Cre) are encapsulated into lipid nanoparticles as previously described. Female, 6-8 week old B6.Cg-Gt(ROSA) 26Sortm9(CAG-tdTomato)Hze/J (Ai9) mice were dosed with lipid nanoparticles at 0.5 mg/kg RNA intravenously. Fluorescent tdTomato protein was transcribed and translated in Ai9 mice upon Cre recombination, meaning circular RNAs have been delivered to and translated in tdTomato+ cells. After 48 hr, mice were euthanized and the spleens were harvested, processed into a single cell suspension, and stained with various fluorophore-conjugated antibodies for immunophenotyping via flow cytometry.

Figure 45A:
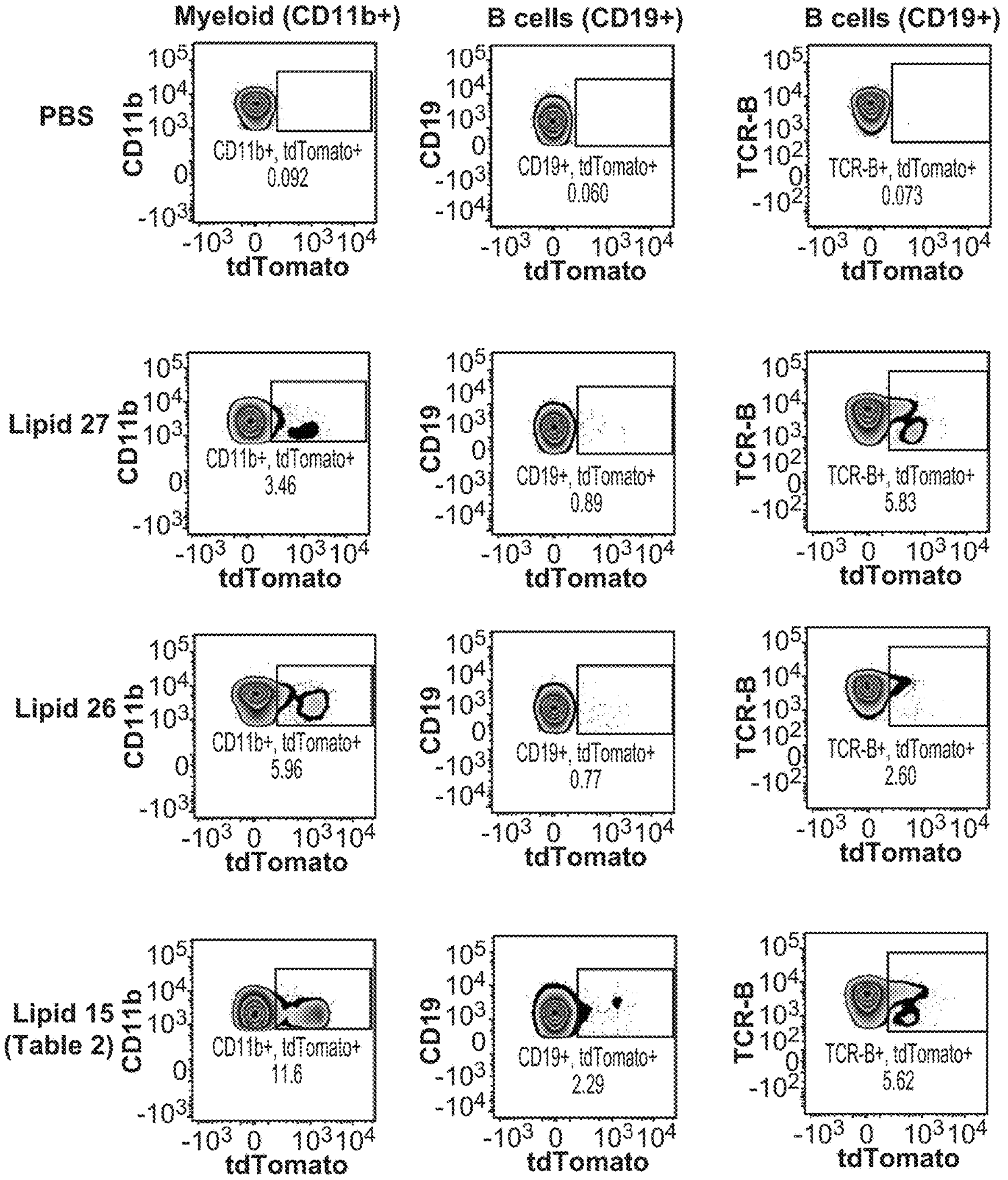
FIG. 45A shows representative FACS plots with frequencies of tdTomato expression in various spleen immune cell subsets following treatment with LNPs formed with Lipid 27 or 26 from Table 10a or Lipid 15 from Table 10b.
Figure 45B:
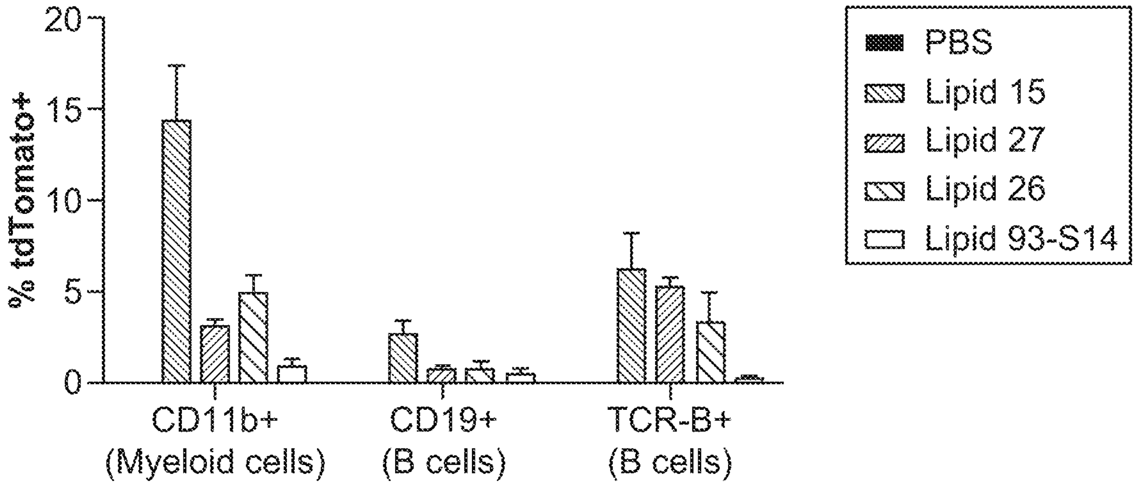
FIG. 45B shows the quantification of the proportion of myeloid cells, B cells, and T cells expressing tdTomato (mean+std. dev., n=3), equivalent to the proportion of each cell population successfully transfected with Cre circular RNA.

FIG. 45A shows representative FACS plots with frequencies of tdTomato expression in various spleen immune cell (CD45+, live) subsets, including total myeloid (CD11b+), B cells (CD19+), and T cells (TCR-B+) following treatment with LNPs formed with Lipid 27 or 26 from Table 10a or Lipid 15 from Table 10b. Ai9 mice injected with PBS represented background tdTomato fluorescence. FIG. 45B quantifies the proportion of myeloid cells, B cells, and T cells expressing tdTomato (mean+std. dev., n=3), which is equivalent to the proportion of each cell population which has been successfully transfected with Cre circular RNA. LNPs made with Lipids 27 and 26 from Table 10a exhibit significantly higher myeloid and T cell transfection compared with Lipid 93-S 14, highlighting the improvements conferred by lipid structural modifications.

Figure 45C:
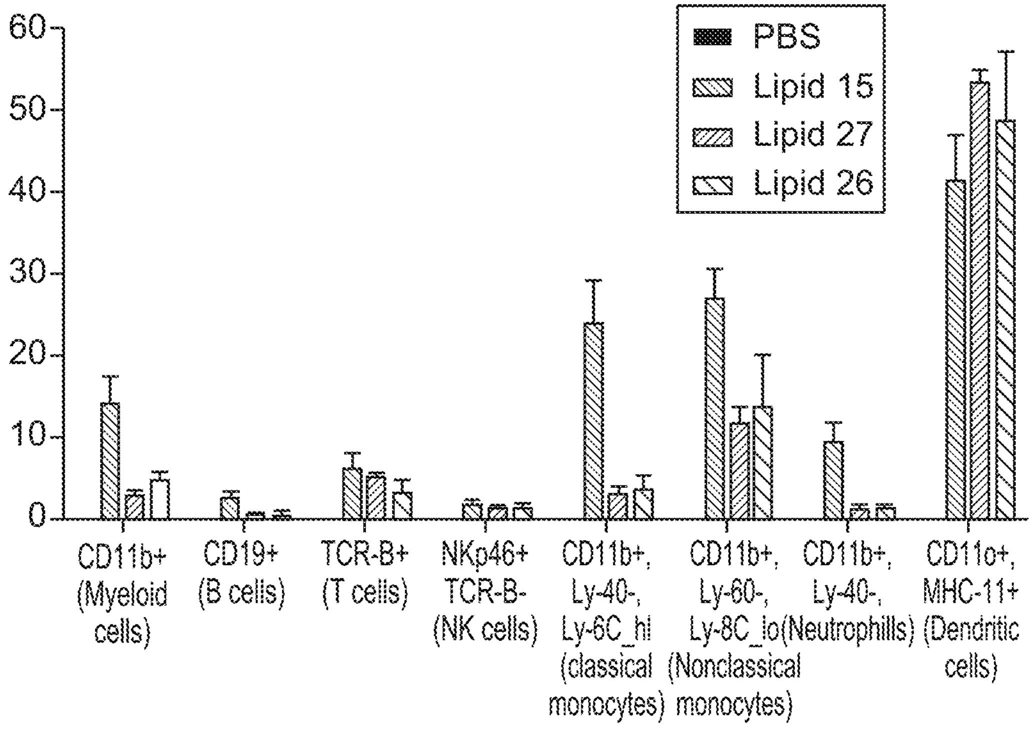
FIG. 45C illustrates the proportion of additional splenic immune cell populations, including NK cells, classical monocytes, nonclassical monocytes, neutrophils, and dendritic cells, expressing tdTomato after treatment with Lipids 27 and 26 (mean+std. dev., n=3).

FIG. 45C illustrates the proportion of additional splenic immune cell populations expressing tdTomato with Lipids 27 and 26 from Table 10a (mean+std. dev., n=3), which also include NKcells (NKp46+, TCR-B-), classical monocytes (CDllb+, Ly-6G−, Ly-6C_hi), nonclassical monocytes (CD11b+, Ly-6G−, Ly-6C_lo), neutrophils (CD11b+, Ly-6G+), and dendritic cells (CD11c+, MHC-II+). These experiments demonstrate that LNPs made with Lipids 27 and 26 from Table 10a and Lipid 15 from Table 10b are effective at delivering circular RNAs to many splenic immune cell subsets in mice and lead to successful protein expression from the circular RNA in those cells.

Example 47

Example 47A: Built-In polyA Sequences and Affinity-Purification to Produce Immue-Silent Circular RNA PolyA sequences (20-30 nt) were inserted into the 5' and 3' ends of the RNA construct (precursor RNA with built-in polyA sequences in the introns). Precursor RNA and introns can alternatively be polyadenylated post-transcriptionally using, e.g., *E coli*. polyA polymerase or yeast polyA polymerase, which requires the use of an additional enzyme.

Circular RNA in this example was circularized by in vitro transcription (IVT) and affinity-purified by washing over a commercially available oligo-dT resin to selectively remove polyA-tagged sequences (including free introns and precursor RNA) from the splicing reaction. The IVT was performed with a commercial IVT kit (New England Biolabs) or a customerized IVT mix (Orna Therapeutics), containing guanosine monophosphate (GMP) and guanosine triphosphate (GTP) at different ratios (GMP:GTP=8, 12.5, or 13.75). In some embodiments, GMP at a high GMP:GTP ratio may be preferentially included as the first nucleotide, yielding a majority of monophosphate-capped precursor RNAs. As a comparison, the circular RNA product was alternatively purified by the treatment with Xrn1, Rnase R, and Dnase I (enzyme purification).

Immunogenicity of the circular RNAs prepared using the affinity purification or enzyme purification process were then assessed. Briefly, the prepared circular RNAs were transfected into A549 cells. After 24 hours, the cells were lysed and interferon beta-1 induction relative to mock samples was measured by qPCR. 3p-hpRNA, a triphosphorylated RNA, was used as a positive control.

Figure 46A:
FIG. 46A depicts an exemplary RNA construct design with built-in polyA sequences in the introns.
Figure 46B:
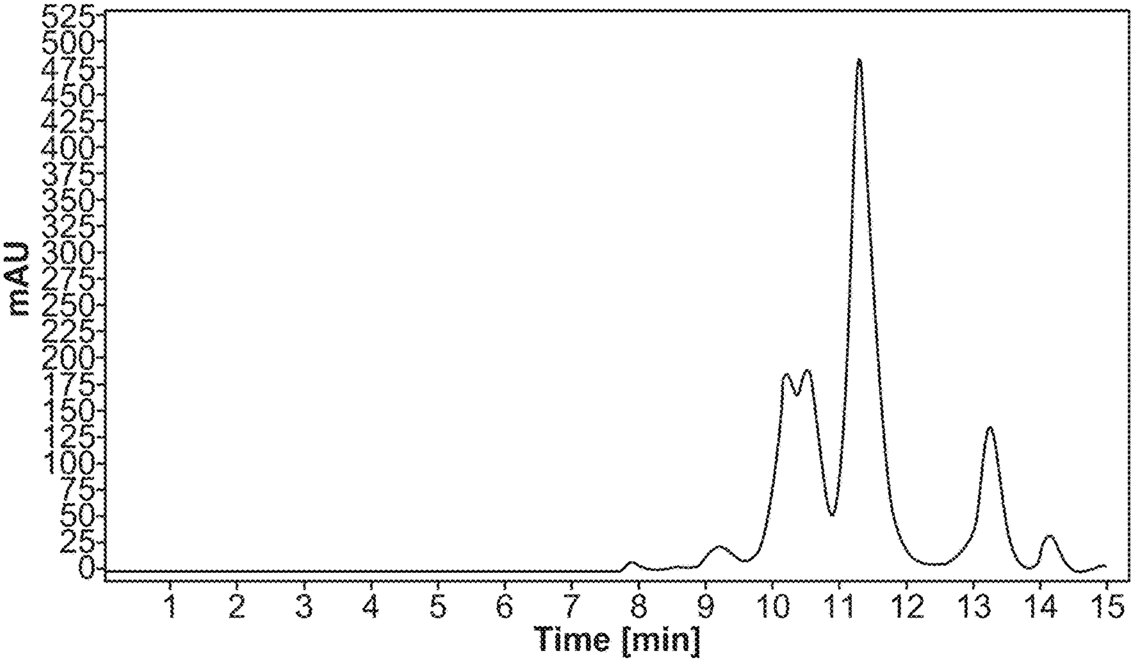
FIG. 46B shows the chromatography trace of unpurified circular RNA.
Figure 46C:
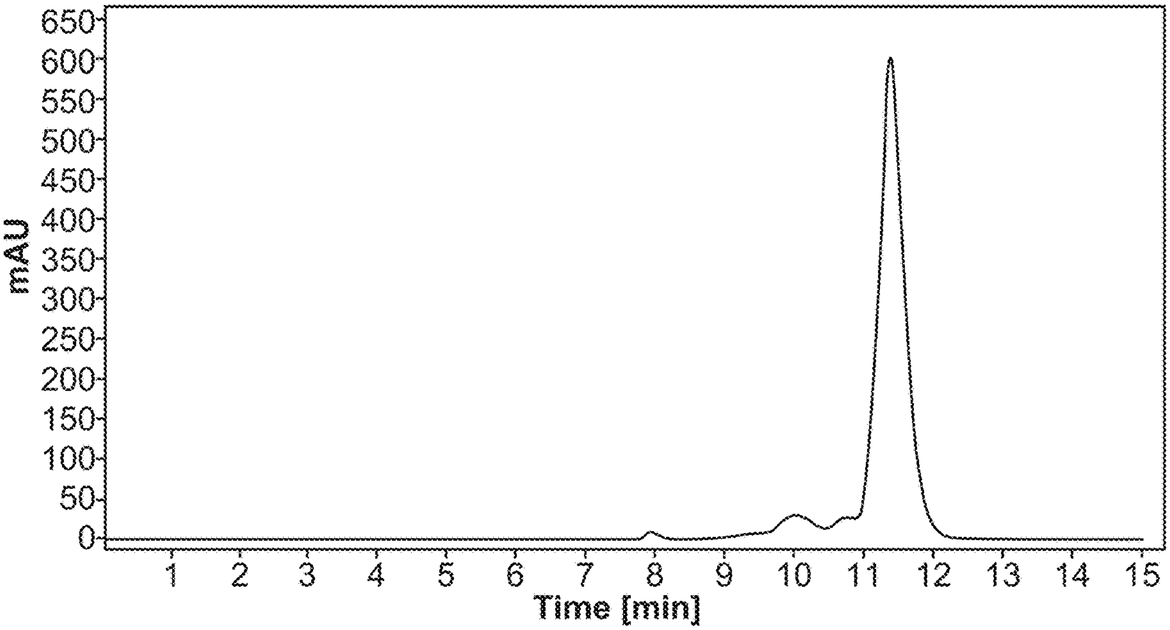
FIG. 46C shows the chromatography trace of affinity-purified circular RNA.
Figure 46D:
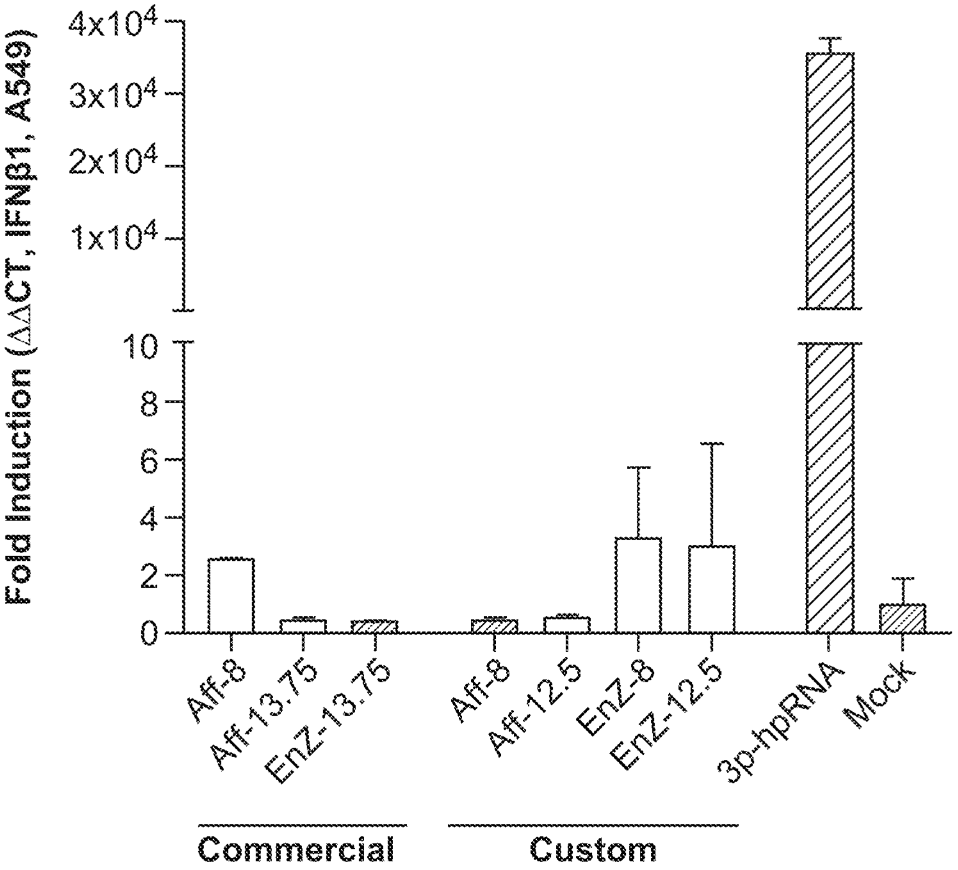
FIG. 46D shows the immunogenicity of the circular RNAs prepared with varying IVT conditions and purification methods. (Commercial=commercial IVT mix; Custom=customerized IVT mix; Aff=affinity purification; Enz=enzyme purification; GMP:GTP ratio=8, 12.5, or 13.75).

FIGS. 46B and 46C show that the negative selection affinity purification removes non-circular products from splicing reactions when polyA sequences are included on elements that are removed during splicing and present in unspliced precursor molecules. FIG. 46D shows circular RNAs prepared with tested IVT conditions and purification methods are all immunoquiescent. These results suggest the negative selection affinity purification is equivalent or superior to enzyme purification for circular RNA purification and that customized circular RNA synthesis conditions (IVT conditions) may reduce the reliance on GMP excess to achieve maximal immunoquiescence.

Example 47B: Dedicated Binding Site and Affinity-Purification for Circular RNA Production Instead of polyA Tags, One can Include Specifically Design Sequences (DBS, Dedicated Binding Site)

Instead of a polyA tag, a dedicated binding site (DBS), such as a specifically designed complementary oligonucleotide that can bind to a resin, may be used to selectively deplete precursor RNA and free introns. In this example, DBS sequences (30 nt) were inserted into the 5' and 3' ends of the precursor RNA. RNA was transcribed and the transcribed product was washed over a custom complementary oligonucleotide linked to a resin.

Figure 47A:
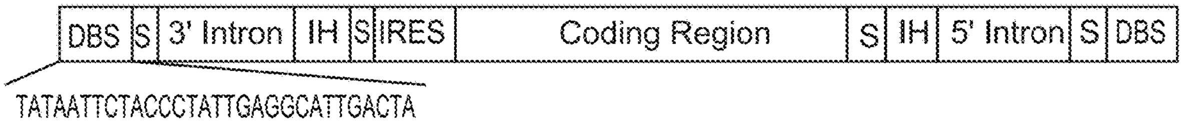
FIG. 47A depicts an exemplary RNA construct design with a dedicated binding sequence as an alternative to polyA for hybridization purification.
Figure 47B:
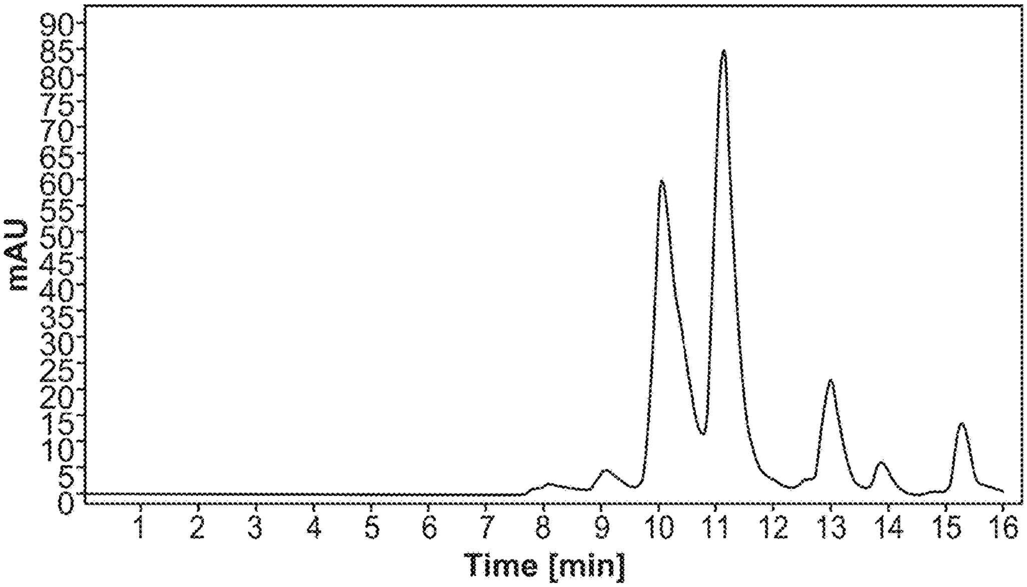
FIG. 47B shows the chromatography trace of unpurified circular RNA.
Figure 47C:
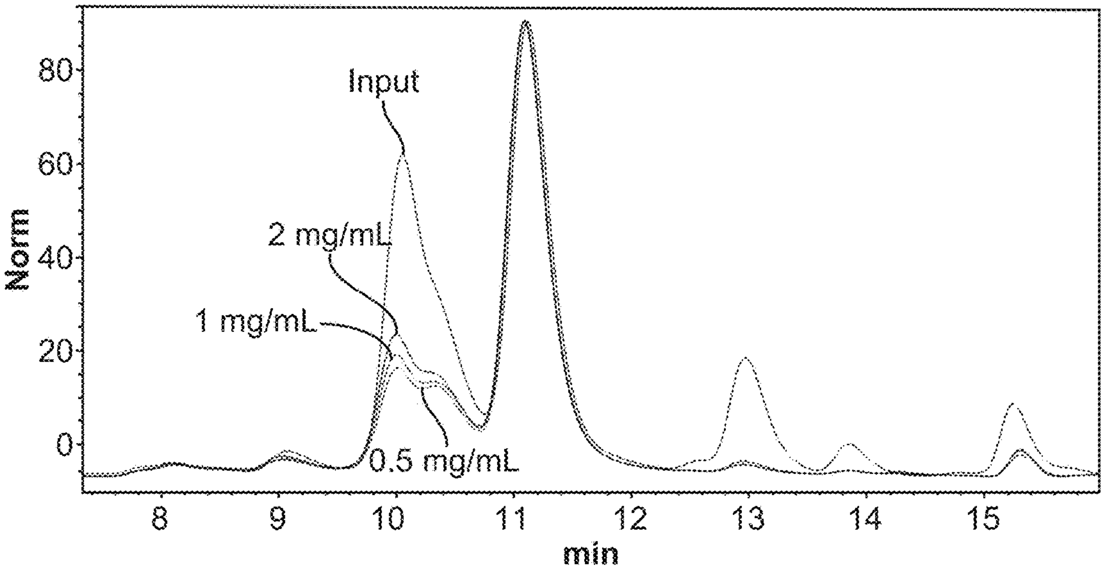

FIGS. 47B and 47C demonstrates that including the designed DBS sequence in elements that are removed during splicing enables the removal of unspliced precursor RNA and free intron components in a splicing reaction, via negative affinity purification.

Example 47C: Production of a Circular RNA Encoding Dystrophin

Figure 48A:
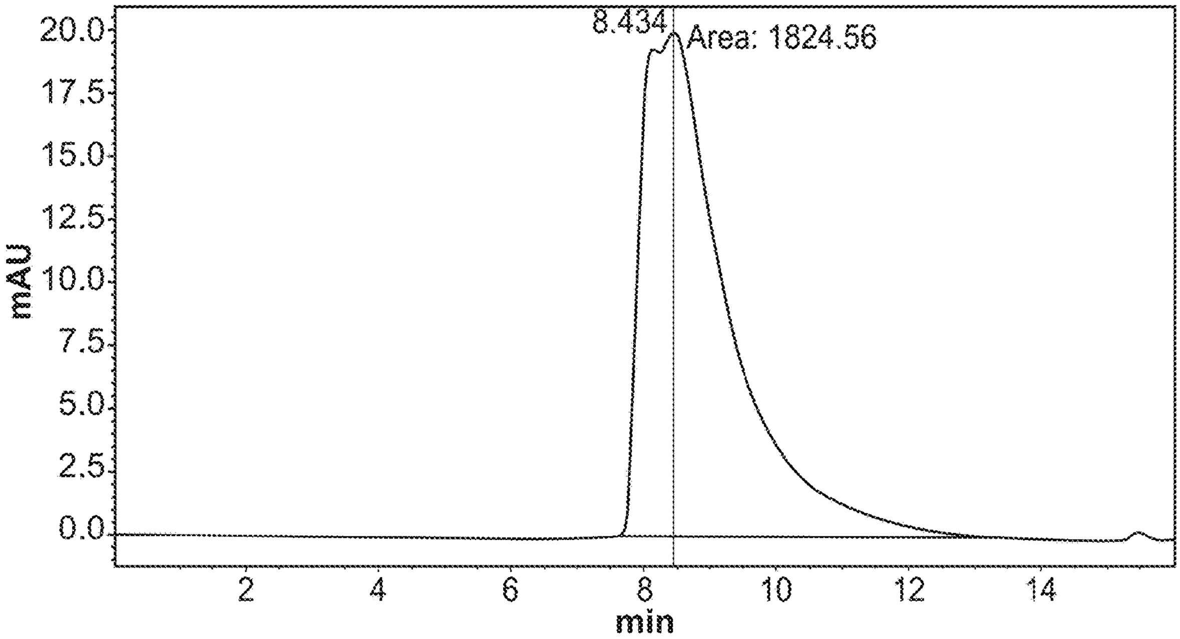
FIG. 48A shows the chromatography trace of unpurified circular RNA encoding dystrophin.
Figure 48B:
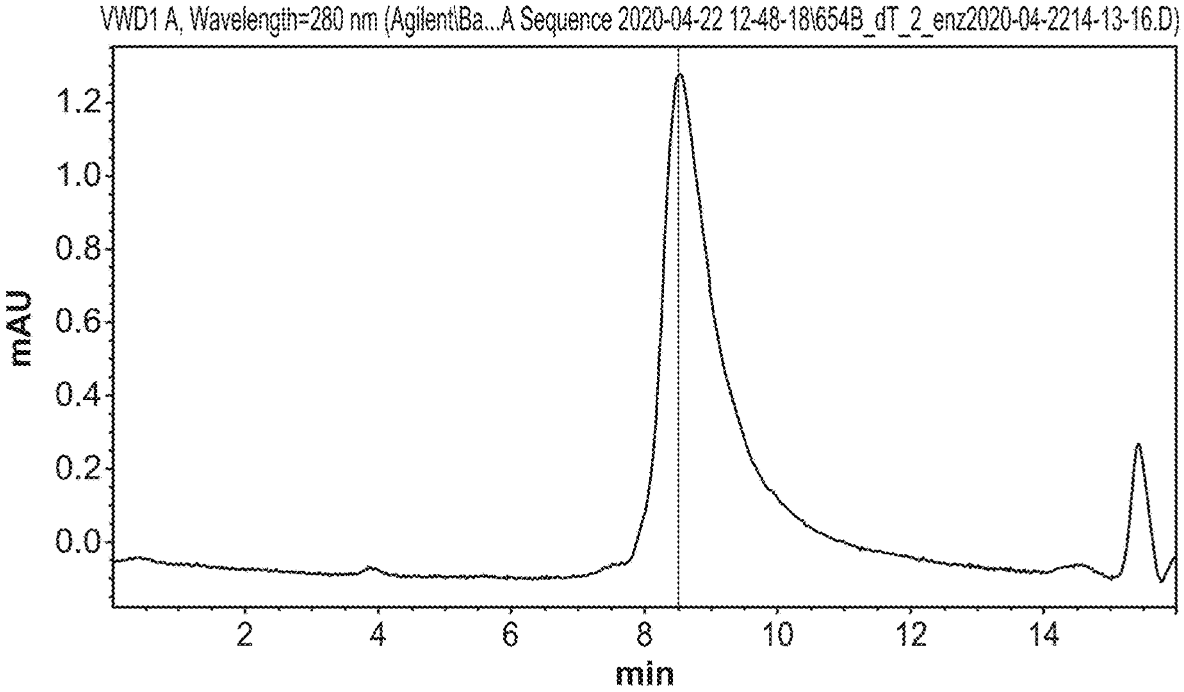
FIG. 48B shows the chromatography trace of enzyme-purified circular RNA encoding dystrophin.

A 12kb12,000 nt circular RNA encoding dystrophin was produced by in vitro transcription of RNA precursors followed by enzyme purification using a mixture of Xrn1, DNase 1, and RNase R to degrade remaining linear components. FIG. 48 shows that the circular RNA encoding dystrophin was successfully produced.

Example 48

5' Spacer Between 3' Intron Fragment and the IRES Improves Circular RNA Expression Expression level of purified circRNAs with different 5' spacers between the 3' intron fragment and the IRES in Jurkat cells were compared. Briefly, luminescence from secreted *Gaussia* luciferase in supernatant was measured 24 hours after electroporation of 60,000 cells with 250ng of each RNA.

Additionally, stability of purified circRNAs with different 5' spacers between the 3' intron fragment and the IRES in Jurkat cells were compared. Briefly, luminescence from secreted *Gaussia* luciferase in supernatant was measured over 2 days after electroporation of 60,000 cells with 250ng of each RNA and normalized to day 1 expression.

Figure 49A:
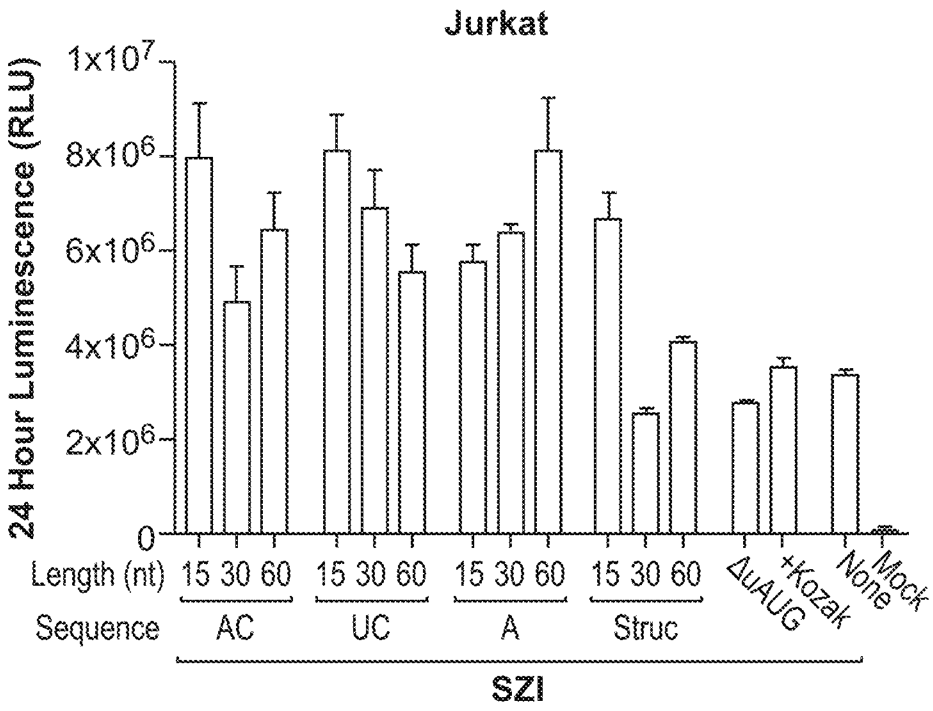
FIGS. 49A and 49B compares the expression (FIG. 49A) and stability (FIG. 49B) of purified circRNAs with different 5' spacers between the 3' intron fragment/5' internal duplex region and the IRES in Jurkat cells. (AC=only A and C were used in the spacer sequence; UC=only U and C were used in the spacer sequence.)
Figure 49B:
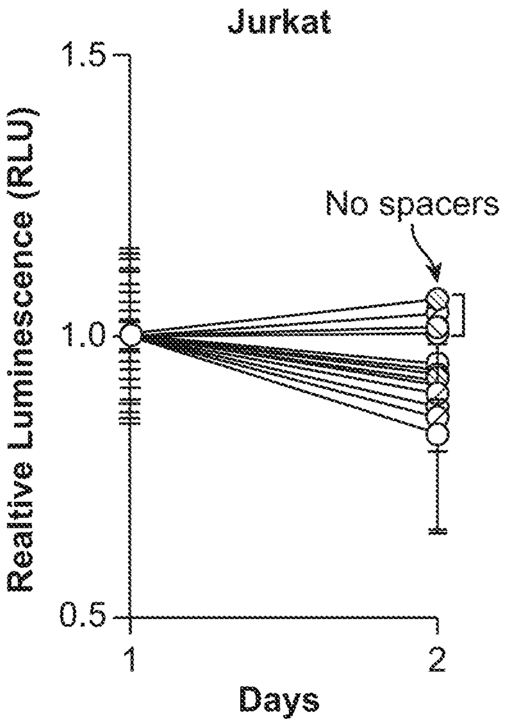

The results are shown in FIGS. 49A and 49B, indicating that adding a spacer can enhance IRES function and the importance of sequence identity and length of the added spacer. A potential explanation is that the spacer is added right before the IRES and likely functions by allowing the IRES to fold in isolation from other structured elements such as the intron fragments.

Example 49

This example describes deletion scanning from 5' or 3' end of the caprine kobuvirus IRES. IRES borders are generally poorly characterized and require empirical analysis, and this example can be used for locating the core functional sequences required for driving translation. Briefly, circular RNA constructs were generated with truncated IRES elements operably linked to a *gaussia* luciferase coding sequence. The truncated IRES elements had nucleotide sequences of the indicated lengths removed from the 5' or 3' end. Luminescence from secreted *gaussia* luciferase in supernatant was measured 24 and 48 hours after electroporation of primary human T cells with RNA. Stability of expression was calculated as the ratio of the expression level at the 48-hour time point relative to that at the 24-hour time point.

Figure 50:
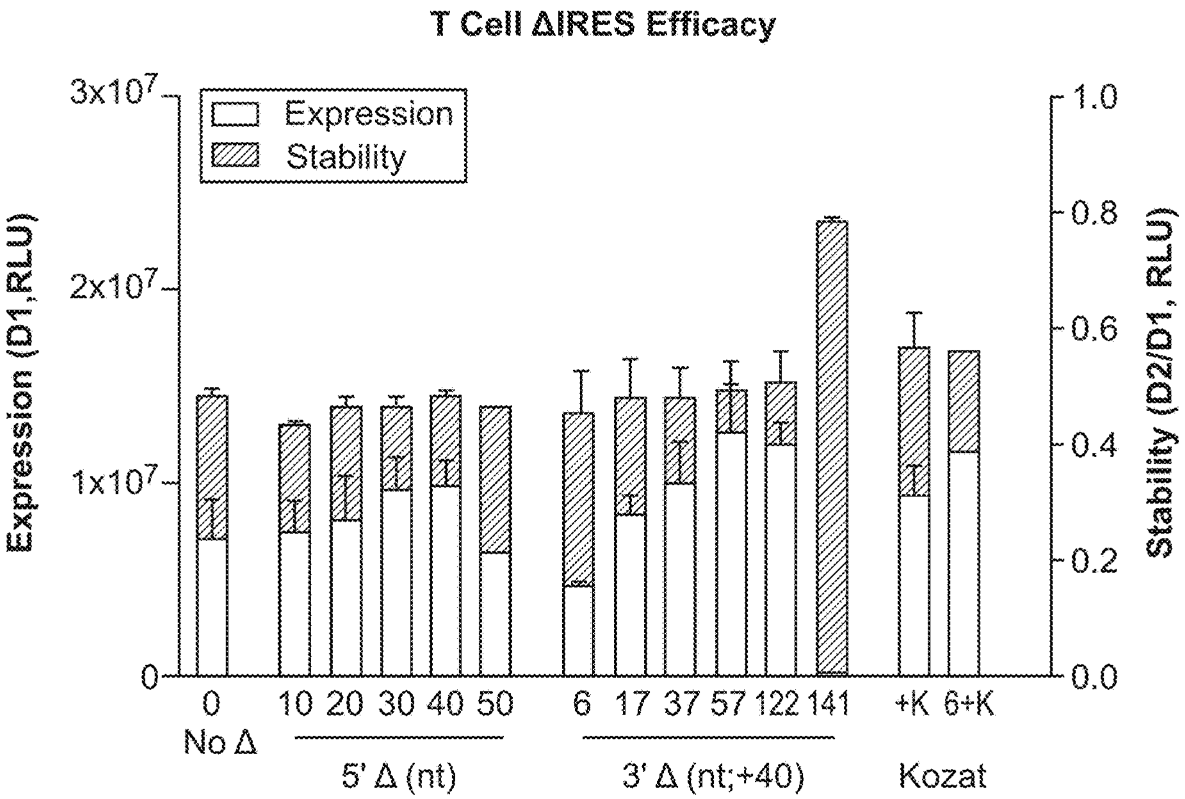
FIG. 50 shows luminescence expression levels and stability of expression in primary T cells from circular RNAs containing the original or modified IRES elements indicated.

As shown in FIG. 50, deletion of more than 40 nucleotides from the 5' end of the IRES reduced expression and disrupted IRES function. Stability of expression was relatively unaffected by the truncation of the IRES element but expression level was substantially reduced by deletion of 141 nucleotides from the 3' end of the IRES, whereas deletion of 57 or 122 nucleotides from the 3' end had a positive impact on the expression level.

It was also observed that deletion of the 6-nucleotide pre-start sequence reduced the expression level of the luciferase reporter. Replacement of the 6-nucleotide sequence with a classical kozak sequence (GCCACC) did not have a significant impact but at least maintained expression.

Example 50

This example describes modifications (e.g., truncations) of selected selected IRES sequences, including Caprine Kobuvirus (CKV) IRES, Parabovirus IRES, Apodemus Picornavirus (AP) IRES, Kobuvirus SZAL6 IRES, Crohivirus B (CrVB) IRES, CVB3 IRES, and SAFV IRES. The sequences of the IRES elements are provided in SEQ ID NOs: 348-389. Briefly, circular RNA constructs were generated with truncated IRES elements operably linked to a *gaussia* luciferase coding sequence. HepG2 cells were transfected with the circular RNAs. Luminescence in the supernatant was assessed 24 and 48 hours after transfection. Stability of expression was calculated as the ratio of the expression level at the 48-hour time point relative to that at the 24-hour time point.

Figure 51:
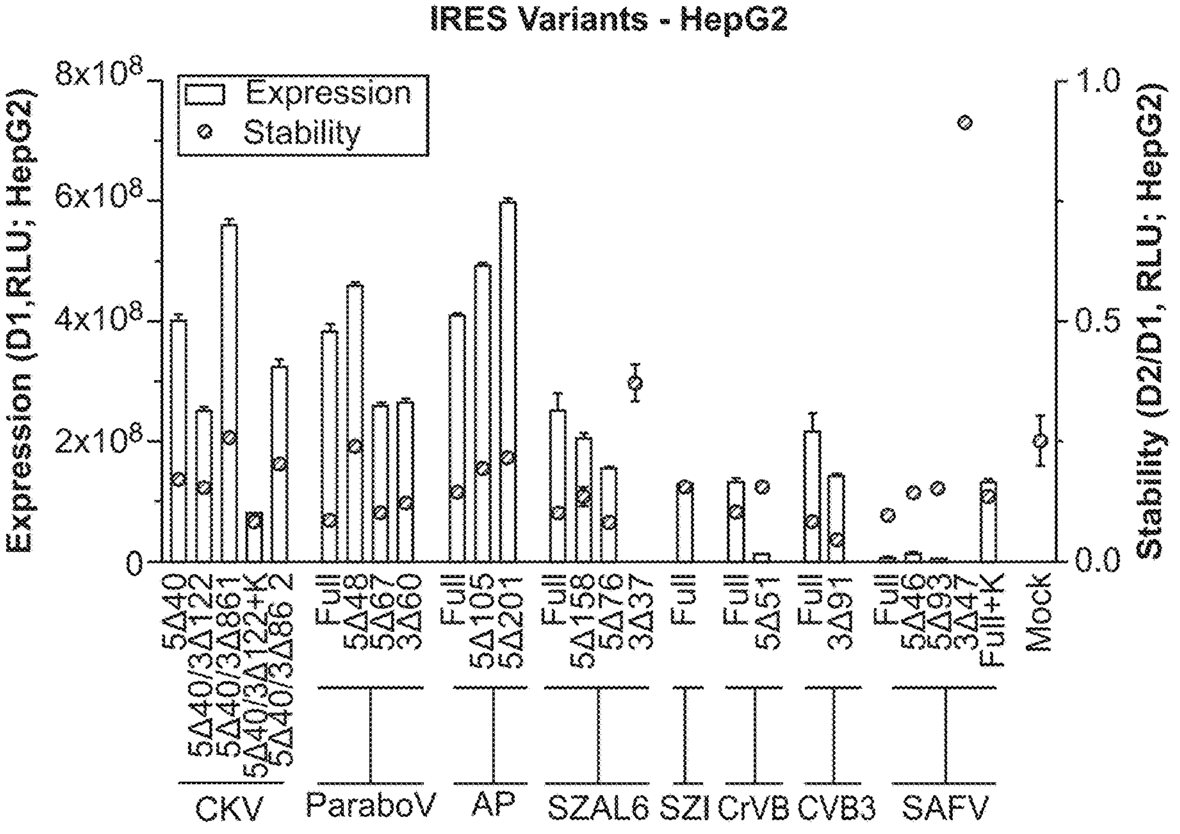
FIG. 51 shows luminescence expression levels and stability of expression in HepG2 cells from circular RNAs containing the original or modified IRES elements indicated.

As shown in FIG. 51, truncations had variable effects depending on the identity of the IRES, which may depend on the initiation mechanism and protein factors used for translation, which often differs between IRESs. 5' and 3' deletions can be effectively combined, for example, in the context of CKV IRES. Addition of a canonical Kozak sequence in some cases significantly improved expression (as in SAFV, Full vs Full+K) or diminished expression (as in CKV, 5d40/3d122 vs 5d40/3d122+K).

Example 51

This example describes modifications of CK-739, AP-748, and PV-743 IRES sequences, including mutations altative translation initiation sites. Briefly, circular RNA constructs were generated with modified IRES elements operably linked to a *gaussia* luciferase coding sequence. Luminescence from secreted *gaussia* luciferase in supernatant was measured 24 and 48 hours after transfection of 1C1C7 cells with RNA.

Figure 52:
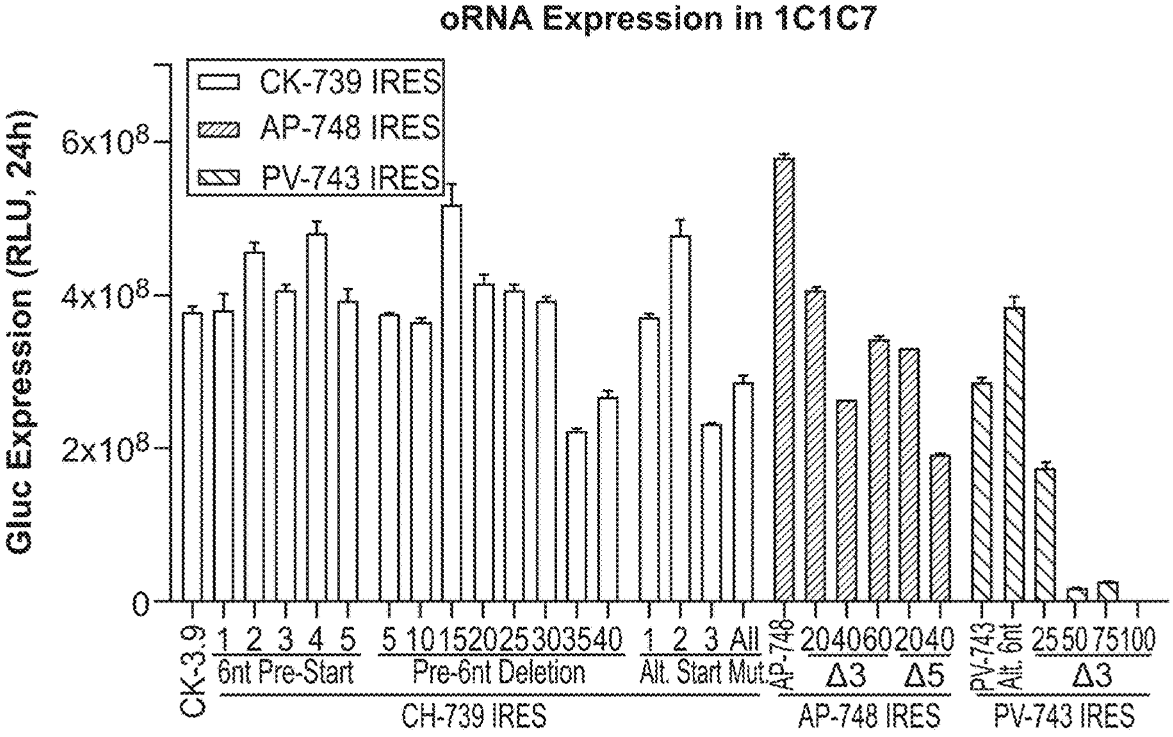
FIG. 52 shows luminescence expression levels and stability of expression in 1C1C7 cells from circular RNAs containing the original or modified IRES elements indicated.

CUG was the most commonly found alternative start site but many others were also characterized. These triplets can be present in the IRES scanning tract prior to the start codon and can affect translation of correct polypeptides. Four alternative start site mutations were created, with the IRES sequnces provided in SEQ ID NOs: 378-380. As shown in FIG. 52, mutations of alternative translation initiation sites in the CK-739 IRES affected translation of correct polypeptides, positively in some instances and negatively in other instances. Mutation of all the alternative translation initiation sites reduced the level of translation.

Alternative Kozak sequences, 6 nucleotides before start codon, can also affect expression levels. The 6-nucleotide sequence upstream of the start codon were gTcacG, aaagtc, gTcacG, gtcatg, gcaaac, and acaacc, respectively, in CK-739 IRES and Sample Nos. 1-5 in the "6 nt Pre-Start" group. As shown in FIG. 52, substitution of certain 6-nucleotide sequences prior to the start codon affected translation.

It was also observed that 5' and 3' terminal deletions in AP-748 and PV-743 IRES sequences reduced expression. However, in the CK-739 IRES, which had a long scanning tract, translation was relatively unaffected by deletions in the scanning tract.

Example 52

This example describes modifications of selected IRES sequences by inserting 5' and/or 3' untranslated regions (UTRs) and creating IRES hybrids. Briefly, circular RNA constructs were generated with modified IRES elements operably linked to a *gaussia* luciferase coding sequence. Luminescence from secreted *gaussia* luciferase in supernatant was measured 24 and 48 hours after transfection of HepG2 cells with RNA.

Figure 53:
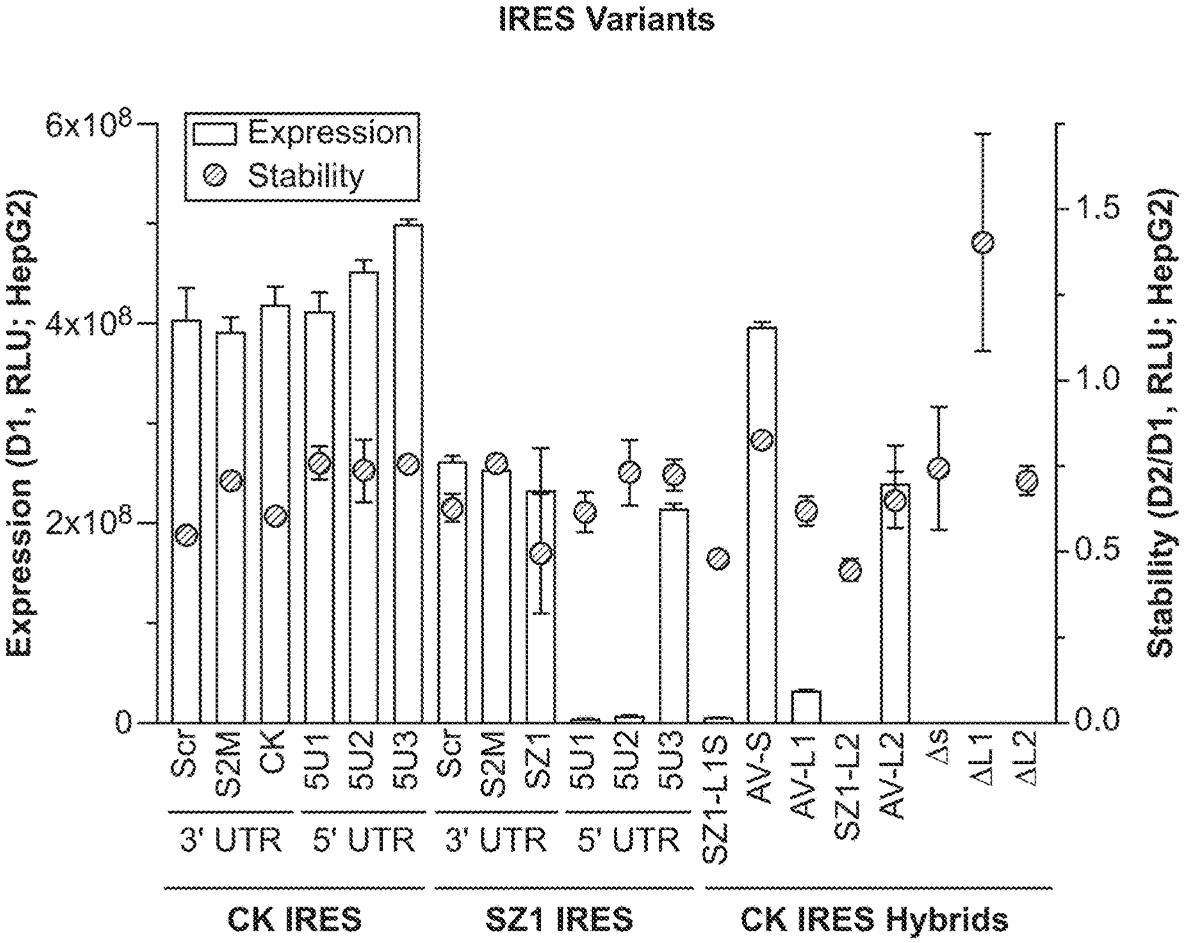
FIG. 53 shows luminescence expression levels and stability of expression in HepG2 cells from circular RNAs containing IRES elements with untranslated regions (UTRs) inserted or hybrid IRES elements. "Scr" means Scrambled, which was used as a control.

IRES sequences with UTRs inserted are provided in SEQ ID NOs: 390-401. As shown in FIG. 53, insertion of 5' UTR right after the 3' end of the IRES and before the start codon slightly increased the translation from Caprine Kobuvirus (CK) IRES but in some instances abrogated translation from Salivirus SZ1 IRES. Insertion of 3' UTR right after the stop cassette had no impact on both IRES sequences.

Hybrid CK IRES sequences are provided in SEQ ID NOs: 390-401. CK IRES was used as a base, and specific regions of the CK IRES were replaced with similar-looking structures from other IRES sequences, for example, SZ1 and AV (Aichivirus). As shown in FIG. 53, certain hybrid synthetic IRES sequences were functional, indicating that hybrid IRES can be constructed using parts from distinct IRES sequences that show similar predicted structures while deleting these structures completely abrogates IRES function.

Example 53

This example describes modifications of circular RNAs by introducing stop codon or cassette variants. Briefly, circular RNA constructs were generated with IRES elements operably linked to a *gaussia* luciferase coding sequence followed by variable stop codon cassettes, which included a stop codon in each frame and two stop codons in the reading frame of the *gaussia* luciferase coding sequence. 1C1C7 cells were transfected with the circular RNAs. Luminescence in supernatant was assessed 24 and 48 hours after transfection.

Figure 54:
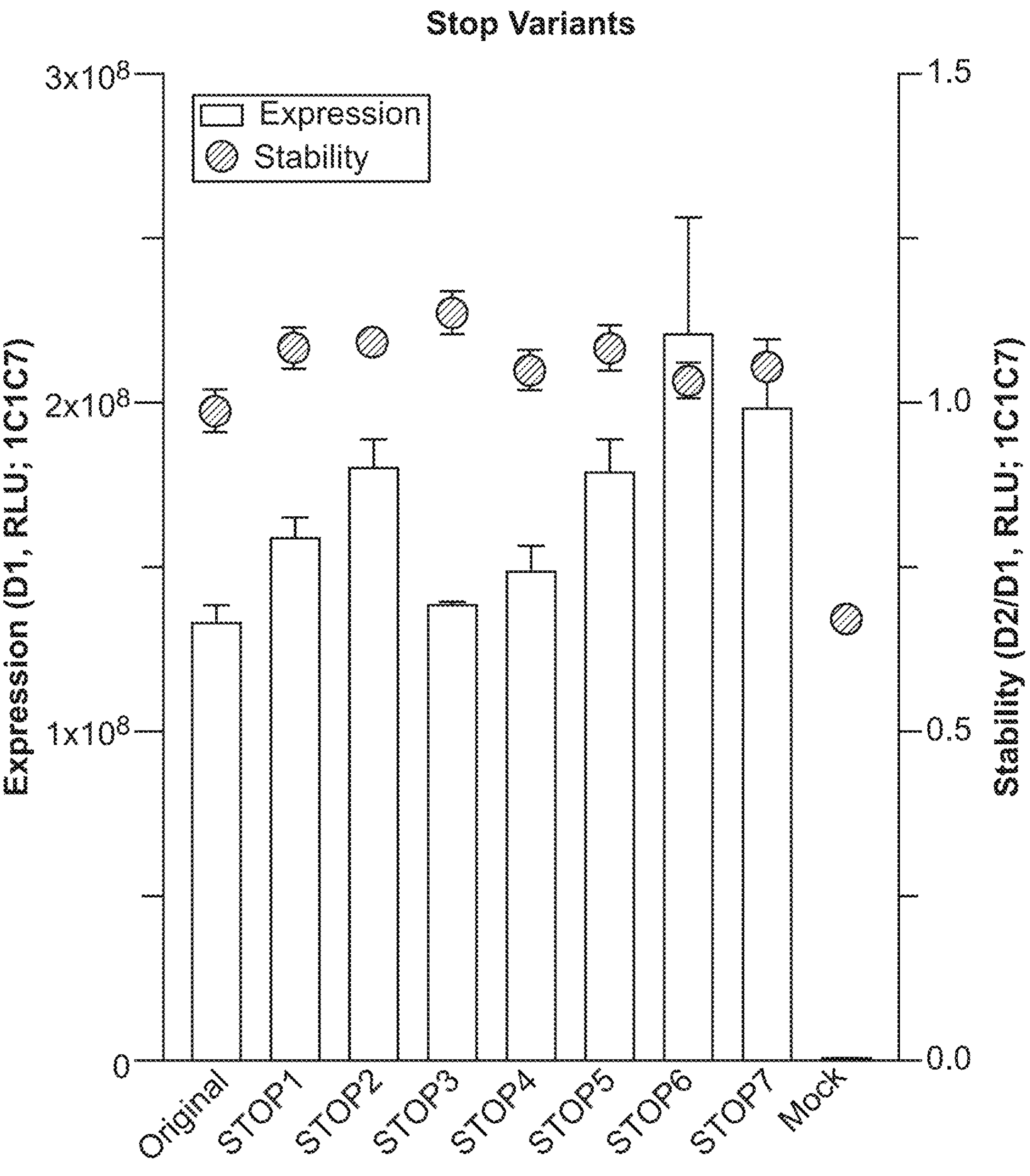
FIG. 54 shows luminescence expression levels and stability of expression in 1C1C7 cells from circular RNAs containing an IRES and variable stop codon cassettes operably linked to a *gaussia* luciferase coding sequence.

The sequences of the stop codon cassettes are set forth in SEQ ID NOs: 406-412. As shown in FIG. 54, certain stop codon cassettes improved expression levels, although they had little impact on expression stability. In particular, a stop cassette with two frame 1 (the reading frame of the *gaussia* luciferase coding sequence) stop codons, the first being TAA, followed by a frame 2 stop codon and a frame 3 stop codon, is effective for promoting functional translation.

Example 54

This example describes modifications of circular RNAs by inserting 5' UTR variants. Briefly, circular RNA constructs were generated with IRES elements with 5' UTR variants inserted between the 3' end of the IRES and the start codon, the IRES being operably linked to a *gaussia* luciferase coding sequence. 1C1C7 cells were transfected with the circular RNAs. Luminescence in supernatant was assessed 24 and 48 hours after transfection.

Figure 55:
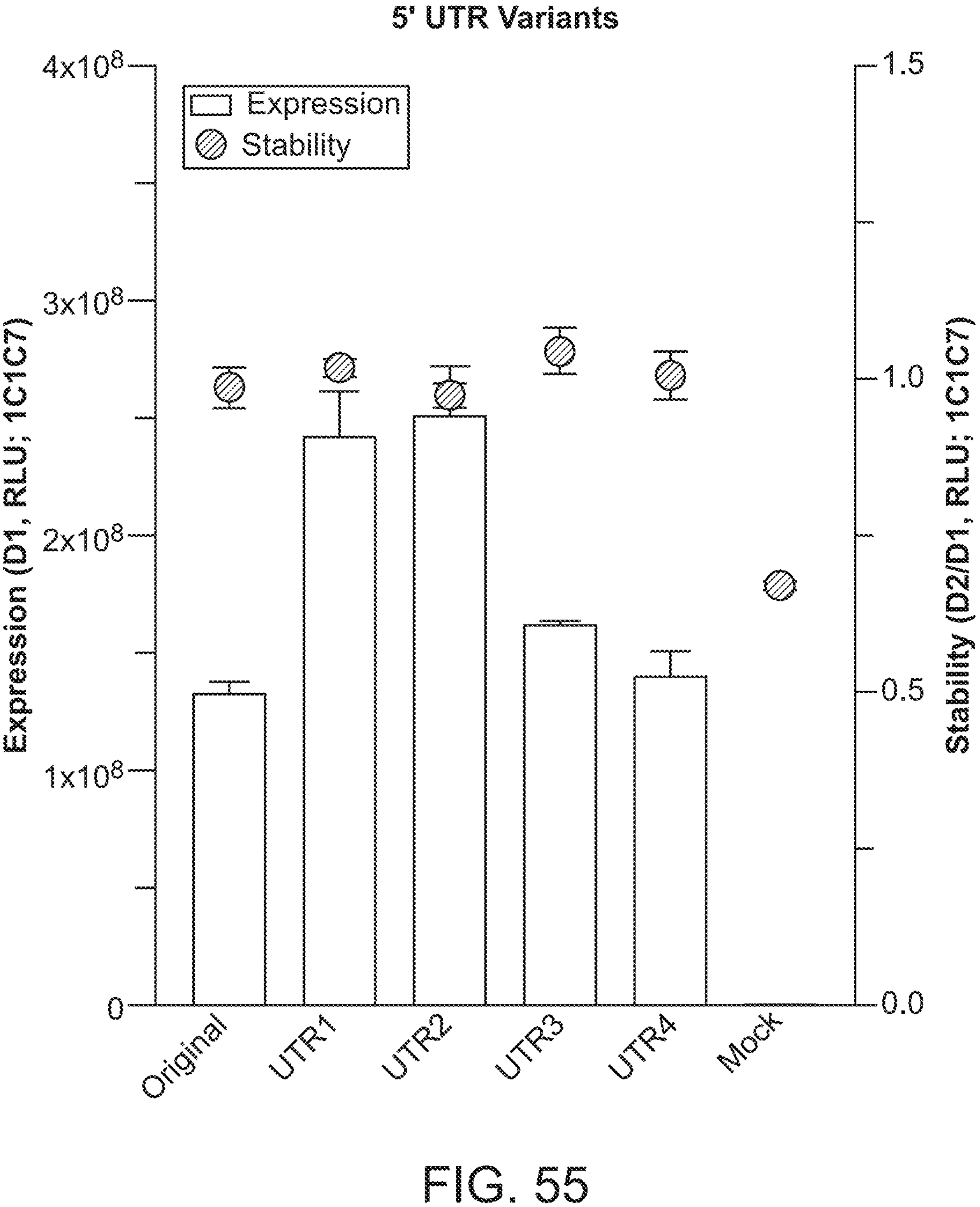
FIG. 55 shows luminescence expression levels and stability of expression in 1C1C7 cells from circular RNAs containing an IRES and variable untranslated regions (UTRs) inserted before the start codon of a gaussian luciferase coding sequence.

The sequences of the 5' UTR variants are set forth in SEQ ID NOs: 402-405. As shown in FIG. 55, a CK IRES with a canonical Kozak sequence (UTR4) was more effective when a 36-nucleotide unstructured/low GC spacer sequence was added (UTR2), suggesting that the GC-rich Kozak sequences may interfere with core IRES folding. Using a higher-GC/structured spacer with a kozak sequence did not show the same benefit (UTR3), possibly due to interference with IRES folding by the spacer itself. Mutating the kozak sequence to gTcacG (UTR1) enhanced translation to the same level as the Kozak+spacer alternative without the need for a spacer.

Example 55

This example describes the impact of miRNA target sites in circular RNAs on expression levels. Briefly, circular RNA constructs were generated with IRES elements operably linked to a human erythropoietin (hEPO) coding sequence, where 2 tandem miR-122 target sites were inserted into the construct. miR-122-expres sing Huh7 cells were transfected with the circular RNAs. hEPO expression in supernatant was assessed 24 and 48 hours after transfection by sandwich ELISA.

Figure 56:
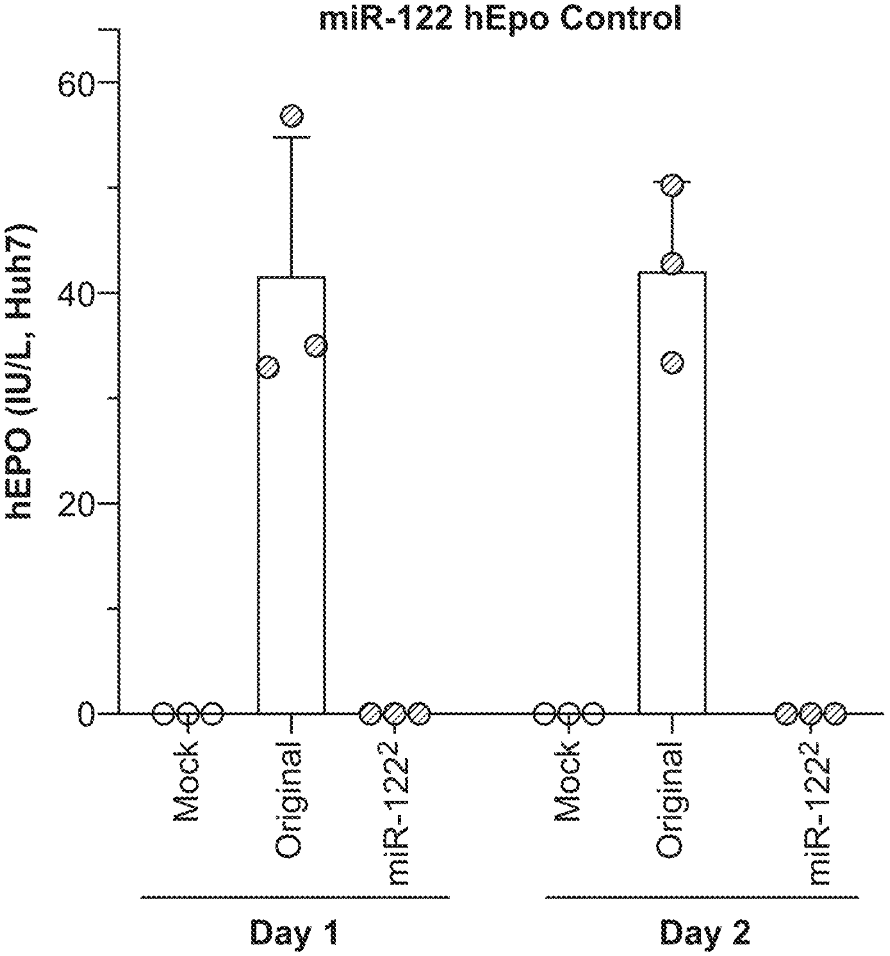
FIG. 56 shows expression levels of human erythropoietin (hEPO) in Huh7 cells from circular RNAs containing two miR-122 target sites downstream from the hEPO coding sequence.

As shown in FIG. 56, the hEPO expression level was obrogated where the miR-122 target sites were inserted into the circular RNA. This result demonstrates that expression from circular RNA can be regulated by miRNA. As such, cell type- or tissue-specific expression can be achieved by incorporating target sites of the miRNAs expressed in the cell types in which expression of the recombinant protein is undesirable.

INCORPORATION BY REFERENCE

All publications, patents, and patent applications mentioned in this specification are herein incorporated by reference to the same extent as if each individual publication, patent, or patent application was specifically and individually indicated as being incorporated by reference herein.

What is claimed is:

1. An ionizable lipid of Formula (1):

Formula (1)

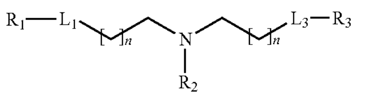

or a pharmaceutically acceptable salt thereof, wherein each n is independently an integer from 2-15;

$L_1$ and $L_3$ are each independently —OC(O)—* or —C(O)O—*, wherein "*" indicates the attachment point to $R_1$ or $R_3$;

$R_1$ and $R_3$ are each independently a linear $C_9$-$C_{20}$ alkyl, a linear or branched $C_9$-$C_{20}$ alkenyl,

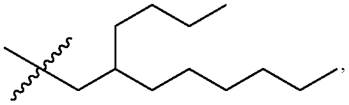,

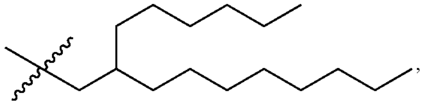,

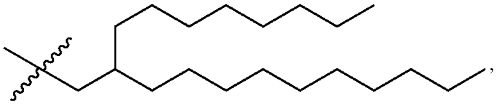,

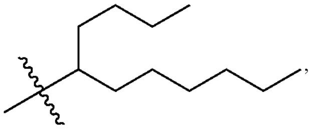,

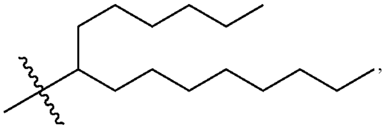,

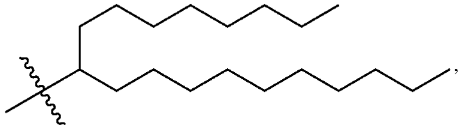,

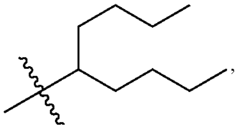, 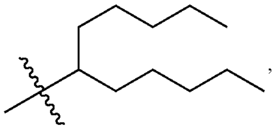,

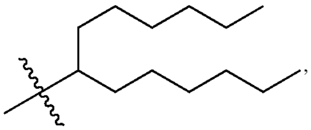, or

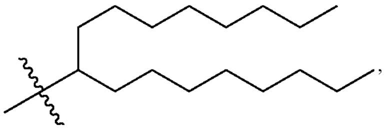, each optionally substituted by one or more substituents selected from a group consisting of oxo, halo, hydroxy, cyano, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ comprises an optionally substituted five-membered heteroaryl selected from imidazolyl, pyrazolyl, or 1,2,4-triazolyl, wherein when $R_2$ comprises imidazolyl, the imidazolyl is not fused with a pyrimidinyl ring.

2. The ionizable lipid of claim 1, wherein $R_2$ comprises an optionally substituted imidazole.

3. The ionizable lipid of claim 1, wherein $R_2$ is selected from a group consisting of:

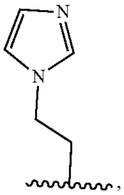, 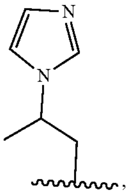, 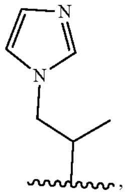,

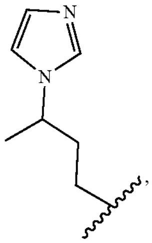, 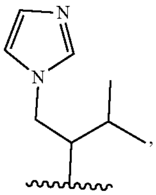, 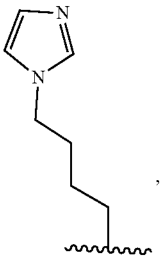,

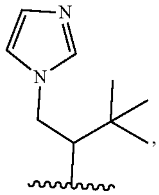, 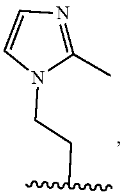, 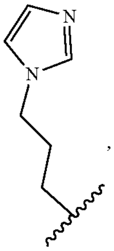, 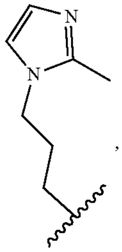,

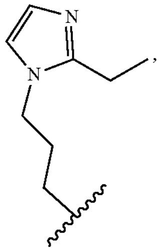, 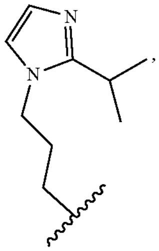, 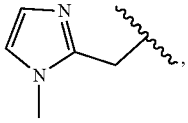,

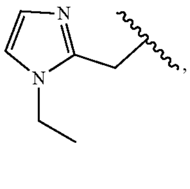, 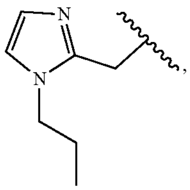,

-continued

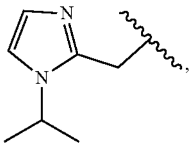,
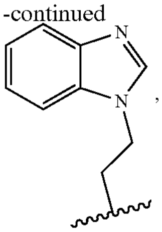,
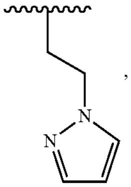,
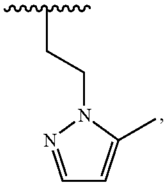, and
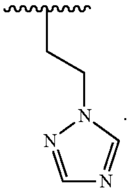.

4. The ionizable lipid of claim 1, wherein the ionizable lipid is represented by Formula (1-1) or Formula (1-2):

Formula (1-1)

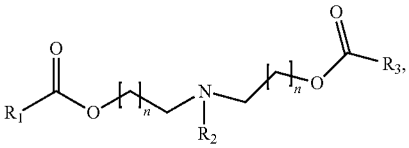

Formula (1-2)

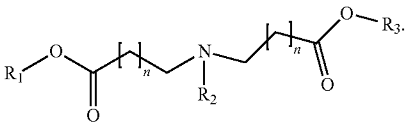

5. The ionizable lipid of claim 1, wherein $R_1$ and $R_3$ are each independently selected from the group consisting of:

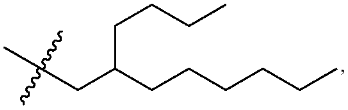,
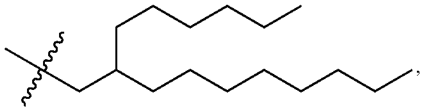,

-continued

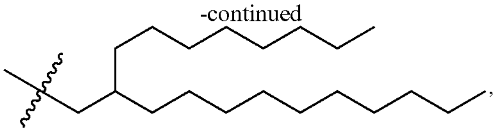,
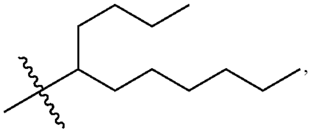,
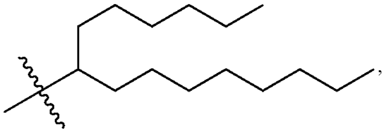,
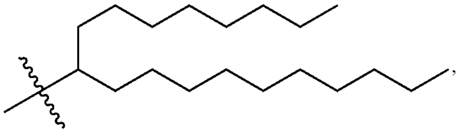,
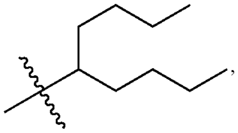,
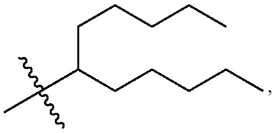,
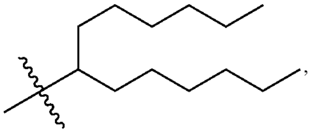,
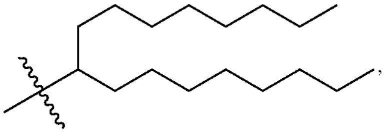, and
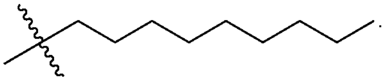.

6. The ionizable lipid of claim 1, wherein $R_1$ and $R_3$ are the same.

7. The ionizable lipid of claim 1, selected from the group consisting of:

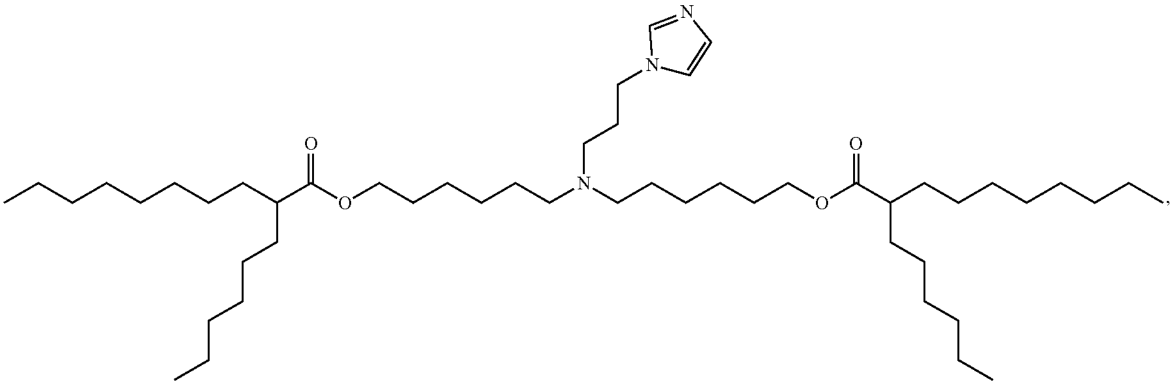,

-continued

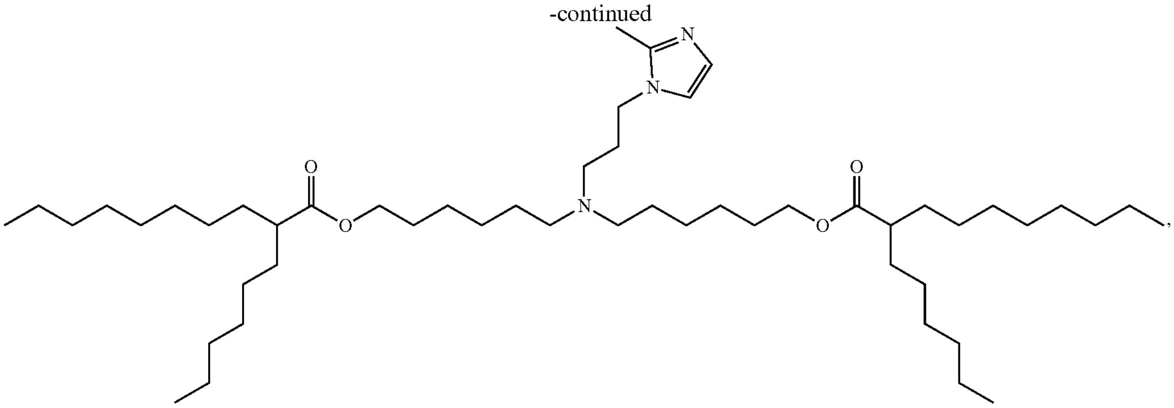

,

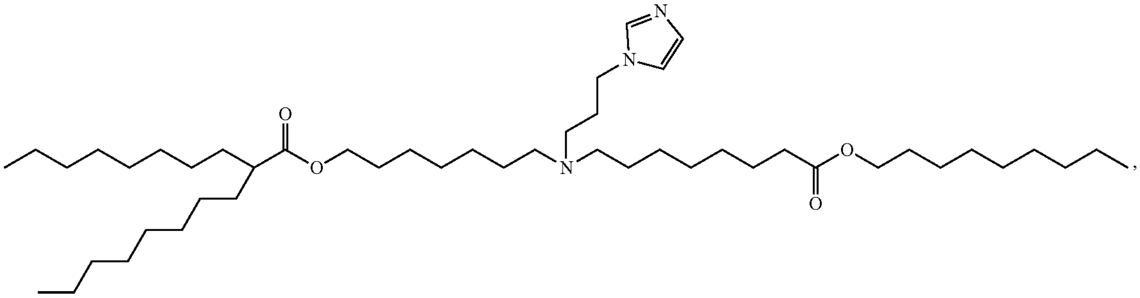

, and

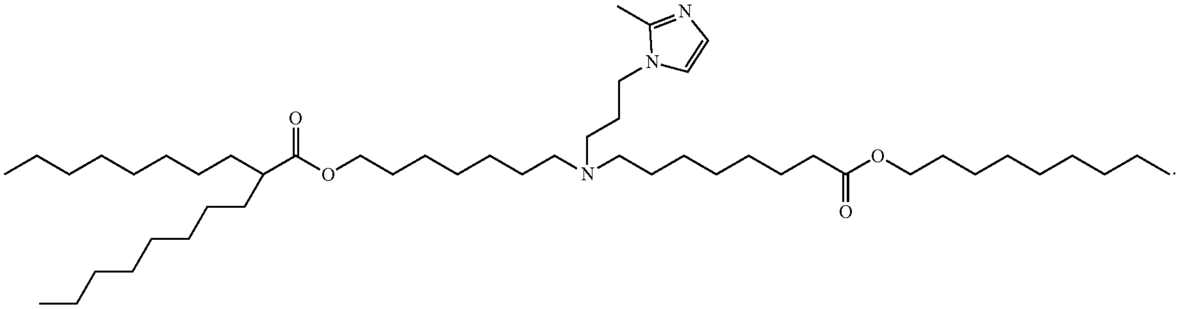

.

8. A pharmaceutical composition comprising a transfer vehicle, wherein the transfer vehicle comprises the ionizable lipid of claim 1.

9. The pharmaceutical composition of claim 8, wherein the transfer vehicle comprises a helper lipid and/or structural lipid.

10. The pharmaceutical composition of claim 9, wherein the structural lipid binds to C1q, and/or promotes the binding of the transfer vehicle comprising said lipid to C1q compared to a control transfer vehicle lacking the structural lipid, and/or increases uptake of C1q-bound transfer vehicle into an immune cell compared to a control transfer vehicle lacking the structural lipid.

11. The pharmaceutical composition of claim 8, wherein the transfer vehicle comprises a PEG-lipid.

12. The pharmaceutical composition of claim 11, wherein the PEG-lipid is a modified PEG-lipid.

13. The pharmaceutical composition of claim 12, wherein the modified PEG-lipid is selected from PEG-c-DOMG, PEG-DMG, PEG-DLPE, PEG-DMPE, PEG-DPPC, PEG-DSPE, PEG-modified phosphatidylethanolamine, PEG-modified phosphatidic acid, PEG-modified ceramide, PEG-modified dialkylamine, PEG-modified diacylglycerol, PEG-modified dialkylglycerol, or a combination thereof.

14. A lipid nanoparticle (LNP) comprising an ionizable lipid, a helper lipid, and a structural lipid, wherein the ionizable lipid is a compound of Formula (1):

Formula (1)

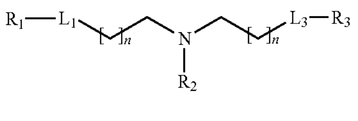

or a pharmaceutically acceptable salt thereof, wherein each n is independently an integer from 2-15;

$L_1$ and $L_3$ are each independently —OC(O)—* or —C(O)O—*, wherein "*" indicates the attachment point to $R_1$ or $R_3$;

$R_1$ and $R_3$ are each independently a linear $C_9$-$C_{20}$ alkyl, a linear or branched $C_9$-$C_{20}$ alkenyl,

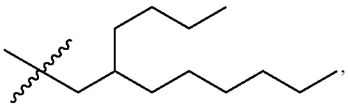

,

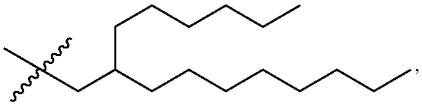

,

-continued

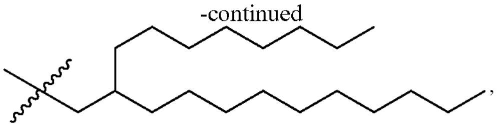,

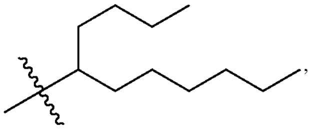,

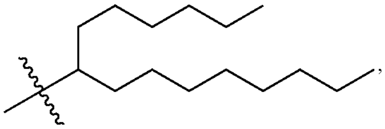,

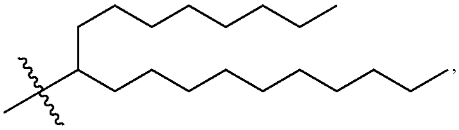,

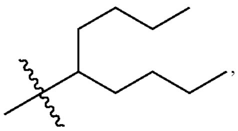,

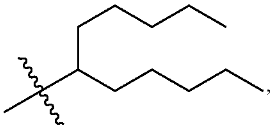,

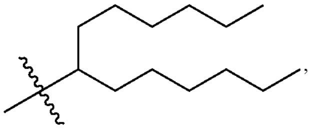, or

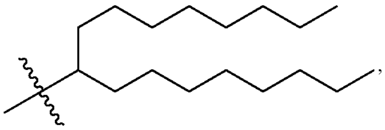, each optionally substituted by one or more substituents selected from a group consisting of oxo, halo, hydroxy, cyano, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ comprises an optionally substituted five-membered heteroaryl selected from imidazolyl, pyrazolyl, or 1,2,4-triazolyl, wherein when $R_2$ comprises imidazolyl, the imidazolyl is not fused with a pyrimidinyl ring.

15. The LNP of claim 14, wherein $R_2$ comprises an optionally substituted imidazole.

16. The LNP of claim 14, wherein $R_2$ is selected from a group consisting of:

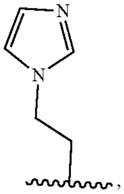, 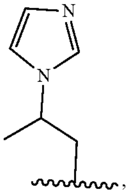, 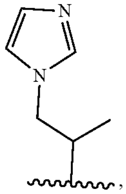,

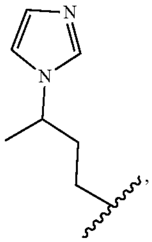, 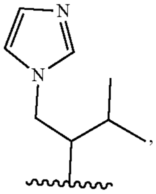, 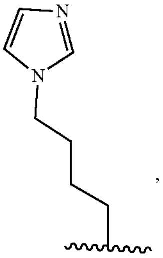,

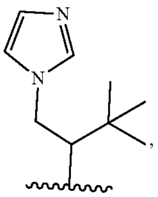, 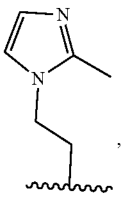, 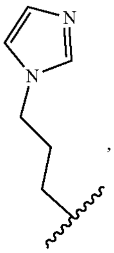, 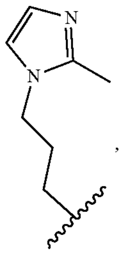,

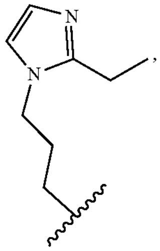, 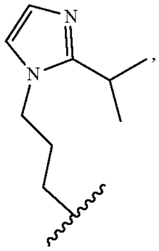, 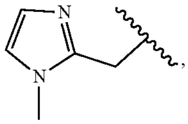,

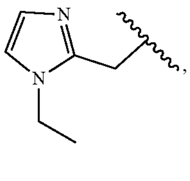, 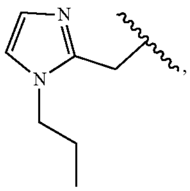,

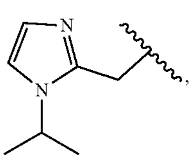, 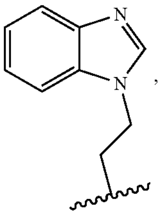, 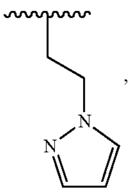,

-continued
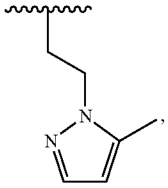
and
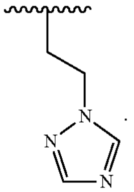
17. The LNP of claim 14, wherein $R_1$ and $R_3$ are each independently selected from the group consisting of:
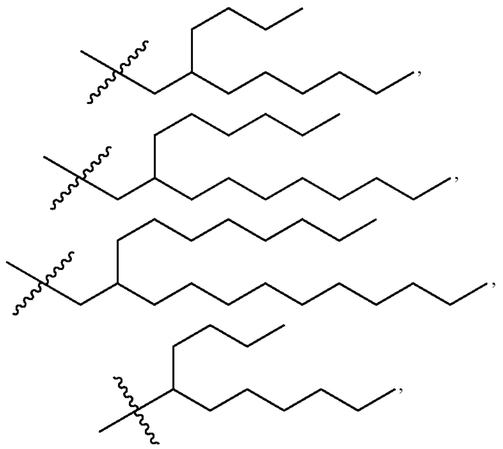
-continued
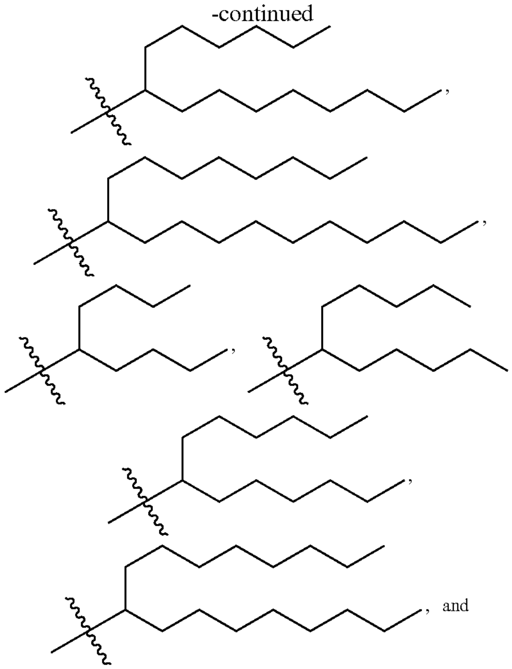
and
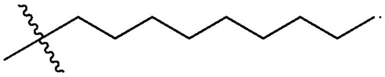
18. The LNP of claim 14, wherein $R_1$ and $R_3$ are the same.
19. The LNP of claim 14, wherein the ionizable lipid is selected from the group consisting of:
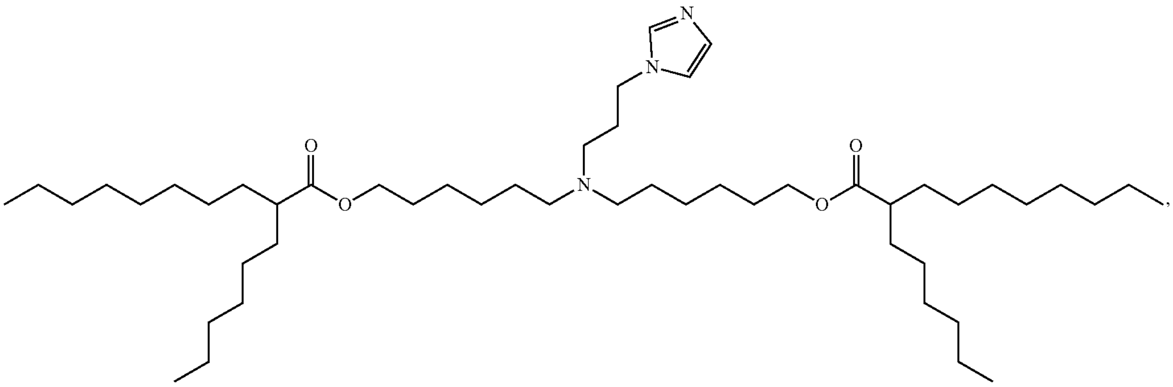
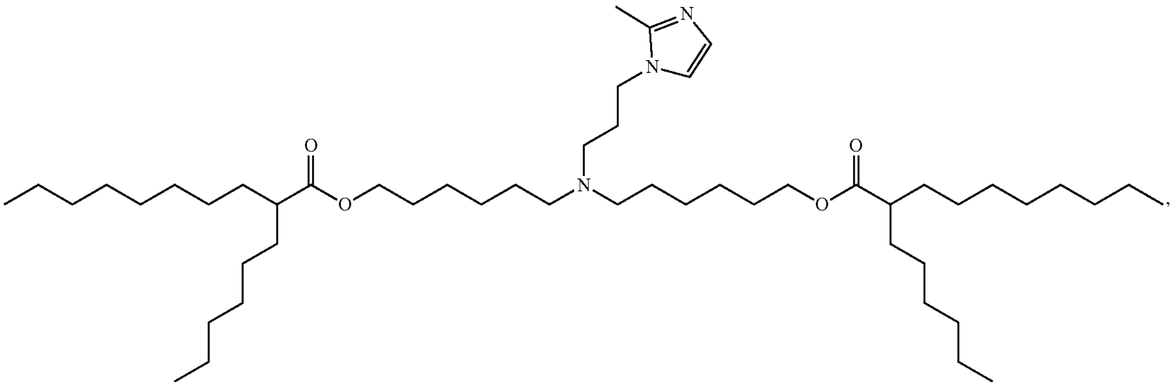

-continued

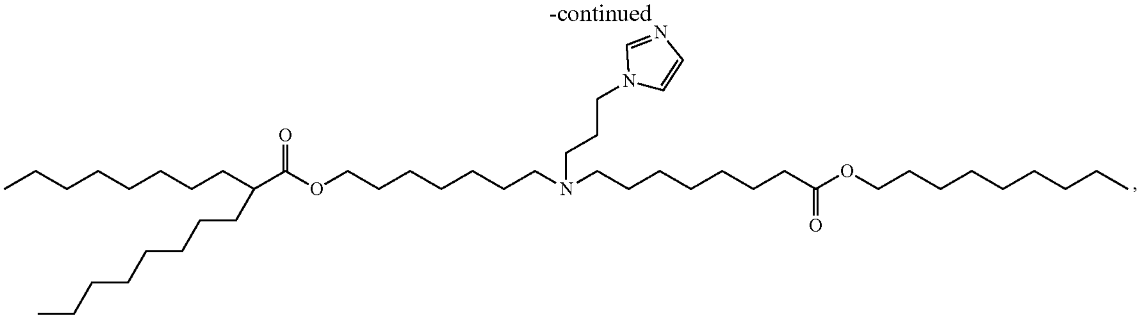

, and

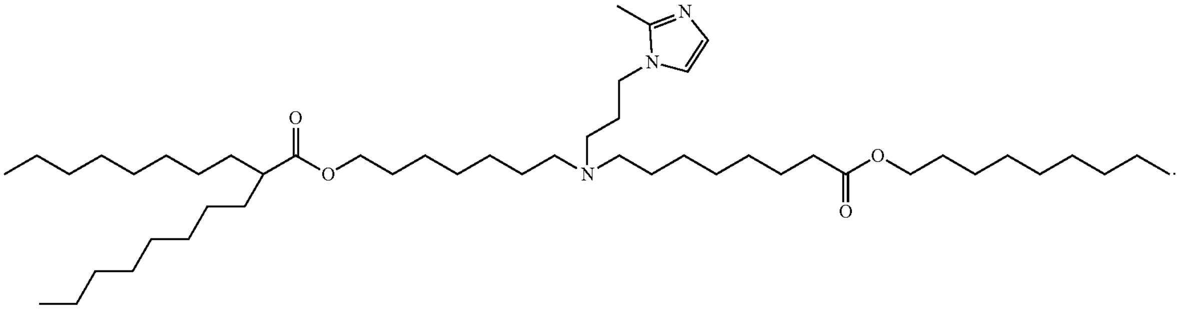

.

20. A pharmaceutical composition comprising: (1) a payload molecule; and (2) a LNP of claim 14.

21. A method of delivering a therapeutic agent to a target cell, comprising administering a LNP of claim 14.

22. The method of claim 21, wherein the therapeutic agent is a RNA polynucleotide.

23. The method of claim 22, wherein the RNA polynucleotide is linear or circular.

24. The method of claim 23, wherein the target cell is a eukaryotic cell.

25. The method of claim 24, wherein the eukaryotic cell is a hepatocyte, a hematopoietic cell, an epithelial cell, an endothelial cell, a lung cell, a bone cell, a stem cell, a mesenchymal cell, a neural cell, a photoreceptor cell, a retinal pigmented epithelial cell, a secretory cell, a cardiac cells, an adipocyte, a vascular smooth muscle cell, a cardiomyocyte, a skeletal muscle cell, a beta cell, a pituitary cell, a synovial lining cell, an ovarian cell, a testicular cell, a fibroblast, a B cell, a T cell, a reticulocyte, a leukocyte, a granulocyte, a tumor cell, an NK cell, an NKT cell, a macrophage, or a neutrophil.

* * * * *

SEQUENCE LISTING

```
<160> NUMBER OF SEQ ID NOS: 717

<210> SEQ ID NO 1
<211> LENGTH: 585
<212> TYPE: DNA
<213> ORGANISM: Unknown
<220> FEATURE:
<223> OTHER INFORMATION: Description of Unknown: Encephalomyocarditis
      virus sequence

<400> SEQUENCE: 1

cccccctctc cctcccccc taacgttact ggccgaagcc gcttggaata aggccggtgt     60

gcgtttgtct atatgttatt ttccaccata ttgccgtctt ttggcaatgt gagggcccgg    120

aaacctggcc ctgtcttctt gacgagcatt cctaggggtc tttcccctct cgccaaagga    180

atgcaaggtc tgttgaatgt cgtgaaggaa gcagttcctc tggaagcttc ttgaagacaa    240

acaacgtctg tagcgaccct ttgcaggcag cggaaccccc cacctggcga caggtgcctc    300

tgcggccaaa agccacgtgt ataagataca cctgcaaagg cggcacaacc ccagtgccac    360

gttgtgagtt ggatagttgt ggaaagagtc aaatggctct cctcaagcgt attcaacaag    420

gggctgaagg atgcccagaa ggtaccccat tgtatgggat ctgatctggg gcctcggtgc    480

acatgcttta catgtgttta gtcgaggtta aaaaacgtct aggccccccg aaccacgggg    540

acgtggtttt cctttgaaaa acacgatgat aatatggcca caacc                    585


<210> SEQ ID NO 2
<211> LENGTH: 568
<212> TYPE: DNA
<213> ORGANISM: Unknown
<220> FEATURE:
<223> OTHER INFORMATION: Description of Unknown: Encephalomyocarditis
      virus sequence

<400> SEQUENCE: 2

ctccccctcc cccccttac tatactggcc gaagccactt ggaataaggc cggtgtgcgt     60

ttgtctacat gctattttct accgcattac cgtcttatgg taatgtgagg gtccagaacc    120

tgaccctgtc ttcttgacga acactcctag ggtctttcc cctctcgaca aaggagtgta    180

aggtctgttg aatgtcgtga aggaagcagt tcctctggaa gcttcttaaa gacaaacaac    240

gtctgtagcg accctttgca ggcagcggaa ccccccacct ggtgacaggt gcctctgcgg    300

ccaaaagcca cgtgtataag atacacctgc aaaggcggca caaccccagt gccacgttgt    360
```

```
gagttggata gttgtggaaa gagtcaaatg gctctcctca agcgtattca acaaggggct    420

gaaggatgcc cagaaggtac ccattgtat gggatctgat ctggggcctc ggtgcacgtg    480

ctttacacgt gttgagtcga ggtgaaaaaa cgtctaggcc ccccgaacca cggggacgtg    540

gttttccttt gaaaaccacg attacaat                                       568
```

<210> SEQ ID NO 3
<211> LENGTH: 696
<212> TYPE: DNA
<213> ORGANISM: Unknown
<220> FEATURE:
<223> OTHER INFORMATION: Description of Unknown: Encephalomyocarditis virus sequence

<400> SEQUENCE: 3

```
ttgccagtct gctcgatatc gcaggctggg tccgtgacta cccactcccc ctttcaacgt     60

gaaggctacg atagtgccag ggcgggtact gccgtaagtg ccaccccaaa caacaacaac    120

aaaacaaact ccccctcccc ccccttacta tactggccga agccacttgg aataaggccg    180

gtgtgcgttt gtctacatgc tattttctac cgcattaccg tcttatggta atgtgagggt    240

ccagaacctg accctgtctt cttgacgaac actcctaggg gtctttcccc tctcgacaaa    300

ggagtgtaag gtctgttgaa tgtcgtgaag gaagcagttc ctctggaagc ttcttaaaga    360

caaacaacgt ctgtagcgac cctttgcagg cagcggaacc ccccacctgg tgacaggtgc    420

ctctgcggcc aaaagccacg tgtataagat acacctgcaa aggcggcaca accccagtgc    480

cacgttgtga gttggatagt tgtggaaaga gtcaaatggc tctcctcaag cgtattcaac    540

aaggggctga aggatgccca gaaggtaccc cattgtatgg gatctgatct ggggcctcgg    600

tgcacgtgct ttacacgtgt tgagtcgagg tgaaaaaacg tctaggcccc ccgaaccacg    660

gggacgtggt tttcctttga aaaccacgat tacaat                              696
```

<210> SEQ ID NO 4
<211> LENGTH: 697
<212> TYPE: DNA
<213> ORGANISM: Unknown
<220> FEATURE:
<223> OTHER INFORMATION: Description of Unknown: Encephalomyocarditis virus sequence

<400> SEQUENCE: 4

```
ttgccagtct gctcgatatc gcaggctggg tccgtgacta cccactcccc ctttcaacgt     60

gaaggctacg atagtgccag ggcgggtact gccgtaagtg ccaccccaaa acaacaacaa    120

cccccccctct ccctcctccc cccctaacgt tactggccga agccgcttgg aataaggccg    180

gtgtgcgttt gtctatatgt tattttccac catattgccg tcttttggca atgtgagggc    240

ccggaaacct ggccctgtct tcttgacgag cattcctagg ggtctttccc ctctcgccaa    300

aggaatgcaa ggtctgttga atgtcgtgaa ggaagcagtt cctctggaag cttcttgaag    360

acaaacaacg tctgtagcga ccctttgcag gcagcggaac cccccacctg gcgacaggtg    420

cctctgcggc caaaagccac gtgtataaga tacacctgca aaggcggcac aaccccagtg    480

ccacgttgtg agttggatag ttgtggaaag agtcaaatgg ctctcctcaa gcgtattcaa    540

caaggggctg aaggatgccc agaaggtacc ccattgtatg ggatctgatc tggggcctcg    600

gtgcacatgc tttacatgtg tttagtcgag gttaaaaaac gtctaggccc cccgaaccac    660

ggggacgtgg ttttcctttg aaaaacacga tgataat                             697
```

<210> SEQ ID NO 5
<211> LENGTH: 562
<212> TYPE: DNA
<213> ORGANISM: Unknown
<220> FEATURE:
<223> OTHER INFORMATION: Description of Unknown: Encephalomyocarditis virus sequence

<400> SEQUENCE: 5

```
ccccccccct aacgttactg gccgaagccg cttggaataa ggccggtgtg cgtttgtcta      60

tatgttattt tccaccatat tgccgtcttt tggcaatgtg agggcccgga aacctggccc     120

tgtcttcttg acgagcattc ctaggggtct ttcccctctc gccaaaggaa tgcaaggtct     180

gttgaatgtc gtgaaggaag cagttcctct ggaagcttct tgaagacaaa caacgtctgt     240

agcgaccctt tgcaggcagc ggaacccccc acctggcgac aggtgcctct gcggccaaaa     300

gccacgtgta taagatacac ctgcaaaggc ggcacaaccc cagtgccacg ttgtgagttg     360

gatagttgtg gaaagagtca aatggctctc ctcaagcgta ttcaacaagg ggctgaagga     420

tgcccagaag gtaccccatt gtatgggatc tgatctgggg cctcggtgca catgctttac     480

atgtgtttag tcgaggttaa aaaacgtcta ggccccccga accacgggga cgtggttttc     540

ctttgaaaaa cacgatgata at                                              562
```

<210> SEQ ID NO 6
<211> LENGTH: 156
<212> TYPE: DNA
<213> ORGANISM: Unknown
<220> FEATURE:
<223> OTHER INFORMATION: Description of Unknown: Picobirnavirus sp. sequence

<400> SEQUENCE: 6

```
gtaaattaaa tgctatttac aaaatttaaa cagaaaggag agatgttatg aaccggtttt      60

acaaggtttc atacatcgaa aatagcacta cctggggcag ccgacacact aacatcgtct     120

gtttaaccag aagtgttact gaaaggaggt tattta                               156
```

<210> SEQ ID NO 7
<211> LENGTH: 340
<212> TYPE: DNA
<213> ORGANISM: Unknown
<220> FEATURE:
<223> OTHER INFORMATION: Description of Unknown: Hepatitis C virus sequence

<400> SEQUENCE: 7

```
acctgcccct aatagggggcg acactccgcc atgaatcact cccctgtgag gaactactgt      60

cttcacgcag aaagcgtcta gccatggcgt tagtatgagt gtcgtacagc ctccaggccc     120

ccccctcccg ggagagccat agtggtctgc ggaaccggtg agtacaccgg aattgccggg     180

aagactgggt cctttcttgg ataaacccac tctatgcccg gacatttggg cgtgcccccg     240

caagactgct agccgagtag cgttgggttg cgaaaggcct tgtggtactg cctgataggg     300

tgcttgcgag tgccccggga ggtctcgtag accgtgcatc                           340
```

<210> SEQ ID NO 8
<211> LENGTH: 315
<212> TYPE: DNA
<213> ORGANISM: Unknown
<220> FEATURE:
<223> OTHER INFORMATION: Description of Unknown: Human Cosavirus sequence

<400> SEQUENCE: 8
ctacaagctt tgtgtaaaca aacttttgtt tggcttttct caagcttctc tcacatcagg 60
ccccaaagat gtcctgaagg taccccgtgt atctgaggat gagcaccatc gactacccgg 120
acctgcaaaa ttttgcaaac gcatgtggta tcccagcccc ctcctctcgg ggagggggct 180
ttgctcactc agcacaggat ctgatcagga gatccacctc cggtgcttta caccggggcg 240
tggatttaaa aattgcccaa ggcctggcgc acaacctagg ggactaggtt ttccttatat 300
tttaaagctg tcaat 315

<210> SEQ ID NO 9
<211> LENGTH: 182
<212> TYPE: DNA
<213> ORGANISM: Unknown
<220> FEATURE:
<223> OTHER INFORMATION: Description of Unknown: Human Cosavirus sequence

<400> SEQUENCE: 9
gtcttaggac gacgcatgtg gtatcccagc cccgcctac attggcgggg gcttttgaag 60
caccagacac tggatctgat caggaggagg gtagctgctt tacagcccct cttaaaaatt 120
gcccaaggtc cggccaccca acctagggga ctaggttttc cttttatttt taaattgtca 180
tt 182

<210> SEQ ID NO 10
<211> LENGTH: 759
<212> TYPE: DNA
<213> ORGANISM: Unknown
<220> FEATURE:
<223> OTHER INFORMATION: Description of Unknown: Human Cosavirus sequence

<400> SEQUENCE: 10
acatggggga gactgcatgt ggcagtcttg aaacgtgtgg tttgacgtct accttatatg 60
gcagtgggtg gagtactgca aagatgtcac cgtgctttac acggtttttg aaccccacac 120
cggctgtttg acgctcgtag ggcagcaggt ttattttcat taaaattctt actttctagc 180
tgcatgagtt ctattcatgc agacggagtg atactcccgt tccttcttgg acaggttgcc 240
tccacgccct ttgtggatct taaggtgacc aagtcactgg tgttggaggt gaagatagag 300
agtcctcttg ggaatgtcat gtggctgtgc caggggttgt agcgatgcca ttcgtgtgtg 360
cggatttcct ctcgtggtga cacgagcctc acaggccaaa agccccgtcc gaaaggaccc 420
gaatggtgga gtgaccctga ctcccccctg catagttttg tgattaggaa cttgaggaat 480
ttctgtcata aatctctatc acatcaggcc ccaaagatgt cctgaaggta ccctgtgtat 540
ctgaggatga gcaccaccga ctacccggac ttgcattagc agacacatgt ggttgcccag 600
ccccacctct tcagaggtgg ggctttgctc actcagcaca ggatctgatc aggagccccg 660
ctcgtgtgct ttacactcga cgcggggtta aaaattgccc aaggcctggc acaacaacct 720
aggggactag gttttcctat ttttgtaaat tatgtcaat 759

<210> SEQ ID NO 11
<211> LENGTH: 478
<212> TYPE: DNA
<213> ORGANISM: Unknown
<220> FEATURE:
<223> OTHER INFORMATION: Description of Unknown: Human rhinovirus sequence

<400> SEQUENCE: 11
gtgacaatca gccagattgt taacggtcaa gcacttctgt ttccccggta cccttgtata 60
cgcttcaccc gaggcgaaaa gtgaggttat cgttatccgc aaagtgccta cgagaagcct 120
agtagcactt ttgaagccta tggctggtcg ctcaactgtt tacccagcag tagacctggc 180
agatgaggct agatgttccc caccagcgat ggtgatctag cctgcgtggc tgcctgcaca 240
ctctattgag tgtgaagcca gaaagtggac aaggtgtgaa gagcctattg tgctcacttt 300
gagtcctccg gcccctgaat gtggctaatc ctaaccccgt agctgttgca tgtaatccaa 360
catgtctgca gtcgtaatgg gcaactatgg gatggaacca actactttgg gtgtccgtgt 420
ttcttgtttt tctttatgct tgcttatggt gacaactgta gttattacat ttgttacc 478

<210> SEQ ID NO 12
<211> LENGTH: 628
<212> TYPE: DNA
<213> ORGANISM: Unknown
<220> FEATURE:
<223> OTHER INFORMATION: Description of Unknown: Human rhinovirus sequence

<400> SEQUENCE: 12
ttaaaacagc ggatgggtat cccaccattc gacccattgg gtgtagtact ctggtactat 60
gtacctttgt acgcctgttt ctccccaacc acccttcctt aaaattccca cccatgaaac 120
gttagaagct tgacattaaa gtacaatagg tggcgccata tccaatggtg tctatgtaca 180
agcacttctg tttcccagga gcgaggtata ggctgtaccc actgccaaaa gcctttaacc 240
gttatccgcc aaccaactac gtaacagtta gtaccatctt gttcttgact ggacgttcga 300
tcaggtggat tttccctcca ctagtttggt cgatgaggct aggaattccc cacgggtgac 360
cgtgtcctag cctgcgtggc ggccaaccca gcttatgctg ggacgccctt ttaaggacat 420
ggtgtgaaga ctcgcatgtg cttggttgtg agtcctccgg cccctgaatg cggctaacct 480
taaccctaga gccttatgcc acgatccagt ggttgtaagg tcgtaatgag caattccggg 540
acgggaccga ctactttggg tgtccgtgtt tctcattttt cttcatattg tcttatggtc 600
acagcatata tatacatata ctgtgatc 628

<210> SEQ ID NO 13
<211> LENGTH: 618
<212> TYPE: DNA
<213> ORGANISM: Unknown
<220> FEATURE:
<223> OTHER INFORMATION: Description of Unknown: Human rhinovirus sequence

<400> SEQUENCE: 13
ttaaaactgg gagtgggttg ttcccactca ctccacccat gcggtgttgt actctgttat 60
tacggtaact ttgtacgcca gtttttccca cccttcccca taatgtaact tagaagtttg 120
tacaatatga ccaataggtg acaatcatcc agactgtcaa aggtcaagca cttctgtttc 180
cccggtcaat gaggatatgc tttacccaag gcaaaaacct tagagatcgt tatccccaca 240
ctgcctacac agagcccagt accatttttg atataattgg gttggtcgct ccctgcaaac 300
ccagcagtag acctggcaga tgaggctgga cattccccac tggcgacagt ggtccagcct 360
gcgtggctgc ctgctcaccc ttcttgggtg agaagcctaa ttattgacaa ggtgtgaaga 420
gccgcgtgtg ctcagtgtgc ttcctccggc ccctgaatgt ggctaacctt aaccctgcag 480
ccgttgccca taatccaatg ggtttgcggt cgtaatgcgt aagtgcggga tgggaccaac 540

```
tactttgggt gtccgtgttt cctgtttttc ttttgattgc attttatggt gacaatttat    600

agtgtataga ttgtcatc                                                  618


<210> SEQ ID NO 14
<211> LENGTH: 610
<212> TYPE: DNA
<213> ORGANISM: Unknown
<220> FEATURE:
<223> OTHER INFORMATION: Description of Unknown: Human rhinovirus
      sequence

<400> SEQUENCE: 14

ttaaaactgg gtacaggttg ttcccacctg tatcacccac gtggtgtggt gctcttgtat     60

tccggtacac ttgcacgcca gtttgccacc cctcacccgt cgtaacttag aagctaacaa    120

ctcgaccaac aggcggtggt aaaccatacc acttacggtc aagcactcct gtttccccgg    180

tatgcgagga atagactcct acagggttga agcctcaagt atcgttatcc gcattggtac    240

tacgcaaagc ttagtagtgc cttgaaagtc ccttggttgg tcgctccgct agtttcccct    300

agtagacctg gcagatgagg caggacactc cccactggcg acagtggtcc tgcctgcgtg    360

gctgcctgcg caccccttagg ggtgcgaagc caagtgacag acaaggtgtg aagagccccg    420

tgtgctacca atgagtcctc cggcccctga atgcggctaa tccaacccca cagctattgc    480

acacaagcca gtgtgtatgt agtcgtaatg agcaattgtg ggacggaacc gactactttg    540

ggtgtccgtg tttcctttta ttcttatcat tctgcttatg gtgacaatac tgtgaaatag    600

tgttgttacc                                                           610


<210> SEQ ID NO 15
<211> LENGTH: 614
<212> TYPE: DNA
<213> ORGANISM: Unknown
<220> FEATURE:
<223> OTHER INFORMATION: Description of Unknown: Human rhinovirus
      sequence

<400> SEQUENCE: 15

taaaactgga tccaggttgt tcccacctgg atctcctatt gggagttgta ctctattatt     60

ccggtaattt tgtacgccag ttttatcttc cccctcccca attgtaactt agaaggttat    120

caatacgacc aataggtggt agttagccaa actaccaaag gtcaagcact tctgtttccc    180

cggtcaaagt tgatatgctc caacagggca aaaacaactg agatcgttat ccgcaaagtg    240

cctacgcaaa gcctagtaac acctttgaag atttatggtt ggtcgttccg ctatttccca    300

tagtagacct ggcagatgag gctagaaatc ccccactggc gacagtgctc tagcctgcgt    360

ggctgcctgc gcaccccttg ggtgcgaagc catacattgg acaaggtgtg aagagccccg    420

tgtgctcact ttgagtcctc cggcccctga atgtggctaa ccttaaccct gcagctagtg    480

catgtaatcc aacatgttgc tagtcgtaat gagtaattgc gggacgggac caactacttt    540

gggtgtccgt gtttcacttt ttccttttaa tattgcttat ggtgacaata tatatagcta    600

tatatattga cacc                                                      614


<210> SEQ ID NO 16
<211> LENGTH: 624
<212> TYPE: DNA
<213> ORGANISM: Unknown
<220> FEATURE:
<223> OTHER INFORMATION: Description of Unknown: Salivirus A sequence
```

<400> SEQUENCE: 16
ttcccctgca accattacgc ttactcgcat gtgcattgag tggtgcatgt gttgaacaaa 60
cagctacact cacatggggg cgggttttcc cgccctacgg cttctcgcga ggcccacccc 120
tcccctttct cccataacta cagtgctttg gtaggtaagc atcctgatcc cccgcggaag 180
ctgctcacgt ggcaactgtg gggacccaga caggttatca aaggcacccg gtctttccgc 240
cttcaggagt atccctgcta gcgaattcta gtagggctct gcttggtgcc aacctccccc 300
aaatgcgcgc tgcgggagtg ctcttcccca actcacccta gtatcctctc atgtgtgtgc 360
ttggtcagca tatctgagac gatgttccgc tgtcccagac cagtccagta atggacgggc 420
cagtgtgcgt agtcgtcttc cggcttgtcc ggcgcatgtt tggtgaaccg gtggggtaag 480
gttggtgtgc ccaacgcccg tactcagggg atacctcaag gcacccagga atgccaggga 540
ggtaccccgc ttcacagcgg gatctgaccc tggggtaaat gtctgcgggg ggtcttcttg 600
gcccacttct cagtactttt cagg 624

<210> SEQ ID NO 17
<211> LENGTH: 730
<212> TYPE: DNA
<213> ORGANISM: Unknown
<220> FEATURE:
<223> OTHER INFORMATION: Description of Unknown: Salivirus FHB sequence

<400> SEQUENCE: 17
acatgggggg tctgcggacg gcttcggccc acccgcgaca agaatgccgt catctgtcct 60
cattacccgt attccttccc ttcccccgca accaccacgc ttactcgcgc acgtgttgag 120
tggcacgtgc gttgtccaaa cagctacacc cacacccttc ggggcgggtt tgtcccgccc 180
tcgggttcct cgcggaaccc ccccctccct ctctctcttt ctatccgccc tcacttccca 240
taactacagt gctttggtag gtgagcaccc tgaccccccg cggaagctgc taacgtggca 300
actgtgggga tccaggcagg ttatcaaagg cacccggtct ttccgccttc aggagtatct 360
ctgccggtga attccggtag ggctctgctt ggtgccaacc tcccccaaat gcgcgctgcg 420
ggagtgctct tccccaactc atcttagtaa cctctcatgt gtgtgcttgg tcagcatatc 480
tgaggcgacg ttccgctgtc ccagaccagt ccagcaatgg acgggccagt gtgcgtagtc 540
gctttccggt tttccggcgc atgtttggcg aaacgctgag gtaaggttgg tgtgcccaac 600
gcccgtaatt tggtgatacc tcaagaccac ccaggaatgc cagggaggta ccccacttcg 660
gtgggatctg accctgggct aattgtctac ggtggttctt cttgcttcca cttctctttt 720
ttctggcatg 730

<210> SEQ ID NO 18
<211> LENGTH: 709
<212> TYPE: DNA
<213> ORGANISM: Unknown
<220> FEATURE:
<223> OTHER INFORMATION: Description of Unknown: Salivirus NG-J1
sequence

<400> SEQUENCE: 18
tatggcaggc gggcttgtgg acggcttcgg cccacccaca gcaagaatgc catcatctgt 60
cctcaccccc aattttccct tttcttcccc tgcaaccatt acgcttactc gcatgtgcat 120
tgagtggtgc atgtgttgaa caaacagcta cactcacatg gggggcgggtt ttcccgccct 180 acggcctctc gcgaggccca ccccttccct ccccttataa ctacagtgct ttggtaggta 240

-continued agcatcctga tcccccgcgg aagctgctca cgtggcaact gtggggaccc agacaggtta 300
tcaaaggcac ccggtctttc cgccttcagg agtatcccta ctagtgaatt ctagcggggc 360
tctgcttggt gccaacctcc cccaaatgcg cgctgcggga gtgctcttcc ccaactcacc 420
ctagtatcct ctcatgtgtg tgcttggtca gcatatctga gacgatgttc cgctgtccca 480
gaccagtcca gtaatggacg ggccagtgcg tgtagtcgtc ttccggcttg tccggggcat 540
gtttggtgaa ccggtggggt aaggttggtg tgcccaacgc ccgtactttg gtgacacctc 600
aagaccaccc aggaatgcca gggaggtacc ccacctcacg gtgggatctg accctgggct 660
aattgtctac ggtggttctt cttgcttcca cttctttctt ctgttcacg 709

<210> SEQ ID NO 19
<211> LENGTH: 708
<212> TYPE: DNA
<213> ORGANISM: Unknown
<220> FEATURE:
<223> OTHER INFORMATION: Description of Unknown: Human Parechovirus sequence

<400> SEQUENCE: 19
tttgaaaggg gtctcctaga gagcttggcc gtcgggcctt ataccccgac ttgctgagtt 60
tctctaggag agccctttc ccagccctga ggcggctggt caataaaagc ctcaaacgta 120
actaacacct aagaagatca tgtaaaccct atgcctggtc tccactattc gaaggcaact 180
tgcaataaga agagtgggat caagacgctt aaagcataga gacagttttc ttttctaacc 240
cacatttgtg tggggtggca gatggcgtgc cataactcta atagtgagat accacgcttg 300
tggaccttat gctcacacag ccatcctcta gtaagtttgt gagacgtctg gtgacgtgtg 360
ggaacttatt ggaaacaaca ttttgctgca aagcatccta ctgccagcgg aaaaacacct 420
ggtaacaggt gcctctgggg ccaaaagcca aggtttaaca gaccctttag gattggttct 480
aaacctgaga tgttgtggaa gatatttagt acctgctgat ctggtagtta tgcaaacact 540
agttgtaagg cccatgaagg atgcccagaa ggtacccgta ggtaacaagt gacactatgg 600
atctgatttg gggccagata cctctatctt ggtgatctgg ttaaaaaaca tctaatgggc 660
caaacccggg ggggatcccc ggtttcctct tattctatca atgccact 708

<210> SEQ ID NO 20
<211> LENGTH: 508
<212> TYPE: DNA
<213> ORGANISM: Unknown
<220> FEATURE:
<223> OTHER INFORMATION: Description of Unknown: Crohivirus B sequence

<400> SEQUENCE: 20
gtataagaga caggtgtttg ccttgtcttc ggactggcat cttgggacca acccccccttt 60 tccccagcca tgggttaaat ggcaataaag gacgtaacaa ctttgtaacc attaagcttt 120
gtaattttgt aaccactaag ctttgtgcac ataatgtaac catcaagctt gttagtccca 180
gcaggaggtt tgcatgcttg tagccgaaat ggggctcgac cccccatagt aggatacttg 240
attttgcatt ccattgtgga cctgcaaact ctacacatag aggctttgtc ttgcatctaa 300
acacctgagt acagtgtgta cctagaccct atagtacggg aggaccgttt gtttcctcaa 360
taaccctaca taataggcta ggtgggcatg cccaatttgc aagatcccag actgggggtc 420
ggtctgggca gggttagatc cctgttagct actgcctgat agggtggtgc tcaaccatgt 480
gtagtttaaa ttgagctgtt catatacc 508

<210> SEQ ID NO 21
<211> LENGTH: 248
<212> TYPE: DNA
<213> ORGANISM: Unknown
<220> FEATURE:
<223> OTHER INFORMATION: Description of Unknown: Picornaviridae sp. sequence

<400> SEQUENCE: 21
actgaagatc ctacagtaac tactgcccca atgaacgcca cagatgggtc tgctgatgac 60
tacctatctt agtgctagtt gaggtttgaa gtgagccggt ttttagaaga accagtttct 120
gaacattatc atccccagca tctattctat acgcacaaga tagatagtca tcagcagaca 180
catctgtgct actgcttgat agagttgcgg ctggtcaact tagattggta taaccagttg 240
agtggcaa 248

<210> SEQ ID NO 22
<211> LENGTH: 516
<212> TYPE: DNA
<213> ORGANISM: Unknown
<220> FEATURE:
<223> OTHER INFORMATION: Description of Unknown: Rosavirus M-7 sequence

<400> SEQUENCE: 22
tatgcatcac tggacggcct aacctcggtc gtggcttctt gccgatttca gcgctaccag 60
gctttctggt ctcgccaggc gttgattagt aggtgcactg tctaagtgaa gacagcagtg 120
ctctctgtga aaagttgatg acactcttca ggtttgtagc gatcactcaa ggctagcgga 180
tttccccgtg tggtaacaca cgcctctagg cccagaaggc acggtgttga cagcacccct 240
tgagtggctg gtcttcccca ccagcacctg atttgtggat tcttcctagt aacggacaag 300
catggctgct cttaagcatt cagtgcgtcc ggggctgaag gatgcccaga aggtacccgc 360
aggtaacgat aagctcactg tggatctgat ctggggctgc gggctgggtg tctttccacc 420
cagccaaaac ccgtaaaacg gtagtcgcag ttaaaaaacg tctaggcccc acccccccag 480
ggatgggggg ttcccttaaa ccctcacaag ttcaac 516

<210> SEQ ID NO 23
<211> LENGTH: 478
<212> TYPE: DNA
<213> ORGANISM: Unknown
<220> FEATURE:
<223> OTHER INFORMATION: Description of Unknown: Shanbavirus A sequence

<400> SEQUENCE: 23
tgaaaagggg gcgcagggtg gtggtggtta ctaaataccc accatcgccc tgcacttccc 60
ttttcccctg tggctcaggg tcacttagcc ccctctttgg gttaccagta gttttctacc 120
cctgggcaca gggttaacta tgcaagacgg aacaacaatc tcttagtccc cctcgccgat 180
agtgggctcg acccccatgt gtaggagtgg ataagggacg gagtgagccg atacggggaa 240
gagtgtgcgg tcacacctta attccatgag cgctgcgaag aaggaagctg tgaacaatgg 300
cgacctgaac cgtacacatg gagctccaca ggcatggtac tcgttagact acgcagcctg 360
gttgggagtg ggtataccct gggtgagccg ccagtgaatg ggagttcact ggttaacaca 420
cactgcctga tagggtcagg gcctcctgtc cccgccgtaa tgaggtagac catatgcc 478

<210> SEQ ID NO 24
<211> LENGTH: 403
<212> TYPE: DNA

<213> ORGANISM: Unknown
<220> FEATURE:
<223> OTHER INFORMATION: Description of Unknown: Pasivirus A sequence

<400> SEQUENCE: 24
gcggctggat attctggccg tgcaactgct tttgaccagt ggctctgggt aacttagcca 60
aagtgtcctt ctccctttcc ctattatatg ttttatggct ttgtctggtc ttgtttagtt 120
tatatataag atcctttccg ccgatataga cctcgacagt ctagtgtagg aggattggtg 180
atattaattt gccccagaag agtgaccgtg acacatagaa accatgagta catgtgtatc 240
cgtggaggat cgcccgggac tggattccat atcccattgc catcccaaca agcggagggt 300
atacccacta tgtgcacgtc tgcagtggga gtctgcagat ttagtcatac tgcctgatag 360
ggtgtgggcc tgcactctgg ggtactcagg ctgtttatat aat 403

<210> SEQ ID NO 25
<211> LENGTH: 404
<212> TYPE: DNA
<213> ORGANISM: Unknown
<220> FEATURE:
<223> OTHER INFORMATION: Description of Unknown: Pasivirus A sequence

<400> SEQUENCE: 25
gctggacttt ctggctgcgc aactgctttt aaccagtggc tctgggttac ttagccaaaa 60
cccccttccc ccgtacccta gtttgtgtgt gtattattat tttgttgttg ttttgtaaat 120
ttttatataa gatcctttcc gccgatatag acctcgacag tctagtgtag gaggattggt 180
gatattaata tgccccagaa gagtgaccgt gacacataga aaccatgagt acatgtgtat 240
ccgtggagga tcgcccggga ctggattcca tatcccattg ccatcccaac aaacggaggg 300
tatacccgct atgtgcgcgt ctacagtggg aatctgtaga tttagtcata ctgcctgata 360
gggtgtgggc ctgcactctg ggtactcag gctgtttata taat 404

<210> SEQ ID NO 26
<211> LENGTH: 744
<212> TYPE: DNA
<213> ORGANISM: Unknown
<220> FEATURE:
<223> OTHER INFORMATION: Description of Unknown: Echovirus E14 sequence

<400> SEQUENCE: 26
ttaaaacagc ctgtgggttg ttcccatcca cagggcccac tgggcgccag cactctggta 60
ttgcggtacc ttagtgcgcc tgttttatat acccgtcccc caaacgtaac ttagacgcat 120
gtcaacgaag accaatagta agcgcagcac accagctgtg ttccggtcaa gcacttctgt 180
taccccggac cgagtatcaa taagctactc acgtggctga aggagaaaac gttcgttacc 240
cgaccaatta cttcaagaaa cctagtaaca ccatgaaggt tgcgcagtgt ttcgctccgc 300
acaaccccag tgtagatcag gtcgatgagt caccgcattc cccacgggtg accgtggcgg 360
tggctgcgct ggcggcctgc ccatggggaa acccatggga cgcttcaata ctgacatggt 420
gcgaagagtc tattgagcta attggtagtc ctccggcccc tgaatgcggc taatcctaac 480
tgcggagcag atacccacac accagtgggc agtctgtcgt aacgggcaac tctgcagcgg 540
aaccgactac tttgggtgtc cgtgtttctc tttatcctta tactggctgc ttatggtgac 600
aattgagaga ttgttaccat atagctattg gattggccat ccggtgacaa atagagcaat 660
tgtgtatttg tttgttggtt tcgtgccatt aaattacaag gttctaaaca cccttaatct 720
tattatagca ttcaacacaa caaa 744

<210> SEQ ID NO 27
<211> LENGTH: 663
<212> TYPE: DNA
<213> ORGANISM: Unknown
<220> FEATURE:
<223> OTHER INFORMATION: Description of Unknown: Human Parechovirus sequence

<400> SEQUENCE: 27

```
gtacattaga tgcgtcatct gcaactttag tcaataaatt acctccaatg tcattaccaa     60
cattccctac cttttcacta acacctaaga caacaagtac ctatgcctgg tctccactat    120
tcgaaggcaa cttgcaataa gaagagtgga attaagacgc ttaaagcata gagctagtta    180
tcttttctaa cccacaaagt tttgtggggt ggcagatggc gtgccataac tctattagtg    240
agataccatg cttgtggatc ttatgctcac acagccatcc tctagtaagt tgataaggtg    300
tctggtgata tgtgggaact cacatgaacc attaatttac cgtaaggtat cctatagcca    360
gcggaatcac atctggtgac agatgcctct ggggccgaaa gccaaggttt aacagaccct    420
ataggattgg tttcaaaacc tgaattgatg tggattgtgt atagtacctg ttgatctggt    480
aacagtgtca acactagttg taaggcccac gaaggatgcc cagaaggtac ccgtaggtaa    540
caagtgacac tatggatctg atctggggcc agctacctct atcatggtga gttggttaaa    600
aaacgtctag tgggccaaac ccagggggga tccctggttt ccttttacct aatcaaagcc    660
act                                                                  663
```

<210> SEQ ID NO 28
<211> LENGTH: 744
<212> TYPE: DNA
<213> ORGANISM: Unknown
<220> FEATURE:
<223> OTHER INFORMATION: Description of Unknown: Aichi virus sequence

<400> SEQUENCE: 28

```
tttgaaaagg gggtgggggg gcctcggccc cctcaccctc ttttccggtg gtctggtccc     60
ggaccaccgt tactccattc agcttcttcg gaacctgttc ggaggaatta aacgggcacc    120
catactcccc ccaccccccct tttgtaacta agtatgtgtg ctcgtgatct tgactcccac   180
ggaacggacc gatccgttgg tgaacaaaca gctaggtcca catcctccct tcccctggga    240
gggcccccgc cctcccacat cctcccccca gcctgacgta tcacaggctg tgtgaagccc    300
ccgcgaaagc tgctcacgtg gcaattgtgg gtccccccctt catcaagaca ccaggtcttt   360
cctccttaag gctagccccg gcgtgtgaat tcacgttggg caactagtgg tgtcactgtg    420
cgctcccaat ctcggccgcg gagtgctgtt ccccaagcca aaccccctggc ccttcactat   480
gtgcctggca agcatatctg agaaggtgtt ccgctgtggc tgccaacctg gtgacaggtg    540
ccccagtgtg cgtaaccttc ttccgtctcc ggacggtagt gattggttaa gatttggtgt    600
aaggttcatg tgccaacgcc ctgtgcggga tgaaacctct actgccctag gaatgccagg    660
caggtacccc acctccgggt gggatctgag cctgggctaa ttgtctacgg gtagtttcat    720
ttccaatcct tttatgtcgg agtc                                           744
```

<210> SEQ ID NO 29
<211> LENGTH: 734
<212> TYPE: DNA
<213> ORGANISM: Unknown
<220> FEATURE:
<223> OTHER INFORMATION: Description of Unknown: Hepatitis A virus sequence

<400> SEQUENCE: 29
ttcaagaggg gtctccggag ttttccggaa cccctcttgg aagtccatgg tgaggggact 60
tgatacctca ccgccgtttg cctaggctat aggctaaatt tccctttccc tgtccttccc 120
ctatttcctt ttgttttgtt tgtaaatatt aattcctgca ggttcagggt tctttaatct 180
gtttctctat aagaacactc aatttttcac gctttctgtc tcctttcttc cagggctctc 240
cccttgccct aggctctggc cgttgcgccc ggcggggtca actccatgat tagcatggag 300
ctgtaggagt ctaaattggg gacgcagatg tttgggacgt cgccttgcag tgttaacttg 360
gctttcatga acctctttga tcttccacaa ggggtaggct acgggtgaaa cctcttaggc 420
taatacttca atgaagagat gccttggata gggtaacagc ggcggatatt ggtgagttgt 480
taagacaaaa accattcaac gccggaggac tggctctcat ccagtggatg cattgaggga 540
attgattgtc agggctgtct ctaggtttaa tctcagacct ctctgtgctt agggcaaaca 600
ctatttggcc ttaaatggga tcctgtgaga gggggtccct ccattgacag ctggactgtt 660
ctttggggcc ttatgtggtg tttgcctctg aggtactcag gggcatttag gtttttcctc 720
attcttaaat aata 734

<210> SEQ ID NO 30
<211> LENGTH: 638
<212> TYPE: DNA
<213> ORGANISM: Unknown
<220> FEATURE:
<223> OTHER INFORMATION: Description of Unknown: Phopivirus sequence

<400> SEQUENCE: 30
gggagtaaac ctcaccaccg tttgccgtgg tttacggcta cctatttttg gatgtaaata 60
ttaattcctg caggttcagg tctcttgaat tatgtccacg ctagtggcac tctcttaccc 120
ataagtgacg ccttagcgga acctttctac acttgatgtg gttaggggtt acattatttc 180
cctgggcctt ctttggccct tttccccctg cactatcatt ctttcttccg ggctctcagc 240
atgccaatgt tccgaccggt gcgcccgccg gggttaactc catggttagc atggagctgt 300
aggccctaaa agtgctgaca ctggaactgg actattgaag catacactgt taactgaaac 360
atgtaactcc aatcgatctt ctacaagggg taggctacgg gtgaaacccc ttaggttaat 420
actcatattg agagatactt ctgataggtt aaggttgctg gataatggtg agtttaacga 480
caaaaaccat tcaacagctg tgggccaacc tcatcaggta gatgcttttg gagccaagtg 540
cgtaggggtg tgtgtggaaa tgcttcagtg gaaggtgccc tcccgaaagg tcgtaggggt 600
aatcaggggc agttaggttt ccacaattac aatttgaa 638

<210> SEQ ID NO 31
<211> LENGTH: 743
<212> TYPE: DNA
<213> ORGANISM: Unknown
<220> FEATURE:
<223> OTHER INFORMATION: Description of Unknown: CVA10 sequence

<400> SEQUENCE: 31
gctcttccga tctgggttgt tcccacccac agggcccact gggcgccagc actctgattc 60
cacggaatct ttgtgcgcct gttttacaac ccttcccaat ttgtaacgta gaagcaatac 120
acactactga tcaatagtag gcatggcgcg ccagtcatgt catgatcaag cacttctgtt 180
cccccggact gagtatcaat agactgctca cgcggttgaa ggagaaaacg ttcgttaccc 240

```
ggctaactac ttcgagaaac ctagtagcac catggaagct gcggagtgtt tcgctcagca    300

ctttccccgt gtagatcagg tcgatgagtc actgcaatcc ccacgggcga ccgtggcagt    360

ggctgcgttg gcggcctgcc tatggggcaa cccataggac gctctaatgt ggacatggtg    420

cgaagagtct attgagctag ttagtagtcc tccggcccct gaatgcggct aatcctaact    480

gcggagcaca tgccttcaac ccaggaggtg gtgtgtcgta acgggtaact ctgcagcgga    540

accgactact ttgggtgtcc gtgtttcctt ttatccttat attggctgct tatggtgaca    600

atcacggaat tgttgccata tagctattgg attggccatc cggtgtctaa cagagctatt    660

gtatacctat ttgttggatt tactccccta tcatacaaat ctctgaacac tttgtgcttt    720

atactgaact taaacacacg aaa                                            743
```

<210> SEQ ID NO 32
<211> LENGTH: 746
<212> TYPE: DNA
<213> ORGANISM: Unknown
<220> FEATURE:
<223> OTHER INFORMATION: Description of Unknown: Enterovirus C sequence

<400> SEQUENCE: 32

```
ttaaaacagc tctggggttg ttcccacccc agaggcccac gtggcggcca gtacaccggt     60

accacggtac ccttgtacgc ctgttttata ctcccctccc cgtaaactag aagcacgaaa    120

cacaagttca atagaagggg gtacagacca gtaccaccac gaacaagcac ttctgttccc    180

ccggtgaggt cacatagact gtccccacgg tcaaaagtga ctgatccgtt atccgctcac    240

gtacttcgga aagcctagta ccaccttgga atctacgatg cgttgcgctc agcactcgac    300

cccggagtgt agcttaggct gatgagtctg gacgttcccc actggtgaca gtggtccagg    360

ctgcgttggc ggcctacctg tggtccaaaa ccacaggacg ctagtagtga acaaggtgtg    420

aagagcccac tgagctacct gagaatcctc cggcccctga atgcggctaa tcccaaccac    480

ggagcaggta atcgcaaacc agcggtcagc ctgtcgtaac gcgtaagtct gtggcggaac    540

cgactacttt gggtgtccgt gtttcctttt atttttatgg tggctgctta tggtgacaat    600

catagattgt tatcataaag caaattggat tggccatccg gagtgagcta aactatctat    660

ttctctgagt gttggattcg tttcacccac attctgaaca atcagcctca ttagtgttac    720

cctgttaata agacgatatc atcacg                                         746
```

<210> SEQ ID NO 33
<211> LENGTH: 726
<212> TYPE: DNA
<213> ORGANISM: Unknown
<220> FEATURE:
<223> OTHER INFORMATION: Description of Unknown: Enterovirus D sequence

<400> SEQUENCE: 33

```
ttaaaacagc tctggggttg ttcccacccc agaggcccac gtggcggcta gtactccggt     60

accccggtac ccttgtacgc ctgttttata ctccctttcc caagtaactt tagaagaaat    120

aaactaatgt tcaacaggag ggggtacaaa ccagtaccac cacgaacaca cacttctgtt    180

tccccggtga agttgcatag actgtaccca cggttgaaag cgatgaatcc gttacccgct    240

taggtacttc gagaagccta gtatcatctt ggaatcttcg atgcgttgcg atcagcactc    300

taccccgagt gtagcttggg tcgatgagtc tggacacccc acaccggcga cgtggtccag    360

gctgcgttgg cggcctaccc atggctagca ccatgggacg ctagttgtga acaaggtgcg    420
```

aagagcctat tgagctacct gagagtcctc cggcccctga atgcggctaa tcccaaccac 480
ggagcaaatg ctcacaatcc agtgagtggt ttgtcgtaat gcgcaagtct gtggcggaac 540
cgactacttt gggtgtccgt gtttcctttt atttttatta tggctgctta tggtgacaat 600
ctgagattgt tatcatatag ctattggatt agccatccgg tgatatcttg aaattttgcc 660
ataacttttt cacaaatcct acaacattac actacacttt ctcttgaata attgagacaa 720
ctcata 726

<210> SEQ ID NO 34
<211> LENGTH: 737
<212> TYPE: DNA
<213> ORGANISM: Unknown
<220> FEATURE:
<223> OTHER INFORMATION: Description of Unknown: Enterovirus J sequence

<400> SEQUENCE: 34
ttaaaatagc ctcagggttg ttcccaccct gagggcccac gtggtgtagt actctggtat 60
tacggtacct ttgtacgcct attttatacc cccttcccca agtaatttag aagcaagcac 120
aaaccagttc agtagtaagc agtacaatcc agtactgtaa tgaacaagta cttctgttac 180
cccggaaggg tctatcggta agctgtaccc acggctgaag aatgacctac cgttaaccgg 240
ctacctactt cgagaagcct agtaatgccg ttgaagtttt attgacgtta cgctcagcac 300
actaccccgt gtgtagtttt ggctgatgag tcacggcact ccccacgggc gaccgtggcc 360
gtggctgcgt tggcggccaa ccaaggagtg caagctcctt ggacgtcata ttacagacat 420
ggtgtgaaga gcctattgag ctaggtggta gtcctccggc ccctgaatgc ggctaatcct 480
aactccggag catatcggtg cgaaccagca cttggtgtgt tgtaatacgt aagtctggag 540
cggaaccgac tactttgggt gtccgtgttt cctgttttaa cttttatggc tgcttatggt 600
gacaatttaa cattgttacc atatagctgt tgggttggcc atccggattt tgttataaaa 660
ccatttcctc gtgccttgac ctttaacaca tttgtgaact tctttaaatc ccttttatta 720
gtccttaaat actaaga 737

<210> SEQ ID NO 35
<211> LENGTH: 327
<212> TYPE: DNA
<213> ORGANISM: Pegivirus sp.

<400> SEQUENCE: 35
aactgttgtt gtagcaatgc gcatattgct acttcggtac gcctaattgg taggcgcccg 60
gccgaccggc cccgcaaggg cctagtagga cgtgtgacaa tgccatgagg gatcatgaca 120
ctggggtgag cggaggcagc accgaagtcg ggtgaactcg actcccagtg cgaccacctg 180
gcttggtcgt tcatggaggg catgcccacg ggaacgctga tcgtgcaaag ggatgggtcc 240
ctgcactggt gccatgcgcg gcaccactcc gtacagcctg atagggtggc ggcgggcccc 300
cccagtgtga cgtccgtgga gcgcaac 327

<210> SEQ ID NO 36
<211> LENGTH: 281
<212> TYPE: DNA
<213> ORGANISM: Unknown
<220> FEATURE:
<223> OTHER INFORMATION: Description of Unknown: GB virus C sequence

<400> SEQUENCE: 36
tgacgtgggg gggttgattt tcccccccccg gcactgggtg caagccccag aaaccgacgc 60

```
ctatctaagt agacgcaatg actcggcgcc gactcggcga ccggccaaaa ggtggtggat    120

gggtgatgac agggttggta ggtcgtaaat cccggtcatc ctggtagcca ctataggtgg    180

gtcttaagag aaggtcaaga ttcctcttac gcctgcggcg agaccgcgca cggtccacag    240

gtgttggccc taccggtgtg aataagggcc cgacatcagg c                        281
```

<210> SEQ ID NO 37
<211> LENGTH: 459
<212> TYPE: DNA
<213> ORGANISM: Unknown
<220> FEATURE:
<223> OTHER INFORMATION: Description of Unknown: GB virus C sequence

<400> SEQUENCE: 37

```
gacgtggggg ggttgatccc ccccctttgg cactgggtgc aagccccaga aaccgacgcc     60

tatttaaaca gacgttaaga accggcgccg acccggcgac cggccaaaag gtggtggatg    120

ggtgatgcca gggttggtag gtcgtaaatc ccggtcatct tggtagccac tataggtggg    180

tcttaagggt tggttaaggt ccctctggcg cttgtggcga gaaagcgcac ggtccacagg    240

tgttggccct accggtgtga ataagggccc gacgtcaggc tcgtcgttaa accgagccca    300

ctacccacct gggcaaacaa cgcccacgta cggtccacgt cgcccttcaa tgtctctctt    360

gaccaatagg cttagccggc gagttgacaa ggaccagtgg gggctgggcg gtaggggaag    420

gacccctgcc gctgcccttc ccggtggagt gggaaatgc                           459
```

<210> SEQ ID NO 38
<211> LENGTH: 350
<212> TYPE: DNA
<213> ORGANISM: Unknown
<220> FEATURE:
<223> OTHER INFORMATION: Description of Unknown: GB virus C sequence

<400> SEQUENCE: 38

```
tgacgtgggg gggttgatcc gcccccccg gcactcggtg caagccccat aaaccgacgc     60

ctatctaagt agacgcaatg actcggcgcc gactcggcga ccggccaaaa ggtggtggat    120

gggtggtgac agggttggta ggtcgtaaat cccggtcatc ctggtagcca ctataggtgg    180

gtcttaagag aaggtcaaga ctcctcttgt gcctgcggcg agaccgcgca cggtccacag    240

gtgctggccc taccggtgtg aataagggcc cgacgtcagg ctcgtcgtta aaccgagccc    300

gtcacccacc tgggcaaacg acgcccacgt acggtccacg tcgcccttca               350
```

<210> SEQ ID NO 39
<211> LENGTH: 318
<212> TYPE: DNA
<213> ORGANISM: Pegivirus A

<400> SEQUENCE: 39

```
tgtagcaatg cgcatattgc tacttcggta cgcctaattg gtaggcgccc ggccgaccgg     60

ccccgcaagg gcctagtagg acgtgtgaca atgccatgcg ggatcatgac actggggtga    120

gcggaggcag caccgaagtc gggtgaactc gactcccagt gcgaccacct ggcttggtcg    180

ttcatggagg gcatgcccac gggaacgctg atcgtgcaaa gggatgggtc cctgcactgg    240

tgccatgcgc ggcaccactc cgtacagcct gatagggtgg cggcgggccc ccccagtgtg    300

acgtccgtgg agcgcaac                                                  318
```

<210> SEQ ID NO 40

<211> LENGTH: 399
<212> TYPE: DNA
<213> ORGANISM: Unknown
<220> FEATURE:
<223> OTHER INFORMATION: Description of Unknown: Pasivirus A sequence

<400> SEQUENCE: 40 atttctggc cgtgtagctg cttttgacca gtggctctgg gttacttagc caaatccccc 60
ttccttcacc cttttaaatt tgatggtctg tgttgtttgt tttgtcttgt ctaaataata 120
tataagatcc ttcccgccga tacagacctc gacagtctgg tgtaggaggg ttggtgttat 180
taatttgccc cagaagagtg accgtgacac atagaaacca tgagtacatg tgtatccgtg 240
gaggatcgcc cgggactgga ttccatatcc cattgccatc ccaacaagcg gagggtatac 300
ccactatgtg cgcgtttgca gtgggaatct gcaaatttag tcatactgcc tgatagggtg 360
tgggcctgca ctctggggta ctcaggctgt tcatataat 399

<210> SEQ ID NO 41
<211> LENGTH: 430
<212> TYPE: DNA
<213> ORGANISM: Sapelovirus sp.

<400> SEQUENCE: 41
cccctccacc cttaaggtgg ttgtatccca cataccccac cctcccttcc aaagtggacg 60
gacaactgga ttttgactaa cggcaagtct gaatggtatg atttggatac gtttaaacgg 120
cagtagcgtg gcgagctatg gaaaaatcgc aattgtcgat agccatgtta gtgacgcgct 180
tcggcgtgct cctttggtga ttcggcgact ggttacagga gagtaggcag tgagctatgg 240
gcaaacctct acagtattac ttagagggaa tgtgcaattg agacttgacg agcgtctctt 300
tgagatgtgg cgcatgctct tggcattacc atagtgagct tccaggttgg gaaacctgga 360
ctgggcctat actacctgat agggtcgcgg ctggccgcct gtaactagta tagtcagttg 420 aaacccccccc 430

<210> SEQ ID NO 42
<211> LENGTH: 504
<212> TYPE: DNA
<213> ORGANISM: Rosavirus B

<400> SEQUENCE: 42
gtctctttag tgtctatgct tcagagagcg gtgaactgac accgttgctt cttgcacagc 60
ccttcgtgcc ggtctttccg gttctcgaca gcgttgggca tcatggctag ttaggctaag 120
atagtggatg atctagtgaa cagttttgga ttgtttggag ttttgtagcg atgctagtag 180
tgtgtgtgga cctccccacg tggtaacacg tgccccacag gccaaaagcc aaggtgttga 240
aagcacccct actagtccca gactcaccca tctgggaact cctctcatga aaaatcttag 300
taacttttga ttcggctatt catcaacctc tctagtcaag ggctgaagga tgcccggaag 360
gtacccgcag gtaacgataa gctcactgtg gatctgatcc ggggctttgg tgcgaccgtc 420
tgtccggcgt agccagagtt aaaaaacgtc taggcccttc caccccaagg gattggggtt 480
tccccaatca tttgaaagtt cact 504

<210> SEQ ID NO 43
<211> LENGTH: 532
<212> TYPE: DNA
<213> ORGANISM: Unknown
<220> FEATURE:
<223> OTHER INFORMATION: Description of Unknown: Bakunsa virus sequence

<400> SEQUENCE: 43
ttttgaacgc cacctcggag cgatatccgg ggaccccctc cccttttttcc ttcctacctt 60 cttcccaaat ttccctcttc ccttgttatt ttggtttgga tttcctggac atgactcgga 120
cggatctatc tcatttgctt tgtgtctgct ccaccagtgg catggtcgaa agatcatcaa 180
cactggacgt gtactgtaat ggccaaacgt gcccacaggg gaaaccatgc cggtcgctgt 240
agcggcgggt ggacgtggtg gacccctctc cctgctcata aactttgggt aggtgaaggg 300
ttcaagcgac gcttgccgtg agggcgcatc cggatggtgg gaaccaacaa actaggctgt 360
aatggccgac ctcaggtgga tgagctaggg ctgctgcacc aaaagggact cgattcgata 420
tcccggcctg gtagcctagt gcagtggact cgtagttggg aatctacgac tggcctagta 480
cagggtgata gccccgtttc ccacgcccac ctgttgtagg gacaccccccc cc 532

<210> SEQ ID NO 44
<211> LENGTH: 494
<212> TYPE: DNA
<213> ORGANISM: Tremovirus A

<400> SEQUENCE: 44
tttgaaagag gcctccggag tgtccggagg ctctctttcg acccaaccca tactgggggg 60
tgtgtgggac cgtacctgga gtgcacggta tatatgcatt cccgcatggc aagggcgtgc 120
taccttgccc cttgacgcat ggtatgcgtc atcatttgcc ttggttaagc cccatagaaa 180
cgaggcgtca cgtgccgaaa atccctttgc gtttcacaga accatcctaa ccatgggtgt 240
agtatgggaa tcgtgtatgg ggatgattag gatctctcgt agagggatag gtgtgccatt 300
caaatccagg gagtactctg gctctgacat tgggacattt gatgtaaccg gacctggttc 360
agtatccggg ttgtcctgta ttgttacggt gtatccgtct tggcacactg aaagggtatt 420
tttgggtaat cctttcctac tgcctgatag ggtggcgtgc ccggccacga gagattaagg 480
gtagcaattt aaac 494

<210> SEQ ID NO 45
<211> LENGTH: 378
<212> TYPE: DNA
<213> ORGANISM: Unknown
<220> FEATURE:
<223> OTHER INFORMATION: Description of Unknown: Swine Pasivirus 1
      sequence

<400> SEQUENCE: 45
gcttttgacc agtggctctg ggttacttag ccaagtccct ttctcttatt ttcactagtt 60
tatgttgtgt gttgtctgtt ttgttttgtt taaattgtat acaagatcct tcccgccgac 120
acagacctcg acagtctggt gtaggagggt tggtgatatt aatttgcccc aaaagagtga 180
ccgtgatacg tggaaaccat gagtacatgt gtatccgtgg aggatcgccc gggactggat 240
tccatatccc attgccatcc caacaaacgg agggtatacc caccacgtgc gcgtttgcag 300
tgggaatctg caaatttagt catactgcct gatagggtgt gggcctgcac tttggggtac 360
tcaggctgtt catataat 378

<210> SEQ ID NO 46
<211> LENGTH: 319
<212> TYPE: DNA
<213> ORGANISM: Unknown
<220> FEATURE:
<223> OTHER INFORMATION: Description of Unknown: Parechovirus-like virus PLV-CHN sequence

<400> SEQUENCE: 46
acatggggta tgttgtctgt cctgttttgt tgaaacaata tataagatcc tttccgccga 60
tatagacctc gacagtctag tgtaggagga ttggtgatag taacttgccc cagaagagtg 120
accgtgacac atagaaacca tgagtacatg tgtatccgtg gaggatcgcc cgggactgga 180
ttccatatcc cattgccatc ccaacaaacg gagggtatac ccactatgtg cgcgtttgca 240
gtgggagcct gcaaatttag tcatactgcc tgatagggtg tgggcctgca ctctggggta 300
ctcaggctgt ttatataat 319

<210> SEQ ID NO 47
<211> LENGTH: 420
<212> TYPE: DNA
<213> ORGANISM: Unknown
<220> FEATURE:
<223> OTHER INFORMATION: Description of Unknown: Pasivirus A sequence

<400> SEQUENCE: 47
tgaaaaagtg gttgtgcagc tggattttcc ggctgtgcaa ctgcttttga ccagtggctc 60
tgggttactt agccaaattc ctttccctta tccctattgg tttgtgttgt gtgttgtttg 120
ttttgttttg tcttaactat atacaagatc cttcccgccg atacagacct cgacagtctg 180
gtgtaggagg gttggtgtta ttaatttgcc ccaaaagagt gaccgtgaca cgtggaaacc 240
atgagtacat gtgtatccgt ggaggatcgc ccgggactgg attccatatc ccattgccat 300
cccaacaaac ggagggtata cccaccacgt gcgcgtttgc agtgggaatc tgcaaattta 360
gtcatactgc ctgatagggt gtgggcctgc actttggggt actcaggctg tttatataat 420

<210> SEQ ID NO 48
<211> LENGTH: 373
<212> TYPE: DNA
<213> ORGANISM: Sicinivirus sp.

<400> SEQUENCE: 48
gtgtcattaa ggtgtgtttg gaagttcgaa ttagctggtt tgtggtgatt agtagacccc 60
ctggaggtac ccaattcgga tctgaccagg gacccgtgac tataccgctc cggtaattcg 120
ggtttaaaac aatgaacgtc accacacaat tacttttctc attttatttt catcattgtc 180
ttcctattta ccgattacac tcgatttcct tggatgttcc tggagatttc cctggttacc 240
tggaccctca ttattgttgt tgtttcaccc agcgagctgt cccaattgct tattatttgc 300
gcttacaact tcgtcctaat atttttctgg ttgatcgggt tgattgagct cccgggctat 360
cctgccattc aac 373

<210> SEQ ID NO 49
<211> LENGTH: 280
<212> TYPE: DNA
<213> ORGANISM: Hepacivirus K

<400> SEQUENCE: 49
gggaacaatg gtccgtccgc ggaacgactc tagccatgag tctagtacga gtgcgtgcca 60
cccattagca caaaaaccac tgactgagcc acacccctcc cggaatcctg agtacaggac 120
attcgctcgg acgacgcatg agcctccatg ccgagaaaat tgggtatacc cacgggtaag 180
gggtggccac ccagcgggaa tctgggggct ggtcactgac tatggtacag cctgataggg 240
tgctgccgca gcgtcagtgg tatgcggctg ttcatggaac 280

<210> SEQ ID NO 50
<211> LENGTH: 384
<212> TYPE: DNA
<213> ORGANISM: Hepacivirus A

<400> SEQUENCE: 50
acctccgtgc taggcacggt gcgttgtcag cgttttgcgc ttgcatgcgc tacacgcgtc 60
gtccaacgcg gagggaactt cacatcacca tgtgtcactc cccctatgga gggttccacc 120
ccgcttacac ggaaatgggt taaccatacc caaagtacgg gtatgcgggt cctcctaggg 180
cccccccggc aggtcgaggg agctggaatt cgtgaattcg tgagtacacg aaaatcgcgg 240
cttgaacgtc tttgaccttc ggagccgaaa tttgggcgtg ccccacgaag gaaggcgggg 300
gcggtgttgg gccgccgccc cctttatccc acggtctgat aggatgcttg cgagggcacc 360
tgccggtctc gtagaccata ggac 384

<210> SEQ ID NO 51
<211> LENGTH: 384
<212> TYPE: DNA
<213> ORGANISM: Unknown
<220> FEATURE:
<223> OTHER INFORMATION: Description of Unknown: Bovine viral diarrhea virus 1 sequence

<400> SEQUENCE: 51
gtatacgaga atttgcctag gacctcgttt acaatatggg caatctaaaa ttataattag 60
gcctaaggga caaatcctcc tcagcgaagg ccgaaaagag gctagccatg cccttagtag 120
gactagcaaa ataagggggg tagcaacagt ggtgagttcg ttggatggct gaagccctga 180
gtacagggta gtcgtcagtg gttcgacgct tcggaggaca agcctcgaga taccacgtgg 240
acgagggcat gcccacagca catcttaacc tggacggggg tcgttcaggt gaaaacggtt 300
taaccaaccg ctacgaatac agcctgatag ggtgctgcag aggcccactg tattgctact 360
gaaaatctct gctgtacatg gcac 384

<210> SEQ ID NO 52
<211> LENGTH: 372
<212> TYPE: DNA
<213> ORGANISM: Unknown
<220> FEATURE:
<223> OTHER INFORMATION: Description of Unknown: Border Disease virus sequence

<400> SEQUENCE: 52
gtatacggga gtagctcatg cccgtataca aaattggata ttccaaaact cgattgggtt 60
agggagccct cctagcgacg gccgaaccgt gttaaccata cacgtagtag gactagcaga 120
cgggaggact agccatcgtg gtgagatccc tgagcagtct aaatcctgag tacaggatag 180
tcgtcagtag ttcaacgcag gcacggttct gccttgagat gctacgtgga cgagggcatg 240
cccaagactt gctttaatct cggcgggggt cgccgaggtg aaaacaccta acggtgttgg 300
ggttacagcc tgatagggtg ctgcagaggc ccacgaatag gctagtataa aaatctctgc 360
tgtacatggc ac 372

<210> SEQ ID NO 53
<211> LENGTH: 388
<212> TYPE: DNA
<213> ORGANISM: Unknown
<220> FEATURE:

-continued

<223> OTHER INFORMATION: Description of Unknown: Bovine viral diarrhea
      virus 2 sequence

<400> SEQUENCE: 53
gtatacgaga ttagctaaag tactcgtata tggattggac gtcaacaaat ttttaattgg 60
caacgtaggg aaccttcccc tcagcgaagg ccgaaaagag gctagccatg ccctttagta 120
ggactagcaa aagtaggggg actagcggta gcagtgagtt cgttggatgg ccgaacccct 180
gagtacaggg gagtcgtcaa tggttcgaca ctccattagt cgaggagtct cgagatgcca 240
tgtggacgag ggcatgccca cggcacatct taacccatgc gggggttgca tgggtgaaag 300
cgctaatcgt ggcgttatgg acacagcctg atagggtgta gcagagacct gctattccgc 360
tagtaaaaaa ctctgctgta catggcac 388

<210> SEQ ID NO 54
<211> LENGTH: 373
<212> TYPE: DNA
<213> ORGANISM: Unknown
<220> FEATURE:
<223> OTHER INFORMATION: Description of Unknown: Classical swine fever
      virus sequence

<400> SEQUENCE: 54
gtatacgagg ttagttcatt ctcgtatgca ttattggaca aatcaaaatt tcaatttggt 60
tcagggcctc cctccagcga cggccgaact gggctagcca tgcccatagt aggactagca 120
aacggaggga ctagccgtag tggcgagctc cctgggtgtt ctaagtcctg agtacaggac 180
agtcgtcagt agttcgacgt gagcagaagc ccacctcgag atgctatgtg gacgagggca 240
tgcccaagac gcaccttaac cctagcgggg gtcgctaggg tgaaatcaca ccacgtgatg 300
ggagtccgac ctgatagggt gctgcagagg ctcactatta ggctagtata aaaatctctg 360
ctgtacatgg cac 373

<210> SEQ ID NO 55
<211> LENGTH: 191
<212> TYPE: DNA
<213> ORGANISM: Unknown
<220> FEATURE:
<223> OTHER INFORMATION: Description of Unknown: Human blood-associated
      dicistrovirus sequence

<400> SEQUENCE: 55
aaaaccgacc ccagagatca gaaagtcgtt gacgcgatct tttattagag gacgttgcgc 60
tggcgcgagc tttaattagc agacgccaaa aataaacaac aaaatgctga tcgcgagact 120
taattgtcag acgattggcc aaatccgatg tgatctttgc tgctcccaga ttgccgaaat 180
aggagtagta g 191

<210> SEQ ID NO 56
<211> LENGTH: 438
<212> TYPE: DNA
<213> ORGANISM: Unknown
<220> FEATURE:
<223> OTHER INFORMATION: Description of Unknown: Hubei Picorna-like
      virus sequence

<400> SEQUENCE: 56
ccccaaaacc ccccccttaa actcaacact gtagtggatt cattttccgt tgcaaaacaa 60
aacattacta cccgcattta tgtaggctct gtgttttcta tgcgaccgtt acattaatct 120
ctactctgac ccactagttt ataaaaccga agacctgaat gaaacgattt tccttctttt 180

```
caacctctaa cgaacctctg acggcttgag aaacctgaag ttagtaatta tgtttaaaag    240

aaaggaaagt caaacgcgat gactcttaca tccctattcc ataccgttgc tccacaatgt    300

gagcgatgcg aggtcgggac tgcagtatta ggggaacgag ctacatggag agttaattat    360

ctctcccctc ctacgggagt ctcatgtgag ctgtagaaag cggttggcac ctctcgttac    420

ctcgcctgta catgatcc                                                  438
```

<210> SEQ ID NO 57
<211> LENGTH: 193
<212> TYPE: DNA
<213> ORGANISM: Cricket paralysis virus

<400> SEQUENCE: 57

```
aaaagcaaaa atgtgatctt gcttgtaaat acaattttga gaggttaata aattacaagt     60

agtgctattt ttgtatttag gttagctatt tagctttacg ttccaggatg cctagtggca    120

gccccacaat atccaggaag ccctctctgc ggtttttcag attaggtagt cgaaaaacct    180

aagaaattta cct                                                       193
```

<210> SEQ ID NO 58
<211> LENGTH: 752
<212> TYPE: DNA
<213> ORGANISM: Unknown
<220> FEATURE:
<223> OTHER INFORMATION: Description of Unknown: Salivirus A sequence

<400> SEQUENCE: 58

```
tttcctcctt tcgaccgcct tacggcaggc gggtccgcgg acggcttcgg cctacccgcg     60

acaagaatgc cgtcatctgt ccttatcacc catattcttt cccttccccc gcaaccatca    120

cgcttactcg cgcacgtgtt gagtggcacg tgcgttgtcc aaacagttac actcacaccc    180

ttggggcggg tttgtcccgc cctcgggttc ctcgcggaac cctccctctt ctctctccct    240

ttctatccgc cttcactttc cataactaca gtgctttggt aggtaagcat cctgaccccc    300

cgcggaagct gccaacgtgg caactgtggg gatccaggca ggttatcaaa ggcacccggt    360

ctttccgcct tcaggagtat ccctgccggt gaattccgac agggctctgc ttggtgccaa    420

cctcccccaa atgcgcgctg cgggagtgct cttccccaac tcatcttagt aacctctcat    480

gtgtgtgctt ggtcagcata tctgaggcga cgttccgctg tcccagacca gtccagcaat    540

ggacgggcca gtgtgcgtag tcgctttccg gtttcccggc gcatgtttgg cgaaacgctg    600

aggtaaggtt ggtgtgccca atgcccgtaa tttggtgaca cctcaagacc acccaggaat    660

gccagggagg taccccactt cggtgggatc tgaccctggg ctaattgtct acggtggttc    720

ttcttgcttc cacttctctt ttttctggca tg                                  752
```

<210> SEQ ID NO 59
<211> LENGTH: 708
<212> TYPE: DNA
<213> ORGANISM: Unknown
<220> FEATURE:
<223> OTHER INFORMATION: Description of Unknown: Salivirus A sequence

<400> SEQUENCE: 59

```
tatggcaggc gggcttgtgg acggcttcgg cccacccaca gcaagaatgc catcatctgt     60

cctcaccccc atgtttcccc tttctttccc tgcaaccgtt acgcttactc gcaggtgcat    120

ttgagtggtg cacgtgttga ataaacagct acactcacat gggggcgggt tttcccgccc    180
```

```
tgcggcctct cgcgaggccc acccctcccc ttcctcccat aactacagtg ctttggtagg    240

taagcatcct gatcccccgc ggaagctgct cacgtggcaa ctgtggggac ccagacaggt    300

tatcaaaggc acccggtctt tccgccttca ggagtatccc tgctagtgaa ttctagtagg    360

gctctgcttg gtgccaacct cccccaaatg cgcgctgcgg gagtgctctt ccccaactca    420

ccctagtatc ctctcatgtg tgtgcttggt cagcatatct gagacgatgt tccgctgtcc    480

cagaccagtc cagtaatgga cgggccagtg tgcgtagtcg tcttccggct tttccggcgc    540

atgtttggtg aaccggtggg gtaaggttgg tgtgcccaac gcccgtactt tggtgatacc    600

tcaagaccac ccaggaatgc cagggaggta ccccgcttca cagcgggatc tgaccctggg    660

ctaattgtct acggtggttc ttcttgcttc cacttctttc tactgttc                708
```

<210> SEQ ID NO 60
<211> LENGTH: 718
<212> TYPE: DNA
<213> ORGANISM: Unknown
<220> FEATURE:
<223> OTHER INFORMATION: Description of Unknown: Salivirus A sequence

<400> SEQUENCE: 60

```
tttcgaccgc cttatggcag gcgggcttgt ggacggcttc ggcccaccca cagcaagaat     60

gccatcatct gtcctcaccc ccatttctcc cctccttccc ctgcaaccat tacgcttact    120

cgcatgtgca ttgagtggtg cacgtgttga acaaacagct acactcacgt gggggcgggt    180

tttcccgccc ttcggcctct cgcgaggccc acccttcccc ttcctcccat aactacagtg    240

ctttggtagg taagcatcct gatcccccgc ggaagctgct cgcgtggcaa ctgtggggac    300

ccagacaggt tatcaaaggc acccggtctt tccgcctcca ggagtatccc tgctagtgaa    360

ttctagtggg gctctgcttg gtgccaacct cccccaaatg cgcgctgcgg gagtgctctt    420

ccccaactca ccctagtatc ctctcatgtg tgtgcttggt cagcatatct gagacgatgt    480

tccgctgtcc cagaccagtc cagcaatgga cgggccagtg tgcgtagtcg tcttccggct    540

tgtccggcgc atgtttggtg aaccggtggg gtaaggttgg tgtgcccaac gcccgtactt    600

tggtgacaac tcaagaccac ccaggaatgc cagggaggta ccccgcctca cggcgggatc    660

tgaccctggg ctaattgtct acggtggttc ttcttgcttc catttctttc ttctgttc      718
```

<210> SEQ ID NO 61
<211> LENGTH: 699
<212> TYPE: DNA
<213> ORGANISM: Unknown
<220> FEATURE:
<223> OTHER INFORMATION: Description of Unknown: Salivirus A sequence

<400> SEQUENCE: 61

```
tatggcaggc gggcttgtgg acggtttcgg cccacccaca gcaagaatgc catcatctgt     60

cctcaccccc aattttccct ttcttcccct gcaatcatca cgcttactcg catgtgcatt    120

gagtggtgca tgtgttgaac aaacagctac actcacatgg gggcgggttt tcccgcccta    180

cggcctctcg cgaggcccac ccttcccctc cccttataac tacagtgctt tggcaggtaa    240

gcatcctgat cccccgcgga agctgctcac gtggcaactg tggggaccca gacaggttat    300

caaaggcacc cggtctttcc gccttcagga gcatccccac tagtgaattc tagtggggct    360

ctgcttggtg ccaacctccc ccaaatgcgc gctgcgggag tgctcttccc caacccatcc    420

tagtatcctc tcatgtgtgt gcttggtcag catatctgag acgacgttcc gctgtcccag    480

accagtccag taatggacgg gccagtgtgc gtagtcgtct tccggcttgt ccggcgcatg    540
```

tttggtgaac cggtggggta aggttggtgt gcccaacgcc cgtactttgg tgacacctca 600
agaccaccca ggaatgccag ggaggtaccc cgcctcacgg cgggatctga ccctgggcta 660
attgtctacg gtggttcttc ttgcttccac ttctttctt 699

<210> SEQ ID NO 62
<211> LENGTH: 624
<212> TYPE: DNA
<213> ORGANISM: Unknown
<220> FEATURE:
<223> OTHER INFORMATION: Description of Unknown: Salivirus A sequence

<400> SEQUENCE: 62
ttctcctgca accattacgc ttaatcgcat gtgcattgag tggtgcatgt gttgaacaaa 60
cagctacaat cacatggggg cgggttttcc cgccccacgg cttctcgcga ggcccatccc 120 tccctttct cccataacta cagtgctttg gtaggtaagc atcccgatct cccgcggaag 180
ctgctcacgt ggcaactgtg gggacccaga caggttatca aaggcacccg gtctttccgc 240
cttcaggagt atccctgcta gcgaattcta gtagggctct gcttggtgcc aacctctccc 300
aaatgcgcgc tgcgggagtg ctcttcccca aatcacccca gtatcctctc atgtgtgtgc 360
ctggtcagca tatctgagac gatgttccgc tgtcccagac cagtccagta atggacgggc 420
cagtgtgcgt agtcgtcctc cggcttgtcc ggcgcatgtt tggtgaaccg gtggggtaag 480
gttggtgtgc ccaacgcccg taatcagggg atacctcaag gcacccagga atgccaggga 540
ggtatcccgc ctcacagcgg gatctgaccc tggggtaaat gtctgcgggg ggtcctcttg 600
gcccaattct cagtaatttt cagg 624

<210> SEQ ID NO 63
<211> LENGTH: 650
<212> TYPE: DNA
<213> ORGANISM: Unknown
<220> FEATURE:
<223> OTHER INFORMATION: Description of Unknown: Salivirus A sequence

<400> SEQUENCE: 63
tctgtcctca ccccatcttc ccttctttcc tgcaccgtta cgcttactcg catgtgcatt 60
gagtggtgca cgtgcttgaa caaacagcta cactcacatg gggcgggtt ttcccgccct 120 gcggcctctc gcgaggccca cccctcccct tcctcccata actacagtgc tttggtaggt 180
aagcatcctg atcccccgcg gaagctgctc acgtggcaac tgtggggacc cagacaggtt 240
atcaaaggca cccggtcttt ccgccttcag gagtatccct gctagtgaat tctagtaggg 300
ctctgcttgg tgccaacctc ccccaaatgc gcgctgcggg agtgctcttc cccaactcac 360
cctagtatcc tctcatgtgt gtgcttggtc agcatatctg agacgatgtt ccgctgtccc 420
agaccagtcc agtaatggac gggccagtgt gcgtagtcgt cttccggctt gtccggcgca 480
tgtttggtga accggtgggg taaggttggt gtgcccaacg cccgtacttt ggtgatacct 540
caagaccacc caggaatgcc agggaggtac cccgcttcac agcgggatct gaccctgggc 600
taattgtcta cggtggttct tcttgcttcc acttctttct actgttcatg 650

<210> SEQ ID NO 64
<211> LENGTH: 730
<212> TYPE: DNA
<213> ORGANISM: Unknown
<220> FEATURE:
<223> OTHER INFORMATION: Description of Unknown: Salivirus FHB sequence

<400> SEQUENCE: 64
acatgggggg tctgcggacg gcttcggccc acccgcgaca agaatgccgt catctgtcct 60
cattacccgt attccttccc ttcccccgca accaccacgc ttactcgcgc acgtgttgag 120
tggcacgtgc gttgtccaaa cagctacacc cacacccttc ggggcgggtt tgtcccgccc 180
tcgggttcct cgcggaaccc cccctccct ctctctcttt ctatccgccc tcacttccca 240
taactacagt gctttggtag gtgagcaccc tgaccccccg cggaagctgc taacgtggca 300
actgtgggga tccaggcagg ttatcaaagg cacccggtct ttccgccttc aggagtatct 360
ctgccggtga attccggtag ggctctgctt ggtgccaacc tcccccaaat gcgcgctgcg 420
ggagtgctct tccccaactc atcttagtaa cctctcatgt gtgtgcttgg tcagcatatc 480
tgaggcgacg ttccgctgtc ccagaccagt ccagcaatgg acgggccagt gtgcgtagtc 540
gctttccggt tttccggcgc atgtttggcg aaacgctgag gtaaggttgg tgtgcccaac 600
gcccgtaatt tggtgatacc tcaagaccac ccaggaatgc cagggaggta ccccacttcg 660
gtgggatctg accctgggct aattgtctac ggtggttctt cttgcttcca cttctctttt 720
ttctggcatg 730

<210> SEQ ID NO 65
<211> LENGTH: 741
<212> TYPE: DNA
<213> ORGANISM: Unknown
<220> FEATURE:
<223> OTHER INFORMATION: Description of Unknown: CVB3 sequence

<400> SEQUENCE: 65
ttaaaacagc ctgtgggttg atcccaccca caggcccatt gggcgctagc actctggtat 60
cacggtacct ttgtgcgcct gttttatacc ccctccccca actgtaactt agaagtaaca 120
cacaccgatc aacagtcagc gtggcacacc agccacgttt tgatcaagca cttctgttac 180
cccggactga gtatcaatag actgctcacg cggttgaagg agaaagcgtt cgttatccgg 240
ccaactactt cgaaaaacct agtaacaccg tggaagttgc agagtgtttc gctcagcact 300
accccagtgt agatcaggtc gatgagtcac cgcattcccc acgggcgacc gtggcggtgg 360
ctgcgttggc ggcctgccca tggggaaacc catgggacgc tctaatacag acatggtgcg 420
aagagtctat tgagctagtt ggtagtcctc cggcccctga atgcggctaa tcctaactgc 480
ggagcacaca ccctcaagcc agagggcagt gtgtcgtaac gggcaactct gcagcggaac 540
cgactacttt gggtgtccgt gtttcatttt attcctatac tggctgctta tggtgacaat 600
tgagagatcg ttaccatata gctattggat tggccatccg gtgactaata gagctattat 660
atatcccttt gttgggttta taccacttag cttgaaagag gttaaaacat tacaattcat 720
tgttaagttg aatacagcaa a 741

<210> SEQ ID NO 66
<211> LENGTH: 741
<212> TYPE: DNA
<213> ORGANISM: Unknown
<220> FEATURE:
<223> OTHER INFORMATION: Description of Unknown: CVB1 sequence

<400> SEQUENCE: 66
ttaaaacagc ctgtgggttg ttcccaccca caggcccatt gggcgctagc actctggtat 60
cacggtacct ttgtgcgcct gttttacatc ccctccccaa attgtaattt agaagtttca 120
cacaccgatc attagcaagc gtggcacacc agccatgttt tgatcaagca cttctgttac 180

```
cccggactga gtatcaatag accgctaacg cggttgaagg agaaaacgtt cgttacccgg    240

ccaactactt cgaaaaacct agtaacacca tggaagttgc ggagtgtttc gctcagcact    300

accccagtgt agatcaggtc gatgagtcac cgcgttcccc acgggcgacc gtggcggtgg    360

ctgcgttggc ggcctgccta cggggaaacc cgtaggacgc tctaatacag acatggtgcg    420

aagagtctat tgagctagtt ggtaatcctc cggcccctga atgcggctaa tcctaactgc    480

ggagcacata ccctcaaacc agggggcagt gtgtcgtaac gggcaactct gcagcggaac    540

cgactacttt gggtgtccgt gtttcatttt attcctatac tggctgctta tggtgacaat    600

tgacaggttg ttaccatata gttattggat tggccatccg gtgactaaca gagcaattat    660

atatctcttt gttgggttta taccacttag cttgaaagag gttaaaacac tacatctcat    720

cattaaacta aatacaacaa a                                              741
```

<210> SEQ ID NO 67
<211> LENGTH: 742
<212> TYPE: DNA
<213> ORGANISM: Unknown
<220> FEATURE:
<223> OTHER INFORMATION: Description of Unknown: Echovirus 7 sequence

<400> SEQUENCE: 67

```
ttaaaacagc ctgtgggttg ttcccaccca cagggcccat tgggcgtcag caccctggta     60

tcacggtacc tttgtgcgcc tgttttatat cccttccccc aattgtaact tagaagaaac    120

acacaccgat caacagcaag cgtggcacac cagccatgtt ttggtcaagc acttctgtta    180

ccccggactg agtatcaata gactgctcac gcggttgaag gagaaagcgt ccgttatccg    240

gccagctact tcgagaaacc tagtaacacc atggaagttg cggagtgttt cgctcagcac    300

taccccagtg tagatcaggt cgatgagtca ccgctttccc cacgggcgac cgtggcggtg    360

gctgcgttgg cggcctgcct atgggggaac ccataggacg ctctaataca gacatggtgc    420

gaagagtcta ttgagctagc tggtattcct ccggcccctg aatgcggcta atcctaactg    480

tggagcacat gcccctaatc caaggggtag tgtgtcgtaa tgagcaattc cgcagcggaa    540

ccgactactt tgggtgtccg tgtttcctct tattcttgta ctggctgctt atggtgacaa    600

ttgagagatt gttaccatat agctattgga ttggccatcc ggtgactaat agagctattg    660

tgtatctctt tgttggattt gtaccactta atttgaaaga aatcaggaca ctacgctaca    720

ttttactatt gaacaccgca aa                                             742
```

<210> SEQ ID NO 68
<211> LENGTH: 743
<212> TYPE: DNA
<213> ORGANISM: Unknown
<220> FEATURE:
<223> OTHER INFORMATION: Description of Unknown: CVB5 sequence

<400> SEQUENCE: 68

```
ttaaaacagc ctgtgggttg tacccaccca cagggcccac tgggcgctag cactctggta     60

tcacggtacc tttgtgcgcc tgttttatgc ccccttcccc caattgaaac ttagaagtta    120

cacacaccga tcaacagcgg gcgtggcata ccagccgcgt cttgatcaag cactcctgtt    180

tccccggacc gagtatcaat agactgctca cgcggttgaa ggagaaaacg ttcgttaccc    240

ggctaactac ttcgagaaac ctagtagcat catgaaagtt gcgaagcgtt tcgctcagca    300

catccccagt gtagatcagg tcgatgagtc accgcattcc ccacgggcga ccgtggcggt    360
```

```
ggctgcgttg gcggcctgcc tacggggcaa cccgtaggac gcttcaatac agacatggtg    420

cgaagagtcg attgagctag ttagtagtcc tccggcccct gaatccggct aatcctaact    480

gcggagcaca taccctcaac ccaggggggca ttgtgtcgta acgggtaact ctgcagcgga    540

accgactact ttgggtgtcc gtgtttcctt ttattcttat aatggctgct tatggtgaca    600

attgaaagat tgttaccata tagctattgg attggccatc cggtgtctaa cagagctatt    660

atatacctct ttgttggatt tgtaccactt gatctaaagg aagtcaagac actacaattc    720

atcatacaat tgaacacagc aaa                                            743
```

<210> SEQ ID NO 69
<211> LENGTH: 743
<212> TYPE: DNA
<213> ORGANISM: Unknown
<220> FEATURE:
<223> OTHER INFORMATION: Description of Unknown: Enterovirus A71
sequence

<400> SEQUENCE: 69

```
ttaaaacagc ctgtgggttg cacccactca cagggcccac tgggcgcaag cactctggca     60

cttcggtacc tttgtgcgcc tgttttatat cccctccccc aatgaaattt agaagcagca    120

aaccccgatc aatagcaggc ataacgctcc agttatgtct tgatcaagca cttctgtttc    180

cccggactga gtatcaatag actgctcacg cggttgaagg agaaaacgtt cgttatccgg    240

ctaactactt cggaaagcct agtaacacca tggaagttgc ggagagtttc gttcagcact    300

tccccagtgt agatcaggtc gatgagtcac cgcattcccc acgggcgacc gtggcggtgg    360

ctgcgttggc ggcctgccca tggggtaacc catgggacgc tctaatacgg acatggtgtg    420

aagagtctac tgagctagtt agtagtcctc cggcccctga atgcggctaa tcccaactgc    480

ggagcacacg cccacaagcc agtgggtagt gtgtcgtaac gggcaactct gcagcggaac    540

cgactacttt gggtgtccgt gtttcctttt attcttatgt tggctgctta tggtgacaat    600

taaagagttg ttaccatata gctattggat tggccatccg gtgtgcaaca gagcgatcgt    660

ttacctattt attggttttg taccattgac actgaagtct gtgatcaccc ttaattttat    720

cttaaccctc aacacagcca aac                                            743
```

<210> SEQ ID NO 70
<211> LENGTH: 742
<212> TYPE: DNA
<213> ORGANISM: Unknown
<220> FEATURE:
<223> OTHER INFORMATION: Description of Unknown: CVA3 sequence

<400> SEQUENCE: 70

```
ttaaaacagc ctgtgggttg tacccaccca cagggcccac tgggcgctag cacactggta     60

ttacggtacc tttgtgcgcc tgttttatac ccccccccaac ctcgaaactt agaagtaaag    120

caaacccgat caatagcagg tgcggcgcac cagtcgcatc ttgatcaagc acttctgtaa    180

ccccggaccg agtatcaata gactgctcac gcggttgaag gagaaaacgt tcgttacccg    240

gctaactact tcgagaaacc cagtagcatc atgaaagttg cagagtgttt cgctcagcac    300

tacccccgtg tagatcaggc cgatgagtca ccgcacttcc ccacgggcga ccgtggcggt    360

ggctgcgttg gcggcctgcc tatggggcaa cccataggac gctctaatac ggacatggtg    420

cgaagagtct attgagctag ttagtagtcc tccggcccct gaatgcggct aatcctaact    480

gcggagcaca taccottaat ccaaagggca gtgtgtcgta acgggtaact ctgcagcgga    540
```

accgactact ttgggtgtcc gtgtttcctt ttaattttta ctggctgctt atggtgacaa 600
ttgaggaatt gttgccatat agctattgga ttggccatcc ggtgactaac agagctattg 660
tgttccaatt tgttggattt accccgctca cactcacagt cgtaagaacc cttcattacg 720
tgttatttct caactcaaga aa 742

<210> SEQ ID NO 71
<211> LENGTH: 745
<212> TYPE: DNA
<213> ORGANISM: Unknown
<220> FEATURE:
<223> OTHER INFORMATION: Description of Unknown: CVA12 sequence

<400> SEQUENCE: 71
ttaaaacagc ctgtgggttg tacccaccca cagggcccac tgggcgctag cactctggta 60
ctacggtacc tttgtgtgcc tgttttaagc ccctaccccc cactcgtaac ttagaaggct 120
tctcacactc gatcaatagt aggtgtggca cgccagtcac accgtgatca agcacttctg 180
ttaccccggt ctgagtacca ataagctgct aacgcggctg aaggggaaaa cgatcgttat 240
ccggctaact acttcgagaa acccagtacc accatgaacg ttgcagggtg tttcgctcgg 300
cacaacccca gtgtagatca ggtcgatgag tcaccgtatt ccccacgggc gaccgtggcg 360
gtggctgcgt tggcggcctg cccatggggt gacccatggg acgctctaat actgacatgg 420
tgcgaagagt ctattgagct agttagtagt cctccggccc ctgaatgcgg ctaatcctaa 480
ctgcggagca catacccta atccaaaggg cagtgtgtcg taacgggcaa ctctgcagcg 540
gaaccgacta ctttgggtgt ccgtgtttcc ttttattctt acattggctg cttatggtga 600
caattgaaaa gttgttacca tatagctatt ggattggcca tccggtgaca aatagagcta 660
ttgtatatct ttttgttggt tacgtacccc ttaattacaa agtggtttca actttgaaat 720
acatcctaac actaaattgt agaaa 745

<210> SEQ ID NO 72
<211> LENGTH: 742
<212> TYPE: DNA
<213> ORGANISM: Unknown
<220> FEATURE:
<223> OTHER INFORMATION: Description of Unknown: Echovirus E24 sequence

<400> SEQUENCE: 72
ttaaaacagc ctgtgggttg cacccaccca cagggcccac agggcgctag cactctggta 60
tcacggtacc tttgtgcgcc tgttttatta ccccttcccc aattgaaaat tagaagcaat 120
gcacaccgat caacagcagg cgtggcgcac cagtcacgtc tcgatcaagc acttctgttt 180
ccccggaccg agtatcaata gactgctcac gcggttgaag gagaaagtgt tcgttatccg 240
gctaaccact tcgagaaacc cagtaacacc atgaaagttg cagggtgttt cgctcagcac 300
ttccccagtg tagatcaggt cgatgagtca ccgcgttccc cacgggcgac cgtggcggtg 360
gctgcgttgg cggcctgcct atgggttaac ccataggacg ctctaataca gacatggtgc 420
gaagagttta ttgagctggt tagtatccct ccggcccctg aatgcggcta atcctaactg 480
cggagcacgt gcctccaatc caggggggttg catgtcgtaa cgggtaactc tgcagcggaa 540
ccgactactt tgggtgtccg tgtttccttt tattcttata ctggctgctt atggtgacaa 600
tcgaggaatt gttaccatat agctattgga ttggccatcc ggtgtctaac agagcgatta 660
tatacctctt tgttggattt atgcagctca ataccaccaa ctttaacaca ttgaaatata 720
tcttaaagtt aaacacagca aa 742

<210> SEQ ID NO 73
<211> LENGTH: 240
<212> TYPE: DNA
<213> ORGANISM: Anabaena sp.

<400> SEQUENCE: 73
gaagaaattc tttaagtgga tgctctcaaa ctcagggaaa cctaaatcta gttatagaca 60
aggcaatcct gagccaagcc gaagtagtaa ttagtaagtt aacaatagat gacttacaac 120
taatcggaag gtgcagagac tcgacgggag ctaccctaac gtcaagacga gggtaaagag 180
agagtccaat tctcaaagcc aataggcagt agcgaaagct gcaagagaat gaaaatccgt 240

<210> SEQ ID NO 74
<211> LENGTH: 239
<212> TYPE: DNA
<213> ORGANISM: Anabaena sp.

<400> SEQUENCE: 74
aagaaattct ttaagtggat gctctcaaac tcagggaaac ctaaatctag ttatagacaa 60
ggcaatcctg agccaagccg aagtagtaat tagtaagtta acaatagatg acttacaact 120
aatcggaagg tgcagagact cgacgggagc taccctaacg tcaagacgag ggtaaagaga 180
gagtccaatt ctcaaagcca ataggcagta gcgaaagctg caagagaatg aaaatccgt 239

<210> SEQ ID NO 75
<211> LENGTH: 238
<212> TYPE: DNA
<213> ORGANISM: Anabaena sp.

<400> SEQUENCE: 75
agaaattctt taagtggatg ctctcaaact cagggaaacc taaatctagt tatagacaag 60
gcaatcctga gccaagccga agtagtaatt agtaagttaa caatagatga cttacaacta 120
atcggaaggt gcagagactc gacgggagct accctaacgt caagacgagg gtaaagagag 180
agtccaattc tcaaagccaa taggcagtag cgaaagctgc aagagaatga aaatccgt 238

<210> SEQ ID NO 76
<211> LENGTH: 190
<212> TYPE: DNA
<213> ORGANISM: Anabaena sp.

<400> SEQUENCE: 76
gttatagaca aggcaatcct gagccaagcc gaagtagtaa ttagtaagtt aacaatagat 60
gacttacaac taatcggaag gtgcagagac tcgacgggag ctaccctaac gtcaagacga 120
gggtaaagag agagtccaat tctcaaagcc aataggcagt agcgaaagct gcaagagaat 180
gaaaatccgt 190

<210> SEQ ID NO 77
<211> LENGTH: 189
<212> TYPE: DNA
<213> ORGANISM: Anabaena sp.

<400> SEQUENCE: 77
ttatagacaa ggcaatcctg agccaagccg aagtagtaat tagtaagtta acaatagatg 60
acttacaact aatcggaagg tgcagagact cgacgggagc taccctaacg tcaagacgag 120
ggtaaagaga gagtccaatt ctcaaagcca ataggcagta gcgaaagctg caagagaatg 180

-continued aaaatccgt 189

<210> SEQ ID NO 78
<211> LENGTH: 188
<212> TYPE: DNA
<213> ORGANISM: Anabaena sp.

<400> SEQUENCE: 78
tatagacaag gcaatcctga gccaagccga agtagtaatt agtaagttaa caatagatga 60
cttacaacta atcggaaggt gcagagactc gacgggagct accctaacgt caagacgagg 120
gtaaagagag agtccaattc tcaaagccaa taggcagtag cgaaagctgc aagagaatga 180
aaatccgt 188

<210> SEQ ID NO 79
<211> LENGTH: 187
<212> TYPE: DNA
<213> ORGANISM: Anabaena sp.

<400> SEQUENCE: 79
atagacaagg caatcctgag ccaagccgaa gtagtaatta gtaagttaac aatagatgac 60
ttacaactaa tcggaaggtg cagagactcg acgggagcta ccctaacgtc aagacgaggg 120
taaagagaga gtccaattct caaagccaat aggcagtagc gaaagctgca agagaatgaa 180
aatccgt 187

<210> SEQ ID NO 80
<211> LENGTH: 186
<212> TYPE: DNA
<213> ORGANISM: Anabaena sp.

<400> SEQUENCE: 80
tagacaaggc aatcctgagc caagccgaag tagtaattag taagttaaca atagatgact 60
tacaactaat cggaaggtgc agagactcga cgggagctac cctaacgtca agacgagggt 120
aaagagagag tccaattctc aaagccaata ggcagtagcg aaagctgcaa gagaatgaaa 180
atccgt 186

<210> SEQ ID NO 81
<211> LENGTH: 139
<212> TYPE: DNA
<213> ORGANISM: Anabaena sp.

<400> SEQUENCE: 81
acaatagatg acttacaact aatcggaagg tgcagagact cgacgggagc taccctaacg 60
tcaagacgag ggtaaagaga gagtccaatt ctcaaagcca ataggcagta gcgaaagctg 120
caagagaatg aaaatccgt 139

<210> SEQ ID NO 82
<211> LENGTH: 138
<212> TYPE: DNA
<213> ORGANISM: Anabaena sp.

<400> SEQUENCE: 82
caatagatga cttacaacta atcggaaggt gcagagactc gacgggagct accctaacgt 60
caagacgagg gtaaagagag agtccaattc tcaaagccaa taggcagtag cgaaagctgc 120
aagagaatga aaatccgt 138

<210> SEQ ID NO 83
<211> LENGTH: 137
<212> TYPE: DNA
<213> ORGANISM: Anabaena sp.

<400> SEQUENCE: 83
aatagatgac ttacaactaa tcggaaggtg cagagactcg acgggagcta ccctaacgtc 60
aagacgaggg taaagagaga gtccaattct caaagccaat aggcagtagc gaaagctgca 120
agagaatgaa aatccgt 137

<210> SEQ ID NO 84
<211> LENGTH: 136
<212> TYPE: DNA
<213> ORGANISM: Anabaena sp.

<400> SEQUENCE: 84
atagatgact tacaactaat cggaaggtgc agagactcga cgggagctac cctaacgtca 60
agacgagggt aaagagagag tccaattctc aaagccaata ggcagtagcg aaagctgcaa 120
gagaatgaaa atccgt 136

<210> SEQ ID NO 85
<211> LENGTH: 135
<212> TYPE: DNA
<213> ORGANISM: Anabaena sp.

<400> SEQUENCE: 85
tagatgactt acaactaatc ggaaggtgca gagactcgac gggagctacc ctaacgtcaa 60
gacgagggta aagagagagt ccaattctca aagccaatag gcagtagcga aagctgcaag 120
agaatgaaaa tccgt 135

<210> SEQ ID NO 86
<211> LENGTH: 134
<212> TYPE: DNA
<213> ORGANISM: Anabaena sp.

<400> SEQUENCE: 86
agatgactta caactaatcg gaaggtgcag agactcgacg ggagctaccc taacgtcaag 60
acgagggtaa agagagagtc caattctcaa agccaatagg cagtagcgaa agctgcaaga 120
gaatgaaaat ccgt 134

<210> SEQ ID NO 87
<211> LENGTH: 133
<212> TYPE: DNA
<213> ORGANISM: Anabaena sp.

<400> SEQUENCE: 87
gatgacttac aactaatcgg aaggtgcaga gactcgacgg gagctaccct aacgtcaaga 60
cgagggtaaa gagagagtcc aattctcaaa gccaataggc agtagcgaaa gctgcaagag 120
aatgaaaatc cgt 133

<210> SEQ ID NO 88
<211> LENGTH: 132
<212> TYPE: DNA
<213> ORGANISM: Anabaena sp.

<400> SEQUENCE: 88
atgacttaca actaatcgga aggtgcagag actcgacggg agctacccta acgtcaagac 60

```
gagggtaaag agagagtcca attctcaaag ccaataggca gtagcgaaag ctgcaagaga    120

atgaaaatcc gt                                                        132


<210> SEQ ID NO 89
<211> LENGTH: 131
<212> TYPE: DNA
<213> ORGANISM: Anabaena sp.

<400> SEQUENCE: 89

tgacttacaa ctaatcggaa ggtgcagaga ctcgacggga gctaccctaa cgtcaagacg     60

agggtaaaga gagagtccaa ttctcaaagc caataggcag tagcgaaagc tgcaagagaa    120

tgaaaatccg t                                                         131


<210> SEQ ID NO 90
<211> LENGTH: 78
<212> TYPE: DNA
<213> ORGANISM: Anabaena sp.

<400> SEQUENCE: 90

caagacgagg gtaaagagag agtccaattc tcaaagccaa taggcagtag cgaaagctgc     60

aagagaatga aaatccgt                                                   78


<210> SEQ ID NO 91
<211> LENGTH: 77
<212> TYPE: DNA
<213> ORGANISM: Anabaena sp.

<400> SEQUENCE: 91

aagacgaggg taaagagaga gtccaattct caaagccaat aggcagtagc gaaagctgca     60

agagaatgaa aatccgt                                                    77


<210> SEQ ID NO 92
<211> LENGTH: 76
<212> TYPE: DNA
<213> ORGANISM: Anabaena sp.

<400> SEQUENCE: 92

agacgagggt aaagagagag tccaattctc aaagccaata ggcagtagcg aaagctgcaa     60

gagaatgaaa atccgt                                                     76


<210> SEQ ID NO 93
<211> LENGTH: 75
<212> TYPE: DNA
<213> ORGANISM: Anabaena sp.

<400> SEQUENCE: 93

gacgagggta aagagagagt ccaattctca aagccaatag gcagtagcga aagctgcaag     60

agaatgaaaa tccgt                                                      75


<210> SEQ ID NO 94
<211> LENGTH: 74
<212> TYPE: DNA
<213> ORGANISM: Anabaena sp.

<400> SEQUENCE: 94

acgagggtaa agagagagtc caattctcaa agccaatagg cagtagcgaa agctgcaaga     60

gaatgaaaat ccgt                                                       74
```

<210> SEQ ID NO 95
<211> LENGTH: 40
<212> TYPE: DNA
<213> ORGANISM: Anabaena sp.

<400> SEQUENCE: 95
aataggcagt agcgaaagct gcaagagaat gaaaatccgt 40

<210> SEQ ID NO 96
<211> LENGTH: 39
<212> TYPE: DNA
<213> ORGANISM: Anabaena sp.

<400> SEQUENCE: 96
ataggcagta gcgaaagctg caagagaatg aaaatccgt 39

<210> SEQ ID NO 97
<211> LENGTH: 38
<212> TYPE: DNA
<213> ORGANISM: Anabaena sp.

<400> SEQUENCE: 97
taggcagtag cgaaagctgc aagagaatga aaatccgt 38

<210> SEQ ID NO 98
<211> LENGTH: 37
<212> TYPE: DNA
<213> ORGANISM: Anabaena sp.

<400> SEQUENCE: 98
aggcagtagc gaaagctgca agagaatgaa aatccgt 37

<210> SEQ ID NO 99
<211> LENGTH: 36
<212> TYPE: DNA
<213> ORGANISM: Anabaena sp.

<400> SEQUENCE: 99
ggcagtagcg aaagctgcaa gagaatgaaa atccgt 36

<210> SEQ ID NO 100
<211> LENGTH: 27
<212> TYPE: DNA
<213> ORGANISM: Anabaena sp.

<400> SEQUENCE: 100
gaaagctgca agagaatgaa aatccgt 27

<210> SEQ ID NO 101
<211> LENGTH: 26
<212> TYPE: DNA
<213> ORGANISM: Anabaena sp.

<400> SEQUENCE: 101
aaagctgcaa gagaatgaaa atccgt 26

<210> SEQ ID NO 102
<211> LENGTH: 25
<212> TYPE: DNA
<213> ORGANISM: Anabaena sp.

<400> SEQUENCE: 102
aagctgcaag agaatgaaaa tccgt 25

<210> SEQ ID NO 103
<211> LENGTH: 24
<212> TYPE: DNA
<213> ORGANISM: Anabaena sp.

<400> SEQUENCE: 103
agctgcaaga gaatgaaaat ccgt 24

<210> SEQ ID NO 104
<211> LENGTH: 23
<212> TYPE: DNA
<213> ORGANISM: Anabaena sp.

<400> SEQUENCE: 104
gctgcaagag aatgaaaatc cgt 23

<210> SEQ ID NO 105
<211> LENGTH: 22
<212> TYPE: DNA
<213> ORGANISM: Anabaena sp.

<400> SEQUENCE: 105
ctgcaagaga atgaaaatcc gt 22

<210> SEQ ID NO 106
<211> LENGTH: 18
<212> TYPE: DNA
<213> ORGANISM: Anabaena sp.

<400> SEQUENCE: 106
aagagaatga aaatccgt 18

<210> SEQ ID NO 107
<211> LENGTH: 17
<212> TYPE: DNA
<213> ORGANISM: Anabaena sp.

<400> SEQUENCE: 107
agagaatgaa aatccgt 17

<210> SEQ ID NO 108
<211> LENGTH: 16
<212> TYPE: DNA
<213> ORGANISM: Anabaena sp.

<400> SEQUENCE: 108
gagaatgaaa atccgt 16

<210> SEQ ID NO 109
<211> LENGTH: 35
<212> TYPE: DNA
<213> ORGANISM: Anabaena sp.

<400> SEQUENCE: 109
gcagtagcga aagctgcaag agaatgaaaa tccgt 35

<210> SEQ ID NO 110
<211> LENGTH: 33
<212> TYPE: DNA
<213> ORGANISM: Anabaena sp.

<400> SEQUENCE: 110
agtagcgaaa gctgcaagag aatgaaaatc cgt 33

<210> SEQ ID NO 111
<211> LENGTH: 32
<212> TYPE: DNA
<213> ORGANISM: Anabaena sp.

<400> SEQUENCE: 111
gtagcgaaag ctgcaagaga atgaaaatcc gt 32

<210> SEQ ID NO 112
<211> LENGTH: 26
<212> TYPE: DNA
<213> ORGANISM: Anabaena sp.

<400> SEQUENCE: 112
acggacttaa ataattgagc cttaaa 26

<210> SEQ ID NO 113
<211> LENGTH: 27
<212> TYPE: DNA
<213> ORGANISM: Anabaena sp.

<400> SEQUENCE: 113
acggacttaa ataattgagc cttaaag 27

<210> SEQ ID NO 114
<211> LENGTH: 28
<212> TYPE: DNA
<213> ORGANISM: Anabaena sp.

<400> SEQUENCE: 114
acggacttaa ataattgagc cttaaaga 28

<210> SEQ ID NO 115
<211> LENGTH: 76
<212> TYPE: DNA
<213> ORGANISM: Anabaena sp.

<400> SEQUENCE: 115
acggacttaa ataattgagc cttaaagaag aaattcttta agtggatgct ctcaaactca 60
gggaaaccta aatcta 76

<210> SEQ ID NO 116
<211> LENGTH: 77
<212> TYPE: DNA
<213> ORGANISM: Anabaena sp.

<400> SEQUENCE: 116
acggacttaa ataattgagc cttaaagaag aaattcttta agtggatgct ctcaaactca 60
gggaaaccta aatctag 77

<210> SEQ ID NO 117
<211> LENGTH: 78
<212> TYPE: DNA
<213> ORGANISM: Anabaena sp.

<400> SEQUENCE: 117
acggacttaa ataattgagc cttaaagaag aaattcttta agtggatgct ctcaaactca 60
gggaaaccta aatctagt 78

<210> SEQ ID NO 118

<211> LENGTH: 79
<212> TYPE: DNA
<213> ORGANISM: Anabaena sp.

<400> SEQUENCE: 118
acggacttaa ataattgagc cttaaagaag aaattcttta agtggatgct ctcaaactca 60
gggaaaccta aatctagtt 79

<210> SEQ ID NO 119
<211> LENGTH: 80
<212> TYPE: DNA
<213> ORGANISM: Anabaena sp.

<400> SEQUENCE: 119
acggacttaa ataattgagc cttaaagaag aaattcttta agtggatgct ctcaaactca 60
gggaaaccta aatctagtta 80

<210> SEQ ID NO 120
<211> LENGTH: 127
<212> TYPE: DNA
<213> ORGANISM: Anabaena sp.

<400> SEQUENCE: 120
acggacttaa ataattgagc cttaaagaag aaattcttta agtggatgct ctcaaactca 60
gggaaaccta aatctagtta tagacaaggc aatcctgagc caagccgaag tagtaattag 120
taagtta 127

<210> SEQ ID NO 121
<211> LENGTH: 128
<212> TYPE: DNA
<213> ORGANISM: Anabaena sp.

<400> SEQUENCE: 121
acggacttaa ataattgagc cttaaagaag aaattcttta agtggatgct ctcaaactca 60
gggaaaccta aatctagtta tagacaaggc aatcctgagc caagccgaag tagtaattag 120
taagttaa 128

<210> SEQ ID NO 122
<211> LENGTH: 129
<212> TYPE: DNA
<213> ORGANISM: Anabaena sp.

<400> SEQUENCE: 122
acggacttaa ataattgagc cttaaagaag aaattcttta agtggatgct ctcaaactca 60
gggaaaccta aatctagtta tagacaaggc aatcctgagc caagccgaag tagtaattag 120
taagttaac 129

<210> SEQ ID NO 123
<211> LENGTH: 130
<212> TYPE: DNA
<213> ORGANISM: Anabaena sp.

<400> SEQUENCE: 123
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca 130

<210> SEQ ID NO 124
<211> LENGTH: 131
<212> TYPE: DNA
<213> ORGANISM: Anabaena sp.

<400> SEQUENCE: 124
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca a 131

<210> SEQ ID NO 125
<211> LENGTH: 132
<212> TYPE: DNA
<213> ORGANISM: Anabaena sp.

<400> SEQUENCE: 125
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca at 132

<210> SEQ ID NO 126
<211> LENGTH: 133
<212> TYPE: DNA
<213> ORGANISM: Anabaena sp.

<400> SEQUENCE: 126
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca ata 133

<210> SEQ ID NO 127
<211> LENGTH: 134
<212> TYPE: DNA
<213> ORGANISM: Anabaena sp.

<400> SEQUENCE: 127
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atag 134

<210> SEQ ID NO 128
<211> LENGTH: 135
<212> TYPE: DNA
<213> ORGANISM: Anabaena sp.

<400> SEQUENCE: 128
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca ataga 135

<210> SEQ ID NO 129
<211> LENGTH: 188
<212> TYPE: DNA
<213> ORGANISM: Anabaena sp.

<400> SEQUENCE: 129
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgt 188

<210> SEQ ID NO 130
<211> LENGTH: 189
<212> TYPE: DNA
<213> ORGANISM: Anabaena sp.

<400> SEQUENCE: 130
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtc 189

<210> SEQ ID NO 131
<211> LENGTH: 190
<212> TYPE: DNA
<213> ORGANISM: Anabaena sp.

<400> SEQUENCE: 131
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca 190

<210> SEQ ID NO 132
<211> LENGTH: 191
<212> TYPE: DNA
<213> ORGANISM: Anabaena sp.

<400> SEQUENCE: 132
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca a 191

<210> SEQ ID NO 133
<211> LENGTH: 192
<212> TYPE: DNA
<213> ORGANISM: Anabaena sp.

<400> SEQUENCE: 133
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca ag 192

<210> SEQ ID NO 134
<211> LENGTH: 226
<212> TYPE: DNA
<213> ORGANISM: Anabaena sp.

<400> SEQUENCE: 134
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagcc 226

<210> SEQ ID NO 135
<211> LENGTH: 227
<212> TYPE: DNA
<213> ORGANISM: Anabaena sp.

<400> SEQUENCE: 135
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagcca 227

<210> SEQ ID NO 136
<211> LENGTH: 228
<212> TYPE: DNA
<213> ORGANISM: Anabaena sp.

<400> SEQUENCE: 136
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaa 228

<210> SEQ ID NO 137
<211> LENGTH: 229
<212> TYPE: DNA
<213> ORGANISM: Anabaena sp.

<400> SEQUENCE: 137
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaat 229

<210> SEQ ID NO 138
<211> LENGTH: 230
<212> TYPE: DNA
<213> ORGANISM: Anabaena sp.

<400> SEQUENCE: 138
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata 230

<210> SEQ ID NO 139
<211> LENGTH: 239
<212> TYPE: DNA
<213> ORGANISM: Anabaena sp.

<400> SEQUENCE: 139

```
acggacttaa ataattgagc cttaaagaag aaattcttta agtggatgct ctcaaactca     60

gggaaaccta aatctagtta tagacaaggc aatcctgagc caagccgaag tagtaattag    120

taagttaaca atagatgact tacaactaat cggaaggtgc agagactcga cgggagctac    180

cctaacgtca agacgagggt aaagagagag tccaattctc aaagccaata ggcagtagc     239


<210> SEQ ID NO 140
<211> LENGTH: 240
<212> TYPE: DNA
<213> ORGANISM: Anabaena sp.

<400> SEQUENCE: 140

acggacttaa ataattgagc cttaaagaag aaattcttta agtggatgct ctcaaactca     60

gggaaaccta aatctagtta tagacaaggc aatcctgagc caagccgaag tagtaattag    120

taagttaaca atagatgact tacaactaat cggaaggtgc agagactcga cgggagctac    180

cctaacgtca agacgagggt aaagagagag tccaattctc aaagccaata ggcagtagcg    240


<210> SEQ ID NO 141
<211> LENGTH: 241
<212> TYPE: DNA
<213> ORGANISM: Anabaena sp.

<400> SEQUENCE: 141

acggacttaa ataattgagc cttaaagaag aaattcttta agtggatgct ctcaaactca     60

gggaaaccta aatctagtta tagacaaggc aatcctgagc caagccgaag tagtaattag    120

taagttaaca atagatgact tacaactaat cggaaggtgc agagactcga cgggagctac    180

cctaacgtca agacgagggt aaagagagag tccaattctc aaagccaata ggcagtagcg    240

a                                                                    241


<210> SEQ ID NO 142
<211> LENGTH: 242
<212> TYPE: DNA
<213> ORGANISM: Anabaena sp.

<400> SEQUENCE: 142

acggacttaa ataattgagc cttaaagaag aaattcttta agtggatgct ctcaaactca     60

gggaaaccta aatctagtta tagacaaggc aatcctgagc caagccgaag tagtaattag    120

taagttaaca atagatgact tacaactaat cggaaggtgc agagactcga cgggagctac    180

cctaacgtca agacgagggt aaagagagag tccaattctc aaagccaata ggcagtagcg    240

aa                                                                   242


<210> SEQ ID NO 143
<211> LENGTH: 243
<212> TYPE: DNA
<213> ORGANISM: Anabaena sp.

<400> SEQUENCE: 143

acggacttaa ataattgagc cttaaagaag aaattcttta agtggatgct ctcaaactca     60

gggaaaccta aatctagtta tagacaaggc aatcctgagc caagccgaag tagtaattag    120

taagttaaca atagatgact tacaactaat cggaaggtgc agagactcga cgggagctac    180

cctaacgtca agacgagggt aaagagagag tccaattctc aaagccaata ggcagtagcg    240

aaa                                                                  243
```

<210> SEQ ID NO 144
<211> LENGTH: 244
<212> TYPE: DNA
<213> ORGANISM: Anabaena sp.

<400> SEQUENCE: 144
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aaag 244

<210> SEQ ID NO 145
<211> LENGTH: 248
<212> TYPE: DNA
<213> ORGANISM: Anabaena sp.

<400> SEQUENCE: 145
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aaagctgc 248

<210> SEQ ID NO 146
<211> LENGTH: 249
<212> TYPE: DNA
<213> ORGANISM: Anabaena sp.

<400> SEQUENCE: 146
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aaagctgca 249

<210> SEQ ID NO 147
<211> LENGTH: 250
<212> TYPE: DNA
<213> ORGANISM: Anabaena sp.

<400> SEQUENCE: 147
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggcagtagcg 240
aaagctgcaa 250

<210> SEQ ID NO 148
<211> LENGTH: 231
<212> TYPE: DNA
<213> ORGANISM: Anabaena sp.

<400> SEQUENCE: 148
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata g 231

<210> SEQ ID NO 149
<211> LENGTH: 233
<212> TYPE: DNA
<213> ORGANISM: Anabaena sp.

<400> SEQUENCE: 149
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggc 233

<210> SEQ ID NO 150
<211> LENGTH: 234
<212> TYPE: DNA
<213> ORGANISM: Anabaena sp.

<400> SEQUENCE: 150
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata ggca 234

<210> SEQ ID NO 151
<211> LENGTH: 104
<212> TYPE: DNA
<213> ORGANISM: Azoarcus sp.

<400> SEQUENCE: 151
tgcgccgatg aaggtgtaga gactagacgg cacccaccta aggcaaacgc tatggtgaag 60
gcatagtcca gggagtggcg aaagtcacac aaaccggaat ccgt 104

<210> SEQ ID NO 152
<211> LENGTH: 141
<212> TYPE: DNA
<213> ORGANISM: Azoarcus sp.

<400> SEQUENCE: 152
ccgggcgtat ggcaacgccg agccaagctt cggcgcctgc gccgatgaag gtgtagagac 60
tagacggcac ccacctaagg caaacgctat ggtgaaggca tagtccaggg agtggcgaaa 120
gtcacacaaa ccggaatccg t 141

<210> SEQ ID NO 153
<211> LENGTH: 78
<212> TYPE: DNA
<213> ORGANISM: Azoarcus sp.

<400> SEQUENCE: 153
acggcaccca cctaaggcaa acgctatggt gaaggcatag tccagggagt ggcgaaagtc 60
acacaaaccg gaatccgt 78

<210> SEQ ID NO 154
<211> LENGTH: 58
<212> TYPE: DNA
<213> ORGANISM: Azoarcus sp.

<400> SEQUENCE: 154
acgctatggt gaaggcatag tccagggagt ggcgaaagtc acacaaaccg gaatccgt 58

<210> SEQ ID NO 155
<211> LENGTH: 75
<212> TYPE: DNA
<213> ORGANISM: Thiomargarita sp.

<400> SEQUENCE: 155
attaaagtta tagaattatc agagaatgat atagtccaag ccttatggta acatgagggc 60
acttgaccct ggtag 75

<210> SEQ ID NO 156
<211> LENGTH: 195
<212> TYPE: DNA
<213> ORGANISM: Staphylococcus virus Twort

<400> SEQUENCE: 156
aagatgtagg caatcctgag ctaagctctt agtaataaga gaaagtgcaa cgactattcc 60
gataggaagt agggtcaagt gactcgaaat ggggattacc cttctagggt agtgatatag 120
tctgaacata tatggaaaca tatagaagga taggagtaac gaacctattc gtaacataat 180
tgaactttta gttat 195

<210> SEQ ID NO 157
<211> LENGTH: 163
<212> TYPE: DNA
<213> ORGANISM: Staphylococcus virus Twort

<400> SEQUENCE: 157
taataagaga aagtgcaacg actattccga taggaagtag ggtcaagtga ctcgaaatgg 60
ggattaccct tctagggtag tgatatagtc tgaacatata tggaaacata tagaaggata 120
ggagtaacga acctattcgt aacataattg aacttttagt tat 163

<210> SEQ ID NO 158
<211> LENGTH: 133
<212> TYPE: DNA
<213> ORGANISM: Staphylococcus virus Twort

<400> SEQUENCE: 158
taggaagtag ggtcaagtga ctcgaaatgg ggattaccct tctagggtag tgatatagtc 60
tgaacatata tggaaacata tagaaggata ggagtaacga acctattcgt aacataattg 120
aacttttagt tat 133

<210> SEQ ID NO 159
<211> LENGTH: 92
<212> TYPE: DNA
<213> ORGANISM: Staphylococcus virus Twort

<400> SEQUENCE: 159
ctagggtagt gatatagtct gaacatatat ggaaacatat agaaggatag gagtaacgaa 60
cctattcgta acataattga acttttagtt at 92

<210> SEQ ID NO 160

<211> LENGTH: 92
<212> TYPE: DNA
<213> ORGANISM: Unknown
<220> FEATURE:
<223> OTHER INFORMATION: Description of Unknown: LSUp1 sequence

<400> SEQUENCE: 160
agttaataaa gatgatgaaa tagtctgaac cattttgaga aaagtggaaa taaaagaaaa 60
tcttttatga taacataaat tgaacaggct aa 92

<210> SEQ ID NO 161
<211> LENGTH: 62
<212> TYPE: DNA
<213> ORGANISM: Unknown
<220> FEATURE:
<223> OTHER INFORMATION: Description of Unknown: Bacteriophage Phi I
sequence

<400> SEQUENCE: 161
caaagactga tgatatagtc cgacactcct agtaatagga gaatacagaa aggatgaaat 60
cc 62

<210> SEQ ID NO 162
<211> LENGTH: 76
<212> TYPE: DNA
<213> ORGANISM: Nostoc sp.

<400> SEQUENCE: 162
agtcgagggt aaagggagag tccaattctc aaagcctatt ggcagtagcg aaagctgcgg 60
gagaatgaaa atccgt 76

<210> SEQ ID NO 163
<211> LENGTH: 76
<212> TYPE: DNA
<213> ORGANISM: Nostoc sp.

<400> SEQUENCE: 163
agccgagggt aaagggagag tccaattctc aaagccaata ggcagtagcg aaagctgcgg 60
gagaatgaaa atccgt 76

<210> SEQ ID NO 164
<211> LENGTH: 89
<212> TYPE: DNA
<213> ORGANISM: Nodularia sp.

<400> SEQUENCE: 164
agccgagggt aaagggagag tccaattctc aaagccgaag gttattaaaa cctggcagca 60
gtgaaagctg cgggagaatg aaaatccgt 89

<210> SEQ ID NO 165
<211> LENGTH: 79
<212> TYPE: DNA
<213> ORGANISM: Pleurocapsa sp.

<400> SEQUENCE: 165
agctgagggt aaagagagag tccaattctc aaagccagca gatggcagta gcgaaagctg 60
cgggagaatg aaaatccgt 79

<210> SEQ ID NO 166
<211> LENGTH: 76
<212> TYPE: DNA

<213> ORGANISM: Planktothrix sp.

<400> SEQUENCE: 166
agccgagggt aaagagagag tccaattctc aaagccaatt ggtagtagcg aaagctacgg 60
gagaatgaaa atccgt 76

<210> SEQ ID NO 167
<211> LENGTH: 118
<212> TYPE: DNA
<213> ORGANISM: Azoarcus sp.

<400> SEQUENCE: 167
gcggactcat atttcgatgt gccttgcgcc gggaaaccac gcaagggatg gtgtcaaatt 60
cggcgaaacc taagcgcccg cccgggcgta tggcaacgcc gagccaagct tcggcgcc 118

<210> SEQ ID NO 168
<211> LENGTH: 81
<212> TYPE: DNA
<213> ORGANISM: Azoarcus sp.

<400> SEQUENCE: 168
gcggactcat atttcgatgt gccttgcgcc gggaaaccac gcaagggatg gtgtcaaatt 60
cggcgaaacc taagcgcccg c 81

<210> SEQ ID NO 169
<211> LENGTH: 144
<212> TYPE: DNA
<213> ORGANISM: Azoarcus sp.

<400> SEQUENCE: 169
gcggactcat atttcgatgt gccttgcgcc gggaaaccac gcaagggatg gtgtcaaatt 60
cggcgaaacc taagcgcccg cccgggcgta tggcaacgcc gagccaagct tcggcgcctg 120
cgccgatgaa ggtgtagaga ctag 144

<210> SEQ ID NO 170
<211> LENGTH: 164
<212> TYPE: DNA
<213> ORGANISM: Azoarcus sp.

<400> SEQUENCE: 170
gcggactcat atttcgatgt gccttgcgcc gggaaaccac gcaagggatg gtgtcaaatt 60
cggcgaaacc taagcgcccg cccgggcgta tggcaacgcc gagccaagct tcggcgcctg 120
cgccgatgaa ggtgtagaga ctagacggca cccacctaag gcaa 164

<210> SEQ ID NO 171
<211> LENGTH: 179
<212> TYPE: DNA
<213> ORGANISM: Thiomargarita sp.

<400> SEQUENCE: 171
aggattagat actacactaa gtgtccccca gactggtgac agtctggtgt gcatccagct 60
atatcggtga aaccccattg gggtaatacc gagggaagct atattatata tatattaata 120
aatagccccg tagagactat gtaggtaagg agatagaaga tgataaaatc aaaatcatc 179

<210> SEQ ID NO 172
<211> LENGTH: 84
<212> TYPE: DNA
<213> ORGANISM: Staphylococcus virus Twort

<400> SEQUENCE: 172
actactgaaa gcataaataa ttgtgccttt atacagtaat gtatatcgaa aaatcctcta 60
attcagggaa cacctaaaca aact 84

<210> SEQ ID NO 173
<211> LENGTH: 116
<212> TYPE: DNA
<213> ORGANISM: Staphylococcus virus Twort

<400> SEQUENCE: 173
actactgaaa gcataaataa ttgtgccttt atacagtaat gtatatcgaa aaatcctcta 60
attcagggaa cacctaaaca aactaagatg taggcaatcc tgagctaagc tcttag 116

<210> SEQ ID NO 174
<211> LENGTH: 146
<212> TYPE: DNA
<213> ORGANISM: Staphylococcus virus Twort

<400> SEQUENCE: 174
actactgaaa gcataaataa ttgtgccttt atacagtaat gtatatcgaa aaatcctcta 60
attcagggaa cacctaaaca aactaagatg taggcaatcc tgagctaagc tcttagtaat 120
aagagaaagt gcaacgacta ttccga 146

<210> SEQ ID NO 175
<211> LENGTH: 187
<212> TYPE: DNA
<213> ORGANISM: Staphylococcus virus Twort

<400> SEQUENCE: 175
actactgaaa gcataaataa ttgtgccttt atacagtaat gtatatcgaa aaatcctcta 60
attcagggaa cacctaaaca aactaagatg taggcaatcc tgagctaagc tcttagtaat 120
aagagaaagt gcaacgacta ttccgatagg aagtagggtc aagtgactcg aaatggggat 180
taccctt 187

<210> SEQ ID NO 176
<211> LENGTH: 216
<212> TYPE: DNA
<213> ORGANISM: Unknown
<220> FEATURE:
<223> OTHER INFORMATION: Description of Unknown: LSUp1 sequence

<400> SEQUENCE: 176
cgctagggat ttataactgt gagtcctcca atattataaa atgttggtaa tatattgggt 60
aaatttcaaa gacaactttt ctccacgtca ggatatagtg tatttgaagc gaaacttatt 120
ttagcagtga aaaagcaaat aaggacgttc aacgactaaa aggtgagtat tgctaacaat 180
aatccttttt tttaatgccc aacatcttta ttaact 216

<210> SEQ ID NO 177
<211> LENGTH: 559
<212> TYPE: DNA
<213> ORGANISM: Unknown
<220> FEATURE:
<223> OTHER INFORMATION: Description of Unknown: Bacteriophage Phi I
sequence

<400> SEQUENCE: 177
gtgggtgcat aaactatttc attgtgcaca ttaaatctgg tgaactcggt gaaaccctaa 60
tggggcaata ccgagccaag ccatagggag gatatatgag aggcaagaag ttaattcttg 120
aggccactga gactggctgt atcatcccta cgtcacacaa acttaatgcc gatggttatt 180
tcagaaagaa aaccaatggc gtcttagaga tgtatcacag aacggtgtgg aaggagcata 240
acggagacat acctgatggc ttcgagatag accataagtg tcgcaatagg gcttgctgta 300
atatagagca tttacagatg cttgagggta cagcccacac tgttaagacc aatcgtgaac 360
gctacgcaga cagaaaggaa acagctaggg aatactggct ggagactgga tgtaccggcc 420
tagcactcgg tgagaagttt ggtgtgtcgt tctcttctgc ttgtaagtgg attagagaat 480
ggaaggcgta gagactatcc gaaaggagta gggccgaggg tgagactccc tcgtaacccg 540
aagcgccaga cagtcaact 559

<210> SEQ ID NO 178
<211> LENGTH: 218
<212> TYPE: DNA
<213> ORGANISM: Nostoc sp.

<400> SEQUENCE: 178
acggacttaa gtaattgagc cttaaagaag aaattcttta agtggcagct ctcaaactca 60
gggaaaccta aatctgttca cagacaaggc aatcctgagc caagccgaaa gagtcatgag 120
tgctgagtag tgagtaaaat aaaagctcac aactcagagg ttgtaactct aagctagtcg 180
gaaggtgcag agactcgacg ggagctaccc taacgtaa 218

<210> SEQ ID NO 179
<211> LENGTH: 165
<212> TYPE: DNA
<213> ORGANISM: Nostoc sp.

<400> SEQUENCE: 179
acggacttaa actgaattga gccttagaga agaaattctt taagtgtcag ctctcaaact 60
cagggaaacc taaatctgtt gacagacaag gcaatcctga gccaagccga gaactctaag 120
ttattcggaa ggtgcagaga ctcgacggga gctaccctaa cgtca 165

<210> SEQ ID NO 180
<211> LENGTH: 181
<212> TYPE: DNA
<213> ORGANISM: Nodularia sp.

<400> SEQUENCE: 180
acggacttag aaaactgagc cttgatcgag aaatctttca agtggaagct ctcaaattca 60
gggaaaccta aatctgttta cagatatggc aatcctgagc caagccgaaa caagtcctga 120
gtgttaaagc tcataactca tcggaaggtg cagagactcg acgggagcta ccctaacgtt 180
a 181

<210> SEQ ID NO 181
<211> LENGTH: 188
<212> TYPE: DNA
<213> ORGANISM: Pleurocapsa sp.

<400> SEQUENCE: 181
acggacttaa aaaaattgag ccttggcaga gaaatctgtc atgcgaacgc tctcaaattc 60
agggaaacct aagtctggca acagatatgg caatcctgag ccaagcctta atcaaggaaa 120
aaaacatttt taccttttac cttgaaagga aggtgcagag actcaacggg agctacccta 180
acaggtca 188

<210> SEQ ID NO 182
<211> LENGTH: 200
<212> TYPE: DNA
<213> ORGANISM: Planktothrix sp.

<400> SEQUENCE: 182
acggacttaa agataaattg agccttgagg cgagaaatct ctcaagtgta agctgtcaaa 60
ttcagggaaa cctaaatctg taaattcaga caaggcaatc ctgagccaag cctaggggta 120
ttagaaatga gggagtttcc ccaatctaag atcaatacct aggaaggtgc agagactcga 180
cgggagctac cctaacgtta 200

<210> SEQ ID NO 183
<211> LENGTH: 166
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 183
agtatataag aaacaaacca ctagatgact tacaactaat cggaaggtgc agagactcga 60
cgggagctac cctaacgtca agacgagggt aaagagagag tccaattctc aaagccaata 120
ggcagtagcg aaagctgcaa gagaatgaaa atccgtggct cgcagc 166

<210> SEQ ID NO 184
<211> LENGTH: 176
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 184
ctgaaattat acttatactc aaacaaacca ctagatgact tacaactaat cggaaggtgc 60
agagactcga cgggagctac cctaacgtca agacgagggt aaagagagag tccaattctc 120
aaagccaata ggcagtagcg aaagctgcaa gagaatgaaa atccgtggct cgcagc 176

<210> SEQ ID NO 185
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 185
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 186
<211> LENGTH: 196
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 186
catcaacaat atgaaattat acttatactc agtatatgac aaacaaacca ctagatgact 60
tacaactaat cggaaggtgc agagactcga cgggagctac cctaacgtca agacgagggt 120
aaagagagag tccaattctc aaagccaata ggcagtagcg aaagctgcaa gagaatgaaa 180
atccgtggct cgcagc 196

<210> SEQ ID NO 187
<211> LENGTH: 206
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 187
catcaacaat atgaaactat acttatactc agtatatgaa gcattatcgc aaacaaacca 60
ctagatgact tacaactaat cggaaggtgc agagactcga cgggagctac cctaacgtca 120
agacgagggt aaagagagag tccaattctc aaagccaata ggcagtagcg aaagctgcaa 180
gagaatgaaa atccgtggct cgcagc 206

<210> SEQ ID NO 188
<211> LENGTH: 166
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 188
tagcgtcagc aaacaaacaa atagatgact tacaactaat cggaaggtgc agagactcga 60
cgggagctac cctaacgtca agacgagggt aaagagagag tccaattctc aaagccaata 120
ggcagtagcg aaagctgcaa gagaatgaaa atccgtggct cgcagc 166

<210> SEQ ID NO 189
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 189
atactcatac tagcgtcagc aaacaaacaa atagatgact tacaactaat cggaaggtgc 60
agagactcga cgggagctac cctaacgtca agacgagggt aaagagagag tccaattctc 120
aaagccaata ggcagtagcg aaagctgcaa gagaatgaaa atccgtggct cgcagc 176

<210> SEQ ID NO 190
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 190
gtgtgaagct atactcatac tagcgtcagc aaacaaacaa atagatgact tacaactaat 60
cggaaggtgc agagactcga cgggagctac cctaacgtca agacgagggt aaagagagag 120

```
tccaattctc aaagccaata ggcagtagcg aaagctgcaa gagaatgaaa atccgtggct    180

cgcagc                                                               186


<210> SEQ ID NO 191
<211> LENGTH: 196
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191

cctcacctga gtgtgaagct atactcatac tagcgtcagc aaacaaacaa atagatgact     60

tacaactaat cggaaggtgc agagactcga cgggagctac cctaacgtca agacgagggt    120

aaagagagag tccaattctc aaagccaata ggcagtagcg aaagctgcaa gagaatgaaa    180

atccgtggct cgcagc                                                    196


<210> SEQ ID NO 192
<211> LENGTH: 206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192

ccgaatgatg cctcacctga gtgtgaagct atactcatac tagcgtcagc aaacaaacaa     60

atagatgact tacaactaat cggaaggtgc agagactcga cgggagctac cctaacgtca    120

agacgagggt aaagagagag tccaattctc aaagccaata ggcagtagcg aaagctgcaa    180

gagaatgaaa atccgtggct cgcagc                                         206


<210> SEQ ID NO 193
<211> LENGTH: 166
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193

cggtgcgagc aaacaaacaa atagatgact tacaactaat cggaaggtgc agagactcga     60

cgggagctac cctaacgtca agacgagggt aaagagagag tccaattctc aaagccaata    120

ggcagtagcg aaagctgcaa gagaatgaaa atccgtggct cgcagc                   166


<210> SEQ ID NO 194
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194

cgctccgacc cagtgcgagc aaacaaacaa atagatgact tacaactaat cggaaggtgc     60

agagactcga cgggagctac cctaacgtca agacgagggt aaagagagag tccaattctc    120

aaagccaata ggcagtagcg aaagctgcaa gagaatgaaa atccgtggct cgcagc        176


<210> SEQ ID NO 195
<211> LENGTH: 186
```

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 195
ctgaaattat actaatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 196
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 196
ctgaaaatat actaatactc actatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 197
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 197
ctgataatat agtaatactc actatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 198
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 198
ctgataataa agtaatacac actataagac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 199
<211> LENGTH: 186
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 199
ctgaaattat acttatactc tctaagttac aaacaaacca ctagatgact tacaactaat     60
cggaaggtgc agagactcga cgggagctac cctaacgtca agacgagggt aaagagagag    120
tccaattctc aaagccaata ggcagtagcg aaagctgcaa gagaatgaaa atccgtggct    180
cgcagc                                                                186

<210> SEQ ID NO 200
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
ctgaaattat gtgtgttaca tctaagttac aaacaaacca ctagatgact tacaactaat     60
cggaaggtgc agagactcga cgggagctac cctaacgtca agacgagggt aaagagagag    120
tccaattctc aaagccaata ggcagtagcg aaagctgcaa gagaatgaaa atccgtggct    180
cgcagc                                                                186

<210> SEQ ID NO 201
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201
gttgatcggt gtgtgttaca tctaagttac aaacaaacca ctagatgact tacaactaat     60
cggaaggtgc agagactcga cgggagctac cctaacgtca agacgagggt aaagagagag    120
tccaattctc aaagccaata ggcagtagcg aaagctgcaa gagaatgaaa atccgtggct    180
cgcagc                                                                186

<210> SEQ ID NO 202
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
ctgaaattat acttatactc agtatatgac aaacaaacca ctagatgact tacaactaat     60
cggaaggtgc agagactcga cgggagctac cctaacgtca agacgagggt aaagagagag    120
tccaattctc aaagccaata ggcagtagcg aaagctgcaa gagaatgaaa atccgtgatt    180
aaacag                                                                186

<210> SEQ ID NO 203
<211> LENGTH: 196
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtgatt 180
cacaatataa attacg 196

<210> SEQ ID NO 204
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 204
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggat 180
catagc 186

<210> SEQ ID NO 205
<211> LENGTH: 196
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 205
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggat 180
cgcagcataa tatccg 196

<210> SEQ ID NO 206
<211> LENGTH: 196
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 206
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagcgcgc ctaccg 196

<210> SEQ ID NO 207
<211> LENGTH: 219
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 207
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagcgcgc ctaccgaaag ccggcgtcga cgttagcgc 219

<210> SEQ ID NO 208
<211> LENGTH: 219
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggat 180
cgcagcataa tatccgaaac gaggatacaa gtgacatgc 219

<210> SEQ ID NO 209
<211> LENGTH: 219
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtgatt 180
cacaatctaa attacgaaac gataaatgat aactctaac 219

<210> SEQ ID NO 210
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210
aaacaaacca ctagatgact tacaactaat cggaaggtgc agagactcga cgggagctac 60
cctaacgtca agacgagggt aaagagagag tccaattctc aaagccaata ggcagtagcg 120
aaagctgcaa gagaatgaaa atccgtggct cgcagc 156

<210> SEQ ID NO 211
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
cgggcaaaca aacaaataga tgacttacaa ctaatcggaa ggtgcagaga ctcgacggga 60
gctaccctaa cgtcaagacg agggtaaaga gagagtccaa ttctcaaagc caataggcag 120
tagcgaaagc tgcaagagaa tgaaaatccg tggctcgcag c 161

<210> SEQ ID NO 212
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 212
cgctccgacg agcttccggc cagtgcgagc aaacaaacaa atagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgtggct 180
cgcagc 186

<210> SEQ ID NO 213
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 213
aaacaaacca cggcagtagc gaaagctgca agagaatgaa aatccgtggc tcgcagc 57

<210> SEQ ID NO 214
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
agtatataag aaacaaacca cggcagtagc gaaagctgca agagaatgaa aatccgtggc 60
tcgcagc 67

<210> SEQ ID NO 215
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
ctgaaattat acttatactc aaacaaacca cggcagtagc gaaagctgca agagaatgaa 60
aatccgtggc tcgcagc 77

<210> SEQ ID NO 216
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216
ctgaaattat acttatactc agtatatgac aaacaaacca cggcagtagc gaaagctgca 60
agagaatgaa aatccgtggc tcgcagc 87

<210> SEQ ID NO 217

<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 217
tagcgtcagc aaacaaacaa aggcagtagc gaaagctgca agagaatgaa aatccgtggc 60
tcgcagc 67

<210> SEQ ID NO 218
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 218
atactcatac tagcgtcagc aaacaaacaa aggcagtagc gaaagctgca agagaatgaa 60
aatccgtggc tcgcagc 77

<210> SEQ ID NO 219
<211> LENGTH: 87
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 219
gtgtgaagct atactcatac tagcgtcagc aaacaaacaa aggcagtagc gaaagctgca 60
agagaatgaa aatccgtggc tcgcagc 87

<210> SEQ ID NO 220
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 220
cggtgcgagc aaacaaacaa aggcagtagc gaaagctgca agagaatgaa aatccgtggc 60
tcgcagc 67

<210> SEQ ID NO 221
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 221
cgctccgacc cagtgcgagc aaacaaacaa aggcagtagc gaaagctgca agagaatgaa 60
aatccgtggc tcgcagc 77

<210> SEQ ID NO 222
<211> LENGTH: 87
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 222
cgctccgacg agcttccggc cagtgcgagc aaacaaacaa aggcagtagc gaaagctgca     60
agagaatgaa aatccgtggc tcgcagc                                          87

<210> SEQ ID NO 223
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
aaacaaacca caagacgagg gtaaagagag agtccaattc tcaaagccaa taggcagtag     60
cgaaagctgc aagagaatga aaatccgtgg ctcgcagc                              98

<210> SEQ ID NO 224
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224
agtatataag aaacaaacca caagacgagg gtaaagagag agtccaattc tcaaagccaa     60
taggcagtag cgaaagctgc aagagaatga aaatccgtgg ctcgcagc                 108

<210> SEQ ID NO 225
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225
ctgaaattat acttatactc aaacaaacca caagacgagg gtaaagagag agtccaattc     60
tcaaagccaa taggcagtag cgaaagctgc aagagaatga aaatccgtgg ctcgcagc      118

<210> SEQ ID NO 226
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226
ctgaaattat acttatactc agtatatgac aaacaaacca caagacgagg gtaaagagag     60
agtccaattc tcaaagccaa taggcagtag cgaaagctgc aagagaatga aaatccgtgg    120
ctcgcagc                                                              128

<210> SEQ ID NO 227
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
tagcgtcagc aaacaaacaa aaagacgagg gtaaagagag agtccaattc tcaaagccaa 60
taggcagtag cgaaagctgc aagagaatga aaatccgtgg ctcgcagc 108

<210> SEQ ID NO 228
<211> LENGTH: 118
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 228
atactcatac tagcgtcagc aaacaaacaa aaagacgagg gtaaagagag agtccaattc 60
tcaaagccaa taggcagtag cgaaagctgc aagagaatga aaatccgtgg ctcgcagc 118

<210> SEQ ID NO 229
<211> LENGTH: 128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 229
gtgtgaagct atactcatac tagcgtcagc aaacaaacaa aaagacgagg gtaaagagag 60
agtccaattc tcaaagccaa taggcagtag cgaaagctgc aagagaatga aaatccgtgg 120
ctcgcagc 128

<210> SEQ ID NO 230
<211> LENGTH: 108
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 230
cggtgcgagc aaacaaacaa aaagacgagg gtaaagagag agtccaattc tcaaagccaa 60
taggcagtag cgaaagctgc aagagaatga aaatccgtgg ctcgcagc 108

<210> SEQ ID NO 231
<211> LENGTH: 118
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 231
cgctccgacc cagtgcgagc aaacaaacaa aaagacgagg gtaaagagag agtccaattc 60
tcaaagccaa taggcagtag cgaaagctgc aagagaatga aaatccgtgg ctcgcagc 118

<210> SEQ ID NO 232
<211> LENGTH: 128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 232
cgctccgacg agcttccggc cagtgcgagc aaacaaacaa aaagacgagg gtaaagagag 60
agtccaattc tcaaagccaa taggcagtag cgaaagctgc aagagaatga aaatccgtgg 120
ctcgcagc 128

<210> SEQ ID NO 233
<211> LENGTH: 176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 233
ctgaaattat acttatactc agtatatgac aaacaaacca ctagatgact tacaactaat 60
cggaaggtgc agagactcga cgggagctac cctaacgtca agacgagggt aaagagagag 120
tccaattctc aaagccaata ggcagtagcg aaagctgcaa gagaatgaaa atccgt 176

<210> SEQ ID NO 234
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 234
ctgaaattat acttatactc agtatatgac aaacaaacca cggcagtagc gaaagctgca 60
agagaatgaa aatccgt 77

<210> SEQ ID NO 235
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 235
ctgaaattat acttatactc agtatatgac aaacaaacca cggcagtagc gaaagctgca 60
agagaatgaa aatccgtgat taaacag 87

<210> SEQ ID NO 236
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 236
ctgaaattat acttatactc agtatatgac aaacaaacca cggcagtagc gaaagctgca 60
agagaatgaa aatccgtgat tcacaatata aattacg 97

<210> SEQ ID NO 237
<211> LENGTH: 87
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 237

```
ctgaaattat acttatactc agtatatgac aaacaaacca cggcagtagc gaaagctgca     60

agagaatgaa aatccgtgga tcatagc                                          87


<210> SEQ ID NO 238
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238

ctgaaattat acttatactc agtatatgac aaacaaacca cggcagtagc gaaagctgca     60

agagaatgaa aatccgtgga tcgcagcata atatccg                               97


<210> SEQ ID NO 239
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239

ctgaaattat acttatactc agtatatgac aaacaaacca cggcagtagc gaaagctgca     60

agagaatgaa aatccgtggc tcgcagcgcg cctaccg                               97


<210> SEQ ID NO 240
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 240

ctgaaattat acttatactc agtatatgac aaacaaacca caagacgagg gtaaagagag     60

agtccaattc tcaaagccaa taggcagtag cgaaagctgc aagagaatga aaatccgt      118


<210> SEQ ID NO 241
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241

ctgaaattat acttatactc agtatatgac aaacaaacca caagacgagg gtaaagagag     60

agtccaattc tcaaagccaa taggcagtag cgaaagctgc aagagaatga aaatccgtga    120

ttaaacag                                                              128


<210> SEQ ID NO 242
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 242

ctgaaattat acttatactc agtatatgac aaacaaacca caagacgagg gtaaagagag     60
```

agtccaattc tcaaagccaa taggcagtag cgaaagctgc aagagaatga aaatccgtga 120
ttcacaatat aaattacg 138

<210> SEQ ID NO 243
<211> LENGTH: 128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 243
ctgaaattat acttatactc agtatatgac aaacaaacca caagacgagg gtaaagagag 60
agtccaattc tcaaagccaa taggcagtag cgaaagctgc aagagaatga aaatccgtgg 120
atcatagc 128

<210> SEQ ID NO 244
<211> LENGTH: 138
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 244
ctgaaattat acttatactc agtatatgac aaacaaacca caagacgagg gtaaagagag 60
agtccaattc tcaaagccaa taggcagtag cgaaagctgc aagagaatga aaatccgtgg 120
atcgcagcat aatatccg 138

<210> SEQ ID NO 245
<211> LENGTH: 138
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 245
ctgaaattat acttatactc agtatatgac aaacaaacca caagacgagg gtaaagagag 60
agtccaattc tcaaagccaa taggcagtag cgaaagctgc aagagaatga aaatccgtgg 120
ctcgcagcgc gcctaccg 138

<210> SEQ ID NO 246
<211> LENGTH: 162
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 246
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aacttatata ct 162

<210> SEQ ID NO 247
<211> LENGTH: 172
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 247
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagagtataa gtataatttc ag 172

<210> SEQ ID NO 248
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 249
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
atattgttga tg 192

<210> SEQ ID NO 250
<211> LENGTH: 202
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagcgataat gcttcatata ctgagtataa 180
gtatagtttc atattgttga tg 202

<210> SEQ ID NO 251
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251

```
gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca aaacaaaaac aagctgacgc ta                      162


<210> SEQ ID NO 252
<211> LENGTH: 172
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252

gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca aaacaaaaac aagctgacgc tagtatgagt at           172


<210> SEQ ID NO 253
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253

gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca aaacaaaaac aagctgacgc tagtatgagt atagcttcac    180

ac                                                                   182


<210> SEQ ID NO 254
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254

gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca aaacaaaaac aagctgacgc tagtatgagt atagcttcac    180

actcaggtga gg                                                        192


<210> SEQ ID NO 255
<211> LENGTH: 202
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255

gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca aaacaaaaac aagctgacgc tagtatgagt atagcttcac    180

actcaggtga ggcatcattc gg                                             202
```

<210> SEQ ID NO 256
<211> LENGTH: 162
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 256
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctcgcac cg 162

<210> SEQ ID NO 257
<211> LENGTH: 172
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 257
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca aaacaaaaac aagctcgcac tgggtcggag cg 172

<210> SEQ ID NO 258
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 258
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 259
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 259
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 260
<211> LENGTH: 182
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 260
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 261
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 262
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 262
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtaactta gagagtataa gtataatttc 180
ag 182

<210> SEQ ID NO 263
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtaactta gatgtaacac acataatttc 180
ag 182

<210> SEQ ID NO 264
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtaactta gatgtaacac acaccgatca 180
ac 182

<210> SEQ ID NO 265
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 265
ctgtttaatc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 266
<211> LENGTH: 192
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 266
cgtaatttat attgtgaatc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca acacaaacac aagtcatata ctgagtataa 180
gtataatttc ag 192

<210> SEQ ID NO 267
<211> LENGTH: 182
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 267
gctatgatcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca acacaaacac aagtcatata ctgagtataa gtataatttc 180
ag 182

<210> SEQ ID NO 268
<211> LENGTH: 192
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 268
cggatattat gctgcgatcc acggacttaa ataattgagc cttaaagaag aaattcttta 60

```
agtggatgct ctcaaactca gggaaaccta aatctagtta tagacaaggc aatcctgagc    120

caagccgaag tagtaattag taagttaaca acacaaacac aagtcatata ctgagtataa    180

gtataatttc ag                                                        192


<210> SEQ ID NO 269
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269

cggtaggcgc gctgcgagcc acggacttaa ataattgagc cttaaagaag aaattcttta     60

agtggatgct ctcaaactca gggaaaccta aatctagtta tagacaaggc aatcctgagc    120

caagccgaag tagtaattag taagttaaca acacaaacac aagtcatata ctgagtataa    180

gtataatttc ag                                                        192


<210> SEQ ID NO 270
<211> LENGTH: 215
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 270

gcgctaacgt cgacgccggc aaacggtagg cgcgctgcga gccacggact taaataattg     60

agccttaaag aagaaattct ttaagtggat gctctcaaac tcagggaaac ctaaatctag    120

ttatagacaa ggcaatcctg agccaagccg aagtagtaat tagtaagtta acaacacaaa    180

cacaagtcat atactgagta taagtataat ttcag                               215


<210> SEQ ID NO 271
<211> LENGTH: 215
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271

gcatgtcact tgtatcctcg aaacggatat tatgctgcga tccacggact taaataattg     60

agccttaaag aagaaattct ttaagtggat gctctcaaac tcagggaaac ctaaatctag    120

ttatagacaa ggcaatcctg agccaagccg aagtagtaat tagtaagtta acaacacaaa    180

cacaagtcat atactgagta taagtataat ttcag                               215


<210> SEQ ID NO 272
<211> LENGTH: 215
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 272

gttagagtta tcatttatcg aaacgtaatt tagattgtga atcacggact taaataattg     60

agccttaaag aagaaattct ttaagtggat gctctcaaac tcagggaaac ctaaatctag    120
```

-continued

```
ttatagacaa ggcaatcctg agccaagccg aagtagtaat tagtaagtta acaacacaaa    180

cacaagtcat atactgagta taagtataat ttcag                               215


<210> SEQ ID NO 273
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273

gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca acacaaacac aa                                  152


<210> SEQ ID NO 274
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 274

gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca aaacaaaaac aagcccg                             157


<210> SEQ ID NO 275
<211> LENGTH: 182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 275

gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca aaacaaaaac aagctcgcac tggccggaag ctcgtcggag    180

cg                                                                   182


<210> SEQ ID NO 276
<211> LENGTH: 251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276

gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca atagatgact tacaactaat cggaaggtgc agagactcga    180

cgggagctac cctaacgtca agacgagggt aaagagagag tccaattctc aaagccaata    240

cacaaacaca a                                                         251
```

<210> SEQ ID NO 277
<211> LENGTH: 261
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277
gctgcgagcc acggacttaa ataattgagc cttaaagaag aaattcttta agtggatgct     60
ctcaaactca gggaaaccta aatctagtta tagacaaggc aatcctgagc caagccgaag    120
tagtaattag taagttaaca atagatgact tacaactaat cggaaggtgc agagactcga    180
cgggagctac cctaacgtca agacgagggt aaagagagag tccaattctc aaagccaata    240
cacaaacaca acttatatac t                                              261

<210> SEQ ID NO 278
<211> LENGTH: 271
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278
gctgcgagcc acggacttaa ataattgagc cttaaagaag aaattcttta agtggatgct     60
ctcaaactca gggaaaccta aatctagtta tagacaaggc aatcctgagc caagccgaag    120
tagtaattag taagttaaca atagatgact tacaactaat cggaaggtgc agagactcga    180
cgggagctac cctaacgtca agacgagggt aaagagagag tccaattctc aaagccaata    240
cacaaacaca agagtataag tataatttca g                                   271

<210> SEQ ID NO 279
<211> LENGTH: 281
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279
gctgcgagcc acggacttaa ataattgagc cttaaagaag aaattcttta agtggatgct     60
ctcaaactca gggaaaccta aatctagtta tagacaaggc aatcctgagc caagccgaag    120
tagtaattag taagttaaca atagatgact tacaactaat cggaaggtgc agagactcga    180
cgggagctac cctaacgtca agacgagggt aaagagagag tccaattctc aaagccaata    240
cacaaacaca agtcatatac tgagtataag tataatttca g                        281

<210> SEQ ID NO 280
<211> LENGTH: 261
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 280
gctgcgagcc acggacttaa ataattgagc cttaaagaag aaattcttta agtggatgct     60
ctcaaactca gggaaaccta aatctagtta tagacaaggc aatcctgagc caagccgaag    120
tagtaattag taagttaaca atagatgact tacaactaat cggaaggtgc agagactcga    180
cgggagctac cctaacgtca agacgagggt aaagagagag tccaattctc aaagccaata 240
aacaaaaaca agctgacgct a 261

<210> SEQ ID NO 281
<211> LENGTH: 271
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctgacgct agtatgagta t 271

<210> SEQ ID NO 282
<211> LENGTH: 281
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 282
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctgacgct agtatgagta tagcttcaca c 281

<210> SEQ ID NO 283
<211> LENGTH: 261
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 283
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctcgcacc g 261

<210> SEQ ID NO 284
<211> LENGTH: 271
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 284
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctcgcact gggtcggagc g 271

<210> SEQ ID NO 285
<211> LENGTH: 281
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 285
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
aacaaaaaca agctcgcact ggccggaagc tcgtcggagc g 281

<210> SEQ ID NO 286
<211> LENGTH: 210
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 286
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa 210

<210> SEQ ID NO 287
<211> LENGTH: 220
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 287
gctgcgagcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa cttatatact 220

<210> SEQ ID NO 288
<211> LENGTH: 230
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 288

-continued

```
gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca atagatgact tacaactaat cggaaggtgc agagactcga    180

cgggagctac cctaacgtcc acaaacacaa gagtataagt ataatttcag               230
```

<210> SEQ ID NO 289
<211> LENGTH: 240
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 289

```
gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca atagatgact tacaactaat cggaaggtgc agagactcga    180

cgggagctac cctaacgtcc acaaacacaa gtcatatact gagtataagt ataatttcag    240
```

<210> SEQ ID NO 290
<211> LENGTH: 220
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 290

```
gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca atagatgact tacaactaat cggaaggtgc agagactcga    180

cgggagctac cctaacgtca acaaaaacaa gctgacgcta                          220
```

<210> SEQ ID NO 291
<211> LENGTH: 230
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 291

```
gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca atagatgact tacaactaat cggaaggtgc agagactcga    180

cgggagctac cctaacgtca acaaaaacaa gctgacgcta gtatgagtat               230
```

<210> SEQ ID NO 292
<211> LENGTH: 240
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 292

```
gctgcgagcc acggacttaa ataattgagc cttaaagaag aaattcttta agtggatgct     60

ctcaaactca gggaaaccta aatctagtta tagacaaggc aatcctgagc caagccgaag    120
```

```
tagtaattag taagttaaca atagatgact tacaactaat cggaaggtgc agagactcga    180

cgggagctac cctaacgtca acaaaaacaa gctgacgcta gtatgagtat agcttcacac    240
```

<210> SEQ ID NO 293
<211> LENGTH: 220
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 293

```
gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca atagatgact tacaactaat cggaaggtgc agagactcga    180

cgggagctac cctaacgtca acaaaaacaa gctcgcaccg                          220
```

<210> SEQ ID NO 294
<211> LENGTH: 230
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 294

```
gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca atagatgact tacaactaat cggaaggtgc agagactcga    180

cgggagctac cctaacgtca acaaaaacaa gctcgcactg ggtcggagcg               230
```

<210> SEQ ID NO 295
<211> LENGTH: 240
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 295

```
gctgcgagcc acggacttaa ataattgagc cttaaagaag aaattcttta agtggatgct     60

ctcaaactca gggaaaccta aatctagtta tagacaaggc aatcctgagc caagccgaag    120

tagtaattag taagttaaca atagatgact tacaactaat cggaaggtgc agagactcga    180

cgggagctac cctaacgtca acaaaaacaa gctcgcactg gccggaagct cgtcggagcg    240
```

<210> SEQ ID NO 296
<211> LENGTH: 172
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 296

```
acggacttaa ataattgagc cttaaagaag aaattcttta agtggatgct ctcaaactca     60

gggaaaccta aatctagtta tagacaaggc aatcctgagc caagccgaag tagtaattag    120

taagttaaca acacaaacac aagtcatata ctgagtataa gtataatttc ag            172
```

<210> SEQ ID NO 297
<211> LENGTH: 271
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 297
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtca agacgagggt aaagagagag tccaattctc aaagccaata cacaaacaca 240
agtcatatac tgagtataag tataatttca g 271

<210> SEQ ID NO 298
<211> LENGTH: 281
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 298
ctgtttaatc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
cacaaacaca agtcatatac tgagtataag tataatttca g 281

<210> SEQ ID NO 299
<211> LENGTH: 291
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 299
cgtaatttat attgtgaatc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtca agacgagggt aaagagagag tccaattctc 240
aaagccaata cacaaacaca agtcatatac tgagtataag tataatttca g 291

<210> SEQ ID NO 300
<211> LENGTH: 281
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 300
gctatgatcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtca agacgagggt aaagagagag tccaattctc aaagccaata 240
cacaaacaca agtcatatac tgagtataag tataatttca g 281

<210> SEQ ID NO 301
<211> LENGTH: 291
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 301
cggatattat gctgcgatcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtca agacgagggt aaagagagag tccaattctc 240
aaagccaata cacaaacaca agtcatatac tgagtataag tataatttca g 291

<210> SEQ ID NO 302
<211> LENGTH: 291
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 302
cggtaggcgc gctgcgagcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtca agacgagggt aaagagagag tccaattctc 240
aaagccaata cacaaacaca agtcatatac tgagtataag tataatttca g 291

<210> SEQ ID NO 303
<211> LENGTH: 230
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 303
acggacttaa ataattgagc cttaaagaag aaattcttta agtggatgct ctcaaactca 60
gggaaaccta aatctagtta tagacaaggc aatcctgagc caagccgaag tagtaattag 120
taagttaaca atagatgact tacaactaat cggaaggtgc agagactcga cgggagctac 180
cctaacgtcc acaaacacaa gtcatatact gagtataagt ataatttcag 230

<210> SEQ ID NO 304
<211> LENGTH: 240
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 304
ctgtttaatc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa gtcatatact gagtataagt ataatttcag 240

<210> SEQ ID NO 305
<211> LENGTH: 250
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 305
cgtaatttat attgtgaatc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtcc acaaacacaa gtcatatact gagtataagt 240
ataatttcag 250

<210> SEQ ID NO 306
<211> LENGTH: 240
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 306
gctatgatcc acggacttaa ataattgagc cttaaagaag aaattcttta agtggatgct 60
ctcaaactca gggaaaccta aatctagtta tagacaaggc aatcctgagc caagccgaag 120
tagtaattag taagttaaca atagatgact tacaactaat cggaaggtgc agagactcga 180
cgggagctac cctaacgtcc acaaacacaa gtcatatact gagtataagt ataatttcag 240

<210> SEQ ID NO 307
<211> LENGTH: 250
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 307
cggatattat gctgcgatcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtcc acaaacacaa gtcatatact gagtataagt 240
ataatttcag 250

<210> SEQ ID NO 308
<211> LENGTH: 250
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 308
cggtaggcgc gctgcgagcc acggacttaa ataattgagc cttaaagaag aaattcttta 60
agtggatgct ctcaaactca gggaaaccta aatctagtta tagacaaggc aatcctgagc 120
caagccgaag tagtaattag taagttaaca atagatgact tacaactaat cggaaggtgc 180
agagactcga cgggagctac cctaacgtcc acaaacacaa gtcatatact gagtataagt 240
ataatttcag 250

<210> SEQ ID NO 309
<211> LENGTH: 1137
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 309
atgctgctgc tggtcacatc tctgctgctg tgcgagctgc cccatcctgc ctttctgctg 60
atccccgaca tccagatgac ccagaccaca agcagcctgt ctgccagcct gggcgataga 120
gtgaccatca gctgtagagc cagccaggac atcagcaagt acctgaactg gtatcagcaa 180
aagcccgacg gcaccgtgaa gctgctgatc taccacacca gcagactgca cagcggcgtg 240
ccaagcagat tttctggcag cggctctggc accgactaca gcctgacaat cagcaacctg 300
gaacaagagg atatcgctac ctacttctgc cagcaaggca acaccctgcc ttacaccttt 360
ggcggaggca ccaagctgga aatcaccggc tctacaagcg gcagcggcaa acctggatct 420
ggcgagggat ctaccaaggg cgaagtgaaa ctgcaagagt ctggccctgg actggtggcc 480
ccatctcagt ctctgagcgt gacctgtaca gtcagcggag tgtccctgcc tgattacggc 540
gtgtcctgga tcagacagcc tcctcggaaa ggcctggaat ggctgggagt gatctggggc 600
agcgagacaa cctactacaa cagcgccctg aagtcccggc tgaccatcat caaggacaac 660
tccaagagcc aggtgttcct gaagatgaac agcctgcaga ccgacgacac cgccatctac 720
tattgcgcca agcactacta ctacggcggc agctacgcca tggattattg gggccagggc 780
accagcgtga ccgtttcttc tgccgccgct atcgaagtga tgtaccctcc tccttacctg 840
gacaacgaga agtccaacgg caccatcatc cacgtgaagg gcaagcacct gtgtccttct 900
ccactgttcc ccggacctag caagcctttc tgggtgctcg ttgttgttgg cggcgtgctg 960
gcctgttaca gcctgctggt taccgtggcc ttcatcatct tttgggtcaa gagaggccgg 1020
aagaaacttc tttatatatt caagcagccc tttatgcgac ccgttcagac tacccaagag 1080
gaagatggat gcagttgccg ctttccagaa gaggaggagg gcgggtgcga actgtaa 1137

<210> SEQ ID NO 310
<211> LENGTH: 1134
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 310
atgctgctgc tggtcacatc tctgctgctg tgcgagctgc cccatcctgc ctttctgctg 60
atccccgaca tccagatgac ccagaccaca agcagcctgt ctgccagcct gggcgataga 120
gtgaccatca gctgtagagc cagccaggac atcagcaagt acctgaactg gtatcagcaa 180
aagcccgacg gcaccgtgaa gctgctgatc taccacacca gcagactgca cagcggcgtg 240
ccaagcagat tttctggcag cggctctggc accgactaca gcctgacaat cagcaacctg 300

```
gaacaagagg atatcgctac ctacttctgc cagcaaggca acaccctgcc ttacaccttt    360

ggcggaggca ccaagctgga aatcaccggc tctacaagcg gcagcggcaa acctggatct    420

ggcgagggat ctaccaaggg cgaagtgaaa ctgcaagagt ctggccctgg actggtggcc    480

ccatctcagt ctctgagcgt gacctgtaca gtcagcggag tgtccctgcc tgattacggc    540

gtgtcctgga tcagacagcc tcctcggaaa ggcctggaat ggctgggagt gatctggggc    600

agcgagacaa cctactacaa cagcgccctg aagtcccggc tgaccatcat caaggacaac    660

tccaagagcc aggtgttcct gaagatgaac agcctgcaga ccgacgacac cgccatctac    720

tattgcgcca agcactacta ctacggcggc agctacgcca tggattattg gggccagggc    780

accagcgtga ccgtttcttc tgccgccgct atcgaagtga tgtaccctcc tccttacctg    840

gacaacgaga agtccaacgg caccatcatc cacgtgaagg gcaagcacct gtgtccttct    900

ccactgttcc ccggacctag caagcctttc tgggtgctcg ttgttgttgg cggcgtgctg    960

gcctgttaca gcctgctggt taccgtggcc ttcatcatct tttgggtccg aagcaagcgg   1020

agccggctgc tgcactccga ctacatgaac atgaccccta gacggcccgg accaaccaga   1080

aagcactacc agccttacgc tcctcctaga gacttcgccg cctaccggtc ctaa         1134
```

```
<210> SEQ ID NO 311
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 311

atgctgctgc tggtcacatc tctgctgctg tgcgagctgc cccatcctgc ctttctgctg     60

atccccgaca tccagatgac ccagaccaca agcagcctgt ctgccagcct gggcgataga    120

gtgaccatca gctgtagagc cagccaggac atcagcaagt acctgaactg gtatcagcaa    180

aagcccgacg gcaccgtgaa gctgctgatc taccacacca gcagactgca cagcggcgtg    240

ccaagcagat tttctggcag cggctctggc accgactaca gcctgacaat cagcaacctg    300

gaacaagagg atatcgctac ctacttctgc cagcaaggca acaccctgcc ttacaccttt    360

ggcggaggca ccaagctgga aatcaccggc tctacaagcg gcagcggcaa acctggatct    420

ggcgagggat ctaccaaggg cgaagtgaaa ctgcaagagt ctggccctgg actggtggcc    480

ccatctcagt ctctgagcgt gacctgtaca gtcagcggag tgtccctgcc tgattacggc    540

gtgtcctgga tcagacagcc tcctcggaaa ggcctggaat ggctgggagt gatctggggc    600

agcgagacaa cctactacaa cagcgccctg aagtcccggc tgaccatcat caaggacaac    660

tccaagagcc aggtgttcct gaagatgaac agcctgcaga ccgacgacac cgccatctac    720

tattgcgcca agcactacta ctacggcggc agctacgcca tggattattg gggccagggc    780

accagcgtga ccgtttcttc tgccgccgct atcgaagtga tgtaccctcc tccttacctg    840

gacaacgaga agtccaacgg caccatcatc cacgtgaagg gcaagcacct gtgtccttct    900

ccactgttcc ccggacctag caagcctttc tgggtgctcg ttgttgttgg cggcgtgctg    960

gcctgttaca gcctgctggt taccgtggcc ttcatcatct tttgggtccg aagcaagcgg   1020

agccggctgc tgcactccga ctacatgaac atgaccccta gacggcccgg accaaccaga   1080

aagcactacc agccttacgc tcctcctaga gacttcgccg cctaccggtc cagagtgaag   1140

ttcagcagat ccgccgatgc tcccgcctat cagcagggcc aaaaccagct gtacaacgag   1200
```

ctgaacctgg ggagaagaga agagtacgac gtgctggaca agcggagagg cagagatcct 1260
gaaatgggcg gcaagcccag acggaagaat cctcaagagg gcctgtataa tgagctgcag 1320
aaagacaaga tggccgaggc ctacagcgag atcggaatga agggcgagcg cagaagaggc 1380
aagggacacg atggactgta ccagggactg agcaccgcca ccaaggatac ctatgacgcc 1440
ctgcacatgc aggccctgcc tccaagataa 1470

<210> SEQ ID NO 312
<211> LENGTH: 1347
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 312
atgctgctgc tggtcacatc tctgctgctg tgcgagctgc cccatcctgc ctttctgctg 60
atccccgaca tccagatgac ccagaccaca agcagcctgt ctgccagcct gggcgataga 120
gtgaccatca gctgtagagc cagccaggac atcagcaagt acctgaactg gtatcagcaa 180
aagcccgacg gcaccgtgaa gctgctgatc taccacacca gcagactgca cagcggcgtg 240
ccaagcagat tttctggcag cggctctggc accgactaca gcctgacaat cagcaacctg 300
gaacaagagg atatcgctac ctacttctgc cagcaaggca acaccctgcc ttacaccttt 360
ggcggaggca ccaagctgga aatcaccggc tctacaagcg gcagcggcaa acctggatct 420
ggcgagggat ctaccaaggg cgaagtgaaa ctgcaagagt ctggccctgg actggtggcc 480
ccatctcagt ctctgagcgt gacctgtaca gtcagcggag tgtccctgcc tgattacggc 540
gtgtcctgga tcagacagcc tcctcggaaa ggcctggaat ggctgggagt gatctggggc 600
agcgagacaa cctactacaa cagcgccctg aagtcccggc tgaccatcat caaggacaac 660
tccaagagcc aggtgttcct gaagatgaac agcctgcaga ccgacgacac cgccatctac 720
tattgcgcca agcactacta ctacggcggc agctacgcca tggattattg gggccagggc 780
accagcgtga ccgtttcttc tgccgccgct atcgaagtga tgtaccctcc tccttacctg 840
gacaacgaga agtccaacgg caccatcatc cacgtgaagg gcaagcacct gtgtccttct 900
ccactgttcc ccggacctag caagcctttc tgggtgctcg ttgttgttgg cggcgtgctg 960
gcctgttaca gcctgctggt taccgtggcc ttcatcatct tttgggtcag agtgaagttc 1020
agcagatccg ccgatgctcc cgcctatcag cagggccaaa accagctgta caacgagctg 1080
aacctgggga gaagagaaga gtacgacgtg ctggacaagc ggagaggcag agatcctgaa 1140
atgggcggca agcccagacg gaagaatcct caagagggcc tgtataatga gctgcagaaa 1200
gacaagatgg ccgaggccta cagcgagatc ggaatgaagg gcgagcgcag aagaggcaag 1260
ggacacgatg gactgtacca gggactgagc accgccacca aggataccta tgacgccctg 1320
cacatgcagg ccctgcctcc aagataa 1347

<210> SEQ ID NO 313
<211> LENGTH: 1461
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 313
atggctctcc cggtcacagc ccttctcctg cccctggcac tcttgctgca tgcggcacga 60

```
cccgacatcc agatgaccca gaccacaagc agcctgtctg ccagcctggg cgatagagtg    120

accatcagct gtagagccag ccaggacatc agcaagtacc tgaactggta tcagcaaaag    180

cccgacggca ccgtgaagct gctgatctac cacaccagca gactgcacag cggcgtgcca    240

agcagatttt ctggcagcgg ctctggcacc gactacagcc tgacaatcag caacctggaa    300

caagaggata tcgctaccta cttctgccag caaggcaaca ccctgcctta cacctttggc    360

ggaggcacca agctggaaat caccggtgga ggtggttctg gcggaggggg atctggtgga    420

ggcggttcag aagtgaaact gcaagagtct ggccctggac tggtggcccc atctcagtct    480

ctgagcgtga cctgtacagt cagcggagtg tccctgcctg attacggcgt gtcctggatc    540

agacagcctc ctcggaaagg cctggaatgg ctgggagtga tctggggcag cgagacaacc    600

tactacaaca gcgccctgaa gtcccggctg accatcatca aggacaactc caagagccag    660

gtgttcctga agatgaacag cctgcagacc gacgacaccg ccatctacta ttgcgccaag    720

cactactact acggcggcag ctacgccatg gattattggg gccagggcac cagcgtgacc    780

gtttcttcta ccacaacgcc cgccccgcga ccgcctactc ccgctcccac aattgcatca    840

caacccctgt ctttgagacc cgaagcttgt cgaccagctg ccggtggcgc ggttcacacg    900

cgggggctcg atttcgcctg tgatatatat atatgggccc cattggctgg aacatgcgga    960

gtattgcttc tgagcctggt gattaccctc tactgtaaga gaggccggaa gaaacttctt   1020

tatatattca agcagccctt tatgcgaccc gttcagacta cccaagagga agatggatgc   1080

agttgccgct ttccagaaga ggaggagggc gggtgcgaac tgagagtgaa gttcagcaga   1140

tccgccgatg ctcccgccta tcagcagggc caaaaccagc tgtacaacga gctgaacctg   1200

gggagaagag aagagtacga cgtgctggac aagcggagag gcagagatcc tgaaatgggc   1260

ggcaagccca gacggaagaa tcctcaagag ggcctgtata atgagctgca gaaagacaag   1320

atggccgagg cctacagcga gatcggaatg aagggcgagc gcagaagagg caagggacac   1380

gatggactgt accagggact gagcaccgcc accaaggata cctatgacgc cctgcacatg   1440

caggccctgc ctccaagata a                                              1461
```

<210> SEQ ID NO 314
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 314

```
atggctctcc cggtcacagc ccttctcctg cccctggcac tcttgctgca tgcggcacga     60

cccgacatcc agatgaccca gaccacaagc agcctgtctg ccagcctggg cgatagagtg    120

accatcagct gtagagccag ccaggacatc agcaagtacc tgaactggta tcagcaaaag    180

cccgacggca ccgtgaagct gctgatctac cacaccagca gactgcacag cggcgtgcca    240

agcagatttt ctggcagcgg ctctggcacc gactacagcc tgacaatcag caacctggaa    300

caagaggata tcgctaccta cttctgccag caaggcaaca ccctgcctta cacctttggc    360

ggaggcacca agctggaaat caccggtgga ggtggttctg gcggaggggg atctggtgga    420

ggcggttcag aagtgaaact gcaagagtct ggccctggac tggtggcccc atctcagtct    480

ctgagcgtga cctgtacagt cagcggagtg tccctgcctg attacggcgt gtcctggatc    540

agacagcctc ctcggaaagg cctggaatgg ctgggagtga tctggggcag cgagacaacc    600
```

tactacaaca gcgccctgaa gtcccggctg accatcatca aggacaactc caagagccag 660
gtgttcctga agatgaacag cctgcagacc gacgacaccg ccatctacta ttgcgccaag 720
cactactact acggcggcag ctacgccatg gattattggg gccagggcac cagcgtgacc 780
gtttcttcta ccacaacgcc cgccccgcga ccgcctactc ccgctcccac aattgcatca 840
caacccctgt ctttgagacc cgaagcttgt cgaccagctg ccggtggcgc ggttcacacg 900
cgggggctcg atttcgcctg tgatatatat atatgggccc cattggctgg aacatgcgga 960
gtattgcttc tgagcctggt gattaccctc tactgtaaga gaggccggaa gaaacttctt 1020
tatatattca agcagccctt tatgcgaccc gttcagacta cccaagagga agatggatgc 1080
agttgccgct ttccagaaga ggaggagggc gggtgcgaac tgagagtgaa gttcagcaga 1140
tccgccgatg ctcccgccta taagcagggc caaaaccagc tgtacaacga gctgaacctg 1200
gggagaagag aagagtacga cgtgctggac aagcggagag gcagagatcc tgaaatgggc 1260
ggcaagccca gacggaagaa tcctcaagag ggcctgtata atgagctgca gaaagacaag 1320
atggccgagg cctacagcga gatcggaatg aagggcgagc gcagaagagg caagggacac 1380
gatggactgt accagggact gagcaccgcc accaaggata cctatgacgc cctgcacatg 1440
caggccctgc ctccaagata a 1461

<210> SEQ ID NO 315
<211> LENGTH: 1452
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 315
atgctgctgc tggtcacatc tctgctgctg tgcgagctgc cccatcctgc ctttctgctg 60
atcccccagg ttcaactcca gcagtctggt cccggcctcg ttaaaccaag ccagactttg 120
tctcttacct gtgctatcag tggcgatagc gtgtctagta attcagccgc atggaactgg 180
atccgacaat caccgagtag gggacttgaa tggctgggta gaacctatta ccggtccaaa 240
tggtacaatg actatgcagt gtctgtaaaa agcaggatca cgatcaaccc tgatacgtct 300
aaaaaccagt tttctctgca acttaatagt gtgacccctg aagacaccgc tgtgtattac 360
tgtgcacggg aggttaccgg tgatcttgaa gatgcttttg atatatgggg ccaaggtacg 420
atggtcacgg tgtctagtgg gggaggcggc agcgacatac agatgacgca gagcccatcc 480
agtctctccg cgtctgttgg tgacagagtg actattacat gtagggcgtc tcagaccatt 540
tggtcttacc tcaattggta tcaacagcga ccaggcaaag caccgaactt gctcatttac 600
gctgccagct cactccaaag tggtgtgccg tccagattta gtggtagggg cagtggcact 660
gatttcactc tgactatttc aagtcttcaa gctgaggatt ttgccacata ctactgccag 720
caaagttact caatacctca gacttttgga caggggacaa aattggagat taaatccgga 780
accacaacgc ccgccccgcg accgcctact cccgctccca caattgcatc acaacccctg 840
tctttgagac ccgaagcttg tcgaccagct gccggtggcg cggttcacac gcgggggctc 900
gatttcgcct gtgatatata tatatgggcc ccattggctg gaacatgcgg agtattgctt 960
ctgagcctgg tgattaccct ctactgtaag agaggccgga agaaacttct ttatatattc 1020
aagcagccct ttatgcgacc cgttcagact acccaagagg aagatggatg cagttgccgc 1080
tttccagaag aggaggaggg cgggtgcgaa ctgagagtga agttcagcag atccgccgat 1140
gctcccgcct ataagcaggg ccaaaaccag ctgtacaacg agctgaacct ggggagaaga 1200
gaagagtacg acgtgctgga caagcggaga ggcagagatc ctgaaatggg cggcaagccc 1260
agacggaaga atcctcaaga gggcctgtat aatgagctgc agaaagacaa gatggccgag 1320
gcctacagcg agatcggaat gaagggcgag cgcagaagag gcaagggaca cgatggactg 1380
taccagggac tgagcaccgc caccaaggat acctatgacg ccctgcacat gcaggccctg 1440
cctccaagat aa 1452

<210> SEQ ID NO 316
<211> LENGTH: 2202
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 316
atgctgctgc tggtcacatc tctgctgctg tgcgagctgc cccatcctgc ctttctgctg 60
atccccgaca tccagatgac ccagaccaca agcagcctgt ctgccagcct gggcgataga 120
gtgaccatca gctgtagagc cagccaggac atcagcaagt acctgaactg gtatcagcaa 180
aagcccgacg gcaccgtgaa gctgctgatc taccacacca gcagactgca cagcggcgtg 240
ccaagcagat tttctggcag cggctctggc accgactaca gcctgacaat cagcaacctg 300
gaacaagagg atatcgctac ctacttctgc cagcaaggca acaccctgcc ttacaccttt 360
ggcggaggca ccaagctgga aatcaccggc ggcggaggat cccaggttca actccagcag 420
tctggtcccg gcctcgttaa accaagccag actttgtctc ttacctgtgc tatcagtggc 480
gatagcgtgt ctagtaattc agccgcatgg aactggatcc gacaatcacc gagtagggga 540
cttgaatggc tgggtagaac ctattaccgg tccaaatggt acaatgacta tgcagtgtct 600
gtaaaaagca ggatcacgat caaccctgat acgtctaaaa accagttttc tctgcaactt 660
aatagtgtga cccctgaaga caccgctgtg tattactgtg cacgggaggt taccggtgat 720
cttgaagatg cttttgatat atggggccaa ggtacgatgg tcacggtgtc tagtggctct 780
acaagcggca gcggcaaacc tggatctggc gagggatcta ccaagggcga catacagatg 840
acgcagagcc catccagtct ctccgcgtct gttggtgaca gagtgactat tacatgtagg 900
gcgtctcaga ccatttggtc ttacctcaat tggtatcaac agcgaccagg caaagcaccg 960
aacttgctca tttacgctgc cagctcactc caaagtggtg tgccgtccag atttagtggt 1020
aggggcagtg gcactgattt cactctgact atttcaagtc ttcaagctga ggattttgcc 1080
acatactact gccagcaaag ttactcaata cctcagactt ttggacaggg gacaaaattg 1140
gagattaaag gggaggcgg cagcgaagtg aaactgcaag agtctggccc tggactggtg 1200
gccccatctc agtctctgag cgtgacctgt acagtcagcg gagtgtccct gcctgattac 1260
ggcgtgtcct ggatcagaca gcctcctcgg aaaggcctgg aatggctggg agtgatctgg 1320
ggcagcgaga caacctacta caacagcgcc ctgaagtccc ggctgaccat catcaaggac 1380
aactccaaga gccaggtgtt cctgaagatg aacagcctgc agaccgacga caccgccatc 1440
tactattgcg ccaagcacta ctactacggc ggcagctacg ccatggatta ttggggccag 1500
ggcaccagcg tgaccgtttc ttcttccgga accacaacgc ccgccccgcg accgcctact 1560
cccgctccca caattgcatc acaacccctg tctttgagac ccgaagcttg tcgaccagct 1620
gccggtggcg cggttcacac gcgggggctc gatttcgcct gtgatatata tatatgggcc 1680

```
ccattggctg gaacatgcgg agtattgctt ctgagcctgg tgattaccct ctactgtaag   1740

agaggccgga agaaacttct ttatatattc aagcagccct ttatgcgacc cgttcagact   1800

acccaagagg aagatggatg cagttgccgc tttccagaag aggaggaggg cgggtgcgaa   1860

ctgagagtga agttcagcag atccgccgat gctcccgcct ataagcaggg ccaaaaccag   1920

ctgtacaacg agctgaacct ggggagaaga gaagagtacg acgtgctgga caagcggaga   1980

ggcagagatc ctgaaatggg cggcaagccc agacggaaga atcctcaaga gggcctgtat   2040

aatgagctgc agaaagacaa gatggccgag gcctacagcg agatcggaat gaagggcgag   2100

cgcagaagag gcaagggaca cgatggactg taccagggac tgagcaccgc caccaaggat   2160

acctatgacg ccctgcacat gcaggccctg cctccaagat aa                       2202
```

<210> SEQ ID NO 317
<211> LENGTH: 2262
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 317

```
atgctgctgc tggtcacatc tctgctgctg tgcgagctgc cccatcctgc ctttctgctg     60

atcccccagg ttcaactcca gcagtctggt cccggcctcg ttaaaccaag ccagactttg    120

tctcttacct gtgctatcag tggcgatagc gtgtctagta attcagccgc atggaactgg    180

atccgacaat caccgagtag ggacttgaa tggctgggta gaacctatta ccggtccaaa     240

tggtacaatg actatgcagt gtctgtaaaa agcaggatca cgatcaaccc tgatacgtct    300

aaaaaccagt tttctctgca acttaatagt gtgacccctg aagacaccgc tgtgtattac    360

tgtgcacggg aggttaccgg tgatcttgaa gatgcttttg atatatgggg ccaaggtacg    420

atggtcacgg tgtctagtgg gggaggcggc agcgacatac agatgacgca gagcccatcc    480

agtctctccg cgtctgttgg tgacagagtg actattacat gtagggcgtc tcagaccatt    540

tggtcttacc tcaattggta tcaacagcga ccaggcaaag caccgaactt gctcatttac    600

gctgccagct cactccaaag tggtgtgccg tccagattta gtggtagggg cagtggcact    660

gatttcactc tgactatttc aagtcttcaa gctgaggatt ttgccacata ctactgccag    720

caaagttact caatacctca gacttttgga caggggacaa aattggagat taaaggggga    780

ggcggatccg gcggtggtgg ctccggcggt ggtggttctg gaggcggcgg aagcggtggg    840

ggtggtagcg acatccagat gacccagacc acaagcagcc tgtctgccag cctgggcgat    900

agagtgacca tcagctgtag agccagccag gacatcagca agtacctgaa ctggtatcag    960

caaaagcccg acggcaccgt gaagctgctg atctaccaca ccagcagact gcacagcggc   1020

gtgccaagca gattttctgg cagcggctct ggcaccgact acagcctgac aatcagcaac   1080

ctggaacaag aggatatcgc tacctacttc tgccagcaag gcaacaccct gccttacacc   1140

tttggcggag gcaccaagct ggaaatcacc ggctctacaa gcggcagcgg caaacctgga   1200

tctggcgagg gatctaccaa gggcgaagtg aaactgcaag agtctggccc tggactggtg   1260

gccccatctc agtctctgag cgtgacctgt acagtcagcg gagtgtccct gcctgattac   1320

ggcgtgtcct ggatcagaca gcctcctcgg aaaggcctgg aatggctggg agtgatctgg   1380

ggcagcgaga caacctacta caacagcgcc ctgaagtccc ggctgaccat catcaaggac   1440

aactccaaga gccaggtgtt cctgaagatg aacagcctgc agaccgacga caccgccatc   1500
```

```
tactattgcg ccaagcacta ctactacggc ggcagctacg ccatggatta ttggggccag   1560

ggcaccagcg tgaccgtttc ttcttccgga accacaacgc ccgccccgcg accgcctact   1620

cccgctccca caattgcatc acaacccctg tctttgagac ccgaagcttg tcgaccagct   1680

gccggtggcg cggttcacac gcgggggctc gatttcgcct gtgatatata tatatgggcc   1740

ccattggctg gaacatgcgg agtattgctt ctgagcctgg tgattaccct ctactgtaag   1800

agaggccgga agaaacttct ttatatattc aagcagccct ttatgcgacc cgttcagact   1860

acccaagagg aagatggatg cagttgccgc tttccagaag aggaggaggg cgggtgcgaa   1920

ctgagagtga agttcagcag atccgccgat gctcccgcct ataagcaggg ccaaaaccag   1980

ctgtacaacg agctgaacct ggggagaaga gaagagtacg acgtgctgga caagcggaga   2040

ggcagagatc ctgaaatggg cggcaagccc agacggaaga atcctcaaga gggcctgtat   2100

aatgagctgc agaaagacaa gatggccgag gcctacagcg agatcggaat gaagggcgag   2160

cgcagaagag gcaagggaca cgatggactg taccagggac tgagcaccgc caccaaggat   2220

acctatgacg ccctgcacat gcaggccctg cctccaagat aa                      2262
```

```
<210> SEQ ID NO 318
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 319
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 320
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 320

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Asp Ile Val Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Arg Tyr Tyr Leu Ser Trp Tyr Gln Gln Lys Pro Gly
                165                 170                 175

Lys Ala Pro Lys Leu Leu Ile Tyr Thr Ala Ser Ile Leu Gln Asn Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Asp Phe Ala Thr Tyr Tyr Cys Leu
    210                 215                 220

Gln Thr Tyr Thr Thr Pro Asp Phe Gly Pro Gly Thr Lys Val Glu Ile
225                 230                 235                 240

Lys

<210> SEQ ID NO 321
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 321

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys

```
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120


<210> SEQ ID NO 322
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105


<210> SEQ ID NO 323
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
```

```
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 324
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 324

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30
```

```
Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 325
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175
```

```
Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 326
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
```

```
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 327
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220
```

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 328
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 329
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

```
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 330
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175
```

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 331
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 331

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Glu Gly Gly Trp Phe Gly Glu Leu Ala Phe Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Arg Val Glu Pro Lys Ser Cys
210 215 220

Asp Lys Thr His Thr Cys Pro Pro Cys Pro Ala Pro Glu Phe Glu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

-continued

Lys Glu Tyr Lys Cys Lys Val Ser Asn Lys Ala Leu Pro Ala Ser Ile
325 330 335

Glu Lys Thr Ile Ser Lys Ala Lys Gly Gln Pro Arg Glu Pro Gln Val
340 345 350

Tyr Thr Leu Pro Pro Ser Arg Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 332
<211> LENGTH: 215
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 332

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Arg Val Ser Ser Ser
20 25 30

Tyr Leu Ala Trp Tyr Gln Gln Lys Pro Gly Gln Ala Pro Arg Leu Leu
35 40 45

Ile Tyr Asp Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Leu Pro
85 90 95

Trp Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys

```
    210                 215


<210> SEQ ID NO 333
<211> LENGTH: 133
<212> TYPE: PRT
<213> ORGANISM: Homo sapiens

<400> SEQUENCE: 333

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 334
<211> LENGTH: 197
<212> TYPE: PRT
<213> ORGANISM: Homo sapiens

<400> SEQUENCE: 334

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
```

```
            180                 185                 190

Tyr Leu Asn Ala Ser
        195


<210> SEQ ID NO 335
<211> LENGTH: 306
<212> TYPE: PRT
<213> ORGANISM: Homo sapiens

<400> SEQUENCE: 335

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 336
<211> LENGTH: 152
<212> TYPE: PRT
<213> ORGANISM: Homo sapiens
```

<400> SEQUENCE: 336

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 337
<211> LENGTH: 160
<212> TYPE: PRT
<213> ORGANISM: Homo sapiens

<400> SEQUENCE: 337

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 338
<211> LENGTH: 114
<212> TYPE: PRT
<213> ORGANISM: Homo sapiens

<400> SEQUENCE: 338

Asn Trp Val Asn Val Ile Ser Asp Leu Lys Lys Ile Glu Asp Leu Ile

-continued

```
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 339
<211> LENGTH: 157
<212> TYPE: PRT
<213> ORGANISM: Homo sapiens

<400> SEQUENCE: 339

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155


<210> SEQ ID NO 340
<211> LENGTH: 209
<212> TYPE: PRT
<213> ORGANISM: Homo sapiens

<400> SEQUENCE: 340

Arg Lys Gly Pro Pro Ala Ala Leu Thr Leu Pro Arg Val Gln Cys Arg
1               5                   10                  15

Ala Ser Arg Tyr Pro Ile Ala Val Asp Cys Ser Trp Thr Leu Pro Pro
            20                  25                  30

Ala Pro Asn Ser Thr Ser Pro Val Ser Phe Ile Ala Thr Tyr Arg Leu
        35                  40                  45

Gly Met Ala Ala Arg Gly His Ser Trp Pro Cys Leu Gln Gln Thr Pro
    50                  55                  60
```

Thr Ser Thr Ser Cys Thr Ile Thr Asp Val Gln Leu Phe Ser Met Ala
65 70 75 80

Pro Tyr Val Leu Asn Val Thr Ala Val His Pro Trp Gly Ser Ser Ser
85 90 95

Ser Phe Val Pro Phe Ile Thr Glu His Ile Ile Lys Pro Asp Pro Pro
100 105 110

Glu Gly Val Arg Leu Ser Pro Leu Ala Glu Arg Gln Leu Gln Val Gln
115 120 125

Trp Glu Pro Pro Gly Ser Trp Pro Phe Pro Glu Ile Phe Ser Leu Lys
130 135 140

Tyr Trp Ile Arg Tyr Lys Arg Gln Gly Ala Ala Arg Phe His Arg Val
145 150 155 160

Gly Pro Ile Glu Ala Thr Ser Phe Ile Leu Arg Ala Val Arg Pro Arg
165 170 175

Ala Arg Tyr Tyr Val Gln Val Ala Ala Gln Asp Leu Thr Asp Tyr Gly
180 185 190

Glu Leu Ser Asp Trp Ser Leu Pro Ala Thr Ala Thr Met Ser Leu Gly
195 200 205

Lys

<210> SEQ ID NO 341
<211> LENGTH: 138
<212> TYPE: PRT
<213> ORGANISM: Homo sapiens

<400> SEQUENCE: 341

Gln Asp Pro Tyr Val Lys Glu Ala Glu Asn Leu Lys Lys Tyr Phe Asn
1 5 10 15

Ala Gly His Ser Asp Val Ala Asp Asn Gly Thr Leu Phe Leu Gly Ile
20 25 30

Leu Lys Asn Trp Lys Glu Glu Ser Asp Arg Lys Ile Met Gln Ser Gln
35 40 45

Ile Val Ser Phe Tyr Phe Lys Leu Phe Lys Asn Phe Lys Asp Asp Gln
50 55 60

Ser Ile Gln Lys Ser Val Glu Thr Ile Lys Glu Asp Met Asn Val Lys
65 70 75 80

Phe Phe Asn Ser Asn Lys Lys Lys Arg Asp Asp Phe Glu Lys Leu Thr
85 90 95

Asn Tyr Ser Val Thr Asp Leu Asn Val Gln Arg Lys Ala Ile His Glu
100 105 110

Leu Ile Gln Val Met Ala Glu Leu Ser Pro Ala Ala Lys Thr Gly Lys
115 120 125

Arg Lys Arg Ser Gln Met Leu Phe Arg Gly
130 135

<210> SEQ ID NO 342
<211> LENGTH: 112
<212> TYPE: PRT
<213> ORGANISM: Homo sapiens

<400> SEQUENCE: 342

Ala Leu Asp Thr Asn Tyr Cys Phe Ser Ser Thr Glu Lys Asn Cys Cys
1 5 10 15

Val Arg Gln Leu Tyr Ile Asp Phe Arg Lys Asp Leu Gly Trp Lys Trp
20 25 30

Ile His Glu Pro Lys Gly Tyr His Ala Asn Phe Cys Leu Gly Pro Cys
35 40 45

Pro Tyr Ile Trp Ser Leu Asp Thr Gln Tyr Ser Lys Val Leu Ala Leu
50 55 60

Tyr Asn Gln His Asn Pro Gly Ala Ser Ala Ala Pro Cys Cys Val Pro
65 70 75 80

Gln Ala Leu Glu Pro Leu Pro Ile Val Tyr Tyr Val Gly Arg Lys Pro
85 90 95

Lys Val Glu Gln Leu Ser Asn Met Ile Val Arg Ser Cys Lys Cys Ser
100 105 110

<210> SEQ ID NO 343
<211> LENGTH: 431
<212> TYPE: PRT
<213> ORGANISM: Homo sapiens

<400> SEQUENCE: 343

Met Pro Asn Pro Arg Pro Gly Lys Pro Ser Ala Pro Ser Leu Ala Leu
1 5 10 15

Gly Pro Ser Pro Gly Ala Ser Pro Ser Trp Arg Ala Ala Pro Lys Ala
20 25 30

Ser Asp Leu Leu Gly Ala Arg Gly Pro Gly Gly Thr Phe Gln Gly Arg
35 40 45

Asp Leu Arg Gly Gly Ala His Ala Ser Ser Ser Ser Leu Asn Pro Met
50 55 60

Pro Pro Ser Gln Leu Gln Leu Pro Thr Leu Pro Leu Val Met Val Ala
65 70 75 80

Pro Ser Gly Ala Arg Leu Gly Pro Leu Pro His Leu Gln Ala Leu Leu
85 90 95

Gln Asp Arg Pro His Phe Met His Gln Leu Ser Thr Val Asp Ala His
100 105 110

Ala Arg Thr Pro Val Leu Gln Val His Pro Leu Glu Ser Pro Ala Met
115 120 125

Ile Ser Leu Thr Pro Pro Thr Thr Ala Thr Gly Val Phe Ser Leu Lys
130 135 140

Ala Arg Pro Gly Leu Pro Pro Gly Ile Asn Val Ala Ser Leu Glu Trp
145 150 155 160

Val Ser Arg Glu Pro Ala Leu Leu Cys Thr Phe Pro Asn Pro Ser Ala
165 170 175

Pro Arg Lys Asp Ser Thr Leu Ser Ala Val Pro Gln Ser Ser Tyr Pro
180 185 190

Leu Leu Ala Asn Gly Val Cys Lys Trp Pro Gly Cys Glu Lys Val Phe
195 200 205

Glu Glu Pro Glu Asp Phe Leu Lys His Cys Gln Ala Asp His Leu Leu
210 215 220

Asp Glu Lys Gly Arg Ala Gln Cys Leu Leu Gln Arg Glu Met Val Gln
225 230 235 240

Ser Leu Glu Gln Gln Leu Val Leu Glu Lys Glu Lys Leu Ser Ala Met
245 250 255

Gln Ala His Leu Ala Gly Lys Met Ala Leu Thr Lys Ala Ser Ser Val
260 265 270

Ala Ser Ser Asp Lys Gly Ser Cys Cys Ile Val Ala Ala Gly Ser Gln
275 280 285

Gly Pro Val Val Pro Ala Trp Ser Gly Pro Arg Glu Ala Pro Asp Ser
290 295 300

Leu Phe Ala Val Arg Arg His Leu Trp Gly Ser His Gly Asn Ser Thr
305 310 315 320

Phe Pro Glu Phe Leu His Asn Met Asp Tyr Phe Lys Phe His Asn Met
325 330 335

Arg Pro Pro Phe Thr Tyr Ala Thr Leu Ile Arg Trp Ala Ile Leu Glu
340 345 350

Ala Pro Glu Lys Gln Arg Thr Leu Asn Glu Ile Tyr His Trp Phe Thr
355 360 365

Arg Met Phe Ala Phe Phe Arg Asn His Pro Ala Thr Trp Lys Asn Ala
370 375 380

Ile Arg His Asn Leu Ser Leu His Lys Cys Phe Val Arg Val Glu Ser
385 390 395 400

Glu Lys Gly Ala Val Trp Thr Val Asp Glu Leu Glu Phe Arg Lys Lys
405 410 415

Arg Ser Gln Arg Pro Ser Arg Cys Ser Asn Pro Thr Pro Gly Pro
420 425 430

<210> SEQ ID NO 344
<211> LENGTH: 417
<212> TYPE: PRT
<213> ORGANISM: Homo sapiens

<400> SEQUENCE: 344

Met Pro Asn Pro Arg Pro Gly Lys Pro Ser Ala Pro Ser Leu Ala Leu
1 5 10 15

Gly Pro Ser Pro Gly Ala Ser Pro Ser Trp Arg Ala Ala Pro Lys Ala
20 25 30

Ser Asp Leu Leu Gly Ala Arg Gly Pro Gly Gly Thr Phe Gln Gly Arg
35 40 45

Asp Leu Arg Gly Gly Ala His Ala Ser Ser Ser Ser Leu Asn Pro Met
50 55 60

Pro Pro Ser Gln Leu Gln Leu Pro Thr Leu Pro Leu Val Met Val Ala
65 70 75 80

Pro Ser Gly Ala Arg Leu Gly Pro Leu Pro His Leu Gln Ala Leu Leu
85 90 95

Gln Asp Arg Pro His Phe Met His Gln Leu Ser Thr Val Asp Ala His
100 105 110

Ala Arg Thr Pro Val Leu Gln Val His Pro Leu Glu Ser Pro Ala Met
115 120 125

Ile Ser Leu Thr Pro Pro Thr Thr Ala Thr Gly Val Phe Ser Leu Lys
130 135 140

Ala Arg Pro Gly Leu Pro Pro Gly Ile Asn Val Ala Ser Leu Glu Trp
145 150 155 160

Val Ser Arg Glu Pro Ala Leu Leu Cys Thr Phe Pro Asn Pro Ser Ala
165 170 175

Pro Arg Lys Asp Ser Thr Leu Ser Ala Val Pro Gln Ser Ser Tyr Pro
180 185 190

Leu Leu Ala Asn Gly Val Cys Lys Trp Pro Gly Cys Glu Lys Val Phe
195 200 205

Glu Glu Pro Glu Asp Phe Leu Lys His Cys Gln Ala Asp His Leu Leu
210 215 220

Asp Glu Lys Gly Arg Ala Gln Cys Leu Leu Gln Arg Glu Met Val Gln
225 230 235 240

Ser Leu Glu Gln Gln Leu Val Leu Glu Lys Glu Lys Leu Ser Ala Met

```
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg


<210> SEQ ID NO 345
<211> LENGTH: 366
<212> TYPE: PRT
<213> ORGANISM: Homo sapiens

<400> SEQUENCE: 345

Gly Gly Ala His Ala Ser Ser Ser Ser Leu Asn Pro Met Pro Pro Ser
1               5                   10                  15

Gln Leu Gln Leu Pro Thr Leu Pro Leu Val Met Val Ala Pro Ser Gly
            20                  25                  30

Ala Arg Leu Gly Pro Leu Pro His Leu Gln Ala Leu Leu Gln Asp Arg
        35                  40                  45

Pro His Phe Met His Gln Leu Ser Thr Val Asp Ala His Ala Arg Thr
    50                  55                  60

Pro Val Leu Gln Val His Pro Leu Glu Ser Pro Ala Met Ile Ser Leu
65                  70                  75                  80

Thr Pro Pro Thr Thr Ala Thr Gly Val Phe Ser Leu Lys Ala Arg Pro
                85                  90                  95

Gly Leu Pro Pro Gly Ile Asn Val Ala Ser Leu Glu Trp Val Ser Arg
            100                 105                 110

Glu Pro Ala Leu Leu Cys Thr Phe Pro Asn Pro Ser Ala Pro Arg Lys
        115                 120                 125

Asp Ser Thr Leu Ser Ala Val Pro Gln Ser Ser Tyr Pro Leu Leu Ala
    130                 135                 140

Asn Gly Val Cys Lys Trp Pro Gly Cys Glu Lys Val Phe Glu Glu Pro
145                 150                 155                 160

Glu Asp Phe Leu Lys His Cys Gln Ala Asp His Leu Leu Asp Glu Lys
                165                 170                 175

Gly Arg Ala Gln Cys Leu Leu Gln Arg Glu Met Val Gln Ser Leu Glu
            180                 185                 190

Gln Gln Leu Val Leu Glu Lys Glu Lys Leu Ser Ala Met Gln Ala His
```

```
        195                 200                 205

Leu Ala Gly Lys Met Ala Leu Thr Lys Ala Ser Ser Val Ala Ser Ser
    210                 215                 220

Asp Lys Gly Ser Cys Cys Ile Val Ala Ala Gly Ser Gln Gly Pro Val
225                 230                 235                 240

Val Pro Ala Trp Ser Gly Pro Arg Glu Ala Pro Asp Ser Leu Phe Ala
                245                 250                 255

Val Arg Arg His Leu Trp Gly Ser His Gly Asn Ser Thr Phe Pro Glu
            260                 265                 270

Phe Leu His Asn Met Asp Tyr Phe Lys Phe His Asn Met Arg Pro Pro
        275                 280                 285

Phe Thr Tyr Ala Thr Leu Ile Arg Trp Ala Ile Leu Glu Ala Pro Glu
    290                 295                 300

Lys Gln Arg Thr Leu Asn Glu Ile Tyr His Trp Phe Thr Arg Met Phe
305                 310                 315                 320

Ala Phe Phe Arg Asn His Pro Ala Thr Trp Lys Asn Ala Ile Arg His
                325                 330                 335

Asn Leu Ser Leu His Lys Cys Phe Val Arg Val Glu Ser Glu Lys Gly
            340                 345                 350

Ala Val Trp Thr Val Asp Glu Leu Glu Phe Arg Lys Lys Arg
        355                 360                 365
```

<210> SEQ ID NO 346
<211> LENGTH: 787
<212> TYPE: PRT
<213> ORGANISM: Homo sapiens

<400> SEQUENCE: 346

```
Met Ala Val Trp Ile Gln Ala Gln Gln Leu Gln Gly Glu Ala Leu His
1               5                   10                  15

Gln Met Gln Ala Leu Tyr Gly Gln His Phe Pro Ile Glu Val Arg His
            20                  25                  30

Tyr Leu Ser Gln Trp Ile Glu Ser Gln Ala Trp Asp Ser Val Asp Leu
        35                  40                  45

Asp Asn Pro Gln Glu Asn Ile Lys Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Asn
                85                  90                  95

Thr Tyr Asp Arg Cys Pro Met Glu Leu Val Arg Cys Ile Arg His Ile
            100                 105                 110

Leu Tyr Asn Glu Gln Arg Leu Val Arg Glu Ala Asn Asn Gly Ser Ser
        115                 120                 125

Pro Ala Gly Ser Leu Ala Asp Ala Met Ser Gln Lys His Leu Gln Ile
    130                 135                 140

Asn Gln Thr Phe Glu Glu Leu Arg Leu Val Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Gly Pro Leu Ala Gln Leu
            180                 185                 190

Ser Pro Gln Glu Arg Leu Ser Arg Glu Thr Ala Leu Gln Gln Lys Gln
        195                 200                 205
```

```
Val Ser Leu Glu Ala Trp Leu Gln Arg Glu Ala Gln Thr Leu Gln Gln
    210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255

Arg Arg Gln Gln Leu Ala Gly Asn Gly Gly Pro Pro Glu Gly Ser Leu
            260                 265                 270

Asp Val Leu Gln Ser Trp Cys Glu Lys Leu Ala Glu Ile Ile Trp Gln
        275                 280                 285

Asn Arg Gln Gln Ile Arg Arg Ala Glu His Leu Cys Gln Gln Leu Pro
    290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
        355                 360                 365

Val Lys Ala Thr Ile Ile Ser Glu Gln Gln Ala Lys Ser Leu Leu Lys
    370                 375                 380

Asn Glu Asn Thr Arg Asn Asp Tyr Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ser Asp Arg Arg Gly Ala
            420                 425                 430

Glu Ser Val Thr Glu Glu Lys Phe Thr Ile Leu Phe Glu Ser Gln Phe
        435                 440                 445

Ser Val Gly Gly Asn Glu Leu Val Phe Gln Val Lys Thr Leu Ser Leu
    450                 455                 460

Pro Val Val Val Ile Val His Gly Ser Gln Asp Asn Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
        515                 520                 525

Asn Leu Val Phe Leu Ala Gln Lys Leu Phe Asn Asn Ser Ser Ser His
    530                 535                 540

Leu Glu Asp Tyr Ser Gly Leu Ser Val Ser Trp Ser Gln Phe Asn Arg
545                 550                 555                 560

Glu Asn Leu Pro Gly Arg Asn Tyr Thr Phe Trp Gln Trp Phe Asp Gly
                565                 570                 575

Val Met Glu Val Leu Lys Lys His Leu Lys Pro His Trp Asn Asp Gly
            580                 585                 590

Ala Ile Leu Gly Phe Val Asn Lys Gln Gln Ala His Asp Leu Leu Ile
        595                 600                 605

Asn Lys Pro Asp Gly Thr Phe Leu Leu Arg Phe Ser Asp Ser Glu Ile
    610                 615                 620

Gly Gly Ile Thr Ile Ala Trp Lys Phe Asp Ser Gln Glu Arg Met Phe
```

-continued

```
625                 630                 635                 640

Trp Asn Leu Met Pro Phe Thr Thr Arg Asp Phe Ser Ile Arg Ser Leu
                645                 650                 655

Ala Asp Arg Leu Gly Asp Leu Asn Tyr Leu Ile Tyr Val Phe Pro Asp
            660                 665                 670

Arg Pro Lys Asp Glu Val Tyr Ser Lys Tyr Tyr Thr Pro Val Pro Cys
        675                 680                 685

Glu Ser Ala Thr Ala Lys Ala Val Asp Gly Tyr Val Lys Pro Gln Ile
    690                 695                 700

Lys Gln Val Val Pro Glu Phe Val Asn Ala Ser Ala Asp Ala Gly Gly
705                 710                 715                 720

Gly Ser Ala Thr Tyr Met Asp Gln Ala Pro Ser Pro Ala Val Cys Pro
                725                 730                 735

Gln Ala His Tyr Asn Met Tyr Pro Gln Asn Pro Asp Ser Val Leu Asp
            740                 745                 750

Thr Asp Gly Asp Phe Asp Leu Glu Asp Thr Met Asp Val Ala Arg Arg
        755                 760                 765

Val Glu Glu Leu Leu Gly Arg Pro Met Asp Ser Gln Trp Ile Pro His
    770                 775                 780

Ala Gln Ser
785


<210> SEQ ID NO 347
<211> LENGTH: 526
<212> TYPE: PRT
<213> ORGANISM: Homo sapiens

<400> SEQUENCE: 347

Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Lys Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Lys Leu
            100                 105                 110

Lys Cys Asp Val Cys Gly Met Val Cys Ile Gly Pro Asn Val Leu Met
        115                 120                 125

Val His Lys Arg Ser His Thr Gly Glu Arg Pro Phe His Cys Asn Gln
    130                 135                 140

Cys Gly Ala Ser Phe Thr Gln Lys Gly Asn Leu Leu Arg His Ile Lys
145                 150                 155                 160

Leu His Ser Gly Glu Lys Pro Phe Lys Cys Pro Phe Cys Ser Tyr Ala
                165                 170                 175

Cys Arg Arg Arg Asp Ala Leu Thr Gly His Leu Arg Thr His Ser Val
            180                 185                 190

Gly Lys Pro His Lys Cys Asn Tyr Cys Gly Arg Ser Tyr Lys Gln Arg
        195                 200                 205
```

```
Ser Ser Leu Glu Glu His Lys Glu Arg Cys His Asn Tyr Leu Gln Asn
    210                 215                 220

Val Ser Met Glu Ala Ala Gly Gln Val Met Ser His His Val Pro Pro
225                 230                 235                 240

Met Glu Asp Cys Lys Glu Gln Glu Pro Ile Met Asp Asn Asn Ile Ser
                245                 250                 255

Leu Val Pro Phe Glu Arg Pro Ala Val Ile Glu Lys Leu Thr Gly Asn
            260                 265                 270

Met Gly Lys Arg Lys Ser Ser Thr Pro Gln Lys Phe Val Gly Glu Lys
        275                 280                 285

Leu Met Arg Phe Ser Tyr Pro Asp Ile His Phe Asp Met Asn Leu Thr
    290                 295                 300

Tyr Glu Lys Glu Ala Glu Leu Met Gln Ser His Met Met Asp Gln Ala
305                 310                 315                 320

Ile Asn Asn Ala Ile Thr Tyr Leu Gly Ala Glu Ala Leu His Pro Leu
                325                 330                 335

Met Gln His Pro Pro Ser Thr Ile Ala Glu Val Ala Pro Val Ile Ser
            340                 345                 350

Ser Ala Tyr Ser Gln Val Tyr His Pro Asn Arg Ile Glu Arg Pro Ile
        355                 360                 365

Ser Arg Glu Thr Ala Asp Ser His Glu Asn Asn Met Asp Gly Pro Ile
    370                 375                 380

Ser Leu Ile Arg Pro Lys Ser Arg Pro Gln Glu Arg Glu Ala Ser Pro
385                 390                 395                 400

Ser Asn Ser Cys Leu Asp Ser Thr Asp Ser Glu Ser Ser His Asp Asp
                405                 410                 415

His Gln Ser Tyr Gln Gly His Pro Ala Leu Asn Pro Lys Arg Lys Gln
            420                 425                 430

Ser Pro Ala Tyr Met Lys Glu Asp Val Lys Ala Leu Asp Thr Thr Lys
        435                 440                 445

Ala Pro Lys Gly Ser Leu Lys Asp Ile Tyr Lys Val Phe Asn Gly Glu
    450                 455                 460

Gly Glu Gln Ile Arg Ala Phe Lys Cys Glu His Cys Arg Val Leu Phe
465                 470                 475                 480

Leu Asp His Val Met Tyr Thr Ile His Met Gly Cys His Gly Tyr Arg
                485                 490                 495

Asp Pro Leu Glu Cys Asn Ile Cys Gly Tyr Arg Ser Gln Asp Arg Tyr
            500                 505                 510

Glu Phe Ser Ser His Ile Val Arg Gly Glu His Thr Phe His
        515                 520                 525
```

<210> SEQ ID NO 348
<211> LENGTH: 625
<212> TYPE: DNA
<213> ORGANISM: Unknown
<220> FEATURE:
<223> OTHER INFORMATION: Description of Unknown: AP1.0 sequence

<400> SEQUENCE: 348

```
attctcgggc tacggccctg gagccactcc ggctcctaaa gatttagaag tttgagcaca      60

cccgcccact agggcccccc atccaggggg gcaacgggca agcacttctg tttccccggt     120

atgatctgat aggctgtaac cacggctgaa acagagatta tcgttatccg cttcactact     180

tcgagaagcc tagtaatgat gggtgaaatt gaatccgttg atccggtgtc tcccccacac     240

cagaaactca tgatgagggt tgccatcccg gctacggcga cgtagcgggc atccctgcgc     300
```

tggcatgagg cctcttagga ggacggatga tatggatctt gtcgtgaaga gcctattgag 360
ctagtgtcga ctcctccgcc cccgtgaatg cggctaatcc taaccccgga gcaggtgggt 420
ccaatccagg gcctggcctg tcgtaatgcg taagtctggg acggaaccga ctactttcgg 480
gaaggcgtgt ttccatttgt tcattatttg tgtgtttatg gtgacaactc tgggtaaacg 540
ttctattgcg tttattgaga gattcccaac aattgaacaa acgagaacta cctgttttat 600
taaatttaca cagagaagaa ttaca 625

<210> SEQ ID NO 349
<211> LENGTH: 549
<212> TYPE: DNA
<213> ORGANISM: Unknown
<220> FEATURE:
<223> OTHER INFORMATION: Description of Unknown: CK1.0 sequence

<400> SEQUENCE: 349
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta ctgctgacaa ctcactgact atccacttgc 540
tctgtcacg 549

<210> SEQ ID NO 350
<211> LENGTH: 630
<212> TYPE: DNA
<213> ORGANISM: Unknown
<220> FEATURE:
<223> OTHER INFORMATION: Description of Unknown: PV1.0 sequence

<400> SEQUENCE: 350
aacaaaaggc tacaccactt gggctacggc ccgcgccacc ttgtggcgca aagacattag 60
aagaatagca taccgcccac tagggccctg cagccagcag ggtaacgggc aagcacttct 120
gtctccccgg tagaacggta taggctgtac ccacggccga aaactgaact atcgttaccc 180
gactccgtac ttcgcaaagc ttagtaggaa actggaaagt tcgagttatt gacccggagt 240
gttcccccca ctccagaaac gcgtgatgag ggttgccacc ccgaccatgg cgacatggtg 300
ggcatccctg cgctggcacg cggcctctaa gaggataact cgctcctact ggtaaccgaa 360
gagccccgtg agctacggtt tattcctccg cctccctgaa tgcggctaat cctaacccat 420
gagcagttgc catagatcca tatggtggac tgtcgtaacg cgtaagttgt gggcggaacc 480
gactactttg ggatggcgtg tttccttgtt ttctccattt gttgttgtat ggtgacaagt 540
tatagatctc gatctatagc gtttcttgag agatttccaa acatttattc aagtcgtaca 600
attcttgtgt ttaagcagta cagtgtaacc 630

<210> SEQ ID NO 351
<211> LENGTH: 653
<212> TYPE: DNA

<213> ORGANISM: Unknown
<220> FEATURE:
<223> OTHER INFORMATION: Description of Unknown: SV1.0 sequence

<400> SEQUENCE: 351
tctgtcctca ccccatcttc ccttctttcc tgcaccgtta cgcttactcg catgtgcatt 60
gagtggtgca cgtgcttgaa caaacagcta cactcacatg gggcgggtt ttcccgccct 120 gcggcctctc gcgaggccca cccctcccct tcctcccata actacagtgc tttggtaggt 180
aagcatcctg atcccccgcg gaagctgctc acgtggcaac tgtggggacc cagacaggtt 240
atcaaaggca cccggtcttt ccgccttcag gagtatccct gctagtgaat tctagtaggg 300
ctctgcttgg tgccaacctc ccccaaatgc gcgctgcggg agtgctcttc cccaactcac 360
cctagtatcc tctcatgtgt gtgcttggtc agcatatctg agacgatgtt ccgctgtccc 420
agaccagtcc agtaatggac gggccagtgt gcgtagtcgt cttccggctt gtccggcgca 480
tgtttggtga accggtgggg taaggttggt gtgcccaacg cccgtacttt ggtgatacct 540
caagaccacc caggaatgcc agggaggtac cccgcttcac agcgggatct gaccctgggc 600
taattgtcta cggtggttct tcttgcttcc acttctttct actgttcgcc acc 653

<210> SEQ ID NO 352
<211> LENGTH: 635
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 352
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta ctgctgacaa ctcactgact atccacttgc 540
tctcttgtgc ctttctgctc tggttcaagt tccttgattg tttttgactg cttttcactg 600
cttttcttct cacaatcctt gctcagttca aagtc 635

<210> SEQ ID NO 353
<211> LENGTH: 513
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 353
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240

```
tcgtcctggc aagactatga cgtcgcatgt tccgctgcgg atgccgaccg ggtaaccggt    300

tccccagtgt gtgtagtgcg atcttccagg tcctcctggt tggcgttgtc cagaaactgc    360

ttcaggtaag tggggtgtgc ccaatcccta caaaggttga ttctttcacc accttaggaa    420

tgctccggag gtaccccagc aacagctggg atctgaccgg aggctaattg tctacgggtg    480

gtgtttcctt tttcttttca cacaactaaa gtc                                 513
```

<210> SEQ ID NO 354
<211> LENGTH: 549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 354

```
gtggccacgc ccgggccacc gatacttccc ttcactcctt cgggactgtt ggggaggaac     60

acaacagggc tcccctgttt tcccattcct tccccctttt cccaacccca accgccgtat    120

ctggtggcgg caagacacac gggtctttcc ctctaaagca caattgtgtg tgtgtcccag    180

gtcctcctgc gtacggtgcg ggagtgctcc cacccaactg ttgtaagcct gtccaacgcg    240

tcgtcctggc aagactatga cgtcgcatgt tccgctgcgg atgccgaccg ggtaaccggt    300

tccccagtgt gtgtagtgcg atcttccagg tcctcctggt tggcgttgtc cagaaactgc    360

ttcaggtaag tggggtgtgc ccaatcccta caaaggttga ttctttcacc accttaggaa    420

tgctccggag gtaccccagc aacagctggg atctgaccgg aggctaattg tctacgggtg    480

gtgtttcctt tttcttttca cacaactcta ctgctgacaa ctcactgact atccacttgc    540

tctaaagtc                                                            549
```

<210> SEQ ID NO 355
<211> LENGTH: 513
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 355

```
gtggccacgc ccgggccacc gatacttccc ttcactcctt cgggactgtt ggggaggaac     60

acaacagggc tcccctgttt tcccattcct tccccctttt cccaacccca accgccgtat    120

ctggtggcgg caagacacac gggtctttcc ctctaaagca caattgtgtg tgtgtcccag    180

gtcctcctgc gtacggtgcg ggagtgctcc cacccaactg ttgtaagcct gtccaacgcg    240

tcgtcctggc aagactatga cgtcgcatgt tccgctgcgg atgccgaccg ggtaaccggt    300

tccccagtgt gtgtagtgcg atcttccagg tcctcctggt tggcgttgtc cagaaactgc    360

ttcaggtaag tggggtgtgc ccaatcccta caaaggttga ttctttcacc accttaggaa    420

tgctccggag gtaccccagc aacagctggg atctgaccgg aggctaattg tctacgggtg    480

gtgtttcctt tttcttttca cacaactgcc acc                                 513
```

<210> SEQ ID NO 356
<211> LENGTH: 549
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 356
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactttc actgcttttc ttctcacaat ccttgctcag 540
ttcaaagtc 549

<210> SEQ ID NO 357
<211> LENGTH: 678
<212> TYPE: DNA
<213> ORGANISM: Parabovirus sp.

<400> SEQUENCE: 357
tgaaccgtta cgcaccactc agttggtgtt tggtggcacc aatgatggaa caaaaggcta 60
caccacttgg gctacggccc gcgccacctt gtggcgcaaa gacattagaa gaatagcata 120
ccgcccacta gggccctgca gccagcaggg taacgggcaa gcacttctgt ctccccggta 180
gaacggtata ggctgtaccc acggccgaaa actgaactat cgttacccga ctccgtactt 240
cgcaaagctt agtaggaaac tggaaagttc gagttattga cccggagtgt tccccccact 300
ccagaaacgc gtgatgaggg ttgccacccc gaccatggcg acatggtggg catccctgcg 360
ctggcacgcg gcctctaaga ggataactcg ctcctactgg taaccgaaga gccccgtgag 420
ctacggttta ttcctccgcc tccctgaatg cggctaatcc taacccatga gcagttgcca 480
tagatccata tggtggactg tcgtaacgcg taagttgtgg gcggaaccga ctactttggg 540
atggcgtgtt tccttgtttt ctccatttgt tgttgtatgg tgacaagtta tagatctcga 600
tctatagcgt ttcttgagag atttccaaac atttattcaa gtcgtacaat tcttgtgttt 660
aagcagtaca gtgtaagg 678

<210> SEQ ID NO 358
<211> LENGTH: 630
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 358
aacaaaaggc tacaccactt gggctacggc ccgcgccacc ttgtggcgca aagacattag 60
aagaatagca taccgcccac tagggccctg cagccagcag ggtaacgggc aagcacttct 120
gtctccccgg tagaacggta taggctgtac ccacggccga aaactgaact atcgttaccc 180
gactccgtac ttcgcaaagc ttagtaggaa actggaaagt tcgagttatt gacccggagt 240
gttcccccca ctccagaaac gcgtgatgag ggttgccacc ccgaccatgg cgacatggtg 300
ggcatccctg cgctggcacg cggcctctaa gaggataact cgctcctact ggtaaccgaa 360
gagccccgtg agctacggtt tattcctccg cctccctgaa tgcggctaat cctaacccat 420
gagcagttgc catagatcca tatggtggac tgtcgtaacg cgtaagttgt gggcggaacc 480
gactactttg ggatggcgtg tttccttgtt ttctccattt gttgttgtat ggtgacaagt 540
tatagatctc gatctatagc gtttcttgag agatttccaa acatttattc aagtcgtaca 600
attcttgtgt ttaagcagta cagtgtaagg 630

<210> SEQ ID NO 359
<211> LENGTH: 611
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 359
tgggctacgg cccgcgccac cttgtggcgc aaagacatta gaagaatagc ataccgccca 60
ctagggccct gcagccagca gggtaacggg caagcacttc tgtctccccg gtagaacggt 120
ataggctgta cccacggccg aaaactgaac tatcgttacc cgactccgta cttcgcaaag 180
cttagtagga aactggaaag ttcgagttat tgacccggag tgttcccccc actccagaaa 240
cgcgtgatga gggttgccac cccgaccatg gcgacatggt gggcatccct gcgctggcac 300
gcggcctcta agaggataac tcgctcctac tggtaaccga agagccccgt gagctacggt 360
ttattcctcc gcctccctga atgcggctaa tcctaaccca tgagcagttg ccatagatcc 420
atatggtgga ctgtcgtaac gcgtaagttg tgggcggaac cgactacttt gggatggcgt 480
gtttccttgt tttctccatt tgttgttgta tggtgacaag ttatagatct cgatctatag 540
cgtttcttga gagatttcca aacatttatt caagtcgtac aattcttgtg tttaagcagt 600
acagtgtaag g 611

<210> SEQ ID NO 360
<211> LENGTH: 618
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 360
tgaaccgtta cgcaccactc agttggtgtt tggtggcacc aatgatggaa caaaaggcta 60
caccacttgg gctacggccc gcgccacctt gtggcgcaaa gacattagaa gaatagcata 120
ccgcccacta gggccctgca gccagcaggg taacgggcaa gcacttctgt ctccccggta 180
gaacggtata ggctgtaccc acggccgaaa actgaactat cgttacccga ctccgtactt 240
cgcaaagctt agtaggaaac tggaaagttc gagttattga cccggagtgt tcccccca ct 300 ccagaaacgc gtgatgaggg ttgccacccc gaccatggcg acatggtggg catccctgcg 360
ctggcacgcg gcctctaaga ggataactcg ctcctactgg taaccgaaga gccccgtgag 420
ctacggttta ttcctccgcc tccctgaatg cggctaatcc taacccatga gcagttgcca 480
tagatccata tggtggactg tcgtaacgcg taagttgtgg gcggaaccga ctactttggg 540
atggcgtgtt tccttgtttt ctccatttgt tgttgtatgg tgacaagtta tagatctcga 600
tctatagcgt ttgtaagg 618

<210> SEQ ID NO 361
<211> LENGTH: 826
<212> TYPE: DNA

<213> ORGANISM: Unknown
<220> FEATURE:
<223> OTHER INFORMATION: Description of Unknown: Apodemus Picornavirus
sequence

<400> SEQUENCE: 361
tttgaaaggg gtgcggatat catggcgttt ctcgccatga tatccgcaca ttgcaaaccc 60
atattgcata cccactgggt atgcattatg gggaggcccc tttcacccct ccccccccaa 120 ttacctttc cccctctagt aaccatacgc tttactcagc gtaactactc cgggttacgt 180
gatgaagaag aggctacgga gattctcggg ctacggccct ggagccactc cggctcctaa 240
agatttagaa gtttgagcac acccgcccac tagggccccc catccagggg ggcaacgggc 300
aagcacttct gtttccccgg tatgatctga taggctgtaa ccacggctga aacagagatt 360
atcgttatcc gcttcactac ttcgagaagc ctagtaatga tgggtgaaat tgaatccgtt 420
gatccggtgt ctcccccaca ccagaaactc atgatgaggg ttgccatccc ggctacggcg 480
acgtagcggg catccctgcg ctggcatgag gcctcttagg aggacggatg atatggatct 540
tgtcgtgaag agcctattga gctagtgtcg actcctccgc ccccgtgaat gcggctaatc 600
ctaaccccgg agcaggtggg tccaatccag ggcctggcct gtcgtaatgc gtaagtctgg 660
gacggaaccg actactttcg ggaaggcgtg tttccatttg ttcattattt gtgtgtttat 720
ggtgacaact ctgggtaaac gttctattgc gtttattgag agattcccaa caattgaaca 780
aacgagaact acctgtttta ttaaatttac acagagaaga attaca 826

<210> SEQ ID NO 362
<211> LENGTH: 721
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 362
cccctccccc cccaattacc ttttcccccct ctagtaacca tacgctttac tcagcgtaac 60
tactccgggt tacgtgatga agaagaggct acggagattc tcgggctacg gccctggagc 120
cactccggct cctaaagatt tagaagtttg agcacacccg cccactaggg ccccccatcc 180
aggggggcaa cgggcaagca cttctgtttc cccggtatga tctgataggc tgtaaccacg 240
gctgaaacag agattatcgt tatccgcttc actacttcga gaagcctagt aatgatgggt 300
gaaattgaat ccgttgatcc ggtgtctccc ccacaccaga aactcatgat gagggttgcc 360
atcccggcta cggcgacgta gcgggcatcc ctgcgctggc atgaggcctc ttaggaggac 420
ggatgatatg gatcttgtcg tgaagagcct attgagctag tgtcgactcc tccgcccccg 480
tgaatgcggc taatcctaac cccggagcag gtgggtccaa tccagggcct ggcctgtcgt 540
aatgcgtaag tctgggacgg aaccgactac tttcgggaag gcgtgtttcc atttgttcat 600
tatttgtgtg tttatggtga caactctggg taaacgttct attgcgttta ttgagagatt 660
cccaacaatt gaacaaacga gaactacctg ttttattaaa tttacacaga gaagaattac 720
a 721

<210> SEQ ID NO 363
<211> LENGTH: 625
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 363
attctcgggc tacggccctg gagccactcc ggctcctaaa gatttagaag tttgagcaca 60
cccgcccact agggcccccc atccaggggg gcaacgggca agcacttctg tttccccggt 120
atgatctgat aggctgtaac cacggctgaa acagagatta tcgttatccg cttcactact 180
tcgagaagcc tagtaatgat gggtgaaatt gaatccgttg atccggtgtc tcccccacac 240
cagaaactca tgatgagggt tgccatcccg gctacggcga cgtagcgggc atccctgcgc 300
tggcatgagg cctcttagga ggacggatga tatggatctt gtcgtgaaga gcctattgag 360
ctagtgtcga ctcctccgcc cccgtgaatg cggctaatcc taaccccgga gcaggtgggt 420
ccaatccagg gcctggcctg tcgtaatgcg taagtctggg acggaaccga ctactttcgg 480
gaaggcgtgt ttccatttgt tcattatttg tgtgtttatg gtgacaactc tgggtaaacg 540
ttctattgcg tttattgaga gattcccaac aattgaacaa acgagaacta cctgttttat 600
taaatttaca cagagaagaa ttaca 625

<210> SEQ ID NO 364
<211> LENGTH: 766
<212> TYPE: DNA
<213> ORGANISM: Kobuvirus sp.

<400> SEQUENCE: 364
tttcacaccc tcttttccgg tggtccggac ccagaccacc gttactccat tcagctactt 60
cggtacctgt tcggaggaat taaacgggca ccctacccaa gggttacatg ggaccatatt 120
cctcctcccc tgtaacttta agttttgtgc ccgtattctt gactccaggc ggatgttgtg 180
tcgcccgtcc tgtgaacaaa cagctagaca ctttcctccc ctccctctgg gctgctccgg 240
cagtccactc cctcccccca gcgtaacatg ccccgctgga gtgatgcacc tggaagtcgt 300
ggacgtgggt tagtaacttc ggtgaaaacc cactataatg acaactggtt gacccccaca 360
ctcaaaggac tcgagtcttt ctcccttaag gctagcccgg ccacatgaat ttgcagctgg 420
caactagtga gtccaccatg tcccgcaacc tcggctgcgg agtgctgttc cccaagcgta 480
tgccttcctt ctgtaagagt gcgcctggca agcacatctg agaagtcgtt ccgctgcgtc 540
gtgccaacct ggcgacaggt gacccagtgt gcgtagactt cttccggatt cgtccggctc 600
ttctctagga aacatgcgtg taaggttcat gtgccaaagc cctgcgcgcg gtgttcttct 660
actgccctag gaatgtgccg caggtacccc tacttcggta gggatctgag cggtagctaa 720
ttgtctacgg gtagtttcat ttccatcttc tcttcaggtc gacatc 766

<210> SEQ ID NO 365
<211> LENGTH: 608
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 365
ttgactccag gcggatgttg tgtcgcccgt cctgtgaaca aacagctaga cactttcctc 60
ccctccctct gggctgctcc ggcagtccac tccctccccc cagcgtaaca tgccccgctg 120
gagtgatgca cctggaagtc gtggacgtgg gttagtaact tcggtgaaaa cccactataa 180
tgacaactgg ttgaccccca cactcaaagg actcgagtct ttctccctta aggctagccc 240

```
ggccacatga atttgcagct ggcaactagt gagtccacca tgtcccgcaa cctcggctgc    300

ggagtgctgt tccccaagcg tatgccttcc ttctgtaaga gtgcgcctgg caagcacatc    360

tgagaagtcg ttccgctgcg tcgtgccaac ctggcgacag gtgacccagt gtgcgtagac    420

ttcttccgga ttcgtccggc tcttctctag gaaacatgcg tgtaaggttc atgtgccaaa    480

gccctgcgcg cggtgttctt ctactgccct aggaatgtgc cgcaggtacc cctacttcgg    540

tagggatctg agcggtagct aattgtctac gggtagtttc atttccatct tctcttcagg    600

tcgacatc                                                              608


<210> SEQ ID NO 366
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 366

gaattaaacg ggcaccctac ccaagggtta catgggacca tattcctcct cccctgtaac     60

tttaagtttt gtgcccgtat tcttgactcc aggcggatgt tgtgtcgccc gtcctgtgaa    120

caaacagcta gacactttcc tcccctccct ctgggctgct ccggcagtcc actccctccc    180

cccagcgtaa catgccccgc tggagtgatg cacctggaag tcgtggacgt gggttagtaa    240

cttcggtgaa aacccactat aatgacaact ggttgacccc cacactcaaa ggactcgagt    300

ctttctccct taaggctagc ccggccacat gaatttgcag ctggcaacta gtgagtccac    360

catgtcccgc aacctcggct gcggagtgct gttccccaag cgtatgcctt ccttctgtaa    420

gagtgcgcct ggcaagcaca tctgagaagt cgttccgctg cgtcgtgcca acctggcgac    480

aggtgaccca gtgtgcgtag acttcttccg gattcgtccg gctcttctct aggaaacatg    540

cgtgtaaggt tcatgtgcca aagccctgcg cgcggtgttc ttctactgcc ctaggaatgt    600

gccgcaggta cccctacttc ggtagggatc tgagcggtag ctaattgtct acgggtagtt    660

tcatttccat cttctcttca ggtcgacatc                                      690


<210> SEQ ID NO 367
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 367

tttcacaccc tcttttccgg tggtccggac ccagaccacc gttactccat tcagctactt     60

cggtacctgt tcggaggaat taaacgggca ccctacccaa gggttacatg ggaccatatt    120

cctcctcccc tgtaacttta agttttgtgc ccgtattctt gactccaggc ggatgttgtg    180

tcgcccgtcc tgtgaacaaa cagctagaca ctttcctccc ctccctctgg gctgctccgg    240

cagtccactc cctcccccca gcgtaacatg ccccgctgga gtgatgcacc tggaagtcgt    300

ggacgtgggt tagtaacttc ggtgaaaacc cactataatg acaactggtt gacccccaca    360

ctcaaaggac tcgagtcttt ctcccttaag gctagcccgg ccacatgaat ttgcagctgg    420

caactagtga gtccaccatg tcccgcaacc tcggctgcgg agtgctgttc cccaagcgta    480

tgccttcctt ctgtaagagt gcgcctggca agcacatctg agaagtcgtt ccgctgcgtc    540

gtgccaacct ggcgacaggt gacccagtgt gcgtagactt cttccggatt cgtccggctc    600
```

ttctctagga aacatgcgtg taaggttcat gtgccaaagc cctgcgcgcg gtgttcttct 660
actgccctag gaatgtgccg caggtacccc tacttcggta gggatctgag cggtagctaa 720
ttggacatc 729

<210> SEQ ID NO 368
<211> LENGTH: 650
<212> TYPE: DNA
<213> ORGANISM: Salivirus sp.

<400> SEQUENCE: 368
tctgtcctca ccccatcttc ccttctttcc tgcaccgtta cgcttactcg catgtgcatt 60
gagtggtgca cgtgcttgaa caaacagcta cactcacatg gggcgggtt ttcccgccct 120 gcggcctctc gcgaggccca cccctcccct tcctcccata actacagtgc tttggtaggt 180
aagcatcctg atcccccgcg gaagctgctc acgtggcaac tgtggggacc cagacaggtt 240
atcaaaggca cccggtcttt ccgccttcag gagtatccct gctagtgaat tctagtaggg 300
ctctgcttgg tgccaacctc ccccaaatgc gcgctgcggg agtgctcttc cccaactcac 360
cctagtatcc tctcatgtgt gtgcttggtc agcatatctg agacgatgtt ccgctgtccc 420
agaccagtcc agtaatggac gggccagtgt gcgtagtcgt cttccggctt gtccggcgca 480
tgtttggtga accggtgggg taaggttggt gtgcccaacg cccgtacttt ggtgatacct 540
caagaccacc caggaatgcc agggaggtac cccgcttcac agcgggatct gaccctgggc 600
taattgtcta cggtggttct tcttgcttcc acttctttct actgttcatg 650

<210> SEQ ID NO 369
<211> LENGTH: 508
<212> TYPE: DNA
<213> ORGANISM: Crohivirus B

<400> SEQUENCE: 369
gtataagaga caggtgtttg ccttgtcttc ggactggcat cttgggacca accccccttt 60
tccccagcca tgggttaaat ggcaataaag gacgtaacaa ctttgtaacc attaagcttt 120
gtaattttgt aaccactaag ctttgtgcac ataatgtaac catcaagctt gttagtccca 180
gcaggaggtt tgcatgcttg tagccgaaat ggggctcgac cccccatagt aggatacttg 240
attttgcatt ccattgtgga cctgcaaact ctacacatag aggctttgtc ttgcatctaa 300
acacctgagt acagtgtgta cctagaccct atagtacggg aggaccgttt gtttcctcaa 360
taaccctaca taataggcta ggtgggcatg cccaatttgc aagatcccag actgggggtc 420
ggtctgggca gggttagatc cctgttagct actgcctgat agggtggtgc tcaaccatgt 480
gtagtttaaa ttgagctgtt catatacc 508

<210> SEQ ID NO 370
<211> LENGTH: 457
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 370 ccccccttt ccccagccat gggttaaatg gcaataaagg acgtaacaac tttgtaacca 60
ttaagctttg taattttgta accactaagc tttgtgcaca taatgtaacc atcaagcttg 120
ttagtcccag caggaggttt gcatgcttgt agccgaaatg gggctcgacc ccccatagta 180

```
ggatacttga ttttgcattc cattgtggac ctgcaaactc tacacataga ggctttgtct    240

tgcatctaaa cacctgagta cagtgtgtac ctagacccta tagtacggga ggaccgtttg    300

tttcctcaat aaccctacat aataggctag gtgggcatgc ccaatttgca agatcccaga    360

ctgggggtcg gtctgggcag ggttagatcc ctgttagcta ctgcctgata gggtggtgct    420

caaccatgtg tagtttaaat tgagctgttc atatacc                             457
```

<210> SEQ ID NO 371
<211> LENGTH: 742
<212> TYPE: DNA
<213> ORGANISM: Unknown
<220> FEATURE:
<223> OTHER INFORMATION: Description of Unknown: CVB3 sequence

<400> SEQUENCE: 371

```
ttaaaacagc ctgtgggttg atcccaccca cagggcccat tgggcgctag cactctggta     60

tcacggtacc tttgtgcgcc tgttttatac cccctccccc aactgtaact tagaagtaac    120

acacaccgat caacagtcag cgtggcacac cagccacgtt ttgatcaagc acttctgtta    180

ccccggactg agtatcaata gactgctcac gcggttgaag gagaaagcgt tcgttatccg    240

gccaactact tcgaaaaacc tagtaacacc gtggaagttg cagagtgttt cgctcagcac    300

taccccagtg tagatcaggt cgatgagtca ccgcattccc cacgggcgac cgtggcggtg    360

gctgcgttgg cggcctgccc atggggaaac ccatgggacg ctctaataca gacatggtgc    420

gaagagtcta ttgagctagt tggtagtcct ccggcccctg aatgcggcta atcctaactg    480

cggagcacac accctcaagc cagagggcag tgtgtcgtaa cgggcaactc tgcagcggaa    540

ccgactactt tgggtgtccg tgtttcattt tattcctata ctggctgctt atggtgacaa    600

ttgagagatt gttaccatat agctattgga ttggccatcc ggtgaccaat agagctatta    660

tatatctctt tgttgggttt ataccactta gcttgaaaga ggttaaaaca ttacaattca    720

ttgttaagtt gaatacagca aa                                             742
```

<210> SEQ ID NO 372
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 372

```
ttaaaacagc ctgtgggttg atcccaccca cagggcccat tgggcgctag cactctggta     60

tcacggtacc tttgtgcgcc tgttttatac cccctccccc aactgtaact tagaagtaac    120

acacaccgat caacagtcag cgtggcacac cagccacgtt ttgatcaagc acttctgtta    180

ccccggactg agtatcaata gactgctcac gcggttgaag gagaaagcgt tcgttatccg    240

gccaactact tcgaaaaacc tagtaacacc gtggaagttg cagagtgttt cgctcagcac    300

taccccagtg tagatcaggt cgatgagtca ccgcattccc cacgggcgac cgtggcggtg    360

gctgcgttgg cggcctgccc atggggaaac ccatgggacg ctctaataca gacatggtgc    420

gaagagtcta ttgagctagt tggtagtcct ccggcccctg aatgcggcta atcctaactg    480

cggagcacac accctcaagc cagagggcag tgtgtcgtaa cgggcaactc tgcagcggaa    540

ccgactactt tgggtgtccg tgtttcattt tattcctata ctggctgctt atggtgacaa    600

ttgagagatt gttaccatat agctattgga ttggccatcc ggtgaagcaa a             651
```

<210> SEQ ID NO 373
<211> LENGTH: 721
<212> TYPE: DNA
<213> ORGANISM: Unknown
<220> FEATURE:
<223> OTHER INFORMATION: Description of Unknown: SAFV sequence

<400> SEQUENCE: 373
cacttattta attcggcctt ttgtgacaag cccctcggtg aaagaacctc tctcttttcg 60
acgtggttgg aattgccatc atttccgacg aaagtgctat catgcctccc cgattatgtg 120
atgttttctg ccctgctggg cggagcattc tcgggttgag aaaccttgaa tctttttctt 180
tggaaccttg gttcccccgg tctaagccgc ttggaatatg acagggttat tttcttgatc 240
ttatttctac ttttgcgggt tctatccgta aaaagggtac gtgctgcccc ttccttctct 300
ggagaattca cacggcggtc tttccgtctc tcaacaagtg tgaatgcagc atgccggaaa 360
cggtgaagaa aacagttttc tgtggaaatt tagagtgcac atcgaaacag ctgtagcgac 420
ctcacagtag cagcggactc ccctcttggc gacaagagcc tctgcggcca aaagccccgt 480
ggataagatc cactgctgtg agcggtgcaa ccccagcacc ctggttcgat gatcattctc 540
tatggaacca gaaaatggtt ttctcaagcc ctccggtaga gaagccaaga atgtcctgaa 600
ggtaccccgc gtgcgggatc tgatcaggag accaattggc ggtgctttac actgtcactt 660
tggtttaaaa attgtcacag cttctccaaa ccaagtggtc ttggttttcc aattttgttg 720
a 721

<210> SEQ ID NO 374
<211> LENGTH: 675
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 374
cctctctctt ttcgacgtgg ttggaattgc catcatttcc gacgaaagtg ctatcatgcc 60
tccccgatta tgtgatgttt tctgccctgc tgggcggagc attctcgggt tgagaaacct 120
tgaatctttt tctttggaac cttggttccc ccggtctaag ccgcttggaa tatgacaggg 180
ttattttctt gatcttattt ctacttttgc gggttctatc cgtaaaaagg gtacgtgctg 240
ccccttcctt ctctggagaa ttcacacggc ggtctttccg tctctcaaca agtgtgaatg 300
cagcatgccg gaaacggtga agaaaacagt tttctgtgga aatttagagt gcacatcgaa 360
acagctgtag cgacctcaca gtagcagcgg actcccctct tggcgacaag agcctctgcg 420
gccaaaagcc ccgtggataa gatccactgc tgtgagcggt gcaaccccag caccctggtt 480
cgatgatcat tctctatgga accagaaaat ggttttctca agccctccgg tagagaagcc 540
aagaatgtcc tgaaggtacc ccgcgtgcgg gatctgatca ggagaccaat tggcggtgct 600
ttacactgtc actttggttt aaaaattgtc acagcttctc caaaccaagt ggtcttggtt 660
ttccaatttt gttga 675

<210> SEQ ID NO 375
<211> LENGTH: 628
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 375
gtgctatcat gcctccccga ttatgtgatg ttttctgccc tgctgggcgg agcattctcg 60
ggttgagaaa ccttgaatct ttttctttgg aaccttggtt cccccggtct aagccgcttg 120
gaatatgaca gggttatttt cttgatctta tttctacttt tgcgggttct atccgtaaaa 180
agggtacgtg ctgccccttc cttctctgga gaattcacac ggcggtcttt ccgtctctca 240
acaagtgtga atgcagcatg ccggaaacgg tgaagaaaac agttttctgt ggaaatttag 300
agtgcacatc gaaacagctg tagcgacctc acagtagcag cggactcccc tcttggcgac 360
aagagcctct gcggccaaaa gccccgtgga taagatccac tgctgtgagc ggtgcaaccc 420
cagcaccctg gttcgatgat cattctctat ggaaccagaa aatggttttc tcaagccctc 480
cggtagagaa gccaagaatg tcctgaaggt accccgcgtg cgggatctga tcaggagacc 540
aattggcggt gctttacact gtcactttgg tttaaaaatt gtcacagctt ctccaaacca 600
agtggtcttg gttttccaat tttgttga 628

<210> SEQ ID NO 376
<211> LENGTH: 674
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 376
cacttattta attcggcctt ttgtgacaag cccctcggtg aaagaacctc tctcttttcg 60
acgtggttgg aattgccatc atttccgacg aaagtgctat catgcctccc cgattatgtg 120
atgttttctg ccctgctggg cggagcattc tcgggttgag aaaccttgaa tctttttctt 180
tggaaccttg gttcccccgg tctaagccgc ttggaatatg acagggttat tttcttgatc 240
ttatttctac ttttgcgggt tctatccgta aaaagggtac gtgctgcccc ttccttctct 300
ggagaattca cacggcggtc tttccgtctc tcaacaagtg tgaatgcagc atgccggaaa 360
cggtgaagaa aacagttttc tgtggaaatt tagagtgcac atcgaaacag ctgtagcgac 420
ctcacagtag cagcggactc ccctcttggc gacaagagcc tctgcggcca aaagccccgt 480
ggataagatc cactgctgtg agcggtgcaa ccccagcacc ctggttcgat gatcattctc 540
tatggaacca gaaaatggtt ttctcaagcc ctccggtaga gaagccaaga atgtcctgaa 600
ggtaccccgc gtgcgggatc tgatcaggag accaattggc ggtgctttac actgtcactt 660
tggtttaatg ttga 674

<210> SEQ ID NO 377
<211> LENGTH: 726
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 377
cacttattta attcggcctt ttgtgacaag cccctcggtg aaagaacctc tctcttttcg 60
acgtggttgg aattgccatc atttccgacg aaagtgctat catgcctccc cgattatgtg 120
atgttttctg ccctgctggg cggagcattc tcgggttgag aaaccttgaa tctttttctt 180
tggaaccttg gttcccccgg tctaagccgc ttggaatatg acagggttat tttcttgatc 240

```
ttatttctac ttttgcgggt tctatccgta aaaagggtac gtgctgcccc ttccttctct    300

ggagaattca cacggcggtc tttccgtctc tcaacaagtg tgaatgcagc atgccggaaa    360

cggtgaagaa aacagttttc tgtggaaatt tagagtgcac atcgaaacag ctgtagcgac    420

ctcacagtag cagcggactc ccctcttggc gacaagagcc tctgcggcca aaagccccgt    480

ggataagatc cactgctgtg agcggtgcaa ccccagcacc ctggttcgat gatcattctc    540

tatggaacca gaaaatggtt ttctcaagcc ctccggtaga gaagccaaga atgtcctgaa    600

ggtaccccgc gtgcgggatc tgatcaggag accaattggc ggtgctttac actgtcactt    660

tggtttaaaa attgtcacag cttctccaaa ccaagtggtc ttggttttcc aattttgttg    720

accgcc                                                               726
```

<210> SEQ ID NO 378
<211> LENGTH: 549
<212> TYPE: DNA
<213> ORGANISM: Unknown
<220> FEATURE:
<223> OTHER INFORMATION: Description of Unknown: GLuc CK dCTG1 sequence

<400> SEQUENCE: 378

```
gtggccacgc ccgggccacc gatacttccc ttcactcctt cgggactgtt ggggaggaac     60

acaacagggc tcccctgttt tcccattcct tccccctttt cccaacccca accgccgtat    120

ctggtggcgg caagacacac gggtctttcc ctctaaagca caattgtgtg tgtgtcccag    180

gtcctcctgc gtacggtgcg ggagtgctcc cacccaactg ttgtaagcct gtccaacgcg    240

tcgtcctggc aagactatga cgtcgcatgt tccgctgcgg atgccgaccg ggtaaccggt    300

tccccagtgt gtgtagtgcg atcttccagg tcctcctggt tggcgttgtc cagaaactgc    360

ttcaggtaag tggggtgtgc ccaatcccta caaaggttga ttctttcacc accttaggaa    420

tgctccggag gtaccccagc aacagctggg atctgaccgg aggctaattg tctacgggtg    480

gtgtttcctt tttcttttca cacaactcta cgtctgacaa ctcactgact atccacttgc    540

tctaaagtc                                                            549
```

<210> SEQ ID NO 379
<211> LENGTH: 549
<212> TYPE: DNA
<213> ORGANISM: Unknown
<220> FEATURE:
<223> OTHER INFORMATION: Description of Unknown: GLuc CK dCTG1_2
      sequence

<400> SEQUENCE: 379

```
gtggccacgc ccgggccacc gatacttccc ttcactcctt cgggactgtt ggggaggaac     60

acaacagggc tcccctgttt tcccattcct tccccctttt cccaacccca accgccgtat    120

ctggtggcgg caagacacac gggtctttcc ctctaaagca caattgtgtg tgtgtcccag    180

gtcctcctgc gtacggtgcg ggagtgctcc cacccaactg ttgtaagcct gtccaacgcg    240

tcgtcctggc aagactatga cgtcgcatgt tccgctgcgg atgccgaccg ggtaaccggt    300

tccccagtgt gtgtagtgcg atcttccagg tcctcctggt tggcgttgtc cagaaactgc    360

ttcaggtaag tggggtgtgc ccaatcccta caaaggttga ttctttcacc accttaggaa    420

tgctccggag gtaccccagc aacagctggg atctgaccgg aggctaattg tctacgggtg    480

gtgtttcctt tttcttttca cacaactcta cgtcgtacaa ctcactgact atccacttgc    540

tctaaagtc                                                            549
```

<210> SEQ ID NO 380
<211> LENGTH: 549
<212> TYPE: DNA
<213> ORGANISM: Unknown
<220> FEATURE:
<223> OTHER INFORMATION: Description of Unknown: GLuc CK dCTG1_2_3 sequence

<400> SEQUENCE: 380
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta cgtcgtacaa ctcacgtact atccacttgc 540
tctaaagtc 549

<210> SEQ ID NO 381
<211> LENGTH: 549
<212> TYPE: DNA
<213> ORGANISM: Unknown
<220> FEATURE:
<223> OTHER INFORMATION: Description of Unknown: GLuc CK dAll sequence

<400> SEQUENCE: 381
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta cgtcgtacaa ctcacgtact actcactgtc 540
tctaaagtc 549

<210> SEQ ID NO 382
<211> LENGTH: 549
<212> TYPE: DNA
<213> ORGANISM: Unknown
<220> FEATURE:
<223> OTHER INFORMATION: Description of Unknown: CK SZ1-L1S sequence

<400> SEQUENCE: 382
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga accacccagg aatgccaggg aggtaccccg cttcacagcg 480
ggatctgacc ctgggctaat tgtctacggt ggttcttctt gcttccactt ctttctactg 540
ttcgccacc 549

<210> SEQ ID NO 383
<211> LENGTH: 553
<212> TYPE: DNA
<213> ORGANISM: Unknown
<220> FEATURE:
<223> OTHER INFORMATION: Description of Unknown: CK Aichi Scan (AV-S) sequence

<400> SEQUENCE: 383
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga ttctttcacc accttaggaa tgctccggag gtaccccagc 480
aacagctggg atctgaccgg aggctaattg tctacgggtg gtgtttcatt tccaatcctt 540
ttatgtcgga gtc 553

<210> SEQ ID NO 384
<211> LENGTH: 667
<212> TYPE: DNA
<213> ORGANISM: Unknown
<220> FEATURE:
<223> OTHER INFORMATION: Description of Unknown: CK Aichi Loop (AV-L1) sequence

<400> SEQUENCE: 384
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga actgccctag gaatgccagg caggtacccc acctccgggt 480
gggatctgag cctgggctaa ttgtctacgg gtagttttcc tttttctttt cacacaactc 540
tactgctgac aactcactga ctatccactt gctctcttgt gcctttctgc tctggttcaa 600
gttccttgat tgtttttgac tgcttttcac tgcttttctt ctcacaatcc ttgctcagtt 660
caaagtc 667

<210> SEQ ID NO 385
<211> LENGTH: 693
<212> TYPE: DNA
<213> ORGANISM: Unknown
<220> FEATURE:
<223> OTHER INFORMATION: Description of Unknown: CK SZ1-L2 sequence

<400> SEQUENCE: 385
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcc tgatcccccg cggaagctgc 300
tcacgtggca actgtgggga cccagacagg ttatcaaagg cacccggtct ttccgccttc 360
aggagtatcc ctgctagtga attctagtag ggctctgctt gcgttgtcca gaaactgctt 420
caggtaagtg gggtgtgccc aatccctaca aaggttgatt ctttcaccac cttaggaatg 480
ctccggaggt accccagcaa cagctgggat ctgaccggag gctaattgtc tacgggtggt 540
gtttcctttt tcttttcaca caactctact gctgacaact cactgactat ccacttgctc 600
tcttgtgcct ttctgctctg gttcaagttc cttgattgtt tttgactgct tttcactgct 660
tttcttctca caatccttgc tcagttcaaa gtc 693

<210> SEQ ID NO 386
<211> LENGTH: 671
<212> TYPE: DNA
<213> ORGANISM: Unknown
<220> FEATURE:
<223> OTHER INFORMATION: Description of Unknown: CK Aichi TriLoop
(AV-L2) sequence

<400> SEQUENCE: 386
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgca tgtgcctggc aagcatatct 300
gagaaggtgt tccgctgtgg ctgccaacct ggtgacaggt gccccagtgt gcgtaacctt 360
cttccgtctc cggacggtgc gttgtccaga aactgcttca ggtaagtggg gtgtgcccaa 420
tccctacaaa ggttgattct ttcaccacct taggaatgct ccggaggtac cccagcaaca 480
gctgggatct gaccggaggc taattgtcta cgggtggtgt ttcctttttc ttttcacaca 540
actctactgc tgacaactca ctgactatcc acttgctctc ttgtgccttt ctgctctggt 600
tcaagttcct tgattgtttt tgactgcttt tcactgcttt tcttctcaca atccttgctc 660
agttcaaagt c 671

<210> SEQ ID NO 387
<211> LENGTH: 523
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 387

```
gggggtgggg ggggcctcgg ccccctcacc ctcttttccg gtggccacgc ccgggccacc     60

gatacttccc ttcactcctt cgggactgtt ggggaggaac acaacagggc tcccctgttt    120

tcccattcct tccccctttt cccaacccca accgccgtat ctggtggcgg caagacacac    180

gggtctttcc ctctaaagca caattgtgtg tgtgtcccag gtcctcctgc gtacggtgcg    240

ggagtgctcc cacccaactg ttgtaagcct gtccaacgcg tcgtcctggc aagactatga    300

cgtcgcatgt tccgctgcgg atgccgaccg ggtaaccggt tccccagtgt gtgtagtgcg    360

atcttccagg tcctcctggt tggcgttgtc cagaaactgc ttcaggtaag tggggtgtgc    420

ccaatcccta caaaggttga ttctttcacc accttaggaa tgctccggag gtaccccagc    480

aacagctggg atctgaccgg aggctaattg tctacgggtg gtg                      523
```

```
<210> SEQ ID NO 388
<211> LENGTH: 592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 388

gggggtgggg ggggcctcgg ccccctcacc ctcttttccg gtggccacgc ccgggccacc     60

gatacttccc ttcactcctt cgggactgtt ggggaggaac acaacagggc tcccctgttt    120

tcccattcct tccccctttt cccaacccca accgccgtat ctggtggcgg caagacacac    180

gggtctttcc ctctaaagca caattgtgtg tgtgtcccag gtcctcctgc gtacggtgcg    240

ggagtgctcc cacccaactg ttgtaagcct gtccaacgcg tcgtcctggc aagactatga    300

cgtcgcatgt tccgctgcgg atgccgaccg ggtaaccggt tccccagtgt gtgtagtgcg    360

atcttccagg tcctcctggt tggcgttgtc cagaaactgc ttcaggtaag tggggtgtgc    420

ccaatcccta caaaggttga tttccttttt cttttcacac aactctactg ctgacaactc    480

actgactatc cacttgctct cttgtgcctt tctgctctgg ttcaagttcc ttgattgttt    540

ttgactgctt ttcactgctt ttcttctcac aatccttgct cagttcaaag tc            592
```

```
<210> SEQ ID NO 389
<211> LENGTH: 572
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 389

gggggtgggg ggggcctcgg ccccctcacc ctcttttccg gtggccacgc ccgggccacc     60

gatacttccc ttcactcctt cgggactgtt ggggaggaac acaacagggc tcccctgttt    120

tcccattcct tccccctttt cccaacccca accgccgtat ctggtggcgg caagacacac    180

gggtctttcc ctctaaagca caattgtgtg tgtgtcccag gtcctcctgc gtacggtgcg    240

ggagtgctcc cacccaactg ttgtaagcct gtccaacgcg cgttgtccag aaactgcttc    300

aggtaagtgg ggtgtgccca atccctacaa aggttgattc tttcaccacc ttaggaatgc    360

tccggaggta ccccagcaac agctgggatc tgaccggagg ctaattgtct acgggtggtg    420

tttccttttt cttttcacac aactctactg ctgacaactc actgactatc cacttgctct    480

cttgtgcctt tctgctctgg ttcaagttcc ttgattgttt ttgactgctt ttcactgctt    540
```

```
ttcttctcac aatccttgct cagttcaaag tc                                  572
```

<210> SEQ ID NO 390
<211> LENGTH: 167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 390

```
ccctgcagcc gtcaccgtaa gtttgaagtt accgcatatc agcctctgct tcccagcgcg    60

tccaattcct gttcttattg tttcccctcc aggcgttacg cgtgacgacg aactgtgtcg   120

cagctaccac attattccgg agccttcatt ctcgcggctc tgatcgt                 167
```

<210> SEQ ID NO 391
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391

```
ggagaccgcg gccacgccga gtaggatcga gggtacagtc tcc                      43
```

<210> SEQ ID NO 392
<211> LENGTH: 167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 392

```
gacaccagga tcactcttgc tctgacccgc cctgtgtaga atagactcat gcttccctaa    60

gacctggatt tcttcccagg cactttcacc cgcctgccct gctccttcag tggactgcac   120

ccagggaggc ggtctctgac tgtcctttac tttctattct ggattgc                 167
```

<210> SEQ ID NO 393
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393

```
aaaccccct aagccgccgc cgccgccacc                                      30
```

<210> SEQ ID NO 394
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394

```
cccccccaac ccgtcacg                                                  18
```

<210> SEQ ID NO 395
<211> LENGTH: 6
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 395 gtcacg 6

<210> SEQ ID NO 396
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396
tctgcgcact cgtaatcagt actaaccccc ctttgtcgga cactatgcga taatcgatcc 60
gcctttttca ccgccttcgg aattttattt acctcaactg atcctggagt ctctcttggt 120
tttcacggag gcctccgccc a 141

<210> SEQ ID NO 397
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
ggagaccgcg gccacgccga gtaggatcga gggtacagtc tcc 43

<210> SEQ ID NO 398
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 398
ccccttgaaa cccccgcccc aggttcagtc tctcttcatc cctctgtcct gcatggtgat 60
acaaagaccc tttgtggacc ctaagccatg tagttgctgc tccctccttc cagttgtgaa 120
tattggtttc tgttaatcac a 141

<210> SEQ ID NO 399
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399 aaaccccct aagccgccgc cgccgccacc 30

<210> SEQ ID NO 400
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
cccccccaac ccgtcacg 18

<210> SEQ ID NO 401
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 401 gtcacg 6

<210> SEQ ID NO 402
<211> LENGTH: 6
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 402 gtcacg 6

<210> SEQ ID NO 403
<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 403
aataagagag aaaagaagag taagaagaaa tataagagcc acc 43

<210> SEQ ID NO 404
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 404
cgaactagta ttcttctggt ccccacagac tcagagagaa cccgccacc 49

<210> SEQ ID NO 405
<211> LENGTH: 7
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 405 agccacc 7

<210> SEQ ID NO 406
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 406
tgatagctaa ctag                                                          14

<210> SEQ ID NO 407
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
tagtagctaa ctag                                                          14

<210> SEQ ID NO 408
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
tgatgactga gtga                                                          14

<210> SEQ ID NO 409
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
tagtagctag gtag                                                          14

<210> SEQ ID NO 410
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410 taa                                                                       3

<210> SEQ ID NO 411
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
taatagctaa ctag                                                          14

<210> SEQ ID NO 412
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
taactagcta actag                                                         15

<210> SEQ ID NO 413
<211> LENGTH: 579
<212> TYPE: DNA
<213> ORGANISM: Rhopalosiphum padi virus

<400> SEQUENCE: 413
gataaaagaa cctataatcc cttcgcacac cgcgtcacac cgcgctatat gctgctcatt 60
aggaattacg gctccttttt tgtggataca atctcttgta tacgatatac ttattgttaa 120
tttcattgac ctttacgcaa tcctgcgtaa atgctggtat agggtgtact tcggatttcc 180
gagcctatat tggttttgaa aggaccttta agtccctact atactacatt gtactagcgt 240
aggccacgta ggcccgtaag atattataac tattttatta tattttattc accccccaca 300
ttaatcccag ttaaagcttt ataactataa gtaagccgtg ccgaaacgtt aatcggtcgc 360
tagttgcgta acaactgtta gtttaatttt ccaaaattta tttttcacaa tttttagtta 420
agattttagc ttgccttaag cagtctttat atcttctgta tattatttta aagtttatag 480
gagcaaagtt cgctttactc gcaatagcta ttttatttat tttaggaata ttatcacctc 540
gtaattattt aattataaca ttagctttat ctatttata 579

<210> SEQ ID NO 414
<211> LENGTH: 675
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 414
cttgattcta accttgccgt atggtgccct aacgggttca tttaatcatg cgatgagggt 60
tgctataccg catccattct aaggcgattc aatgcttcat ttaggaattt tgttgacgat 120
taaaaggtac ccccacaaaa acaaaaccaa tcttacttga ttttcgtttt aactgaccac 180
tgcgatccca aattttcgcc ttcttatcaa agtatgttgt gttctttggg tgtacaacct 240
gagaacttgt ctacaactac atattactcg aggaagaaat tcggtttaag ccgtgccttc 300
tcacgtttag tatatctatc tggacacacc ttcttcatct tctaatcccc atctagtctc 360
ctgatcagag acgtcgttat taacaaataa cccccccttgt taataagaga caaagtacaa 420
tcaagctaag ttctcttgga gttcctgtag gaacttagcc attgtgatag agtcataagt 480
ctatgtgcat agacagctct agctcaccat ttccttccca acccatcttt tcatcagctt 540
aactctatga atccgatgca aaaaccattc taacatctta tggtgctttc caagccaaat 600
gagagctcac tcttttgagc cgctatttaa tggacaataa acgttttata gtgtacatca 660
tattgtaaaa acaaa 675

<210> SEQ ID NO 415
<211> LENGTH: 636
<212> TYPE: DNA
<213> ORGANISM: Oscivirus sp.

<400> SEQUENCE: 415
cctcggtccc tctttccgtc gccgcccacg acgttaaatg cggtgttgtg gtgcttaggt 60
gccacaccac tgctatttgg gtcccccttt cccctatata tgtttgtttg tttatttcaa 120
tttcttgagg attggcacct ccttatgcca aatctaaatc gtggaggatc ccaggctttc 180
tggtctttaa cagaactcca cgtccaggtc atagaaactg gttggtaggc tgcctgagta 240

-continued gtccatttgc tagtagtccc ttgtgaacag ggtggctccc gtttactgct ggtattcccg 300
gtgtaggtcg ccatggtggt aacaccatcc tgcattgtgt gtgaaccagt accgcaagga 360
tagcaaggta tgaacacttg tggacgaaat ggtaagtgat caattcactt tcatggccgg 420
aaggtcacgt ggcaatcatg ccacccaggt accctcctct gggaggatct gagggtgggc 480
taagcagacc ctgccatgtg gctgaacttt tcccttattg ttttactttg taacatttat 540
agttgtgtta gtgatttgtg tgttgtgccc ttgtgagcta tatccagtat aagttcgcag 600
ctagaagtta atccttcgac atcggctgta ttggaa 636

<210> SEQ ID NO 416
<211> LENGTH: 675
<212> TYPE: DNA
<213> ORGANISM: Cadicivirus B

<400> SEQUENCE: 416
caccaaccct tgacctgtaa tgtcagtgga cagagtgctc ctctgttccc ggttaccgtg 60
ttccaggaca cgattgtaat cctgcgcctc accagcgctg cgtgcacgtc tgcataagga 120
aacgtgcctt ccccatgtct ctatcaattc tttggtgagt gaccgcccta gttgctcatc 180
ctatgggatt cttctctcat gggttctttg tggcatgcga atgtcacctt aattggaggt 240
ctttaattag atatcctttc ttcatctttg atatgagtgt cggaatttga ttcctagtct 300
ctgcaaaaca accccacttg atgaattcaa cttttcaacc gcacaaacat aatcaggttt 360
ttaaattgaa tgtttctaaa ttctaaattt agtttattta agtagtttgc catcttgact 420
cgatgtaaaa ttgtcataca agtcttcttt tcttttcttt acactttgaa gtttgcactt 480
agcagtcgtt ctgcacagct ttcgagtttt gtttgatcga catcgcaact tccacccacc 540
tctctttttc tagtgttgaa tgcggctaat cctaacccga gagcaataaa cccaggttta 600
ttgtcgtaac gcgcaagtct tggacggaac cgactataca cacacctctt taccctttag 660
tacacccttg gtacg 675

<210> SEQ ID NO 417
<211> LENGTH: 570
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 417
gcaaaatggg tacgtagtta accactgcgt atcaggattg caggccacga agggtatttg 60
catatctttc tatgcggtat tacggcttaa aacccgttgt atcttgttgt ttgactgcct 120
gtatcactag tggccatttt atttaggtta gagacccctg atagtaggag agttacaaac 180
tctttaaaaa ttgttgaccc cggaaaagat ggtgacccct gtaagtagtt gatcaagaag 240
atctatgcgc tggcatagta atccagtgtt tcctgtttta ggatgacctc tgaaagtaga 300
tgaccgtgga aagtcacgta gtgccccaat aagcacgttt gggcagcgtg cgctatcaca 360
aggcttgatc tccgaggagc cccttgtttt agctggctgg aagccaatga tcttaagtag 420
ataagtgctg ttgcttgtag ttcaacagaa agctttgagt acgtctttct tgcgagaaag 480
aacacatgca ttcttatgct ctcaattcta ttatttttat tttgggcgaa aggaaagctc 540
tcacgcgagt acgaatagcc aaccctttat 570

<210> SEQ ID NO 418
<211> LENGTH: 145
<212> TYPE: DNA
<213> ORGANISM: Plautia stali intestine virus

<400> SEQUENCE: 418
gctgactatg tgatcttatt aaaattaggt taaatttcga ggttaaaaat agttttaata 60
ttgctatagt cttagaggtc ttgtatattt atacttacca cacaagatgg accggagcag 120
ccctccaata tctagtgtac cctcg 145

<210> SEQ ID NO 419
<211> LENGTH: 312
<212> TYPE: DNA
<213> ORGANISM: Unknown
<220> FEATURE:
<223> OTHER INFORMATION: Description of Unknown: PV Mahoney sequence

<400> SEQUENCE: 419
atgagtctgg acatccctca ccggtgacgg tggtccaggc tgcgttggcg gcctacctat 60
ggctaacgcc atgggacgct agttgtgaac aaggtgtgaa gagcctattg agctacataa 120
gaatcctccg gcccctgaat gcggctaatc ccaacctcgg agcaggtggt cacaaaccag 180
tgattggcct gtcgtaacgc gcaagtccgt ggcggaaccg actactttgg gtgtccgtgt 240
ttccttttat tttattgtgg ctgcttatgg tgacaatcac agattgttat cataaagcga 300
attggattgg cc 312

<210> SEQ ID NO 420
<211> LENGTH: 577
<212> TYPE: DNA
<213> ORGANISM: Reticuloendotheliosis virus

<400> SEQUENCE: 420
ggggtcgccg tcctacacat tgttgtgacg tgcggcccag attcgaatct gtaataaaag 60
ctttttcttc tatatcctca gattggcagt gagaggagat tttgttcgtg gtgttggctg 120
gcctactggg tggggtaggg atccggactg aatccgtagt atttcggtac aacatttggg 180
ggctcgtccg ggattcctcc ccatcggcag aggtgcctac tgtttcttcg aactccggcg 240
ccggtaagta agtacttgat tttggtacct cgcgagggtt tgggaggatc ggagtggcgg 300
gacgctgccg ggaagctcca cctccgctca gcaggggacg ccctggtctg agctctgtgg 360
tatctgattg ttgttgaacc gtctctaaga cggtgatact ataagtcgtg gtttgtgtgt 420
ttgtttgtta ccttgtgttt gttcgtcact tgtcgacagc gccctgcgaa ttggtgtacc 480
cacaccgcgc ggcttgcgaa taatactttg gagagtcttt tgcctccagt gtcttccgtt 540
tgtactcgtc ctcctctccc tctccggccg ggatggg 577

<210> SEQ ID NO 421
<211> LENGTH: 675
<212> TYPE: DNA
<213> ORGANISM: Tropivirus A

<400> SEQUENCE: 421
tgtcgcatgt tgccaacatc aaaattctgg gagagtcgcg aactccttaa cactgccttg 60
cctcgacgga gccgttgtta tagtgtcgac gggatacaaa cattaaacta aacccacttg 120
cctcgacgga accccttacc ttttatttta ttttatagta tgaaagtgaa tcttgtatga 180
atgttcatag aaaactgcaa atgagtacca cgtctaacat gagagaatga tactggagaa 240

-continued

```
atccaagttt agaagtcact acgaatccca gcggaaacaa gggaattctg agcttctaat    300

aggcgtttaa gactatttgc aaaattctgg tgcgtaagtg atattttcat tgcgtagaac    360

gctggtaacc actccggcta gtataagcat tgttagtcac ttattatgaa actccacact    420

atcctttctg gagaagcaca caaacttaca tggtaaagct agaccattat cttaagcggt    480

gagtacactg caaccttgta acaatgcttg tatgactact ttttgtatat cttgagcaat    540

attgttgagg tggacatgtc caaaggtaat gttgttggga atggaggggt ccattttccc    600

gtgcacgtag tgtactagta ttgggtgata gccttgcggc ggatcaacca tgtattttaa    660

tccgttgact ttcac                                                     675


<210> SEQ ID NO 422
<211> LENGTH: 592
<212> TYPE: DNA
<213> ORGANISM: Symapivirus A

<400> SEQUENCE: 422

ttgggaaatc cccaatgctt ctttcaacac cgcctgacta tgcggtggcg cttcggctca     60

aacaactagt cacttccccc tcttaactac tacccaagac ttctaactac ccttacctac    120

ttatttgtct aaatttcaaa cttttattct cacgcgtctt ataaacatct tttctatttg    180

ttatggtatg ttttgtgatt tgtgtggtgt atttcattta atgggatcta gtggaccgtg    240

ccccggttgg gtatccgctc cctttaaatg tttgcaagca ctcttgacat tataacctat    300

catttagttt acttgtttgt atgatcgtat ttctgaatcg taacatttat gcaattcttt    360

ctcgccgaga cttgtctagg agataaagtt cctgcatatt tagtgttacg gttgtataat    420

ggagacttag atagcttcac actgaggacg ctttttcgct atccttttga cctgattcag    480

gccagtgtgg agttaatgat tgtatggatg ggccctacaa tttgtctaag acttggtgat    540

agcctcgcgg ccgctcgcca tttatacaac tgaatagcgg ttgaaactct ct            592


<210> SEQ ID NO 423
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 423

tcacgcgctt ttccggtggt cacccaccgt tagggagcgc cagcgttcgc gcttccgcta     60

ccaggtgaca cactcctttc ccctccccca ttcccgttcc catcctctgg actggtttct    120

cctcacgatt gaccagcagc tgggagctgt taccagacgt tggacagtaa gtcccggatg    180

cactataggg ctggtggcta gtgcttggta agcactcaac gccataccta atgtgtacct    240

cggcttgccc tcctggtcgt ggtgaccggc tgtttctctt cccttggctc cagacgggct    300

ggtgtcctac caccaccgtt gcatgcagac ctccccctgc gcactcgaac gccctgtccc    360

agcagggtta gtatgtgctg tgcagatctg catgtgacac cccatccact ggtagagcag    420

gaagttgccc tagctaacgc ggcaagtatt actttccgct acacgtcctt gagattcctc    480

ggacctctgg aactagggtg actgtgggct tgggaaaacc caccttggtc ctgtactgcc    540

tgatagggtc gcggctggcc gaccagtgga tgtagccagt tgttttggga t             591


<210> SEQ ID NO 424
<211> LENGTH: 538
<212> TYPE: DNA
```

<213> ORGANISM: Rosavirus C

<400> SEQUENCE: 424
cagggagatc tccatgaata atcttttcca ccctctttag cgtctatgct attgaggacg 60
ggttggagcc ccgttgaccc agcgtcagag tgtgtcggta gcaggctttc tgctctcgcc 120
ccatgccggc cacacctccc attagtgatg tgaaggttgt aagttacatg tgaaaaggtt 180
tctaataatt gagctgaatg tagcgattac ctaaggtgag cggattcccc cacgtggtaa 240
cacgtgcctc tcaggccaaa agccaaggtg ttaaaagcac cccttaggta ggccactacc 300
ccgtggcctc agttctctta gaagattcac ttagtagtgt gtgcactggc aactcttaag 360
cagagctagt gagtgggcta aggatgccct gaaggtaccc gcaggtaacg ttaagacact 420
gtggatctga tcaggggctc gagtgctgaa gctttacaga ggtagctcga gttaaaaaac 480
gtctatgccc ctcccccacg ggagtggggg ttcccccaca ccaattttag attgcact 538

<210> SEQ ID NO 425
<211> LENGTH: 675
<212> TYPE: DNA
<213> ORGANISM: Rosavirus sp.

<400> SEQUENCE: 425
ccaggcatgg cgttaaacat gcattccctt cccctagtaa cctcccttcg ccccttcccc 60
acgttgtacc ccctccgaga tggctgctaa ggcgcttgct gctacagcag tctcgtgttt 120
cgggtgttat aagtgctttc ttttccactc cactccctgc ctatggggag cggaacggcc 180
ttgtctcggt cgttgcttct tgcagatctt caccccctcca ggctttctgg actcgccagg 240
ggtggagtag taggcgcact gtctaagtga aggtagcagt gttgttggcg aagagttgtg 300
gacctacttt gagtttgtag cgatcatcca gagctagcgg atctccccac gcggtaacgc 360
gtgcctctag gcccaaaagg cacggtgttc acagcaccct ttggatggcg ggggtgcccc 420
cctccgcact taaagtagaa aaacagctta gtagtcaaat aacatggctt tcctcaagca 480
ttcagtgcta catgggactg aaggatgccc agaaggtacc cgcaggcaac gataagctca 540
ctgtggatct gatctggggc cctgggccag gtgctataca cctggttaaa accaaatctg 600
gtagtcaggg ttaaaaaacg tctaagtccc accccccccgg ggacgggggg ttcccttaaa 660
ccctcaactg acacc 675

<210> SEQ ID NO 426
<211> LENGTH: 656
<212> TYPE: DNA
<213> ORGANISM: Unknown
<220> FEATURE:
<223> OTHER INFORMATION: Description of Unknown: Rhimavirus A sequence

<400> SEQUENCE: 426
cgaattccgg acatctcctt tcgggggcga gcgtcaccgt gcccctcatg gaggcaactg 60
tgcctctaat cggtgaccca ctgagaaaat tttctttcta cgtggctaaa caatgcaact 120
ttataataac acaaatttaa tgcttaatct taacaccaaa gatttgaaca tatgtttgga 180
aagtggcaca cttcaaacat tgcatagttg ctaggggtga agtcccttta aggggttgca 240
gaggatcttt cctctttatg agcggctagg agtatcttct tgatattatg tggtcgtgca 300
actcacttcc cagatgtatg acggtgtact aagcgattgg aactagtcat aacctctttg 360
aattttggta ttgcgagtct agcaggggga tatttaccgc taaagggtga cacactcgtg 420
agggtggcct ttggtgtgtg tatatttatt ccgcccatct tgcatggggt gctaaaattc 480

```
taatgctgtg aaataaccat tttctgaata cattctctac atttggagtc aaatatgagg    540

aatgccactc aggtaccctt gacatgatct tggatctgag agtgggctaa ttatctaatt    600

atttggcgac tttctaaaat cttctgtttt tagtggtgac aatttatggt tataaa        656


<210> SEQ ID NO 427
<211> LENGTH: 487
<212> TYPE: DNA
<213> ORGANISM: Rafivirus sp.

<400> SEQUENCE: 427

gtgtccggga agcgactcaa gcttttgact gagtctctac accttcatcc gtaacatctt     60

taagtttatg tgcctatgga cctctagtgc actgccatca ccgggggtgt attggactgg    120

tttttccaca atccattcat cctgaggaat tttggctttg ttactaggat ggtcccacca    180

cacgcttatc tgtgcctatt gtgtcaacca tgttcttaag tagttgtgcc cgtgggtgag    240

tagataacca caacaatccg ataaagcatc tcgcaaggat gtgagtaatg gagtgtatgt    300

gctacagaga cccacaacct gaaccaagag agacacagtg aggattgtaa agggggaact    360

ctttgaaagg gcatgtcccg caattcctac tgactgacac cgggggttgg tgtcggtgga    420

ttttagcaaa tcctgttact gggtgatagc cttgtgcact tcacttggtt cttgtataag    480

tgctgta                                                              487


<210> SEQ ID NO 428
<211> LENGTH: 560
<212> TYPE: DNA
<213> ORGANISM: Rafivirus sp.

<400> SEQUENCE: 428

tgcgaattta ttcgcacagt ctcttttccc ccatcttgtg tgtgtgatgg ggtaagccgc     60

agagtaatac ctactctgct gcaaacacac tcactctttt ctatctactt tatatcatgt    120

aataataagt agggaacata ttcaattcat attgttcatc tcactgaacc cgcatgaagg    180

actgcattgc atatcctgga cgaagtgacg tggaatattt ggacatttat ggattggaca    240

ccattacgct ttgtgcctct acggagatgt aaccataatc ttaagtagta gtaccccagc    300

acaagaggat aaagtggcat acacgacaac gggtgttgct cgcaccttag taatgtggat    360

gttcaccctt ggagcgtgct gaaactctgt gggtaaagac acacattagt acaaatgtgg    420

gggaactcac tgaaagggca tgtcccgtgt actggtgtgc cggaaagtgg gggtcgcttt    480

ctggagaact tagtagttct tgttattggg tgatagcctt gcggcggatc aactcacagt    540

tttaatccgt tgttttgcat                                                560


<210> SEQ ID NO 429
<211> LENGTH: 675
<212> TYPE: DNA
<213> ORGANISM: Poecivirus sp.

<400> SEQUENCE: 429

actacacaat cgcaacacgc gcaagtttgt agtttgattg gcgtgcaaat gtcaaatcaa     60

gcatataaca caatttggtg gctgttggtg tttgttatag gaattttggt tgtgttgaaa    120

ttgtggatgt gtaggaaata tgcacaatta cgtcagcgtc aggagtttta taacctggcg    180

caacaccaaa atggtcttcg cgctttaaca tcaccagcga ggtgtaaaca aattgaagtt    240

gaattagatc gtgtataggc cagggaacca tccctcccaa cgccacatct tgtggggaag    300
```

ttgggataat ggtgggtcta tatgaattgg tctgtagacc cacagtgaag agtgaatagt 360
atgcttgcgg ttccatttgt taatggtcta gcatgggtgg gggcggcaac cccgtgaggg 420
gttccccact ggccaaaagc ccaggggtta gtcatttcaa ccaaggaagc tggtaacctg 480
gtgacctgaa cttgagtggt gagaccccct tgctagagtg tgtaaaccga ttgtaagcat 540
tttgtttgct tagtatctgt ggtataagca gtcaattttg tataggctca aggctgtggt 600
agttagtaga tgcccggaag gttattactg atccggggac cgtgactata cattaggtaa 660
accggtttaa aaacc 675

<210> SEQ ID NO 430
<211> LENGTH: 519
<212> TYPE: DNA
<213> ORGANISM: Unknown
<220> FEATURE:
<223> OTHER INFORMATION: Description of Unknown: Megirivirus A LY sequence

<400> SEQUENCE: 430
ttcgggacac tggatgggcg acttggtggg gctgccactc tatcttgacc tttcgttact 60
gactttcgga tctctgactc ctccttgtct cttgcgtttg gtccacggac ggactaattg 120
gaatgtttac tggctaagcc tcgttctgaa ataccctagc caatgggttg tagtaggatc 180
ctggtgtttc cattaaacct cttccgacca tagtagctag agttatggct gtgtaggatg 240
tgggtaagac cgctttttgc gtatctccca caagacaccg gattatggat gtgtccgctg 300
gataaggctc gaaacctccc aactgaaggt ggtgctgaaa tattgcaagc ctaggttgtg 360
tagaggcaag tagatgcctg ccgcgacatt cgtcttccgc ccttttgggt tagtagtgta 420
cctacatgga cgtggggctg ggaatcccca ccttgcataa cactggttga tagacctgcg 480
gctggtcaag ttactatggt ataaccagtt gaaatggct 519

<210> SEQ ID NO 431
<211> LENGTH: 675
<212> TYPE: DNA
<213> ORGANISM: Unknown
<220> FEATURE:
<223> OTHER INFORMATION: Description of Unknown: Megirivirus E sequence

<400> SEQUENCE: 431
gcttggcaac ctcatatcgt tactctgccg accagtctgg gtcgtgtggc cacacaatgg 60
gattcgttct gttgtgtaga gtcacatggc attactgggc tgatcggtgg ggatccgttg 120
ccacccctaa acccttacat ttactggact gcttttcttg gccccggaat gattcgctca 180
cccgcgatga ggactgttgt tcttattatg gcaggattac gcgtctggtc cgcgtaagga 240
ctaattccta tgtttatacg ttactacctt gttctgaacg gtgggcgcca ccccgcctag 300
taggatcctg gcttatcgtg tagacctcta gggaccacat tagctagagt gtaggctgct 360
atggatggag tagtgacccc tttttgggta tcactctcta agactccgga atgtgtcata 420
gtacgctgga aatccttact tgtttttcca tgagggggag gtggtgctga aatattgcaa 480
gccacccctc ggttaaaaca gtttggtgcc gcttatgcca tattaccgcc ccttgtagtt 540
gggctgtttt tgcagctccg ggttagtaga gtaccatagt ggacgcggtg ttgggaatca 600
ccgccttggc tgcacactgc ttgatagagc tgcggctggt caagctaatt gtggtataac 660
cagttgattt ggcat 675

<210> SEQ ID NO 432

<211> LENGTH: 639
<212> TYPE: DNA
<213> ORGANISM: Unknown
<220> FEATURE:
<223> OTHER INFORMATION: Description of Unknown: Megirivirus C sequence

<400> SEQUENCE: 432
ttcccgaccg gtctggcaaa ccggacggtt atcctggtta gatgtctgat ggttgctgga 60
acgtggtggc tactgctgcc accttctggc ttcctttaat gggcatctag ctgggttctt 120
tgccacaatc catcttactc tcttacccat tttctattac ccagacttgt tgttaactgg 180
taaagttgac ctactggctt cgttttgaga ctattctggt gttggtggac actctttcca 240
caagtagatt gtatggagtt catgctcgtt ttgaaccggg aatggcacaa cccgtagtag 300
gatcttgcct ctgccatact aatctgcgcc tgttgctttt agactatggg ctgctaagga 360
tgacattgga accccttttt ggatattcca tgtcaagtca actgtttcat ctggtgtacg 420
ctggaaatcc ttgttccgag gtcttgtctg gaggtggtgc tgaaatattg caagccacag 480
gcagttcctt ggacttggtg ccgctatcag atgctacacc ctctatgggc aaatgttgaa 540
ccttagtgga cgcgtgagat gggaatccac gccggccata gactggctga taagctcgcg 600
gctgatcgag ttgcaacagt aatcagttga tttgccact 639

<210> SEQ ID NO 433
<211> LENGTH: 497
<212> TYPE: DNA
<213> ORGANISM: Ludopivirus sp.

<400> SEQUENCE: 433
tagaccccca cctagccctt ttccccgtca gtggggggct tactcactgg gcatctgtta 60
atctggccta actagattga caccactccc ttggaacgta actccacgct aactcactgg 120
ctctacgcac agacacacgg tctttctgct atccccgggg aagataccag atggcgaccg 180
gctgtcccag cggcctagta gctactcggg ttgagtaccc accacggttt tgacgcctgc 240
taaaattcaa gagacagagg taggggtgct tagtgtgtgg gggaagttcc cacaagcgag 300
gcaaagcatt gctccctcgc gtcaccgggt gcaaggtaaa ttggctggac ttccgctcta 360
cccttgctac tcgccctctt cggagggttc gaagtgacac taggtatacg catggttggg 420
aaaccatgcc tggcctacta ctgggtgata gcctggcggc gggtccgtct cttggcttat 480
acccgttgat ttgggat 497

<210> SEQ ID NO 434
<211> LENGTH: 610
<212> TYPE: DNA
<213> ORGANISM: Livupivirus sp.

<400> SEQUENCE: 434
tatctacatg gggatccagg ctgtatggaa tgtctgtctt aacaagcact ataccagaaa 60
gatccaccca aagtggtggg actgggactg tgaggtgaga aatcccgaaa ccagccttct 120
caagcgtcgg acgatctttc tgttttagtg aacaccttgc cttttaaatg gatgacaaca 180
ccccttcagc aaatcgcaat ctgaaatccc aaaagactgt ttagccgaac tctggtaatc 240
actccggaga agtaggatac gcagcccctg tggactcttg atttcaggac tcaaggtagc 300
tagagctgga acttcatgga atgacaaagg aatatatgca cattgtgcgc tttcctggcc 360
ttgtagcccg tcgtgaggat atgtcgttgg gaatcgacat cttagtccag tactgcttga 420
tagagtgtcg gctggcacag ttacctgaga ataagtcagt tgtacttaac atgaacaaaa 480
aaaataacta ccacaactac cacaatctac caatacttga attatgctga atctcgtaca 540
gtaaaaacgt tccgtggaag gacaagtatt gaagtgcggt tacatcatcc gatacgcgct 600
ggatccctca 610

<210> SEQ ID NO 435
<211> LENGTH: 629
<212> TYPE: DNA
<213> ORGANISM: Aichivirus A

<400> SEQUENCE: 435
cacccataca cccccacccc cttttctgta actcaagtat gtgtgctcgt aatcttgact 60
cccacggaat ggatcgatcc gctggagaac aaactgctag atccacatcc tccctcccct 120
tgggaggacc tcggtcctcc cacatcctcc ctccagcctg acgtatcaca ggctgtgtga 180
agcccccgcg aaagctgctc acgtggcaat tgtgggtccc cccttcatca agacaccagg 240
tctttcctcc ttaaggctag ccccgatgtg tgaattcaca ttgggcaact agtggtgtca 300
ctgtgcgctc ccaatctcgg ccgcggagtg ctgttcccca agccaaaccc ctggcccttc 360
actatgtgcc tggcaagcat atctgagaag gtgttccgct gtggctgcca gcctggtaac 420
aggtgcccca gtgtgcgtaa ccttcttccg tctccggacg gtagtgattg gttaagattt 480
ggtgtaaggt tcatgtgcca acgccctgtg cgggatgaaa cctctactgc cctaggaatg 540
ccaggcaggt accccacctt cgggtgggat ctgagcctgg gctaattgtc tacgggtagt 600
ttcatttcca attcttttat gctggagtc 629

<210> SEQ ID NO 436
<211> LENGTH: 675
<212> TYPE: DNA
<213> ORGANISM: Aichivirus sp.

<400> SEQUENCE: 436
tactccattc agcttcttcg gaacctgttc ggaggaatta aacgggcacc catactcccc 60
cccacccccc ttttgtaact aagtatgtgt gctcgtgacc ttgactccca cggaacggac 120
cgatccgttg gtgaacaaac agctaggtcc acatcctcct ttcccctggg agggtccccg 180
ccctcccaca tccccccccc agcctgacgt gtcacaggct gtgtgaagcc cccgcgaaag 240
ctgctcacgt ggcaattgtg ggtcccccct tcatcaagac accaggtctt tcctccttaa 300
ggctagcccc ggcgtgtgaa ctcacgttgg gcaactagtg gtgtcactgt gcgctcccaa 360
tctcggccgc ggagtgctgt tccccaagcc aaacccctgg cccttcacta tgtgcctggc 420
aagcacacct gagaaggtgt tccgctgtgg ctgccagcct ggtaacaggt gccccagtgt 480
gcgtaacctt cttccgtctt cggacggtgg tgattggtta agatttggtg taaggttcat 540
gtgccaacgc cctgtgcggg atgaaacctc tactgcccta ggaatgccag gcaggtaccc 600
caccttcggg tgggatctga gcctgggcta attgtctacg ggtggtttca tttccaattc 660
tttcatgtcg gagtc 675

<210> SEQ ID NO 437
<211> LENGTH: 675
<212> TYPE: DNA
<213> ORGANISM: Aichivirus sp.

<400> SEQUENCE: 437
tactccattc agcttcttcg gaacctgttc ggaggaatta aacgggcacc catacacccc 60

-continued

```
cacccccttt tctgcaactt aagtatgtgt gctcgtaatc ttgactccca cggaacggat    120

cgatccgctg gagaacaaac tgctagatcc acatcctccc ttcccctggg aggaccccgg    180

tcctcccaca tcctcccccc agcctgacgt aacacaggct gtgtgaagtc cccgcgaaag    240

ctgctcacgt ggcaattgtg ggtcccccct tcaccaagac accaggtctt tcctccttaa    300

ggctagcccc gatgtgtgaa ttcacattgg gcaactagtg gtgtcactgt gcgctcccaa    360

tctcggccgc ggagtgctgt tccccaagcc aaacccctgg cccttcacta tgtgcctggc    420

aagcatatct gagaaggtgt tccgctgtgg ctgccagcct ggtaacaggt gccccagtgt    480

gcgtaacctt cttccgtctc cggacggtag tgattggtta agatttggtg taaggttcat    540

gtgccaacgc cctgtgcggg atgaaacctc tactgcccta ggaatgccag gcaggtaccc    600

caccttcggg tgggatctga gcctgggcta attgtctacg ggtagtttca tttccaattc    660

ttttatgtcg gagtc                                                     675
```

<210> SEQ ID NO 438
<211> LENGTH: 610
<212> TYPE: DNA
<213> ORGANISM: Kobuvirus sp.

<400> SEQUENCE: 438

```
gtaacttcaa gtgtgtgtgc tcgtaatctt gactcctgcc ggaatgccgc ccggttcagt     60

gaacaaacag ctaggcaagt ccctcccttc ccctgtggtc ggttctcacc ggccaccatc    120

cctcccccag cctgacgtgt tacaggctgt gcaaagcccc cgcgaaagct gctcacgtgg    180

caattgtggg tccccccttt gtcaagacac cgagtctttc tcccttaagg ctagcccggt    240

cccacgaacg tggaactggc aactagtggt gtcactacac gcctccgacc tcggacgcgg    300

agtgctgttc cccaagctgt aaccctgacc caagactgtg ctgcctggca agcaccgtct    360

gggaagatgt tccgctgtgg ctgccaaacc tggtaacagg tgccccagtg tgtgtagtct    420

tcctccagtc tccggactgg cagtcttgtg taaagatgca gtgtaaggtt caagtgccaa    480

atccctggaa ggagtgaccc tctactgccc taggaatgct gtgcaggtac cccaacttc     540

ggttggggat ctgagcacag gctaattgtc tacgggtagt ttcatttccc atcctctctt    600

ttttggcatc                                                           610
```

<210> SEQ ID NO 439
<211> LENGTH: 576
<212> TYPE: DNA
<213> ORGANISM: Kobuvirus sp.

<400> SEQUENCE: 439

```
tttgaaaagg gggtgggggg gcctcggccc cctcaccctc ttttccggtg gccacccgcc     60

cgggccaccg ttactccact ccactccttc gggactggtt tggaggaaca taacagggct    120

tcccatccct gtttaccctt actccactca cccctcccct tgaccaaccc tatccacacc    180

ccactgactg actcctttgg atcttgacct cggaatgcct acttgacctc ccacttgcct    240

ctcccttttc ggattgccgg tggtgcctgg cggaaaaagc acaagtgtgt tgttggctac    300

caaactccta cccgacaaag gtgcgtgtcc gcgtgctgag taatgggata ggagatgcca    360

ataacaggct cgcccatgag tagagcatgg actgcggtgc atgtgacttc ggtcaccagg    420

ggcatagcat tgctcacccc tgaatcaagt catcgagatt tctctgacct ctgaagtgca    480

ctgtggttgc gtggctggga atccacgctt gaccatgtac tgcttgatag agtcgcggct    540

ggccgactca tgggttaaag tcagttgaca agacac                              576
```

<210> SEQ ID NO 440
<211> LENGTH: 513
<212> TYPE: DNA
<213> ORGANISM: Kobuvirus sp.

<400> SEQUENCE: 440
ccaccgttac ttcactccac tccctcggga ctggtttgga ggagcataac agggcttccc 60
atccctgttc accctcaata ccacccaccc tttccctcaa ccatccctat ccacacccca 120
ctgactgatt cccttggatt ttgacctcag aacgcctact tgacctccca cttgcctttc 180
ccttctcgga ttgccggtgg tgcctggcgg aaaaagcaca agtgtgttgc aggctaccaa 240
actcctaccc gacaaaggta cgtgtccgcg tgctgagtaa tgggatagga gatgcctaca 300
acaggctcgc ccatgagtag agcatggact gcggtgcatg tgacttcggt caccacgggc 360
atagcattgc tcacccgtga atcaagtcat tgagattcct ctgacctctg aagtgcactg 420
tggttgcgtg gctgggaatc cacgcttgac catgtactgc ttgatagagt cgcggctggc 480
cgactcatgg gttaaagtca gttgataaga cac 513

<210> SEQ ID NO 441
<211> LENGTH: 675
<212> TYPE: DNA
<213> ORGANISM: Kobuvirus sp.

<400> SEQUENCE: 441
gggggtgggg ggggcctcgg ccccctcacc ctcttttccg gtggccacgc ccgggccacc 60
gatacttccc ttcactcctt cgggactgtt ggggaggaac acaacagggc tcccctgttt 120
tcccattcct tccccctttt cccaacccca accgccgtat ctggtggcgg caagacacac 180
gggtctttcc ctctaaagca caattgtgtg tgtgtcccag gtcctcctgc gtacggtgcg 240
ggagtgctcc cacccaactg ttgtaagcct gtccaacgcg tcgtcctggc aagactatga 300
cgtcgcatgt tccgctgcgg atgccgaccg ggtaaccggt tccccagtgt gtgtagtgcg 360
atcttccagg tcctcctggt tggcgttgtc cagaaactgc ttcaggtaag tggggtgtgc 420
ccaatcccta caaaggttga ttctttcacc accttaggaa tgctccggag gtaccccagc 480
aacagctggg atctgaccgg aggctaattg tctacgggtg gtgtttcctt tttcttttca 540
cacaactcta ctgctgacaa ctcactgact atccacttgc tctcttgtgc ctttctgctc 600
tggttcaagt tccttgattg tttttgactg cttttcactg cttttcttct cacaatcctt 660
gctcagttca aagtc 675

<210> SEQ ID NO 442
<211> LENGTH: 675
<212> TYPE: DNA
<213> ORGANISM: Kobuvirus sp.

<400> SEQUENCE: 442
gggctataaa tatgggcatt cctcttcccc cttccccttt tgaagatgag tgcgcatatt 60
cttgactccg cctggattgg ccgcccaagg cgtgaacaag cagctaggcc accatgacac 120
tgcggtggtg tccgaacccg cgggtgcctt cacgggcacc tgtggtatgt aggactccca 180
ccgtggtctt ccctttcccc ctcaatcttt ccccctggtt cgactaacgg gaccagtgct 240
ggaacctgtc cggtgaacgg tatagcaggc ccccccggca gaaacacccg gtgcttaccc 300
cttaaggcta gccccccttcc atgaatttgg ttggggcaac tagtgggtgt acagttggcg 360

```
tgaaccctcc ggtctaggag tgctcttgcc caatcctctg tgtgtgcctt gcagtaggga    420

ctggcaatcc ttcgcgtagg tgatccgctg tgccatgcca tcctggcgac aggaggccca    480

gtgtgcgcaa cctacgtccc ttctgggtgc tgcattgcat tacctttgga gtaagcttgg    540

tgtgccgaaa ccccagggtt tacgtaccac tcgtggtgtg aggaatgtgc cgcaggtacc    600

ccatccttga ggtgggatct gagcggtagc taattgtcta gcaccacttt cttccttttt    660

tctttgctgg tcacg                                                     675
```

```
<210> SEQ ID NO 443
<211> LENGTH: 604
<212> TYPE: DNA
<213> ORGANISM: Aalivirus sp.

<400> SEQUENCE: 443

ttgaaagggg gtgctcaggg tagctccctg agctcttccc tccaccctct ttcaacgtct     60

ggcccacgat acgggccacc tttcaatctt aactaactat ccctttaatc tatttggatt    120

ttctggttta gaataatttg gaacacataa ttggattatc ttttaggatt gtggatagga    180

tttgttcggg atatcactcc cttcctgtgc taacacatat tctaattccc tcctttgtct    240

attatctctt ggaggtggtg ctgaaatatt gcaagccact tgagtgtata gatgaagtag    300

gctcaagatg aatgttgtgt tactcaaggc aagtgtagct atcactaaga tattggtaac    360

gtgaaacgga ttaccggtag tagcgtgatc ttccgtctta gtgctctagt gactagagga    420

caacgacatg gcatcacata tcttaaccct ccagttttgg catccgggac agaatgggct    480

ggatatccgc tttctttctg ggtatgtga tgggtggtat tggggtaacc accttgacca    540

tgacgctcga taagagtgac cgcctgatca ttgaaacctc tagtataaaa ttcaggctga    600

aatc                                                                 604
```

```
<210> SEQ ID NO 444
<211> LENGTH: 445
<212> TYPE: DNA
<213> ORGANISM: Grusopivirus A

<400> SEQUENCE: 444

tgcctgagta ggattgtgaa tttaggtatg agagggttag ccaacccatt ctgaaccata     60

atagatacgt caatctgaat ccatctaaat ctatctctta ggcagtggtg ctgaaatatt    120

gcaagctact agggatagac gtgatctgat tcaagaacct atctaatgtg gtgatgagaa    180

ggctaggttt atccatagta atcccttgtt ctgaacaggc aatgcacatg ctctagtagg    240

atctcgggct ctgcgattgg ctctaaaccg accaatccag gtagaggcac taagtgtagg    300

acttgccaaa atgtattaca tgctggtacc gactcactag tctggaaact ccacactgaa    360

agtgactggg gggggcccca tcacatttgt gctactgctt gatagagttg cggctggtca    420

acttggattg gtataaccag ttgaa                                          445
```

```
<210> SEQ ID NO 445
<211> LENGTH: 537
<212> TYPE: DNA
<213> ORGANISM: Grusopivirus B

<400> SEQUENCE: 445

gccatccgta ggttctggta aggttccatc aactgttggg gcgctagttg ctatgaccgc     60

attcacggac ggatgattta tagtatcacc caatccgggc acaacttctt tagccacttc    120

ttccacatta ctaagggctc tcttgccgag tttcaacgtc tagtccacga cacggacctt    180
```

cctacttttc tatcttctta ttttctctac taaattggta tctggtactg aagatatgcg 240
gattgtgatt ttgtgcctgt ctaaactaac cctattctag ggttaggtgg gtaccatata 300
ctaatggtga acaggattac ctatgtatcc attagtccct atggatctgg cgacccacaa 360
actcatgttc atagagaggc taagctgagt gctcgccgaa taagcattgc ttcaggtgcc 420
gactattgtc tggaaaccac tcagtgatag ctataggggg gggccccgta gcatctgcct 480
tactgcctga tagggtggcg gctggtccat gaacatgcag taaccagttg acttgac 537

<210> SEQ ID NO 446
<211> LENGTH: 562
<212> TYPE: DNA
<213> ORGANISM: Unknown
<220> FEATURE:
<223> OTHER INFORMATION: Description of Unknown: Yancheng osbecks grenadier anchovy picornavirus sequence

<400> SEQUENCE: 446
ccttagggtc tggaatgcgt cctttctggg cacttccaca atcctaaggt aattttcaac 60
gccagcgatg gagcgatatc caaagaacct ttatgtttta gttcgtcttg tatgtttata 120
aaatataaaa ttgggattag caacccacaa aaacattttt gttattctca ccacatgaga 180
gggtggttaa acctcttcgt aacctatctt gcttgattgg ctacttgggc tagatttagg 240
acaacctctt tagcaagcct aaattactcc tcgtacttgc acctggtaac aggcgtacct 300
ggaggttacg gtggcgctaa cttggacttc tcgttaattc gtgcaagttt aaatgatgcc 360
tattttgaat acaagaaagt atgatagtaa cttagggcgt gaagttccgc ttaacataag 420
gcagtataag tactaagata aggtgtaaga cctaccttaa taactgttgt cttttctcat 480
ggtctttccg tgggagccct tgctaggggt aaagttaagt attctcaaat aatttttcat 540
tcaaactctt tctctctgtt tt 562

<210> SEQ ID NO 447
<211> LENGTH: 675
<212> TYPE: DNA
<213> ORGANISM: Gallivirus sp.

<400> SEQUENCE: 447
ccactcgcac ttcctggata gtgcgttaga tatgcccgac atatcgcttc caggaccaaa 60 gcccccccttt tctctttccc aaccagcttc gccactcaag ctgtaattcc atgtccggtc 120
tttccggcct tagtatcatg gaaatgtggt cgtgctcaaa tgaaattgag ttgacattga 180
tcaatgaaag ttgcactgaa ctttgctaaa ctggctagcg ccacctggtg tgtgccgttg 240
gtctcctcac atggtaacat gtgccaacgg gcccgaaagg ctagtgggca attaccgctc 300
caagggaggg gtacccaccc cgacctgaac agcggtaatg aagctcacct cccaggctct 360
gaccccgaga agtttagtta tttagtaggt gtaattagta cttgtgattg gtcaatttga 420
tagtagtttg aaacgttatg gatgaatgag tagaccccct gaaggtaccc cattacatgg 480
gatctgatca gggccacatt ctgcgtgtct ccccgcactt gtggttaaaa ccatgaaagt 540
tcatcccaaa caatcttttc ctcttctttt tcttttagtg gtgacaacct actggattgg 600
tgattaccaa tctgtactag tgttgtatta agacttgttg tgtggagaaa atggactctt 660
tcaagaagat ttttg 675

<210> SEQ ID NO 448
<211> LENGTH: 673

-continued

<212> TYPE: DNA
<213> ORGANISM: Unknown
<220> FEATURE:
<223> OTHER INFORMATION: Description of Unknown: Falcovirus A1 sequence

<400> SEQUENCE: 448
taaaagggga cgcggtgtgg cagctttggc tgtcatgccg tgttctcctt ttaccccaag 60
gactagcctt gggggttttc caaattcctt tccctgtagg ctttacttct ctttatctat 120
cttttctgta actaagtttt gcctattcta aaaatatttt agaatgtgtt tggatgtaac 180
taagtttgtg cctgccctaa aaatatttta gggcttgttt ggataacctc gtcccttgtg 240
ttcagtgccg cacaatttgc taggcactgt tcacttcctt tgtttgtcca ttatgtatgc 300
taaggtatga attccatcat atgcttagcc tctacatgca taatcttatt ccctccctgg 360
tgcaaactac gcccccaaca tatgtgaatc ttttaagcat attcctgacc ccacacatat 420
atatgtgttc tcgtgaattc ccccaccgtg aggtggtcac ttggacgtgg tgtgtgtcac 480
acagcatata tatgatgcag gatgttgttt ttaagataag catatgtcct tagtgctttg 540
catcatttcc tccacacccc gtgaatgcgg ctaatcttaa ccctgttggg tccgtgggta 600
aaccaaccca ttaaccacag gacggaaccg actactttcg ggagtgtgtg tttctttttc 660
ttcttttgtc act 673

<210> SEQ ID NO 449
<211> LENGTH: 665
<212> TYPE: DNA
<213> ORGANISM: Tremovirus B

<400> SEQUENCE: 449
ttcaaatggc ccctgggttg atacccagtg gtcatttgga cactttggta aggaggtgta 60
attatccttc ccatgtggaa cctagtgctt aggtttactt tatatgttct ttgtttgtcc 120
tttgtacttt ctatcgggca atcttgttgt tcaatacaat atgtatttga actgcctaag 180
ataaattcag ttttcaacca acccctctct tggggttgtg tctttctttc tttcttatat 240
cctcttaagc tgacttactt gctaatccga ctcctcgtca acgggagggt aaagcagtat 300
cactagggta ttgtgatgta ggagaaaaag taagtagaga tagtgcatgt aacgaaagtg 360
acttggtact ttaaactctc ttaatcccaa agtgtggtat tggtcatgtt ggagtaggct 420
acgggtgaaa ctccttcaca tttagtaatg tgttcacacg ctaacgctac ggtagatgac 480
agactaggtc ttattctcaa cgtaggggga cgggtgtatg ttcatgatta gccacatatt 540
aaggttttga ggggctgagt catataagta tgtgcattaa tttctggtac tggtccctgg 600
ggactggccc ttttctaggt tgattttagt ttccccaatt tttaaaaact aatgagattt 660
acgac 665

<210> SEQ ID NO 450
<211> LENGTH: 675
<212> TYPE: DNA
<213> ORGANISM: Hepatovirus A

<400> SEQUENCE: 450
tctttggtct ggggaactaa aataccagac ccgcgtttgc ctagcgatat aggctttaat 60
tgttgtttgt cattgtgcgt ttgatatgtg ttttaatgta aataataatt ctagcaggtt 120
ctagttcttg atcatgtcct ctttaaggca ctcatttcaa cttgctatct ttcttttctt 180
ccttggttct ccctacacca aatgcactgg ccgctgcgcc cggcggggtc aaccacatga 240

-continued

```
ttagcatgtg gctgtaggtg ttgaaggctg ggacatgaac atcaatggaa tagtgcgcat    300

gcttactggg gtccattgaa gtagtgggat ctttctattg ggtaggcta cgggtgaaac    360

cccttaggtt aatactcata ttgagagata ccttggatag gttaactgtg ctggatatgg    420

ttgagtttaa cgacaaaaag ccatcaacag ctgtggacag aacctcatcc ttagattgct    480

cactatggat atgtgctctg ggcgtgtttc ttgcatgatg gccattggtc aattcatgcc    540

tgggccaatg taggattagc cttaaattac tttttaaaag tagcctcatt tagctggact    600

aatggtgggg cgtatgatcc tgcatttggc ctctggggta atcaggggca tttaggtttc    660

cacataatag caaat                                                      675
```

<210> SEQ ID NO 451
<211> LENGTH: 675
<212> TYPE: DNA
<213> ORGANISM: Hepatovirus sp.

<400> SEQUENCE: 451

```
gcaaggggtg gttttaacct tgcacgcgtt taccgtgcgt taacggtttt ccatgtttgt     60

atgtcttgtt tgtattatgt gttttgtaaa tattaattcc tgcaggttca gggttcttta    120

atcatgttgg gctgtaccca cactcaactt ttggccataa gtgagtttct taacgaacct    180

tttaacacag gatgttatta gggcccaata ttttccctga ggccttcttt ggcctctatt    240

ttttcccctt ttctatctcc ttgtattccg ggctcacgtg atgccaatgg actgacccat    300

gcgcccgtgg gggttaacta ctggagtagc cagtagctgt aggtgctaaa agtcacgtac    360

gtgtaagact ggacgagacc tctcagctat aactgaaagt agtaagtatg tctgaacttc    420

ttgaaggggt aggctacggg tgaaacccct taggttaata ctcatattga gagatacctc    480

tgataggtga aggtttccgg tagaggtgag tttaacgaca aagcctctca acggatgtgg    540

gcccacctca tcagcaagat gctttcatac ccaataccgt aggggctggg ttgttgagtt    600

cagtcccaag cgtccctccc gcaaggttgt aggggtactc aggggcattt aggtttccac    660

aattaaacaa ataca                                                      675
```

<210> SEQ ID NO 452
<211> LENGTH: 675
<212> TYPE: DNA
<213> ORGANISM: Hepatovirus D

<400> SEQUENCE: 452

```
ctttggatgc ccatagtgcg ggggtataaa taccgcactc cctttagctg ttccgagggt     60

atcggaacct atatgtttgt tttctgtctg tctgtcagct ttatgtgtgc tcgtcccctt    120

tagggcactc atttcagctt gctttcattc ttttcttccc cggttctcac cttaccggag    180

gcactggccg ttgcgcccgg cggggtcaac ctagtgatta gcactaggct gtaggtgtct    240

aaagtggtga cattaagact tggtaactga tttcagcact gttaactgat gttggggatg    300

acttgattga tcttctggaa ggggtaggct acgggtgaaa ccccttatct taataccact    360

atgtagagat agattcagta ggttaagggc agtggataag gttgagttca ttttggacaa    420

taaaccttca acactggtgg acccaatctc actgaccaga tgctttcttg actgatcctt    480

cagaggggtg attcttctga ataggttgcc ttgacactga tgcctgagac ccattgggtc    540

gggccttaaa tcatggaact ccactggact ttcatggcct agcttctgcc ttagacagac    600

tctggggccc cacgaccctc tgggcccttc ggggtactca ggggcattta ggtttttcca    660

caattaaaag agtta                                                      675
```

<210> SEQ ID NO 453
<211> LENGTH: 560
<212> TYPE: DNA
<213> ORGANISM: Hepatovirus sp.

<400> SEQUENCE: 453
gtcatgtttc tctttaagaa cactcaattt tggccataag tgagactctt gtcgaacctt 60
tcatgtcagg accatgttag ggccattatc cttttccctg gggcattctt cttgcccctg 120
tttcatcttt ctatcatctt tcttccgggc tctcacaatg ccaatggagc gaccgatgcg 180
cacgtcgggg ttaacccatg gattagccat gggctgtagc tgctaaaagt tgtgactcct 240
gaagcatact atcaatggta gtagatgtaa ctgaaacact gaagcttctc tgatcttgaa 300
agaagggtag gctacgggtg aaacccttca ggttaatact catattgaga gatacctttg 360
gtaggttaac gttggcggat aatgttgagt ttaacgacaa taaacattca acgcctgtgg 420
gcgaacctca ccaatttcat gctttgaagt gaatgtgcgt agggtctcta tcggagatgc 480
tatgtggatg gtgccctccc tggaaacagg ttgtaggggt actcaggtgc acttaggttt 540
ccacatttta aagatttttc 560

<210> SEQ ID NO 454
<211> LENGTH: 675
<212> TYPE: DNA
<213> ORGANISM: Hepatovirus I
<400> SEQUENCE: 454
ggctgcctgt gtctcagggg taagtactgg ggccgcgttg accgtgcggt acggttatgc 60
ttttagatta ggatgtccgt ctgtccggca ctctcttttg cttaaaatgg ccttaaatcc 120
atgggaggcg taaccatggg ccctttgtta cctagacatg attgcattgg gggccgtcct 180
tggggcttag gccccagcca tttctcttga ctcgtctaag agtttacttc atccttttct 240
ttactttatt ttccaggctc tcagcatgcc gacggctctg accactgcgc ccggtggggt 300
taactgcatg attagcatgc agctgtagga gttaaaagtg ctgacaggcc aattctgacg 360
taagtccact ctatattaac ttgatcaagt aaggttgatt gatctttgtg agagggtagg 420
ctacgggtga aaccctctag gttaatactc atattgagag atacctccag aaggtgaagg 480
ttggcggata ttggtgagtt cttttaggac aaaaaccttt caacgcctgt gggcccacct 540
cactggcaca atgctttcat ccccaattgt gatgggtagt ttggactgaa atcaggagta 600
acctgcccta cgagtttagg ggtagttcag gggtatttag gcttccacat ttgatagagt 660
ttatgagagt gagcc 675

<210> SEQ ID NO 455
<211> LENGTH: 527
<212> TYPE: DNA
<213> ORGANISM: Hepatovirus C
<400> SEQUENCE: 455
ttcaaaagcc ccagcggggt ttcattaccc cgctgtggct tttggacttc cctaggatgg 60
ggaagtaaat taccatcctc gcgtttgccg tgcgttaacg gctacttttc ttctagctgt 120
agaagtaaaa ttcagcatgt tttatgtttg tttgtcttgt ttgttatata catttttaca 180
ctcctacaaa tgcacatgaa gaacagtttg tagagattaa caaacgctta gctgaaccta 240
ggtggtgaat ctagtagtaa gataagtaga ggaagctata ccttaagttg gttgggccct 300
cgtgtttgct ctataaacaa aaccaagtga gtagagtgga tgaacagtac taaatccctg 360
agtacaggga acctcacagg tgtgatacac ttatgtctat gtgacctggt tggaggttgg 420
gcgtgcccta tgatactgga gtgggagatc ttttggggaa cccacgtttt cacactgcct 480
gatagggtct tgccgagaga ctcacttgtt tcggctgtac ttgtaac 527

<210> SEQ ID NO 456
<211> LENGTH: 665
<212> TYPE: DNA
<213> ORGANISM: Fipivirus A

<400> SEQUENCE: 456
tgcgggtaaa ctcccgcatg tgtgaatgag gcgatgtccc aggaactaac tgccgatcct 60
ggttttaact acgatccgta tttgttacta atgcgatatc cccccattgt ttgcctccat 120
gttgttttca acgcttttgg ccttgagtgt tatcaagtgt tttagcgaca tagtgggaag 180
ctacggctgc gtccccattt ttgagtggcg acccagtttt agtggccact ctgtccctga 240
actgcgctat aatgtgaatt tatgttcaca aaaacggact gatgtaactg ttaatgacta 300
aggaatagta cctcactgaa gtatcaagac cccgttcgag cggtgtacat atatggatgg 360
aaaccttgtc tgagtcatct cgaatactaa tcaatgaggg atgtcgagta agcatatcat 420
gaaccacata gaatagtggg gtttcggggt tagaggctct ctgcagcaat gtatctctaa 480
caccatggcc gaaatgagag atagagacca cgatgtttgt gtgtaagtaa tgatgtgtgg 540
aaagaaaatt ctgaatgttg gtatgatatc agtctaaggg gagtggctca cctaagagct 600
acccaaacat ttcacagcag acaacataac gtactgagag tagttggaag gttccagaaa 660
tcagt 665

<210> SEQ ID NO 457
<211> LENGTH: 467
<212> TYPE: DNA
<213> ORGANISM: Fipivirus C

<400> SEQUENCE: 457
cgcggttaaa cccgcgcaac cttctttcag ccgcgtctga gtagcgcggt tagtcctgat 60
acacagtttc ctgttgggta ctgtgtcttc gggtgaatgc tcttgtgtga atgttttagg 120
ctgtttaagg gaagcgtttc cccgtgcgct gtgagggttt ctcacgctct ttcggggtgc 180
agtctcttct gttgttcatt aagatgtatg gatgcactgt tgtgaaggat ttgtgaactg 240
gggatcgaca ccccgtgagg ggtgccccag tgtccatagg agtttgctgg agaggtgtgt 300
tgctgtagtg actatccgtg acctggcatt ctaaggtgtt gaccccaacc tgtgagggtc 360
tggatcgcag tgttgaagtg ctttggaggg ttcaatgggg tttctgtagt ggatattatg 420
tgcttgacga ctactggtac gagtgtattg ggggtctaca tgtgtga 467

<210> SEQ ID NO 458
<211> LENGTH: 657
<212> TYPE: DNA
<213> ORGANISM: Fipivirus E

<400> SEQUENCE: 458
ctcttccgat cttgggggtt cgccccccatg tctcatttca actagccgtg tgtctagtta 60
acgcaccgcc tcaccctggt cgttatcggg tcggttcttg cgaccgttag atcgtgagcg 120
tttctgagga tcagttcgta taagttctcc ggtgtggcga ccgtaaaatc gtcacgtccc 180
atgcaataga tgacgttaaa ctcgtttgcc agttacataa aggaatgttg ttacttttaa 240

```
attgtctgtt acatttaaca tcttgccagt atgatgctac tgtacactac gggtgtagga    300

accttgtagt gtgacgtatc actcatatgt ggatgggtgc tccagacctt tatggaagct    360

ctcagttagt agtgatcctt gacttcattg agccctggta acagtggaag tcaagatgta    420

tatgttgctc aacacacttc ggtgctacga agctgtttgt ggaagtactg gcgaggttca    480

ttctgaatca tatgtttgtc acatagtcag ggagtgccgt cgcttacgac ggaccctttt    540

tctttataat tacaaatctg tgtctcaagt gttgttggct ggttttcttc ttctgttttc    600

attgttcata tatatacgtc agagtgaaag actcggtata tacaaaactg atccaga       657
```

<210> SEQ ID NO 459
<211> LENGTH: 506
<212> TYPE: DNA
<213> ORGANISM: Aquamavirus sp.

<400> SEQUENCE: 459

```
ttcaaaggtg gcgggagagt tggcctcacg ctgtttagcg tgagagctgg ctctcctgcc     60

ccttcccctg agccggggat cttggctcat tcccctcttt tctatcctcc ctcattggac    120

tttacggatg acccggcata aacttgacaa ccgatgttgg atttcccttg tggctgtgat    180

ggaggacata ccctcgggtg tagttgtgtg cgtgtcgctc tgcgactcga gcttcaaagt    240

ggtgctgaaa tattgcaagc gtcgttgctc gattaacgga gtggtacaat cctatgaacc    300

caagtgcatt catgcgaaag ccccggaggg gtgagtagca tggactcgaa tcagaagagc    360

tggagctcgc ttggtacggc acgtagcatt gctttgccta aagaccaagg gggtatggct    420

ataggtgggg gcctatagct tgtccagtgc tggttgacag actcgtgcta cgcgtctggt    480

tcgagtataa gtagctgcaa ctcact                                         506
```

<210> SEQ ID NO 460
<211> LENGTH: 548
<212> TYPE: DNA
<213> ORGANISM: Avisivirus A

<400> SEQUENCE: 460

```
ttcactcgct ttcccccccct ctctataggg gcggtctttt aattcttatt aatttcctac     60

tttactatca aatttcttct aagtagggac tgaggtcact tagccctccc tctcctgggc    120

tttccagggt tatagaggtt ctaaagctaa gccatgtgtc ttgagctaca cttagtacaa    180

aggtttagta atgattgtac atgccagtaa ccttctagtg cccatggatt aaagagtggt    240

aacactctcc atggggcccg aaaggctagt gggcatagtt ggcatcaagg aaggggtccc    300

caccccaacc tgaattgctg gctagaagct caccttagaa gaagtgctgg gtgacaacgt    360

gtccaatcgt gaacgactga tggaaacgtg tggagatgga tatgtggggg ttcactgagt    420

agatgccctg aaggagaaat ctgatcaggg gcccgtgact atacgctagg taaaccgggt    480

ataaaaacca tgaaaggtgg cccaaaatct cttcctttta ttttatttct atgttggtga    540

cagtcaag                                                             548
```

<210> SEQ ID NO 461
<211> LENGTH: 492
<212> TYPE: DNA
<213> ORGANISM: Avisivirus B

<400> SEQUENCE: 461

```
cacccctac tgccctaacc cccaaagtta gttatagggt ggctccctac ccttactcca     60
```

cggggtaagc cctaacccgg ttgaatctca agatcagcct tagcgaggac tattagtacc 120
gctcaaaccc tttgcctgta gtgcccaggg gtcacagagg ggtgaccctc tccctggggc 180
ccaaaaggct aggtggcaag acagggtcca agtgaggggc tactctaagt agccccaagc 240
tgaacatcct gtctgaagcc acccttgcag ggccaggttt gattggggaa actagacacc 300
agctttgtcc tgggattggg gggatatcga gttagtccag gaggtgcgag tagatgcccc 360
cgaaggtacc ccaggcacat ctgggatctg atcgggggcc cgtgactata caataggtaa 420
accgggttaa aaaacatgaa agcgcctctc tctttcctac ttcttttatt gactggtgac 480
aaaaatagca gt 492

<210> SEQ ID NO 462
<211> LENGTH: 517
<212> TYPE: DNA
<213> ORGANISM: Crohivirus A

<400> SEQUENCE: 462
gttgaagtcc atttcttgct tgcccccgat gaatcctgtt aaggcctcac ggccctaagg 60
gtgaaactcg gttatcccct cctgtacttc gagaagatta gtacaacact atgaaatcta 120
catcttgtga tccgggataa ccccaatccc agaaacctgt gatgggcgtc accacccctc 180
ttatggtaac ataagggtgt cgccgcgttg gcacaggacc ctttgggctg gatgttttta 240
gtaatggtgt cgaaggtcct attgagctac aggagtttcc tccgccctgg tgaatgcggc 300
taatcttatc cctgagccta aggttgcgat ccagcaactt gatggtcgta atgcgtaagt 360
tgggggcgga accgactact ttccagaagg cgtgtttctt tgttttgtct gttactatgg 420
tgcatgatat agatattgaa tatttgatct ttttgagctg tttcttatct tattgctaca 480
tcctttcagg tgttggattt acattttggt taataag 517

<210> SEQ ID NO 463
<211> LENGTH: 393
<212> TYPE: DNA
<213> ORGANISM: Kunsagivirus B

<400> SEQUENCE: 463
gattttctgg ttatcccttt tggacttggt aggggcccac gtgcccaccc acctctgtgt 60
gtgttgattt ctaatcgatg cctggcagtg gcggccacct ctccttactg gtaaacctcc 120
ggtgagtgaa gttgtcaagc tacaggtacc gtgcaggatg aaatgcgcac atgtgaacaa 180
actaggagtc atacaccggg tcaaactctg gaaacggagt ccgggactct gaccttggtt 240
gggtgagctc gaggcatcac attgatggac gcgattcgct atccttccct agtaggacct 300
tgtggtgtac ccctggttgg gaatccaggg ctggtcgggt gcagggtgac agcctgttct 360
ccacctcaac cattgtagga gaaatcaacc cct 393

<210> SEQ ID NO 464
<211> LENGTH: 675
<212> TYPE: DNA
<213> ORGANISM: Limnipivirus A

<400> SEQUENCE: 464
ttctttggat atccatttaa cgtgtaccct atacgataat tggggtggat tctggatgcc 60
tagttccagt gattggttaa gaactcgttt actacgtata gtatgattag caaagtgctc 120
gattgatcac gtaatgatct atgtggttaa aaacccagta gtatggtata tactcagtag 180
tgtacactgt gagtacaact cttggcgtag agagaacaat tcacccgaat ccgtggcgta 240

```
tccatggaaa taagtttacc taattgtatg ttacaaggca tatgagacat ttatgagata    300

tggtttattt tgactaaacg agtgtagagg tggtggagtc tatccaactt caagccatgc    360

aattgttgtg ttgattgata tcattgacca tttttgtgga ttgtgtacac atacaatttg    420

aaaattaacc ccctcaagaa taagacatgg gaccattcgt ggtagatacc gtgctcggat    480

gcttgagatt agatgggtta gactagtttt ggaatgagat tgccgagaaa gtcccgctag    540

acatgtttta caagtcgtgg tattccgcta gactttttcg cagacacatg gaagggtcca    600

tgtgttgtgc aattgcaggg tgacagccca actgcagagt tttccttact agaataaaaa    660

tctgttgtca atttt                                                     675
```

<210> SEQ ID NO 465
<211> LENGTH: 501
<212> TYPE: DNA
<213> ORGANISM: Limnipivirus C

<400> SEQUENCE: 465

```
gtttctgagc actggtaaga gcttagacaa acgtttttaa aatttatttt ctctgcaact     60

tttgtttgtg tttattttta tttgttaatt ttgcgcctaa gcatttgttg cgaagtattt    120

gattcattag taatattact tattgtttat ttagatggta ttcaaagtgg tgggagtatc    180

gaacccaagc gtcgtatgct atctccttga acaattttta atcattgcga agtgatcatt    240

gaaaaggata ggtgtttaag aactcaaaga gtgttaataa tgttgggtga caggtgtccc    300

catagaattt attaacatga tttggactgg ttatctagta agaagaacca tcgaacgcac    360

gagcgagcat tgcttgcggg gcagttaccc tgcgtcgatg taagtgtgta ccggggggtg    420

cacatgttga ttctttatgg cctgataggg tgcgtcattc gcgcctagat aattagtata    480

atgcgaatgg aataaattta c                                              501
```

<210> SEQ ID NO 466
<211> LENGTH: 675
<212> TYPE: DNA
<213> ORGANISM: Orivirus sp.

<400> SEQUENCE: 466

```
ggtcccaggc caatattctt cgtaaggctt ggttccaatt ttccaccact cgtgtttggg     60

ttctggccta tggtacccag aggggcggtt tgggggaatt aactcccccct cccctgtggt    120

cctataccac cccacacctc tgtgggcttt ctttactatc ttcttgtttt ccgactttta    180

aacactaggc aggcgcgcct agtcatacac cgcccggctg gtctttccag ctcttgtggg    240

cggtgcgcgc tggtccatcg tgcccagcga catagcacct tgtggacacc tccgaacgcc    300

ctcccctgta tggggtggtg cccaggggtt tcagtgtggt gacacactcc ctggggcccg    360

aaaggctagt gtgcaacagg tgaggtacag ccagctgccc ccgtggctgg agggaccaag    420

cttgtgaagc acacctcacc ttcttggggg tgggctagta agtggtgaaa gcatagtgtc    480

cgtgtcgctg gccaacactt tgggtcaagt ccagccactc agtgagtaga tgcccaggag    540

gtacccctag tggatctgac ttggggcctg ttacttaatg caggttaaaa actatgaaag    600

ctgagtagtg tagcccggct ggtggcttct cttccttatt cattctattt tatggtgaca    660

aacgcaactg aagcc                                                     675
```

<210> SEQ ID NO 467
<211> LENGTH: 675
<212> TYPE: DNA

<213> ORGANISM: Hepatovirus A

<400> SEQUENCE: 467

```
cttgatacct caccgccgtt tgcctaggct ataggctaaa tttccctttc cctgtccttt     60
ccctatttcc ttttgttttg tttgtaaata ttaattcctg caggttcagg gttctttaat    120
ctgtttctct ataagaacac tcaattttca cgctttctgt ctcctttctt ccagggctct    180
ccccttgccc taggctctgg ccgttgcgcc cggcggggtc aactccatga ttagcatgga    240
gctgtaggag tctaaattgg ggacgcagat gtttgggacg tcgccttgca gtgttaactt    300
ggctttcatg aacctctttg atcttccaca aggggtaggc tacgggtgaa acctcttagg    360
ctaatacttc tatgaagaga tgccttggat agggtaacag cggcggatat tggtgagttg    420
ttaagacaaa aaccattcaa cgccgaagga ctggctctca tccagtggat gcattgaggg    480
aattgattgt cagggctgtc tctaggttta atctcagacc tctctgtgct tagggcaaac    540
actatttggc cttaaatggg atcctgtgag agggggtccc tccattgaca gctggactgt    600
tctttggggc cttatgtggt gtttgcctct gaggtactca ggggcattta ggtttttcct    660
cattcttaaa caata                                                     675
```

<210> SEQ ID NO 468
<211> LENGTH: 675
<212> TYPE: DNA
<213> ORGANISM: Hepatovirus A

<400> SEQUENCE: 468

```
cgccgtttgc ctaggctata ggctaaattt tccctttccc ttttcccttt cctattccct     60
ttgttttgct tgtaaatatt gatttgtaaa tattgattcc tgcaggttca gggttcttaa    120
atctgtttct ctataagaac actcatttca cgctttctgt cttctttctt ccagggctct    180
ccccttgccc taggctctgg ccgttgcgcc cggcggggtc aactccatga ttagcatgga    240
gctgtaggag tctaaattgg ggacacagat gtttggaacg tcaccttgca gtgttaactt    300
ggctttcatg aatctctttg atcttccaca aggggtaggc tacgggtgaa acctcttagg    360
ctaatacttc tatgaagaga tgccttggat agggtaacag cggcggatat tggtgagttg    420
ttaagacaaa aaccattcaa cgccggagga ctgactctca tccagtggat gcattgagtg    480
gattgactgt cggggctgtc tttaggctta attccagacc tctctgtgct tggggcaaac    540
atcatttggc cttaaatggg attctgtgag aggggatccc tccattgcca gctggactgt    600
tctttggggc cttatgtggt gtttgccgct gaggtactca ggggcattta ggtttttcct    660
cattcttaaa taata                                                     675
```

<210> SEQ ID NO 469
<211> LENGTH: 519
<212> TYPE: DNA
<213> ORGANISM: Parechovirus F

<400> SEQUENCE: 469

```
ggtcggggag atgtgttcat gatcggttaa caccatcatg gatcatctct ccccgacctc     60
tttttgaccc agctatgggt taaatagtac ttttcttttc tcttttgctt tcttttgtgt    120
tttgtttgtt ttgcaacata taacaagcat tttatcagta ttagtgtctg caactgtata    180
acaagcaagg tggagcaatc atgcgagtat atctcaattg aattgtgaca cacaagtgtg    240
cactatgtgg aataaatgcc attttggcca aacctggtta gccagaccag tagtaggaca    300
atttggcacc cttagtgggc gcgacctaga tgctagggat gagcaaacct atttcccctg    360
```

agtacagggg ctctccttca cctctacatt ttggacctct ttttgagtat cctcgataga 420
aggtgaagtg acggtgtacc ggatggttaa ttgatctcat tgctgggtga cagcccgcta 480
ggaccaggca gcatctttgt atggacctgt acatgtaac 519

<210> SEQ ID NO 470
<211> LENGTH: 343
<212> TYPE: DNA
<213> ORGANISM: Parechovirus D

<400> SEQUENCE: 470
acatggggca ggtgtgctgt gccaagagca acactacggt ggccgagccg atggttcgtc 60
accacgtagt aggactccgt agtgcttggt tacggcggac gtaagtcagt tgagtgatgt 120
ctaagtggca aaccatgagt acatggtaac cttgtgtgga ctcgcgggac ggaatttcct 180
atcccattga ctccttgtag caaggtgggt atacccaacc acaatggcag caccctgggt 240
gggaacccag gggcctggat tagtatccag tcacacagcc tgatagggtg gcggctcagc 300
cactgaccag cgtctctaaa taattgtgag ctgttcatgc acc 343

<210> SEQ ID NO 471
<211> LENGTH: 675
<212> TYPE: DNA
<213> ORGANISM: Parechovirus C

<400> SEQUENCE: 471
cggtcatccc cctttcccca cagccggtgt gggttctaat cggctcctac taaacaccta 60
agcatcactg cgcctctatc tctcctatcc acaggtctaa gacgcttgga ataagacatg 120
tgggtgcaat aggaagatta gctagtccaa tctctccttc cagctacgct tctcccttcg 180
atgagcgtag ggggggcccc cacctccctc atctctggat agggctcttg ctacggggct 240
ttcccgtctg gaccagcagg cccactggtg cgcttccatt caagtttagt gtgcattact 300
gtctgaaata ttgctttgct aggatctagt gtagcgacct gcatattgcc agcggacttc 360
cccacatggt aacatgtgcc tctgggccca aaaggcatgt ctttgaccgt atgcagtaca 420
accccagtat aggtcctttc tatggcagta tggatctcag tgatgagtct atacagaata 480
tggaagtggt tcggatatgt cagcccgaag gatgcccaga aggtacccgc agataacctt 540
aagagactgt ggatctgatc tggggcccac caccttcggg tgggtagaag ctaaccatgc 600
cttgggttaa aaaacgtcta agggctgacc agacccgggg gatccgggtt ttccctatct 660
tgacctactc taatc 675

<210> SEQ ID NO 472
<211> LENGTH: 675
<212> TYPE: DNA
<213> ORGANISM: Unknown
<220> FEATURE:
<223> OTHER INFORMATION: Description of Unknown: Ljungan Virus 87-012 sequence

<400> SEQUENCE: 472
ctcattgccc acacctggtt ggttcccagg ttcatacaat aaccatcaat aaacttttaa 60
catctaagat agtattatcc catactagac tggacgaagc cgcttggaat aagtctagtc 120
ttatcttgta tgtgtcctgc actgaacttg tttctgtctc tggagtgctc tacacttcag 180
taggggctgt acccgggcgg tcccactctt cacaggaatc tgcacaggtg gctttcacct 240
ctggacagtg cattccacac ccgctccacg gtagaagatg atgtgtgtct ttgcttgtga 300

```
aaagcttgtg aaaatcgtgt gtaggcgtag cggctacttg agtgccagcg gattacccct    360

agtggtaaca ctagcctctg ggcccaaaag gcatgtcatt tgaccactca ggtacacaac    420

cccagtgatg cacacgctta gtaatggctt agtaacaaac attgattgat catttgaaag    480

ctgttaggag gtttaggtat gacgggctga aggatgccct gaaggtaccc ataggtaacc    540

ttaagcgact atggatctga tcaggggccc accatgtaac acatgggtag aagtcttcgg    600

accttgggtt aaaaaacgtc taggcccgcc ccccacaggg atgtggggtt tcccttataa    660

ccccaatatt gtata                                                     675
```

<210> SEQ ID NO 473
<211> LENGTH: 675
<212> TYPE: DNA
<213> ORGANISM: Parechovirus sp.

<400> SEQUENCE: 473

```
gccgtcgggc cttacacccc gacttgctga gtttctctag gagagtccct ttcccagcca     60

gaggtggctg gtcaaacaat accaaacgta actaaacatc taagataaca tagccctatg    120

cctggtctcc accagttgaa ggcatcttgc aataaaatgg gtggattaag acgcttaaag    180

catggagtca attatctttt ctaactagtg atcttcactg ggtggcagat ggcgtgccat    240

aactctatta gtgggatacc acgctcgtgg atcttatgcc cacacagcca tcctctagta    300

agtttgcaag gtgtctgatg aggcgtggga acttattgga aataattact tgctgcgaag    360

catcctactg ccagcggatc aacacctggt aacaggtgcc cctggggcca aaagccacgg    420

tttaacagac cctttaggat tggttaaaac ctgagtaatt atggaagata cttagtacct    480

accaacttgg taacagtgca aacactagtt gtaaggccca cgaaggatgc ccagaaggta    540

cccgcaggta acaagagaca ctgtggatct gatctggggc cacctacctc tatcctggtg    600

aggtggttaa aaaacgtcta gtgggccaaa cccagggggg atccctggtt tccttatttt    660

agtgtaaatg tcatt                                                     675
```

<210> SEQ ID NO 474
<211> LENGTH: 631
<212> TYPE: DNA
<213> ORGANISM: Parechovirus sp.

<400> SEQUENCE: 474

```
agagtccttt tcccagccag aggtggctgg ttaaataata cctactgtaa caaaacatct     60

aagatgtaac aaccacacac ctggtctcca ctggccgaag gcaactagca ataaggcagg    120

tgggttcaga cgcttaaagt gtgttgtaca tattcttttc taacctgtgt tttacacagg    180

gtggcagatg gcgtgccata actctaacag tgagatacca cgcttgtgga ccttatgctc    240

acacagccat cctctagtaa gtttgtaaga tgtctgatga cgtgtgggaa cctgttggag    300

ataacagttt gctgcaaagc atcccactgc cagcggatct acatctggta acagatgcct    360

ctggggccaa aagccaaggt ttaacagacc ctttgggatt ggttcaaacc tgaactgtta    420

tggaagacat ttagtacctg ctgatttggt agtaatgcaa acactagttg taaggcccac    480

gaaggatgcc cagaaggtac ccgtaggtaa caagtggcac tatggatctg atctggggcc    540

agctacctct atcttggtga gttggttaaa aaacgtctag tgggccaaac ccaggggga    600

tcctggtttc tttttaattt aagtaatcac t                                   631
```

<210> SEQ ID NO 475

<211> LENGTH: 675
<212> TYPE: DNA
<213> ORGANISM: Parechovirus sp.

<400> SEQUENCE: 475
gggccttata ccccgacttg ctgagtttct ctaggagagt ccctttccca gccctgaggc 60
ggctggataa taaaggcctc acatgtaaca aacatctaag acaaaataat ttgccttgca 120
cctggtcccc actagttgaa ggcatctagc aataagatga gtggaacaag gacgcttaaa 180
gtgcaatgat agttatcttt tctaacccac tatttatagt ggggtggtgg atggcgcacc 240
ataattctaa tagtgagata ccacgcttgt ggaccttatg ctcacacagc catcctctag 300
taagtttgtg agacgtctgg tgacgtgtgg gaacttactg gaaacaatgc tttgccgtaa 360
ggctttcatt agccagcgga ccaccacctg gtaacaggtg cctctggggc caaaagccaa 420
ggtttaatag accctaatgg aatggttcaa acctggagca ttgtggaaag tacttagtac 480
ctgctgatct ggtagtaatg caaacactag ttgtacggcc cacgaaggat gcccagaagg 540
tacccgtagg taacaagtga cactatggat ctgatctggg gccaactacc tctatcttgg 600
tgagttggtt aaaaaacgtc tagtgggcca aacccagggg ggatccctgg tttcctttta 660
ttttactttg tcaat 675

<210> SEQ ID NO 476
<211> LENGTH: 433
<212> TYPE: DNA
<213> ORGANISM: Parechovirus sp.

<400> SEQUENCE: 476
ctctattagt gagataccac gcttgtggac cttatgctca cacagccatc ctctagtaag 60
tttgtaagac gtctggtgac gtgtgggaac ttgtgggaat caatattttg ctttaaagca 120
tccattagcc agcggataaa acacctggta acaggtgcct ctggggccaa aagccaaggt 180
ttaacagacc ctagtggatt ggtttcaaaa cctgaaatat tgtggaacac actcagtacc 240
tactgatctg gtagtaatgc aagcactagt tgtaaggccc acgaaggatg cccagaaggt 300
acctgtaggg aacaagagac actatagatc tgatctgggg ctggctacct ctattttggt 360
gagtcagtta aaaaacgtct agtgggccaa acccaggggg gaccctggtt tccatttatt 420
ttacaaaggc act 433

<210> SEQ ID NO 477
<211> LENGTH: 488
<212> TYPE: DNA
<213> ORGANISM: Potamipivirus A

<400> SEQUENCE: 477
cacatggaaa gcttttcgct tccatgttta cgcacacact ctctttgaca ccctgttgta 60
tggtgttaaa ctacaacatt tgtctgtcta taatcgttta ttttgtttac cctatatgta 120
cccaagtatt tgattgcttg actcacataa gcatcggtaa cccatactgt tttatgagct 180
actacctctg ctgtctacat acattttata tgaatggttt gagctctgcc tcaggatcaa 240
acatggtaac atgttccttt ggtcagttag aatcttattg tataatctaa ggtgtctatt 300
agtacgtaga aagttgtaac acatatgggg cctgatagcc gctatctctg atggatgtaa 360
ggtaaccttc tttaggtctg atacattctg cacaggatcc aattttcggt gccctgtacg 420
agtgcactct tatgcacgag gacgagatat gctacaaccc actgcaaatt taaacccaaa 480
ctttaaca 488

<210> SEQ ID NO 478
<211> LENGTH: 675
<212> TYPE: DNA
<213> ORGANISM: Potamipivirus B

<400> SEQUENCE: 478
tttcaacgtc gtggctgacg ttaaaaagcc acaattccac ttacctttta ccttttatgt 60
ttaatgtttg ttagttttgt gatctttaac aaatagatct aaataatttg ttggtaacca 120
atctcggatg tttcggctgc attgtagttt atttatttca ttttagttgt aggtggccac 180
tacgtcctgg aatcatacat ggtaacatgt acctcggcgg ttatccacta ttacgctaat 240
ctaagaatat ttaaatgaaa atgtaagtgt tacggctgac tttgggcctg atagttaaat 300
gctcgcactg acagatagta ccctccttta ggatcgattc tgttacatgg gatccatttt 360
ggtgccccac tgattcaacc tctttgttga aaaagagtta gcatactaca aattttccaa 420
acaaaaaccc tttttaatga ctacaactta tgattttatg aattttactg ctcttgaaaa 480
agatattttg acattgatcg ctgtactgtt tcagacattc attgcatcca tttttgttgg 540
ctactcctca caaactcaaa acttttccac acgagaaacc ttgtttattg aattttgcct 600
ttatattttg gaacttgttg ttggatttat tgtttgctta attattgacc tcacacctgt 660
tttaaacact acaat 675

<210> SEQ ID NO 479
<211> LENGTH: 546
<212> TYPE: DNA
<213> ORGANISM: Unknown
<220> FEATURE:
<223> OTHER INFORMATION: Description of Unknown: Beihai Conger Picornavirus sequence

<400> SEQUENCE: 479
gggacaaccc cacagctggt acaaccattg tgggttggtc tccacccttt ttcaaccgtg 60
gcaacttcgg ttaaagttgc aaatcccccc tctccctatt ccacctccct tactttcact 120
ccccatatat ggtcccagat tttattctac ctctttatat ttttatttag tacagtggtg 180
gtgaattact cccagcataa actttgctgg atcagtgttc atcaagcata ctaattacta 240
atgtactgag ctatactatt atctggcatc tcacctggat aaccggtgtg accatatttc 300
ctaggttgcc tccctatgta ttttgtagca cctgtgcatc tgcacgttgg ggcgacaaat 360
tgtaggtttc ctggcacggg taagaattgt ggaaagctag tatgcagtta atgcaagggc 420
gcgtttttcg ctaccccgac actgctaaag tttttgggag gggtccctta aacatttcta 480
gtattgagtg atagctttgc ggcaggtcac cacaacctta ctataaataa acctgttgaa 540
tctcac 546

<210> SEQ ID NO 480
<211> LENGTH: 457
<212> TYPE: DNA
<213> ORGANISM: Sapelovirus sp.

<400> SEQUENCE: 480
tacgcatgta ttccacactc atttcccccc tccaccctta aggtggttgt atccccatac 60
cttaccctcc cttccacaat ggacggacaa atggatttga cctcacggca aacacatatg 120
gtatgatttc ggatacacct taacggcagt agcgtggcga gctatggaaa aatcgcaatt 180
gtcgatagcc atgttagtga cgcgcttcgg cgtgctcctt tggtgattcg gcgactggtt 240
acaggagagt aggcagtgag ctatgggcaa acctctacag tattacttag agggaatgtg 300
caattgagac ttgacgagcg tctcctcgga gatgtggcgc atgctcttgg cattaccata 360
gtgagcttcc aggttgggaa acctggactg ggcctatact acctgatagg gtcgcggctg 420
gccgcctgta actagtatag tcagttgaaa ccccccc 457

<210> SEQ ID NO 481
<211> LENGTH: 489
<212> TYPE: DNA
<213> ORGANISM: Sapelovirus sp.

<400> SEQUENCE: 481
ttgaaatggg tgtggggtac atgcgtatta cggtacgcat atattccaca ctcatttccc 60
cccctccacc cttaaggtgg ttgtatcccc ataccttacc ctcccttcta aaacagatgg 120
acaaatggat ttgaacttat ggcaagtgaa tatggtatga ctttggatac actttaacgg 180
cagtagcgtg gcgagctatg gaaaaatcgc aattgtcgat agccatgtta gtgacgcgct 240
tcggcgtgct cctttggtga ttcggcgact ggttacagga gagtaggcag tgagctatgg 300
gcaaacctct acagtattac ttagagggaa tgtgcaattg agacttgacg agcgtctctt 360
agagatgtgg cgcatgctct tggcattacc atagtgagct tccaggttgg gaaacctgga 420
ctgggcctat actacctgat agggtcgcgg ctggccgcct gtaactagta tagtcagttg 480
aaaccccc 489

<210> SEQ ID NO 482
<211> LENGTH: 675
<212> TYPE: DNA
<213> ORGANISM: Sapelovirus sp.

<400> SEQUENCE: 482
ccaaggatct gttgcatagg cgttgtatcc cctaaccttt tacctaccca tcccaatagg 60
actggtattt cggttttgat tgagtaatgg atactgattc tatacctgtt acccattcag 120
gggaaaaatg gagtttcttt catggatctg acttgatatg accaagagtc aacactttgc 180
gtgttggccg tatggaatgc tttaaggttt attctttgga ttatgacttc agggttggcc 240
gcccaggata aaaggcaatt gtggtaagtg atgttagtca ttggtggttg aaacctgcct 300
aagacgtcct aggtctacgc tgtgcgggcc gaagtaagct taggaataac agggagtatg 360
ccattttctg ctttcaccca acacgaccgt acacgaaaga gctagaggca ctttggggca 420
aagggaaaag ctttgcttag cccgaatgtt catttgagtc cttgacgaat gcgtcccgtc 480
tgtcccgacg gtgaggcgta tggcgcatgc tcatggcatt acccaatggt gtatctgtga 540
ggggggggct cctcacactt agtctagtgc tacctgacag ggccgcggct ggtcgtttgt 600
gtatggtata accagtagta atcccccatg gattgcttta acttcccctc ctcccttacc 660
aagacattct ctaag 675

<210> SEQ ID NO 483
<211> LENGTH: 579
<212> TYPE: DNA
<213> ORGANISM: Sapelovirus sp.

<400> SEQUENCE: 483
ttttaacttg ttatgacatt caaggaaaaa atgtcttttt cattatggga ctgacctgtt 60
tatgaacatg agcagcggca ctgctccacg ggctatccgt gtaagaaata ttgattattc 120

-continued

```
ttatggatca tgatttcagg gttggccgcc cagtctaaaa ggcaattgtg gtaagctatg    180

taagtagttg gctgttgaaa ggagccaagt acatcctagg tctacgctgt gcgggccgaa    240

gtaagacttg gaacaactct gagtaggcag tttttctctt tagcccaaca cgaccgcata    300

ctgaagagct agaggcactt tggggcaaag gtaaaagcat tgcttagacc gaatgttcaa    360

tgagaccttg acgagtgctg tcacagtgtc ccctgatggc agtatggcgc atgctcttgg    420

cattacccat atgtgtatct atagggggggg ggccccctat acttagtcta gtgctacctg    480

acagggccgc ggctggtcgt cggtgtgtgg tataaccagt agtaatcccc catggattgc    540

tttaactccc cctcctccct caacaaaact ttctctaag                           579
```

<210> SEQ ID NO 484
<211> LENGTH: 522
<212> TYPE: DNA
<213> ORGANISM: Rabovirus C

<400> SEQUENCE: 484

```
ccgggtataa cccggagttt tggggcaggt ccaagcccca cataggaaca tacgatccac     60

ggatcgtgtg ttcttttatg ctttctaacc ttaccctttg taaccattac gctttacgcc    120

gcatggtgtt tggcggcacc atgacgtgga caagaggtta cgccattacg atatgtaccc    180

tccccttttg gggagagacc gaccaattat ggtacagtat ccaactgtat tgtggtcaag    240

tacttctgtt tccccggtga tgcgggatag gctgtaccca cggccaaaac ctgctgatcc    300

gttacccgac tcacatctac gaggaggcta gtaaaaggca tgaagttcaa gagtatgatc    360

caaccagatc cccactggta aactagtgat gagggttccc gttccgaaca tggcaacatg    420

tgggttccct gcgttggcac taggcccctt ccgaggggtg ctctgaagat ggattgttga    480

tgaagaccaa tttgtgcatg tgtttatcct ccggccctct ga                       522
```

<210> SEQ ID NO 485
<211> LENGTH: 551
<212> TYPE: DNA
<213> ORGANISM: Rabovirus A

<400> SEQUENCE: 485

```
ccgaccccac tggtcgaagg ccacttggca ataagactgg tggaacaagg tcgcctgtag     60

ttgattggaa ccttctttct aatgacttat gtcagcggtg ctactcacac cgtaactctc    120

ctaccctatc cccacgcttg tggaactagg aggggatgag tgattcaagt aagtactgtc    180

agaatggtga aaataatctg attctgaaac gctatggatc catcgaaaga tggggctaca    240

cgcctgcgga acaacacatg gtaacatgtg ccccaggggc cgaaagccac ggtgatagga    300

tcacccgtgt agtttgagat catatcaatg ttcatagtct agtaagatga tttgaaatct    360

aactggtctg atggctaact gcttgtctta ttgcggccta aggatgtcct gcaggtacct    420

ttagagaacc ttaagagact attgatctga gcaggagcca aggtggtctt tcccagcctt    480

ggttaaaaag cgtctaagcc gcggcagggg gcgggaggcc ccctttcctc ccaaactata    540

atatagattg t                                                         551
```

<210> SEQ ID NO 486
<211> LENGTH: 675
<212> TYPE: DNA
<213> ORGANISM: Parabovirus C

<400> SEQUENCE: 486

```
gatgtatccc catcccccag tgtgtatgcc atactgcata gctcgcctat gccctatgga     60
```

ttcacaaccc tttcatatac cctccctacc caaccccgta accacatgct ttactccgct 120
tggggttttg cggccccatg ttgtgacgaa atggctacgc aatcaatgcg gctaatgggg 180
cctgccgctt ttaagtggcc ccagttagaa gtttatgcac acccgcccat taggaggcca 240
ccagccaggt ggtcagaggg caagcacttc tgtttccccg gtgaagtttg ataagctgtg 300
cccacggctg aagcagacag atccgttacc cgcctcacta ctacgagacg gctagtagtg 360
tgtaatatcc gaatttcatt gatccgggtg ttccccccac ccagaaacgt gtgatgagga 420
gcggcacccc tcctatggca acatagggcc tctcctgcgc tggcacacgg gctctatgag 480
catgaaatca ggagaaagtc acacgaagac cttattgtgc tagtgttgat tcctccgccc 540
ccctgaatgc ggctaatccc aactccggag cgcccgctgg caaacccgcc agaagagcgt 600
cgtaatgcgt aagtctggag cggaaccgac tactttgggt gtggcgtgtt tcctttattt 660
cctttgtatt tgtat 675

<210> SEQ ID NO 487
<211> LENGTH: 675
<212> TYPE: DNA
<213> ORGANISM: Parabovirus B

<400> SEQUENCE: 487
aacccataat ccattgtcca tcaatgtttt atgggggga ccctttctcc cctccccctc 60
caaatacctt ttacccctct gtaaccaaga gtgtgcaaaa tctatttact agcccagaat 120
tgcggcttct ggggaggttt attcctcatg cctaacaaga tgttacgcaa actccgggct 180
acggccctgg gcttttgccc taaagattta gaagtttaca ctatcgtcca acaggaggac 240
aacaaaccag ttgttctaag gacaagcact tctgtttccc cggtgagact ggatagactg 300
tacccacggt tgaaactggt tgatccgtta cccgactcac tacttcgaga agattagtag 360
gaaactgtga aactgattcc attgatccgg atactttccc cgtatccaga aactactgat 420
gagggttgac ttcccgacta cggcgacgta gtgtcatccc tgcgctggca gtaggcctct 480
ttgaggatgg aagatgtgga tcggtaaccg aaggtcctat tgagctagtg tttatacctc 540
cggcctcctg aatgcggcta atcctaaccc atgatctagt gctcacaaac cagtgagtag 600
ctagtcgtaa cgcgtaagtc gtgggcggaa ccgactactt tggagtgacc gtgtttccta 660
ttttactttt gtttg 675

<210> SEQ ID NO 488
<211> LENGTH: 675
<212> TYPE: DNA
<213> ORGANISM: Parabovirus sp.

<400> SEQUENCE: 488
accgttacgc accactcagt tggtgtttgg tggcaccaat gatggaacaa aaggctacac 60
cacttgggct acggcccgcg ccaccttgtg gcgcaaagac attagaagaa tagcataccg 120
cccactaggg ccctgcagcc agcagggtaa cgggcaagca cttctgtctc cccggtagaa 180
cggtataggc tgtacccacg gccgaaaact gaactatcgt tacccgactc cgtacttcgc 240
aaagcttagt aggaaactgg aaagttcgag ttattgaccc ggagtgttcc ccccactcca 300
gaaacgcgtg atgagggttg ccacccccgac catggcgaca tggtgggcat ccctgcgctg 360
gcacgcggcc tctaagagga taactcgctc ctactggtaa ccgaagagcc ccgtgagcta 420
cggtttattc ctccgcctcc ctgaatgcgg ctaatcctaa cccatgagca gttgccatag 480
atccatatgg tggactgtcg taacgcgtaa gttgtgggcg gaaccgacta ctttgggatg 540
gcgtgtttcc ttgttttctc catttgttgt tgtatggtga caagttatag atctcgatct 600
atagcgtttc ttgagagatt tccaaacatt tattcaagtc gtacaattct tgtgtttaag 660
cagtacagtg taagg 675

<210> SEQ ID NO 489
<211> LENGTH: 316
<212> TYPE: DNA
<213> ORGANISM: Felipivirus sp.

<400> SEQUENCE: 489
gatgtcggat gacggctggc caccggggaa aaacggcaaa tgtgcaccac ctctgcaacc 60
cacgccgacc acgtttaacc atggcgttag taggagtgga ccactgcagt gggctctggt 120
gtgcgacagt cagtggtaga gtagacagtc ctgactgggc aatgggaccg cgttgcgtat 180
ccctaggtgg catcgagatt cctctgctac ccaccagcgt ggactcctat ggggggggcc 240
ccataggcta ggtctatact gcctgatagg gtcgcggctg gtcgaccact gactgtataa 300
ccagttgtaa ctcact 316

<210> SEQ ID NO 490
<211> LENGTH: 553
<212> TYPE: DNA
<213> ORGANISM: Boosepivirus A

<400> SEQUENCE: 490
ttgaaagacc tcggcatata tcgttgtcac aacggtatat gtcgagatct ttctccccac 60
cccctccaat tccctttcc ccctcttgca acttagaagt ttgtacacac agggcaatag 120
gatacgtgat ccagccagga cacgtgagct caagcacttc tgtttccccg tccccttcac 180
gtactacggg aatgttagta atttgtgtgc actttagtaa ggttgatccg ggattaaccc 240
caaatcccag aaactggtga tgagcgttac cacccccgcc gggcgaccgg aaggtttcgc 300
tgcgttggca ccagggcttc ggcaccagaa aaaggtaaag caaatgaagg cgctactgtg 360
ctacgagaag tttcctccag gcccctgaat gcggctaatc ctaaccagtg atccaccggt 420
gcaaaaccat gtactaggtg gtcgtaacgc gcaagtcgct ggcggaaccg actactttgg 480
gtgtcctgtg tttccatatt ttattttatt caattttatg gtgacaagag taaagagata 540
cagatttgca gcc 553

<210> SEQ ID NO 491
<211> LENGTH: 512
<212> TYPE: DNA
<213> ORGANISM: Boosepivirus B

<400> SEQUENCE: 491
ttttctcccc tccccctcca actacctttt ccccctcttg taacgctaga agtttgtgca 60
aaccgcctgt agggtactgc aatccagcag tgcataggct aagcttttct tgttacccca 120
ccccacatta tactgaggag gattgtgaaa ttgtgttagt atgggttagt agcggtgacc 180
cgggtaaccc caacccagaa actcacggat gagatgaaca ggaccccaca tggtaacgtg 240
tgtgttcgtc tgccccgcaa ggtgaggccg tgagagcttt gcacgcgaaa accttgaaaa 300
cccaaaagta ccttgagctc ttcgctattt tgtgtttcct ccaggaccct gaatgcggct 360
aaacctaacc cgcgatccgc acgtagcaac ccagctagag tgtggtcgta atgcgcaagt 420
tgcgggcggt accgactact ttggtgttcc tgtgtttcct ttattttatt ttgaattttt 480
atggtgacaa cagctagaaa ataagagtga ac 512

<210> SEQ ID NO 492
<211> LENGTH: 506
<212> TYPE: DNA
<213> ORGANISM: Unknown
<220> FEATURE:
<223> OTHER INFORMATION: Description of Unknown: Phacovirus Pf-CHK1
sequence

<400> SEQUENCE: 492
gtgtgtcatt tctcccctcc ccctcccaaa ccttttcccc ctctaatcgg attgattaac 60
ccggttaaag atgattaatg gtttgtgagt tgatatgatg gcccggcatt gaatccggga 120
attcttaagt aatggaattg catccaatat gaaagtgagt gtggcaagct cacaagtagt 180
acttggctct gcccattatt tgaggaccaa ctcttcttga ctacaatgtg tttaaagtaa 240
actggaccac attgtgtatc cagacaactc catttgataa tgtacgctgg aaacgttttc 300
agtgcatagg gtcctaaagt ggtgctgaaa tattgcaagc tcaatgggat actgaacgct 360
gaaaaccgcc gctgttatca tatgggcccc tagtgggtaa atgttggctt taggcatata 420
ctgcttggga atgcagtact ggttgtagac agggtgatag cctaccggct ggcgtagttg 480
agttggtata gccagttgat tgccat 506

<210> SEQ ID NO 493
<211> LENGTH: 612
<212> TYPE: DNA
<213> ORGANISM: Rhinovirus sp.

<400> SEQUENCE: 493
ttaaagctgg atcatggttg ttcccaccat gattacccac gcggtgcagt ggtcttgtat 60
tacggtacat ttccatacca gttttataca ccccaccccg aaactcatag aagtttgtac 120
acaatgacca ataggtggtg gccatccagg tcgctaatgg tcaagcactt ctgtttcccc 180
ggcacccttg tatacgcttc acccgaggcg aaaaatgagg ttgtcgttat ccgcaaagtg 240
cctacgaaaa gcctagtaac actttgaaaa cccatggttg gtcgctcagc tgtttaccca 300
acagtagacc tggcagatga ggctagacat tccccaccag cgatggtggt ctagcctgcg 360
tggctgcctg cacaccctgc cgggtgtgaa gccagaaagt ggacaaggtg tgaagagcct 420
attgtgctca ctttgagtcc tccggcccct gaatgtggct aaccctaacc ccgtagctgt 480
tgcatgtaac ccaacatgta tgcagtcgta atgggcaact atgggatggg accaactact 540
ttgggtgtcc gtgtttcctg ttttactttt tcattgctta tggtgacaat tgtatctgat 600
acacttgtta cc 612

<210> SEQ ID NO 494
<211> LENGTH: 627
<212> TYPE: DNA
<213> ORGANISM: Rhinovirus sp.

<400> SEQUENCE: 494
ttaaaacagc ggatgggtat cccaccatcc gacccacagg gtgtagtgct ctggtatttt 60
gtacctttgc acgcctgttt ccccattgta cccctcctta aatttcctcc ccaagtaacg 120
ttagaagttt aaggaaacaa atgtacaata ggaagcatca catccagtgg tgttatgtac 180
aagcacttct gtttccccgg agcgaggtat aagtggtacc caccgccgaa agcctttaac 240
cgttatccgc caatcaacta cgtaatggct agtattacca tgtttgtgac ttggtgttcg 300
atcaggtggt tccccccact agtttggtcg atgaggctag gaactcccca cgggtgaccg 360
tgtcctagcc tgcgtggcgg ccaacccagc ttttgctggg acgccttttt acagacatgg 420
tgtgaagacc tgcatgtgct tgattgtgag tcctccggcc cctgaatgcg gctaacctta 480
accccggagc cttgcaacat aatccaatgt tgttgaggtc gtaatgagta attctgggat 540
gggaccgact actttgggtg tccgtgtttc cttttattct ttatattgtc ttatggtcac 600
agcatatata gcatatatac tgtgatc 627

<210> SEQ ID NO 495
<211> LENGTH: 615
<212> TYPE: DNA
<213> ORGANISM: Rhinovirus sp.

<400> SEQUENCE: 495
ttaaaactgg gtttgggttg ttcccaccca aaccacccac gcggtgttgt acactgttat 60
tccggtaacc ttgtacgcca gttttatatc ccttcccccc cttgtaactt agaagacatg 120
cgaatcgacc aatagcaggc aatcaaccag attgtcaccg gtcaagcact tctgtttccc 180
cggctctcgt tgatatgctc caacagggca aaaacaattg gagtcgttac ccgcaagatg 240
cctacgcaaa acctagtagc atcttcgaag atttttggtt ggtcgctcag ttgctacccc 300
agcaatagac ctggcagatg aggctagaaa taccccactg gtgacagtgt tctagcctgc 360
gtggctgcct gcacacccac acgggtgtga agccaaagat tggacaaggt gtgaagagtc 420
acgtgtgctc atcttgagtc ctccggcccc tgaatgcggc taaccttaac cccgtagcca 480
ttgctcgcaa tccagcgagt atatggtcgt aatgagtaat tacgggatgg gaccgactac 540
tttgggtgtc cgtgtttcac tttttactta tcaatttgct tatggtgaca atatatatag 600
atatatattg acacc 615

<210> SEQ ID NO 496
<211> LENGTH: 660
<212> TYPE: DNA
<213> ORGANISM: Enterovirus L

<400> SEQUENCE: 496
acatgggcca gcccaccaca cccactgggt gtagtagtct ggttctatgg aacctttcta 60
cgcctctttt gcttccctcc cccatttctc cttcgattgc tccacctgtg atctttgcaa 120
cttagaagaa ataatgaacc cgcacaatag cgggcgctga gccacagcgt caatgtgcaa 180
gcacttctgt ttccccggaa tgggcccata ggctgtaccc acggctgaaa gggaccggcc 240
cgttacccgc cttggtactg cgagaatgtt agtaactccc tcgatagctt taggcgttac 300
gctcagccct ttgagcccga agggtagttc gggtcgatga ggctcgtcat tccccactgg 360
cgacagtgtg acttgcctgc gttggcggcc cggggtgggg ggcaaccccc atccacgcct 420
actgaaggac agggtgtgaa ggcgctattg cgctactaag gagtcctccg gcccctgaat 480
gcggctaacc cgaaccccga gcccacggtg gtaaacccgc cacaagtggg tcgtaatgag 540
taatttgggg cagggaccga ctactttggg tgtccgtgtt tcctgttttt ccatacgatg 600
gctgcttatg gtgacaacca taagcaattg gattggccat ccggtgttca tattgcgaat 660

<210> SEQ ID NO 497
<211> LENGTH: 675
<212> TYPE: DNA
<213> ORGANISM: Enterovirus K

<400> SEQUENCE: 497
tcagcctgac gcaagtgcct ccattggagt ctctccaagc cctccggggc ttggagggcg 60
ccgacccccct gcctaggggg agcccacgac acggctggag tccattggca caccgcagcc 120
acgattcaag ccagaattga aagcgggaag cacttctgtc tccccggtgt ggatcatacg 180
ctgtacccac ggcgaaaagt gaagcatcgt tacccgactc ggtacttcga gaagcccagt 240
acagttgtgg atctctgcag ggtatacgct cagcgtgacc cctacgtagt tccttgagat 300
ggctgagaga acaccccacg ggcgaccgtg tctctcggcg cgtggctcaa ggccgggcct 360
tcagtggctc ggtgccttgc agagtgaagc ctccgaacag cctattgagc taccgtttag 420
cctccgccct cttgaatgcg gctaatccta accatggagc gcccgcccac agtccagtgg 480
gtagagcgtc gtaacgcgca agtccgtggc ggaaccgact actttagagt ggcgtgtttc 540
caatttatcc tttataaagt tgcttatggt gacaccacaa gagatccacg atttcttgtt 600
tcttatcact gagacacaag tcatattcat caatctttat tgcggaatta acttggtgcg 660
tccaaacaca tcagc 675

<210> SEQ ID NO 498
<211> LENGTH: 675
<212> TYPE: DNA
<213> ORGANISM: Enterovirus sp.

<400> SEQUENCE: 498
caccctgagg gcccacgtgg cgtagtactc tggtatcaag gtacctttgt acgcctattt 60
tatttccctt cccccacagt aacttagaag cttatctcat agttcaacag tagggtcact 120
aaccaagtgg ctcagcgaac aagcacttct gtttccccgg tcctagtacc tgtgaagctg 180
tacccacggc ggaaggggaa aaagatcgtt atccggcccc ctacttcgga aagcctagta 240
acaccattga agcaatcgag tgttgcgctc agcacagtaa cccctgtgta gctttggttg 300
atgagtctgg gcactcccca ctggcgacag cggcccaggc tgcgttggcg gccaaccgac 360
tcgggcaacc gggtcggacg ctcgtttgtg gacatggtgt gaagagccta ctgagctaga 420
gggtagtcct ccggcccctg aatgcggata atcctaaccc cggagcaccc acactcaatc 480
cagagtgcag gatgtcgtaa cgcgtaagtc tgggacggaa ccgactactt tgggtgtccg 540
tgtttcctgt tttacttact ttggctgctt atggtgacaa tctagtgttg ttaccatata 600
gctattggat tggccatccg gtgttttgaa ttgtgtgttt atactaattc ttttacatat 660
cacagacaac caaat 675

<210> SEQ ID NO 499
<211> LENGTH: 675
<212> TYPE: DNA
<213> ORGANISM: Enterovirus sp.

<400> SEQUENCE: 499
cggtaccttt gtacgcctat tttacccccct tccccttgta acttagaagc aaagcaaacc 60
agttcaatag taagcaacac aacccagtgt tgtgacgaac aagtacttct gtttccccgg 120
gagggtctga cggtaagctg tacccacggc tgaagtatga cctaccgtta accggctacc 180
tacttcgaga agtctagtaa taccattgaa gttttgttgg cgttacgctc aacacactac 240
cccgtgtgta gttttggctg atgagtcacg gcattcccca cgggcgaccg tggccgtggc 300
tgcgttgcgg ccaaccaagg ggcgcaagct ccttggacgt cacttaacag acatggtgtg 360
aagaacctat tgagctaggt agtagtcctc cggcccctga atgcggctaa tcctaactcc 420

```
ggagcacatc agtgcaaccc agcatttggt gtgttgtaat acgcaagtct ggagcggaac    480

cgactacttt gggtgtccgt gtttcctgtt ttaccttatt tggctgctta tggtgacaat    540

ttgatattgt taccatatag ctgttggatt ggccatccgg atttttgaaa gagacccaaa    600

actttcttct ctacttcaga ttcaagtgcg aagttttcct tttcatatat tacttactaa    660

tttgaagtac caaag                                                     675


<210> SEQ ID NO 500
<211> LENGTH: 675
<212> TYPE: DNA
<213> ORGANISM: Enterovirus I

<400> SEQUENCE: 500

ttagtacttt ctcacgggga tagtggtatc cctccctagt aatttagaag acttgaaaaa     60

ccgaccaata ggcacctcgc atccagcggg gtaaaggtca agcacttctg tttccccggg    120

tcgagtagcg atagactgtg cccacggtcg aaggtgaaac aacccgttat ccgactttgt    180

acttcgggaa gcctagtacc accaaagatt atgcttgggg tttcgctcag cacgaccctg    240

gtgtagatca ggccgatgga tcaccgcatt cctcacaggc gactgtggcg gtggtcgcgt    300

ggcagcctgc cgatggggca acccatcgga cgccaagcat atgacagggt gtgaagagcc    360

tactgagcta caaagtattc ctccggcccc tgaatgcggc taatcccaac cacggagcat    420

ttgctaccaa accaggtagt ggaatgtcgt aacgggtaac tctgtggcgg aaccgactac    480

tttgggtgtc cgtgtttcct tttaatttat cattctgtat atggtgacaa ctatagtgct    540

atctcgattt gcattactat tgttgagatt aaaactttat tacattgttg cattttaccc    600

tttgagtgag ttttcacctg aacagattaa tttactcatc ctgtttatat attacaagca    660

gaaatacttg caaag                                                     675


<210> SEQ ID NO 501
<211> LENGTH: 675
<212> TYPE: DNA
<213> ORGANISM: Enterovirus sp.

<400> SEQUENCE: 501

gcaatgctgc accagtgcac tggtacgcta gtaccttttc acggagtaga tggtatccct     60

taccccggaa cctagaagat tgcacacaaa ccgaccaata ggcgcaccgc atccagccgt    120

gcagcggtca agcacttctg tctccccggt ctgtaaagat cgttatccgc ccgacccact    180

acgaaaagcc tagtaactgg ccaagtgaac gcgaagttgc gctccgccac aaccccagtg    240

gtagctctgg aagatggggc tcgcaccacc cccgtggtaa cacggttgcc tgcccgcgtg    300

tgcttccggg ttcggtctcg tgccgttcac ttcaacttca cgcaaccagc caagagccta    360

ttgtgctggg acggttttcc tccggggccg tgaatgctgc taatcccaac ctccgagcgt    420

gtgcgcacaa tccagtgttg ctacgtcgta acgcgtaagt tggaggcgga acagactact    480

ttcggtaccc cgtgtttcct ctcattttat ttaatatttt atggtgacaa ttgttgagat    540

ttgcgctctt gcaacgttgc cattgaatat tggcttatac tatttggttg ccttttacaa    600

aacctctgat atacccagtt cttacattga tctgcttgtt tttctcaatt tgaagtatag    660

actacaaata gcaaa                                                     675


<210> SEQ ID NO 502
<211> LENGTH: 675
<212> TYPE: DNA
```

<213> ORGANISM: Enterovirus sp.

<400> SEQUENCE: 502
cgtggcggcc agtactctgg tatcacggta cctttgtacg cctgttttat atccccttcc 60
cccgcaactt agaagaaaac aaatcaagtt cactaggagg gggtacaaac cagtaccacc 120
acgaacaagc acttctgttt ccccggtgat gtcgtataga ctgtaaccac ggttgaaaac 180
gattgatccg ttatccgctc ttgtacttcg aaaagcccag tatcaccttg gaatcttcga 240
tgcgttgcgc tcagcactca accccagagt gtagcttagg tcgatgagtc tggacactcc 300
tcaccggcga cggtggtcca ggctgcgttg gcggcctacc tgtggtccaa agccacagga 360
cgctagttgt gaacaaggtg tgaagagcct attgagctac aagagaatcc tccggcccct 420
gaatgcggct aatcctaacc acggagcaag ggtacacaaa ccagtgtata tcttgtcgta 480
acgcgcaagt ctgtggcgga accgactact ttgggtgtcc gtgtttcctt ttgtttttat 540
catggctgct tatggtgaca atctaagatt gttatcatat agctgttgga ttggccatcc 600
ggtaatttat tgagatttga gcatttgctt gtttcttcaa caatttcacc tattcattgc 660
atttcagcag tcaaa 675

<210> SEQ ID NO 503
<211> LENGTH: 675
<212> TYPE: DNA
<213> ORGANISM: Unknown
<220> FEATURE:
<223> OTHER INFORMATION: Description of Unknown: PV3 sequence

<400> SEQUENCE: 503
tacctttgta cgcctgtttt atactccctc ccccgcaact tagaagcata caattcaagc 60
tcaataggag ggggtgcaag ccagcgcctc cgtgggcaag cactactgtt tccccggtga 120
ggccgcatag actgttccca cggttgaaag tggccgatcc gttatccgct catgtacttc 180
gagaagccta gtatcgctct ggaatcttcg acgcgttgcg ctcagcactc aaccccggag 240
tgtagcttgg gccgatgagt ctggacagtc cccactggcg acagtggtcc aggctgcgct 300
ggcggcccac ctgtggccca aagccacggg acgctagttg tgaacagggt gtgaagagcc 360
tattgagcta catgagagtc ctccggcccc tgaatgcggc taatcctaac catggagcag 420
gcagctgcaa cccagcagcc agcctgtcgt aacgcgcaag tccgtggcgg aaccgactac 480
tttgggtgtc cgtgtttcct tttattcttg aatggctgct tatggtgaca atcatagatt 540
gttatcataa agcgagttgg attggccatc cagtgtgaat cagattaatt actcccttgt 600
ttgttggatc cactcccgaa acgttttact ccttaactta ttgaaattgt ttgaagacag 660
gatttcagtg tcaca 675

<210> SEQ ID NO 504
<211> LENGTH: 675
<212> TYPE: DNA
<213> ORGANISM: Enterovirus sp.

<400> SEQUENCE: 504
ctttgtacgc ctgttttaca tcccctcccc cacgtaactt tagaagcaat tcaacaagtt 60
caatagaggg ggtacaaacc agtatcacca cgaacaagca cttctgtttc cccggtgatt 120
ttacataagc tgtgcccacg gctgaaagtg aatgatccgt tacccgctcg agtacttcga 180
aaagcctagt atcgctttgg gatcttcgac gcgttgcgct cagcactcta ccccgagtgt 240
agcttaggct gatgagtctg ggcattcccc atcggcgacg atggcccagg ctgcgttggc 300

-continued ggcctaccca tggctaacgc catgggacgc tagttgtgaa caaggtgtga agagcctatt 360
gagctactcg agagtcctcc ggcccctgaa tgcggctaat cccaaccacg gatcaggtgc 420
ctccaaccca ggaggtggcc tgtcgtaacg cgcaagtctg tggcggaacc gactactttg 480
ggtgtccgtg tttcctttta tcttttaaat ggctgcttat ggtgacaatc atagattgtt 540
atcataaagc gaattggatt ggccatccgg tgaaatacaa acacattatt tacttgtttg 600
ttggatttac tccgctcaca cagcttactc ctaagataat atttattgta ttgctggtaa 660
ggagacacta ttata 675

<210> SEQ ID NO 505
<211> LENGTH: 636
<212> TYPE: DNA
<213> ORGANISM: Enterovirus sp.

<400> SEQUENCE: 505
aagcaaggca aacctgacca atagtaggtg tggcacacca gccgcatttt ggtcaagcac 60
ttctgtttcc ccggaccgag tatcaataag ctgctcacgc ggctgaagga gaaaccgttc 120
gttacccgac cagctacttc gagaaaccta gtaacactat gaacgttgcg gagtgtttcg 180
ttcagcactt cccccgtgta gatcaggtcg atgagtcacc gcattcctca cgggtgaccg 240
tggcggtggc tgcgttggcg gcctgcctac gggttcgccc gtaggacgct ctaataccga 300
catggtgtga agagtccatt gagctagctg gtagtcctcc ggcccctgaa tgcggctaat 360
cctaactgcg gagcaggtgc tcacagacca gtgagtagcc tgtcgtaacg ggcaactctg 420
cagcggaacc gactactttg ggtgtttttc ctttttttctt ctcttatatt ggctgcttat 480
ggtgacaatt aaagaattgt taccatatag ctattggatt ggccatccgg tgacgagcag 540
agccattgtt tacctctttg ttggatttgt acctttgaac cacaaagtct tgaataccat 600
tcatctcatt ttaaagttca actcagctaa aagaaa 636

<210> SEQ ID NO 506
<211> LENGTH: 675
<212> TYPE: DNA
<213> ORGANISM: Unknown
<220> FEATURE:
<223> OTHER INFORMATION: Description of Unknown: SA5 sequence

<400> SEQUENCE: 506
agtacttggt attccggtac ctttgtacac ctatttacaa accctacccc ttgtaacctt 60
agaagcaatt atttaaccgc tcactagggg gtgtgctatc caagcacatc aagagcaagc 120
acttctgtct ccccgggagg ggctaatggt acgctgtgcc cacggcggaa atgagcccta 180
ccgttaaccg gcagtctact tcgggaagcc cagtaactac attgaaactt tgaggcgtta 240
cactcagcac ataaccccaa tgtgtagttc tggtcgatga gccttggcat cccccacagg 300
cgactgtggc caaggctgcg ttggcggcca gcctgcggac caaaagtccg taggacgcct 360
aattgtggac atggtgtgaa gagcctactg agctagactg tagtcctccg gcccctgaat 420
gcggctaatc ctaaccctgg agcatccgcg tgcaacccag tacgtagggt gtcgtaatgc 480
gtaagtctgg gatggaaccg actactttgg gtgtccgtgt ttcttgtttt tcatactggg 540
tcgcttatgg ttacaactaa ttgttgtaat cattggcagt gcgcgctgac cacgcgatta 600
ttgatatttc catttgttgg atactccaat agtgtcaact catatacaca acttttacca 660
ctgatcaaga taaaa 675

<210> SEQ ID NO 507
<211> LENGTH: 675
<212> TYPE: DNA
<213> ORGANISM: Enterovirus sp.

<400> SEQUENCE: 507
tgtgcgcctg ttttgaaacc ccctccccca actcgaaacg tagaagtaat gtacactact 60
gatcagtagc aggcgtggcg caccagccat gtctcgatca agcacttctg tttccccgga 120
ctgagtatca atagactgct cacgcggttg aaggtgaaaa cgtccgttac ccggctaact 180
acttcgagaa acctagtagc accatagaaa ctgcagagtg tttcgctcag cacttccccc 240
gtgtagatca ggtcgatgag tcactgcaat ccccacgggt gaccgtggca gtggctgcgt 300
tggcggcctg cctatggggc aacccatagg acgctctaag gtggacatgg tgtgaagagt 360
ctattgagct agttagtagt cctccggccc ctgaatgcgg ctaatcctaa ctgtggagcg 420
catactccca aaccagggag cagtgcgtcg taacgggcaa ctccgcagcg gaaccgacta 480
ctttgggtgt ccgtgtttcc ttttattcct atactggctg cttatggtga caattgagag 540
attgttacca tatagctatt ggattggcca tccagtgtgt aatagagcaa tcatttacca 600
atttgttgga tttactccat taacccacac gtctctcaac acactacatt tcatcttact 660
actgaacact agaaa 675

<210> SEQ ID NO 508
<211> LENGTH: 675
<212> TYPE: DNA
<213> ORGANISM: Unknown
<220> FEATURE:
<223> OTHER INFORMATION: Description of Unknown: Mobovirus A sequence

<400> SEQUENCE: 508
tattctccca caaaccttct tgtaactctg ttaagccttt tacatccatg taatttaatt 60
ttctccacct aaaaggattt cccccatggt ccttttttggc tcgaacaaat gctacatagg 120
gtcttgtttt ctccccctgg ctctcttgcc agggttccat accccaattc ctctatttcc 180
atgatttttc atcatggttt atttttactg tcttcttatt ttctgaggtg accaactcct 240
aagccgactg ggtcgcggaa gcccggactc ctcgcatcac tagggtgcgt agcgatgtag 300
gcgaaaatat tggttgctag atgcatacat atagtgaatt gatactacac caaactctgt 360
tctttttgaa actagctatt ttctaagtaa ggtaggctac gggtgaaacc ttaccattgc 420
aggtacgtga accgcaacgg acatttggcc gaagactggt gtacccacgt cagttatagg 480
acctcttcaa cgttggtgga cggcatgtca ctgattagtt aggctagtga atttaagttc 540
agggggtatc ttttagctta agcgtgtatt ctagtaggac ttgcagagcc tccccaccta 600
ggaggatctc tgtttatagc cccttttcct tgttccgtta gttttccaca cttttacaat 660
atttgatgat ttgtt 675

<210> SEQ ID NO 509
<211> LENGTH: 509
<212> TYPE: DNA
<213> ORGANISM: Unknown
<220> FEATURE:
<223> OTHER INFORMATION: Description of Unknown: Burpengary Virus
sequence

<400> SEQUENCE: 509
ctcccccccc ttccccttcc cgagtaggag attggcatgt atgctctaca tgcccgattc 60

-continued

```
tctcttgctc actctcttaa atcctggtgg cggtctcgga ttaaacattt atgtcgtatc    120

tgggatcgtc ttacttggtg gtaattcctc tgttgcctag ggacctccgg actgccggat    180

taaaggtctc aacagagggc aatgtacaag gaagtcatta tacgctaatt aagtatttga    240

tgaatgacta gtgtgacagg gctgaggaac tccccccggg taaccggtgc ctcagcgtcc    300

gaaagacacg tggataggat ccaccctgtt atacccagca cgatgtaata gtcaaatacc    360

tctgatttgt gtaggatgta taaattgtgc attgtaaatt ttgggcgtag agatgctccg    420

aaggtacccc gttttacggg atctgatcgg aggctaatta cccaatgcgc cctaaataac    480

ttcatataat ttctttttct ttattcaaa                                      509


<210> SEQ ID NO 510
<211> LENGTH: 675
<212> TYPE: DNA
<213> ORGANISM: Hunnivirus sp.

<400> SEQUENCE: 510

taacgtttgg caagaaccct cacctgtcaa ttgggaccac cactttcagt gaccccatgc     60

gaagtagtga gagagaataa gctttcttac ccttcatttg tgaacccttc agtcgaagcc    120

gcttggaata agataggagg aaaagttcat tctaaatgga gtgaaacatg tacttcagaa    180

tttctagcac gcgctgggct ttcttgcgtg tgacggcact gtcttgccgg agctctccac    240

actgacaccc cacgcttgtg gaccttggtg gcagatgaca acactgcagc tggaattgag    300

tgtctggtac actctgtgta acagtgaaaa caatgtgatc acttcggtga gctagtagcc    360

tgtggaccaa caactggtaa cagttgcctc aggggccaaa agccacggtg tttacagcac    420

cctactggtt tgattggagc aatccaagat gtcacagagt tagtaattgc caagcagtcc    480

gtactggtat cttgacatac cgtgcagttt tggatagtga aggatgccct gacggtaccc    540

ataggtaaca agtgacacta tggatctaag caggggctca ctctacgctg ctttacagct    600

ggctgtgagt taaaaaacgt ctagctatcc acaacctagg ggactaggtt ttccttttat    660

ttagattaca attat                                                     675


<210> SEQ ID NO 511
<211> LENGTH: 675
<212> TYPE: DNA
<213> ORGANISM: Hunnivirus sp.

<400> SEQUENCE: 511

acagttttg acaaggaccc tcacctgtca atcgggacca ccactttcag tgaccccgtg      60

cgaagtgttg agagaaagtg agctttctta cccttcattt gtgaaccctt cagtcgaagc    120

cgcttggaat aagatggaag gaaatgttca ttctaaatgg agtgaaacat atacttaatt    180

tccagtgttt agtggtcttt ccactagaca acggcactgt cttgccggaa ctctacacac    240

caacattcca cgcttgtggg actcaaatgt tggatgacac agttgtagct ggaactgagt    300

gtttagtgca ctctgtgtaa cagtgaaaac aatgtgatca cttcggtggg ctagtagcct    360

gtggactaac aactggtaac agttgcctca ggggccaaaa gccacggtgt taacagcacc    420

ctactagttt gattggagca atccatgatg ttacagagtt agtaactgcc aaacagattg    480

tactggtatc ttggcatacc gtgcaactta ggatagtgaa ggatgccctg gcggtaccca    540

taggtaacaa gtgacactat ggatctaaac aggggctcac tctacgttgc tttacaacta    600

gctgtgagtt aaaaaacgtc taactatcca caacctaggg gactaggttt tcctttttat    660

ttttatacac aacta                                                     675
```

<210> SEQ ID NO 512
<211> LENGTH: 240
<212> TYPE: DNA
<213> ORGANISM: Unknown
<220> FEATURE:
<223> OTHER INFORMATION: Description of Unknown: Ia Io sequence

<400> SEQUENCE: 512
ggtgtccggg tgtgtgggat agacccagat gtgcagtgga tgcgagcatt tgagtcagag 60
taggagcaag cccaggggca aagggaccac attgtgtatc ccgaatgaag gatcgagatt 120
tctctcctca ttacccggtg tcttgtcact gttggggggg cccaacagtc ttagtcctat 180
actgcctgat agggtcgcgg ctggccggac tcaagtgcta tagtcagttg attttcactc 240

<210> SEQ ID NO 513
<211> LENGTH: 416
<212> TYPE: DNA
<213> ORGANISM: Taura Syndrome Virus

<400> SEQUENCE: 513
ctttaaaagt cgtgcgtggc ttcaccacgc acgatcagta ctatcagtta accactcttg 60
aatatgctca atgaccctat tcaacactgg tgtctcttag tacattattt tagcacttaa 120
cgtgcatgag ttttgcccat ttctttcaaa aaaatgagta ttcgaggaga cgtcccgctc 180
cccgtcttat ttcaaccgta gactcgacat ctattggtgg acatttaatt ccagtcgccg 240
taagttgctt ctgccccgcg ctatattttc ttatacttat ggttctatag gtctggttta 300
aaacgtaaat agacggccca caaactatag aacgcgtacc cggaacgcca atcccggata 360
agtccctgga tatatagatg caccgcaata taagcctgca gactgtctca tatact 416

<210> SEQ ID NO 514
<211> LENGTH: 604
<212> TYPE: DNA
<213> ORGANISM: Acute bee paralysis virus

<400> SEQUENCE: 514
cccgtcaaaa taacaactta taacacgatg ttacccgaag aaaccatttt agtgtaacat 60
ttaagattag aagtagttca tctaatagag ataggcacta ttagaaggag gccttttcta 120
aaggagccgt tagtcagccc agacaagcgc agtactttag aagagagaag ttccccgata 180
gcgaccgaaa agacgcgttt tccgtgctaa ctaatttaaa tgtgggaacg aatattatta 240
ttgaaattat gtgagccacg tagcaatcaa gtcatgtttt tgtcactacg tttactcatc 300
taatgtagat aattttgttt aagtacctat ttaggtgtca tcccaccaga gaagaaataa 360
tacgtaccgg aacccagagt acacccctta ttttaagcct tactgggctt ctctgttagt 420
tagtaatctg gcccacgttt tgcgttgagt ggggtcccaa cagtaggaat tcgacggaca 480
agtagcaagc gagtcggtac caattggttt agccttcgaa attactctgg gcaggaagtt 540
actaaacgag aactttctgc ttaaatccca acgcacaaac aaatagagta aataaataat 600
tata 604

<210> SEQ ID NO 515
<211> LENGTH: 539
<212> TYPE: DNA
<213> ORGANISM: Bovine rhinitis A virus

<400> SEQUENCE: 515

-continued

```
tttgttttgc ggctttgccg ttgttcgggt tttacctgtt ttcacacagc aaaacaggcc     60
ttctagtttc gtgcttaaac gagatcatgc tcgaactaga actacatagc tggtcactgg    120
actcatacca caccttgtgg agctttatgg gaaaggtggc tagtgggctg tggaagtgac    180
tctgaccaca tgcctctcaa gtgtgggaaa tcacggatcg gtgtagcgac gacaacaggc    240
cttgggacac cctctccagt aatggagacc caaggggcca aaagccacgc ctcgtgccct    300
gttgttcaca accccagtgc gacccgtgtt agtacctatt tgcgagaact gtgtctggac    360
agctaaacac aaccctagtg ggagactaag gatgcccagg aggtacccgg aggtaacaag    420
tgacactctg gatctgacct ggggagagag ggcttgcttt acaggcgcct ctctttaaaa    480
agcttctatg tctcatcagg caccggaggc cgggcctttt ccttttaaaa ttacactta     539
```

```
<210> SEQ ID NO 516
<211> LENGTH: 608
<212> TYPE: DNA
<213> ORGANISM: Bovine rhinitis B virus

<400> SEQUENCE: 516 cccccctac ttaaagatgt acggttttgc tgctttcaca gagtaaagca gatagaggtt      60
ctgaactggc aaactttacc tcgaaacacg cccgtttttc tgctgtgtct cacagactgt    120
cctgtcacac ttgtggcggc ttgtgacact gtgaacatag tgagaccgac caagacaaca    180
gtttcaagtg atgaacatcg aacgtctaaa ctggatccgt aactggacat gttagggcaa    240
ggacttcccc cctggtaaca ggagcctggc tggccaaaag ccccgctcat tgagcctagc    300
atgttgtcga ccctggactg ttcagtttag ttagtacatg gaattcactt gtcacggttc    360
ttctgaactc ggtctctagt atgacagcct aaggatgccc tccaggtacc ccggggtaac    420
aagtgacacc cgggatctga ggaggggact actttacgta gtttaaaaaa cgtctaagct    480
gttatggtga ccagaggctg gcacctttca cttttaaaat tacactactg actacaattg    540
aagtgataac ggttttacag gctttcaaac tagttacaca agcactgttt tcctgacaca    600
cacacttt                                                              608
```

```
<210> SEQ ID NO 517
<211> LENGTH: 576
<212> TYPE: DNA
<213> ORGANISM: Equine rhinitis A virus

<400> SEQUENCE: 517
aatattggcg cgcgcatttg cgcgcccccc cccatttcag ccccctgtca ttgactggtc     60
gaaggcgttc gcaataagac tggtcgtcac ttggctgttc tatcgtttca ggctttagcg    120
cgccctcgcg cggcgggccg tcaagcccgt gcgctgtata gcgccaggta accggacagc    180
ggcttgctgg attttcccgg tgccattgct ctggatggtg tcaccaagct gacaaatgcg    240
gactgaacct cacaaagcga cacacctgtg gtagcgctgc ccaaaaggga gcggaactcc    300
cccgccgcga ggcggtcctc tctggccaaa agcccagcgt taatagcgcc ttttgggatg    360
caggagcccc acctgccagg tgtgaagtgg agtgagtgga tctccaattt ggtctgttct    420
gaactacacc atctactgct gtgaagaatg ccctggaggc aagctggtta cagccctgac    480
caggggccct gcccgtgact ctcgatcggc gcagggtcaa aaattgtcta agcagcagca    540
ggaacgcggg agcgtttctt ttccctttgt atcgac                              576
```

```
<210> SEQ ID NO 518
<211> LENGTH: 466
```

<212> TYPE: DNA
<213> ORGANISM: Unknown
<220> FEATURE:
<223> OTHER INFORMATION: Description of Unknown: GFTV sequence

<400> SEQUENCE: 518
atggggaagg gtatgacgtg ccccttcctt cttcggagaa ctcgctctag tggtctttcc 60
acttctggaa aagagtgagt gcacgtgatc aggaccgtcg aagacgacaa atacctggtg 120
ctctatctca tagacgtttc acagctgtag cgacccctca gtagcagcgg aagccccctc 180
ctggtgacag gagcctctgc ggccaaaagc cacgtggata agatccactg ctgagggcgg 240
tgcgacccta gcaccctgtg atgcatacta gttgtagcgt gccggactat tggtctgtca 300
taagacacct gatagagaga ccaagaatgt cctggaggta ccccgcgtgc gggatctgac 360
caggagacca ttgcccaatg ctttacaacg ggtctatggt ttaaaaactg tcgcagtctc 420
tccaaaccaa gtggtcttgg ttttcaatta ctttgaatat ttcact 466

<210> SEQ ID NO 519
<211> LENGTH: 675
<212> TYPE: DNA
<213> ORGANISM: Unknown
<220> FEATURE:
<223> OTHER INFORMATION: Description of Unknown: SAFV V13C sequence

<400> SEQUENCE: 519
ttttcgacgt ggttggaatt gccatcattt ccgacgaaag tgctatcatg cctccccgat 60
tatgtgatgt tttctgccct gctgggcgga gcattctcgg gttgagaaac cttgaatctt 120
tttctttgga accttggttc cccggtcta agccgcttgg aatatgacag ggttattttc 180
ttgatcttat ttctactttt gcgggttcta tccgtaaaaa gggtacgtgc tgccccttcc 240
ttctctggag aattcacacg gcggtctttc cgtctctcaa caagtgtgaa tgcagcatgc 300
cggaaacggt gaagaaaaca gttttctgtg gaaatttaga gtgcacatcg aaacagctgt 360
agcgacctca cagtagcagc ggactcccct cttggcgaca agagcctctg cggccaaaag 420
ccccgtggat aagatccact gctgtgagcg gtgcaacccc agcaccctgg ttcgatgatc 480
attctctatg gaaccagaaa atggttttct caagccctcc ggtagagaag ccaagaatgt 540
cctgaaggta ccccgcgtgc gggatctgat caggagacca attggcggtg ctttacactg 600
tcactttggt ttaaaaattg tcacagcttc tccaaaccaa gtggtcttgg ttttccaatt 660
ttgttgaatg gcaat 675

<210> SEQ ID NO 520
<211> LENGTH: 675
<212> TYPE: DNA
<213> ORGANISM: Unknown
<220> FEATURE:
<223> OTHER INFORMATION: Description of Unknown: SAV P-113 sequence

<400> SEQUENCE: 520
ggagatctaa gtcaaccgac tccgacgaaa ctaccatcat gcctccccga ttatgtgatg 60
ctttctgccc tgctgggtgg agcatcctcg ggttgagaaa accttcttcc tttttccttg 120
gaccccggtc cccggtcta agccgcttgg aataagacag ggttatcttc acctcttcct 180
tcttctactt catagtgttc tatactatga aagggtatgt gtcgcccctt ccttctttgg 240
agaacacgcg cggcggtctt tccgtctctc gaaaagcgcg tgtgcgacat gcagagaacc 300
gtgaagaaag cagtttgcgg actagcttta gtgcccacaa gaaaacagct gtagcgacca 360
cacaaaggca gcggaccccc cctcctggca acaggagcct ctgcggccaa aagccacgtg 420
gataagatcc acctttgtgt gcggcacaac cccagtgccc tggtttcttg gtgacacttc 480
agtgaaaacg caaatggcga tctgaagcgc ctctgtagga aagccaagaa tgtccaggag 540
gtaccccttc cctcgggaag ggatctgacc tggagacaca tcacatgtgc tttacacctg 600
tgcttgtgtt taaaaattgt cacagctttc ccaaaccaag tggtcttggt tttcactctt 660
taaactgatt tcact 675

<210> SEQ ID NO 521
<211> LENGTH: 612
<212> TYPE: DNA
<213> ORGANISM: Unknown
<220> FEATURE:
<223> OTHER INFORMATION: Description of Unknown: VHEV sequence

<400> SEQUENCE: 521
aattccttct tcctttctcc ttggacctcg gtcccccggt ctaagccgct cggaatatga 60
cagggttatt ttcacctctt ctctcttcta cttcatagtg ttctatacta tgaaagggta 120
tgtgtcgccc cttccttctt ggagaacgtg cgtggcggtc tttccgtctc tcgaaaaacg 180
tgcgtgcgac atgcagagta acgcaaagaa agcagttctt ggtctagctc tggtgcccac 240
aagaaaacag ctgtagcgac cacacaaagg cagcggaaac cccctcctgg taacaggagc 300
ctctgcggcc aaaagccacg tggataagat ccacctttgt gtgcggtgca accccagcac 360
cctggtttct tggtgacacc ttagtgaacc ctcgaatggc aatctcaagc gcctctgtag 420
gaaagccaag aatgtccagg aggtacccct tcctcatgga gggatctgac ctggagacac 480
atcacacgtg ctatacactt gtgcttgtgt ttaaaaattg tcacagcttt cccaaaccaa 540
gtggtcttgg ttttccctta acttcgaaaa gtcactatgg cctgcaaaca tggataccca 600
gacgtgtgcc ct 612

<210> SEQ ID NO 522
<211> LENGTH: 675
<212> TYPE: DNA
<213> ORGANISM: Unknown
<220> FEATURE:
<223> OTHER INFORMATION: Description of Unknown: TRV NGS910 sequence

<400> SEQUENCE: 522
atgcgacgtg gttggagatt aaaccgactc cgacgaaagt gctatcatgc ctccccgatt 60
atgtgatgtt ttctgccctg ctgggcggag cattctcggg ttgatacacc ttgaatcctt 120
catccttgga cctcaggtcc cccggtctaa gccgcttgga atacgacagg gttattttcc 180
aatcttctcc tttctacttt catgagtcct attcatgaaa agggtctgtg ctgccccttc 240
cttcttggag aatctgcgcg gcggtctttc cgtctctcga aaagcgcaga tgcagcatgc 300
tggaaccggt gaagaaaaca gttctttgtg gaaacttaga gcagacatcg aaacagctgt 360
agtgacctca cagtagcagc ggaaccccct cctggtaaca ggagcctctg cggccaaaag 420
ccccgtggat aagatccact gctgtgagcg gtgcaacccc agcaccctgg ttcgatggtt 480
gttctctgtg gaaccagaga atggtctttc tcaagccctc cagtagagaa gccaagaatg 540
tcctgaaggt accccgcatg cgggatctga tcaggagacc aatcgtcagt gctttacact 600
ggcgctttgg tttaaaaact gtcacagctt ctccaaacca agtggtcttg gttttcactt 660
ttatcaaact gtttc 675

<210> SEQ ID NO 523
<211> LENGTH: 551
<212> TYPE: DNA
<213> ORGANISM: Unknown
<220> FEATURE:
<223> OTHER INFORMATION: Description of Unknown: EMCV2 RD1338 sequence

<400> SEQUENCE: 523
aaatactggt cgaaaccgct tgggataaga ccggggtttg ttaatgtctc aatgttattc 60
tccacccaat tgacgtcttt tgtcaattgg agggcagtga aaccttgccc ttgcttcttg 120
cagaggattc ccagtggtct ttccgctctc gacaagggaa ttcatgatcc accaaaagtt 180
gtgaagagag caggtcccat ggaagctttc tgacgactga tgatgactgt agcgaccctt 240
tgcaggcagc ggaccccccc acctggtgac aggtgcctct gcggccaaaa gccacgtgtt 300
taacagacac ctgcaaaggc ggcacaaccc cagtgcctca tcaaaagtct gatgactgtg 360
gaaatagtca accggctttt cttaagcaaa tttggtgtcg gggctgaagg atgcccggaa 420
ggtaccacac tggttgtgat ctgatccggg gccacagtac atgtgcttta cacatgtagc 480
tgcggttaaa aaacgtctag gccccccgaa ccacggggac gtggttttcc tttgaaaacc 540
acgattacaa t 551

<210> SEQ ID NO 524
<211> LENGTH: 675
<212> TYPE: DNA
<213> ORGANISM: Unknown
<220> FEATURE:
<223> OTHER INFORMATION: Description of Unknown: EMCV1 JZ1203 sequence

<400> SEQUENCE: 524
gtctgctcga tatcgcaggc tgggtccgtg actacccact ccccctttca acgtgaaggc 60
tacgatagtg ccagggcggg tactgccgta agtgccaccc caaaacaaca acaaaccccc 120
cctaacatta ctggccgacg ccgcttggaa taaggccggt gtgcgtttgt ctatatgtta 180
tttcccacca cattgccgtc ttttggcaat gtgtgggccc ggaaacctgg ccctgtcttc 240
ttgacgagca ttcctagggg tctttcccct ctcgccaaag gaatgcaagg tctgttgaat 300
gtcgtgaagg aagcagttcc tctggaagct tcttgaagac aaacaacgtc tgtagcggcc 360
ctttgcaggc agcggaaccc cccacctggc gacaggtgcc tctgcggcca aaagccacgt 420
gtataagata cacctgcaaa ggcggcacaa ccccagtgcc acgttgtgag ttggatagtt 480
gtggaaagag tcaaatggct ctcctcaagc gtattcaaca aggggctgaa ggatgcccag 540
aaggtacccc attgtatggg atctgatctg gggcctcggt gcacatgctt tacatgtgtt 600
tagtcgaggt taaaaaacgt ctaggccccc cgaaccacgg ggacgtggtt ttcctttgaa 660
aaacacgatg ataat 675

<210> SEQ ID NO 525
<211> LENGTH: 544
<212> TYPE: DNA
<213> ORGANISM: Unknown
<220> FEATURE:
<223> OTHER INFORMATION: Description of Unknown: EMCV1 AnrB-3741
sequence

<400> SEQUENCE: 525
atgtggtcga agccacttgg aataagaccg gcgtgcgctt gtctatatgt tacttccacc 60
acattgccgt cttttggcaa tgtgagggcc cggaacctgg ccctgtcttc ttgacgaaca 120
ttcctagggg actttcccct ctcgccaaag gaatgtaagg tctgttgaat gtcgtgaagg 180
aagcagttcc tctggaagct tcttgaagac aaacagcgtc tgtagcgacc ctttgcaggc 240
agcggaaccc cccacctggt aacaggtgcc tctgcggccg aaagccacgt gtataagata 300
cacctgcaaa ggcggcacaa ccccagtgcc acgttgtgcg ttggatagtt gtggaaagag 360
tcaaatggct ttccccaagc gtattcaaca aggggctgaa ggatgcccag aaggtacccc 420
actggttggg atctgatctg gggcctcggt gcaggtgctt tacacctgtt gagtcgaggt 480
taaaaaacgt ctaggccccc cgaaccacgg ggacgtggtt ttcctagaaa accactatga 540
caat 544

<210> SEQ ID NO 526
<211> LENGTH: 675
<212> TYPE: DNA
<213> ORGANISM: Cosavirus sp.

<400> SEQUENCE: 526
cgtgctttac acggtttttg aaccccacac cggctgtttg gcgcttgcag gacagtaggt 60
atattttctt tcatttctct tttctagccg cgtaggttct atctacgcgg gcggagtgat 120
actcccgctc cttcttggac aggcggcctc cacgctcttt gtggatctta aggctgccaa 180
gtcactggtg tttgaagtga agaatggaga gacactaggg cgtttcatgt ggctttgcca 240
gggattgtag cgatgctgtg tgtgtgtgcg gatttcccct cgtggcgaca cgagcctcac 300
aggccaaaag ccctgtccga aaggacccac acagtggggt tgccccgacc cctcccttca 360
aagctttgtg taaacaaact tttgtttaga ctttcttaag cttctctcac atcaggcccc 420
aaagatgtcc tgaaggtacc ctgtgtatct gaggatgagc accaccaact acccggactt 480
gtgggacgtg tcccacagac gcatgtggta ttccagcccc ctccttttga ggagggggct 540
tttgctcgct cagcacagga tctgatcagg agattcatct ctggtgcttt acaccagagc 600
atggatttaa aaattgccca aggcctggca aacaacctag gggactaggt tttctctatt 660
ttaaaagatg tcaat 675

<210> SEQ ID NO 527
<211> LENGTH: 675
<212> TYPE: DNA
<213> ORGANISM: Cosavirus sp.

<400> SEQUENCE: 527
cgtgctttac acggtttttg aaccccacac cggctgtttg gcgcttgcag gacagcaggt 60
ttattttctt ttaactctct ctttctagcc acacacgatc tatgtgtgtg ggcggagtga 120
tactcccgtt ccttcttgga caggcggcct ccacgccctt tgtggatctt aaggctacca 180
agtcactggt gttggaaagt gaagagaaag gagttccttg ggaactacat gtggcattga 240
cagaggttgt agcgatgctg tgtgtgtgtg cggattaccc ccgtggcgac acggacccca 300
caggccaaaa gccctgtccg aaaggaccca cacagtggag caaccccagc tcccctcttc 360
aatgttttgt gttagcaacc ttggtattat tttctctcaa gcttccaata caccgggccc 420
caaagatgtc ctgaaggtac cccgtgtatc tgaggatgag caccatcaac tacccggact 480
tgttctttcg agaacagacg catgtggtaa cccagccccg atcctaaggg gtcggggctt 540
ttgctcactc agcacaggat ctgatcagga gacctccccc ccctgcttta caggggggcgg 600 gggtttaaaa attgcccaag gcctggcaaa taacctaggg gactaggttt tcctttttat 660
tttaaagttg tcaat 675

<210> SEQ ID NO 528
<211> LENGTH: 675
<212> TYPE: DNA
<213> ORGANISM: Cosavirus A

<400> SEQUENCE: 528
ccgtgcttta cacggttttt gaaccccaca ccggctgttt ggcgcttgca ggacagcagg 60
tttattttct tatgctcttt atttctagcc aacagggttc tatcctgttg ggcggagtga 120
tactcccgtt ccttcttgga cagattgcct ccacgatctt tgtggatctc aaggtgatca 180
agtcactggt aaatagagcg aaggttgagg aaacctgagg aatttccatg tggttttgcc 240
aggagttgta gcgatgctgt gtgtgtgtgc ggatttcccc tcatggcaac atgagcctca 300
caggccaaaa gccctgtccg aaaggaccca cacagtggag caatcccagc tccctcctac 360
aaagctttgt gagaatgaac tcacgtttat tcttctttat tctctgttta catcaggccc 420
caaagatgtc ctgaaggtac cttgtgtatc tgggcatgag caccatcaac tacccggact 480
tgcatttcgg tgcagacaca tgtggttacc cagcccctct gctttggcag aggggctttt 540
gctcgctcag cacgagatct gatcaggagc ccttcccagt gtgctttaca cctggcgggg 600
ggttaaaaat tgcccaaggc ctggcaaaat aacctagggg actaggtttt ccttttatta 660
acaatgtctg tcatt 675

<210> SEQ ID NO 529
<211> LENGTH: 660
<212> TYPE: DNA
<213> ORGANISM: Malagasivirus B

<400> SEQUENCE: 529
ctttattttc ttatgtaact cttcttttta agttttattt tgcctacttg tgagcttatg 60
cgggaccact gtcttagaca accccacatt tgtcatgagt aagtacacgc aaccattacg 120
attacttttt aaccgtctga ccttttgata acaactgaag ttaggcgtga aacatgcatt 180
tataccaaag tagccccgca tttccccact acggtggggg ggctacccta ctggctttgg 240
aactgtagcc attatgtgtt gcctggcttt caggatctca caacacaaca gttctctcac 300
aatggaatat gggtgagatt gcagtgacat gaacaagtat ctagtagtac atagactcaa 360
gcctagttgc ctgcggaaca acatgtggta acacatgccc cagggtccaa aagacaaggg 420
ttaacagccc cttctaggtg tctgtgtgtg aagaatactt tagtagtgtt gttatgatct 480
cacctgttag tacagaatga gtatggcttg gtgaaggatg tcctacaggt acccattata 540
tggatctgag taggagacca ctagtggtgg ctttaccgcc aggtgagtgg tttaaaaagc 600
gtctagccaa gccaacagca ctagggatag tgctttctat attttatatt ttcagtgtat 660

<210> SEQ ID NO 530
<211> LENGTH: 654
<212> TYPE: DNA
<213> ORGANISM: Mosavirus sp.

<400> SEQUENCE: 530
cccccccctc aaattgcaac gatatagcta atggcgagat tgagatgcta tatcacctct 60
tctaagttat agacctcatc tgattgataa ggacgtaatt tggtcgaaac cgcttggaat 120
aagaccgatg cgcgtagtca tgatgatgat gtaagatcta ggaacttatc caatctgctt 180
atgtctatgt aagtagaggg gcaggcctca ttgccctaat tctttctacc gagtatctgc 240
tagggtttct agcggcttga atacttggat tgagggatac aagatactac tgatcgattg 300
tcgattggga aacttgtaga tacttcaaag ctaccagtag cgtggactca cagccagcgg 360 actaccccte atggtaacat gagcctctgg gcccacaagg cacgtcgcaa gacctgtgag 420
acggcaaccc cagcctagct ttgttgagga aacaagcgat aacatgacat gagagaccgg 480
aaggattctt gtattgtgag ccgaaggatg gcctctaggt acctcatttt atgagatctg 540
aggaggtgct cttgagttgg tgctttacac tgacaacaca gagttaaaaa gcgtctaagc 600
tcacccggaa attgggaaat ttccgttatt tccattttgt ttgcaaagtc gttc 654

<210> SEQ ID NO 531
<211> LENGTH: 654
<212> TYPE: DNA
<213> ORGANISM: Unknown
<220> FEATURE:
<223> OTHER INFORMATION: Description of Unknown: SVV sequence

<400> SEQUENCE: 531
ctgggccctc atgcccagtc cttcctttcc ccttccgggg ggtaaaccgg ctgtgtttgc 60
tagaggcaca gaggagcaac atccaacctg cttttgtggg gaacggtgcg gctccaattc 120
ctgcgtcgcc aaaggtgtta gcgcacccaa acggcgcatc taccaatgct attggtgtgg 180
tctgcgagtt ctagcctact cgtttctccc ctatccactc actcacgcac aaaaagtgtg 240
ctgtaattac aagatttagc cctcgcacga gatgtgcgat aaccgcaaga ttgactcaag 300
cgcggaaagc gctgtaacca catgctgtta gtcccttcat ggctgcgaga tggctatcca 360
cctcggatca ctgaactgga gctcgaccct ccttagtaag ggaaccgaga ggccttcttg 420
caacaagctc cgacacagag tccacgtgat tgctaccacc atgagtacat ggttctcccc 480
tctcgaccca ggacttcttt ttgaatatcc acggctcgat ccagagggtg gggcatgatc 540
cccctagcat agcgagctac agcgggaact gtagctaggc cttagcgtgc cttggatact 600
gcctgatagg gcgacggcct agtcgtgtcg gttctatagg tagcacatac aaat 654

<210> SEQ ID NO 532
<211> LENGTH: 331
<212> TYPE: DNA
<213> ORGANISM: Teschovirus A

<400> SEQUENCE: 532
actagtcctt ggacttttgt tgtgtttaaa cacagaaatt taattacctg gccatgaatt 60
cattggatta acccttctga aagacttgct ctggcgcgag ctaaagcgca attgtcacca 120
ggtattgcac cagtggtggc gacagggtac agaagagcaa gtactcctga ccgggcaatg 180
ggactgcatt gcatatccct aggcacctat tgagatttct ctggggccca ccggcgtgga 240
gttcctgtat gggaatgcag gactggactt gtgctgcctg acagggtcgc ggctggccgt 300
ctgtactttg tatagtcagt tgaaactcac c 331

<210> SEQ ID NO 533
<211> LENGTH: 416
<212> TYPE: DNA
<213> ORGANISM: Teschovirus B

<400> SEQUENCE: 533
cttcctttta attcgtaact gataagtgat agtccttgga agctaggtat ttgttacgct 60
agttttggat tatcttgtgc ccaacatttg ttttcgaaca tatgttgtgt ttaaacacag 120
aaatctagtt tctttggtta tgagtttaat ggaatatcct tttgaaagac ttgccttggc 180

-continued

```
gcgggctaga gcgcaattgt caccaggtat tgcaccaatg gtggcgacag ggtacagaag    240

agcaagtact cctgactggg taatgggact gcattgcata tccctaggca tctattgaga    300

tttctctgga gcccaccagc atggagttcc tgtatgggaa tgcaggactg gacttgtgct    360

gcctgacagg gtcgcggctg gccgtctgta ctttgtatag tcagttgaaa ctcatt        416
```

<210> SEQ ID NO 534
<211> LENGTH: 664
<212> TYPE: DNA
<213> ORGANISM: Tottorivirus sp.

<400> SEQUENCE: 534

```
cccctttacg taactgcaac ttaaagagta ccctactgca ttggatgtgt ggtaaacttt     60

tacgcacaca tttgtagtag tgttagttat gttctaccta atgagtatgc atgcacccgt    120

cgaaacacgc ttgtgataag ataggtgagt ccatgtgact aatctcatta agataaataa    180

gcaccctaca acgcacggca cgctcgtgtc ttccgtgcgg ggccgggaca acagcggcct    240

aaatcttcta ggtgaccacc atgcttttgg gactatggca ccactgtgga cgtgagtacc    300

tggcagtaag tctgtgaaaa gatggaaggt gtcccaagct atggggcgta tgcatatagc    360

ctgcggaaca aacaacggcg acgttgtccc cagggcccaa aaggcacgtg gataagatcc    420

acctatatgt ttaccccata gtgtaagtca ctggaagtcc tagtaatgga tgtctggagt    480

aaggctcacg gggtagggcg aaggatgccc agaaggtacc cgtaggtaac cttaagagac    540

tatggatctg atctggggac cggatggcgc catcaccatg acgtggaggc cggtttaaaa    600

aacgtctaag cccgaccaac aacctagggg actaggtttt cctttttat tcatgtatga     660

cgtt                                                                 664
```

<210> SEQ ID NO 535
<211> LENGTH: 675
<212> TYPE: DNA
<213> ORGANISM: Unknown
<220> FEATURE:
<223> OTHER INFORMATION: Description of Unknown: Posavirus 1 sequence

<400> SEQUENCE: 535

```
acatttcctt gcgtgcgcac ccgaaaattt attgaacttg gcttgaatca taagtaatgc     60

ttcttatagc ggacactttg agaatataat gcttgtatgg attaatgtat actgttttaa    120

ataacaaacc tagacacgca gttgcgttga tggttgtatc aatcacatat aagtgttgaa    180

ctcgtgttaa tcctcgatcg ctatatgttt gccgcctact tccaataaaa tagattacat    240

gcgcgtcatg cctttgtggg ttacctattg gcctctgaca aaaacaagtc gtaagatttg    300

tagcttcccg gtgtaaaaag ctgggcgcgg tctggctctc gtagggtgga aaggtccacc    360

aatggctggt tgagtgtaag ctccggtgtc ctggttgtcg caattccagg cgtcgtaata    420

acctatattg catctgactc taactcttgt ggctctactg tatctagttc ttgttctact    480

aactctaata atactactgg ctctaatact gaaaaactta catatgttaa tatagataat    540

atccttgatc ctgatatccc tcacgtcact gaagttcgcc gaaaacgaat ttcagatcat    600

atcattgaat ctcaaggatg tacttgctct gaacctacta taactcctca tgcgttttca    660

ttttctactc ttggc                                                     675
```

<210> SEQ ID NO 536
<211> LENGTH: 675
<212> TYPE: DNA
<213> ORGANISM: Unknown

<220> FEATURE:
<223> OTHER INFORMATION: Description of Unknown: A105-675 sequence

<400> SEQUENCE: 536
ccacccacag caagaatgcc atcatctgtc ctcaccccca tttctcccct ccttcccctg 60
caaccattac gcttactcgc atgtgcattg agtggtgcac gtgttgaaca aacagctaca 120
ctcacgtggg ggcgggtttt cccgcccttc ggcctctcgc gaggcccacc cttccccttc 180
ctcccataac tacagtgctt tggtaggtaa gcatcctgat cccccgcgga agctgctcgc 240
gtggcaactg tggggaccca gacaggttat caaaggcacc cggtctttcc gcctccagga 300
gtatccctgc tagtgaattc tagtggggct ctgcttggtg ccaacctccc ccaaatgcgc 360
gctgcgggag tgctcttccc caactcaccc tagtatcctc tcatgtgtgt gcttggtcag 420
catatctgag acgatgttcc gctgtcccag accagtccag caatggacgg gccagtgtgc 480
gtagtcgtct tccggcttgt ccggcgcatg tttggtgaac cggtggggta aggttggtgt 540
gcccaacgcc cgtactttgg tgacaactca agaccaccca ggaatgccag ggaggtaccc 600
cgcctcacgg cgggatctga ccctgggcta attgtctacg gtggttcttc ttgcttccat 660
ttctttcttc tgttc 675

<210> SEQ ID NO 537
<211> LENGTH: 675
<212> TYPE: DNA
<213> ORGANISM: Unknown
<220> FEATURE:
<223> OTHER INFORMATION: Description of Unknown: A110-675 sequence

<400> SEQUENCE: 537
acctttgtgc gcctgtttta taccccctcc cccaactgta acttagaagt aacacacacc 60
gatcaacagt cagcgtggca caccagccac gttttgatca agcacttctg ttaccccgga 120
ctgagtatca atagactgct cacgcggttg aaggagaaag cgttcgttat ccggccaact 180
acttcgaaaa acctagtaac accgtggaag ttgcagagtg tttcgctcag cactacccca 240
gtgtagatca ggtcgatgag tcaccgcatt ccccacgggc gaccgtggcg gtggctgcgt 300
tggcggcctg cccatgggga aacccatggg acgctctaat acagacatgg tgcgaagagt 360
ctattgagct agttggtagt cctccggccc ctgaatgcgg ctaatcctaa ctgcggagca 420
cacaccctca agccagaggg cagtgtgtcg taacgggcaa ctctgcagcg gaaccgacta 480
ctttgggtgt ccgtgtttca ttttattcct atactggctg cttatggtga caattgagag 540
atcgttacca tatagctatt ggattggcca tccggtgact aatagagcta ttatatatcc 600
ctttgttggg tttataccac ttagcttgaa agaggttaaa acattacaat tcattgttaa 660
gttgaataca gcaaa 675

<210> SEQ ID NO 538
<211> LENGTH: 675
<212> TYPE: DNA
<213> ORGANISM: Unknown
<220> FEATURE:
<223> OTHER INFORMATION: Description of Unknown: 18-675 sequence

<400> SEQUENCE: 538
cccacagcaa gaatgccatc atctgtcctc acccccaatt ttcccttttc ttcccctgca 60
accattacgc ttactcgcat gtgcattgag tggtgcatgt gttgaacaaa cagctacact 120
cacatggggg cgggttttcc cgccctacgg cctctcgcga ggcccacccc ttccctcccc 180

```
ttataactac agtgctttgg taggtaagca tcctgatccc ccgcggaagc tgctcacgtg    240

gcaactgtgg ggacccagac aggttatcaa aggcacccgg tctttccgcc ttcaggagta    300

tccctactag tgaattctag cggggctctg cttggtgcca acctccccca aatgcgcgct    360

gcgggagtgc tcttccccaa ctcaccctag tatcctctca tgtgtgtgct tggtcagcat    420

atctgagacg atgttccgct gtcccagacc agtccagtaa tggacgggcc agtgcgtgta    480

gtcgtcttcc ggcttgtccg gggcatgttt ggtgaaccgg tggggtaagg ttggtgtgcc    540

caacgcccgt actttggtga cacctcaaga ccacccagga atgccaggga ggtaccccac    600

ctcacggtgg gatctgaccc tgggctaatt gtctacggtg gttcttcttg cttccacttc    660

tttcttctgt tcacg                                                     675
```

<210> SEQ ID NO 539
<211> LENGTH: 675
<212> TYPE: DNA
<213> ORGANISM: Unknown
<220> FEATURE:
<223> OTHER INFORMATION: Description of Unknown: A115-675 sequence

<400> SEQUENCE: 539

```
acctttgtgc gcctgtttta tacccccccc aacctcgaaa cttagaagta aagcaaaccc     60

gatcaatagc aggtgcggcg caccagtcgc atcttgatca agcacttctg taaccccgga    120

ccgagtatca atagactgct cacgcggttg aaggagaaaa cgttcgttac ccggctaact    180

acttcgagaa acccagtagc atcatgaaag ttgcagagtg tttcgctcag cactaccccc    240

gtgtagatca ggccgatgag tcaccgcact tccccacggg cgaccgtggc ggtggctgcg    300

ttggcggcct gcctatgggg caacccatag gacgctctaa tacggacatg gtgcgaagag    360

tctattgagc tagttagtag tcctccggcc cctgaatgcg gctaatccta actgcggagc    420

acataccctt aatccaaagg gcagtgtgtc gtaacgggta actctgcagc ggaaccgact    480

actttgggtg tccgtgtttc cttttaattt ttactggctg cttatggtga caattgagga    540

attgttgcca tatagctatt ggattggcca tccggtgact aacagagcta ttgtgttcca    600

atttgttgga tttaccccgc tcacactcac agtcgtaaga acccttcatt acgtgttatt    660

tctcaactca agaaa                                                     675
```

<210> SEQ ID NO 540
<211> LENGTH: 675
<212> TYPE: DNA
<213> ORGANISM: Unknown
<220> FEATURE:
<223> OTHER INFORMATION: Description of Unknown: A73-675 sequence

<400> SEQUENCE: 540

```
ttactccatt cagcttcttc ggaacctgtt cggaggaatt aaacgggcac ccatactccc     60

cccacccccc ttttgtaact aagtatgtgt gctcgtgatc ttgactccca cggaacggac    120

cgatccgttg gtgaacaaac agctaggtcc acatcctccc ttcccctggg agggcccccg    180

ccctcccaca tcctcccccc agcctgacgt atcacaggct gtgtgaagcc cccgcgaaag    240

ctgctcacgt ggcaattgtg ggtccccccct tcatcaagac accaggtctt tcctccttaa   300

ggctagcccc ggcgtgtgaa ttcacgttgg gcaactagtg gtgtcactgt gcgctcccaa    360

tctcggccgc ggagtgctgt tccccaagcc aaacccctgg cccttcacta tgtgcctggc    420

aagcatatct gagaaggtgt tccgctgtgg ctgccaacct ggtgacaggt gccccagtgt    480

gcgtaacctt cttccgtctc cggacggtag tgattggtta agatttggtg taaggttcat    540
```

gtgccaacgc cctgtgcggg atgaaacctc tactgcccta ggaatgccag gcaggtaccc 600
cacctccggg tgggatctga gcctgggcta attgtctacg ggtagtttca tttccaatcc 660
ttttatgtcg gagtc 675

<210> SEQ ID NO 541
<211> LENGTH: 675
<212> TYPE: DNA
<213> ORGANISM: Kobuvirus sp.

<400> SEQUENCE: 541
ttactccatt cagcttcttc ggaacctgtt cggaggaatt aaacgggcac ccatacaccc 60
ccatcccctt tctgcaactt aagtatgtgt gctcgtgatc ttgactccca cggaatggat 120
cgatccgctg gagaacaaac tgctagatcc acatcctccc ttcccctggg aggaccttgg 180
tcctcccaca tcctcccccc agcctgacgt accacaggct gtgtgaagcc cccgcgaaag 240
ctgctcacgt ggcaattgtg ggtcccccct tcatcaagac accaggtctt tcctccttaa 300
ggctagcccc gatgtgtgaa ttcacattgg gcaactagtg gtgtcactgt gcgctcccaa 360
tctcggccgc ggagtgctgt tccccaagcc aaacccctgg cccttcacta tgtgcctggc 420
aagcatacct gagaaggtgt tccgctgtgg ctgccagcct ggtaacaggt gccccagtgt 480
gcgtaacctt cttccgtctt cggacggtag tgattggtta agatttggtg taaggtccat 540
gtgccaacgc cctgtgcggg atgaaacctc tactgcccta ggaatgccag gcaggtaccc 600
cacccccggg tgggatctga gcctgggcta attgtctacg ggtagtttca tttccaattc 660
ttttatgtcg gagtc 675

<210> SEQ ID NO 542
<211> LENGTH: 675
<212> TYPE: DNA
<213> ORGANISM: Aichivirus sp.

<400> SEQUENCE: 542
ttactccatt cagcttcttc ggaacctgtt cggaggaatt aaacgggcac ccatacatcc 60
ccatcccctt tctgtaactt aagtatgtgt gcttgtaatc ttgactccca cggaatggat 120
cgatccgctg gagaacaaac tgctagatcc acatcctccc ttcccctggg aggaccttgg 180
tcctcccaca tcctcccccc agcctgacgt accacaggct gtgtgaagcc cccgcgaaag 240
ctgctcacgt ggcaattgtg ggtcccccct tcatcaagac accaggtctt tcctccttaa 300
ggctagcccc gatgtgtgaa ttcacattgg gcaactagtg gtgtcactgt gcgctcccaa 360
tctcggccgc ggagtgctgt tccccaagcc aaacccctgg cccttcacta tgtgcctggc 420
aagcatatct gagaaggtgt tccgctgtgg ctgccagcct ggtaacaggt gccccagtgt 480
gcgtaacctt cttccgtctc cggacggtag tgattggtta agatttggtg taaggttcat 540
gtgccaacgc cctgtgcggg atgaaatctc tactgcccta ggaatgccag gcaggtaccc 600
caccctcggg tgggatctga gcctgggcta attgtctacg ggtagtttca tttccaatcc 660
ttttatgtcg gagtc 675

<210> SEQ ID NO 543
<211> LENGTH: 675
<212> TYPE: DNA
<213> ORGANISM: Aichivirus sp.

<400> SEQUENCE: 543

```
actccattca gcttcttcgg aacctgttcg gaggaattaa acgggcaccc atacaccccc     60

atccccttttt ttgcaactta agtatgtgtg ctcgtaatct tgactcccac ggaatggatc    120

gatccgctgg agaacaaact gctagatcca catcctccct ccccccctgggg aggacctcgg    180

tcctcccaca tcctcccccc agcctgacgt atcacaggct gtgtgaagcc cccgcgaaag    240

ctgctcacgt ggcaattgtg ggtcccccct tcatcaagac accaggtctt tcctccttaa    300

ggctagtccc gatgtgtgaa ttcacatcgg gcaactagtg gtgtcactgt gcgctcccaa    360

tctcggccgc ggagtgctgt tccccaagcc aaacccctgg cccttcacta tgtgcctggc    420

aagcatatct gagaaggcgt tccgctgtgg ctgccagcct ggtaacaggt gccccagtgt    480

gcgtaacctt cttccgtccc cggacggtag tgattggtta agacttggcg taaggttcat    540

gtgccaacgc cctgtgcggg atgaaacctc tactgcccta ggaatgccag gcaggtaccc    600

caccttcggg tgggatctga gcctgggcta attgtctacg ggtagtttca tttctaattc    660

tttcatgtcg gagtc                                                      675
```

<210> SEQ ID NO 544
<211> LENGTH: 675
<212> TYPE: DNA
<213> ORGANISM: Aichivirus sp.

<400> SEQUENCE: 544

```
ttactccatt cagcttcttc ggaacctgtt cggaggaatt aaacgggcac ccatacaccc     60

ccaccccctt tttgcaactt aagtatgtgt gctcgtgatc ttgactccca cggaatggat    120

cgatccgctg gagaacaaac tgctagatcc acatcctccc ttcccttggg aggacctcgg    180

tcctcccaca tcctcccccc agcctgacgt accacaggct gtgtgaagcc cccgcgaaag    240

ccgctcacgt ggcaattgtg ggtcccccct tcattaagac accaggtctt tcctccttaa    300

ggctagtccc gatgtgtgaa ttcacattgg gcaactagtg gtgtcactgt gcgctcccaa    360

tctcggccgc ggagtgctgt tccccaagcc aaacccctgg cccttcacta tgtgcctggc    420

aagcatatct gagaaggtgt tccgctgtgg ctgccagcct ggtaacaggt gccccagtgt    480

gcgtaacctt cttccgtctt cggacggtag tgattggtta agatttggcg taaggttcat    540

gtgccaacgc cctgtgcggg atgaaacctc tactacccta ggaatgccag gcaggtaccc    600

caccctcggg tgggatctga gcctgggcta attgtctacg ggtagtttca tttccaattc    660

ttctatgtcg gagtc                                                      675
```

<210> SEQ ID NO 545
<211> LENGTH: 675
<212> TYPE: DNA
<213> ORGANISM: Aichivirus sp.

<400> SEQUENCE: 545

```
tactccattc agcttcttcg gaacctgttc ggaggaatta aacgggcacc catacacccc     60

caccccccttt tctgcaactt aagtatgtgt gctcgtaatc ttgactccca cggaatggat    120

cgatccgctg gagaacaaac tgctagatcc acatcctccc ttcccctggg aggaccccgg    180

tcctcccaca tcctcccccc agcctgacgt atcacaggct gtgtgaagtc cccgcgaaag    240

ctgctcacgt ggcaattgtg ggtcccccct tcatcaagac accaggtctt tcctccttaa    300

ggctagcccc gatgtgtgaa ttcacattgg gcaactagtg gtgtcactgt gcgctcccaa    360

tctcggccgc ggagtgctgt tccccaagcc aaacccctgg cccttcacta tgtgcctggc    420

aagcatatct gagaaggtgt tccgctgtgg ctgccagcct ggtaacaggt gccccagtgt    480
```

gcgtaacctt cttccgtctc cggacggtag tgattggtta agatttggtg taaggttcat 540
gtgccaacgc cctgtgcggg atgaaacctc tactgcccta ggaatgccag gcaggtaccc 600
caccttcggg tgggatctga gcctgggcta attgtctacg ggtagtttca tttccaattc 660
ttttatgtcg gagtc 675

<210> SEQ ID NO 546
<211> LENGTH: 664
<212> TYPE: DNA
<213> ORGANISM: Aichivirus sp.

<400> SEQUENCE: 546
gcttcttcgg aacctgttcg gaggaattaa acgggcaccc atacaccccc accccctttt 60
ctgcaactta agtatgtgtg ctcgtaatct tgactcccac ggaatggatc gatccgctgg 120
agaacaaact gctagatcca catcctccct tcccctggga ggaccccggt cctcccacat 180
cctcccccca gcctgacgta tcacaggctg tgtgaagtcc ccgcgaaagc tgctcacgtg 240
gcaattgtgg gtcccccctt catcaagaca ccaggtcttt cctccttaag gctagccccg 300
atgtgtgaat tcacattggg caactagtgg tgtcactgtg cgctcccaat ctcggccgcg 360
gagtgctgtt ccccaagcca aacccctggc ccttcactat gtgcctggca agcatatctg 420
agaaggtgtt ccgctgtggc tgccagcctg gtaacaggtg ccccagtgtg cgtaaccttc 480
ttccgtctcc ggacggtagt gattggttaa gatttggtgt aaggttcatg tgccaacgcc 540
ctgtgcggga tgaaacctct actgccctag gaatgccagg caggtacccc accttcgggt 600
gggatctgag cctgggctaa ttgtctacgg gtagtttcat ttccaattct tttatgtcgg 660
agtc 664

<210> SEQ ID NO 547
<211> LENGTH: 675
<212> TYPE: DNA
<213> ORGANISM: Aichivirus sp.

<400> SEQUENCE: 547
tactccattc agcttcttcg gaacctgttc ggaggaatta aacgggcacc cactttcctg 60
tcctctcccc ttttctgtaa ctccaagtgt gtgctcgtaa tcttgactcc cgcggattga 120
ccgctccgct ggtgaacaaa ctgctaggtc atctcctccc cacccttggg cgtccttccg 180
ggcgtccaca ccctcccccc agcctgacgt gtcacaggct gtacaaagac cccgcgaaag 240
ctgctaacgt ggcaattgtg ggtcccccct ttgtaaagga accgagtctt tctcccttaa 300
ggctagaccc ctgtgtgaat tcacaggtgg caactagtgg ttccactgca tgctcccgac 360
ctcggccgcg gagtgctgtt ccccaagtcg taacactgac cttcacttat gtgcctggca 420
agcatatctg agaagatgtt ccgctgtggc tgccaaacct ggtaacaggt gccccagtgt 480
gcgtagtctt cttccgtctt cggacggtag gtgttaggta aagatgcggc gtaaggttca 540
agtgccaacg ccctggaagg gatgaccctt ctactgccct aggaatgccg cgcaggtacc 600
ccaggttcgc ctgggatctg agcgcgggct aattgtctac gggtagtttc atttccctct 660
tcttccactg gcatc 675

<210> SEQ ID NO 548
<211> LENGTH: 675
<212> TYPE: DNA
<213> ORGANISM: Aichivirus sp.

<400> SEQUENCE: 548
actccattca gcttcttcgg aacctgttcg gaggaattaa acgggcaccc actttcctgt 60
cctctccccc tttctgcaac tcaagtgtgt gctcgtaatc ctgactccca cgggttgacc 120
gccccgttgg tgaacaaaca gctaggtcat tccctcccta cccctgggcg ccatttcagt 180
ggcgttcata tcctcccccc agcctgacgt gtcacaggct gtgcaaagtc cccgcgaaag 240
ctgctcacgt ggcaattgtg ggtccccccct ttgtgaagga accgagtctt tctcccttaa 300
ggctagaccc ctgtgtgaac tcacaggtgg caactagtgg ttccactgca tgctcccgac 360
ctcggccgcg gagtgctgtt ccccaagtcg tgacactgac ctccacttat gtgcctggca 420
agcatatctg agaagatgtt ccgctgtggc tgccaaacct ggtaacaggt gccccagtgc 480
gtgtagtctt cttccgtctc cggacggtaa gtgtgtggta aagatgcggc gtaaggttca 540
agtgccaacg ccctggaagg gatgaccctt ctactgccct aggaatgccg cgcaggtacc 600
ccaggttcgc ctgggatctg agcgcgggct aattgtctac gggtagtttc atttccctct 660
cttttcactg gcatc 675

<210> SEQ ID NO 549
<211> LENGTH: 498
<212> TYPE: DNA
<213> ORGANISM: Pestivirus sp.

<400> SEQUENCE: 549
gtataagggt tgggaacctt gtaccaagct acctctgcca ttcagtattt gggagtagaa 60
gtagatgtgt ttacaaactc acacgtgtgg gggcggggat agactgtgcc agcggtcgtg 120
taccagcacc tacgcatacg tgtggactgc gaaccaggag agcacctagg tctgacaagc 180
tgtgagaaca cagtagtcgt cagtgagtca gctggtaagg atcacccacc tggatactca 240
cgtggacgag ggagtttccc agtcagaaac ctacaccaga ggaggggtcc tctggagaca 300
tggatggtct gagtaacaga ctatctactg ggtgtgctg cctgacaggg tctcggctga 360
tagcctggct agcagtataa aaatcagttg aattggcata tgagttgtga acatctagta 420
aacaatgaaa gacaaaaaca aaaaatgagc ataataaaaa aattgtacaa tccactactc 480
aggtgtggct gcagactt 498

<210> SEQ ID NO 550
<211> LENGTH: 576
<212> TYPE: DNA
<213> ORGANISM: Kobuvirus sp.

<400> SEQUENCE: 550
tttgaaaagg gggtgggggg gcctcggccc cctcaccctc ttttccggtg gccattcgcc 60
cgggccaccg ttactccact ccactccttc gggactggtt tggaggaaca caacagggct 120
tcccatccct gtttaccctt tattccatca tcctttcccc aagtttaccc tatccacacc 180
ccactgactg actcctttgg attttgacct cagaatgcct atttgacctc ccactcgcct 240 ctccctttc ggattgccgg tggtgcctgg cggaaaaagc acaagtgtgt tgcaggctac 300
caaactccta cccgacaaag gtgcgtgtcc gcgtgctgag taatgggata ggagatgcct 360
acaacaggct cgcccatgag tagagcatgg actgcggtgc atgtgacttc ggtcaccacg 420
ggcatagcat tgctcacccg tgaatcaagt catcgagatt tctctgacct ctgaagtgca 480
ctgtggttgc gtggctggga atccacgctt gaccatgtac tgcttgatag agtcgcggct 540
ggccgactca tgggttaaag tcagttgaca agacac 576

<210> SEQ ID NO 551
<211> LENGTH: 675
<212> TYPE: DNA
<213> ORGANISM: Kobuvirus sp.

<400> SEQUENCE: 551
cctacccaag ggttacatgg gaccatattc ctcctcccct gtaactttaa gttttgtgcc 60
cgtattcttg actccaggcg gatgttgtgt cgcccgtcct gtgaacaaac agctagacac 120
tttcctcccc tccctctggg ctgctccggc agtccactcc ctccccccag cgtaacatgc 180
cccgctggag tgatgcacct ggaagtcgtg gacgtgggtt agtaacttcg gtgaaaaccc 240
actataatga caactggttg acccccacac tcaaaggact cgagtctttc tcccttaagg 300
ctagcccggc cacatgaatt tgcagctggc aactagtgag tccaccatgt cccgcaacct 360
cggctgcgga gtgctgttcc ccaagcgtat gccttccttc tgtaagagtg cgcctggcaa 420
gcacatctga gaagtcgttc cgctgcgtcg tgccaacctg gcgacaggtg acccagtgtg 480
cgtagacttc ttccggattc gtccggctct tctctaggaa acatgcgtgt aaggttcatg 540
tgccaaagcc ctgcgcgcgg tgttcttcta ctgccctagg aatgtgccgc aggtacccct 600
acttcggtag ggatctgagc ggtagctaat tgtctacggg tagtttcatt tccatcttct 660
cttcaggtcg acatc 675

<210> SEQ ID NO 552
<211> LENGTH: 675
<212> TYPE: DNA
<213> ORGANISM: Kobuvirus sp.

<400> SEQUENCE: 552
gaccttctgg tacttcttcg cctgggtcac aaaagcgaag aacctgcctc tctaacgcca 60
gacgagcggc attaaacttg aacttctggc actctccact ctccttttc cctgtccctt 120 tccccactgc gctctcaagg tcgcgcaatc ctgggactag cccagtttta aaagttcctg 180
gcaccctttg cccctctagg cccttaaggt aggaactgac cttgtgctgt gatctcggtg 240
cgggagtgct accacgtagt catcgtaagc ctcgtttctg gttctgccct ggcaaggcta 300
cagagtaccg tgttccgctg tggatgccat ccgggtaacc ggacccccag tgtgtgtagc 360
ggtatgttca cggtccgccg tgttcaccag attcctgacc tggctttgct agaaatggtg 420
tgtgcccaat ccctgtgacc agtatcaatt acatcaccta ggaatgctag gaaggtaccc 480
cagtcctgag ctgggatctg atcctaggct aattgtctac ggtgatgctc cttttatttt 540
cttacaactg ctattgactg tctgattgct gattctgctc ttgtgctctt ctgctctggc 600
tcattctcaa gggttctctt tgtccaagat cctttggttc tctccttgtt ccacttgcca 660
ctgccaacgc ttgtc 675

<210> SEQ ID NO 553
<211> LENGTH: 369
<212> TYPE: DNA
<213> ORGANISM: Pestivirus sp.

<400> SEQUENCE: 553
gtatacgcag ttagttcatc ctgtgtatac agattggaga ctctaaaaac aacgattcgg 60
aataggggcc cgcggcgaag accgaagaca ggctaaccat gccgttagta gggctagcac 120
caaaacgcgg gaactagaca cttaggagag tggtctggct actctaagag gtgagtacac 180

-continued

```
cttaaccgtc aagggttcta ctcctcagtt gaggactaga gatgccctgt ggacgggggc    240

atgcccaaga gttagcttag ccggggcggg ggttgttccg gtgaaagtag caatattgac    300

cacactgcct gatagggcgg agcaggcccc ctaggtagtc tagtataaaa tgtctgctgt    360

acatggcac                                                            369
```

<210> SEQ ID NO 554
<211> LENGTH: 399
<212> TYPE: DNA
<213> ORGANISM: Pestivirus sp.

<400> SEQUENCE: 554

```
tacgcggggt ataacgacag tagttcaagt gtcgttatgc atcattggcc ataacaaatt     60

atctaatttg gaatagggac ctgcgacctg tacgaaggcc gagcgtcggt agccattccg    120

actagtagga ctagtacaaa taggtcaact ggttgagcag gtgagtgtgc tgcagcggct    180

aagcggtgag tacaccgtat tcgtcaacag gtgctactgg aaaggatcac ccactagcga    240

tgcctgtgtg gacgaggaca tgtccaagcc aatgttatca gtagcggggg tcgttactga    300

gaaagctgcc cagaatgggt agttgcacat acagtctgat aggatgccgg cggatgccct    360

gtattttgac cagtataaat attatccgtt gtaaagcat                          399
```

<210> SEQ ID NO 555
<211> LENGTH: 123
<212> TYPE: DNA
<213> ORGANISM: Pestivirus sp.

<400> SEQUENCE: 555

```
gcagatatcg gtggtggacc tgggggttgg gctcaccgtg ccccttcatg ggtagacct      60

cactgcttga tagagtgccg gcggatgcct caggtaagag tataaaatcc gttgttcact    120

aac                                                                  123
```

<210> SEQ ID NO 556
<211> LENGTH: 382
<212> TYPE: DNA
<213> ORGANISM: Pestivirus sp.

<400> SEQUENCE: 556

```
gtatacgagt ttagctcaat cctcgtatac aatattgggc gtcaccaaat atagatttgg     60

cataggcaac accccgatgc gaaggccgaa aagggctaac catgccctta gtaggactag    120

caaaaaatcg gggactagcc caggtggtga gcttcctgga tgaccgaagc cctgagtaca    180

gggcagtcgt caacagttca acacgcagaa taggtttgcg tcttgatatg ctgtgtggac    240

gagggcatgc ccacggtaca tcttaaccta tccgggggtc ggataggcga aagtccagta    300

ttggactggg agtacagcct gatagggtgt tgcagagacc catctgatag gctagtataa    360

aaaactctgc tgtacatggc ac                                             382
```

<210> SEQ ID NO 557
<211> LENGTH: 373
<212> TYPE: DNA
<213> ORGANISM: Unknown
<220> FEATURE:
<223> OTHER INFORMATION: Description of Unknown: Classical swine fever
      virus sequence

<400> SEQUENCE: 557

```
gtatacgagg ttagttcatt ctcgtatgca tgattggaca aattaaaatt tcaatttgga     60
```

```
tcagggcctc cctccagcga cggccgaact gggctagcca tgcccacagt aggactagca    120

aacggaggga ctagccgtag tggcgagctc cctgggtggt ctaagtcctg agtacaggac    180

agtcgtcagt agttcgacgt gagcagaagc ccacctcgat atgctatgtg gacgagggca    240

tgcccaagac acaccttaac cctagcgggg gtcgctaggg tgaaatcaca ccacgtgatg    300

ggagtacgac ctgatagggt gctgcagagg cccactatta ggctagtata aaaatctctg    360

ctgtacatgg cac                                                       373


<210> SEQ ID NO 558
<211> LENGTH: 222
<212> TYPE: DNA
<213> ORGANISM: Pegivirus sp.

<400> SEQUENCE: 558

tcagggttgg taggtcgtaa atcccggtca ccttggtagc cactataggt gggtcttaag     60

agaaggttaa gattcctctt gtgcctgcgg cgagaccgcg cacggtccac aggtgttggc    120

cctaccggtg ggaataaggg cccgacgtca ggctcgtcgt taaaccgagc ccgtcaccca    180

cctgggcaaa cgacgcccac gtacggtcca cgtcgccctt ca                       222


<210> SEQ ID NO 559
<211> LENGTH: 527
<212> TYPE: DNA
<213> ORGANISM: Pegivirus sp.

<400> SEQUENCE: 559

cccggcactg ggtgcaagcc ccagaaaccg acgcctattt aaacagacgt tatgaaccgg     60

cgccgacccg gcgaccggcc aaaaggtggt ggatgggtga tgccagggtt ggtaggtcgt    120

aaatcccggt catcttggta gccactatag gtgggtctta agggttggtc aaggtccctc    180

tggcgcttgt ggcgagaaag cgcacggtcc acaggtgttg gccctaccgg tgtgaataag    240

ggcccgacgt caggctcgtc gttaaaccga gcccattacc cacctgggca aacaacgccc    300

acgtacggtc cacgtcgccc tacaatgtct ctcttgacca ataggctttg ccggcgagtt    360

gacaaggacc agtgggggct gggcgacggg ggtcgtatag gaagaaaaat gccacccgcc    420

ctcacccgaa ggttcttggg ctaccccggc tgcaggccgc cgcggagctg ggtagcccca    480

agaaccttcg ggtgagggcg ggtggcattt ttcttcctat accgatc                  527


<210> SEQ ID NO 560
<211> LENGTH: 402
<212> TYPE: DNA
<213> ORGANISM: Pegivirus sp.

<400> SEQUENCE: 560

tggtcacctt ggtagccact ataggtgggt cttaagagaa ggttaagatt cctcttgtgc     60

ctgcggcgag accgcgcacg gtccacaggt gttggcccta ccggtgtgaa taagggcccg    120

acgtcaggct cgtcgttaaa ccgagcccat ttcccgcctg ggcaaacgac gcccacgtac    180

ggtccacgtc gccctttaa tgtctctctt gaccaatagg ttcatccggc gagttgacaa     240

ggaccagtgg gggccggggg tcacagggat ggaccctggg ccctgccctt cccggcgggg    300

tggggaaagc atggggccac ccagctccgc ggcggcctgc agccggggta gcccaagaac    360

cttcgggtga gggcgggtgg cattttctt cctataccga tc                        402


<210> SEQ ID NO 561
<211> LENGTH: 531
```

<212> TYPE: DNA
<213> ORGANISM: Unknown
<220> FEATURE:
<223> OTHER INFORMATION: Description of Unknown: Hepatitis GB virus A sequence
<400> SEQUENCE: 561
gccgggtgga aggcccggaa ccgccccacc acctcaacta ggtggtaagg gtacgtctat 60
cggtccggct ggcccgaaag gcggtggatc ctgtgtgtta gggttcgtag gtggtaaatc 120
ccagcacagg tggtaatcgc tatagggcag gcttatcccg gtgaccgctt ccctggatcc 180
tggagcgggt cgtggcggca cggtccacag gagtggggcc tccggtgtga ataagccctc 240
gtctggagca tcagacgtta aactgagacg tcccgaagag atcggaacga cgccccacgt 300
atggcaacgc cgcttaaaac ccttcgggga cagctatgcg ggttgacaat gccagtgggg 360
ggccgggccc actattgttg tgggctccga gttcctctag ggatggccga aaggcagcca 420
tggggccacc caggcggcgc cgtgctacag gcggcaaggg gaaaaatcct tcgggtgacc 480
ccgggtggca ttccctccct tagcagcatg agtgtggtgg tagctgcaac c 531

<210> SEQ ID NO 562
<211> LENGTH: 520
<212> TYPE: DNA
<213> ORGANISM: Pegivirus sp.

<400> SEQUENCE: 562
ggggaatctc accccccgtc cggttccgga agaatcggaa accgacaccc tgaccaatca 60
ttcttgatca tagagtggat gttagtgaaa gccagacgaa agccggcgga tgggtggtga 120
cagggttggt aggtcgtaaa tcccggccac cctggtaccc ggtataagtt gggcggaagc 180
tgactgaagc tccgtgctct tttctgtgcg ttcttggtgc acggtccaca ggtgacgcct 240
ataccggtgt gaataatagg ccgactcgag cggagtcgtt aaactgagaa cctccatacg 300
gatggcaact tggcttgcgt acggggacgc cgctaaagtc acagtgggtt aagtccggcg 360
ggttgacaac cccagcaagg cgagggggtc ctattgttgg actctgccag ttcccggtgg 420
aggtaggcat ggggtggccc agctccgcgg cgcgctacag ccggggtagc ccaaaatccg 480
aaaggtgagg gcgggccaca tgtccgaaat ttagtcaagc 520

<210> SEQ ID NO 563
<211> LENGTH: 524
<212> TYPE: DNA
<213> ORGANISM: Pegivirus I
<400> SEQUENCE: 563
agaatggtct aagtggttgc caccgtggtc cgaaggggag gaggacctac gctgccaggg 60
ttggcaggtc gtaaatcccg ggtgtaggag atccctcctt gttaggactg ctggtagctg 120
gggggtcggt gaccccctgg gcaaccgcca aacccggacg accgggtggc ggctccatgt 180
tggcacggtc cacaggtgtg aaccctaccg gtgtgaataa gggttggtgg ttgcggtcca 240
ccttaaacgt agtatgcatt gggcttggta aaacaccgct cgtagtacgg aacgccgcct 300
ttaaagacac agtaggcgta gccggcgggt tgacaatcca tacggggggt ggggtgtggt 360
catggatctg tccacaccac cttcatgcgg ccctctaagc aagccatacc ggggggaggc 420
gcgcggcacc gcactgccgg gcaaggggaa gaaccttcgg gtgacccccc cccaaccacc 480
gtccgatcaa tgctaatgtt gcgtttaggc gtgacaccgg caca 524

<210> SEQ ID NO 564
<211> LENGTH: 537
<212> TYPE: DNA
<213> ORGANISM: Pegivirus K

<400> SEQUENCE: 564
agaatggtgt gatccgtcgc cgctccagcg gaaagcgggc gggatctagt ggttagggtt 60
gttcgcgtaa atcccacact agtggtacgc tcgtataacg tgggagcagc cggtggggtc 120
gaccccccac ctggcggctg ctgagcaccg gacgaagcgc ggggggtgaa cgctaacccg 180
cggcccgggc tgccaacgtt aggcacgtct tggctggaag acgttaaaca cagggccccc 240
cctcaaccct gatccgaggc cagagaccaa ggtacgccgc ccttttaaag gcgttactcg 300
tccaatagga tctctccggc gggttgtcaa accttgctgg ccctggtgat ggttacggga 360
gggggtgggg cggggagtag aagccccgcc cggcatgggg gtaccaagct cggcacgccc 420
agcacgcgtg gcgtagggga aaaatccttc gggtgacccc tggtaccata aagtaattaa 480
catgagcatg ccgctagggt gtgctttttc ttccttcctt gggaaggcgg tggcacc 537

<210> SEQ ID NO 565
<211> LENGTH: 617
<212> TYPE: DNA
<213> ORGANISM: Unknown
<220> FEATURE:
<223> OTHER INFORMATION: Description of Unknown: Theiler's disease-
associated virus sequence

<400> SEQUENCE: 565
tgataccgtg tcccggtacg acctcgcgcg tccccaagct cgccctgagg ggggagcgta 60
agggcgcgta gtggggtagc cccccaaacc gagccaccct agtgagtgac tttagaatgg 120
ttagggagac taccgccttc gctgtttggg gacctaatga tccgcgtgcc agggttcttc 180
gggtaaatcc cggcgcggtg ttttgggttc agggcagtag gggcagacgg gccagcagtc 240
gctggttcct ggtaccacca ccctatccgg acgacctccc tcacgaaagg tcgccacggt 300
ctgtggctcg acgacgccta taattcagtc cgaggggcgc agccctcgtt aaacttaggc 360
aaggttcctc gccattgatt tggccagggg tttaagtgaa cgccgccctt ttaatgttta 420
atagggttct ttcccggcgg gttgacaaac acttccctgg gctcttcgtt ggcctcggtt 480
ccttgatgct tcggcaccca tgagcgcaca gggggggac cctgcgacag tccgccaaga 540
ggaaaatcct tcgggtgacc tcgtgcgcaa cccaatccct tcttcttcca catggcgtgt 600
ctgtggtgca tgctgtg 617

<210> SEQ ID NO 566
<211> LENGTH: 349
<212> TYPE: DNA
<213> ORGANISM: Pegivirus sp.

<400> SEQUENCE: 566
ggacttcggt ccccctgtta ctctgcgagc caccgcagag ccagggttgg tacgcccgag 60
gtgttagacc ccggccgaaa gctcctaacc atggggttag taggacgtgg taaatgccac 120
tgaggggttg gagagctggt agagcgagta agtcggcgta aggcccgagt acgggcctcc 180
cagcccgggt cagcctaaac ctggctgtga tacccggtgc atggagggcg tgtcccaacg 240
ctcgatcgct gtagggtggg tccctgcagt tgggtgtggc taccctgctc gtactgcttg 300
atagagtccc ggcggacgga ccagctctcg tcagtccgtg gagttgcac 349

<210> SEQ ID NO 567
<211> LENGTH: 327
<212> TYPE: DNA
<213> ORGANISM: Pegivirus sp.

<400> SEQUENCE: 567
aactgttgtt gtagcaatgc gcatattgct acttcggtac gcctaattgg taggcgcccg 60
gccgaccggc cccgcaaggg cctagtagga cgtgtgacaa tgccatgagg gatcatgaca 120
ctggggtgag cggaggcagc accgaagtcg ggtgaactcg actcccagtg cgaccacctg 180
gcttggtcgt tcatggaggg catgcccacg ggaacgctga tcgtgcaaag ggatgggtcc 240
ctgcactggt gccatgcgcg gcaccactcc gtacagcctg atagggtggc ggcgggcccc 300
cccagtgtga cgtccgtgga gcgcaac 327

<210> SEQ ID NO 568
<211> LENGTH: 436
<212> TYPE: DNA
<213> ORGANISM: Unknown
<220> FEATURE:
<223> OTHER INFORMATION: Description of Unknown: GB virus C/Hepatitis G virus sequence

<400> SEQUENCE: 568
cccccggcac tgggtgcaag ccccagaaac cgacgcctat ctaagtagac gcaatgactc 60
ggcgccgact cggcgaccgg ccaaaaggtg gtggatgggt gatgacaggg ttggtaggtc 120
gtaaatcccg gtcaccttgg tagccactat aggtgggtct taagagaagg ttaagattcc 180
tcttgtgcct gcggcgagac cgcgcacggt ccacaggtgt tggccctacc ggtgggaata 240
agggcccgac gtcaggctcg tcgttaaacc gagcccgtta cccacctggg caaacgacgc 300
ccacgtacgg tccacgtcgc ccttcaatgt ctctcttgac caataggcgt agccggcgag 360
ttgacaagga ccagtggggg ccgggggctt ggagagggac tccaagtccc gcccttcccg 420
gtgggccggg aaatgc 436

<210> SEQ ID NO 569
<211> LENGTH: 393
<212> TYPE: DNA
<213> ORGANISM: Pegivirus sp.

<400> SEQUENCE: 569
agaatgggga gttaactcct ggcactggcc cgaagcatga actgatcgcg gtggcagggt 60
tcttcgggta aatcccggcc gcgtgttgtg attgtgttag ggcaggtgac agtcggcagg 120
gtcgaccccc tgcttcagga ccactgtctt cctggacgac cgttgctgaa aaagggccgc 180
cacggtctgt agctcgccga cgcttctaat tcaggccgga ggaccacgct ccgtaatcga 240
gcccaagtac tcaaacccca gcacccctgg gtcacgccct acgccgccct tttaacgctt 300
cggctaatag ggtctatccg gcgggttgac aaagggcgca gggttacctg gtactacgag 360
cttgggtgtc cctgggagta atcccagggt gcc 393

<210> SEQ ID NO 570
<211> LENGTH: 343
<212> TYPE: DNA
<213> ORGANISM: Flavivirus sp.

<400> SEQUENCE: 570
atataaatcc cagtttggtt aaacctattt caaggcttaa gttgtttatt attttatcgc 60
cgctcgtgac tataaagttg cctagcggag agagataaag aagaaggagt tcaaggctca 120
gggcagggcg caagttccct ggtccctagg ccgctcgcag gaaggaggag tgaagaagaa 180
gaaagagaag gagaggacca ccgccgaaag aaggcaggtg cctcacaaga gggccaacca 240
gcgtgttgga ccagtggcca acgccggacg gcgtggtggc ctgctgggac gcctggggat 300
tggatggagt gccttcctac aggaagacat cgttcaagcc atc 343

<210> SEQ ID NO 571
<211> LENGTH: 104
<212> TYPE: DNA
<213> ORGANISM: Unknown
<220> FEATURE:
<223> OTHER INFORMATION: Description of Unknown: Bussuquara virus sequence

<400> SEQUENCE: 571
agtatttctt ctgcgtgaga ccattgcgac agttcgtacc ggtgagtttt gacttaacgc 60
agtgagaaaa gttttcgagg aaagacgaga agcgaattct ctga 104

<210> SEQ ID NO 572
<211> LENGTH: 106
<212> TYPE: DNA
<213> ORGANISM: Zika virus

<400> SEQUENCE: 572
agttgttgat ctgtgtgagt cagactgcga cagttcgagt ctgaagcgag agctaacaac 60
agtatcaaca ggtttaattt ggatttggaa acgagagttt ctggtc 106

<210> SEQ ID NO 573
<211> LENGTH: 150
<212> TYPE: DNA
<213> ORGANISM: Yokose virus

<400> SEQUENCE: 573
agtaaatttt gcgtgctagt cgctgagcgt cagaccgcaa agtgagtttt tagtgatcta 60
aagtgaggag ttattcttac tgtcatcaaa cactacaaat aaacacgttg aaattatttc 120
cggaagaaca actgtccgga atcaaagacg 150

<210> SEQ ID NO 574
<211> LENGTH: 118
<212> TYPE: DNA
<213> ORGANISM: Wesselsbron virus

<400> SEQUENCE: 574
agtatattct gcgtgctaat cgttcgacgt tagtccgtgg agtgagcttc tattagagtc 60
gttaacacgt ttgaataatt tctactgaaa ggagtagaag aaaggagatt cattccca 118

<210> SEQ ID NO 575
<211> LENGTH: 389
<212> TYPE: DNA
<213> ORGANISM: Hepacivirus sp.

<400> SEQUENCE: 575
acctccgtgc tatgcacggt gcgttgtcag cgttttgcgc ttgcatgcgc tacacgcgtc 60
gtccaacgcg gagggattct tccacattac catgtgtcac tccccctatg gagggttcca 120
ccccgcccac acggaaatag gttaaccata cctatagtac gggtgagcgg gtcctcctag 180
ggcccccccg gcaggtcgag ggagctgaaa ttcgtgaatc cgtgagtaca cggaaatcgc 240
ggcttgaacg tcatacgtga ccttcggagc cgaaatttgg gcgtgcccca cgaaggaagg 300
cgggggcggt gttgggccgc cgcccccttt atcccacggt ctgataggat gcttgcgagg 360
gcacctgccg gtctcgtaga ccataggac 389

<210> SEQ ID NO 576
<211> LENGTH: 445
<212> TYPE: DNA
<213> ORGANISM: Hepacivirus B

<400> SEQUENCE: 576
accacaaaca ctccagtttg ttacactccg ctaggaatgc tcctggagca ccccccctag 60
cagggcgtgg gggatttccc ctgcccgtct gcagaagggt ggagccaacc accttagtat 120
gtaggcggcg ggactcatga cgctcgcgtg atgacaagcg ccaagcttga cttggatggc 180
cctgatgggc gttcatgggt tcggtggtgg tggcgcttta ggcagcctcc acgcccacca 240
cctcccagat agagcggcgg cactgtaggg aagaccgggg accggtcact accaaggacg 300
cagacctctt tttgagtatc acgcctccgg aagtagttgg gcaagcccac ctatatgtgt 360
tgggatggtt ggggttagcc atccataccg tactgcctga tagggtcctt gcgaggggat 420
ctgggagtct cgtagaccgt agcac 445

<210> SEQ ID NO 577
<211> LENGTH: 379
<212> TYPE: DNA
<213> ORGANISM: Hepacivirus I

<400> SEQUENCE: 577
cagggtttcg accctggccc ggatacctat cgccttacgc cgaaaggtaa cgagtaggag 60
tcgggtcccc aggcccttac cgccaccaag ccaggtgggg aggtatggga gccgggggt 120 gcagctggta gctccatggg ggacgccccg tgagcggatg ctgcatcgat accgggttag 180
ctctctggga gagcggcact tgacaccacg aatccgggaa ccggacaatc gccggcgtgg 240
gacgcgttgc ctccgtggcc gagcaatttg gcatgcccgt ggtgaagagt gatggtgggg 300
gggggccccc cttccagtac cgtactgcct gatagggtct tgcctcaagc ccagagagtc 360
gaggctgaaa accgccatc 379

<210> SEQ ID NO 578
<211> LENGTH: 557
<212> TYPE: DNA
<213> ORGANISM: Hepacivirus J

<400> SEQUENCE: 578
gccgctcccg aaagggagtc cggcgcgtca tcccactccg aggagtgggg tggcgtcccc 60
gtgtgccggg gaaccatgaa gcctaagggc atccacattt tagaatgaac ttgaagcttc 120
gtttcgctgg ccggaaagtc ctgggttccc atggccaggg ttccgcaggt gggtaaatcc 180
cggtggggtt ccatccagga tatacggcag gcgggcgtag tccggcggtt cggacgacgt 240
gtgggtcgcc tacggtggat tgttcacagg atgggcactc cggtgtgaat aggccccgtc 300
agggtgcgct gacgttaaac tcaggccttg cctggtgttc ggggaggatt gcagggccac 360
gccgcctcta agggccgtat ggcacagtac ttcttcgggc gggttgtcaa ggccctccaa 420
cgcgacacca gtgcctcggc aggcatgggg ccacccagct cggcgtcccg cacacagacg 480
gcgtagggga aaatcagcaa tgtgaccccg ggtggcattt tccttctctc tacttccatg 540
catgatcaac cgcaatc 557

<210> SEQ ID NO 579
<211> LENGTH: 280
<212> TYPE: DNA
<213> ORGANISM: Hepacivirus K

<400> SEQUENCE: 579
gggaacaatg gtccgtccgc ggaacgactc tagccatgag tctagtacga gtgcgtgcca 60
cccattagca caaaaaccac tgactgagcc acacccctcc cggaatcctg agtacaggac 120
attcgctcgg acgacgcatg agcctccatg ccgagaaaat tgggtatacc cacgggtaag 180
gggtggccac ccagcgggaa tctgggggct ggtcactgac tatggtacag cctgataggg 240
tgctgccgca gcgtcagtgg tatgcggctg ttcatggaac 280

<210> SEQ ID NO 580
<211> LENGTH: 675
<212> TYPE: DNA
<213> ORGANISM: Unknown
<220> FEATURE:
<223> OTHER INFORMATION: Description of Unknown: Icavirus sequence

<400> SEQUENCE: 580
cgaagtttaa gctaagcacc ctcgggcgtt cccggattat gtgatcacat caatttgatg 60
gctggtcacc acgcaacgcc tggagagata ctcttacttt tctcttaaga tccccggtca 120
tttgacgctt gtaggatgat agggttattt tccactataa atactttcat actcttggat 180
gttctatatc caagacggga ggacctaccc cgtacccctt agaggtgaga tgccaagaac 240
aggccctttc tgttctctcg acaatggcat cataggcaac aagcatcaca ccaagattgc 300
taagttttgt taagagttct tcaagctata gggtggctgt agcgaccttc tgatgcctgc 360
ggatttcccc acggagcgat ccgtgccaca ggggccaaaa gccacggcta acgcccatca 420
ggagcggcac ttaccccgtg ccccaccctt gaaacttgaa tgttcacact ggcttctctc 480
ggctttctga actgtctgct tgttggggcc ccgaaggatg ccctggaggt accccatttt 540
atgggatctg accaggggac acctcagctc tctaagttgc tggtgtttaa aaaacgtcta 600
agggccccca ccccttaggt ggagggatcc acctttcctt tattttttaa aactctttta 660
tggtcacaat tgttt 675

<210> SEQ ID NO 581
<211> LENGTH: 113
<212> TYPE: DNA
<213> ORGANISM: Unknown
<220> FEATURE:
<223> OTHER INFORMATION: Description of Unknown: Antarctic penguin virus
A sequence

<400> SEQUENCE: 581
ctaggagact acgcagtggg ataagatgac tatgatgtcg tacgggcaga agccagtaca 60
gtcgaagtcg agaccgacgt cgaggatttg actctgcctg acctagtgcc atc 113

<210> SEQ ID NO 582
<211> LENGTH: 214
<212> TYPE: DNA
<213> ORGANISM: Unknown
<220> FEATURE:
<223> OTHER INFORMATION: Description of Unknown: Forest pouched giant
rat arterivirus sequence

<400> SEQUENCE: 582
tattggatcc gcctccgggc aaaggttact ttcttgtacc tcggcttagc cacagggtga 60

```
ccccttgtac gtaggggccc cgacgtagca ctggtctgac aacaccttct cggcatttca    120

ccttctgccc gctcttccgg gcggtggtgt caagaagcag cagtgctctt ctcttttctt    180

cctgcagttc accgagccct acggggggta ggtg                                214
```

<210> SEQ ID NO 583
<211> LENGTH: 561
<212> TYPE: DNA
<213> ORGANISM: Avisivirus sp.

<400> SEQUENCE: 583

```
cattcccctt tccccagcca tgggttaaat ggcccctcac caggttcggt gctgtctagg     60

cttccagtaa agaagtcaac cgagcattga acaaaacctc agtgggtatg gtagttaacc    120

ccgtccactg gacaactttg tcctcttaaa agtggatcaa tccaccccaa ctcccccccct   180

agccacctga gccatggtgg atagcagtga cgaaactagg gaccccaata cctctagtgc    240

caagagaatt ccccccctcgc gagaggtgct cttgggcccg aaaggctagt tggcagggtg   300

aagtgaagga agctgctagc gtggcaacct taagcgtagc ccgaagctga ccttagaggt    360

taaccctagt ggaccactgg atgaagctgt ggaggtggtg gataggaaag ttggccactt    420

gtgagtagat gcccagaagg cataaggctg atctggggcc agtgactata ccgttccggt    480

aaacctggta taaaaaccat gaaagcaagt gggtttaaaa tttcttctaa ttccttcatt    540

tcagtagtga taactggcag a                                              561
```

<210> SEQ ID NO 584
<211> LENGTH: 134
<212> TYPE: DNA
<213> ORGANISM: Unknown
<220> FEATURE:
<223> OTHER INFORMATION: Description of Unknown: Avian paramyxovirus
      penguin sequence

<400> SEQUENCE: 584

```
accaaacaag gactagataa cccacgtgac cgttaactgg aaaataagat gttgtagggg     60

cgacctagtt ggaattcgac cccggctccg aaacctctaa ttgtggttat tggcagtcta    120

gtctacttct aacg                                                      134
```

<210> SEQ ID NO 585
<211> LENGTH: 121
<212> TYPE: DNA
<213> ORGANISM: Unknown
<220> FEATURE:
<223> OTHER INFORMATION: Description of Unknown: Newcastle disease virus
      sequence

<400> SEQUENCE: 585

```
accaaacaga gaatctgtga ggtacgataa aaggcgaaga agcaatcgag atcgtacggg     60

tagaaggtgt gaaccccgag cgcgaggccg aagctcgaac ctgagggaac cttctaccga    120

t                                                                    121
```

<210> SEQ ID NO 586
<211> LENGTH: 302
<212> TYPE: DNA
<213> ORGANISM: Bat Hp-betacoronavirus

<400> SEQUENCE: 586

```
ttaagcttcg gcttgttgca taggaccgga aaggtactat ctaccctaac tcttgtagtt     60
```

-continued

```
agactctcta aacgaacttt aaaactggtt gtgtccttca gtagtctgta tggccattgg    120

aggcacaccg gtaattatca aatactaaga agattcatag tacatccttg tctagctttt    180

ggttggcagt gagcctacgg tttcgtccgt gtcgctcaca attatccaca cagtaggttt    240

cgtccgctgt ggttgagttg ctagtccgtt gctgtttcgt cagccatcta caactcgaca    300

cc                                                                   302
```

```
<210> SEQ ID NO 587
<211> LENGTH: 458
<212> TYPE: DNA
<213> ORGANISM: Unknown
<220> FEATURE:
<223> OTHER INFORMATION: Description of Unknown: Basella alba
      endornavirus sequence

<400> SEQUENCE: 587

ggaatatggc taatcggctt attctaatca aacgcaaaag acttatgaca cagaccggac     60

ctgaacgagg tgataaaaca cctcgttcag gttcaaaacg tagaagattc attcctccga    120

ttagaaatac aactacgtct aagcacgata gagatggtat caagatcggt tttagaccac    180

gagaaaatcg gcaaatgaaa gtacaagttg ggtggtttaa attaccaaga acagtaacat    240

tcaagaacaa cggcaacccg tttgttacct catttcgtaa attgtttaga agtaacaaag    300

ataaattatt taatggtggg aagaacctaa gtacagtacc agccagaagt agtgaaatga    360

cagaaatgtt tatgttcatg tccacgctag agggccaatt gtcaatccaa gatcgagatc    420

caaaaataat caataagtct atatacatga tagaggta                            458
```

```
<210> SEQ ID NO 588
<211> LENGTH: 675
<212> TYPE: DNA
<213> ORGANISM: Ball python nidovirus

<400> SEQUENCE: 588

ccccttcacc cataggcact aggagaacag gataacccct aacggggcat cctgcctgtg     60

acctttcaga ttcgctagtt agatatcttc acagactctg ctaggcttct gacccagtcc    120

gttcccaaag tccgttaccg cccgagtagc gcttaggcgc gaaagggacg gaagtacctc    180

cagtaagcga aagctgaagt aagggaaata cggcaagact aacttgttag tcttacagtg    240

tggataacct ggtagttatc cccgacaaga gacctgactc gatgtgaaaa catccaacta    300

ggttggcttc aaactagcta caggcaggat atcccccaac ggggcctcca aggaatcgag    360

aaccaaccct cattccacgt ctgtagtaag caaaaacagg ggcgatcttc accgacacct    420

ctcaccacag agcacaccaa cctctgtgaa gccaatttcc tcgtccaagg acaggttatt    480

gagggtcaac tttcttccga ccagaagaag ggatttccta ccaaaagaaa aaccaaatcc    540

accaacacca caaggtaaaa caacaacttg tgaagccaat acttagtcaa agactaacta    600

ttgagggtca actttctctt caatagagaa gggatttcct ggtaaaacaa ataacaacaa    660

ctaacatcag caact                                                     675
```

```
<210> SEQ ID NO 589
<211> LENGTH: 150
<212> TYPE: DNA
<213> ORGANISM: Sapelovirus sp.

<400> SEQUENCE: 589

gacaggtgtt ttggagggcg gatgacgata tctggctggc caccagggaa taacggcaaa     60
```

```
tgtctgatca tacggttcac aagtctaccg gcgatagtgg ttcaacacca tgtgtagcag    120

ggattcttgc gtatgtgaag gcgacagtgc                                     150


<210> SEQ ID NO 590
<211> LENGTH: 496
<212> TYPE: DNA
<213> ORGANISM: Unknown
<220> FEATURE:
<223> OTHER INFORMATION: Description of Unknown: Bat Picornavirus 3
      sequence

<400> SEQUENCE: 590

taagcggaaa gcattcttgt cccccggtca gtaacctata ggctgttccc acggctgaaa     60

gggtgaacat ccgttacccg cctcagtact tcgagaaacc tagtacgcct gatgattcca    120

aattggtatg atccggtcaa ccccagacca gaaactgtgg atgggggtca ccattcctag    180

tatggcaaca tacaggtgtc cccgcgtgtg tcacaggccc ttacgggtgc catttcggat    240

gagtctggcc gaagagtcta ttgagctact gttgatacct ccggccccct gaatgcggct    300

aatctcaacc ccggagccac tgggtggtga accaaccact tggtggtcgt aatgagcaat    360

tctgggacgg aaccgactac tttggggtgt ccgtgtttct tttgttcata ttaaactgtt    420

ttatggtcac aacacaactt ggtacgattt gtgattattc actgctcact tgtcacagta    480

aatatacaca atcatc                                                    496


<210> SEQ ID NO 591
<211> LENGTH: 419
<212> TYPE: DNA
<213> ORGANISM: Unknown
<220> FEATURE:
<223> OTHER INFORMATION: Description of Unknown: Bat Picornavirus 2
      sequence

<400> SEQUENCE: 591

gggttttacg aaacccgtat acaccagacc ttttctcccc tccccctcca cctacctttt     60

ccccctcttt ggaccgaaac aaggacacgt aagtggaaac gcgattttat atgtggttgg    120

ccaccacgga ataacggcaa ttgtctacat gtgggaagtg caacctccct agccgataac    180

ccctgaccgg gtgtgtagga taggaaaggt gcccactgtg ggcgacaggt tatggtagag    240

tggataccta gccaggggca atgggactgc tttgcatatc cctaatgaag tattgagatt    300

tctctgctca ttacccggtg atggttgtgt ggggggggcc ccatacacta gatccatact    360

gcctgatagg gtcgcggctg gccgaccata acctgtatag tcagttgaat tcagccaag     419


<210> SEQ ID NO 592
<211> LENGTH: 410
<212> TYPE: DNA
<213> ORGANISM: Unknown
<220> FEATURE:
<223> OTHER INFORMATION: Description of Unknown: Bat Picornavirus 1
      sequence

<400> SEQUENCE: 592

gaaacccgta tacaccggac cttttctccc ctccctctcc acttaccttt ttcccctctt     60

cggcatgaaa caaggattat tcaagtggaa acgcgattta atatgcggct ggccaccgcg    120

gaataacggc aattgtgtat ctgctggaag ccaagcctgc ctagccgata gcccttgacc    180

gggtgtgtag gatagcccag gaaccagcaa tacgcgacag gttatggtag agtagatacc    240

tagccagggg caatgggact gcattgcata tccctaatga accattgaga tttctctggt    300
```

-continued cattacccgg tgatggttac tagagggggg cctctagtac tagatctata ctgcctgata 360
gggtcgcggc tggccgacca tgacctgtat agtcagttga tttgagcaat 410

<210> SEQ ID NO 593
<211> LENGTH: 675
<212> TYPE: DNA
<213> ORGANISM: Iflavirus sp.

<400> SEQUENCE: 593
acgaatcggt atacgcttcg gtacctattg ttgcaagttc gttccctatt ttcgatttgc 60
ctgcccgaat ttgactcaaa caattgtgac atactatgtc tctgtttgaa agcactacac 120
gagtttgcgc ccagcatgta tgttttcaag tcttttgtat aagtctgcct ctatagtggt 180
tttctttgac cttaaagcct tgtcaaccat cctatatgct gcatcgagac ttgatgtcaa 240
tctgcctcta ctacgcaaat gtctagtaat tagttataag gttttactat tttccctcat 300
ttccaatttt agtttgtagt gtatgtgagt atcattctta ctccgactgt taagagaaac 360
caatttatag tcgttaaata tgataaatgg aatgaatgat ggtgtcattt taaaaacact 420
cttctctata ggcgtaagca ttctcgctct tagagtcgta aagaagaaat gccgtgtcta 480
tcagtatgtt atgcgattta ttttctgcca cgcgcttcta gtgcaatcta gttgacatac 540
agacattgcc taccactcgc gagggtcgac cggtagtgta aggagtaagt gatgatttcc 600
gcttattctg taccctttgc ctggtgagga cagatcctga ctaattttaa atataaatga 660
acactagctt ccaag 675

<210> SEQ ID NO 594
<211> LENGTH: 210
<212> TYPE: DNA
<213> ORGANISM: Unknown
<220> FEATURE:
<223> OTHER INFORMATION: Description of Unknown: Bat dicibavirus
      sequence

<400> SEQUENCE: 594
gtatagcacc ggaatggtat tttactactc caagtatacg tactaggagt taaaccctgt 60
aatttacagg ggatttagtg acttttatcc gtaaaagtcg attggacgtt aatcggtaac 120
gaggccaagt accgtgaacc aatttaaaaa cgtattttct catgtggtag aaccaacttg 180
gaaatagcat ggcatatagg ttgtttaggg 210

<210> SEQ ID NO 595
<211> LENGTH: 212
<212> TYPE: DNA
<213> ORGANISM: Betacoronavirus sp.

<400> SEQUENCE: 595
gataaagtgt gaatcgcttc cgtagcatcg caccctcgat ctcttgttag atctaatcta 60
atctaaactt tataaaaaca ctaggtccct gctagcctat gcctgagggt ttaggcgttg 120
catactagtg tcttaggaat ttgactgata acacttccct gctaacggcg tgttgcactc 180
tcagtctaag cctcccaccc ataggaggta tc 212

<210> SEQ ID NO 596
<211> LENGTH: 277
<212> TYPE: DNA
<213> ORGANISM: Betacoronavirus sp.

<400> SEQUENCE: 596

```
atttaagtga atagcttggc tatctcactt cccctcgttc tcttgcagaa ctttgatttt     60

aacgaactta aataaaagcc ctgttgttta gcgtattgtt gcacttgtct ggtgggattg    120

tggcattaat ttgcctgctc atctaggcag tggacatatg ctcaacactg ggtataattc    180

taattgaata ctatttttca gttagagcgt cgtgtctctt gtacgtctcg gtcacaatac    240

acggtttcgt ccggtgcgtg gcaattcggg gcacatc                             277


<210> SEQ ID NO 597
<211> LENGTH: 675
<212> TYPE: DNA
<213> ORGANISM: Cardiovirus sp.

<400> SEQUENCE: 597

tacgatcgct gtacattcca ctactgccaa ttagctcccc cttcccgttg ctcccctcta     60

taaggagagc cttctcttgc aaaggtgaag ccttcacccc cggtcgaagc cgcttggaat    120

aagacagggt tattttctcc tctcctcggc gcttgcctct tctaagctga ataggttcta    180

tctattcagg cggatggtct ggtccgttcc ttcttggaca gagtgtgtat ctgggttttc    240

cggatctcga ccacacactc accagagctc aggagtgatt aagtcaaggc ccgatctgcg    300

gcgaaaagga aatgaagtat tttgcagctg tagcgacctc tcaaggccag cggatttccc    360

cacctggtga caggtgcctc tggggccaaa agccacgtgt taatagcacc cttgagagcg    420

gtggtacccc accaccctgc aaattatgga tttgacttag taactaaaag attgacttgg    480

catacctcaa cctgagcggc ggctaaggat gccctgaagg tacccgtgtt gaaatcgctt    540

cggcgaccat ggatctgatc aggggccctg cctggagtgg ttctatccca cacagcgtag    600

ggttaaaaaa cgtctaaccg ccccacaaag accccggcag ggatgccggt ttcctttttta   660

ccaattcttg acact                                                     675


<210> SEQ ID NO 598
<211> LENGTH: 675
<212> TYPE: DNA
<213> ORGANISM: Unknown
<220> FEATURE:
<223> OTHER INFORMATION: Description of Unknown: Breda virus sequence

<400> SEQUENCE: 598

atcacctagt acttacaagc gggtcaaacc gccctccgga acggtcataa ccccctcccg     60

aacgtgcgct tgacgtgact ggtctttcag tctagctttc tgagaaatac tccggggttg    120

taacccacca ttttgacctt tggtcagttt ggtaacactc caaccaaaca gcatctgacc    180

cacctccagc ttgctgcagg ccatttggac caaacgggtt cagatatctt gtggctaaac    240

ctctgaccca cctccagttt actgcaggcc ttttggacta aacgggtaca gactctttgt    300

ggttagtttt taactaccca ctgtttagcc gccaacctga tttttattgt tacaaaattt    360

tgtgtttaca cattattttc ttacggttgg cagtttgttt ggttgtttgc acagtttttg    420

ctgataccaa tttttactgt gcttttggtg ttttcggcta aggctgtttt tcacatactt    480

agtttgcttg aagtaacctt cacaacatct gttttgtttt tggtttctaa ggtaaagagt    540

ttcaggaaaa aacataggcg cccatcttgt ggtgtctagt tttaattaat ctggcaaaca    600

agtatcaagt catcgactcc ctttggagtg agacttacga gtaccaattc gcctattttg    660

gccatccata taaaa                                                     675


<210> SEQ ID NO 599
<211> LENGTH: 383
```

<212> TYPE: DNA
<213> ORGANISM: Unknown
<220> FEATURE:
<223> OTHER INFORMATION: Description of Unknown: Bovine viral diarrhea virus 3 sequence

<400> SEQUENCE: 599
gtatacgccc agttagttca ggtggacgtg tacgattggg tatcccaaat taataatttg 60
gtttagggac taaatcccct ggcgaaggcc gaaacaggtt aaccatacct ttagtaggac 120
gagcataatg gggactagt ggtggcagtg agctccctgg atcaccgaag ccccgagtac 180
ggggtagtcg tcaatggttc gacgcatcaa ggaatgcctc gagatgccat gtggacgagg 240
gcgtgcccac ggtgtatctt aacccaggcg gggccgctt gggtgaaata gggttgttat 300
acaagccttt gggagtacag cctgataggg tgttgcagag acctgctaca ccactagtat 360
aaaaactctg ctgtacatgg cac 383

<210> SEQ ID NO 600
<211> LENGTH: 537
<212> TYPE: DNA
<213> ORGANISM: Bovine rhinitis A virus

<400> SEQUENCE: 600
ttttgcggct ctgccgccgt tcgggtttta cctgttttca cagagcaaaa caggacctct 60
agtttcgtgc ttaaacgaga tcatgctcga actagaacta taacgctggt cactggaccc 120
gtgccgcgcc ttgcggatct ttgcgggaat ggtggctagt gggctgtgga agtgactcta 180
accacacgcc cctcaagtgt gggaaaacac gaactggtgt agcgacgacg ataggccttg 240
ggacaccctc tccagtgatg gagacccaag gggccaaaag ccacgccttg tgccctgtcg 300
ttcacaaccc cagtgcagtt cgtgccagta cctgcttttg ggaagtgtgc tttggacagc 360
tgaaaacagt cctagtggga gactaaggat gcccaggagg tacccggagg taacaagtga 420
cactctggat ctgacttggg gagagcgggt ctgctttaca gacgccactc tttaaaaaac 480
ttctatgtct cgtcaggcac cggaggccgg gccttttcct ttaaaacaat acacttt 537

<210> SEQ ID NO 601
<211> LENGTH: 248
<212> TYPE: DNA
<213> ORGANISM: Unknown
<220> FEATURE:
<223> OTHER INFORMATION: Description of Unknown: Bovine picornavirus isolate TCH6 sequence

<400> SEQUENCE: 601
ttggatctga gcaggggccc cctttgggtt gctttacaac tcaactgggg gttaaaaaac 60
gtctaacccg acacgccaga gggatctggt ttccttttat ttcttttact caccactgga 120
tgcagattga cgataaacgt tgttgtttgt gactattgac ttgatctgct tctacgggtt 180
tactttcact gttatacttc ttgctttgtt tggtgttcac tgtactttgt ctccttctac 240
atttcaca 248

<210> SEQ ID NO 602
<211> LENGTH: 486
<212> TYPE: DNA
<213> ORGANISM: Bovine nidovirus

<400> SEQUENCE: 602
caccaataga ttagtcaagc tgtctatagg cataaactaa cccccaaccc cattaccccg 60

-continued

```
gggccaggtg ggccgccgcc ttcgggcaaa cccgtgcgct ggtataatca aggttcacag    120

ccagattcac tgccggttag ctagtggggc ggtagcctgg caaaacccga agaggttgga    180

aagggaactt cagggtagtt tatcctaggc tagcgtagct acagttcggt caagataacc    240

gtcctggtgc tagggctagt agagacagtg gtaacttgga caagggtcca gggccacttt    300

agggaatacc ctacggaagg ctaggtccgt aaggaagacc cccgcagttg tccgcggttg    360

agcagagctc ctgcgtagac aaaaggcaaa aagtggatta cattcgcctg caggaaaagg    420

caaacgtcgt tggagtcgga gctaaagtac tggacgattg ataccacgcc tgctgcggta    480

gataaa                                                                486
```

<210> SEQ ID NO 603
<211> LENGTH: 293
<212> TYPE: DNA
<213> ORGANISM: Hepacivirus sp.

<400> SEQUENCE: 603

```
ccatcgacac tccaggctca cggattaagt taggttccgc cgaagcgggc taaccaggcc     60

cctagtagga ggcgcctatc ccgtgagccc tttccccacg gattgagtgg agctggagct    120

gggaaggacc gagtacggtc caatcgagaa gaaccctgat gaacattcca ggcctcttcg    180

gtagatttgg atatatccac cagtgaaggc ggggtcgtgg gtacaggccc cctagtccac    240

acagcctgat agggtcctgc cgcaggatcc gtgggtgcgg ctgtacatgt acc           293
```

<210> SEQ ID NO 604
<211> LENGTH: 472
<212> TYPE: DNA
<213> ORGANISM: Mitovirus sp.

<400> SEQUENCE: 604

```
gccccgccga ccttcctatt tatttctaaa taggaaggtc ccgactagtc ggataattcg     60

gtttaacgaa ttatggttag atctattaaa gttaaaatag attgaatttc tttctcatcc    120

tccttattcc tatactttgg gagtaaatga caaatgtcta tcctcaaacc gaaatggctt    180

aagtgatgaa tttgaaagaa aggtaggttt taagaatata aggcatcaat atattatacc    240

cttgaatgtt aagtgaccac ggcgtgacga ttagggctat cttaggatag acagccatct    300

aacgcgacag cagtggaaat cagcttagca tctcaagatc atgtataata tatacataac    360

cttacaatta taaaaccaaa ccaaaacaca ctataatttt atataaatta tagaagtatc    420

ggacctggac ggtacctact attaactgat agtagccaaa tgcaggaagc tc            472
```

<210> SEQ ID NO 605
<211> LENGTH: 315
<212> TYPE: DNA
<213> ORGANISM: Mitovirus sp.

<400> SEQUENCE: 605

```
ggaacttttc agttccagaa gtggctttat taagccttca aagtttacac tttgaacctg     60

cgattaattc cccatagtga ctcttgttac tgtgaattag gaatagttgt agttcaactt    120

ctaatgaggt gaacaatata ataactcatc ttattaaccc tatacgtaga caattgtcca    180

aagagacagt tggaattctg ccaatctgga atgtttggta cgcgtagaag ataataagag    240

accctctatt cccctgcctc atgactaagt catggcccgg ggtgtaatag agatactttt    300

atatattata caatc                                                      315
```

<210> SEQ ID NO 606
<211> LENGTH: 675
<212> TYPE: DNA
<213> ORGANISM: Unknown
<220> FEATURE:
<223> OTHER INFORMATION: Description of Unknown: Canine
picodicistrovirus strain 209 sequence

<400> SEQUENCE: 606
cgctctttat acaaatctgt caaccctttg tataactcta agccgaacaa ttatagctag 60
gctttttatt atataacatt aattaggcat tagcgttgtc gccaatctct tggtaatcct 120
aaggatacct ttcctgttga ctaagatgaa gcgccttcgg ttaccgatgc ccggtgtcca 180
cgaagccatc gtggtcggcc gcgtccccca cctctcccaa cttggactcc atgttttcag 240
taggtgtaat gattagtatt attgattctg ctcgttcaat gtgtttatct tcacgatctg 300
ggacccaaca catgcttcac tcatgtttaa atgttggttc cctcattttg aagacaccca 360
aaccatagag tgcgagaatg aggatttcta cttccattct ggtaacagaa atgaattcct 420
gcgtgtgtct cgtaaatgga atctttaaga acttcagata aatcgaacaa tacactaata 480
caagttgttt tctaccaaca tgttcaatgc ggctaatctg accgtggagc tgtgaagcgc 540
tcaaacccga gtgttgtata cagtcgtaat gcgtaagtcc atgaggaacc gactactgtt 600
acctctgttg gtgtgtttct cctttcctct cttttattat tatttgttat tgcaaatact 660
acaactttga tcaac 675

<210> SEQ ID NO 607
<211> LENGTH: 107
<212> TYPE: DNA
<213> ORGANISM: Canine morbillivirus

<400> SEQUENCE: 607
accagacaaa gttggctaag gatagttaaa ttattgaata ttttattaaa aacttagggt 60
caatgatcct accttaaaga acaaggctag ggttcagacc taccaat 107

<210> SEQ ID NO 608
<211> LENGTH: 601
<212> TYPE: DNA
<213> ORGANISM: Kobuvirus sp.

<400> SEQUENCE: 608
tttaagtgtt gtgcccaatc tcttgactcc tgctggaacc accgaccagt agtgtccaaa 60
atgccaggtg gaaaatcctc ccttcccctc tgggcttcat gcccggcatc ctccccccag 120
cctgacgtgc cacaggctgt gcaaagaccc cgcgaaagct gccaaaagtg gcaattgtgg 180
gtcccccctt tgtcaaggcg tcgagtcttt ctcccttaag gctagtcctg tcagtgaact 240
ctgtcgggca actagtgacg ccactgcatg cctccgacct cggccgcgga gtgctgcccc 300
ccaagtcatg cccctgacca caagttgtgc tgtctggcaa acattgtctg tgagaatgtt 360
ccgctgtggc tgccaagcct ggtaacaggc tgccccagtg tgcgtaattc tcatccagac 420
ttcggtctgg caacttgctg ttaagacatg gcgtaagggg cgtgtgccaa cgccctggaa 480
cgagtgtcca ctctaatacc ccgaggaatg ctacgcaggt acccctggct cgccagggat 540
ctgagcgtag gctaattgtc taagggtatt ttcatttccc accctcttct tcttgttcat 600
a 601

<210> SEQ ID NO 609
<211> LENGTH: 291

<212> TYPE: DNA
<213> ORGANISM: Alphacoronavirus sp.

<400> SEQUENCE: 609
cttaagtgtc ttatctatct atagatagaa aagtcgcttt ttagactttg tgtctactct 60
tctcaactaa acgaaatttt tgctacggcc ggcatctctg atgctggagt cgtggcgtaa 120
ttgaaatttc atttgggttg caacagtttg gaaataagtg ctgtgcgtcc tagtctaagg 180
gttctgtgtt ctgtcacggg attccattct acaaacgcct tactcgaggt tctgtctcgt 240
gtttgtgtgg aagcaaagtt ctgtctttgt ggaaaccagt aactgttcct a 291

<210> SEQ ID NO 610
<211> LENGTH: 623
<212> TYPE: DNA
<213> ORGANISM: Cripavirus sp.

<400> SEQUENCE: 610
gcaaaatcgg tagtacgtta aacgtacgac caccgatgag actgaaatga cactagttga 60
gattatttca atatcctagt gttataaagt caatatttgt tggttgatcg tttcgtcaat 120
cgatggcgct gacagccgga aagacggcaa taataaaaac caagatttag tttttaagtt 180
ttgattgaat tgcaaaagct atcttgaata gacaatcaaa atattaagta aagcaaaagc 240
ttcttaaaga agacaatatt taattagtta gtaaccaaac ctcatcgtgc ccctaagggt 300
taaccggtta cgtaaaagcg tagaggtatt aaggtcactg cggagaccta aaatccgcaa 360
ttttatgttt tgtaatgttt tagttataga cttagatgta actataagag tttataaata 420
cttgtttcaa gatttataga caagatctga tcctatggat tttagataac cttcatgtta 480
gtggatagtg tgtgtaccta tctaaacgca taaggctctt atttcatatt taaagtagga 540
ctatgtatta cggcgcatct aacggtaacg ttagtcaaga ccggagaatc tcggaatgaa 600
ttttagtaat tcccaaattt ata 623

<210> SEQ ID NO 611
<211> LENGTH: 675
<212> TYPE: DNA
<213> ORGANISM: Unknown
<220> FEATURE:
<223> OTHER INFORMATION: Description of Unknown: Human coxsackievirus A2 sequence

<400> SEQUENCE: 611
acctttgtgc gcctgtttta tatccccacc ccgagtaaac gttagaagtt acgcaacccc 60
gatcaatagt aggtgtagca ctccagctgc atcgagatca agcacttctg tctccccgga 120
ccgagtatca atagactgct aacgcggttg aaggagaaaa cgttcgttac ccggccaatt 180
acttcgagaa gcccagtagt gccgtgaaag ttgcggagtg tttcgctcag cacttccccc 240
gtgtagatca ggctgatgag tcaccgcgat ccccacaggt gactgtggcg gtggctgcgt 300
tggcggcctg cctatggggc aacccatagg acgctctaat acagacatgg tgcgaagagc 360
ctattgagct aattggtagt cctccggccc ctgaatgcgg ctaatcctaa ctgcggagca 420
catgccctca aaccaggggg tggtgtgtcg taacgggtaa ctctgcagcg gaaccgacta 480
ctttgggtgt ccgtgtttct ttttattctt ataatggctg cttatggtga caattaaaga 540
attgttacca tatagctatt ggattggcca tccggtgact aacaaatcgc tcatatacca 600
gtttgttggt tttgttccct tatcacatac agctcataac accctcttat atttactaca 660
attgaatagc aagaa 675

<210> SEQ ID NO 612
<211> LENGTH: 436
<212> TYPE: DNA
<213> ORGANISM: Unknown
<220> FEATURE:
<223> OTHER INFORMATION: Description of Unknown: Coronavirus AcCoV-JC34 sequence

<400> SEQUENCE: 612
agaaacaagt agtgttttaa aaaccttcaa attagtgcct gtaacatctt tgcaatgaaa 60
gtagcgctca ctagcctcta tgcaaagaat gttaaaagaa atacgaagca tttaaagaat 120
acaatctatc taggataggt acaattctcc tccccctctt gacttcggtc aactcaactc 180
aactaaacga aatccccctt gcatggttcc gacccgtgta aggttgtgta tttcgtgcag 240
tcgttgccct tactagtgta agcgtaacgg catctaggtt tgcacgtctt ggaggaaacg 300
gtgtgtacgt ttctagtgtt tacgccgtat cggttccggc ccgataggta ttgcattaga 360
cgtcctgggt ggttctgcct gcccttgtgt gattcggctg ttccgtcagt ttggtcacct 420
cacacgtcct taagac 436

<210> SEQ ID NO 613
<211> LENGTH: 457
<212> TYPE: DNA
<213> ORGANISM: Unknown
<220> FEATURE:
<223> OTHER INFORMATION: Description of Unknown: Chicken picornavirus 3 sequence

<400> SEQUENCE: 613
gggtatggtg gttaaccccg tccactgggc atctttgccc tctcagaagt ggatcaatcc 60
accccaactc ccccctggt tacctgagcc acagtggact ccggtgacga agctagggac 120
cccaatacct caagtgccaa gagagtcccc ccctcgcgag aggtgctctt gggcccaaaa 180
ggctagttgg cagagtgaag tgaaggaagc tgctaacgtg gtgaccttaa gcgtaattcg 240
aagctgacct ttgaggttaa ccctagtgga ccactggagg aatctgtgga ggtggtggtt 300
aggaaagttg gccacttgtg agtagatgcc cagaaggcat aaggctgatc tggggccagt 360
gactataccg ttccggtaaa cctggtataa aaaccatgaa agcaagtggg tgaaattttc 420
tctttttatc cttcattcag cagttgatat tggcaaa 457

<210> SEQ ID NO 614
<211> LENGTH: 675
<212> TYPE: DNA
<213> ORGANISM: Unknown
<220> FEATURE:
<223> OTHER INFORMATION: Description of Unknown: Chicken picornavirus 1 sequence

<400> SEQUENCE: 614
gtggccgact tgcagaactt cctaccgaac caccacctca cccccataac tccttccctc 60
tacaccttcc gctatggtgg ttaccactgc tttattgcct tgactgagaa tggccacccc 120
ctcgacacct gccccctact gccccaccgc gcaacctttt gcttgtccac tcggttggag 180
aggcatgggg gccccgttca tatccccagt ccagttggtg accttccccc tccccgtccg 240
gtagatggtc cagagggctt tgccgacgcc ctctatgatg cttgcttgtc tttcctccgt 300
cagcgcgagc atgcacttgt cgagcccacg gaaacacagc ctagcttttg cttctctcac 360
cctgcgtacc ctgggcgcct tccgctcgag attcgctttg ttcgacaccc tggcgtcccc 420
ccaccgctac gtgattttac tcgtggcata caccgccctg gcgttcagta cattccactg 480
cctaatttgg gtggcctccc tcaatctccc gcacccccca ttgcgcacgt catcaccgcc 540
gccgctaacg cgatccggcg cggttctcac tggcactgtc ccctcgtccg ccgggtttcc 600
actcatggtt ggcttttcac ttattctggt tactggtgtt ccatcctact tcatgatggt 660
cgccatgacc atgac 675

<210> SEQ ID NO 615
<211> LENGTH: 675
<212> TYPE: DNA
<213> ORGANISM: Orivirus sp.

<400> SEQUENCE: 615
aaaccctcac gagtgcttgt ggtaggtccc aggccaatat tcttcgtaag gcttggttcc 60
aattttccac cactcgtgtt tgggttctgg cctatggtac ccagaggggc ggtttggggg 120
aattaactcc ccctcccctg tggtcctata ccaccccaca cctctgtggg ctttctttac 180
tatcttcttg ttttccgact tttaaacact aggcaggcgc gcctagtcat acaccgcccg 240
gctggtcttt ccagctcttg tgggcggtgc gcgctggtcc atcgtgccca gcgacatagc 300
accttgtgga cacctccgaa cgccctcccc tgtatggggt ggtgcccagg ggtttcagtg 360
tggtgacaca ctccctgggg cccgaaaggc tagtgtgcaa caggtgaggt acagccagct 420
gcccccgtgg ctggagggac caagcttgtg aagcacacct caccttcttg gggggtgggct 480 agtaagtggt gaaagcatag tgtccgtgtc gctggccaac actttgggtc aagtccagcc 540
actcagtgag tagatgccca ggaggtaccc ctagtggatc tgacttgggg cctgttactt 600
aatgcaggtt aaaaactatg aaagctgagt agtgtagccc ggctggtggc ttctcttcct 660
tattcattct atttt 675

<210> SEQ ID NO 616
<211> LENGTH: 651
<212> TYPE: DNA
<213> ORGANISM: Gallivirus sp.

<400> SEQUENCE: 616
ggttaacttg tttaaccaag gcttccgtgc agggcttgca cgttaggagt tcatgttgat 60
tcatgctcca atgcccaaaa ctttgtgtgt ttgtttatgt ctttcccaaa gtttccccca 120
aggtttcggt actcaaacct taattcctag tcccatcttt tgggccttag tatctaggaa 180
atgtacccgt gccttgacga acgtaagaaa gctgtctttt attgaacggt tctaatgaac 240
taagtataac tggctcgcgc cacctggtgt gtgccgttgg aattccccca tggtaacatg 300
gtccaacggg cccgaaaggc tagtgggcaa tcggtcctcc aaggaagggg ttcccacccc 360
gacctgaaca ggatttgatg aagctcacct cccaggctcc taaccccaag gaagtttact 420
tatagtaatt agaatttagt atgtaattgc tggcaatctt gctagtagtc aggaacgtta 480
tgaccaaatg agtagacccc cagaaggtac cccattatat gggatctgat ctgggcctca 540
tactgtgtgt ctccccacat atgaggttaa aaccatgaaa gtttggtcca aaatattctt 600
ttccttttat cttttcttta gtggtgacgc cattatatca gcagtttgct g 651

<210> SEQ ID NO 617
<211> LENGTH: 303
<212> TYPE: DNA
<213> ORGANISM: Unknown
<220> FEATURE:

<223> OTHER INFORMATION: Description of Unknown: Chicken calicivirus
      sequence

<400> SEQUENCE: 617
ggtgcatcat cactgaacac cctcgggcag agatgcaagg gtggaagtca ctcctgcccc 60
ctggcaacat gcaggtgccc gatcccaagc ttagttctga cttcctctcc tgggtggtgc 120
aacactccaa ggttgatgaa caaacctgga gggacctctg ggcaacctgg tctctcgagg 180
atctccggcg catctccaca gactacctca tgctcccgga acctgagaag aacactgatg 240
cctatgatgg ctggctgatg gtcggcgaga tgttgacctt tgccggtctc attggctggg 300
agg 303

<210> SEQ ID NO 618
<211> LENGTH: 524
<212> TYPE: DNA
<213> ORGANISM: Unknown
<220> FEATURE:
<223> OTHER INFORMATION: Description of Unknown: Carp picornavirus 1
      sequence

<400> SEQUENCE: 618
agctacagga aagagagaga taatcacagc acataaatac aactacagaa gagagccttt 60
ccctgagcac tatttacagc aaaccacgct gggaaaagtg gtagcatgac ccacttacgg 120
gttacttagt ataggatttt aatatcttcg attctttatt ttcttttctt aactaagttc 180
gcccggactt tatccgtgtt ttattttagt ttaagcaaaa ttgagtaact aagtttttaa 240
cctgccaaat ggtgagaagt aactctgtga aaataccatt tgtgcatgaa attgtcttga 300
aaactcttag gcttttgggg ggtcccactg ctgtttggag gactattgac agactctatt 360
gtagttgagt agtgactaat gataacgatt tgcgtattac gcaatgggct gtacccgtta 420
gatttagtat gccgggggga ggggtcccac tggattgcac tatgtaacct gacagggcgt 480
ctgccgacgc actacaatga ggataagatc ggctgttttt attt 524

<210> SEQ ID NO 619
<211> LENGTH: 675
<212> TYPE: DNA
<213> ORGANISM: Unknown
<220> FEATURE:
<223> OTHER INFORMATION: Description of Unknown: Falcon picornavirus
      sequence

<400> SEQUENCE: 619
cgcttggaat aagttgagag gaattatgca tgctagttgt gtttgtttac aactaattgt 60
tctaatccaa gtgaagctct tcgcttgggg cggcacgaca cttgccgtaa ttcttctacc 120
gtccctccac accttgtgga tgaagggccg gatgtgtggc ctctggctaa cccctctctc 180
tggggtgatg ctactggatg ttttactcct agaccaaatc acatgaactc ctcttgatcc 240
acttcggtgg ggctatgagc ctgcggatta atagctggcg acagctaccc caggggccaa 300
aagccacggt gttagcagca ccctcatagt ctgatgccca agggctgatg ttgggagcta 360
gtagtgtgtg tctggcctat gtttaggact tctggccaag cgcagaggag tggggctgaa 420
ggatgcccag aaggtacccg taggtaacct taagagacta tggatctgat ctggggcccc 480
ctcacgtggc tttaccacgt gttgggggtt aaaaaacgtc taggccccac cagcccacgg 540
gagtgggctt tcccttaaaa agcccaacaa tatttatggt gacaattcac tgtttcttct 600
ttgcaatttt tgtattcttg gactccttat tttttgtttg cttgatttta gtggacattc 660
agattcaaat acaaa 675

<210> SEQ ID NO 620
<211> LENGTH: 675
<212> TYPE: DNA
<213> ORGANISM: Unknown
<220> FEATURE:
<223> OTHER INFORMATION: Description of Unknown: Equine rhinitis B virus 1 sequence

<400> SEQUENCE: 620
cgacaggcac aggtcgctcc gagttctagt agtgtgggaa cttgttacta ctgatgaaac 60
gaggtagtga cactcagtac ctgcgaacga ggtcggggcc ctcccttctt ccttcaccca 120
actttcactt ttcgttccac tttagcaggg gtcttctttc tatccccctg gcggcattgg 180
aactagccgt cgcgtcttaa cgcgcagccc tgaaggcccc acaccttgtg gatcttgccg 240
tgggtatgtt tctggcatgt gtttctcaag cctgcaaccg aagccgaaca gccacatgaa 300
cagtttgagc gtggtagcgc tgtgtgagtt ggcggtggat ccccctcgtg gtaacacgag 360
cccccgtggc caaaagccca gtgtttacag cacctctcac atccaggacg accccatcct 420
ggcgctcact cttagtagta tggcttagta cgcattaggt ggtaagccga gctctccctc 480
ggccttgttc tgaatgcaca catgtctagg ggctaaggat gtcctacagg tacccgcacg 540
taaccttcag agagtgcgga tctgagtagg agaccgtggt gcactgcttt acagatgcag 600
cccggtttaa aaagcgtcta tgcccctaca gggtagcggt gggccgcgcc ctttcctttt 660
aaaactactt gttct 675

<210> SEQ ID NO 621
<211> LENGTH: 675
<212> TYPE: DNA
<213> ORGANISM: Equine rhinitis A virus

<400> SEQUENCE: 621
aagggttact gctcgtaatg agagcacatg acattttgcc aagatttcct ggcaattgtc 60
acgggagaga ggagcccgtt ctcgggcact tttctctcaa acaatgttgg cgcgcctcgg 120
cgcgcccccc ctttttcagc cccctgtcat tgactggtcg aaggcgctcg caataagact 180
ggtcgttgct tggcttttct attgtttcag gctttagcgc gcccttgcgc ggcgggccgt 240
caagcccgtg tgctgtacag caccaggtaa ccggacagcg gcttgctgga ttttcccggt 300
gccattgctc tggatggtgt caccaagctg gcagatgcgg agtgaacctt acgaagcgac 360
acacctgtgg tagcgctgcc cagaagggag cggagctccc ccgccgcgag gcggtcctct 420
ctggccaaaa gcccagcgtt aatagcgcct tctgggatgc aggaacccca cctgccaggt 480
gtgaagtgga ctaagtggat ctccaatttg gcctgttctg aactacacca tctactgctg 540
tgaagaatgt cctgaaggca agctggttac agccctgatc aggagccccg ctcgtgactc 600
tcgatcgacg cggggtcaaa aactgtctaa gcagcagcag aaacgcggga gcgtttcttt 660
ttcctcattt gtttc 675

<210> SEQ ID NO 622
<211> LENGTH: 224
<212> TYPE: DNA
<213> ORGANISM: Unknown
<220> FEATURE:
<223> OTHER INFORMATION: Description of Unknown: Equine arteritis virus sequence

<400> SEQUENCE: 622

```
gctcgaagtg tgtatggtgc catatacggc tcaccaccat atacactgca agaattacta     60

ttcttgtggg cccctctcgg taaatcctag agggctttcc tctcgttatt gcgagattcg    120

tcgttagata acggcaagtt ccctttctta ctatcctatt ttcatcttgt ggcttgacgg    180

gtcactgcca tcgtcgtcga tctctatcaa ctacccttgc gact                     224


<210> SEQ ID NO 623
<211> LENGTH: 675
<212> TYPE: DNA
<213> ORGANISM: Enterovirus sp.

<400> SEQUENCE: 623

actctggtat cacggtacct ttgcacgcct attttatacc ccttccccat cgtaacttag     60

aagcaacaaa caaactgccc aatagcagca caacacccag ttgtgttagg ggcaagcact    120

tctgtttccc cggaagggtc tgacggtatg ctgtacccac ggcagaagta tgacctaccg    180

ttaaccggcc atgtacttcg agaagcctag taccattatg aaggttgatt gatgttacgc    240

tccccagcaa ccccagctgg tagttctggt cgatgagtct cggcattccc cacgggcgac    300

cgtggccgag gctgcgttgg cggccagcct acaccatacg gtgtaggacg tcaagatact    360

gacatggtgt gaagagccta ttgagctacg tggtagtcct ccggcccctg aatgcggcta    420

atcctaactc cggagcatcc gccagtaagc ccactggaag ggtgtcgtaa tgcgaaagtc    480

tggagcggaa ccgactactt tgggtgtccg tgtttcctgt tttacttatt gtttggctgc    540

ttatggtgac aacttatagt tatcatcata agctacttgg tcttgccaac cggagaatta    600

tttggttatt tgttggtttc ataaacctac agtcgtattt tcctgtctta ttaattgttc    660

tcaaaattaa caaca                                                     675


<210> SEQ ID NO 624
<211> LENGTH: 675
<212> TYPE: DNA
<213> ORGANISM: Enterovirus sp.

<400> SEQUENCE: 624

taccgctgca ccagtgagct ggtacgctag taccttcgca cggagtagat ggcatccccc     60

accccgtaac ttagaagcaa agtacacatc tggccaatag tggcgctgca tccagccgcg    120

caacggtcaa gcacttctgt ttccccggtc cgcaagggtc gttatccgcc cagtccacta    180

cggaaagcct actaaccatt gaagctatcg agaggttgcg ctcggccacg accccggtgg    240

tagctctgag tgatggggct cgcaaacacc cccgtggtaa cacggatgct tgcccgcgcg    300

tgcactcggg ttcagcctat tggttgttca cctcaacata gtgtaaatgg ccaagagcct    360

actgtgctgg attggttttc ctccggagcc gtgaatgctg ctaatcccaa cctccgagcg    420

tgtgcgcaca atccagtgtt gctacgtcgt aacgcgtaag ttggaggcgg aacagactac    480

tttcggtact ccgtgtttct tttgttttat tttgaatttt atggtgacaa ttgctgagat    540

ttgcgaatta gcgactctac cgctgaacat tgccctgtac tacctaatcg catttcacaa    600

aacctcagag ataccaagct cttacattga tctgcttgtt ttcctgaatc tcaaatataa    660

attggaacaa gcaaa                                                     675


<210> SEQ ID NO 625
<211> LENGTH: 107
<212> TYPE: DNA
<213> ORGANISM: Morbillivirus sp.
```

<400> SEQUENCE: 625
accagacaaa gctggctagg ggtagaataa cagataatga taaattatca tacttaggat 60
taatgatcct atcaattggc acaggatttg gataaaggtt cacagtc 107

<210> SEQ ID NO 626
<211> LENGTH: 348
<212> TYPE: DNA
<213> ORGANISM: Unknown
<220> FEATURE:
<223> OTHER INFORMATION: Description of Unknown: Dianke virus sequence

<400> SEQUENCE: 626
tgttttcaac cataatacta ctactacaag tataaaaccc cgtccgtctg tcggagacgc 60
taaactctga ccaccaatct agccacatca gttgcttaaa gaacctcttg agacactctc 120
ccacttaaca tcttttagga atcttcgatg ctacaacaac ttggctagtg aacaataaat 180
ccgtacaatt cacagttgta agaggccata ggtccagact ttgaaaggtt tgtttctatt 240
gttacaaata cttagattaa cagaggctat ttaatagtgc tcatcacgtt aacagagtaa 300
ccttgtgcaa tagtatgagc ttgttgtaaa acgtcttgat acgacacc 348

<210> SEQ ID NO 627
<211> LENGTH: 270
<212> TYPE: DNA
<213> ORGANISM: Hepacivirus sp.

<400> SEQUENCE: 627
cactcaatac tacactccgc atttggggag aagcgctggc gttcgcggaa ccgcgttaac 60
catacgcgta gtacgagtgc gacagacccc ggtgctactg gtggtagcga gacacgagcc 120
gaagtctgtg gggggaactc cacttagagg gcatgcccgg gcgtaggctt ctgagttggg 180
atgggcccca acttggcccc tgagtggggg ggtgttacga cctgataggg tgcgggctgg 240
cgcctaccac tttccagtcg tacatgagtc 270

<210> SEQ ID NO 628
<211> LENGTH: 415
<212> TYPE: DNA
<213> ORGANISM: Narnavirus sp.

<400> SEQUENCE: 628
gcccgggggg tgcagtcctg tgaaagggtc tgcaccatac tatatatgta tatgattaca 60
tcccaaaagg cgacttcgtt caggttttaa atctgacgta ggtccagtaa ataagcatgt 120
caaaacatgt aagtttatcc tgtaatctac tctcataaga tgagataaga tgatattgca 180
gttcccatgt aaataaatcc attatgaatt cattcatata aggtagaagt ggtaactatg 240
gttgaaacat taatataaaa cggtcatttt gcatgaacgt cattaaggaa ctggcatacc 300
aatgtctatt tagtgactat gatatttaga gtatccctta tattaattaa caattattcc 360
ttttagcata tcatccgaca acaaatttta aaagaagaaa tattactcat taaaa 415

<210> SEQ ID NO 629
<211> LENGTH: 675
<212> TYPE: DNA
<213> ORGANISM: Torovirus sp.

<400> SEQUENCE: 629
gtacttacaa gcgggttaaa ccgccctccg gaacggttac aaccccctcc cgaacgtgcg 60
cttgacgtga ctggttctca gtctggcttt ctgagaaata ctccagggtt gtatcccacc 120
atcttgacct ctggtcattt tggtaacacc ataaccaaac aaactctaca cacctaaccc 180
acctccagct tgctgcaggc cttttggact aaacgggttt aggtgttttg tgaccaactc 240
gtctacccac ctccagtttt actgcaggcc tttttggact aaacggcttt agacttttgt 300
ggttagtttt taactaccca ctgtttagcc gccaacctga ttttcattgt tgtaaaattt 360
tgtgtttata cactattttc atacggttgg cagtttgttt ggttgtttgc acagtttttg 420
ttgataccaa tttttactgt gcttttagtg tattctgcta aggctgtatt ttacatactt 480
agtttggttg aagcaatttt tacaacattt atattgtttt tgatttctaa ggtaaagagt 540
cttaggaaac accatagacg ccattcttgt ggtgtctagt tccaactaat ctggcaaaca 600
agtaccaagt cattgactca ctttggagtg agacttacga gtaccaattt gcctatttcg 660
gacatccata taaag 675

<210> SEQ ID NO 630
<211> LENGTH: 675
<212> TYPE: DNA
<213> ORGANISM: Foot-and-mouth disease virus

<400> SEQUENCE: 630
acaagcttga caccgcctgt cccggcgtta aagggaagta accacaagct tacaaccgcc 60
taccccggtg ttaatgggat gtaaccacaa gatacacctt cacccggaag taaaacggca 120
aattcacaca gttttgcccg tttttcatga gaaacgggac gtctgcgcac gaaacgcgcc 180
gtcgcttgag gaggacttgt acaaacacga tctaaacagg tttccccaac tgacatacac 240
cgtgcaattt gaaactccgc ctggtctttc caggtctaga ggggtaacac tttgtactgt 300
gcttgactcc acgctcggtc cactggcgag tgttagtaac agcactggtg cttcgtagcg 360
gagcatggtg gccgtgggaa ctcctccttg gtaacaagga cccacggggc cgaaagccac 420
gtcctgacgg acccaccatg tgtgcaaccc cagcacggca acttttctgt gaaactcact 480
ctaaggtgac actgatactg gtattcaagt actggtgaca ggctaaggat gcccttcagg 540
taccccgagg taacacgcga cactcgggat ctgagaaggg gactggggct tctgtaaaag 600
cgcccagttt aaaaagcttc tatgcctgga taggtgaccg gaggccggcg cctttccatt 660
ataactactg acttt 675

<210> SEQ ID NO 631
<211> LENGTH: 310
<212> TYPE: DNA
<213> ORGANISM: Unknown
<220> FEATURE:
<223> OTHER INFORMATION: Description of Unknown: Feline infectious
peritonitis virus sequence

<400> SEQUENCE: 631
acttttaaag taaagtgagt gtagcgtggc tataactctt cttttacttt aactagcctt 60
gtgctagatt tgtcttcgga caccaactcg aactaaacga aatatttgtc tctctatgaa 120
accatagaag acaagcgttg attatttcac cagtttggca atcactccta ggaacggggt 180
tgagagaacg gcgcaccagg gttccgtccc tgtttggtaa gtcgtctagt attagctgcg 240
gcggttccgc ccgtcgtagt tgggtagacc gggttccgtc ctgtgatctc cctcgccggc 300
cgccaggaga 310

<210> SEQ ID NO 632
<211> LENGTH: 143

<212> TYPE: DNA
<213> ORGANISM: Unknown
<220> FEATURE:
<223> OTHER INFORMATION: Description of Unknown: Farmington virus sequence

<400> SEQUENCE: 632
acgacgcata agcagagaaa cataagagac tatgttcata gtcaccctgt attcattatt 60
gacttttatg acctattatt agacccttca cgggtaaatc cttctccttg cagttctcgc 120
caagtacctc caaagtcaga acg 143

<210> SEQ ID NO 633
<211> LENGTH: 528
<212> TYPE: DNA
<213> ORGANISM: Unknown
<220> FEATURE:
<223> OTHER INFORMATION: Description of Unknown: Avian infectious bronchitis virus sequence

<400> SEQUENCE: 633
acttaagata gatattaata tatatctatt acactagcct tgcgctagat ttttaactta 60
acaaaacgga cttaaatacc tacagctggt cctcataggt gttccattgc agtgcacttt 120
agtgccctgg atggcacctg gccacctgtc aggtttttgt tattaaaatc ttattgttgc 180
tggtatcact gcttgttttg ccgtgtctca ctttatacat ctgttgcttg ggctacctag 240
tgtccagcgt cctacgggcg tcgtggctgg ttcgagtgcg aggaacctct ggttcatcta 300
gcggtaggcg ggtgtgtgga agtagcactt cagacgtacc ggttctgttg tgtgaaatac 360
ggggtcacct ccccccacat acctctaagg gcttttgagc ctagcgttgg gctacgttct 420
cgcataaggt cggctatacg acgtttgtag gggtagtgc caaacaaccc ctgaggtgac 480
aggttctggt ggtgtttagt gagcagacat acaatagaca gtgacaac 528

<210> SEQ ID NO 634
<211> LENGTH: 626
<212> TYPE: DNA
<213> ORGANISM: Rhinovirus sp.

<400> SEQUENCE: 634
ttaaaactgg gtgtgggttg ttcccaccca caccacccaa tgggtgttgt actctgttat 60
tccggtaact ttgtacgcca gtttttccct cccctcccca tccttttacg taacttagaa 120
gttttaaata caagaccaat agtaggcaac tctccaggtt gtctaaggtc aagcacttct 180
gtttccccgg ttgatgttga tatgctccaa cagggcaaaa acaacagata ccgttatccg 240
caaagtgcct acacagagct tagtaggatt ctgaaagatc tttggttggt cgttcagctg 300
catacccagc agtagacctt gcagatgagg ctggacattc cccactggta acagtggtcc 360
agcctgcgtg gctgcctgcg cacctctcat gaggtgtgaa gccaaagatc ggacagggtg 420
tgaagagccg cgtgtgctca ctttgagtcc tccggcccct gaatgcggct aaccttaaac 480
ctgcagccat ggctcataag ccaatgagtt tatggtcgta acgagtaatt gcgggatggg 540
accgactact ttgggtgtcc gtgtttcact ttttccttta ttaattgctt atggtgacaa 600
tatatatatt gatatatatt ggcatc 626

<210> SEQ ID NO 635
<211> LENGTH: 675
<212> TYPE: DNA
<213> ORGANISM: Unknown
<220> FEATURE:

<223> OTHER INFORMATION: Description of Unknown: EV22 sequence

<400> SEQUENCE: 635
ccttataacc cgacttgctg agcttctata ggaaaaaacc ctttcccagc cttggggtgg 60
ctggtcaata aaaacccccca tagtaaccaa cacctaagac aatttgatca accctatgcc 120
tggtccccac tattcgaagg caacttgcaa taagaagagt ggaacaagga tgcttaaagc 180
atagtgtaaa tgatcttttc taacctgtat tatgtacagg gtggcagatg gcgtgccata 240
aatctattag tgggatacca cgcttgtgga ccttatgccc acacagccat cctctagtaa 300
gtttgtaaaa tgtctggtga gatgtgggaa cttattggaa acaacaattt gcttaatagc 360
atcctagtgc cagcggaaca acatctggta acagatgcct ctggggccaa aagccaaggt 420
ttgacagacc cattaggatt ggtttcaaaa cctgaattgt tgtggaagat attcagtacc 480
tatcaatctg gtagtggtgc aaacactagt tgtaaggccc acgaaggatg cccagaaggt 540
acccgcaggt aacaagagac actgtggatc tgatctgggg ccaactacct ctatcaggtg 600
agttagttaa aaaacgtcta gtgggccaaa cccagggggg atccctggtt tccttttatt 660
gttaatattg acatt 675

<210> SEQ ID NO 636
<211> LENGTH: 675
<212> TYPE: DNA
<213> ORGANISM: Cardiovirus sp.

<400> SEQUENCE: 636
tccgacgtgg ttggaattaa catcttttcc gacgaaagtg ctattatgcc tccccgattg 60
tgtgatgctt tctgccctgc tgggcggagc gtcctcgggt tgagaaacct tgaatctttt 120
cctttggagc cttggctccc ccggtctaag ccgcttggaa tatgacaggg ttattttcca 180
aactctttat ttctactttc atgggttcta tccatgaaaa gggtatgtgt tgccccttcc 240
ttctttggag aatctgcgcg gcggtctttc cgtctctcaa caggcgtgga tgcaacatgc 300
cggaaacggt gaagaaaaca gttttctgtg gaaatttaga gtggacatcg aaacagctgt 360
agcgacctca cagtagcagc ggattcccct cttggcgaca agagcctctg cggccaaaag 420
ccccgtggat aagatccact gctgtgagcg gtgcaacccc agcaccctgg ttcgatggcc 480
attctctatg gaaccagaaa atggttttct caagccctcc ggtagagaag ccaagaatgt 540
cctgaaggta ccccgcgcgc gggatctgat caggagacca attggcagtg ctttacgctg 600
ccactttggt ttaaaaactg tcacagcttc tccaaaccaa gtggtcttgg ttttccaatt 660
ttgttgactg acaat 675

<210> SEQ ID NO 637
<211> LENGTH: 292
<212> TYPE: DNA
<213> ORGANISM: Human coronavirus 229E

<400> SEQUENCE: 637
acttaagtac cttatctatc tacagataga aaagttgctt tttagacttt gtgtctactt 60
ttctcaacta aacgaaattt ttgctatggc cggcatcttt gatgctggag tcgtagtgta 120
attgaaattt catttgggtt gcaacagttt ggaagcaagt gctgtgtgtc ctagtctaag 180
ggtttcgtgt tccgtcacga gattccattc tacaaacgcc ttactcgagg ttccgtctcg 240
tgtttgtgtg gaagcaaagt tctgtctttg tggaaaccag taactgttcc ta 292

<210> SEQ ID NO 638
<211> LENGTH: 282
<212> TYPE: DNA
<213> ORGANISM: Unknown
<220> FEATURE:
<223> OTHER INFORMATION: Description of Unknown: Hubei zhaovirus-like virus 1 sequence

<400> SEQUENCE: 638
gtgcaggatg gcctttccca tcttaagtgg tttgtaggat ttcgtgggtc catacccccc 60
gatttcttgg tacgtattcc atgcacggag aatacgacca aaactcttat ttcaaaaaat 120
attatttttt actcttgtgg gctgagtgcg acccaccagt tccagcttag caacctggaa 180
gttgttggag atttatggaa ccaaattaca catgcgtgga gtgccgccac tccgtatctg 240
ttcactcatt acgcgattaa gttctgcgac gagacgagcg aa 282

<210> SEQ ID NO 639
<211> LENGTH: 600
<212> TYPE: DNA
<213> ORGANISM: Unknown
<220> FEATURE:
<223> OTHER INFORMATION: Description of Unknown: Hubei tombus-like virus 9 sequence

<400> SEQUENCE: 639
ggaccatcca ggcaggtgta ggctagtacc ctcacctgac ctgtcgcgat gtttggcttt 60
gtgaggcttg tgggaggatc ccttggccca tgcattgctg ctgtcatcgt gaaaaatgtt 120
gtatgctcgc acctggcgtg gaggaaacgg catttgacgg atgctaagga ggatttgaag 180
gtcctcaact cccatgcctt attacaagtc ccctttcctt caagcttcga gcccacgtct 240
gtgacgagca gaggtgaggt tggagtcaag aggagtccta ttcaagctgt tcgcagcaag 300
aaccataaaa ctttcattgc tcaatgggca agagcggcta aggctcggtt ctcgtttgca 360
cgacagtgtg agcggagccc tgtaaatgtc gcggcccttc atcggtggtt tgcatcggag 420
tttaagaaaa ttggcatgaa cttgctccag gtttcgtacg tgatcgatga ggttgttgaa 480
cttagtttgg aaccaacgta tgagcgtatg gtgtccgaaa ctaagaagca attccgtcat 540
cgggcacgta tggaatacta caacgagaaa aaatgccttg aaaagatcca ctaggaacgc 600

<210> SEQ ID NO 640
<211> LENGTH: 251
<212> TYPE: DNA
<213> ORGANISM: Unknown
<220> FEATURE:
<223> OTHER INFORMATION: Description of Unknown: Hubei tombus-like virus 32 sequence

<400> SEQUENCE: 640
ttcgggttta cccgcgtaag cggccacact gactggttgt cggtgttgaa tttgtatacc 60
agatgaggag acgttaccac cgtctcggca gtgctacgtc tgggaaagga ctgtgatagt 120
ggacagtcct accgtcttta gatacattgc gttgtgtata gcccgggagg gattaactaa 180
tagcaacgca atgcacacgg cggttcggat ttgcttgact gatggaaaga catctaagtt 240
ctaattgaac c 251

<210> SEQ ID NO 641
<211> LENGTH: 341
<212> TYPE: DNA
<213> ORGANISM: Unknown
<220> FEATURE:
<223> OTHER INFORMATION: Description of Unknown: Hubei sobemo-like virus 3 sequence

<400> SEQUENCE: 641
gagatgtttg cgtgggccgt tgcgctgcgg gcggcccacc tccctacggg gaccgtgaga 60
caccgctggg gaaggccccc acccccggcc aaggggatcc tgccgagagg caggagaaag 120
aggcccagcc ctctggggcg cctttagggg tgcctgggag ggaagtaccc gagccgggcg 180
gccggtcggg tgcggctgtg cagttcgagg ctaaccgtaa ggaaggcctg agctgcctcg 240
gcttgtcgga aaggaagacg aaggcactta tcaaggcttt caggaagcag gagcgcaatt 300
acagcgcgcg ccgtgcggcc tggattaacc gcatttggcc g 341

<210> SEQ ID NO 642
<211> LENGTH: 675
<212> TYPE: DNA
<213> ORGANISM: Unknown
<220> FEATURE:
<223> OTHER INFORMATION: Description of Unknown: Hubei picorna-like virus 2 sequence

<400> SEQUENCE: 642
agcaacttct ttctgaaaac tagctagagt tcgacgatct ctctggctaa tgacaaataa 60
ccaatcaaaa agtcaaatgt tcatgtatat atatatttag tagtgacctt tatttagaaa 120
aactttagat gatttatcgt caagttgccc tttgtgaagc gatcagcttt ttatatcgtt 180
tcatttttgt atacgtctta attgacgttg taagtacgtt ttgcatacct cacattgagg 240
atagtatcgt ttcctgacta agaagttaaa ctagtctacc aatagcaacc atataggata 300
tagctttgtt tttaacaagg tttaatctga tcttatgctc ttgcttacgg tgttttatgt 360
atagaaaagt ttttataaaa actacataat tgtcaaaaga aaaagcgtta cgtactgacg 420
catttatgtt cacagtgtga cacaaacctt ctatattttg attgtaaaat aggctttgcc 480
tgaccattta tcaaatacaa actgtttcaa acgcctctcc gagccatatt ggccgacgcg 540
aatcgacata acagggtgag tttacagctg cagttgcagc cgaggatcca cttatttgag 600
agagaattac tcttaacgaa attttgaagt cacttctaca cagttaagtc tgagtaggcg 660
ttatccaaac gtaaa 675

<210> SEQ ID NO 643
<211> LENGTH: 174
<212> TYPE: DNA
<213> ORGANISM: Hepacivirus sp.

<400> SEQUENCE: 643
acatgggggg gggctgacag tgagtacact gtgccaagca ggtgctacgc tatgcctagg 60
tgctgctgta ggccaaggac atgtcccagt catcccaggt gagggggggg gttcccctca 120
ccgctgccac tgcctgatag ggtcctgccg gagggtctcg gtgtccggct gtac 174

<210> SEQ ID NO 644
<211> LENGTH: 675
<212> TYPE: DNA
<213> ORGANISM: Unknown
<220> FEATURE:
<223> OTHER INFORMATION: Description of Unknown: Harrier picornavirus 1 sequence

<400> SEQUENCE: 644
gatgtgtgac ggtgtaatta ctttccggat cccactttcc tattataact ctttcatccc 60
aaggttaggg aaagaacctg gctcggtacc accagaccct ccgccacgct agtggactct 120
ccggagataa cggtaccccc tttgtagtca cctgtgctgg tgaagaacca cctagtattg 180
cttgggtgcg tgccgcctag cttccatttc ttctggagca ctgtgcaatg aggtttcccc 240
acttggtaac aagtgcctca ggtcccgcaa ggatactgtg gggtggtgtg accgcaggga 300
gctgtctcca cggctcctct aatgttacgc cgctatccac aggccagtgc gtgtcatcga 360
tcccggatga cagagctagt attgcgaacc cccaagtaag aaaagtggct agtaacctga 420
tagctggtga agagggtggg tcagttgagt agatgcccta gaggtacccg aaaggatctg 480
actagggacc cgtgactata cattaggtaa accgggtata aaaaccatga aaaactgacc 540
acttttcttt taacctcttc tttcttttta tgtgtgttaa gtgttttgag tttggactgt 600
accttgcccg cctttcttgg attttctcta tcgctcttct tacacctact gttatcaagg 660
cactctttag agata 675

<210> SEQ ID NO 645
<211> LENGTH: 500
<212> TYPE: DNA
<213> ORGANISM: Kunsagivirus sp.

<400> SEQUENCE: 645
tttcaaatcg gactccggta gttataccgg agcccggttt ggacgcttgg gccgcgttaa 60
cagcccccca cccctttccc actgactgat ttctcggatt ggactcattt gcattgctaa 120
ctctgattct ggatttcccc gtttatgtcg tcgcggtcgg aagtgcacgt acttcgacgt 180
tgatctgatg gcgtttgttt ccagggggga ggtggcggca gaaacgcccc cgccgtaaac 240
ttcggcgggc cacgcctgtc aagccactcc ctggggccga gcgcctgagg tgatacagag 300
agataagcac actgggcgct gacaacgccc gggacctcag tgagaagagc agtagggccg 360
tgtttatggg actccattgg atatccccg cttgtcggaa ctcacggcta ctccgggttg 420
ggaagcccgc gactggtact gtactgggtg atagcctggt gccttccctc tcactgttgt 480
atgaaggctg aaaacccccct 500

<210> SEQ ID NO 646
<211> LENGTH: 675
<212> TYPE: DNA
<213> ORGANISM: Kobuvirus sp.

<400> SEQUENCE: 646
tatagtttgc ctgtttctcg caccgttacc gctcgttcgg gaatgtgaaa ctggcacccc 60
tcctctcccc taccaccctt tctccttcgc ccccattcat aatttacaac gccgcacaca 120
gcggcggccg ccaagggcta gcctggcggt tataaaagga acctgggtct ttccctcttc 180
aagccaaaag gtaggttccc tgtgtccctg aatgctcggt gaggaatgct gcaccgtaac 240
gctttgtgaa gtgtttgcaa gttctggccc ggcaagccta cagagtgctg tgatccgctg 300
cggacgccat cctggtaaca ggacccccag tgtgcgcaac agtatgttca gacttcggtt 360
tgttcacttg ctttcatgga ccattgcgcg aaagtgcgtg cgccatatcc ctgtacttca 420
ggtgtgcttc tctggaccct aggaatgctg cgaaggtacc ccgtttcggc gggatctgat 480
cgcaggctaa ttgtctatgg gttcagtttc ctttttcttt actccacaat tgactgctta 540
actgactctg gatcttgtgc ttccactgct ctttctgctc tcaaaacggc ttcacttacc 600
aactctcacc tttcgaccaa caccatttac acactaactt ttttcgactc ttctgactcc 660
tggcttggtg aagac 675

<210> SEQ ID NO 647
<211> LENGTH: 608
<212> TYPE: DNA
<213> ORGANISM: Kashmir bee virus

<400> SEQUENCE: 647
tacgtacaat tttgacgctt cgttcatgca acaatgaact cacatgtggc gctcggtagt 60
aaccagaggg gcgtcattcc cccgtatgga gtggagaata taagctaccg actcgagctg 120
tagaataatt cagcaactta taacgaacac gaattttagt cgacgaaacc attttagcct 180
ttaattctat gatttgatta taatgataaa cagctcatgt aactgtctaa actacataaa 240
tacaactgga ttacgaacct ttaagtaact atcttagatg aagtctagta gtctcccaat 300
atttccgtga aaagaatgag ggacgagata gctctattta aagacgtgag gctttaaatt 360
ctgataaata cattacctga gaattcctcc tttaggagtt agaatttgaa aagattagta 420
cctatactta atagaattta aatatgttaa taatgctgaa gacaagtatt tcgattatta 480
acctctatat ttctatataa agtatctgtg agtctcagtg gacatcacag taaggtcgca 540
gttaacttgt aatcttttca ttcctgtgtc ggagcagtgg taatggagcc ggacgatttc 600
gccaaaac 608

<210> SEQ ID NO 648
<211> LENGTH: 332
<212> TYPE: DNA
<213> ORGANISM: Unknown
<220> FEATURE:
<223> OTHER INFORMATION: Description of Unknown: Jingmen picorna-like virus sequence

<400> SEQUENCE: 648
tgtgtttttg tcaagataat tgttctgtga ttaacagtga ttgtggttcg tgtaatgcga 60
cgcagtcaaa tgctagtttt gatgaagtgt atgagagagt ggaaaactta tctcataaga 120
agattgaaga gtgtgtagat caggctattg atcgagcttc taagcttcgt gattacaagc 180
ttaatgttca caatggctcc cgacgggaat catctgatcc tctctttatt tcgccccatt 240
cgttgttatc gcttggggta tctaagtttg ttgcgtttga gcagcatcac agtttcgctt 300
cagttgagtc tctgaagttg cttgctctgt ct 332

<210> SEQ ID NO 649
<211> LENGTH: 145
<212> TYPE: DNA
<213> ORGANISM: Mumps orthorubulavirus

<400> SEQUENCE: 649
accaagggga aaatgaagat gggatgttgg tagaacaaat agtgtaagaa acagtaagcc 60
cggaagtggt gttttgcgat ttcgaggccg ggctcgatcc tcacctttca ttgtcgatag 120
gggacatttt gacactacct ggaaa 145

<210> SEQ ID NO 650
<211> LENGTH: 138
<212> TYPE: DNA
<213> ORGANISM: Mosavirus sp.

<400> SEQUENCE: 650
gaagttgatc atgaacttgg ttattggtgg aacgcacatg aactcccaac aatgatcttg 60
aagacacagc gtggtaacaa ttaccatgcc cttgtggctg cccaagacat tgatggctat 120

```
tgggtgattt atgatgac                                                138


<210> SEQ ID NO 651
<211> LENGTH: 675
<212> TYPE: DNA
<213> ORGANISM: Unknown
<220> FEATURE:
<223> OTHER INFORMATION: Description of Unknown: Miniopterus
      schreibersii picornavirus 1 sequence

<400> SEQUENCE: 651

gttgtcgacc cgttgcttgg tttaagcatg aggtggattc ccccgattat gtctacccgt     60

tactatggcg ggcggtcgtt tcagggtgtt tctactgagg actgcaccaa gtctttatct    120

tttattctca gatctccggc tgtttgacgc ttgtaggaca gcaggactat tttctcttaa    180

tctttttcta cccactaggg tcctatccta gtggagggag ggtgccaccc cttctctctt    240

tagagagtgc gcctggcggt ctttccgtct ctggaaaaag gagcacatgg catgctacaa    300

ttggcacaag aaaacaagct ttgcggattc tttctttgta ctagaggaag ctgtagcgac    360

cctgtatggc gagcggactc ccctctcggc gacgagagcc tctcgggcca aaagccaagt    420

gttaatagca cccatacagg cggcagtacc ccactgccct ttctcaacat acaatgactg    480

atgaaccact gttggttttt ctgacacctt tgtagtagga ttccaaggaa tgtcctgaag    540

gtaccctgtt agcttacgcg caggatctga tcaggagtct ctttacagtg ctgtacactg    600

tgcaagggat taaaaattgt ttgaggaatc cccgagatag tggtctatct cttcctattt    660

tgttttacag acacg                                                   675


<210> SEQ ID NO 652
<211> LENGTH: 381
<212> TYPE: DNA
<213> ORGANISM: Unknown
<220> FEATURE:
<223> OTHER INFORMATION: Description of Unknown: Linda virus sequence

<400> SEQUENCE: 652

gtatagcagc agtagctcaa ggctgctata cgattggaca taccaaattc caattggtgt     60

tagggaccac ctaggtgaag gccgacgaca ggtagccatt cctgttagta ggacgaaccg    120

ttatggtgga ctggttgctc aggtgagcag gctgcaatgc gtaagtggtg agtacaccac    180

agccgtcaaa ggtgccactg gtaaggatca cccactggcg atgccttgtg gacgggggcg    240

tgcccaacgc aatgttagcg gtggcggggg ctgccatcgt gaaagctagg tcttgatgga    300

ccttgttgcc tgtacagtct gataggatgc cggcggatgc cctgtgacag ccagtataaa    360

gaatatccgt tgtgattgca c                                            381


<210> SEQ ID NO 653
<211> LENGTH: 675
<212> TYPE: DNA
<213> ORGANISM: Unknown
<220> FEATURE:
<223> OTHER INFORMATION: Description of Unknown: Lesavirus 2 sequence

<400> SEQUENCE: 653

tctttcttta ttttcttatg taactcttct ttttaagttt tattttgcct acttgtgagc     60

ttatgcggga ccactgtctt agacaacccc acatttgtca tgagtaagta cacgcaacca    120

ttacgattac tttttaaccg tctgaccttt tgataacaac tgaagttagg cgtgaaacat    180

gcatttatac caaagtagcc ccgcatttcc ccactacggt ggggggggcta ccctactggc    240
```

-continued

```
tttggaactg tagccattat gtgttgcctg gctttcagga tctcacaaca caacagttct    300

ctcacaatgg aatatgggtg agattgcagt gacatgaaca agtatctagt agtacataga    360

ctcaagccta gttgcctgcg gaacaacatg tggtaacaca tgccccaggg tccaaaagac    420

aagggttaac agccccttct aggtgtctgt gtgtgaagaa tactttagta gtgttgttat    480

gatctcacct gttagtacag aatgagtatg gcttggtgaa ggatgtccta caggtaccca    540

ttatatggat ctgagtagga gaccactagt ggtggcttta ccgccaggtg agtggtttaa    600

aaagcgtcta gccaagccaa cagcactagg gatagtgctt tctatatttt atattttcag    660

tgtatatggt gacaa                                                     675
```

<210> SEQ ID NO 654
<211> LENGTH: 675
<212> TYPE: DNA
<213> ORGANISM: Unknown
<220> FEATURE:
<223> OTHER INFORMATION: Description of Unknown: Lesavirus 1 sequence

<400> SEQUENCE: 654

```
gtaactaata agcaagtttt actgcctgca aactgcttca atgggaccac cgcttcggcg     60

accccttgt  tgagtttgta tgtttttaag taatctttgc aaccatacga ttattttagc    120

cgcctctcta taatgatctt gttatagtgg gacgtgaaac attggttttt ctcacacacg    180

tccggtcacc cgggcgtgtg ttcttccgta agtcctatcc acataccatc gtgggtaggc    240

cagcatgttt gcacaggctg tgacagtgtg ggtgggcttt ccacctctca acaacacact    300

gaattgcaat gcactcacgg aggaaatgac aatttggtta tagttttgaa ctgtgctagt    360

aatttctttc acattaagcc atgttgcctg cggaatcaca tgtggtaaca catgcctcag    420

ggcccaaaag gcacgggtta gcagcccctt catggtgtgt tagaagtgaa aacacatagt    480

atgagctata atatctttgt tgtcttctct gtagtgtacc ccgccaaatg taaggatgcc    540

cagcaggtac ccattttatg gatctgagct ggggattgat agtgtatcta taaatgcact    600

gatcaattta aaaagcgtct aagtttggca caaacactgg ggacagtgtt tttcctttat    660

tcttttattt gatta                                                     675
```

<210> SEQ ID NO 655
<211> LENGTH: 638
<212> TYPE: DNA
<213> ORGANISM: Unknown
<220> FEATURE:
<223> OTHER INFORMATION: Description of Unknown: Phopivirus strain
      NewEngland sequence

<400> SEQUENCE: 655

```
gggagtaaac ctcaccaccg tttgccgtgg tttacggcta cctatttttg gatgtaaata     60

ttaattcctg caggttcagg tctcttgaat tatgtccacg ctagtggcac tctcttaccc    120

ataagtgacg ccttagcgga acctttctac acttgatgtg gttaggggtt acattatttc    180

cctgggcctt ctttggccct ttttcccctg cactatcatt ctttcttccg ggctctcagc    240

atgccaatgt tccgaccggt gcgcccgccg gggttaactc catggttagc atggagctgt    300

aggccctaaa agtgctgaca ctggaactgg actattgaag catacactgt taactgaaac    360

atgtaactcc aatcgatctt ctacaagggg taggctacgg gtgaaacccc ttaggttaat    420

actcatattg agagatactt ctgataggtt aaggttgctg gataatggtg agtttaacga    480

caaaaaccat tcaacagctg tgggccaacc tcatcaggta gatgcttttg gagccaagtg    540
```

cgtaggggtg tgtgtggaaa tgcttcagtg gaaggtgccc tcccgaaagg tcgtaggggt 600
aatcaggggc agttaggttt ccacaattac aatttgaa 638

<210> SEQ ID NO 656
<211> LENGTH: 377
<212> TYPE: DNA
<213> ORGANISM: Pestivirus sp.

<400> SEQUENCE: 656
gtatacgaga ttagctcata ctcgtgtaca aattggacgt agcaaattta aaaattcgga 60
tagggtcccc atccagcgac ggccgaacgg ggttaaccat acctctagta ggactagcag 120
acggatggac tagccacagt ggtgagctcc ctgggaggtc taagttctga gtacagaaca 180
gtcgtcagta gttcaacgct ggtaaacccc agccttgaga tgctacgtgg acgagggcat 240
gcccaagaca caccttaacc tggacggggg tcgtccaggt gaaagtaccc atctttgggt 300
gctgggagta cagcctgata gggcgctgca gaggcccact gacaggctag tataaaaatc 360
tctgctgtac atggaac 377

<210> SEQ ID NO 657
<211> LENGTH: 494
<212> TYPE: DNA
<213> ORGANISM: Unknown
<220> FEATURE:
<223> OTHER INFORMATION: Description of Unknown: Quail picornavirus QPV1
sequence

<400> SEQUENCE: 657
tttgcatcag ttcgcccctc ccctcaccat accttttttcc cctctttagg actgatactt 60
ggttatgatg agcagaggat ttcgcaagtt atgcttcttg ataaaaagta attcacgaat 120
catgggatta tagcctggaa gtgaacactc atgtggcaag tgggttagta gctctccatg 180
ttcccatgtg cagtggactg acaacagtga gttcggggtt gtgtagtaaa gggaaagtat 240
tacttacccg cacctgctat acgtggtgta cgtaggatac gagttagtag tgcttagcaa 300
ctttaaactg gtgctgaaat attgcaaggt cactgaagtt gtgaacgcga acgctccgcc 360
actgccatgt atagcgtgca atgcataaat ggtgcactac atgatacgag ggaatgggaa 420
accctccatg gccgaatgca gggtgacagc ctgccggcgg atgcctgttg ttagtataat 480
ccgttgtttg ccac 494

<210> SEQ ID NO 658
<211> LENGTH: 443
<212> TYPE: DNA
<213> ORGANISM: Sapelovirus sp.

<400> SEQUENCE: 658
acactcattt cccccctcca cccttaaggt ggttgtatcc cctacaccct accctccctt 60
ccacatagga cgaataaacg gacttgagat taaggcaagt acataaggta tggtttttgg 120
atacacttaa atggcagtag cgtggcgagc tatggaaaaa tcgcaattgt cgatagccat 180
gttagcgacg cgcttcggcg tgctcctttg gtgattcggc gactggttac aggagagtag 240
acagtgagct atgggcaaac ccctacagta ttacttaggg gaatgtgcaa ttgagacttg 300
acgagcgtct ctttgagatg tggcgcatgc tcttggcatt accatagtga gcttccaggt 360
tgggaaacct ggactgggtc tatactgcct gatagggtcg cggctggccg cctgtaacta 420
gtatagtcag ttgaaaaccc ccc 443

<210> SEQ ID NO 659
<211> LENGTH: 189
<212> TYPE: DNA
<213> ORGANISM: Unknown
<220> FEATURE:
<223> OTHER INFORMATION: Description of Unknown: Porcine reproductive and respiratory syndrome virus 2 sequence

<400> SEQUENCE: 659
atgacgtata ggtgttggct ctatgccttg gcatttgtat tgtcaggagc tgtgaccatt 60
ggcacagccc aaaacttgct gcacagaaac acccttctgt gatagcctcc ttcaggggag 120
cttagggttt gtccctagca ccttgcttcc ggagttgcac tgctttacgg tctctccacc 180
cctttaacc 189

<210> SEQ ID NO 660
<211> LENGTH: 675
<212> TYPE: DNA
<213> ORGANISM: Enterovirus sp.

<400> SEQUENCE: 660
gaaccttaga agtttacaca aacaaagacc aataggagtc caacacccag ttggattgcg 60
gtcaagcact tctgtttccc cggacctagt agtgataggc tgtacccacg gccgaagatg 120
aacccgtccg ttatccggct acctacttcg ggaagcctag taacattctg aagtctctga 180
ggcgtttcgc tcagcacgac cccggtgtag atcgggctga tgggtctccg catacccac 240 gggcgaccgt ggcggaggcc gcgttggcgg cccgcctatg gcgaaagcca taggacgcct 300
cttagatgac agggtgtgaa gagcctactg agctgggtag tagtcctccg gcccctgaat 360
gcggctaatc ctaaccacgg agcgtccacc agcaatccag ctggcagggc gtcgtaacgg 420
gcaactctgt ggcggaaccg actactttgg gtgtccgtgt ttccttttga tcctattttg 480
gctgcttatg gtgacaacga taagttgtta tcataaagct cttgggttgg ccacctggaa 540
aaagttatca gtgtttgata ttgttcggct ctcacgccta ccaataagac aagccctata 600
tttacttgtt gcattttact cgtcagaaga aatcacagag tatcatttgg atttgttact 660
cacattaagg acaag 675

<210> SEQ ID NO 661
<211> LENGTH: 591
<212> TYPE: DNA
<213> ORGANISM: Unknown
<220> FEATURE:
<223> OTHER INFORMATION: Description of Unknown: Pigeon picornavirus B sequence

<400> SEQUENCE: 661
tttatttagc tgttaagttt tatttgtgcc gagaccccat agtaggatct tggtgttcca 60
cattaagctc tcccgaccac acatccaaac gataggcggt gtaagggctc cctggctaag 120
tgtttactca ttgctaggga agtgttgcga cccgttacca gtaggaatac aggaggtctt 180
agttgcctaa ccagataaag tggtgctgaa atattgcaag ctcaatgtct ggcgaacgac 240
ggactaccgt tgaactattg ttaacgcccg cgtgtgtagg caacacacgg gttagtaggt 300
cacttacatt gacatccgtg ccgggaaagc ggatctgagc tatcgattgc ctgatagggt 360
gccggcgggc gcggtacgtg tggtatagtc cgctgtcttg gggtatggcg tctactcggt 420
tttgttgtcg ttttggaatg tcccatgtcg gagatgtcgt taccggtgtt tgctttactt 480
gtgcacgaat aagaaaacag agtttggagt tttggaagtt aatggataac atcaagtttc 540
cattgcgttc ctcgtgcatt ttaggccaga aaatcgacca caaaatcgag a 591

<210> SEQ ID NO 662
<211> LENGTH: 620
<212> TYPE: DNA
<213> ORGANISM: Unknown
<220> FEATURE:
<223> OTHER INFORMATION: Description of Unknown: Picornavirus HK21 sequence

<400> SEQUENCE: 662
aaacgggagg atcggctttg gcttatcctc ttaatagtct acaaaactgg gctgactggt 60
gggggagcta ctagatccgg gagaggacta gttaccccgc gtaacttccc tttttgtcac 120
tccctccacc taccccttcc ctgtccctta gactcttaag taggtgtgca ggcctggccc 180
cccggaaatg ggcaaatcgg acgtttgcgt gtagggtcgt tctgaaaggt ggggcccact 240
ccaccgtagt aggatcttcc tgtttcacgt ttaaacctct ccgggcaggt atcgctagac 300
actaggctgt ataggatggc acgcacttag gtttcgcacc ttcctagtgc gccaagatcc 360
cgcttttgag ctcaagtaca tggttctttg taagatgtct aaccagagga ggtggtgctg 420
aaatattgca agccactctg gcgaacgtcc actgcattgc ctggaacagg ctctctagcg 480
ccctccactg gtagcgcggt ggtgggttag taggatacct atatggacag gggatgcggg 540
aatacccctc actagctagt gactggttga tcgactggcg gcggatccag tgatacttgc 600
ataatccgca gacttgggag 620

<210> SEQ ID NO 663
<211> LENGTH: 675
<212> TYPE: DNA
<213> ORGANISM: Unknown
<220> FEATURE:
<223> OTHER INFORMATION: Description of Unknown: Picornavirales Tottori-HG1 sequence

<400> SEQUENCE: 663
agccatgaac tagtgtgcga ttcccacagt gttggtcgaa agccccgcac tgtctactcg 60
catatttgac tccagtcctt ccgcagccag cggttaggtt ctggttaaag tgcattatgt 120
gcacggcgcc acgcagaact gccagaaatg gtaagctgcg cccaacgcca acggtttgtg 180
tatcccgtta gtcacacgtt tacagctgtt cgttaacagt agggttttgt cgacccggac 240
cccttaatgc gcgcgaattc aaccgcgcct agtcggcaat ggtatcattt aatcccatgc 300
actacgggag aaatttgaga ccaaagaatt cctgagggcc actgcttgct ctaagtgcaa 360
tgcctcggga gacttctgtc aggagcctag cggctttcaa ccgcgacagc taactcctgc 420
gggatgtttg gtgtccatac ttactggcgt cctcacaacg ctaagtggat gttgtccaca 480
ggtaggcaaa caccgagccc cacattcagg agacctgtat gaacgatcct atcagcatta 540
gagttggaat tgggtgtgct aacgtccgca taagtgcacc ccgtggtaac gctgggaaac 600
tatccagcgc aacgtactgt cctcaatgtc tagggaagga ccgccctaag cgtacaaccg 660
ggccatgtgt cgagc 675

<210> SEQ ID NO 664
<211> LENGTH: 549
<212> TYPE: DNA
<213> ORGANISM: Hepatovirus sp.

<400> SEQUENCE: 664
ttcaaagagg ggtccgggat tttcctggtc cccctctttg ggcacccttg gctcgggggt 60
gtgaataccg tgctcgcgtt tgccgtgcgt taacggcttc atttatgttt gtttgtctgt 120
tttattatgt tggtttgtct gtttgttatg ttggtattgt tcgtgtttaa tgttatgacc 180
acattacact ccagccaatg aagaacagat ggtgcggtta ttgctggcgg aattcctaac 240
gtcctggatc cgttggtacg catcacaaaa caatttgcag agagagtggt gaaacggctt 300
gggaatccct gagtacaggg aaatcacact gatagctcat cttggctgtt ttcagtcatg 360
gaccttatgc agtgtaattt gggtgtaccc cccatagctt aggaggaatg ttctgtcttg 420
gcactagagt gggacgctga tgcctccgtg tctaggatgg tctaagggac agaatggggt 480
gcctctgatg ccatactacc tgatagggtg ctctcacggc ctctgcatct tagtgagaag 540
ttcaatttt 549

<210> SEQ ID NO 665
<211> LENGTH: 107
<212> TYPE: DNA
<213> ORGANISM: Unknown
<220> FEATURE:
<223> OTHER INFORMATION: Description of Unknown: Rinderpest virus sequence

<400> SEQUENCE: 665
accaaacaaa gttgggtaag gatcggtcta tcaatgatta tgatttagca cacttaggat 60
tcaagatcct atcgactgga gcaggcttaa ggtaaaggtt ctttaaa 107

<210> SEQ ID NO 666
<211> LENGTH: 675
<212> TYPE: DNA
<213> ORGANISM: Rabovirus A

<400> SEQUENCE: 666
ctacggatat ttgcatgacc cgctttctat cgccccaaca atcccctttg taaccacaag 60
ctttactcag gctagcagcc cgactagctg tttggaagaa aaggctaggg cacacaccaa 120
caacaccgac cccactggtc gaaggccgct tggcaataag actggtggaa cagggtcgcc 180
tgtagttgtt tggaacattc tttctaatga ctttgtcagc ggtgctactc acaccgtaac 240
tcttctaccc tatccccacg cttgtggaac taggagggga tgagtgattc aagtaagtac 300
tgtcagaatg gtgaaaatga tctgattctg aaacgctatg gatccatcga aagatggggc 360
tacacgcctg cggaacaaca catggtaaca tgtgccccag gggccgaaag ccacggtgat 420
aggatcaccc gtgtagtttg agatcatatc aatgttcata gtctagtaag atgatttgaa 480
atctaactga gctgatggct aactgcttgt cttattgcgg cctaaggatg tcctgcaggt 540
acctttagat aaccttaaga gactattgat ctgagcagga gccaaagtgg tctttcccag 600
ctttggttaa aaaacgtcta agccgcggca gggggcggga ggccccccttt cctcccaaaa 660 cttaatattg attgt 675

<210> SEQ ID NO 667
<211> LENGTH: 410
<212> TYPE: DNA
<213> ORGANISM: Shingleback nidovirus 1

<400> SEQUENCE: 667
ctgtgagtac cgacaggctc gaagtctatt atgaggcgtc gaaacagaaa acctgtaaca 60
actccggttt catctatcac tgccgtcaag aggcagaaga ggacgaccac gtgtcaccag 120

-continued

```
atcacttgta tctgtttcag tcaggaagtc aacttttcga cgaagttcga ccattcatcg    180

acccgctgaa aagcgtagaa gtcgatgaag atgagctcca aagagccatc gccgatttcg    240

acaaccaaag tgactgtttc cactccttcg agctcgtgaa tttcgagctg aaacaacaaa    300

tcaacgagaa cgagtggtac ggttattata attacgacaa ccaaaactgc aaagttcagt    360

tgccagtcac atgtcgaatc gaggacgtaa cctgggatca ggtttacgtg               410
```

<210> SEQ ID NO 668
<211> LENGTH: 666
<212> TYPE: DNA
<213> ORGANISM: Unknown
<220> FEATURE:
<223> OTHER INFORMATION: Description of Unknown: Seneca valley virus sequence

<400> SEQUENCE: 668

```
tttgaaatgg ggggctgggc cctgatgccc agtccttcct ttccccttcc ggggggttaa     60

ccggctgtgt ttgctagagg cacagagggg caacatccaa cctgcttttg cggggaacgg    120

tgcggctccg attcctgcgt cgccaaaggt gttagcgcac ccaaacggcg cacctaccaa    180

tgttattggt gtggtctgcg agttctagcc tactcgtttc tcccccgacc attcactcac    240

ccacgaaaag tgtgttgtaa ccataagatt taaccccgc acgggatgtg cgataaccgt     300

aagactggct caagcgcgga aagcgctgta accacatgct gttagtccct ttatggctgc    360

aagatggcta cccacctcgg atcactgaac tggagctcga ccctccttag taagggaacc    420

gagaggcctt cgtgcaacaa gctccgacac agagtccacg tgactgctac caccatgagt    480

acatggttct cccctctcga cccaggactt ctttttgaat atccacggct cgatccagag    540

ggtggggcat gacccctagc atagcgagct acagcgggaa ctgtagctag gccttagcgt    600

gccttggata ctgcctgata gggcgacggc ctagtcgtgt cggttctata ggtagcacat    660

acaaat                                                               666
```

<210> SEQ ID NO 669
<211> LENGTH: 675
<212> TYPE: DNA
<213> ORGANISM: Unknown
<220> FEATURE:
<223> OTHER INFORMATION: Description of Unknown: Sclerotinia sclerotiorum dsRNA mycovirus-L sequence

<400> SEQUENCE: 669

```
ttgaattaat cttttacgtt tacgcgcata aaatcaggac acatctcttg tatactttag     60

tatatcaatg atgtttttgt tttatgcgat taatcgtaag agaacttctt tccatccgcc    120

tgtatgggcg ggataataag ttcaccgcct tggtcgaggc gcaaacttgt atgtgcaaag    180

gtgagctata tgctcgaaat agtcgtaact aacacacagc cactacctgt agagctctat    240

tgatccggaa tcctttagtg ggaatgcaga gctcacaccg gacctgcggg tatcttcggc    300

gttagggact tctgtttcag ccttgaatca tttaccttta taccttctct gaggcgcctg    360

ggccgggcgc gatattaagt acaagtcaag gacatcgcgg gtagtggtct aatcagccgc    420

tagtcctgct ggagagttcc aacttagttg ggtgtggtgc atactagctg gatagagtag    480

gtatgtattg ctaacgtatg ccggaggcta tccgtcctcg gtagaacgtg ccgaggagta    540

gtctctgcag acccccgaac gcgtggggtc tttacttaaa tgtaggcgga gggagcgctc    600

gtaggtggaa cgactgcctc ccagtcgaat gcaagatttt gcacgcggac cagtctgccc    660

ggcaattccc gggtg                                                     675
```

<210> SEQ ID NO 670
<211> LENGTH: 675
<212> TYPE: DNA
<213> ORGANISM: Enterovirus sp.

<400> SEQUENCE: 670
ctccggcaca gccgcaccag tgcactggta cgctagtacc ttttcacggg gtagtcggta 60 tcccccccg taacttagaa gcatgtaaca aaccgaccaa taggtgcgcg gcagccagct 120
gcgttgcggt caagcacttc tgtctccccg gtccgcaagg atcgttaccc gcccactcca 180
ctacgaggag cctagtaact ggccaagtga ttgcggagtt gcgttcagcc acaaccccag 240
tggtagctct ggaagatggg gctcgcacat cccccgtggt aacacggttg cttgcccgcg 300
tgtgcttccg ggttcagtct ccgactgttc acttcaacat cacgcaacca gccaagagcc 360
gattgtgctg gagtggtctt cctccggggc cgtgaatgct gctaatccta acctccgagc 420
gtgtgcgcac aatccagtgt tgctacgtcg taacgcgtaa gttggaggcg gaacagacta 480
ctttcggcac cccgtgtttc ctttatttta ttcttatttt atggtgacaa ttgcagagat 540
ttgtgatatt gcgactttac cgttaaacat agcactgcat tacctggttg cattccacaa 600
aacttcagag attcctagtt cctacattga cctacttgtt tatttgaatc ttaaatacaa 660
acttgagcaa gtgaa 675

<210> SEQ ID NO 671
<211> LENGTH: 245
<212> TYPE: DNA
<213> ORGANISM: Unknown
<220> FEATURE:
<223> OTHER INFORMATION: Description of Unknown: Wobbly possum disease
virus sequence

<400> SEQUENCE: 671
cggctgtgag tgcttagcat atgctagagt actacagccg ggtgttggag tcatatgcac 60
tggttgcctg tataatagtc gggatctgtc tgacctacat tatctttggg agttgcttat 120
cacgacaatt ctcgaagtgt ctgtcgacag cttacccccg attcgacaag gccccttgtc 180
caccgcagac ctatcgattt tcaacgagaa cactatcaga ggtttaaatt taaaactcac 240
caaca 245

<210> SEQ ID NO 672
<211> LENGTH: 631
<212> TYPE: DNA
<213> ORGANISM: Avian orthoreovirus

<400> SEQUENCE: 672
gctttttcaa tcccttgtgt cgatgttccc gtatgtcatc tggttcatgt aacggtgcaa 60
cttctatttt tggtaacgtt cactgtcagg cagcgcaaaa ctcggcgggt ggtgatcttc 120
aagcgacttc ctctcttgtt gcttattggc cctacttggc tgcgggcggt ggtctgctcg 180
ttgttattat tataattgtt ggcgctgttt gttgttgcaa ggctaaggtt aaagcggacg 240
cagcccgaaa cgttttctac cgagagctgt tcgcacttaa ttcgggtaaa agtgatgcag 300
gacctccgat ttaccaggtt tagtgtacga cgatttgagt tttcaccttt cgtcttagag 360
gagtgcacta ctccatcttt cacgactata actaataccg atccggctct ctactttaac 420
attgagtttc cgtcaagtca tcgtctctcc cccttcattc cagaactgtt gtctcagcct 480
tgtaccgttc acgtttcatt gattcggaga ttcgctctct gtgcaacctt atctagtatt 540
tgtgaatacg actgtgcgct actgccatcc atcaacgcta ttacgacgat ccctacacca 600
ggtgcgtcat catctctgat tgttcattgg g 631

<210> SEQ ID NO 673
<211> LENGTH: 665
<212> TYPE: DNA
<213> ORGANISM: Kobuvirus sp.

<400> SEQUENCE: 673
ggggcctcgg ccccctcacc ctcttttccg gtggccacgc ccgggccacc gatacttccc 60
ttcactcctt cgggactgtt ggggaggaac acaacagggc tcccctgttt tcccattcct 120
tccccctttt cccaacccca accgccgtat ctggtggcgg caagacacac gggtctttcc 180
ctctaaagca caattgtgtg tgtgtcccag gtcctcctgc gtacggtgcg ggagtgctcc 240
cacccaactg ttgtaagcct gtccaacgcg tcgtcctggc aagactatga cgtcgcatgt 300
tccgctgcgg atgccgaccg ggtaaccggt tccccagtgt gtgtagtgcg atcttccagg 360
tcctcctggt tggcgttgtc cagaaactgc ttcaggtaag tggggtgtgc ccaatcccta 420
caaaggttga ttctttcacc accttaggaa tgctccggag gtaccccagc aacagctggg 480
atctgaccgg aggctaattg tctacgggtg gtgtttcctt tttcttttca cacaactcta 540
ctgctgacaa ctcactgact atccacttgc tctcttgtgc ctttctgctc tggttcaagt 600
tccttgattg tttttgactg cttttcactg cttttcttct cacaatcctt gctcagttca 660
aagtc 665

<210> SEQ ID NO 674
<211> LENGTH: 655
<212> TYPE: DNA
<213> ORGANISM: Kobuvirus sp.

<400> SEQUENCE: 674
ccccctcacc ctcttttccg gtggccacgc ccgggccacc gatacttccc ttcactcctt 60
cgggactgtt ggggaggaac acaacagggc tcccctgttt tcccattcct tccccctttt 120
cccaacccca accgccgtat ctggtggcgg caagacacac gggtctttcc ctctaaagca 180
caattgtgtg tgtgtcccag gtcctcctgc gtacggtgcg ggagtgctcc cacccaactg 240
ttgtaagcct gtccaacgcg tcgtcctggc aagactatga cgtcgcatgt tccgctgcgg 300
atgccgaccg ggtaaccggt tccccagtgt gtgtagtgcg atcttccagg tcctcctggt 360
tggcgttgtc cagaaactgc ttcaggtaag tggggtgtgc ccaatcccta caaaggttga 420
ttctttcacc accttaggaa tgctccggag gtaccccagc aacagctggg atctgaccgg 480
aggctaattg tctacgggtg gtgtttcctt tttcttttca cacaactcta ctgctgacaa 540
ctcactgact atccacttgc tctcttgtgc ctttctgctc tggttcaagt tccttgattg 600
tttttgactg cttttcactg cttttcttct cacaatcctt gctcagttca aagtc 655

<210> SEQ ID NO 675
<211> LENGTH: 645
<212> TYPE: DNA
<213> ORGANISM: Kobuvirus sp.

<400> SEQUENCE: 675
ctcttttccg gtggccacgc ccgggccacc gatacttccc ttcactcctt cgggactgtt 60
ggggaggaac acaacagggc tcccctgttt tcccattcct tccccctttt cccaacccca 120
accgccgtat ctggtggcgg caagacacac gggtctttcc ctctaaagca caattgtgtg 180
tgtgtcccag gtcctcctgc gtacggtgcg ggagtgctcc cacccaactg ttgtaagcct 240
gtccaacgcg tcgtcctggc aagactatga cgtcgcatgt tccgctgcgg atgccgaccg 300
ggtaaccggt tccccagtgt gtgtagtgcg atcttccagg tcctcctggt tggcgttgtc 360
cagaaactgc ttcaggtaag tggggtgtgc ccaatcccta caaaggttga ttctttcacc 420
accttaggaa tgctccggag gtaccccagc aacagctggg atctgaccgg aggctaattg 480
tctacgggtg gtgtttcctt tttcttttca cacaactcta ctgctgacaa ctcactgact 540
atccacttgc tctcttgtgc ctttctgctc tggttcaagt tccttgattg tttttgactg 600
cttttcactg cttttcttct cacaatcctt gctcagttca aagtc 645

<210> SEQ ID NO 676
<211> LENGTH: 635
<212> TYPE: DNA
<213> ORGANISM: Kobuvirus sp.

<400> SEQUENCE: 676
gtggccacgc ccgggccacc gatacttccc ttcactcctt cgggactgtt ggggaggaac 60
acaacagggc tcccctgttt tcccattcct tccccctttt cccaacccca accgccgtat 120
ctggtggcgg caagacacac gggtctttcc ctctaaagca caattgtgtg tgtgtcccag 180
gtcctcctgc gtacggtgcg ggagtgctcc cacccaactg ttgtaagcct gtccaacgcg 240
tcgtcctggc aagactatga cgtcgcatgt tccgctgcgg atgccgaccg ggtaaccggt 300
tccccagtgt gtgtagtgcg atcttccagg tcctcctggt tggcgttgtc cagaaactgc 360
ttcaggtaag tggggtgtgc ccaatcccta caaaggttga ttctttcacc accttaggaa 420
tgctccggag gtaccccagc aacagctggg atctgaccgg aggctaattg tctacgggtg 480
gtgtttcctt tttcttttca cacaactcta ctgctgacaa ctcactgact atccacttgc 540
tctcttgtgc ctttctgctc tggttcaagt tccttgattg tttttgactg cttttcactg 600
cttttcttct cacaatcctt gctcagttca aagtc 635

<210> SEQ ID NO 677
<211> LENGTH: 625
<212> TYPE: DNA
<213> ORGANISM: Kobuvirus sp.

<400> SEQUENCE: 677
ccgggccacc gatacttccc ttcactcctt cgggactgtt ggggaggaac acaacagggc 60
tcccctgttt tcccattcct tccccctttt cccaacccca accgccgtat ctggtggcgg 120
caagacacac gggtctttcc ctctaaagca caattgtgtg tgtgtcccag gtcctcctgc 180
gtacggtgcg ggagtgctcc cacccaactg ttgtaagcct gtccaacgcg tcgtcctggc 240
aagactatga cgtcgcatgt tccgctgcgg atgccgaccg ggtaaccggt tccccagtgt 300
gtgtagtgcg atcttccagg tcctcctggt tggcgttgtc cagaaactgc ttcaggtaag 360
tggggtgtgc ccaatcccta caaaggttga ttctttcacc accttaggaa tgctccggag 420
gtaccccagc aacagctggg atctgaccgg aggctaattg tctacgggtg gtgtttcctt 480
tttcttttca cacaactcta ctgctgacaa ctcactgact atccacttgc tctcttgtgc 540
ctttctgctc tggttcaagt tccttgattg tttttgactg cttttcactg cttttcttct 600
cacaatcctt gctcagttca aagtc 625

-continued

<210> SEQ ID NO 678
<211> LENGTH: 675
<212> TYPE: DNA
<213> ORGANISM: Unknown
<220> FEATURE:
<223> OTHER INFORMATION: Description of Unknown: Picornavirales sp. isolate RtMruf-PicoV sequence

<400> SEQUENCE: 678
tttgctcagc gtaacttctc cgggttacgt ggagaccaaa aggctacgga gactcgggct 60
acggccctgg agcacctagg tgctcctaaa gacgttagaa gttgtacaaa ctcgcccaat 120
agggcccccc aaccaggggg gtagcgggca agcacttctg tttccccggt atgatctcat 180
aggctgtacc cacggctgaa agagagatta tcgttacccg cctcactact tcgagaagcc 240
cagtaatggt tcatgaagtt gatctcgttg acccggtgtt tcccccacac cagaaacctg 300
tgatgggggt ggtcatcccg gtcatggcga catgacggac ctccccgcgc cggcacaggg 360
cctcttcgga ggacgagtga catggattca accgtgaaga gcctattgag ctagtgttga 420
ttcctccgcc cccgtgaatg cggctaatcc caactccgga gcaggcgggc ccaaaccagg 480
gtctggcctg tcgtaacgcg aaagtctgga gcggaaccga ctactttcgg gaaggcgtgt 540
ttccttttgt tccttttatc aagttttatg gtgacaactc ctggtagacg ttttattgcg 600
tttattgaga gatttccaac aattgaacag actagaacca cttgttttat caaaccctca 660
cagaataaga taaca 675

<210> SEQ ID NO 679
<211> LENGTH: 675
<212> TYPE: DNA
<213> ORGANISM: Unknown
<220> FEATURE:
<223> OTHER INFORMATION: Description of Unknown: Apodemus agrarius picornavirus strain Longquan-Aa118 sequence

<400> SEQUENCE: 679
ttactcagcg taactactcc gggttacgtg atgaagaaga ggctacggag attctcgggc 60
tacggccctg gagccactcc ggctcctaaa gatttagaag tttgagcaca cccgcccact 120
agggcccccc atccaggggg gcaacgggca agcacttctg tttccccggt atgatctgat 180
aggctgtaac cacggctgaa acagagatta tcgttatccg cttcactact tcgagaagcc 240
tagtaatgat gggtgaaatt gaatccgttg atccggtgtc tcccccacac cagaaactca 300
tgatgagggt tgccatcccg gctacggcga cgtagcgggc atccctgcgc tggcatgagg 360
cctcttagga ggacggatga tatggatctt gtcgtgaaga gcctattgag ctagtgtcga 420
ctcctccgcc cccgtgaatg cggctaatcc taaccccgga gcaggtgggt ccaatccagg 480
gcctggcctg tcgtaatgcg taagtctggg acggaaccga ctactttcgg gaaggcgtgt 540
ttccatttgt tcattatttg tgtgtttatg gtgacaactc tgggtaaacg ttctattgcg 600
tttattgaga gattcccaac aattgaacaa acgagaacta cctgttttat taaatttaca 660
cagagaagaa ttaca 675

<210> SEQ ID NO 680
<211> LENGTH: 675
<212> TYPE: DNA
<213> ORGANISM: Unknown
<220> FEATURE:
<223> OTHER INFORMATION: Description of Unknown: Niviventer confucianus picornavirus sequence

<400> SEQUENCE: 680

```
ccctttcata accccccccct tttaacccaa cccttcgtaa ccgtacgctt cactcgcctt     60

tgggtatagc ggcccaatgt gctgaagaaa aggatacgct ataaggggcc aacgggtggt    120

ggcccttaag accacccaac ctagaagctt gtacactcgg gcaatagtga ggcccacatc    180

cagtgggtca agcccaaagc attcttgttc cccggtatga tctcataagc tgtacccacg    240

gctgaaagag tgattatcgt tatcccactc agtacttcgg agagcctagt acaccacttg    300

gaaatggaag tctgtgatcc ggggttgacc ctgaacccca gaaactcatg atgaggctaa    360

ccttcccgaa cacggcgacg tgtggttagc ctgcgctggc atgaggcctc tttgtaggca    420

gactgaaatg gaagggtgac gaagagccga ctgagctact gttttattcc tccggccccc    480

tgaatgcggc taatcctaac tcctggtcca gtacttgtaa cccaacaggt ggctggtcgt    540

aatgcgtaag ccgggagcgg aaccgactac tttggggcgt ccgtgtttct caatattatt    600

catttctagc ttatggtgac aatttatgat tgcagagatt gtgctgtatt tgtgtctgag    660

agaagaagta acaat                                                     675
```

<210> SEQ ID NO 681
<211> LENGTH: 619
<212> TYPE: DNA
<213> ORGANISM: Unknown
<220> FEATURE:
<223> OTHER INFORMATION: Description of Unknown: Bat picornavirus isolate BtRs-PicoV sequence

<400> SEQUENCE: 681

```
tttcaaaagg ccctgggcat acggcgttat tcgtaacgtc gtatgtccag ggcggtagca     60

tcaggccaag gcctgatgct accacgtgtg gactaaacca cacactcttc ttgtgacacg    120

ttgtgtcacc tatccctttc ttggtaactt agaagcttgt acacttacgc acgtaggtgc    180

cccacatcca gtggggtttg tgcaaagcaa tcttgttccc cggtaaaccc tgataggctg    240

taaccacggc cgaaacaagg tttgtcgtta cccgactcac tactacacaa agcctagtaa    300

agttcaatga aagtgcgcag cgtgatccgg tcaaaacccc cttgaccaga aacacatgat    360

gagggtcacc aacccccact ggcgacagtg tggtgtccct gcgttggcat gtggcctcgt    420

agaggcgttg caatctggat ttgctccgaa gagccccgtg tgctagtgtt tatacctccg    480

gccccttgaa tgcggctaat cctaaccccc gagcatgtac acacaagcca gtgtgtagca    540

tgtcgtaatg agcaatttgg ggatggaacc gactacttta gggtgtccgt gtttctcatt    600

attctttgtt tgatgtttt                                                 619
```

<210> SEQ ID NO 682
<211> LENGTH: 593
<212> TYPE: DNA
<213> ORGANISM: Unknown
<220> FEATURE:
<223> OTHER INFORMATION: Description of Unknown: Rhinolophus picornavirus strain Guizhou-Rr100 sequence

<400> SEQUENCE: 682

```
tttttttttct caggcggtag catccagcca aggcctgatg ctaccaacgt gtgactaaac     60

cacactctct ttttgtgata cattgtgtca cctatccctt tcttggtaac ttagaagctt    120

gtacacccac gcacgtaggt accccacatc cagtggggtt tgtgcaaagc attcttgttc    180

cccggtaaac cctgataggc tgtaaccacg gctgaaacaa ggtttgtcgt tacccgactc    240

actactacgc aaagcctagt aaagttcaat gaaagtgcgc agcgtgatcc ggtcaaaacc    300
```

cccttgacca gaaacacatg atgagggtca ccaaccccca ctggcgacag tgtggtgtcc 360
ctgcgttggc atgtggcctc atagaggcgt tgcaatctgg atttgctccg aagagccccg 420
tgtgctagtg tttatacctc cggccccttg aatgcggcta atcctaaccc ccgagcatgt 480
acacacacgc cagtgtgcag catgtcgtaa tgagcaattt ggggatggaa ccgactactt 540
tagggtgtcc gtgtttctca ttattctttg tttgatgttt tatggtgaca aca 593

<210> SEQ ID NO 683
<211> LENGTH: 597
<212> TYPE: DNA
<213> ORGANISM: Unknown
<220> FEATURE:
<223> OTHER INFORMATION: Description of Unknown: Rhinolophus
picornavirus strain Henan-Rf265 sequence

<400> SEQUENCE: 683
cggaacgttg tatgctcagg gcgtaggcac cacccacggg tggtgcctac acgtgtggac 60
taaaccacac actcttttca gcacttagtg ctgctatctc tttttgtaac ttagaagttt 120
gtacacaatg cgttagggcc acacatccag tgtggtatcg caaagcactt ctgtttcccc 180
ggtgctagta ggagggtggc tgctccacgg ccacttgccg aacccatcgt tacccgactc 240
attacttcgc aaagcctagt aacccagttg aagcaagccc ggcgtgttcc ggtcaggaaa 300
aaccccccct ggccagaaac atgtgatgag ggtgggctat ccccactggt gacagtgagc 360
cctccctgcg ttggcacatg gcccgatctg ggcgtggttc ttgtggatgc tgccgaagag 420
ccccgtgagc tagtgtttat accgccggcc tcgtgaatgc ggctaaccct aaccccggag 480
cagaggctac tgaagccaca gtagtcgctg tcgtaacgag taattctggg atgggaccga 540
ctactttcga gtgtccgtgt ttcctttatt cttttattgt tgtttatggt gacaaac 597

<210> SEQ ID NO 684
<211> LENGTH: 636
<212> TYPE: DNA
<213> ORGANISM: Enterovirus sp.

<400> SEQUENCE: 684
cccctaggat ccactggatg tcagtacact ggtatcgtgg tacctttgta cgcctgtttt 60
ataccccctt ccccgcaact ttagaagcat caaaagcacc gctcaatagt caccacaccc 120
ccagtgtggt ttcgagcaag cacttctgtt ttcccggttg cgtcccatat gctgtgcaaa 180
cggcaaaaag ggacaatatc gttacccgct tgtatactac gggaaaccta gtaccaccat 240
tgattgtgtt gagagttgcg ctcatcacct ttccccggtg tagctcaggc cgatgaggct 300
cagaatcccc cacaggtgac tgtgtctgag cctgcgttgg cggcctgccc tcgccttatg 360
gcgtgggacg cttgatacat gacatggtgc gaagagtcta ctgtgctatg caagagtcct 420
ccggcccctg aatgtggcta atcctaacca ctgatcccac gcacgcaaac cagtgtgtag 480
tgggtcgtaa cgcgcaagtc ggtggcggaa ccaactactt tgggtgaccg tgtttccttt 540
attacttatt gaatgtttat ggtgacaatt gtttgattca gttgttgcca ttctctacat 600
tcatttaccc agcatcaaac caattgaact gttaca 636

<210> SEQ ID NO 685
<211> LENGTH: 421
<212> TYPE: DNA
<213> ORGANISM: Unknown
<220> FEATURE:
<223> OTHER INFORMATION: Description of Unknown: Human poliovirus 1
strain NIE1116623 sequence

<400> SEQUENCE: 685
agtctggaca tccctcaccg gcgacggtgg tccaggctgc gctggcggcc tacctgtggt 60
ccaaagccac gggacgctac atgtgaacaa ggtgtgaaga gcctattgag ctacaaaaga 120
gtcctccggc ccctgaatgc ggctaatccc aaccacggat caagggtgca caaaccagtg 180
tacaccttgt cgtaacgcgc aagtctgtgg cggaaccgac tactttgggt gtccgtgttt 240
cctttttaat tttgatggct gcttatggtg acaatcatag attgttatca taaagctaat 300
tggattggcc atccggtgag agtgaaatat attgtttacc tccctgttgg gtttactcta 360
actaacttct ccatttataa acttgtcatc acagttttaa taattagaag tgcagtttac 420
a 421

<210> SEQ ID NO 686
<211> LENGTH: 663
<212> TYPE: DNA
<213> ORGANISM: Enterovirus sp.

<400> SEQUENCE: 686
tttaaaacag cctgggggtt gttcccaccc ccagggccca ctgggcgtta gtactctggt 60
atcgcggtac cttagtatgc ctgttttatg tctcctttcc cccgcaactt tagaagtaat 120
caagttatgg ctcaacagtc gccacacccc cagtgtggtt ccgagcaagc acttctgttc 180
cccggttgcg tcttatatgc tgtgtgaacg gcagaaaggg acaatatcgt tatccgctca 240
actactacgg gaagcctagt accaccatgg attgacctga aagttgcgtt cagcgcaccc 300
ccagcgcagc tcaggccgat gaggctccga ataccccacg ggcgaccgtg tcggagcctg 360
cgttggcggc ctgcccacgt tgcaaaacgt gggacgctca tttcatgaca tggtgcgaag 420
agcctactgt gctagttgag agtcctccgg cccctgaatg tggataatcc taaccactga 480
acctacgggc gcaaaccagc gtctggtagg ccgtaacgcg caagtcggtg gcggaaccaa 540
ctactttggg tgtccgtgtt tccttttatc tttttgaatg tttatggtga caattgttgt 600
gtacagttgt taccatagtt tgcattcaga aataaaccta acactttcca attatttgtt 660
aca 663

<210> SEQ ID NO 687
<211> LENGTH: 675
<212> TYPE: DNA
<213> ORGANISM: Unknown
<220> FEATURE:
<223> OTHER INFORMATION: Description of Unknown: Human poliovirus 2
strain NIE0811460 sequence

<400> SEQUENCE: 687
ttgtgcgcct gttttatatt cccccccgc aacttagaag cacgaaacca agttcaatag 60
aagggggtac aaaccagtac caccacgaac aagcacttct gtttccccgg tgacattgca 120
tagactgctc acgcggttga aagtgatcga tccgttaccc gcttgtgtac ttcgaaaagc 180
ctagtattgc cttggaatct tcgacgcgtt gcgctcagca cccgaccccg gggtgtagct 240
taggctgatg agtctggaca ttcctcaccg gtgacggtgg tccaggctgc gttggcggcc 300
tacctatggc taatgccata ggacgctaga tgtgaacaag gtgtgaagag cctattgagc 360
tacataagag tcctccggcc cctgaatgcg gctaatccta accacggagc aggcggtcgc 420
aaaccagtga ctagcttgtc gtaacgcgca agtctgtggc ggaaccgact actttgggtg 480
tccgtgtttc ctgttatttt tattatggct gcttatggtg acaatcagag attgttatca 540
taaagcgaat tggattggcc atccggtgag tgttgtgtca ggtatacaac tgtttgttgg 600
aaccactgtg ttagtttaac ctctctttca accaattagt caaaaacaat acgaagatag 660
aacaacaata ctaca 675

<210> SEQ ID NO 688
<211> LENGTH: 512
<212> TYPE: DNA
<213> ORGANISM: Unknown
<220> FEATURE:
<223> OTHER INFORMATION: Description of Unknown: Bovine picornavirus sequence

<400> SEQUENCE: 688
ttttctcccc tccccctcca actacctttt ccccctcttg taacgctaga agtttgtgca 60
aaccgcctgt agggtactgc aatccagcag tgcataggct aagcttttct tgttacccca 120
ccccacatta tactgaggag gattgtgaaa ttgtgttagt atgggttagt agcggtgacc 180
cgggtaaccc caacccagaa actcacggat gagatgaaca ggaccccaca tggtaacgtg 240
tgtgttcgtc tgccccgcaa ggtgaggccg tgagagcttt gcacgcgaaa accttgaaaa 300
cccaaaagta ccttgagctc ttcgctattt tgtgtttcct ccaggaccct gaatgcggct 360
aaacctaacc cgcgatccgc acgtagcaac ccagctagag tgtggtcgta atgcgcaagt 420
tgcgggcggt accgactact ttggtgttcc tgtgtttcct ttattttatt ttgaattttt 480
atggtgacaa cagctagaaa ataagagtga ac 512

<210> SEQ ID NO 689
<211> LENGTH: 675
<212> TYPE: DNA
<213> ORGANISM: Unknown
<220> FEATURE:
<223> OTHER INFORMATION: Description of Unknown: Human poliovirus 1 strain EQG1419328 sequence

<400> SEQUENCE: 689
acccttgtac gcctgtttta tactcccctc cccgtaactt agaagaaaca aaataagttc 60
aataggaggg ggtacaaacc agtaccacca cgaacaagca cttctgtctc cccggtgaca 120
ttgcatagac tgtccccacg gttgaaagca attgatccgt tacccgctct tgtacttcga 180
gaagcctagt accatcttgg aatcatcgat gcgttgcgct ccacactcag tcccagagtg 240
tagcttaggc tgatgagtct ggacattcct caccggcgac ggtggtccag gctgcgttgg 300
cggcctacct gtggcccaaa gccacaggac gctagatgtg aacaaggtgt gaagagccta 360
ttgagctata agagagtcct ccggcccctg aatgcggcta atcccaacca cggatcaagg 420
gtgcacgaac cagtgtatac cttgtcgtaa cgcgcaagtc cgtggcggaa ccgactactt 480
tgggtgaccg tgtttccttt tattatttca atggctgctt atggtgacaa tcattgattg 540
ttatcataaa gcgaattgga ctggccatcc ggtgaaagtg aaacatattg tttgcctcct 600
cgttgggtct acttcaacca atctttactt acaatcttac cactacagtt ttgctggtta 660
gaagtgtgtt tcacg 675

<210> SEQ ID NO 690
<211> LENGTH: 675
<212> TYPE: DNA
<213> ORGANISM: Unknown
<220> FEATURE:
<223> OTHER INFORMATION: Description of Unknown: Human poliovirus 2 isolate IS_061 sequence
<400> SEQUENCE: 690
ttgtgcgcct gttttatact cccctcccgc aacttagaag cacgaaacca agttcaatag 60
aagggggtac aaaccagtac cactacgaac aagcacttct gtttccccgg tgacattgca 120
tagactgctc acgcggttga aagtgatcga tccgttaccc gcttgtgtac ttcgaaaagc 180
ctagtatcgc cttggaatct tcgacgcgtt gcgctcagca cccgaccccg gggtgtagct 240
taggccgatg agtctggaca ttcctcaccg gtgacggtgg tccaggctgc gttggcggcc 300
tacctatggc taacgccata ggacgttaga tgtgaacaag gtgtgaagag cctattgagc 360
tacataagag tcctccggcc cctgaatgcg gctaatccta accacggagc aggcggtcgc 420
gaaccagtga ctggcttgtc gtaacgcgca agtctgtggc ggaaccgact actttgggtg 480
tccgtgtttc ctgttatttt tatcatggct gcttatggtg acaatcagag attgttatca 540
taaagcgaat tggattggcc atccggtgag tgttgtgtca ggtatacaac tgtttgttgg 600
aaccactgtg ttagctttgc ttctcattta accaattaat caaaaacaat acgaggataa 660
aacaacaata ctaca 675

<210> SEQ ID NO 691
<211> LENGTH: 675
<212> TYPE: DNA
<213> ORGANISM: Unknown
<220> FEATURE:
<223> OTHER INFORMATION: Description of Unknown: Coxsackievirus B5
sequence <400> SEQUENCE: 691
cctttgtgcg cctgttttat gccccccttcc cccaattgaa acttagaagt tacacacacc 60
gatcaacagc gggcgtggca taccagccgc gtcttgatca agcactcctg tttccccgga 120
ccgagtatca atagactgct cacgcggttg aaggagaaaa cgttcgttac ccggctaact 180
acttcgagaa acctagtagc atcatgaaag ttgcgaagcg tttcgctcag cacatcccca 240
gtgtagatca ggtcgatgag tcaccgcatt ccccacgggc gaccgtggcg gtggctgcgt 300
tggcggcctg cctacggggc aacccgtagg acgcttcaat acagacatgg tgcgaagagt 360
cgattgagct agttagtagt cctccggccc ctgaatccgg ctaatcctaa ctgcggagca 420
cataccctca acccaggggg cattgtgtcg taacgggtaa ctctgcagcg gaaccgacta 480
ctttgggtgt ccgtgtttcc ttttattctt ataatggctg cttatggtga caattgaaag 540
attgttacca tatagctatt ggattggcca tccggtgtct aacagagcta ttatatacct 600
ctttgttgga tttgtaccac ttgatctaaa ggaagtcaag acactacaat tcatcataca 660
attgaacaca gcaaa 675

<210> SEQ ID NO 692
<211> LENGTH: 675
<212> TYPE: DNA
<213> ORGANISM: Unknown
<220> FEATURE:
<223> OTHER INFORMATION: Description of Unknown: Coxsackievirus A10
sequence <400> SEQUENCE: 692
tttgtgcgcc tgttttacaa cccttcccca acttgtaacg tagaagtaat acacactact 60
gatcaatagc aggcatggcg cgccagtcat gtctcgatca agcacttctg ttcccccgga 120
ctgagtatca atagactgct cacgcggttg aaggagaaaa cgttcgttac ccggctaact 180
acttcgagaa acctagtagc accatagaag ctgcagagtg tttcgctcag cacttccccc 240
gtgtagatca ggctgatgag tcactgcaat ccccacgggt gaccgtggca gtggctgcgt 300
tggcggcctg cctatggggc aacccatagg acgctctaat gtggacatgg tgcgaagagt 360
ctattgagct agttagtagt cctccggccc ctgaatgcgg ctaatcctaa ctgcggagca 420
catgccttca acccagaagg tagtgtgtcg taacgggcaa ctctgcagcg gaaccgacta 480
ctttgggtgt ccgtgtttct ttttattcct atattggctg cttatggtga caatcacgga 540
attgttgcca tatagctatt ggattggcca tccggtgtct aatagagcta ttgtgtacct 600
atttgttgga tttactccgc tatcacataa atctctgaac actttgtgct ttatattgaa 660
cttaaacacc cgaaa 675

<210> SEQ ID NO 693
<211> LENGTH: 18
<212> TYPE: PRT
<213> ORGANISM: Unknown
<220> FEATURE:
<223> OTHER INFORMATION: Description of Unknown: Liver targeting moiety sequence

<400> SEQUENCE: 693

Cys Lys Asn Glu Lys Lys Asn Ile Glu Arg Asn Asn Lys Leu Lys Gln
1 5 10 15

Pro Pro

<210> SEQ ID NO 694
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 694
tataattcta ccctattgag gcattgacta 30

<210> SEQ ID NO 695
<211> LENGTH: 493
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 695

Met Ala Leu Pro Val Thr Ala Leu Leu Leu Pro Leu Ala Leu Leu Leu
1 5 10 15

His Ala Ala Arg Pro Asp Ile Val Leu Thr Gln Ser Pro Ala Ser Leu
20 25 30

Ala Val Ser Leu Gly Glu Arg Ala Thr Ile Asn Cys Arg Ala Ser Glu
35 40 45

Ser Val Ser Val Ile Gly Ala His Leu Ile His Trp Tyr Gln Gln Lys
50 55 60

Pro Gly Gln Pro Pro Lys Leu Leu Ile Tyr Leu Ala Ser Asn Leu Glu
65 70 75 80

Thr Gly Val Pro Ala Arg Phe Ser Gly Ser Gly Ser Gly Thr Asp Phe
85 90 95

Thr Leu Thr Ile Ser Ser Leu Gln Ala Glu Asp Ala Ala Ile Tyr Tyr
100 105 110

```
Cys Leu Gln Ser Arg Ile Phe Pro Arg Thr Phe Gly Gln Gly Thr Lys
        115                 120                 125

Leu Glu Ile Lys Gly Ser Thr Ser Gly Ser Gly Lys Pro Gly Ser Gly
    130                 135                 140

Glu Gly Ser Thr Lys Gly Gln Val Gln Leu Val Gln Ser Gly Ser Glu
145                 150                 155                 160

Leu Lys Lys Pro Gly Ala Ser Val Lys Val Ser Cys Lys Ala Ser Gly
                165                 170                 175

Tyr Thr Phe Thr Asp Tyr Ser Ile Asn Trp Val Arg Gln Ala Pro Gly
            180                 185                 190

Gln Gly Leu Glu Trp Met Gly Trp Ile Asn Thr Glu Thr Arg Glu Pro
        195                 200                 205

Ala Tyr Ala Tyr Asp Phe Arg Gly Arg Phe Val Phe Ser Leu Asp Thr
    210                 215                 220

Ser Val Ser Thr Ala Tyr Leu Gln Ile Ser Ser Leu Lys Ala Glu Asp
225                 230                 235                 240

Thr Ala Val Tyr Tyr Cys Ala Arg Asp Tyr Ser Tyr Ala Met Asp Tyr
                245                 250                 255

Trp Gly Gln Gly Thr Leu Val Thr Val Ser Ser Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 696
<211> LENGTH: 207
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 696

Lys Asn Gln Val Glu Gln Ser Pro Gln Ser Leu Ile Ile Leu Glu Gly
1 5 10 15

Lys Asn Cys Thr Leu Gln Cys Asn Tyr Thr Val Ser Pro Phe Ser Asn
20 25 30

Leu Arg Trp Tyr Lys Gln Asp Thr Gly Arg Gly Pro Val Ser Leu Thr
35 40 45

Ile Met Thr Phe Ser Glu Asn Thr Lys Ser Asn Gly Arg Tyr Thr Ala
50 55 60

Thr Leu Asp Ala Asp Thr Lys Gln Ser Ser Leu His Ile Thr Ala Ser
65 70 75 80

Gln Leu Ser Asp Ser Ala Ser Tyr Ile Cys Val Val Asn His Ser Gly
85 90 95

Gly Ser Tyr Ile Pro Thr Phe Gly Arg Gly Thr Ser Leu Ile Val His
100 105 110

Pro Tyr Ile Gln Lys Pro Asp Pro Ala Val Tyr Gln Leu Arg Asp Ser
115 120 125

Lys Ser Ser Asp Lys Ser Val Cys Leu Phe Thr Asp Phe Asp Ser Gln
130 135 140

Thr Asn Val Ser Gln Ser Lys Asp Ser Asp Val Tyr Ile Thr Asp Lys
145 150 155 160

Thr Val Leu Asp Met Arg Ser Met Asp Phe Lys Ser Asn Ser Ala Val
165 170 175

Ala Trp Ser Asn Lys Ser Asp Phe Ala Cys Ala Asn Ala Phe Asn Asn
180 185 190

Ser Ile Ile Pro Glu Asp Thr Phe Phe Pro Ser Pro Glu Ser Ser
195 200 205

<210> SEQ ID NO 697
<211> LENGTH: 246
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 697

Asp Val Lys Val Thr Gln Ser Ser Arg Tyr Leu Val Lys Arg Thr Gly
1 5 10 15

Glu Lys Val Phe Leu Glu Cys Val Gln Asp Met Asp His Glu Asn Met
20 25 30

Phe Trp Tyr Arg Gln Asp Pro Gly Leu Gly Leu Arg Leu Ile Tyr Phe
35 40 45

Ser Tyr Asp Val Lys Met Lys Glu Lys Gly Asp Ile Pro Glu Gly Tyr
50 55 60

Ser Val Ser Arg Glu Lys Lys Glu Arg Phe Ser Leu Ile Leu Glu Ser
65 70 75 80

Ala Ser Thr Asn Gln Thr Ser Met Tyr Leu Cys Ala Ser Ser Phe Leu
85 90 95

Met Thr Ser Gly Asp Pro Tyr Glu Gln Tyr Phe Gly Pro Gly Thr Arg
100 105 110

Leu Thr Val Thr Glu Asp Leu Lys Asn Val Phe Pro Pro Glu Val Ala
115 120 125

Val Phe Glu Pro Ser Glu Ala Glu Ile Ser His Thr Gln Lys Ala Thr

```
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp
                245


<210> SEQ ID NO 698
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 698

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr
        115


<210> SEQ ID NO 699
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 699

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
```

```
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110


<210> SEQ ID NO 700
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 700

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165


<210> SEQ ID NO 701
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 701

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
```

-continued

```
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450
```

<210> SEQ ID NO 702
<211> LENGTH: 1462
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 702

```
Leu Ser Val Lys Ala Gln Thr Ala His Ile Val Leu Glu Asp Gly Thr
1               5                   10                  15

Lys Met Lys Gly Tyr Ser Phe Gly His Pro Ser Ser Val Ala Gly Glu
            20                  25                  30

Val Val Phe Asn Thr Gly Leu Gly Gly Tyr Pro Glu Ala Ile Thr Asp
        35                  40                  45

Pro Ala Tyr Lys Gly Gln Ile Leu Thr Met Ala Asn Pro Ile Ile Gly
    50                  55                  60

Asn Gly Gly Ala Pro Asp Thr Thr Ala Leu Asp Glu Leu Gly Leu Ser
65                  70                  75                  80

Lys Tyr Leu Glu Ser Asn Gly Ile Lys Val Ser Gly Leu Leu Val Leu
                85                  90                  95

Asp Tyr Ser Lys Asp Tyr Asn His Trp Leu Ala Thr Lys Ser Leu Gly
            100                 105                 110

Gln Trp Leu Gln Glu Glu Lys Val Pro Ala Ile Tyr Gly Val Asp Thr
        115                 120                 125

Arg Met Leu Thr Lys Ile Ile Arg Asp Lys Gly Thr Met Leu Gly Lys
    130                 135                 140

Ile Glu Phe Glu Gly Gln Pro Val Asp Phe Val Asp Pro Asn Lys Gln
145                 150                 155                 160

Asn Leu Ile Ala Glu Val Ser Thr Lys Asp Val Lys Val Tyr Gly Lys
                165                 170                 175

Gly Asn Pro Thr Lys Val Val Ala Val Asp Cys Gly Ile Lys Asn Asn
            180                 185                 190

Val Ile Arg Leu Leu Val Lys Arg Gly Ala Glu Val His Leu Val Pro
        195                 200                 205

Trp Asn His Asp Phe Thr Lys Met Glu Tyr Asp Gly Ile Leu Ile Ala
    210                 215                 220

Gly Gly Pro Gly Asn Pro Ala Leu Ala Glu Pro Leu Ile Gln Asn Val
225                 230                 235                 240

Arg Lys Ile Leu Glu Ser Asp Arg Lys Glu Pro Leu Phe Gly Ile Ser
                245                 250                 255

Thr Gly Asn Leu Ile Thr Gly Leu Ala Ala Gly Ala Lys Thr Tyr Lys
            260                 265                 270

Met Ser Met Ala Asn Arg Gly Gln Asn Gln Pro Val Leu Asn Ile Thr
        275                 280                 285

Asn Lys Gln Ala Phe Ile Thr Ala Gln Asn His Gly Tyr Ala Leu Asp
    290                 295                 300

Asn Thr Leu Pro Ala Gly Trp Lys Pro Leu Phe Val Asn Val Asn Asp
305                 310                 315                 320

Gln Thr Asn Glu Gly Ile Met His Glu Ser Lys Pro Phe Phe Ala Val
                325                 330                 335

Gln Phe His Pro Glu Val Thr Pro Gly Pro Ile Asp Thr Glu Tyr Leu
            340                 345                 350

Phe Asp Ser Phe Phe Ser Leu Ile Lys Lys Gly Lys Ala Thr Thr Ile
        355                 360                 365

Thr Ser Val Leu Pro Lys Pro Ala Leu Val Ala Ser Arg Val Glu Val
    370                 375                 380

Ser Lys Val Leu Ile Leu Gly Ser Gly Gly Leu Ser Ile Gly Gln Ala
```

```
385                 390                 395                 400

Gly Glu Phe Asp Tyr Ser Gly Ser Gln Ala Val Lys Ala Met Lys Glu
                405                 410                 415

Glu Asn Val Lys Thr Val Leu Met Asn Pro Asn Ile Ala Ser Val Gln
            420                 425                 430

Thr Asn Glu Val Gly Leu Lys Gln Ala Asp Thr Val Tyr Phe Leu Pro
        435                 440                 445

Ile Thr Pro Gln Phe Val Thr Glu Val Ile Lys Ala Glu Gln Pro Asp
    450                 455                 460

Gly Leu Ile Leu Gly Met Gly Gly Gln Thr Ala Leu Asn Cys Gly Val
465                 470                 475                 480

Glu Leu Phe Lys Arg Gly Val Leu Lys Glu Tyr Gly Val Lys Val Leu
                485                 490                 495

Gly Thr Ser Val Glu Ser Ile Met Ala Thr Glu Asp Arg Gln Leu Phe
            500                 505                 510

Ser Asp Lys Leu Asn Glu Ile Asn Glu Lys Ile Ala Pro Ser Phe Ala
        515                 520                 525

Val Glu Ser Ile Glu Asp Ala Leu Lys Ala Ala Asp Thr Ile Gly Tyr
    530                 535                 540

Pro Val Met Ile Arg Ser Ala Tyr Ala Leu Gly Gly Leu Gly Ser Gly
545                 550                 555                 560

Ile Cys Pro Asn Arg Glu Thr Leu Met Asp Leu Ser Thr Lys Ala Phe
                565                 570                 575

Ala Met Thr Asn Gln Ile Leu Val Glu Lys Ser Val Thr Gly Trp Lys
            580                 585                 590

Glu Ile Glu Tyr Glu Val Val Arg Asp Ala Asp Asp Asn Cys Val Thr
        595                 600                 605

Val Cys Asn Met Glu Asn Val Asp Ala Met Gly Val His Thr Gly Asp
    610                 615                 620

Ser Val Val Val Ala Pro Ala Gln Thr Leu Ser Asn Ala Glu Phe Gln
625                 630                 635                 640

Met Leu Arg Arg Thr Ser Ile Asn Val Val Arg His Leu Gly Ile Val
                645                 650                 655

Gly Glu Cys Asn Ile Gln Phe Ala Leu His Pro Thr Ser Met Glu Tyr
            660                 665                 670

Cys Ile Ile Glu Val Asn Ala Arg Leu Ser Arg Ser Ser Ala Leu Ala
        675                 680                 685

Ser Lys Ala Thr Gly Tyr Pro Leu Ala Phe Ile Ala Ala Lys Ile Ala
    690                 695                 700

Leu Gly Ile Pro Leu Pro Glu Ile Lys Asn Val Val Ser Gly Lys Thr
705                 710                 715                 720

Ser Ala Cys Phe Glu Pro Ser Leu Asp Tyr Met Val Thr Lys Ile Pro
                725                 730                 735

Arg Trp Asp Leu Asp Arg Phe His Gly Thr Ser Ser Arg Ile Gly Ser
            740                 745                 750

Ser Met Lys Ser Val Gly Glu Val Met Ala Ile Gly Arg Thr Phe Glu
        755                 760                 765

Glu Ser Phe Gln Lys Ala Leu Arg Met Cys His Pro Ser Ile Glu Gly
    770                 775                 780

Phe Thr Pro Arg Leu Pro Met Asn Lys Glu Trp Pro Ser Asn Leu Asp
785                 790                 795                 800

Leu Arg Lys Glu Leu Ser Glu Pro Ser Ser Thr Arg Ile Tyr Ala Ile
                805                 810                 815
```

-continued

```
Ala Lys Ala Ile Asp Asp Asn Met Ser Leu Asp Glu Ile Glu Lys Leu
            820                 825                 830

Thr Tyr Ile Asp Lys Trp Phe Leu Tyr Lys Met Arg Asp Ile Leu Asn
        835                 840                 845

Met Glu Lys Thr Leu Lys Gly Leu Asn Ser Glu Ser Met Thr Glu Glu
    850                 855                 860

Thr Leu Lys Arg Ala Lys Glu Ile Gly Phe Ser Asp Lys Gln Ile Ser
865                 870                 875                 880

Lys Cys Leu Gly Leu Thr Glu Ala Gln Thr Arg Glu Leu Arg Leu Lys
                885                 890                 895

Lys Asn Ile His Pro Trp Val Lys Gln Ile Asp Thr Leu Ala Ala Glu
            900                 905                 910

Tyr Pro Ser Val Thr Asn Tyr Leu Tyr Val Thr Tyr Asn Gly Gln Glu
        915                 920                 925

His Asp Val Asn Phe Asp Asp His Gly Met Met Val Leu Gly Cys Gly
    930                 935                 940

Pro Tyr His Ile Gly Ser Ser Val Glu Phe Asp Trp Cys Ala Val Ser
945                 950                 955                 960

Ser Ile Arg Thr Leu Arg Gln Leu Gly Lys Lys Thr Val Val Val Asn
                965                 970                 975

Cys Asn Pro Glu Thr Val Ser Thr Asp Phe Asp Glu Cys Asp Lys Leu
            980                 985                 990

Tyr Phe Glu Glu Leu Ser Leu Glu  Arg Ile Leu Asp Ile  Tyr His Gln
        995                 1000                1005

Glu Ala  Cys Gly Gly Cys Ile  Ile Ser Val Gly Gly  Gln Ile Pro
    1010                1015                1020

Asn Asn  Leu Ala Val Pro Leu  Tyr Lys Asn Gly Val  Lys Ile Met
    1025                1030                1035

Gly Thr  Ser Pro Leu Gln Ile  Asp Arg Ala Glu Asp  Arg Ser Ile
    1040                1045                1050

Phe Ser  Ala Val Leu Asp Glu  Leu Lys Val Ala Gln  Ala Pro Trp
    1055                1060                1065

Lys Ala  Val Asn Thr Leu Asn  Glu Ala Leu Glu Phe  Ala Lys Ser
    1070                1075                1080

Val Asp  Tyr Pro Cys Leu Leu  Arg Pro Ser Tyr Val  Leu Ser Gly
    1085                1090                1095

Ser Ala  Met Asn Val Val Phe  Ser Glu Asp Glu Met  Lys Lys Phe
    1100                1105                1110

Leu Glu  Glu Ala Thr Arg Val  Ser Gln Glu His Pro  Val Val Leu
    1115                1120                1125

Thr Lys  Phe Val Glu Gly Ala  Arg Glu Val Glu Met  Asp Ala Val
    1130                1135                1140

Gly Lys  Asp Gly Arg Val Ile  Ser His Ala Ile Ser  Glu His Val
    1145                1150                1155

Glu Asp  Ala Gly Val His Ser  Gly Asp Ala Thr Leu  Met Leu Pro
    1160                1165                1170

Thr Gln  Thr Ile Ser Gln Gly  Ala Ile Glu Lys Val  Lys Asp Ala
    1175                1180                1185

Thr Arg  Lys Ile Ala Lys Ala  Phe Ala Ile Ser Gly  Pro Phe Asn
    1190                1195                1200

Val Gln  Phe Leu Val Lys Gly  Asn Asp Val Leu Val  Ile Glu Cys
    1205                1210                1215
```

-continued

```
Asn Leu  Arg Ala Ser Arg Ser  Phe Pro Phe Val Ser  Lys Thr Leu
    1220                 1225                 1230

Gly Val  Asp Phe Ile Asp Val  Ala Thr Lys Val Met  Ile Gly Glu
    1235                 1240                 1245

Asn Val  Asp Glu Lys His Leu  Pro Thr Leu Asp His  Pro Ile Ile
    1250                 1255                 1260

Pro Ala  Asp Tyr Val Ala Ile  Lys Ala Pro Met Phe  Ser Trp Pro
    1265                 1270                 1275

Arg Leu  Arg Asp Ala Asp Pro  Ile Leu Arg Cys Glu  Met Ala Ser
    1280                 1285                 1290

Thr Gly  Glu Val Ala Cys Phe  Gly Glu Gly Ile His  Thr Ala Phe
    1295                 1300                 1305

Leu Lys  Ala Met Leu Ser Thr  Gly Phe Lys Ile Pro  Gln Lys Gly
    1310                 1315                 1320

Ile Leu  Ile Gly Ile Gln Gln  Ser Phe Arg Pro Arg  Phe Leu Gly
    1325                 1330                 1335

Val Ala  Glu Gln Leu His Asn  Glu Gly Phe Lys Leu  Phe Ala Thr
    1340                 1345                 1350

Glu Ala  Thr Ser Asp Trp Leu  Asn Ala Asn Asn Val  Pro Ala Thr
    1355                 1360                 1365

Pro Val  Ala Trp Pro Ser Gln  Glu Gly Gln Asn Pro  Ser Leu Ser
    1370                 1375                 1380

Ser Ile  Arg Lys Leu Ile Arg  Asp Gly Ser Ile Asp  Leu Val Ile
    1385                 1390                 1395

Asn Leu  Pro Asn Asn Asn Thr  Lys Phe Val His Asp  Asn Tyr Val
    1400                 1405                 1410

Ile Arg  Arg Thr Ala Val Asp  Ser Gly Ile Pro Leu  Leu Thr Asn
    1415                 1420                 1425

Phe Gln  Val Thr Lys Leu Phe  Ala Glu Ala Val Gln  Lys Ser Arg
    1430                 1435                 1440

Lys Val  Asp Ser Lys Ser Leu  Phe His Tyr Arg Gln  Tyr Ser Ala
    1445                 1450                 1455

Gly Lys  Ala Ala
    1460


<210> SEQ ID NO 703
<211> LENGTH: 1053
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 703

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95
```

-continued

```
Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510
```

```
Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
```

```
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                 1005

Asn Asp  Lys Arg Pro Pro Arg  Ile Ile Lys Thr Ile  Ala Ser Lys
    1010                 1015                 1020

Thr Gln  Ser Ile Lys Lys Tyr  Ser Thr Asp Ile Leu  Gly Asn Leu
    1025                 1030                 1035

Tyr Glu  Val Lys Ser Lys Lys  His Pro Gln Ile Ile  Lys Lys Gly
    1040                 1045                 1050


<210> SEQ ID NO 704
<211> LENGTH: 1353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 704

Ala Ala Gly Gly Ile Leu His Leu Glu Leu Leu Val Ala Val Gly Pro
1               5                   10                  15

Asp Val Phe Gln Ala His Gln Glu Asp Thr Glu Arg Tyr Val Leu Thr
            20                  25                  30

Asn Leu Asn Ile Gly Ala Glu Leu Leu Arg Asp Pro Ser Leu Gly Ala
        35                  40                  45

Gln Phe Arg Val His Leu Val Lys Met Val Ile Leu Thr Glu Pro Glu
    50                  55                  60

Gly Ala Pro Asn Ile Thr Ala Asn Leu Thr Ser Ser Leu Leu Ser Val
65                  70                  75                  80

Cys Gly Trp Ser Gln Thr Ile Asn Pro Glu Asp Asp Thr Asp Pro Gly
                85                  90                  95

His Ala Asp Leu Val Leu Tyr Ile Thr Arg Phe Asp Leu Glu Leu Pro
            100                 105                 110

Asp Gly Asn Arg Gln Val Arg Gly Val Thr Gln Leu Gly Gly Ala Cys
        115                 120                 125

Ser Pro Thr Trp Ser Cys Leu Ile Thr Glu Asp Thr Gly Phe Asp Leu
    130                 135                 140

Gly Val Thr Ile Ala His Glu Ile Gly His Ser Phe Gly Leu Glu His
145                 150                 155                 160

Asp Gly Ala Pro Gly Ser Gly Cys Gly Pro Ser Gly His Val Met Ala
                165                 170                 175

Ser Asp Gly Ala Ala Pro Arg Ala Gly Leu Ala Trp Ser Pro Cys Ser
            180                 185                 190

Arg Arg Gln Leu Leu Ser Leu Leu Ser Ala Gly Arg Ala Arg Cys Val
        195                 200                 205

Trp Asp Pro Pro Arg Pro Gln Pro Gly Ser Ala Gly His Pro Pro Asp
    210                 215                 220

Ala Gln Pro Gly Leu Tyr Tyr Ser Ala Asn Glu Gln Cys Arg Val Ala
225                 230                 235                 240
```

```
Phe Gly Pro Lys Ala Val Ala Cys Thr Phe Ala Arg Glu His Leu Asp
                245                 250                 255

Met Cys Gln Ala Leu Ser Cys His Thr Asp Pro Leu Asp Gln Ser Ser
            260                 265                 270

Cys Ser Arg Leu Leu Val Pro Leu Leu Asp Gly Thr Glu Cys Gly Val
        275                 280                 285

Glu Lys Trp Cys Ser Lys Gly Arg Cys Arg Ser Leu Val Glu Leu Thr
    290                 295                 300

Pro Ile Ala Ala Val His Gly Arg Trp Ser Ser Trp Gly Pro Arg Ser
305                 310                 315                 320

Pro Cys Ser Arg Ser Cys Gly Gly Gly Val Val Thr Arg Arg Arg Gln
                325                 330                 335

Cys Asn Asn Pro Arg Pro Ala Phe Gly Gly Arg Ala Cys Val Gly Ala
            340                 345                 350

Asp Leu Gln Ala Glu Met Cys Asn Thr Gln Ala Cys Glu Lys Thr Gln
        355                 360                 365

Leu Glu Phe Met Ser Gln Gln Cys Ala Arg Thr Asp Gly Gln Pro Leu
    370                 375                 380

Arg Ser Ser Pro Gly Gly Ala Ser Phe Tyr His Trp Gly Ala Ala Val
385                 390                 395                 400

Pro His Ser Gln Gly Asp Ala Leu Cys Arg His Met Cys Arg Ala Ile
                405                 410                 415

Gly Glu Ser Phe Ile Met Lys Arg Gly Asp Ser Phe Leu Asp Gly Thr
            420                 425                 430

Arg Cys Met Pro Ser Gly Pro Arg Glu Asp Gly Thr Leu Ser Leu Cys
        435                 440                 445

Val Ser Gly Ser Cys Arg Thr Phe Gly Cys Asp Gly Arg Met Asp Ser
    450                 455                 460

Gln Gln Val Trp Asp Arg Cys Gln Val Cys Gly Gly Asp Asn Ser Thr
465                 470                 475                 480

Cys Ser Pro Arg Lys Gly Ser Phe Thr Ala Gly Arg Ala Arg Glu Tyr
                485                 490                 495

Val Thr Phe Leu Thr Val Thr Pro Asn Leu Thr Ser Val Tyr Ile Ala
            500                 505                 510

Asn His Arg Pro Leu Phe Thr His Leu Ala Val Arg Ile Gly Gly Arg
        515                 520                 525

Tyr Val Val Ala Gly Lys Met Ser Ile Ser Pro Asn Thr Thr Tyr Pro
    530                 535                 540

Ser Leu Leu Glu Asp Gly Arg Val Glu Tyr Arg Val Ala Leu Thr Glu
545                 550                 555                 560

Asp Arg Leu Pro Arg Leu Glu Glu Ile Arg Ile Trp Gly Pro Leu Gln
                565                 570                 575

Glu Asp Ala Asp Ile Gln Val Tyr Arg Arg Tyr Gly Glu Glu Tyr Gly
            580                 585                 590

Asn Leu Thr Arg Pro Asp Ile Thr Phe Thr Tyr Phe Gln Pro Lys Pro
        595                 600                 605

Arg Gln Ala Trp Val Trp Ala Ala Val Arg Gly Pro Cys Ser Val Ser
    610                 615                 620

Cys Gly Ala Gly Leu Arg Trp Val Asn Tyr Ser Cys Leu Asp Gln Ala
625                 630                 635                 640

Arg Lys Glu Leu Val Glu Thr Val Gln Cys Gln Gly Ser Gln Gln Pro
                645                 650                 655

Pro Ala Trp Pro Glu Ala Cys Val Leu Glu Pro Cys Pro Pro Tyr Trp
```

-continued

```
            660                 665                 670

Ala Val Gly Asp Phe Gly Pro Cys Ser Ala Ser Cys Gly Gly Gly Leu
        675                 680                 685

Arg Glu Arg Pro Val Arg Cys Val Glu Ala Gln Gly Ser Leu Leu Lys
    690                 695                 700

Thr Leu Pro Pro Ala Arg Cys Arg Ala Gly Ala Gln Gln Pro Ala Val
705                 710                 715                 720

Ala Leu Glu Thr Cys Asn Pro Gln Pro Cys Pro Ala Arg Trp Glu Val
                725                 730                 735

Ser Glu Pro Ser Ser Cys Thr Ser Ala Gly Gly Ala Gly Leu Ala Leu
            740                 745                 750

Glu Asn Glu Thr Cys Val Pro Gly Ala Asp Gly Leu Glu Ala Pro Val
        755                 760                 765

Thr Glu Gly Pro Gly Ser Val Asp Glu Lys Leu Pro Ala Pro Glu Pro
    770                 775                 780

Cys Val Gly Met Ser Cys Pro Pro Gly Trp Gly His Leu Asp Ala Thr
785                 790                 795                 800

Ser Ala Gly Glu Lys Ala Pro Ser Pro Trp Gly Ser Ile Arg Thr Gly
                805                 810                 815

Ala Gln Ala Ala His Val Trp Thr Pro Ala Ala Gly Ser Cys Ser Val
            820                 825                 830

Ser Cys Gly Arg Gly Leu Met Glu Leu Arg Phe Leu Cys Met Asp Ser
        835                 840                 845

Ala Leu Arg Val Pro Val Gln Glu Glu Leu Cys Gly Leu Ala Ser Lys
    850                 855                 860

Pro Gly Ser Arg Arg Glu Val Cys Gln Ala Val Pro Cys Pro Ala Arg
865                 870                 875                 880

Trp Gln Tyr Lys Leu Ala Ala Cys Ser Val Ser Cys Gly Arg Gly Val
                885                 890                 895

Val Arg Arg Ile Leu Tyr Cys Ala Arg Ala His Gly Glu Asp Asp Gly
            900                 905                 910

Glu Glu Ile Leu Leu Asp Thr Gln Cys Gln Gly Leu Pro Arg Pro Glu
        915                 920                 925

Pro Gln Glu Ala Cys Ser Leu Glu Pro Cys Pro Pro Arg Trp Lys Val
    930                 935                 940

Met Ser Leu Gly Pro Cys Ser Ala Ser Cys Gly Leu Gly Thr Ala Arg
945                 950                 955                 960

Arg Ser Val Ala Cys Val Gln Leu Asp Gln Gly Gln Asp Val Glu Val
                965                 970                 975

Asp Glu Ala Ala Cys Ala Ala Leu Val Arg Pro Glu Ala Ser Val Pro
            980                 985                 990

Cys Leu Ile Ala Asp Cys Thr Tyr  Arg Trp His Val Gly  Thr Trp Met
        995                 1000                1005

Glu Cys  Ser Val Ser Cys Gly  Asp Gly Ile Gln Arg  Arg Arg Asp
    1010                1015                1020

Thr Cys  Leu Gly Pro Gln Ala  Gln Ala Pro Val Pro  Ala Asp Phe
    1025                1030                1035

Cys Gln  His Leu Pro Lys Pro  Val Thr Val Arg Gly  Cys Trp Ala
    1040                1045                1050

Gly Pro  Cys Val Gly Gln Gly  Thr Pro Ser Leu Val  Pro His Glu
    1055                1060                1065

Glu Ala  Ala Ala Pro Gly Arg  Thr Thr Ala Thr Pro  Ala Gly Ala
    1070                1075                1080
```

Ser Leu Glu Trp Ser Gln Ala Arg Gly Leu Leu Phe Ser Pro Ala
1085 1090 1095

Pro Gln Pro Arg Arg Leu Leu Pro Gly Pro Gln Glu Asn Ser Val
1100 1105 1110

Gln Ser Ser Ala Cys Gly Arg Gln His Leu Glu Pro Thr Gly Thr
1115 1120 1125

Ile Asp Met Arg Gly Pro Gly Gln Ala Asp Cys Ala Val Ala Ile
1130 1135 1140

Gly Arg Pro Leu Gly Glu Val Val Thr Leu Arg Val Leu Glu Ser
1145 1150 1155

Ser Leu Asn Cys Ser Ala Gly Asp Met Leu Leu Leu Trp Gly Arg
1160 1165 1170

Leu Thr Trp Arg Lys Met Cys Arg Lys Leu Leu Asp Met Thr Phe
1175 1180 1185

Ser Ser Lys Thr Asn Thr Leu Val Val Arg Gln Arg Cys Gly Arg
1190 1195 1200

Pro Gly Gly Gly Val Leu Leu Arg Tyr Gly Ser Gln Leu Ala Pro
1205 1210 1215

Glu Thr Phe Tyr Arg Glu Cys Asp Met Gln Leu Phe Gly Pro Trp
1220 1225 1230

Gly Glu Ile Val Ser Pro Ser Leu Ser Pro Ala Thr Ser Asn Ala
1235 1240 1245

Gly Gly Cys Arg Leu Phe Ile Asn Val Ala Pro His Ala Arg Ile
1250 1255 1260

Ala Ile His Ala Leu Ala Thr Asn Met Gly Ala Gly Thr Glu Gly
1265 1270 1275

Ala Asn Ala Ser Tyr Ile Leu Ile Arg Asp Thr His Ser Leu Arg
1280 1285 1290

Thr Thr Ala Phe His Gly Gln Gln Val Leu Tyr Trp Glu Ser Glu
1295 1300 1305

Ser Ser Gln Ala Glu Met Glu Phe Ser Glu Gly Phe Leu Lys Ala
1310 1315 1320

Gln Ala Ser Leu Arg Gly Gln Tyr Trp Thr Leu Gln Ser Trp Val
1325 1330 1335

Pro Glu Met Gln Asp Pro Gln Ser Trp Lys Gly Lys Glu Gly Thr
1340 1345 1350

<210> SEQ ID NO 705
<211> LENGTH: 431
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 705

Met Pro Asn Pro Arg Pro Gly Lys Pro Ser Ala Pro Ser Leu Ala Leu
1 5 10 15

Gly Pro Ser Pro Gly Ala Ser Pro Ser Trp Arg Ala Ala Pro Lys Ala
20 25 30

Ser Asp Leu Leu Gly Ala Arg Gly Pro Gly Gly Thr Phe Gln Gly Arg
35 40 45

Asp Leu Arg Gly Gly Ala His Ala Ser Ser Ser Ser Leu Asn Pro Met
50 55 60

Pro Pro Ser Gln Leu Gln Leu Pro Thr Leu Pro Leu Val Met Val Ala

-continued

```
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430


<210> SEQ ID NO 706
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 706
```

-continued

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160


<210> SEQ ID NO 707
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 707

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 708
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
```

<223> OTHER INFORMATION: This sequence may encompass 1-10 "Gly Ser" repeating units

<400> SEQUENCE: 708

```
Gly Ser Gly Ser Gly Ser Gly Ser Gly Ser Gly Ser Gly Ser Gly Ser
1               5                   10                  15

Gly Ser Gly Ser
            20
```

<210> SEQ ID NO 709
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(30)
<223> OTHER INFORMATION: This sequence may encompass 1-10 "Gly Gly Ser" repeating units

<400> SEQUENCE: 709

```
Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30
```

<210> SEQ ID NO 710
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly Ser" repeating units

<400> SEQUENCE: 710

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40
```

<210> SEQ ID NO 711
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(40)
<223> OTHER INFORMATION: This sequence may encompass 1-10 "Gly Gly Ser Gly" repeating units

<400> SEQUENCE: 711

```
Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30
```

Gly Gly Ser Gly Gly Gly Ser Gly
35 40

<210> SEQ ID NO 712
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(50)
<223> OTHER INFORMATION: This sequence may encompass 1-10 "Gly Gly Ser Gly Gly" repeating units

<400> SEQUENCE: 712

Gly Gly Ser Gly Gly Gly Gly Ser Gly Gly Gly Gly Ser Gly Gly Gly
1 5 10 15

Gly Ser Gly Gly Gly Gly Ser Gly Gly Gly Gly Ser Gly Gly Gly Gly
20 25 30

Ser Gly Gly Gly Gly Ser Gly Gly Gly Gly Ser Gly Gly Gly Gly Ser
35 40 45

Gly Gly
50

<210> SEQ ID NO 713
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly Gly Ser" repeating units

<400> SEQUENCE: 713

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser
50

<210> SEQ ID NO 714
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly Gly Gly" repeating units

<400> SEQUENCE: 714

Gly Gly Gly Gly Gly Gly Gly Gly Gly Gly Gly Gly Gly Gly Gly Gly
1 5 10 15

-continued

Gly Gly Gly Gly Gly Gly Gly Gly Gly Gly Gly Gly Gly Gly Gly Gly
20 25 30

Gly Gly Gly Gly Gly Gly Gly Gly Gly Gly Gly Gly Gly Gly Gly Gly
35 40 45

Gly Gly
50

<210> SEQ ID NO 715
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(30)
<223> OTHER INFORMATION: This sequence may encompass 1-10 “Gly Gly Gly” repeating units

<400> SEQUENCE: 715

Gly Gly Gly Gly Gly Gly Gly Gly Gly Gly Gly Gly Gly Gly Gly Gly
1 5 10 15

Gly Gly Gly Gly Gly Gly Gly Gly Gly Gly Gly Gly Gly Gly
20 25 30

<210> SEQ ID NO 716
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 716

Gly Gly Gly Gly Ser Gly Gly Gly Gly Ser Gly Gly Gly Gly Ser Gly
1 5 10 15

Gly Gly Gly Ser
20

<210> SEQ ID NO 717
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 717

Gly Gly Gly Gly Ser Gly Gly Gly Gly Ser Gly Gly Gly Gly Ser
1 5 10 15